US012479840B2

(12) United States Patent
Choi et al.

(10) Patent No.: US 12,479,840 B2
(45) Date of Patent: Nov. 25, 2025

(54) HMG-CoA REDUCTASE DEGRADATION INDUCING COMPOUND

(71) Applicant: Uppthera, Incheon (KR)

(72) Inventors: Si Woo Choi, Incheon (KR); Soo Hee Ryu, Incheon (KR); Ji Hoon Ryu, Seoul (KR); San Ha Son, Incheon (KR); Hwa Jin Lee, Incheon (KR); Seong Hoon Kim, Incheon (KR); Eun Bin Lee, Incheon (KR); Hye Guk Ryu, Incheon (KR); Im Suk Min, Gyeonggi-do (KR); Jun Kyu Lee, Gyeonggi-do (KR)

(73) Assignee: UPPTHERA INC., Incheon (KR)

( * ) Notice: Subject to any disclaimer, the term of this patent is extended or adjusted under 35 U.S.C. 154(b) by 1110 days.

(21) Appl. No.: 17/428,564

(22) PCT Filed: Mar. 30, 2021

(86) PCT No.: PCT/KR2021/003955

§ 371 (c)(1),
(2) Date: Aug. 4, 2021

(87) PCT Pub. No.: WO2021/201577

PCT Pub. Date: Oct. 7, 2021

(65) Prior Publication Data

US 2023/0078961 A1 Mar. 16, 2023

(30) Foreign Application Priority Data

Mar. 30, 2020 (KR) ........................ 10-2020-0037908

(51) Int. Cl.

| | |
|---|---|
| ***C07D 417/14*** | (2006.01) |
| ***A61K 47/55*** | (2017.01) |
| ***C07D 309/30*** | (2006.01) |
| ***C07D 405/14*** | (2006.01) |
| *A61K 31/366* | (2006.01) |
| *A61K 31/427* | (2006.01) |
| *A61K 31/454* | (2006.01) |
| *A61P 3/06* | (2006.01) |
| *A61P 9/00* | (2006.01) |

(52) U.S. Cl.

CPC ............ *C07D 417/14* (2013.01); *A61K 47/55* (2017.08); *C07D 309/30* (2013.01); *C07D 405/14* (2013.01)

(58) Field of Classification Search

CPC .. C07D 417/14; C07D 309/30; C07D 405/14; A61K 47/55; A61K 31/366; A61K 31/427; A61K 31/454; A61P 3/06; A61P 9/00

See application file for complete search history.

(56) References Cited

FOREIGN PATENT DOCUMENTS

| | | | |
|---|---|---|---|
| KR | 1020180035779 | | 4/2018 |
| WO | WO 2007/005941 | A2 | 1/2007 |
| WO | WO-2019109415 | A1 * | 6/2019 |
| WO | WO 2019/195609 | A2 | 10/2019 |
| WO | WO 2019/246570 | A1 | 12/2019 |

OTHER PUBLICATIONS

Lim SY. Role of statins in coronary artery disease. Chonnam Med J. Apr. 2013;49(1):1-6. doi: 10.4068/cmj.2013.49.1.1. Epub Apr. 25, 2013. PMID: 23678470; PMCID: PMC3651980. (Year: 2013).*

Akuffo, Afua A., et al. "Ligand-mediated protein degradation reveals functional conservation among sequence variants of the CUL4-type E3 ligase substrate receptor cereblon." Journal of Biological Chemistry 293.16 (2018): 6187-6200.

Buckley, Dennis L., et al. "Targeting the von Hippel-Lindau E3 ubiquitin ligase using small molecules to disrupt the VHL/HIF-1α interaction." Journal of the American Chemical Society 134.10 (2012): 4465-4468.

Buckley, Dennis L., and Craig M. Crews. "Small-Molecule Control of Intracellular Protein Levels through Modulation of the Ubiquitin Proteasome System." Angewandte Chemie International Edition 53.9 (2014): 2312-2330.

Burslem, George M., et al. "The advantages of targeted protein degradation over inhibition: an RTK case study." Cell chemical biology 25.1 (2018): 67-77.

Burslem, George M., and Craig M. Crews. "Small-molecule modulation of protein homeostasis." Chemical reviews 117.17 (2017): 11269-11301.

Chamberlain, Philip P., and Brian E. Cathers. "Cereblon modulators: Low molecular weight inducers of protein degradation." Drug Discovery Today: Technologies 31 (2019): 29-34.

Galdeano, Carles, et al. "Structure-guided design and optimization of small molecules targeting the protein-protein interaction between the von Hippel-Lindau (VHL) E3 ubiquitin ligase and the hypoxia inducible factor (HIF) alpha subunit with in vitro nanomolar affinitixes." Journal of Medicinal Chemistry 57.20 (2014): 8657-8663.

Istvan, Eva, "Statin inhibition of HMG-CoA reductase:a 3-dimensional view", Atherosclerosis Supplements 4 (2003): 3-8.

Istvan, Eva et al., "Structural Mechanism for Statin Inhibition of HMG-COA Reductase" Science 292 (May 2001): 1160-1164.

Ito, Takumi, et al. "Identification of a primary target of thalidomide teratogenicity." Science 327.5971 (2010): 1345-1350.

(Continued)

*Primary Examiner* — Jeffrey H Murray
*Assistant Examiner* — Kevin S Martin
(74) *Attorney, Agent, or Firm* — Klarquist Sparkman, LLP

(57) ABSTRACT

The present invention relates HMG-CoA reductase degradation inducing compounds. Specifically, the present invention relates a bifunctional compound in which a HMG-CoA reductase binding moiety and an E3 ubiquitin ligase-binding moiety are linked by a chemical linker. The present invention also relates a method for preparing the compounds, and a method for degradation of HMG-CoA reductase using the compounds, as well as use for prevention or treatment of HMG-CoA reductase related diseases using the compounds.

3 Claims, 3 Drawing Sheets

(56) References Cited

OTHER PUBLICATIONS

Kim, Min Kyoung, et al. "Evaluation of short-term Hypolipidemic Effect and Safety of Simvastatin (Zocor®) in Patients with Hyperlipidemia", Yeungnam University Journal of Medicine, 20.2 (Dec. 2003): 152-159.
Naito, Mikihiko, "SNIPERs-Hijacking IAP activity to induce protein degradation", Drug Discovery Today: Technologies, 31 (2019): 35-42.
Rodriguez-Gonzalez, A., et al. "Targeting steroid hormone receptors for ubiquitination and degradation in breast and prostate cancer." Oncogene 27.57 (2008): 7201-7211.
Schneekloth, John S., et al. "Chemical genetic control of protein levels: selective in vivo targeted degradation." Journal of the American Chemical Society 126.12 (2004): 3748-3754.
Soares, Michael J. et al. "Hypoxia and placental development." Birth Defects Research 109.17 (2017): 1309-1329.
Wang, Yang et al. "Degradation of proteins by PROTACs and other strategies" Acta Pharmaceutica Sinica B 10.2 (2020): 207-238.
Korean Intellectual Property Office, Decision for Grant of Patent for Korean Application No. 10-2021-0041514, dated Nov. 9, 2021, with English Translation.

* cited by examiner

【Figure 1】
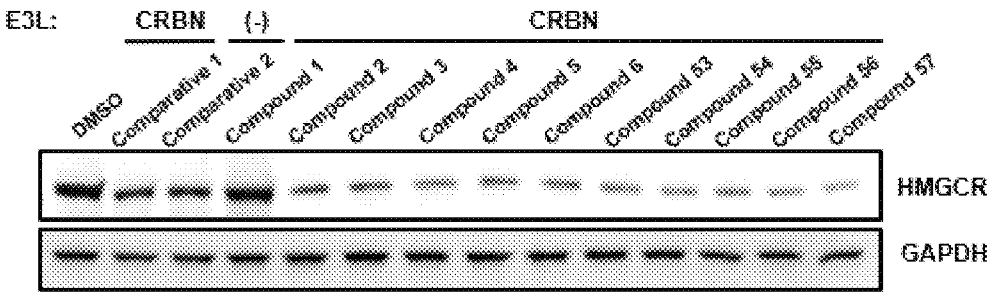
【Figure 2】
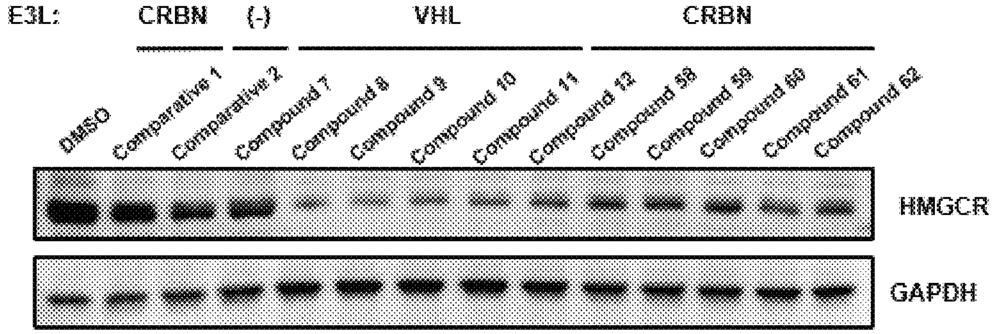
【Figure 3】
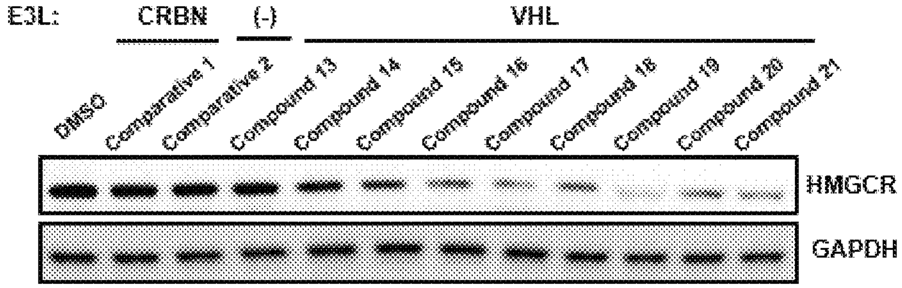
【Figure 4】
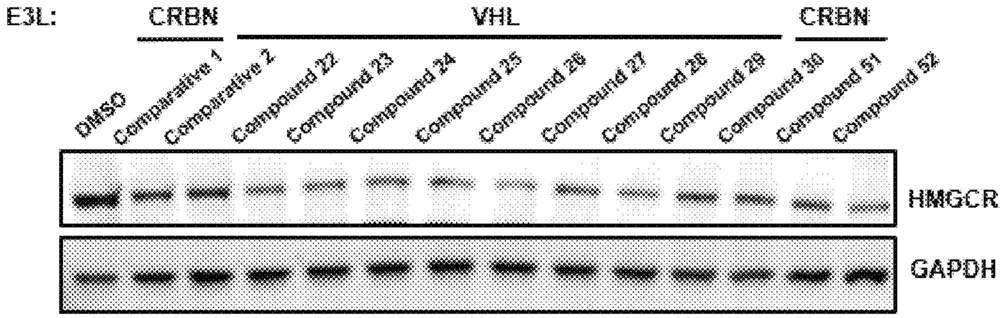

【Figure 5】
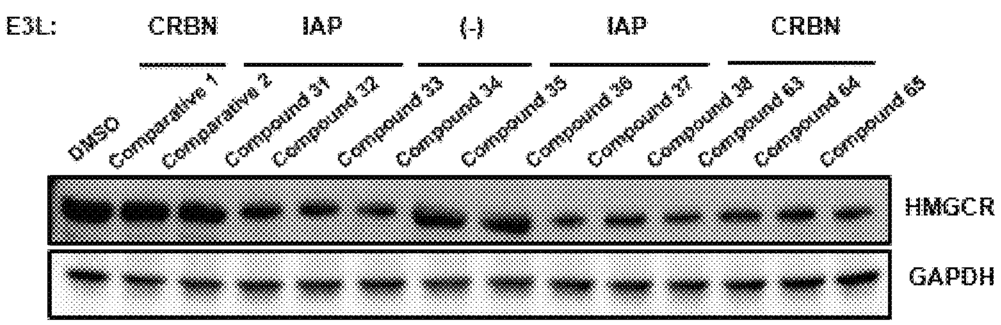
【Figure 6】
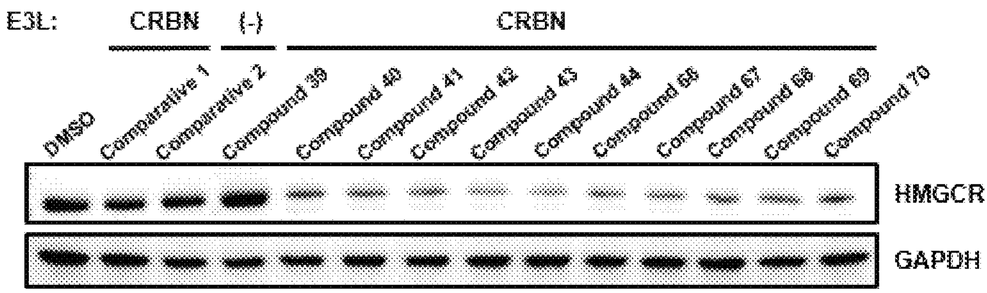
【Figure 7】
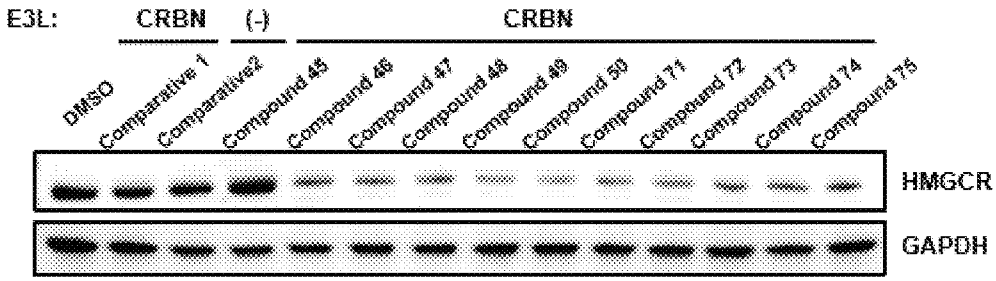
【Figure 8】
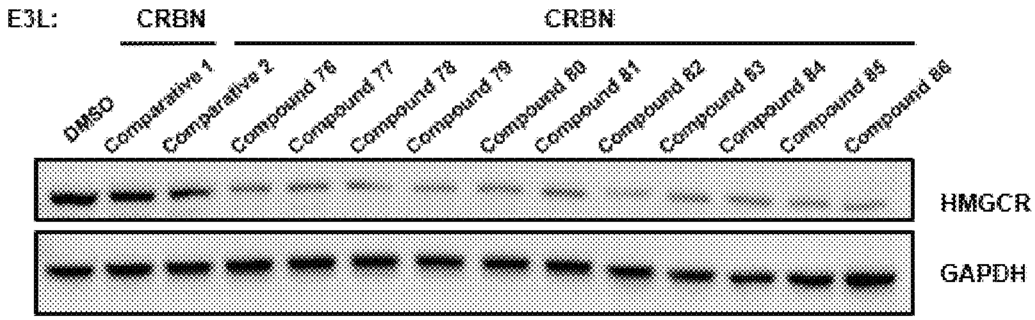

【Figure 9】
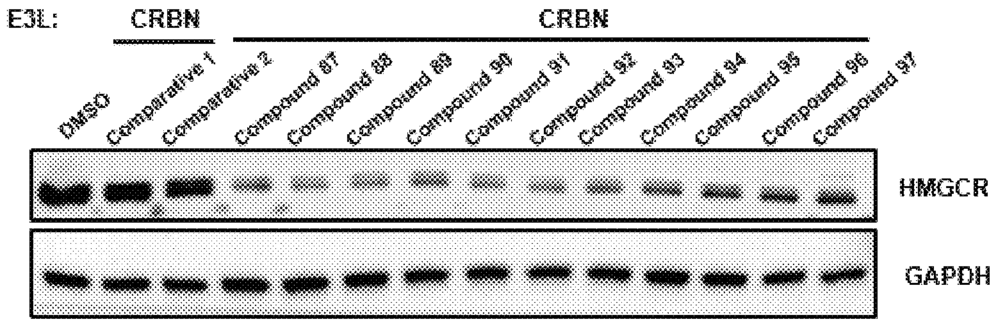
【Figure 10】
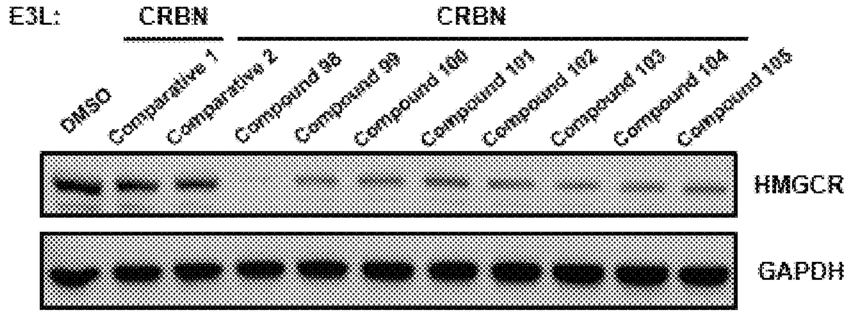

HMG-CoA REDUCTASE DEGRADATION INDUCING COMPOUND

TECHNICAL FIELD

The present invention relates to a HMG-CoA reductase degradation inducing compound, a method for preparing the same, and the use thereof.

BACKGROUND ART

Intracellular cholesterol homeostasis may be maintained through transcriptional regulation of HMG-CoA reductase through a sterol regulatory element-binding protein (SREBP) pathway. The SREBP is a transcriptional regulator present in the endoplasmic reticulum membrane, which forms a complex with SREBP cleavage-activating protein (SCAP). When the concentration of the intracellular cholesterol drops, the complex moves to the Golgi apparatus to induce cleavage of the SREBP, and the activated SREBP enters cell's nucleus to promote transcription of HMG-CoA reductase. On the other hand, when the concentration of the intracellular cholesterol elevates, INSIG (insulin-induced gene) binds to SCAP and inhibits the movement of the SREBP-SCAP complex to the Golgi apparatus, thereby inhibiting the transcription of HMG-CoA reductase.

The HMG-CoA reductase is involved in conversion of HMG-CoA to mevalonate in a mevalonate pathway, which is a pathway for cholesterol biosynthesis in hepatocytes, with the cholesterol as the end product. Statin-based compounds are designed to bind the active site of HMG-CoA reductase, thereby inhibiting enzyme activity. Through the drug mechanism, the statin-based compounds may inhibit intracellular cholesterol production and lower blood cholesterol concentration and reduce the risk of cardiovascular disease. However, when the intracellular cholesterol concentration is lowered by statin, the SREBP pathway may be activated to increase expression of the HMG-CoA as a compensatory mechanism. As a result, in addition to weakening effect of statin, higher dose of statin is necessary, which may lead to risk of type 2 diabetes, muscle pain, or the like. In addition, patients taking high dose of statins for a long period of time in which HMG-CoA reductase are induced, the prognosis may worsen if the patient stops taking the drug. Therefore, there is a demand for alternative drug capable of solving the disadvantages of statin therapy as described above.

Recently, a proteolysis targeting chimera (PROTAC) has been proposed as a small molecule-based platform technology capable of inducing proteolysis of a target protein in the human body. The PROTAC is a bifunctional compound in which a ligand molecule that binds to disease-related target protein and an E3 ubiquitin ligase binding moiety are linked by a chemical linker. Theoretically, the PROTAC compound is capable of inducing degradation of the target protein by placing the disease-related target protein near the E3 ubiquitin ligase. In the case of the PROTAC compound having the HMG-CoA reductase as a target protein, International Patent Publication No. WO2019/109415 A1 discloses some bifunctional compounds in which atorvastatin and a binding moiety for E3 ubiquitin ligase CRBN are linked by a triazole group linker.

However, the above document only describes a synthesis example of only one type of atorvastatin statin-derived PROTAC compound. In addition, the above document merely shows partial confirmation of degradation effects of HMG-CoA reductase in CHO cell line (SRD-15) artificially mutated to lack the function of INSIG, etc. The CHO cell line is histologically different from the hepatocyte environment in which statins actually act, and has basically different expression and activity characteristics of HMG-CoA reductase. In addition, the cell line is engineered to maintain a constant level of expression of HMG-CoA reductase through artificially mutating a gene. Thus, unlike the hepatocyte environment, the compensatory mechanism of HMG-CoA reductase depending on the intracellular cholesterol concentration does not occur. In other words, in actual hepatocytes, when the intracellular cholesterol concentration is lowered by administering statins, the HMG-CoA reductase is overexpressed as a compensatory mechanism, and as a result, the pharmacological effect of statins is weakened, but the SRD-15 cell line does not reflect these hepatocyte characteristics. Therefore, it is not sufficient to conclude from the above document that the PROTAC compound using atorvastatin as a binding moiety to the HMG-CoA reductase effectively induces degradation of the HMG-CoA reductase while overcoming the compensation mechanism caused by atorvastatin action in the actual hepatocyte environment.

In addition, the target protein degradation effect of the PROTAC compound may vary depending on the type of the target protein ligand and the E3 ubiquitin ligase binding moiety constituting the PROTAC compound (see Burslem and Crews, 2017, etc.). Therefore, it is extremely difficult to predict a structure of a compound capable of effectively inducing the degradation of the HMG-CoA reductase among a wide range of statin-derived PROTAC compounds that are not described in WO2019/109415 A1.

DISCLOSURE

Technical Problem

An object of the present invention is to provide HMG-CoA reductase degradation inducing compounds.

Another object of the present invention is to provide a method for preparing the compounds.

Still another object of the present invention is to provide a use of the compounds.

Technical Solution

HMG-CoA Reductase Degradation Inducing Compounds

The present invention provides novel compounds that induce HMG-CoA reductase degradation. Specifically, the present invention provides a bifunctional compound in which a HMG-CoA reductase binding moiety and an E3 ubiquitin ligase-binding moiety are linked by a chemical linker.

In one general aspect, there is provided a compound represented by the following Formula I, a stereoisomer thereof or a pharmaceutically acceptable salt thereof:

ULM-Linker-PTM [Formula I]

in the Formula I above,

ULM is CRBN, VHL or IAP E3 ubiquitin ligase binding moiety;

PTM is HMG-CoA reductase binding moiety represented by the following Formula II:

[Formula II]

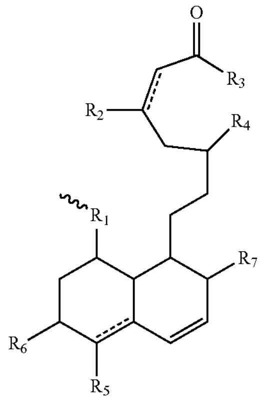

{in the Formula II above, $R_1$ is

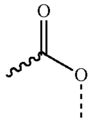

or

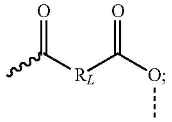

$R_L$ is a single bond or $C_{1-6}$ alkylene that is optionally substituted by 1-4 substituents selected from the group consisting of —$CH_3$, —CN, $NH_2$, —OH and halogen;

$R_2$ is selected from the group consisting of hydrogen, halogen, —OH, —O($C_{1-6}$ alkyl), —O($C_{3-8}$ cycloalkyl), —OCO($C_{1-6}$ alkyl), —O($C_{3-8}$ cycloalkyl) and silyl ether, optionally substituted by one or more straight- or branched-$C_{1-4}$ alkyl, 5- to 10-membered heterocyclyl, 6- to 10-membered aryl, 6- to 10-membered heteroaryl, halogen, $NH_3$, OH, or $CF_3$;

$R_3$ and $R_4$ are each independently —OH or —O($C_{1-3}$ alkyl); or $R_3$ and $R_4$ together form —O—;

$R_5$ and $R_6$ are each independently hydrogen, halogen, OH, $C_{1-4}$ alkyl, $C_{1-4}$ alkenyl, $OC_{1-4}$ alkyl, $CF_3$, $NH_3$, $NO_2$ or CN;

$R_7$ is hydrogen or $C_{1-3}$ alkyl; and

 is a single bond or a double bond}; and

Linker is a chemical group that links ULM and PTM.

In the Formula II,  indicates a covalent bond that links PTM into Linker.

(1) E3 Ubiquitin Ligase Binding Moiety (ULM)

In one embodiment of the present invention, ULM is a CRBN E3 ubiquitin ligase binding moiety.

In the present invention, CRBN means Cereblon E3 ubiquitin ligase. CRBN constitutes an E3 ubiquitin ligase complex together with DDB1, Cul4A and ROC1, wherein the CRBN is a substrate recognition subunit of the complex.

Some compounds capable of binding to the CRBN E3 ubiquitin ligase are known in the art. For example, after it was known that thalidomide binds to the CRBN E3 ubiquitin ligase (see Ito et al. 2010), it has been reported that a number of immunomodulatory imide drugs (IMiD) including lenalidomide and pomalidomide have CRBN binding ability (see Chamberlain and Brian. 2019; Akuffo et al. 2018; and Burslem et al. 2018, etc.).

In one embodiment, the CRBN E3 ubiquitin ligase binding moiety in Formula I is represented by the following Formula A-1:

[Formula A-1]

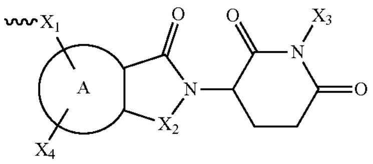

wherein:

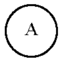

is a ring selected from the group consisting of

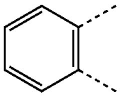

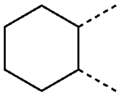

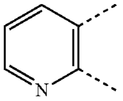

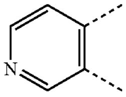

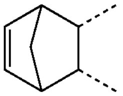

and

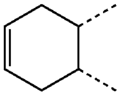

;

$X_1$ is a single bond, —$CH_2$—, —NH—, —O—, —$CH_2CH_2$—, —CC— —CO—, —COO—, —NHCO— or —CONH—;

$X_2$ is —$CH_2$—, —CH($C_{1-4}$ alkyl)-, —NH—, —N($C_{1-4}$ alkyl)-, —O—, —CO—, —$CH_2$—$CH_2$—, —NH—$CH_2$—, —NH—CH($C_{1-4}$ alkyl)-, —N═CH—, —N═C($C_{1-4}$ alkyl)- or —N═N—;

$X_3$ is hydrogen or $C_{1-4}$ alkyl; and $X_4$ is hydrogen, halogen, $C_{1-6}$ alkyl, CN, $NH_2$, $NO_2$, OH, COH, COOH or $CF_3$.

In one embodiment, Formula A-1 is represented by the following Formula A-2:

[Formula A-2]

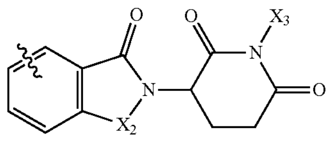

wherein:

$X_2$ is —$CH_2$—, —CH($C_{1-4}$ alkyl)-, —CO— or —N═N—; and $X_3$ is hydrogen or $C_{1-3}$ alkyl.

In certain embodiment, Formula A-2 is selected from the group consisting of:

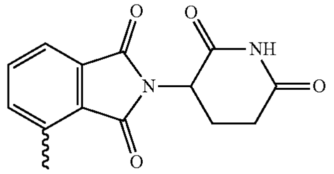

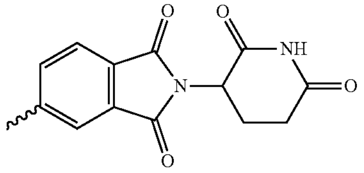

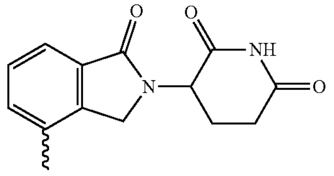

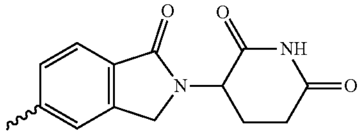

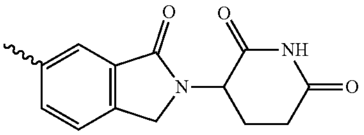

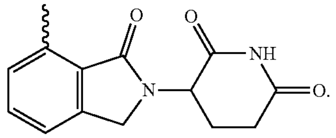

One example of CRBN E3 ubiquitin ligase binding moieties of Formula A-1 or A-2 may be derived from the compounds having the following structures (Chamberlain and Brian. 2019; Akuffo et al. 2018; etc.):

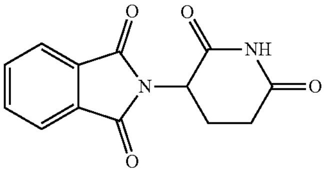

Thalidomide

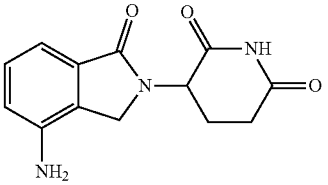

Lenalidomide

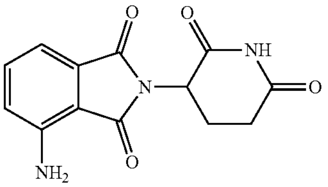

Pomalidomide

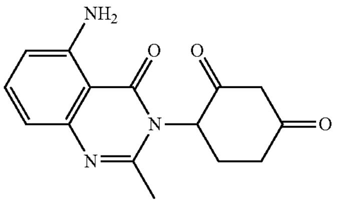

Avadomide (CC-122)

Another example of CRBN E3 ubiquitin ligase binding moieties of Formula A-1 or A-2 may be derived from the compounds having the following structures (Burslem et al. 2018; etc.):

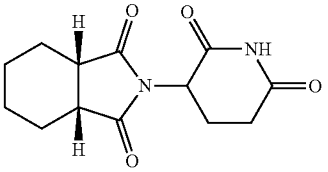

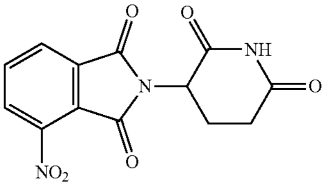

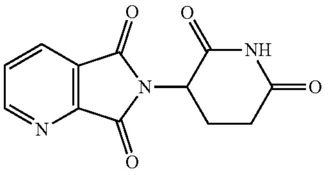

-continued
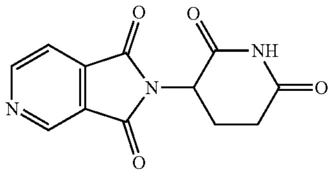
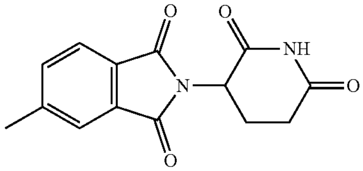
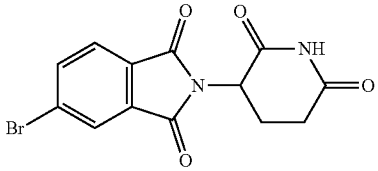
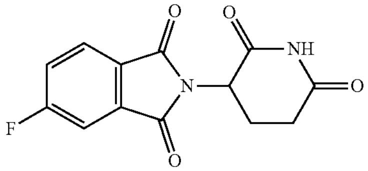
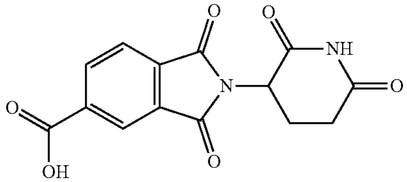
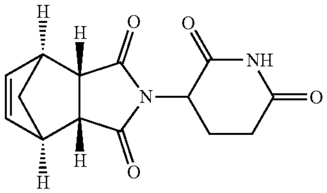
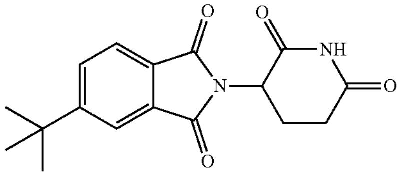
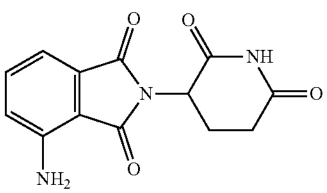
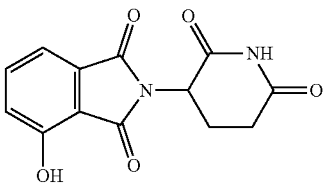
-continued
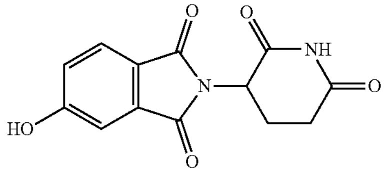
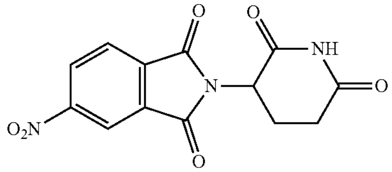
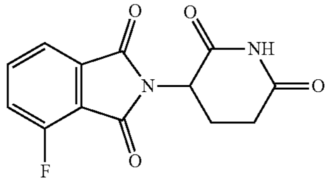
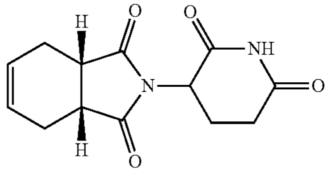
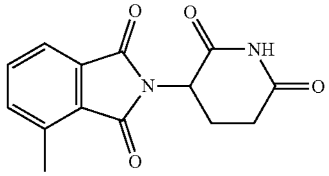
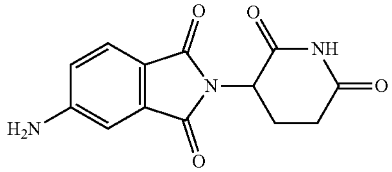
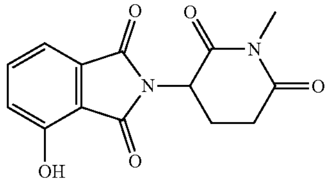
In another embodiment of the present invention, ULM is a VHL E3 ubiquitin ligase ligand binding moiety.
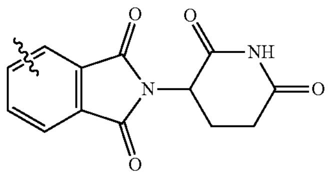
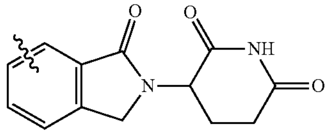

-continued

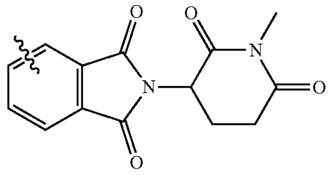

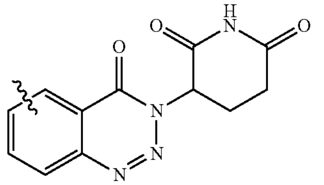

In the present invention, VHL means a von Hippel-Lindau tumor suppressor. VHL constitutes a VCB E3 ligation complex together with Elongin B, Elongin C, CUL2 and Rbx1, wherein VHL is a substrate recognition subunit of the complex. Some compounds capable of binding to the VHL E3 ubiquitin ligase are known in the art. For example, after it was known that peptide such as Ala-Leu-Ala-(Hy)Pro-Tyr-Ile-Pro heptapeptide (see Schneekloth et al. 2004) and Leu-Ala-(Hy)Pro-Tyr-Ile pentapeptide (see Rodriguez-Gonzalez et al. 2008), an improved low-molecular VHL E3 ubiquitin ligase binding compound has been reported (see Buckley et al. J. Am. Chem. Soc. 2012; Buckley et al. Ang. Chem. Int. Ed. 2012; Galdeano et al. 2014; Soares et al. 2017, etc.).

In one embodiment, the VHL E3 ubiquitin ligase binding moiety in Formula I is represented by the following Formula B-1:

[Formula B-1]

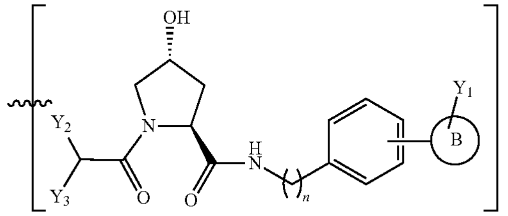

wherein:

n is an integer from 1 to 3;

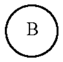

is 5- to 6-membered cycloalkyl, phenyl, 5- to 6-membered heterocycloalkyl, or 5- to 6-membered heteroaryl, wherein the heterocycloalkyl or the heteroaryl contains one to three N, O or S atoms;

$Y_1$ is hydrogen or $C_{1-4}$ alkyl;

$Y_2$ is $C_{1-4}$alkyl, hydroxy($C_{1-4}$alkyl), —($C_{0-2}$alkyl)-COH, $C_{3-8}$cycloalkyl, or phenyl;

$Y_3$ is hydrogen,  or

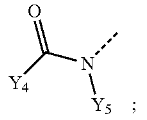

$Y_4$ is hydrogen, halogen, $C_{1-4}$ alkyl, —O($C_{1-4}$ alkyl), $C_{3-6}$ cycloalkyl or 4- to 6-membered heterocycloalkyl, optionally substituted by halogen, —OH, —CN, —NHCOH, —$NHCOCH_3$, —COH or —$COCH_3$; and $Y_5$ is hydrogen or $C_{1-4}$ alkyl.

In one embodiment, the VHL E3 ubiquitin ligase binding moiety in Formula B-1 is selected from the group consisting of the following Formula B-2-1 and B-2-2:

[Formula B-2-1]

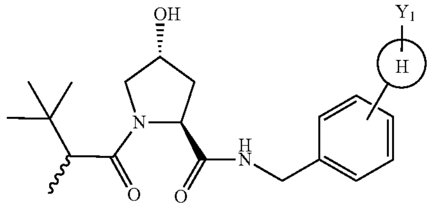

[Formula B-2-2]

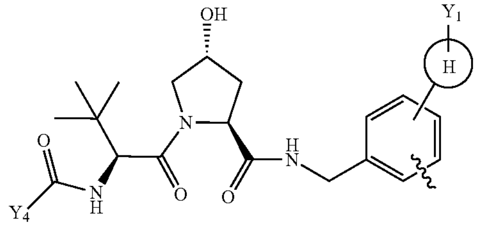

wherein:

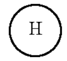

is 5-membered heteroaryl ring selected from the group consisting of oxazole, isoxazole, thiazole, isothiazole, imidazole, pyrazole, triazole, oxadiazole, pyrrole, pyrrolidine, furan, dihydrofuran and tetrahydrofuran;

$Y_1$ is hydrogen or $C_{1-3}$ alkyl; and $Y_4$ is $C_{1-4}$ alkyl or $C_{3-5}$ cycloalkyl, optionally substituted by hydrogen or halogen.

In certain example, Formula B-2-1 is represented by the moiety selected from the group consisting of:

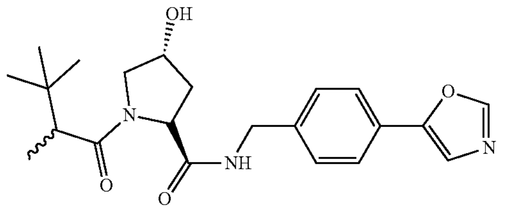

-continued
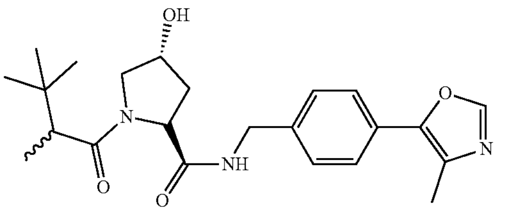
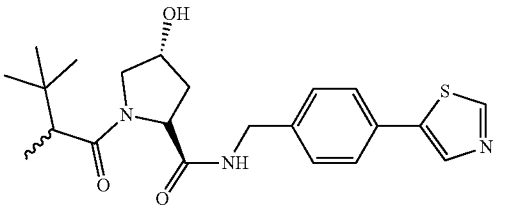
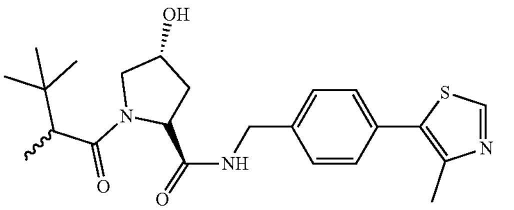
In certain example, Formula B-2-2 is represented by the moiety selected from the group consisting of:
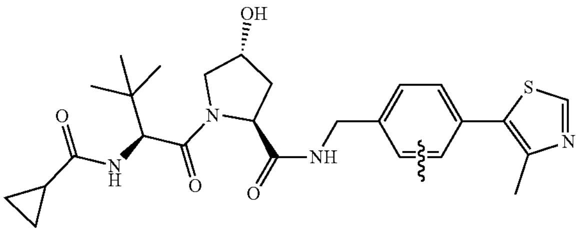
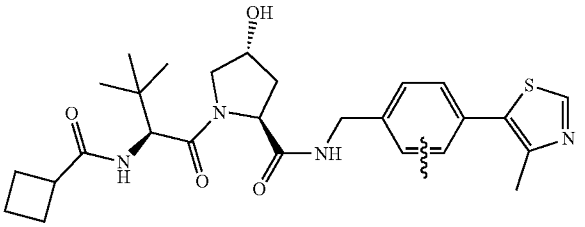
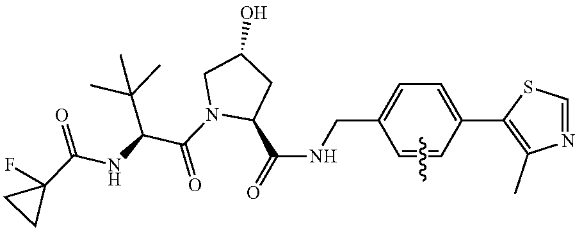
One example of VHL E3 ubiquitin ligase binding moieties of Formula B-1, B-2-1 or B-2-2 may be derived from the compounds having the following structures (Galdeano et al. (2014); etc.).
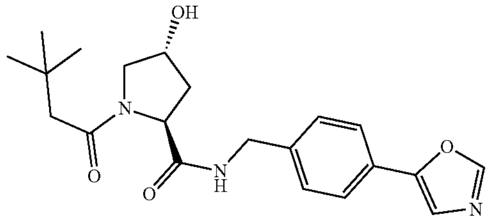
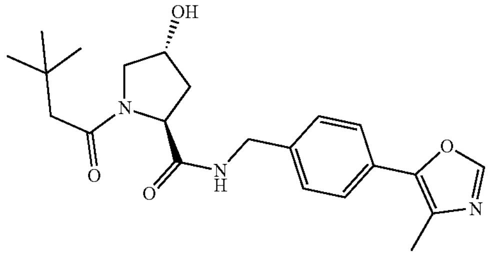
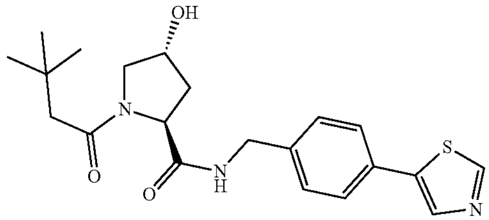
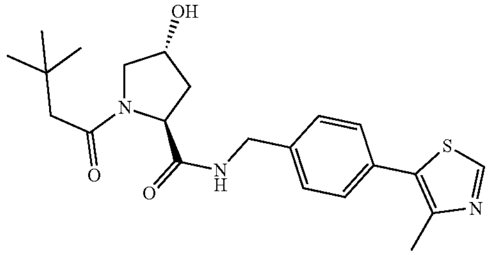
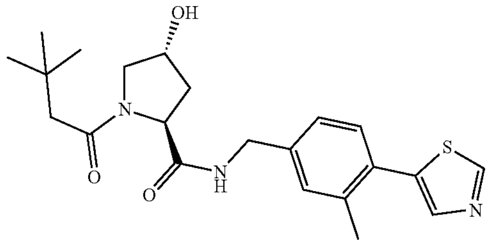
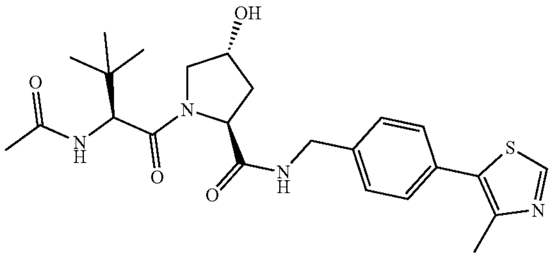
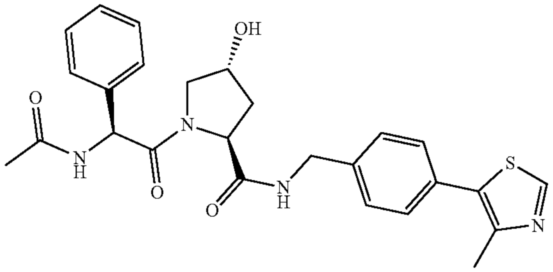

-continued
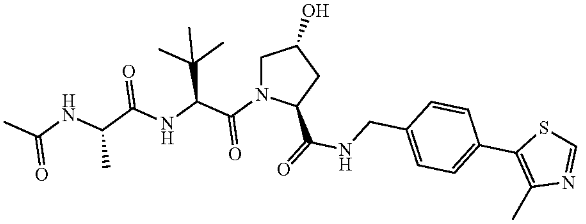
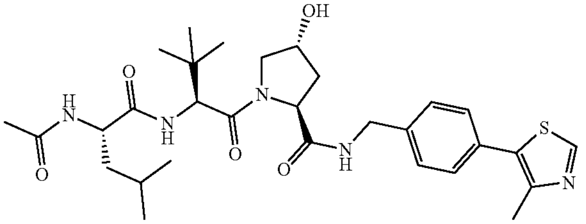
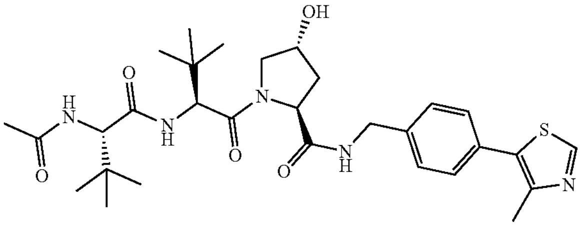
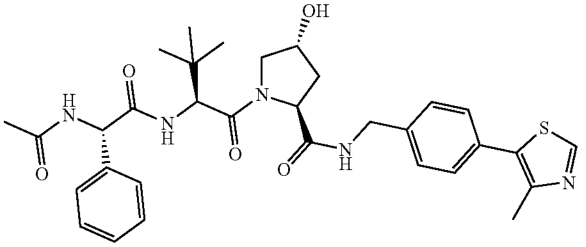
Another example of VHL E3 ubiquitin ligase binding moieties of Formula B-1, B-2-1 or B-2-2 may be derived from the compounds having the following structures (Soares et al. 2017; etc.).
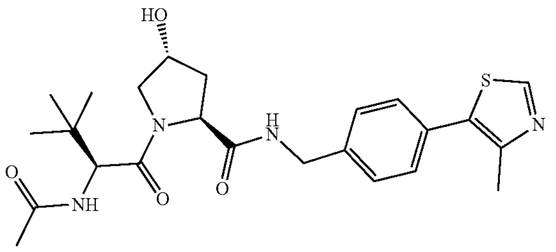
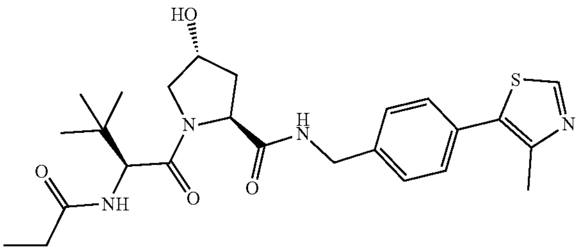
-continued
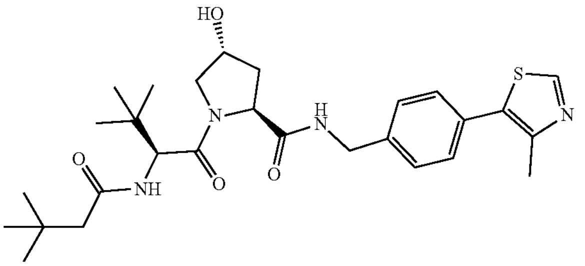
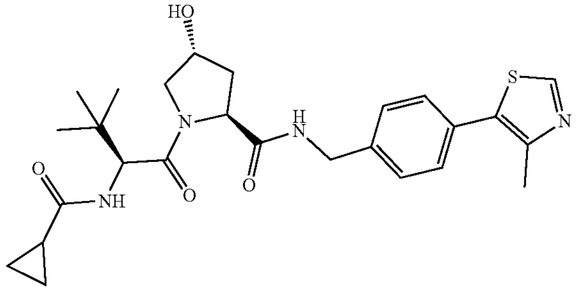
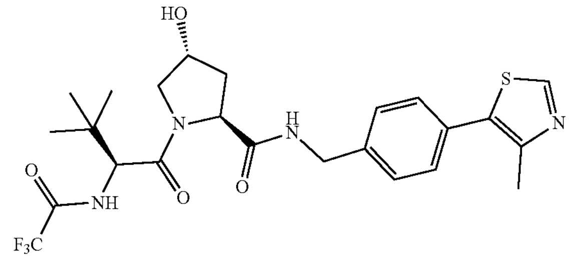
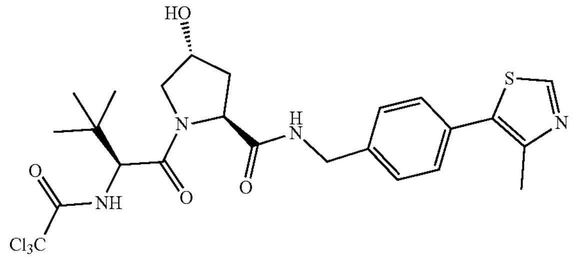
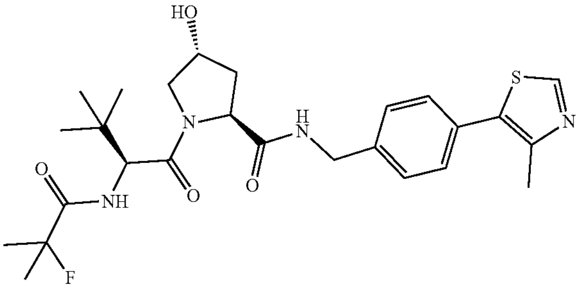
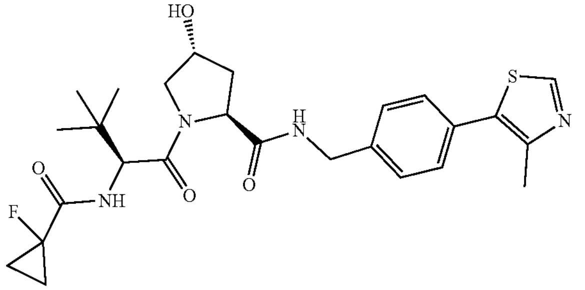

-continued

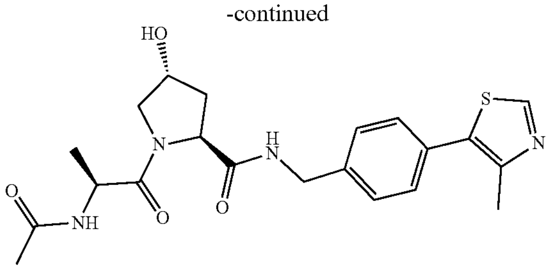

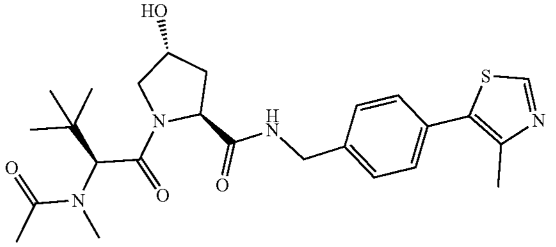

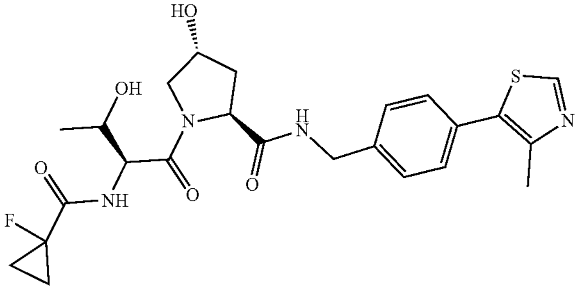

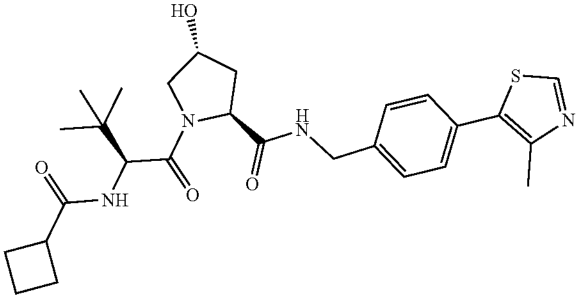

In one embodiment, ULM of Formula I is IAP E3 ubiquitin ligase binding moeity.

In the present invention, IAP (inhibitor of apoptosis protein) refers to a protein family including 1 to 3 BIR (baculoviral IAP repeat) domains. In human, total 8 IAP members (XIAP, cIAP1, cIAP2, Livin, ILP2, Survivin, NAIP, Apollon) have been reported and are known to inhibit apoptosis in various cellular systems. Since IAP contains an E3 ubiquitin ligase-specific domain that recognizes a substrate and promotes its ubiquitination, it has been reported that it can be used as an E3 ubiquitin ligase target of PROTAC compounds together with CRBN and VHL (see Naito, Mikihiko, Nobumichi Ohoka, and Norihito Shibata. "SNIPERs—Hijacking IAP activity to induce protein degradation." Drug Discovery Today: Technologies 31 (2019): 35-42; et al.).

In one embodiment, IAP E3 ubiquitin ligase binding moiety is represented by the following Formula C-1:

[Formula C-1]

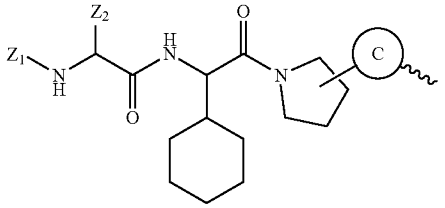

wherein:

$Z_1$ and $Z_2$ are each independently hydrogen, $C_{1-4}$ alkyl or $C_{3-6}$ cycloalkyl;

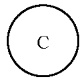

is phenyl or 5- to 6-membered heteroaryl.

In one embodiment, Formula C-1 is represented by the following Formula C-2:

[Formula C-2]

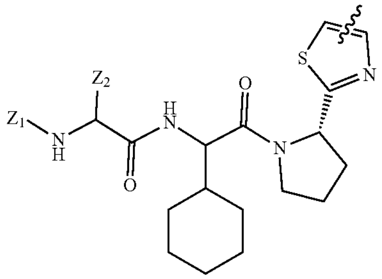

wherein, $Z_1$ and $Z_2$ are as same defined in the above.

In the present invention, Linker may be attached into ULM at a position necessary to exhibit the bifunctionality of PROTAC. In Formulas A-1, A-2, B-1, B-2-1, B-2-2, C-1 and C-2 of the present invention, the Linker may be covalently linked through . If there  is not indicated, one hydrogen in the moiety of E3 ubiquitin ligase binding compound may be substituted into a single bond to be connected to the Linker.

(2) Protein Target Moiety (PTM)

In the compound represented by Formula I of the present invention, PTM, a moiety that performs a target protein ligand function, is a Type 1 statin or a derivative thereof.

Statins are low-molecular compounds that inhibit HMG-CoA reductase (3-hydroxy-3-methylglutaryl-coenzyme A), and are known to bind to HMG-CoA binding sites and inhibit the enzymatic activity of HMG-CoA reductase. Various types of statins are known, and they can be largely classified into Type 1 statins and Type 2 statins according to their molecular structure (see E S Istvan, J Deisenhofer, Science (2001); Istvan, Eva. Atherosclerosis Supplements (2003); etc.).

Type 1 statins share the form of a decalin ring, and can bind to the active site of HMG-CoA reductase through the decalin ring. Examples of known Type 1 statins include compactin, pravastatin, simvastatin, lovastin, and the like.

On the other hand, Type 2 statins are distinguished from Type 1 statins in that they have a fluorophenyl and/or methylethyl group form instead of the decalin ring structure of Type 1 statins, and bind to HMG-CoA reductase through the group. Examples of type 2 statins include rosuvastatin, atorvastatin, cerivastatin, fluvastatin, and the like.

In the compound represented by Formula I of the present invention, Type 1 statin derivative refers to a chemical analog containing a substituent that can be suitably modified to exhibit bifunctionality while sharing the core structure of a known Type 1 statin. Specifically, Type 1 statin is a moiety represented by Formula II described above.

In one embodiment of Formula II of the present invention is represented by the following Formula III-1:

[Formula III-1]

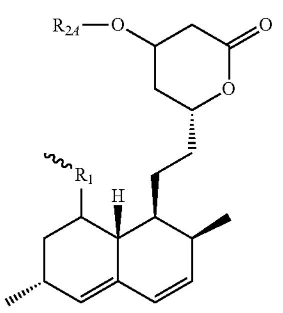

wherein:

$R_1$ is

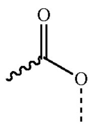 or 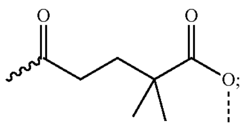

$R_{2A}$ is selected from the group consisting of hydrogen, $C_{1-6}$ alkyl, $C_{3-6}$ cycloalkyl, 5-6-membered heterocyclyl, phenyl, 5-6-membered heteroaryl and

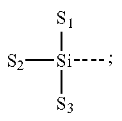

and $S_1$ to $S_3$ are each independently hydrogen, $C_{1-6}$ alkyl, $C_{3-6}$ cycloalkyl, 5-6-membered heterocyclyl, phenyl or 5-6-membered heteroaryl.

In Formula III-1, in one embodiment, $R_{2A}$—O— is hydroxy.

In Formula III-1, in one embodiment, $R_{2A}$—O— is silyl ether. In this case, $R_{2A}$ may be selected from the group consisting of:

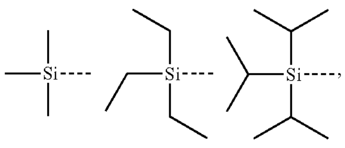

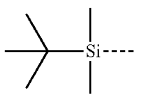 and 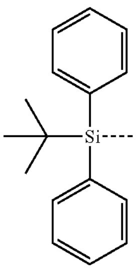

(see Examples 19-22, 27-30, 35-38, 46-57, 65, 67, 70, 71, 72, 74, 76, 78, 80, 82, 84, 86, 88, 90, 92, 94, 96, 98, 100, 102, 104, 108-109, 114, 116, 118, 120, 122, 124-125, 128, 130, 132, 134, 136, 138, 140, 142, 144, 146, 148, 150 or 155).

In Formula III-1, in one embodiment, $R_{2A}$—O— is selected from the group consisting of methoxy, ethoxy, propoxy and butoxy (see Examples 69, 110).

In one embodiment, Formula II is represented by the following Formula III-2 (see Example 153):

[Formula III-2]

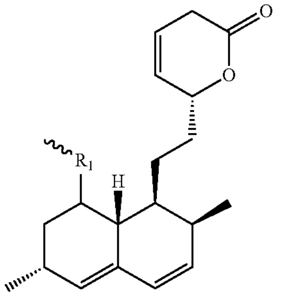

wherein $R_1$ is

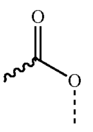 or 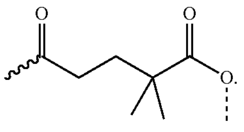

In one embodiment, Formula II is represented by the following Formula III-3 (see Examples 106, 107 and 154):

[Formula III-3]

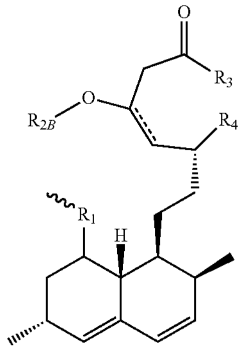

wherein $R_1$ is

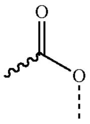 or 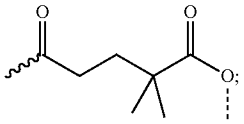

$R_{2B}$ is selected from the group consisting of hydrogen, $C_{1-6}$ alkyl, $C_{3-6}$ cycloalkyl, 5-6-membered heterocyclyl, phenyl, 5-6-membered heteroaryl and

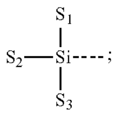

$S_1$ to $S_3$ are each independently hydrogen, $C_{1-6}$ alkyl, $C_{3-6}$ cycloalkyl, 5-6-membered heterocyclyl, phenyl or 5-6-membered heteroaryl; and $R_3$ and $R_4$ are each independently —OH or —$OCH_3$.

In Formula II, in one embodiment, $R_2$ is hydrogen (see Example 153) or halogen (see Example 113).

In Formula II, in one embodiment, $R_2$ is $CH_3COO$— (see Example 111);

In Formula II, in one embodiment, $R_2$ is Ph-$CH_2O$— (see Example 112).

In one embodiment, the PTM moiety is PTM moiety that is included in the compound selected from the group consisting of Compound 1 to 169.

(3) Linker

In one embodiment of the present invention, the Linker as defined in Formula I is represented by the following Formula L:

[Formula L]

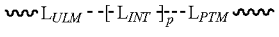

wherein:

and ----- are each independently bond;

$L_{ULM}$ is covalently bonded to ULM moiety through  that is linked thereto, $L_{PTM}$ is covalently bonded to PTM moiety through  that is linked thereto, $L_{ULM}$, $L_{PTM}$ and $L_{INT}$ are independently selected from the group consisting of null, a single bond, —$CH_2$—, —NH—, —O—, —S—, —SO—, —$SO_2$—, —CO—, —$CH_2CH_2$—, —CHCH—, —CC—, —$CH_2CH_2O$—, —$OCH_2CH_2$—, —$CH_2CH_2S$—, —$SCH_2CH_2$—, —COO—, —CONH—, —NHCO— and

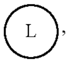, optionally substituted by one or more $C_{1-6}$ alkyl, $C_{3-8}$ cycloalkyl, halogen, hydroxy, amino, nitro, cyano or haloalkyl {wherein

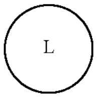

is cycloalkyl, heterocycloalkyl, aryl, or heteroaryl}; and p is an integer from 1 to 30.

In one embodiment, p is 1 or more; 5 or more; 10 or more; 15 or more; 20 or more; or 25 or more. In another embodiment, p is 25 or less; 20 or less; 15 or less; 10 or less; 5 or less.

In Formula L above, $L_{ULM}$ may be

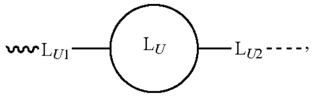, wherein:

$L_{U1}$ is selected from the group consisting of a single bond, —$CH_2$—, —$CH_2CH_2$—, —CH═CH—, —CC—, —NH—, —$NCH_3$—, —CO—, —NHCO— and —O—;

$L_{U2}$ is selected from the group consisting of a single bond, —$CH_2$—, —NH—, —O—, —CO— and —CONH—; and

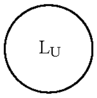

is null, $C_{1-6}$ alkyl or a ring selected from the group consisting of 3- to 10-membered cycloalkyl, 4- to 10-membered heterocycloalkyl, 6- to 10-membered aryl and 5- to 10-membered heteroaryl.

In certain embodiment,

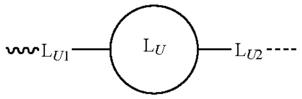

is selected from the group consisting of —$CH_2$—, —NH—, —O—, —NHCO—, —CC—, —$O(CH_2)$—CO— and —$O(CH_2)$CONH—.

In certain embodiment,

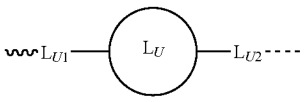

is selected from the group consisting of

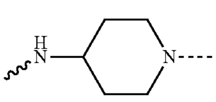
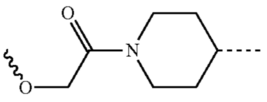
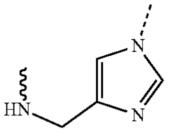
and
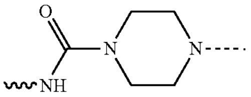

In Formula L above, $L_{PTM}$ may be

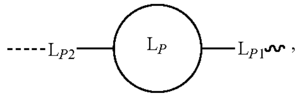

wherein:

$L_{P1}$ is selected from the group consisting of a single bond, —O—, —S—, —NH—, —N($C_{1-4}$ alkyl)-, —$CH_2$—, —CH($C_{1-4}$ alkyl)-, —$CH_2$NH—, and —$CH_2CH_2$—;

$L_{P2}$ is selected from the group consisting of a single bond, —CO—, —$COCH_2$—, —NHCO—, —$NHCOCH_2$—, -HET- and -HET-$CH_2$— {wherein HET is 5- to 6-membered heterocyclyl or heteroaryl containing one ore more N, S or O atoms}; and

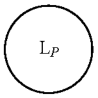

is null, amino substituted $C_{1-8}$ alkyl, or a ring selected from the group consisting of 3- to 10-membered cycloalkyl, 4- to 10-membered heterocycloalkyl, 6- to 10-membered aryl and 5- to 10-membered heteroaryl.

In certain embodiment,

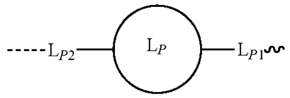

is selected from the group consisting of

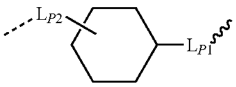
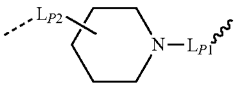

-continued

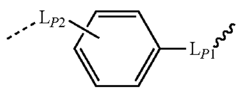
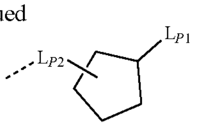
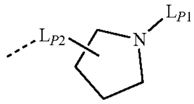
and
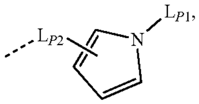

and, and for example, is

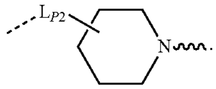

In certain embodiment, is

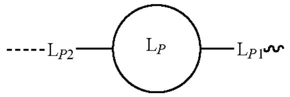

is

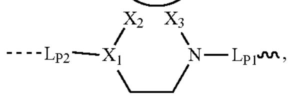

wherein $X_1$ is CH or N; $X_2$ and $X_3$ are each independently hydrogen, $CH_3$ or $CH_2CH_3$.

In Formula L above,

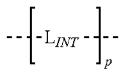

may be

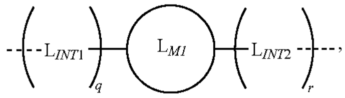

wherein:

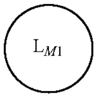

is null or a ring selected from the group consisting of 3- to 10-membered cycloalkyl, 4- to 10-membered heterocycloalkyl, 6- to 10-membered aryl and 5- to 10-membered heteroaryl;

$L_{INT1}$ and $L_{INT2}$ are each independently selected from the group consisting of —$CH_2$—, —NH—, —$NCH_3$—, —O—, —S—, —SO—, —$SO_2$—, —CO—, —$CH_2CH_2O$—, —$OCH_2CH_2$—, —$CH_2CH_2S$—, —$SCH_2CH_2$—, —COO—, —CONH— and —NHCO—; and q and r are each independently an integer from 1 to 10.

In one embodiment,

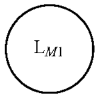

is selected from the group consisting of

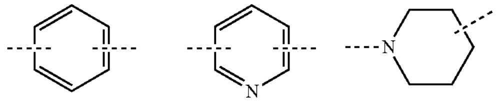

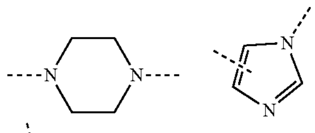

and

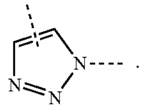

.

In one embodiment, Linker is a linker that is included in the compound selected from the group consisting of Compound 1 to 169.

In a certain embodiment of the present invention, the compound represented by Formula I is a compound that is selected from the group consisting of Compound 2-6, 8-12, 14-33, 36-38, 40-44 and 46-169.

In the present invention, a pharmaceutically acceptable salt refers to any organic or inorganic acid addition salt with a concentration that is relatively non-toxic, is harmless, and has effective action to patients, wherein side effects caused by this salt does not deteriorate beneficial efficacy of the compound represented by Formula I. For example, the pharmaceutically acceptable salt may be an inorganic acid such as hydrochloric acid, phosphoric acid, sulfuric acid, nitric acid, or the like, or an organic acid such as methanesulfonic acid, p-toluenesulfonic acid, acetic acid, trifluoroacetic acid, maleic acid, succinic acid, oxalic acid, benzoic acid, tartaric acid, fumaric acid, manderic acid, propionic acid, citric acid, lactic acid, glycolic acid, gluconic acid, galacturonic acid, glutamic acid, glutaric acid, glucuronic acid, aspartic acid, ascorbic acid, carbonic acid, vanillic acid or hydroiodic acid, but is not limited thereto.

Method for the Preparing the HMG-CoA Reductase Degradation Inducing Compounds

In the present invention, the compound represented by Formula I above, a stereoisomer thereof, or a pharmaceutically acceptable salt thereof may be prepared through reactions such as the following Reaction Schemes 1 to 3 by a synthetic method known in the field of organic chemistry or a modification technique apparent to those skilled in the art.

[Reaction Scheme 1]

PTM-$RG^1$ $\xrightarrow{RG^2\text{-Linker-}RG^3}$ PTM-Linker-$RG^3$ $\xrightarrow{ULM\text{-}RG^4}$ PTM-Linker-ULM

[Reaction Scheme 2]

ULM—$RG^4$ $\xrightarrow{RG^2\text{—Linker—}RG^3}$ $RG^2$—Linker—ULM $\xrightarrow{PTM\text{—}RG^1}$ PTM—Linker—ULM

[Reaction Scheme 3]

(i)

PTM-$RG^1$ $\xrightarrow{RG^{2a}\text{-Linker 1-}RG^{2b}}$ PTM-Linker 1-$RG^{2b}$ (ii)

ULM-$RG^4$ $\xrightarrow{RG^{3a}\text{-Linker 2-}RG^{3b}}$ $RG^{3a}$-Linker 2-ULM (iii)

PTM-Linker 1-$RG^{2b}$ + $RG^{3a}$-Linker 2-ULM ⟶ PTM-Linker 1-Linker 2-ULM ⟶ PTM-Linker-ULM In the Reaction Schemes 1 to 3 above, PTM, Linker and ULM are a group defined in the above, or a suitable derivative thereof. $RG^1$, $RG^2$, $RG^{2a}$, $RG^{2b}$, $RG^3$, $RG^{3a}$, $RG^{3b}$ and $RG^4$ are moieties including a suitable reactive group capable of linking together with an intermediate of the PROTAC compound represented by Formula I through formation of the covalent bond in the field of organic synthesis. The formation of the covalent bond may be achieved by synthetic reactions such as amide formation, ester formation, carbamate formation, urea formation, ether formation, amine formation, and single bonds, double bond formation between various carbons, click chemistry and the like, depending on specific reaction groups, but is not limited thereto.

Variations of each step in the above Reaction Scheme may include one or multiple synthesis steps. Isolation and purification of the product may be accomplished by standard procedures known to those skilled in the art of organic chemistry.

In one embodiment, the compounds of the present invention can be prepared through Reaction Scheme 1 by one or multiple synthetic steps.

In one example of Reaction Scheme 1, when ULM is Formula A-1, the compound of the present invention may be prepared through the following Reaction Scheme 1-A.

[Reaction Scheme 1-A]

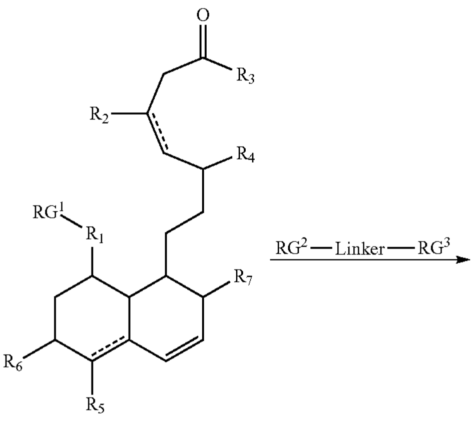

-continued
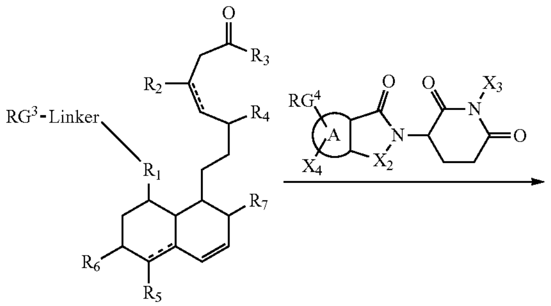
-continued
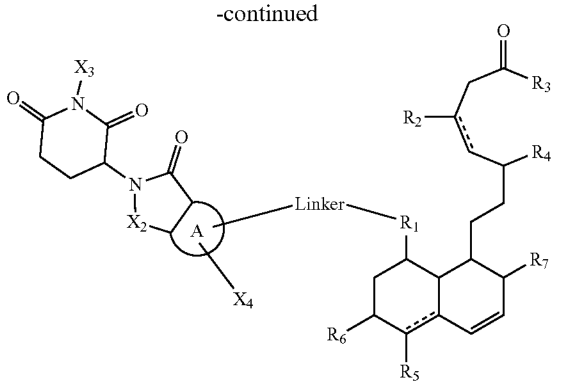
Formula 1A
In one example of Reaction Scheme 1, when ULM is Formula B-1, the compound of the present invention may be prepared through the following Reaction Scheme 1-B.
[Reaction Scheme 1-B]
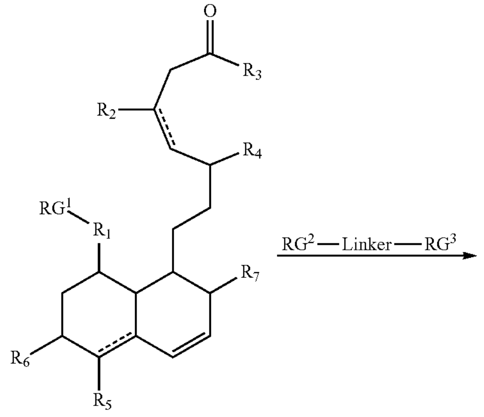
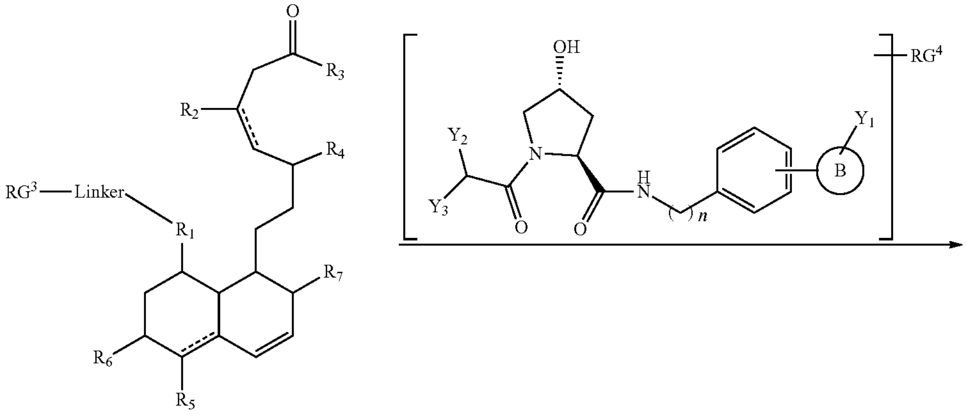

-continued

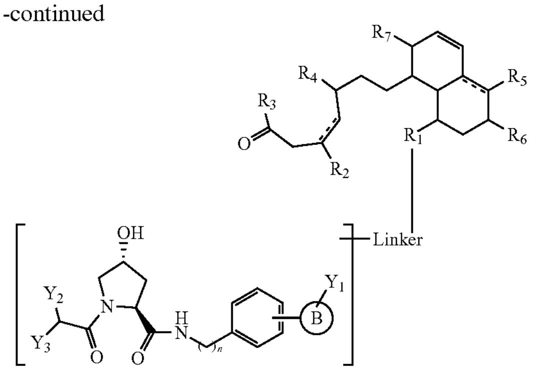

Formula 1B

In one example of Reaction Scheme 2, when ULM is Formula A-1, the compound of the present invention may be prepared through the following Reaction Scheme 2-A (see Examples 2-6, 31-38, 40-44, 46-105, 106-153 and 155-157).

[Reaction Scheme 2-A]

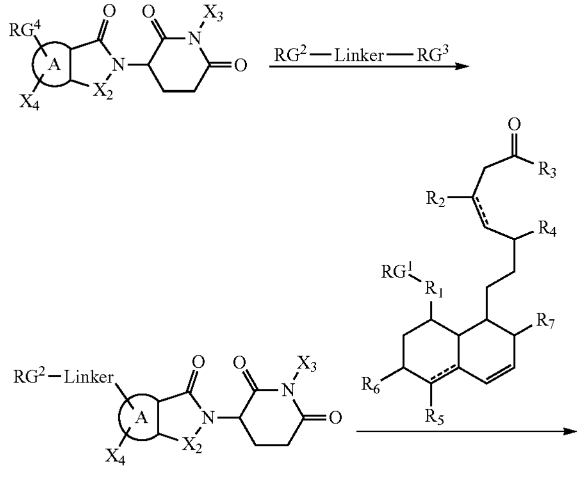

-continued

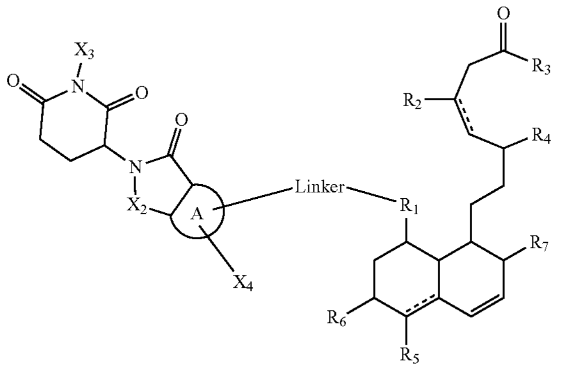

Formula 2A

In one example of Reaction Scheme 2, when ULM is Formula B-1, the compound of the present invention may be prepared through the following Reaction Scheme 2-B (see Examples 8-12, 14-30, 154, 158-169)

[Reaction Scheme 2-B]

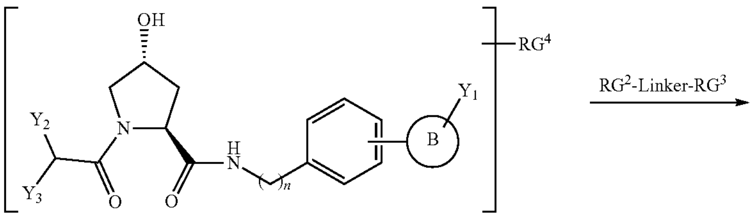

-continued
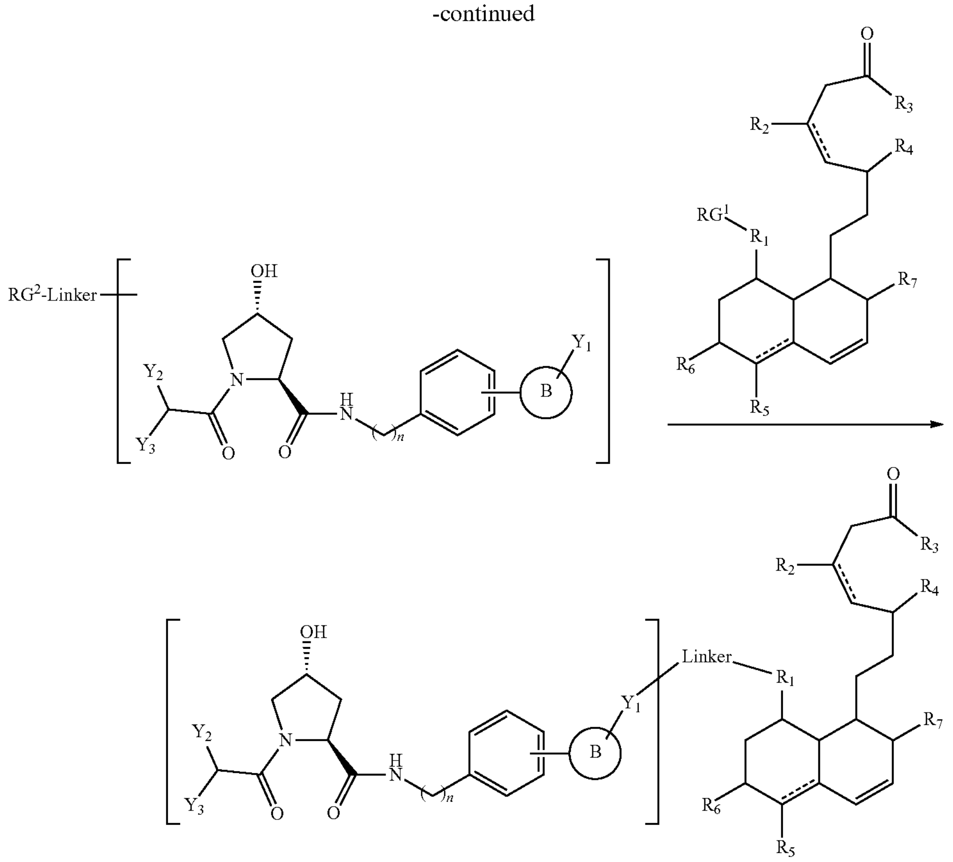
Formula 2B
In one example of Reaction Scheme 3, when ULM is Formula A-1, the compound of the present invention may be prepared through the following Reaction Scheme 3-A.
[Reaction Scheme 3-A]
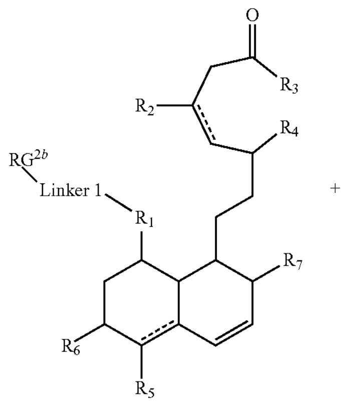
-continued
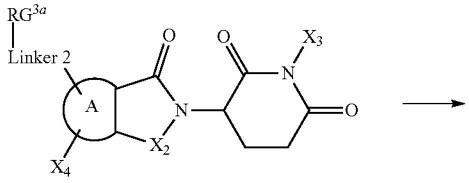
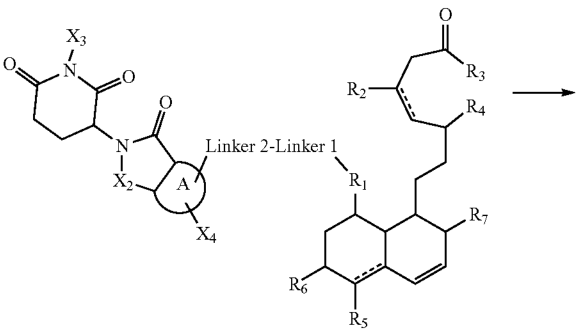

-continued
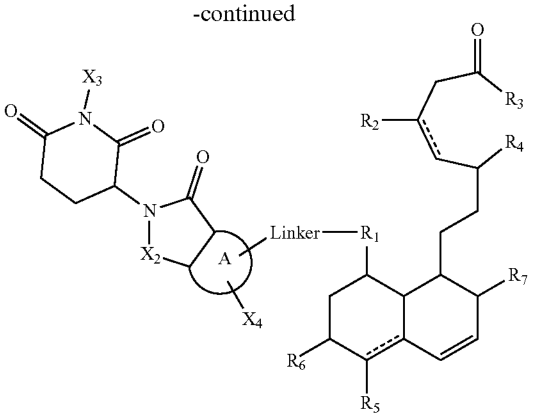
Formula 3A
In one example of Reaction Scheme 3, when ULM is Formula B-1, the compound of the present invention may be prepared through the following Reaction Scheme 3-B.
[Reaction Scheme 3-B]
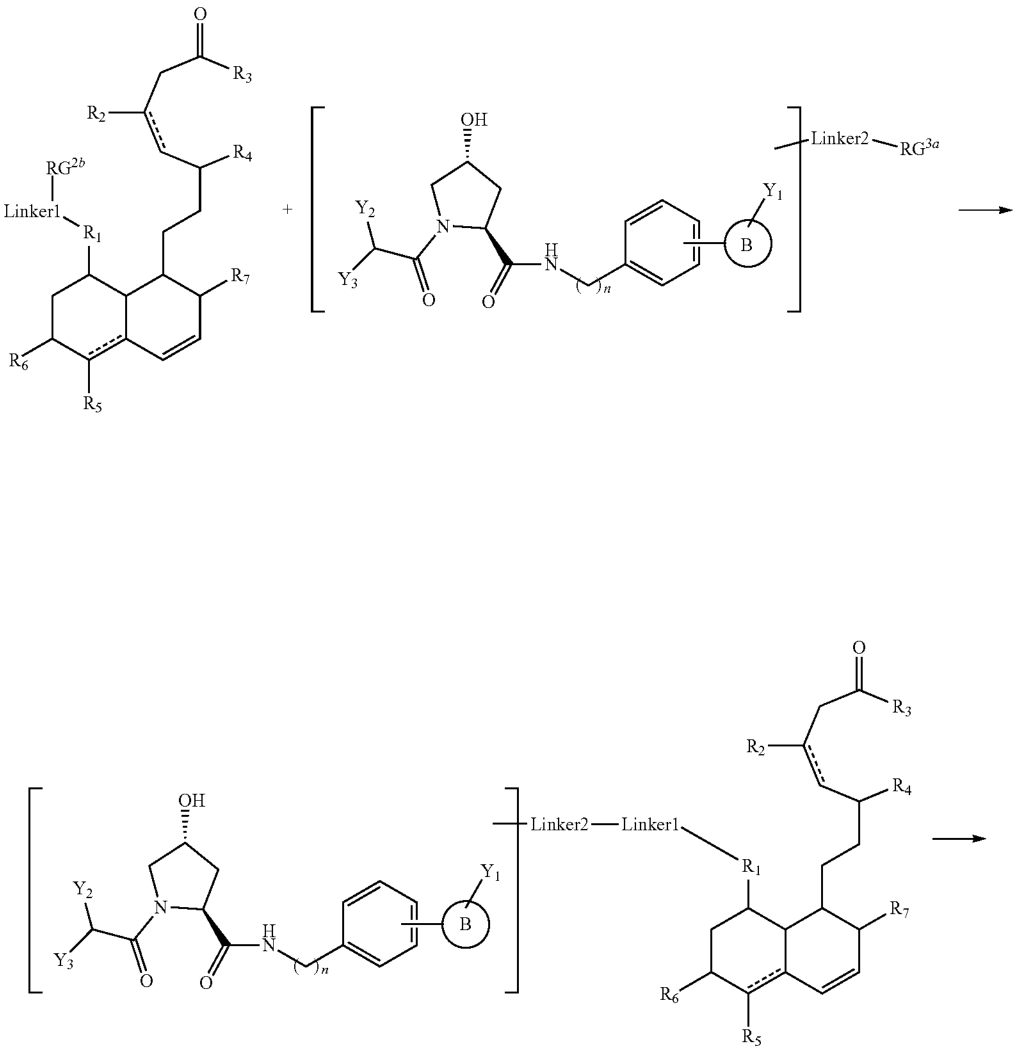

-continued

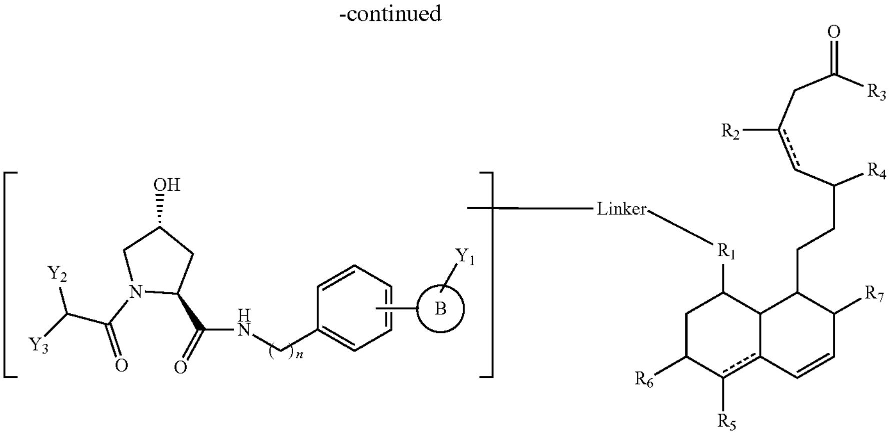

Formula 3B

In the above schemes, $RG^1$, $RG^2$, and $RG^{2a}$ are each independently $L_{PTM}$ or any reaction precursor thereof, $RG^3$, $RG^4$ and $RG^{3a}$ are each independently $L_{ULM}$ or any reaction precursor thereof, and $RG^1$, $RG^2$, $RG^{2a}$, $RG^3$, $RG^{3a}$ and $RG^4$ may be appropriately selected according to the structure and linker position of the target compound.

In the above Reaction Scheme, each compound represented by PTM and ULM may be synthesized by a person skilled in the art with reference to documents known in the field of organic chemistry, descriptions of Examples of the present invention, and the like.

The present invention also provides the compounds represented by PTM-Linker-$RG^3$ or PTM-Linker 1-$RG^{2b}$ that are the reaction intermediates of the compounds represented by Formula I.

Use of the HMG-CoA Reductase Degradation Inducing Compounds

Another embodiment of the present invention is a composition for inducing HMG-CoA reductase degradation comprising the compound represented by Formula I, stereoisomer, or a pharmaceutically acceptable salt thereof. Formula I is the same as defined above.

HMG-CoA reductase (3-hydroxy-3-methylglutaryl-CoA reductase) is an enzyme in an endoplasmic reticulum membrane and catalyzes conversion of HMG-CoA to mevalonate which is a rate-limiting step of intracellular cholesterol biosynthesis.

In Experimental Examples of the present invention, it was confirmed that the compound according to the present invention effectively induced the degradation of HMG-CoA reductase in a hepatocyte model. Surprisingly, it was confirmed that the compound of the present invention had remarkably excellent degradability of HMG-CoA reductase in hepatocytes as compared to the atorvastatin-based PROTAC compound described in WO 2019/109415 A1 (see FIGS. 1 to 10). Accordingly, the composition comprising the compound represented by Formula I of the present invention may be effectively employed for inducing degradation of HMG-CoA reductase.

An embodiment of the present invention is a composition for preventing or treating HMG-CoA reductase-related diseases comprising a compound represented by Formula I, a stereoisomer or a pharmaceutically acceptable salt thereof. An another embodiment of the present invention is a method for prevention or treatment of HMG-CoA reductase-related diseases by administering a therapeutically effective amount of compound represented by Formula I, a stereoisomer or a pharmaceutically acceptable salt thereof into a patient. Formula I is the same as defined above.

In the present invention, the HMGCR-related disease refers to any disease or condition capable of being treated, alleviated, delayed, inhibited or prevented from induction of degradation or inhibition of activity of HMGCR. In an embodiment, the HMG-CoA reductase-related disease may be cardiovascular disease or hyperlipidemia. The cardiovascular disease may include, for example, myocardial infarction, stroke, angina, heart failure, atherosclerosis, or arteriosclerosis, and the hyperlipidemia may include, for example, primary hypercholesterolemia (family and non-family), mixed dyslipidemia, primary dysbetalipoproteinemia, or hypertriglyceridemia. However, examples thereof are not limited thereto.

It was confirmed from Experimental Examples of the present invention that the compound according to the present invention has an excellent effect of inducing protein degradation of HMG-CoA reductase. Therefore, the pharmaceutical composition comprising the compound represented by Formula I, a stereoisomer or a pharmaceutically acceptable salt thereof may be effectively employed for the prevention or treatment of HMG-CoA-related diseases.

The pharmaceutical composition of the present invention may further include one or more pharmaceutically acceptable carriers in addition to the compound represented by Formula I for administration. These formulations may be prepared by referring to conventional methods or literature (see Remington's Pharmaceutical Science, Mack Publishing Company, Easton PA) used for formulation in the art, and may be formulated into various formulations according to each disease or ingredient.

The pharmaceutical composition of the present invention may be administered orally or parenterally according to a desired method (e.g., intravenously, subcutaneously, intraperitoneally or topically applied), and the dosage range may vary according to be the patient's weight, age, sex, and health status, diet, administration time, administration method, excretion rate, and the severity of the disease, etc.

The pharmaceutical composition of the present invention may further include one or more active ingredients exhibiting the same or similar medicinal effects in addition to the compound represented by Formula I above, or the pharmaceutically acceptable salt thereof.

An embodiment of the present invention is a method of degrading HMG-CoA reductase by administering a compound represented by Formula I, a stereoisomer or a pharmaceutically acceptable salt thereof to mammals including humans.

Another embodiment of the present invention is a method of degrading HMG-CoA reductase by administering the compound represented by Formula I, a stereoisomer or a pharmaceutically acceptable salt thereof to a sample in vitro. The sample may be a cell, a cell culture, a body fluid or tissue of a mammal including a human, but is not limited thereto.

Advantageous Effects

The compound of the present invention exhibits an effect of inducing HMG-CoA reductase degradation. Therefore, the pharmaceutical compound of the present invention may be effectively utilized for preventing or treating HMG-CoA reductase-related diseases.

DESCRIPTION OF DRAWINGS

FIGS. 1 to 10 show the western blotting results from the measurement of the protein degradability of HMG-CoA reductase according to the bifunctional compound of the present invention.

DETAILED DESCRIPTION

Unless otherwise defined, all technical and scientific terms used herein have the same meaning as commonly understood by one of ordinary skill in the art to which this disclosure belongs. The terminology used in the description is for describing particular embodiments only and is not intended to be limiting of the disclosure.

Examples 2 to 6, 8 to 12, 14 to 38, 40 to 44, 46 to 105 and 106 to 169 are examples for synthesis of Compounds 2 to 6, 8 to 12, 14 to 38, 40 to 44 and 46 to 105 and 106 to 169 which are HMGCR decomposition-inducing bifunctional compounds according to the present invention. Examples of 1, 7, 13, 39 and 45 are examples for synthesis of Compounds 1, 7, 13, 39 and 45, which are comparative compounds that lack the E3 ubiquitin ligase ligand. Comparative Examples 1 and 2 are examples for synthesis of Comparative Compounds 1 and 2 disclosed in WO2019/109415 A1.

The present invention provides synthetic methods for Compound 1 to 169 shown in the table below.

TABLE 1

| Compound | Structure |
|---|---|
| 1 | 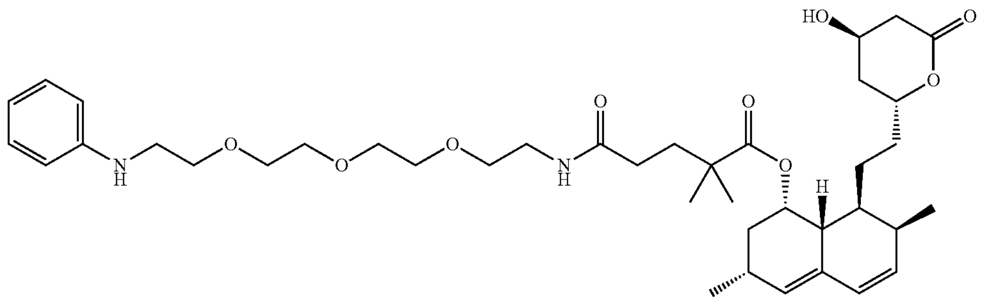 [SMILES: C[C@H]1C=C2C=C[C@H](C)[C@H](CC[C@@H]3C[C@@H](O)CC(=O)O3)[C@H]2[C@@H](OC(=O)C(C)(C)CCC(=O)NCCOCCOCCOCCNc2ccccc2)C1] |
| 2 | 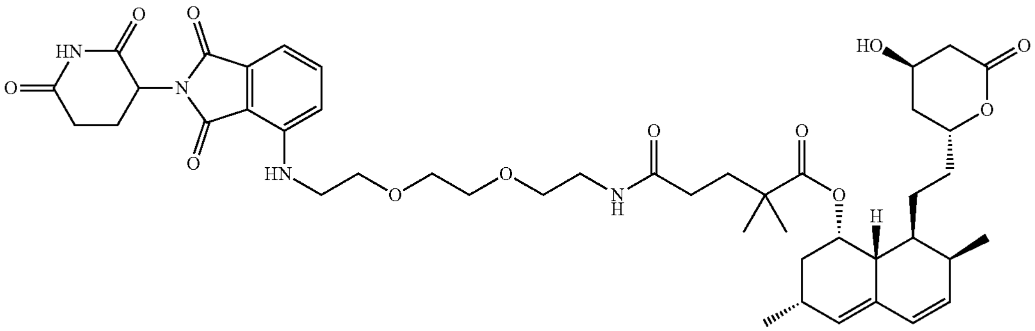 [SMILES: C[C@H]1C=C2C=C[C@H](C)[C@H](CC[C@@H]3C[C@@H](O)CC(=O)O3)[C@H]2[C@@H](OC(=O)C(C)(C)CCC(=O)NCCOCCOCCNc2cccc3c2C(=O)N(C2CCC(=O)NC2=O)C3=O)C1] |

TABLE 1-continued
| Compound | Structure |
| --- | --- |
| 3 | 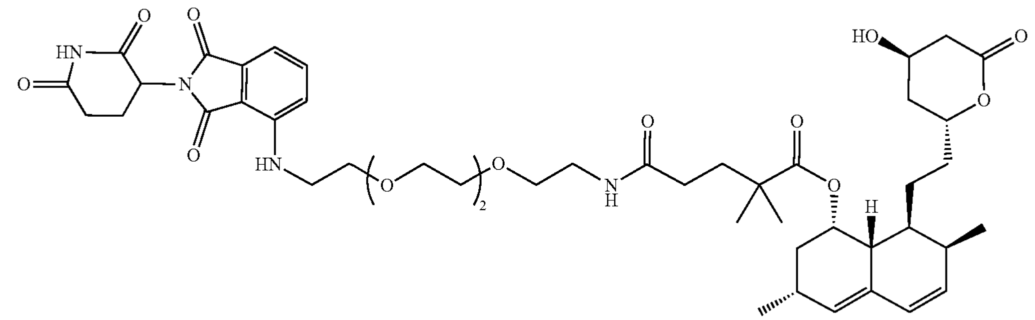 |
| 4 | 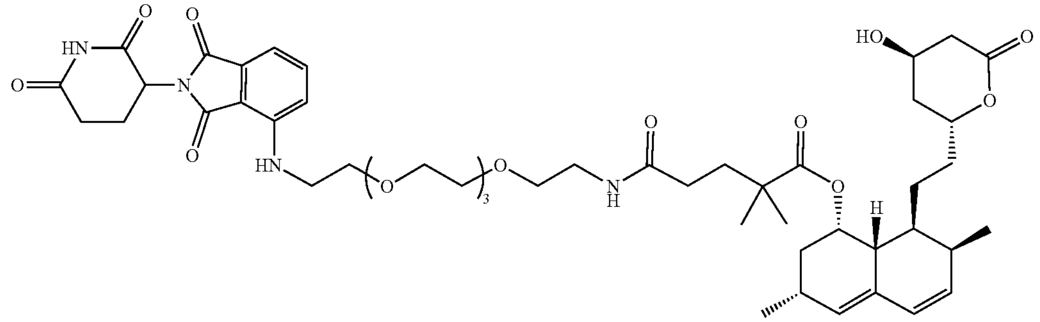 |
| 5 | 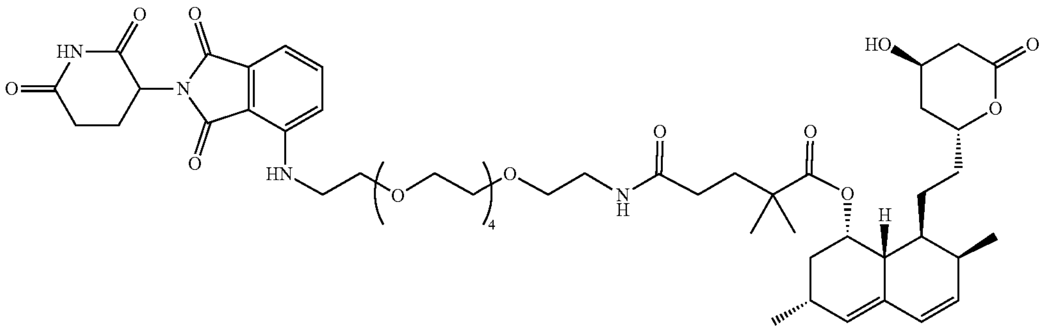 |
| 6 | 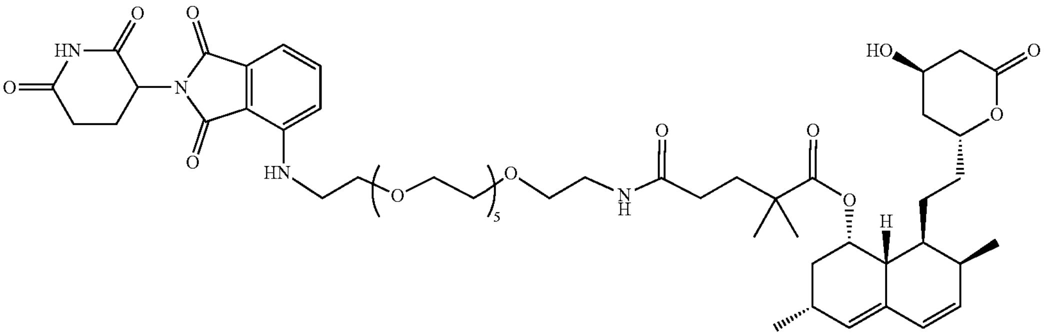 |

TABLE 1-continued
| Compound | Structure |
| --- | --- |
| 7 | 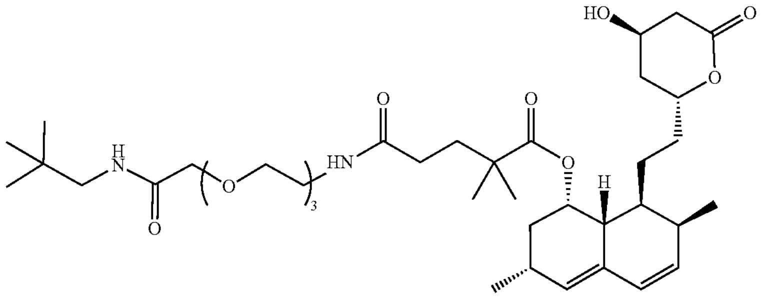 |
| 8 | 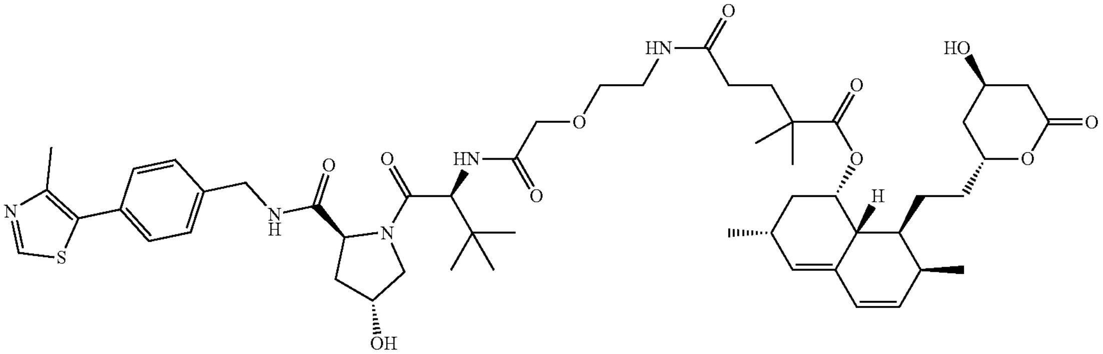 [SMILES: Cc1ncsc1-c1ccc(CNC(=O)[C@@H]2C[C@@H](O)CN2C(=O)[C@@H](NC(=O)COCCNC(=O)CCC(C)(C)C(=O)O[C@H]2C[C@@H](C)C=C3C=C[C@H](C)[C@H](CC[C@@H]4C[C@@H](O)CC(=O)O4)[C@H]32)C(C)(C)C)cc1] |
| 9 | 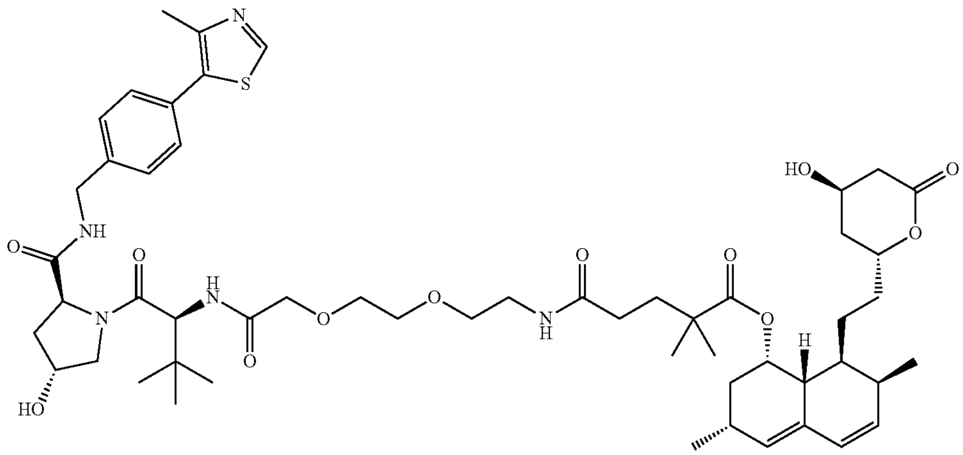 [SMILES: Cc1ncsc1-c1ccc(CNC(=O)[C@@H]2C[C@@H](O)CN2C(=O)[C@@H](NC(=O)COCCOCCNC(=O)CCC(C)(C)C(=O)O[C@H]2C[C@@H](C)C=C3C=C[C@H](C)[C@H](CC[C@@H]4C[C@@H](O)CC(=O)O4)[C@H]32)C(C)(C)C)cc1] |
| 10 | 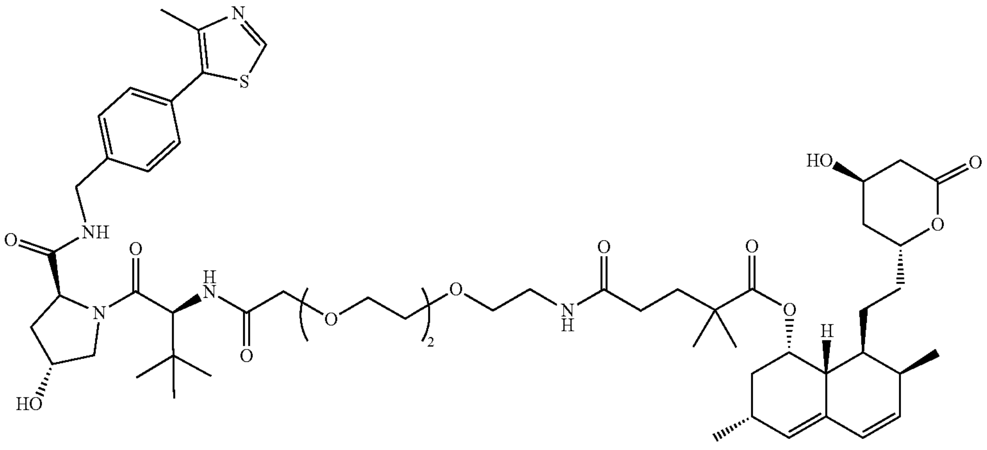 |

TABLE 1-continued
| Compound | Structure |
| --- | --- |
| 11 | 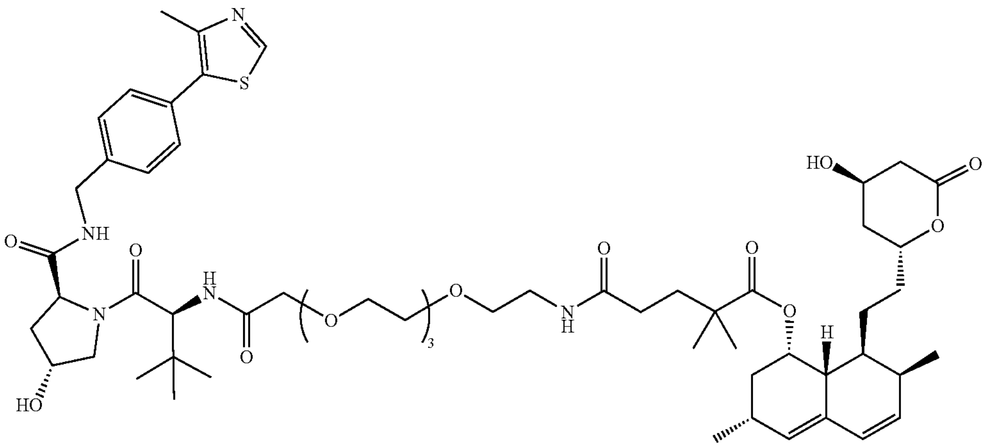 |
| 12 | 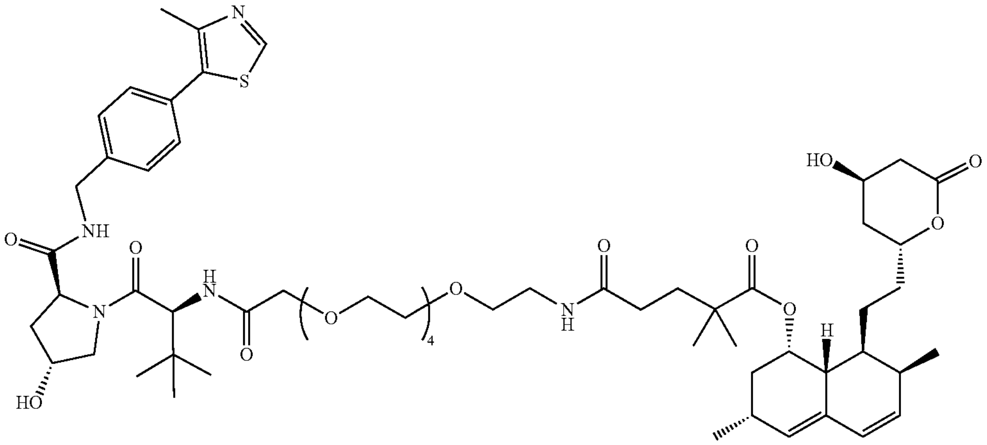 |
| 13 | 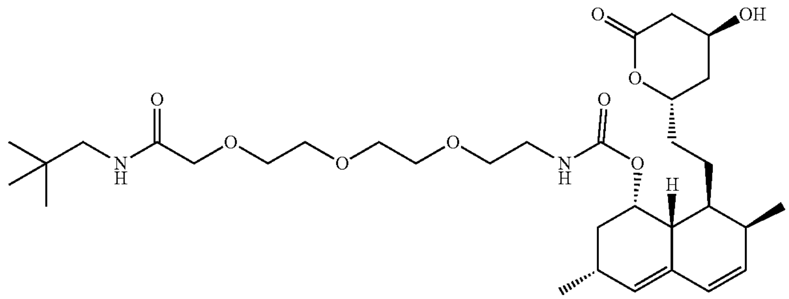 [SMILES: C[C@H]1C=C2C=C[C@H](C)[C@H](CC[C@H]3C[C@H](O)CC(=O)O3)[C@H]2[C@@H](OC(=O)NCCOCCOCCOCC(=O)NCC(C)(C)C)C1] |
| 14 | 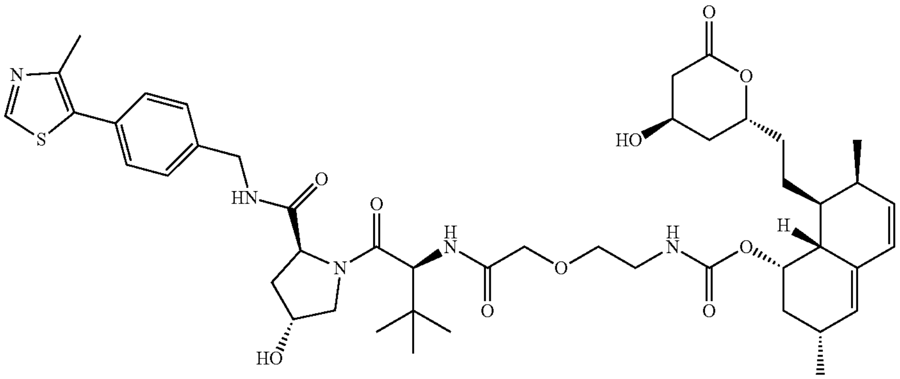 [SMILES: Cc1ncsc1-c1ccc(CNC(=O)[C@@H]2C[C@@H](O)CN2C(=O)[C@@H](NC(=O)COCCNC(=O)O[C@H]2C[C@@H](C)C=C3C=C[C@H](C)[C@H](CC[C@@H]4C[C@@H](O)CC(=O)O4)[C@H]32)C(C)(C)C)cc1] |

TABLE 1-continued
| Compound | Structure |
|---|---|
| 15 | 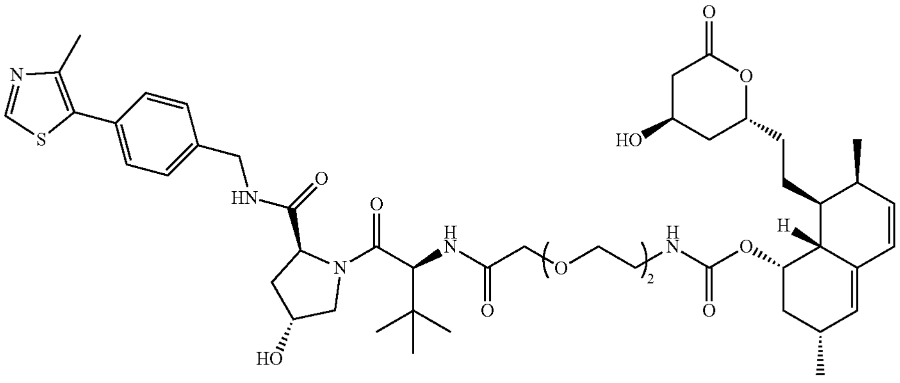 |
| 16 | 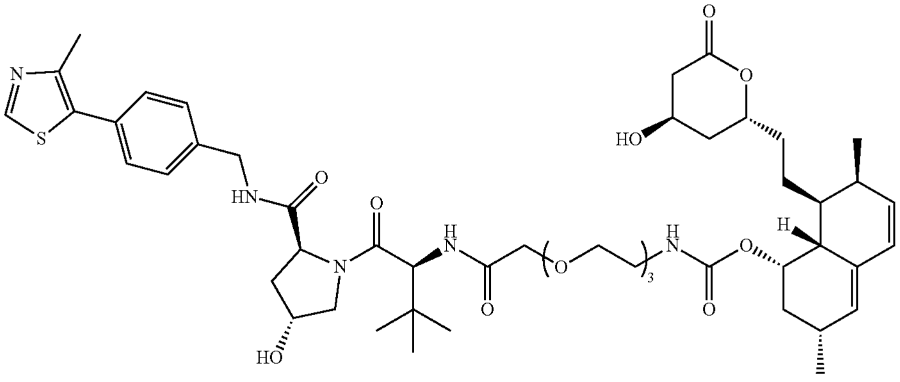 |
| 17 | 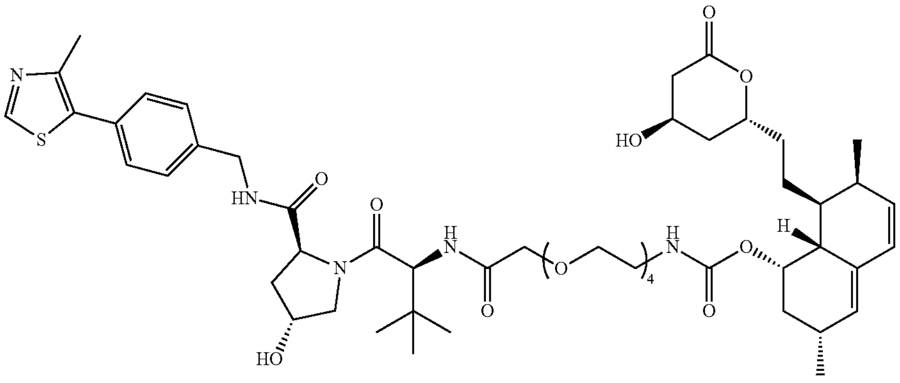 |
| 18 | 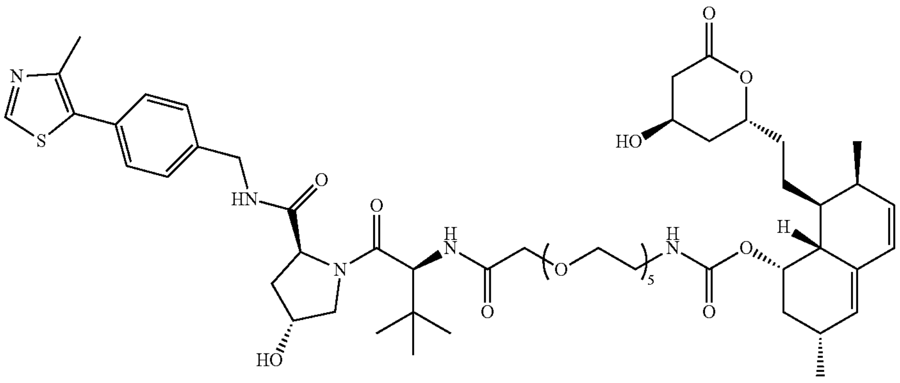 |

TABLE 1-continued
| Compound | Structure |
| --- | --- |
| 19 | 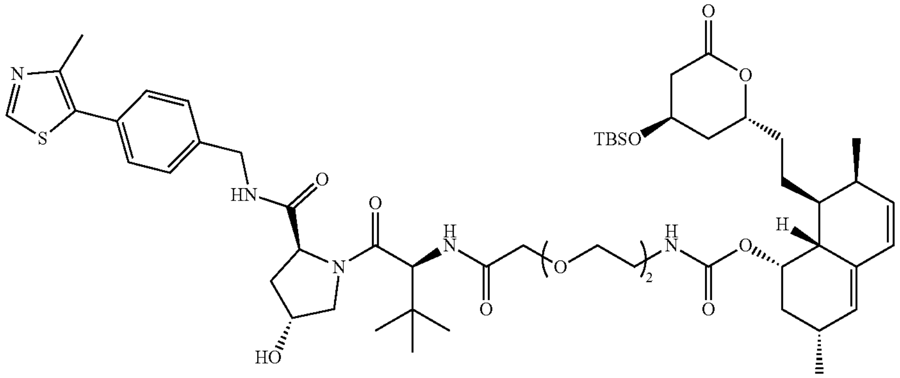 TBS = tert-Butyldimethylsilyl |
| 20 | 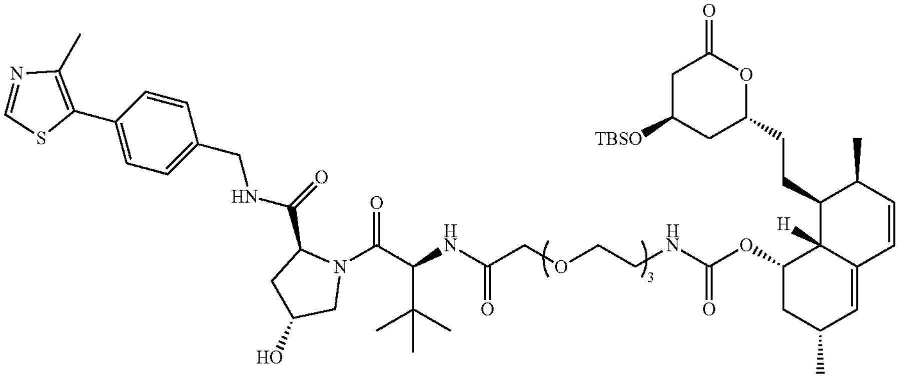 |
| 21 | 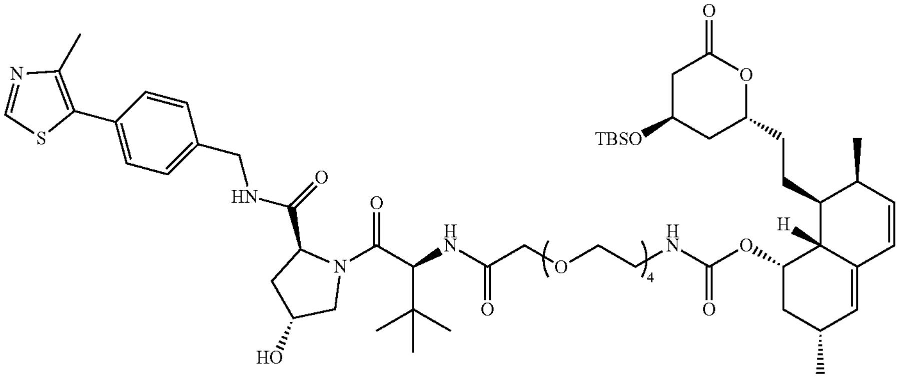 |
| 22 | 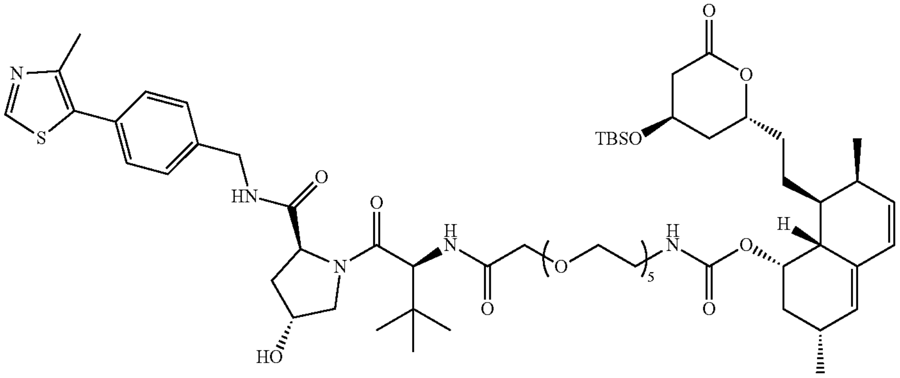 |

TABLE 1-continued
| Compound | Structure |
| --- | --- |
| 23 | 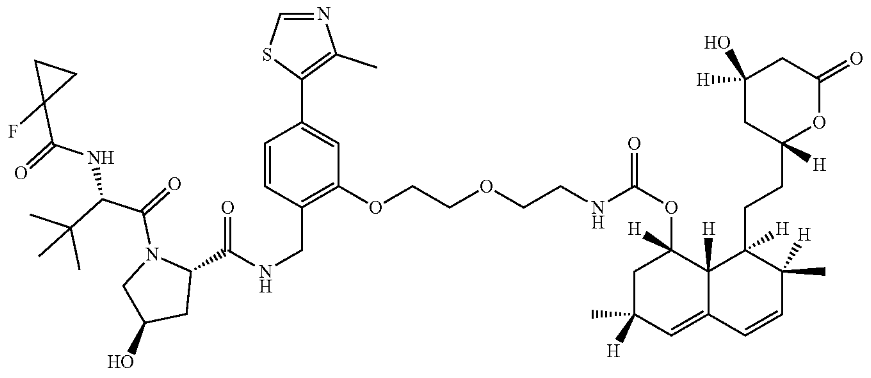 [SMILES: Cc1ncsc1-c1ccc(CNC(=O)[C@@H]2C[C@@H](O)CN2C(=O)[C@@H](NC(=O)C2(F)CC2)C(C)(C)C)c(OCCOCCNC(=O)O[C@H]2C[C@@H](C)C=C3C=C[C@H](C)[C@H](CC[C@@H]4C[C@@H](O)CC(=O)O4)[C@H]32)c1] |
| 24 | 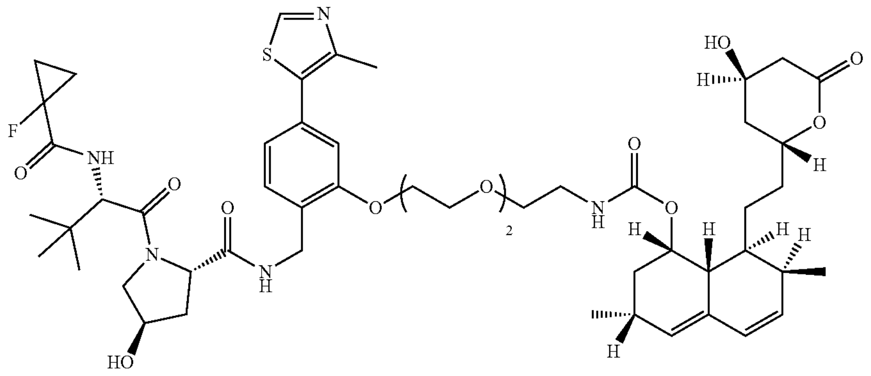 |
| 25 | 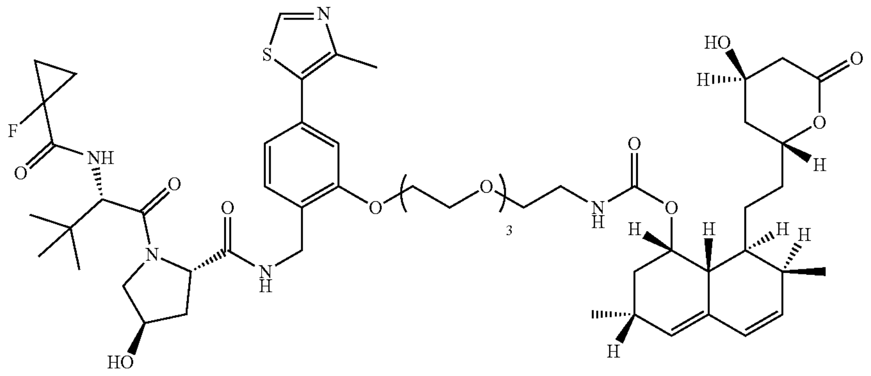 |
| 26 | 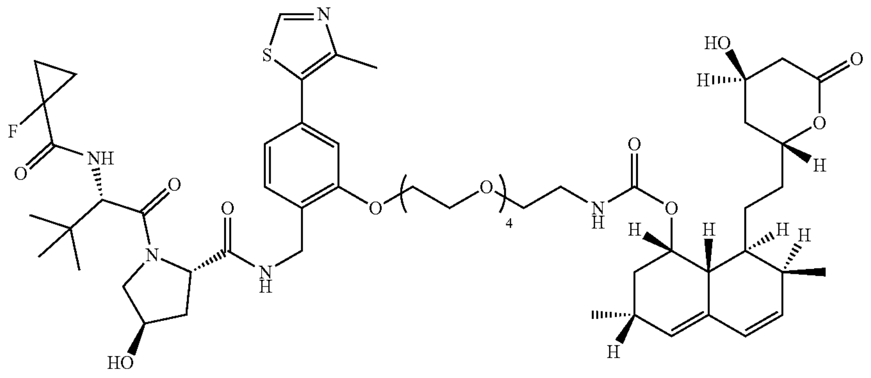 |

TABLE 1-continued
| Com-pound | Structure |
| --- | --- |
| 27 | 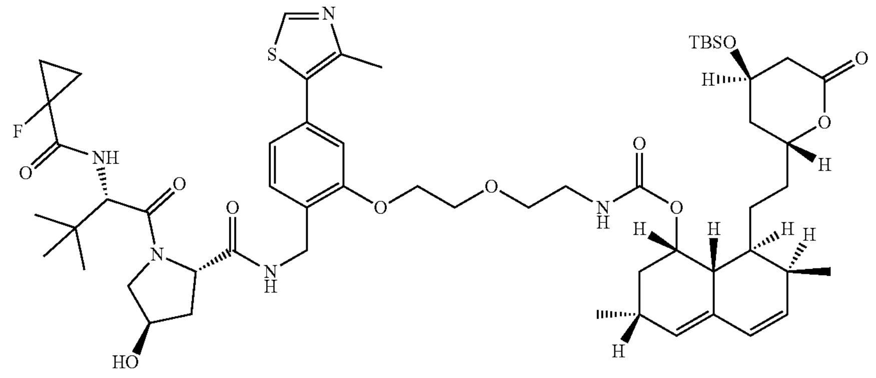 [SMILES: Cc1ncsc1-c1ccc(CNC(=O)[C@@H]2C[C@@H](O)CN2C(=O)[C@@H](NC(=O)C2(F)CC2)C(C)(C)C)c(OCCOCCNC(=O)O[C@H]2C[C@@H](C)C=C3C=C[C@H](C)[C@H](CC[C@@H]4C[C@@H](O[Si](C)(C)C(C)(C)C)CC(=O)O4)[C@H]32)c1] |
| 28 | 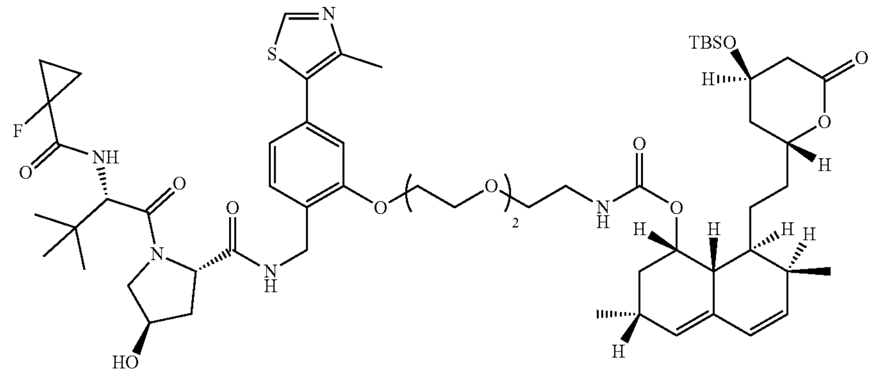 |
| 29 | 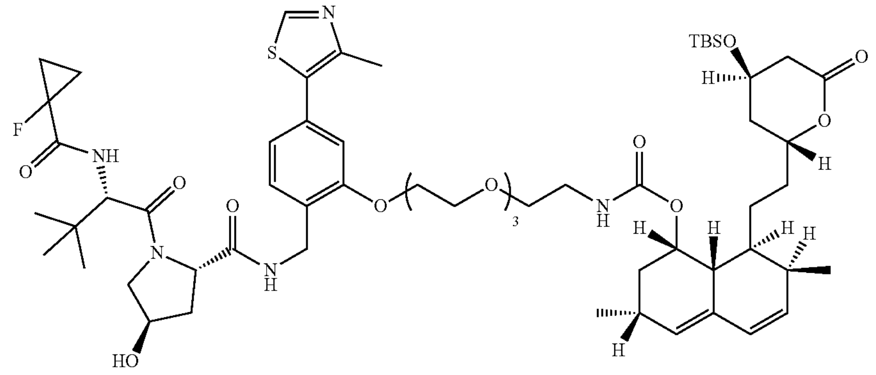 |
| 30 | 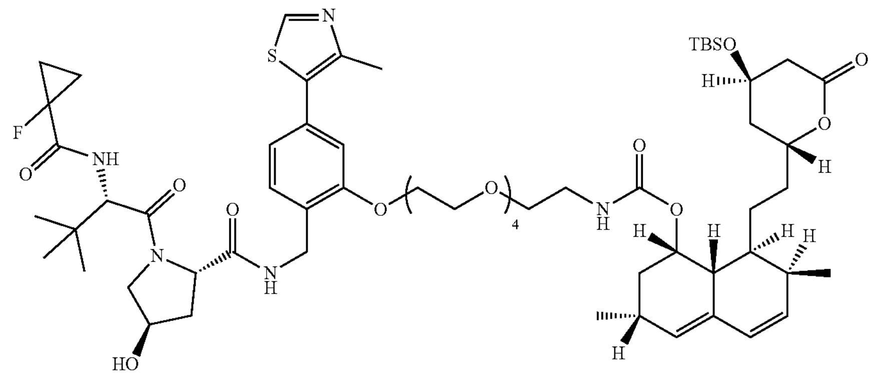 |

TABLE 1-continued
| Compound | Structure |
|---|---|
| 31 | 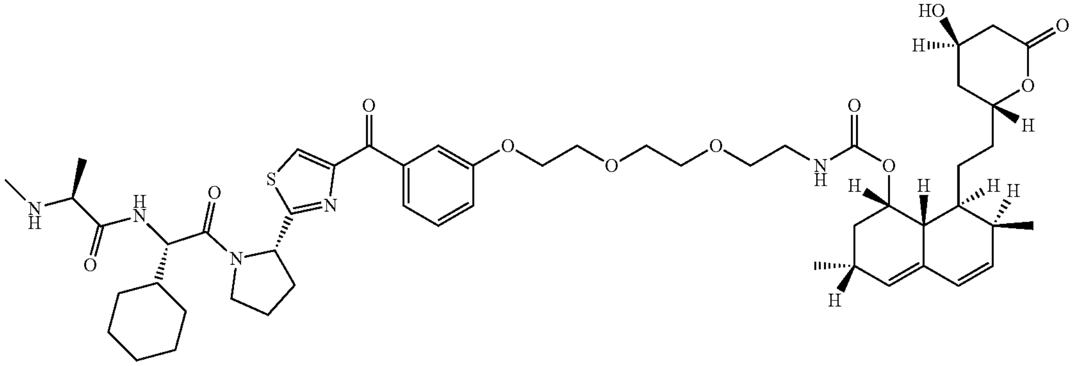 [SMILES: CN[C@@H](C)C(=O)N[C@H](C(=O)N1CCC[C@H]1c1nc(C(=O)c2cccc(OCCOCCOCCNC(=O)O[C@H]3C[C@@H](C)C=C4C=C[C@H](C)[C@H](CC[C@@H]5C[C@@H](O)CC(=O)O5)[C@H]43)c2)cs1)C1CCCCC1] |
| 32 | 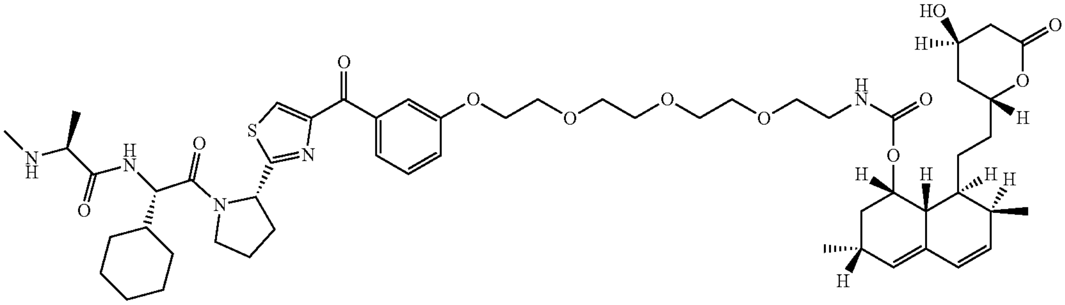 [SMILES: CN[C@@H](C)C(=O)N[C@H](C(=O)N1CCC[C@H]1c1nc(C(=O)c2cccc(OCCOCCOCCOCCNC(=O)O[C@H]3C[C@@H](C)C=C4C=C[C@H](C)[C@H](CC[C@@H]5C[C@@H](O)CC(=O)O5)[C@H]43)c2)cs1)C1CCCCC1] |
| 33 | 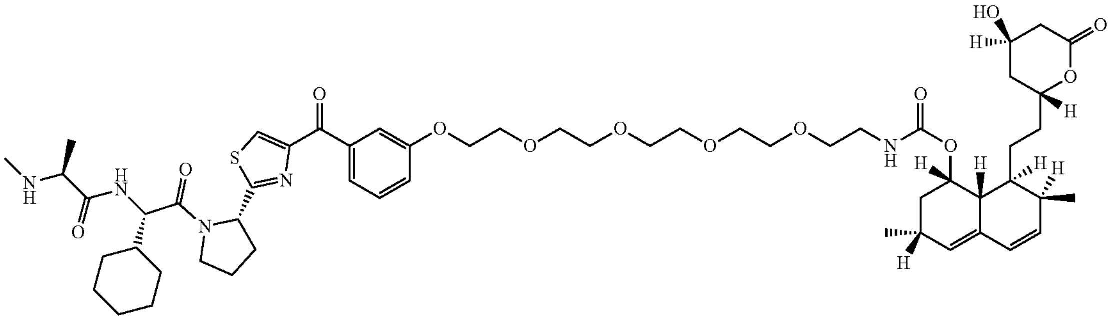 [SMILES: CN[C@@H](C)C(=O)N[C@H](C(=O)N1CCC[C@H]1c1nc(C(=O)c2cccc(OCCOCCOCCOCCOCCNC(=O)O[C@H]3C[C@@H](C)C=C4C=C[C@H](C)[C@H](CC[C@@H]5C[C@@H](O)CC(=O)O5)[C@H]43)c2)cs1)C1CCCCC1] |
| 34 | 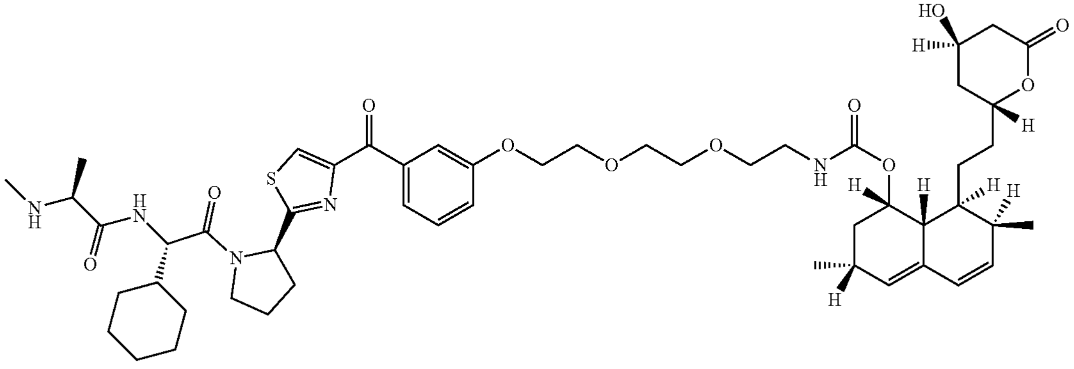 [SMILES: CN[C@@H](C)C(=O)N[C@H](C(=O)N1CCC[C@@H]1c1nc(C(=O)c2cccc(OCCOCCOCCNC(=O)O[C@H]3C[C@@H](C)C=C4C=C[C@H](C)[C@H](CC[C@@H]5C[C@@H](O)CC(=O)O5)[C@H]43)c2)cs1)C1CCCCC1] |

TABLE 1-continued
| Compound | Structure |
| --- | --- |
| 35 | 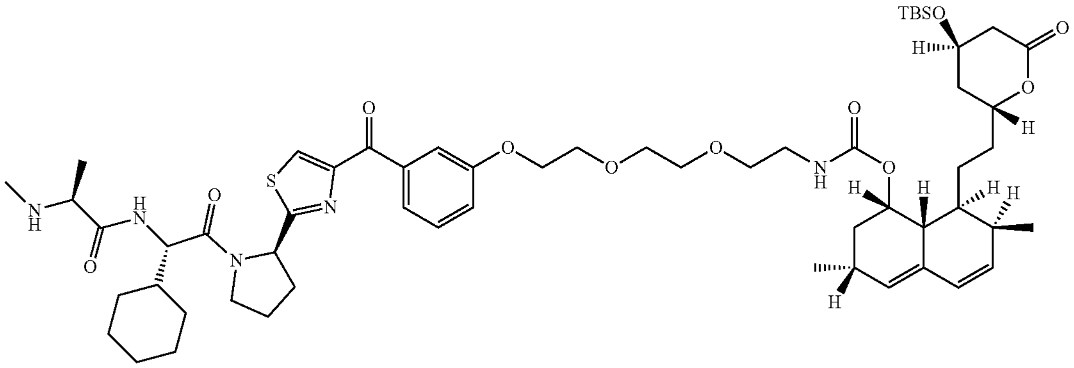 [SMILES: CN[C@@H](C)C(=O)N[C@H](C(=O)N1CCC[C@@H]1c1nc(C(=O)c2cccc(OCCOCCOCCNC(=O)O[C@H]3C[C@@H](C)C=C4C=C[C@H](C)[C@H](CC[C@@H]5C[C@@H](O[Si](C)(C)C(C)(C)C)CC(=O)O5)[C@H]43)c2)cs1)C1CCCCC1] |
| 36 | 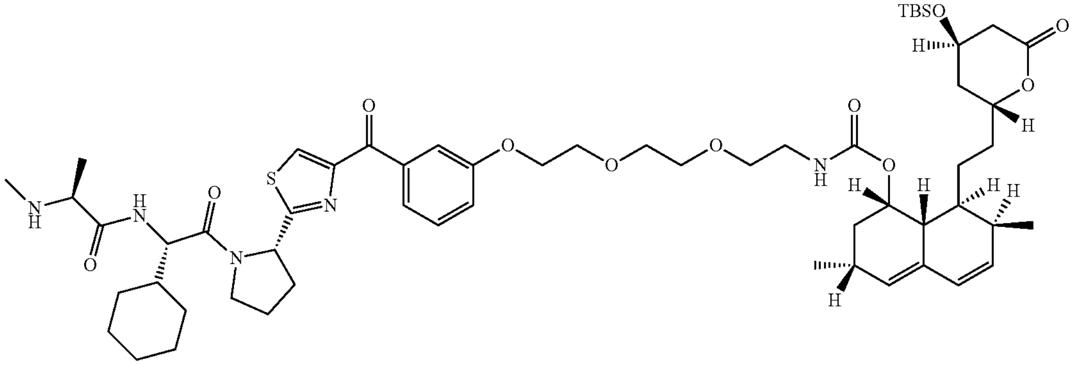 [SMILES: CN[C@@H](C)C(=O)N[C@H](C(=O)N1CCC[C@H]1c1nc(C(=O)c2cccc(OCCOCCOCCNC(=O)O[C@H]3C[C@@H](C)C=C4C=C[C@H](C)[C@H](CC[C@@H]5C[C@@H](O[Si](C)(C)C(C)(C)C)CC(=O)O5)[C@H]43)c2)cs1)C1CCCCC1] |
| 37 | 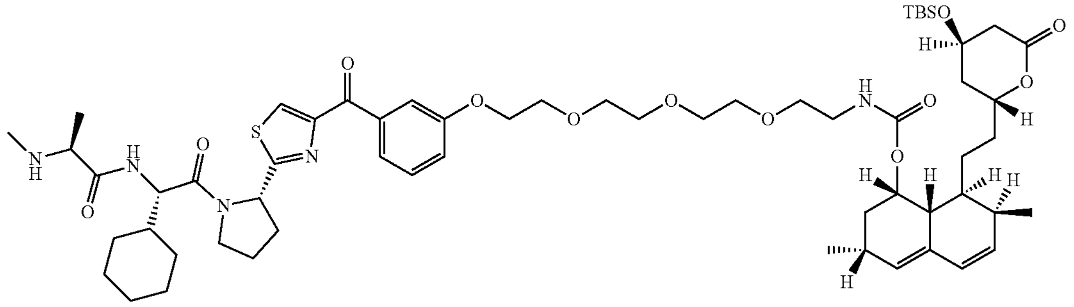 [SMILES: CN[C@@H](C)C(=O)N[C@H](C(=O)N1CCC[C@H]1c1nc(C(=O)c2cccc(OCCOCCOCCOCCNC(=O)O[C@H]3C[C@@H](C)C=C4C=C[C@H](C)[C@H](CC[C@@H]5C[C@@H](O[Si](C)(C)C(C)(C)C)CC(=O)O5)[C@H]43)c2)cs1)C1CCCCC1] |
| 38 | 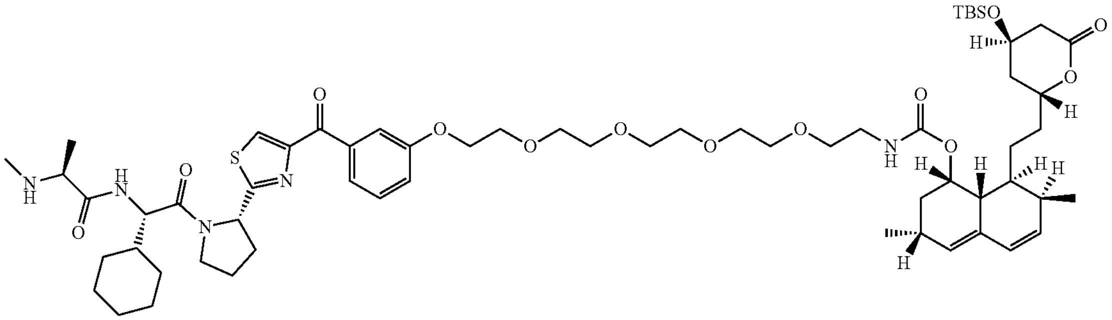 [SMILES: CN[C@@H](C)C(=O)N[C@H](C(=O)N1CCC[C@H]1c1nc(C(=O)c2cccc(OCCOCCOCCOCCOCCNC(=O)O[C@H]3C[C@@H](C)C=C4C=C[C@H](C)[C@H](CC[C@@H]5C[C@@H](O[Si](C)(C)C(C)(C)C)CC(=O)O5)[C@H]43)c2)cs1)C1CCCCC1] |

TABLE 1-continued
| Compound | Structure |
|---|---|
| 39 | 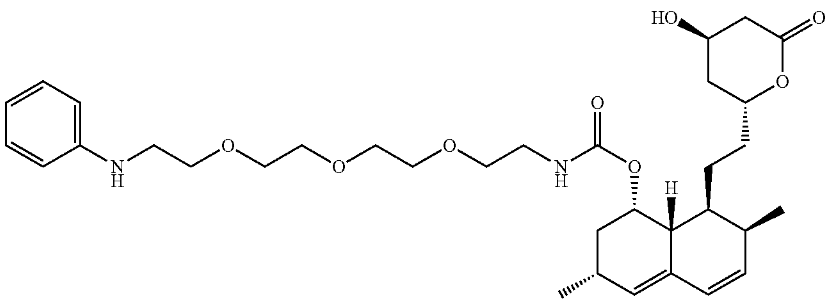 [SMILES: C[C@H]1C=C2C=C[C@H](C)[C@H](CC[C@@H]3C[C@@H](O)CC(=O)O3)[C@H]2[C@@H](OC(=O)NCCOCCOCCOCCNc2ccccc2)C1] |
| 40 | 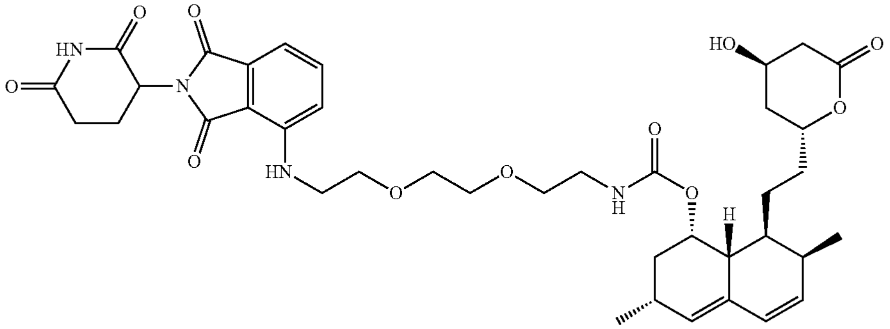 [SMILES: C[C@H]1C=C2C=C[C@H](C)[C@H](CC[C@@H]3C[C@@H](O)CC(=O)O3)[C@H]2[C@@H](OC(=O)NCCOCCOCCNc2cccc3c2C(=O)N(C2CCC(=O)NC2=O)C3=O)C1] |
| 41 | 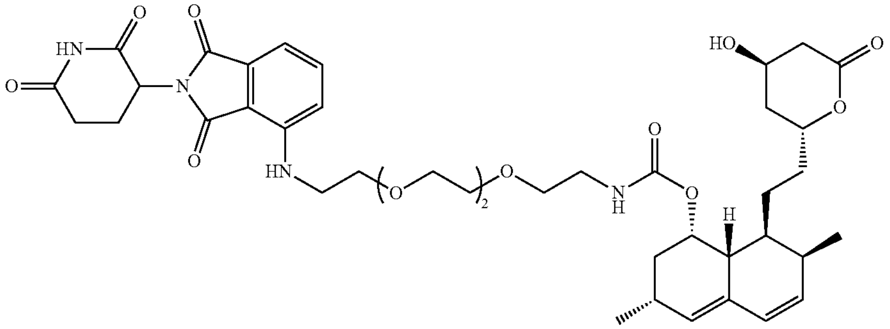 |
| 42 | 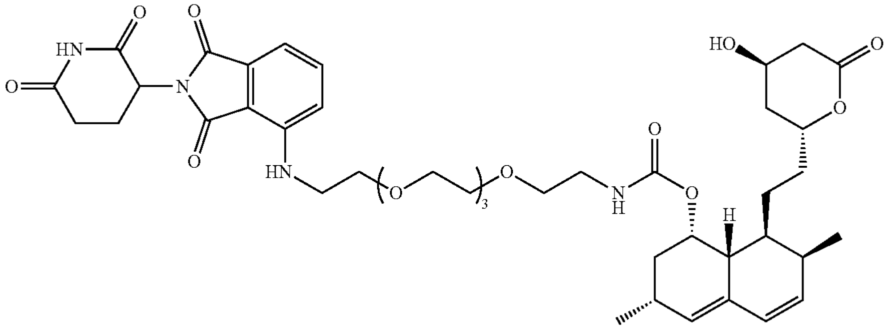 |

TABLE 1-continued
| Compound | Structure |
|---|---|
| 43 | 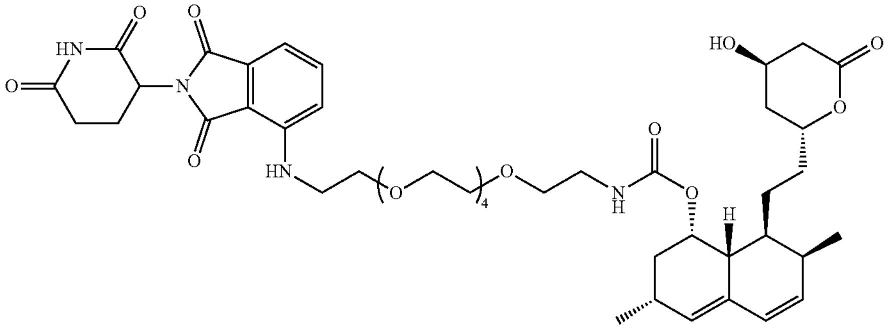 |
| 44 | 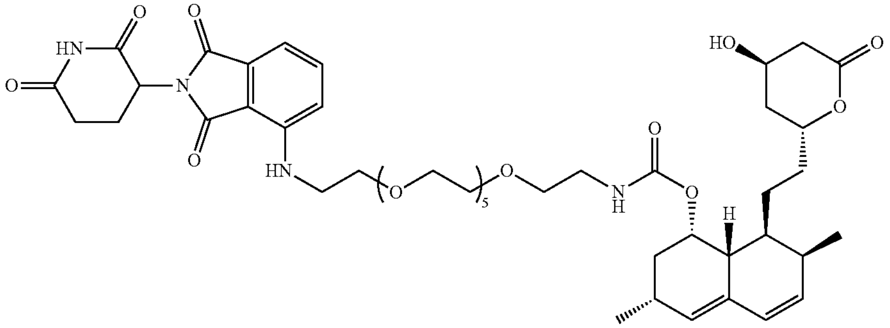 |
| 45 | 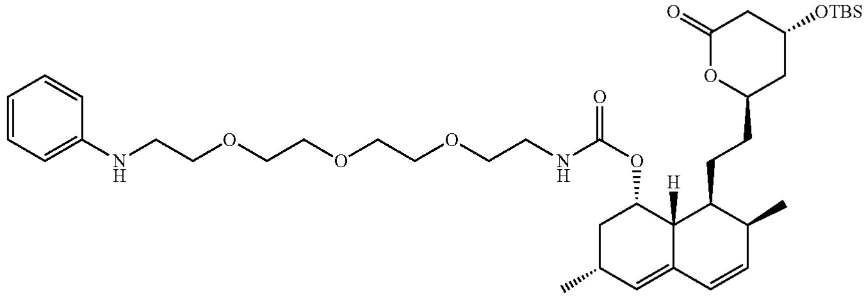 [SMILES: C[C@H]1C=C2C=C[C@H](C)[C@H](CC[C@@H]3C[C@@H](O[Si](C)(C)C(C)(C)C)CC(=O)O3)[C@H]2[C@@H](OC(=O)NCCOCCOCCOCCNc2ccccc2)C1] |
| 46 | 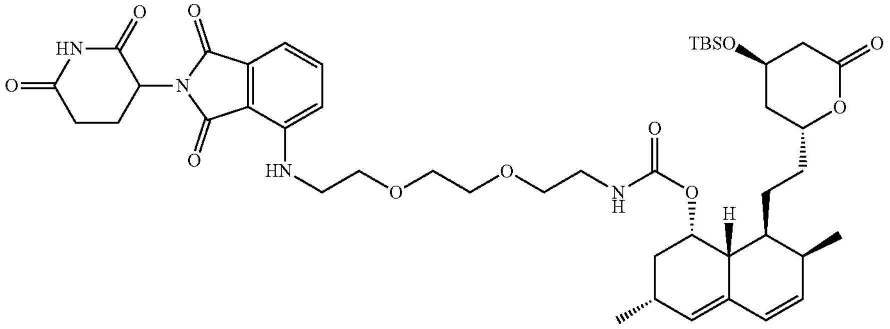 [SMILES: C[C@H]1C=C2C=C[C@H](C)[C@H](CC[C@@H]3C[C@@H](O[Si](C)(C)C(C)(C)C)CC(=O)O3)[C@H]2[C@@H](OC(=O)NCCOCCOCCNc2cccc3c2C(=O)N(C2CCC(=O)NC2=O)C3=O)C1] |

TABLE 1-continued
| Compound | Structure |
|---|---|
| 47 | 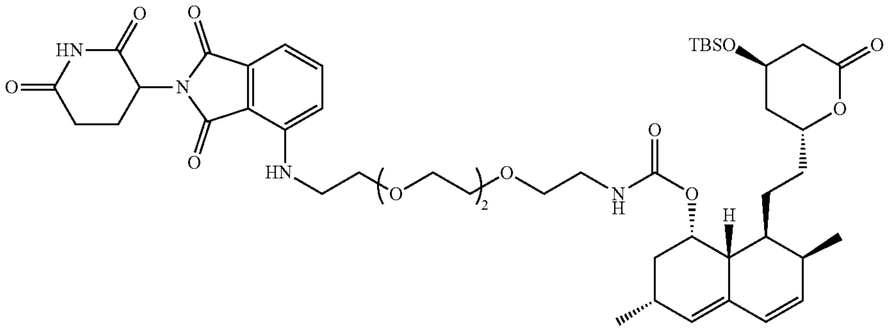 |
| 48 | 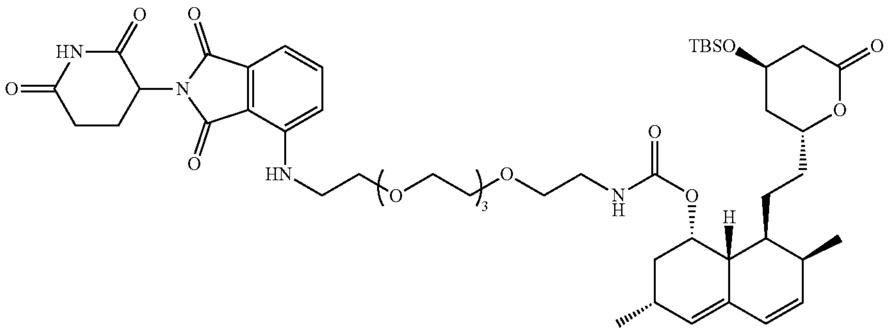 |
| 49 | 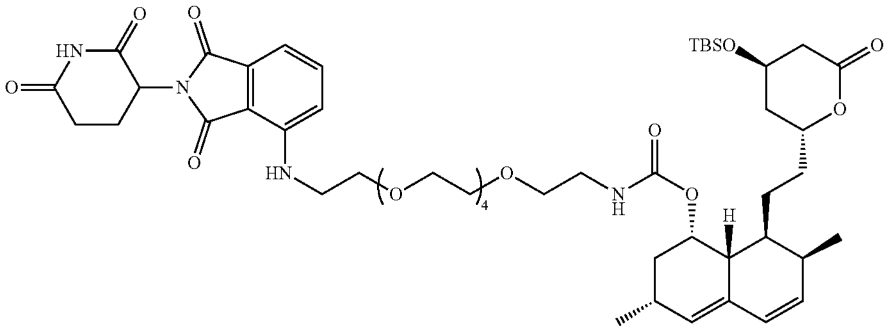 |
| 50 | 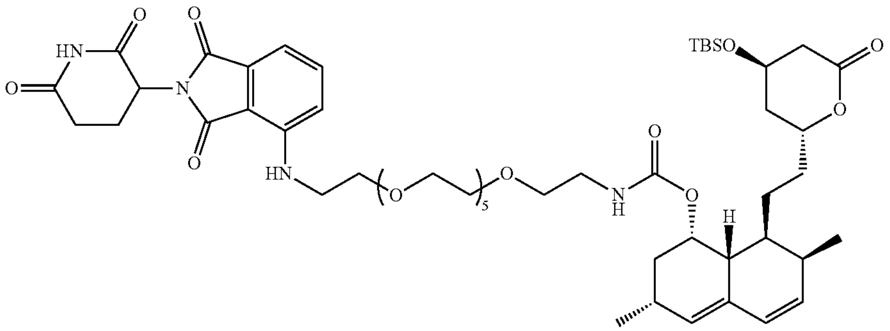 |

TABLE 1-continued
| Compound | Structure |
| --- | --- |
| 51 | 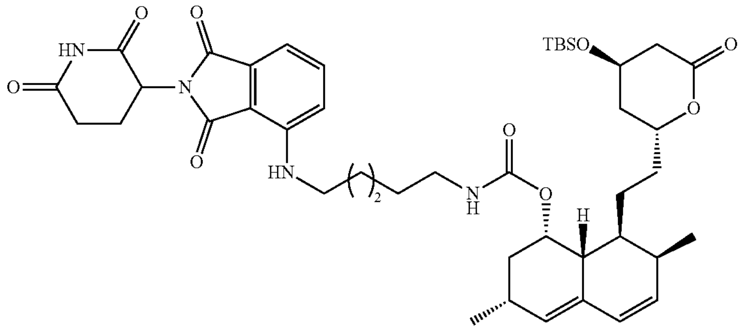 |
| 52 | 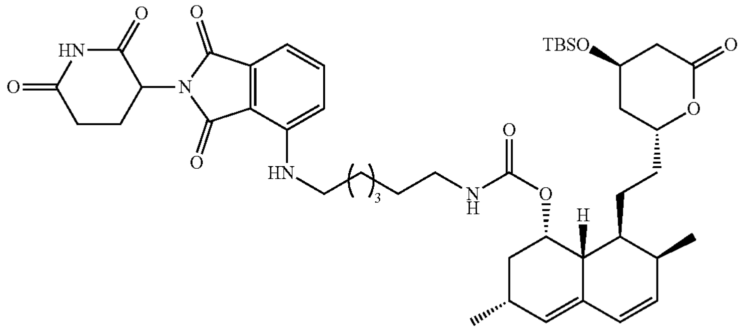 |
| 53 | 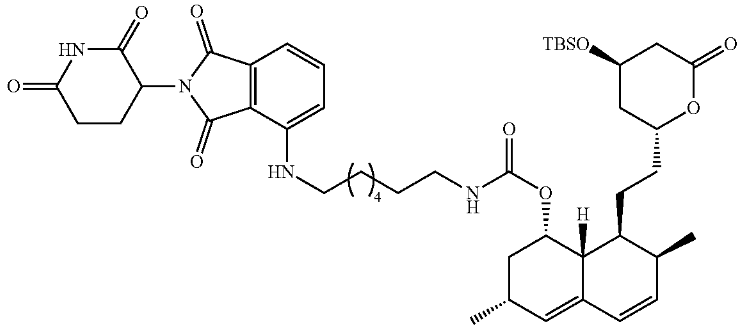 |
| 54 | 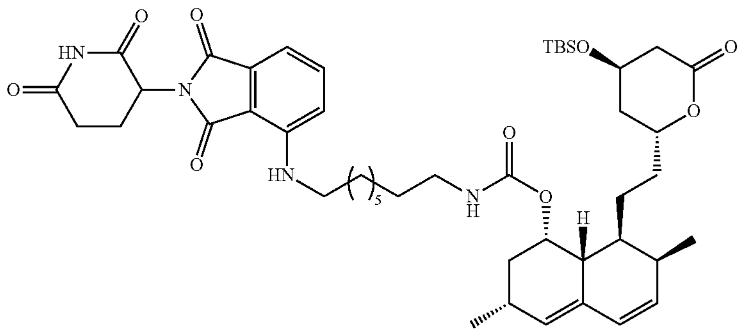 |

TABLE 1-continued
| Compound | Structure |
| --- | --- |
| 55 | 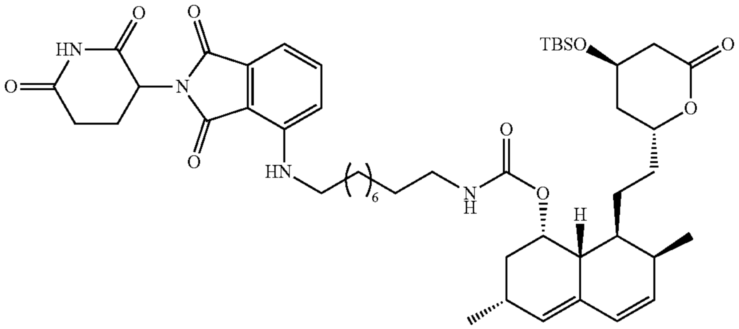 |
| 56 | 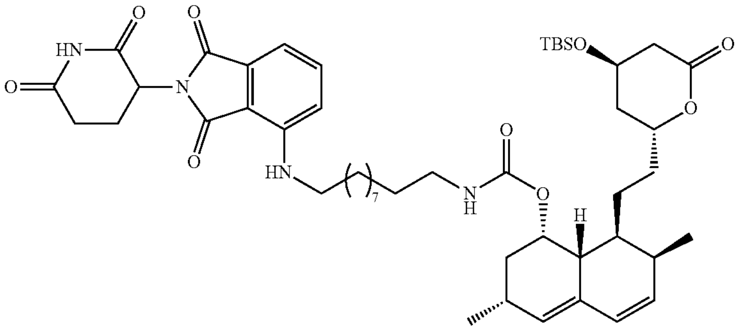 |
| 57 | 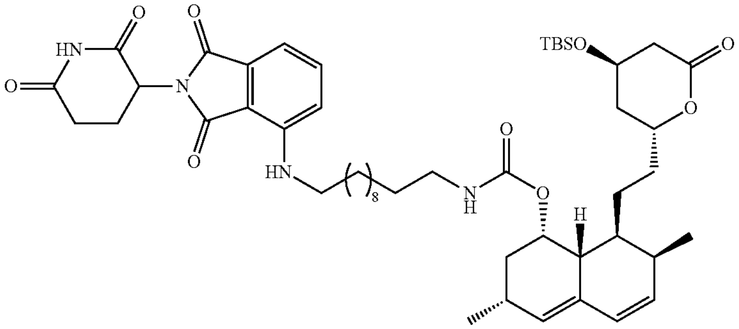 |
| 58 | 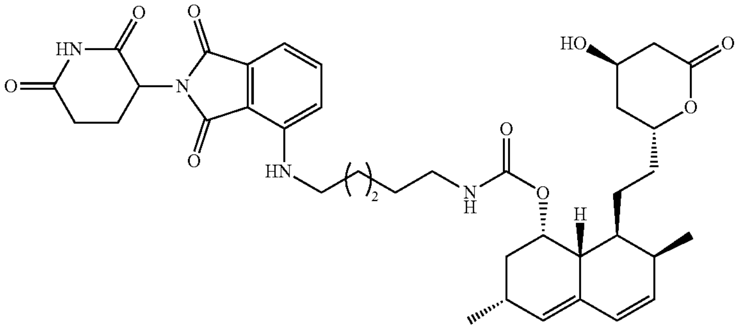 |

TABLE 1-continued
| Compound | Structure |
| --- | --- |
| 59 | 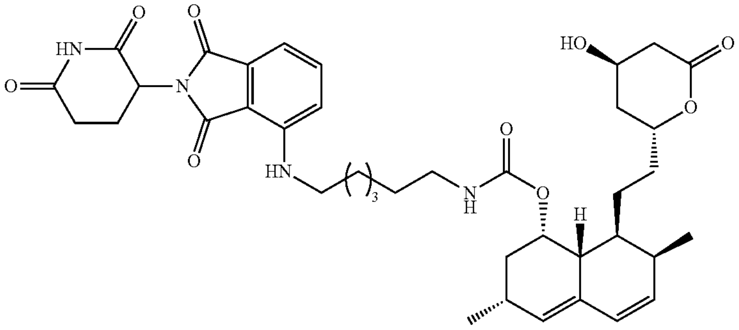 |
| 60 | 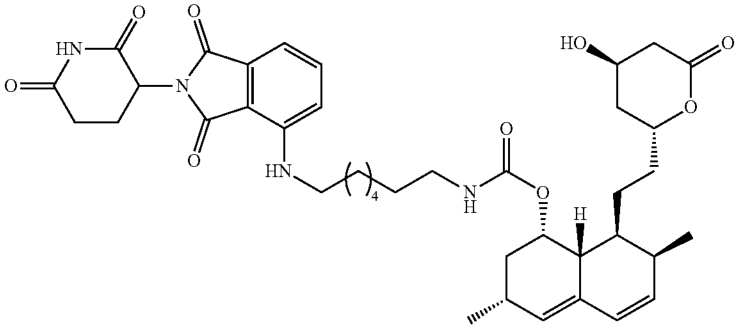 |
| 61 | 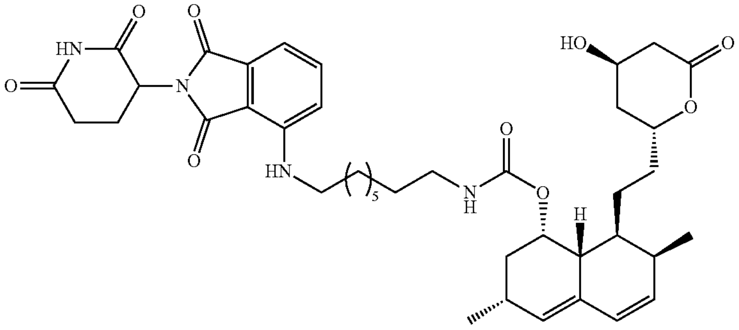 |
| 62 | 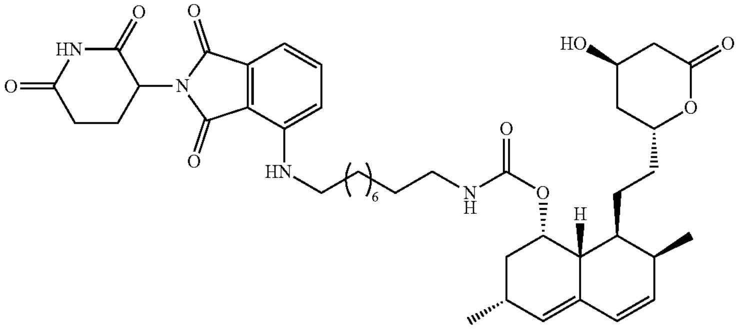 |

TABLE 1-continued
| Compound | Structure |
|---|---|
| 63 | 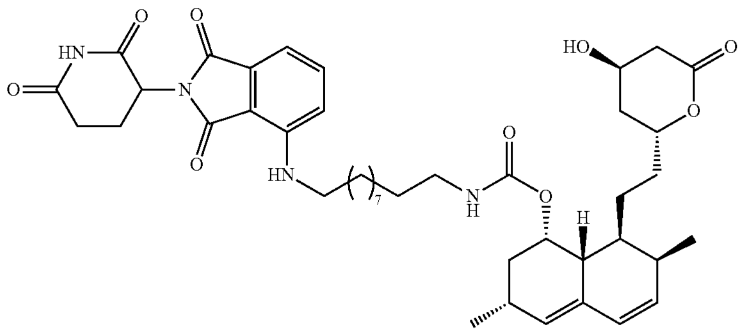 |
| 64 | 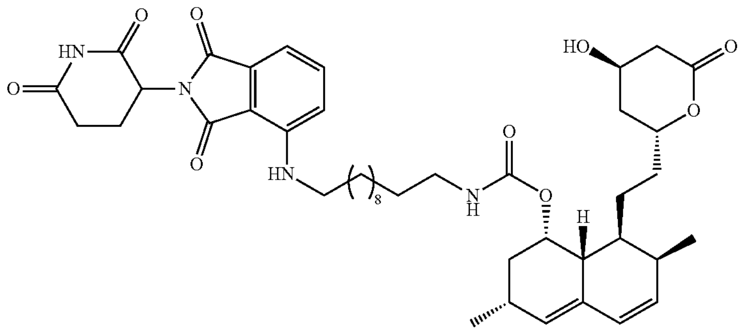 |
| 65 | 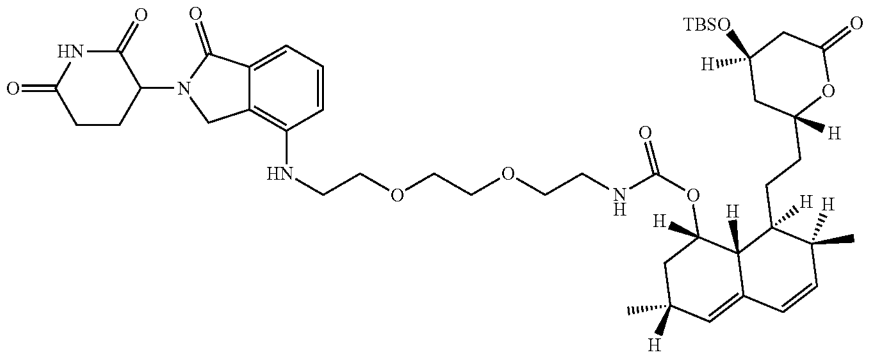 [SMILES: C[C@H]1C=C2C=C[C@H](C)[C@H](CC[C@@H]3C[C@@H](O[Si](C)(C)C(C)(C)C)CC(=O)O3)[C@H]2[C@@H](OC(=O)NCCOCCOCCNc2cccc3c2CN(C2CCC(=O)NC2=O)C3=O)C1] |
| 66 | 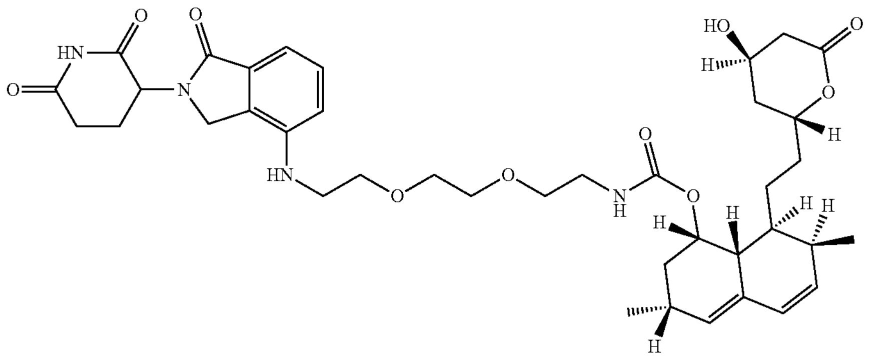 [SMILES: C[C@H]1C=C2C=C[C@H](C)[C@H](CC[C@@H]3C[C@@H](O)CC(=O)O3)[C@H]2[C@@H](OC(=O)NCCOCCOCCNc2cccc3c2CN(C2CCC(=O)NC2=O)C3=O)C1] |

TABLE 1-continued
| Compound | Structure |
| --- | --- |
| 67 | 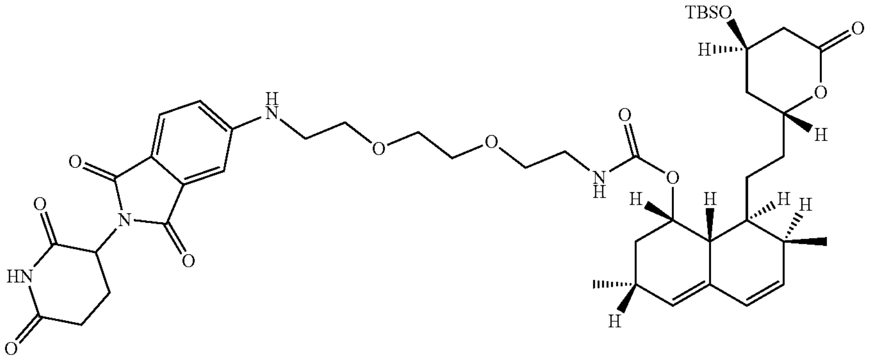 [SMILES: C[C@H]1C=C2C=C[C@H](C)[C@H](CC[C@@H]3C[C@@H](O[Si](C)(C)C(C)(C)C)CC(=O)O3)[C@H]2[C@@H](OC(=O)NCCOCCOCCNc2ccc3c(c2)C(=O)N(C2CCC(=O)NC2=O)C3=O)C1] |
| 68 | 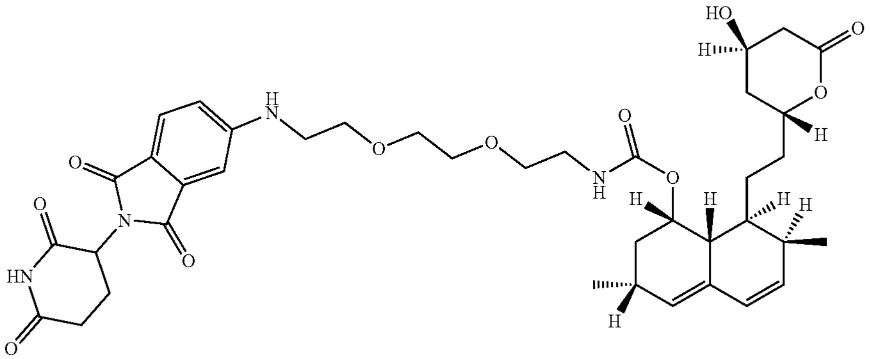 [SMILES: C[C@H]1C=C2C=C[C@H](C)[C@H](CC[C@@H]3C[C@@H](O)CC(=O)O3)[C@H]2[C@@H](OC(=O)NCCOCCOCCNc2ccc3c(c2)C(=O)N(C2CCC(=O)NC2=O)C3=O)C1] |
| 69 | 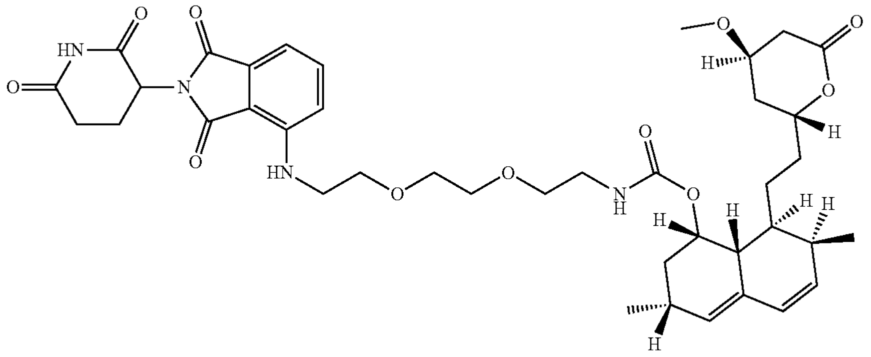 [SMILES: CO[C@H]1CC(=O)O[C@H](CC[C@@H]2[C@@H]3C(=C[C@H](C)C[C@@H]3OC(=O)NCCOCCOCCNc3cccc4c3C(=O)N(C3CCC(=O)NC3=O)C4=O)C=C[C@@H]2C)C1] |
| 70 | 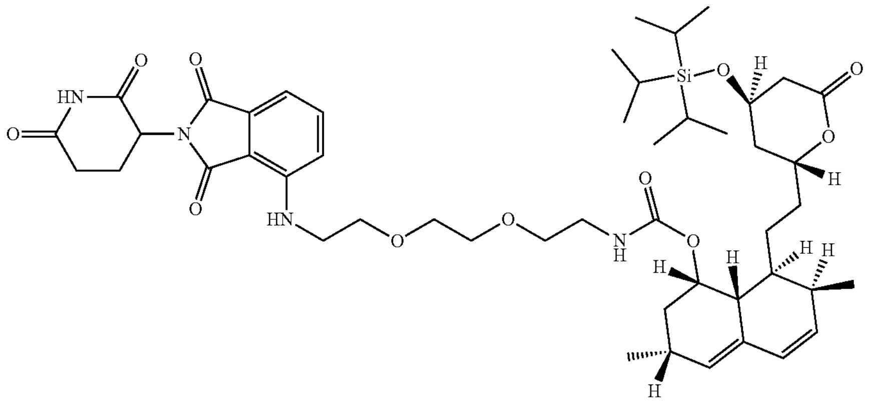 [SMILES: CC(C)[Si](O[C@H]1CC(=O)O[C@H](CC[C@@H]2[C@@H]3C(=C[C@H](C)C[C@@H]3OC(=O)NCCOCCOCCNc3cccc4c3C(=O)N(C3CCC(=O)NC3=O)C4=O)C=C[C@@H]2C)C1)(C(C)C)C(C)C] |

TABLE 1-continued
| Compound | Structure |
| --- | --- |
| 71 | 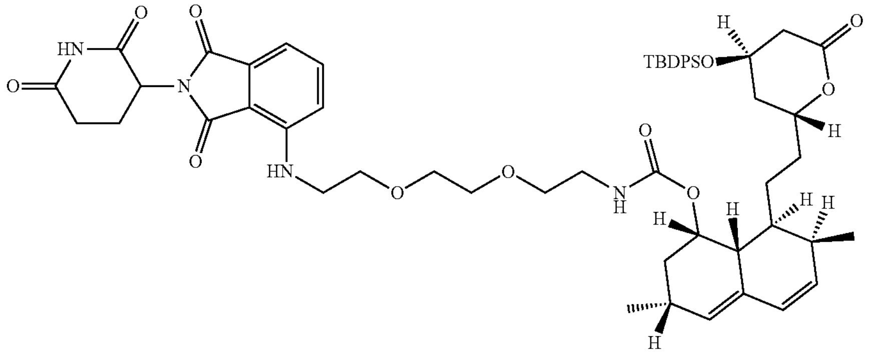<br>TBDPS = tert-Butyldiphenylsilyl |
| 72 | 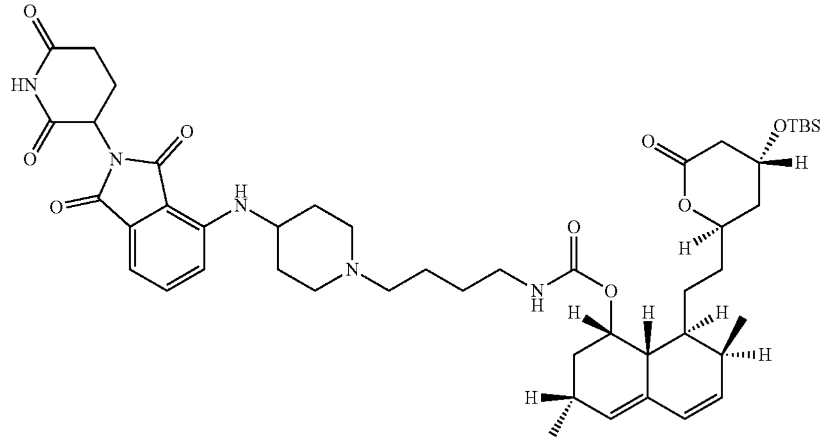 [SMILES: C[C@H]1C=C2C=C[C@H](C)[C@H](CC[C@@H]3C[C@@H](O[Si](C)(C)C(C)(C)C)CC(=O)O3)[C@H]2[C@@H](OC(=O)NCCCCN2CCC(Nc3cccc4c3C(=O)N(C3CCC(=O)NC3=O)C4=O)CC2)C1] |
| 73 | 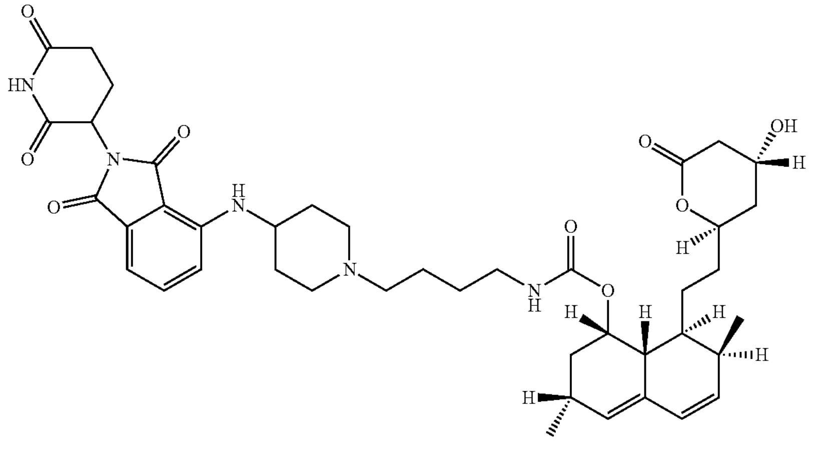 [SMILES: C[C@H]1C=C2C=C[C@H](C)[C@H](CC[C@@H]3C[C@@H](O)CC(=O)O3)[C@H]2[C@@H](OC(=O)NCCCCN2CCC(Nc3cccc4c3C(=O)N(C3CCC(=O)NC3=O)C4=O)CC2)C1] |

TABLE 1-continued
| Compound | Structure |
| --- | --- |
| 74 | 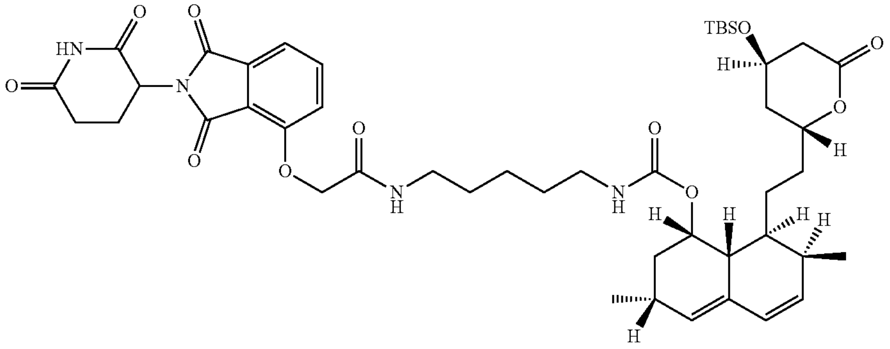 |
| 75 | 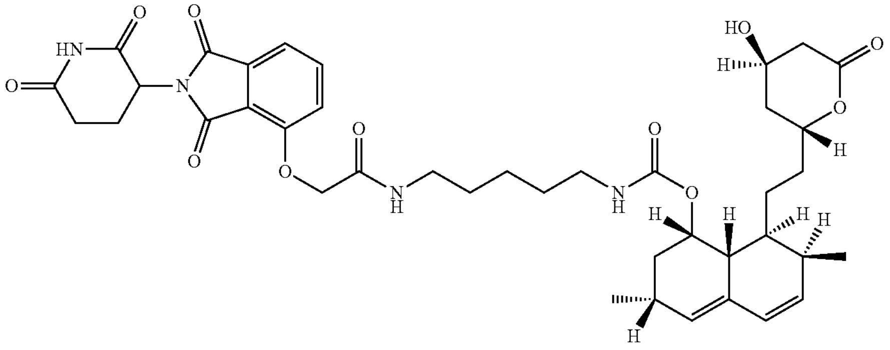 [SMILES: C[C@H]1C=C2C=C[C@H](C)[C@H](CC[C@@H]3C[C@@H](O)CC(=O)O3)[C@H]2[C@@H](OC(=O)NCCCCCNC(=O)COc2cccc3c2C(=O)N(C2CCC(=O)NC2=O)C3=O)C1] |
| 76 | 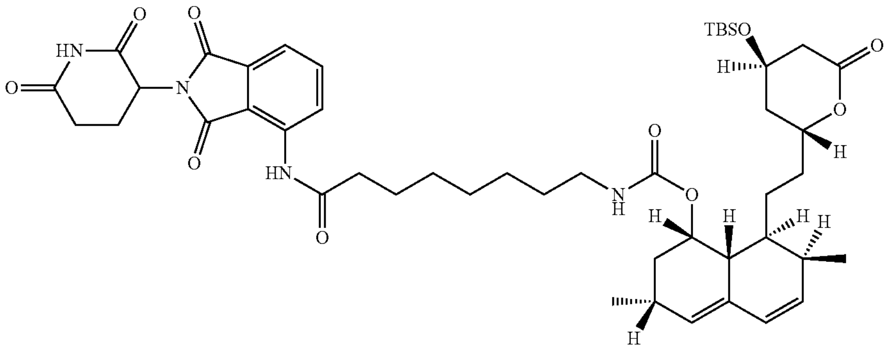 [SMILES: C[C@H]1C=C2C=C[C@H](C)[C@H](CC[C@@H]3C[C@@H](O[Si](C)(C)C(C)(C)C)CC(=O)O3)[C@H]2[C@@H](OC(=O)NCCCCCCCC(=O)Nc2cccc3c2C(=O)N(C2CCC(=O)NC2=O)C3=O)C1] |
| 77 | 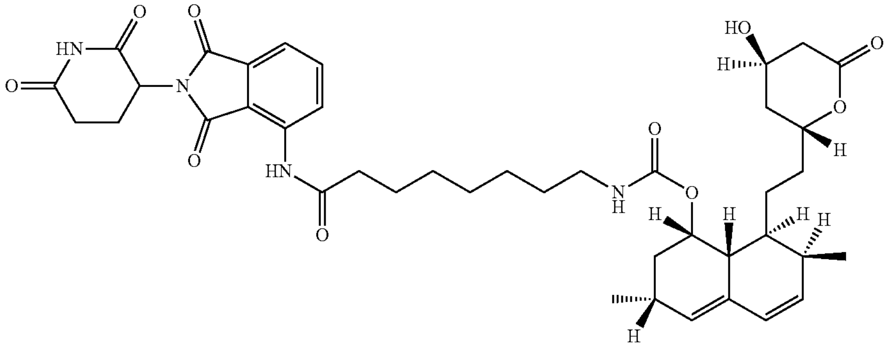 [SMILES: C[C@H]1C=C2C=C[C@H](C)[C@H](CC[C@@H]3C[C@@H](O)CC(=O)O3)[C@H]2[C@@H](OC(=O)NCCCCCCCC(=O)Nc2cccc3c2C(=O)N(C2CCC(=O)NC2=O)C3=O)C1] |

TABLE 1-continued
| Compound | Structure |
| --- | --- |
| 78 | 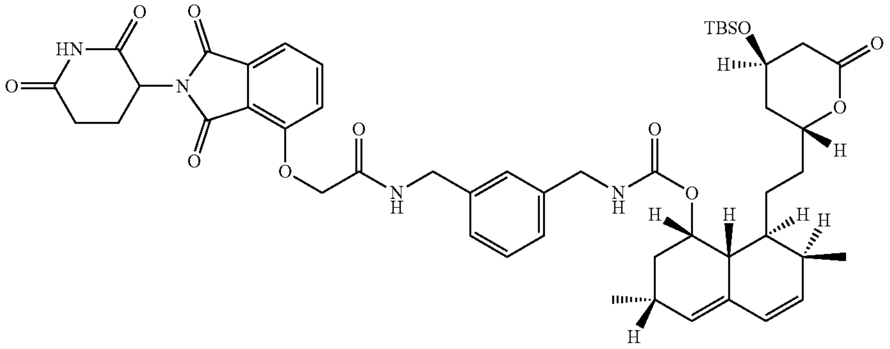 [SMILES: C[C@H]1C=C2C=C[C@H](C)[C@H](CC[C@@H]3C[C@@H](O[Si](C)(C)C(C)(C)C)CC(=O)O3)[C@H]2[C@@H](OC(=O)NCc2cccc(CNC(=O)COc3cccc4c3C(=O)N(C3CCC(=O)NC3=O)C4=O)c2)C1] |
| 79 | 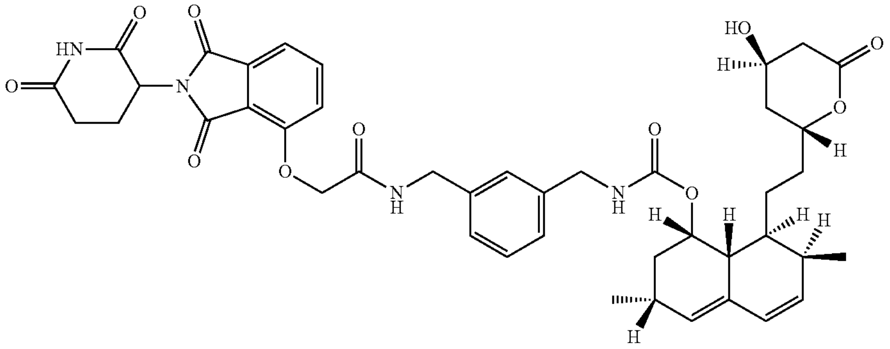 [SMILES: C[C@H]1C=C2C=C[C@H](C)[C@H](CC[C@@H]3C[C@@H](O)CC(=O)O3)[C@H]2[C@@H](OC(=O)NCc2cccc(CNC(=O)COc3cccc4c3C(=O)N(C3CCC(=O)NC3=O)C4=O)c2)C1] |
| 80 | 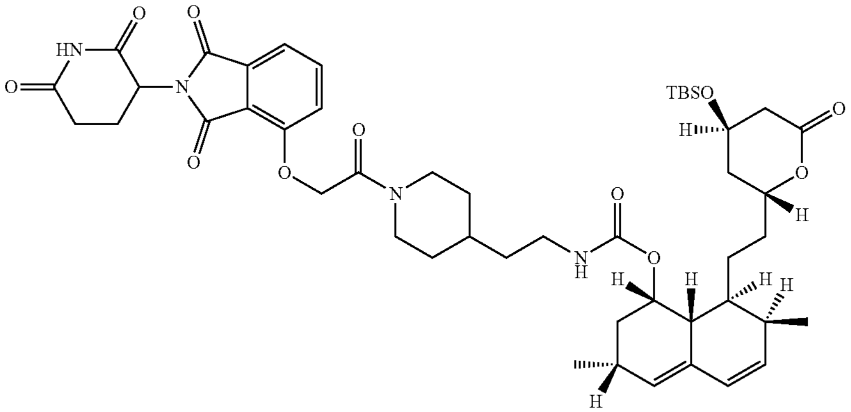 [SMILES: C[C@H]1C=C2C=C[C@H](C)[C@H](CC[C@@H]3C[C@@H](O[Si](C)(C)C(C)(C)C)CC(=O)O3)[C@H]2[C@@H](OC(=O)NCCC2CCN(C(=O)COc3cccc4c3C(=O)N(C3CCC(=O)NC3=O)C4=O)CC2)C1] |
| 81 | 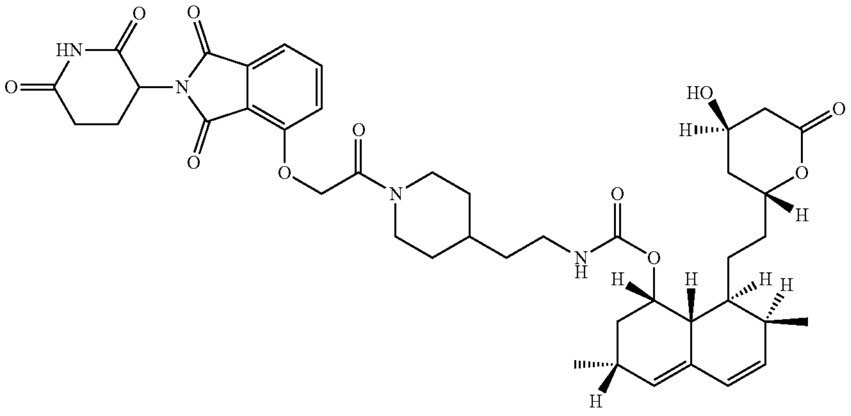 [SMILES: C[C@H]1C=C2C=C[C@H](C)[C@H](CC[C@@H]3C[C@@H](O)CC(=O)O3)[C@H]2[C@@H](OC(=O)NCCC2CCN(C(=O)COc3cccc4c3C(=O)N(C3CCC(=O)NC3=O)C4=O)CC2)C1] |

TABLE 1-continued
| Compound | Structure |
|---|---|
| 82 | 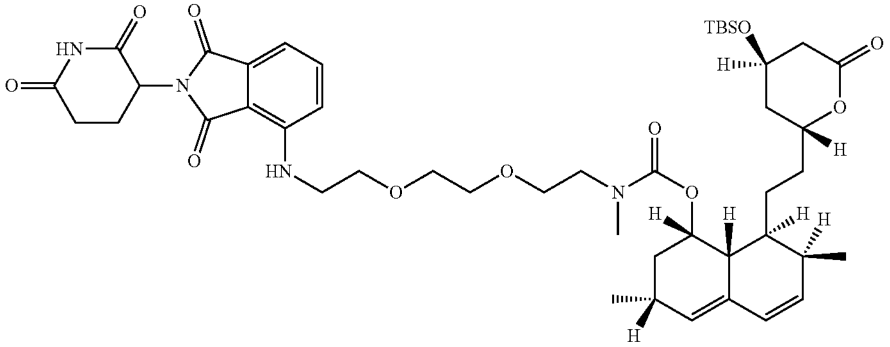 [SMILES: C[C@H]1C=C2C=C[C@H](C)[C@H](CC[C@@H]3C[C@@H](O[Si](C)(C)C(C)(C)C)CC(=O)O3)[C@H]2[C@@H](OC(=O)N(C)CCOCCOCCNc2cccc3c2C(=O)N(C2CCC(=O)NC2=O)C3=O)C1] |
| 83 | 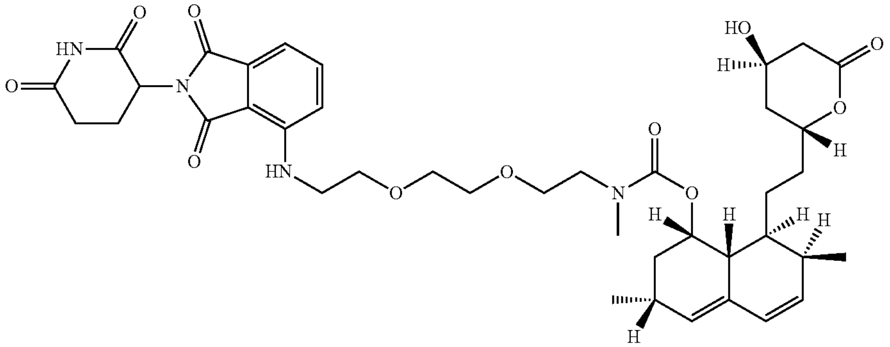 [SMILES: C[C@H]1C=C2C=C[C@H](C)[C@H](CC[C@@H]3C[C@@H](O)CC(=O)O3)[C@H]2[C@@H](OC(=O)N(C)CCOCCOCCNc2cccc3c2C(=O)N(C2CCC(=O)NC2=O)C3=O)C1] |
| 84 | 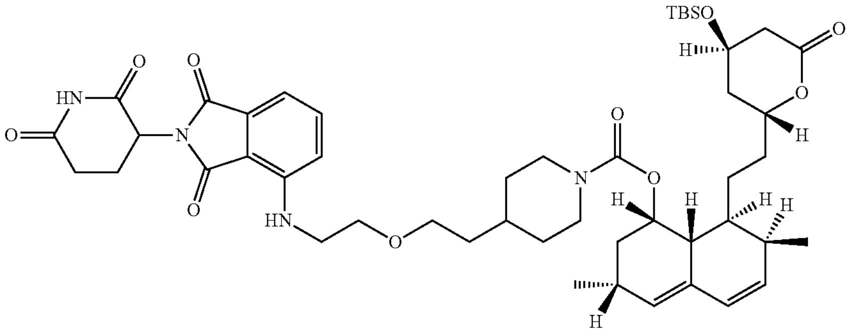 [SMILES: C[C@H]1C=C2C=C[C@H](C)[C@H](CC[C@@H]3C[C@@H](O[Si](C)(C)C(C)(C)C)CC(=O)O3)[C@H]2[C@@H](OC(=O)N2CCC(CCOCCNc3cccc4c3C(=O)N(C3CCC(=O)NC3=O)C4=O)CC2)C1] |
| 85 | 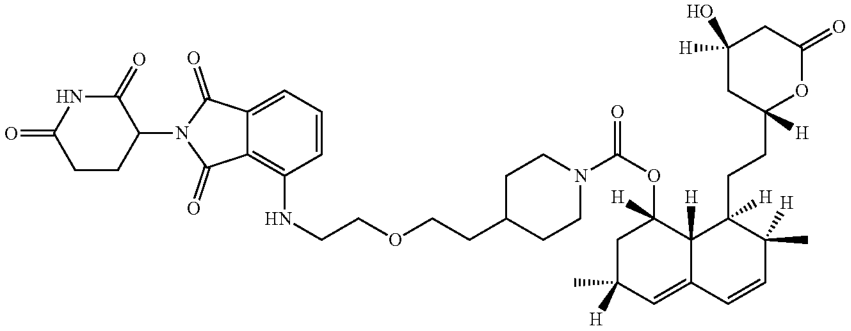 [SMILES: C[C@H]1C=C2C=C[C@H](C)[C@H](CC[C@@H]3C[C@@H](O)CC(=O)O3)[C@H]2[C@@H](OC(=O)N2CCC(CCOCCNc3cccc4c3C(=O)N(C3CCC(=O)NC3=O)C4=O)CC2)C1] |

TABLE 1-continued
| Compound | Structure |
|---|---|
| 86 | 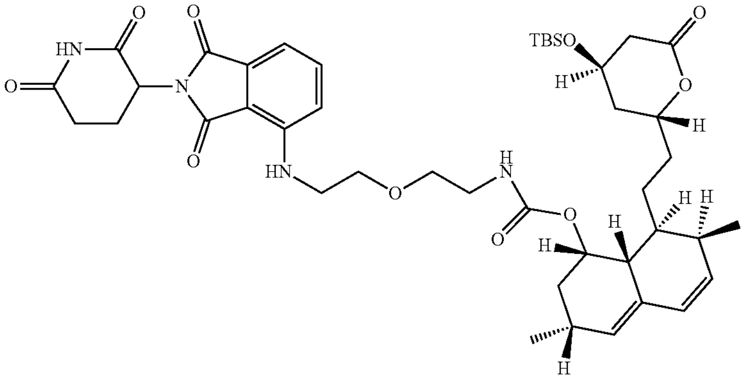 [SMILES: C[C@H]1C=C2C=C[C@H](C)[C@H](CC[C@@H]3C[C@@H](O[Si](C)(C)C(C)(C)C)CC(=O)O3)[C@H]2[C@@H](OC(=O)NCCOCCNc2cccc3c2C(=O)N(C2CCC(=O)NC2=O)C3=O)C1] |
| 87 | 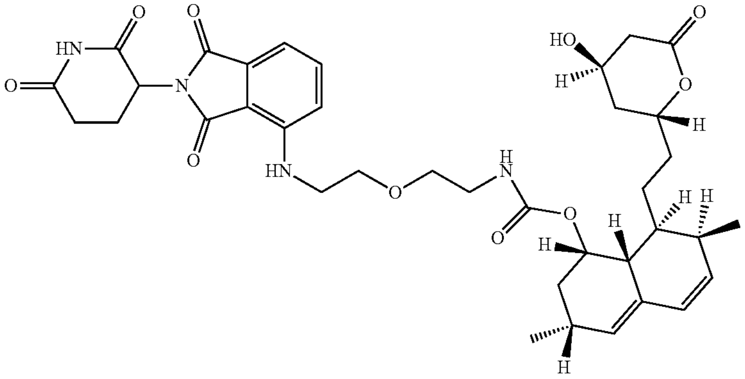 [SMILES: C[C@H]1C=C2C=C[C@H](C)[C@H](CC[C@@H]3C[C@@H](O)CC(=O)O3)[C@H]2[C@@H](OC(=O)NCCOCCNc2cccc3c2C(=O)N(C2CCC(=O)NC2=O)C3=O)C1] |
| 88 | 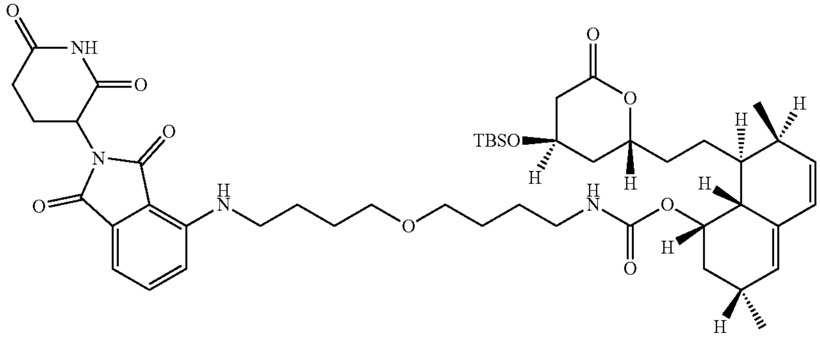 [SMILES: C[C@H]1C=C2C=C[C@H](C)[C@H](CC[C@@H]3C[C@@H](O[Si](C)(C)C(C)(C)C)CC(=O)O3)[C@H]2[C@@H](OC(=O)NCCCCOCCCCNc2cccc3c2C(=O)N(C2CCC(=O)NC2=O)C3=O)C1] |
| 89 | 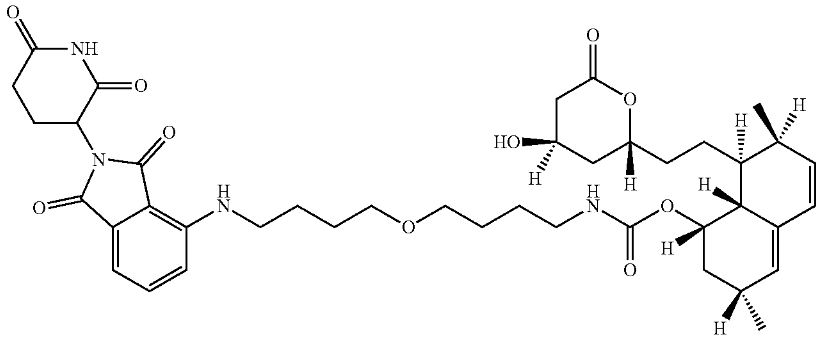 [SMILES: C[C@H]1C=C2C=C[C@H](C)[C@H](CC[C@@H]3C[C@@H](O)CC(=O)O3)[C@H]2[C@@H](OC(=O)NCCCCOCCCCNc2cccc3c2C(=O)N(C2CCC(=O)NC2=O)C3=O)C1] |

TABLE 1-continued
| Compound | Structure |
|---|---|
| 90 | 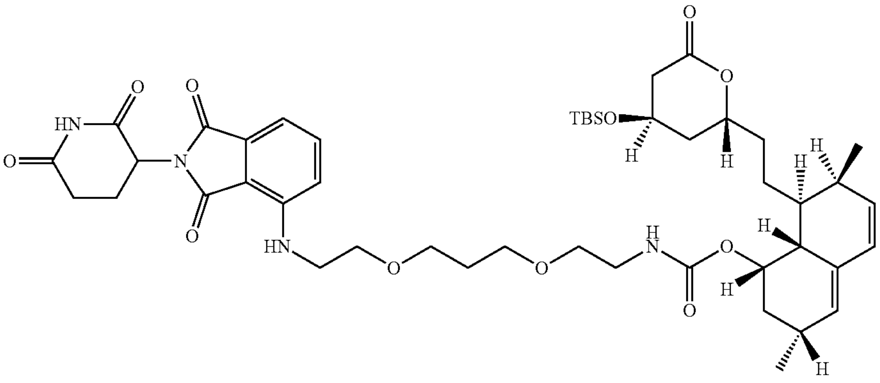 [SMILES: C[C@H]1C=C2C=C[C@H](C)[C@H](CC[C@@H]3C[C@@H](O[Si](C)(C)C(C)(C)C)CC(=O)O3)[C@H]2[C@@H](OC(=O)NCCOCCCOCCNc2cccc3c2C(=O)N(C2CCC(=O)NC2=O)C3=O)C1] |
| 91 | 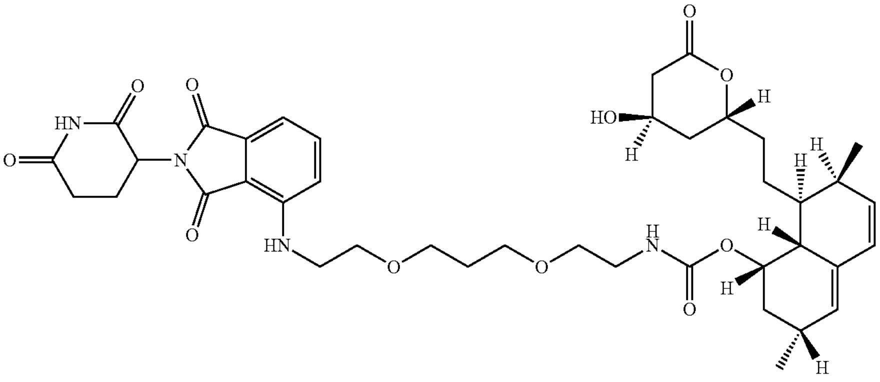 |
| 92 | 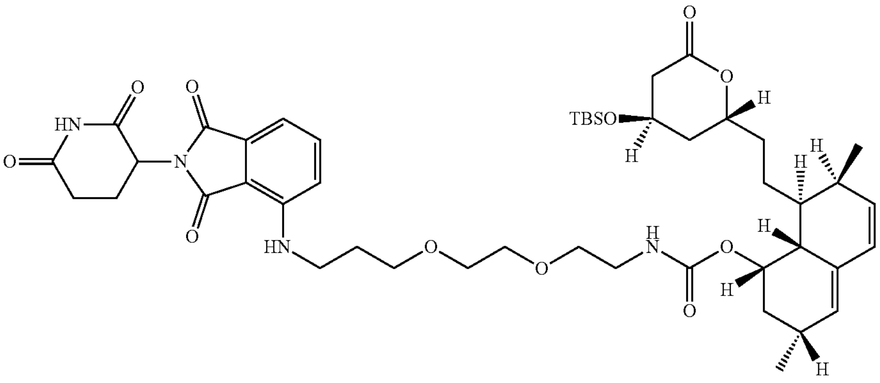 [SMILES: C[C@H]1C=C2C=C[C@H](C)[C@H](CC[C@@H]3C[C@@H](O[Si](C)(C)C(C)(C)C)CC(=O)O3)[C@H]2[C@@H](OC(=O)NCCOCCOCCCNc2cccc3c2C(=O)N(C2CCC(=O)NC2=O)C3=O)C1] |
| 93 | 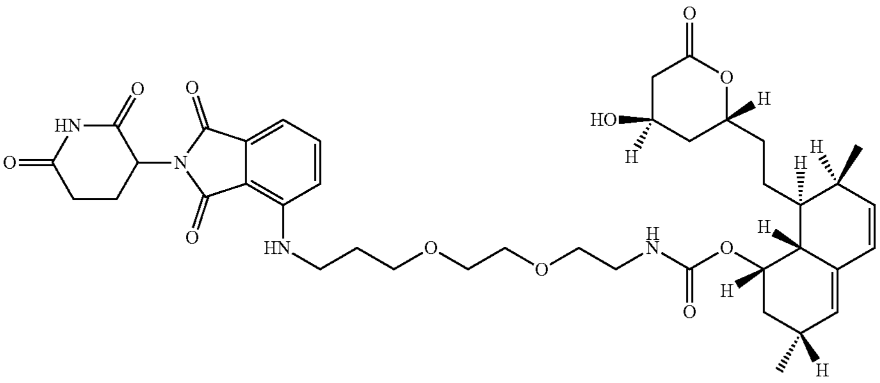 [SMILES: C[C@H]1C=C2C=C[C@H](C)[C@H](CC[C@@H]3C[C@@H](O)CC(=O)O3)[C@H]2[C@@H](OC(=O)NCCOCCOCCCNc2cccc3c2C(=O)N(C2CCC(=O)NC2=O)C3=O)C1] |

TABLE 1-continued
| Compound | Structure |
|---|---|
| 94 | 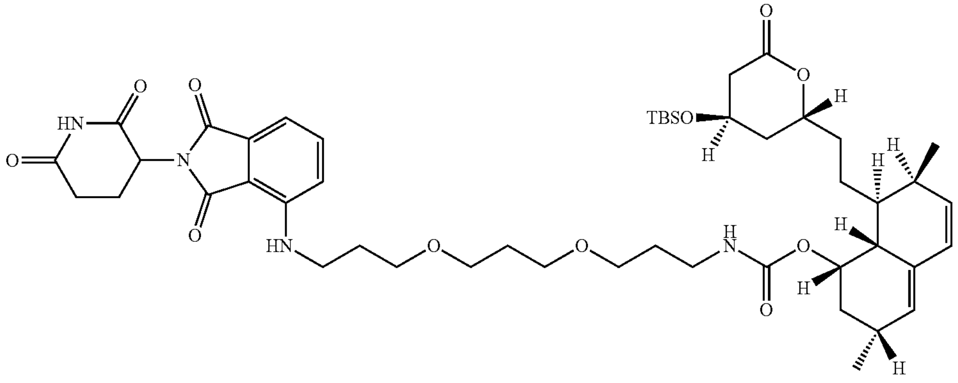 [SMILES: C[C@H]1C=C2C=C[C@H](C)[C@H](CC[C@@H]3C[C@@H](O[Si](C)(C)C(C)(C)C)CC(=O)O3)[C@H]2[C@@H](OC(=O)NCCCOCCCOCCCNc2cccc3c2C(=O)N(C2CCC(=O)NC2=O)C3=O)C1] |
| 95 | 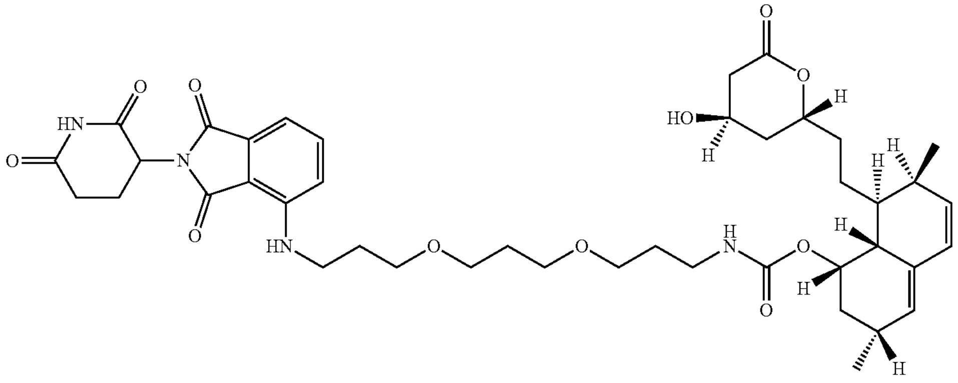 [SMILES: C[C@H]1C=C2C=C[C@H](C)[C@H](CC[C@@H]3C[C@@H](O)CC(=O)O3)[C@H]2[C@@H](OC(=O)NCCCOCCCOCCCNc2cccc3c2C(=O)N(C2CCC(=O)NC2=O)C3=O)C1] |
| 96 | 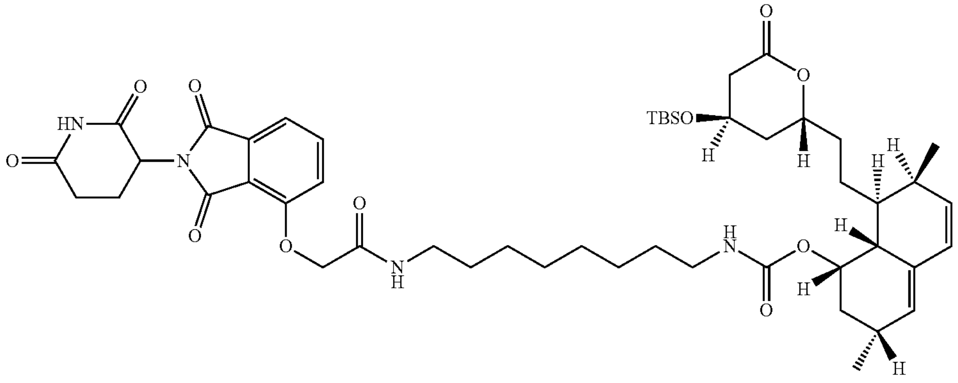 [SMILES: C[C@H]1C=C2C=C[C@H](C)[C@H](CC[C@@H]3C[C@@H](O[Si](C)(C)C(C)(C)C)CC(=O)O3)[C@H]2[C@@H](OC(=O)NCCCCCCCCNC(=O)COc2cccc3c2C(=O)N(C2CCC(=O)NC2=O)C3=O)C1] |
| 97 | 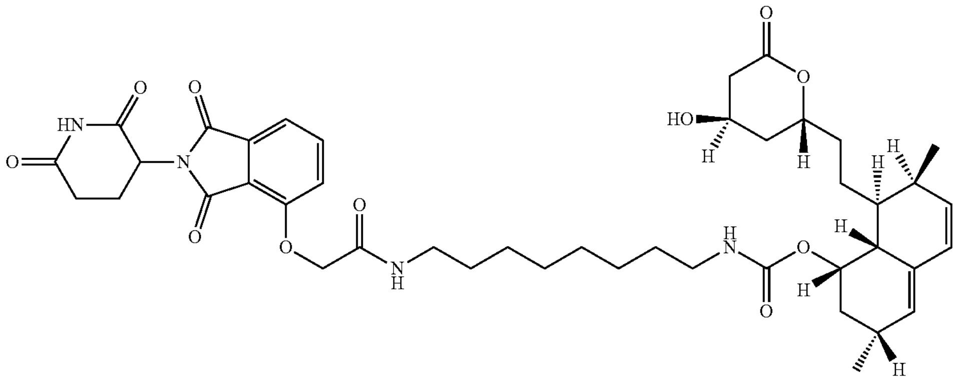 [SMILES: C[C@H]1C=C2C=C[C@H](C)[C@H](CC[C@@H]3C[C@@H](O)CC(=O)O3)[C@H]2[C@@H](OC(=O)NCCCCCCCCNC(=O)COc2cccc3c2C(=O)N(C2CCC(=O)NC2=O)C3=O)C1] |

TABLE 1-continued
| Compound | Structure |
|---|---|
| 98 | 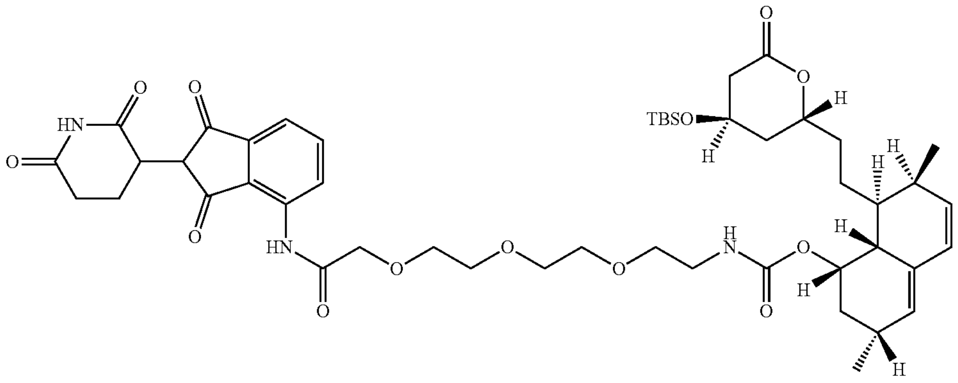 [SMILES: C[C@H]1C=C2C=C[C@H](C)[C@H](CC[C@@H]3C[C@@H](O[Si](C)(C)C(C)(C)C)CC(=O)O3)[C@H]2[C@@H](OC(=O)NCCOCCOCCOCC(=O)Nc2cccc3c2C(=O)C(C2CCC(=O)NC2=O)C3=O)C1] |
| 99 | 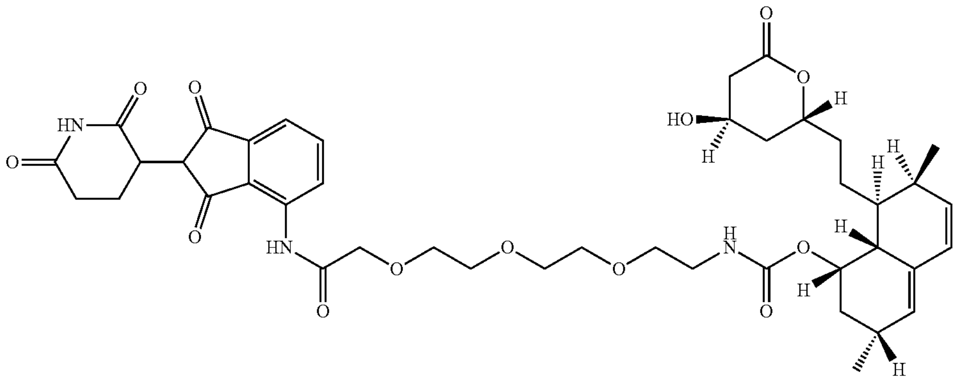 |
| 100 | 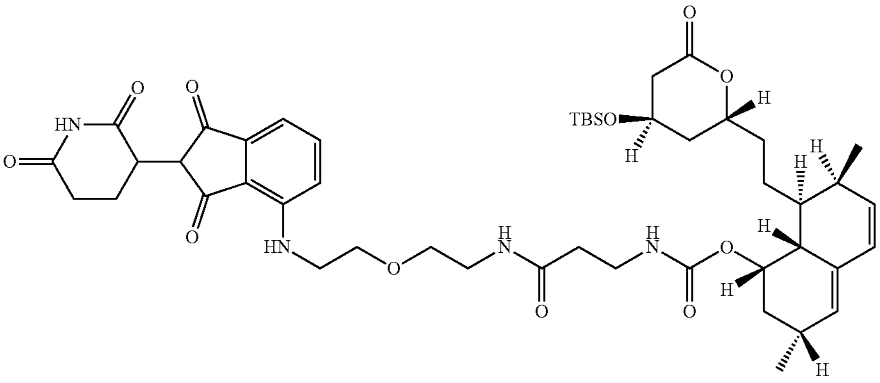 [SMILES: C[C@H]1C=C2C=C[C@H](C)[C@H](CC[C@@H]3C[C@@H](O[Si](C)(C)C(C)(C)C)CC(=O)O3)[C@H]2[C@@H](OC(=O)NCCC(=O)NCCOCCNc2cccc3c2C(=O)C(C2CCC(=O)NC2=O)C3=O)C1] |
| 101 | 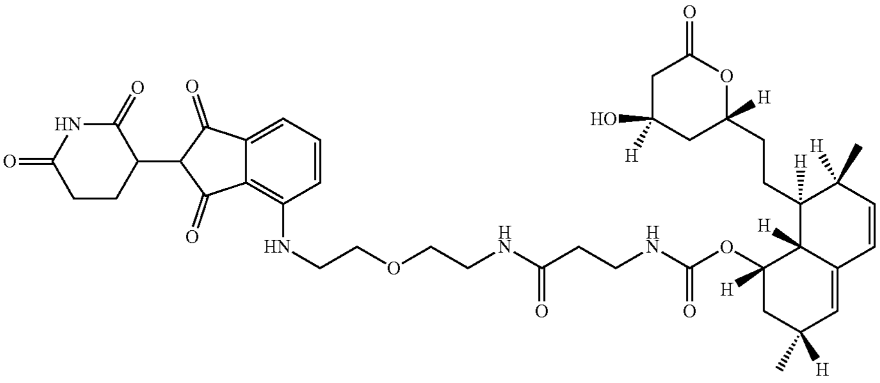 [SMILES: C[C@H]1C=C2C=C[C@H](C)[C@H](CC[C@@H]3C[C@@H](O)CC(=O)O3)[C@H]2[C@@H](OC(=O)NCCC(=O)NCCOCCNc2cccc3c2C(=O)C(C2CCC(=O)NC2=O)C3=O)C1] |

TABLE 1-continued
| Compound | Structure |
| --- | --- |
| 102 | 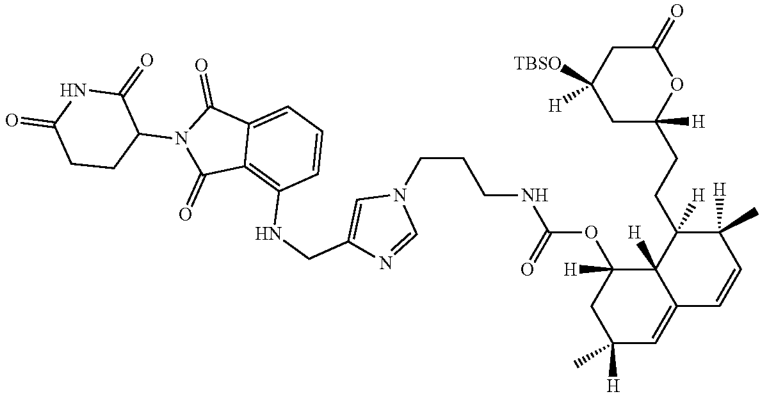 [SMILES: C[C@H]1C=C2C=C[C@H](C)[C@H](CC[C@@H]3C[C@@H](O[Si](C)(C)C(C)(C)C)CC(=O)O3)[C@H]2[C@@H](OC(=O)NCCCn2cnc(CNc3cccc4c3C(=O)N(C3CCC(=O)NC3=O)C4=O)c2)C1] |
| 103 | 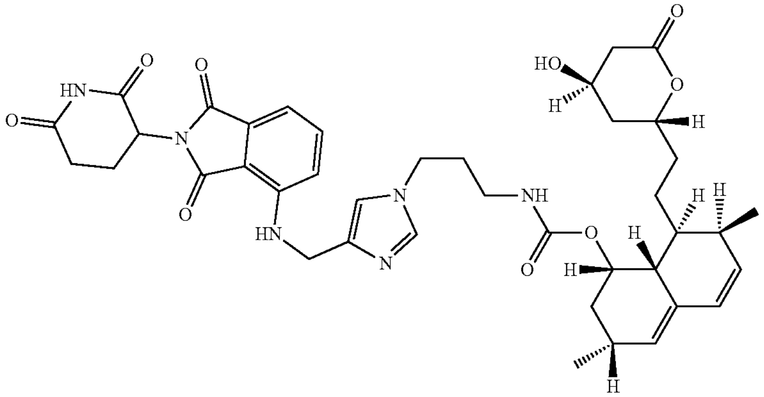 [SMILES: C[C@H]1C=C2C=C[C@H](C)[C@H](CC[C@@H]3C[C@@H](O)CC(=O)O3)[C@H]2[C@@H](OC(=O)NCCCn2cnc(CNc3cccc4c3C(=O)N(C3CCC(=O)NC3=O)C4=O)c2)C1] |
| 104 | 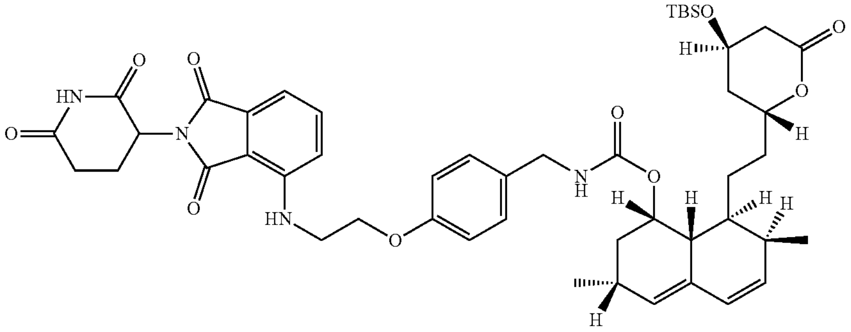 [SMILES: C[C@H]1C=C2C=C[C@H](C)[C@H](CC[C@@H]3C[C@@H](O[Si](C)(C)C(C)(C)C)CC(=O)O3)[C@H]2[C@@H](OC(=O)NCc2ccc(OCCNc3cccc4c3C(=O)N(C3CCC(=O)NC3=O)C4=O)cc2)C1] |
| 105 | 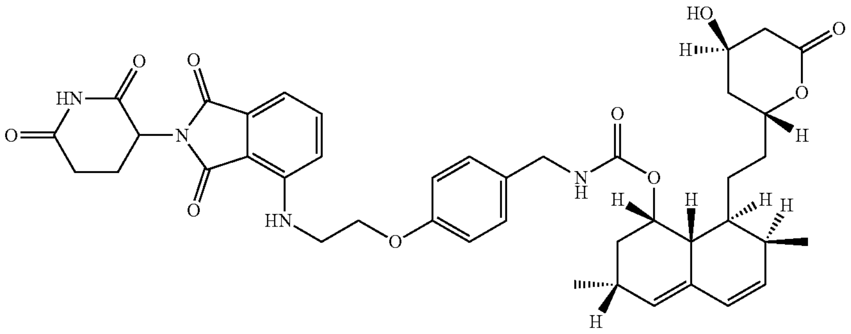 [SMILES: C[C@H]1C=C2C=C[C@H](C)[C@H](CC[C@@H]3C[C@@H](O)CC(=O)O3)[C@H]2[C@@H](OC(=O)NCc2ccc(OCCNc3cccc4c3C(=O)N(C3CCC(=O)NC3=O)C4=O)cc2)C1] |

TABLE 1-continued
| Compound | Structure |
|---|---|
| 106 | 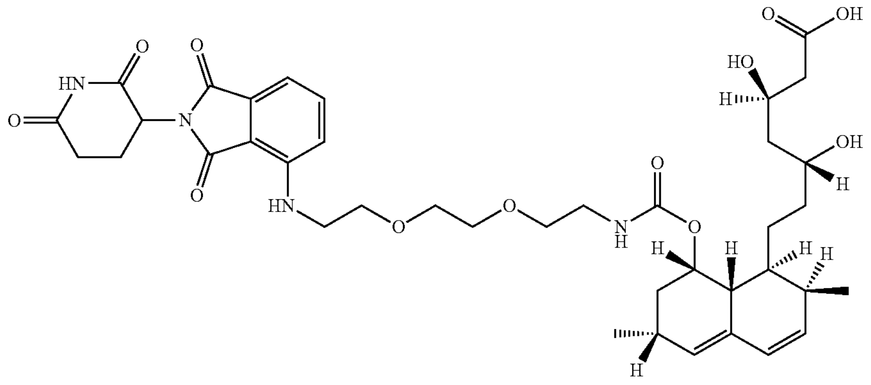 |
| 107 | 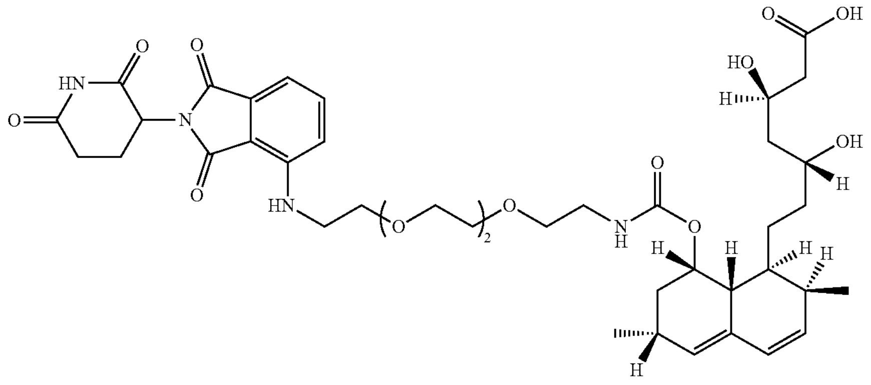 |
| 108 | 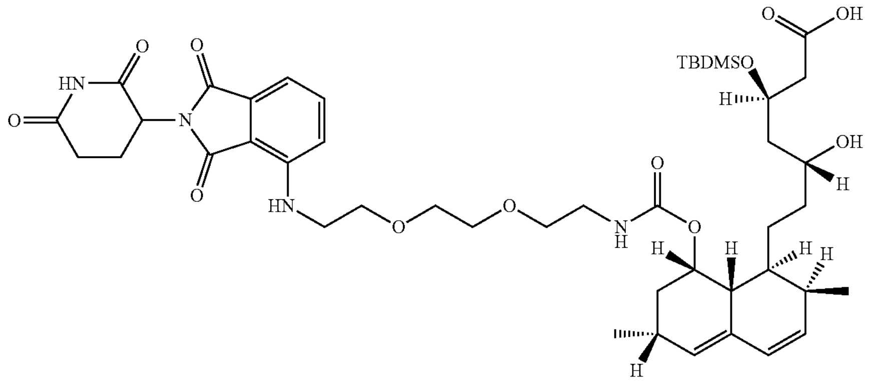 [SMILES: C[C@H]1C=C2C=C[C@H](C)[C@H](CC[C@@H](O)C[C@H](CC(=O)O)O[Si](C)(C)C(C)(C)C)[C@H]2[C@@H](OC(=O)NCCOCCOCCNc2cccc3c2C(=O)N(C2CCC(=O)NC2=O)C3=O)C1] |
| 109 | 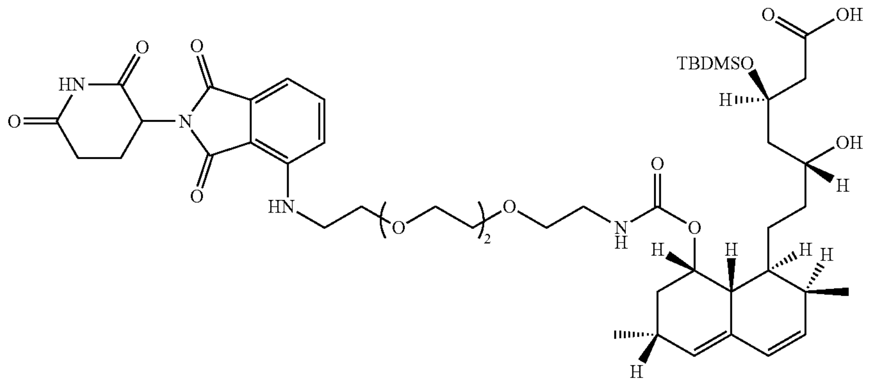 |

TABLE 1-continued
| Compound | Structure |
|---|---|
| 110 | 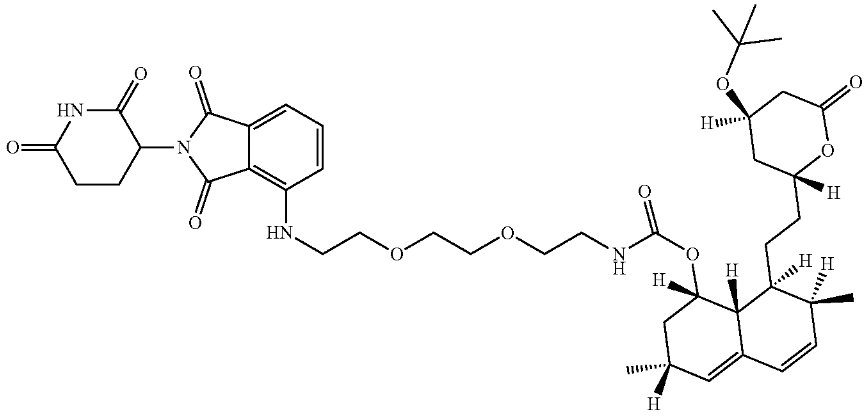 [SMILES: C[C@H]1C=C2C=C[C@H](C)[C@H](CC[C@@H]3C[C@@H](OC(C)(C)C)CC(=O)O3)[C@H]2[C@@H](OC(=O)NCCOCCOCCNc2cccc3c2C(=O)N(C2CCC(=O)NC2=O)C3=O)C1] |
| 111 | 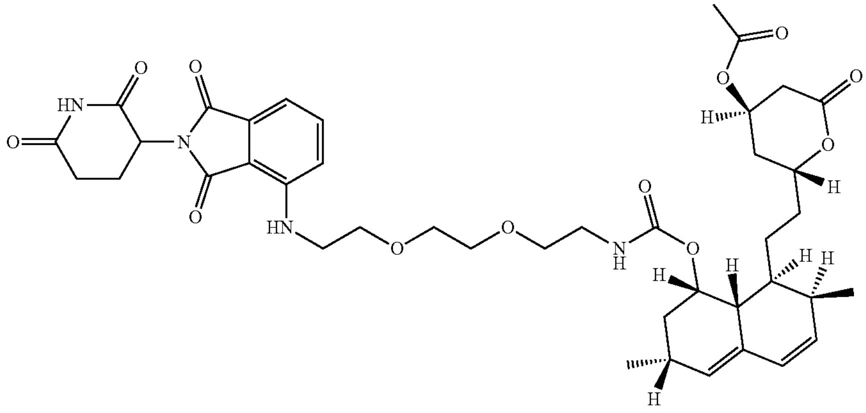 [SMILES: CC(=O)O[C@H]1CC(=O)O[C@H](CC[C@@H]2[C@@H]3C(=C[C@H](C)C[C@@H]3OC(=O)NCCOCCOCCNc3cccc4c3C(=O)N(C3CCC(=O)NC3=O)C4=O)C=C[C@@H]2C)C1] |
| 112 | 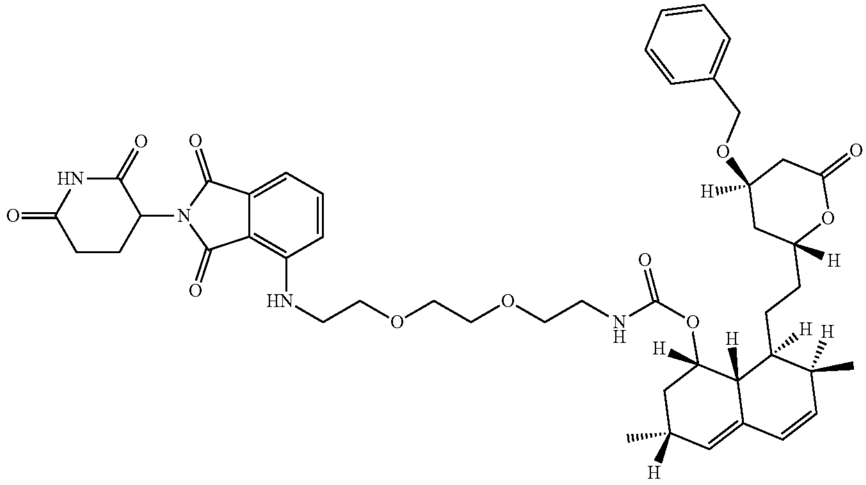 [SMILES: C[C@H]1C=C2C=C[C@H](C)[C@H](CC[C@@H]3C[C@@H](OCc4ccccc4)CC(=O)O3)[C@H]2[C@@H](OC(=O)NCCOCCOCCNc2cccc3c2C(=O)N(C2CCC(=O)NC2=O)C3=O)C1] |

TABLE 1-continued
| Compound | Structure |
| --- | --- |
| 113 | 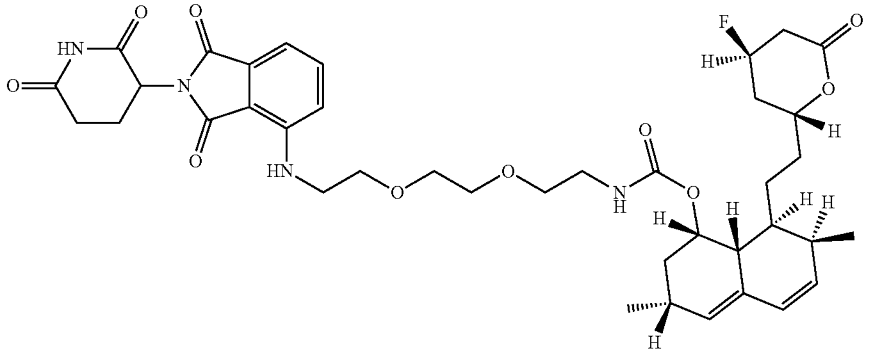 [SMILES: C[C@H]1C=C2C=C[C@H](C)[C@H](CC[C@@H]3C[C@@H](F)CC(=O)O3)[C@H]2[C@@H](OC(=O)NCCOCCOCCNc2cccc3c2C(=O)N(C2CCC(=O)NC2=O)C3=O)C1] |
| 114 | 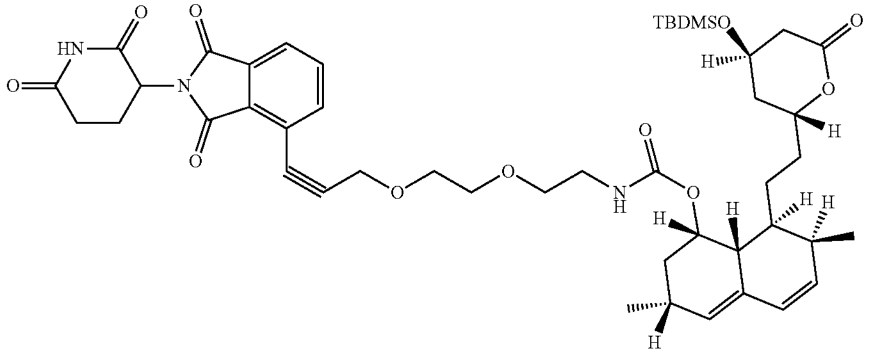 [SMILES: C[C@H]1C=C2C=C[C@H](C)[C@H](CC[C@@H]3C[C@@H](O[Si](C)(C)C(C)(C)C)CC(=O)O3)[C@H]2[C@@H](OC(=O)NCCOCCOCC#Cc2cccc3c2C(=O)N(C2CCC(=O)NC2=O)C3=O)C1] |
| 115 | 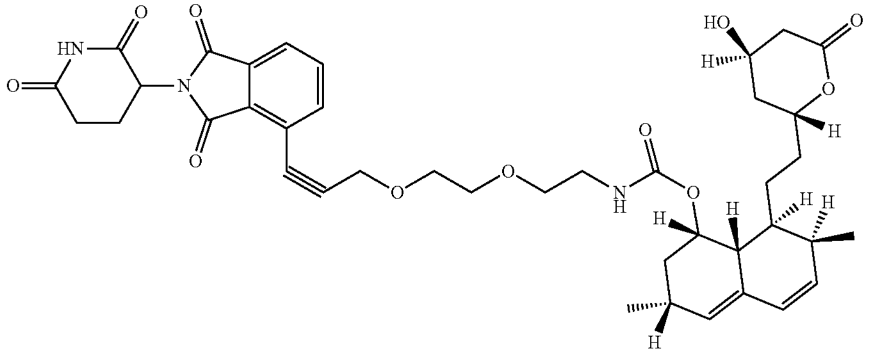 [SMILES: C[C@H]1C=C2C=C[C@H](C)[C@H](CC[C@@H]3C[C@@H](O)CC(=O)O3)[C@H]2[C@@H](OC(=O)NCCOCCOCC#Cc2cccc3c2C(=O)N(C2CCC(=O)NC2=O)C3=O)C1] |
| 116 | 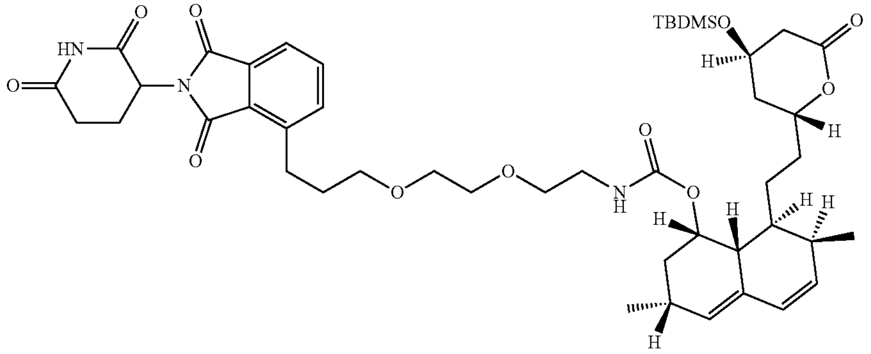 [SMILES: C[C@H]1C=C2C=C[C@H](C)[C@H](CC[C@@H]3C[C@@H](O[Si](C)(C)C(C)(C)C)CC(=O)O3)[C@H]2[C@@H](OC(=O)NCCOCCOCCCc2cccc3c2C(=O)N(C2CCC(=O)NC2=O)C3=O)C1] |

TABLE 1-continued
| Compound | Structure |
| --- | --- |
| 117 | 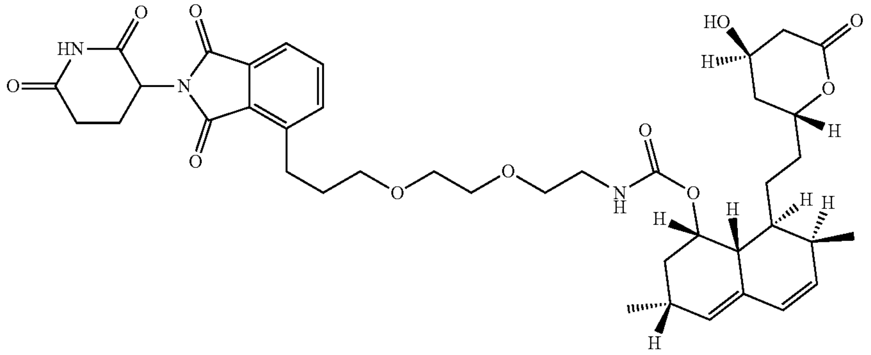 [SMILES: C[C@H]1C=C2C=C[C@H](C)[C@H](CC[C@@H]3C[C@@H](O)CC(=O)O3)[C@H]2[C@@H](OC(=O)NCCOCCOCCCc2cccc3c2C(=O)N(C2CCC(=O)NC2=O)C3=O)C1] |
| 118 | 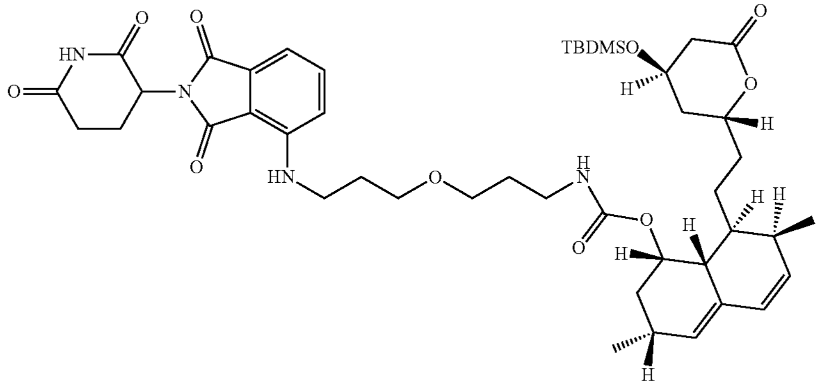 [SMILES: C[C@H]1C=C2C=C[C@H](C)[C@H](CC[C@@H]3C[C@@H](O[Si](C)(C)C(C)(C)C)CC(=O)O3)[C@H]2[C@@H](OC(=O)NCCCOCCCNc2cccc3c2C(=O)N(C2CCC(=O)NC2=O)C3=O)C1] |
| 119 | 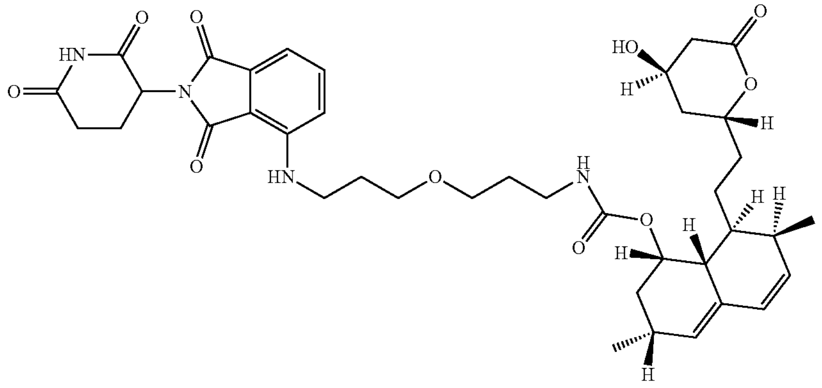 [SMILES: C[C@H]1C=C2C=C[C@H](C)[C@H](CC[C@@H]3C[C@@H](O)CC(=O)O3)[C@H]2[C@@H](OC(=O)NCCCOCCCNc2cccc3c2C(=O)N(C2CCC(=O)NC2=O)C3=O)C1] |
| 120 | 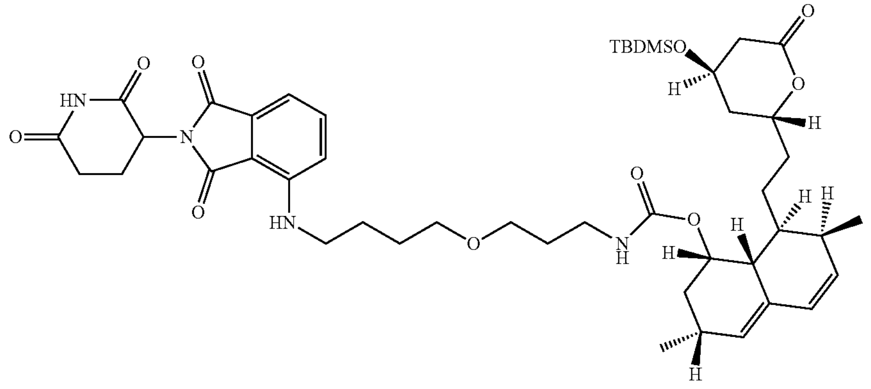 [SMILES: C[C@H]1C=C2C=C[C@H](C)[C@H](CC[C@@H]3C[C@@H](O[Si](C)(C)C(C)(C)C)CC(=O)O3)[C@H]2[C@@H](OC(=O)NCCCOCCCCNc2cccc3c2C(=O)N(C2CCC(=O)NC2=O)C3=O)C1] |

TABLE 1-continued
| Compound | Structure |
|---|---|
| 121 | 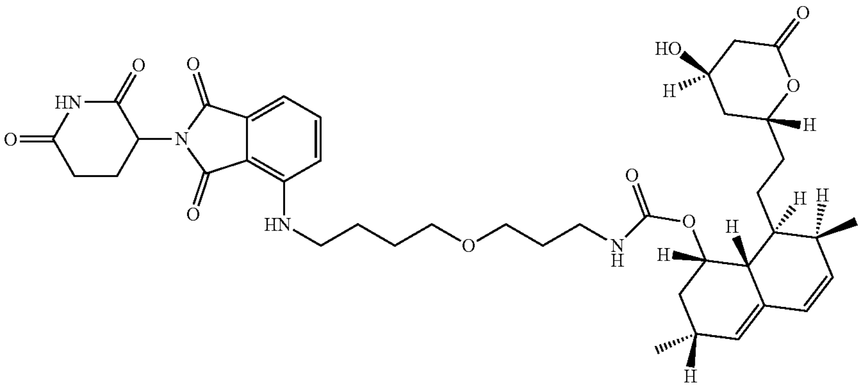 [SMILES: C[C@H]1C=C2C=C[C@H](C)[C@H](CC[C@@H]3C[C@@H](O)CC(=O)O3)[C@H]2[C@@H](OC(=O)NCCCOCCCCNc2cccc3c2C(=O)N(C2CCC(=O)NC2=O)C3=O)C1] |
| 122 | 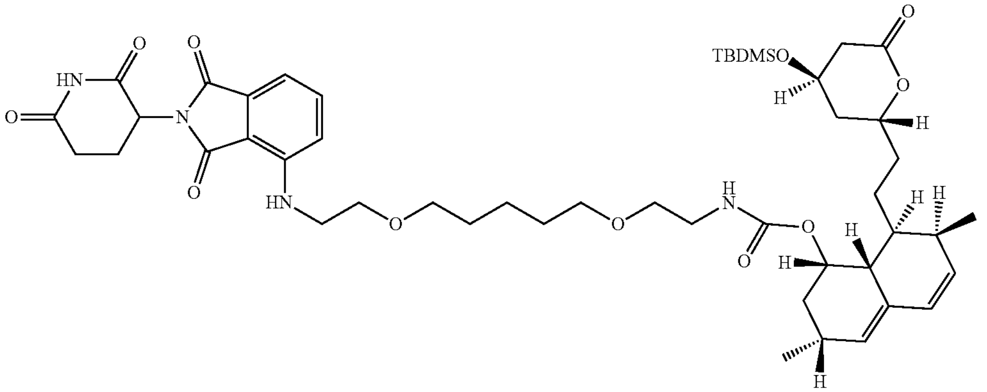 [SMILES: C[C@H]1C=C2C=C[C@H](C)[C@H](CC[C@@H]3C[C@@H](O[Si](C)(C)C(C)(C)C)CC(=O)O3)[C@H]2[C@@H](OC(=O)NCCOCCCCCOCCNc2cccc3c2C(=O)N(C2CCC(=O)NC2=O)C3=O)C1] |
| 123 | 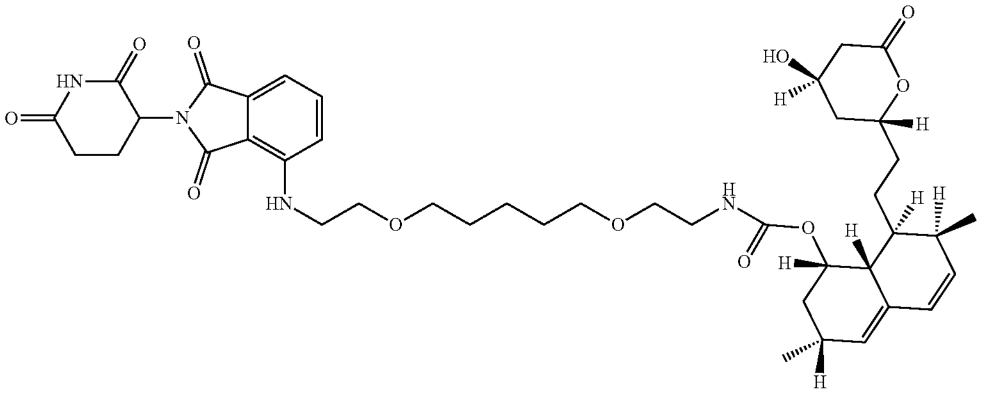 [SMILES: C[C@H]1C=C2C=C[C@H](C)[C@H](CC[C@@H]3C[C@@H](O)CC(=O)O3)[C@H]2[C@@H](OC(=O)NCCOCCCCCOCCNc2cccc3c2C(=O)N(C2CCC(=O)NC2=O)C3=O)C1] |
| 124 | 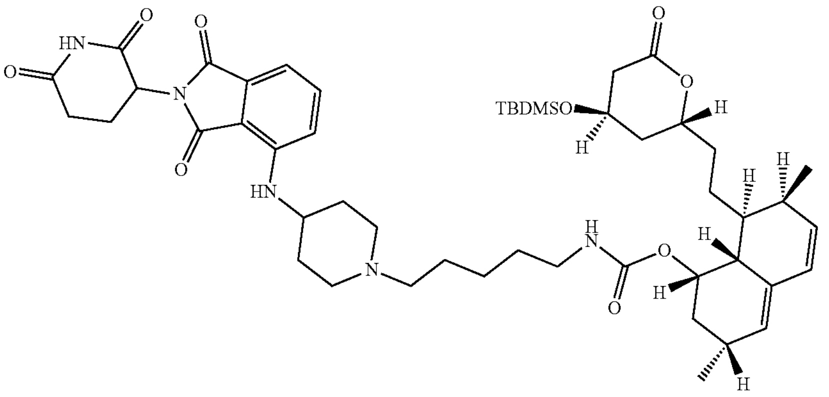 [SMILES: C[C@H]1C=C2C=C[C@H](C)[C@H](CC[C@@H]3C[C@@H](O[Si](C)(C)C(C)(C)C)CC(=O)O3)[C@H]2[C@@H](OC(=O)NCCCCCN2CCC(Nc3cccc4c3C(=O)N(C3CCC(=O)NC3=O)C4=O)CC2)C1] |

TABLE 1-continued
| Compound | Structure |
|---|---|
| 125 | 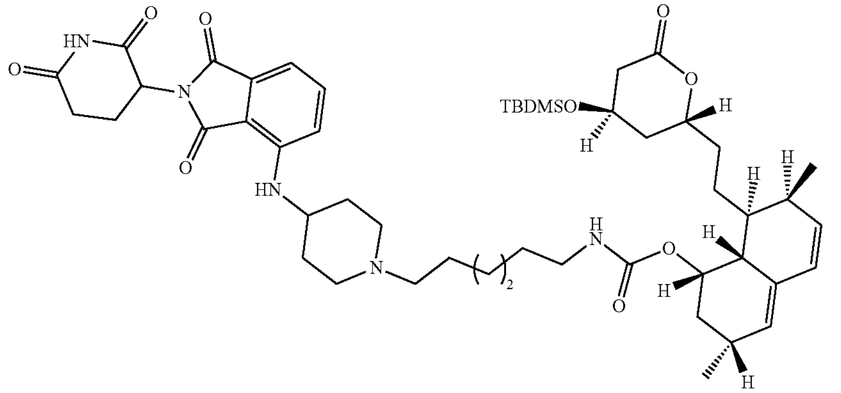 |
| 126 | 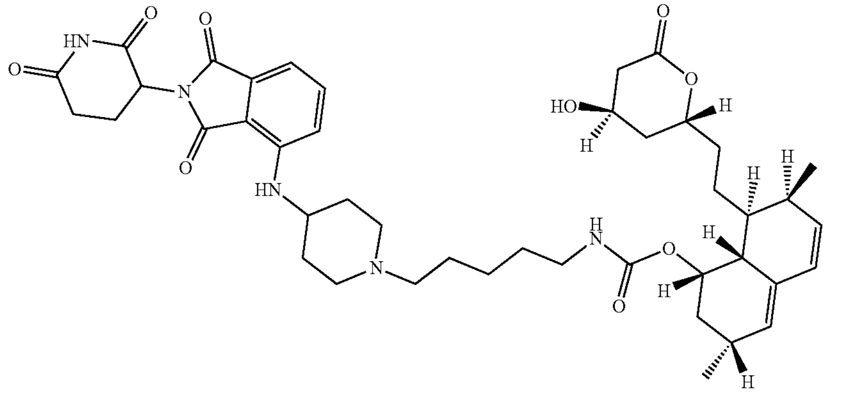 [SMILES: C[C@H]1C=C2C=C[C@H](C)[C@H](CC[C@@H]3C[C@@H](O)CC(=O)O3)[C@H]2[C@@H](OC(=O)NCCCCCN2CCC(Nc3cccc4c3C(=O)N(C3CCC(=O)NC3=O)C4=O)CC2)C1] |
| 127 | 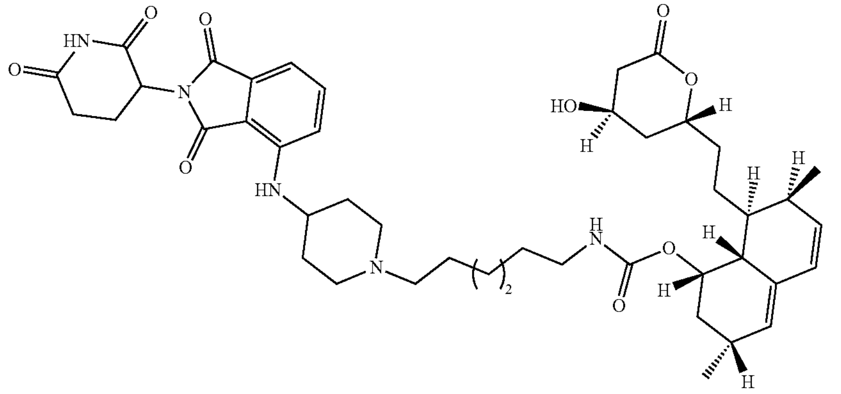 |
| 128 | 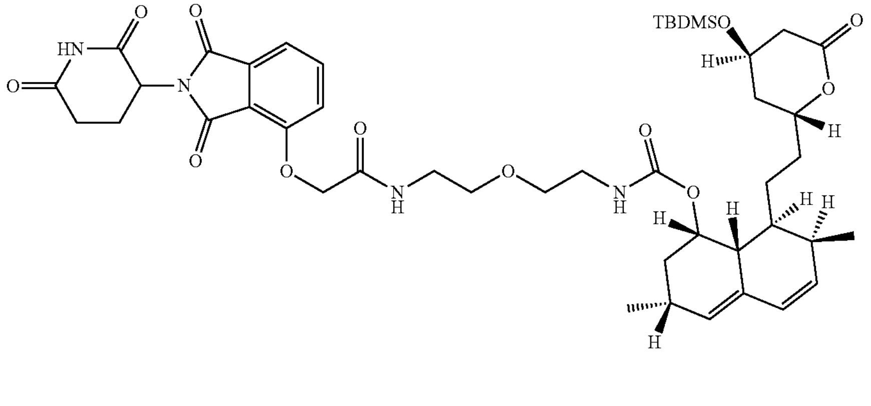 [SMILES: C[C@H]1C=C2C=C[C@H](C)[C@H](CC[C@@H]3C[C@@H](O[Si](C)(C)C(C)(C)C)CC(=O)O3)[C@H]2[C@@H](OC(=O)NCCOCCNC(=O)COc2cccc3c2C(=O)N(C2CCC(=O)NC2=O)C3=O)C1] |

TABLE 1-continued
| Compound | Structure |
|---|---|
| 129 | 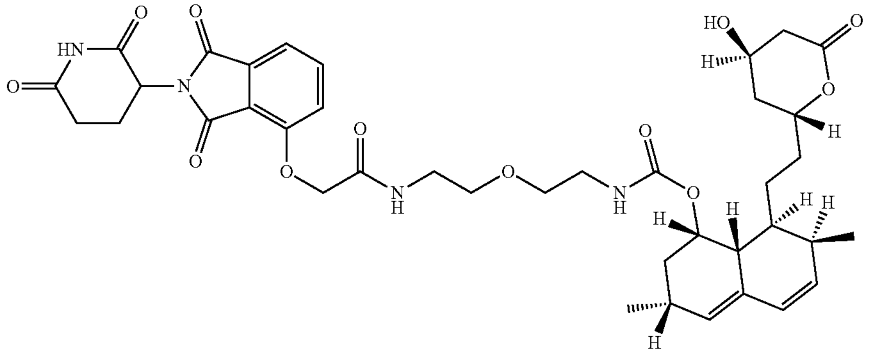 [SMILES: C[C@H]1C=C2C=C[C@H](C)[C@H](CC[C@@H]3C[C@@H](O)CC(=O)O3)[C@H]2[C@@H](OC(=O)NCCOCCNC(=O)COc2cccc3c2C(=O)N(C2CCC(=O)NC2=O)C3=O)C1] |
| 130 | 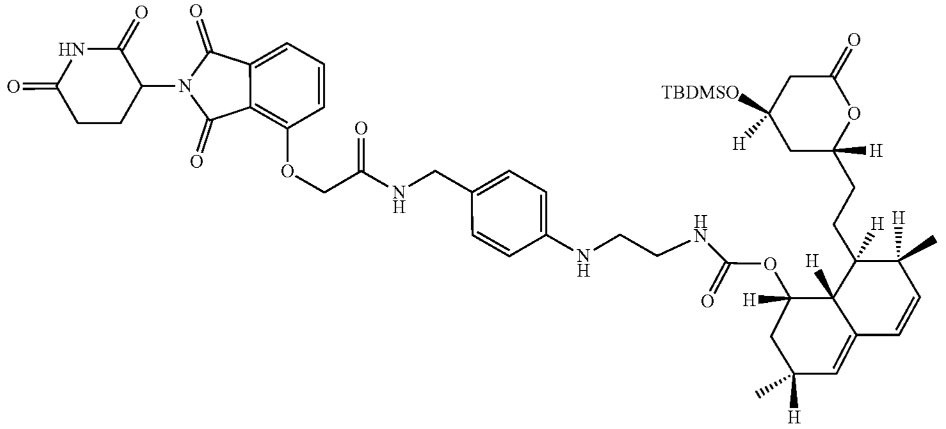 [SMILES: C[C@H]1C=C2C=C[C@H](C)[C@H](CC[C@@H]3C[C@@H](O[Si](C)(C)C(C)(C)C)CC(=O)O3)[C@H]2[C@@H](OC(=O)NCCNc2ccc(CNC(=O)COc3cccc4c3C(=O)N(C3CCC(=O)NC3=O)C4=O)cc2)C1] |
| 131 | 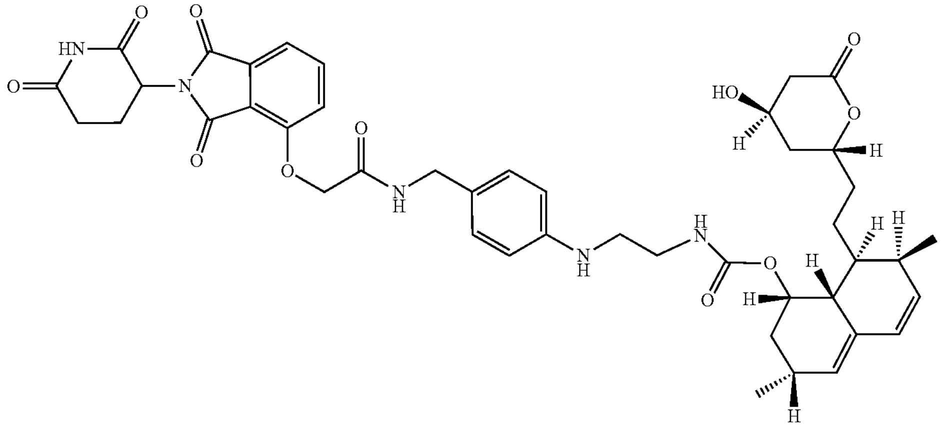 [SMILES: C[C@H]1C=C2C=C[C@H](C)[C@H](CC[C@@H]3C[C@@H](O)CC(=O)O3)[C@H]2[C@@H](OC(=O)NCCNc2ccc(CNC(=O)COc3cccc4c3C(=O)N(C3CCC(=O)NC3=O)C4=O)cc2)C1] |
| 132 | 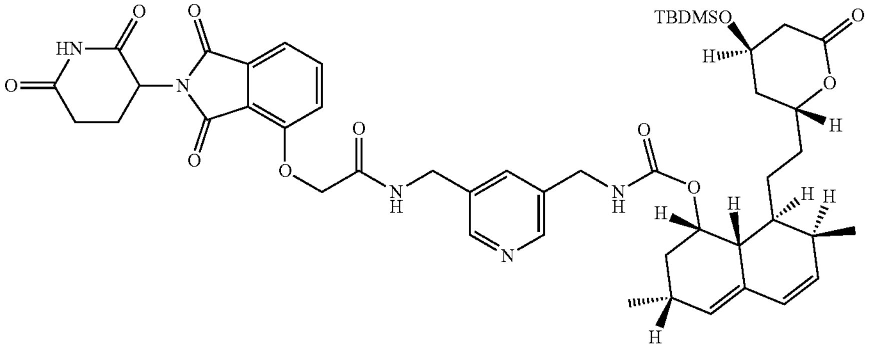 [SMILES: C[C@H]1C=C2C=C[C@H](C)[C@H](CC[C@@H]3C[C@@H](O[Si](C)(C)C(C)(C)C)CC(=O)O3)[C@H]2[C@@H](OC(=O)NCc2cncc(CNC(=O)COc3cccc4c3C(=O)N(C3CCC(=O)NC3=O)C4=O)c2)C1] |

TABLE 1-continued
| Compound | Structure |
|---|---|
| 133 | 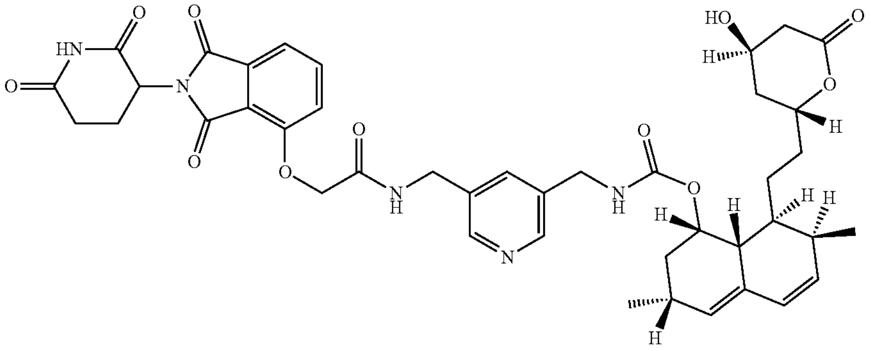 [SMILES: C[C@H]1C=C2C=C[C@H](C)[C@H](CC[C@@H]3C[C@@H](O)CC(=O)O3)[C@H]2[C@@H](OC(=O)NCc2cncc(CNC(=O)COc3cccc4c3C(=O)N(C3CCC(=O)NC3=O)C4=O)c2)C1] |
| 134 | 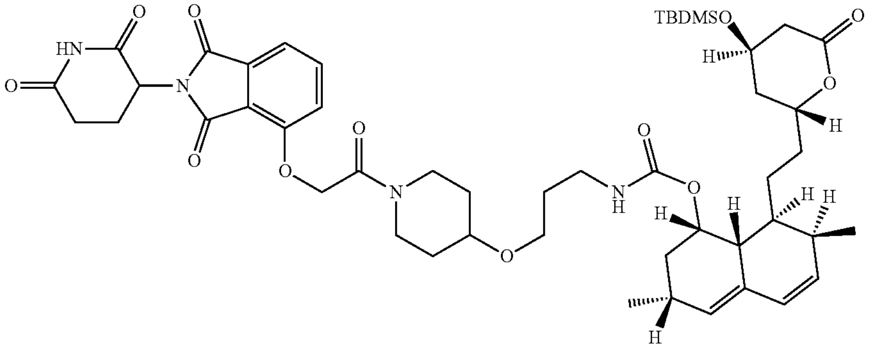 [SMILES: C[C@H]1C=C2C=C[C@H](C)[C@H](CC[C@@H]3C[C@@H](O[Si](C)(C)C(C)(C)C)CC(=O)O3)[C@H]2[C@@H](OC(=O)NCCCOC2CCN(C(=O)COc3cccc4c3C(=O)N(C3CCC(=O)NC3=O)C4=O)CC2)C1] |
| 135 | 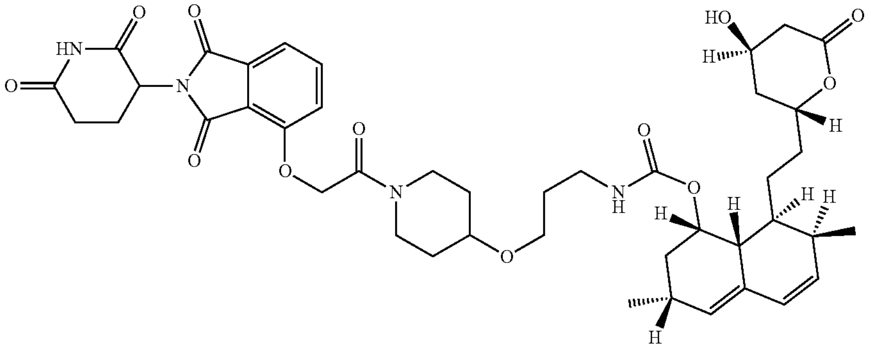 [SMILES: C[C@H]1C=C2C=C[C@H](C)[C@H](CC[C@@H]3C[C@@H](O)CC(=O)O3)[C@H]2[C@@H](OC(=O)NCCCOC2CCN(C(=O)COc3cccc4c3C(=O)N(C3CCC(=O)NC3=O)C4=O)CC2)C1] |
| 136 | 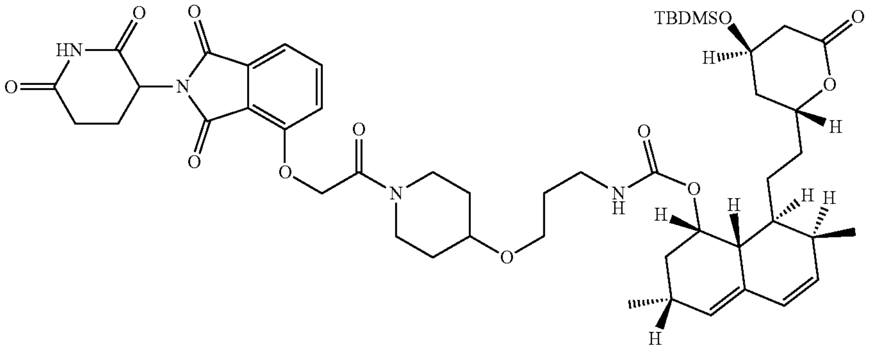 [SMILES: C[C@H]1C=C2C=C[C@H](C)[C@H](CC[C@@H]3C[C@@H](O[Si](C)(C)C(C)(C)C)CC(=O)O3)[C@H]2[C@@H](OC(=O)NCCCOC2CCN(C(=O)COc3cccc4c3C(=O)N(C3CCC(=O)NC3=O)C4=O)CC2)C1] |

TABLE 1-continued
| Compound | Structure |
|---|---|
| 137 | 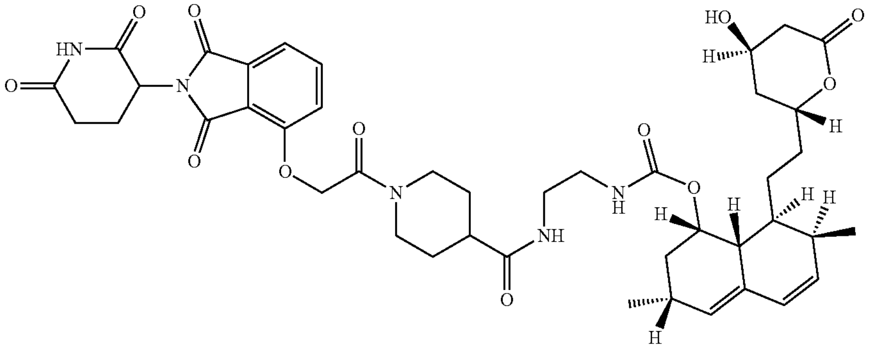 [SMILES: C[C@H]1C=C2C=C[C@H](C)[C@H](CC[C@@H]3C[C@@H](O)CC(=O)O3)[C@H]2[C@@H](OC(=O)NCCNC(=O)C2CCN(C(=O)COc3cccc4c3C(=O)N(C3CCC(=O)NC3=O)C4=O)CC2)C1] |
| 138 | 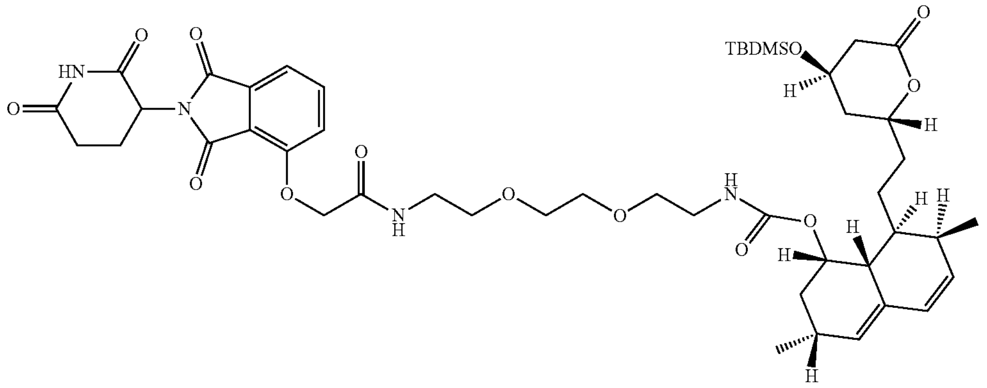 [SMILES: C[C@H]1C=C2C=C[C@H](C)[C@H](CC[C@@H]3C[C@@H](O[Si](C)(C)C(C)(C)C)CC(=O)O3)[C@H]2[C@@H](OC(=O)NCCOCCOCCNC(=O)COc2cccc3c2C(=O)N(C2CCC(=O)NC2=O)C3=O)C1] |
| 139 | 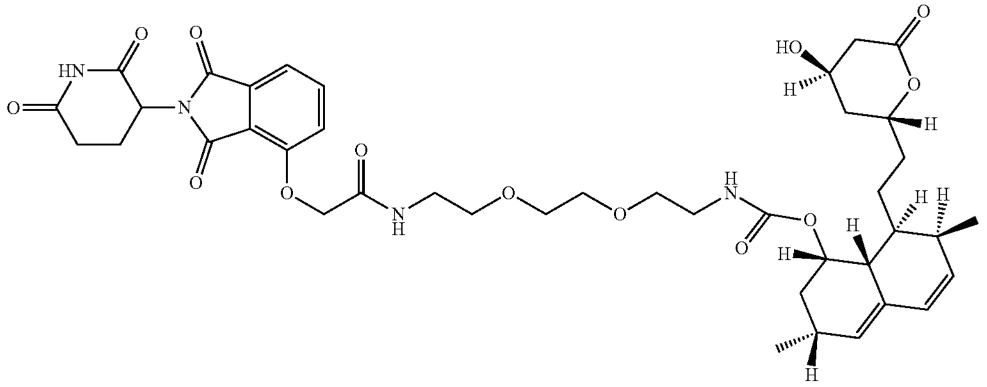 [SMILES: C[C@H]1C=C2C=C[C@H](C)[C@H](CC[C@@H]3C[C@@H](O)CC(=O)O3)[C@H]2[C@@H](OC(=O)NCCOCCOCCNC(=O)COc2cccc3c2C(=O)N(C2CCC(=O)NC2=O)C3=O)C1] |
| 140 | 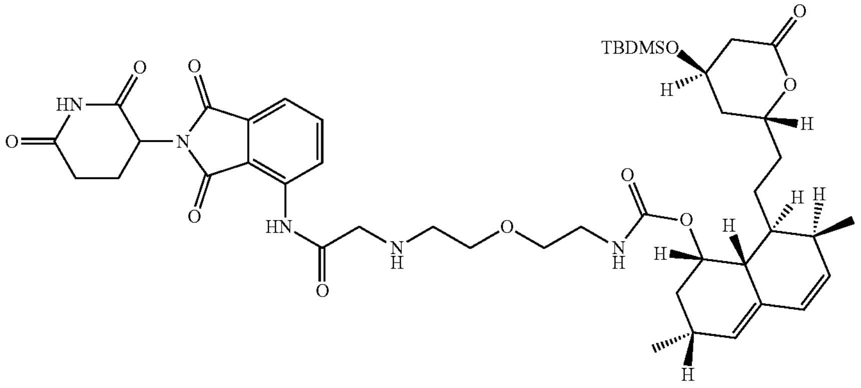 [SMILES: C[C@H]1C=C2C=C[C@H](C)[C@H](CC[C@@H]3C[C@@H](O[Si](C)(C)C(C)(C)C)CC(=O)O3)[C@H]2[C@@H](OC(=O)NCCOCCNCC(=O)Nc2cccc3c2C(=O)N(C2CCC(=O)NC2=O)C3=O)C1] |

TABLE 1-continued
| Compound | Structure |
|---|---|
| 141 | 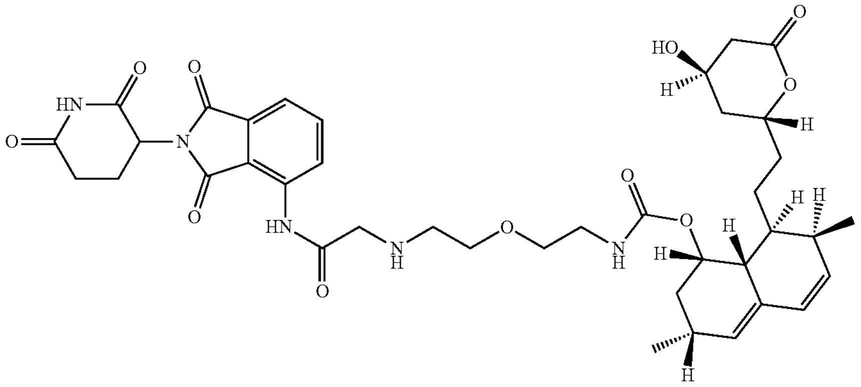 [SMILES: C[C@H]1C=C2C=C[C@H](C)[C@H](CC[C@@H]3C[C@@H](O)CC(=O)O3)[C@H]2[C@@H](OC(=O)NCCOCCNCC(=O)Nc2cccc3c2C(=O)N(C2CCC(=O)NC2=O)C3=O)C1] |
| 142 | 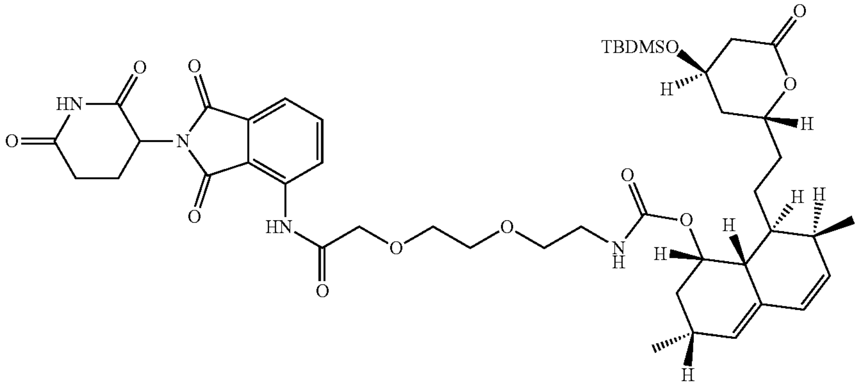 [SMILES: C[C@H]1C=C2C=C[C@H](C)[C@H](CC[C@@H]3C[C@@H](O[Si](C)(C)C(C)(C)C)CC(=O)O3)[C@H]2[C@@H](OC(=O)NCCOCCOCC(=O)Nc2cccc3c2C(=O)N(C2CCC(=O)NC2=O)C3=O)C1] |
| 143 | 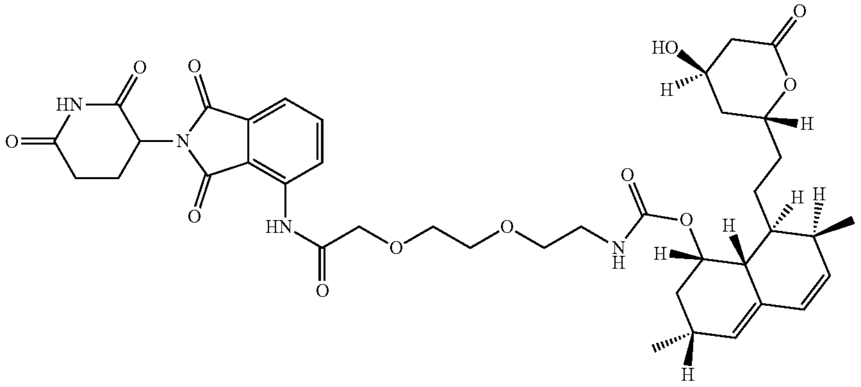 [SMILES: C[C@H]1C=C2C=C[C@H](C)[C@H](CC[C@@H]3C[C@@H](O)CC(=O)O3)[C@H]2[C@@H](OC(=O)NCCOCCOCC(=O)Nc2cccc3c2C(=O)N(C2CCC(=O)NC2=O)C3=O)C1] |
| 144 | 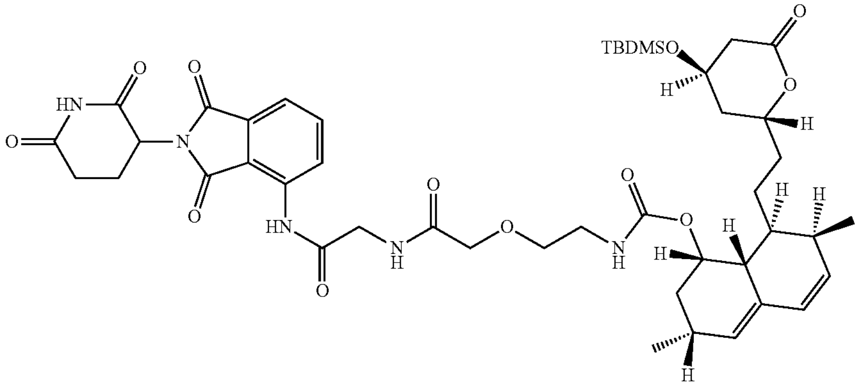 [SMILES: C[C@H]1C=C2C=C[C@H](C)[C@H](CC[C@@H]3C[C@@H](O[Si](C)(C)C(C)(C)C)CC(=O)O3)[C@H]2[C@@H](OC(=O)NCCOCC(=O)NCC(=O)Nc2cccc3c2C(=O)N(C2CCC(=O)NC2=O)C3=O)C1] |

TABLE 1-continued
| Compound | Structure |
|---|---|
| 145 | 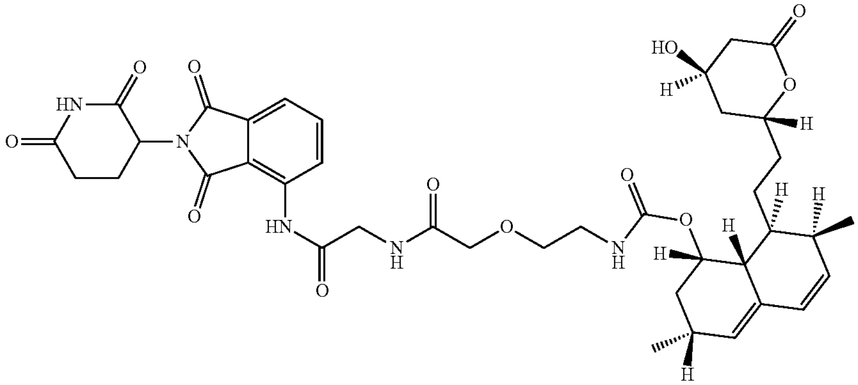 [SMILES: C[C@H]1C=C2C=C[C@H](C)[C@H](CC[C@@H]3C[C@@H](O)CC(=O)O3)[C@H]2[C@@H](OC(=O)NCCOCC(=O)NCC(=O)Nc2cccc3c2C(=O)N(C2CCC(=O)NC2=O)C3=O)C1] |
| 146 | 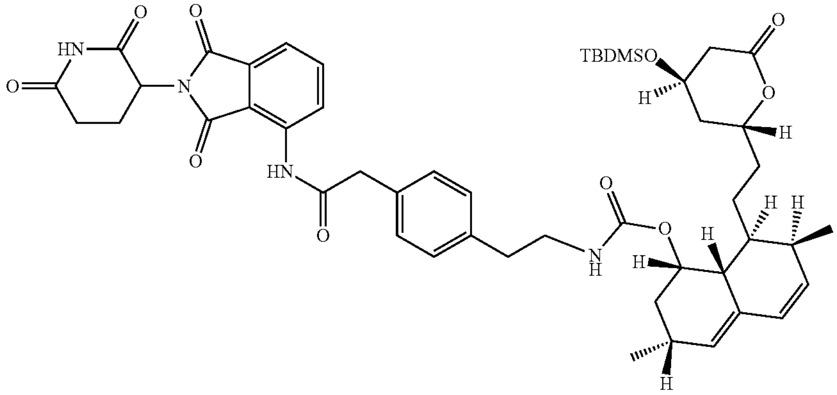 [SMILES: C[C@H]1C=C2C=C[C@H](C)[C@H](CC[C@@H]3C[C@@H](O[Si](C)(C)C(C)(C)C)CC(=O)O3)[C@H]2[C@@H](OC(=O)NCCc2ccc(CC(=O)Nc3cccc4c3C(=O)N(C3CCC(=O)NC3=O)C4=O)cc2)C1] |
| 147 | 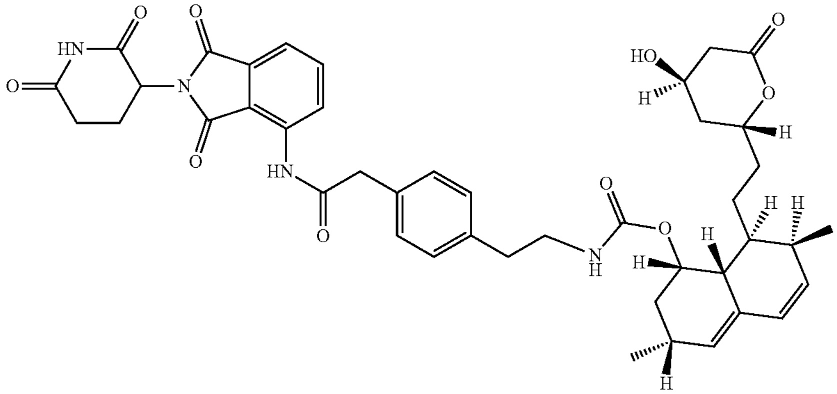 [SMILES: C[C@H]1C=C2C=C[C@H](C)[C@H](CC[C@@H]3C[C@@H](O)CC(=O)O3)[C@H]2[C@@H](OC(=O)NCCc2ccc(CC(=O)Nc3cccc4c3C(=O)N(C3CCC(=O)NC3=O)C4=O)cc2)C1] |
| 148 | 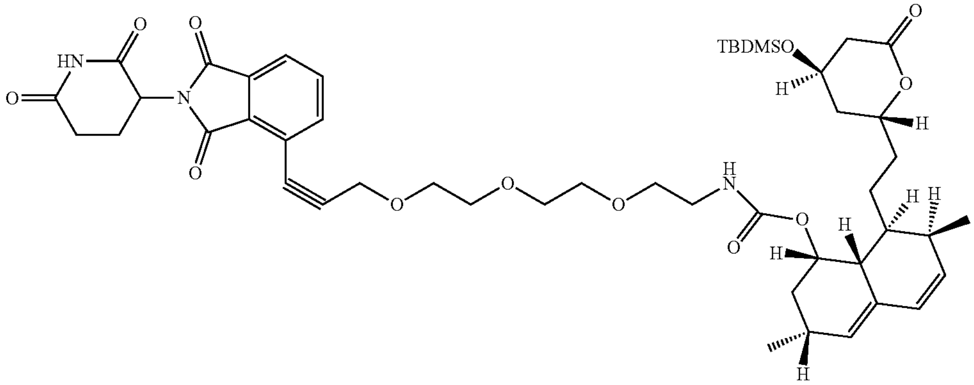 [SMILES: C[C@H]1C=C2C=C[C@H](C)[C@H](CC[C@@H]3C[C@@H](O[Si](C)(C)C(C)(C)C)CC(=O)O3)[C@H]2[C@@H](OC(=O)NCCOCCOCCOCC#Cc2cccc3c2C(=O)N(C2CCC(=O)NC2=O)C3=O)C1] |

TABLE 1-continued
| Compound | Structure |
| --- | --- |
| 149 | 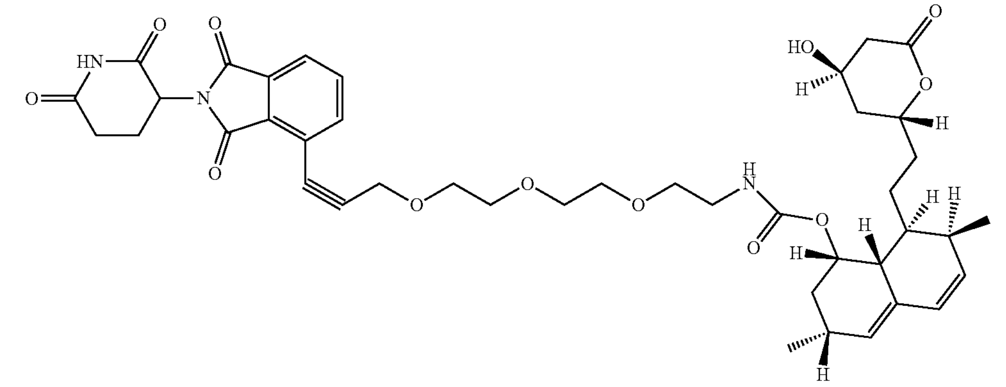 [SMILES: C[C@H]1C=C2C=C[C@H](C)[C@H](CC[C@@H]3C[C@@H](O)CC(=O)O3)[C@H]2[C@@H](OC(=O)NCCOCCOCCOCC#Cc2cccc3c2C(=O)N(C2CCC(=O)NC2=O)C3=O)C1] |
| 150 | 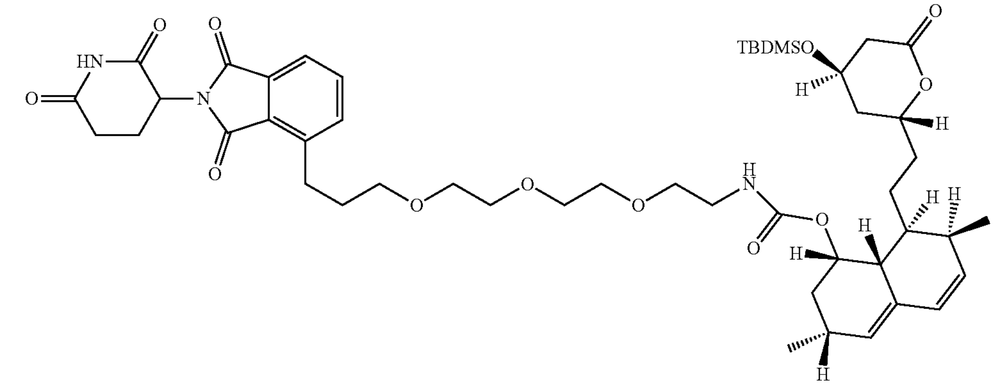 [SMILES: C[C@H]1C=C2C=C[C@H](C)[C@H](CC[C@@H]3C[C@@H](O[Si](C)(C)C(C)(C)C)CC(=O)O3)[C@H]2[C@@H](OC(=O)NCCOCCOCCOCCCc2cccc3c2C(=O)N(C2CCC(=O)NC2=O)C3=O)C1] |
| 151 | 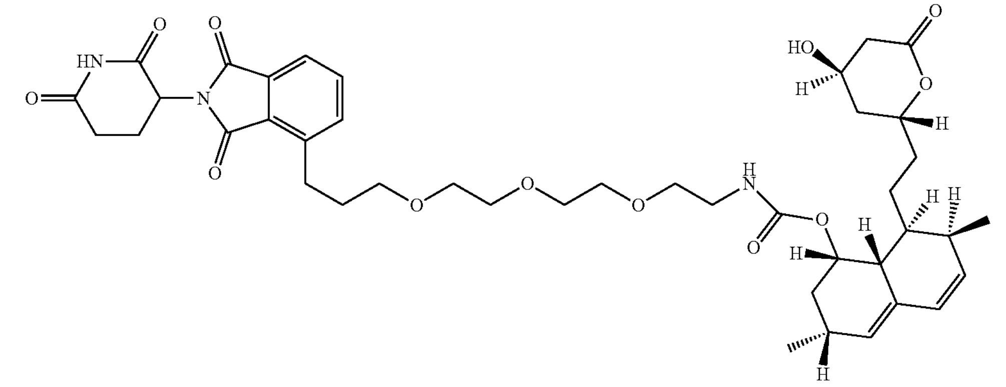 [SMILES: C[C@H]1C=C2C=C[C@H](C)[C@H](CC[C@@H]3C[C@@H](O)CC(=O)O3)[C@H]2[C@@H](OC(=O)NCCOCCOCCOCCCc2cccc3c2C(=O)N(C2CCC(=O)NC2=O)C3=O)C1] |
| 152 | 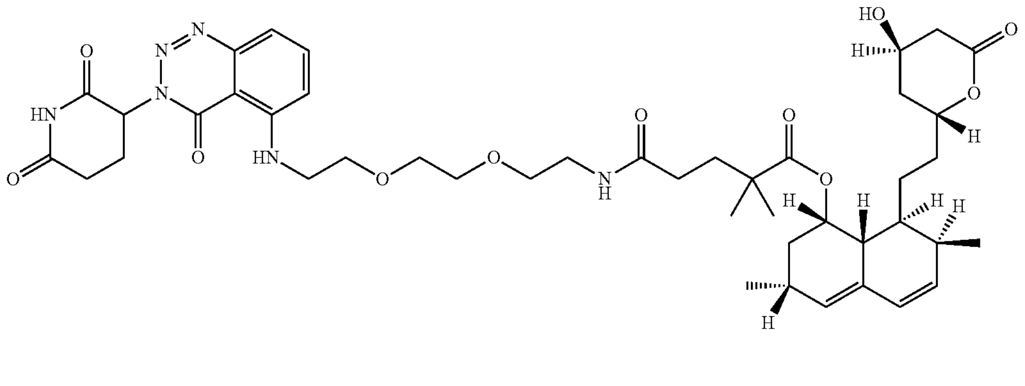 [SMILES: C[C@H]1C=C2C=C[C@H](C)[C@H](CC[C@@H]3C[C@@H](O)CC(=O)O3)[C@H]2[C@@H](OC(=O)C(C)(C)CCC(=O)NCCOCCOCCNc2cccc3nnn(C4CCC(=O)NC4=O)c(=O)c23)C1] |

TABLE 1-continued
| Compound | Structure |
| --- | --- |
| 153 | 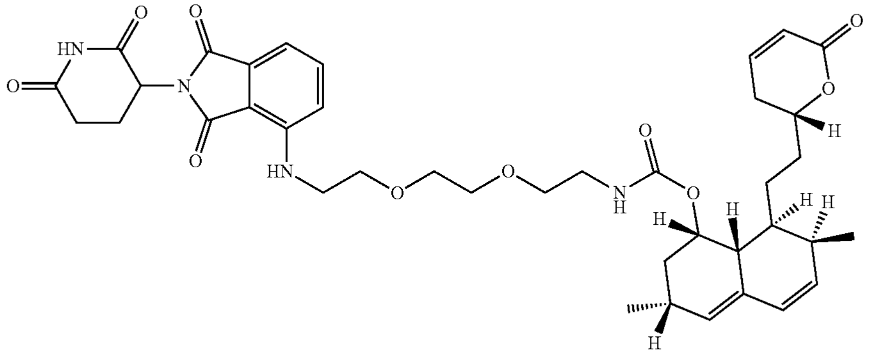 [SMILES: C[C@H]1C=C2C=C[C@H](C)[C@H](CC[C@@H]3CC=CC(=O)O3)[C@H]2[C@@H](OC(=O)NCCOCCOCCNc2cccc3c2C(=O)N(C2CCC(=O)NC2=O)C3=O)C1] |
| 154 | 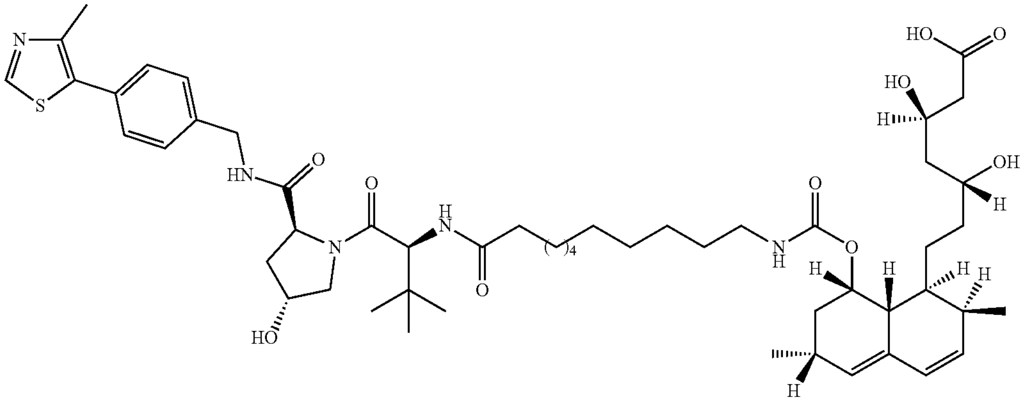 |
| 155 | 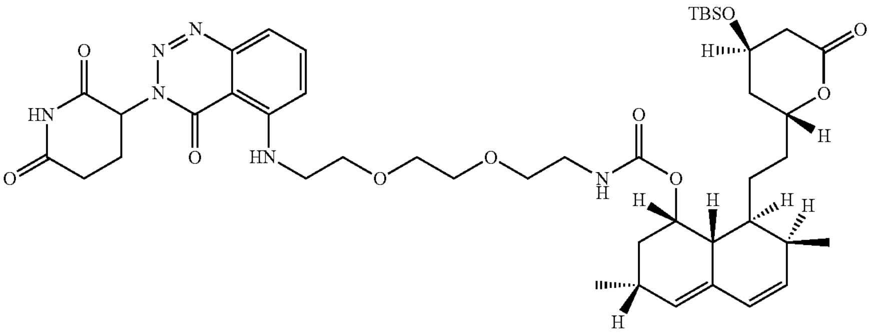 [SMILES: C[C@H]1C=C2C=C[C@H](C)[C@H](CC[C@@H]3C[C@@H](O[Si](C)(C)C(C)(C)C)CC(=O)O3)[C@H]2[C@@H](OC(=O)NCCOCCOCCNc2cccc3nnn(C4CCC(=O)NC4=O)c(=O)c23)C1] |
| 156 | 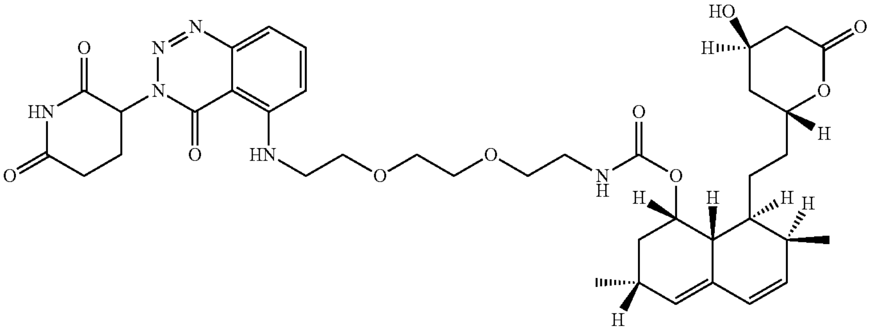 [SMILES: C[C@H]1C=C2C=C[C@H](C)[C@H](CC[C@@H]3C[C@@H](O)CC(=O)O3)[C@H]2[C@@H](OC(=O)NCCOCCOCCNc2cccc3nnn(C4CCC(=O)NC4=O)c(=O)c23)C1] |

TABLE 1-continued
| Compound | Structure |
| --- | --- |
| 157 | 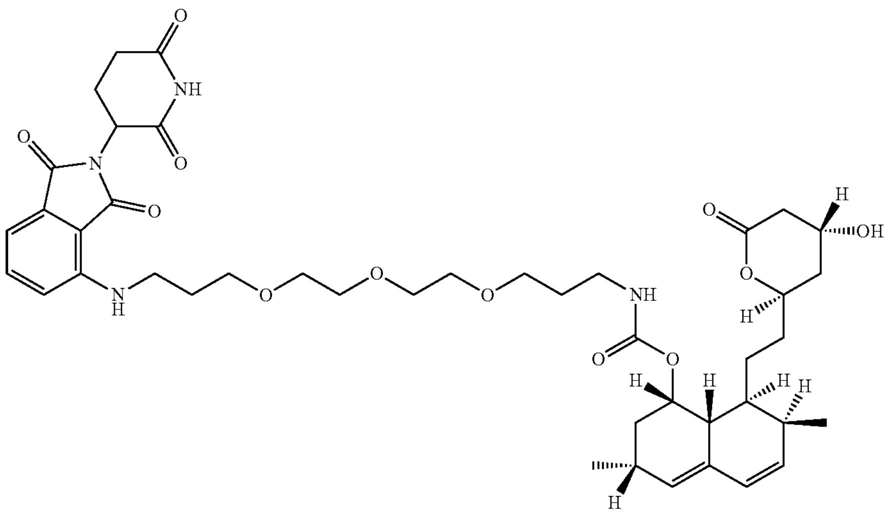 [SMILES: C[C@H]1C=C2C=C[C@H](C)[C@H](CC[C@@H]3C[C@@H](O)CC(=O)O3)[C@H]2[C@@H](OC(=O)NCCCOCCOCCOCCCNc2cccc3c2C(=O)N(C2CCC(=O)NC2=O)C3=O)C1] |
| 158 | 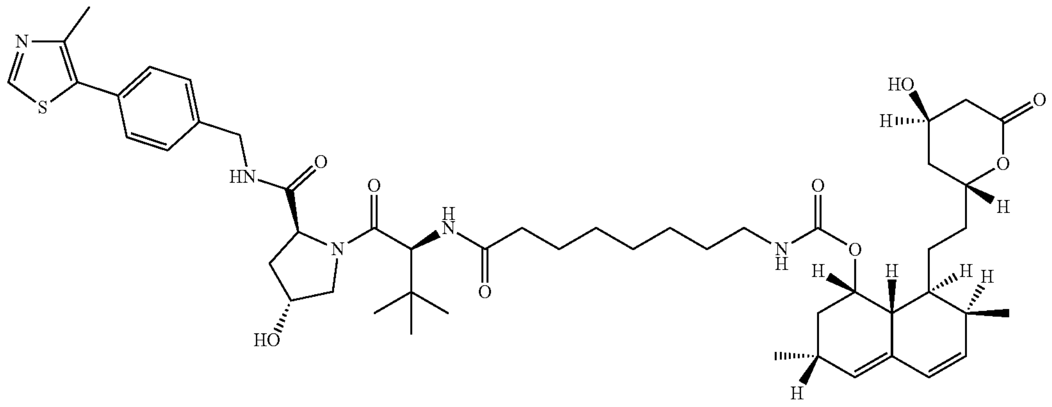 [SMILES: Cc1ncsc1-c1ccc(CNC(=O)[C@@H]2C[C@@H](O)CN2C(=O)[C@@H](NC(=O)CCCCCCCNC(=O)O[C@H]2C[C@@H](C)C=C3C=C[C@H](C)[C@H](CC[C@@H]4C[C@@H](O)CC(=O)O4)[C@H]32)C(C)(C)C)cc1] |
| 159 | 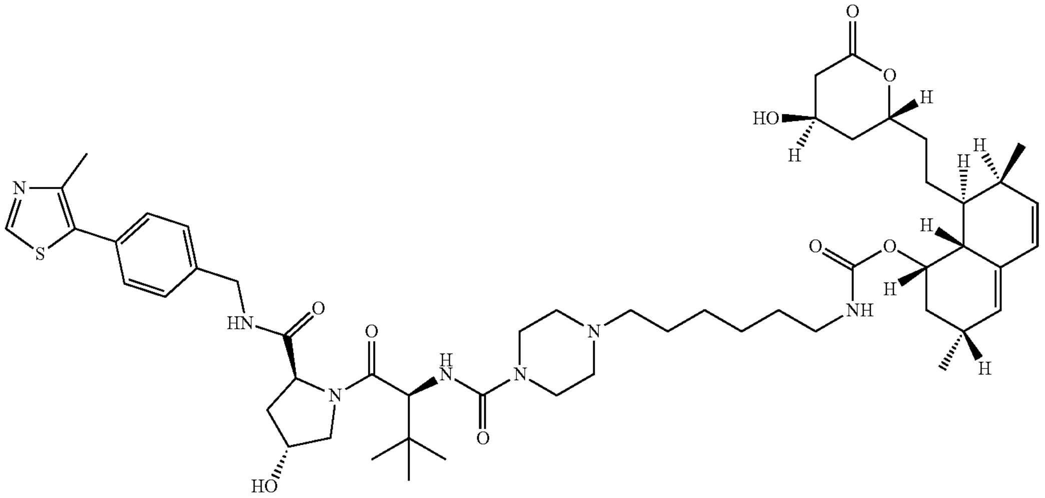 [SMILES: Cc1ncsc1-c1ccc(CNC(=O)[C@@H]2C[C@@H](O)CN2C(=O)[C@@H](NC(=O)N2CCN(CCCCCCNC(=O)O[C@H]3C[C@@H](C)C=C4C=C[C@H](C)[C@H](CC[C@@H]5C[C@@H](O)CC(=O)O5)[C@H]43)CC2)C(C)(C)C)cc1] |

TABLE 1-continued
| Compound | Structure |
|---|---|
| 160 | 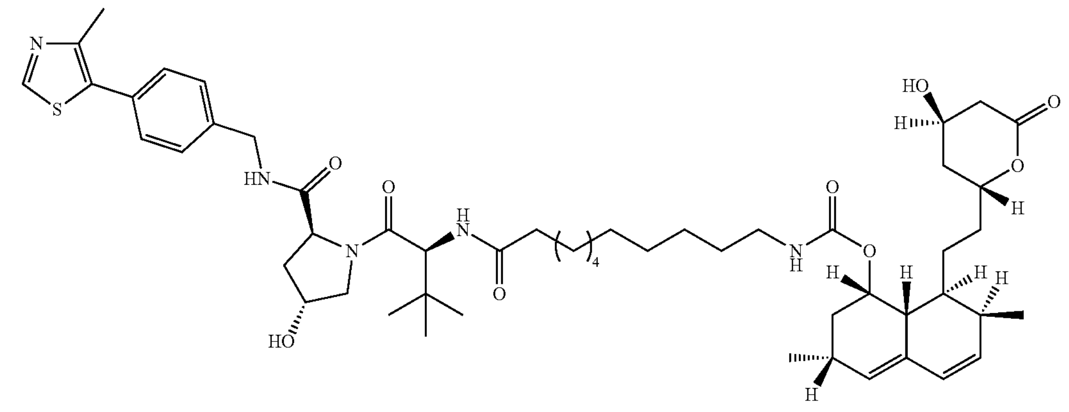 |
| 161 | 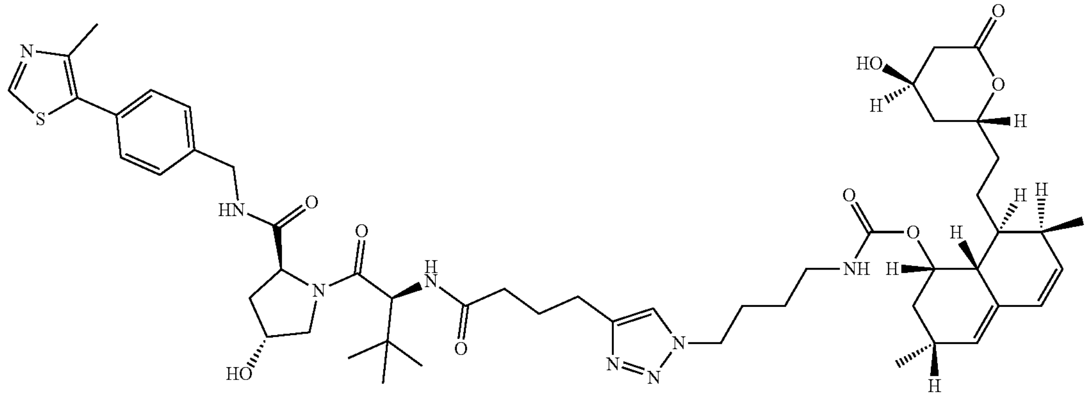 [SMILES: Cc1ncsc1-c1ccc(CNC(=O)[C@@H]2C[C@@H](O)CN2C(=O)[C@@H](NC(=O)CCCc2cn(CCCCNC(=O)O[C@H]3C[C@@H](C)C=C4C=C[C@H](C)[C@H](CC[C@@H]5C[C@@H](O)CC(=O)O5)[C@H]43)nn2)C(C)(C)C)cc1] |
| 162 | 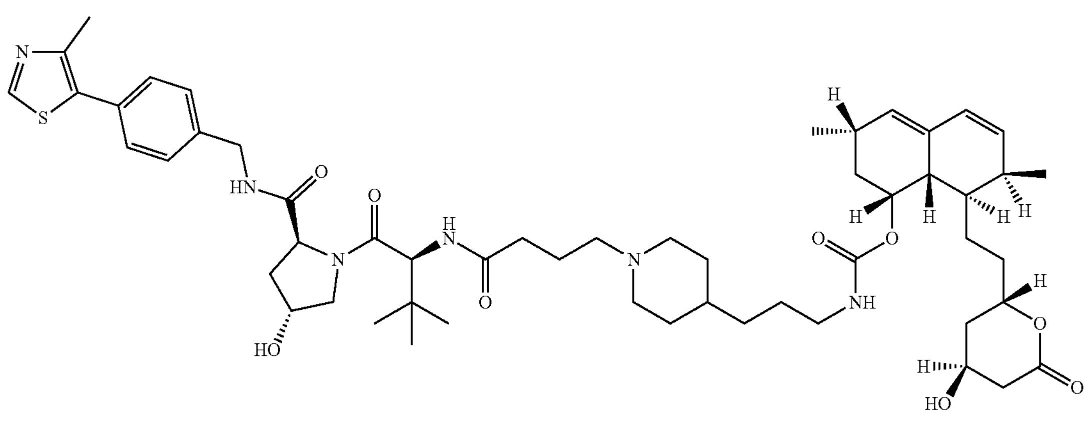 [SMILES: Cc1ncsc1-c1ccc(CNC(=O)[C@@H]2C[C@@H](O)CN2C(=O)[C@@H](NC(=O)CCCN2CCC(CCCNC(=O)O[C@@H]3C[C@H](C)C=C4C=C[C@@H](C)[C@@H](CC[C@H]5C[C@H](O)CC(=O)O5)[C@@H]43)CC2)C(C)(C)C)cc1] |

TABLE 1-continued
| Compound | Structure |
|---|---|
| 163 | 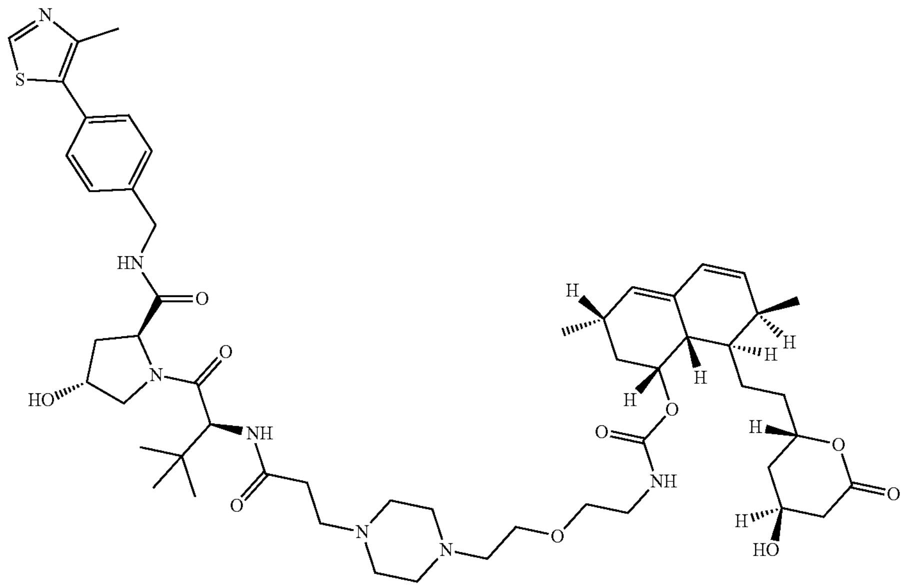 [SMILES: Cc1ncsc1-c1ccc(CNC(=O)[C@@H]2C[C@@H](O)CN2C(=O)[C@@H](NC(=O)CCN2CCN(CCOCCNC(=O)O[C@@H]3C[C@H](C)C=C4C=C[C@@H](C)[C@@H](CC[C@H]5C[C@H](O)CC(=O)O5)[C@@H]43)CC2)C(C)(C)C)cc1] |
| 164 | 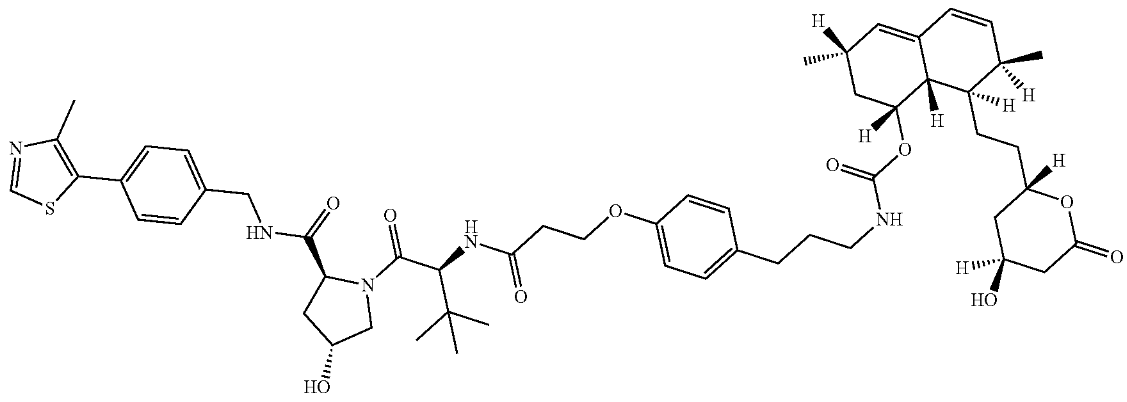 [SMILES: Cc1ncsc1-c1ccc(CNC(=O)[C@@H]2C[C@@H](O)CN2C(=O)[C@@H](NC(=O)CCOc2ccc(CCCNC(=O)O[C@@H]3C[C@H](C)C=C4C=C[C@@H](C)[C@@H](CC[C@H]5C[C@H](O)CC(=O)O5)[C@@H]43)cc2)C(C)(C)C)cc1] |
| 165 | 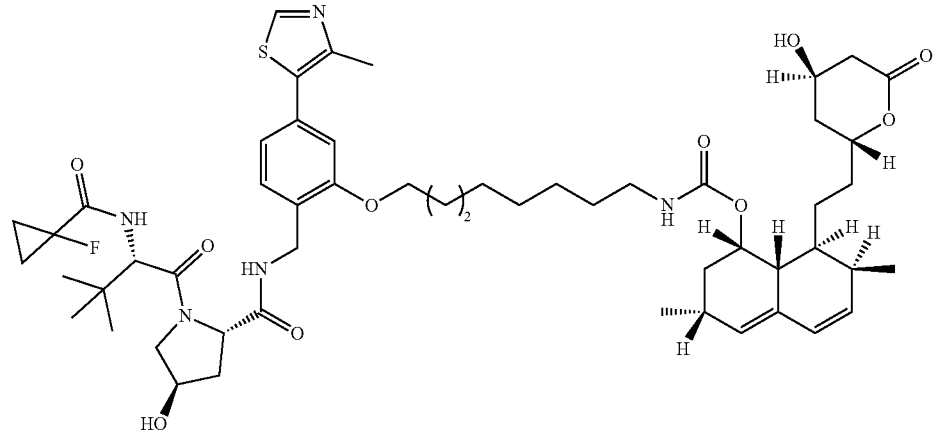 |

TABLE 1-continued
| Compound | Structure |
| --- | --- |
| 166 | 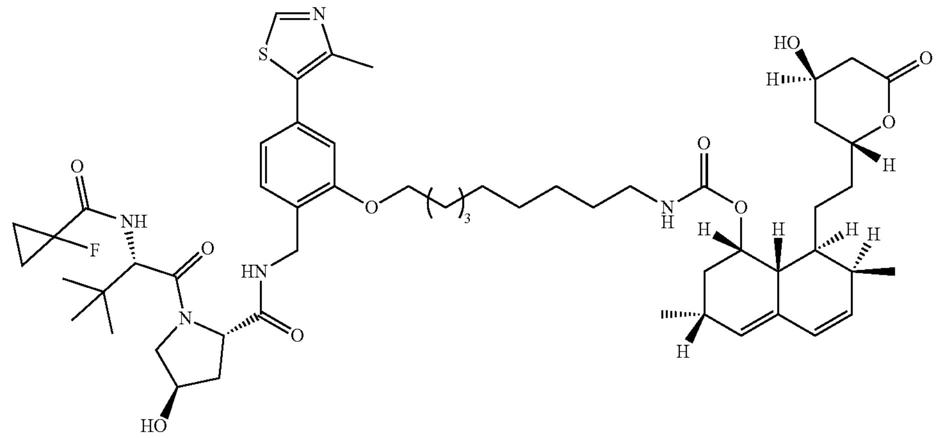 |
| 167 | 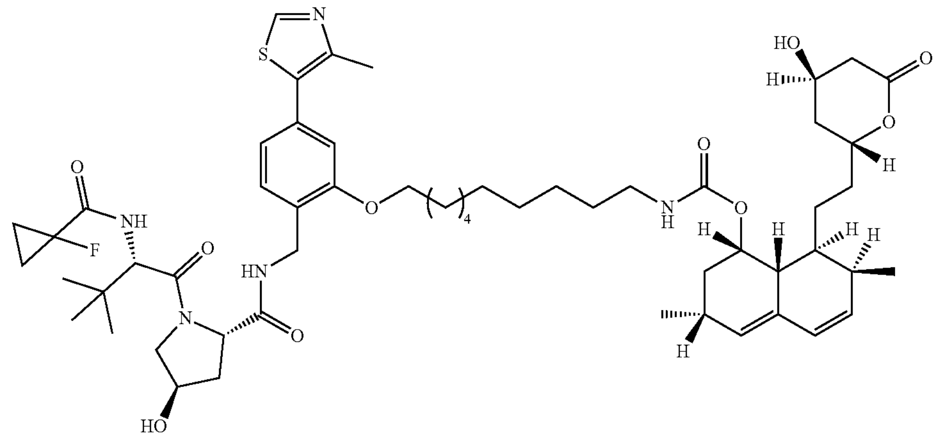 |
| 168 | 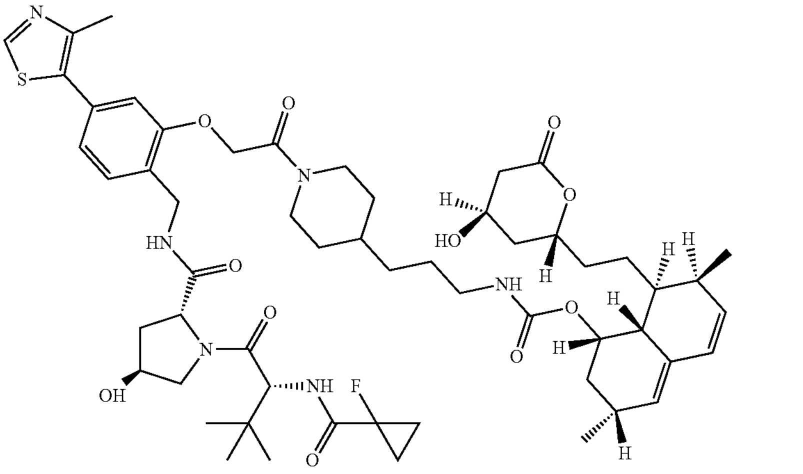 [SMILES: Cc1ncsc1-c1ccc(CNC(=O)[C@H]2C[C@H](O)CN2C(=O)[C@H](NC(=O)C2(F)CC2)C(C)(C)C)c(OCC(=O)N2CCC(CCCNC(=O)O[C@H]3C[C@@H](C)C=C4C=C[C@H](C)[C@H](CC[C@@H]5C[C@@H](O)CC(=O)O5)[C@H]43)CC2)c1] |

TABLE 1-continued

| Compound | Structure |
| --- | --- |
| 169 | 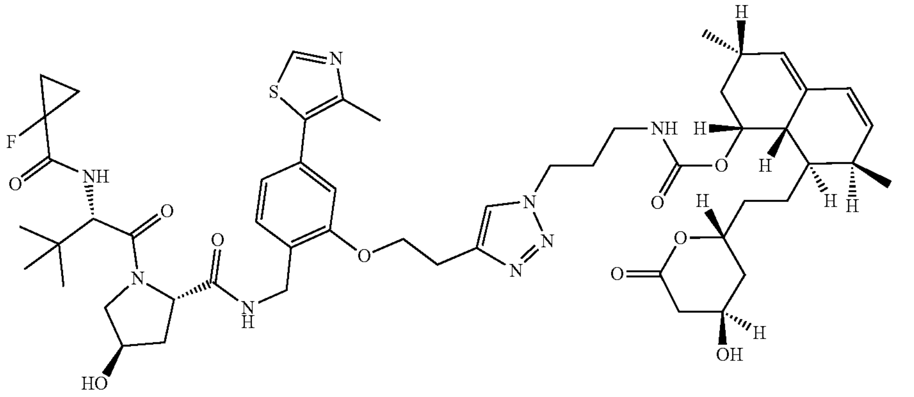 |

The compounds of the present invention were purified according to the following method and the structure was analyzed.

Instruments

LCMS: Shimadzu LCMS-2020

NMR: BRUKER AVANCE III 400 MHz, Bruker A V-600 600 Mhz

HPLC: Shimadzu LC-20AB, Shimadzu LC-20AD, Agilent 1100 LC, Agilent 1200 LC, Agilent 1290 LC SFC: SHIMADZU LC-30ADsf LCSM Analysis LCMS data were recorded with Shimadzu LCMS-2020 equipped with an electron spray ionization device. 0.0375% TFA in water (solvent A) and 0.01875% TFA in acetonitrile (solvent B) were used as mobile phases. As a column, Kinetex EVO C18 (2.1*30) mm, 5 μm was used.

HPLC Analysis

In HPLC analysis, Shimadzu LC-20AB, Shimadzu LC-20AD, Agilent 1100 LC, Agilent 1200 LC or Agilent 1290 LC was used. 0.0375% TFA in water (solvent A) and 0.01875% TFA in acetonitrile (solvent B) or 0.025% $NH_3$·H2O in water (solvent A) and acetonitrile (Solvent B) was used as the mobile phase. As a column, XBridge C18 (2.1*50) mm, 5 μm or Kinetex C18 LC column (4.6*50) mm, 5 μm or Eclipse plus C18 (4.6*150) mm, 3.5 μm or Waters XBridge® C18 (4.6*150) mm, 3.5 m was used.

NMR Analysis $^1$H NMR spectrum was recorded with Bruker AVANCE III 400 MHz/5 mm Probe (BBO) and Bruker A V-600 600 Mhz.

SFC Analysis

In SFC analysis, SHIMADZU LC-30ADsf was used, and $CO_2$ (solvent A) and 0.05% DEA in isopropanol (solvent B) or 0.05% DEA in methanol (solvent B) or 0.05% DEA in ethanol (solvent B) or 0.05% DEA in isopropanol:acetonitrile (1:1) (solvent B) was used as the mobile phase. Columns were Cellucoat 50×4.6 mm, 3 μm or Chiralcel OD-3 50×4.6 mm, 3 μm or Chiralcel OJ-3 50×4.6 mm, 3 μm or Chiralpak AD-3 50×4.6 mm, 3 μm or Chiralpak AS-3 50×4.6 mm, 3 μm or Chiralpak IG-3 50×4.6 mm, 3 μm or (S,S) Whelk-01 100×4.6 mm, 3.5 μm Chiralcel OD-3 50×4.6 mm, 3 μm or Chiralcel OJ-3 50×4.6 mm, 3 μm or Chiralpak AD-3 50×4.6 mm, 3 μm or Chiralpak AS-3 50×4.6 mm, 3 μm.

Example 1. Synthesis of (1S,3R,7S,8S,8aR)-8-(2-((2R,4R)-4-hydroxy-6-oxotetrahydro-2H-pyran-2-yl)ethyl)-3,7-dimethyl-1,2,3,7,8,8a-hexahydronaphthalen-1-yl 16,16-dimethyl-13-oxo-1-(phenylamino)-3,6,9-trioxa-12-azaheptadecan-17-oate (Compound 1)

Step 1: Synthesis of 5-(allyloxy)-2,2-dimethyl-5-oxopentanoic acid (2)

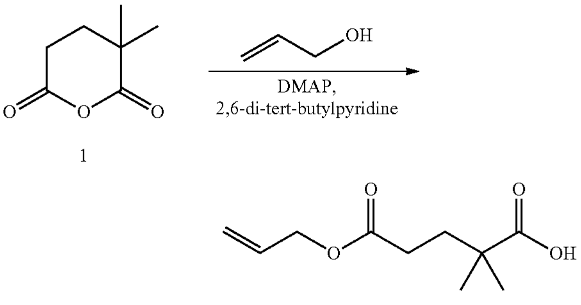

1

2

To a mixture of 3,3-dimethyltetrahydropyran-2,6-dione (10 g, 70.35 mmol) and prop-2-en-1-ol (4.09 g, 70.35 mmol, 4.78 mL) in 2,6-di-tert-butylpyridine (40 mL) was added DMAP (866.67 mg, 7.09 mmol). The mixture was stirred at 25° C. for 15 h. TLC (Petroleum ether:Ethyl acetate=2:1) showed two new spots were formed. The mixture was added to water (100 mL), the aqueous phase was extracted with EtOAc (50 mL×3). The combined organic layer was concentrated under vacuum. The residue was purified by silica gel column chromatography (Petroleum ether:Ethyl acetate=1:0 to 2:1) to afford 5-(allyloxy)-2,2-dimethyl-5-oxopentanoic acid (10 g, 49.94 mmol, 70.99% yield) and 5-(allyloxy)-2,2-dimethyl-5-oxopentanoic acid (2 g, crude) was obtained as colorless oil.

$^1$H NMR (400 MHz, $CDCl_3$) δ 5.84-6.01 (m, 1H), 5.29-5.37 (m, 1H), 5.25 (dd, J=1.16, 10.45 Hz, 1H), 4.58 (d, J=5.75 Hz, 2H), 2.33-2.46 (m, 2H), 1.88-2.00 (m, 2H), 1.23 (s, 6H)

Step 2: Synthesis of 5-(allyloxy)-2,2-dimethyl-5-oxopentanoic acid (2)

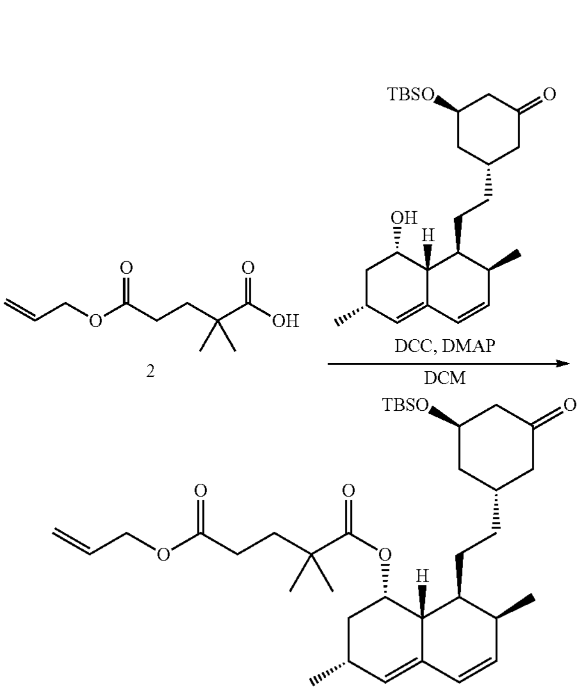

2

3

To a solution of 5-allyloxy-2,2-dimethyl-5-oxo-pentanoic acid (2 g, 9.99 mmol), (4R,6R)-6-[2-[(1S,2S,6R,8S,8aR)-8-hydroxy-2,6-dimethyl-1,2,6,7,8,8a-hexahydronaphthalen-1-yl]ethyl]-4-[tert-butyl(dimethyl)silyl]oxy-tetrahydropyran-2-one (1.45 g, 3.33 mmol) and DMAP (1.45 g, 11.85 mmol) in DCM (30 mL) was added and DCC (2.03 g, 9.82 mmol, 1.99 mL) and the resulting mixture was stirred at 25° C. for 15 h. TLC (Petroleum ether:Ethyl acetate=2:1) showed desired spot was formed and the starting material remained. The mixture was filtered. The filtrate was concentrated under vacuum. The residue was purified by reversed-phase HPLC (neutral, 100% ACN) to afford 5-allyl 1-((1S,3R,7S,8S,8aR)-8-(2-((2R,4R)-4-((tert-butyldimethylsilyl)oxy)-6-oxo-tetrahydro-2H-pyran-2-yl)ethyl)-3,7-dimethyl-1,2,3,7,8,8a-hexahydronaphthalen-1-yl) 2,2-dimethylpentanedioate (1.5 g, 2.43 mmol, 36.51% yield) as yellow oil.

$^1$H NMR (400 MHz, $CDCl_3$) δ 6.01 (s, 1H), 5.94-5.84 (m, 1H), 5.79 (dd, J=6.11, 9.66 Hz, 1H), 5.53 (s, 1H), 5.36 (d, J=2.57 Hz, 1H), 5.32-5.27 (m, 1H), 5.23-5.20 (m, 1H), 4.64-4.56 (m, 1H), 4.56-4.54 (m, 2H), 4.32-4.28 (m, 1H), 2.56-2.61 (m, 2H), 2.48-2.34 (m, 2H), 2.32-2.16 (m, 3H), 2.03-1.97 (m, 4H), 1.93-1.80 (m, 5H), 1.74-1.63 (m, 2H), 1.54-1.44 (m, 1H), 1.35 (t, J=7.89 Hz, 2H), 1.19 (d, J=3.91 Hz, 5H), 1.06 (d, J=7.46 Hz, 3H), 0.92-0.88 (m, 12H), 0.09 (d, J=1.47 Hz, 6H).

Step 3: Synthesis of 5-(((1S,3R,7S,8S,8aR)-8-(2-((2R,4R)-4-((tert-butyldimethylsilyl)oxy)-6-oxotetrahydro-2H-pyran-2-yl)ethyl)-3,7-dimethyl-1,2,3,7,8,8a-hexahydronaphthalen-1-yl)oxy)-4,4-dimethyl-5-oxopentanoic acid (4)

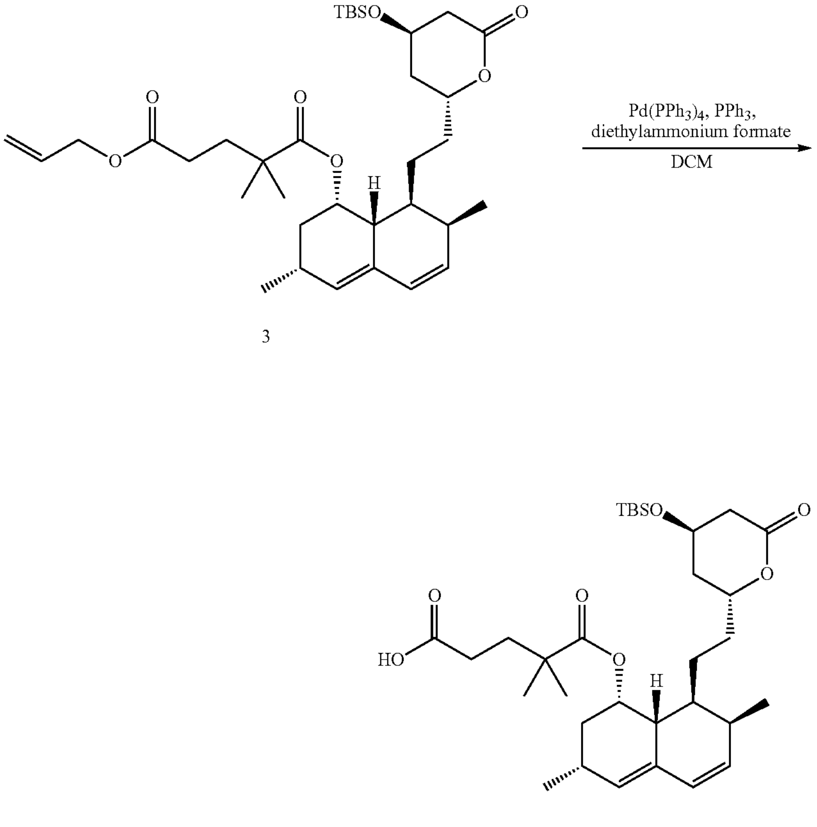

3

4

To a solution of 5-allyl 1-((1S,3R,7S,8S,8aR)-8-(2-((2R,4R)-4-((tert-butyldimethylsilyl)oxy)-6-oxotetrahydro-2H-pyran-2-yl)ethyl)-3,7-dimethyl-1,2,3,7,8,8a-hexahydronaphthalen-1-yl) 2,2-dimethylpentanedioate (1.5 g, 2.43 mmol) and $PPh_3$ (95.66 mg, 364.73 μmol) in DCM (20 mL) was added diethylammonium formate (2 M, 2.40 mL) followed by $Pd(PPh_3)_4$ (210.00 mg, 0.18 mmol) and the resulting mixture was stirred at 25° C. for 15 h. LCMS showed a peak with desired mass and starting material remained. The mixture was filtered, the filtrate was concentrated under vacuum. The residue was purified by reversed-phase HPLC (neutral, 89% ACN) to afford 5-(((1S,3R,7S,8S,8aR)-8-(2-((2R,4R)-4-((tert-butyldimethylsilyl)oxy)-6-oxotetrahydro-2H-pyran-2-yl)ethyl)-3,7-dimethyl-1,2,3,7,8,8a-hexahydronaphthalen-1-yl)oxy)-4,4-dimethyl-5-oxopentanoic acid (0.9 g, 1.56 mmol, 64.17% yield) as yellow oil. MS $(M+H)^+$=577.2

Step 4: Synthesis of 5-(((1S,3R,7S,8S,8aR)-8-(2-((2R,4R)-4-hydroxy-6-oxotetrahydro-2H-pyran-2-yl)ethyl)-3,7-dimethyl-1,2,3,7,8,8a-hexahydronaphthalen-1-yl)oxy)-4,4-dimethyl-5-oxopentanoic acid (5)

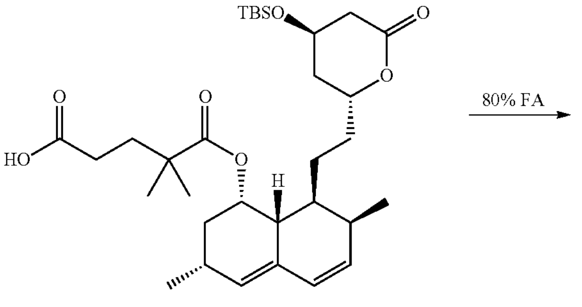

4

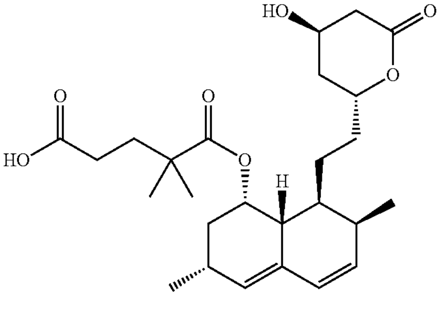

5

A mixture of 5-(((1S,3R,7S,8S,8aR)-8-(2-((2R,4R)-4-((tert-butyldimethylsilyl)oxy)-6-oxotetrahydro-2H-pyran-2-yl)ethyl)-3,7-dimethyl-1,2,3,7,8,8a-hexahydronaphthalen-1-yl)oxy)-4,4-dimethyl-5-oxopentanoic acid (0.9 g, 1.56 mmol) in formic acid (24.40 g, 424.11 mmol, 20 mL, 80% purity) was stirred at 25° C. for 1 h. LCMS showed a main peak with desired mass. The mixture was concentrated under vacuum. The residue was purified by reversed-phase HPLC (neutral, 50% ACN) to afford 5-(((1S,3R,7S,8S,8aR)-8-(2-((2R,4R)-4-hydroxy-6-oxotetrahydro-2H-pyran-2-yl)ethyl)-3,7-dimethyl-1,2,3,7,8,8a-hexahydronaphthalen-1-yl)oxy)-4,4-dimethyl-5-oxopentanoic acid (0.28 g, 0.61 mmol, 38.80% yield) as white solid. MS $(M+H)^+$=463.0

Step 5: Synthesis of benzyl (2-(2-(2-(2-hydroxyethoxy)ethoxy)ethoxy)ethyl)carbamate (7)

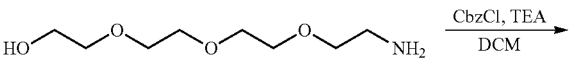

6

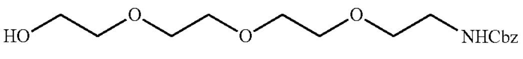

7

To a solution of 2-[2-[2-(2-aminoethoxy)ethoxy]ethoxy] ethanol (1 g, 5.17 mmol) and TEA (1.05 g, 10.35 mmol, 1.44 mL) in DCM (20 mL) was added CbzCl (971.08 mg, 5.69 mmol, 0.81 mL), the mixture was stirred at 25° C. for 2 h. LCMS showed a peak with desired mass. The mixture was concentrated under vacuum to give benzyl (2-(2-(2-(2-hydroxyethoxy)ethoxy) ethoxy)ethyl)carbamate (1.7 g, crude) as white solid, which was used for next step directly.

MS $(M+H)^+$=328.0

Step 6: Synthesis of 3-oxo-1-phenyl-2,7,10,13-tetraoxa-4-azapentadecan-15-yl 4-methylbenzenesulfonate (8)

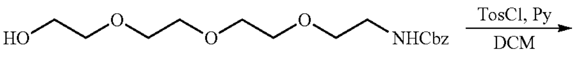

7

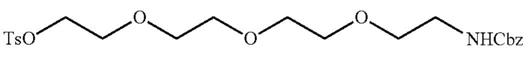

8

To a solution of benzyl (2-(2-(2-(2-hydroxyethoxy)ethoxy)ethoxy)ethyl)carbamate (1.7 g, crude) and pyridine (821.51 mg, 10.39 mmol) in DCM (20 mL) was added p-TsCl (1.49 g, 7.79 mmol), the mixture was stirred at 25° C. for 16 h. LCMS showed a peak with desired mass. The mixture was concentrated under vacuum. The residue was purified by silica gel column chromatography (Petroleum ether/EtOAc=1/0 to 1/1) to afford 3-oxo-1-phenyl-2,7,10,13-tetraoxa-4-azapentadecan-15-yl 4-methylbenzenesulfonate (0.9 g, 1.87 mmol, 35.99% yield) as yellow oil. MS $(M+H)^+$=482.2

Step 7: Synthesis of benzyl (2-(2-(2-(2-(phenylamino)ethoxy)ethoxy)ethoxy)ethyl)carbamate (9)

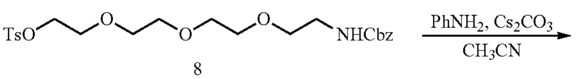

8

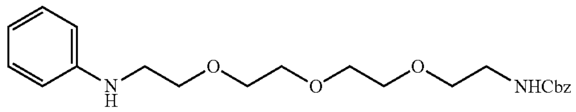

9

To a mixture of 3-oxo-1-phenyl-2,7,10,13-tetraoxa-4-azapentadecan-15-yl 4-methylbenzenesulfonate (0.9 g, 1.87 mmol) and aniline (1.74 g, 18.69 mmol, 1.71 mL) in $CH_3CN$ (15 mL) was added $Cs_2CO_3$ (1.83 g, 5.61 mmol), the mixture was stirred at 90° C. for 15 h. LCMS showed a peak (50%) with desired mass. The mixture was filtered and the filtrate was concentrated under vacuum to give a residue. The residue was purified by reversed-phase HPLC (0.1% FA condition, 50% ACN) to afford benzyl (2-(2-(2-(2-(phenylamino)ethoxy)ethoxy)ethoxy) ethyl)carbamate (0.11 g, 0.27 mmol, 14.62% yield) as yellow oil. MS $(M+H)^+$=403.2

Step 8: Synthesis of N-(2-(2-(2-(2-aminoethoxy) ethoxy)ethoxy)ethyl)aniline (10)

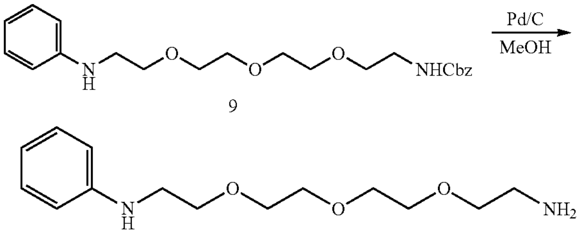

9

10

To a solution of benzyl (2-(2-(2-(2-(phenylamino)ethoxy) ethoxy)ethoxy)ethyl)carbamate (0.11 g, 0.27 mmol) in MeOH (10 mL) was added Pd/C (0.05 g, 10% purity), the mixture was stirred at 40° C. for 16 h. LCMS showed a peak with desired and a little starting material remained. The mixture was filtered and the filtrate was concentrated under vacuum to give N-(2-(2-(2-(2-aminoethoxy)ethoxy)ethoxy) ethyl)aniline (60 mg, 0.22 mmol, 81.81% yield) as yellow oil, which was used directly in the next step. MS $(M+H)^+$=269.3

Step 9: Synthesis of (1S,3R,7S,8S,8aR)-8-(2-((2R, 4R)-4-hydroxy-6-oxotetrahydro-2H-pyran-2-yl) ethyl)-3,7-dimethyl-1,2,3,7,8,8a-hexahydronaphthalen-1-yl 16,16-dimethyl-13-oxo-1-(phenylamino)-3, 6,9-trioxa-12-azaheptadecan-17-oate (Compound 1)

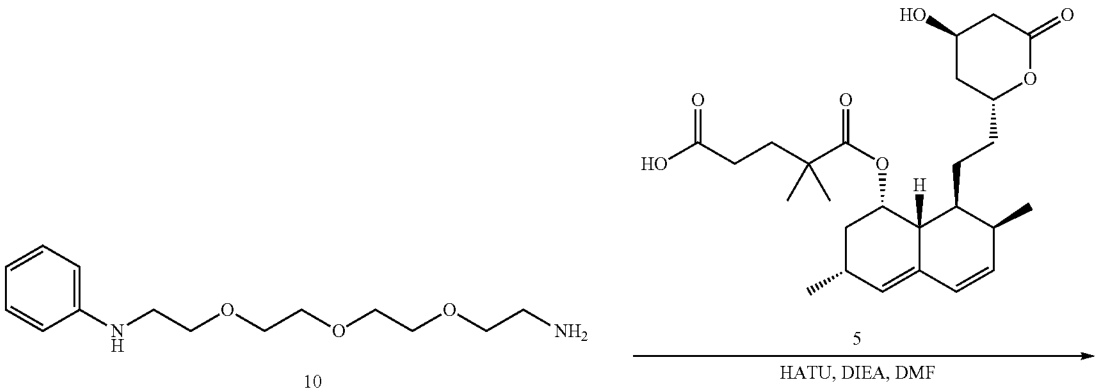

10

5

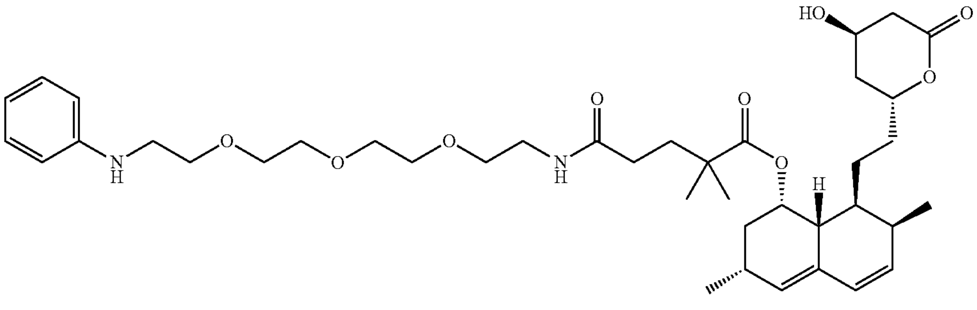

Compound 1

To a solution of 5-[[(1S,3R,7S,8S,8aR)-8-[2-[(2R,4R)-4-hydroxy-6-oxo-tetrahydropyran-2-yl] ethyl]-3,7-dimethyl-1,2,3,7,8,8a-hexahydronaphthalen-1-yl]oxy]-4,4-dimethyl-5-oxo-pentanoic acid (0.1 g, 0.21 mmol) and DIEA (55.88 mg, 0.43 mmol, 0.075. mL) in DMF (2 mL) was added HATU (0.1 g, 0.26 mmol), the mixture was stirred at 25° C. for 15 min, to the mixture was added N-[2-[2-[2-(2-amino-ethoxy)ethoxy]ethoxy]ethyl]aniline (58.01 mg, 0.216 mmol), the mixture was stirred at 25° C. for 1 h. LCMS showed a peak (53%) with desired mass. The pH was adjusted to 7-8 with 50% FA, the mixture was filtered and the filtrate was collected. The filtrate was purified by prep-HPLC (column: Phenomenex luna C18 150*25 mm*10 μm; mobile phase: [water (0.1% TFA)-ACN]; B %: 37%-67%, 10 min) to give a crude product (HPLC: EW15926-241-P1C), The crude product was re-purified by prep-HPLC (column: UniSil 3-100 C18 Ultra (150*25 mm*3 μm); mobile phase: [water (0.225% FA)-ACN]; B %: 46%-76%, 10 min) followed by lyophilization to afford (1S,3R,7S,8S,8aR)-8-(2-((2R,4R)-4-hydroxy-6-oxotetrahydro-2H-pyran-2-yl)ethyl)-3,7-dimethyl-1,2,3,7,8,8a-hexahydronaphthalen-1-yl 16,16-dimethyl-13-oxo-1-(phenylamino)-3,6,9-trioxa-12-azaheptadecan-17-oate (12.8 mg, 0.017 mmol, 8.06% yield, 97% purity) as yellow oil. MS (M+H)+=713.2 $^1$H NMR (400 MHz, DMSO-$d_6$) δ 7.47 (t, J=5.6 Hz, 1H), 7.05 (dd, J=8.5, 7.2 Hz, 2H), 6.60-6.54 (m, 2H), 6.51 (t, J=7.2 Hz, 1H), 5.94 (d, J=9.6 Hz, 1H), 5.77 (dd, J=9.6, 6.0 Hz, 1H), 5.51-5.42 (m, 2H), 5.18 (d, J=3.4 Hz, 2H), 4.55-4.43 (m, 1H), 4.14-4.06 (m, 1H), 3.57-3.51 (m, 6H), 3.51-3.45 (m, 4H), 3.36 (d, J=6.4 Hz, 2H), 3.20-3.13 (m, 4H), 2.61 (dd, J=17.3, 4.5 Hz, 1H), 2.42-2.40 (m, 1H), 2.38-2.34 (m, 2H), 2.27 (d, J=12.5 Hz, 1H), 2.22-2.11 (m, 1H), 2.09-1.97 (m, 1H), 1.94-1.75 (m, 3H), 1.72-1.57 (m, 5H), 1.41-1.27 (m, 2H), 1.27-1.20 (m, 1H), 1.03 (d, J=5.3 Hz, 6H), 0.99 (d, J=7.3 Hz, 3H), 0.83 (d, J=6.9 Hz, 3H).

Example 2. Synthesis of (1S,3R,7S,8S,8aR)-8-(2-((2R,4R)-4-hydroxy-6-oxotetrahydro-2H-pyran-2-yl)ethyl)-3,7-dimethyl-1,2,3,7,8,8a-hexahydronaphthalen-1-yl 5-((2-(2-(2-((2-(2,6-dioxopiperidin-3-yl)-1,3-dioxoisoindolin-4-yl)amino)ethoxy)ethoxy)ethyl)amino)-2,2-dimethyl-5-oxopentanoate (Compound 2)

Step 1: Synthesis of tert-butyl (2-(2-(2-((2-(2,6-dioxopiperidin-3-yl)-1,3-dioxoisoindolin-4-yl)amino)ethoxy)ethoxy)ethyl)carbamate (13a)

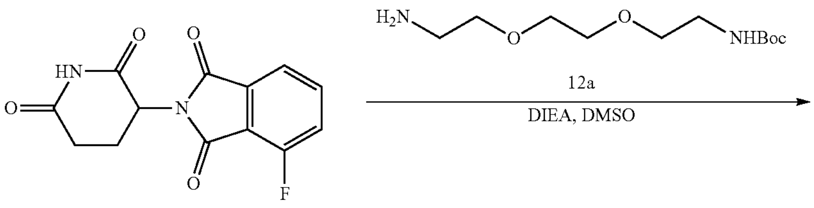

11

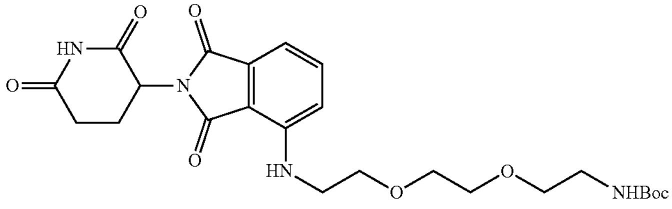

13a

To a solution of 2-(2,6-dioxo-3-piperidyl)-4-fluoro-isoindoline-1,3-dione (1 g, 3.62 mmol, 1 eq) and tert-butyl N-[2-[2-(2-aminoethoxy)ethoxy]ethyl]carbamate (0.9 g, 3.62 mmol) in DMSO (10 mL) was added DIEA (935.80 mg, 7.24 mmol, 1.26 mL), the mixture was stirred at 90° C. for 16 h. LCMS showed a main peak with desired mass. The pH was adjusted to 7-8 by 1N HCl, the mixture was filtered and the filtrate was purified directly by reversed-phase HPLC (0.1% FA condition, 65% ACN) to afford tert-butyl (2-(2-(2-((2-(2,6-dioxopiperidin-3-yl)-1,3-dioxoisoindolin-4-yl)amino)ethoxy)ethoxy)ethyl)carbamate (1.3 g, 2.58 mmol, 71.17% yield) as black oil.

Step 2: Synthesis of 4-((2-(2-(2-aminoethoxy)ethoxy)ethyl)amino)-2-(2,6-dioxopiperidin-3-yl)isoindoline-1,3-dione (14a)

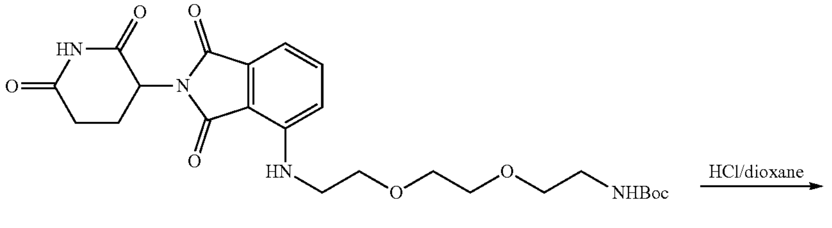

13a

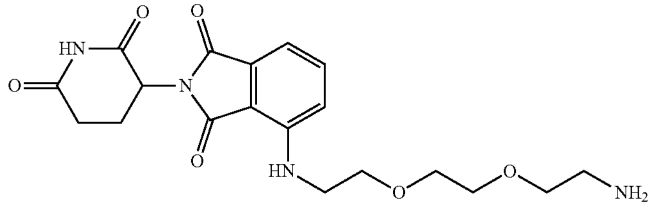

14a

To a solution of tert-butyl (2-(2-(2-((2-(2,6-dioxopiperidin-3-yl)-1,3-dioxoisoindolin-4-yl)amino)ethoxy)ethoxy)ethyl)carbamate (1.3 g, 2.58 mmol) in dioxane (5 mL) was added HCl/dioxane (4 M, 15 mL) and the resulting mixture was stirred at 25° C. for 3 h. LCMS showed a main peak with desired mass. The mixture was concentrated under vacuum to give 4-((2-(2-(2-aminoethoxy)ethoxy)ethyl)amino)-2-(2,6-dioxopiperidin-3-yl)isoindoline-1,3-dione (1.2 g, crude, HCl salt) as brown oil, which was used directly in the next step. MS $(M+H)^+$=405.3

Step 3: Synthesis of (1S,3R,7S,8S,8aR)-8-(2-((2R,4R)-4-hydroxy-6-oxotetrahydro-2H-pyran-2-yl)ethyl)-3,7-dimethyl-1,2,3,7,8,8a-hexahydronaphthalen-1-yl 5-((2-(2-(2-((2-(2,6-dioxopiperidin-3-yl)-1,3-dioxoisoindolin-4-yl)amino)ethoxy)ethoxy)ethyl)amino)-2,2-dimethyl-5-oxopentanoate (Compound 2)

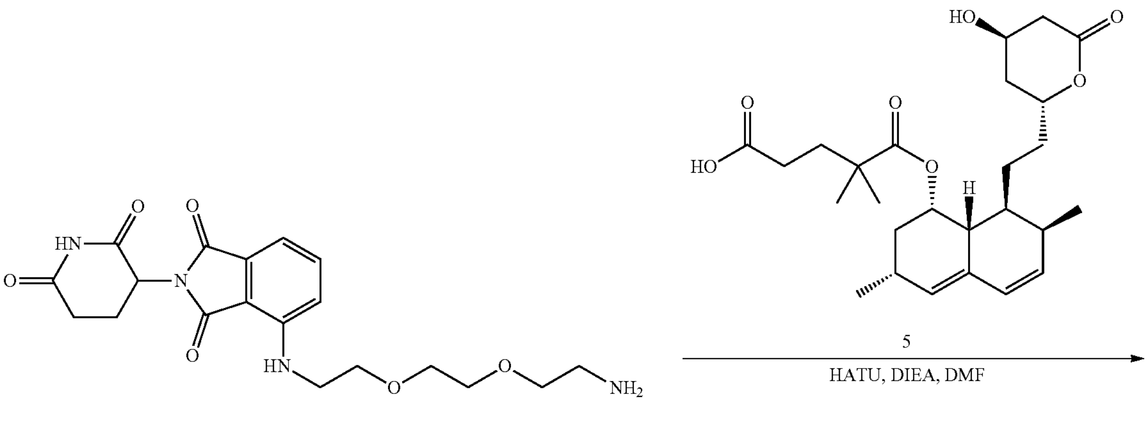

14a

-continued

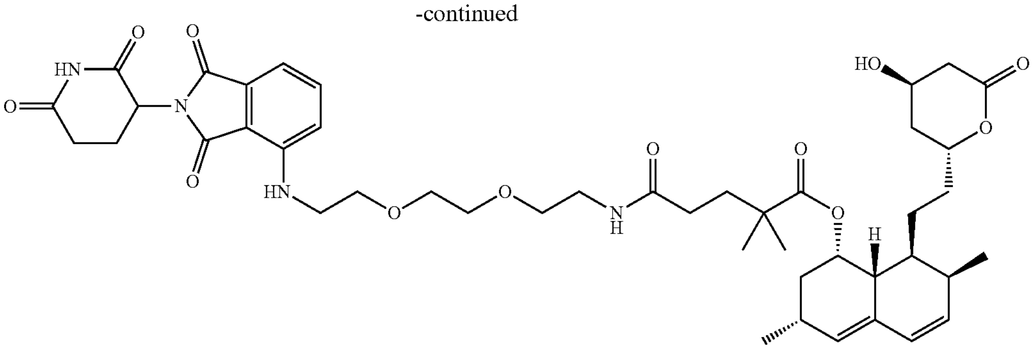

Compound 2

To a solution of 5-[[(1S,3R,7S,8S,8aR)-8-[2-[(2R,4R)-4-hydroxy-6-oxo-tetrahydropyran-2-yl]ethyl]-3,7-dimethyl-1,2,3,7,8,8a-hexahydronaphthalen-1-yl]oxy]-4,4-dimethyl-5-oxo-pentanoic acid (0.12 g, 0.26 mmol) and DIEA (74.20 mg, 0.57 mmol, 0.1 mL) in DMF (2 mL) was added HATU (0.12 g, 315.60 μmol) at 25° C., the resulting mixture was stirred at 25° C. for 0.5 h. To the mixture was added 4-[2-[2-(2-aminoethoxy)ethoxy]ethylamino]-2-(2,6-dioxo-3-piperidyl) isoindoline-1,3-dione (0.12 g, 272.18 μmol, HCl), the resulting mixture was stirred at 25° C. for 2.5 h. LCMS showed a peak with desired mass. The pH was adjusted 7-8 with 1 N HCl, the mixture was filtered, the filtrated was purified directly by prep-HPLC (column: Uni-Sil 3-100 C18 Ultra (150*25 mm*3 μm); mobile phase: [water (0.225% FA)-ACN]; B %: 43%-73%, 10 min) followed by lyophilization to afford (1S,3R,7S,8S,8aR)-8-(2-((2R,4R)-4-hydroxy-6-oxotetrahydro-2H-pyran-2-yl)ethyl)-3,7-dimethyl-1,2,3,7,8,8a-hexahydronaphthalen-1-yl 5-((2-(2-(2-((2-(2,6-dioxopiperidin-3-yl)-1,3-dioxoisoindolin-4-yl)amino)ethoxy)ethoxy)ethyl)amino)-2,2-dimethyl-5-oxopentanoate (98.7 mg, 0.10 mmol, 42.13% yield, 94% purity) as yellow solid. MS $(M+H)^+$=849.3.

$^1$H NMR (400 MHz, DMSO-$d_6$) δ 11.09 (s, 1H), 7.58 (dd, J=7.4, 8.4 Hz, 1H), 7.45 (t, J=5.6 Hz, 1H), 7.14 (d, J=8.6 Hz, 1H), 7.04 (d, J=7.0 Hz, 1H), 6.60 (t, J=5.8 Hz, 1H), 5.93 (d, J=9.8 Hz, 1H), 5.76 (dd, J=6.0, 9.6 Hz, 1H), 5.47 (s, 1H), 5.18 (d, J=3.2 Hz, 2H), 5.05 (dd, J=5.4, 12.8 Hz, 1H), 4.53-4.43 (m, 1H), 4.10 (d, J=3.2 Hz, 1H), 3.63-3.58 (m, 2H), 3.56-3.51 (m, 2H), 3.51-3.43 (m, 4H), 3.34-3.39 (m, 2H), 3.17 (q, J=6.0 Hz, 2H), 2.94-2.82 (m, 1H), 2.64-2.52 (m, 3H), 2.40 (d, J=1.8 Hz, 1H), 2.38-2.30 (m, 2H), 2.30-2.23 (m, 1H), 2.22-2.12 (m, 1H), 2.06-1.98 (m, 2H), 1.93-1.74 (m, 3H), 1.71-1.56 (m, 5H), 1.39-1.20 (m, 3H), 1.02 (d, J=5.0 Hz, 6H), 0.98 (d, J=7.4 Hz, 3H), 0.83 (d, J=6.8 Hz, 3H).

Example 3. Synthesis of (1S,3R,7S,8S,8aR)-8-(2-((2R,4R)-4-hydroxy-6-oxotetrahydro-2H-pyran-2-yl)ethyl)-3,7-dimethyl-1,2,3,7,8,8a-hexahydronaphthalen-1-yl 1-((2-(2,6-dioxopiperidin-3-yl)-1,3-dioxoisoindolin-4-yl)amino)-16,16-dimethyl-13-oxo-3,6,9-trioxa-12-azaheptadecan-17-oate (Compound 3)

Step 1: Synthesis of tert-butyl (2-(2-(2-(2-((2-(2,6-dioxopiperidin-3-yl)-1,3-dioxoisoindolin-4-yl)amino)ethoxy)ethoxy)ethoxy)ethyl)carbamate (13b)

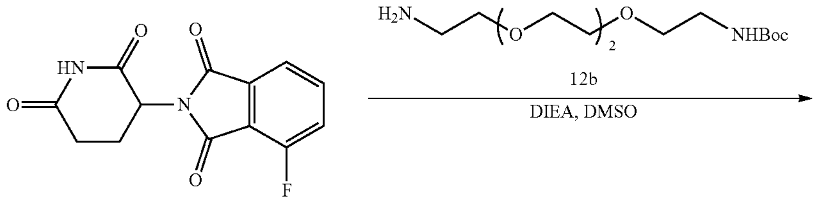

11

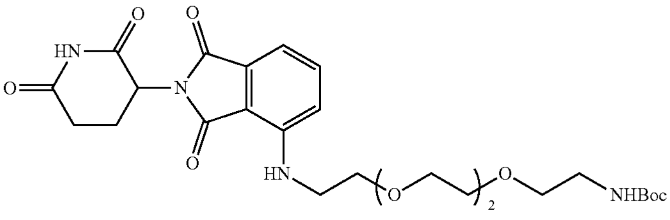

13b

In a manner similar to Step 1 of Example 2, the titled compound (0.78 g, 1.42 mmol, 41.57% yield) was obtained as a black oil.

Step 2: 4-((2-(2-(2-(2-aminoethoxy)ethoxy)ethoxy)ethyl)amino)-2-(2,6-dioxopiperidin-3-yl)isoindoline-1,3-dione (14b)

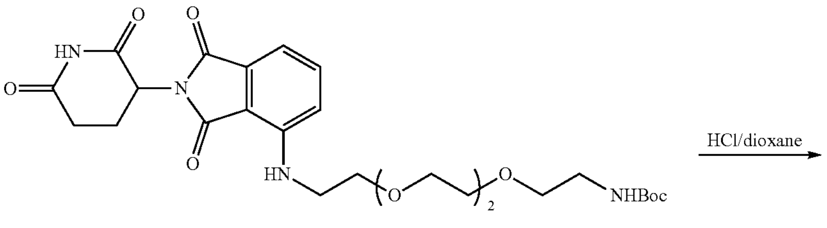

13b

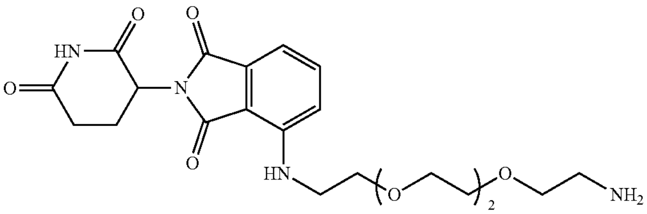

14b

In a manner similar to Step 2 of Example 2, the titled compound (0.7 g, crude, HCl) was obtained as a brown oil. MS $(M+H)^+$=449.0

Step 3: Synthesis of (1S,3R,7S,8S,8aR)-8-(2-((2R,4R)-4-hydroxy-6-oxotetrahydro-2H-pyran-2-yl)ethyl)-3,7-dimethyl-1,2,3,7,8,8a-hexahydronaphthalen-1-yl 1-((2-(2,6-dioxopiperidin-3-yl)-1,3-dioxoisoindolin-4-yl)amino)-16,16-dimethyl-13-oxo-3,6,9-trioxa-12-azaheptadecan-17-oate (Compound 3)

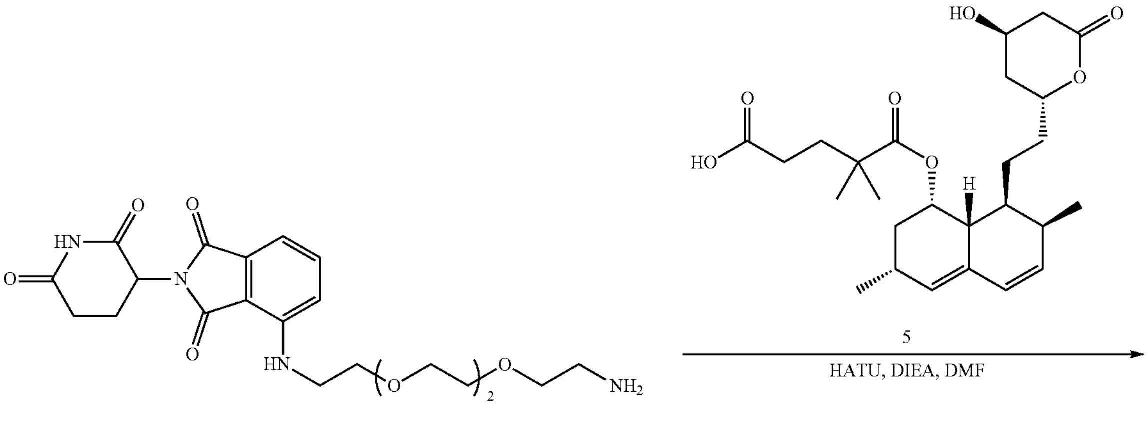

14b

-continued

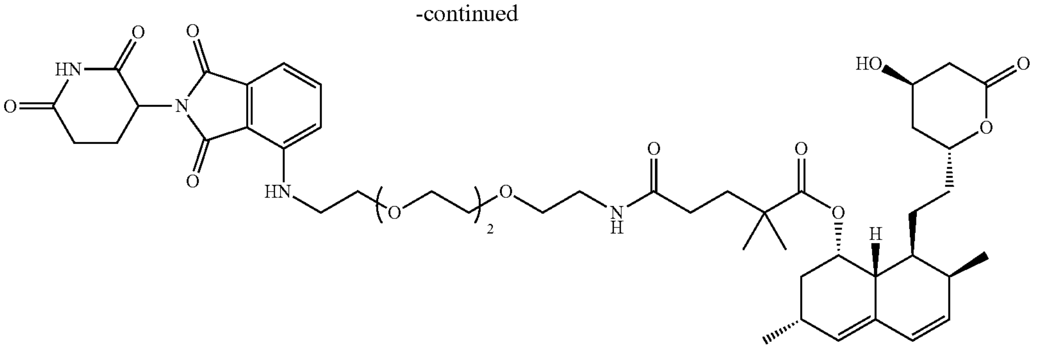

Compound 3

In a manner similar to Step 3 of Example 2, the titled compound (22.0 mg, 23.28 μmol, 17.95% yield, 94.5% purity) was obtained as a yellow solid.

MS $(M+H)^+$=893.3.

$^1H$ NMR (400 MHz, DMSO-$d_6$) δ 11.08 (s, 1H), 7.58 (dd, J=8.6, 7.1 Hz, 1H), 7.46 (t, J=5.7 Hz, 1H), 7.14 (d, J=8.6 Hz, 1H), 7.04 (d, J=7.0 Hz, 1H), 6.60 (t, J=5.9 Hz, 1H), 5.93 (d, J=9.7 Hz, 1H), 5.76 (dd, J=9.6, 6.0 Hz, 1H), 5.48 (s, 1H), 5.18 (d, J=3.3 Hz, 2H), 5.05 (dd, J=12.9, 5.4 Hz, 1H), 4.54-4.40 (m, 1H), 4.10 (d, J=4.1 Hz, 1H), 3.62 (t, J=5.4 Hz, 2H), 3.58-3.54 (m, 2H), 3.54-3.51 (m, 2H), 3.50-3.43 (m, 6H), 3.16 (q, J=6.0 Hz, 2H), 2.95-2.82 (m, 1H), 2.65-2.52 (m, 4H), 2.42-2.34 (m, 3H), 2.27 (d, J=12.6 Hz, 2H), 2.23-2.10 (m, 1H), 2.10-1.98 (m, 2H), 1.94-1.74 (m, 3H), 1.74-1.56 (m, 5H), 1.42-1.19 (m, 3H), 1.03 (d, J=5.4 Hz, 6H), 0.98 (d, J=7.3 Hz, 3H), 0.83 (d, J=6.9 Hz, 3H).

Example 4. Synthesis of (1S,3R,7S,8S,8aR)-8-(2-((2R,4R)-4-hydroxy-6-oxotetrahydro-2H-pyran-2-yl)ethyl)-3,7-dimethyl-1,2,3,7,8,8a-hexahydronaphthalen-1-yl 1-((2-(2,6-dioxopiperidin-3-yl)-1,3-dioxoisoindolin-4-yl)amino)-19,19-dimethyl-16-oxo-3,6,9,12-tetraoxa-15-azaicosan-20-oate (Compound 4)

Step 1: Synthesis of tert-butyl (14-((2-(2,6-dioxopiperidin-3-yl)-1,3-dioxoisoindolin-4-yl)amino)-3,6,9,12-tetraoxatetradecyl)carbamate (13c)

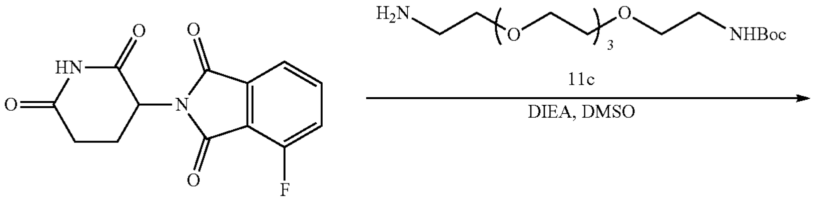

11

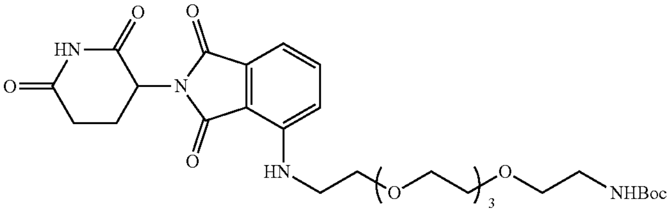

13c

In a manner similar to Step 1 of Example 2, the titled compound (1 g, 1.69 mmol, 18.92% yield) was obtained as a brown oil.

Step 2: Synthesis of 4-((14-amino-3,6,9,12-tetraoxatetradecyl)amino)-2-(2,6-dioxopiperidin-3-yl) isoindoline-1,3-dione (14c)

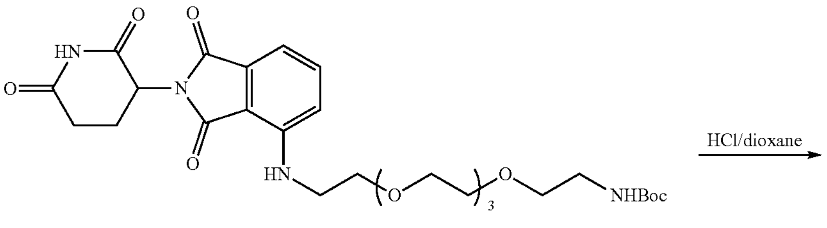

13c

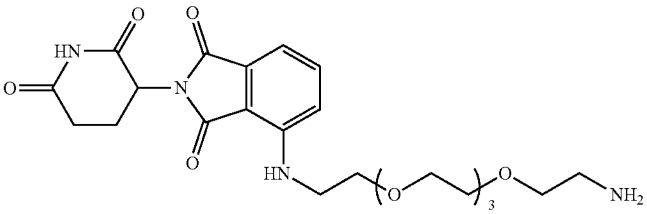

14c

In a manner similar to Step 2 of Example 2, the titled compound (0.3 g, 0.6 mmol, 36.10% yield) was obtained as a brown oil.

Step 3: Synthesis of (1S,3R,7S,8S,8aR)-8-(2-((2R, 4R)-4-hydroxy-6-oxotetrahydro-2H-pyran-2-yl) ethyl)-3,7-dimethyl-1,2,3,7,8,8a-hexahydronaphthalen-1-yl 1-((2-(2,6-dioxopiperidin-3-yl)-1,3-dioxoisoindolin-4-yl)amino)-19,19-dimethyl-16-oxo-3,6,9,12-tetraoxa-15-azaicosan-20-oate (Compound 4)

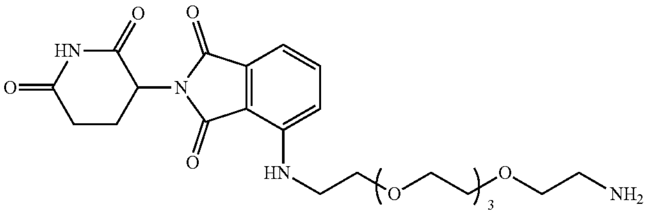

14c

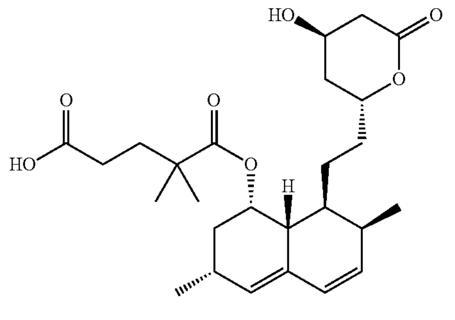

5

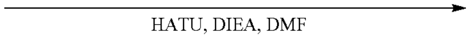

-continued

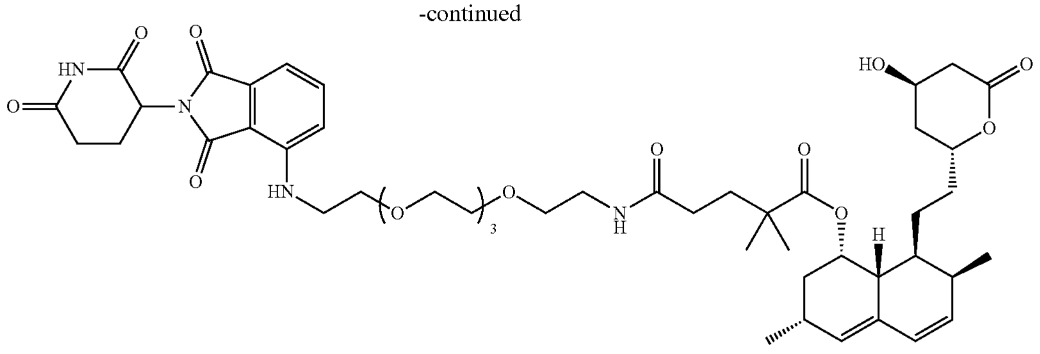

Compound 4

In a manner similar to Step 3 of Example 2, the titled compound (16.6 mg, 0.016 mmol, 7.76% yield, 94.7% purity) was obtained as a yellow solid.

MS $(M+H)^+$=937.3

$^1$H NMR (400 MHz, DMSO-$d_6$) δ 11.09 (s, 1H), 7.62-7.55 (m, 1H), 7.46 (t, J=5.6 Hz, 1H), 7.15 (d, J=8.6 Hz, 1H), 7.04 (d, J=7.0 Hz, 1H), 6.60 (t, J=5.6 Hz, 1H), 5.93 (d, J=9.6 Hz, 1H), 5.77 (dd, J=5.8, 9.6 Hz, 1H), 5.48 (s, 1H), 5.18 (d, J=2.8 Hz, 2H), 5.05 (dd, J=5.4, 12.8 Hz, 1H), 4.48 (dd, J=7.6, 11.2 Hz, 1H), 4.10 (d, J=3.2 Hz, 1H), 3.64-3.59 (m, 2H), 3.58-3.51 (m, 4H), 3.50-3.43 (m, 8H), 3.37-3.34 (m, 4H), 3.16 (q, J=6.2 Hz, 2H), 2.94-2.82 (m, 1H), 2.65-2.54 (m, 2H), 2.42-2.30 (m, 4H), 2.26 (d, J=14.0 Hz, 1H), 2.22-2.12 (m, 1H), 2.07-1.98 (m, 2H), 1.93-1.74 (m, 3H), 1.71-1.55 (m, 5H), 1.40-1.21 (m, 3H), 1.08-1.01 (m, 6H), 0.98 (d, J=7.4 Hz, 3H), 0.83 (d, J=7.0 Hz, 3H).

Example 5. Synthesis of (1S,3R,7S,8S,8aR)-8-(2-((2R,4R)-4-hydroxy-6-oxotetrahydro-2H-pyran-2-yl)ethyl)-3,7-dimethyl-1,2,3,7,8,8a-hexahydronaphthalen-1-yl 1-((2-(2,6-dioxopiperidin-3-yl)-1,3-dioxoisoindolin-4-yl)amino)-22,22-dimethyl-19-oxo-3,6,9,12,15-pentaoxa-18-azatricosan-23-oate (Compound 5)

Step 1: Synthesis of tert-butyl (17-((2-(2,6-dioxopiperidin-3-yl)-1,3-dioxoisoindolin-4-yl)amino)-3,6,9,12,15-pentaoxaheptadecyl)carbamate (13d)

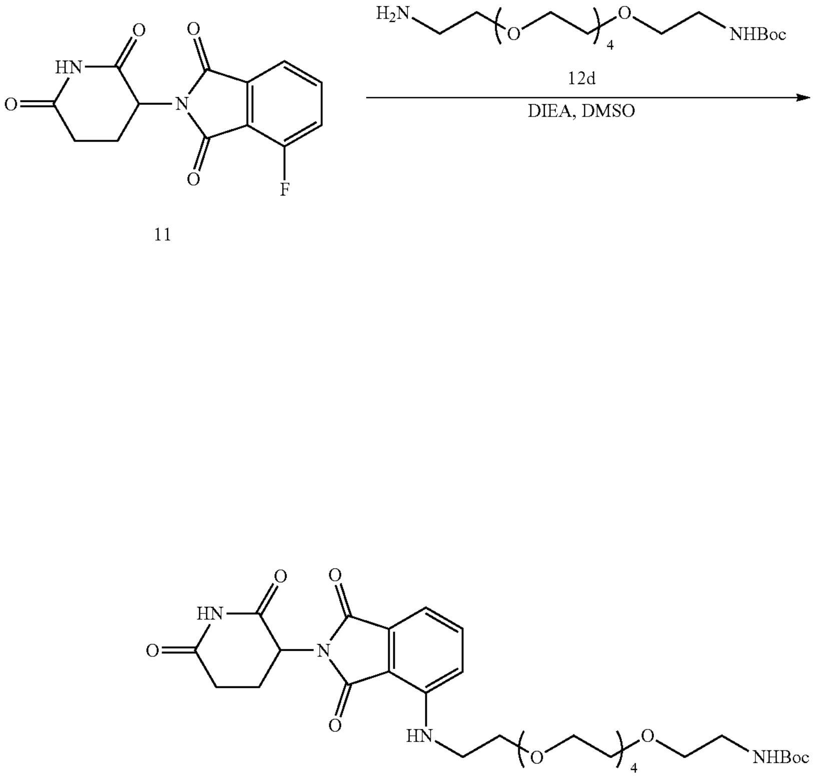

11

13d

In a manner similar to Step 1 of Example 2, the titled compound (0.4 g, 0.63 mmol, 23.90% yield) was obtained as a black oil.

Step 2: Synthesis of 4-((17-amino-3,6,9,12,15-pentaoxaheptadecyl)amino)-2-(2,6-dioxopiperidin-3-yl) isoindoline-1,3-dione (14d)

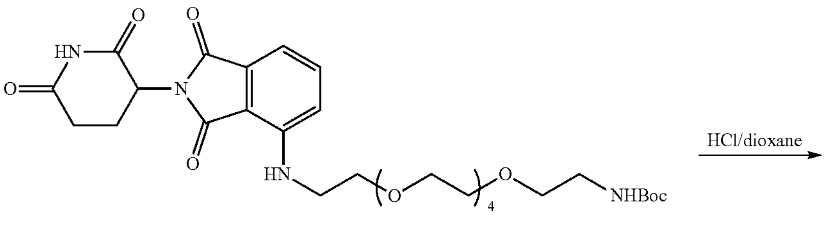

13d

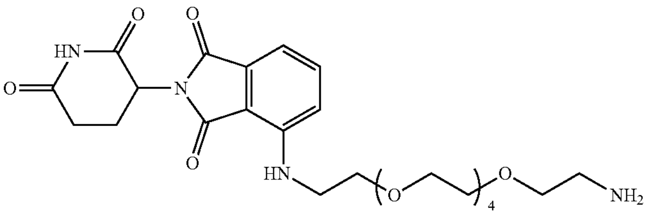

14d

In a manner similar to Step 2 of Example 2, the titled compound (0.4 g, crude, HCl) was obtained as a brown oil. MS $(M+H)^+=537.2$ Step 3: Synthesis of (1S,3R,7S,8S,8aR)-8-(2-((2R, 4R)-4-hydroxy-6-oxotetrahydro-2H-pyran-2-yl) ethyl)-3,7-dimethyl-1,2,3,7,8,8a-hexahydronaphthalen-1-yl 1-((2-(2,6-dioxopiperidin-3-yl)-1,3-dioxoisoindolin-4-yl)amino)-22,22-dimethyl-19-oxo-3,6,9,12,15-pentaoxa-18-azatricosan-23-oate (Compound 5)

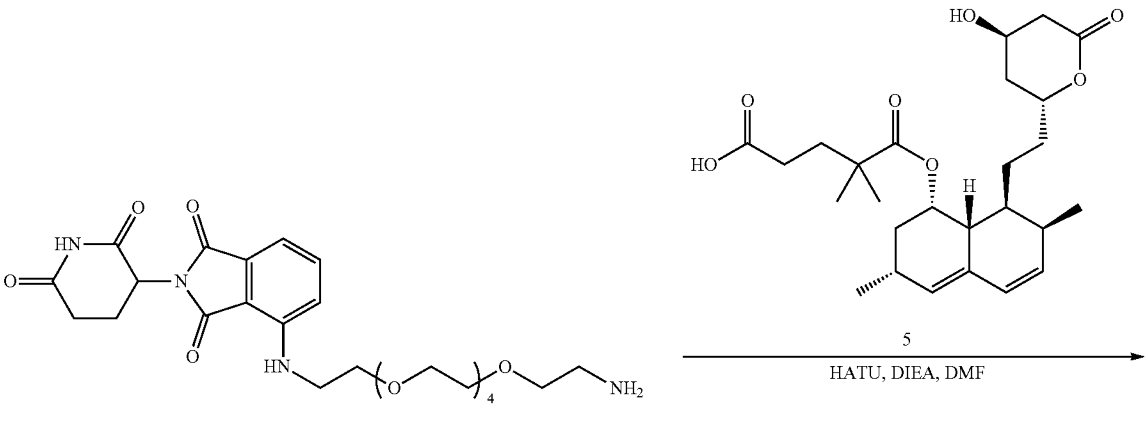

14d

-continued

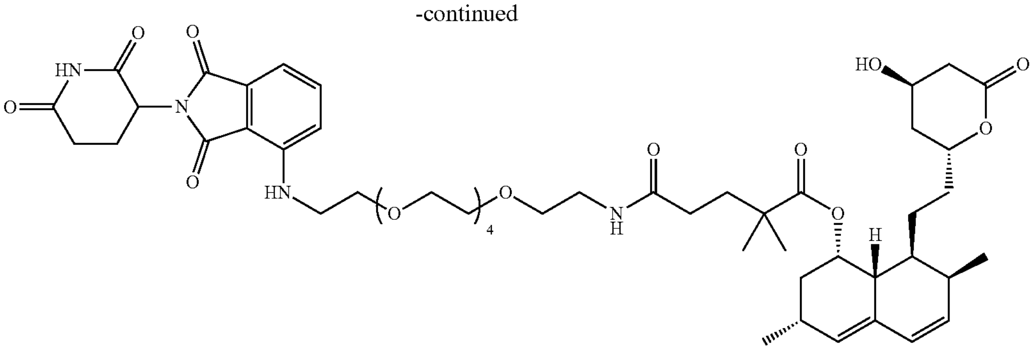

Compound 5

In a manner similar to Step 3 of Example 2, the titled compound (22.1 mg, 0.02 mmol, 13.84% yield, 94% purity) was obtained as a yellow solid.

MS $(M+H)^+$=981.3

$^1$H NMR (400 MHz, DMSO-$d_6$) δ 11.1 (s, 1H), 7.58 (dd, J=7.2, 8.4 Hz, 1H), 7.47 (t, J=5.6 Hz, 1H), 7.15 (d, J=8.6 Hz, 1H), 7.04 (d, J=7.0 Hz, 1H), 6.60 (t, J=5.6 Hz, 1H), 5.93 (d, J=9.8 Hz, 1H), 5.77 (dd, J=5.8, 9.4 Hz, 1H), 5.48 (s, 1H), 5.18 (d, J=2.8 Hz, 2H), 5.05 (dd, J=5.2, 12.8 Hz, 1H), 4.53-4.42 (m, 1H), 4.10 (d, J=2.8 Hz, 1H), 3.64-3.59 (m, 2H), 3.58-3.51 (m, 4H), 3.51-3.44 (m, 14H), 3.37-3.34 (m, 2H), 3.16 (q, J=6.0 Hz, 2H), 2.96-2.82 (m, 1H), 2.64-2.52 (m, 2H), 2.42-2.30 (m, 4H), 2.27 (d, J=12.2 Hz, 1H), 2.22-2.11 (m, 1H), 2.07-1.97 (m, 2H), 1.93-1.74 (m, 3H), 1.71-1.56 (m, 5H), 1.41-1.19 (m, 3H), 1.03 (d, J=5.2 Hz, 6H), 0.99 (d, J=7.4 Hz, 3H), 0.83 (d, J=6.8 Hz, 3H).

Example 6. Synthesis of (1S,3R,7S,8S,8aR)-8-(2-((2R,4R)-4-hydroxy-6-oxotetrahydro-2H-pyran-2-yl)ethyl)-3,7-dimethyl-1,2,3,7,8,8a-hexahydronaphthalen-1-yl 1-((2-(2,6-dioxopiperidin-3-yl)-1,3-dioxoisoindolin-4-yl)amino)-25,25-dimethyl-22-oxo-3,6,9,12,15,18-hexaoxa-21-azahexacosan-26-oate (Compound 6)

Step 1: Synthesis of tert-butyl (20-((2-(2,6-dioxopiperidin-3-yl)-1,3-dioxoisoindolin-4-yl)amino)-3,6,9,12,15,18-hexaoxaicosyl)carbamate (13e)

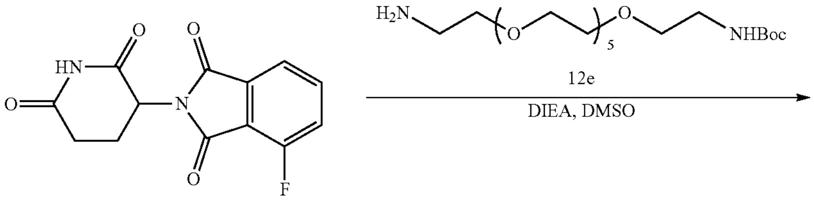

11

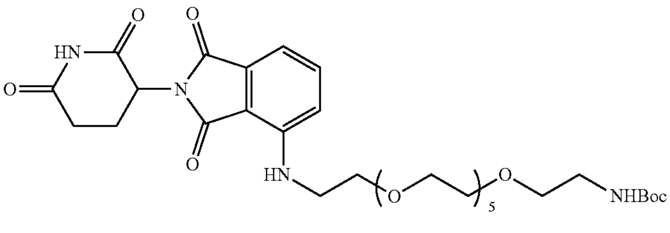

13e

In a manner similar to Step 1 of Example 2, the titled compound (0.8 g, 0.93 mmol, 39.46% yield, 79% purity) was obtained as a brown oil.

Step 2: Synthesis of 4-((20-amino-3,6,9,12,15,18-hexaoxaicosyl)amino)-2-(2,6-dioxopiperidin-3-yl) isoindoline-1,3-dione (14e)

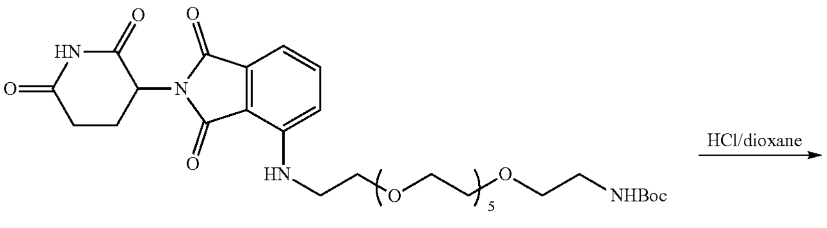

13e

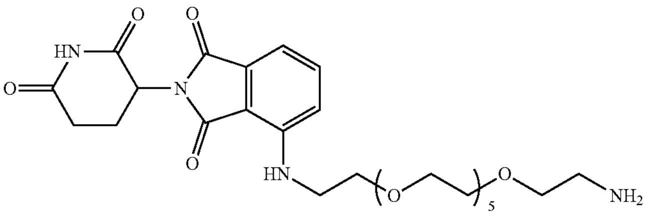

14e

In a manner similar to Step 2 of Example 2, the titled compound (0.8 g, crude, HCl) was obtained as a brown oil. MS $(M+H)^+=581.2$.

Step 3: Synthesis of (1S,3R,7S,8S,8aR)-8-(2-((2R,4R)-4-hydroxy-6-oxotetrahydro-2H-pyran-2-yl)ethyl)-3,7-dimethyl-1,2,3,7,8,8a-hexahydronaphthalen-1-yl 1-((2-(2,6-dioxopiperidin-3-yl)-1,3-dioxoisoindolin-4-yl)amino)-25,25-dimethyl-22-oxo-3,6,9,12,15,18-hexaoxa-21-azahexacosan-26-oate (Compound 6)

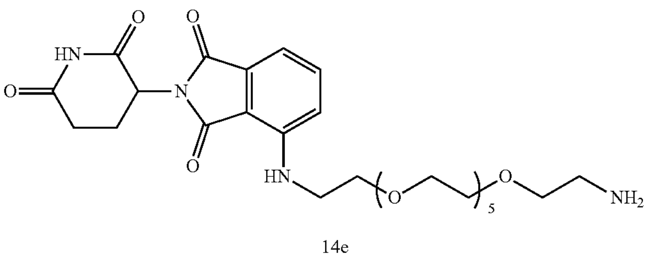

14e

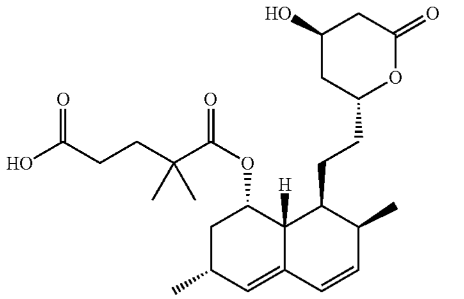

5

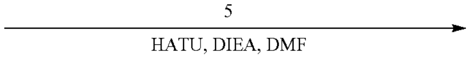

-continued

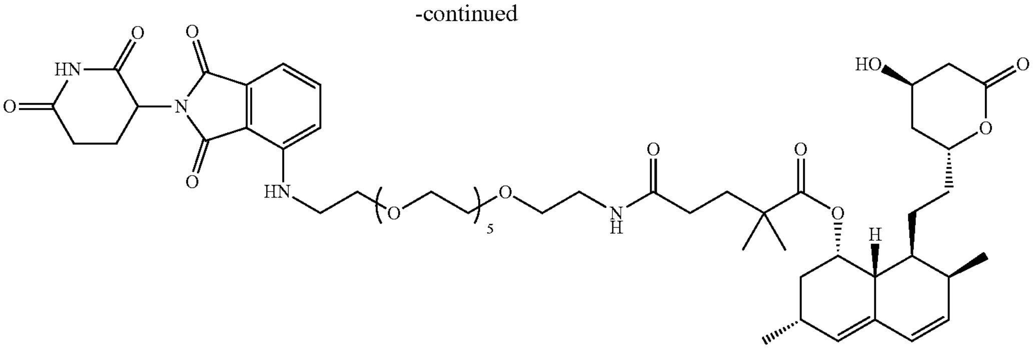

Compound 6

In a manner similar to Step 3 of Example 2, the titled compound (40.4 mg, 0.034 mmol, 16.15% yield, 88.6% purity) was obtained as a yellow solid.

MS $(M+H)^+$=1025.4

$^1$H NMR (400 MHz, DMSO-$d_6$) δ 11.10 (s, 1H), 7.59 (dd, J=8.6, 7.1 Hz, 1H), 7.49 (t, J=5.6 Hz, 1H), 7.15 (d, J=8.6 Hz, 1H), 7.05 (d, J=7.0 Hz, 1H), 6.61 (t, J=5.8 Hz, 1H), 5.94 (d, J=9.7 Hz, 1H), 5.78 (dd, J=9.6, 5.9 Hz, 1H), 5.49 (d, J=4.5 Hz, 1H), 5.25-5.13 (m, 2H), 5.06 (dd, J=12.9, 5.4 Hz, 1H), 4.57-4.42 (m, 1H), 4.11 (s, 1H), 3.63 (t, J=5.4 Hz, 2H), 3.59-3.55 (m, 2H), 3.55-3.52 (m, 2H), 3.52-3.44 (m, 18H), 3.17 (q, J=6.0 Hz, 2H), 2.95-2.83 (m, 1H), 2.65-2.54 (m, 3H), 2.44-2.24 (m, 5H), 2.23-2.12 (m, 1H), 2.10-1.99 (m, 2H), 1.95-1.75 (m, 3H), 1.75-1.56 (m, 5H), 1.43-1.22 (m, 3H), 1.04 (d, J=5.4 Hz, 6H), 0.99 (d, J=7.4 Hz, 3H), 0.84 (d, J=7.0 Hz, 3H).

Example 7. Synthesis of (1S,3R,7S,8S,8aR)-8-(2-((2R,4R)-4-hydroxy-6-oxotetrahydro-21H-pyran-2-yl)ethyl)-3,7-dimethyl-1,2,3,7,8,8a-hexahydronaphthalen-1-yl 2,2,20,20-tetramethyl-5,17-dioxo-7,10,13-trioxa-4,16-diazahenicosan-21-oate (Compound 7)

Step 1: Synthesis of (1S,3R,7S,8S,8aR)-8-(2-((2R,4R)-4-hydroxy-6-oxotetrahydro-2H-pyran-2-yl)ethyl)-3,7-dimethyl-1,2,3,7,8,8a-hexahydronaphthalen-1-yl 2,2,20,20-tetramethyl-5,17-dioxo-7,10,13-trioxa-4,16-diazahenicosan-21-oate (Compound 7)

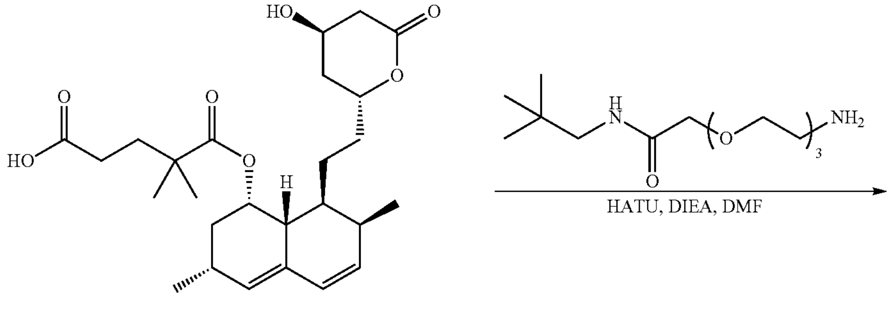

5

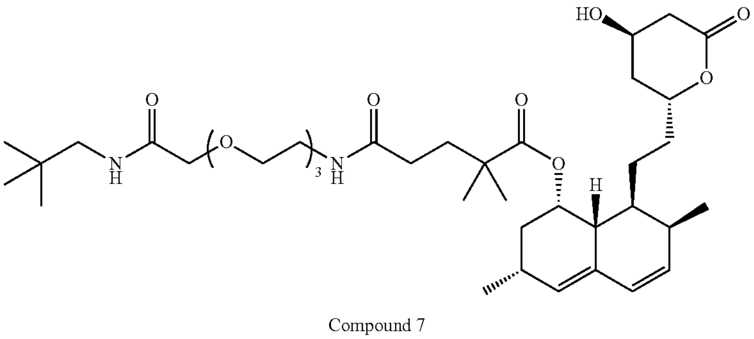

Compound 7

In a manner similar to Step 3 of Example 2, the titled compound (42.2 mg, 53.85 μmol, 35.59% yield, 92% purity) was obtained as a yellow oil.

MS $(M+H)^+=721.3$ $^1H$ NMR (400 MHz, DMSO-$d_6$) δ 7.52-7.41 (m, 2H), 5.94 (d, J=9.5 Hz, 1H), 5.78 (dd, J=6.0, 9.6 Hz, 1H), 5.49 (s, 1H), 5.18 (d, J=3.2 Hz, 2H), 4.55-4.48 (m, 1H), 4.10 (d, J=3.3 Hz, 1H), 3.90 (s, 2H), 3.60-3.54 (m, 4H), 3.53-3.46 (m, 4H), 3.39-3.33 (m, 2H), 3.17 (q, J=6.0 Hz, 2H), 2.94 (d, J=6.5 Hz, 2H), 2.61 (dd, J=4.5, 17.2 Hz, 1H), 2.43-2.31 (m, 4H), 2.28 (d, J=12.1 Hz, 1H), 2.22-2.13 (m, 1H), 2.07-1.99 (m, 1H), 1.94-1.74 (m, 3H), 1.73-1.56 (m, 5H), 1.41-1.22 (m, 3H), 1.03 (d, J=5.2 Hz, 6H), 0.99 (d, J=7.3 Hz, 3H), 0.84 (s, 12H).

Example 8. Synthesis of (1S,3R,7S,8S,8aR)-8-(2-((2R,4R)-4-hydroxy-6-oxotetrahydro-2H-pyran-2-yl)ethyl)-3,7-dimethyl-1,2,3,7,8,8a-hexahydronaphthalen-1-yl 5-((2-(2-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-2-oxoethoxy)ethyl)amino)-2,2-dimethyl-5-oxopentanoate (Compound 8)

Step 1: Synthesis of tert-butyl (2-(2-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-2-oxoethoxy)ethyl)carbamate (16a)

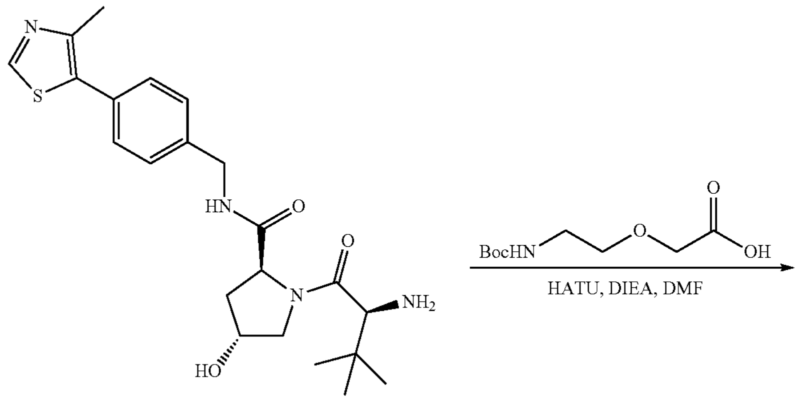

15

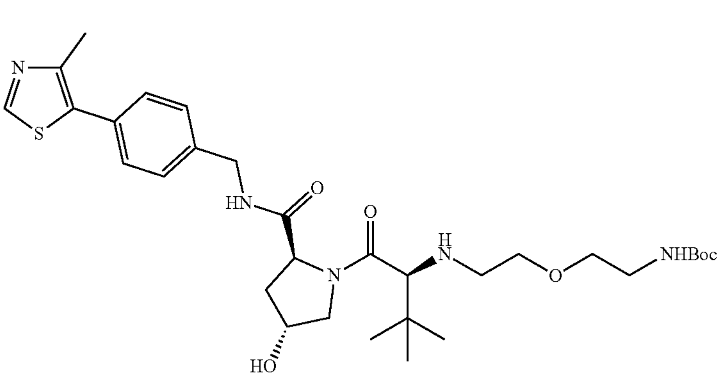

16a

To a mixture of 2-(2-((tert-butoxycarbonyl)amino) ethoxy)acetic acid (250.00 mg, 1.14 mmol) and DIEA (450.25 mg, 3.48 mmol, 0.6 mL, 3 eq) in DMF (6 mL) was added HATU (500.00 mg, 1.31 mmol), the mixture was stirred at 25° C. for 10 min, and then a solution of (2S,4R)-1-((S)-2-amino-3,3-dimethylbutanoyl)-4-hydroxy-N-(4-(4-methylthiazol-5-yl)benzyl)pyrrolidine-2-carboxamide (0.5 g, 1.16 mmol, 1 eq) in DMF (2 mL) was added, the resulting mixture was stirred at 25° C. for 3 h. LCMS showed a peak (40%) with desired mass. The mixture was filtered and the filtrate was purified by reversed-phase HPLC (0.1% FA condition, 48% ACN) to give tert-butyl (2-(2-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-2-oxoethoxy)ethyl)carbamate (0.5 g, 0.79 mmol, 34.08% yield) as brown oil. MS $(M+H)^+$=632.3

Step 2: Synthesis of (2S,4R)-1-((S)-2-(2-(2-amino-ethoxy)acetamido)-3,3-dimethylbutanoyl)-4-hydroxy-N-(4-(4-methylthiazol-5-yl)benzyl)pyrrolidine-2-carboxamide (17a)

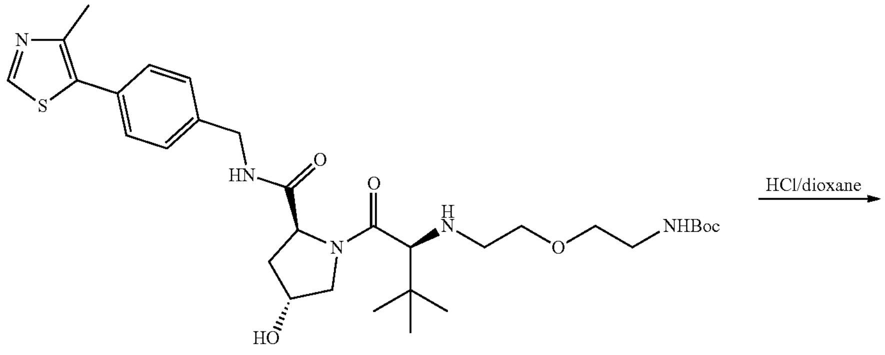

16a

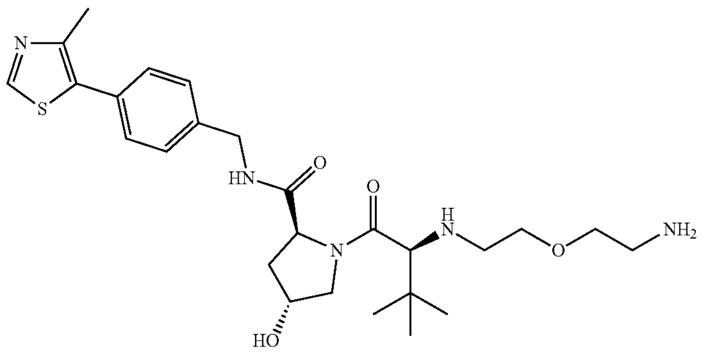

17a

A mixture of tert-butyl (2-(2-(((S)-1-((2S,4R)-4-hydroxy-2-((4-(4-methylthiazol-5-yl)benzyl) carbamoyl)pyrrolidin-1-yl)-3,3-dimethyl-1-oxobutan-2-yl)amino)-2-oxoethoxy) ethyl)carbamate (0.5 g, 0.79 mmol) in HCl/dioxane (4 M, 20 mL) was stirred at 25° C. for 3 h. LCMS showed a main peak with desired mass. The mixture was concentrated under vacuum to give (2S,4R)-1-((S)-2-(2-(2-aminoethoxy)acetamido)-3,3-dimethylbutanoyl)-4-hydroxy-N-(4-(4-methylthiazol-5-yl)benzyl)pyrrolidine-2-carboxamide (0.4 g, 0.7 mmol, 88.96% yield, HCl) as yellow solid which was used directly in the next step. MS $(M+H)^+$=532.5

Step 3: Synthesis of (1S,3R,7S,8S,8aR)-8-(2-((2R,4R)-4-hydroxy-6-oxotetrahydro-2H-pyran-2-yl)ethyl)-3,7-dimethyl-1,2,3,7,8,8a-hexahydronaphthalen-1-yl 5-((2-(2-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-2-oxoethoxy)ethyl)amino)-2,2-dimethyl-5-oxopentanoate (Compound 8)

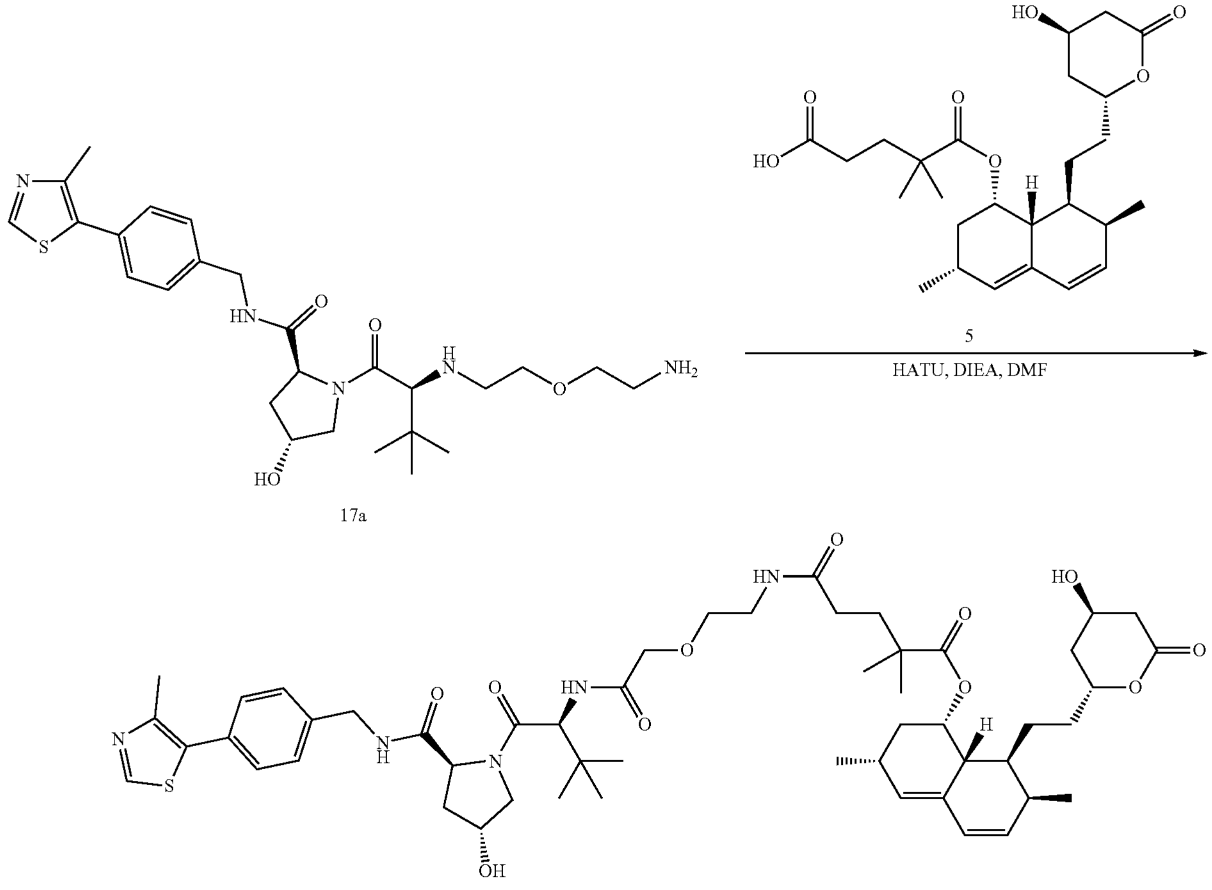

17a

5

Compound 8

To a solution of 5-[[(1S,3R,7S,8S,8aR)-8-[2-[(2R,4R)-4-hydroxy-6-oxo-tetrahydropyran-2-yl]ethyl]-3,7-dimethyl-1,2,3,7,8,8a-hexahydronaphthalen-1-yl]oxy]-4,4-dimethyl-5-oxo-pentanoic acid (60 mg, 0.129 mmol), DIPEA (33.53 mg, 0.259 mmol, 45.19 μL) in DMF (2 mL) was added HATU (59.18 mg, 0.155 mmol) and the resulting mixture was stirred at 25° C. for 10 min. Then (2S,4R)-1-((S)-2-(2-(2-aminoethoxy)acetamido)-3,3-dimethylbutanoyl)-4-hydroxy-N-(4-(4-methylthiazol-5-yl)benzyl)pyrrolidine-2-carboxamide (75 mg, 0.13 mmol, HCl salt) was added, the mixture was stirred at 25° C. for 1 h. LCMS showed a peak (42%) with desired mass. The pH was adjusted to 7-8 with 50% formic acid and filtered. The filtrate was purified by prep-HPLC (column: UniSil 3-100 C18 Ultra (150*25 mm*3 μm); mobile phase: [water (0.225% FA)-ACN]; B %: 45%-75%, 10 min) followed by lyophilization to afford (1S,3R,7S,8S,8aR)-8-(2-((2R,4R)-4-hydroxy-6-oxotetrahydro-2H-pyran-2-yl)ethyl)-3,7-dimethyl-1,2,3,7,8,8a-hexahydronaphthalen-1-yl 5-((2-(2-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-2-oxoethoxy)ethyl)amino)-2,2-dimethyl-5-oxopentanoate (10.2 mg, 0.097 mmol, 7.51% yield, 93.2% purity) as white solid. MS $(M+H)^+$=976.3

$^1H$ NMR (400 MHz, DMSO-$d_6$) δ 8.98 (s, 1H), 8.58 (t, J=5.9 Hz, 1H), 7.58 (t, J=5.5 Hz, 1H), 7.44 (d, J=9.5 Hz, 1H), 7.40 (s, 4H), 5.93 (d, J=9.6 Hz, 1H), 5.81-5.73 (m, 1H), 5.48 (s, 1H), 5.18 (d, J=3.4 Hz, 2H), 5.14 (d, J=3.6 Hz, 1H), 4.56 (d, J=9.5 Hz, 1H), 4.52-4.33 (m, 4H), 4.25 (dd, J=15.8, 5.6 Hz, 1H), 4.15-4.07 (m, 1H), 3.93 (d, J=2.0 Hz, 2H), 3.70-3.57 (m, 2H), 3.46 (t, J=6.0 Hz, 2H), 3.26-3.18 (m, 2H), 2.61 (dd, J=17.3, 4.5 Hz, 1H), 2.44 (s, 3H), 2.41-2.34 (m, 3H), 2.30-2.23 (m, 1H), 2.23-2.12 (m, 1H), 2.09-2.00 (m, 2H), 1.94-1.86 (m, 2H), 1.85-1.74 (m, 2H), 1.71-1.56 (m, 5H), 1.42-1.21 (m, 3H), 1.04 (d, J=4.8 Hz, 6H), 0.98 (d, J=7.2 Hz, 3H), 0.94 (s, 9H), 0.83 (d, J=6.9 Hz, 3H).

Example 9. Synthesis of (S)-(1S,3R,7S,8S,8aR)-8-(2-((2R,4R)-4-hydroxy-6-oxotetrahydro-2H-pyran-2-yl)ethyl)-3,7-dimethyl-1,2,3,7,8,8a-hexahydronaphthalen-1-yl 3-((2S,4R)-4-hydroxy-2-((4-(4-methylthiazol-5-yl)benzyl)carbamoyl)pyrrolidine-1-carbonyl)-2,2,17,17-tetramethyl-5,14-dioxo-7,10-dioxa-4,13-diazaoctadecan-18-oate (Compound 9)

Step 1: Synthesis of tert-butyl (2-(2-(2-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-2-oxoethoxy)ethoxy)ethyl) carbamate (16b)

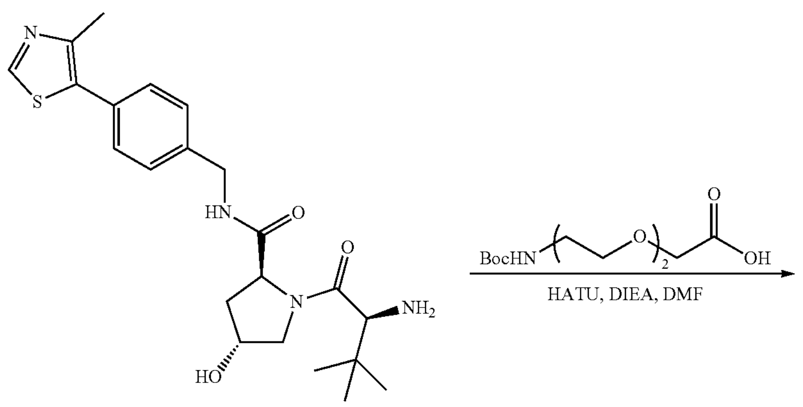

15

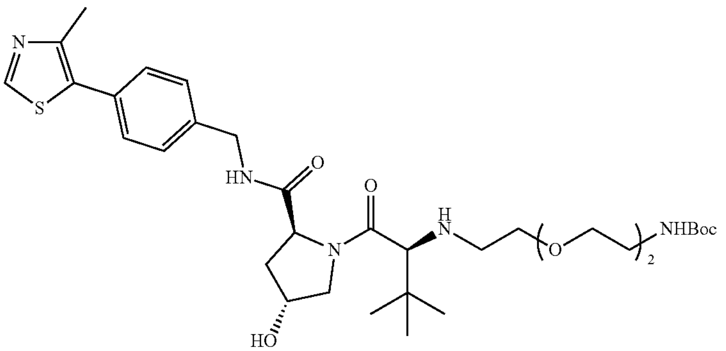

16b

In a manner similar to Step 1 of Example 8, the titled compound (0.6 g, 0.89 mmol, 54.61% yield) was obtained as a brown oil.

Step 2: Synthesis of (2S,4R)-1-((S)-2-(2-(2-(2-aminoethoxy)ethoxy)acetamido)-3,3-dimethylbutanoyl)-4-hydroxy-N-(4-(4-methylthiazol-5-yl)benzyl)pyrrolidine-2-carboxamide (17b)
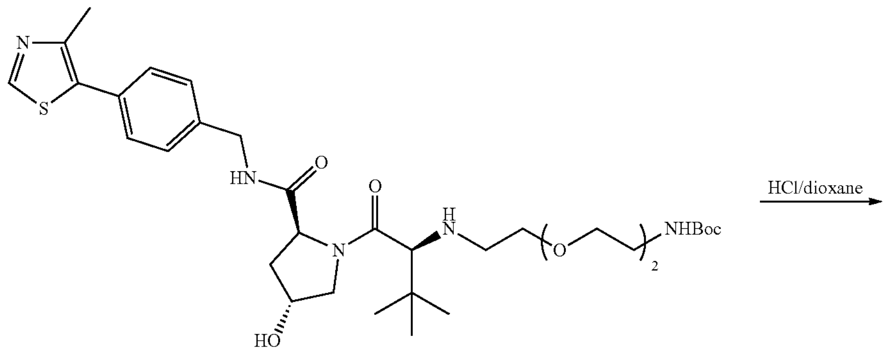
16b
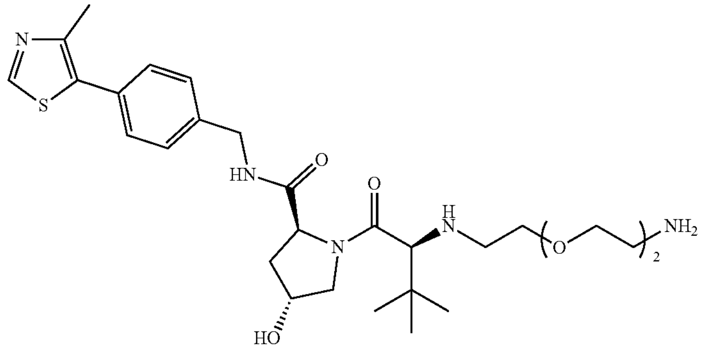
17b
In a manner similar to Step 2 of Example 8, the titled compound (0.5 g, 0.82 mmol, 92.00% yield, HCl salt) was obtained as a yellow solid.

Step 3: Synthesis of (S)-(1S,3R,7S,8S,8aR)-8-(2-((2R,4R)-4-hydroxy-6-oxotetrahydro-2H-pyran-2-yl)ethyl)-3,7-dimethyl-1,2,3,7,8,8a-hexahydronaphthalen-1-yl 3-((2S,4R)-4-hydroxy-2-((4-(4-methylthiazol-5-yl)benzyl)carbamoyl)pyrrolidine-1-carbonyl)-2,2,17,17-tetramethyl-5,14-dioxo-7,10-dioxa-4,13-diazaoctadecan-18-oate (Compound 9)

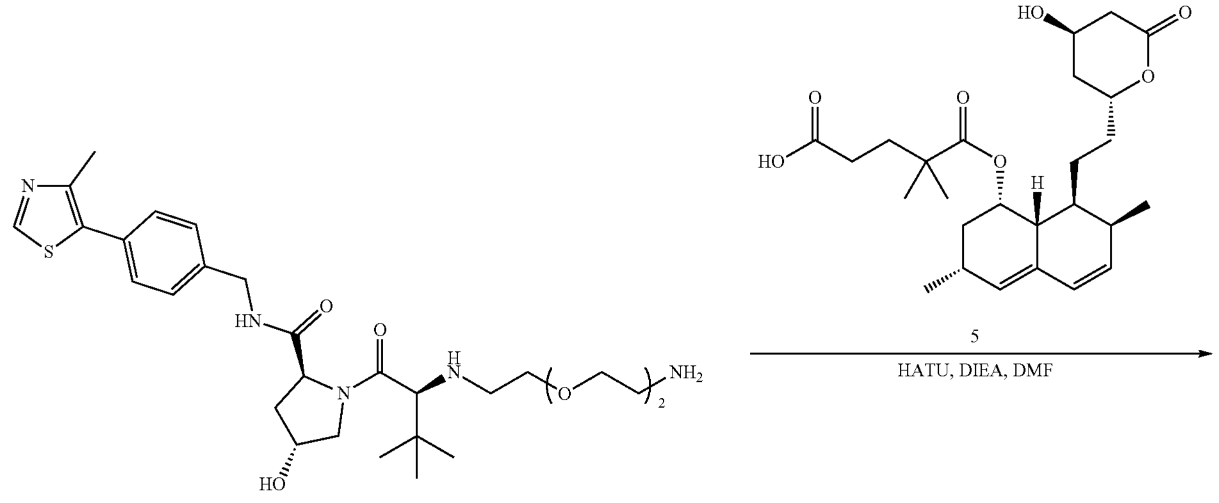

5

17b

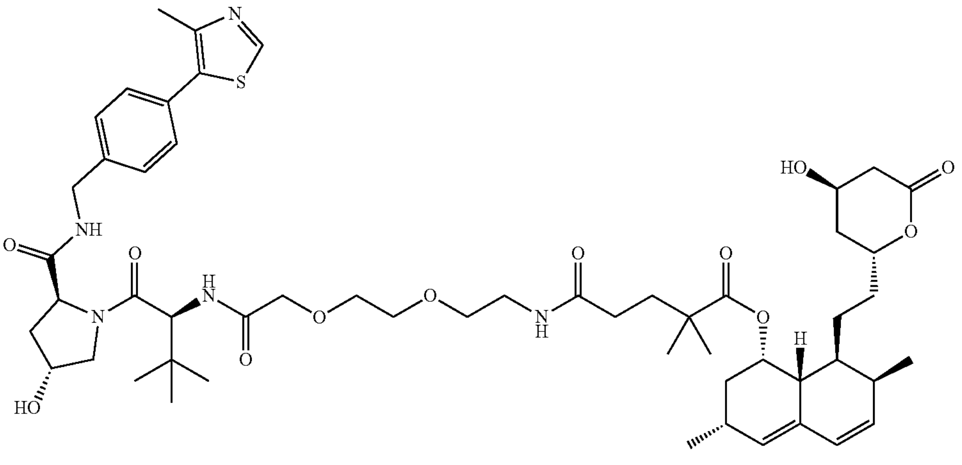

Compound 9

In a manner similar to Step 3 of Example 8, the titled compound (11.2 mg, 0.1 mmol, 7.68% yield, 90.7% purity) was obtained as a white solid.

MS $(M+H)^+$=1020.4

$^1$H NMR (400 MHz, DMSO-$d_6$) δ 8.98 (s, 1H), 8.58 (t, J=5.9 Hz, 1H), 7.57-7.35 (m, 6H), 5.94 (d, J=9.7 Hz, 1H), 5.83-5.73 (m, 1H), 5.49 (s, 1H), 5.18 (dd, J=11.3, 3.5 Hz, 3H), 4.58 (d, J=9.6 Hz, 1H), 4.53-4.39 (m, 2H), 4.39-4.34 (m, 1H), 4.31-4.21 (m, 1H), 4.14-4.06 (m, 1H), 3.96 (s, 2H), 3.72-3.65 (m, 1H), 3.63-3.58 (m, 2H), 3.53 (d, J=5.1 Hz, 2H), 3.43-3.38 (m, 2H), 3.30-3.27 (m, 1H), 3.23-3.17 (m, 2H), 2.69-2.66 (m, 1H), 2.62 (dd, J=17.3, 4.6 Hz, 1H), 2.45 (s, 3H), 2.42-2.38 (m, 1H), 2.38-2.36 (m, 1H), 2.36-2.31 (m, 2H), 2.27 (d, J=13.2 Hz, 1H), 2.22-2.12 (m, 1H), 2.10-1.99 (m, 2H), 1.95-1.86 (m, 2H), 1.86-1.76 (m, 2H), 1.72-1.57 (m, 5H), 1.42-1.21 (m, 3H), 1.03 (d, J=5.5 Hz, 6H), 0.99 (d, J=7.3 Hz, 3H), 0.95 (s, 9H), 0.84 (d, J=6.9 Hz, 3H).

Example 10. Synthesis of (S)-(1S,3R,7S,8S,8aR)-8-(2-((2R,4R)-4-hydroxy-6-oxotetrahydro-2H-pyran-2-yl)ethyl)-3,7-dimethyl-1,2,3,7,8,8a-hexahydronaphthalen-1-yl 3-((2S,4R)-4-hydroxy-2-((4-(4-methylthiazol-5-yl)benzyl)carbamoyl)pyrrolidine-1-carbonyl)-2,2,17,17-tetramethyl-5,14-dioxo-7,10-dioxa-4,13-diazaoctadecan-18-oate (Compound 10)

Step 1: Synthesis of tert-butyl ((S)-13-((2R,4R)-4-hydroxy-2-((4-(4-methylthiazol-5-yl)benzyl)carbamoyl)pyrrolidine-1-carbonyl)-14,14-dimethyl-11-oxo-3,6,9-trioxa-12-azapentadecyl)carbamate (16c)

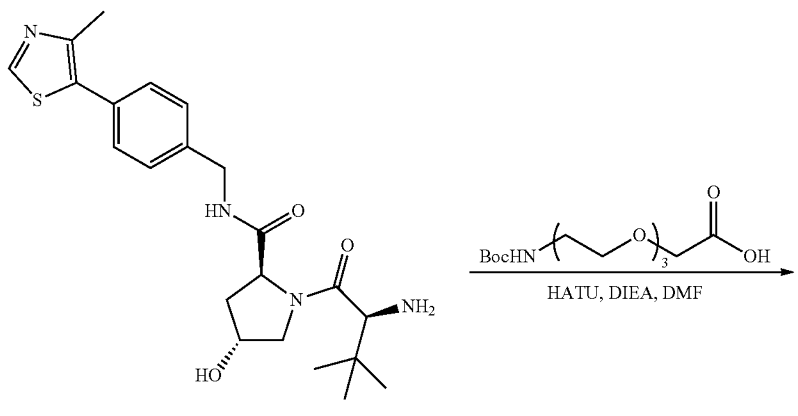

15

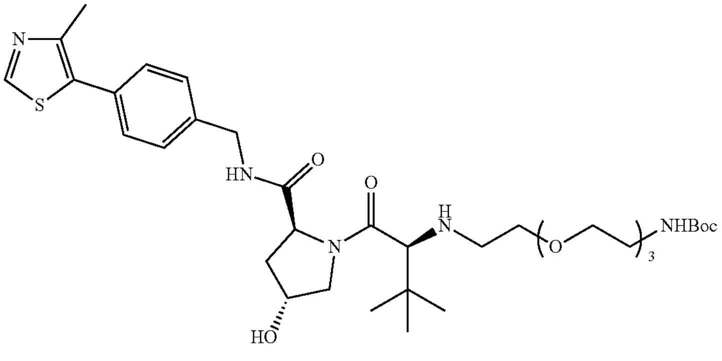

16c

In a manner similar to Step 1 of Example 8, the titled compound (0.7 g, 0.97 mmol, 59.81% yield) was obtained as a brown oil.
MS $(M+H)^+$=720.4
Step 2: Synthesis of (2R,4R)-1-((S)-14-amino-2-(tert-butyl)-4-oxo-6,9,12-trioxa-3-azatetradecan-1-oyl)-4-hydroxy-N-(4-(4-methylthiazol-5-yl)benzyl) pyrrolidine-2-carboxamide (17c)
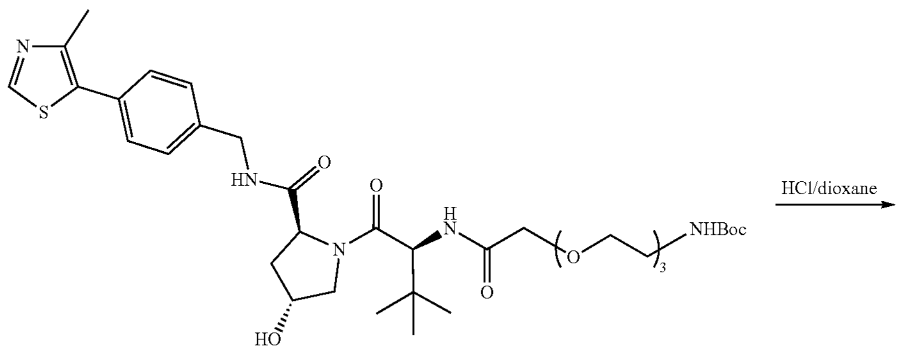
16c
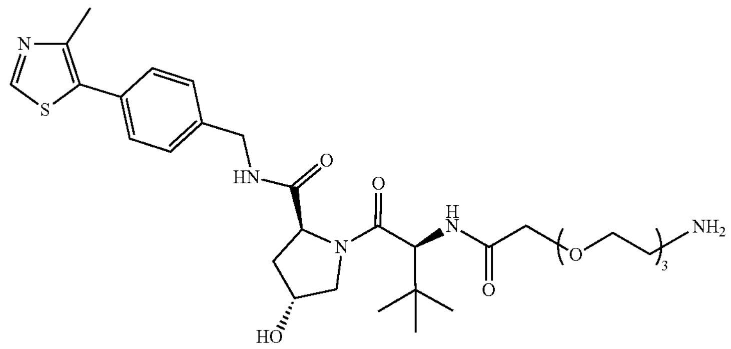
17c
In a manner similar to Step 2 of Example 8, the titled compound (0.6 g, 0.91 mmol, 94.03% yield, HCl) was obtained as a yellow solid.

Step 3: Synthesis of (S)-(1S,3R,7S,8S,8aR)-8-(2-((2R,4R)-4-hydroxy-6-oxotetrahydro-2H-pyran-2-yl)ethyl)-3,7-dimethyl-1,2,3,7,8,8a-hexahydronaphthalen-1-yl 3-((2S,4R)-4-hydroxy-2-((4-(4-methylthiazol-5-yl)benzyl)carbamoyl)pyrrolidine-1-carbonyl)-2,2,17,17-tetramethyl-5,14-dioxo-7,10-dioxa-4,13-diazaoctadecan-18-oate (Compound 10)

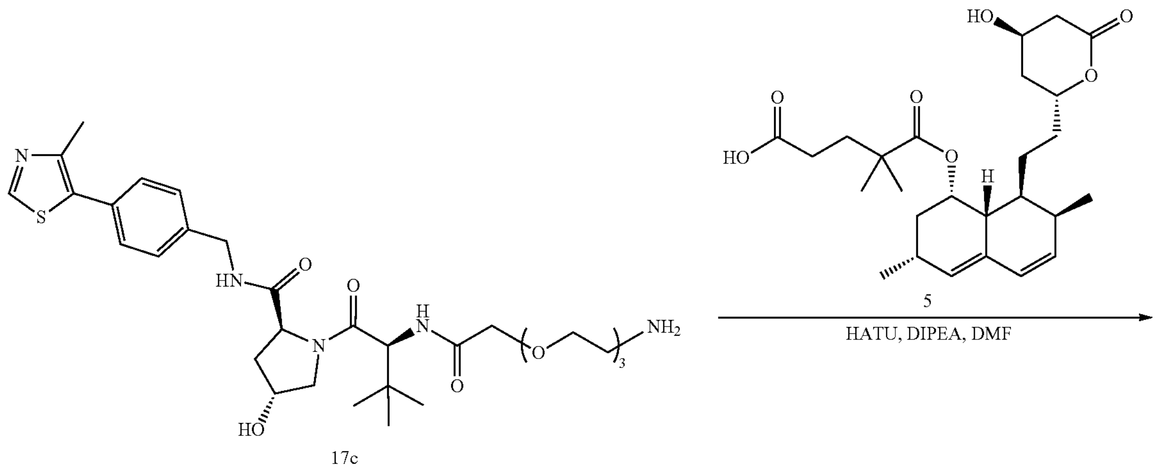

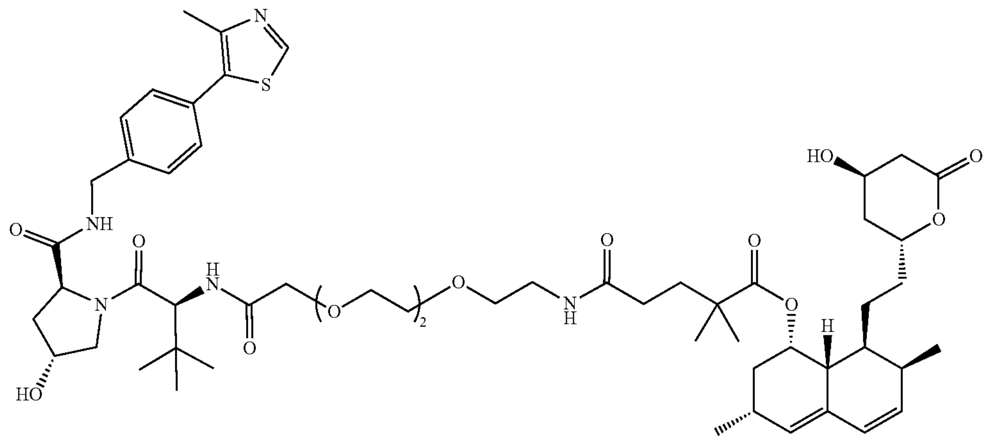

Compound 10

In a manner similar to Step 3 of Example 8, the titled compound (11.6 mg, 0.00985 mmol, 9.12% yield, 90.4% purity) was obtained as a white solid.

MS $(M+H)^+$=1064.4

$^1H$ NMR (400 MHz, DMSO-$d_6$) δ 8.99 (s, 1H), 8.59 (t, J=6.0 Hz, 1H), 7.49-7.43 (m, 2H), 7.40 (s, 4H), 5.94 (d, J=9.7 Hz, 1H), 5.83-5.74 (m, 1H), 5.49 (s, 1H), 5.18 (d, J=3.5 Hz, 2H), 5.15 (d, J=3.6 Hz, 1H), 4.57 (d, J=9.5 Hz, 1H), 4.47-4.33 (m, 3H), 4.26 (dd, J=15.7, 5.6 Hz, 1H), 4.14-4.07 (m, 1H), 3.97 (s, 2H), 3.71-3.65 (m, 1H), 3.61 (d, J=5.6 Hz, 3H), 3.59-3.51 (m, 4H), 3.49 (d, J=4.2 Hz, 2H), 3.21-3.13 (m, 2H), 2.62 (dd, J=17.2, 4.5 Hz, 1H), 2.45 (s, 3H), 2.42-2.40 (m, 1H), 2.38-2.37 (m, 1H), 2.31-2.24 (m, 2H), 2.23-2.11 (m, 1H), 2.11-1.97 (m, 1H), 1.97-1.75 (m, 3H), 1.74-1.57 (m, 5H), 1.39-1.23 (m, 3H), 1.03 (d, J=5.7 Hz, 6H), 0.99 (d, J=7.3 Hz, 3H), 0.95 (s, 9H), 0.84 (d, J=6.9 Hz, 3H).

Example 11. Synthesis of (S)-(1S,3R,7S,8S,8aR)-8-(2-((2R,4R)-4-hydroxy-6-oxotetrahydro-2H-pyran-2-yl)ethyl)-3,7-dimethyl-1,2,3,7,8,8a-hexahydronaphthalen-1-yl 3-((2S,4R)-4-hydroxy-2-((4-(4-methylthiazol-5-yl)benzyl)carbamoyl)pyrrolidine-1-carbonyl)-2,2,23,23-tetramethyl-5,20-dioxo-7,10,13,16-tetraoxa-4,19-diazatetracosan-24-oate (Compound 11)

Step 1: Synthesis of tert-butyl ((S)-16-((2S,4R)-4-hydroxy-2-((4-(4-methylthiazol-5-yl)benzyl)carbamoyl)pyrrolidine-1-carbonyl)-17,17-dimethyl-14-oxo-3,6,9,12-tetraoxa-15-azaoctadecyl)carbamate (16d)

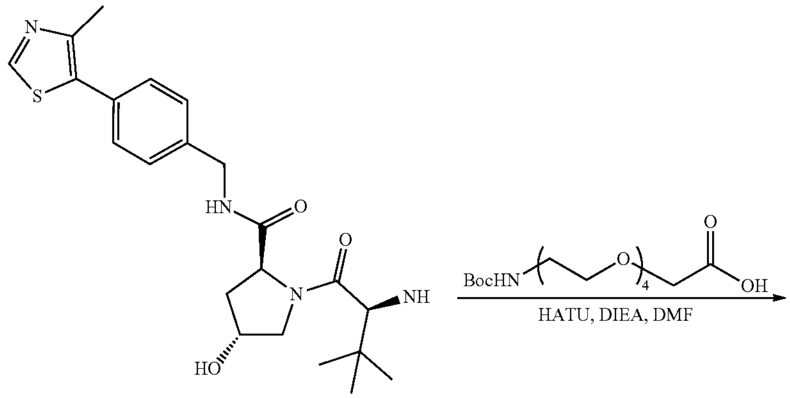

15

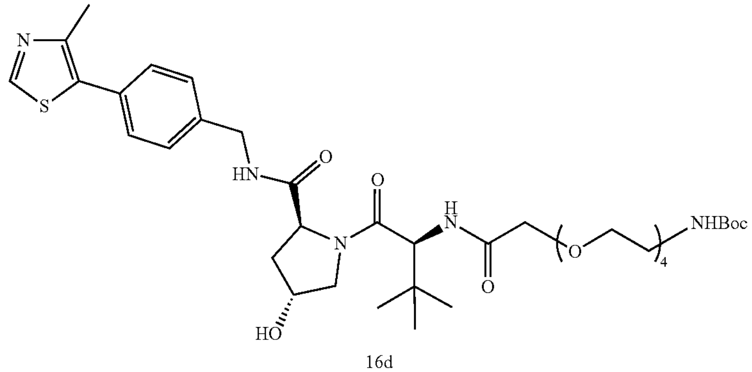

16d

In a manner similar to Step 1 of Example 8, the titled compound (0.45 g, 0.59 mmol, 36.14% yield) was obtained as a brown oil.

MS $(M+H)^+$=764.2

Step 2: Synthesis of (2S,4R)-1-((S)-17-amino-2-(tert-butyl)-4-oxo-6,9,12,15-tetraoxa-3-azaheptadecan-1-oyl)-4-hydroxy-N-(4-(4-methylthiazol-5-yl)benzyl)pyrrolidine-2-carboxamide (17d)
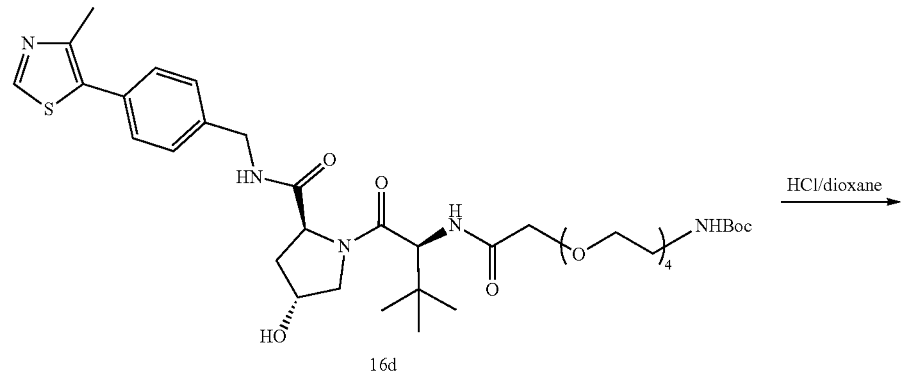
16d
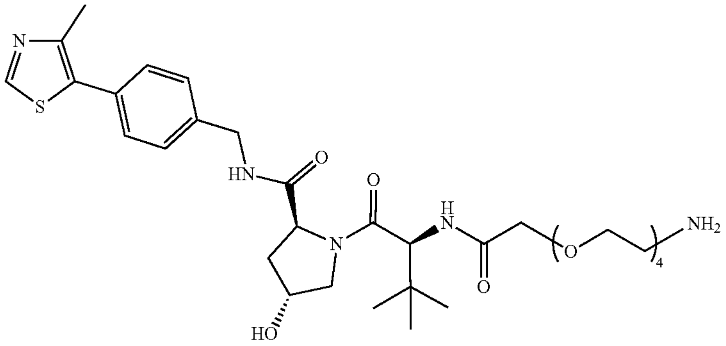
17d
In a manner similar to Step 2 of Example 8, the titled compound (0.4 g, 0.57 mmol, 96.97% yield, HCl) was obtained as a yellow oil.
MS $(M+H)^+$=664.2

Step 3: Synthesis of (S)-(1S,3R,7S,8S,8aR)-8-(2-((2R,4R)-4-hydroxy-6-oxotetrahydro-2H-pyran-2-yl)ethyl)-3,7-dimethyl-1,2,3,7,8,8a-hexahydronaphthalen-1-yl 3-((2S,4R)-4-hydroxy-2-((4-(4-methylthiazol-5-yl)benzyl)carbamoyl)pyrrolidine-1-carbonyl)-2,2,23,23-tetramethyl-5,20-dioxo-7,10,13,16-tetraoxa-4,19-diazatetracosan-24-oate (Compound 11)

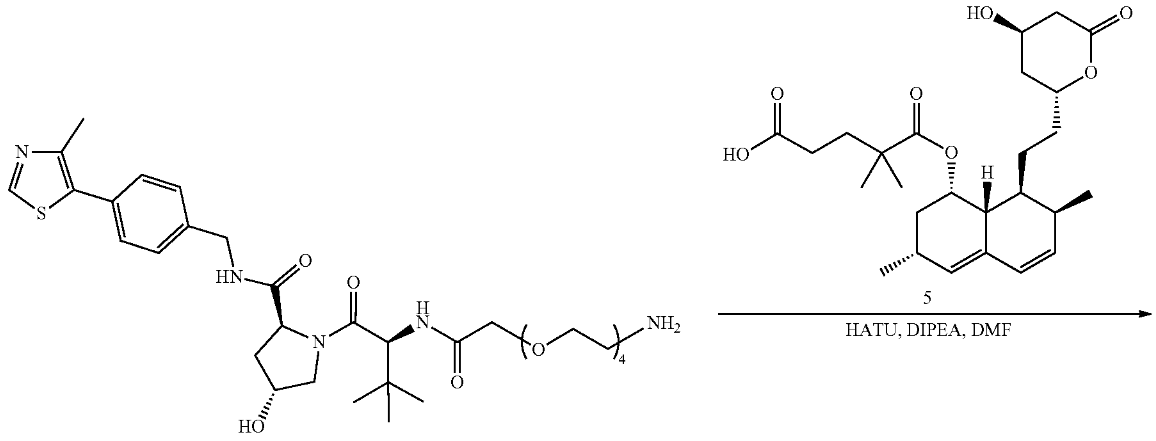

17d

5

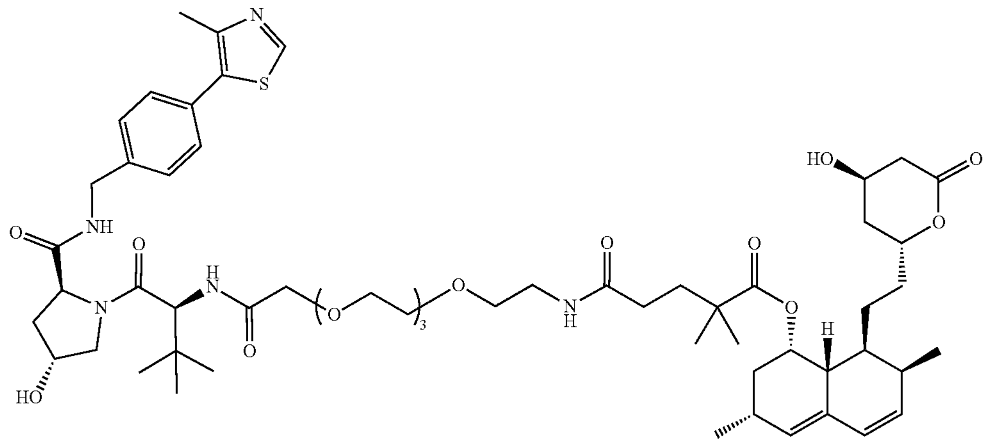

Compound 11

In a manner similar to Step 3 of Example 8, the titled compound (17 mg, 0.014 mmol, 13.31% yield, 93.8% purity) was obtained as a white solid.

MS $(M+H)^+$=1108.4

$^1$H NMR (400 MHz, DMSO-$d_6$) δ 8.98 (s, 1H), 8.59 (t, J=5.87 Hz, 1H), 7.48-7.35 (m, 6H), 5.93 (d, J=9.54 Hz, 1H), 5.81-5.73 (m, 1H), 5.48 (s, 1H), 5.16 (dd, J=3.36, 13.02 Hz, 3H), 4.56 (d, J=9.66 Hz, 1H), 4.51-4.40 (m, 3H), 4.39-4.32 (m, 2H), 4.29-4.21 (m, 1H), 4.10-4.05 (m, 1H), 3.96 (s, 2H), 3.70-3.63 (m, 1H), 3.63-3.49 (m, 16H), 3.19-3.13 (m, 2H), 2.65-2.57 (m, 1H), 2.46-2.43 (m, 3H), 2.30-2.42 (m, 2H), 2.30-2.13 (m, 1H), 2.09-1.99 (m, 1H), 1.95-1.74 (m, 4H), 1.71-1.56 (m, 5H), 1.40-1.14 (m, 3H), 1.03 (d, J=5.75 Hz, 6H), 0.98 (d, J=7.34 Hz, 3H), 0.96-0.92 (m, 9H), 0.83 (d, J=6.97 Hz, 3H).

Example 12. Synthesis of (S)-(1S,3R,7S,8S,8aR)-8-(2-((2R,4R)-4-hydroxy-6-oxotetrahydro-2H-pyran-2-yl)ethyl)-3,7-dimethyl-1,2,3,7,8,8a-hexahydronaphthalen-1-yl 3-((2S,4R)-4-hydroxy-2-((4-(4-methylthiazol-5-yl)benzyl)carbamoyl)pyrrolidine-1-carbonyl)-2,2,26,26-tetramethyl-5,23-dioxo-7,10,13,16,19-pentaoxa-4,22-diazaheptacosan-27-oate (Compound 12)

Step 1: Synthesis of (9H-fluoren-9-yl)methyl ((S)-19-((2S,4R)-4-hydroxy-2-((4-(4-methylthiazol-5-yl)benzyl)carbamoyl)pyrrolidine-1-carbonyl)-20,20-dimethyl-17-oxo-3,6,9,12,15-pentaoxa-18-azahenicosyl)carbamate (16e)

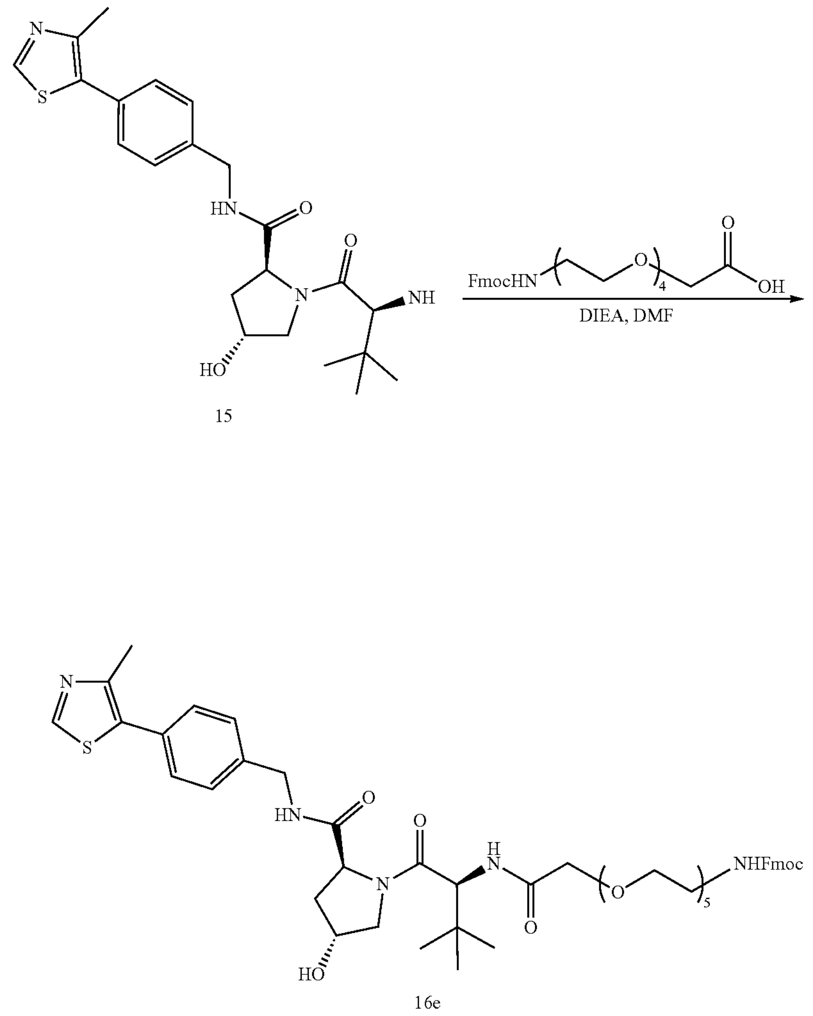

15

16e

To a solution of 1-(9H-fluoren-9-yl)-3-oxo-2,7,10,13,16,19-hexaoxa-4-azahenicosan-21-oic acid (0.35 g, 0.67 mmol, 1 eq) and DIEA (104.88 mg, 0.81 mmol, 0.14 mL) in DMF (5 mL) was added (2S,4R)-1-((S)-2-amino-3,3-dimethylbutanoyl)-4-hydroxy-N-(4-(4-methylthiazol-5-yl)benzyl)pyrrolidine-2-carboxamide (208.33 mg, 0.74 mmol) at 0° C., the mixture was stirred at 0-25° C. for 30 min, and then (2S,4R)-1-((S)-2-amino-3,3-dimethylbutanoyl)-4-hydroxy-N-(4-(4-methylthiazol-5-yl)benzyl)pyrrolidine-2-carboxamide (291.16 mg, 0.67 mmol) was added, the resulting mixture was stirred at 25° C. for 1 h. LCMS showed a peak with desired mass. The mixture was filtered, the filtrate was purified by reversed-phase HPLC (0.1% FA condition, 70% ACN) to afford (9H-fluoren-9-yl)methyl ((S)-19-((2S,4R)-4-hydroxy-2-((4-(4-methylthiazol-5-yl)benzyl)carbamoyl)pyrrolidine-1-carbonyl)-20,20-dimethyl-17-oxo-3,6,9,12,15-pentaoxa-18-azahenicosyl)carbamate (0.8 g, 0.86 mmol, 63.59% yield) as brown oil.

MS $(M+H)^+$=930.2

Step 2: Synthesis of (2S,4R)-1-((S)-20-amino-2-(tert-butyl)-4-oxo-6,9,12,15,18-pentaoxa-3-azaicosan-1-oyl)-4-hydroxy-N-(4-(4-methylthiazol-5-yl)benzyl)pyrrolidine-2-carboxamide (17e)

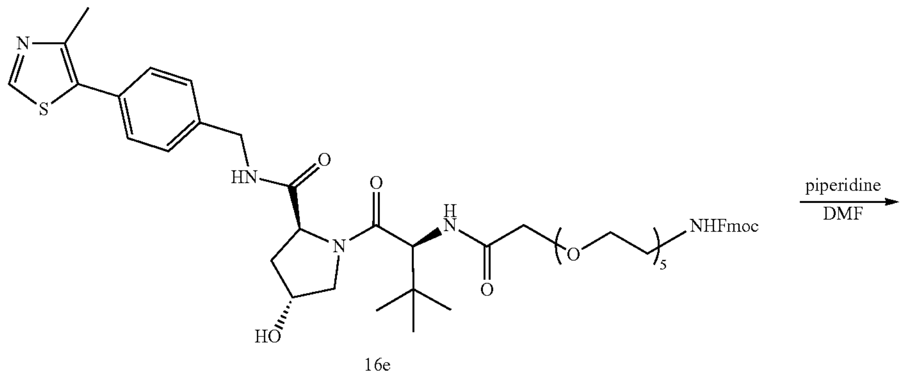

16e

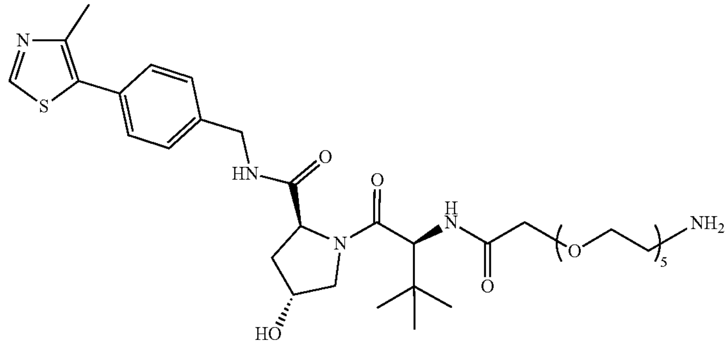

17e

To a solution of (9H-fluoren-9-yl)methyl ((S)-19-((2S,4R)-4-hydroxy-2-((4-(4-methylthiazol-5-yl) benzyl)carbamoyl)pyrrolidine-1-carbonyl)-20,20-dimethyl-17-oxo-3,6,9,12,15-pentaoxa-18-azahenicosyl)carbamat (0.8 g, 0.86 mmol) in DMF (8 mL) was added piperidine (1.72 g, 20.25 mmol, 2 mL), the resulting mixture was stirred at 25° C. for 1 h. LCMS showed a peak with desired mass. The pH was adjusted to 8-9 by 1 N HCl, the mixture was extracted with EA (20 mL×3), the aqueous phase was concentrated under high vacuum, The solution was purified directly by reversed-phase HPLC (0.1% $NH_3 \cdot H_2O$) followed by lyophilization to afford (2S,4R)-1-((S)-20-amino-2-(tert-butyl)-4-oxo-6,9,12,15,18-pentaoxa-3-azaicosan-1-oyl)-4-hydroxy-N-(4-(4-methylthiazol-5-yl)benzyl)pyrrolidine-2-carboxamide (0.4 g, 0.565 mmol, 65.70% yield) as yellow oil.

MS $(M+H)^+$=708.3

Step 3: Synthesis of (S)-(1S,3R,7S,8S,8aR)-8-(2-((2R,4R)-4-hydroxy-6-oxotetrahydro-2H-pyran-2-yl)ethyl)-3,7-dimethyl-1,2,3,7,8,8a-hexahydronaphthalen-1-yl 3-((2S,4R)-4-hydroxy-2-((4-(4-methylthiazol-5-yl)benzyl)carbamoyl)pyrrolidine-1-carbonyl)-2,2,26,26-tetramethyl-5,23-dioxo-7,10,13,16,19-pentaoxa-4,22-diazaheptacosan-27-oate (Compound 12)

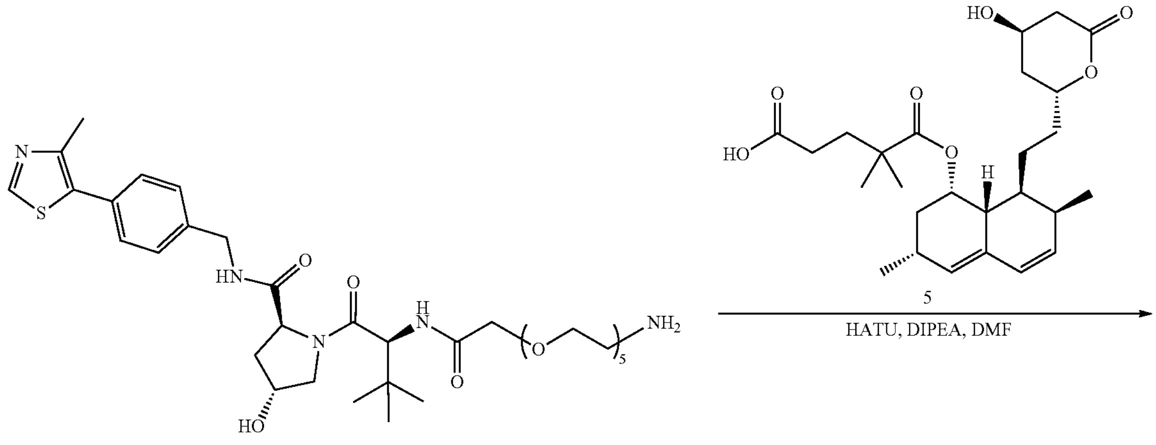

17e

5

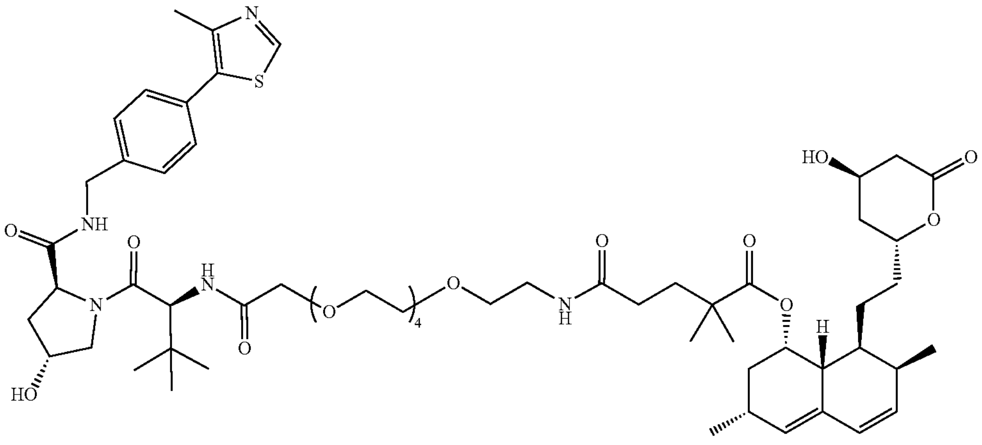

Compound 12

In a manner similar to Step 3 of Example 8, the titled compound (70.5 mg, 0.054 mmol, 41.98% yield, 89% purity) was obtained as a white solid.

MS $(M+H)^+$=1152.4

$^1$H NMR (400 MHz, DMSO-$d_6$) δ 8.98 (s, 1H), 8.59 (t, J=6.0 Hz, 1H), 7.49-7.38 (m, 6H), 5.93 (d, J=9.6 Hz, 1H), 5.81-5.73 (m, 1H), 5.48 (s, 1H), 5.16 (dd, J=13.1, 3.5 Hz, 3H), 4.56 (d, J=9.5 Hz, 1H), 4.52-4.33 (m, 4H), 4.25 (dd, J=15.8, 5.6 Hz, 1H), 4.13-4.05 (m, 1H), 3.96 (s, 2H), 3.69-3.64 (m, 1H), 3.63-3.59 (m, 3H), 3.59-3.56 (m, 2H), 3.56-3.52 (m, 2H), 3.52-3.49 (m, 2H), 3.46 (d, J=5.5 Hz, 8H), 3.36-3.34 (m, 2H), 3.16 (q, J=6.0 Hz, 2H), 2.61 (dd, J=17.2, 4.5 Hz, 1H), 2.44 (s, 3H), 2.41-2.39 (m, 1H), 2.37-2.35 (m, 1H), 2.27 (d, J=12.9 Hz, 2H), 2.22-2.13 (m, 1H), 2.08-1.99 (m, 2H), 1.93-1.87 (m, 2H), 1.85-1.82 (m, 1H), 1.81-1.78 (m, 1H), 1.78-1.74 (m, 1H), 1.71-1.56 (m, 5H), 1.42-1.21 (m, 3H), 1.03 (d, J=5.4 Hz, 6H), 0.99 (d, J=7.3 Hz, 3H), 0.94 (s, 9H), 0.83 (d, J=6.9 Hz, 3H).

Example 13. Synthesis of (1S,3R,7S,8S,8aR)-8-(2-((2S,4S)-4-hydroxy-6-oxotetrahydro-2H-pyran-2-yl)ethyl)-3,7-dimethyl-1,2,3,7,8,8a-hexahydronaphthalen-1-yl (14,14-dimethyl-11-oxo-3,6,9-trioxa-12-azapentadecyl) carbamate (Compound 13)

Step 1: Synthesis of (4R,6R)-4-hydroxy-6-(2-((1S,2S,6R,8S,8aR)-8-hydroxy-2,6-dimethyl-1,2,6,7,8,8a-hexahydronaphthalen-1-yl)ethyl)tetrahydro-2H-pyran-2-one (20)

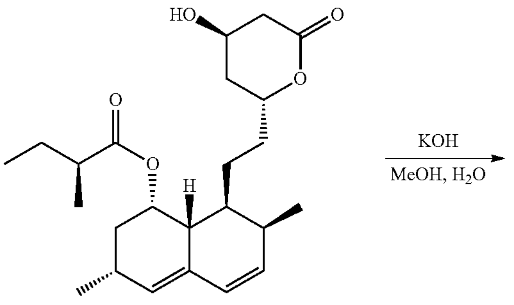

19

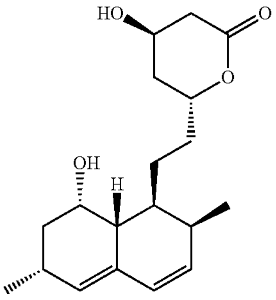

20

To a solution of [(1S,3R,7S,8S,8aR)-8-[2-[(2R,4R)-4-hydroxy-6-oxo-tetrahydropyran-2-yl]ethyl]-3,7-dimethyl-1,2,3,7,8,8ahexahydronaphthalen-1-yl] (2S)-2-methylbutanoate (10 g, 24.72 mmol) in MeOH (60 mL) H2O (10 mL) was added KOH (13.87 g, 247.19 mmol) and the reaction mixture was heated at 100° C. for 12 h. TLC showed the reaction was completed. The reaction mixture was cooled to rt, water (50 mL) was added. The mixture was concentrated under reduced pressure. The residue was dissolved in DCM (100 mL) and adjusted by 5 M HCl to pH=2. The resulting material was stirred for 4 h. Then the organic layer was separated, washed brine (50 mL) and dried over $Na_2SO_4$, filtered. The filtrate was concentrated under reduced pressure to give (4R,6R)-4-hydroxy-6-(2-((1S,2S,6R,8S,8aR)-8-hydroxy-2,6-dimethyl-1,2,6,7,8,8a-hexahydronaphthalen-1-yl)ethyl)tetrahydro-2H-pyran-2-one (9.6 g, crude) as yellow solid, which was used for next step without purification.

Step 2: Synthesis of (4R,6R)-4-((tert-butyldimethylsilyl)oxy)-6-(2-((1S,2S,6R,8S,8aR)-8-hydroxy-2,6-dimethyl-1,2,6,7,8,8a-hexahydronaphthalen-1-yl)ethyl)tetrahydro-2H-pyran-2-one (21)

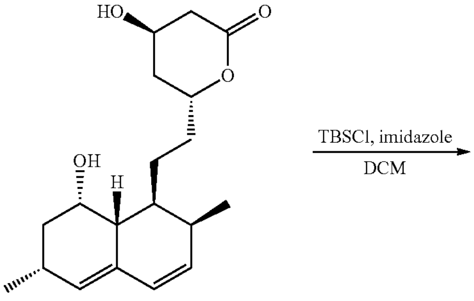

20

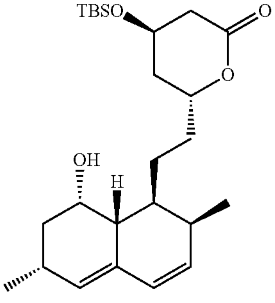

21

To a solution of (4R,6R)-4-hydroxy-6-(2-((1S,2S,6R,8S,8aR)-8-hydroxy-2,6-dimethyl-1,2,6,7,8,8a-hexahydronaphthalen-1-yl)ethyl)tetrahydro-2H-pyran-2-one (9.6 g, 29.96 mmol) in DCM (100 mL) was added TBSCl (6.77 g, 44.94 mmol, 5.51 mL) and Imidazole (4.08 g, 59.92 mmol). The reaction mixture was stirred for 12 h at 20° C. TLC showed the reaction was completed. The reaction mixture was quenched with water (100 mL), extracted with DCM (300 mL). The organic layer washed with brine (100 mL), dried over $Na_2SO_4$, filtered and the filtrate was concentrated under reduced pressure. The residue was purified by silica gel column (PE/EtOAc=30/1 to 5/1) to give (4R,6R)-4-((tert-butyldimethylsilyl)oxy)-6-(2-((1S,2S,6R,8S,8aR)-8-hydroxy-2,6-dimethyl-1,2,6,7,8,8a-hexahydronaphthalen-1-yl)ethyl)tetrahydro-2H-pyran-2-one (5.9 g, 13.57 mmol, 45.30% yield) as white solid.

Step 3: Synthesis of (1S,3R,7S,8S,8aR)-8-(2-((2R, 4R)-4-((tert-butyldimethylsilyl)oxy)-6-oxotetrahydro-2H-pyran-2-yl)ethyl)-3,7-dimethyl-1,2,3,7,8,8a-hexahydronaphthalen-1-yl (4-nitrophenyl) carbonate (18)

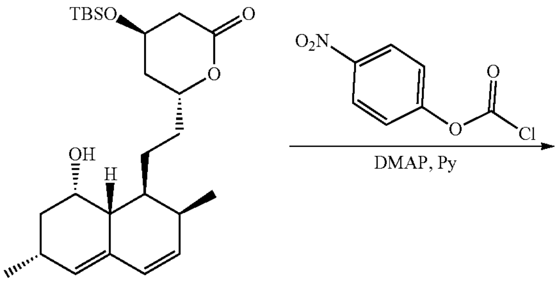

21

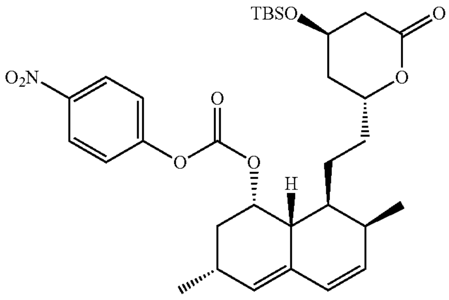

18

To a mixture of (4R,6R)-4-((tert-butyldimethylsilyl)oxy)-6-(2-((1S,2S,6R,8S,8aR)-8-hydroxy-2,6-dimethyl-1,2,6,7,8,8a-hexahydronaphthalen-1-yl)ethyl)tetrahydro-2H-pyran-2-one (5.00 g, 11.50 mmol) and DMAP (10.00 g, 81.85 mmol) in pyridine (80 mL) was added (4-nitrophenyl) carbonochloridate (16.23 g, 80.52 mmol) and the resulting mixture was stirred at 25° C. for 16 h. LCMS showed a peak with desired mass and the starting material was consumed. The mixture was poured into water (100 mL) and extracted with EtOAc (100 mL×3), the organic phase was washed with 1N HCL (100 mL×3), brine (100 mL×2) and concentrated under vacuum. The residue was purified by silica gel column chromatography (PE:EtOAc=10:1 to 4:1) to afford (1S,3R,7S,8S,8aR)-8-(2-((2R,4R)-4-((tert-butyldimethylsilyl)oxy)-6-oxotetrahydro-2H-pyran-2-yl)ethyl)-3,7-dimethyl-1,2,3,7,8,8a-hexahydronaphthalen-1-yl (4-nitrophenyl) carbonate (1.3 g, 2.17 mmol, 18.84% yield) as white solid and (1S,3R,7S,8S,8aR)-8-(2-((2R,4R)-4-((tert-butyldimethylsilyl)oxy)-6-oxotetrahydro-2H-pyran-2-yl)ethyl)-3,7-dimethyl-1,2,3,7,8,8a-hexahydronaphthalen-1-yl (4-nitrophenyl) carbonate (9 g, 7.20 mmol, 62.62% yield, 48% purity) as white solid.

$^1$H NMR (400 MHz, DMSO-$d_6$) δ 8.26-8.32 (m, 2H), 7.47-7.54 (m, 2H), 5.97 (d, J=9.66 Hz, 1H), 5.81 (dd, J=6.05, 9.60 Hz, 1H), 5.54 (br d, J=2.45 Hz, 1H), 5.25 (br d, J=2.81 Hz, 1H), 4.50-4.62 (m, 1H), 4.28 (t, J=3.30 Hz, 1H), 2.69 (dd, J=4.16, 17.24 Hz, 1H), 2.32-2.48 (m, 4H), 2.04 (br d, J=2.93 Hz, 2H), 1.67-1.84 (m, 4H), 1.45-1.64 (m, 2H), 1.28-1.40 (m, 1H), 1.11 (d, J=7.34 Hz, 3H), 0.82-0.91 (m, 3H), 0.77-0.80 (m, 9H), 0.01 (d, J=5.87 Hz, 6H)

Step 4: Synthesis of (1S,3R,7S,8S,8aR)-8-(2-((2S, 4S)-4-((tert-butyldimethylsilyl)oxy)-6-oxotetrahydro-2H-pyran-2-yl)ethyl)-3,7-dimethyl-1,2,3,7,8,8a-hexahydronaphthalen-1-yl (14,14-dimethyl-11-oxo-3,6,9-trioxa-12-azapentadecyl) carbamate (22)

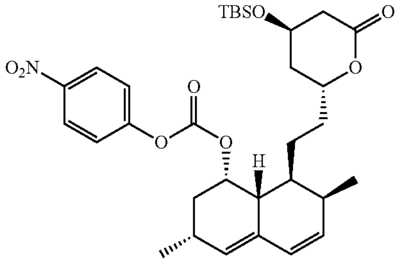

18

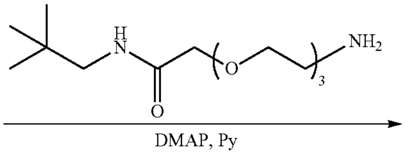

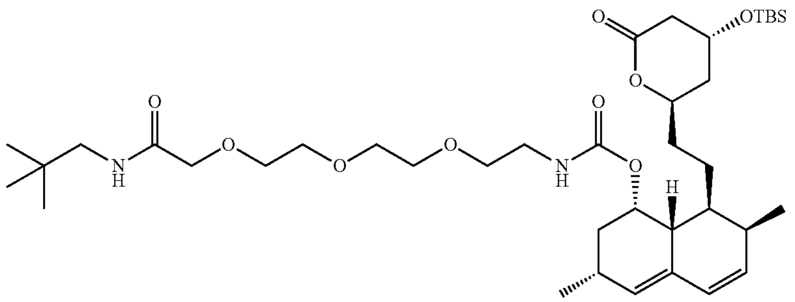

22

To a solution of 2-(2-(2-(2-aminoethoxy)ethoxy)ethoxy)-N-neopentylacetamide (0.15 g, 384.23 μmol, TFA) and (1S,3R,7S,8S,8aR)-8-(2-((2R,4R)-4-((tert-butyldimethylsilyl)oxy)-6-oxotetrahydro-2H-pyran-2-yl)ethyl)-3,7-dimethyl-1,2,3,7,8,8a-hexahydronaphthalen-1-yl(4-nitrophenyl) carbonate (480.11 mg, 384.23 μmol) in pyridine (5 mL) was added DMAP (93.88 mg, 768.45 μmol), the resulting mixture was stirred at 25° C. for 20 h. LCMS showed a peak (22%) with desired mass. The mixture was concentrated under vacuum. The residue was purified by reversed-phase HPLC (0.1% FA condition, 93% ACN) to give (1S,3R,7S,8S,8aR)-8-(2-((2S,4S)-4-((tert-butyldimethylsilyl)oxy)-6-oxotetrahydro-2H-pyran-2-yl)ethyl)-3,7-dimethyl-1,2,3,7,8,8a-hexahydronaphthalen-1-yl (14,14-dimethyl-11-oxo-3,6,9-trioxa-12-azapentadecyl)carbamate (0.17 g, 0.23 mmol, 60.03% yield) as light yellow oil.

MS $(M+H)^+$=737.2

Step 5: Synthesis of (1S,3R,7S,8S,8aR)-8-(2-((2S,4S)-4-hydroxy-6-oxotetrahydro-2H-pyran-2-yl)ethyl)-3,7-dimethyl-1,2,3,7,8,8a-hexahydronaphthalen-1-yl (14,14-dimethyl-11-oxo-3,6,9-trioxa-12-azapentadecyl) carbamate (Compound 13)

A mixture of (1S,3R,7S,8S,8aR)-8-(2-((2S,4S)-4-((tert-butyldimethylsilyl)oxy)-6-oxotetrahydro-2H-pyran-2-yl)ethyl)-3,7-dimethyl-1,2,3,7,8,8a-hexahydronaphthalen-1-yl (14,14-dimethyl-11-oxo-3,6,9-trioxa-12-azapentadecyl) carbamate (0.17 g, 0.231 mmol) in formic acid (12.20 g, 212.06 mmol, 10 mL, 80% purity) was stirred at 25° C. for 1 h. LCMS showed a peak (72%) with desired mass. The mixture was concentrated under vacuum. The residue was purified by prep-HPLC (column: Waters Xbridge 150*25 mm*5 μm; mobile phase: [water (10 mM $NH_4HCO_3$)-ACN]; B %: 38%-68%, 10 min) followed by lyophilization to give (1S,3R,7S,8S,8aR)-8-(2-((2S,4S)-4-hydroxy-6-oxotetrahydro-2H-pyran-2-yl)ethyl)-3,7-dimethyl-1,2,3,7,8,8a-hexahydronaphthalen-1-yl (14,14-dimethyl-11-oxo-3,6,9-trioxa-12-azapentadecyl) carbamate (123.6 mg, 0.173 mmol, 75.20% yield, 87.4% purity) as light yellow oil.

MS $(M+H)^+$=623.5

$^1H$ NMR (400 MHz, $CDCl_3$) δ 6.92 (s, 1H), 5.97 (d, J=9.7 Hz, 1H), 5.78 (dd, J=9.7, 6.0 Hz, 1H), 5.51 (s, 1H), 5.30 (t, J=5.9 Hz, 1H), 5.21 (s, 1H), 4.64 (s, 1H), 4.31 (t, J=4.3 Hz, 1H), 4.03 (s, 2H), 3.67 (d, J=3.3 Hz, 4H), 3.64-3.59 (m, 4H), 3.57-3.47 (m, 2H), 3.35 (s, 2H), 3.08 (dd, J=6.5, 4.7 Hz, 2H), 2.75-2.58 (m, 2H), 2.45-2.34 (m, 2H), 2.25 (d, J=12.4 Hz, 1H), 2.09 (d, J=15.1 Hz, 1H), 1.96 (d, J=14.6 Hz, 1H), 1.90-1.81 (m, 2H), 1.80-1.67 (m, 6H), 1.07 (d, J=7.4 Hz, 3H), 0.94-0.88 (m, 12H).

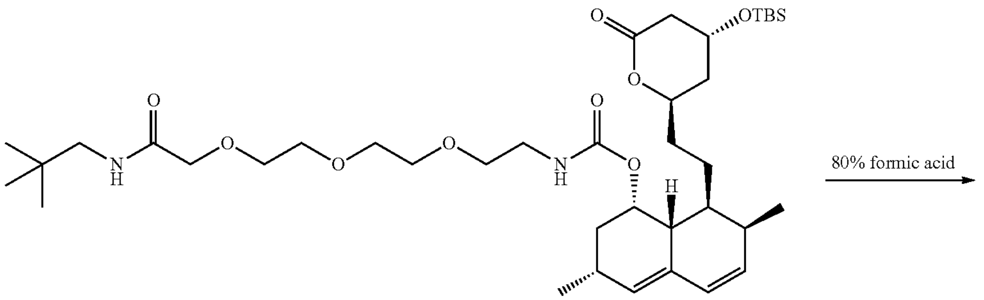

22

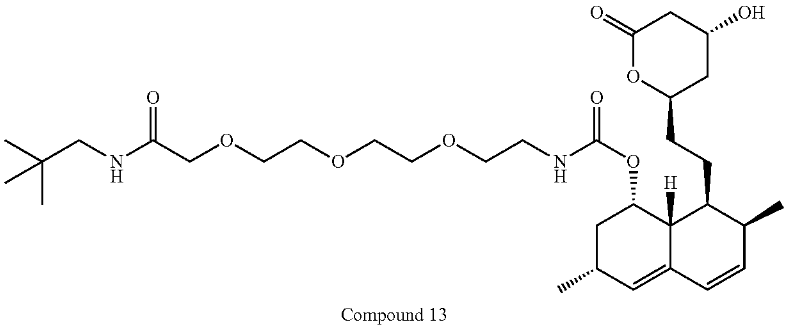

Compound 13

Example 14. Synthesis of (1S,3R,7S,8S,8aR)-8-(2-((2R,4R)-4-hydroxy-6-oxotetrahydro-2H-pyran-2-yl)ethyl)-3,7-dimethyl-1,2,3,7,8,8a-hexahydronaphthalen-1-yl (2-(2-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-2-oxoethoxy)ethyl)carbamate (Compound 14)

Step 1: Synthesis of (1S,3R,7S,8S,8aR)-8-(2-((2R,4R)-4-((tert-butyldimethylsilyl)oxy)-6-oxotetrahydro-2H-pyran-2-yl)ethyl)-3,7-dimethyl-1,2,3,7,8,8a-hexahydronaphthalen-1-yl (2-(2-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-2-oxoethoxy)ethyl)carbamate (23)

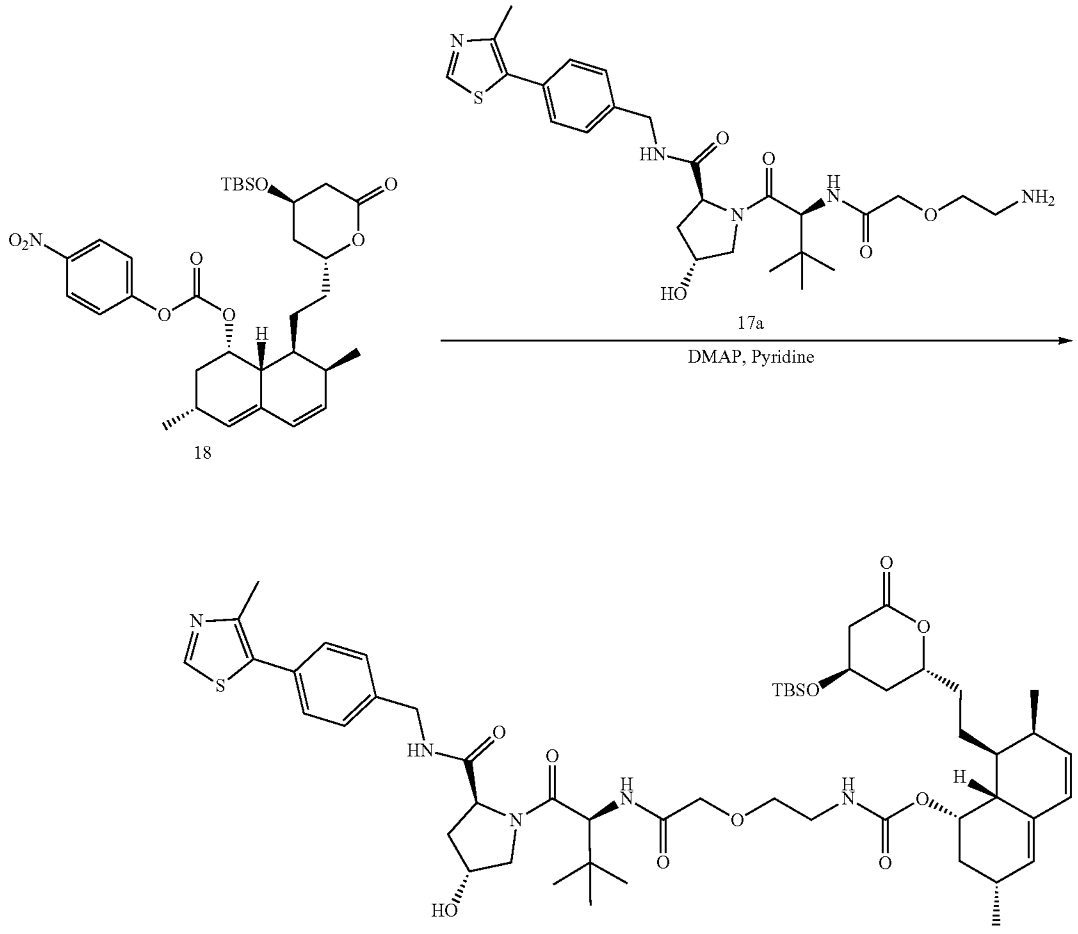

18

23

To a solution of (2S,4R)-1-((S)-2-(2-(2-aminoethoxy)acetamido)-3,3-dimethylbutanoyl)-4-hydroxy-N-(4-(4-methylthiazol-5-yl)benzyl)pyrrolidine-2-carboxamide (0.2 g, 0.35 mmol, HCl) and (1S,3R,7S,8S,8aR)-8-(2-((2R,4R)-4-((tert-butyldimethylsilyl)oxy)-6-oxotetrahydro-2H-pyran-2-yl)ethyl)-3,7-dimethyl-1,2,3,7,8,8a-hexahydronaphthalen-1-yl(4-nitrophenyl)carbonate (439.88 mg, 0.35 mmol) in pyridine (2 mL) was added DMAP (215.04 mg, 1.76 mmol), the resulting mixture was stirred at 25° C. for 15 h. LCMS showed a peak (17.5%) with desired mass. The mixture was concentrated under vacuum. The residue was purified by reversed-phase HPLC (0.1% FA condition, 95% ACN) to give (1S,3R,7S,8S,8aR)-8-(2-((2R,4R)-4-((tert-butyldimethylsilyl)oxy)-6-oxotetrahydro-2H-pyran-2-yl)ethyl)-3,7-dimethyl-1,2,3,7,8,8a-hexahydronaphthalen-1-yl (2-(2-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-2-oxoethoxy)ethyl)carbamate (0.12 g, 0.12 mmol, 34.35% yield) as yellow solid. MS $(M+H)^+=992.7$ Step 2: Synthesis of (1S,3R,7S,8S,8aR)-8-(2-((2R,4R)-4-hydroxy-6-oxotetrahydro-2H-pyran-2-yl)ethyl)-3,7-dimethyl-1,2,3,7,8,8a-hexahydronaphthalen-1-yl (2-(2-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-2-oxoethoxy)ethyl)carbamate (Compound 14)

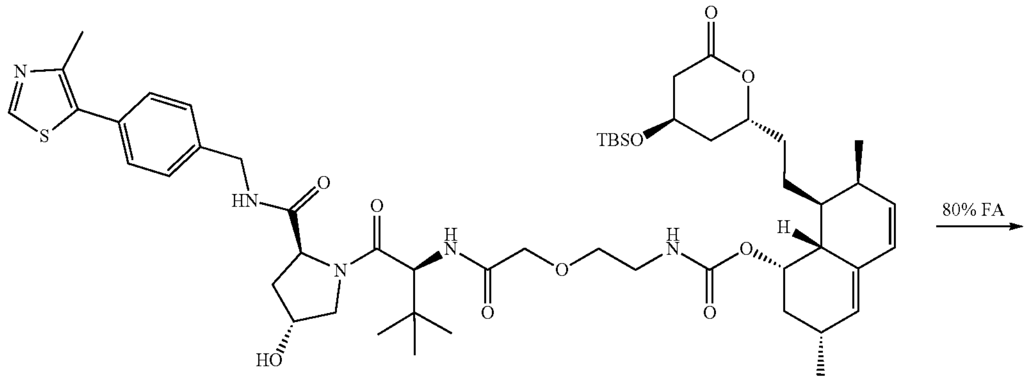

23

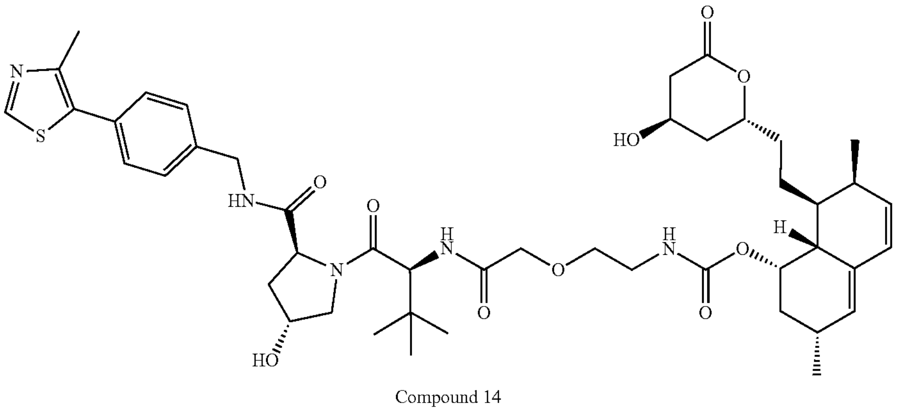

Compound 14

A mixture of (1S,3R,7S,8S,8aR)-8-(2-((2R,4R)-4-hydroxy-6-oxotetrahydro-2H-pyran-2-yl) ethyl)-3,7-dimethyl-1,2,3,7,8,8a-hexahydronaphthalen-1-yl(2-(2-(((S)-1-((2S,4R)-4-hydroxy-2-((4-(4-methylthiazol-5-yl)benzyl) carbamoyl)pyrrolidin-1-yl)-3,3-dimethyl-1-oxobutan-2-yl) amino)-2-oxoethoxy)ethyl)carbamate (0.12 g, 0.12 mmol) in formic acid (12.20 g, 212.06 mmol, 10 mL, 80% purity) was stirred at 25° C. for 1 h. LCMS showed a peak with desired mass. The mixture was concentrated under vacuum. The residue was purified by prep-HPLC (column: Phenomenex Synergi C18 150*30 mm*4 μm; mobile phase: [water (0.225% FA)-ACN]; B %: 36%-66%, 10 min) followed by lyophilization to give (1S,3R,7S,8S,8aR)-8-(2-((2R,4R)-4-hydroxy-6-oxotetrahydro-2H-pyran-2-yl)ethyl)-3,7-dimethyl-1,2,3,7,8,8a-hexahydronaphthalen-1-yl (2-(2-(((S)-1-((2S,4R)-4-hydroxy-2-((4-(4-methylthiazol-5-yl)benzyl) carbamoyl)pyrrolidin-1-yl)-3,3-dimethyl-1-oxobutan-2-yl) amino)-2-oxoethoxy)ethyl)carbamate (34.1 mg, 0.037 mmol, 30.44% yield, 94.8% purity) as white solid.

MS $(M+H)^+$=878.3

$^1H$ NMR (400 MHz, DMSO-$d_6$) δ 8.99 (s, 1H), 8.58 (t, J=6.0 Hz, 1H), 7.45-7.39 (m, 5H), 7.14 (t, J=5.8 Hz, 1H), 5.90 (d, J=9.7 Hz, 1H), 5.76 (dd, J=9.4, 6.1 Hz, 1H), 5.46 (s, 1H), 5.17 (dd, J=9.8, 3.4 Hz, 2H), 5.08-5.01 (m, 1H), 4.56 (d, J=9.6 Hz, 1H), 4.52-4.34 (m, 4H), 4.26 (dd, J=15.8, 5.6 Hz, 1H), 4.14-4.07 (m, 1H), 3.93 (s, 2H), 3.69-3.58 (m, 2H), 3.47 (t, J=6.1 Hz, 2H), 3.16 (dd, J=11.2, 5.9 Hz, 2H), 2.68-2.59 (m, 1H), 2.45 (s, 3H), 2.38-2.30 (m, 3H), 2.26-2.21 (m, 1H), 2.09-2.03 (m, 1H), 1.94-1.79 (m, 4H), 1.71-1.57 (m, 3H), 1.52-1.43 (m, 1H), 1.37-1.25 (m, 2H), 1.04 (d, J=7.4 Hz, 3H), 0.95-0.92 (m, 9H), 0.84 (d, J=6.9 Hz, 3H).

Example 15 & Example 19. Synthesis of (1S,3R,7S,8S,8aR)-8-(2-((2R,4R)-4-hydroxy-6-oxotetrahydro-2H-pyran-2-yl)ethyl)-3,7-dimethyl-1,2,3,7,8,8a-hexahydronaphthalen-1-yl (2-(2-(2-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-2-oxoethoxy)ethoxy)ethyl)carbamate (Compound 15) and (1S,3R,7S,8S,8aR)-8-(2-((2R,4R)-4-((tert-butyldimethylsilyl)oxy)-6-oxotetrahydro-2H-pyran-2-yl)ethyl)-3,7-dimethyl-1,2,3,7,8,8a-hexahydronaphthalen-1-yl (2-(2-(2-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-2-oxoethoxy)ethoxy)ethyl)carbamate (Compound 19)

Step 1: Synthesis of (1S,3R,7S,8S,8aR)-8-(2-((2R,4R)-4-((tert-butyldimethylsilyl)oxy)-6-oxotetrahydro-2H-pyran-2-yl)ethyl)-3,7-dimethyl-1,2,3,7,8,8a-hexahydronaphthalen-1-yl (2-(2-(2-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-2-oxoethoxy)ethoxy)ethyl)carbamate (Compound 19)

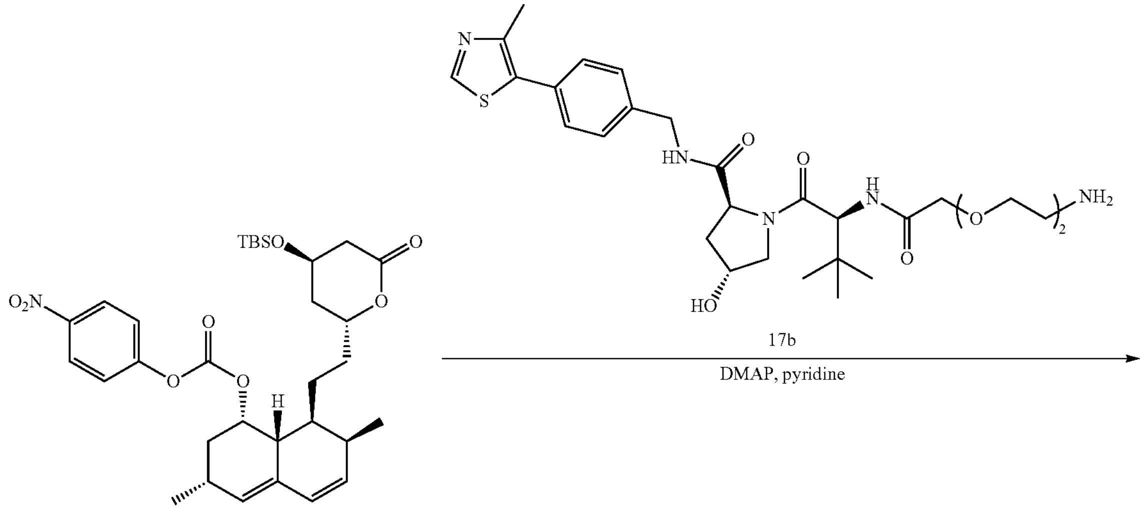

17b

18

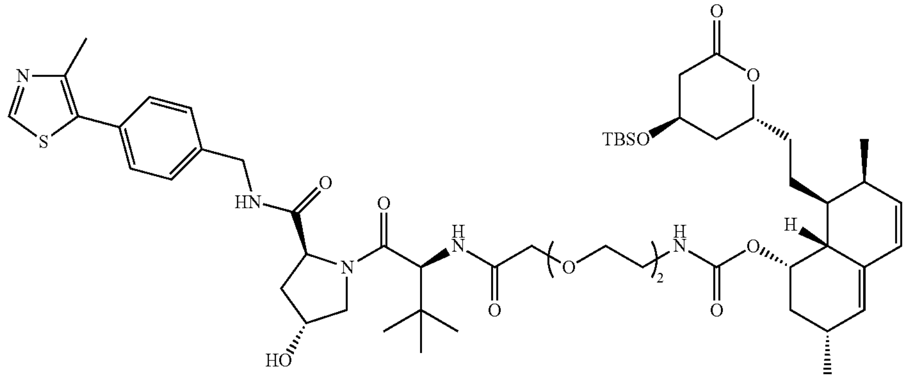

Compound 19

In a manner similar to Step 1 of Example 14, the titled compound (0.15 g, 0.145 mmol, 35.44% yield, 97% purity) was obtained as a yellow solid.

MS $(M+H)^+$=1036.5

$^1$H NMR (400 MHz, DMSO-$d_6$) δ 8.99 (s, 1H), 8.52 (d, J=5.9 Hz, 1H), 7.40 (s, 5H), 7.03 (t, J=5.7 Hz, 1H), 5.92 (d, J=9.7 Hz, 1H), 5.77 (dd, J=9.6, 5.9 Hz, 1H), 5.47 (s, 1H), 5.16 (d, J=3.5 Hz, 1H), 5.06 (s, 1H), 4.57 (d, J=9.6 Hz, 1H), 4.51-4.34 (m, 4H), 4.26 (dd, J=16.6, 6.4 Hz, 2H), 3.96 (s, 2H), 3.70-3.49 (m, 6H), 3.45-3.38 (m, 2H), 3.20-3.06 (m, 2H), 2.71-2.65 (m, 1H), 2.45 (s, 3H), 2.39-2.30 (m, 3H), 2.28-2.21 (m, 1H), 2.10-2.02 (m, 1H), 1.95-1.77 (m, 4H), 1.74-1.61 (m, 3H), 1.52-1.45 (m, 1H), 1.33-1.23 (m, 2H), 1.03 (d, J=7.2 Hz, 3H), 0.96-0.92 (m, 9H), 0.86-0.83 (m, 12H), 0.06 (d, J=0.8 Hz, 6H).

Step 2: Synthesis of (1S,3R,7S,8S,8aR)-8-(2-((2R,4R)-4-hydroxy-6-oxotetrahydro-2H-pyran-2-yl)ethyl)-3,7-dimethyl-1,2,3,7,8,8a-hexahydronaphthalen-1-yl (2-(2-(2-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-2-oxoethoxy)ethoxy)ethyl)carbamate (Compound 15)

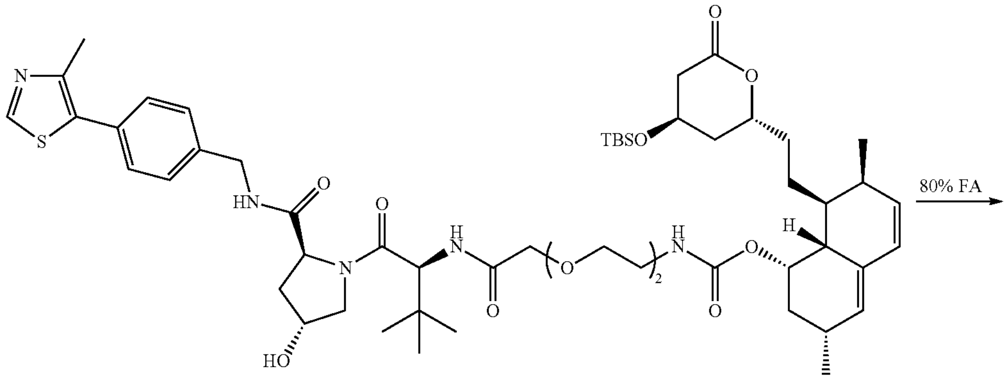

Compound 19

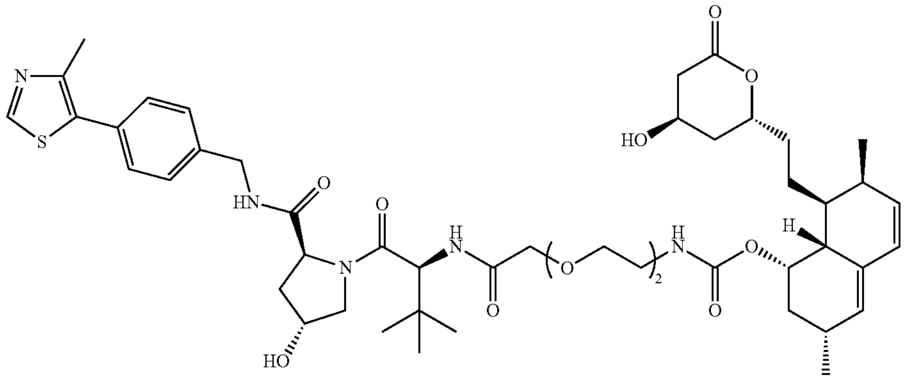

Compound 15

In a manner similar to Step 2 of Example 14, the titled compound (35.0 mg, 0.0366 mmol, 25.25% yield, 96.3% purity) was obtained as a white solid.

MS $(M+H)^+$=922.2

$^1$H NMR (400 MHz, DMSO-$d_6$) δ 8.98 (s, 1H), 8.52 (t, J=6.1 Hz, 1H), 7.40 (s, 5H), 7.03 (t, J=5.8 Hz, 1H), 5.91 (d, J=9.6 Hz, 1H), 5.76 (dd, J=9.6, 5.9 Hz, 1H), 5.46 (t, J=3.2 Hz, 1H), 5.17 (dd, J=8.9, 3.3 Hz, 2H), 5.05 (d, J=3.4 Hz, 1H), 4.56 (d, J=9.4 Hz, 1H), 4.52-4.33 (m, 4H), 4.30-4.21 (m, 1H), 4.13-4.07 (m, 1H), 3.95 (s, 2H), 3.71-3.47 (m, 6H), 3.41-3.37 (m, 2H), 3.19-3.05 (m, 2H), 2.65-2.57 (m, 1H), 2.45 (s, 3H), 2.38-2.30 (m, 3H), 2.26-2.18 (m, 1H), 2.10-2.02 (m, 1H), 1.95-1.76 (m, 4H), 1.70-1.56 (m, 3H), 1.46 (d, J=9.4 Hz, 1H), 1.34-1.21 (m, 2H), 1.02 (d, J=7.2 Hz, 3H), 0.97-0.90 (m, 9H), 0.83 (d, J=6.8 Hz, 3H).

Example 16 & Example 20. Synthesis of (1S,3R,7S,8S,8aR)-8-(2-((2R,4R)-4-hydroxy-6-oxotetrahydro-2H-pyran-2-yl)ethyl)-3,7-dimethyl-1,2,3,7,8,8a-hexahydronaphthalen-1-yl ((S)-13-((2S,4R)-4-hydroxy-2-((4-(4-methylthiazol-5-yl)benzyl)carbamoyl)pyrrolidine-1-carbonyl)-14,14-dimethyl-11-oxo-3,6,9-trioxa-12-azapentadecyl)carbamate (Compound 16) and (1S,3R,7S,8S,8aR)-8-(2-((2R,4R)-4-((tert-butyldimethylsilyl)oxy)-6-oxotetrahydro-2H-pyran-2-yl)ethyl)-3,7-dimethyl-1,2,3,7,8,8a-hexahydronaphthalen-1-yl ((S)-13-((2S,4R)-4-hydroxy-2-((4-(4-methylthiazol-5-yl)benzyl)carbamoyl)pyrrolidine-1-carbonyl)-14,14-dimethyl-11-oxo-3,6,9-trioxa-12-azapentadecyl)carbamate (Compound 20)

Step 1: Synthesis of (1S,3R,7S,8S,8aR)-8-(2-((2R,4R)-4-((tert-butyldimethylsilyl)oxy)-6-oxotetrahydro-2H-pyran-2-yl)ethyl)-3,7-dimethyl-1,2,3,7,8,8a-hexahydronaphthalen-1-yl ((S)-13-((2S,4R)-4-hydroxy-2-((4-(4-methylthiazol-5-yl)benzyl)carbamoyl)pyrrolidine-1-carbonyl)-14,14-dimethyl-11-oxo-3,6,9-trioxa-12-azapentadecyl)carbamate (Compound 20)

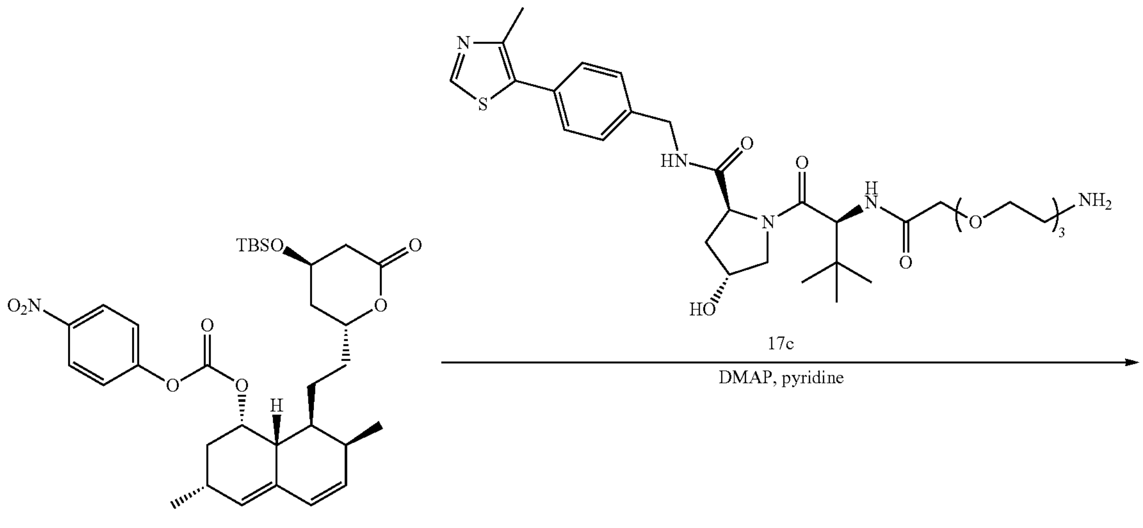

18

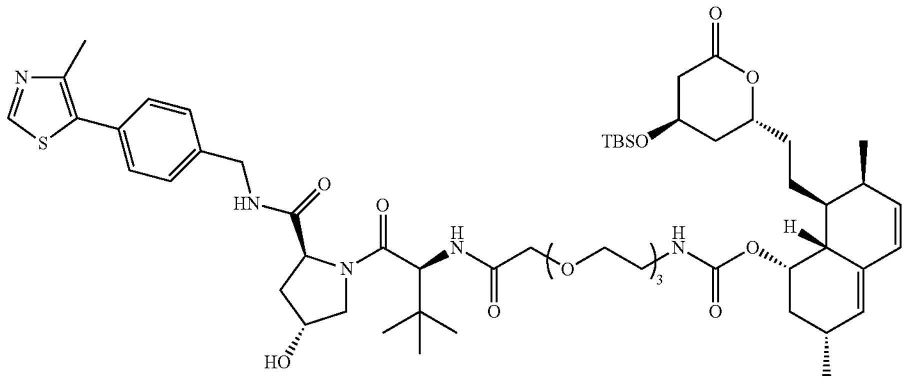

Compound 20

In a manner similar to Step 1 of Example 14, the titled compound (0.13 g, 0.12 mmol, 31.58% yield, 97% purity) was obtained as a white solid.

MS $(M+H)^+$=1080.5

$^1$H NMR (400 MHz, $CDCl_3$) δ 8.68 (s, 1H), 7.35 (d, J=2.9 Hz, 5H), 7.25 (s, 1H), 5.96 (d, J=9.6 Hz, 1H), 5.83-5.72 (m, 1H), 5.50 (s, 1H), 5.37 (s, 1H), 5.19 (s, 1H), 4.73 (t, J=7.9 Hz, 1H), 4.68-4.45 (m, 4H), 4.34 (dd, J=14.9, 5.3 Hz, 1H), 4.28 (t, J=3.8 Hz, 1H), 4.11-4.05 (m, 1H), 4.06-3.92 (m, 2H), 3.66 (s, 4H), 3.61-3.56 (m, 4H), 3.53-3.47 (m, 2H), 3.42-3.20 (m, 2H), 2.62-2.51 (m, 6H), 2.42-2.30 (m, 2H), 2.24-2.02 (m, 3H), 1.89-1.79 (m, 3H), 1.79-1.66 (m, 4H), 1.50-1.23 (m, 3H), 1.05 (d, J=7.0 Hz, 3H), 0.98-0.93 (m, 9H), 0.89-0.87 (m, 12H), 0.07 (d, J=0.9 Hz, 6H).

Step 2: Synthesis of (1S,3R,7S,8S,8aR)-8-(2-((2R, 4R)-4-hydroxy-6-oxotetrahydro-2H-pyran-2-yl) ethyl)-3,7-dimethyl-1,2,3,7,8,8a-hexahydronaphthalen-1-yl ((S)-13-((2S,4R)-4-hydroxy-2-((4-(4-methylthiazol-5-yl)benzyl)carbamoyl)pyrrolidine-1-carbonyl)-14,14-dimethyl-11-oxo-3,6,9-trioxa-12-azapentadecyl)carbamate (Compound 16)

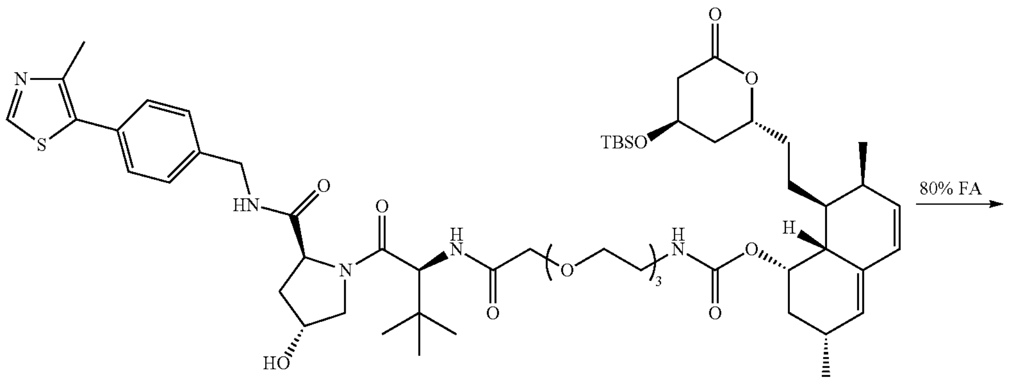

Compound 20

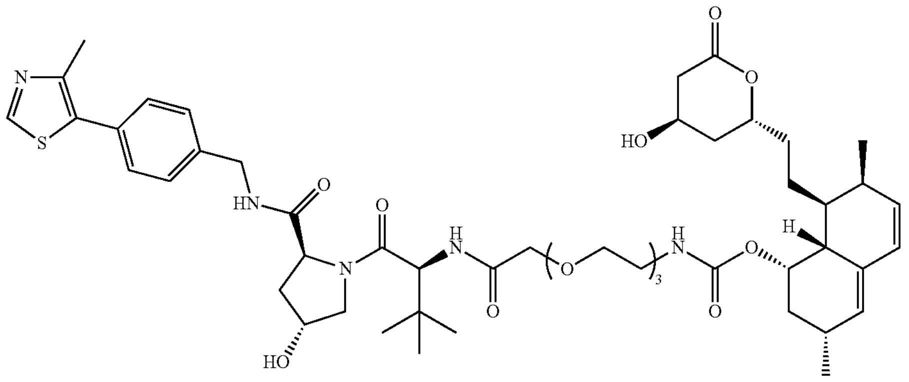

Compound 16

In a manner similar to Step 2 of Example 14, the titled compound (36.0 mg, 0.035 mmol, 29.20% yield, 94.3% purity) was obtained as a white solid.

MS $(M+H)^+$=966.3

$^1$H NMR (400 MHz, DMSO-$d_6$) δ 8.98 (s, 1H), 8.58 (t, J=6.0 Hz, 1H), 7.40 (s, 5H), 6.99 (s, 1H), 5.91 (d, J=9.6 Hz, 1H), 5.79-5.73 (m, 1H), 5.45 (s, 1H), 5.16 (dd, J=3.4, 10.6 Hz, 2H), 5.04 (s, 1H), 4.56 (d, J=9.6 Hz, 1H), 4.51-4.33 (m, 4H), 4.29-4.22 (m, 1H), 4.10 (s, 1H), 3.96 (s, 2H), 3.60-3.40 (m, 10H), 3.41-3.37 (m, 2H), 3.19-3.05 (m, 2H), 2.70-2.66 (m, 1H), 2.46-2.43 (m, 3H), 2.39-2.34 (m, 3H), 2.26-2.20 (m, 1H), 2.09-2.00 (m, 1H), 1.94-1.77 (m, 4H), 1.71-1.61 (m, 3H), 1.53-1.44 (m, 1H), 1.35-1.22 (m, 2H), 1.02 (d, J=7.46 Hz, 3H), 0.96-0.91 (m, 9H), 0.84 (d, J=6.9 Hz, 3H).

Example 17 & Example 21. Synthesis of (1S,3R,7S,8S,8aR)-8-(2-((2R,4R)-4-hydroxy-6-oxotetrahydro-2H-pyran-2-yl)ethyl)-3,7-dimethyl-1,2,3,7,8,8a-hexahydronaphthalen-1-yl ((S)-16-((2S,4R)-4-hydroxy-2-((4-(4-methylthiazol-5-yl)benzyl)carbamoyl)pyrrolidine-1-carbonyl)-17,17-dimethyl-14-oxo-3,6,9,12-tetraoxa-15-azaoctadecyl)carbamate (Compound 17) and (1S,3R,7S,8S,8aR)-8-(2-((2R,4R)-4-((tert-butyldimethylsilyl)oxy)-6-oxotetrahydro-2H-pyran-2-yl)ethyl)-3,7-dimethyl-1,2,3,7,8,8a-hexahydronaphthalen-1-yl ((S)-16-((2S,4R)-4-hydroxy-2-((4-(4-methylthiazol-5-yl)benzyl)carbamoyl)pyrrolidine-1-carbonyl)-17,17-dimethyl-14-oxo-3,6,9,12-tetraoxa-15-azaoctadecyl)carbamate (Compound 21)

Step 1: Synthesis of (1S,3R,7S,8S,8aR)-8-(2-((2R,4R)-4-((tert-butyldimethylsilyl)oxy)-6-oxotetrahydro-2H-pyran-2-yl)ethyl)-3,7-dimethyl-1,2,3,7,8,8a-hexahydronaphthalen-1-yl ((S)-16-((2S,4R)-4-hydroxy-2-((4-(4-methylthiazol-5-yl)benzyl)carbamoyl)pyrrolidine-1-carbonyl)-17,17-dimethyl-14-oxo-3,6,9,12-tetraoxa-15-azaoctadecyl)carbamate (Compound 21)

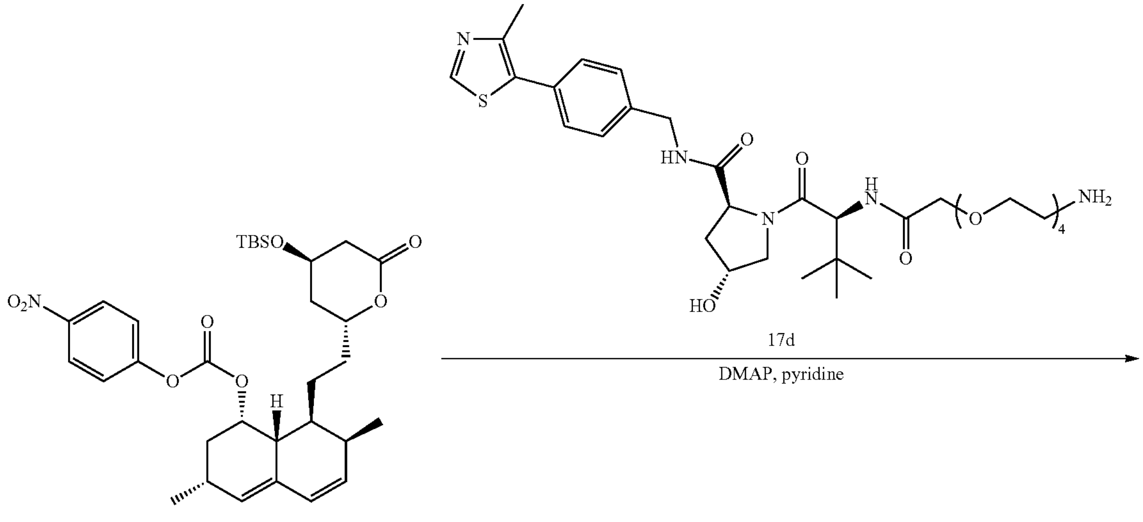

17d

18

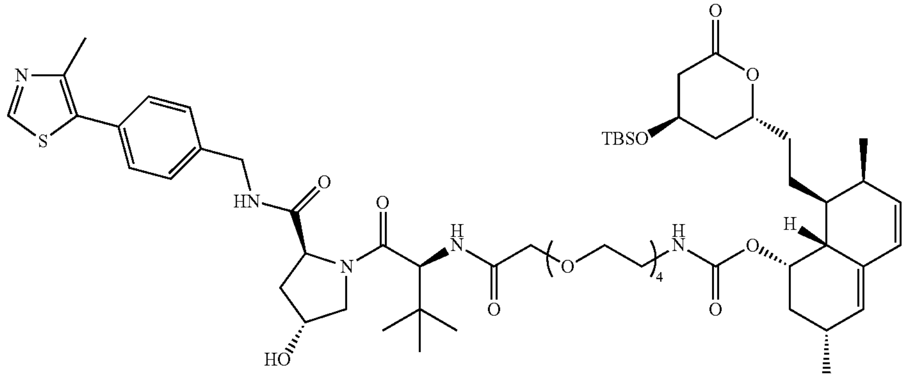

Compound 21

In a manner similar to Step 1 of Example 14, the titled compound (0.14 g, 124.50 μmol, 41.32% yield) was obtained as a yellow oil.

MS $(M+H)^+$=1124.6

$^1$H NMR (400 MHz, $CDCl_3$) δ 8.68 (s, 1H), 7.41-7.31 (m, 5H), 7.25 (s, 1H), 5.96 (d, J=9.7 Hz, 1H), 5.77 (dd, J=9.6, 6.0 Hz, 1H), 5.50 (s, 1H), 5.35 (s, 1H), 5.20 (s, 1H), 4.73 (t, J=7.9 Hz, 1H), 4.68-4.45 (m, 4H), 4.35 (dd, J=14.9, 5.2 Hz, 1H), 4.32-4.25 (m, 1H), 4.11 (d, J=11.5 Hz, 1H), 4.09-3.93 (m, 2H), 3.69-3.64 (m, 4H), 3.64-3.59 (m, 4H), 3.60-3.55 (m, 4H), 3.54-3.46 (m, 2H), 3.42-3.23 (m, 2H), 2.61-2.49 (m, 6H), 2.44-2.31 (m, 2H), 2.28-2.03 (m, 3H), 1.92-1.68 (m, 7H), 1.49-1.23 (m, 3H), 1.06 (d, J=7.3 Hz, 3H), 0.96-0.93 (m, 9H), 0.91-0.85 (m, 12H), 0.08 (d, J=0.9 Hz, 6H).

Step 2: Synthesis of (1S,3R,7S,8S,8aR)-8-(2-((2R,4R)-4-hydroxy-6-oxotetrahydro-2H-pyran-2-yl)ethyl)-3,7-dimethyl-1,2,3,7,8,8a-hexahydronaphthalen-1-yl ((S)-16-((2S,4R)-4-hydroxy-2-((4-(4-methylthiazol-5-yl)benzyl)carbamoyl)pyrrolidine-1-carbonyl)-17,17-dimethyl-14-oxo-3,6,9,12-tetraoxa-15-azaoctadecyl)carbamate (Compound 17)

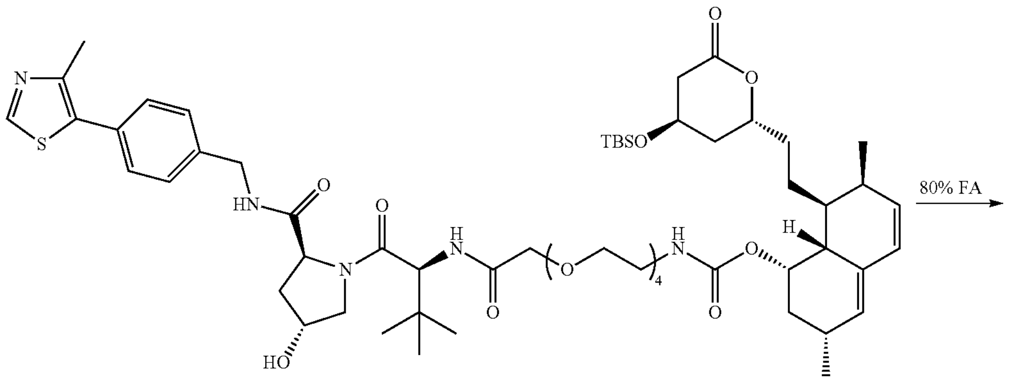

Compound 21

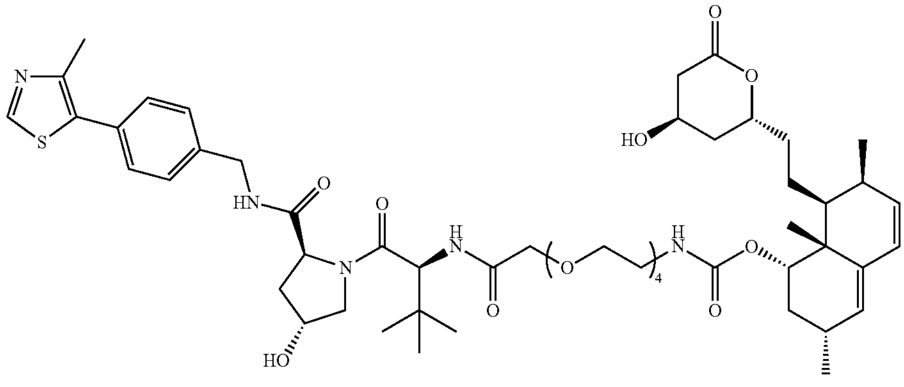

Compound 17

In a manner similar to Step 2 of Example 14, the titled compound (39.4 mg, 0.034 mol, 27.25% yield, 87% purity) was obtained as a white solid.

MS $(M+H)^+=1010.3$ $^1H$ NMR (400 MHz, DMSO-$d_6$) δ 8.98 (s, 1H), 8.60 (t, J=6.1 Hz, 1H), 7.40 (s, 5H), 7.00 (t, J=5.7 Hz, 1H), 5.91 (d, J=9.6 Hz, 1H), 5.76 (dd, J=9.6, 6.0 Hz, 1H), 5.46 (t, J=3.4 Hz, 1H), 5.04 (q, J=3.2 Hz, 1H), 4.56 (d, J=9.5 Hz, 1H), 4.52-4.32 (m, 4H), 4.25 (dd, J=15.8, 5.6 Hz, 1H), 4.09 (p, J=3.8 Hz, 1H), 3.96 (s, 2H), 3.67 (dd, J=10.7, 4.0 Hz, 2H), 3.62-3.58 (m, 4H), 3.58-3.52 (m, 8H), 3.34 (s, 2H), 3.07 (q, J=7.2, 6.6 Hz, 2H), 2.62 (dd, J=17.2, 4.6 Hz, 1H), 2.44 (s, 3H), 2.33 (dd, J=12.6, 7.8 Hz, 3H), 2.26-2.17 (m, 1H), 2.10-2.00 (m, 1H), 1.95-1.78 (m, 4H), 1.73-1.57 (m, 3H), 1.52-1.42 (m, 1H), 1.36-1.22 (m, 2H), 1.04-0.99 (m, 3H), 0.97-0.91 (m, 9H), 0.83 (d, J=6.8 Hz, 3H).

Example 18 & Example 22. Synthesis of (1S,3R,7S,8S,8aR)-8-(2-((2R,4R)-4-hydroxy-6-oxotetrahydro-2H-pyran-2-yl)ethyl)-3,7-dimethyl-1,2,3,7,8,8a-hexahydronaphthalen-1-yl ((S)-19-((2S,4R)-4-hydroxy-2-((4-(4-methylthiazol-5-yl)benzyl)carbamoyl)pyrrolidine-1-carbonyl)-20,20-dimethyl-17-oxo-3,6,9,12,15-pentaoxa-18-azahenicosyl)carbamate (Compound 18) and (1S,3R,7S,8S,8aR)-8-(2-((2R,4R)-4-((tert-butyldimethylsilyl)oxy)-6-oxotetrahydro-2H-pyran-2-yl)ethyl)-3,7-dimethyl-1,2,3,7,8,8a-hexahydronaphthalen-1-yl ((S)-19-((2S,4R)-4-hydroxy-2-((4-(4-methylthiazol-5-yl)benzyl)carbamoyl)pyrrolidine-1-carbonyl)-20,20-dimethyl-17-oxo-3,6,9,12,15-pentaoxa-18-azahenicosyl)carbamate (Compound 22)

Step 1: Synthesis of (1S,3R,7S,8S,8aR)-8-(2-((2R,4R)-4-((tert-butyldimethylsilyl)oxy)-6-oxotetrahydro-2H-pyran-2-yl)ethyl)-3,7-dimethyl-1,2,3,7,8,8a-hexahydronaphthalen-1-yl ((S)-19-((2S,4R)-4-hydroxy-2-((4-(4-methylthiazol-5-yl)benzyl)carbamoyl)pyrrolidine-1-carbonyl)-20,20-dimethyl-17-oxo-3,6,9,12,15-pentaoxa-18-azahenicosyl)carbamate (Compound 22)

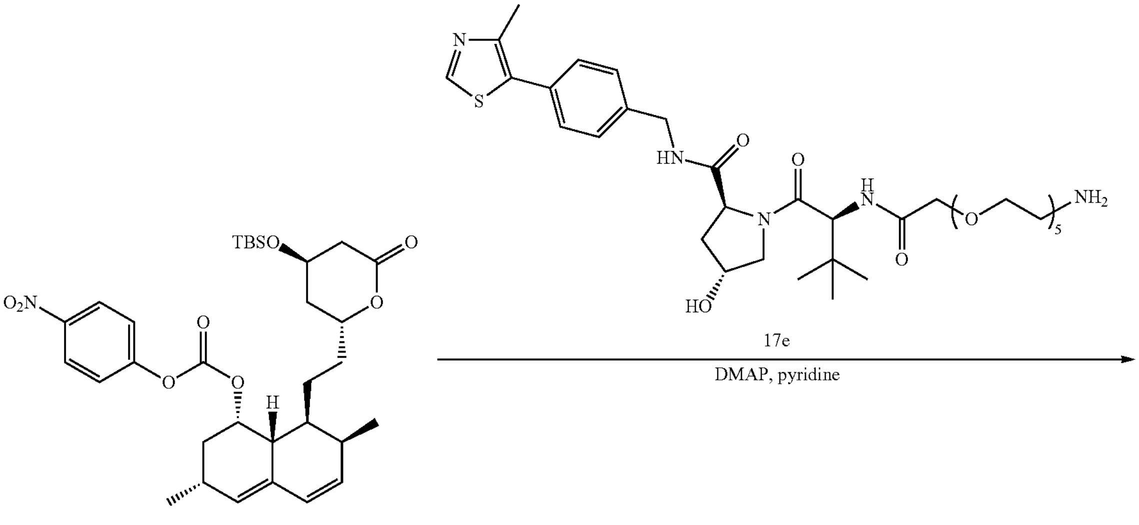

17e

18

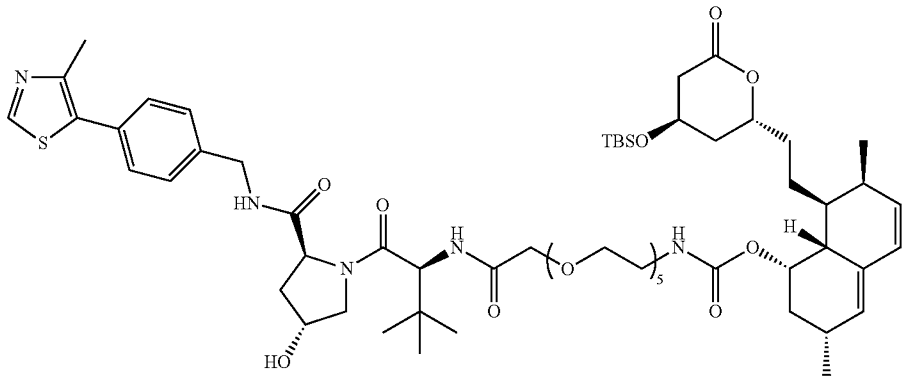

Compound 22

In a manner similar to Step 1 of Example 14, the titled compound (0.12 g, 0.1 mmol, 36.35% yield) was obtained as a yellow oil.

MS $(M+H)^+$=1168.8

$^1$H NMR (400 MHz, $CDCl_3$) δ 8.68 (s, 1H), 7.39-7.31 (m, 5H), 7.27 (s, 1H), 5.96 (d, J=9.6 Hz, 1H), 5.77 (dd, J=9.6, 6.1 Hz, 1H), 5.50 (s, 1H), 5.31 (t, J=5.7 Hz, 1H), 5.20 (s, 1H), 4.73 (t, J=7.9 Hz, 1H), 4.68-4.45 (m, 4H), 4.34 (dd, J=14.9, 5.3 Hz, 1H), 4.30-4.25 (m, 1H), 4.09 (d, J=11.4 Hz, 1H), 4.06-3.94 (m, 2H), 3.70-3.64 (m, 4H), 3.62 (s, 4H), 3.60 (s, 4H), 3.59-3.55 (m, 4H), 3.51 (d, J=6.3 Hz, 2H), 3.30 (d, J=5.4 Hz, 2H), 2.63-2.50 (m, 6H), 2.46-2.32 (m, 2H), 2.26-2.04 (m, 3H), 1.88-1.63 (m, 7H), 1.60-1.15 (m, 3H), 1.06 (d, J=7.3 Hz, 3H), 0.98-0.91 (m, 9H), 0.91-0.87 (m, 12H), 0.07 (d, J=0.9 Hz, 6H).

Step 2: Synthesis of (1S,3R,7S,8S,8aR)-8-(2-((2R,4R)-4-hydroxy-6-oxotetrahydro-2H-pyran-2-yl)ethyl)-3,7-dimethyl-1,2,3,7,8,8a-hexahydronaphthalen-1-yl ((S)-19-((2S,4R)-4-hydroxy-2-((4-(4-methylthiazol-5-yl)benzyl)carbamoyl)pyrrolidine-1-carbonyl)-20,20-dimethyl-17-oxo-3,6,9,12,15-pentaoxa-18-azahenicosyl)carbamate (Compound 18)

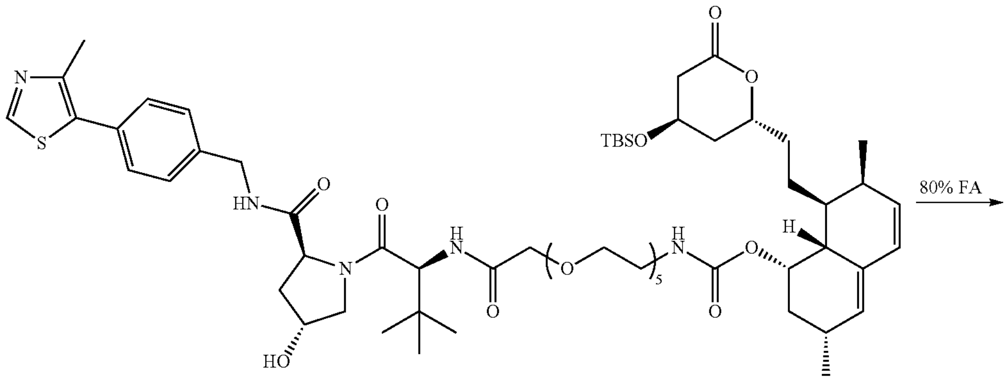

Compound 22

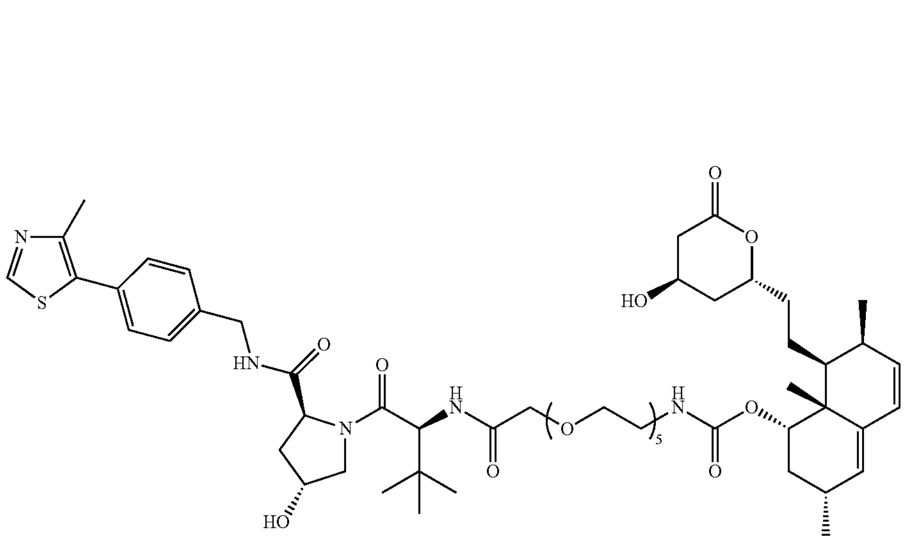

Compound 18

In a manner similar to Step 2 of Example 14, the titled compound (65.5 mg, 0.054. mmol, 53.12% yield, 87.8% purity) was obtained as a white solid.

MS $(M+H)^+$=1054.6

$^1$H NMR (400 MHz, DMSO-$d_6$) δ 8.99 (s, 1H), 8.62 (t, J=6.0 Hz, 1H), 7.45-7.38 (m, 5H), 7.05-6.94 (m, 1H), 5.91 (d, J=9.6 Hz, 1H), 5.77 (dd, J=9.6, 6.0 Hz, 1H), 5.46 (d, J=3.7 Hz, 1H), 5.05 (q, J=3.3 Hz, 1H), 4.57 (d, J=9.6 Hz, 1H), 4.53-4.35 (m, 4H), 4.25 (dd, J=15.7, 5.6 Hz, 1H), 4.10 (q, J=3.8 Hz, 1H), 3.97 (s, 2H), 3.68 (dd, J=10.6, 3.9 Hz, 2H), 3.62-3.52 (m, 10H), 3.48-3.46 (m, 8H), 3.13-3.06 (m, 2H), 2.62 (dd, J=17.2, 4.6 Hz, 1H), 2.45 (s, 3H), 2.43-2.18 (m, 5H), 2.08-2.04 (m, 1H), 1.96-1.74 (m, 5H), 1.72-1.58 (m, 3H), 1.53-1.43 (m, 1H), 1.33-1.24 (m, 2H), 1.03 (dd, J=7.1, 4.9 Hz, 3H), 0.96-0.92 (m, 9H), 0.83 (d, J=6.6 Hz, 3H).

Example 23 & Example 27. (1S,3R,7S,8S,8aR)-8-(2-((2R,4R)-4-hydroxy-6-oxotetrahydro-2H-pyran-2-yl)ethyl)-3,7-dimethyl-1,2,3,7,8,8a-hexahydronaphthalen-1-yl (2-(2-(2-(((2S,4R)-1-((S)-2-(1-fluorocyclopropane-1-carboxamido)-3,3-dimethylbutanoyl)-4-hydroxypyrrolidine-2-carboxamido)methyl)-5-(4-methylthiazol-5-yl) phenoxy)ethoxy)ethyl)carbamate (Compound 23) and (1S,3R,7S,8S,8aR)-8-(2-((2R,4R)-4-((tert-butyldimethylsilyl)oxy)-6-oxotetrahydro-2H-pyran-2-yl)ethyl)-3,7-dimethyl-1,2,3,7,8,8a-hexahydronaphthalen-1-yl (2-(2-(2-(((2S,4R)-1-((S)-2-(1-fluorocyclopropane-1-carboxamido)-3,3-dimethylbutanoyl)-4-hydroxypyrrolidine-2-carboxamido)methyl)-5-(4-methylthiazol-5-yl) phenoxy)ethoxy)ethyl)carbamate (Compound 27)

Step 1: Synthesis of tert-butyl N-[2-(2-hydroxyethoxy) ethyl] carbamate (28a)

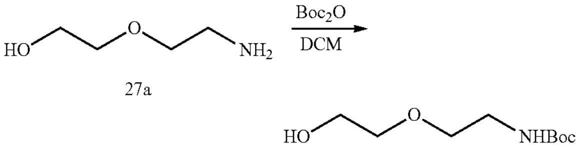

27a

28a

To a solution of 2-(2-aminoethoxy) ethanol (5.3 g, 50.41 mmol, 5.05 mL) in DCM (20 mL) was added Boc$_2$O (11.00 g, 50.41 mmol, 11.58 mL). The mixture was stirred at 25° C. for 3 h. TLC showed a main new spot was formed. DCM (80 mL) and water (100 mL) were added and layers were separated. The aqueous phase was extracted with DCM (80 mL×2). Combined extracts were washed with brine (100 mL), dried over $Na_2SO_4$, filtered. The filtrate was concentrated under vacuum. The residue was purified by silica gel chromatography (Petroleum ether/Ethyl acetate=1/1) to afford tert-butyl N-[2-(2-hydroxyethoxy)ethyl]carbamate (9.1 g, 44.34 mmol, 87.95% yield) as a colorless oil.

$^1$H NMR (400 MHz, $CDCl_3$) δ=5.18 (s, 1H), 3.70 (d, J=3.6 Hz, 2H), 3.63-3.43 (m, 4H), 3.30 (d, J=4.2 Hz, 2H), 2.89 (dd, J=3.2, 5.2 Hz, 1H), 1.41 (s, 9H).

Step 2: Synthesis of 2-[2-(tert-butoxycarbonylamino)ethoxy] ethyl 4-methylbenzenesulfonate (29a)

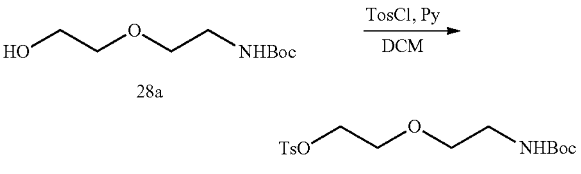

28a

29a

To a solution of tert-butyl N-[2-(2-hydroxyethoxy) ethyl] carbamate (4 g, 19.49 mmol) in DCM (40 mL) was added pyridine (1.54 g, 19.49 mmol, 1.57 mL) and TosCl (4.09 g, 21.44 mmol) at 0° C. and the resulting mixture was stirred at 25° C. for 2 h. LCMS showed 32% desired mass was detected. DCM (150 mL) and water (200 mL) were added and layers were separated. The aqueous phase was extracted with DCM (100 mL×2). Combined extracts were washed with brine (20 mL), dried over $Na_2SO_4$, filtered. The filtrate was concentrated under vacuum. The residue was purified by silica gel chromatography (Petroleum ether:Ethyl acetate=2:1) to afford 2-[2-(tert-butoxycarbonylamino) ethoxy] ethyl 4-methylbenzenesulfonate (3.9 g, 10.85 mmol, 55.68% yield) as a yellow oil. MS $(M+H)^+$=360.1

Step 3: Synthesis of (2S, 4R)-1-[(2S)-2-[(1-fluoro-cyclopropanecarbonyl) amino]-3, 3-dimethyl-butanoyl]-4-hydroxy-N-[[2-hydroxy-4-(4-methylthiazol-5-yl) phenyl] methyl] pyrrolidine-2-carboxamide (24)

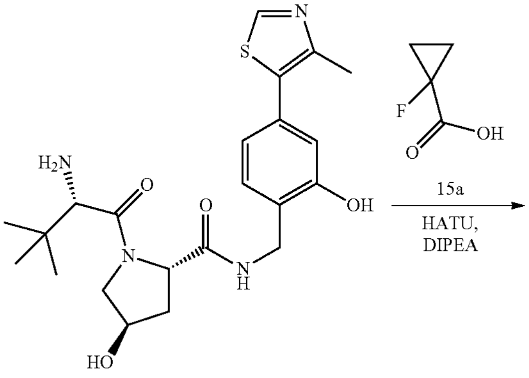

15

-continued

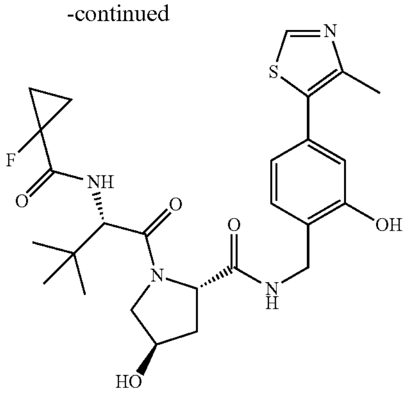

24

To a solution of 1-fluorocyclopropanecarboxylic acid (2.68 g, 25.74 mmol) in DMF (150 mL) was added HATU (12.23 g, 32.17 mmol) followed by DIPEA (13.86 g, 107.24 mmol, 18.68 mL). The mixture was stirred at 25° C. for 15 minutes. Then (2S, 4R)-1-[(2S)-2-amino-3, 3-dimethyl-butanoyl]-4-hydroxy-N-[[2-hydroxy-4-(4-methylthiazol-5-yl) phenyl] methyl] pyrrolidine-2-carboxamide (10.36 g, 21.45 mmol, HCl salt) was added and the resulting mixture was stirred at 25° C. for 2 h. LCMS showed starting material was consumed completely and 17% of desired mass and 63% of the mass of (2S, 4R)-1-[(2S)-2-[(1-fluorocyclopropanecarbonyl) amino]-3, 3-dimethyl-butanoyl]-4-hydroxy-N-[[2-hydroxy-4-(4-methylthiazol-5-yl) phenyl] methyl] pyrrolidine-2-carboxamide was detected. The mixture was quenched by addition of $H_2O$ (500 mL) and extracted with EtOAc (500 mL×3). The combined organic layers were washed with $CaCl_2$) (sat.aq, 300 mL×3), dried over $Na_2SO_4$, filtered. The filtrate was concentrated under reduced pressure. The residue was dissolved in MeOH (100 mL) and $NaHCO_3$ (sat.aq, 100 mL) was added. The mixture was stirred at 25° C. for 0.5 h. LCMS showed 95% of desired mass was detected. The mixture was concentrated under reduced pressure to remove most of MeOH and extracted with EtOAc (200 mL×2). The combined organic layers were washed with brine (300 mL), dried over $Na_2SO_4$, filtered and concentrated under reduced pressure. The residue was purified by silica gel column chromatography ($SiO_2$, 100~200 mesh, Petroleum ether/Ethyl acetate=1/1 to 0/1) to afford (2S, 4R)-1-[(2S)-2-[(1-fluorocyclopropanecarbonyl) amino]-3, 3-dimethyl-butanoyl]-4-hydroxy-N-[[2-hydroxy-4-(4-methylthiazol-5-yl) phenyl] methyl] pyrrolidine-2-carboxamide (5.24 g, 9.25 mmol, 43.13% yield, 94% purity)) as a brown solid. SFC (retention time=1.805, analysis method: "Column: Chiralpak IC-3 50×4.6 mm I.D., 3 μm; Mobile phase: Phase A for $CO_2$, and Phase B for MeOH (0.05% DEA); Gradient elution: MeOH (0.05% DEA) in $CO_2$ from 5% to 40%; Flow rate: 3 mL/min; Detector: PDA; Column Temp: 35C; Back Pressure: 100 Bar").

MS $(M+H)^+$=533.1

$^1H$ NMR (400 MHz, DMSO-$d_6$) δ=9.80 (s, 1H), 8.95 (s, 1H), 8.52 (t, J=5.8 Hz, 1H), 7.45-7.21 (m, 2H), 6.96-6.81 (m, 2H), 5.16 (d, J=3.4 Hz, 1H), 4.59 (d, J=9.1 Hz, 1H), 4.51 (t, J=8.2 Hz, 1H), 4.35 (s, 1H), 4.29-4.15 (m, 2H), 3.71-3.55 (m, 2H), 2.45 (s, 3H), 2.13-2.03 (m, 1H), 1.92 (ddd, $J_1$=12.6 Hz, $J_2$=8.6 Hz, $J_3$=3.9 Hz, 1H), 1.42-1.31 (m, 2H), 1.25-1.20 (m, 2H), 0.96 (s, 9H).

Step 4: Synthesis of tert-butyl N-[2-[2-[2-[[[(2S, 4R)-1-[(2S)-2-[(1-fluorocyclopropanecarbonyl) amino]-3, 3-dimethyl-butanoyl]-4-hydroxy-pyrrolidine-2-carbonyl] amino] methyl]-5-(4-methylthiazol-5-yl) phenoxy] ethoxy] ethyl] carbamate (25a)

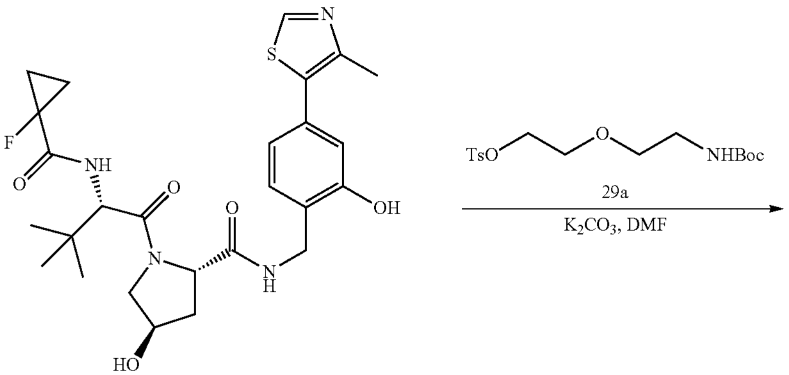

24

-continued

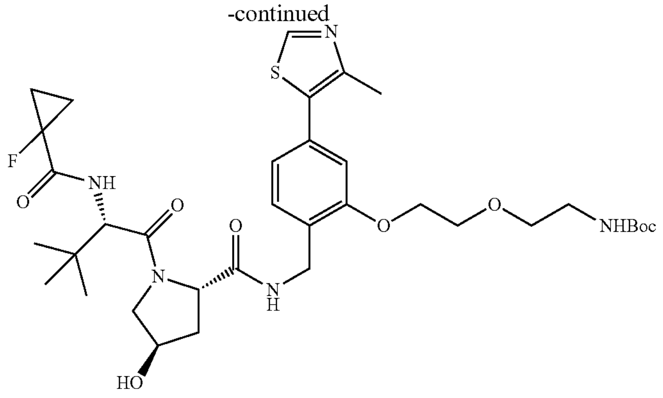

25a

To a solution of (2S, 4R)-1-[(2S)-2-[(1-fluorocyclopropanecarbonyl) amino]-3, 3-dimethyl-butanoyl]-4-hydroxy-N-[[2-hydroxy-4-(4-methylthiazol-5-yl) phenyl] methyl] pyrrolidine-2-carboxamide (1.5 g, 2.65 mmol) and 2-[2-(tert-butoxycarbonylamino) ethoxy]ethyl 4-methylbenzenesulfonate (1.60 g, 3.97 mmol) in DMF (25 mL) was added $K_2CO_3$ (2.20 g, 15.88 mmol) and the resulting mixture was stirred at 40° C. for 12 h. LCMS showed the starting material was consumed completely and 93% of desired mass was detected. The reaction mixture was diluted with brine (40 mL), and extracted with EtOAc (50 mL×3). The combined organic layers were washed with $CaCl_2$ (sat.aq, 50 mL×2), dried over $Na_2SO_4$, filtered. The filtrate was concentrated under reduced pressure. The residue was purified by silica gel column chromatography ($SiO_2$, 100~200 mesh, EtOAc:MeOH=1:0~20:1). Compound (tert-butyl N-[2-[2-[2-[[[(2S, 4R)-1-[(2S)-2-[(1-fluorocyclopropanecarbonyl) amino]-3, 3-dimethyl-butanoyl]-4-hydroxy-pyrrolidine-2-carbonyl] amino] methyl]-5-(4-methylthiazol-5-yl) phenoxy] ethoxy] ethyl] carbamate (1.74 g, 2.32 mmol, 87.65% yield, 96% purity)) was obtained as a colourless oil. MS $(M+H)^+$=720.1.

Step 5: Synthesis of (2S, 4R)—N-[[2-[2-(2-aminoethoxy) ethoxyl-4-(4-methylthiazol-5-yl) phenyl] methyl]-1-[(2S)-2-[(1-fluorocyclopropanecarbonyl) amino]-3, 3-dimethyl-butanoyl]-4-hydroxy-pyrrolidine-2-carboxamide (26a)

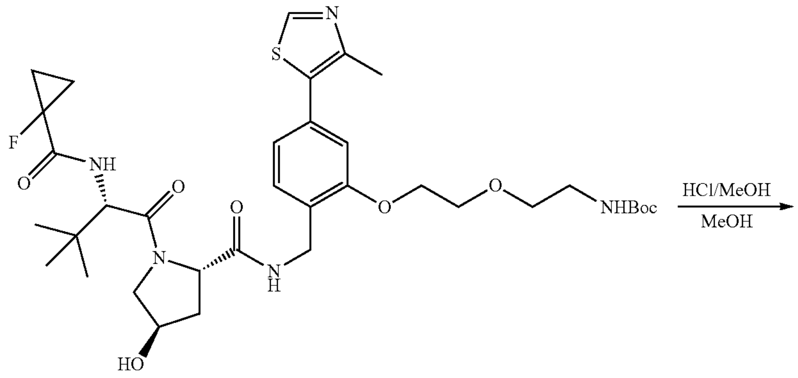

25a

-continued

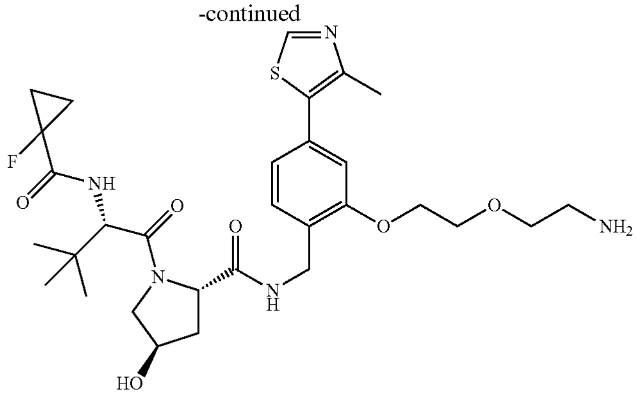

26a

To a solution of tert-butyl N-[2-[2-[2-[[[(2S, 4R)-1-[(2S)-2-[(1-fluorocyclopropanecarbonyl) amino]-3, 3-dimethyl-butanoyl]-4-hydroxy-pyrrolidine-2-carbonyl] amino] methyl]-5-(4-methylthiazol-5-yl) phenoxy] ethoxy] ethyl] carbamate (1.74 g, 2.42 mmol) in MeOH (10 mL) was added HCl/MeOH (4 M, 15.92 mL). The mixture was stirred at 25° C. for 2 h. LCMS showed 75% of desired mass was detected. The reaction mixture was concentrated under reduced pressure. Compound ((2S, 4R)—N-[[2-[2-(2-aminoethoxy) ethoxy]-4-(4-methylthiazol-5-yl) phenyl] methyl]-1-[(2S)-2-[(1-fluorocyclopropanecarbonyl) amino]-3, 3-dimethyl-butanoyl]-4-hydroxy-pyrrolidine-2-carboxamide (1.94 g, crude, HCl)) was obtained as a yellow solid, which was used for next step without any further purification. MS $(M+H)^+$=620.3.

Step 6: Synthesis of (1S,3R,7S,8S,8aR)-8-(2-((2R, 4R)-4-((tert-butyldimethylsilyl)oxy)-6-oxotetrahydro-2H-pyran-2-yl)ethyl)-3,7-dimethyl-1,2,3,7,8, 8a-hexahydronaphthalen-1-yl (2-(2-(2-(((2S,4R)-1-((S)-2-(1-fluorocyclopropane-1-carboxamido)-3,3-dimethylbutanoyl)-4-hydroxypyrrolidine-2-carboxamido)methyl)-5-(4-methylthiazol-5-yl)phenoxy) ethoxy)ethyl)carbamate (Compound 27)

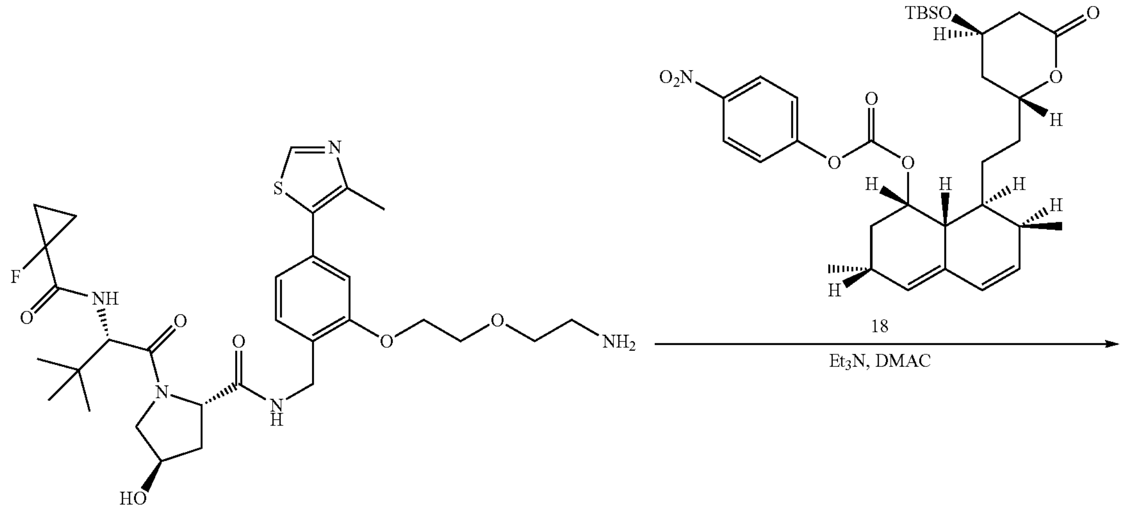

26a

-continued

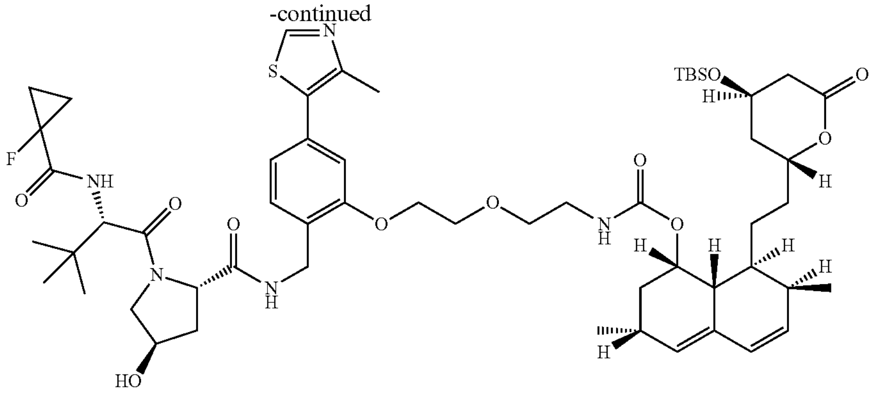

Compound 27

A mixture of (2S, 4R)—N-[[2-[2-(2-aminoethoxy) ethoxy]-4-(4-methylthiazol-5-yl) phenyl] methyl]-1-[(2S)-2-[(1-fluorocyclopropanecarbonyl) amino]-3, 3-dimethyl-butanoyl]-4-hydroxy-pyrrolidine-2-carboxamide (252 mg, 303.38 μmol, HCl salt), [(1S, 3R, 7S, 8S, 8aR)-8-[2-[(2R, 4R)-4-[tert-butyl (dimethyl) silyl]oxy-6-oxo-tetrahydropyran-2-yl]ethyl]-3, 7-dimethyl-1, 2, 3, 7, 8, 8a-hexahydronaphthalen-1-yl] (4-nitrophenyl) carbonate (568.63 mg, 455.07 μmol) and TEA (153.50 mg, 1.52 mmol, 211.13 μL) in DMAC (3 mL) was stirred at 25° C. for 12 h. LCMS showed 41% of desired mass was detected. The reaction mixture was quenched by addition of $H_2O$ (20 mL) and extracted with EtOAc (40 mL×3). The combined organic layers were washed with $CaCl_2$ (sat.aq, 50 mL×2), dried over $Na_2SO_4$, filtered and concentrated under reduced pressure. The residue was purified by prep-HPLC (column: Phenomenex Synergi C18 150*25*10 μm; mobile phase: [water (0.225% FA)-ACN]; B %$_0$: 70%-1000%, 8 min). Compound ((1S,3R,7S,8S,8aR)-8-(2-((2R,4R)-4-((tert-butyldimethylsilyl)oxy)-6-oxotetrahydro-2H-pyran-2-yl) ethyl)-3,7-dimethyl-1,2,3,7,8,8a-hexahydronaphthalen-1-yl (2-(2-(2-(((2S,4R)-1-((S)-2-(1-fluorocyclopropane-1-carboxamido)-3,3-dimethylbutanoyl)-4-hydroxypyrrolidine-2-carboxamido)methyl)-5-(4-methylthiazol-5-yl)phenoxy) ethoxy)ethyl)carbamate (92 mg, 83.45 μmol, 27.51% yield, 9800 purity) was obtained as a white solid. SFC: (retention time=1.973, analysis method: "Column: Cellucoat 50×4.6 mm I.D., 3 μm; Mobile phase: Phase A for $CO_2$, and Phase B for IPA (0.05% DEA); Gradient elution: IPA (0.05% DEA) in $CO_2$ from 5% to 40% Flow rate: 3 mL/min; Detector: PDA; Column Temp: 35 C; Back Pressure: 100 Bar").

MS $(M+H)^+$=1080.3.

$^1$H NMR (400 MHz, DMSO-$d_6$) δ 8.99 (s, 1H), 8.50 (t, J=6.0 Hz, 1H), 7.42 (d, J=7.7 Hz, 1H), 7.32-7.26 (m, 1H), 7.09-6.96 (m, 3H), 5.92 (d, J=9.6 Hz, 1H), 5.79-5.71 (m, 1H), 5.47 (s, 1H), 5.18 (d, J=3.6 Hz, 1H), 5.06 (s, 1H), 4.61 (d, J=9.2 Hz, 1H), 4.55-4.45 (m, 2H), 4.40-4.25 (m, 4H), 4.25-4.09 (m, 4H), 3.76 (s, 2H), 3.68-3.59 (m, 2H), 3.49 (t, J=6.2 Hz, 2H), 3.18-3.09 (m, 2H), 2.70-2.67 (m, 1H), 2.46 (s, 3H), 2.37-2.33 (m, 2H), 2.26-2.22 (m, 1H), 2.13-2.07 (m, 1H), 1.95-1.90 (m, 1H), 1.86-1.82 (m, 2H), 1.74-1.65 (m, 3H), 1.52-1.45 (m, 1H), 1.41-1.32 (m, 3H), 1.28-1.21 (m, 3H), 1.04 (d, J=7.3 Hz, 3H), 0.98-0.95 (m, 9H), 0.85-0.81 (m, 12H), 0.06 (s, 6H).

Step 7: Synthesis of (1S,3R,7S,8S,8aR)-8-(2-((2R,4R)-4-hydroxy-6-oxotetrahydro-2H-pyran-2-yl) ethyl)-3,7-dimethyl-1,2,3,7,8,8a-hexahydronaphthalen-1-yl (2-(2-(2-(((2S,4R)-1-((S)-2-(1-fluorocyclopropane-1-carboxamido)-3,3-dimethylbutanoyl)-4-hydroxypyrrolidine-2-carboxamido)methyl)-5-(4-methylthiazol-5-yl) phenoxy)ethoxy)ethyl)carbamate (Compound 23)

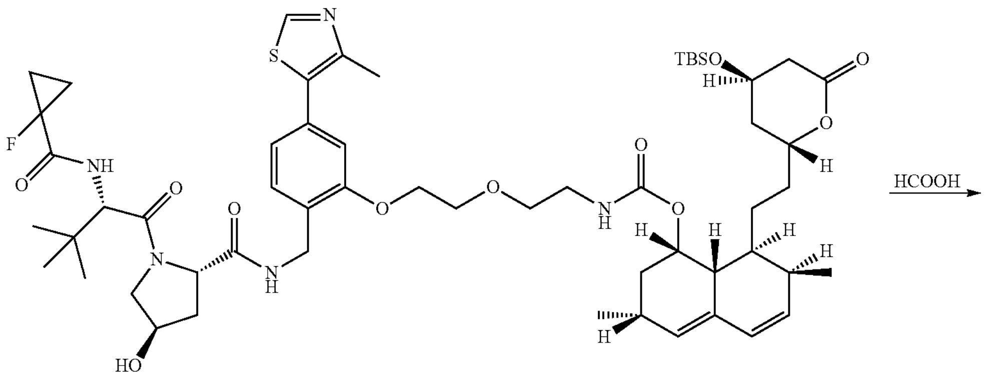

Compound 27

-continued

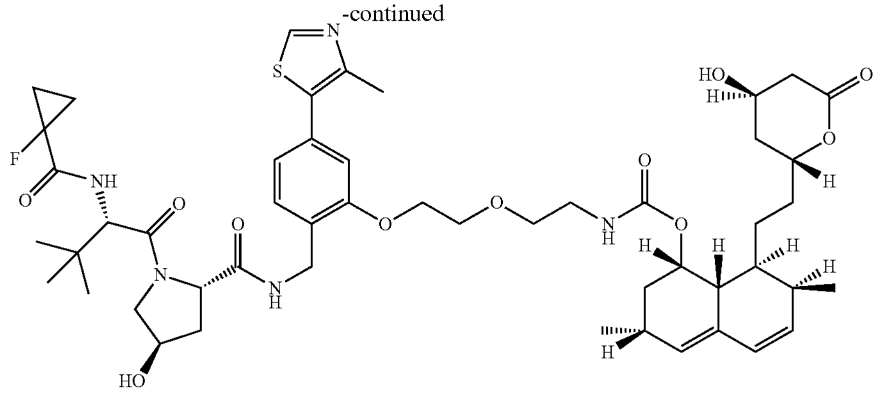

Compound 23

The mixture of (1S,3R,7S,8S,8aR)-8-(2-((2R,4R)-4-((tert-butyldimethylsilyl)oxy)-6-oxotetrahydro-2H-pyran-2-yl)ethyl)-3,7-dimethyl-1,2,3,7,8,8a-hexahydronaphthalen-1-yl (2-(2-(2-(((2S,4R)-1-((S)-2-(1-fluorocyclopropane-1-carboxamido)-3,3-dimethylbutanoyl)-4-hydroxypyrrolidine-2-carboxamido)methyl)-5-(4-methylthiazol-5-yl)phenoxy)ethoxy)ethyl)carbamate (500 mg, 462.78 μmol) in HCOOH (2 mL) was stirred at 20° C. for 3 h. LCMS showed that 45% desired mass was detected. The mixture was adjusted pH=~5 with $NaHCO_3$ solid. The resulting mixture was purified by prep-HPLC (column: Phenomenex luna C18 150*40 mm*15 μm; mobile phase: [water (0.225% FA)-ACN]; B %: 42%-72%, 11 min) followed by prep-TLC (Ethylacetate:Methanol=10/1) to obtain 70 mg of crude product, the crude product was re-purified by prep-HPLC (column: 3_Phenomenex Luna C18 75*30 mm*3 μm; mobile phase: [water (0.225% FA)-ACN]; B %: 48%-68%, 8 min) to afford (1S,3R,7S,8S,8aR)-8-(2-((2R,4R)-4-hydroxy-6-oxotetrahydro-2H-pyran-2-yl)ethyl)-3,7-dimethyl-1,2,3,7,8,8a-hexahydronaphthalen-1-yl (2-(2-(2-(((2S,4R)-1-((S)-2-(1-fluorocyclopropane-1-carboxamido)-3,3-dimethylbutanoyl)-4-hydroxypyrrolidine-2-carboxamido)methyl)-5-(4-methylthiazol-5-yl)phenoxy)ethoxy)ethyl)carbamate (24.4 mg, 24.24 μmol, 5.24% yield, 93% purity) as white solid.

SFC: (retention time=2.083 min, analysis method: "Column: Chiralcel OD-3 50×4.6 mm I.D., 3 μm Mobile phase: Phase A for $CO_2$, and Phase B for MeOH (0.05% DEA); Gradient elution: MeOH (0.05% DEA) in $CO_2$ from 5% to 40% Flow rate: 3 mL/min; Detector: PDA, Column Temp: 35° C.; Back Pressure: 100 Bar.")

MS $(M+H)^+$=966.4.

$^1H$ NMR (400 MHz, $CDCl_3$) δ 8.68 (s, 1H), 7.34 (d, J=7.7 Hz, 1H), 7.20-7.10 (m, 1H), 6.98 (dd, J=7.7, 1.6 Hz, 1H), 6.88 (d, J=1.6 Hz, 1H), 5.96 (d, J=9.6 Hz, 1H), 5.78 (dd, J=9.6, 6.1 Hz, 1H), 5.49 (s, 1H), 5.23 (s, 1H), 5.14 (s, 1H), 4.72-4.44 (m, 6H), 4.30-4.11 (m, 3H), 3.98 (d, J=11.1 Hz, 1H), 3.88 (s, 2H), 3.70-3.28 (m, 6H), 2.73-2.53 (m, 2H), 2.53 (s, 3H), 2.49-2.15 (m, 5H), 2.04-1.69 (m, 6H), 1.42-1.17 (m, 7H), 1.04 (d, J=6.8 Hz, 3H), 1.02-0.90 (m, 9H), 0.88 (d, J=7.0 Hz, 3H).

Example 24 & Example 28. Synthesis of (1S,3R,7S,8S,8aR)-8-(2-((2R,4R)-4-hydroxy-6-oxotetrahydro-2H-pyran-2-yl)ethyl)-3,7-dimethyl-1,2,3,7,8,8a-hexahydronaphthalen-1-yl (2-(2-(2-(2-(((2S,4R)-1-((S)-2-(1-fluorocyclopropane-1-carboxamido)-3,3-dimethylbutanoyl)-4-hydroxypyrrolidine-2-carboxamido)methyl)-5-(4-methylthiazol-5-yl)phenoxy)ethoxy)ethoxy)ethyl)carbamate (Compound 24) and (1S,3R,7S,8S,8aR)-8-(2-((2R,4R)-4-((tert-butyldimethylsilyl)oxy)-6-oxotetrahydro-2H-pyran-2-yl)ethyl)-3,7-dimethyl-1,2,3,7,8,8a-hexahydronaphthalen-1-yl (2-(2-(2-(2-(((2S,4R)-1-((S)-2-(1-fluorocyclopropane-1-carboxamido)-3,3-dimethylbutanoyl)-4-hydroxypyrrolidine-2-carboxamido)methyl)-5-(4-methylthiazol-5-yl)phenoxy)ethoxy)ethoxy)ethyl)carbamate (Compound 28)

Step 1: Synthesis of tert-butyl N-[2-[2-(2-hydroxyethoxy) ethoxy] ethyl]carbamate (28b)

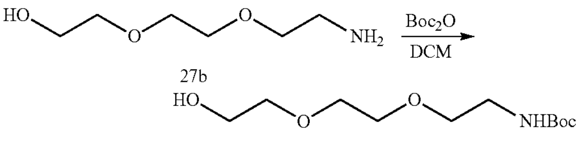

27b

28b

In a manner similar to Step 1 of Example 23, 27, the titled compound (4.7 g, 18.85 mmol, 93.75% yield) was obtained as a colorless oil.

$^1H$ NMR (400 MHz, $CDCl_3$) δ=5.20 (s, 1H), 3.84-3.46 (m, 11H), 3.30 (d, J=4.9 Hz, 2H), 1.53-1.41 (m, 9H).

Step 2: Synthesis of 2-[2-[2-(tert-butoxycarbonylamino) ethoxy] ethoxy] ethyl 4-methylbenzenesulfonate (29b)

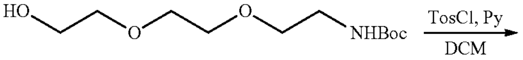

28b

-continued

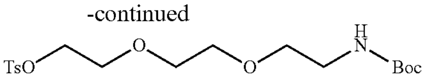

29b

In a manner similar to Step 2 of Example 23, 27, the titled compound (3.4 g, 6.40 mmol, 33.97% yield, 76% purity) was obtained as a colorless oil.

MS $(M+H)^+$=404.2

Step 3: Synthesis of tert-butyl (2-(2-(2-(2-(((2S, 4R)-1-((S)-2-(1-fluorocyclopropane-1-carboxamido)-3,3-dimethylbutanoyl)-4-hydroxypyrrolidine-2-carboxamido)methyl)-5-(4-methylthiazol-5-yl)phenoxy)ethoxy)ethoxy)ethyl)carbamate (25b)

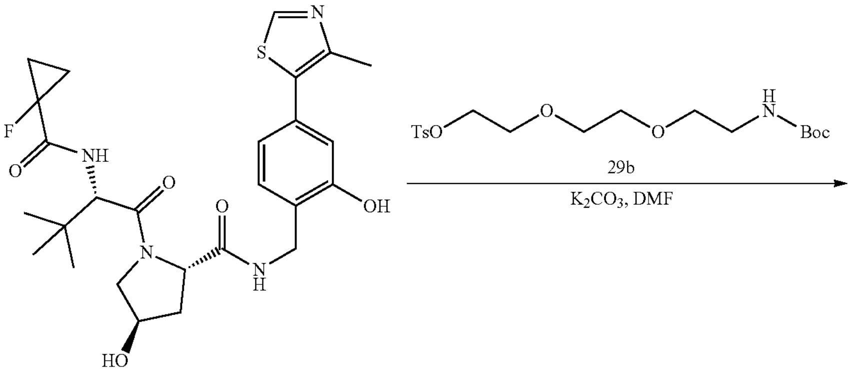

24

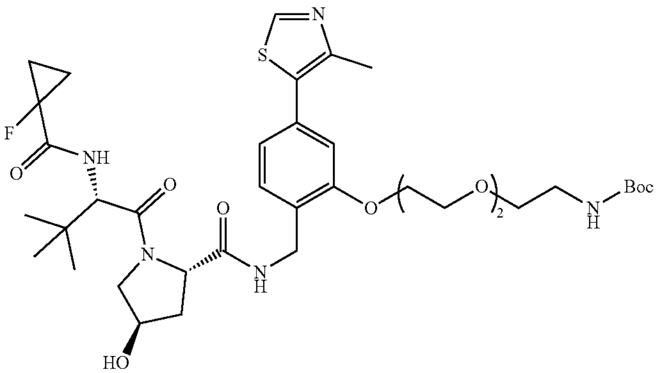

25b

In a manner similar to Step 4 of Example 23, 27, the titled compound (1.72 g, 2.18 mmol, 82.50% yield, 97% purity) was obtained as a yellowish oil.

MS $(M+H)^+$=764.2.

Step 4: Synthesis of (2S, 4R)—N-[[2-[2-[2-(2-aminoethoxy) ethoxy] ethoxy]-4-(4-methylthiazol-5-yl) phenyl] methyl]-1-[(2S)-2-[(1-fluorocyclopropanecarbonyl) amino]-3, 3-dimethyl-butanoyl]-4-hydroxy-pyrrolidine-2-carboxamide (26b)

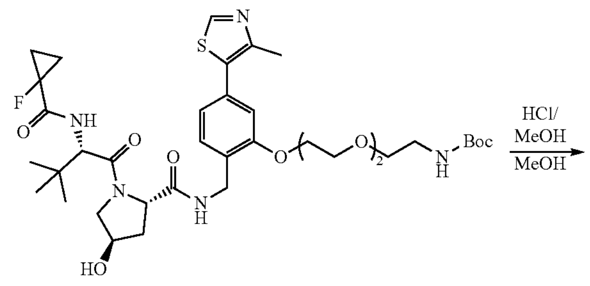

25b

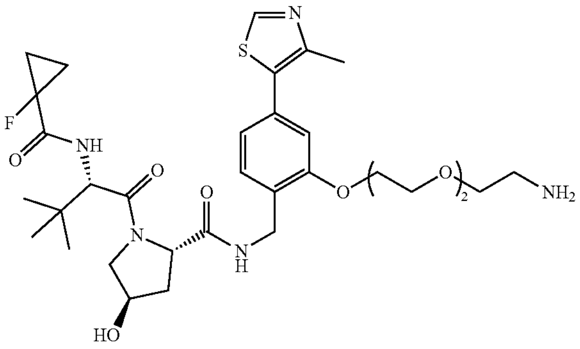

26b

In a manner similar to Step 5 of Example 23, 27, the titled compound (1.75 g, crude, HCl salt) was obtained as a yellow solid.

MS $(M+H)^+$=664.4.

Step 5: Synthesis of (1S,3R,7S,8S,8aR)-8-(2-((2R, 4R)-4-((tert-butyldimethylsilyl)oxy)-6-oxotetrahydro-2H-pyran-2-yl)ethyl)-3,7-dimethyl-1,2,3,7,8, 8a-hexahydronaphthalen-1-yl (2-(2-(2-(2-(((2S,4R)-1-((S)-2-(1-fluorocyclopropane-1-carboxamido)-3,3-dimethylbutanoyl)-4-hydroxypyrrolidine-2-carboxamido)methyl)-5-(4-methylthiazol-5-yl) phenoxy)ethoxy)ethoxy)ethyl)carbamate (Compound 28)

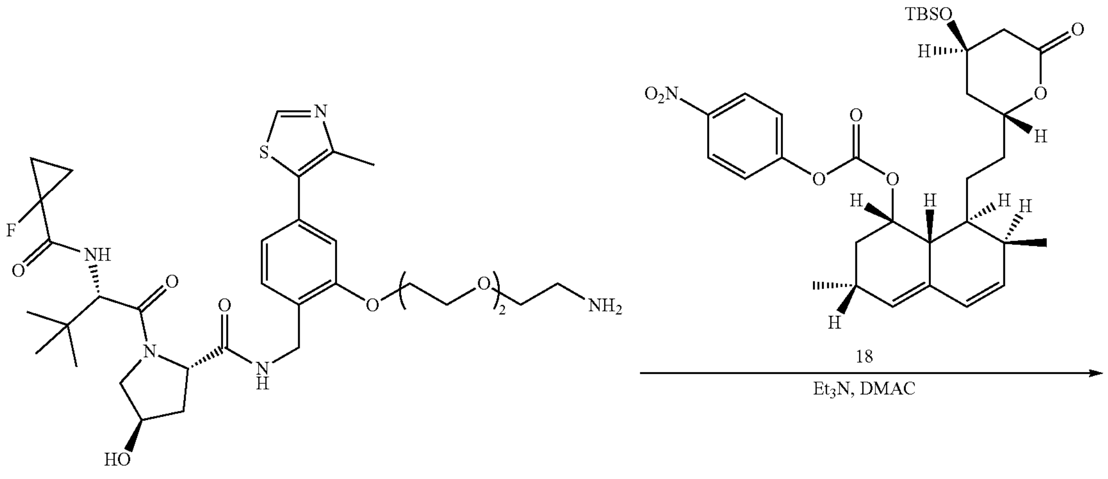

18

26b

-continued

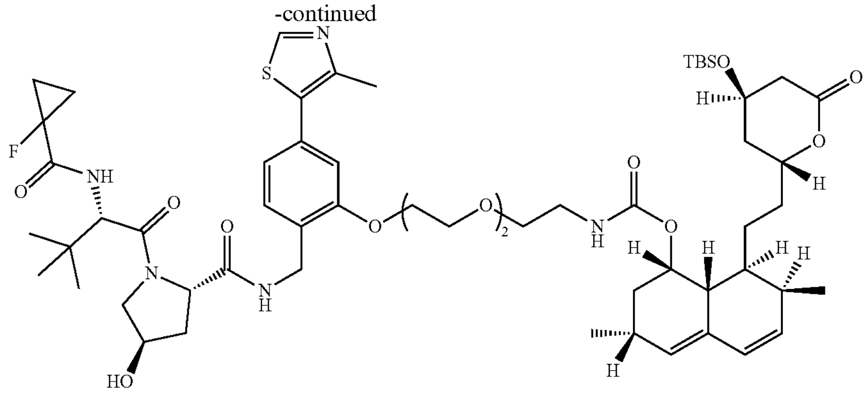

Compound 28

In a manner similar to Step 6 of Example 23, 27, the titled compound (135.5 mg, 115.68 μmol, 4.63% yield, 96% purity) was obtained as a white solid.

SFC: (retention time: 0.616, analysis method: "Column: Chiralpak IG-3 50×4.6 mm I.D., 3 μm; Mobile phase: Phase A for $CO_2$, and Phase B for IPA+ACN (0.05% DEA); Gradient elution: 50% IPA+ACN (0.05% DEA) in $CO_2$; Flow rate: 3 mL/min; Detector: PDA; Column Temp: 35 C; Back Pressure: 100 Bar").

MS $(M+H)^+$=1124.2

$^1$H NMR (400 MHz, DMSO-$d_6$) δ 8.98 (s, 1H), 8.54-8.43 (m, 1H), 7.41 (d, J=7.8 Hz, 1H), 7.29 (dd, J=9.4, 2.8 Hz, 1H), 7.04-6.95 (m, 3H), 5.90 (d, J=9.7 Hz, 1H), 5.74 (s, 1H), 5.45 (s, 1H), 5.17 (d, J=3.6 Hz, 1H), 5.09-5.01 (m, 1H), 4.60 (d, J=9.2 Hz, 1H), 4.54-4.44 (m, 2H), 4.39-4.10 (m, 8H), 3.78 (t, J=4.6 Hz, 2H), 3.67-3.59 (m, 4H), 3.53-3.49 (m, 2H), 3.40-3.36 (m, 2H), 3.09 (t, J=6.1 Hz, 2H), 2.71-2.66 (m, 1H), 2.46 (s, 3H), 2.37-2.32 (m, 2H), 2.27-2.21 (m, 1H), 2.12-2.05 (m, 1H), 1.95-1.88 (m, 1H), 1.84-1.77 (m, 3H), 1.73-1.64 (m, 3H), 1.51-1.45 (m, 1H), 1.39-1.33 (m, 2H), 1.26-1.20 (m, 3H), 1.03 (d, J=7.3 Hz, 3H), 0.98-0.93 (m, 9H), 0.85-0.81 (m, 12H), 0.05 (s, 6H).

Step 6: Synthesis of (1S,3R,7S,8S,8aR)-8-(2-((2R, 4R)-4-hydroxy-6-oxotetrahydro-2H-pyran-2-yl) ethyl)-3,7-dimethyl-1,2,3,7,8,8a-hexahydronaphthalen-1-yl (2-(2-(2-(2-(((2S,4R)-1-((S)-2-(1-fluorocyclopropane-1-carboxamido)-3,3-dimethylbutanoyl)-4-hydroxypyrrolidine-2-carboxamido)methyl)-5-(4-methylthiazol-5-yl) phenoxy)ethoxy)ethoxy)ethyl)carbamate (Compound 24)

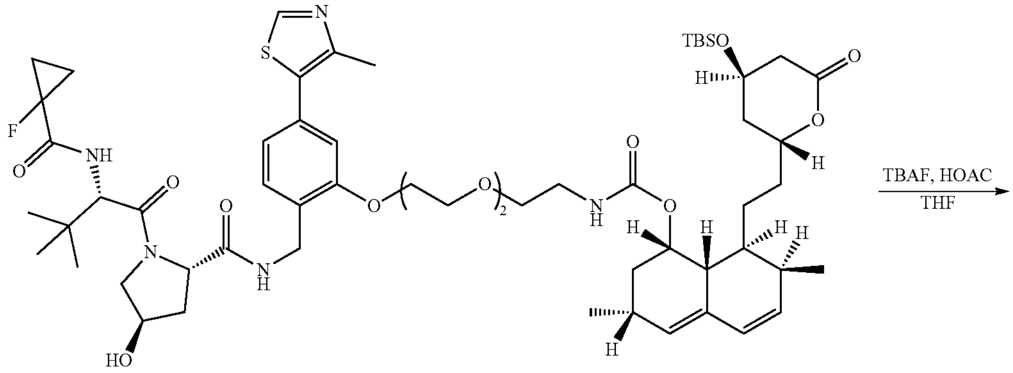

Compound 28

-continued

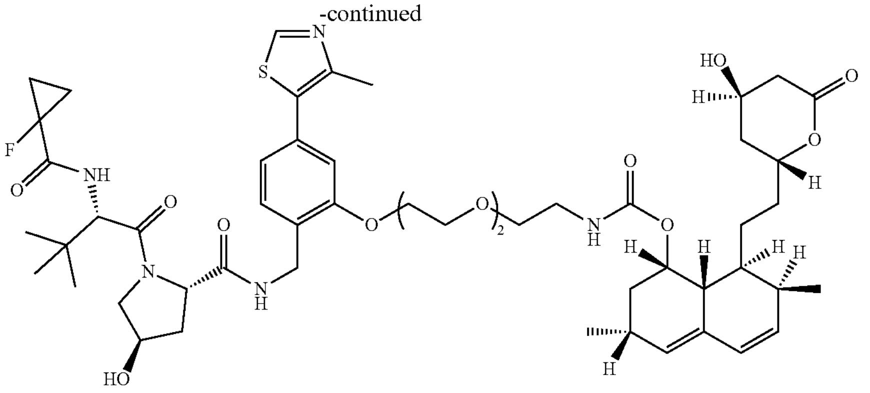

Compound 24

The mixture of (1S,3R,7S,8S,8aR)-8-(2-((2R,4R)-4-((tert-butyldimethylsilyl)oxy)-6-oxotetrahydro-2H-pyran-2-yl)ethyl)-3,7-dimethyl-1,2,3,7,8,8a-hexahydronaphthalen-1-yl (2-(2-(2-(2-(((2S,4R)-1-((S)-2-(1-fluorocyclopropane-1-carboxamido)-3,3-dimethylbutanoyl)-4-hydroxypyrrolidine-2-carboxamido)methyl)-5-(4-methylthiazol-5-yl)phenoxy)ethoxy)ethoxy)ethyl) carbamate (300 mg, 266.79 μmol) in THE (10 mL) was added TBAF (1 M, 1.07 mL) and AcOH (80.11 mg, 1.33 mmol, 76.29 μL) and the resulting mixture was stirred at 25° C. for 12 h. LCMS showed 71% desired mass was detected. The mixture was poured into water (50 mL) and extracted with EtOAc (50 mL×3). The combined organic layer was washed with brine (100 mL), dried over $Na_2SO_4$, filtered and concentrated. The residue was purified by prep-TLC (Ethylacetate:Methanol=10:1) followed by prep-HPLC (column: Shim-pack C18 150*25*10 μm; mobile phase: [water (0.225% FA)-ACN]; B %: 54%-74%, 9 min) to afford (1S,3R,7S,8S,8aR)-8-(2-((2R,4R)-4-hydroxy-6-oxotetrahydro-2H-pyran-2-yl)ethyl)-3,7-dimethyl-1,2,3,7,8,8a-hexahydronaphthalen-1-yl (2-(2-(2-(2-(((2S,4R)-1-((S)-2-(1-fluorocyclopropane-1-carboxamido)-3,3-dimethylbutanoyl)-4-hydroxypyrrolidine-2-carboxamido) methyl)-5-(4-methylthiazol-5-yl)phenoxy)ethoxy)ethoxy) ethyl)carbamate (70.4 mg, 68.99 μmol, 25.86% yield, 99% purity) as white solid.

SFC: (retention time=2.083 min, Column: Chiralcel OD-3 50×4.6 mm I.D., 3 μm Mobile phase: Phase A for $CO_2$, and Phase B for MeOH (0.05% DEA); Gradient elution: MeOH (0.05% DEA) in $CO_2$ from 5% to 40%, Flow rate: 3 mL/min; Detector: PDA Column Temp: 35° C.; Back Pressure: 100 Bar").

MS $(M+H)^+$=1011.0

$^1H$ NMR (400 MHz, $CDCl_3$) δ 8.70 (s, 1H), 7.39-7.35 (m, 1H), 7.13 (s, 1H), 7.00 (dd, J=7.7, 1.6 Hz, 1H), 6.92 (s, 1H), 5.97 (d, J=9.7 Hz, 1H), 5.77 (s, 1H), 5.52 (s, 1H), 5.32-5.20 (m, 2H), 4.70-4.46 (m, 6H), 4.31-4.16 (m, 3H), 4.00 (d, J=11.4 Hz, 1H), 3.97-3.87 (m, 2H), 3.79-3.61 (m, 6H), 3.61-3.45 (m, 2H), 3.37-3.19 (m, 2H), 2.75-2.58 (m, 2H), 2.55 (s, 3H), 2.48-2.20 (m, 5H), 2.07-1.67 (m, 6H), 1.42-1.25 (m, 7H), 1.08 (d, J=7.4 Hz, 3H), 1.04-1.00 (m, 9H), 0.89 (d, J=6.9 Hz, 3H).

Example 25 & Example 29. Synthesis of (1S,3R,7S,8S,8aR)-8-(2-((2R,4R)-4-hydroxy-6-oxotetrahydro-2H-pyran-2-yl)ethyl)-3,7-dimethyl-1,2,3,7,8,8a-hexahydronaphthalen-1-yl (2-(2-(2-(2-(2-(((2S,4R)-1-((S)-2-(1-fluorocyclopropane-1-carboxamido)-3,3-dimethylbutanoyl)-4-hydroxypyrrolidine-2-carboxamido)methyl)-5-(4-methylthiazol-5-yl)phenoxy)ethoxy)ethoxy)ethoxy) ethyl)carbamate (Compound 25) and (1S,3R,7S,8S,8aR)-8-(2-((2R,4R)-4-((tert-butyldimethylsilyl)oxy)-6-oxotetrahydro-2H-pyran-2-yl)ethyl)-3,7-dimethyl-1,2,3,7,8,8a-hexahydronaphthalen-1-yl (2-(2-(2-(2-(2-(((2S,4R)-1-((S)-2-(1-fluorocyclopropane-1-carboxamido)-3,3-dimethylbutanoyl)-4-hydroxypyrrolidine-2-carboxamido)methyl)-5-(4-methylthiazol-5-yl)phenoxy)ethoxy)ethoxy)ethoxy) ethyl)carbamate (Compound 29)

Step 1: Synthesis of tert-butyl N-[2-[2-[2-(2-hydroxyethoxy) ethoxy] ethoxy] ethyl]carbamate (28c)

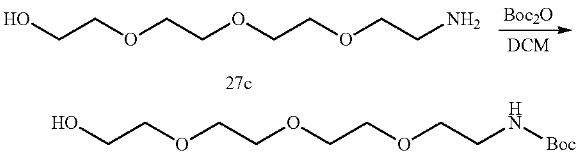

27c

28c

In a manner similar to Step 1 of Example 23, 27, the titled compound (3.9 g, crude) was obtained as a colorless oil.

Step 2: Synthesis of 2-[2-[2-[2-(tert-butoxycarbonylamino) ethoxy] ethoxy] ethoxy] ethyl 4-methylbenzenesulfonate (29c)

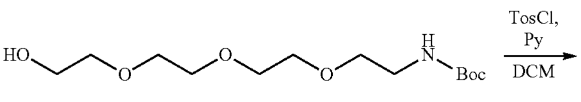

28c

-continued

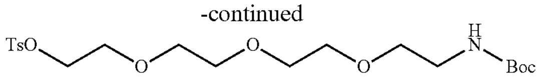

29c

In a manner similar to Step 2 of Example 23, 27, the titled compound (3.1 g, 5.61 mmol, 42.20% yield, 81% purity) was obtained as a colorless oil.

MS $(M+H)^+$=448.2

Step 3: Synthesis of tert-butyl (2-(2-(2-(2-(2-(((2S, 4R)-1-((S)-2-(1-fluorocyclopropane-1-carboxamido)-3,3-dimethylbutanoyl)-4-hydroxypyrrolidine-2-carboxamido)methyl)-5-(4-methylthiazol-5-yl)phenoxy)ethoxy)ethoxy)ethoxy)ethyl)carbamate (25c)

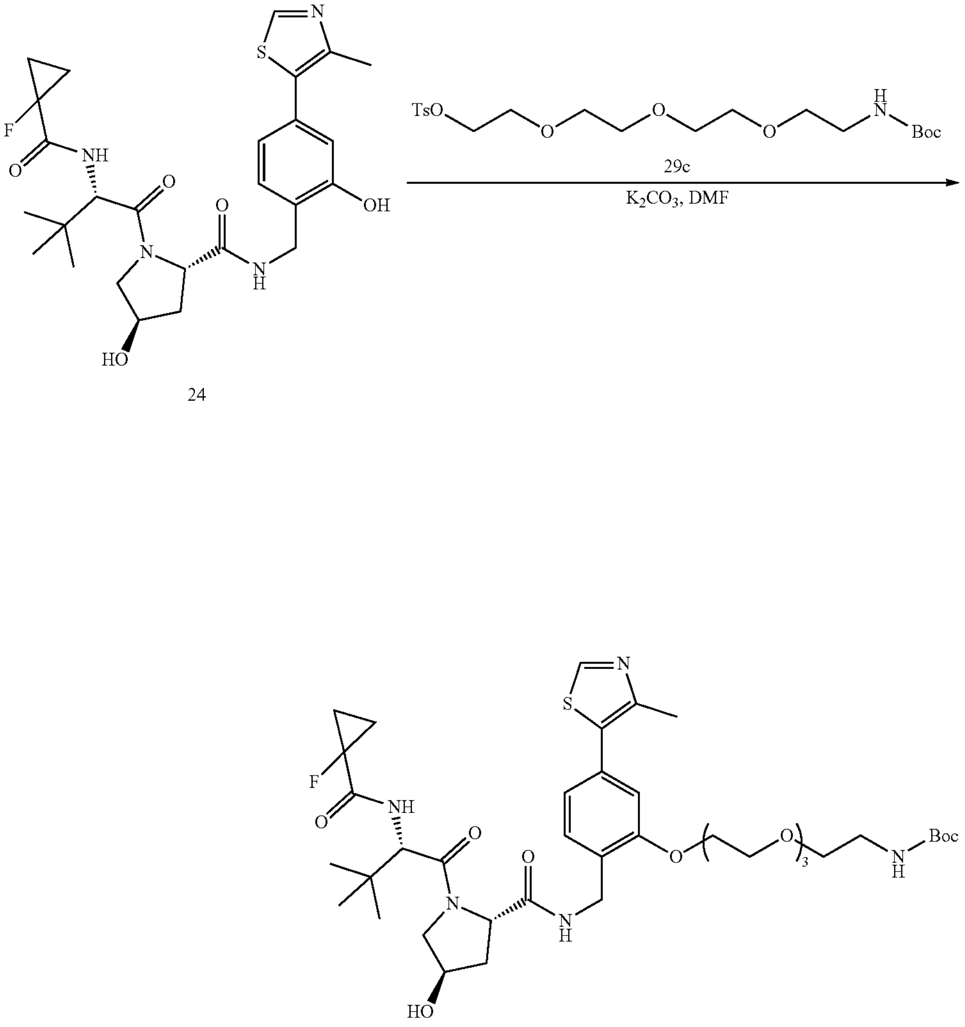

24

25c

In a manner similar to Step 4 of Example 23, 27, the titled compound (1.68 g, 1.68 mmol, 63.62% yield, 81% purity) was obtained as a yellowish oil.

MS $(M+H)^+$=808.2

Step 4: Synthesis of (2S, 4R)—N-[[2-[2-[2-[2-(2-aminoethoxy) ethoxy] ethoxy] ethoxy]-4-(4-methylthiazol-5-yl) phenyl] methyl]-1-[(2S)-2-[(1-fluorocyclopropanecarbonyl) amino]-3, 3-dimethylbutanoyl]-4-hydroxy-pyrrolidine-2-carboxamide (26c)

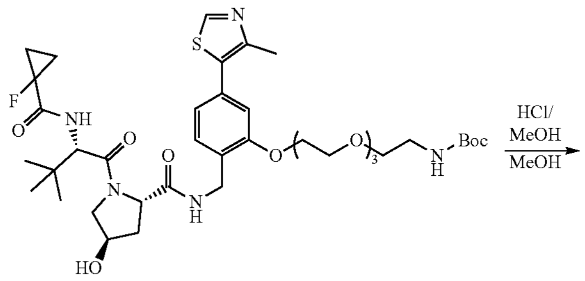

25c

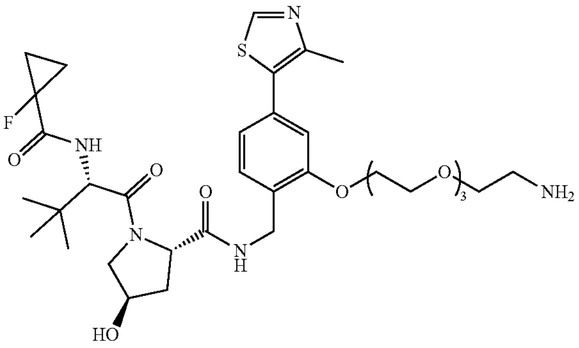

26c

To a solution of tert-butyl (2-(2-(2-(2-(2-(((2S,4R)-1-((S)-2-(1-fluorocyclopropane-1-carboxamido)-3,3-dimethylbutanoyl)-4-hydroxypyrrolidine-2-carboxamido)methyl)-5-(4-methylthiazol-5-yl)phenoxy)ethoxy)ethoxy)ethoxy)ethyl) carbamate (1.68 g, 2.08 mmol) in MeOH (10 mL) was added HCl/MeOH (4 M, 15 mL). The reaction mixture was stirred at 25° C. for 2 h. LCMS showed the starting material was consumed completely. The reaction mixture was concentrated under reduced pressure. Compound ((2S, 4R)—N-[[2-[2-[2-[2-(2-aminoethoxy) ethoxy] ethoxy] ethoxy]-4-(4-methylthiazol-5-yl) phenyl] methyl]-1-[(2S)-2-[(1-fluorocyclopropanecarbonyl) amino]-3,3-dimethylbutanoyl]-4-hydroxy-pyrrolidine-2-carboxamide (1.78 g, crude, HCl salt)) was obtained as a yellow solid, which was used for next step without any further purification.

MS $(M+H)^+$=708.4.

Step 5: Synthesis of (1S,3R,7S,8S,8aR)-8-(2-((2R, 4R)-4-((tert-butyldimethylsilyl)oxy)-6-oxotetrahydro-2H-pyran-2-yl)ethyl)-3,7-dimethyl-1,2,3,7,8, 8a-hexahydronaphthalen-1-yl (2-(2-(2-(2-(2-(((2S, 4R)-1-((S)-2-(1-fluorocyclopropane-1-carboxamido)-3,3-dimethylbutanoyl)-4-hydroxypyrrolidine-2-carboxamido)methyl)-5-(4-methylthiazol-5-yl)phenoxy)ethoxy)ethoxy)ethoxy) ethyl)carbamate (Compound 29)

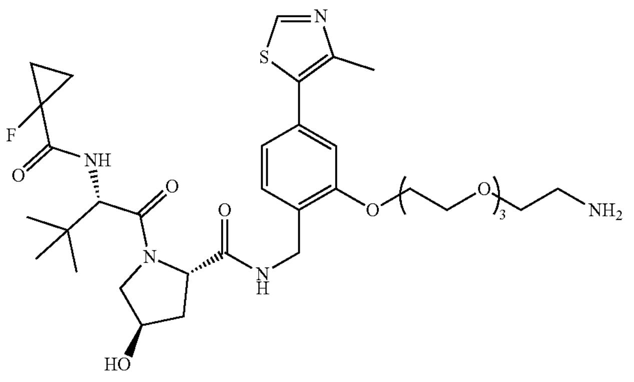

26c

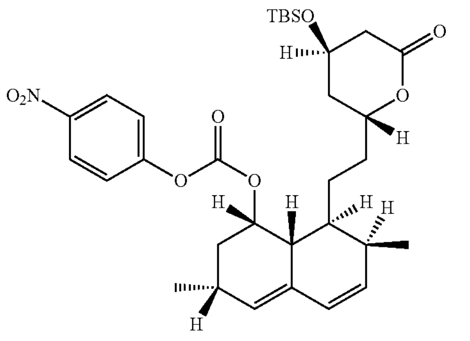

18

$Et_3N$, DMAC

-continued

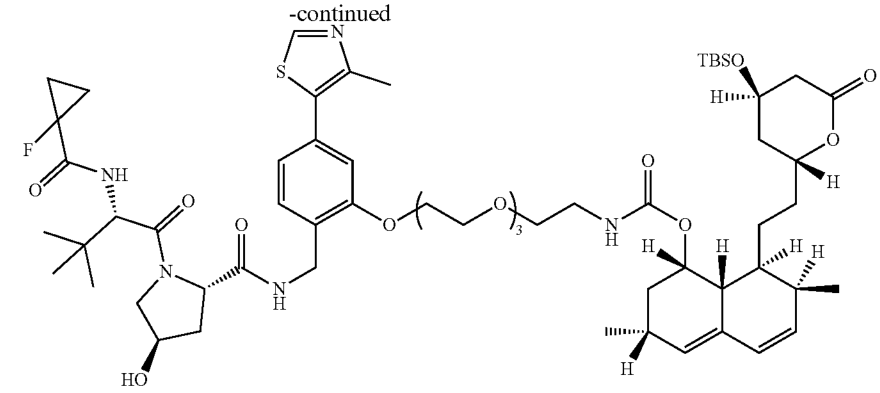

Compound 29

In a manner similar to Step 6 of Example 23, 27, the titled compound (148.9 mg, 124.88 μmol, 4.97% yield, 98% purity) was obtained as a white solid.

MS $(M+H)^+$=1168.2

$^1$H NMR (400 MHz, DMSO-$d_6$) δ 8.99 (s, 1H), 8.49 (t, J=6.0 Hz, 1H), 7.41 (d, J=7.8 Hz, 1H), 7.29 (dd, J=9.4, 2.8 Hz, 1H), 7.04 (d, J=1.6 Hz, 1H), 7.01-6.95 (m, 2H), 5.90 (d, J=9.7 Hz, 1H), 5.75 (dd, J=9.6, 5.9 Hz, 1H), 5.46 (s, 1H), 5.17 (d, J=3.6 Hz, 1H), 5.08-5.01 (m, 1H), 4.60 (d, J=9.2 Hz, 1H), 4.55-4.45 (m, 2H), 4.44-4.06 (m, 8H), 3.81-3.76 (m, 2H), 3.67-3.60 (m, 4H), 3.56-3.52 (m, 2H), 3.50-3.46 (m, 4H), 3.38-3.35 (m, 2H), 3.14-3.03 (m, 2H), 2.71-2.66 (m, 1H), 2.47 (s, 3H), 2.36-2.31 (m, 2H), 2.26-2.21 (m, 1H), 2.14-2.06 (m, 1H), 1.95-1.89 (m, 1H), 1.86-1.78 (m, 3H), 1.73-1.64 (m, 3H), 1.53-1.44 (m, 1H), 1.41-1.35 (m, 2H), 1.28-1.20 (m, 3H), 1.03 (d, J=7.3 Hz, 3H), 0.98-0.95 (m, 9H), 0.85-0.83 (m, 12H), 0.06 (s, 6H).

Step 6: Synthesis of (1S,3R,7S,8S,8aR)-8-(2-((2R, 4R)-4-hydroxy-6-oxotetrahydro-2H-pyran-2-yl) ethyl)-3,7-dimethyl-1,2,3,7,8,8a-hexahydronaphthalen-1-yl (2-(2-(2-(2-(2-(((2S,4R)-1-((S)-2-(1-fluorocyclopropane-1-carboxamido)-3,3-dimethylbutanoyl)-4-hydroxypyrrolidine-2-carboxamido)methyl)-5-(4-methylthiazol-5-yl) phenoxy)ethoxy)ethoxy)ethoxy)ethyl)carbamate (Compound 25)

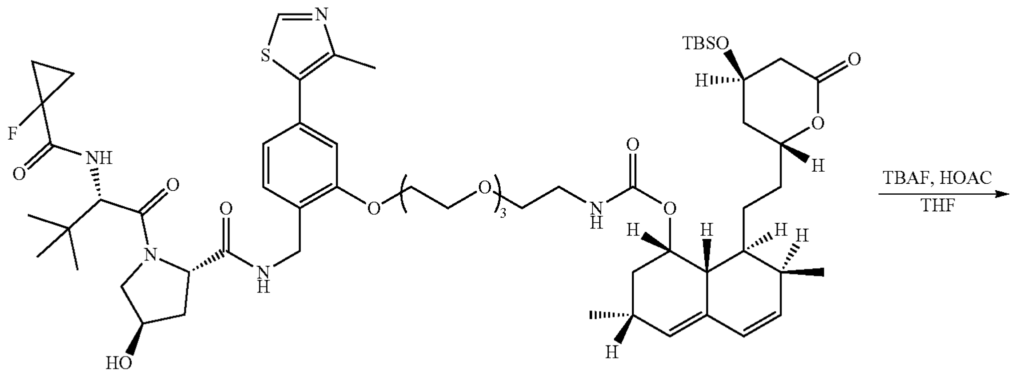

Compound 29

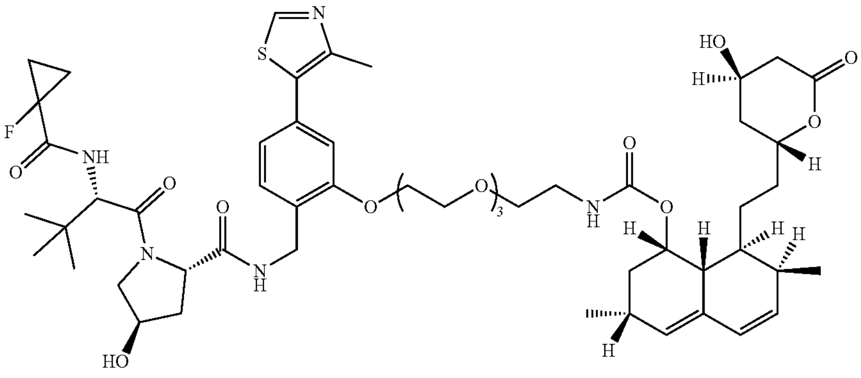

Compound 25

The mixture of (1S,3R,7S,8S,8aR)-8-(2-((2R,4R)-4-((tert-butyldimethylsilyl)oxy)-6-oxotetrahydro-2H-pyran-2-yl)ethyl)-3,7-dimethyl-1,2,3,7,8,8a-hexahydronaphthalen-1-yl (2-(2-(2-(2-(2-(((2S,4R)-1-((S)-2-(1-fluorocyclopropane-1-carboxamido)-3,3-dimethylbutanoyl)-4-hydroxypyrrolidine-2-carboxamido)methyl)-5-(4-methylthiazol-5-yl)phenoxy)ethoxy)ethoxy)ethoxy)ethyl)carbamate (300 mg, 256.73 μmol) in THF (10 mL) was added TBAF (1 M, 1.03 mL) and AcOH (77.09 mg, 1.28 mmol, 73.42 μL) and the resulting mixture was stirred at 20° C. for 12 h. LCMS showed that 66% desired mass was detected. The mixture was poured into water (50 mL) and extracted with EtOAc (50 mL×3). The combined organic layer was washed with brine (100 mL), dried over $Na_2SO_4$, filtered and concentrated. The residue was purified by prep-TLC (Ethylacetate:Methanol=10/1) followed by prep-HPLC (column: Shim-pack C18 150*25*10 μm; mobile phase: [water (0.225% FA)-ACN]; B %: 52%-72%, 9 min) to afford (1S,3R,7S,8S,8aR)-8-(2-((2R,4R)-4-hydroxy-6-oxotetrahydro-2H-pyran-2-yl)ethyl)-3,7-dimethyl-1,2,3,7,8,8a-hexahydronaphthalen-1-yl (2-(2-(2-(2-(2-(((2S,4R)-1-((S)-2-(1-fluorocyclopropane-1-carboxamido)-3,3-dimethylbutanoyl)-4-hydroxypyrrolidine-2-carboxamido)methyl)-5-(4-methylthiazol-5-yl)phenoxy)ethoxy)ethoxy)ethoxy)ethyl)carbamate (63 mg, 59.16 μmol, 23.04% yield, 99% purity) as white solid.

SFC: (retention time=2.170 min, analysis method: "Column: Chiralcel OD-3 50×4.6 mm I.D., 3 μm Mobile phase: Phase A for $CO_2$, and Phase B for MeOH (0.05% DEA); Gradient elution:MeOH (0.05% DEA) in $CO_2$ from 5% to 40% Flow rate: 3 mL/min; Detector: PDA, Column Temp: 35° C.; Back Pressure: 100 Bar").

MS $(M+H)^+$=1055.1.

$^1$H NMR (400 MHz, $CDCl_3$) δ 8.68 (s, 1H), 7.35 (d, J=7.7 Hz, 1H), 7.12 (s, 1H), 6.98 (dd, J=7.7, 1.6 Hz, 1H), 6.90 (s, 1H), 5.95 (d, J=9.7 Hz, 1H), 5.76 (dd, J=9.6, 6.0 Hz, 1H), 5.50 (s, 1H), 5.40-5.17 (m, 2H), 4.65-4.46 (m, 6H), 4.28-4.16 (m, 3H), 3.97-3.86 (m, 3H), 3.79-3.65 (m, 6H), 3.61-3.46 (m, 6H), 3.34-3.22 (m, 2H), 2.71-2.56 (m, 2H), 2.53 (s, 3H), 2.45-2.17 (m, 5H), 2.10-1.69 (m, 6H), 1.42-1.21 (m, 7H), 1.06 (d, J=7.4 Hz, 3H), 1.02-0.96 (m, 9H), 0.88 (d, J=7.0 Hz, 3H).

Example 26 & Example 30. (1S,3R,7S,8S,8aR)-8-(2-((2R,4R)-4-hydroxy-6-oxotetrahydro-2H-pyran-2-yl)ethyl)-3,7-dimethyl-1,2,3,7,8,8a-hexahydronaphthalen-1-yl (14-(2-(((2S,4R)-1-((S)-2-(1-fluorocyclopropane-1-carboxamido)-3,3-dimethylbutanoyl)-4-hydroxypyrrolidine-2-carboxamido)methyl)-5-(4-methylthiazol-5-yl)phenoxy)-3,6,9,12-tetraoxatetradecyl)carbamate (Compound 26) and (1S,3R,7S,8S,8aR)-8-(2-((2R,4R)-4-((tert-butyldimethylsilyl)oxy)-6-oxotetrahydro-2H-pyran-2-yl)ethyl)-3,7-dimethyl-1,2,3,7,8,8a-hexahydronaphthalen-1-yl (14-(2-(((2S,4R)-1-((S)-2-(1-fluorocyclopropane-1-carboxamido)-3,3-dimethylbutanoyl)-4-hydroxypyrrolidine-2-carboxamido)methyl)-5-(4-methylthiazol-5-yl)phenoxy)-3,6,9,12-tetraoxatetradecyl)carbamate (Compound 30)

Step 1: Synthesis of benzyl N-[2-[2-[2-[2-(2-hydroxyethoxy)ethoxy]ethoxy]ethoxy]ethyl]carbamate (28d)

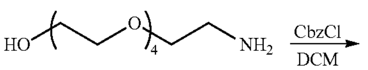

27d

-continued

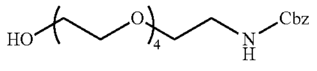

28d

To a solution of 2-[2-[2-[2-(2-aminoethoxy)ethoxy]ethoxy]ethoxy]ethanol (1 g, 4.21 mmol) in DCM (40 mL) was added CbzCl (718.91 mg, 4.21 mmol, 599.10 μL) and DIPEA (1.09 g, 8.43 mmol, 1.47 mL) and the resulting mixture was added at 25° C. for 16 h. LCMS showed desired mass was detected. The reaction mixture was concentrated in vacuum. Compound benzyl N-[2-[2-[2-[2-(2-hydroxyethoxy)ethoxy]ethoxy]ethoxy]ethyl]carbamate (1.5 g, crude) was obtained as a yellow oil, which was used into the next step without further purification.

Step 2: Synthesis of 2-[2-[2-[2-[2-(benzyloxycarbonylamino)ethoxy]ethoxy]ethoxy]ethoxy]ethyl 4-methylbenzenesulfonate (29d)

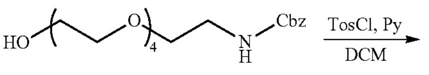

28d

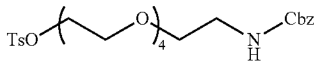

29d

In a manner similar to Step 2 of Example 23, 27, the titled compound (540 mg, 945.19 μmol, 23.40% yield, 92% purity) was obtained as a yellow oil.

MS $(M+H)^+$=526.1

Step 3: Synthesis of benzyl (14-(2-(((2S,4R)-1-((S)-2-(1-fluorocyclopropanecarboxamido)-3,3-dimethylbutanoyl)-4-hydroxypyrrolidine-2-carboxamido)methyl)-5-(4-methylthiazol-5-yl)phenoxy)-3,6,9,12-tetraoxatetradecyl)carbamate (25d)

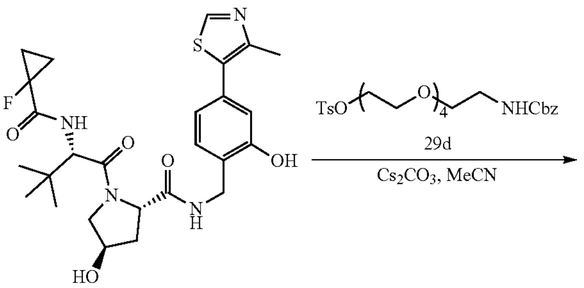

24

-continued

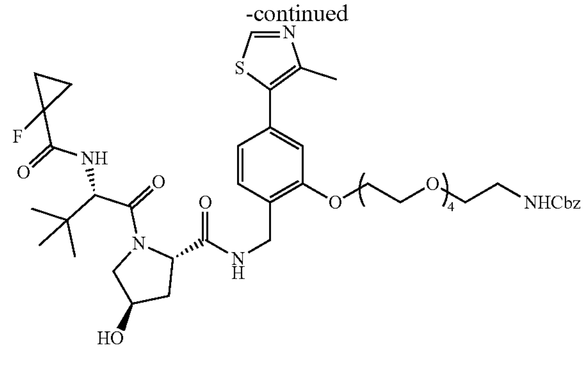

25d

-continued

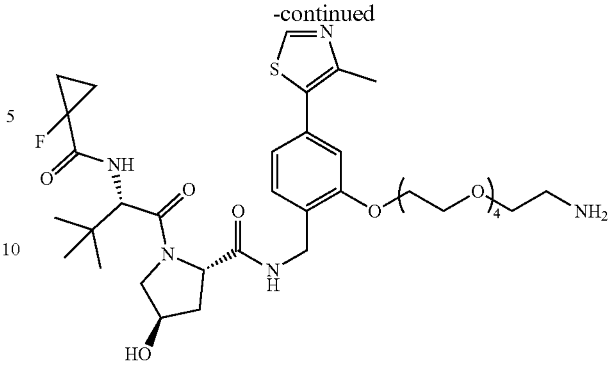

26d

In a manner similar to Step 4 of Example 23, 27, the titled compound (490 mg, 508.78 μmol, 54.20% yield, 92% purity) was obtained as a yellow oil.

MS $(M+H)^+$=886.0

Step 4: Synthesis of (2S,4R)—N-(2-((14-amino-3,6,9,12-tetraoxatetradecyl)oxy)-4-(4-methylthiazol-5-yl)benzyl)-1-((S)-2-(1-fluorocyclopropanecarboxamido)-3,3-dimethylbutanoyl)-4-hydroxypyrrolidine-2-carboxamide (26d)

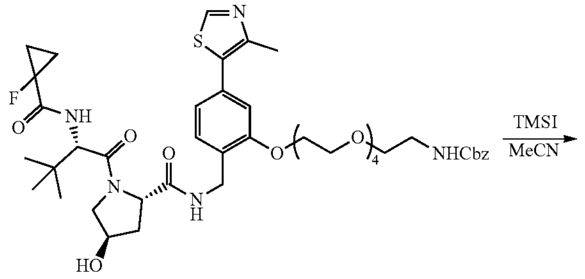

25d

To the solution of benzyl (14-(2-(((2S,4R)-1-((S)-2-(1-fluorocyclopropanecarboxamido)-3,3-dimethylbutanoyl)-4-hydroxypyrrolidine-2-carboxamido)methyl)-5-(4-methylthiazol-5-yl)phenoxy)-3,6,9,12-tetraoxatetradecyl) carbamate (380 mg, 428.88 μmol) in ACN (40 mL) was added TMSI (188.79 mg, 943.53 μmol, 128.43 μL) and the resulting mixture was stirred at 25° C. for 2 h. LCMS showed that the reaction was completed. $Et_3N$ (0.2 mL) was added into the mixture and the resulting mixture was stirred for another 0.5 h. The mixture was concentrated to afford (2S,4R)—N-(2-((14-amino-3,6,9,12-tetraoxatetradecyl)oxy)-4-(4-methylthiazol-5-yl)benzyl)-1-((S)-2-(1-fluorocyclopropanecarboxamido)-3,3-dimethylbutanoyl)-4-hydroxypyrrolidine-2-carboxamide (322 mg, crude) as yellow oil, which was used for next step directly. MS $(M+H)^+$ =752.3

Step 5: Synthesis of (1S,3R,7S,8S,8aR)-8-(2-((2R,4R)-4-((tert-butyldimethylsilyl)oxy)-6-oxotetrahydro-2H-pyran-2-yl)ethyl)-3,7-dimethyl-1,2,3,7,8,8a-hexahydronaphthalen-1-yl (14-(2-(((2S,4R)-1-((S)-2-(1-fluorocyclopropane-1-carboxamido)-3,3-dimethylbutanoyl)-4-hydroxypyrrolidine-2-carboxamido)methyl)-5-(4-methylthiazol-5-yl)phenoxy)-3,6,9,12-tetraoxatetradecyl)carbamate (Compound 30)

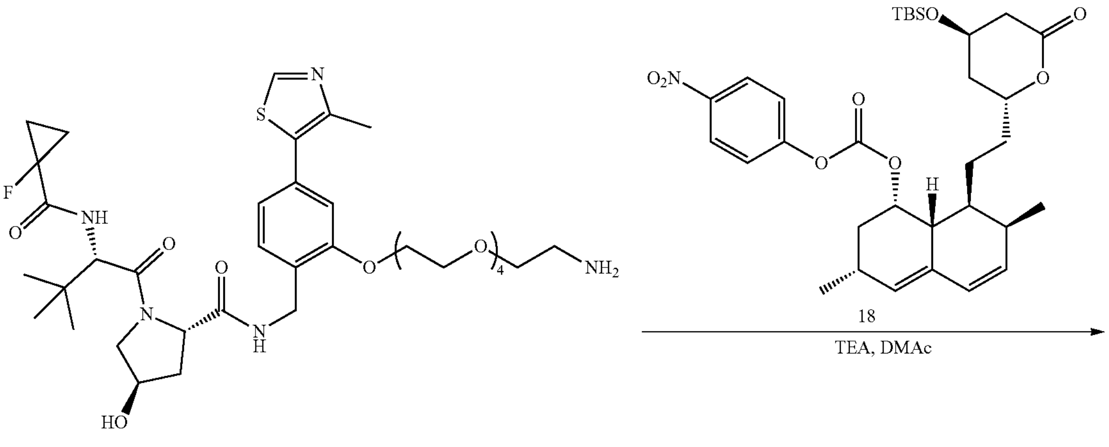

26d

-continued

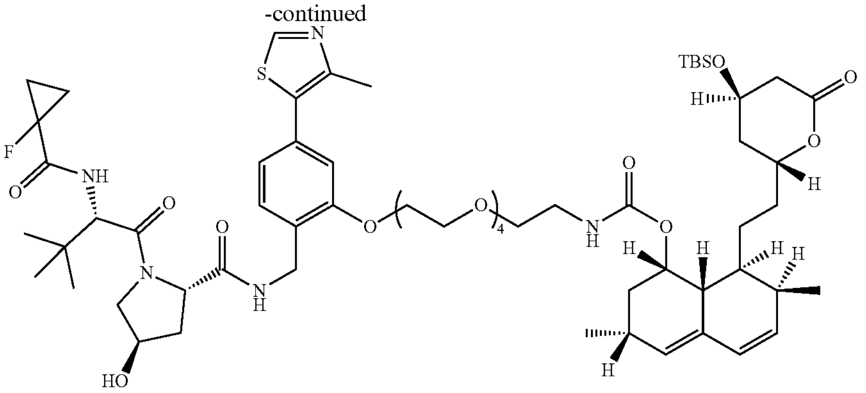

Compound 30

In a manner similar to Step 6 of Example 23, 27, the titled compound (227.5 mg, 183.86 μmol, 29.28% yield, 98% purity) was obtained as a brown solid.

MS $(M+H)^+=1212.7$ $^1H$ NMR (400 MHz, $CDCl_3$) δ 8.68 (s, 1H), 7.33 (d, J=7.7 Hz, 2H), 7.08-7.02 (m, 1H), 6.97 (dd, J=7.7, 1.7 Hz, 1H), 6.90 (d, J=1.6 Hz, 1H), 5.96 (d, J=9.6 Hz, 1H), 5.76 (dd, J=9.6, 6.0 Hz, 1H), 5.50 (s, 1H), 5.43-5.32 (m, 1H), 5.20 (s, 1H), 4.69-4.61 (m, 2H), 4.55-4.45 (m, 4H), 4.28-4.15 (m, 3H), 3.96-3.87 (m, 3H), 3.74-3.55 (m, 14H), 3.53-3.46 (m, 2H), 3.42-3.24 (m, 2H), 2.63-2.54 (m, 2H), 2.52 (s, 3H), 2.44-2.31 (m, 3H), 2.27-2.20 (m, 1H), 2.16-2.05 (m, 2H), 1.89-1.83 (m, 2H), 1.67-1.60 (m, 3H), 1.45-1.38 (m, 1H), 1.36-1.22 (m, 6H), 1.06 (d, J=7.4 Hz, 3H), 0.98-0.94 (m, 9H), 0.89-0.87 (m, 12H), 0.07 (d, J=0.9 Hz, 6H).

Step 6: Synthesis of (1S,3R,7S,8S,8aR)-8-(2-((2R,4R)-4-hydroxy-6-oxotetrahydro-2H-pyran-2-yl)ethyl)-3,7-dimethyl-1,2,3,7,8,8a-hexahydronaphthalen-1-yl (14-(2-(((2S,4R)-1-((S)-2-(1-fluorocyclopropane-1-carboxamido)-3,3-dimethylbutanoyl)-4-hydroxypyrrolidine-2-carboxamido)methyl)-5-(4-methylthiazol-5-yl)phenoxy)-3,6,9,12-tetraoxatetradecyl)carbamate (Compound 26)

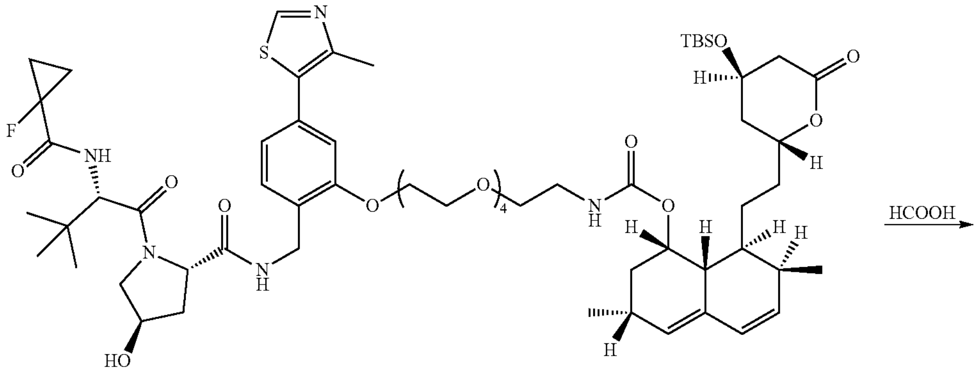

Compound 30

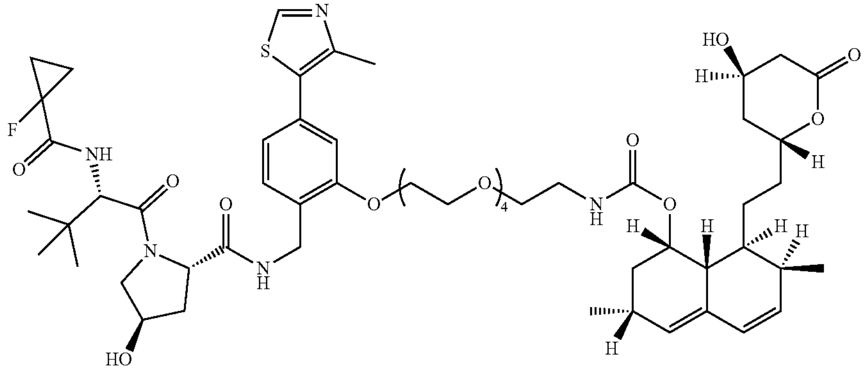

Compound 26

In a manner similar to Step 7 of Example 23, 27, the titled compound (15.8 mg, 13.81 μmol, 54.17% yield, 94% purity) was obtained as a white solid.

MS $(M+H)^+$=1098.6

$^1$H NMR (400 MHz, $CDCl_3$) δ 8.68 (s, 1H), 7.35 (d, J=7.7 Hz, 1H), 7.11 (s, 1H), 6.98 (d, J=8.5 Hz, 1H), 6.91 (s, 1H), 5.95 (d, J=9.6 Hz, 1H), 5.76 (dd, J=9.6, 6.1 Hz, 1H), 5.50 (s, 1H), 5.40-5.13 (m, 2H), 4.66-4.44 (m, 6H), 4.32-4.16 (m, 3H), 3.95-3.86 (m, 3H), 3.79-3.65 (m, 6H), 3.62-3.46 (m, 10H), 3.34-3.22 (m, 2H), 2.71-2.56 (m, 2H), 2.53 (s, 3H), 2.45-2.17 (m, 5H), 2.07-1.68 (m, 6H), 1.35-1.25 (m, 7H), 1.06 (d, J=7.4 Hz, 3H), 1.00-0.94 (m, 9H), 0.87 (d, J=3.2 Hz, 3H).

Example 31 & Example 36. Synthesis of (1S,3R,7S,8S,8aR)-8-(2-((2R,4R)-4-hydroxy-6-oxotetrahydro-2H-pyran-2-yl)ethyl)-3,7-dimethyl-1,2,3,7,8,8a-hexahydronaphthalen-1-yl (2-(2-(2-(3-(2-((S)-1-((S)-2-cyclohexyl-2-((S)-2-(methylamino)propanamido)acetyl)pyrrolidin-2-yl)thiazole-4-carbonyl)phenoxy)ethoxy)ethoxy)ethyl)carbamate (Compound 31) and (1S,3R,7S,8S,8aR)-8-(2-((2R,4R)-4-((tert-butyldimethylsilyl)oxy)-6-oxotetrahydro-2H-pyran-2-yl)ethyl)-3,7-dimethyl-1,2,3,7,8,8a-hexahydronaphthalen-1-yl (2-(2-(2-(3-(2-((S)-1-((S)-2-cyclohexyl-2-((S)-2-(methylamino)propanamido)acetyl)pyrrolidin-2-yl)thiazole-4-carbonyl)phenoxy)ethoxy)ethoxy)ethyl)carbamate (Compound 36)

Step 1: Synthesis of tert-butyl (2S)-2-carbamothioylpyrrolidine-1-carboxylate (31)

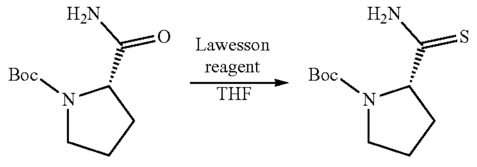

30 31

To a mixture of tert-butyl (2S)-2-carbamoylpyrrolidine-1-carboxylate (50.00 g, 233.36 mmol) in THE (500 mL) was added 2,4-bis(4-methoxyphenyl)-2,4-dithioxo-1,3,2,4dithiadiphosphetane (47.19 g, 116.68 mmol) at 30° C. under $N_2$. The mixture was stirred at 30° C. for 3 h. TLC ($SiO_2$, Dichloromethane:Methanol=10:1) indicated starting material was consumed completely and three new spots were detected. The reaction mixture was filtrated, the cake was dried in vacuum to afford tert-butyl (2S)-2-carbamothioylpyrrolidine-1-carboxylate (50 g, 217.08 mmol, 93.02% yield) as a white solid.

Step 2: Synthesis of tert-butyl (S)-2-(4-(3-ethoxybenzoyl)thiazol-2-yl)pyrrolidine-1-carboxylate (32)

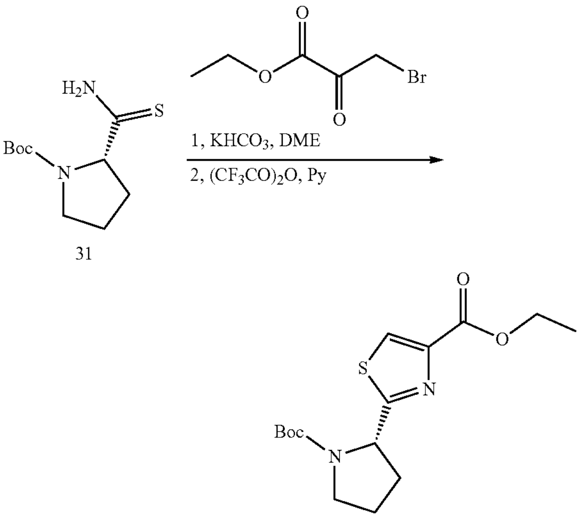

31

32

To a mixture of tert-butyl (2S)-2-carbamothioylpyrrolidine-1-carboxylate (50 g, 217.08 mmol) and $KHCO_3$ (217.33 g, 2.17 mol) in DME (500 mL) was added ethyl 3-bromo-2-oxo-propanoate (63.50 g, 325.62 mmol, 40.71 mL) at 25° C. under $N_2$. The mixture was stirred at 25° C. for 10 min, then to the mixture was added pyridine (154.54 g, 1.95 mol, 157.70 mL) and $(CF_3CO)_2O$ (319.16 g, 1.52 mol, 211.36 mL) and the resulting mixture was stirred at 0° C. for 1 h. LCMS showed 38% of intermediate state remained and 52% desired mass was detected. TLC ($SiO_2$, Petroleum ether:Ethyl acetate=2:1) indicated starting material was consumed completely and four new spots were detected. The reaction mixture was combined with another batch (2 g scale) for work-up, the reaction mixture was concentrated in vacuum, the residue was diluted with $H_2O$ (300 mL) and extracted with EtOAc (300 mL×5). The combined organic layer was dried over $Na_2SO_4$, filtrated and concentrated. The residue was purified by column chromatography ($SiO_2$, Petroleum ether/Ethyl acetate=10/1 to 3/1) to afford tert-butyl (S)-2-(4-(3-ethoxybenzoyl)thiazol-2-yl)pyrrolidine-1-carboxylate (34.5 g, 105.70 mmol, 48.69% yield) as a yellow oil.

Step 3: Synthesis of (S)-2-(1-(tert-butoxycarbonyl)pyrrolidin-2-yl)thiazole-4-carboxylic acid (33)

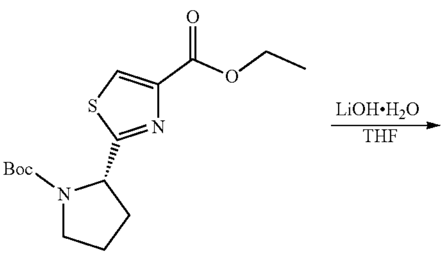

32

-continued

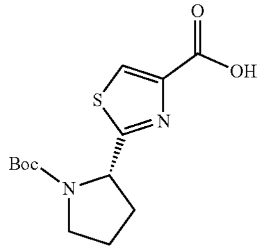

33

To a mixture of tert-butyl (S)-2-(4-(3-ethoxybenzoyl) thiazol-2-yl)pyrrolidine-1-carboxylate (34.5 g, 105.70 mmol) in THF (350 mL) and was added a solution of $LiOH \cdot H_2O$ (22.18 g, 528.48 mmol) in $H_2O$ (350 mL) dropwise at 0° C. The mixture was stirred at 25° C. for 2 h. LCMS showed starting material was consumed completely and 98% desired mass was detected. The reaction mixture was diluted with ice-$H_2O$ (100 mL) and added HCl (6 M) to adjust the PH to 5-6. The reaction mixture was extracted with EtOAc (50 mL×3). The combined organic layer was dried over $Na_2SO_4$, filtered, and concentrated to afford (S)-2-(1-(tert-butoxycarbonyl)pyrrolidin-2-yl)thiazole-4-carboxylic acid (29.5 g, 95.91 mmol, 90.74% yield, 97% purity) as a yellow oil. MS $(M+H)^+$=299.2

Step 4: Synthesis of tert-butyl (S)-2-(4-(methoxy (methyl)carbamoyl)thiazol-2-yl)pyrrolidine-1-carboxylate (34)

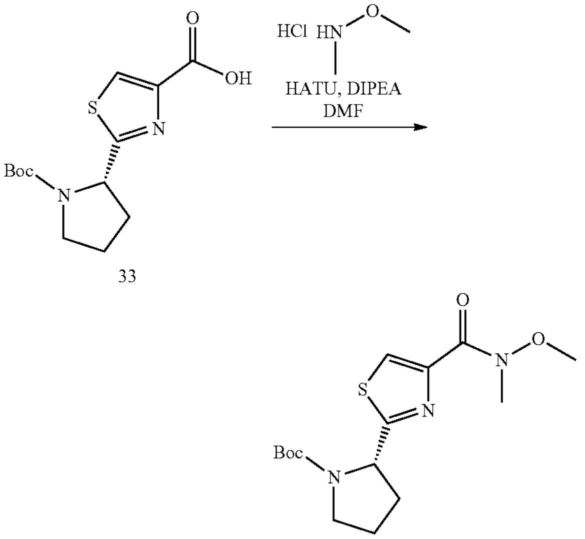

33

34

To a solution of (S)-2-(1-(tert-butoxycarbonyl)pyrrolidin-2-yl)thiazole-4-carboxylic acid (27.5 g, 92.17 mmol) in DMF (200 mL) was added DIPEA (35.74 g, 276.51 mmol, 48.16 mL) and HATU (42.06 g, 110.61 mmol). The mixture was stirred at 25° C. for 30 min and a solution of N-methoxymethanamine (13.76 g, 141.02 mmol, HCl salt) in DMF (200 mL) with DIPEA (71.48 g, 553.03 mmol, 96.33 mL) was added and the resulting mixture was stirred at 25° C. for 2 h. LCMS showed starting material was consumed completely and desired mass was detected. TLC ($SiO_2$, Petroleum ether:Ethyl acetate=2:1) indicated starting material was consumed and one major new spot was detected. The reaction mixture was combined with another batch (2 g scale) for work-up, the combined reaction mixture was diluted with $H_2O$ (120 mL) and extracted with EtOAc (120 mL×3), the organic layer was washed with brine (120 mL×5) and citric acid (120 mL×3). The combined organic layer was dried over $Na_2SO_4$, filtrated and concentrated. The residue was purified by column chromatography ($SiO_2$, Petroleum ether/Ethyl acetate=8/1 to 2/1) to afford tert-butyl (S)-2-(4-(methoxy(methyl)carbamoyl)thiazol-2-yl)pyrrolidine-1-carboxylate (29.4 g, 80.94 mmol, 87.82% yield, 94% purity) as a yellow oil. MS $(M+H)^+$=362.4

Step 5: Synthesis of tert-butyl (S)-2-(4-(3-methoxybenzoyl)thiazol-2-yl)pyrrolidine-1-carboxylate (35)

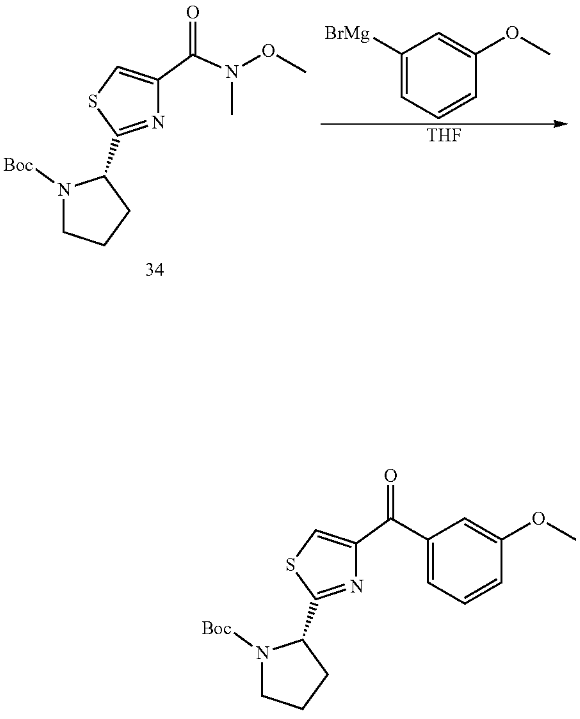

34

35

To a mixture of tert-butyl (S)-2-(4-(methoxy(methyl)carbamoyl)thiazol-2-yl)pyrrolidine-1-carboxylate (29 g, 84.94 mmol) in THF (300 mL) was added bromo-(3-methoxyphenyl)magnesium (1 M, 169.88 mL) dropwise at −70° C. under $N_2$ and the resulting mixture was stirred at −70° C. for 0.5 h. LCMS showed starting material was consumed completely and desired mass was detected. TLC ($SiO_2$, Petroleum ether:Ethyl acetate=5:1) indicated starting material was consumed completely and one major new spot was detected. The reaction mixture was combined with another batch (3 g, scale) for work-up, the combined reaction mixture was quenched with $NH_4Cl$ (sat.aq, 200 mL) and extracted with EtOAc (200 mL×3). The combined organic lawyer was dried over $Na_2SO_4$, filtrated and concentrated. The residue was purified by column chromatography ($SiO_2$, Petroleum ether/Ethyl acetate=10/1 to 5/1) to afford tert-butyl (S)-2-(4-(3-methoxybenzoyl)thiazol-2-yl)pyrrolidine-1-carboxylate (16 g, 41.19 mmol, 48.49% yield) as a yellow oil, which is checked by SFC (retention time: 1.117, 71% ee, analysis method: Column: Chiralpak AD-3 50×4.6 mm I.D., 3 μm; Mobile phase: Phase A for $CO_2$, and Phase B for EtOH (0.05% DEA); Gradient elution: B in A from 5% to 40%; Flow rate: 3 mL/min; Detector: DAD; Column Temp: 35 C; Back Pressure: 100 Bar).

MS $(M+H)^+$=389.1

Step 6: Synthesis of tert-butyl (2S)-2-[4-(3-hydroxybenzoyl)thiazol-2-yl]pyrrolidine-1-carboxylate (36)

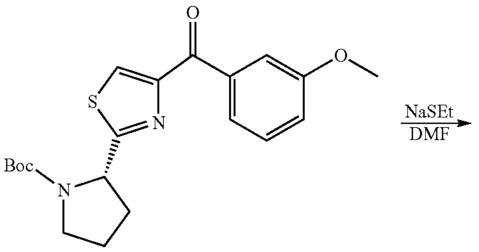

35

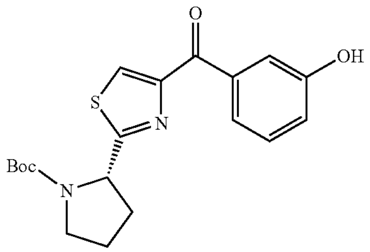

36

Two batches in parallel: To a mixture of tert-butyl (S)-2-(4-(3-methoxybenzoyl)thiazol-2-yl)pyrrolidine-1-carboxylate (7.5 g, 19.31 mmol) in DMF (75 mL) was added NaSEt (12.99 g, 154.45 mmol) in one portion at 25° C. and the resulting mixture was stirred at 100° C. for 16 h. LCMS showed the starting material was consumed completely and desired mass was detected. TLC ($SiO_2$, Petroleum ether: Ethyl acetate=2:1) indicated starting material was consumed completely and two new spots were formed. Two parallel batches and combined with another batch (1 g scale) for work-up, the combined reaction mixture was diluted with $H_2O$ (150 mL) and extracted with EtOAc (150 mL×3). The organic layer was washed with brine (150 mL×3). The organic layer was dried over $Na_2SO_4$, filtrated and concentrated. The residue was purified by column chromatography ($SiO_2$, Petroleum ether/Ethyl acetate=8/1 to 2/1) to afford tert-butyl (2S)-2-[4-(3-hydroxybenzoyl)thiazol-2-yl]pyrrolidine-1-carboxylate (9.4 g, 25.10 mmol, 65.01% yield) as a yellow oil, which is checked by SFC (two peaks on SFC (ratio is about 1/1), retention time: 0.976 and 1.069, analysis method: Column: Chiralcel OJ-3 50×4.6 mm I.D., 3 μm; Mobile phase: Phase A for $CO_2$, and Phase B for MEOH (0.05% DEA); Gradient elution: B in A from 5% to 40%; Flow rate: 3 mL/min; Detector: DAD; Column Temp: 35 C; Back Pressure: 100 Bar). MS $(M+H)^+$=375.1

Step 7: Synthesis of (3-hydroxyphenyl)-[2-[(2S)-pyrrolidin-2-yl]thiazol-4-yl]methanone (37)

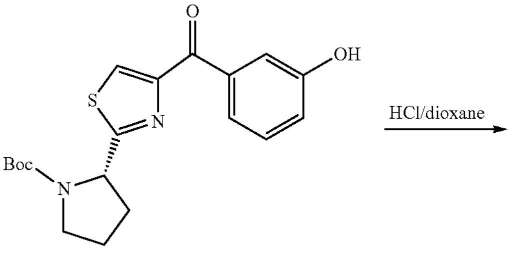

36

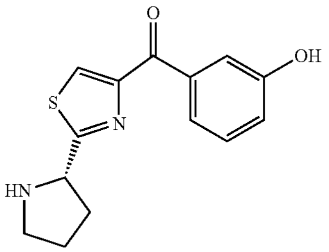

37

To a mixture of tert-butyl (2S)-2-[4-(3-hydroxybenzoyl)thiazol-2-yl]pyrrolidine-1-carboxylate (9.4 g, 25.10 mmol) in dioxane (20 mL) was added HCl/dioxane (80 mL) at 25° C. The mixture was stirred at 25° C. for 1 h. LCMS showed the starting material was consumed completely and 84% desired mass was detected. The reaction mixture was concentrated in vacuum to afford (3-hydroxyphenyl)-[2-[(2S)-pyrrolidin-2-yl]thiazol-4-yl]methanone (8.1 g, crude) as a yellow oil, which was used in the next step.

MS $(M+H)^+$=275.0

Step 8: Synthesis of tert-butyl ((S)-1-cyclohexyl-2-((S)-2-(4-(3-hydroxybenzoyl)thiazol-2-yl)pyrrolidin-1-yl)-2-oxoethyl)carbamate (38)

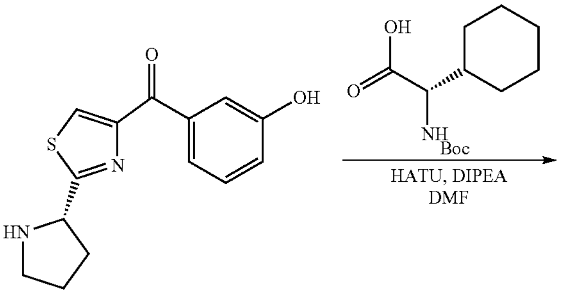

37

-continued

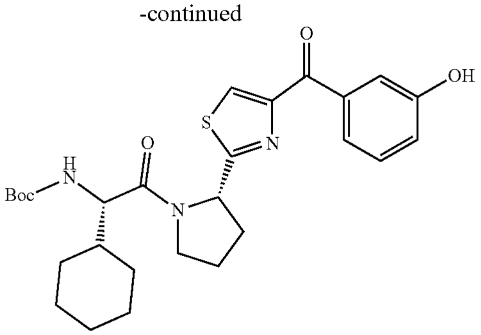

38

To a solution of (2S)-2-(tert-butoxycarbonylamino)-2-cyclohexyl-acetic acid (3.35 g, 13.03 mmol) in DMF (20 mL) was added DIPEA (5.05 g, 39.09 mmol, 6.81 mL) and HATU (5.45 g, 14.33 mmol), the mixture was stirred at 0° C. for 15 min, then a solution of (3-hydroxyphenyl)-[2-[(2S)-pyrrolidin-2-yl]thiazol-4-yl]methanone (4.05 g, 13.03 mmol, HCl salt) in DMF (20 mL) with DIPEA (10.10 g, 78.19 mmol, 13.62 mL) was added and the resulting mixture was stirred at 0° C. for 3 h. LCMS showed the starting material was consumed completely and desired mass was detected. The reaction mixture was combined with another batch (4.05 g scale) for work-up, the combined reaction mixture was diluted with $H_2O$ (20 mL) and extracted with EtOAc (20 mL). The organic layer was washed with brine (20 mL×3), dried over $Na_2SO_4$, filtrated and concentrated. The residue was purified by column chromatography ($SiO_2$, Petroleum ether/Ethyl acetate=8/1 to 1/1) to afford tert-butyl ((S)-1-cyclohexyl-2-((S)-2-(4-(3-hydroxybenzoyl)thiazol-2-yl)pyrrolidin-1-yl)-2-oxoethyl)carbamate (4.9 g, 9.16 mmol, 70.29% yield, 96% purity) as a yellow oil, which is checked by SFC (two peaks on SFC (ratio is about 1/1), retention time: 3.052 and 3.485, analysis method: Column: (R,R)Whelk-01 100×4.6 mm I.D., 3.5 μm; Mobile phase: Phase A for CO2, and Phase B for MEOH (0.05% DEA); Gradient elution: B in A from 5% to 40%; Flow rate: 3 mL/min; Detector: DAD; Column Temp: 35 C; Back Pressure: 120 Bar).

MS $(M+H)^+$=514.2

Step 9: Synthesis of (2S)-2-amino-2-cyclohexyl-1-[(2S)-2-[4-(3-hydroxybenzoyl)thiazol-2-yl]pyrrolidin-1-yl]ethenone (39)

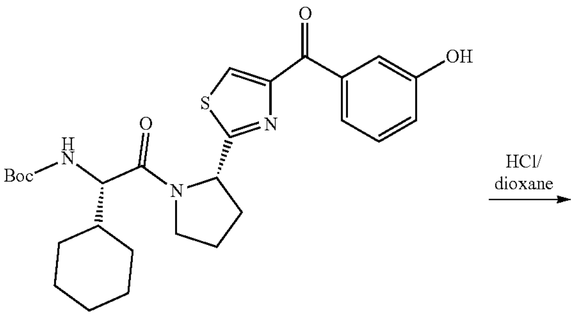

38

-continued

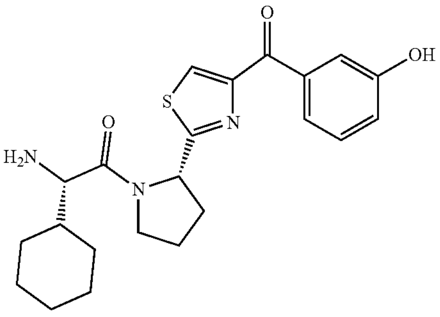

39

To a mixture of tert-butyl ((S)-1-cyclohexyl-2-((S)-2-(4-(3-hydroxybenzoyl)thiazol-2-yl)pyrrolidin-1-yl)-2-oxoethyl)carbamate (4.9 g, 9.54 mmol) in dioxane (10 mL) was added HCl/dioxane (4 M, 50 mL) and the resulting mixture was stirred at 30° C. for 1 h. LCMS showed starting material was consumed and desired mass was detected. The reaction mixture was concentrated in vacuum to afford (2S)-2-amino-2-cyclohexyl-1-[(2S)-2-[4-(3-hydroxybenzoyl)thiazol-2-yl]pyrrolidin-1-yl]ethanone (4.7 g, crude, HCl salt) as a yellow oil, which was used in the next step directly.

MS $(M+H)^+$=414.3

Step 10: Synthesis of tert-butyl ((S)-1-(((S)-1-cyclohexyl-2-((S)-2-(4-(3-hydroxybenzoyl)thiazol-2-yl)pyrrolidin-1-yl)-2-oxoethyl)amino)-1-oxopropan-2-yl)(methyl)carbamate (40-Int-1) and tert-butyl ((S)-1-(((S)-1-cyclohexyl-2-((R)-2-(4-(3-hydroxybenzoyl)thiazol-2-yl)pyrrolidin-1-yl)-2-oxoethyl)amino)-1-oxopropan-2-yl)(methyl)carbamate (40-Int-2)

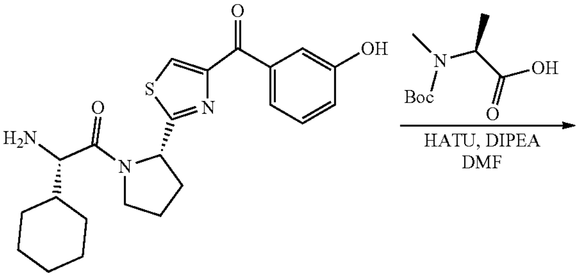

39

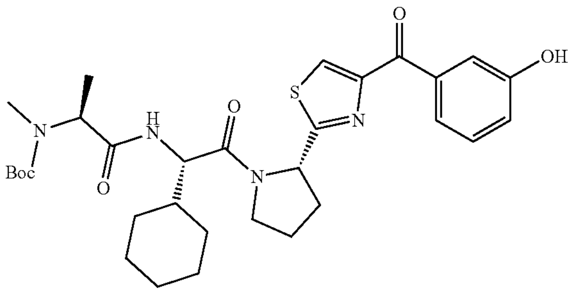

40-Int-1

-continued

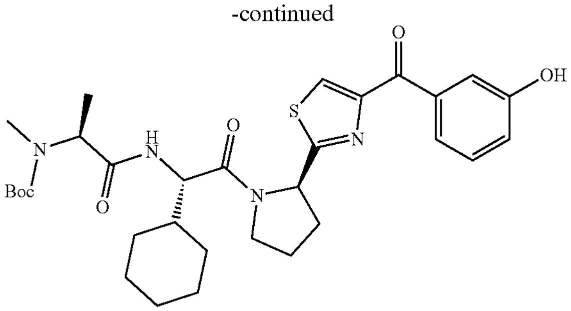

40-Int-2

To a solution of (2S)-2-[tert-butoxycarbonyl(methyl) amino]propanoic acid (2.12 g, 10.44 mmol) in DMF (20 mL) was added DIPEA (4.05 g, 31.33 mmol, 5.46 mL) and HATU (4.77 g, 12.53 mmol), the mixture was stirred at 0° C. for 15 min and a solution of (2S)-2-amino-2-cyclohexyl-1-[(2S)-2-[4-(3-hydroxybenzoyl)thiazol-2-yl]pyrrolidin-1-yl]ethanone (4.7 g, 10.44 mmol, HCl salt) in DMF (20 mL) with DIPEA (8.10 g, 62.67 mmol, 10.92 mL) was added and the resulting mixture was stirred at 0° C. for 3 h. LCMS showed desired mass was detected. TLC ($SiO_2$, Petroleum ether:Ethyl acetate=2:1) indicated starting material remained and two new spots were detected. The reaction mixture was diluted with $H_2O$ (120 mL) and extracted with EtOAc (120 mL×3). The organic layer was washed with brine (120 mL×3), dried over $Na_2SO_4$, filtrated and concentrated. The residue was purified by column chromatography ($SiO_2$, Petroleum ether/Ethyl acetate=8/1 to 1/1) to afford tert-butyl ((S)-1-(((S)-1-cyclohexyl-2-((R)-2-(4-(3-hydroxybenzoyl)thiazol-2-yl)pyrrolidin-1-yl)-2-oxoethyl) amino)-1-oxopropan-2-yl)(methyl)carbamate (40-Int-2) (1.3 g, 2.06 mmol, 19.75% yield, 95% purity) as a yellow oil, which is checked by SFC (retention time: 1.355, analysis method: "Column: Cellucoat 50×4.6 mm I.D., 3 μm Mobile phase: Phase A for $CO_2$, and Phase B for MeOH (0.05% DEA); Gradient elution: MeOH (0.05% DEA) in CO2 from 5% to 40%; Flow rate: 3 mL/min; Detector: PDA; Column Temp: 35 C; Back Pressure: 100 Bar") and tert-butyl ((S)-1-(((S)-1-cyclohexyl-2-((S)-2-(4-(3-hydroxybenzoyl)thiazol-2-yl)pyrrolidin-1-yl)-2-oxoethyl)amino)-1-oxopropan-2-yl)(methyl)carbamate (40-Int-1) (1.4 g, 2.15 mmol, 20.60% yield, 92% purity) as a yellow oil, which is checked by SFC (retention time: 1.406, analysis method: "Column: Cellucoat 50×4.6 mm I.D., 3 μm Mobile phase: Phase A for $CO_2$, and Phase B for MeOH (0.05% DEA); Gradient elution: MeOH (0.05% DEA) in $CO_2$ from 5% to 40%; Flow rate: 3 mL/min; Detector: PDA; Column Temp: 35 C; Back Pressure: 100 Bar").

Step 11: Synthesis of tert-butyl ((S)-1-(((S)-1-cyclohexyl-2-((S)-2-(4-(3-((2,2-dimethyl-4-oxo-3,8,11-trioxa-5-azatridecan-13-yl)oxy)benzoyl)thiazol-2-yl) pyrrolidin-1-yl)-2-oxoethyl)amino)-1-oxopropan-2-yl)(methyl)carbamate (42a)

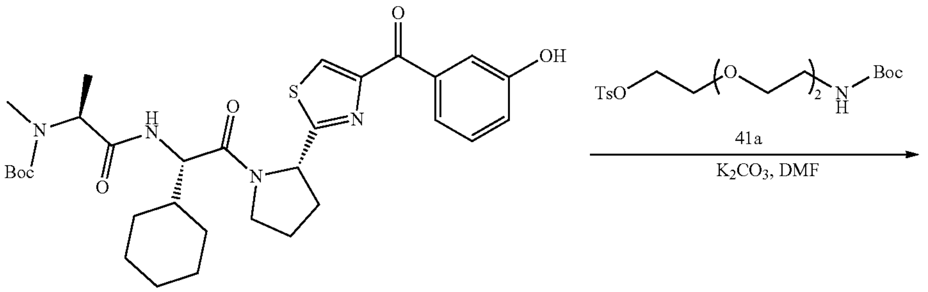

40-Int-1

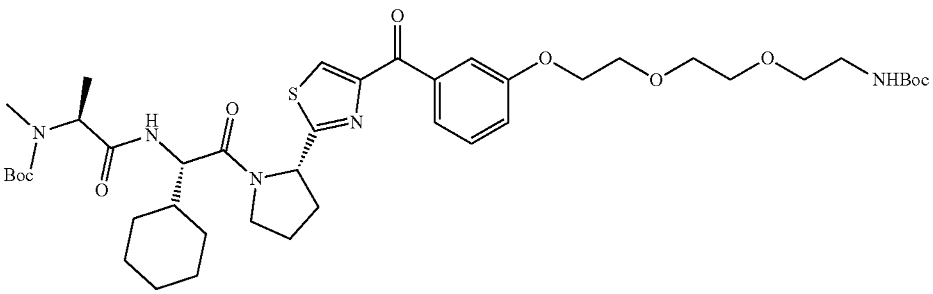

42a

To a mixture of tert-butyl ((S)-1-(((S)-1-cyclohexyl-2-((S)-2-(4-(3-hydroxybenzoyl)thiazol-2-yl)pyrrolidin-1-yl)-2-oxoethyl)amino)-1-oxopropan-2-yl)(methyl)carbamate (200 mg, 334.03 μmol) and 2,2-dimethyl-4-oxo-3,8,11-trioxa-5-azatridecan-13-yl 4-methylbenzenesulfonate (195.07 mg, 367.43 μmol) in DMF (4 mL) was added $K_2CO_3$ (92.33 mg, 668.06 μmol) in one portion at 30° C. under $N_2$. The mixture was stirred at 50° C. for 16 h. LCMS showed the starting material was consumed completely and desired mass was detected. TLC ($SiO_2$, Petroleum ether:Ethyl acetate=1:3) indicated the starting material was consumed completely and one major new spot was detected. The reaction mixture was diluted with $H_2O$ (15 mL) and extracted with EtOAc (15 mL×3). The combined organic layer was dried over $Na_2SO_4$, filtrated and concentrated. The residue was purified by column chromatography ($SiO_2$, Petroleum ether/Ethyl acetate=3/1 to 1/3) to afford tert-butyl ((S)-1-(((S)-1-cyclohexyl-2-((S)-2-(4-(3-((2,2-dimethyl-4-oxo-3,8,11-trioxa-5-azatridecan-13-yl)oxy)benzoyl)thiazol-2-yl)pyrrolidin-1-yl)-2-oxoethyl)amino)-1-oxopropan-2-yl)(methyl)carbamate (216 mg, 257.63 μmol, 77.13% yield, 99% purity) as a yellow oil. MS $(M+H)^+$=830.4

Step 12: Synthesis of (2S)—N-[(1S)-2-[(2S)-2-[4-[3-[2-[2-(2-aminoethoxy)ethoxy]ethoxy]benzoyl]thiazol-2-yl]pyrrolidin-1-yl]-1-cyclohexyl-2-oxo-ethyl]-2-(methylamino)propenamide (43a)

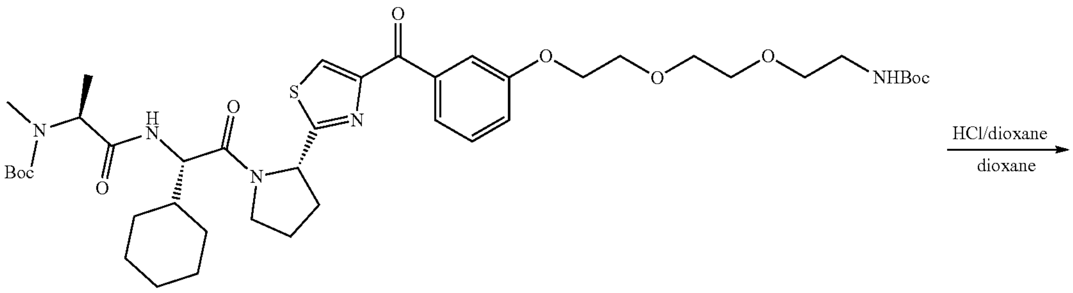

42a

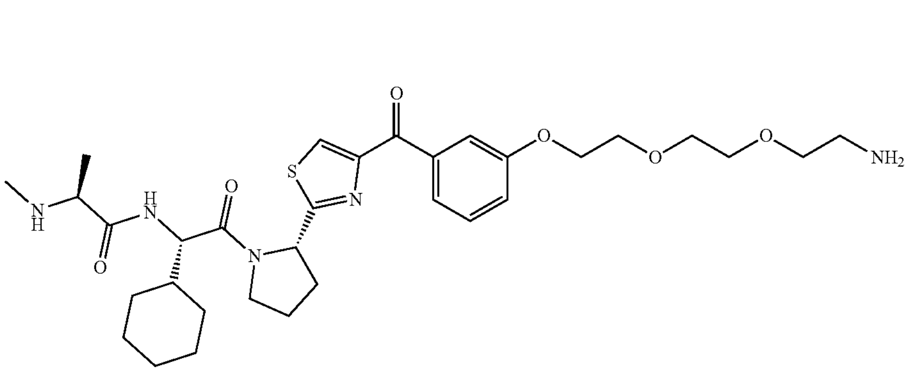

43a

To a mixture of tert-butyl ((S)-1-(((S)-1-cyclohexyl-2-((S)-2-(4-(3-((2,2-dimethyl-4-oxo-3,8,11-trioxa-5-azatridecan-13-yl)oxy)benzoyl)thiazol-2-yl)pyrrolidin-1-yl)-2-oxoethyl)amino)-1-oxopropan-2-yl)(methyl)carbamate (216.00 mg, 260.23 μmol) in dioxane (2 mL) was added HCl/dioxane (4 M, 4 mL) and the resulting mixture was stirred at 25° C. for 1 h. LCMS showed starting material was consumed and desired mass was detected. The reaction mixture was concentrated in vacuum to afford (2S)—N-[(1S)-2-[(2S)-2-[4-[3-[2-[2-(2-aminoethoxy)ethoxy]ethoxy]benzoyl]thiazol-2-yl]pyrrolidin-1-yl]-1-cyclohexyl-2-oxo-ethyl]-2-(methylamino)propanamide (174 mg, crude, HCl salt) as a yellow solid.

MS $(M+H)^+$=630.2

Step 13: Synthesis of (1S,3R,7S,8S,8aR)-8-(2-((2R,4R)-4-((tert-butyldimethylsilyl)oxy)-6-oxotetrahydro-2H-pyran-2-yl)ethyl)-3,7-dimethyl-1,2,3,7,8,8a-hexahydronaphthalen-1-yl (2-(2-(2-(3-(2-((S)-1-((S)-2-cyclohexyl-2-((S)-2-(methylamino)propanamido)acetyl)pyrrolidin-2-yl)thiazole-4-carbonyl)phenoxy)ethoxy)ethoxy)ethyl)carbamate (Compound 36)

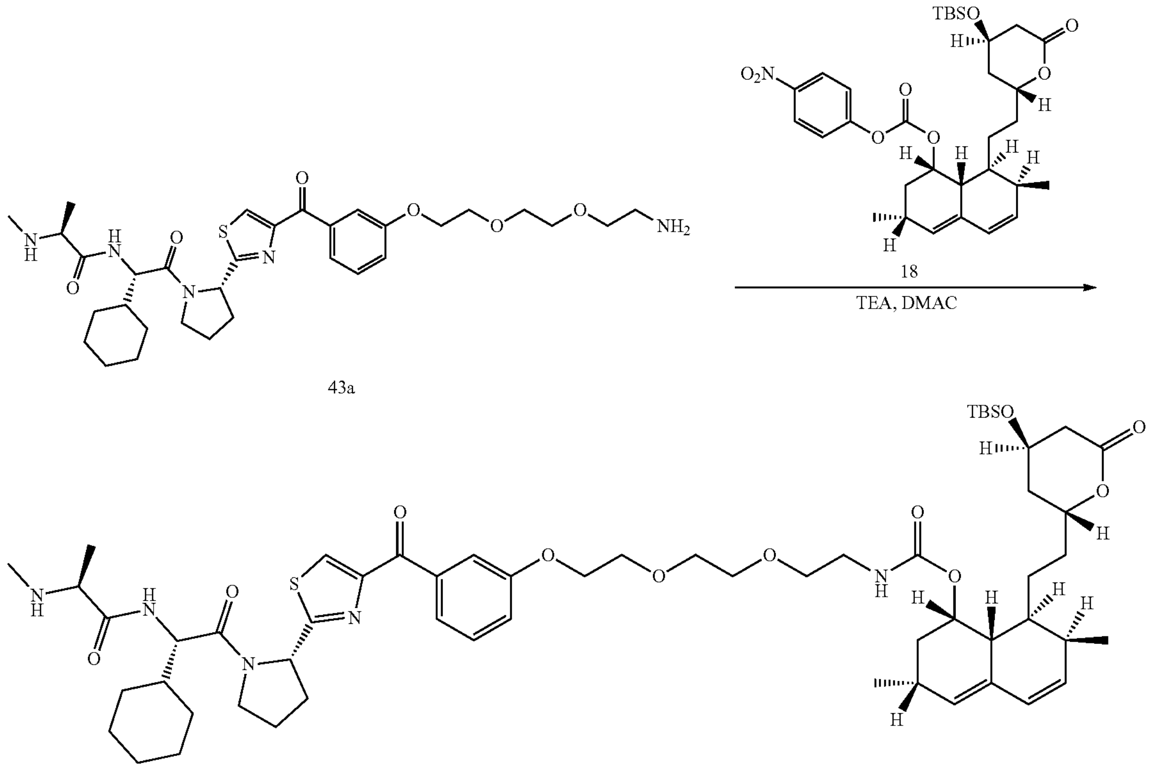

43a

18

Compound 36

To a mixture of (2S)—N-[(1S)-2-[(2S)-2-[4-[3-[2-[2-(2-aminoethoxy)ethoxy]ethoxy]benzoyl]thiazol-2-yl]pyrrolidin-1-yl]-1-cyclohexyl-2-oxo-ethyl]-2-(methylamino)propanamide (174 mg, 276.27 μmol, HCl salt) and [(1S,3R,7S,8S,8aR)-8-[2-[(2R,4R)-4-[tert-butyl(dimethyl)silyl]oxy-6-oxo-tetrahydropyran-2-yl]ethyl]-3,7-dimethyl-1,2,3,7,8,8a-hexahydronaphthalen-1-yl](4-nitrophenyl) carbonate (167.38 mg, 276.27 μmol) in DMAC (3 mL) was added TEA (83.87 mg, 828.82 μmol, 115.36 μL) at 25° C. and the resulting mixture was stirred at 25° C. for 16 h. LCMS showed 63% desired mass was detected. The reaction mixture was diluted with $H_2O$ (12 mL) and extracted with EtOAc (12 mL×3). The organic layer was dried over $Na_2SO_4$, filtrated and concentrated in vacuum. The residue was purified by prep-HPLC (column: Unisil 3-100 C18 Ultra 150*50 mm*3 μm; mobile phase: [water (0.225% FA)-ACN]; B %: 48%-78%, 10 min) to afford (1S,3R,7S,8S,8aR)-8-(2-((2R,4R)-4-((tert-butyldimethylsilyl)oxy)-6-oxotetrahydro-2H-pyran-2-yl)ethyl)-3,7-dimethyl-1,2,3,7,8,8a-hexahydronaphthalen-1-yl (2-(2-(2-(3-(2-((S)-1-((S)-2-cyclohexyl-2-((S)-2-(methylamino)propanamido)acetyl)pyrrolidin-2-yl)thiazole-4-carbonyl)phenoxy)ethoxy)ethoxy)ethyl)carbamate (122.3 mg, 111.03 μmol, 40.19% yield, 99% purity) as a white solid, which is checked SFC (retention time: 0.952, method: "Column: Chiralpak AD-3 50×4.6 mm I.D., 3 μm; Mobile phase: Phase A for $CO_2$, and Phase B for IPA (0.05% DEA); Gradient elution: 40% IPA (0.05% DEA) in $CO_2$; Flow rate: 3 mL/min; Detector: PDA; Column Temp: 35 C; Back Pressure: 100 Bar").

MS $(M+H)^+$=1090.6

$^1$H NMR (400 MHz, $CDCl_3$) δ 8.11 (s, 1H), 7.80 (d, J=7.7 Hz, 1H), 7.71-7.61 (m, 2H), 7.37 (t, J=7.9 Hz, 1H), 7.19-7.09 (m, 1H), 5.96 (d, J=9.6 Hz, 1H), 5.76 (dd, J=9.6, 6.0 Hz, 1H), 5.56 (dd, J=7.9, 2.7 Hz, 1H), 5.50 (s, 1H), 5.27-5.18 (m, 2H), 4.64 (dd, J=9.1, 6.0 Hz, 2H), 4.30-4.25 (m, 1H), 4.18 (t, J=4.8 Hz, 2H), 3.99-3.73 (m, 5H), 3.72-3.67 (m, 2H), 3.64-3.60 (m, 2H), 3.57-3.49 (m, 2H), 3.43-3.27 (m, 2H), 2.63-2.55 (m, 2H), 2.47-2.40 (m, 5H), 2.36-2.26 (m, 4H), 2.23-2.14 (m, 4H), 2.09-2.04 (m, 4H), 1.91-1.84 (m, 2H), 1.75-1.70 (m, 4H), 1.38-1.29 (m, 5H), 1.19-0.98 (m, 9H), 0.89-0.87 (m, 12H), 0.07 (s, 6H).

Step 14: Synthesis of (1S,3R,7S,8S,8aR)-8-(2-((2R,4R)-4-hydroxy-6-oxotetrahydro-2H-pyran-2-yl)ethyl)-3,7-dimethyl-1,2,3,7,8,8a-hexahydronaphthalen-1-yl (2-(2-(2-(3-(2-((S)-1-((S)-2-cyclohexyl-2-((S)-2-(methylamino)propanamido)acetyl)pyrrolidin-2-yl)thiazole-4-carbonyl)phenoxy)ethoxy)ethoxy)ethyl)carbamate (Compound 31)

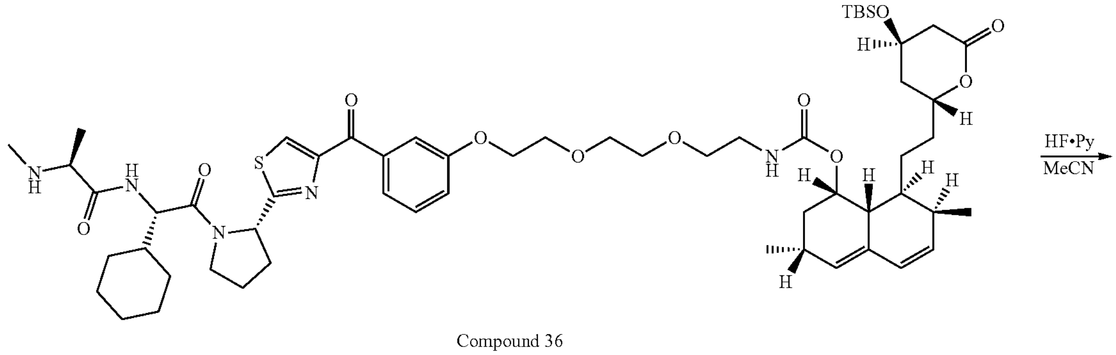

Compound 36

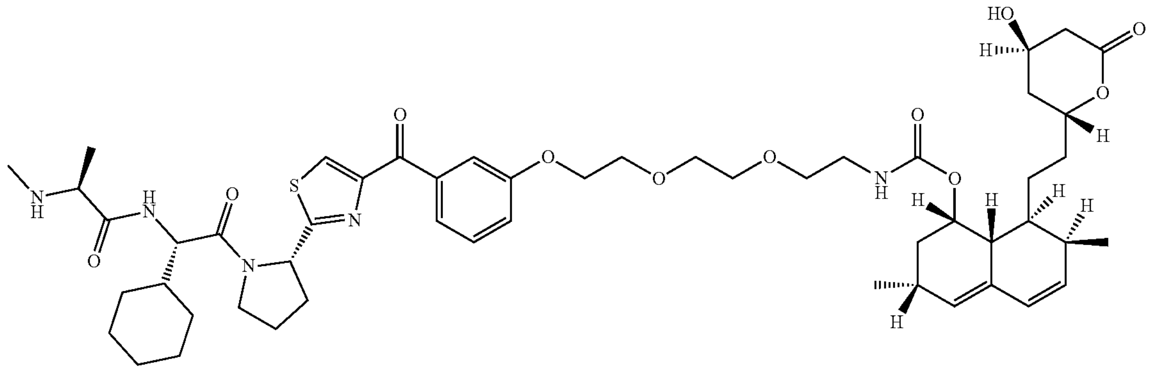

Compound 31

To a mixture of (1S,3R,7S,8S,8aR)-8-(2-((2R,4R)-4-((tert-butyldimethylsilyl)oxy)-6-oxotetrahydro-2H-pyran-2-yl)ethyl)-3,7-dimethyl-1,2,3,7,8,8a-hexahydronaphthalen-1-yl (2-(2-(2-(3-(2-((S)-1-((S)-2-cyclohexyl-2-((S)-2-(methylamino)propanamido)acetyl)pyrrolidin-2-yl)thiazole-4-carbonyl)phenoxy)ethoxy)ethoxy)ethyl)carbamate (250 mg, 204.04 μmol) in ACN (5 mL) was added HF·Pyridine (612.11 μmol, 0.75 mL) in one portion at 15° C. The mixture was stirred at 15° C. for 2 h. LCMS showed starting material was consumed completely and desired mass was detected. The reaction mixture was concentrated in vacuum. The residue was purified by prep-HPLC (column: Phenomenex Luna C18 150*25 mm*10 μm; mobile phase: [water (0.225% FA)-ACN]; B %: 23%-53%, 10 min). Compound (1S,3R,7S,8S,8aR)-8-(2-((2R,4R)-4-hydroxy-6-oxotetrahydro-2H-pyran-2-yl)ethyl)-3,7-dimethyl-1,2,3,7,8,8a-hexahydronaphthalen-1-yl (2-(2-(2-(3-(2-((S)-1-((S)-2-cyclohexyl-2-((S)-2-(methylamino)propanamido)acetyl)pyrrolidin-2-yl)thiazole-4-carbonyl)phenoxy)ethoxy)ethoxy)ethyl)carbamate (42 mg, 37.80 μmol, 18.53% yield, 92% purity, FA salt) was obtained as an off-white solid, which is checked by SFC (retention time=3.566, SFC analysis method: "Column: (S,S)Whelk-01 100×4.6 mm I.D., 3.5 μm; Mobile phase: Phase A for $CO_2$, and Phase B for EtOH (0.05% DEA); Gradient elution: 60% EtOH (0.05% DEA) in $CO_2$; Flow rate: 3 mL/min; Detector: PDA; Column Temp: 35 C; Back Pressure: 100 Bar").

MS $(M+H)^+$=976.6

$^1$H NMR (400 MHz, $CDCl_3$) δ 8.12 (s, 1H), 7.81-7.77 (m, 1H), 7.77-7.68 (m, 2H), 7.38 (t, J=8.0 Hz, 1H), 7.17-7.11 (m, 1H), 5.95 (d, J=9.7 Hz, 1H), 5.76 (dd, J=9.7, 6.0 Hz, 1H), 5.54 (dd, J=7.8, 2.9 Hz, 1H), 5.50 (s, 1H), 5.28 (s, 1H), 5.22-5.14 (m, 1H), 4.69-4.52 (m, 2H), 4.31-4.24 (m, 1H), 4.22-4.13 (m, 2H), 3.95-3.80 (m, 4H), 3.76-3.65 (m, 3H), 3.65-3.59 (m, 2H), 3.58-3.49 (m, 2H), 3.39-3.31 (m, 2H), 2.67-2.59 (m, 2H), 2.50-2.46 (m, 3H), 2.44-2.38 (m, 3H), 2.35-2.30 (m, 3H), 2.27-2.19 (m, 3H), 2.15-2.04 (m, 3H), 1.97-1.86 (m, 2H), 1.85-1.77 (m, 2H), 1.74-1.68 (m, 4H), 1.44-1.29 (m, 5H), 1.21-0.95 (m, 9H), 0.87 (d, J=7.0 Hz, 3H).

Example 32 & Example 37. Synthesis of (1S,3R,7S,8S,8aR)-8-(2-((2R,4R)-4-hydroxy-6-oxotetrahydro-2H-pyran-2-yl)ethyl)-3,7-dimethyl-1,2,3,7,8,8a-hexahydronaphthalen-1-yl (2-(2-(2-(2-(3-(2-((S)-1-((S)-2-cyclohexyl-2-((S)-2-(methylamino)propanamido)acetyl)pyrrolidin-2-yl)thiazole-4-carbonyl)phenoxy)ethoxy)ethoxy)ethoxy)ethyl) carbamate (Compound 32) and (1S,3R,7S,8S,8aR)-8-(2-((2R,4R)-4-((tert-butyldimethylsilyl)oxy)-6-oxotetrahydro-2H-pyran-2-yl)ethyl)-3,7-dimethyl-1,2,3,7,8,8a-hexahydronaphthalen-1-yl (2-(2-(2-(2-(3-(2-((S)-1-((S)-2-cyclohexyl-2-((S)-2-(methylamino)propanamido)acetyl)pyrrolidin-2-yl)thiazole-4-carbonyl)phenoxy)ethoxy)ethoxy)ethoxy)ethyl) carbamate (Compound 37)

Step 1: Synthesis of tert-butyl ((S)-1-(((S)-1-cyclohexyl-2-((S)-2-(4-(3-((2,2-dimethyl-4-oxo-3,8,11,14-tetraoxa-5-azahexadecan-16-yl)oxy)benzoyl)thiazol-2-yl)pyrrolidin-1-yl)-2-oxoethyl)amino)-1-oxopropan-2-yl)(methyl)carbamate (42b)

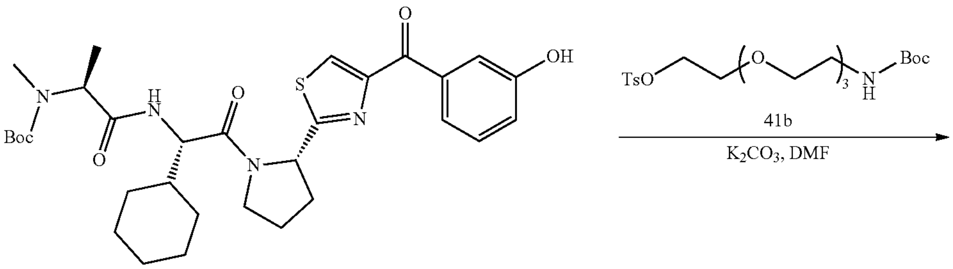

40-Int-1

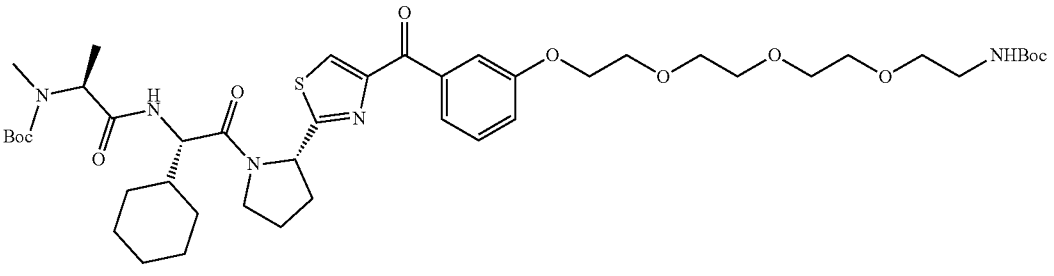

42b

In a manner similar to Step 11 of Example 31, 36, the titled compound (948 mg, 1.15 mmol, 57.41% yield, 94% purity) was obtained as a yellow oil.

MS $(M+H)^+$=874.1

Step 2: Synthesis of (S)—N—((S)-2-((S)-2-(4-(3-(2-(2-(2-(2-aminoethoxy)ethoxy)ethoxy)ethoxy)benzoyl)thiazol-2-yl)pyrrolidin-1-yl)-1-cyclohexyl-2-oxoethyl)-2-(methylamino)propanamide (43b)

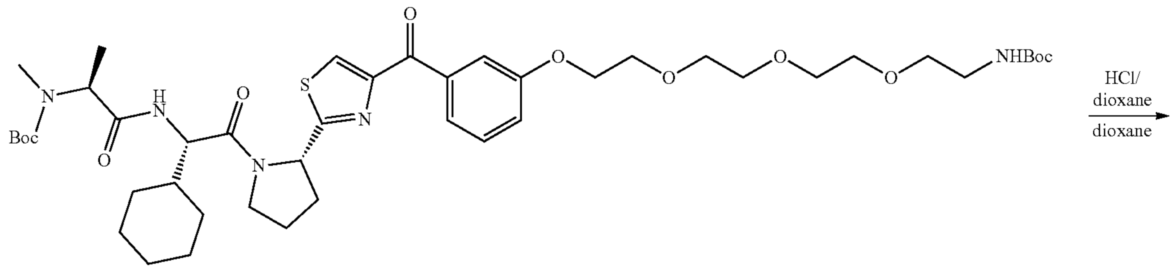

42b

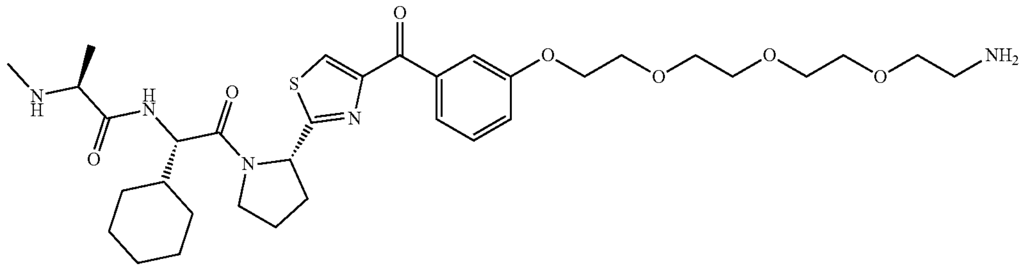

43b

In a manner similar to Step 12 of Example 31, 36, the titled compound (771 mg, crude, HCl salt) was obtained as a yellow solid.

MS $(M+H)^+=674.2$

Step 3: Synthesis of (1S,3R,7S,8S,8aR)-8-(2-((2R,4R)-4-((tert-butyldimethylsilyl)oxy)-6-oxotetrahydro-2H-pyran-2-yl)ethyl)-3,7-dimethyl-1,2,3,7,8,8a-hexahydronaphthalen-1-yl (2-(2-(2-(2-(3-(2-((S)-1-((S)-2-cyclohexyl-2-((S)-2-(methylamino)propanamido)acetyl)pyrrolidin-2-yl)thiazole-4-carbonyl)phenoxy)ethoxy)ethoxy)ethoxy)ethyl)carbamate (Compound 37)

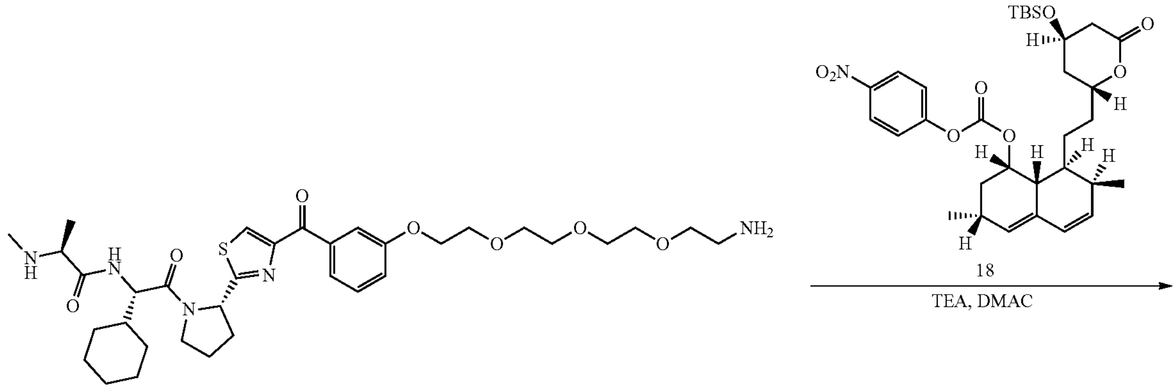

43b

-continued

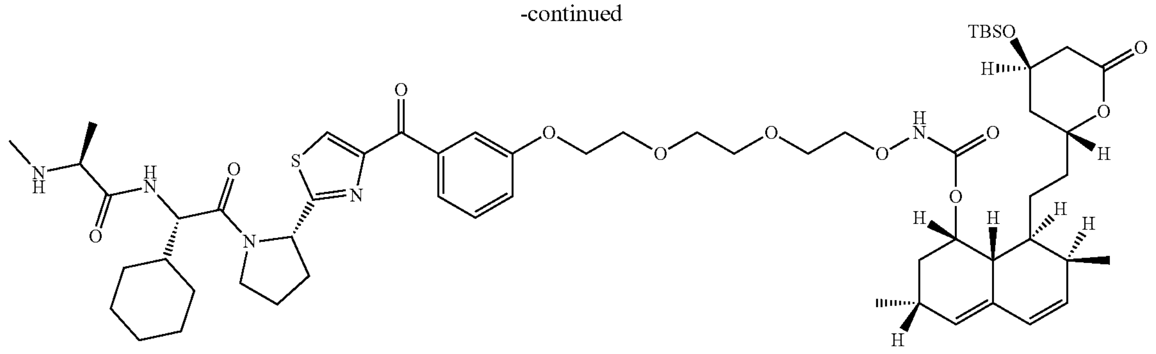

Compound 37

In a manner similar to Step 13 of Example 31, 36, the titled compound (647 mg, 537.08 μmol, 49.48% yield, 98% purity, FA salt) was obtained as a white solid.

MS $(M+H)^+$=1134.6

$^1$H NMR (400 MHz, $CDCl_3$) δ=8.11 (s, 1H), 7.81 (d, J=7.4 Hz, 1H), 7.70-7.63 (m, 2H), 7.38 (t, J=8.0 Hz, 1H), 7.16 (dd, J=2.0, 8.3 Hz, 1H), 5.97 (d, J=9.5 Hz, 1H), 5.78 (dd, J=6.0, 9.7 Hz, 1H), 5.56 (dd, J=2.6, 7.9 Hz, 1H), 5.51 (brs, 1H), 5.29-5.25 (m, 1H), 5.20 (brs, 1H), 4.65 (dd, J=6.0, 9.0 Hz, 2H), 4.29-4.26 (m, 1H), 4.20 (t, J=4.8 Hz, 2H), 3.92-3.86 (m, 3H), 3.75-3.71 (m, 2H), 3.69-3.65 (m, 2H), 3.65-3.58 (m, 4H), 3.56-3.50 (m, 2H), 3.46-3.38 (m, 1H), 3.35-3.22 (m, 2H), 2.60-2.55 (m, 2H), 2.46 (s, 3H), 2.41-2.27 (m, 12H), 1.88-1.85 (m, 2H), 1.81-1.60 (m, 9H), 1.46-1.32 (m, 4H), 1.27-0.98 (m, 9H), 0.89 (s, 9H), 0.08 (s, 6H)

Step 4: Synthesis of (1S,3R,7S,8S,8aR)-8-(2-((2R, 4R)-4-hydroxy-6-oxotetrahydro-2H-pyran-2-yl) ethyl)-3,7-dimethyl-1,2,3,7,8,8a-hexahydronaphthalen-1-yl (2-(2-(2-(2-(3-(2-((S)-1-((S)-2-cyclohexyl-2-((S)-2-(methylamino)propanamido)acetyl) pyrrolidin-2-yl)thiazole-4-carbonyl)phenoxy)ethoxy) ethoxy)ethoxy)ethyl)carbamate (Compound 32)

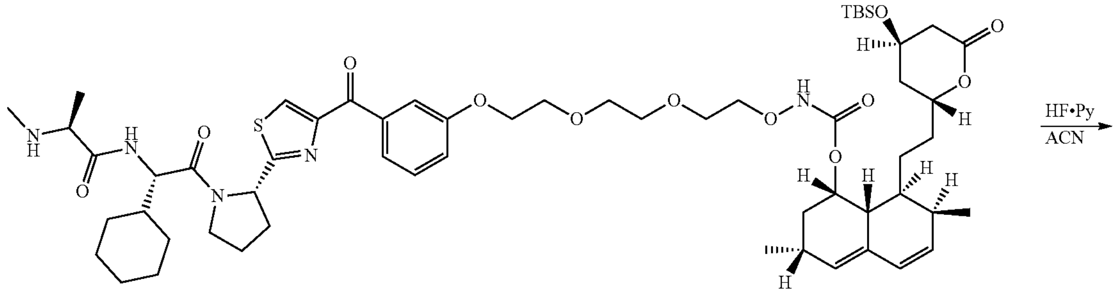

Compound 37

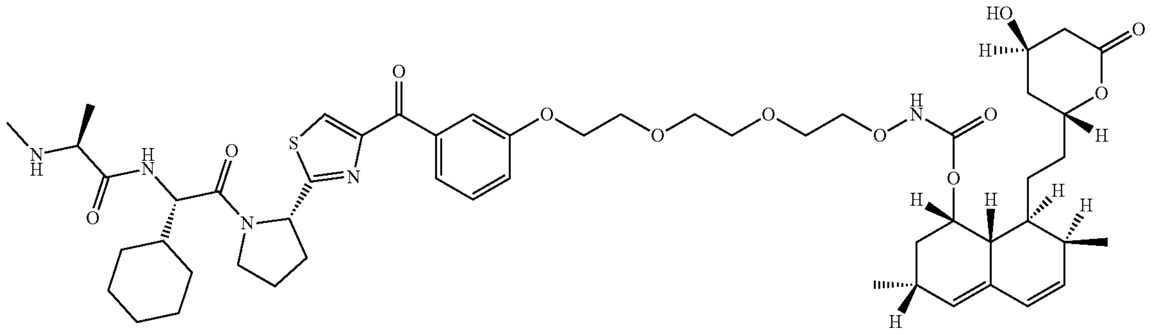

Compound 32

In a manner similar to Step 14 of Example 31, 36, the titled compound (176.7 mg, 157.43 μmol, 25.44% yield, 95% purity, FA salt) was obtained as a white solid.

MS $(M+H)^+=1020.6$ $^1$H NMR (400 MHz, $CDCl_3$) δ 8.10 (s, 1H), 8.00-7.59 (m, 3H), 7.38 (t, J=7.9 Hz, 1H), 7.18-7.12 (m, 1H), 5.95 (d, J=9.6 Hz, 1H), 5.76 (dd, J=9.6, 6.0 Hz, 1H), 5.55 (dd, J=7.6, 3.4 Hz, 1H), 5.50 (s, 1H), 5.33-5.25 (m, 1H), 5.19 (s, 1H), 4.62 (d, J=7.7 Hz, 2H), 4.32-4.25 (m, 1H), 4.23-4.15 (m, 2H), 3.90-3.75 (m, 5H), 3.73-3.68 (m, 2H), 3.67-3.64 (m, 2H), 3.63-3.57 (m, 4H), 3.54-3.47 (m, 2H), 3.37-3.29 (m, 2H), 2.69-2.53 (m, 5H), 2.44-2.31 (m, 4H), 2.27-2.03 (m, 4H), 1.97-1.61 (m, 12H), 1.48-1.30 (m, 5H), 1.21-0.95 (m, 9H), 0.87 (d, J=7.0 Hz, 3H).

Example 33 & Example 38. Synthesis of (1S,3R,7S,8S,8aR)-8-(2-((2R,4R)-4-hydroxy-6-oxotetrahydro-2H-pyran-2-yl)ethyl)-3,7-dimethyl-1,2,3,7,8,8a-hexahydronaphthalen-1-yl (14-(3-(2-((S)-1-((S)-2-cyclohexyl-2-((S)-2-(methylamino)propanamido)acetyl)pyrrolidin-2-yl)thiazole-4-carbonyl)phenoxy)-3,6,9,12-tetraoxatetradecyl)carbamate (Compound 33) and (1S,3R,7S,8S,8aR)-8-(2-((2R,4R)-4-((tert-butyldimethylsilyl)oxy)-6-oxotetrahydro-2H-pyran-2-yl)ethyl)-3,7-dimethyl-1,2,3,7,8,8a-hexahydronaphthalen-1-yl (14-(3-(2-((S)-1-((S)-2-cyclohexyl-2-((S)-2-(methylamino)propanamido)acetyl)pyrrolidin-2-yl)thiazole-4-carbonyl)phenoxy)-3,6,9,12-tetraoxatetradecyl)carbamate (Compound 38)

Step 1: Synthesis of tert-butyl ((S)-1-(((S)-1-cyclohexyl-2-((S)-2-(4-(3-((2,2-dimethyl-4-oxo-3,8,11,14,17-pentaoxa-5-azanonadecan-19-yl)oxy)benzoyl)thiazol-2-yl)pyrrolidin-1-yl)-2-oxoethyl)amino)-1-oxopropan-2-yl)(methyl)carbamate (42c)

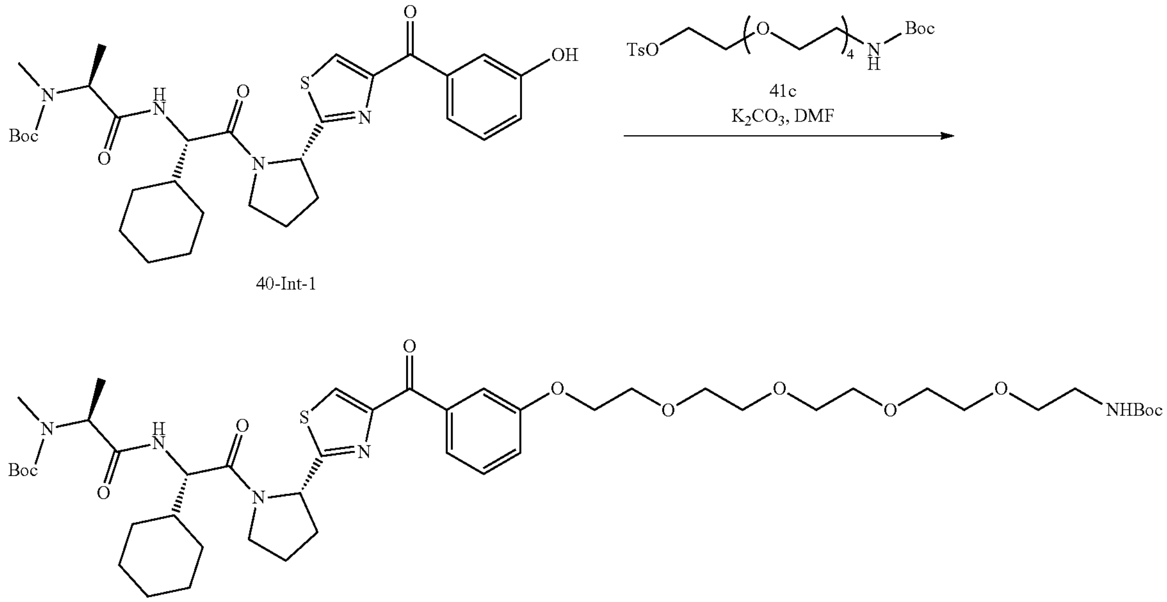

40-Int-1

42c

In a manner similar to Step 11 of Example 31, 36, the titled compound (1.1 g, 1.19 mmol, 71.02% yield, 99% purity) was obtained as a yellow oil.

MS $(M+H)^+=918.1$

Step 2: Synthesis of (S)—N—((S)-2-((S)-2-(4-(3-((14-amino-3,6,9,12-tetraoxatetradecyl)oxy)benzoyl)thiazol-2-yl)pyrrolidin-1-yl)-1-cyclohexyl-2-oxo-ethyl)-2-(methylamino)propanamide (43c)

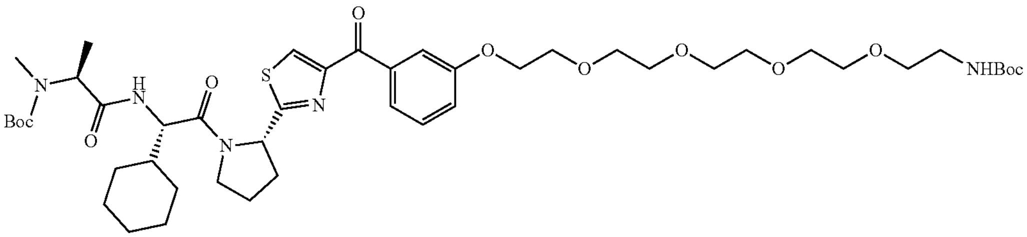

42c

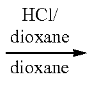

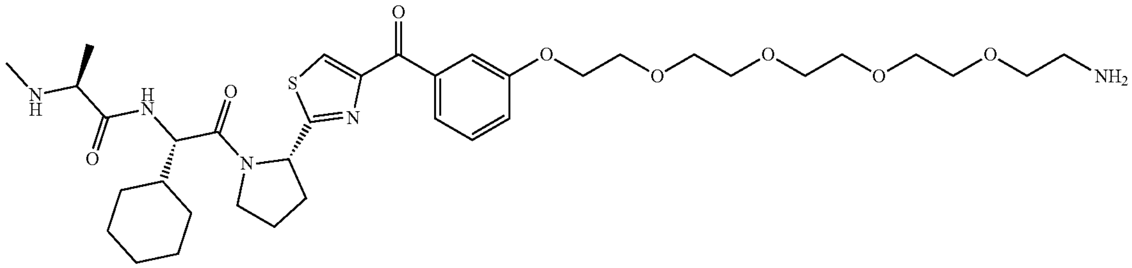

43c

In a manner similar to Step 12 of Example 31, 36, the titled compound (906 mg, crude, HCl salt) was obtained as a yellow oil.

MS $(M+H)^+$=718.1

Step 3: Synthesis of (1S,3R,7S,8S,8aR)-8-(2-((2R,4R)-4-((tert-butyldimethylsilyl)oxy)-6-oxotetrahydro-2H-pyran-2-yl)ethyl)-3,7-dimethyl-1,2,3,7,8,8a-hexahydronaphthalen-1-yl (14-(3-(2-((S)-1-((S)-2-cyclohexyl-2-((S)-2-(methylamino)propanamido)acetyl)pyrrolidin-2-yl)thiazole-4-carbonyl)phenoxy)-3,6,9,12-tetraoxatetradecyl)carbamate (Compound 38)

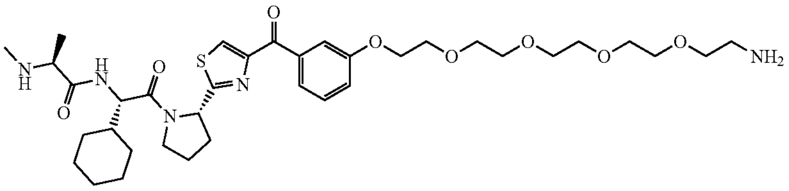

43c

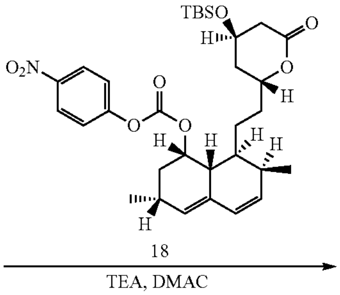

18

TEA, DMAC

-continued

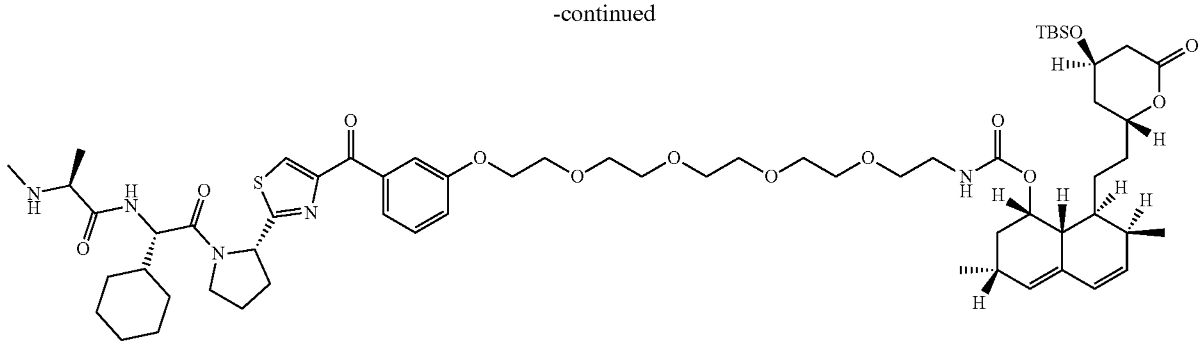

Compound 38

In a manner similar to Step 13 of Example 31, 36, the titled compound (726 mg, 603.67 μmol, 50.26% yield, 98% purity) was obtained as a white solid.

MS $(M+H)^+$=1178.6

$^1H$ NMR (400 MHz, $CDCl_3$) δ=8.10 (s, 1H), 7.80 (d, J=7.6 Hz, 1H), 7.72-7.66 (m, 2H), 7.38 (t, J=7.8 Hz, 1H), 7.16 (dd, J=2.2, 7.8 Hz, 1H), 5.97 (d, J=9.8 Hz, 1H), 5.78 (dd, J=6.1, 9.6 Hz, 1H), 5.57 (dd, J=2.6, 7.9 Hz, 1H), 5.49 (brs, 1H), 5.30-5.19 (m, 2H), 4.64 (dd, J=6.2, 9.0 Hz, 2H), 4.31-4.27 (m, 1H), 4.20 (t, J=4.7 Hz, 2H), 3.97-3.87 (m, 3H), 3.84-3.78 (m, 1H), 3.75-3.72 (m, 2H), 3.68 (m, 2H), 3.64 (s, 3H), 3.62-3.56 (m, 5H), 3.55-3.48 (m, 2H), 3.46-3.36 (m, 1H), 3.30-3.28 (m, 1H), 3.16-3.14 (m, 1H), 2.64-2.56 (m, 2H), 2.50-2.41 (m, 5H), 2.38-2.20 (m, 3H), 1.92-1.84 (m, 6H), 1.78-1.68 (m, 5H), 1.68-1.59 (m, 4H), 1.48-1.27 (m, 5H), 1.26-0.97 (m, 9H), 0.89 (s, 9H), 0.08 (s, 6H).

Step 4: Synthesis of (1S,3R,7S,8S,8aR)-8-(2-((2R,4R)-4-hydroxy-6-oxotetrahydro-2H-pyran-2-yl)ethyl)-3,7-dimethyl-1,2,3,7,8,8a-hexahydronaphthalen-1-yl (14-(3-(2-((S)-1-((S)-2-cyclohexyl-2-((S)-2-(methylamino)propanamido)acetyl)pyrrolidin-2-yl)thiazole-4-carbonyl)phenoxy)-3,6,9,12-tetraoxatetradecyl)carbamate (Compound 33)

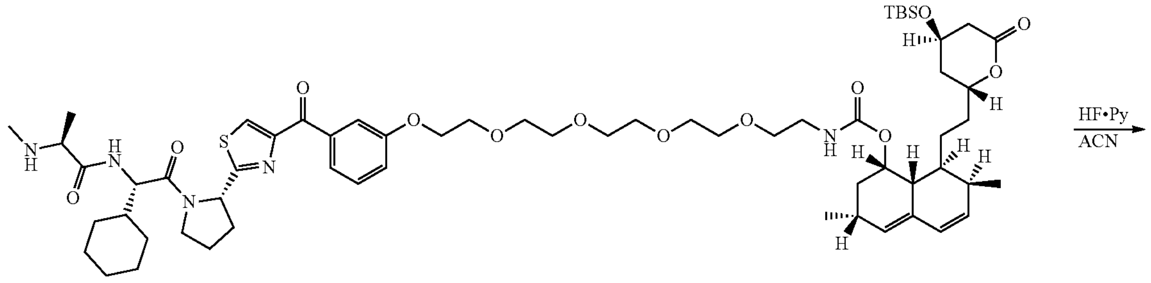

Compound 38

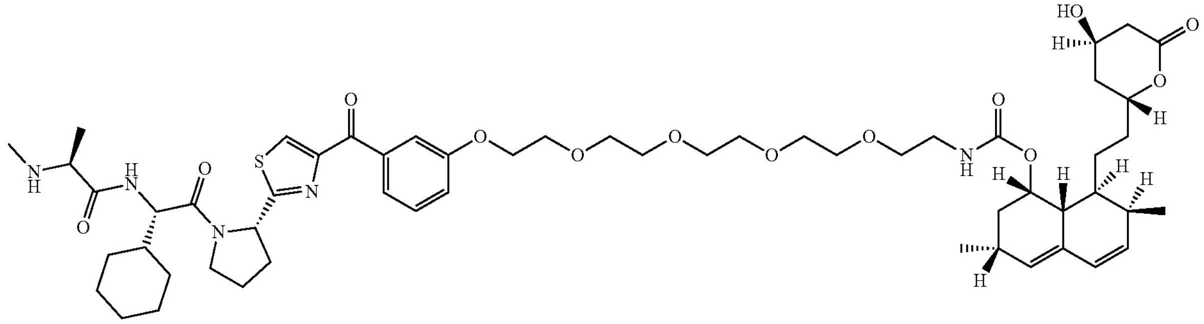

Compound 33

In a manner similar to Step 14 of Example 31, 36, the titled compound (21 mg, 19.34 μmol, 11.39% yield, 98% purity) was obtained as a white solid.

MS $(M+H)^+$=1064.8

$^1$H NMR (400 MHz, $CDCl_3$) δ 8.11 (s, 1H), 7.83-7.66 (m, 3H), 7.37 (t, J=8.0 Hz, 1H), 7.18-7.12 (m, 1H), 5.95 (d, J=9.7 Hz, 1H), 5.76 (dd, J=9.7, 6.0 Hz, 1H), 5.54 (dd, J=8.0, 2.7 Hz, 1H), 5.50 (s, 1H), 5.34-5.16 (m, 2H), 4.66-4.57 (m, 2H), 4.29 (t, J=4.3 Hz, 1H), 4.19 (t, J=4.7 Hz, 2H), 3.98-3.74 (m, 5H), 3.75-3.69 (m, 2H), 3.67-3.64 (m, 2H), 3.64-3.61 (m, 4H), 3.61-3.56 (m, 4H), 3.55-3.46 (m, 2H), 3.37-3.29 (m, 2H), 2.71-2.54 (m, 2H), 2.49-2.41 (m, 2H), 2.39 (s, 3H), 2.36-2.27 (m, 2H), 2.25-2.15 (m, 2H), 2.15-2.07 (m, 2H), 2.06-1.94 (m, 2H), 1.92-1.79 (m, 4H), 1.77-1.69 (m, 6H), 1.40-1.28 (m, 5H), 1.20-0.99 (m, 9H), 0.88 (d, J=7.0 Hz, 3H).

Example 34 & Example 35. Synthesis of (1S,3R,7S,8S,8aR)-8-(2-((2R,4R)-4-hydroxy-6-oxotetrahydro-2H-pyran-2-yl)ethyl)-3,7-dimethyl-1,2,3,7,8,8a-hexahydronaphthalen-1-yl (2-(2-(2-(3-(2-((R)-1-((S)-2-cyclohexyl-2-((S)-2-(methylamino)propanamido)acetyl)pyrrolidin-2-yl)thiazole-4-carbonyl)phenoxy)ethoxy)ethoxy)ethyl)carbamate (Compound 34) and (1S,3R,7S,8S,8aR)-8-(2-((2R,4R)-4-((tert-butyldimethylsilyl)oxy)-6-oxotetrahydro-2H-pyran-2-yl)ethyl)-3,7-dimethyl-1,2,3,7,8,8a-hexahydronaphthalen-1-yl (2-(2-(2-(3-(2-((R)-1-((S)-2-cyclohexyl-2-((S)-2-(methylamino)propanamido)acetyl)pyrrolidin-2-yl)thiazole-4-carbonyl)phenoxy)ethoxy)ethoxy)ethyl)carbamate (Compound 35)

Step 1: Synthesis of tert-butyl ((S)-1-(((S)-1-cyclohexyl-2-((R)-2-(4-(3-((2,2-dimethyl-4-oxo-3,8,11-trioxa-5-azatridecan-13-yl)oxy)benzoyl)thiazol-2-yl)pyrrolidin-1-yl)-2-oxoethyl)amino)-1-oxopropan-2-yl)(methyl)carbamate (42d)

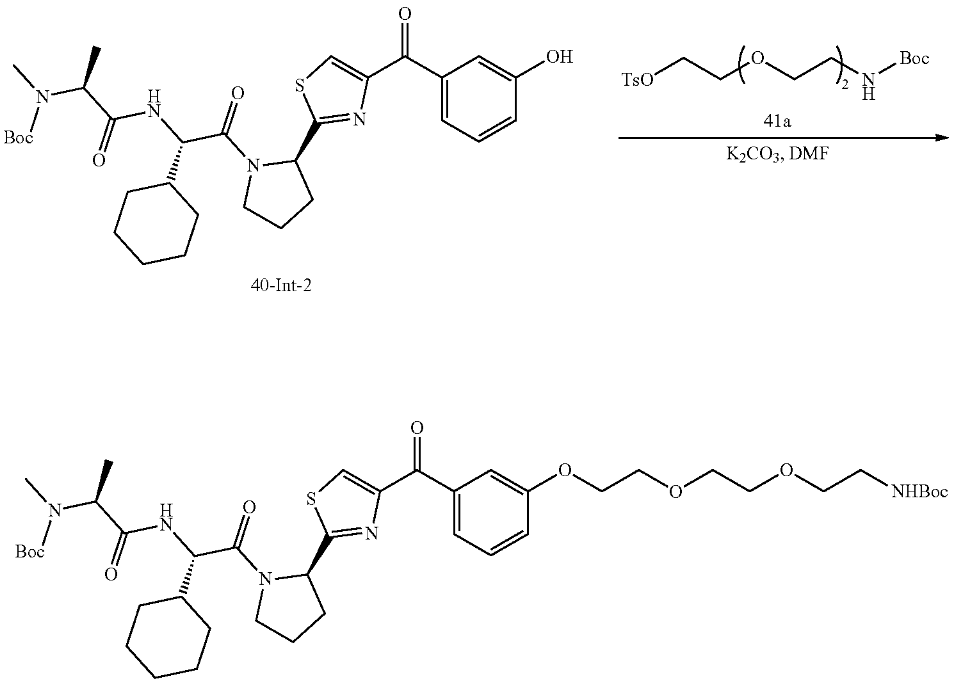

40-Int-2

42d

To a mixture of tert-butyl N-[(1S)-2-[[(1S)-1-cyclohexyl-2-[(2R)-2-[4-(3-hydroxybenzoyl)thiazol-2-yl]pyrrolidin-1-yl]-2-oxo-ethyl]amino]-1-methyl-2-oxo-ethyl]-N-methyl-carbamate (1.5 g, 2.51 mmol) and 2-[2-[2-(tert-butoxycarbonylamino)ethoxy]ethoxy]ethyl 4-methylbenzenesulfonate (1.33 g, 2.51 mmol) in DMF (10 mL) was added $K_2CO_3$ (1.04 g, 7.52 mmol) and the resulting mixture was stirred at 50° C. for 16 h. LCMS showed the starting material was consumed completely and 78% desired mass was detected. TLC ($SiO_2$, Petroleum ether:Ethyl acetate=1:3) indicated the starting material was consumed completely and one major new spot was detected. The reaction mixture was diluted with $H_2O$ (30 mL) and extracted with EtOAc (30 mL×3). The combined organic layer was washed with brine (30 mL×3), dried over $Na_2SO_4$, filtrated and concentrated. The residue was purified by column chromatography ($SiO_2$, Petroleum ether/Ethyl acetate=2/1 to 1/3) to afford tert-butyl ((S)-1-(((S)-1-cyclohexyl-2-((R)-2-(4-(3-((2,2-dimethyl-4-oxo-3,8,11-trioxa-5-azatridecan-13-yl)oxy)benzoyl)thiazol-2-yl)pyrrolidin-1-yl)-2-oxoethyl)amino)-1-oxopropan-2-yl)(methyl) carbamate (1.7 g, 1.93 mmol, 76.85% yield, 94% purity) as a yellow oil.

MS $(M+H)^+$=830.1

Step 2: Synthesis of (2S)—N-[(1S)-2-[(2R)-2-[4-[3-[2-[2-(2-aminoethoxy)ethoxy]ethoxy]benzoyl]thiazol-2-yl]pyrrolidin-1-yl]-1-cyclohexyl-2-oxo-ethyl]-2-(methylamino)propanamide (43d)

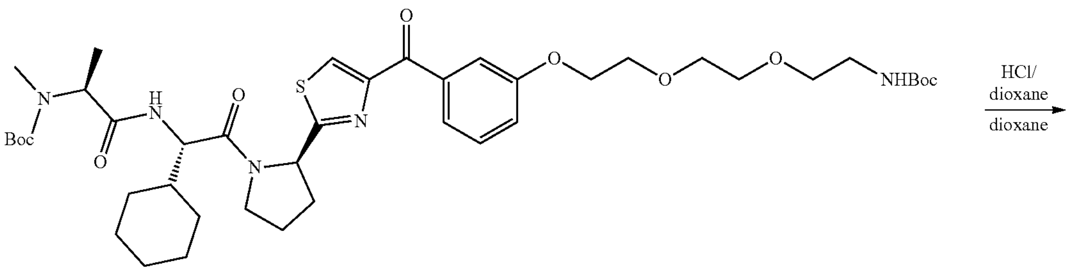

42d

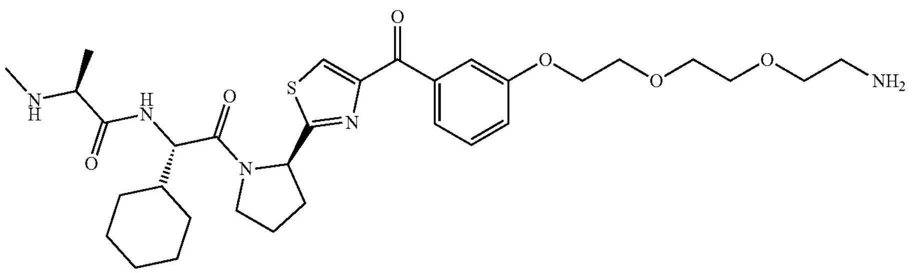

43d

To a mixture of tert-butyl ((S)-1-(((S)-1-cyclohexyl-2-((R)-2-(4-(3-((2,2-dimethyl-4-oxo-3,8,11-trioxa-5-azatridecan-13-yl)oxy)benzoyl)thiazol-2-yl)pyrrolidin-1-yl)-2-oxo-ethyl)amino)-1-oxopropan-2-yl)(methyl)carbamate (1.7 g, 2.05 mmol) in dioxane (10 mL) was added HCl/dioxane (4 M, 20 mL) and the resulting mixture was stirred at 25° C. for 1 h. LCMS showed starting material was consumed completely and 86% desired mass was detected. The reaction mixture was concentrated in vacuum to afford (2S)—N-[(1S)-2-[(2R)-2-[4-[3-[2-[2-(2-aminoethoxy)ethoxy]ethoxy]benzoyl]thiazol-2-yl]pyrrolidin-1-yl]-1-cyclohexyl-2-oxo-ethyl]-2-(methylamino)propanamide (1.36 g, crude, HCl salt) as a yellow solid, which was used in the next step. MS $(M+H)^+$=630.3

Step 3: Synthesis of (1S,3R,7S,8S,8aR)-8-(2-((2R,4R)-4-((tert-butyldimethylsilyl)oxy)-6-oxotetrahydro-2H-pyran-2-yl)ethyl)-3,7-dimethyl-1,2,3,7,8,8a-hexahydronaphthalen-1-yl (2-(2-(2-(3-(2-((R)-1-((S)-2-cyclohexyl-2-((S)-2-(methylamino)propanamido)acetyl)pyrrolidin-2-yl)thiazole-4-carbonyl)phenoxy)ethoxy)ethoxy)ethyl)carbamate (Compound 35)

resulting mixture was stirred at 25° C. for 16 h. LCMS showed the starting material was consumed completely and 70% desired mass was detected. The reaction was diluted with $H_2O$ (30 mL) and extracted with EtOAc (30 mL×3). The combined organic layer was dried over $Na_2SO_4$, filtrated and concentrated in vacuum. The residue was purified by prep-HPLC (column: Phenomenex luna C18 150*40 mm*15 μm; mobile phase: [water (0.225% FA)-ACN]; B %: 50%-80%, 11 min) to afford (1S,3R,7S,8S,8aR)-8-(2-((2R,4R)-4-((tert-butyldimethylsilyl)oxy)-6-oxotetrahydro-2H-pyran-2-yl)ethyl)-3,7-dimethyl-1,2,3,7,8,8a-hexahydronaphthalen-1-yl (2-(2-(2-(3-(2-((R)-1-((S)-2-cyclohexyl-2-((S)-2-(methylamino)propanamido)acetyl)pyrrolidin-2-yl)thiazole-4-carbonyl)phenoxy)ethoxy)ethoxy)ethyl) carbamate (579.7 mg, 499.87 μmol, 23.15% yield, 98% purity, FA salt) as a white solid, which is checked by SFC (retention time: 1.368, analysis method: "Column: Chiralpak AD-3 50 ¡ Á4.6 mm I.D., 3 μm; Mobile phase: Phase A for $CO_2$, and Phase B for IPA (0.05% DEA); Gradient elution: 40% IPA (0.05% DEA) in $CO_2$; Flow rate: 3 mL/min; Detector: PDA; Column Temp: 35 C; Back Pressure: 100 Bar").

MS $(M+H)^+$=1090.6

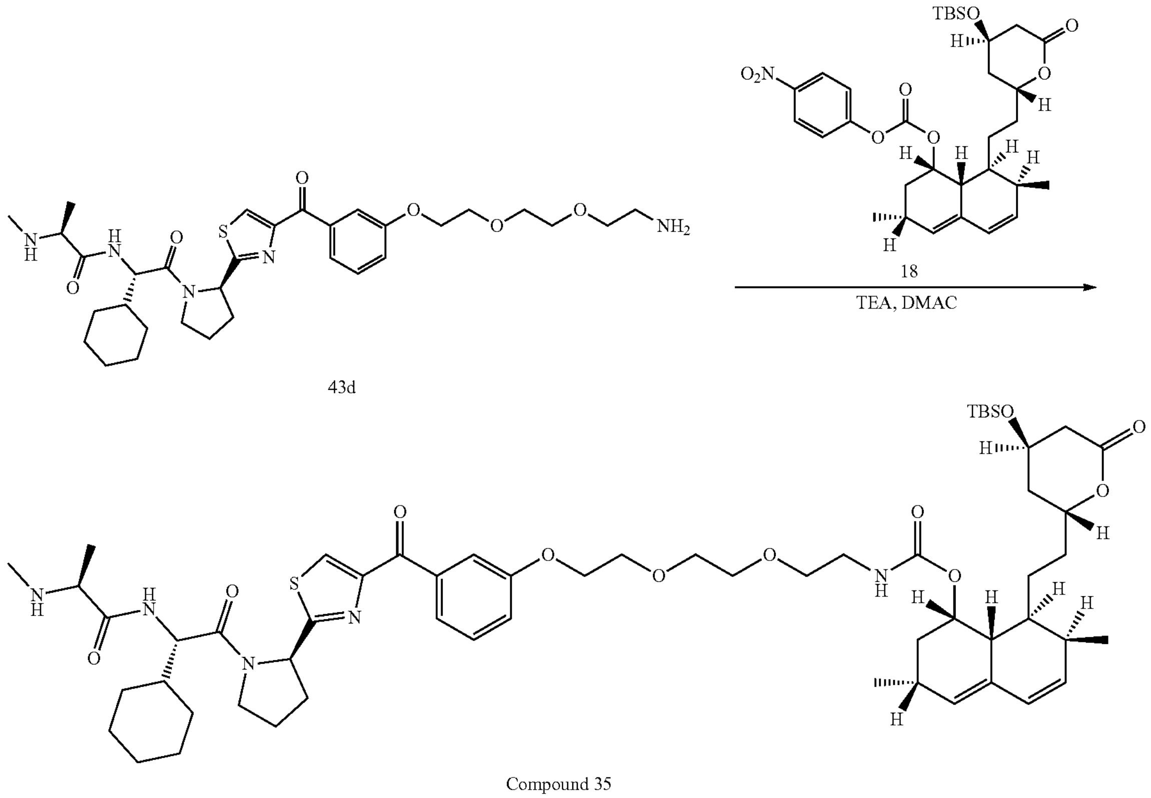

43d

Compound 35

To a mixture of (2S)—N-[(1S)-2-[(2R)-2-[4-[3-[2-[2-(2-aminoethoxy)ethoxy]ethoxy]benzoyl]thiazol-2-yl]pyrrolidin-1-yl]-1-cyclohexyl-2-oxo-ethyl]-2-(methylamino)propanamide (1.36 g, 2.16 mmol, HCl salt) and [(1S,3R,7S,8S,8aR)-8-[2-[(2R,4R)-4-[tert-butyl(dimethyl)silyl]oxy-6-oxo-tetrahydropyran-2-yl]ethyl]-3,7-dimethyl-1,2,3,7,8,8a-hexahydronaphthalen-1-yl] (4-nitrophenyl) carbonate (1.30 g, 2.16 mmol) in DMAC (15 mL) was added TEA (655.52 mg, 6.48 mmol, 901.68 μL) in one portion at 25° C. and the $^1$H NMR (400 MHz, $CDCl_3$) δ 8.05 (s, 1H), 7.77 (d, J=7.5 Hz, 1H), 7.64 (s, 1H), 7.53-7.46 (m, 1H), 7.38 (t, J=8.0 Hz, 1H), 7.15 (dd, J=8.2, 2.5 Hz, 1H), 5.95 (d, J=9.6 Hz, 1H), 5.76 (dd, J=9.6, 6.0 Hz, 1H), 5.54-5.48 (m, 2H), 5.28-5.17 (m, 2H), 4.62 (t, J=8.9 Hz, 2H), 4.28 (t, J=3.7 Hz, 1H), 4.18 (t, J=4.8 Hz, 2H), 4.12 (t, J=8.3 Hz, 1H), 3.88-3.84 (m, 2H), 3.76-3.65 (m, 4H), 3.64-3.60 (m, 2H), 3.54 (d, J=5.3 Hz, 2H), 3.43-3.29 (m, 2H), 2.64-2.40 (m, 5H), 2.36-2.33 (m, 3H), 2.27-2.20 (m, 2H), 1.90-1.75 (m, 9H), 1.74-1.66 (m, 4H), 1.64-1.58 (m, 2H), 1.39-1.03 (m, 14H), 0.89-0.87 (m, 12H), 0.07 (s, 6H).

Step 4: Synthesis of (1S,3R,7S,8S,8aR)-8-(2-((2R,4R)-4-hydroxy-6-oxotetrahydro-2H-pyran-2-yl)ethyl)-3,7-dimethyl-1,2,3,7,8,8a-hexahydronaphthalen-1-yl (2-(2-(2-(3-(2-((R)-1-((S)-2-cyclohexyl-2-((S)-2-(methylamino)propanamido)acetyl)pyrrolidin-2-yl)thiazole-4-carbonyl)phenoxy)ethoxy)ethoxy)ethyl)carbamate (Compound 34)

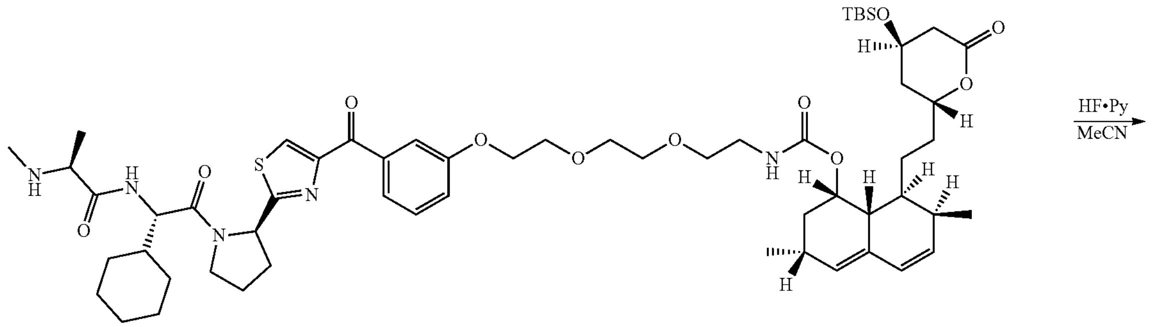

Compound 35

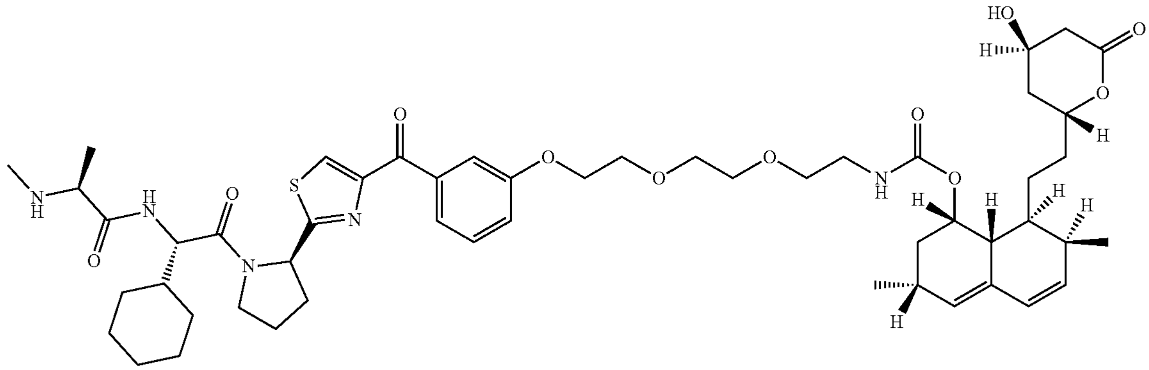

Compound 34

To a mixture of (1S,3R,7S,8S,8aR)-8-(2-((2R,4R)-4-((tert-butyldimethylsilyl)oxy)-6-oxotetrahydro-2H-pyran-2-yl)ethyl)-3,7-dimethyl-1,2,3,7,8,8a-hexahydronaphthalen-1-yl (2-(2-(2-(3-(2-((R)-1-((S)-2-cyclohexyl-2-((S)-2-(methylamino)propanamido)acetyl)pyrrolidin-2-yl)thiazole-4-carbonyl)phenoxy)ethoxy)ethoxy)ethyl)carbamate (201 mg, 184.32 μmol) in ACN (3 mL) was added HF·Pyridine (552.96 mol, 0.6 mL) at 0° C. The mixture was stirred at 15° C. for 16 h. LCMS showed starting material was consumed completely and desired mass was detected. The reaction mixture was concentrated in vacuum. The residue was purified by prep-HPLC (column: Phenomenex luna C18 150*40 mm*15 μm; mobile phase: [water (0.225% FA)-ACN]; B %: 24%-54%, 10 min) to afford (1S,3R,7S,8S,8aR)-8-(2-((2R,4R)-4-hydroxy-6-oxotetrahydro-2H-pyran-2-yl)ethyl)-3,7-dimethyl-1,2,3,7,8,8a-hexahydronaphthalen-1-yl (2-(2-(2-(3-(2-((R)-1-((S)-2-cyclohexyl-2-((S)-2-(methylamino)propanamido)acetyl)pyrrolidin-2-yl)thiazole-4-carbonyl)phenoxy)ethoxy)ethoxy)ethyl) carbamate (72.8 mg, 69.79 μmol, 37.86% yield, 98% purity, FA salt) as a white solid, which is checked by SFC (retention time=2.780, SFC analysis method: "Column: (S,S)Whelk-O1 100×4.6 mm I.D., 3.5 μm Mobile phase: Phase A for $CO_2$, and Phase B for EtOH (0.05% DEA); Gradient elution: 60% EtOH (0.05% DEA) in $CO_2$, Flow rate: 3 mL/min; Detector: PDA, Column Temp: 35 C; Back Pressure: 100 Bar").

MS $(M+H)^+$=976.6

$^1H$ NMR (400 MHz, $CDCl_3$) δ 8.05 (s, 1H), 7.79-7.58 (m, 3H), 7.40-7.34 (m, 1H), 7.18-7.11 (m, 1H), 5.95 (d, J=9.6 Hz, 1H), 5.76 (dd, J=9.7, 6.0 Hz, 1H), 5.51 (d, J=9.8 Hz, 2H), 5.24 (d, J=39.6 Hz, 2H), 4.61 (t, J=8.9 Hz, 2H), 4.29-4.17 (m, 3H), 4.15-4.07 (m, 1H), 3.88-3.82 (m, 2H), 3.74-3.65 (m, 4H), 3.65-3.52 (m, 4H), 3.39-3.31 (m, 2H), 2.66-2.59 (m, 2H), 2.49-2.41 (m, 3H), 2.41-2.37 (m, 2H), 2.35-2.29 (m, 2H), 2.26-2.18 (m, 2H), 2.17-2.00 (m, 4H), 1.94-1.84 (m, 2H), 1.84-1.74 (m, 4H), 1.74-1.67 (m, 4H), 1.38-1.30 (m, 5H), 1.24-0.96 (m, 9H), 0.87 (d, J=7.0 Hz, 3H).

Example 39 & Example 45. Synthesis of (1S,3R,7S,8S,8aR)-8-(2-((2R,4R)-4-hydroxy-6-oxotetrahydro-2H-pyran-2-yl)ethyl)-3,7-dimethyl-1,2,3,7,8,8a-hexahydronaphthalen-1-yl (2-(2-(2-(2-(phenylamino)ethoxy)ethoxy)ethoxy)ethyl) carbamate (Compound 39) and (1S,3R,7S,8S,8aR)-8-(2-((2R,4R)-4-((tert-butyldimethylsilyl)oxy)-6-oxotetrahydro-2H-pyran-2-yl)ethyl)-3,7-dimethyl-1,2,3,7,8,8a-hexahydronaphthalen-1-yl (2-(2-(2-(2-(phenylamino)ethoxy)ethoxy)ethoxy)ethyl) carbamate (Compound 45)

Step 1: Synthesis of (1S,3R,7S,8S,8aR)-8-(2-((2R,4R)-4-((tert-butyldimethylsilyl)oxy)-6-oxotetrahydro-2H-pyran-2-yl)ethyl)-3,7-dimethyl-1,2,3,7,8,8a-hexahydronaphthalen-1-yl (2-(2-(2-(2-(phenylamino)ethoxy)ethoxy)ethoxy)ethyl) carbamate (Compound 45)

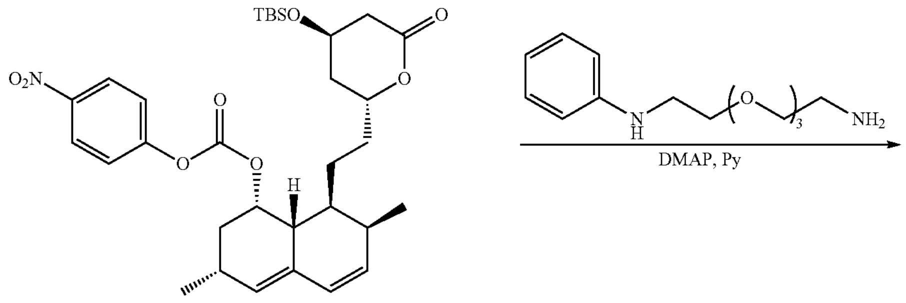

18

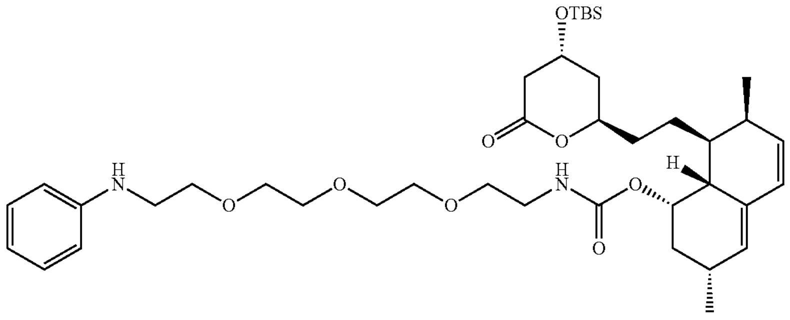

Compound 45

To a solution of (1S,3R,7S,8S,8aR)-8-(2-((2R,4R)-4-((tert-butyldimethylsilyl)oxy)-6-oxotetrahydro-2H-pyran-2-yl)ethyl)-3,7-dimethyl-1,2,3,7,8,8a-hexahydronaphthalen-1-yl (4-nitrophenyl) carbonate (325.95 mg, 0.26 mmol) and N-[2-[2-[2-(2-aminoethoxy)ethoxy]ethoxy]ethyl]aniline (70 mg, 0.26 mmol) in pyridine (0.5 mL) was added DMAP (223.07 mg, 1.83 mmol) and the mixture was stirred at 25° C. for 16 h. LCMS showed a peak (14.7%) with desired mass. The mixture was concentrated under vacuum. The residue was purified by prep-HPLC (column: Phenomenex Synergi C18 150*25*10 μm; mobile phase: [water (0.225% FA)-ACN]; B %: 75%-100%, 10 min) followed by lyophilization to afford (1S,3R,7S,8S,8aR)-8-(2-((2R,4R)-4-((tert-butyldimethylsilyl)oxy)-6-oxotetrahydro-2H-pyran-2-yl)ethyl)-3,7-dimethyl-1,2,3,7,8,8a-hexahydronaphthalen-1-yl (2-(2-(2-(2-(phenylamino)ethoxy)ethoxy)ethoxy)ethyl) carbamate (9.1 mg, 0.011 mmol, 4.46% yield, 93.2% purity) as yellow oil and (1S,3R,7S,8S,8aR)-8-(2-((2R,4R)-4-((tert-butyldimethylsilyl)oxy)-6-oxotetrahydro-2H-pyran-2-yl)ethyl)-3,7-dimethyl-1,2,3,7,8,8a-hexahydronaphthalen-1-yl (2-(2-(2-(2-(phenylamino)ethoxy)ethoxy)ethoxy)ethyl) carbamate (90 mg, 123.45 μmol, 47.33% yield, 93.2% purity) as yellow oil.

MS $(M+H)^+$=729.6

$^1$H NMR (400 MHz, DMSO-$d_6$) δ 7.10-7.02 (m, 2H), 6.99 (t, J=5.7 Hz, 1H), 6.57 (dd, J=0.9, 8.5 Hz, 2H), 6.54-6.47 (m, 1H), 5.91 (d, J=9.7 Hz, 1H), 5.76 (dd, J=6.5, 8.8 Hz, 1H), 5.51-5.42 (m, 2H), 5.05 (d, J=2.81 Hz, 1H), 4.48-4.47 (m, 1H), 4.33-4.25 (m, 1H), 3.57-3.43 (m, 10H), 3.39-3.34 (m, 2H), 3.16 (q, J=5.8 Hz, 2H), 3.12-3.02 (m, 2H), 2.72-2.64 (m, 1H), 2.40-2.29 (m, 2H), 2.23-2.20 (m, 1H), 1.88-1.75 (m, 3H), 1.73-1.59 (m, 3H), 1.48 (t, J=11.6 Hz, 1H), 1.38-1.21 (m, 2H), 1.03 (d, J=7.3 Hz, 3H), 0.89-0.80 (m, 12H), 0.08-0.06 (m, 6H).

Step 2: Synthesis of (1S,3R,7S,8S,8aR)-8-(2-((2R,4R)-4-hydroxy-6-oxotetrahydro-2H-pyran-2-yl)ethyl)-3,7-dimethyl-1,2,3,7,8,8a-hexahydronaphthalen-1-yl (2-(2-(2-(2-(phenylamino)ethoxy)ethoxy)ethoxy)ethyl)carbamate (Compound 39)

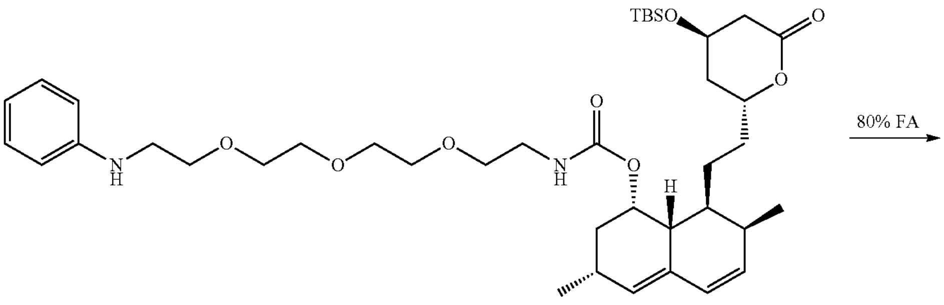

Compound 45

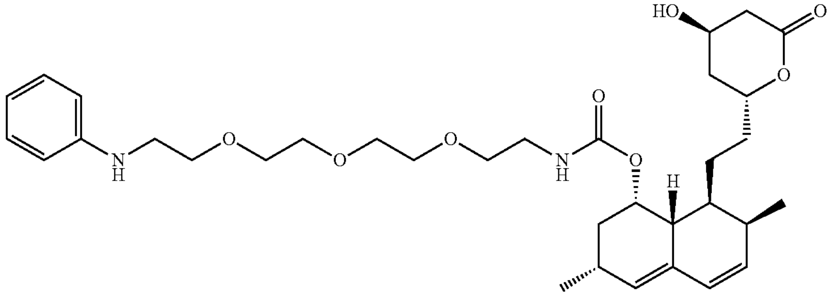

Compound 39

A mixture of (1S,3R,7S,8S,8aR)-8-(2-((2R,4R)-4-((tert-butyldimethylsilyl)oxy)-6-oxotetrahydro-2H-pyran-2-yl)ethyl)-3,7-dimethyl-1,2,3,7,8,8a-hexahydronaphthalen-1-yl (2-(2-(2-(2-(phenylamino)ethoxy)ethoxy)ethoxy)ethyl)carbamate (90 mg, 0.12 mmol) in formic acid (2.44 g, 42.41 mmol, 2.00 mL, 80% purity) was stirred at 25° C. for 30 min. LCMS showed a main peak with desired mass and a little starting material remained. The mixture was stirred at 25° C. for 30 min. The mixture was concentrated under vacuum. The residue was purified by prep-HPLC (column: Phenomenex Synergi C18 150*25*10 μm; mobile phase: [water (0.225% FA)-ACN]; B %: 37%-67%, 10 min) followed by lyophilization to afford (1S,3R,7S,8S,8aR)-8-(2-((2R,4R)-4-hydroxy-6-oxotetrahydro-2H-pyran-2-yl)ethyl)-3,7-dimethyl-1,2,3,7,8,8a-hexahydronaphthalen-1-yl (2-(2-(2-(2-(phenylamino)ethoxy)ethoxy)ethoxy)ethyl)carbamate (37.8 mg, 0.057 mmol, 46.72% yield, 93.8% purity) as yellow oil.

MS $(M+H)^+$=615.4

$^1$H NMR (400 MHz, DMSO-$d_6$) δ 7.09-7.02 (m, 2H), 6.99 (t, J=5.6 Hz, 1H), 6.57 (dd, J=0.9, 8.5 Hz, 2H), 6.51 (t, J=7.21 Hz, 1H), 5.91 (d, J=9.5 Hz, 1H), 5.76 (dd, J=5.9, 9.4 Hz, 1H), 5.49-5.42 (m, 2H), 5.18 (d, J=3.30 Hz, 1H), 5.05 (d, J=3.0 Hz, 1H), 4.49-4.46 (m, 1H), 4.15-4.05 (m, 1H), 3.57-3.32 (m, 12H), 3.16-3.14 (m, 2H), 3.09-3.05 (m, 2H), 2.62-2.60 (m, 1H), 2.41 (m, 2H), 2.36 (d, J=3.5 Hz, 1H), 1.89-1.77 (m, 3H), 1.72-1.57 (m, 3H), 1.50-1.40 (m, 1H), 1.38-1.20 (m, 2H), 1.03 (d, J=7.3 Hz, 3H), 0.83 (d, J=6.9 Hz, 3H).

Example 40 & Example 46. Synthesis of (1S,3R,7S,8S,8aR)-8-(2-((2R,4R)-4-hydroxy-6-oxotetrahydro-2H-pyran-2-yl)ethyl)-3,7-dimethyl-1,2,3,7,8,8a-hexahydronaphthalen-1-yl (2-(2-(2-((2-(2,6-dioxopiperidin-3-yl)-1,3-dioxoisoindolin-4-yl)amino)ethoxy)ethoxy)ethyl)carbamate (Compound 40) and (1S,3R,7S,8S,8aR)-8-(2-((2R,4R)-4-((tert-butyldimethylsilyl)oxy)-6-oxotetrahydro-2H-pyran-2-yl)ethyl)-3,7-dimethyl-1,2,3,7,8,8a-hexahydronaphthalen-1-yl (2-(2-(2-((2-(2,6-dioxopiperidin-3-yl)-1,3-dioxoisoindolin-4-yl)amino)ethoxy)ethoxy)ethyl)carbamate (Compound 46)

Step 1: Synthesis of (1S,3R,7S,8S,8aR)-8-(2-((2R,4R)-4-((tert-butyldimethylsilyl)oxy)-6-oxotetrahydro-2H-pyran-2-yl)ethyl)-3,7-dimethyl-1,2,3,7,8,8a-hexahydronaphthalen-1-yl (2-(2-(2-((2-(2,6-dioxopiperidin-3-yl)-1,3-dioxoisoindolin-4-yl)amino)ethoxy)ethoxy)ethyl)carbamate (Compound 46)

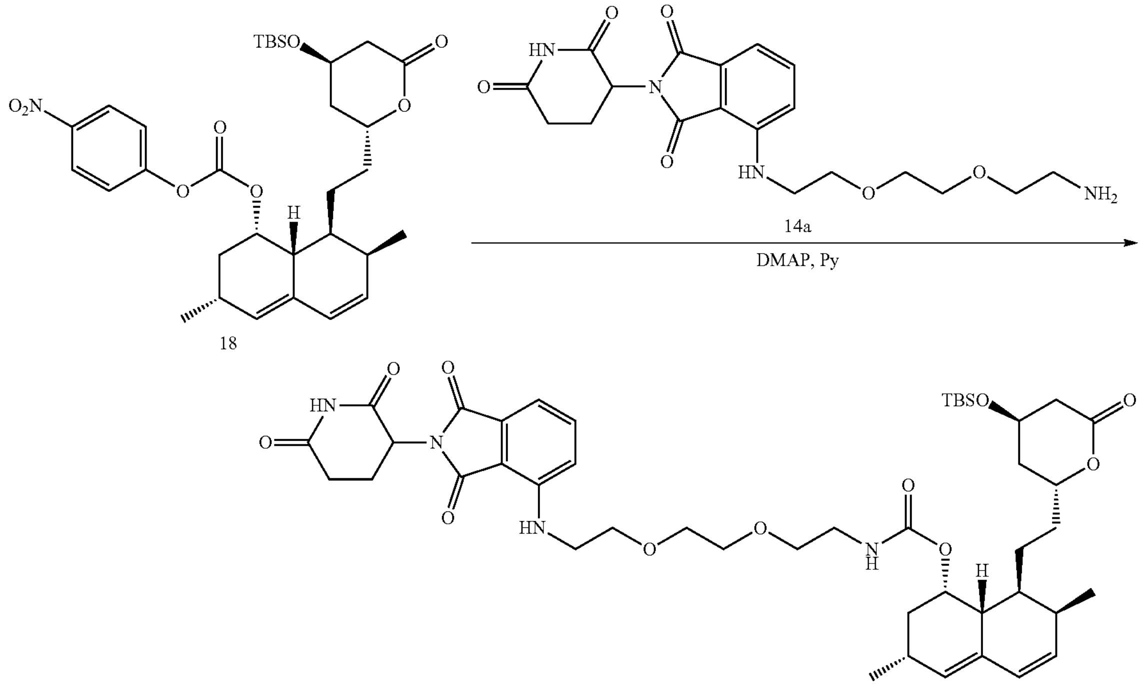

18

Compound 46

A mixture of [(1S,3R,7S,8S,8aR)-8-[2-[(2R,4R)-4-[tert-butyl(dimethyl)silyl]oxy-6-oxo-tetrahydropyran-2-yl]ethyl]-3,7-dimethyl-1,2,3,7,8,8a-hexahydronaphthalen-1-yl] (4-nitrophenyl) carbonate (0.3 g, 0.50 mmol), 4-[2-[2-(2-aminoethoxy)ethoxy]ethylamino]-2-(2,6-dioxo-3-piperidyl)isoindoline-1,3-dione (0.3 g, 680.46 μmol, HCl salt) and DMAP (0.43 g, 3.52 mmol, 7.04 eq) in pyridine (3 mL) was stirred at 25° C. for 16 h. LCMS showed a main peak with desired mass. The mixture was concentrated. The residue was purified by prep-HPLC (column: Phenomenex Synergi Max-RP 150*50 mm*10 μm; mobile phase: [water (0.2% FA)-ACN]; B %: 3%-33%, 11 min) followed by lyophilization to afford (1S,3R,7S,8S,8aR)-8-(2-((2R,4R)-4-((tert-butyldimethylsilyl)oxy)-6-oxotetrahydro-2H-pyran-2-yl)ethyl)-3,7-dimethyl-1,2,3,7,8,8a-hexahydronaphthalen-1-yl (2-(2-(2-((2-(2,6-dioxopiperidin-3-yl)-1,3-dioxoisoindolin-4-yl)amino)ethoxy)ethoxy)ethyl)carbamate (19.4 mg, 0.021 mmol, 4.37% yield, 97.5% purity) as yellow solid and (1S,3R,7S,8S,8aR)-8-(2-((2R,4R)-4-((tert-butyldimethylsilyl)oxy)-6-oxotetrahydro-2H-pyran-2-yl)ethyl)-3,7-dimethyl-1,2,3,7,8,8a-hexahydronaphthalen-1-yl(2-(2-(2-((2-(2,6-dioxopiperidin-3-yl)-1,3-dioxoisoindolin-4-yl)amino)ethoxy)ethoxy)ethyl)carbamate (100 mg, 0.115 mmol, 23.11% yield, 98% purity) as yellow solid.

MS $(M+H)^+$=865.4

$^1$H NMR (400 MHz, DMSO-$d_6$) δ 11.08 (s, 1H), 7.58 (dd, J=8.5, 7.1 Hz, 1H), 7.13 (d, J=8.6 Hz, 1H), 7.04 (d, J=7.0 Hz, 1H), 6.97 (t, J=5.7 Hz, 1H), 6.59 (t, J=5.8 Hz, 1H), 5.90 (d, J=9.6 Hz, 1H), 5.74 (dd, J=9.6, 5.9 Hz, 1H), 5.45 (s, 1H), 5.12-4.96 (m, 2H), 4.53-4.41 (m, 1H), 4.33-4.21 (m, 1H), 3.60 (t, J=5.4 Hz, 2H), 3.57-3.41 (m, 6H), 3.37 (t, J=6.2 Hz, 2H), 3.29 (s, 2H), 3.09 (p, J=6.5 Hz, 2H), 2.94-2.82 (m, 1H), 2.70 (d, J=4.3 Hz, 1H), 2.62-2.55 (m, 1H), 2.40-2.36 (m, 1H), 2.23 (d, J=11.7 Hz, 1H), 2.08-1.97 (m, 1H), 1.88-1.75 (m, 3H), 1.75-1.58 (m, 3H), 1.54-1.43 (m, 1H), 1.39-1.21 (m, 2H), 1.03 (d, J=7.4 Hz, 3H), 0.85-0.82 (m, 12H), 0.05 (s, 6H).

Step 2: Synthesis of (1S,3R,7S,8S,8aR)-8-(2-((2R,4R)-4-hydroxy-6-oxotetrahydro-2H-pyran-2-yl)ethyl)-3,7-dimethyl-1,2,3,7,8,8a-hexahydronaphthalen-1-yl (2-(2-(2-((2-(2,6-dioxopiperidin-3-yl)-1,3-dioxoisoindolin-4-yl)amino)ethoxy)ethoxy)ethyl) carbamate (Compound 40)

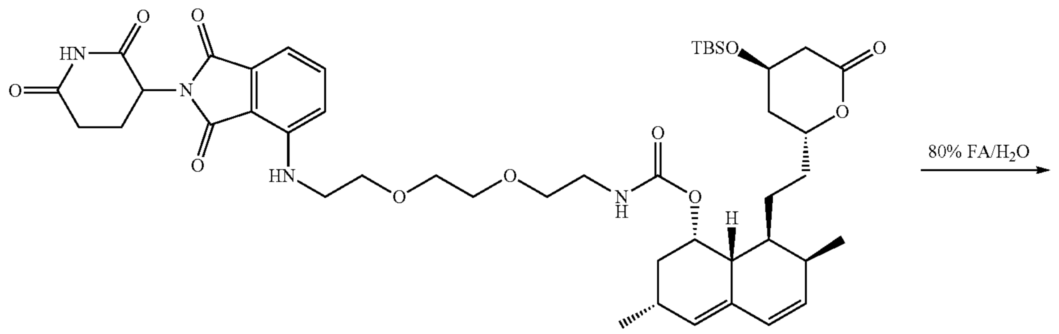

Compound 46

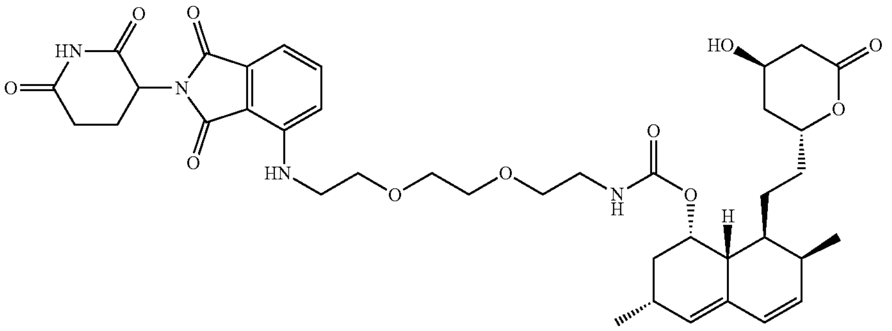

Compound 40

A mixture of (1S,3R,7S,8S,8aR)-8-(2-((2R,4R)-4-((tert-butyldimethylsilyl)oxy)-6-oxotetrahydro-2H-pyran-2-yl)ethyl)-3,7-dimethyl-1,2,3,7,8,8a-hexahydronaphthalen-1-yl (2-(2-(2-((2-(2,6-dioxopiperidin-3-yl)-1,3-dioxoisoindolin-4-yl)amino)ethoxy)ethoxy)ethyl)carbamate (95 mg, 109.81 μmol) in FA (109.81 μmol, 10 mL, 80% purity) was stirred at 25° C. for 1 h. LCMS showed a main peak (68%) with desired mass. The mixture was concentrated under vacuum. The residue was purified by prep-HPLC (column: Phenomenex Synergi C18 150*25*10 μm; mobile phase: [water (0.225% FA)-ACN]; B %: 48%-78%, 9 min) followed by lyophilization to afford (1S,3R,7S,8S,8aR)-8-(2-((2R,4R)-4-hydroxy-6-oxotetrahydro-2H-pyran-2-yl)ethyl)-3,7-dimethyl-1,2,3,7,8,8a-hexahydronaphthalen-1-yl (2-(2-(2-((2-(2,6-dioxopiperidin-3-yl)-1,3-dioxoisoindolin-4-yl)amino)ethoxy)ethoxy)ethyl)carbamate (64.9 mg, 0.084 mmol, 76.11% yield, 96.7% purity) as yellow solid.

MS $(M+H)^+$=751.4

$^1H$ NMR (400 MHz, DMSO-$d_6$) δ 11.08 (s, 1H), 7.61-7.55 (m, 1H), 7.13 (d, J=8.6 Hz, 1H), 7.04 (d, J=7.09 Hz, 1H), 6.98 (t, J=5.4 Hz, 1H), 6.59 (t, J=5.6 Hz, 1H), 5.90 (d, J=9.54 Hz, 1H), 5.79-5.71 (m, 1H), 5.45 (brs, 1H), 5.17 (d, J=3.1 Hz, 1H), 5.09-5.01 (m, 2H), 4.48-4.46 (m, 1H), 4.09 (m, 1H), 3.63-3.58 (m, 2H), 3.56-3.42 (m, 6H), 3.40-3.37 (m, 2H), 3.13-3.05 (m, 2H), 2.94-2.82 (m, 1H), 2.65-2.53 (m, 3H), 2.41 (s, 1H), 2.36 (s, 1H), 2.22 (d, J=10.7 Hz, 1H), 2.07 (s, 1H), 2.05-1.98 (m, 1H), 1.86-1.75 (m, 3H), 1.70-1.57 (m, 3H), 1.49-1.23 (m, 1H), 1.36-1.21 (m, 2H), 1.02 (d, J=7.2 Hz, 3H), 0.83 (d, J=6.9 Hz, 3H).

Example 41 & Example 47. Synthesis of (1S,3R,7S,8S,8aR)-8-(2-((2R,4R)-4-hydroxy-6-oxotetrahydro-2H-pyran-2-yl)ethyl)-3,7-dimethyl-1,2,3,7,8,8a-hexahydronaphthalen-1-yl (2-(2-(2-(2-((2-(2,6-dioxopiperidin-3-yl)-1,3-dioxoisoindolin-4-yl)amino)ethoxy)ethoxy)ethoxy)ethyl)carbamate (Compound 41) and (1S,3R,7S,8S,8aR)-8-(2-((2R,4R)-4-((tert-butyldimethylsilyl)oxy)-6-oxotetrahydro-2H-pyran-2-yl)ethyl)-3,7-dimethyl-1,2,3,7,8,8a-hexahydronaphthalen-1-yl (2-(2-(2-(2-((2-(2,6-dioxopiperidin-3-yl)-1,3-dioxoisoindolin-4-yl)amino)ethoxy)ethoxy)ethoxy)ethyl)carbamate (Compound 47)

Step 1: Synthesis of (1S,3R,7S,8S,8aR)-8-(2-((2R,4R)-4-((tert-butyldimethylsilyl)oxy)-6-oxotetrahydro-2H-pyran-2-yl)ethyl)-3,7-dimethyl-1,2,3,7,8,8a-hexahydronaphthalen-1-yl (2-(2-(2-(2-((2-(2,6-dioxopiperidin-3-yl)-1,3-dioxoisoindolin-4-yl)amino)ethoxy)ethoxy)ethoxy)ethyl)carbamate (Compound 47)

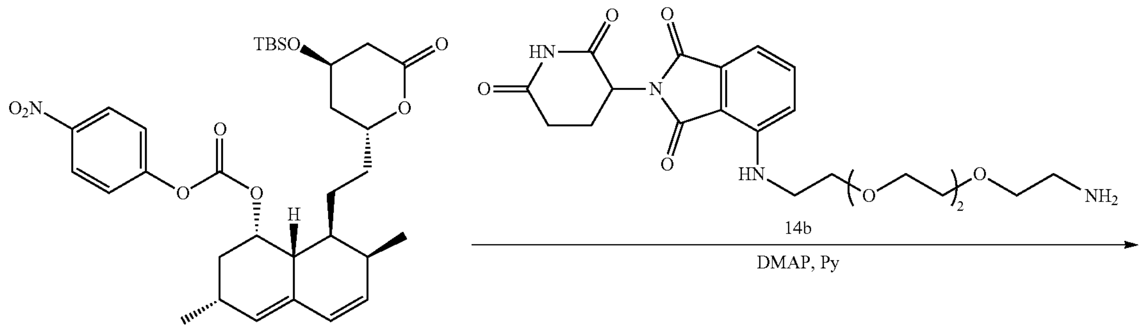

18

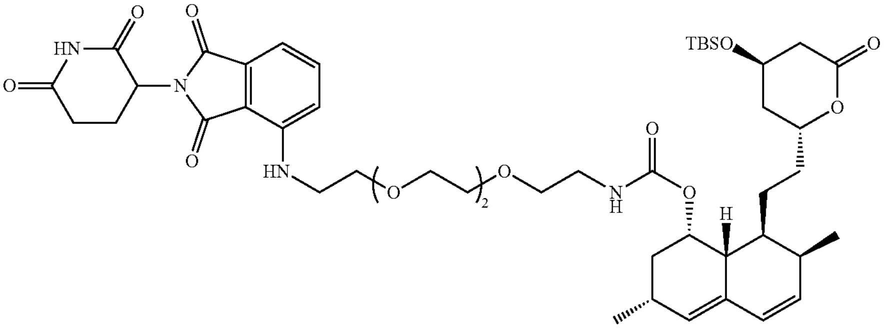

Compound 47

In a manner similar to Step 1 of Example 40, 46, the titled compound (0.13 g, 0.14 mmol, 28.66% yield, 99.1% purity) was obtained as a white solid.

MS $(M+H)^+$=909.5

$^1$H NMR (400 MHz, DMSO-$d_6$) δ 11.09 (s, 1H), 7.58 (dd, J=8.6, 7.0 Hz, 1H), 7.14 (d, J=8.6 Hz, 1H), 7.04 (d, J=7.0 Hz, 1H), 6.97 (t, J=5.7 Hz, 1H), 6.60 (t, J=5.8 Hz, 1H), 5.90 (d, J=9.6 Hz, 1H), 5.75 (dd, J=9.6, 5.9 Hz, 1H), 5.46 (d, J=3.8 Hz, 1H), 5.10-4.99 (m, 2H), 4.55-4.42 (m, 1H), 4.32-4.25 (m, 1H), 3.61 (t, J=5.4 Hz, 2H), 3.58-3.53 (m, 2H), 3.53-3.50 (m, 2H), 3.50-3.42 (m, 6H), 3.38-3.34 (m, 2H), 3.15-3.01 (m, 2H), 2.95-2.81 (m, 1H), 2.72-2.64 (m, 1H), 2.58-2.53 (m, 1H), 2.36-2.30 (m, 2H), 2.23 (d, J=12.2 Hz, 1H), 2.06-1.98 (m, 1H), 1.90-1.75 (m, 3H), 1.75-1.60 (m, 3H), 1.54-1.42 (m, 1H), 1.41-1.17 (m, 2H), 1.03 (d, J=7.3 Hz, 3H), 0.88-0.79 (m, 12H), 0.05 (s, 6H).

Step 2: Synthesis of (1S,3R,7S,8S,8aR)-8-(2-((2R,4R)-4-hydroxy-6-oxotetrahydro-2H-pyran-2-yl)ethyl)-3,7-dimethyl-1,2,3,7,8,8a-hexahydronaphthalen-1-yl (2-(2-(2-(2-((2-(2,6-dioxopiperidin-3-yl)-1,3-dioxoisoindolin-4-yl)amino)ethoxy)ethoxy)ethoxy)ethyl)carbamate (Compound 41)

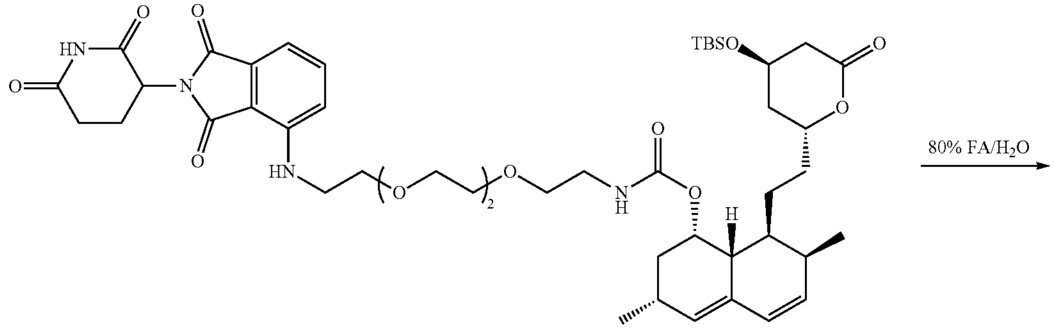

Compound 47

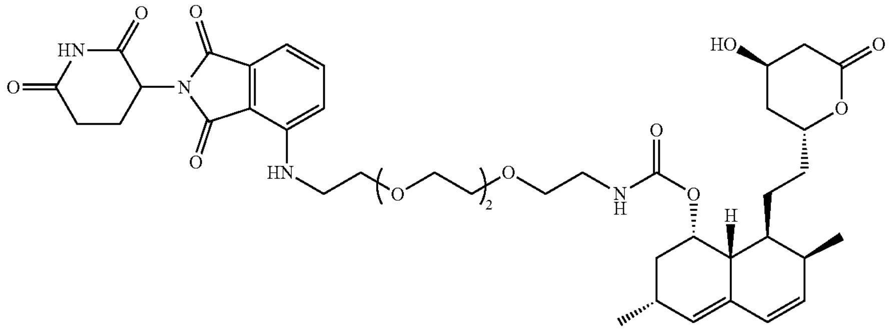

Compound 41

In a manner similar to Step 2 of Example 40, 46, the titled compound (71.5 mg, 0.086 mmol, 60.58% yield, 96.3% purity) was obtained as a yellow solid.

MS $(M+H)^+$=795.4

$^1H$ NMR (400 MHz, DMSO-$d_6$) δ 11.08 (s, 1H), 7.61-7.55 (m, 1H), 7.14 (d, J=8.6 Hz, 1H), 7.04 (d, J=6.9 Hz, 1H), 6.98 (t, J=5.4 Hz, 1H), 6.60 (t, J=5.9 Hz, 1H), 5.90 (d, J=9.6 Hz, 1H), 5.75 (dd, J=6.1, 9.3 Hz, 1H), 5.45 (brs, 1H), 5.17 (d, J=2.9 Hz, 1H), 5.10-4.99 (m, 2H), 4.49-4.46 (m, 1H), 4.09-4.06 (m, 1H), 3.63-3.59 (m, 2H), 3.57-3.44 (m, 12H), 3.11-3.05 (m, 2H), 2.93-2.82 (m, 1H), 2.65-2.54 (m, 3H), 2.41 (m, 1H), 2.34 (m, 2H), 2.06-1.97 (m, 1H), 1.88-1.74 (m, 3H), 1.72-1.56 (m, 3H), 1.49-1.28 (m, 1H), 1.36-1.21 (m, 2H), 1.02 (d, J=7.2 Hz, 3H), 0.83 (d, J=6.9 Hz, 3H).

Example 42 & Example 48. Synthesis of (1S,3R,7S,8S,8aR)-8-(2-((2R,4R)-4-hydroxy-6-oxotetrahydro-2H-pyran-2-yl)ethyl)-3,7-dimethyl-1,2,3,7,8,8a-hexahydronaphthalen-1-yl (14-((2-(2,6-dioxopiperidin-3-yl)-1,3-dioxoisoindolin-4-yl)amino)-3,6,9,12-tetraoxatetradecyl)carbamate (Compound 42) and (1S,3R,7S,8S,8aR)-8-(2-((2R,4R)-4-((tert-butyldimethylsilyl)oxy)-6-oxotetrahydro-2H-pyran-2-yl)ethyl)-3,7-dimethyl-1,2,3,7,8,8a-hexahydronaphthalen-1-yl (14-((2-(2,6-dioxopiperidin-3-yl)-1,3-dioxoisoindolin-4-yl)amino)-3,6,9,12-tetraoxatetradecyl)carbamate (Compound 48)

Step 1: Synthesis of (1S,3R,7S,8S,8aR)-8-(2-((2R,4R)-4-((tert-butyldimethylsilyl)oxy)-6-oxotetrahydro-2H-pyran-2-yl)ethyl)-3,7-dimethyl-1,2,3,7,8,8a-hexahydronaphthalen-1-yl (14-((2-(2,6-dioxopiperidin-3-yl)-1,3-dioxoisoindolin-4-yl)amino)-3,6,9,12-tetraoxatetradecyl)carbamate (Compound 48)

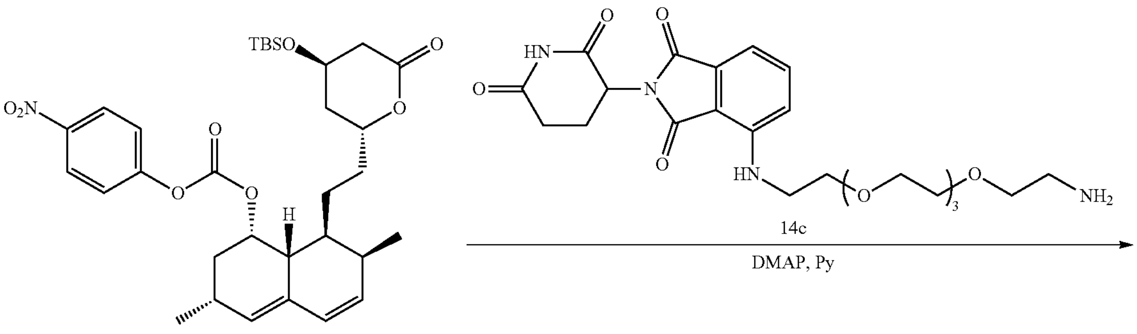

18

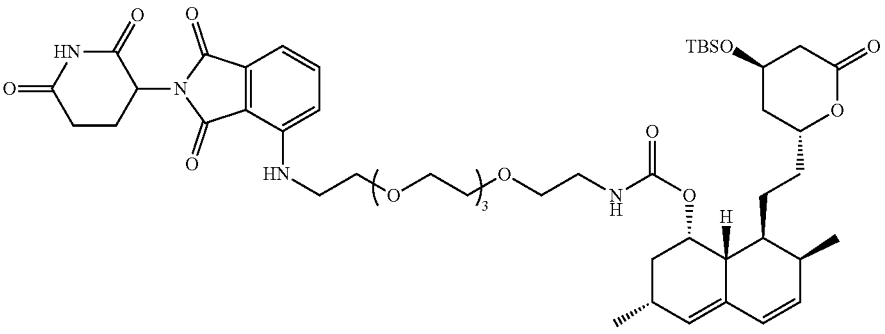

Compound 48

In a manner similar to Step 1 of Example 40, 46, the titled compound (50 mg, 51.46 μmol, 10.31% yield, 98.1% purity) was obtained as a yellow solid.

MS $(M+H)^+$=953.3.

$^1$H NMR (400 MHz, DMSO-$d_6$) δ=11.09 (s, 1H), 7.58-7.56 (m, 1H), 7.14 (d, J=8.6 Hz, 1H), 7.07-7.02 (m, 1H), 6.98 (t, J=5.7 Hz, 1H), 6.64-6.57 (m, 1H), 5.90 (d, J=9.6 Hz, 1H), 5.75 (dd, J=9.5 Hz, 5.9 Hz, 1H), 5.45 (s, 1H), 5.11-4.98 (m, 2H), 4.53-4.41 (m, 1H), 4.33-4.24 (m, 1H), 3.64-3.59 (m, 2H), 3.58-3.54 (m, 2H), 3.54-3.43 (m, 12H), 3.50-3.30 (m, 2H), 3.15-3.00 (m, 2H), 2.94-2.81 (m, 1H), 2.73-2.58 (m, 2H), 2.57-2.54 (m, 1H), 2.40-2.31 (m, 3H), 2.23 (d, J=11.8 Hz, 1H), 2.06-1.98 (m, 1H), 1.90-1.76 (m, 3H), 1.74-1.60 (m, 3H), 1.53-1.42 (m, 1H), 1.36-1.22 (m, 2H), 1.07-0.99 (m, 3H), 0.83-0.84 (m, 12H), 0.08-0.05 (m, 6H).

Step 2: Synthesis of (1S,3R,7S,8S,8aR)-8-(2-((2R,4R)-4-hydroxy-6-oxotetrahydro-2H-pyran-2-yl)ethyl)-3,7-dimethyl-1,2,3,7,8,8a-hexahydronaphthalen-1-yl (14-((2-(2,6-dioxopiperidin-3-yl)-1,3-dioxoisoindolin-4-yl)amino)-3,6,9,12-tetraoxatetradecyl)carbamate (Compound 42)

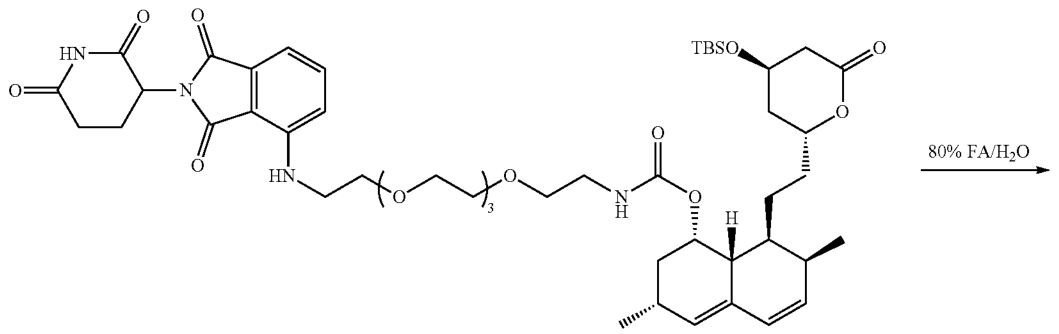

Compound 48

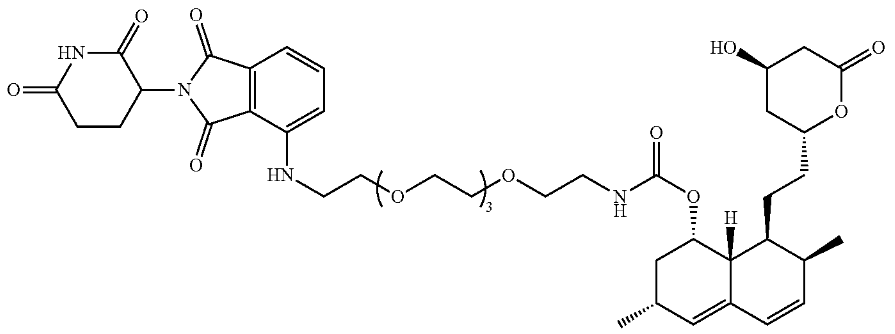

Compound 42

In a manner similar to Step 2 of Example 40, 46, the titled compound (26.6 mg, 0.03 mmol, 57.91% yield, 95.8% purity) was obtained as a yellow solid.

MS $(M+H)^+$=839.5

$^1$H NMR (400 MHz, DMSO-$d_6$) δ 11.09 (s, 1H), 7.64 (dd, J=7.2, 8.4 Hz, 1H), 7.15 (d, J=8.6 Hz, 1H), 7.04 (d, J=7.0 Hz, 1H), 6.99 (t, J=5.5 Hz, 1H), 6.60 (t, J=5.7 Hz, 1H), 5.90 (d, J=9.6 Hz, 1H), 5.76 (dd, J=6.0, 9.5 Hz, 1H), 5.46 (brs, 1H), 5.17 (d, J=3.3 Hz, 1H), 5.08-5.01 (m, 2H), 4.48 (brs, 1H), 4.09 (m, 1H), 3.65-3.59 (m, 2H), 3.58-3.43 (m, 16H), 3.13-3.04 (m, 2H), 2.94-2.83 (m, 1H), 2.65-2.55 (m, 4H), 2.41-2.39 (m, 1H), 2.36 (m, 1H), 2.23 (d, J=10.0 Hz, 1H), 2.06-1.97 (m, 1H), 1.88-1.76 (m, 3H), 1.72-1.56 (m, 3H), 1.48-1.40 (m, 1H), 1.37-1.21 (m, 2H), 1.03 (d, J=7.4 Hz, 3H), 0.83 (d, J=6.9 Hz, 3H).

Example 43 & Example 49. Synthesis of (1S,3R,7S,8S,8aR)-8-(2-((2R,4R)-4-hydroxy-6-oxotetrahydro-2H-pyran-2-yl)ethyl)-3,7-dimethyl-1,2,3,7,8,8a-hexahydronaphthalen-1-yl (17-((2-(2,6-dioxopiperidin-3-yl)-1,3-dioxoisoindolin-4-yl)amino)-3,6,9,12,15-pentaoxaheptadecyl)carbamate (Compound 43) and (1S,3R,7S,8S,8aR)-8-(2-((2R,4R)-4-((tert-butyldimethylsilyl)oxy)-6-oxotetrahydro-2H-pyran-2-yl)ethyl)-3,7-dimethyl-1,2,3,7,8,8a-hexahydronaphthalen-1-yl (17-((2-(2,6-dioxopiperidin-3-yl)-1,3-dioxoisoindolin-4-yl)amino)-3,6,9,12,15-pentaoxaheptadecyl)carbamate (Compound 49)

Step 1: Synthesis of (1S,3R,7S,8S,8aR)-8-(2-((2R,4R)-4-((tert-butyldimethylsilyl)oxy)-6-oxotetrahydro-2H-pyran-2-yl)ethyl)-3,7-dimethyl-1,2,3,7,8,8a-hexahydronaphthalen-1-yl (17-((2-(2,6-dioxopiperidin-3-yl)-1,3-dioxoisoindolin-4-yl)amino)-3,6,9,12,15-pentaoxaheptadecyl)carbamate (Compound 49)

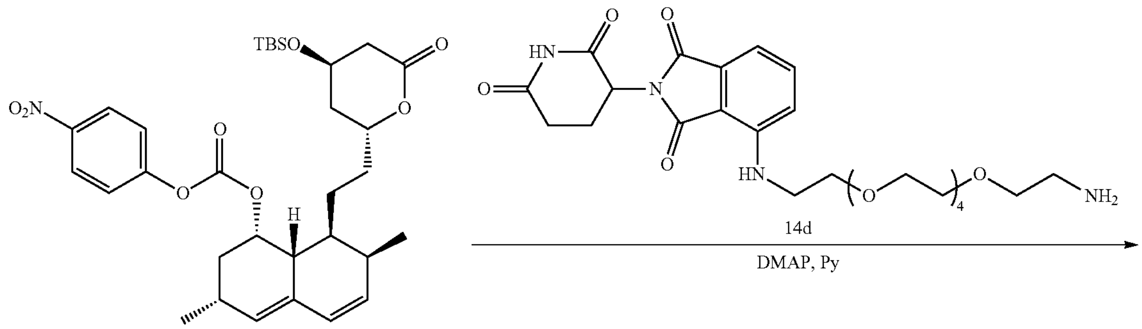

18

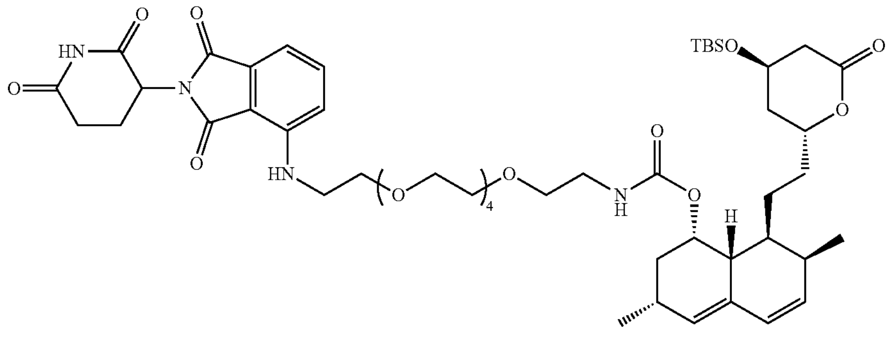

Compound 49

In a manner similar to Step 1 of Example 40, 46, the titled compound (180 mg, 0.18 mmol, 27.15% yield, 98.9% purity) was obtained as a yellow solid.

MS $(M+H)^+$=997.6

$^1$H NMR (400 MHz, DMSO-$d_6$) δ 11.09 (s, 1H), 7.61-7.55 (m, 1H), 7.15 (d, J=8.5 Hz, 1H), 7.04 (d, J=7.0 Hz, 1H), 6.98 (t, J=5.0 Hz, 1H), 6.60 (t, J=5.6 Hz, 1H), 5.90 (d, J=9.5 Hz, 1H), 5.79-5.72 (m, 1H), 5.46 (brs, 1H), 5.11-4.99 (m, 2H), 4.46-4.43 (m, 1H), 4.29 (s, 1H), 3.62 (t, J=5.3 Hz, 2H), 3.59-3.43 (m, 18H), 3.39-3.33 (m, 2H), 3.15-3.01 (m, 2H), 2.95-2.82 (m, 1H), 2.72-2.65 (m, 1H), 2.63-2.56 (m, 2H), 2.40-2.29 (m, 1H), 2.23 (d, J=10.5 Hz, 1H), 2.06-1.98 (m, 1H), 1.89-1.60 (m, 7H), 1.53-1.19 (m, 2H), 1.03 (d, J=7.1 Hz, 3H), 0.77-0.90 (m, 12H), 0.08-0.06 (m, 6H).

Step 2: Synthesis of (1S,3R,7S,8S,8aR)-8-(2-((2R,4R)-4-hydroxy-6-oxotetrahydro-2H-pyran-2-yl)ethyl)-3,7-dimethyl-1,2,3,7,8,8a-hexahydronaphthalen-1-yl (17-((2-(2,6-dioxopiperidin-3-yl)-1,3-dioxoisoindolin-4-yl)amino)-3,6,9,12,15-pentaoxaheptadecyl)carbamate (Compound 43)

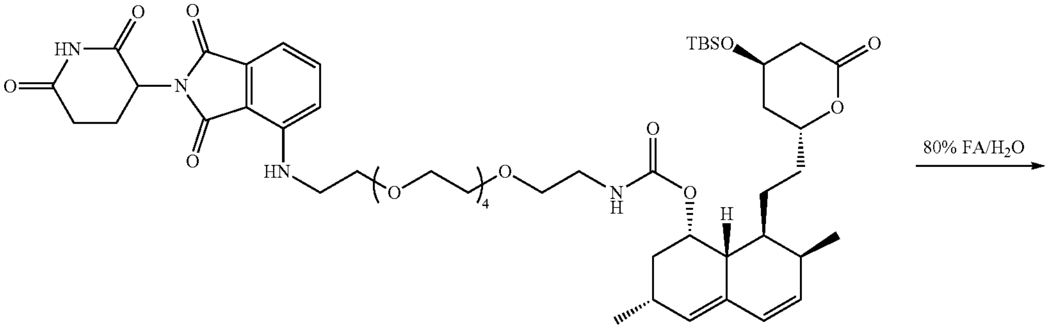

Compound 49

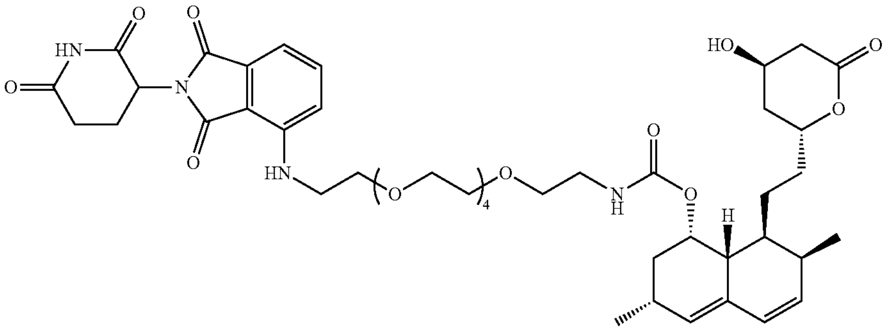

Compound 43

In a manner similar to Step 1 of Example 40, 46, the titled compound (157.0 mg, 0.174 mmol, 96.34% yield, 97.8% purity) was obtained as a yellow solid.

MS $(M+H)^+$=883.5

$^1$H NMR (400 MHz, DMSO-$d_6$) δ 11.09 (s, 1H), 7.58 (dd, J=7.2, 8.4 Hz, 1H), 7.14 (d, J=8.6 Hz, 1H), 7.04 (d, J=7.0 Hz, 1H), 6.99 (t, J=5.4 Hz, 1H), 6.60 (t, J=5.7 Hz, 1H), 5.90 (d, J=9.8 Hz, 1H), 5.80-5.72 (m, 1H), 5.46 (brs, 1H), 5.18 (brs, 1H), 5.10-5.00 (m, 2H), 4.54-4.43 (m, 1H), 4.13-4.07 (m, 1H), 3.65-3.59 (m, 2H), 3.58-3.44 (m, 22H), 3.13-3.04 (m, 2H), 2.95-2.65 (m, 1H), 2.64-2.54 (m, 2H), 2.41 (m, 1H), 2.36 (m, 1H), 2.23 (d, J=10.3 Hz, 1H), 2.06-1.99 (m, 1H), 1.88-1.77 (m, 3H), 1.72-1.56 (m, 3H), 1.49 (m, 1H), 1.37-1.22 (m, 2H), 1.02 (d, J=7.6 Hz, 3H), 0.83 (d, J=6.9 Hz, 3H).

Example 44 & Example 50. Synthesis of (1S,3R,7S,8S,8aR)-8-(2-((2R,4R)-4-hydroxy-6-oxotetrahydro-2H-pyran-2-yl)ethyl)-3,7-dimethyl-1,2,3,7,8,8a-hexahydronaphthalen-1-yl (20-((2-(2,6-dioxopiperidin-3-yl)-1,3-dioxoisoindolin-4-yl)amino)-3,6,9,12,15,18-hexaoxaicosyl)carbamate (Compound 44) and (1S,3R,7S,8S,8aR)-8-(2-((2R,4R)-4-((tert-butyldimethylsilyl)oxy)-6-oxotetrahydro-2H-pyran-2-yl)ethyl)-3,7-dimethyl-1,2,3,7,8,8a-hexahydronaphthalen-1-yl (20-((2-(2,6-dioxopiperidin-3-yl)-1,3-dioxoisoindolin-4-yl)amino)-3,6,9,12,15,18-hexaoxaicosyl)carbamate (Compound 50)

Step 1: Synthesis of (1S,3R,7S,8S,8aR)-8-(2-((2R,4R)-4-((tert-butyldimethylsilyl)oxy)-6-oxotetrahydro-2H-pyran-2-yl)ethyl)-3,7-dimethyl-1,2,3,7,8,8a-hexahydronaphthalen-1-yl (20-((2-(2,6-dioxopiperidin-3-yl)-1,3-dioxoisoindolin-4-yl)amino)-3,6,9,12,15,18-hexaoxaicosyl)carbamate (Compound 50)

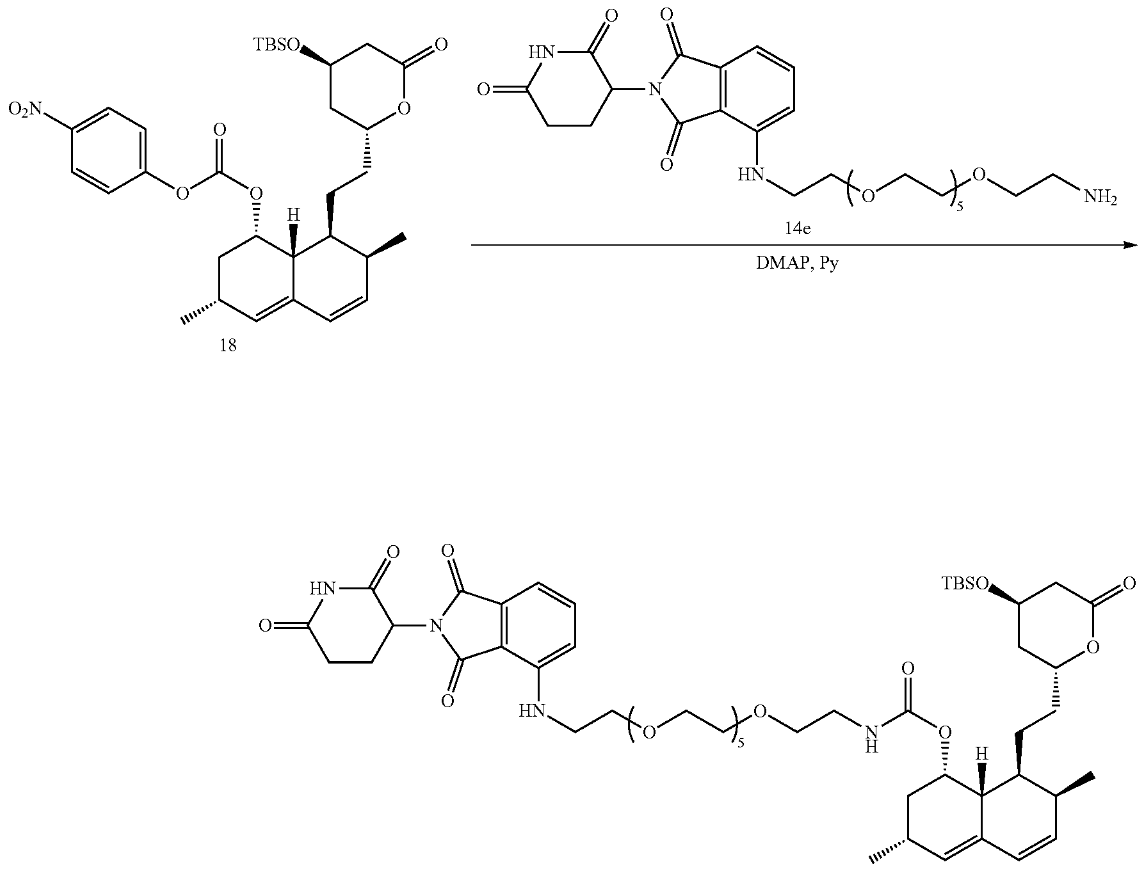

18

Compound 50

In a manner similar to Step 1 of Example 40, 46, the titled compound (0.24 g, 0.23 mmol, 33.46% yield, 99.5% purity) was obtained as a yellow solid.

MS $(M+H)^+$=1041.6

$^1$H NMR (400 MHz, DMSO-$d_6$) δ 11.09 (s, 1H), 7.58 (dd, J=7.2, 8.6 Hz, 1H), 7.14 (d, J=8.6 Hz, 1H), 7.04 (d, J=7.0 Hz, 1H), 6.98 (t, J=5.8 Hz, 1H), 6.60 (t, J=6.0 Hz, 1H), 5.90 (d, J=9.8 Hz, 1H), 5.77-5.74 (m, 1H), 5.46 (brs, 1H), 5.10-5.00 (m, 2H), 4.47-4.46 (m, 1H), 4.32-4.29 (m, 1H), 3.64-3.60 (m, 2H), 3.58-3.52 (m, 5H), 3.51-3.44 (m, 20H), 3.11-3.04 (m, 2H), 2.93-2.83 (m, 1H), 2.71-2.67 (m, 1H), 2.60-2.57 (m, 1H), 2.58-2.56 (m, 1H), 2.39-2.34 (m, 1H), 2.23 (d, J=10.8 Hz, 1H), 2.03-2.00 (m, 1H), 1.86-1.76 (m, 3H), 1.72-1.59 (m, 3H), 1.47 (t, J=12.2 Hz, 1H), 1.38-1.21 (m, 2H), 1.03 (d, J=7.4 Hz, 3H), 0.90-0.84 (m, 12H), 0.08-0.06 (m, 6H).

Step 2: Synthesis of (1S,3R,7S,8S,8aR)-8-(2-((2R,4R)-4-hydroxy-6-oxotetrahydro-2H-pyran-2-yl)ethyl)-3,7-dimethyl-1,2,3,7,8,8a-hexahydronaphthalen-1-yl (20-((2-(2,6-dioxopiperidin-3-yl)-1,3-dioxoisoindolin-4-yl)amino)-3,6,9,12,15,18-hexaoxaicosyl)carbamate (Compound 44)

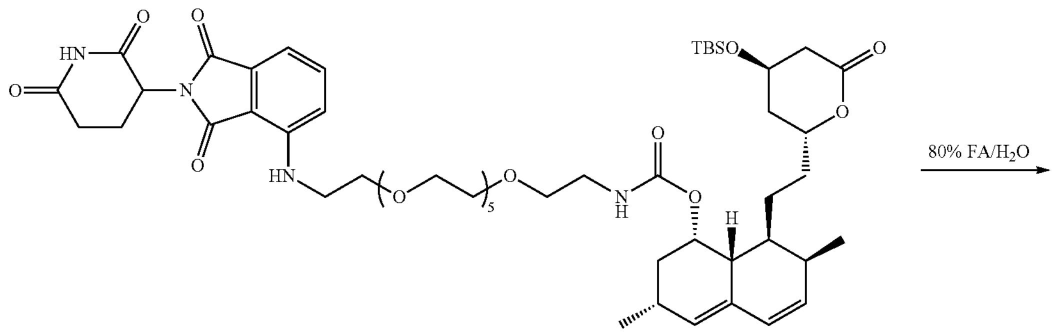

Compound 50

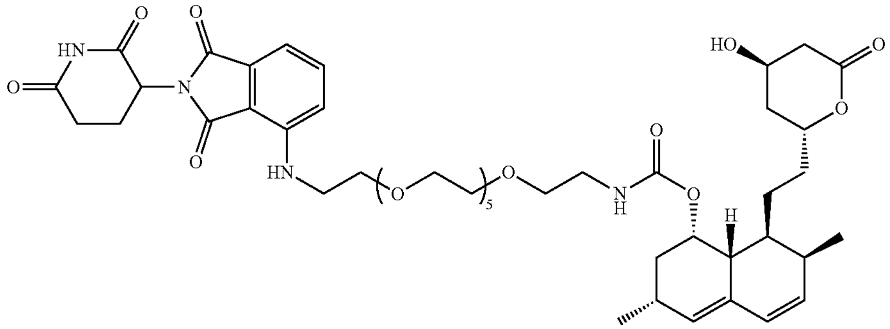

Compound 44

In a manner similar to Step 1 of Example 40, 46, the titled compound (65.8 mg, 0.068 mmol, 29.56% yield, 99% purity) was obtained as a yellow solid.

MS $(M+H)^+$=927.5

$^1H$ NMR (400 MHz, DMSO-$d_6$) δ 11.10 (s, 1H), 7.58 (dd, J=7.2, 8.4 Hz, 1H), 7.15 (d, J=8.6 Hz, 1H), 6.98-7.07 (m, 2H), 6.61 (t, J=5.6 Hz, 1H), 5.91 (d, J=9.8 Hz, 1H), 5.80-5.76 (m, 1H), 5.46 (brs, 1H), 5.18 (d, J=3.0 Hz, 1H), 5.09-5.02 (m, 2H), 4.56-4.41 (m, 1H), 4.09-4.05 (m, 1H), 3.64-3.59 (m, 2H), 3.58-3.51 (m, 5H), 3.51-3.44 (m, 20H), 3.14-3.04 (m, 2H), 2.95-2.81 (m, 1H), 2.67-2.53 (m, 2H), 2.43-2.30 (m, 3H), 2.23 (d, J=13.0 Hz, 1H), 2.06-1.98 (m, 1H), 1.88-1.77 (m, 3H), 1.72-1.56 (m, 3H), 1.49 (d, J=11.6 Hz, 1H), 1.36-1.20 (m, 2H), 1.03 (d, J=7.4 Hz, 3H), 0.83 (d, J=6.8 Hz, 3H).

Example 51 & Example 58. Synthesis of (1S,3R,7S,8S,8aR)-8-(2-((2R,4R)-4-((tert-butyldimethylsilyl)oxy)-6-oxotetrahydro-2H-pyran-2-yl)ethyl)-3,7-dimethyl-1,2,3,7,8,8a-hexahydronaphthalen-1-yl (5-((2-(2,6-dioxopiperidin-3-yl)-1,3-dioxoisoindolin-4-yl)amino)pentyl)carbamate (Compound 51) and (1S,3R,7S,8S,8aR)-8-(2-((2R,4R)-4-hydroxy-6-oxotetrahydro-2H-pyran-2-yl)ethyl)-3,7-dimethyl-1,2,3,7,8,8a-hexahydronaphthalen-1-yl (5-((2-(2,6-dioxopiperidin-3-yl)-1,3-dioxoisoindolin-4-yl)amino)pentyl)carbamate (Compound 58)

Step 1: Synthesis of tert-butyl N-[5-[[2-(2,6-dioxo-3-piperidyl)-1,3-dioxo-isoindolin-4-yl]amino]pentyl]carbamate (45a)

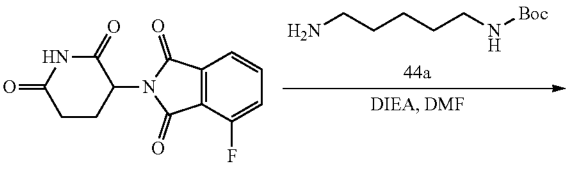

11

-continued

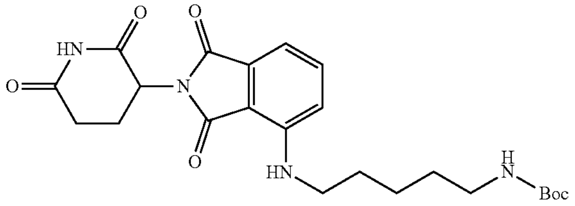

45a

-continued

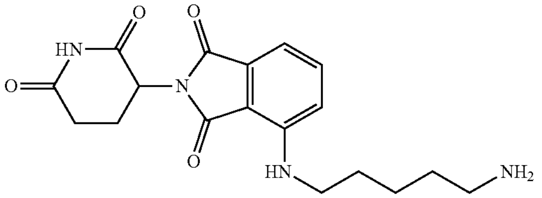

46a

To the solution of 2-(2,6-dioxo-3-piperidyl)-4-fluoro-isoindoline-1,3-dione (1 g, 3.62 mmol) and tert-butyl N-(5-aminopentyl)carbamate (732.36 mg, 3.62 mmol, 753.46 μL) in DMF (10 mL) was added DIPEA (935.80 mg, 7.24 mmol, 1.26 mL) and the resulting mixture was stirred at 90° C. for 12 hr. LCMS showed 49% desired mass was detected. The mixture was poured into $H_2O$ (50 mL) and extracted with EtOAc (50 mL×3). The combined organic layer was washed with brine (50 mL) and concentrated. The residue was purified by silica gel column (Petroleum ether:Ethyl acetate=1:0-1:1) to afford tert-butyl N-[5-[[2-(2,6-dioxo-3-piperidyl)-1,3-dioxo-isoindolin-4-yl]amino]pentyl]carbamate (1.3 g, 1.76 mmol, 48.56% yield, 62% purity) as yellow oil MS $(M+H)^+$=459.3

Step 2: Synthesis of 4-(5-aminopentylamino)-2-(2,6-dioxo-3-piperidyl)isoindoline-1,3-dione (46a)

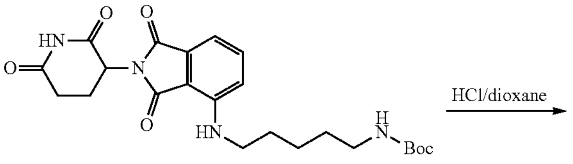

45a

To a solution of tert-butyl N-[5-[[2-(2,6-dioxo-3-piperidyl)-1,3-dioxo-isoindolin-4-yl]amino]pentyl]carbamate (1.0 g, 2.18 mmol) in dioxane (10 mL) was added HCl/dioxane (4 M, 9.09 mL). The mixture was stirred at 25° C. for 3 hr. LCMS showed starting material was consumed and 83% desired mass was detected. The mixture was concentrated under vacuum. The residue was purified by reverse HPLC (FA). Compound 4-(5-aminopentylamino)-2-(2,6-dioxo-3-piperidyl)isoindoline-1,3-dione (540 mg, 1.51 mmol, 69.08% yield, 100% purity) was obtained as a yellow oil. MS $(M+H)^+$=359.2

Step 3: Synthesis of (1S,3R,7S,8S,8aR)-8-(2-((2R,4R)-4-((tert-butyldimethylsilyl)oxy)-6-oxotetrahydro-2H-pyran-2-yl)ethyl)-3,7-dimethyl-1,2,3,7,8,8a-hexahydronaphthalen-1-yl (5-((2-(2,6-dioxopiperidin-3-yl)-1,3-dioxoisoindolin-4-yl)amino)pentyl)carbamate (Compound 51)

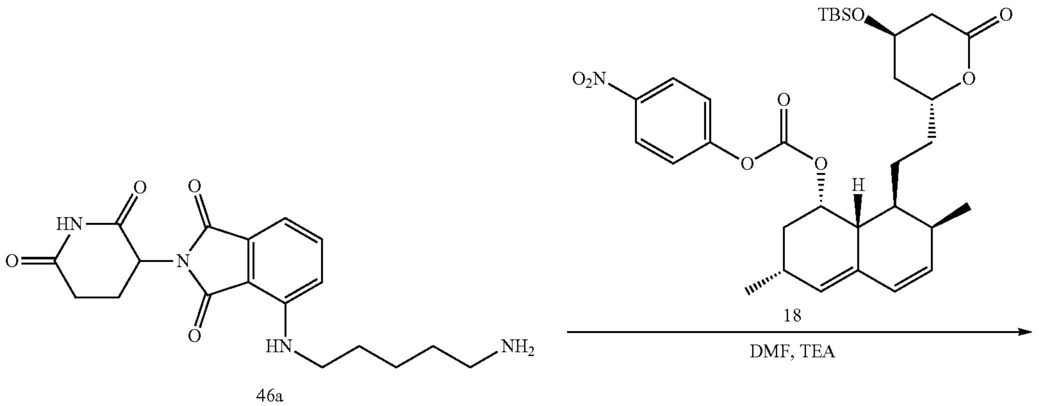

46a

-continued

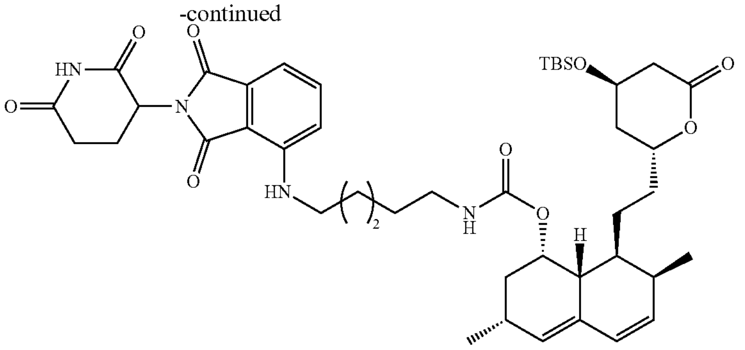

Compound 51

To the solution of 4-(5-aminopentylamino)-2-(2,6-dioxo-3-piperidyl)isoindoline-1,3-dione (540 mg, 1.51 mmol, HCl salt) and [(1S,3R,7S,8S,8aR)-8-[2-[(2R,4R)-4-[tert-butyl (dimethyl)silyl]oxy-6-oxo-tetrahydropyran-2-yl]ethyl]-3,7-dimethyl-1,2,3,7,8,8a-hexahydronaphthalen-1-yl] (4-nitrophenyl) carbonate (994.09 mg, 1.66 mmol) in DMF (10 mL) was added TEA (457.40 mg, 4.52 mmol, 629.16 μL) and the resulting mixture was stirred at 25° C. for 12 hr. LCMS showed that starting material was consumed and 57% desired mass was detected. The mixture was poured into water (50 mL) and extracted with EtOAc (50 mL×3). The combined organic layer was washed with brine (50 mL), dried over $Na_2SO_4$, filtered and concentrated. The residue was purified by prep-HPLC (column: Phenomenex luna C18 150*40 mm*15 μm; mobile phase: [water (0.225% FA)-ACN]; B %: 75%-100%, 11 min). Compound (1S,3R,7S,8S,8aR)-8-(2-((2R,4R)-4-((tert-butyldimethylsilyl)oxy)-6-oxotetrahydro-2H-pyran-2-yl)ethyl)-3,7-dimethyl-1,2,3,7,8,8a-hexahydronaphthalen-1-yl (5-((2-(2,6-dioxopiperidin-3-yl)-1,3-dioxoisoindolin-4-yl)amino)pentyl)carbamate (550 mg, 664.78 μmol, 44.12% yield, 99% purity) was obtained as yellow solid.

MS $(M+H)^+$=819.4

$^1$H NMR (400 MHz, $CDCl_3$) δ=8.00 (brs, 1H), 7.50 (dd, J=7.3, 8.4 Hz, 1H), 7.10 (d, J=7.1 Hz, 1H), 6.88 (d, J=8.4 Hz, 1H), 6.24-6.21 (m, 1H), 5.98 (d, J=9.7 Hz, 1H), 5.78 (dd, J=6.0, 9.4 Hz, 1H), 5.53 (brs, 1H), 5.17 (brs, 1H), 4.99-4.82 (m, 2H), 4.75-4.55 (m, 1H), 4.35-4.23 (m, 1H), 3.26 (q, J=6.8 Hz, 3H), 3.16-3.04 (m, 1H), 2.96-2.69 (m, 3H), 2.66-2.50 (m, 2H), 2.47-2.30 (m, 2H), 2.26 (d, J=12.2 Hz, 1H), 2.18-2.08 (m, 2H), 1.91-1.79 (m, 3H), 1.73-1.62 (m, 4H), 1.60-1.52 (m, 3H), 1.44-1.22 (m, 3H), 1.08 (d, J=7.3 Hz, 3H), 0.94-0.85 (m, 12H), 0.08-0.06 (m, 6H).

Step 4: Synthesis of (1S,3R,7S,8S,8aR)-8-(2-((2R,4R)-4-hydroxy-6-oxotetrahydro-2H-pyran-2-yl)ethyl)-3,7-dimethyl-1,2,3,7,8,8a-hexahydronaphthalen-1-yl (5-((2-(2,6-dioxopiperidin-3-yl)-1,3-dioxoisoindolin-4-yl)amino)pentyl)carbamate (Compound 58)

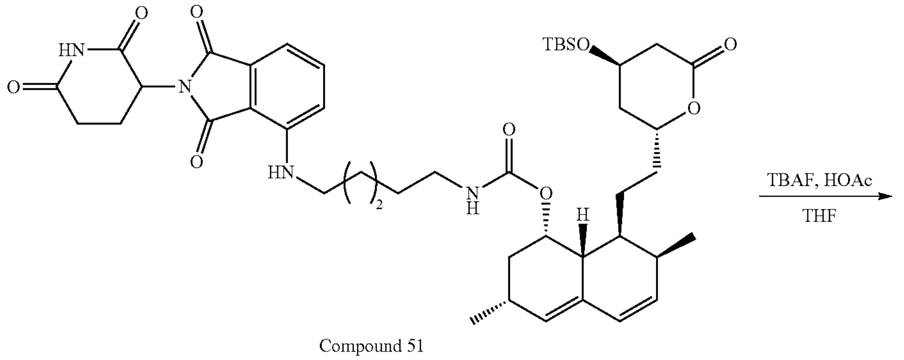

Compound 51

-continued

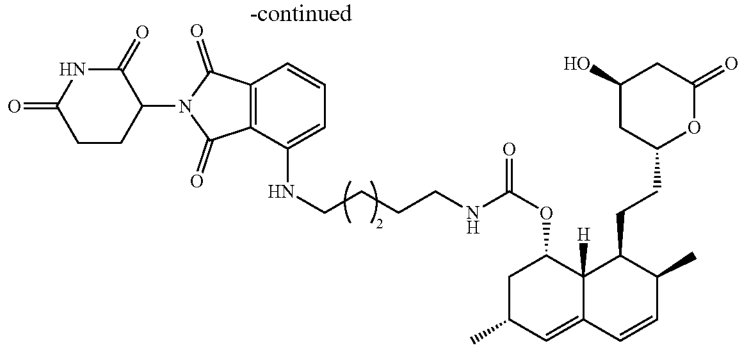

Compound 58

To a stirred solution of (1S,3R,7S,8S,8aR)-8-(2-((2R,4R)-4-((tert-butyldimethylsilyl)oxy)-6-oxotetrahydro-2H-pyran-2-yl)ethyl)-3,7-dimethyl-1,2,3,7,8,8a-hexahydronaphthalen-1-yl (5-((2-(2,6-dioxopiperidin-3-yl)-1,3-dioxoisoindolin-4-yl)amino)pentyl)carbamate (0.3 g, 366.27 μmol) in THE (10 mL) was added a premixed solution of TBAF (1 M, 1.47 mL) and AcOH (105.58 mg, 1.76 mmol, 100.55 μL) and the resulting solution was heated at 25° C. for 12 h. LCMS showed that 94% desired mass was detected. The mixture was poured into water (50 mL) and extracted with EtOAc (50 mL×3). The combined organic layer was washed with brine (100 mL), dried over $Na_2SO_4$, filtered and concentrated. The residue was purified by silica gel column (Petroleum ether:Ethyl acetate=1:1-0:1) twice. Compound (1S,3R,7S,8S,8aR)-8-(2-((2R,4R)-4-hydroxy-6-oxotetrahydro-2H-pyran-2-yl)ethyl)-3,7-dimethyl-1,2,3,7,8,8a-hexahydronaphthalen-1-yl (5-((2-(2,6-dioxopiperidin-3-yl)-1,3-dioxoisoindolin-4-yl)amino)pentyl)carbamate (93 mg, 127.99 μmol, 34.94% yield, 97% purity) was obtained as yellow solid.

MS $(M+H)^+$=705.6

$^1H$ NMR (400 MHz, $CDCl_3$) δ=8.14 (brs, 1H), 7.50 (dd, J=7.2, 8.3 Hz, 1H), 7.10 (d, J=7.1 Hz, 1H), 6.89 (d, J=8.6 Hz, 1H), 6.25-6.23 (m, 1H), 5.99 (d, J=9.5 Hz, 1H), 5.84-5.74 (m, 1H), 5.53 (brs, 1H), 5.21 (brs, 1H), 4.95-4.89 (m, 1H), 4.84 (brs, 1H), 4.69-4.59 (m, 1H), 4.32 (d, J=4.0 Hz, 1H), 3.32-3.10 (m, 4H), 2.93-2.68 (m, 4H), 2.62-2.55 (m, 1H), 2.48-2.35 (m, 2H), 2.26 (d, J=9.7 Hz, 1H), 2.18-2.05 (m, 2H), 1.99-1.81 (m, 3H), 1.77-1.65 (m, 5H), 1.54 (d, J=7.0 Hz, 3H), 1.47-1.36 (m, 4H), 1.08 (d, J=7.3 Hz, 3H), 0.90 (d, J=7.0 Hz, 3H).

Example 52 & Example 59. Synthesis of (1S,3R,7S,8S,8aR)-8-(2-((2R,4R)-4-((tert-butyldimethylsilyl)oxy)-6-oxotetrahydro-2H-pyran-2-yl)ethyl)-3,7-dimethyl-1,2,3,7,8,8a-hexahydronaphthalen-1-yl (6-((2-(2,6-dioxopiperidin-3-yl)-1,3-dioxoisoindolin-4-yl)amino)hexyl)carbamate (Compound 52) and (1S,3R,7S,8S,8aR)-8-(2-((2R,4R)-4-hydroxy-6-oxo-tetrahydro-2H-pyran-2-yl)ethyl)-3,7-dimethyl-1,2,3,7,8,8a-hexahydronaphthalen-1-yl (6-((2-(2,6-dioxopiperidin-3-yl)-1,3-dioxoisoindolin-4-yl)amino)hexyl)carbamate (Compound 59)

Step 1: Synthesis of tert-butyl N-[6-[[2-(2,6-dioxo-3-piperidyl)-1,3-dioxo-isoindolin-4-yl]amino]hexyl]carbamate (45b)

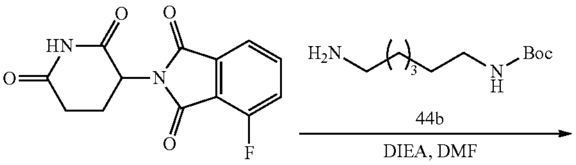

11

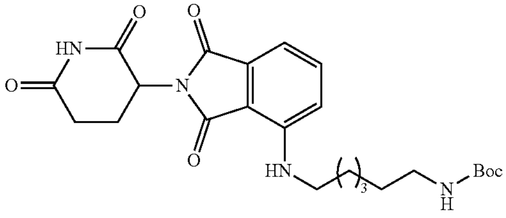

45b

In a manner similar to Step 1 of Example 51, 58, the titled compound (1.04 g, 2.20 mmol, 60.79% yield) was obtained as a yellow oil.

MS $(M+H)^+$=473.2

Step 2: Synthesis of 4-(6-aminohexylamino)-2-(2,6-dioxo-3-piperidyl)isoindoline-1,3-dione (46b)

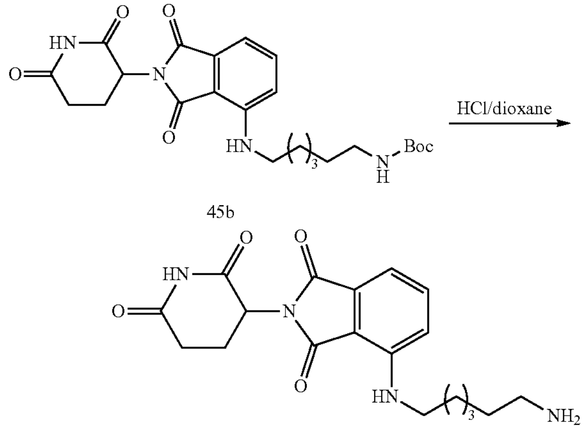

45b

46b

In a manner similar to Step 2 of Example 51, 58, the titled compound (590 mg, 1.24 mmol, 56.38% yield, 86% purity, HCl) was obtained as a yellow oil.

MS $(M+H)^+$=373.2

Step 3: Synthesis of (1S,3R,7S,8S,8aR)-8-(2-((2R,4R)-4-((tert-butyldimethylsilyl)oxy)-6-oxotetrahydro-2H-pyran-2-yl)ethyl)-3,7-dimethyl-1,2,3,7,8,8a-hexahydronaphthalen-1-yl (6-((2-(2,6-dioxopiperidin-3-yl)-1,3-dioxoisoindolin-4-yl)amino)hexyl)carbamate (Compound 52)

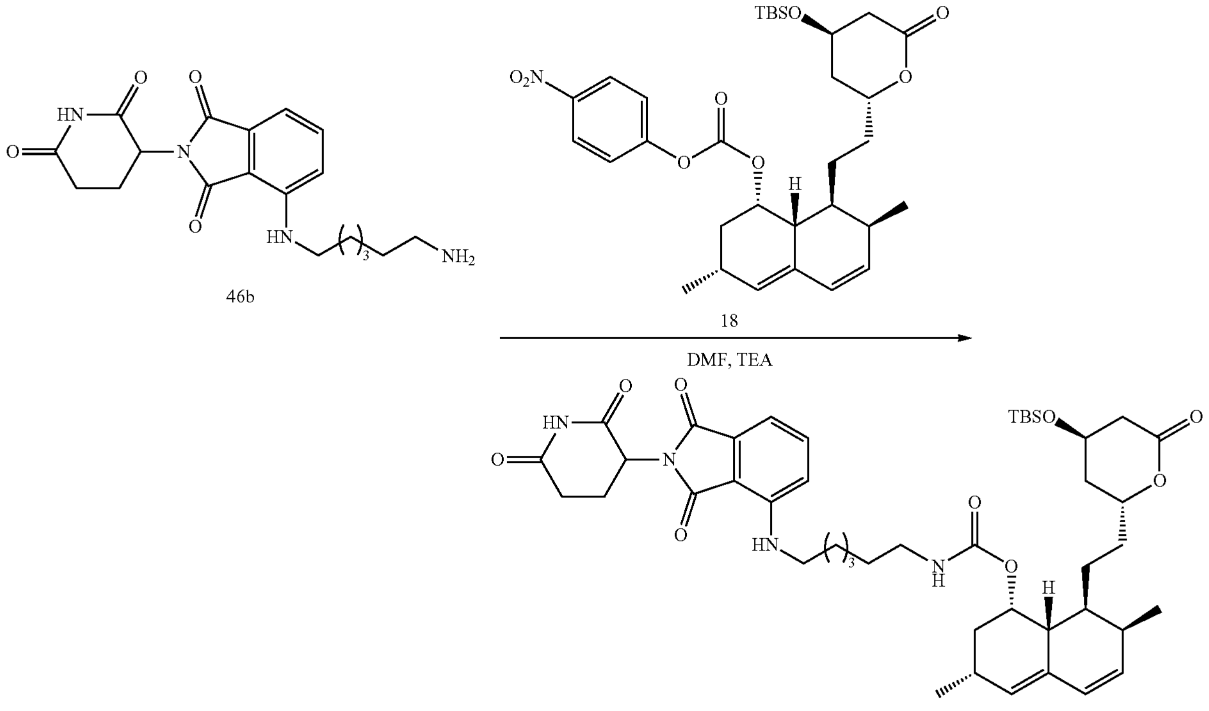

46b

18

Compound 52

In a manner similar to Step 3 of Example 51, 58, the titled compound (0.5 g, 594.17 μmol, 41.18% yield, 99% purity) was obtained as a yellow solid.

MS $(M+H)^+$=833.4

$^1H$ NMR (400 MHz, $CDCl_3$) δ=8.00 (brs, 1H), 7.52 (dd, J=7.3, 8.4 Hz, 1H), 7.11 (d, J=7.0 Hz, 1H), 6.89 (d, J=8.6 Hz, 1H), 6.24 (t, J=5.4 Hz, 1H), 6.00 (d, J=9.8 Hz, 1H), 5.85-5.75 (m, 1H), 5.54 (brs, 1H), 5.20 (brs, 1H), 4.97-4.90 (m, 1H), 4.85 (brs, 1H), 4.66 (brs, 1H), 4.30 (t, J=3.5 Hz, 1H), 3.25 (q, J=6.7 Hz, 3H), 3.20-3.10 (m, 1H), 2.96-2.70 (m, 3H), 2.66-2.52 (m, 2H), 2.50-2.34 (m, 2H), 2.27 (d, J=10.1 Hz, 1H), 2.19-2.10 (m, 2H), 1.92-1.80 (m, 3H), 1.74-1.63 (m, 4H), 1.55-1.32 (m, 8H), 1.10 (d, J=7.3 Hz, 3H), 0.94-0.89 (m, 12H), 0.08-0.06 (m, 6H).

Step 4: Synthesis of (1S,3R,7S,8S,8aR)-8-(2-((2R,4R)-4-hydroxy-6-oxotetrahydro-2H-pyran-2-yl)ethyl)-3,7-dimethyl-1,2,3,7,8,8a-hexahydronaphthalen-1-yl (6-((2-(2,6-dioxopiperidin-3-yl)-1,3-dioxoisoindolin-4-yl)amino)hexyl)carbamate (Compound 59)

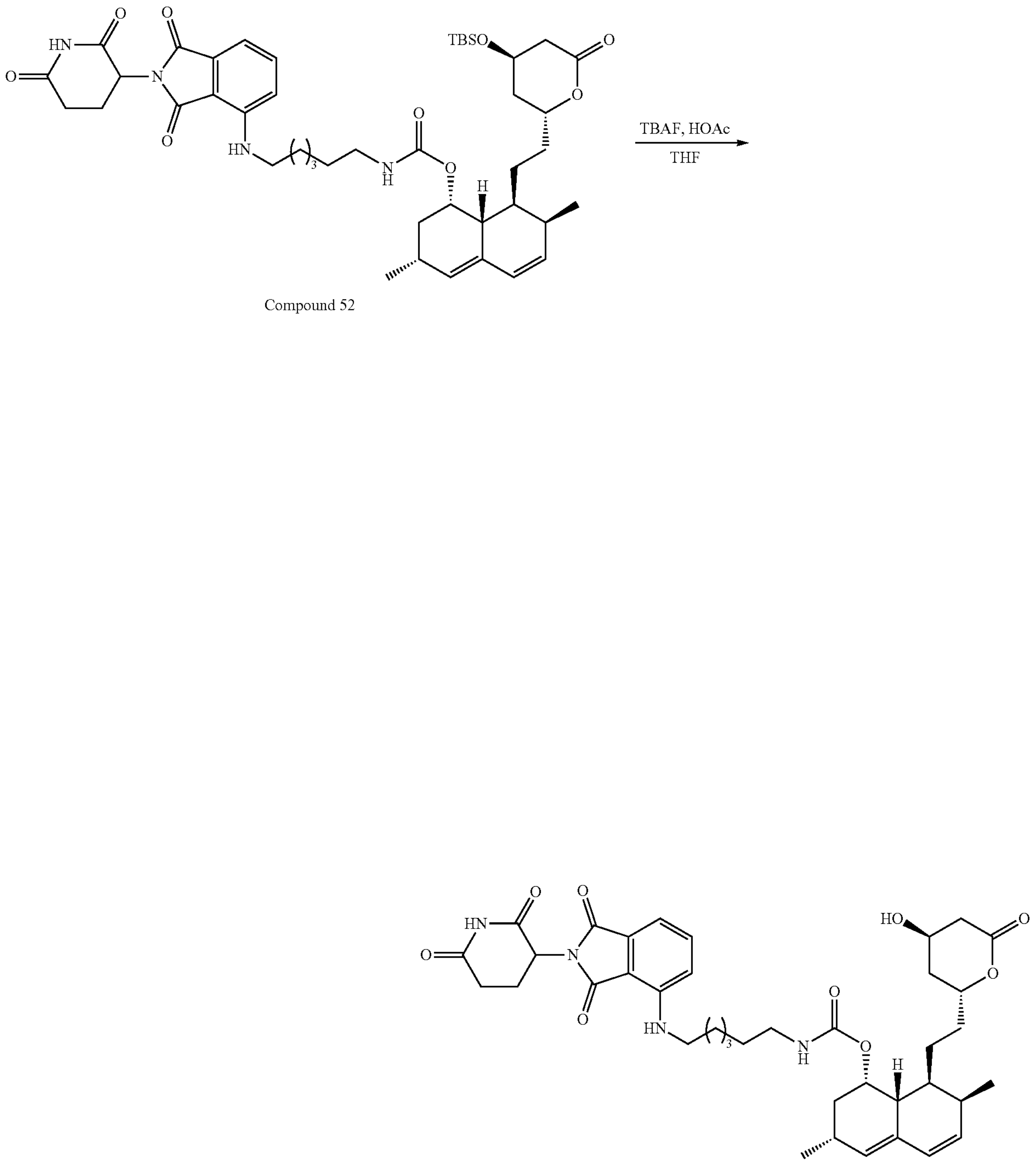

Compound 52

Compound 59

In a manner similar to Step 4 of Example 51, 58, the titled compound (48 mg, 65.44 μmol, 18.17% yield, 98% purity) was obtained as a yellow solid.

MS $(M+H)^+$=719.6

$^1$H NMR (400 MHz, $CDCl_3$) δ=8.17 (brs, 1H), 7.50-7.34 (m, 1H), 7.02 (d, J=7.2 Hz, 1H), 6.81 (d, J=8.6 Hz, 1H), 6.14 (t, J=5.4 Hz, 1H), 5.90 (d, J=9.8 Hz, 1H), 5.75-5.65 (m, 1H), 5.45 (brs, 1H), 5.14 (brs, 1H), 4.90-4.81 (m, 1H), 4.73 (d, J=4.4 Hz, 1H), 4.56 (brs, 1H), 4.25 (brs, 1H), 3.24-3.03 (m, 4H), 2.86-2.60 (m, 4H), 2.55-2.46 (m, 1H), 2.41-2.25 (m, 3H), 2.18 (d, J=10.0 Hz, 1H), 2.10-1.96 (m, 2H), 1.92-1.72 (m, 3H), 1.69-1.55 (m, 4H), 1.48-1.24 (m, 8H), 1.00 (d, J=7.2 Hz, 3H), 0.82 (d, J=7.0 Hz, 3H).

Example 53 & Example 50. Synthesis of (1S,3R,7S,8S,8aR)-8-(2-((2R,4R)-4-((tert-butyldimethylsilyl)oxy)-6-oxotetrahydro-2H-pyran-2-yl)ethyl)-3,7-dimethyl-1,2,3,7,8,8a-hexahydronaphthalen-1-yl (7-((2-(2,6-dioxopiperidin-3-yl)-1,3-dioxoisoindolin-4-yl)amino)heptyl)carbamate (Compound 53) and (1S,3R,7S,8S,8aR)-8-(2-((2R,4R)-4-hydroxy-6-oxo-tetrahydro-2H-pyran-2-yl)ethyl)-3,7-dimethyl-1,2,3,7,8,8a-hexahydronaphthalen-1-yl (7-((2-(2,6-dioxopiperidin-3-yl)-1,3-dioxoisoindolin-4-yl)amino)heptyl)carbamate (Compound 60)

Step 1: Synthesis of tert-butyl N-(7-aminoheptyl)carbamate (44c)

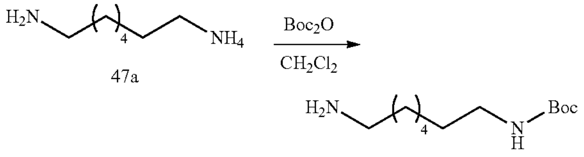

44c

To the solution of heptane-1,7-diamine (9 g, 69.11 mmol) in DCM (450 mL) was added $Boc_2O$ (4.52 g, 20.73 mmol, 4.76 mL) in DCM (90 mL) and the resulting mixture was stirred at 25° C. for 12 hr. TLC (Dichloromethane:Methanol: $NH_3{\cdot}H_2O$=10/1/0.01) showed some of starting material was consumed and new spot was detected. The mixture was concentrated. The residue was purified by base $Al_2O_3$ column (Ethyl acetate). Compound tert-butyl N-(7-aminoheptyl)carbamate (4 g, 17.37 mmol, 25.13% yield) was obtained as yellow oil.

Step 2: Synthesis of tert-butyl N-[7-[[2-(2,6-dioxo-3-piperidyl)-1,3-dioxo-isoindolin-4-yl]amino]heptyl]carbamate (45c)

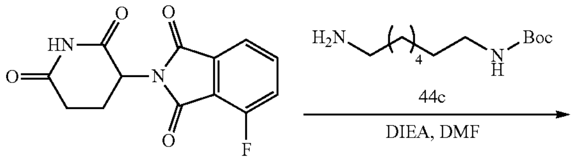

11

-continued

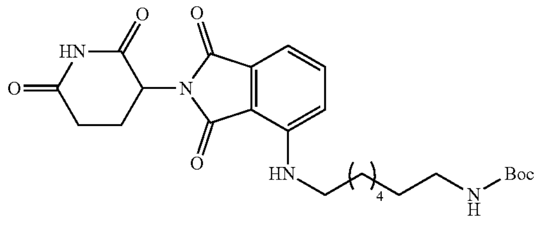

45c

In a manner similar to Step 1 of Example 51, 58, the titled compound (1.1 g, 1.09 mmol, 14.99% yield, 48% purity) was obtained as a yellow oil.

MS $(M+H)^+$=487.1

Step 3: Synthesis of 4-(7-aminoheptylamino)-2-(2,6-dioxo-3-piperidyl)isoindoline-1,3-dione (46c)

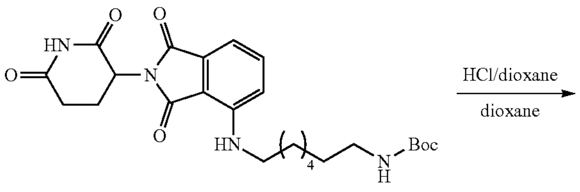

45c

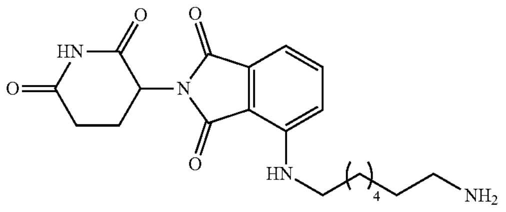

46c

In a manner similar to Step 2 of Example 51, 58, the titled compound (0.49 g, 1.14 mmol, 65.77% yield, 98% purity, HCl salt) was obtained as a yellow oil.

MS $(M+H)^+$=387.2

Step 4: Synthesis of (1S,3R,7S,8S,8aR)-8-(2-((2R,4R)-4-((tert-butyldimethylsilyl)oxy)-6-oxotetrahydro-2H-pyran-2-yl)ethyl)-3,7-dimethyl-1,2,3,7,8,8a-hexahydronaphthalen-1-yl (7-((2-(2,6-dioxopiperidin-3-yl)-1,3-dioxoisoindolin-4-yl)amino)heptyl)carbamate (Compound 53)

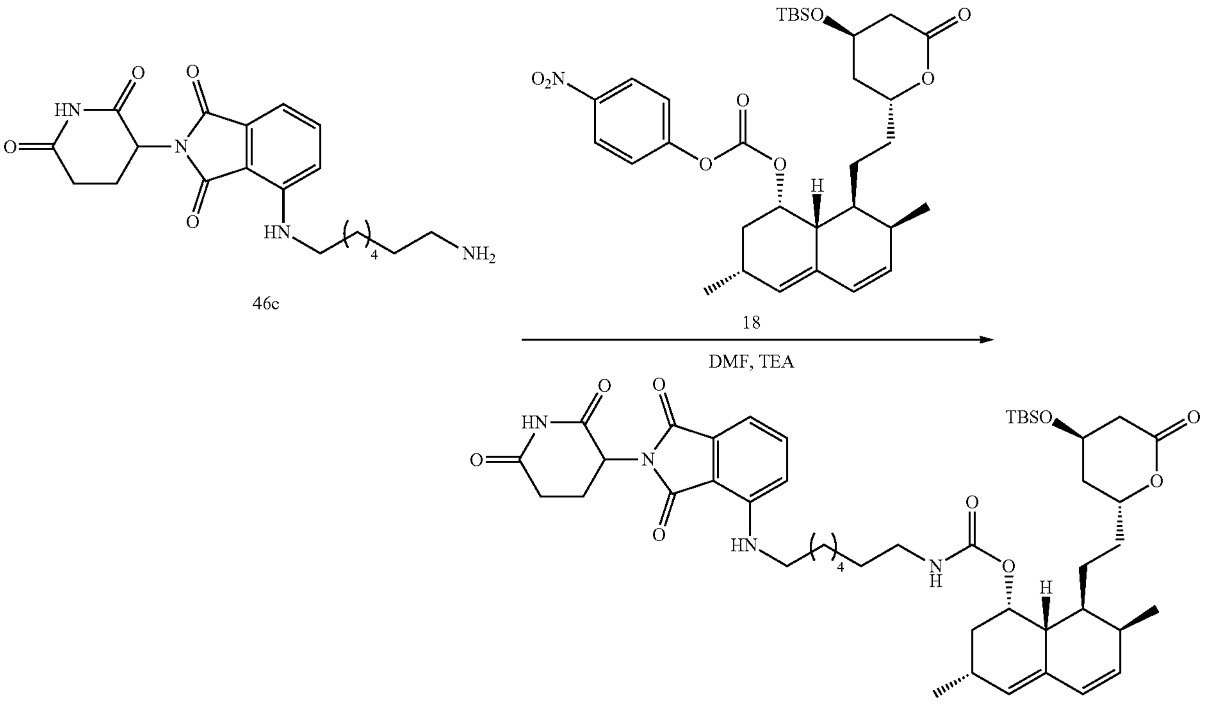

46c

18

Compound 53

In a manner similar to Step 3 of Example 51, 58, the titled compound (480.2 mg, 561.19 μmol, 44.26% yield, 99% purity) was obtained as a yellow solid.

MS $(M+H)^+$=847.5

$^1$H NMR (400 MHz, $CDCl_3$) δ=7.99 (brs, 1H), 7.50 (t, J=7.8 Hz, 1H), 7.10 (d, J=7.1 Hz, 1H), 6.89 (d, J=8.3 Hz, 1H), 6.23 (brs, 1H), 5.98 (d, J=9.5 Hz, 1H), 5.87-5.72 (m, 1H), 5.53 (brs, 1H), 5.19 (brs, 1H), 4.92 (dd, J=5.4, 12.2 Hz, 1H), 4.82 (brs, 1H), 4.66 (brs, 1H), 4.29 (brs, 1H), 3.26 (q, J=6.7 Hz, 3H), 3.08-3.04 (m, 1H), 2.94-2.69 (m, 3H), 2.64-2.51 (m, 2H), 2.48-2.32 (m, 2H), 2.25 (d, J=12.5 Hz, 1H), 2.19-2.08 (m, 2H), 1.93-1.71 (m, 4H), 1.71-1.60 (m, 4H), 1.52-1.23 (m, 10H), 1.08 (d, J=7.6 Hz, 3H), 0.92-0.87 (m, 12H), 0.08 (s, 6H).

Step 5: Synthesis of (1S,3R,7S,8S,8aR)-8-(2-((2R,4R)-4-hydroxy-6-oxotetrahydro-2H-pyran-2-yl)ethyl)-3,7-dimethyl-1,2,3,7,8,8a-hexahydronaphthalen-1-yl (7-((2-(2,6-dioxopiperidin-3-yl)-1,3-dioxoisoindolin-4-yl)amino)heptyl)carbamate (Compound 60)

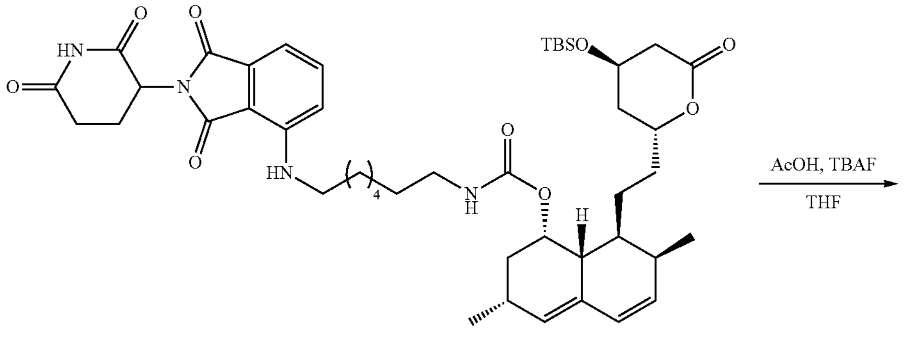

Compound 53

-continued

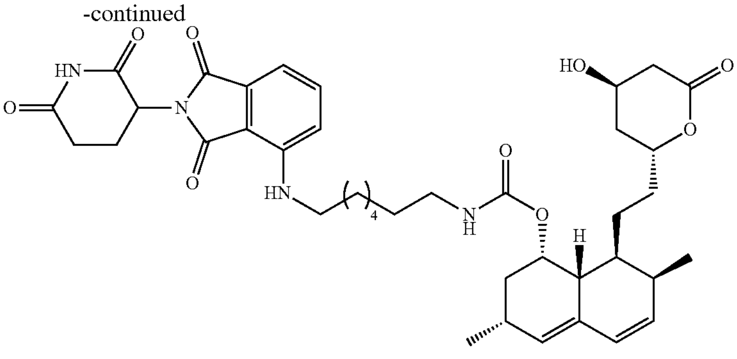

Compound 60

In a manner similar to Step 4 of Example 51, 58, the titled compound (212.7 mg, 287.33 μmol, 60.85% yield, 99% purity) was obtained as a yellow solid.

MS $(M+H)^+=733.5$ $^1H$ NMR (400 MHz, $CDCl_3$) δ=8.16 (d, J=15.5 Hz, 1H), 7.51 (t, J=7.8 Hz, 1H), 7.10 (d, J=6.7 Hz, 1H), 6.89 (d, J=8.4 Hz, 1H), 6.23 (brs, 1H), 5.99 (d, J=9.7 Hz, 1H), 5.86-5.73 (m, 1H), 5.53 (brs, 1H), 5.22-5.21 (m, 1H), 4.92 (d, J=11.9 Hz, 1H), 4.79-4.76 (m, 1H), 4.64 (brs, 1H), 4.33 (brs, 1H), 3.36-3.03 (m, 3H), 2.94-2.69 (m, 4H), 2.65-2.54 (m, 1H), 2.50-2.34 (m, 2H), 2.25 (d, J=11.1 Hz, 1H), 2.18-2.05 (m, 2H), 1.98 (d, J=13.8 Hz, 1H), 1.91-1.80 (m, 2H), 1.78-1.61 (m, 6H), 1.51-1.31 (m, 10H), 1.08 (d, J=7.5 Hz, 3H), 0.90 (d, J=6.8 Hz, 3H).

Example 54 & Example 51. Synthesis of (1S,3R,7S,8S,8aR)-8-(2-((2R,4R)-4-((tert-butyldimethylsilyl)oxy)-6-oxotetrahydro-2H-pyran-2-yl)ethyl)-3,7-dimethyl-1,2,3,7,8,8a-hexahydronaphthalen-1-yl (8-((2-(2,6-dioxopiperidin-3-yl)-1,3-dioxoisoindolin-4-yl)amino)octyl)carbamate (Compound 54) and (1S,3R,7S,8S,8aR)-8-(2-((2R,4R)-4-hydroxy-6-oxo-tetrahydro-2H-pyran-2-yl)ethyl)-3,7-dimethyl-1,2,3,7,8,8a-hexahydronaphthalen-1-yl (8-((2-(2,6-dioxopiperidin-3-yl)-1,3-dioxoisoindolin-4-yl)amino)octyl)carbamate (Compound 61)

Step 1: Synthesis of tert-butyl N-[8-[[2-(2,6-dioxo-3-piperidyl)-1,3-dioxo-isoindolin-4-yl]amino]octyl]carbamate (45d)

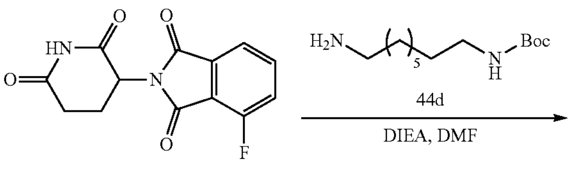

11

-continued

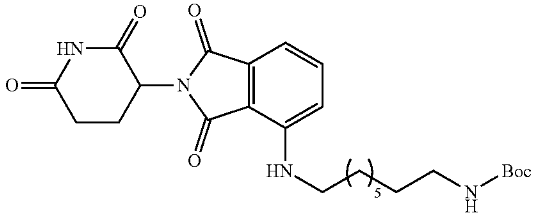

45d

In a manner similar to Step 1 of Example 51, 58, the titled compound (1.2 g, 2.40 mmol, 66.22% yield) was obtained as a yellow oil.

MS $(M+H)^+=401.2$

Step 2: Synthesis of 4-(8-aminooctylamino)-2-(2,6-dioxo-3-piperidyl)isoindoline-1,3-dione (46d)

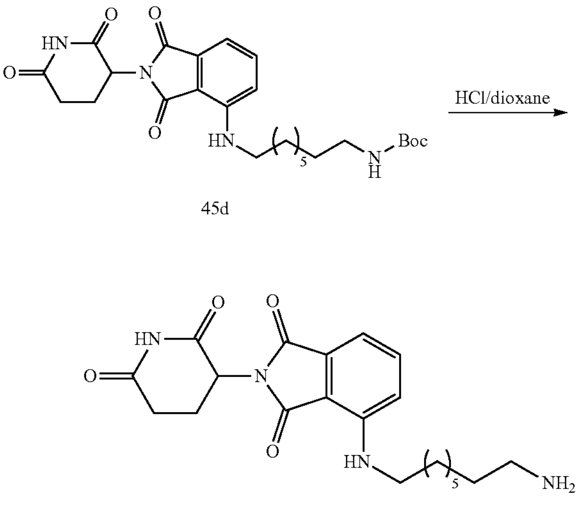

45d

46d

In a manner similar to Step 2 of Example 51, 58, the titled compound (600 mg, 1.48 mmol, 61.87% yield, 99% purity) was obtained as a yellow oil.

MS $(M+H)^+=401.2$

Step 3: Synthesis of (1S,3R,7S,8S,8aR)-8-(2-((2R,4R)-4-((tert-butyldimethylsilyl)oxy)-6-oxotetrahydro-2H-pyran-2-yl)ethyl)-3,7-dimethyl-1,2,3,7,8,8a-hexahydronaphthalen-1-yl (8-((2-(2,6-dioxopiperidin-3-yl)-1,3-dioxoisoindolin-4-yl)amino)octyl)carbamate (Compound 54)

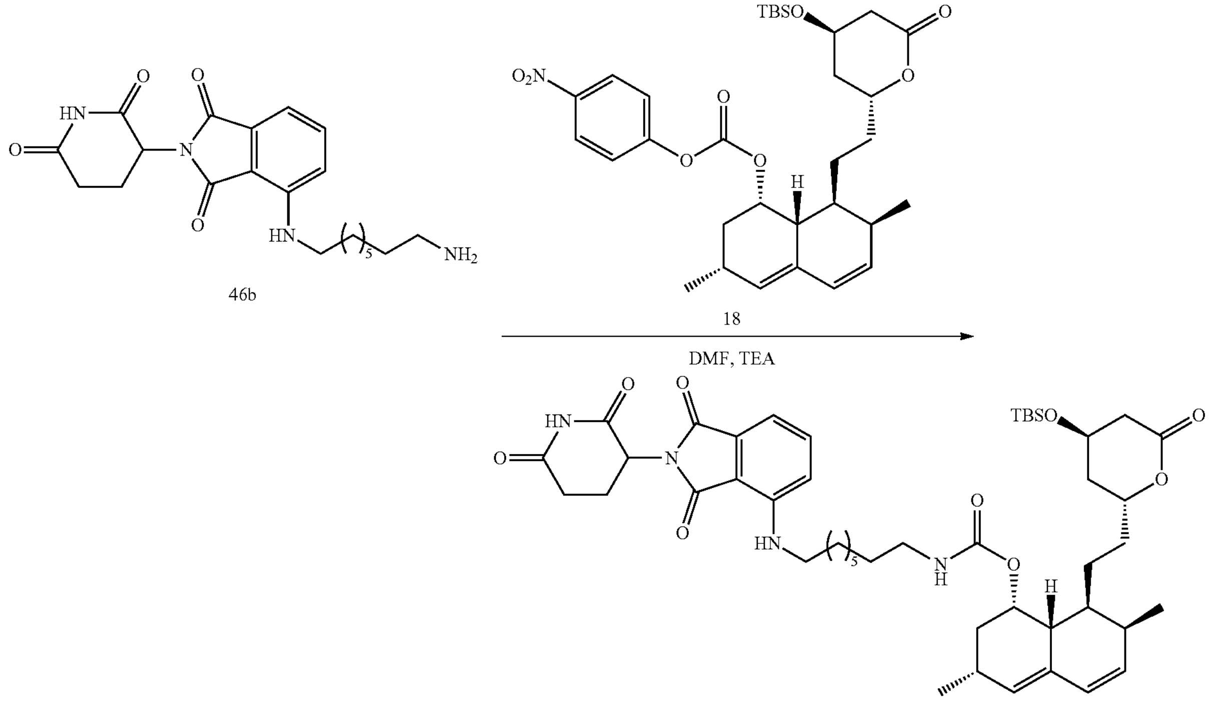

46b

18

Compound 54

In a manner similar to Step 3 of Example 51, 58, the titled compound (600 mg, 668.88 μmol, 44.64% yield, 96% purity) was obtained as a yellow solid.

MS $(M+H)^+$=861.5

$^1$H NMR (400 MHz, $CDCl_3$) δ=8.06 (brs, 1H), 7.54-7.49 (m, 1H), 7.11 (d, J=7.1 Hz, 1H), 6.90 (d, J=8.7 Hz, 1H), 6.25 (brs, 1H), 6.00 (d, J=9.7 Hz, 1H), 5.80 (dd, J=6.4, 9.4 Hz, 1H), 5.54 (brs, 1H), 5.20 (brs, 1H), 4.94 (dd, J=5.1, 12.2 Hz, 1H), 4.81 (brs, 1H), 4.66 (brs, 1H), 4.30 (brs, 1H), 3.34-3.20 (m, 3H), 3.14-3.04 (m, 1H), 2.94-2.72 (m, 3H), 2.66-2.54 (m, 2H), 2.49-2.35 (m, 2H), 2.27 (d, J=14.2 Hz, 1H), 2.20-2.09 (m, 2H), 1.95-1.75 (m, 4H), 1.73-1.64 (m, 4H), 1.53-1.23 (m, 12H), 1.10 (d, J=7.3 Hz, 3H), 0.93-0.90 (m, 12H), 0.10 (s, 6H).

Step 4: Synthesis of (1S,3R,7S,8S,8aR)-8-(2-((2R,4R)-4-hydroxy-6-oxotetrahydro-2H-pyran-2-yl)ethyl)-3,7-dimethyl-1,2,3,7,8,8a-hexahydronaphthalen-1-yl (8-((2-(2,6-dioxopiperidin-3-yl)-1,3-dioxoisoindolin-4-yl)amino)octyl)carbamate (Compound 61)

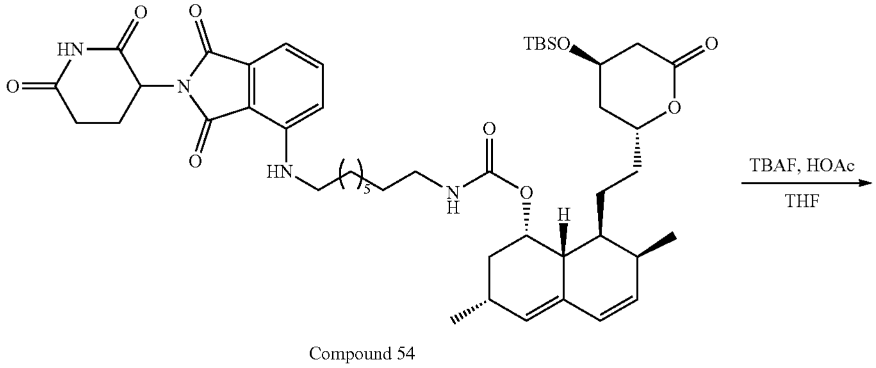

Compound 54

-continued

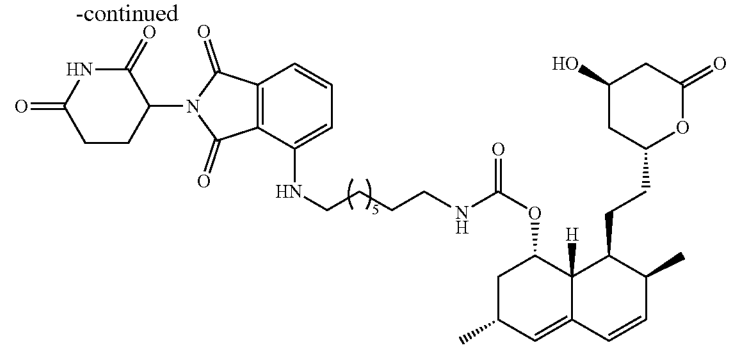

Compound 61

In a manner similar to Step 4 of Example 51, 58, the titled compound (125 mg, 164.01 μmol, 47.08% yield, 98% purity) was obtained as a yellow solid.

MS $(M+H)^+$=747.7

$^1$H NMR (400 MHz, $CDCl_3$) δ=8.37 (br d, J=15.2 Hz, 1H), 7.47-7.37 (m, 1H), 7.02 (d, J=7.0 Hz, 1H), 6.81 (d, J=8.6 Hz, 1H), 6.16 (br s, 1H), 5.90 (d, J=9.7 Hz, 1H), 5.76-5.64 (m, 1H), 5.45 (br s, 1H), 5.15 (br s, 1H), 4.92-4.78 (m, 1H), 4.70 (br s, 1H), 4.56 (br s, 1H), 4.25 (br s, 1H), 3.25-2.96 (m, 4H), 2.84-2.60 (m, 4H), 2.57-2.47 (m, 1H), 2.41-2.25 (m, 2H), 2.18 (br d, J=12.0 Hz, 1H), 2.11-1.87 (m, 4H), 1.79 (br dd, J=8.4, 13.4 Hz, 3H), 1.70-1.58 (m, 4H), 1.44-1.21 (m, 12H), 1.00 (d, J=7.3 Hz, 3H), 0.82 (dd, J=1.3, 7.0 Hz, 3H).

Example 55 & Example 52. Synthesis of (1S,3R,7S,8S,8aR)-8-(2-((2R,4R)-4-((tert-butyldimethylsilyl)oxy)-6-oxotetrahydro-2H-pyran-2-yl)ethyl)-3,7-dimethyl-1,2,3,7,8,8a-hexahydronaphthalen-1-yl (9-((2-(2,6-dioxopiperidin-3-yl)-1,3-dioxoisoindolin-4-yl)amino)nonyl)carbamate (Compound 55) and (1S,3R,7S,8S,8aR)-8-(2-((2R,4R)-4-hydroxy-6-oxo-tetrahydro-2H-pyran-2-yl)ethyl)-3,7-dimethyl-1,2,3,7,8,8a-hexahydronaphthalen-1-yl (9-((2-(2,6-dioxopiperidin-3-yl)-1,3-dioxoisoindolin-4-yl)amino)nonyl)carbamate (Compound 62)

Step 1: Synthesis of tert-butyl N-(9-aminononyl)carbamate (44e)

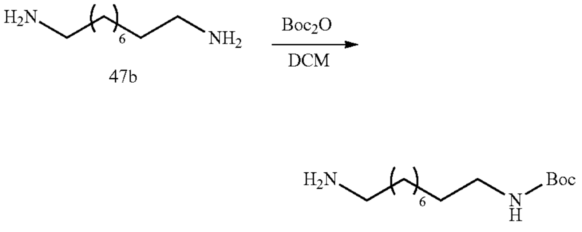

47b

44e

In a manner similar to Step 1 of Example 53, 60, the titled compound (1.6 g, 6.19 mmol, 19.60% yield) was obtained as a yellow oil.

Step 2: Synthesis of tert-butyl (9-((2-(2,6-dioxopiperidin-3-yl)-1,3-dioxoisoindolin-4-yl)amino)nonyl) carbamate (45e)

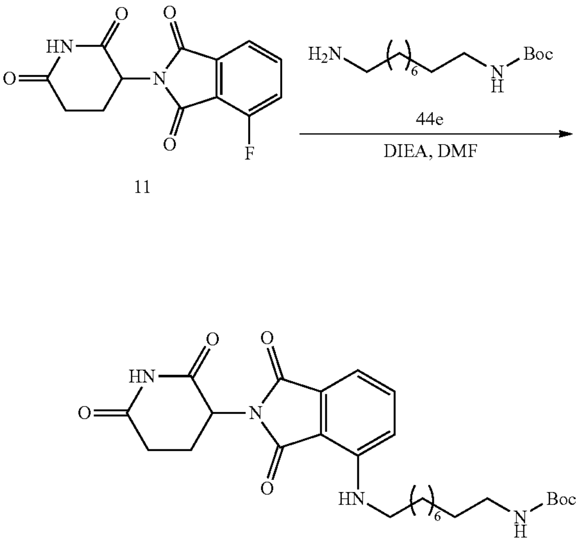

11

45e

In a manner similar to Step 1 of Example 51, 58, the titled compound (0.93 g, 1.61 mmol, 44.43% yield, 89% purity) was obtained as a yellow oil.

MS $(M+H)^+$=515.3

Step 3: Synthesis of 4-((9-aminononyl)amino)-2-(2,6-dioxopiperidin-3-yl)isoindoline-1,3-dione (46e)

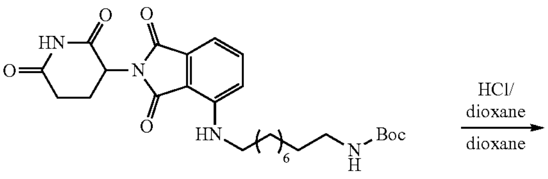

45e

-continued
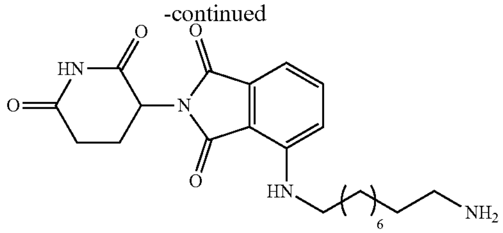
46e
In a manner similar to Step 2 of Example 51, 58, the titled compound (814 mg, 1.81 mmol, 99.88% yield, HCl salt) was obtained as a yellow oil.
Step 4: Synthesis of (1S,3R,7S,8S,8aR)-8-(2-((2R, 4R)-4-((tert-butyldimethylsilyl)oxy)-6-oxotetrahydro-2H-pyran-2-yl)ethyl)-3,7-dimethyl-1,2,3,7,8, 8a-hexahydronaphthalen-1-yl (9-((2-(2,6-dioxopiperidin-3-yl)-1,3-dioxoisoindolin-4-yl) amino)nonyl)carbamate (Compound 55)
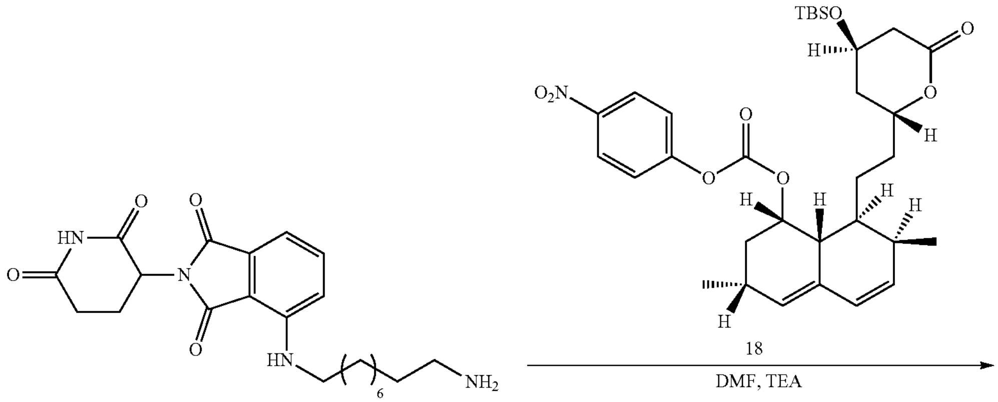
46e
18
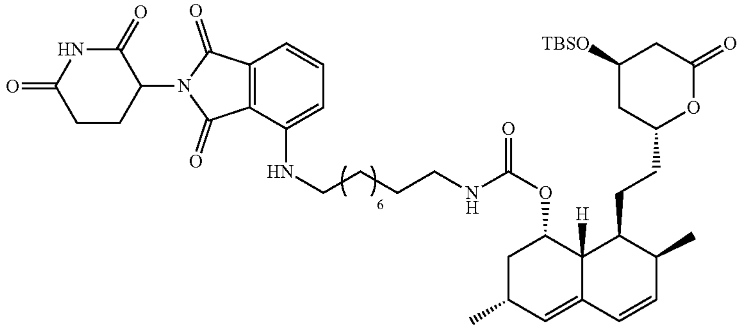
Compound 55

In a manner similar to Step 3 of Example 51, 58, the titled compound (599 mg, 677.59 μmol, 37.54% yield, 99% purity) was obtained as a yellow solid.

MS $(M+H)^+$=875.6

$^1H$ NMR (400 MHz, $CDCl_3$) δ=8.05 (s, 1H), 7.50 (dd, J=7.2, 8.5 Hz, 1H), 7.09 (d, J=7.0 Hz, 1H), 6.89 (d, J=8.6 Hz, 1H), 6.23 (brs, 1H), 5.98 (d, J=9.7 Hz, 1H), 5.79 (dd, J=6.1, 9.4 Hz, 1H), 5.53 (brs, 1H), 5.19 (brs, 1H), 4.97-4.87 (m, 1H), 4.79 (brs, 1H), 4.65-4.55 (m, 1H), 4.29 (t, J=3.5 Hz, 1H), 3.31-3.17 (m, 2H), 3.15-3.08 (m, 1H), 2.94-2.68 (m, 3H), 2.66-2.51 (m, 2H), 2.48-2.33 (m, 2H), 2.25 (d, J=12.1 Hz, 1H), 2.20-2.07 (m, 2H), 1.94-1.72 (m, 4H), 1.71-1.62 (m, 4H), 1.50-1.23 (m, 14H), 1.08 (d, J=7.3 Hz, 3H), 0.93-0.87 (m, 12H), 0.09 (s, 6H)

Step 5: Synthesis of (1S,3R,7S,8S,8aR)-8-(2-((2R, 4R)-4-hydroxy-6-oxotetrahydro-2H-pyran-2-yl) ethyl)-3,7-dimethyl-1,2,3,7,8,8a-hexahydronaphthalen-1-yl (9-((2-(2,6-dioxopiperidin-3-yl)-1,3-dioxoisoindolin-4-yl)amino)nonyl)carbamate (Compound 62)

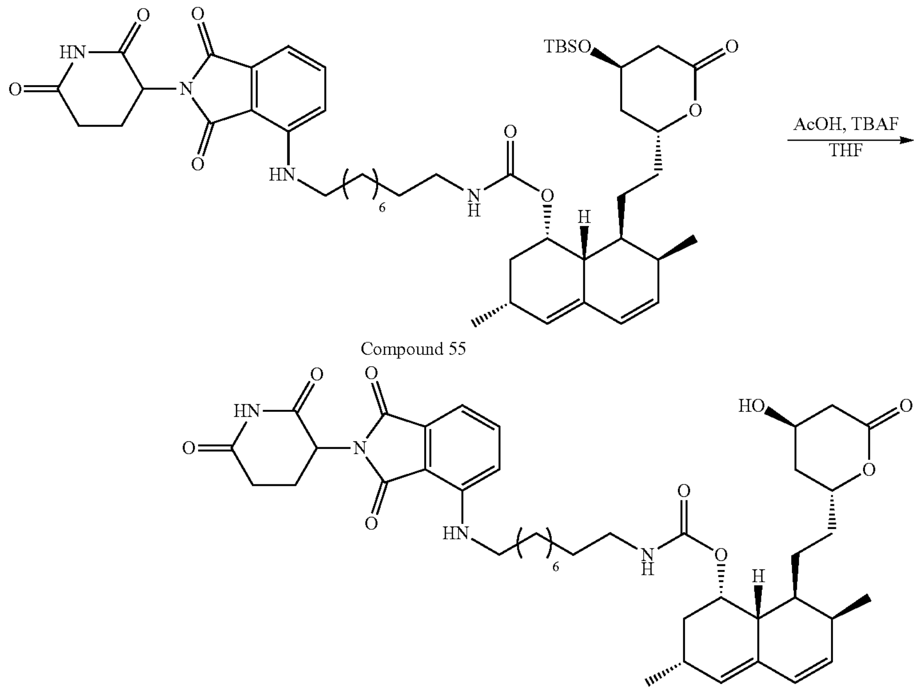

Compound 55

Compound 62

In a manner similar to Step 4 of Example 51, 58, the titled compound (200.5 mg, 258.23 μmol, 56.50% yield, 98% purity) was obtained as a yellow solid.

MS $(M+H)^+$=761.5

$^1H$ NMR (400 MHz, $CDCl_3$) δ=8.38-7.94 (m, 1H), 7.48-7.37 (m, 1H), 7.02 (d, J=7.1 Hz, 1H), 6.81 (d, J=8.6 Hz, 1H), 6.16 (br s, 1H), 5.91 (d, J=9.5 Hz, 1H), 5.76-5.67 (m, 1H), 5.45 (br s, 1H), 5.15 (br s, 1H), 4.92-4.80 (m, 1H), 4.68 (br d, J=5.8 Hz, 1H), 4.56 (br s, 1H), 4.25 (br s, 1H), 3.28-3.00 (m, 4H), 2.87-2.59 (m, 4H), 2.57-2.46 (m, 1H), 2.40-2.26 (m, 2H), 2.22-1.87 (m, 5H), 1.81 (br d, J=8.1 Hz, 2H), 1.70-1.54 (m, 5H), 1.43-1.12 (m, 14H), 1.01 (d, J=7.4 Hz, 3H), 0.85-0.79 (m, 3H)

Example 56 & Example 53. Synthesis of (1S,3R,7S,8S,8aR)-8-(2-((2R,4R)-4-((tert-butyldimethylsilyl)oxy)-6-oxotetrahydro-2H-pyran-2-yl)ethyl)-3,7-dimethyl-1,2,3,7,8,8a-hexahydronaphthalen-1-yl (10-((2-(2,6-dioxopiperidin-3-yl)-1,3-dioxoisoindolin-4-yl)amino)decyl)carbamate (Compound 56) and (1S,3R,7S,8S,8aR)-8-(2-((2R,4R)-4-hydroxy-6-oxotetrahydro-2H-pyran-2-yl)ethyl)-3,7-dimethyl-1,2,3,7,8,8a-hexahydronaphthalen-1-yl (10-((2-(2,6-dioxopiperidin-3-yl)-1,3-dioxoisoindolin-4-yl)amino)decyl)carbamate (Compound 63)

Step 1: Synthesis of tert-butyl N-[10-[[2-(2,6-dioxo-3-piperidyl)-1,3-dioxo-isoindolin-4-yl]amino]decyl]carbamate (45f)

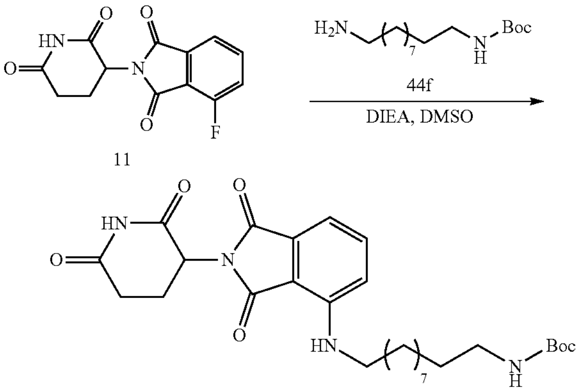

11

44f

45f

In a manner similar to Step 1 of Example 51, 58, the titled compound (600 mg, 601.54 μmol, 20.77% yield, 53% purity) was obtained as a yellow oil.

MS (M−100+H)+=429.3

Step 2: Synthesis of 4-(10-aminodecylamino)-2-(2,6-dioxo-3-piperidyl)isoindoline-1,3-dione (46f)

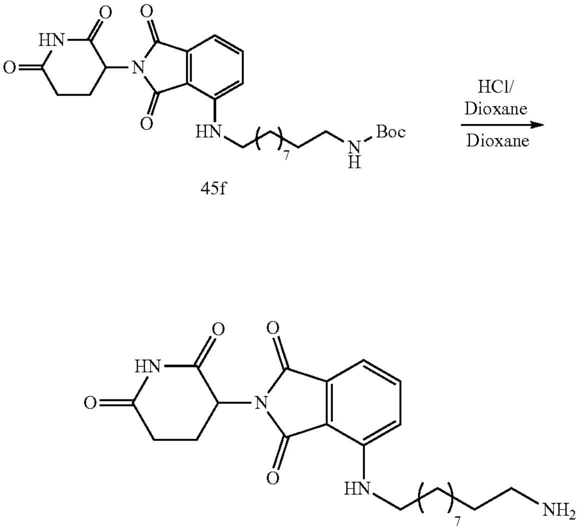

45f

46f

In a manner similar to Step 2 of Example 51, 58, the titled compound (360 mg, 394.85 μmol, 65.64% yield, 51% purity, HCl salt) was obtained as a yellow oil.

MS $(M+H)^+$=429.1

Step 3: Synthesis of (1S,3R,7S,8S,8aR)-8-(2-((2R,4R)-4-((tert-butyldimethylsilyl)oxy)-6-oxotetrahydro-2H-pyran-2-yl)ethyl)-3,7-dimethyl-1,2,3,7,8,8a-hexahydronaphthalen-1-yl (10-((2-(2,6-dioxopiperidin-3-yl)-1,3-dioxoisoindolin-4-yl)amino)decyl)carbamate (Compound 56)

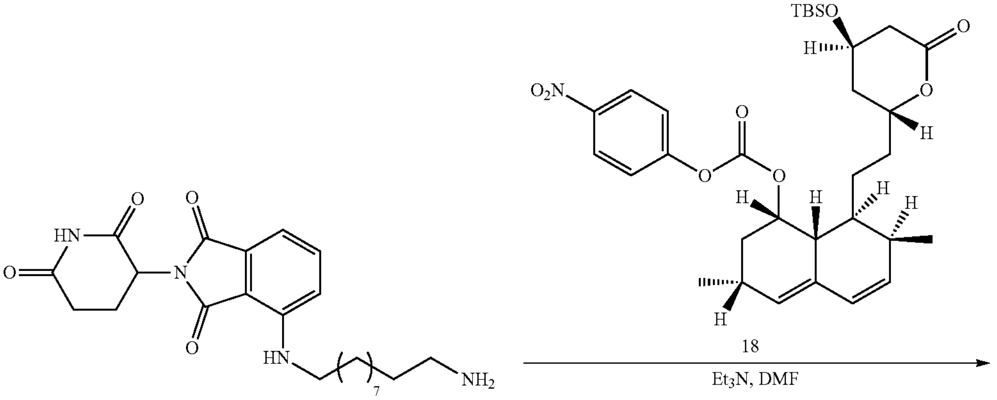

18

46f

-continued

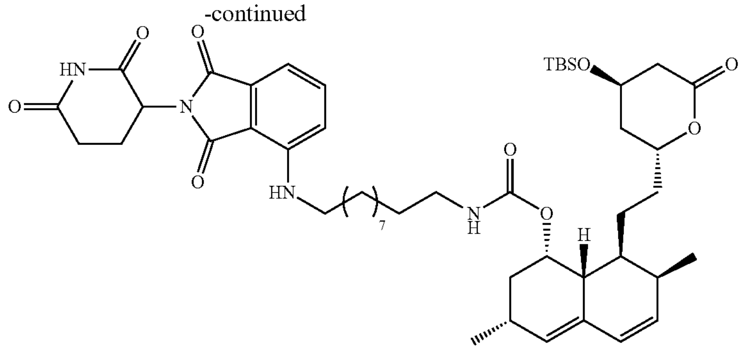

Compound 56

In a manner similar to Step 3 of Example 51, 58, the titled compound (298.9 mg, 332.78 μmol, 39.61% yield, 99% purity) was obtained as a yellow oil.

MS $(M+H)^+$=889.6

$^1$H NMR (400 MHz, $CDCl_3$) δ=7.93 (brs, 1H), 7.41 (dd, J=7.2, 8.2 Hz, 1H), 7.01 (d, J=7.0 Hz, 1H), 6.80 (d, J=8.6 Hz, 1H), 6.15 (t, J=5.4 Hz, 1H), 5.90 (d, J=9.6 Hz, 1H), 5.70 (dd, J=6.2, 9.6 Hz, 1H), 5.44 (brs, 1H), 5.11 (brs, 1H), 4.84 (dd, J=5.4, 12.0 Hz, 1H), 4.69 (brs, 1H), 4.56 (dd, J=3.0, 8.0 Hz, 1H), 4.20 (t, J=3.6 Hz, 1H), 3.23-3.08 (m, 3H), 3.00 (dd, J=5.8, 12.8 Hz, 1H), 2.85-2.61 (m, 3H), 2.56-2.42 (m, 2H), 2.40-2.22 (m, 2H), 2.20-2.11 (m, 1H), 2.09-1.98 (m, 2H), 1.84-1.64 (m, 4H), 1.62-1.52 (m, 4H), 1.40-1.29 (m, 5H), 1.19 (brs, 11H), 1.00 (d, J=7.4 Hz, 3H), 0.83-0.80 (m, 12H), 0.07 (s, 6H).

Step 4: Synthesis of (1S,3R,7S,8S,8aR)-8-(2-((2R, 4R)-4-hydroxy-6-oxotetrahydro-2H-pyran-2-yl) ethyl)-3,7-dimethyl-1,2,3,7,8,8a-hexahydronaphthalen-1-yl (10-((2-(2,6-dioxopiperidin-3-yl)-1,3-dioxoisoindolin-4-yl)amino)decyl)carbamate (Compound 63)

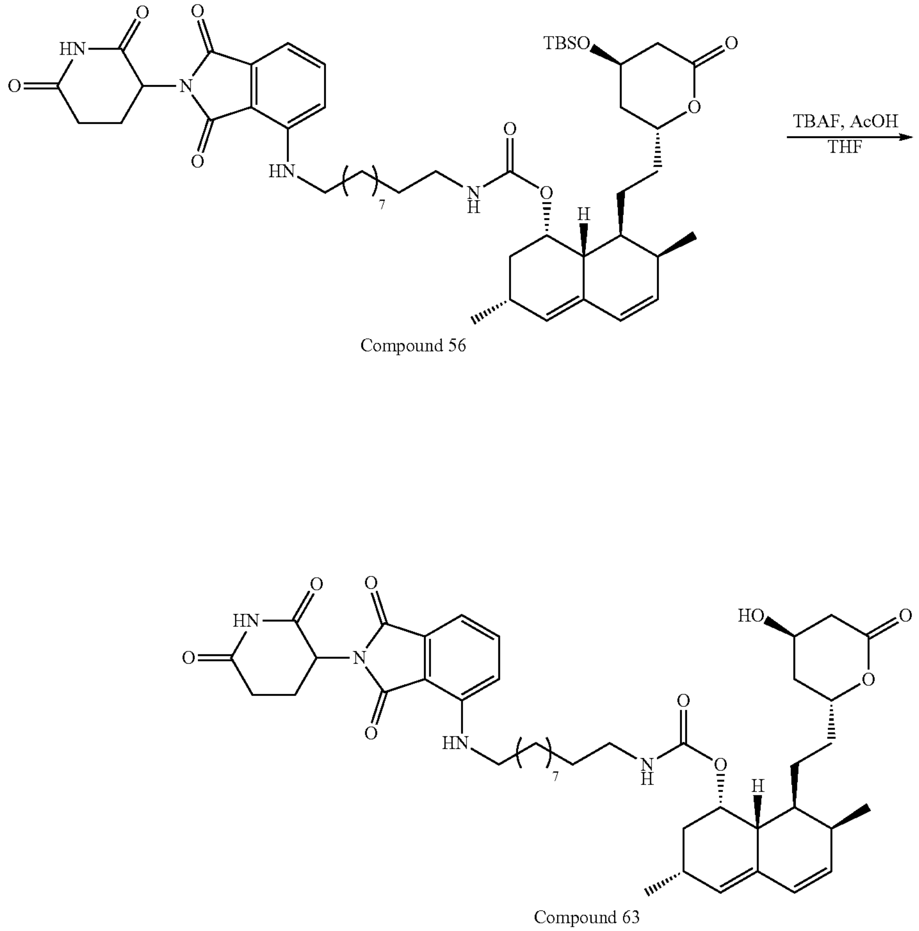

Compound 56

Compound 63

In a manner similar to Step 4 of Example 51, 58, the titled compound (37.8 mg, 47.31 μmol, 21.04% yield, 97% purity) was obtained as a yellow solid.

MS $(M+H)^+=775.6$ $^1H$ NMR (400 MHz, $CDCl_3$) δ=8.39-8.14 (m, 1H), 7.56-7.45 (m, 1H), 7.10 (d, J=7.2 Hz, 1H), 6.89 (d, J=8.4 Hz, 1H), 6.23 (br s, 1H), 5.99 (d, J=9.6 Hz, 1H), 5.84-5.73 (m, 1H), 5.53 (br s, 1H), 5.23 (br s, 1H), 4.99-4.87 (m, 1H), 4.75 (br s, 1H), 4.64 (br s, 1H), 4.34 (br s, 1H), 3.32-3.24 (m, 3H), 3.12 (br s, 1H), 2.95-2.67 (m, 4H), 2.66-2.52 (m, 1H), 2.49-2.32 (m, 2H), 2.29-1.95 (m, 5H), 1.87 (br d, J=7.6 Hz, 2H), 1.77-1.63 (m, 4H), 1.50-1.18 (m, 16H), 1.09 (d, J=7.6 Hz, 3H), 0.90 (d, J=7.2 Hz, 3H).

Example 57 & Example 54. Synthesis of (1S,3R,7S,8S,8aR)-8-(2-((2R,4R)-4-((tert-butyldimethylsilyl)oxy)-6-oxotetrahydro-2H-pyran-2-yl)ethyl)-3,7-dimethyl-1,2,3,7,8,8a-hexahydronaphthalen-1-yl (11-((2-(2,6-dioxopiperidin-3-yl)-1,3-dioxoisoindolin-4-yl)amino)undecyl)carbamate (Compound 57) and (1S,3R,7S,8S,8aR)-8-(2-((2R,4R)-4-hydroxy-6-oxotetrahydro-2H-pyran-2-yl)ethyl)-3,7-dimethyl-1,2,3,7,8,8a-hexahydronaphthalen-1-yl (11-((2-(2,6-dioxopiperidin-3-yl)-1,3-dioxoisoindolin-4-yl)amino)undecyl)carbamate (Compound 64)

Step 1: Synthesis of tert-butyl N-(11-aminoundecyl)carbamate (44g)

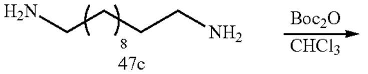

47c

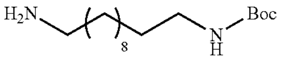

44g

In a manner similar to Step 1 of Example 53, 60, the titled compound (2.3 g, 8.03 mmol, 22.00% yield) was obtained as a white solid.

$^1H$ NMR (400 MHz, $CDCl_3$) δ=4.52 (br s, 1H), 3.15-3.09 (m, 2H), 2.70 (t, J=7.0 Hz, 2H), 1.46 (s, 9H), 1.35-1.22 (m, 20H) Step 2: Synthesis of tert-butyl N-[11-[[2-(2,6-dioxo-3-piperidyl)-1,3-dioxo-isoindolin-4-yl]amino]undecyl]carbamate (45g)

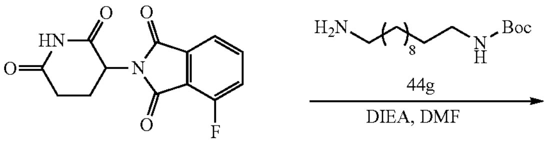

11

-continued

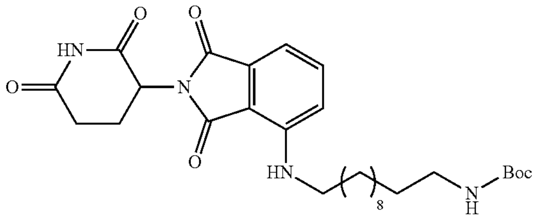

45g

In a manner similar to Step 1 of Example 51, 58, the titled compound (0.6 g, 961.92 μmol, 26.57% yield, 87% purity) was obtained as a yellow oil.

MS $(M+H)^+=443.2$

Step 3: Synthesis of 4-(11-aminoundecylamino)-2-(2,6-dioxo-3-piperidyl)isoindoline-1,3-dione (46g)

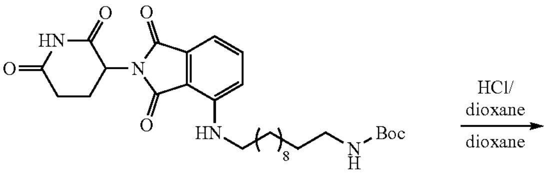

45g

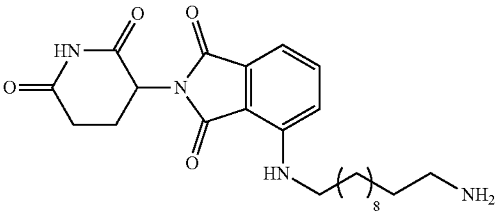

46g

In a manner similar to Step 2 of Example 51, 58, the titled compound (529 mg, 1.10 mmol, 99.88% yield, HCl salt) was obtained as a yellow oil.

MS $(M+H)^+=443.2$

Step 4: Synthesis of (1S,3R,7S,8S,8aR)-8-(2-((2R,4R)-4-((tert-butyldimethylsilyl)oxy)-6-oxotetrahydro-2H-pyran-2-yl)ethyl)-3,7-dimethyl-1,2,3,7,8,8a-hexahydronaphthalen-1-yl (11-((2-(2,6-dioxopiperidin-3-yl)-1,3-dioxoisoindolin-4-yl)amino)undecyl)carbamate (Compound 57)

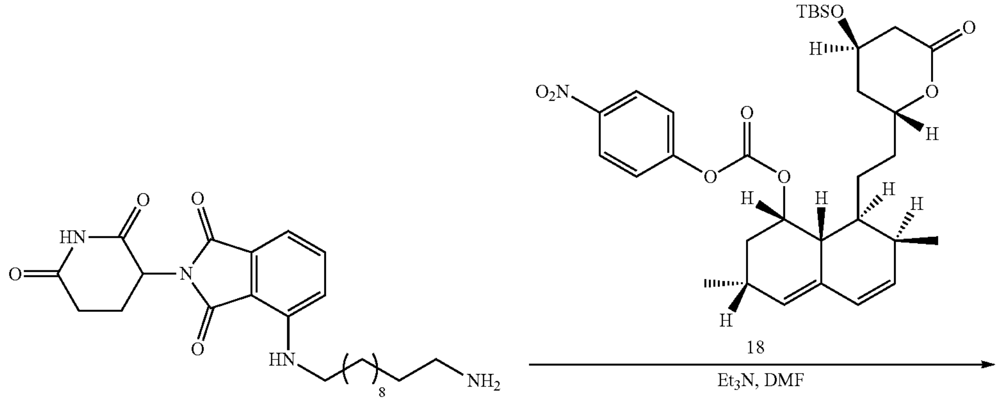

46g

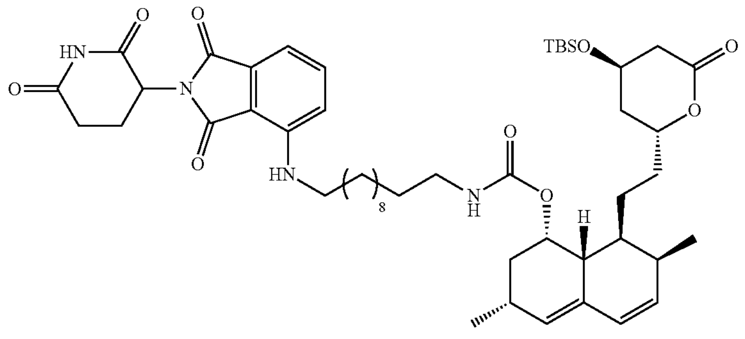

Compound 57

In a manner similar to Step 3 of Example 51, 58, the titled compound (592.5 mg, 616.62 μmol, 55.84% yield, 94% purity) was obtained as a yellow solid.

MS $(M+H)^+$=903.6

$^1H$ NMR (400 MHz, $CDCl_3$) δ=8.06 (brs, 1H), 7.50 (dd, J=7.2, 8.2 Hz, 1H), 7.09 (d, J=7.0 Hz, 1H), 6.89 (d, J=8.6 Hz, 1H), 6.24-6.23 (m, 1H), 5.98 (d, J=9.6 Hz, 1H), 5.79 (dd, J=6.0, 9.2 Hz, 1H), 5.53 (brs, 1H), 5.19 (brs, 1H), 4.96-4.88 (m, 1H), 4.78 (brs, 1H), 4.70-4.60 (m, 1H), 4.33-4.25 (m, 1H), 3.32-3.15 (m, 3H), 3.13-3.03 (m, 1H), 2.96-2.68 (m, 3H), 2.65-2.51 (m, 2H), 2.47-2.31 (m, 2H), 2.25 (d, J=12.2 Hz, 1H), 2.19-2.04 (m, 2H), 1.93-1.72 (m, 4H), 1.69-1.59 (m, 4H), 1.50-1.37 (m, 5H), 1.35-1.25 (m, 13H), 1.08 (d, J=7.4 Hz, 3H), 0.92-0.88 (m, 12H), 0.09 (s, 6H).

Step 5: Synthesis of (1S,3R,7S,8S,8aR)-8-(2-((2R,4R)-4-hydroxy-6-oxotetrahydro-2H-pyran-2-yl)ethyl)-3,7-dimethyl-1,2,3,7,8,8a-hexahydronaphthalen-1-yl (11-((2-(2,6-dioxopiperidin-3-yl)-1,3-dioxoisoindolin-4-yl)amino)undecyl)carbamate (Compound 64)

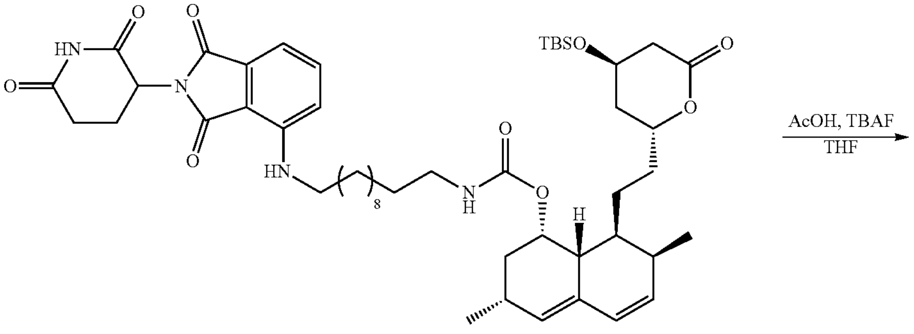

Compound 57

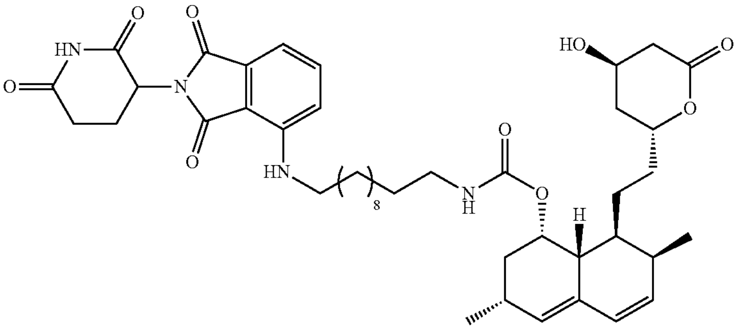

Compound 64

In a manner similar to Step 4 of Example 51, 58, the titled compound (89 mg, 110.55 μmol, 33.28% yield, 98% purity) was obtained as a yellow solid

MS $(M+H)^+$=789.6

$^1$H NMR (400 MHz, $CDCl_3$) δ=8.20 (br s, 1H), 7.55-7.45 (m, 1H), 7.10 (d, J=7.2 Hz, 1H), 6.89 (d, J=8.6 Hz, 1H), 6.23 (s, 1H), 5.99 (d, J=9.8 Hz, 1H), 5.85-5.72 (m, 1H), 5.53 (br s, 1H), 5.24 (br s, 1H), 4.93 (br d, J=8.8 Hz, 1H), 4.74 (br s, 1H), 4.64 (br s, 1H), 4.35 (br s, 1H), 3.32-3.23 (m, 3H), 3.22-3.00 (m, 2H), 2.93-2.85 (m, 1H), 2.84-2.69 (m, 3H), 2.63 (s, 1H), 2.50-2.33 (m, 2H), 2.26 (br d, J=12.2 Hz, 1H), 2.19-1.95 (m, 4H), 1.92-1.81 (m, 2H), 1.78-1.60 (m, 4H), 1.48-1.20 (m, 18H), 1.09 (d, J=7.5 Hz, 3H), 0.91 (d, J=7.0 Hz, 3H).

Example 65 & Example 66. Synthesis of (1S,3R,7S,8S,8aR)-8-(2-((2R,4R)-4-((tert-butyldimethylsilyl)oxy)-6-oxotetrahydro-2H-pyran-2-yl)ethyl)-3,7-dimethyl-1,2,3,7,8,8a-hexahydronaphthalen-1-yl (2-(2-(2-((2-(2,6-dioxopiperidin-3-yl)-1-oxoisoindolin-4-yl)amino)ethoxy)ethoxy)ethyl)carbamate (Compound 65) and (1S,3R,7S,8S,8aR)-8-(2-((2R,4R)-4-hydroxy-6-oxotetrahydro-2H-pyran-2-yl)ethyl)-3,7-dimethyl-1,2,3,7,8,8a-hexahydronaphthalen-1-yl (2-(2-(2-((2-(2,6-dioxopiperidin-3-yl)-1-oxoisoindolin-4-yl)amino)ethoxy)ethoxy)ethyl)carbamate (Compound 66)

Step 1: Synthesis of tert-butyl (2-(2-(2-((2-(2,6-dioxopiperidin-3-yl)-1-oxoisoindolin-4-yl)amino)ethoxy)ethoxy)ethyl)carbamate (49)

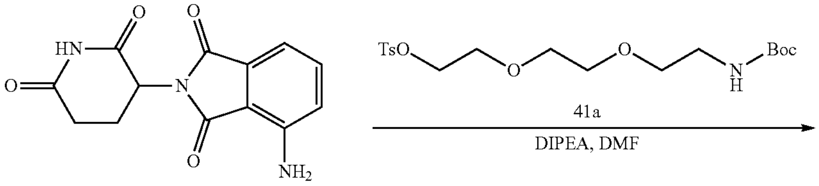

48

-continued

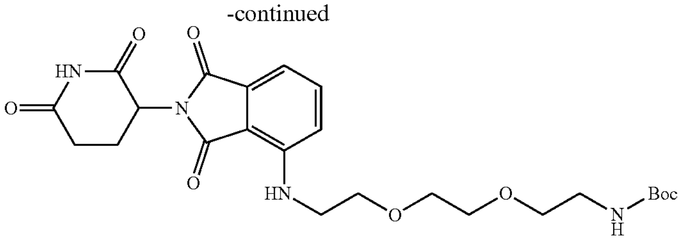

49

To a mixture of 3-(4-amino-1-oxoisoindolin-2-yl)piperidine-2,6-dione (3 g, 11.57 mmol) and 2-[2-[2-(tert-butoxycarbonylamino)ethoxy]ethoxy]ethyl 4-methylbenzenesulfonate (6.50 g, 12.73 mmol) in DMF (30 mL) was added DIPEA (4.49 g, 34.71 mmol, 6.05 mL) in one portion at 25° C. The mixture was stirred at 110° C. for 12 h. LCMS showed starting material was consumed completely and desired mass was detected. TLC ($SiO_2$, Petroleum ether: Ethyl acetate=10:1) indicated starting material was consumed completely and one major new spot was formed. The reaction mixture was diluted with $H_2O$ (90 mL) and extracted with EtOAc (90 mL×3). The organic layer was washed with brine (90 mL×3), dried over $Na_2SO_4$, filtrated and concentrated. The residue was purified by column chromatography ($SiO_2$, Petroleum ether/Ethyl acetate=2/1 to 0/1) to afford tert-butyl (2-(2-(2-((2-(2,6-dioxopiperidin-3-yl)-1-oxoisoindolin-4-yl)amino)ethoxy)ethoxy)ethyl)carbamate (2.1 g, 4.28 mmol, 37.00% yield) as a reddish brown solid.

MS $(M+H)^+$=491.3

Step 2: Synthesis of 3-(4-((2-(2-(2-aminoethoxy)ethoxy)ethyl)amino)-1-oxoisoindolin-2-yl)piperidine-2,6-dione (50)

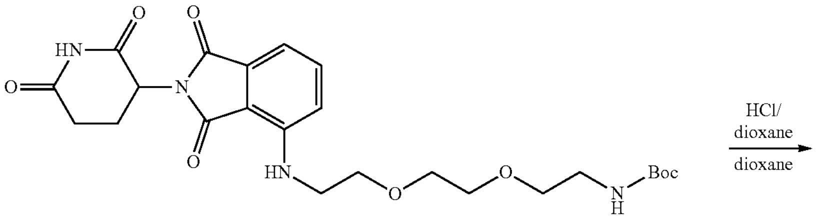

49

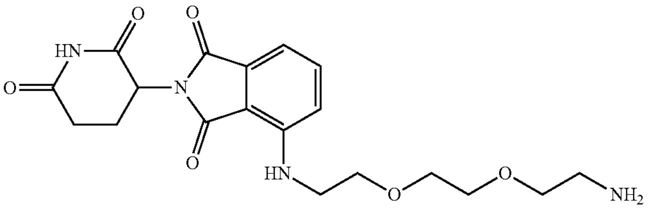

50

To a mixture of tert-butyl (2-(2-(2-((2-(2,6-dioxopiperidin-3-yl)-1-oxoisoindolin-4-yl)amino)ethoxy)ethoxy)ethyl) carbamate (2.1 g, 4.28 mmol) in dioxane (10 mL) was added HCl/dioxane (4 M, 20 mL) in one portion at 25° C. and the mixture was stirred at 25° C. for 16 h. LCMS showed starting material was consumed completely and desired mass was detected. The reaction mixture was concentrated in vacuum to afford 3-(4-((2-(2-(2-aminoethoxy)ethoxy) ethyl)amino)-1-oxoisoindolin-2-yl)piperidine-2,6-dione (1.7 g, crude, HCl salt) as a reddish brown solid.

MS $(M+H)^+$=391.2

Step 3: Synthesis of (1S,3R,7S,8S,8aR)-8-(2-((2R, 4R)-4-((tert-butyldimethylsilyl)oxy)-6-oxotetrahydro-2H-pyran-2-yl)ethyl)-3,7-dimethyl-1,2,3,7,8,8a-hexahydronaphthalen-1-yl (2-(2-(2-((2-(2,6-dioxopiperidin-3-yl)-1-oxoisoindolin-4-yl)amino) ethoxy)ethoxy)ethyl)carbamate (Compound 65)

stirred at 15° C. for 16 h. LCMS showed starting material was consumed completely and desired mass was detected. The reaction mixture was diluted with $H_2O$ (45 mL) and extracted with EtOAc (45 mLx3). The organic layer was washed with brine (45 mLx3), dried over $Na_2SO_4$, filtrated and concentrated. The residue was purified by prep-HPLC (column: Waters Xbridge C18 150*50 mm*10 μm; mobile phase: [water (10 mM $NH_4HCO_3$)-ACN]; B %: 60%-90%, 11.5 min) to afford (1S,3R,7S,8S,8aR)-8-(2-((2R,4R)-4-((tert-butyldimethylsilyl)oxy)-6-oxotetrahydro-2H-pyran-2-yl)ethyl)-3,7-dimethyl-1,2,3,7,8,8a-hexahydronaphthalen-1-yl (2-(2-(2-((2-(2,6-dioxopiperidin-3-yl)-1-oxoisoindolin-4-yl)amino)ethoxy)ethoxy)ethyl)carbamate (886 mg, 957.71 μmol, 24.05% yield, 92% purity) as a white solid.

MS $(M+H)^+$=851.8

$^1H$ NMR (400 MHz, Chloroform-d) δ 8.23 (d, J=18.0 Hz, 1H), 7.35 (t, J=7.7 Hz, 1H), 7.33-7.28 (m, 1H), 6.79 (d, J=7.9 Hz, 1H), 5.97 (d, J=9.6 Hz, 1H), 5.83-5.74 (m, 1H), 5.51 (s, 1H), 5.40-5.08 (m, 3H), 4.74-4.59 (m, 1H), 4.41-4.24 (m, 2H), 4.22-4.13 (m, 1H), 4.08-3.95 (m, 1H), 3.71 (t, J=5.0 Hz, 2H), 3.67-3.57 (m, 4H), 3.57-3.49 (m, 2H), 3.47-3.24 (m, 4H), 2.96-2.74 (m, 2H), 2.64-2.47 (m, 2H), 2.47-2.28 (m, 3H), 2.28-2.16 (m, 2H), 2.09 (d, J=14.4 Hz, 1H), 1.91-1.71 (m, 4H), 1.70-1.60 (m, 3H), 1.50-1.37 (m, 1H), 1.35-1.22 (m, 1H), 1.06 (dd, J=7.4, 2.0 Hz, 3H), 0.93-0.79 (m, 12H), 0.12-0.04 (m, 6H).

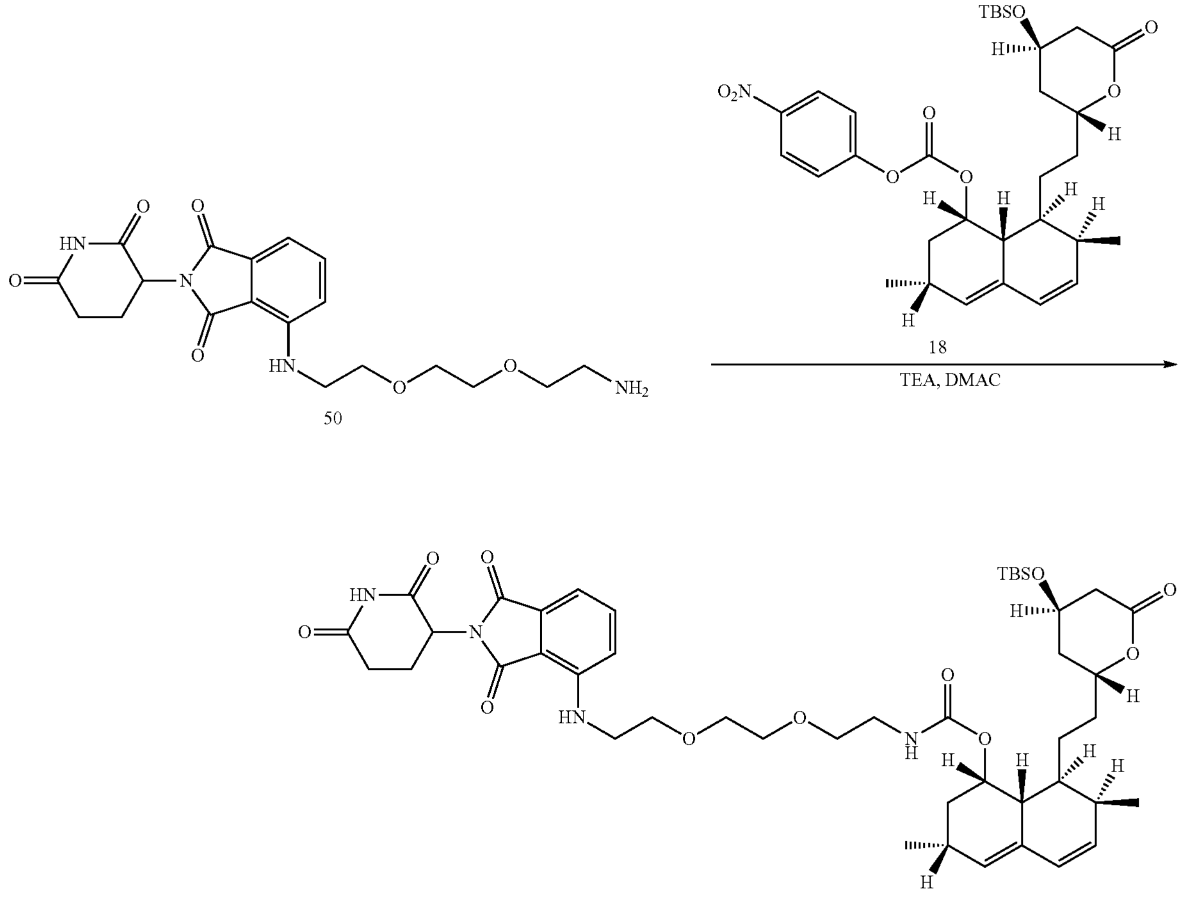

50
18

Compound 65

To a mixture of 3-(4-((2-(2-(2-aminoethoxy)ethoxy)ethyl) amino)-1-oxoisoindolin-2-yl)piperidine-2,6-dione (1.7 g, 3.98 mmol, HCl salt) and (1S,3R,7S,8S,8aR)-8-(2-((2R, 4R)-4-((tert-butyldimethylsilyl)oxy)-6-oxotetrahydro-2H-pyran-2-yl)ethyl)-3,7-dimethyl-1,2,3,7,8,8a-hexahydronaphthalen-1-yl (4-nitrophenyl) carbonate (3.73 g, 3.98 mmol) in DMAC (15 mL) was added TEA (1.21 g, 11.95 mmol, 1.66 mL) in one portion at 15° C. The mixture was Step 4: Synthesis of (1S,3R,7S,8S,8aR)-8-(2-((2R,4R)-4-hydroxy-6-oxotetrahydro-2H-pyran-2-yl)ethyl)-3,7-dimethyl-1,2,3,7,8,8a-hexahydronaphthalen-1-yl (2-(2-(2-((2-(2,6-dioxopiperidin-3-yl)-1-oxoisoindolin-4-yl)amino)ethoxy)ethoxy)ethyl) carbamate (Compound

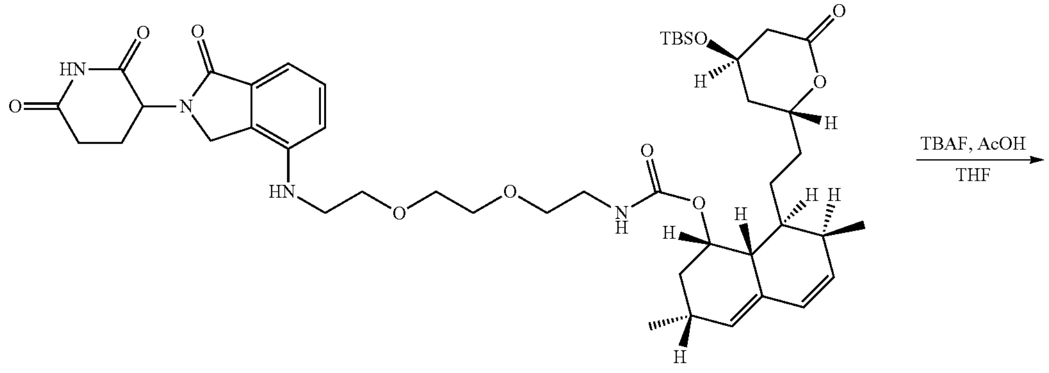

Compound 65

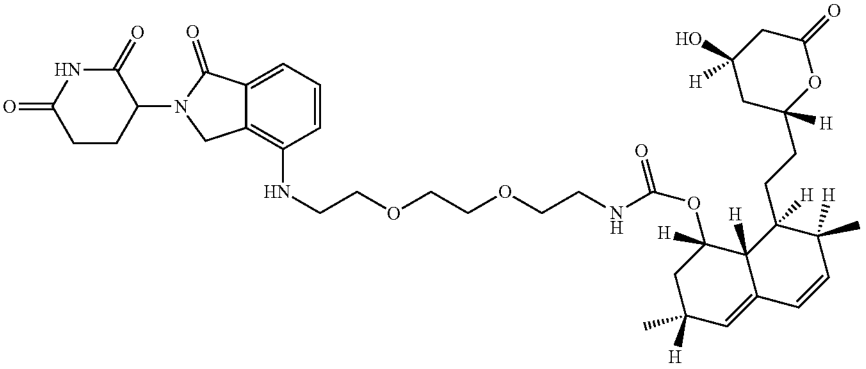

Compound 66

To a mixture of (1S,3R,7S,8S,8aR)-8-(2-((2R,4R)-4-((tert-butyldimethylsilyl)oxy)-6-oxotetrahydro-2H-pyran-2-yl)ethyl)-3,7-dimethyl-1,2,3,7,8,8a-hexahydronaphthalen-1-yl (2-(2-(2-((2-(2,6-dioxopiperidin-3-yl)-1-oxoisoindolin-4-yl)amino)ethoxy)ethoxy)ethyl)carbamate (670 mg, 787.21 μmol) in THF (6 mL) was added TBAF (1 M, 3.15 mL) and AcOH (236.36 mg, 3.94 mmol, 225.10 μL) in one portion at 15° C. The mixture was stirred at 15° C. for 16 h. LCMS showed starting material was consumed completely and desired mass was detected. TLC ($SiO_2$, Dichloromethane:Methanol=10:1) indicated starting material was consumed completely and one major new spot was detected. The reaction mixture was quenched with saturated $NH_4Cl$ (20 mL) and extracted with EtOAc (20 mL×3). The organic layer was dried over $Na_2SO_4$, filtrated and concentrated. The residue was purified by column chromatography ($SiO_2$, Dichloromethane/Methanol=1/0 to 8/1) followed by prep-HPLC (column: Phenomenex luna C18 150*40 mm*15 μm; mobile phase: [water (0.225% FA)-ACN]; B %: 35%-65%, 10 min) to afford 160 mg with 72% purity of product. The less pure product was re-purified by prep-HPLC (column: Unisil 3-100 C18 Ultra 150*50 mm*3 μm; mobile phase: [water (0.225% FA)-ACN]; B %: 40%-60%, 10 min) followed by prep-TLC ($SiO_2$, DCM:MeOH:THF=10:10:1) to afford (1S,3R,7S,8S,8aR)-8-(2-((2R,4R)-4-hydroxy-6-oxotetrahydro-2H-pyran-2-yl)ethyl)-3,7-dimethyl-1,2,3,7,8,8a-hexahydronaphthalen-1-yl (2-(2-(2-((2-(2,6-dioxopiperidin-3-yl)-1-oxoisoindolin-4-yl)amino)ethoxy)ethoxy)ethyl) carbamate (94.1 mg, 123.87 μmol, 15.74% yield, 97% purity) as a white solid.

MS $(M+H)^+$=737.5

$^1$H NMR (400 MHz, Chloroform-d) δ 7.39-7.32 (m, 1H), 7.31-7.27 (m, 1H), 6.79 (d, J=7.9 Hz, 1H), 5.96 (dd, J=9.6, 5.1 Hz, 1H), 5.83-5.72 (m, 1H), 5.50 (s, 1H), 5.35-5.11 (m, 3H), 4.65-4.50 (m, 1H), 4.42-4.14 (m, 3H), 3.76-3.67 (m, 2H), 3.66-3.55 (m, 5H), 3.53-3.33 (m, 4H), 3.32-3.17 (m, 1H), 2.93-2.74 (m, 2H), 2.73-2.55 (m, 2H), 2.50-2.27 (m, 3H), 2.27-2.15 (m, 2H), 2.06 (d, J=14.6 Hz, 1H), 1.95-1.70 (m, 5H), 1.65-1.53 (m, 2H), 1.46-1.26 (m, 2H), 1.06 (dd, J=7.4, 3.7 Hz, 3H), 0.87 (dd, J=7.0, 4.6 Hz, 3H).

Example 67 & Example 68: Synthesis of (1S,3R,7S,8S,8aR)-8-(2-((2R,4R)-4-((tert-butyldimethylsilyl)oxy)-6-oxotetrahydro-2H-pyran-2-yl)ethyl)-3,7-dimethyl-1,2,3,7,8,8a-hexahydronaphthalen-1-yl (2-(2-(2-((2-(2,6-dioxopiperidin-3-yl)-1,3-dioxoisoindolin-5-yl)amino)ethoxy)ethoxy)ethyl)carbamate (Compound 67) and (1S,3R,7S,8S,8aR)-8-(2-((2R,4R)-4-hydroxy-6-oxotetrahydro-2H-pyran-2-yl)ethyl)-3,7-dimethyl-1,2,3,7,8,8a-hexahydronaphthalen-1-yl (2-(2-(2-((2-(2,6-dioxopiperidin-3-yl)-1,3-dioxoisoindolin-5-yl)amino)ethoxy)ethoxy)ethyl)carbamate (Compound 68)

Step 1: Synthesis of 2-(2,6-dioxo-3-piperidyl)-5-fluoro-isoindoline-1,3-dione (52)

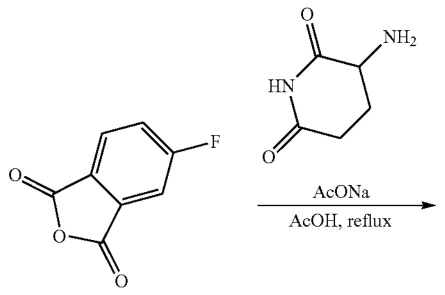

51

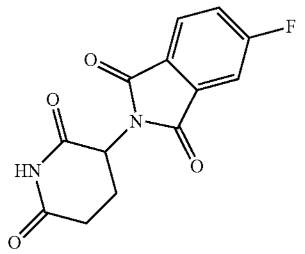

52

To a solution of 5-fluoroisobenzofuran-1,3-dione (4 g, 24.08 mmol) and 3-aminopiperidine-2,6-dione (3.96 g, 24.08 mmol, HCl salt) in HOAc (80 mL) was added sodium acetate (2.96 g, 36.12 mmol). The mixture was then stirred at 130° C. for 16 hr. LCMS showed 100% desired mass was detected. The reaction mixture was cooled to room temperature and concentrated under vacuum. The crude product was triturated with $H_2O$ (100 mL) at 25° C. for 10 min. Compound 2-(2,6-dioxo-3-piperidyl)-5-fluoro-isoindoline-1,3-dione (5.5 g, 19.91 mmol, 82.69% yield) was obtained as a white solid.

MS $(M+H)^+$=277.1

Step 2: Synthesis of tert-butyl N-[2-[2-[2-[[2-(2,6-dioxo-3-piperidyl)-1,3-dioxo-isoindolin-5-yl]amino]ethoxy]ethoxy]ethyl]carbamate (53)

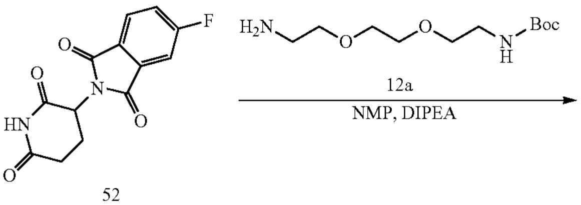

52

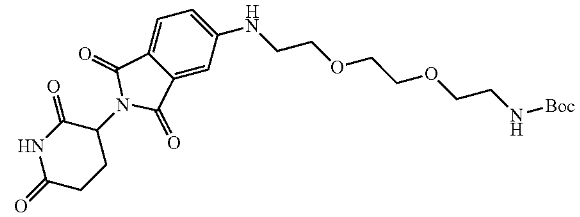

53

To the solution of 2-(2,6-dioxo-3-piperidyl)-5-fluoro-isoindoline-1,3-dione (2 g, 7.24 mmol) and tert-butyl N-[2-[2-(2-aminoethoxy)ethoxy]ethyl]carbamate (1.80 g, 7.24 mmol) in NMP (20 mL) was added DIPEA (1.87 g, 14.48 mmol, 2.52 mL) and the resulting mixture was stirred at 90° C. for 16 hr. LCMS showed that desired mass was detected. The reaction mixture was cooled to room temperature. EtOAc (150 mL) and water (150 mL) were added and layers were separated. The aqueous phase was extracted with EtOAc (200 mL×2). Combined extracts were washed with brine (300 mL), dried over $Na_2SO_4$, filtered and concentrated under vacuum. The residue was purified by silica gel chromatography (Petroleum ether:Ethyl acetate 1:1 to 0:1). Compound tert-butyl N-[2-[2-[2-[[2-(2,6-dioxo-3-piperidyl)-1,3-dioxo-isoindolin-5-yl]amino]ethoxy]ethoxy]ethyl]carbamate (1.1 g, 1.77 mmol, 24.39% yield, 81% purity) was obtained as a black brown oil.

MS $(M+H)^+$=505.1

Step 3: Synthesis of 5-[2-[2-(2-aminoethoxy)ethoxy]ethylamino]-2-(2,6-dioxo-3-piperidyl)isoindoline-1,3-dione (54)

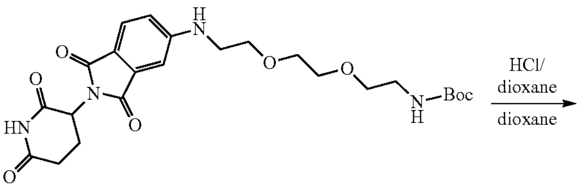

53

-continued

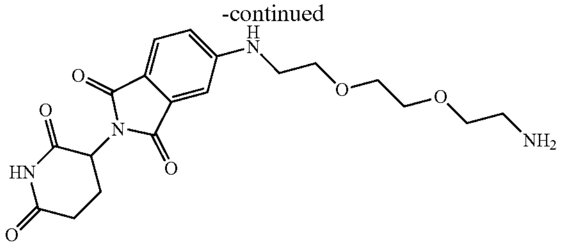

54

To a solution of tert-butyl N-[2-[2-[2-[[2-(2,6-dioxo-3-piperidyl)-1,3-dioxo-isoindolin-5-yl]amino]ethoxy]ethoxy]ethyl]carbamate (1 g, 1.61 mmol) in dioxane (20 mL) was added HCl/dioxane (4 M, 20 mL). The mixture was then stirred at 25° C. for 6 hr. LCMS showed that starting material was consumed and 77% desired mass was detected. The residue was combined with another batch (100 mg scale) and concentrated under vacuum. Compound 5-[2-[2-(2-aminoethoxy)ethoxy]ethylamino]-2-(2,6-dioxo-3-piperidyl)isoindoline-1,3-dione (1.3 g, crude, HCl salt) was obtained as a yellow oil

MS $(M+H)^+$=405.1

Step 4: Synthesis of (1S,3R,7S,8S,8aR)-8-(2-((2R,4R)-4-((tert-butyldimethylsilyl)oxy)-6-oxotetrahydro-2H-pyran-2-yl)ethyl)-3,7-dimethyl-1,2,3,7,8,8a-hexahydronaphthalen-1-yl (2-(2-(2-((2-(2,6-dioxopiperidin-3-yl)-1,3-dioxoisoindolin-5-yl)amino)ethoxy)ethoxy)ethyl)carbamate (Compound 67)

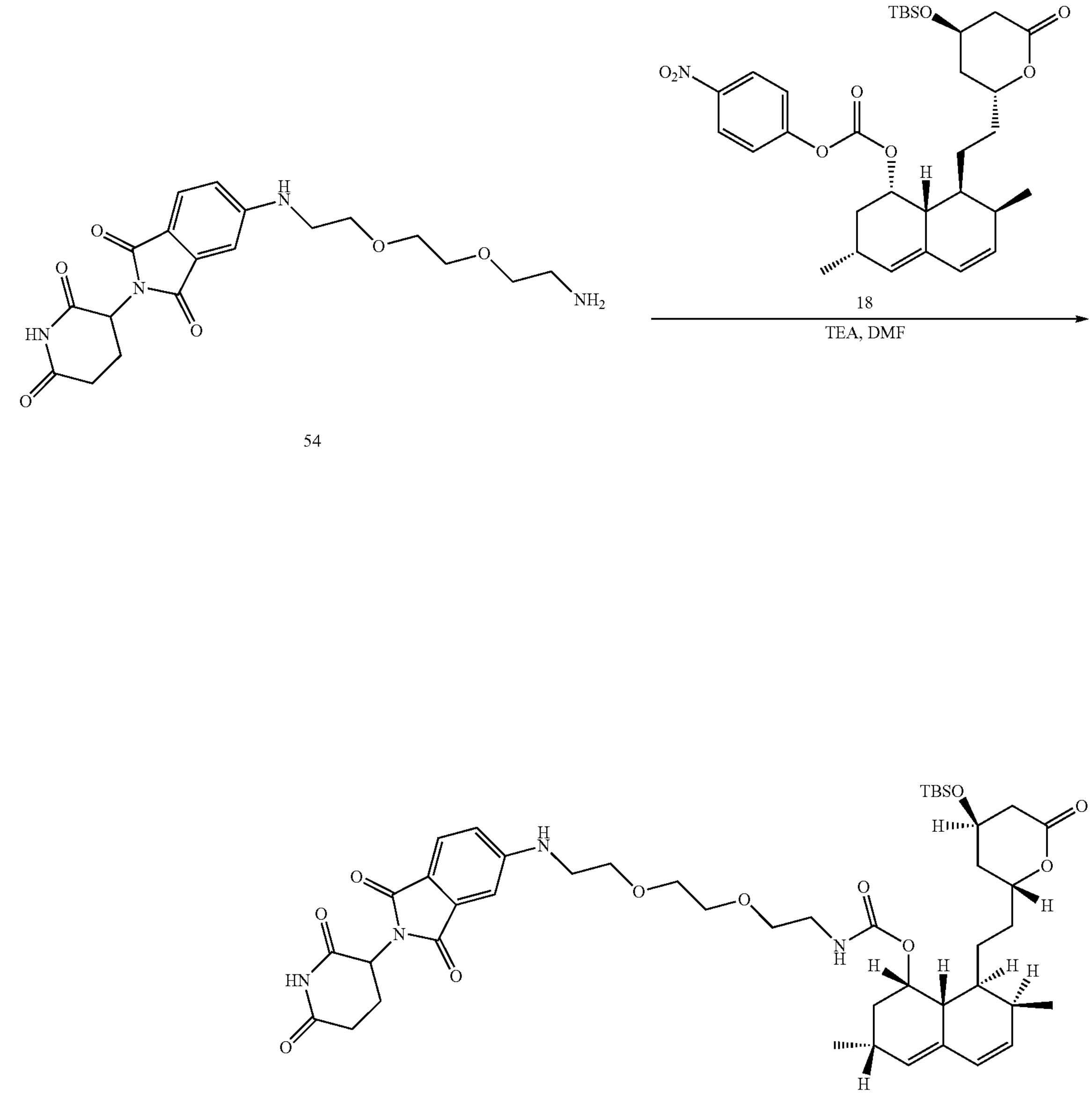

54

18

Compound 67

To the solution of 5-[2-[2-(2-aminoethoxy)ethoxy]ethylamino]-2-(2,6-dioxo-3-piperidyl)isoindoline-1,3-dione (600 mg, 1.48 mmol, HCl salt) and [(1S,3R,7S,8S,8aR)-8-[2-[(2R,4R)-4-[tert-butyl(dimethyl)silyl]oxy-6-oxo-tetrahydropyran-2-yl]ethyl]-3,7-dimethyl-1,2,3,7,8,8a-hexahydronaphthalen-1-yl] (4-nitrophenyl) carbonate (1.01 mg, 1.68 μmol) in DMF (10 mL) was added TEA (450.38 mg, 4.45 mmol, 619.51 μL) and the resulting mixture was stirred at 25° C. for 12 hr. LCMS showed that the starting material was consumed and 35% desired mass was detected. The mixture was poured into water (50 mL) and extracted with EtOAc (50 mL×3). The combined organic layer was washed with brine (50 mL), dried over $Na_2SO_4$, filtered and concentrated. The residue was purified by prep-HPLC (column: Phenomenex luna C18 150*40 mm*15 μm; mobile phase: [water (0.225% FA)-ACN]; B %: 68%-98%, 11 min). Compound (1S,3R,7S,8S,8aR)-8-(2-((2R,4R)-4-((tert-butyldimethylsilyl)oxy)-6-oxotetrahydro-2H-pyran-2-yl)ethyl)-3,7-dimethyl-1,2,3,7,8,8a-hexahydronaphthalen-1-yl (2-(2-(2-((2-(2,6-dioxopiperidin-3-yl)-1,3-dioxoisoindolin-5-yl)amino)ethoxy)ethoxy)ethyl)carbamate (105 mg, 120.16 μmol, 8.10% yield, 99% purity) was obtained as yellow solid.

MS $(M+H)^+$=865.8

$^1H$ NMR (400 MHz, $CDCl_3$) δ=8.07 (s, 1H), 7.61 (d, J=8.3 Hz, 1H), 6.99 (d, J=1.7 Hz, 1H), 6.79 (br d, J=8.4 Hz, 1H), 5.98 (d, J=9.7 Hz, 1H), 5.79 (dd, J=6.1, 9.5 Hz, 1H), 5.52 (br s, 1H), 5.21 (br s, 2H), 4.93 (dd, J=5.3, 12.3 Hz, 1H), 4.66 (br s, 1H), 4.34-4.25 (m, 1H), 3.72 (t, J=5.0 Hz, 2H), 3.63 (s, 4H), 3.58-3.51 (m, 2H), 3.50-3.36 (m, 3H), 3.36-3.26 (m, 1H), 2.94-2.69 (m, 3H), 2.65-2.51 (m, 2H), 2.44 (br s, 1H), 2.35 (br s, 1H), 2.26 (br d, J=12.5 Hz, 1H), 2.17-2.07 (m, 2H), 1.92-1.81 (m, 2H), 1.78-1.65 (m, 4H), 1.45 (br s, 1H), 1.36-1.25 (m, 1H), 1.08-1.07 (m, 3H), 0.92-0.86 (m, 12H), 0.08 (s, 6H).

Step 5: Synthesis of (1S,3R,7S,8S,8aR)-8-(2-((2R,4R)-4-hydroxy-6-oxotetrahydro-2H-pyran-2-yl)ethyl)-3,7-dimethyl-1,2,3,7,8,8a-hexahydronaphthalen-1-yl (2-(2-(2-((2-(2,6-dioxopiperidin-3-yl)-1,3-dioxoisoindolin-5-yl)amino)ethoxy)ethoxy)ethyl)carbamate (Compound 68)

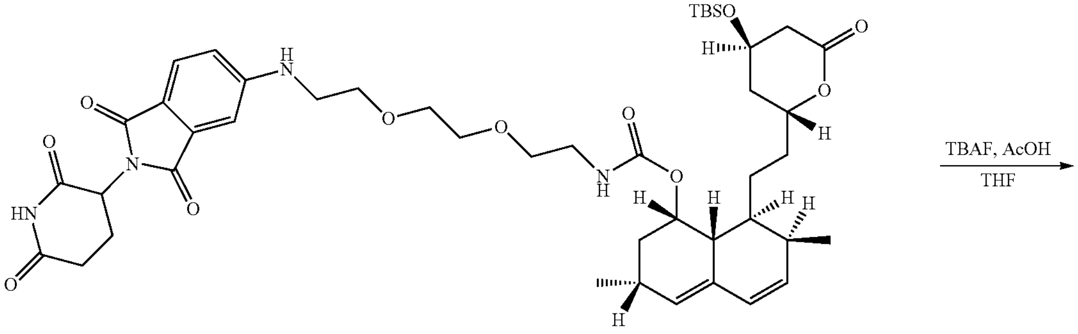

Compound 67

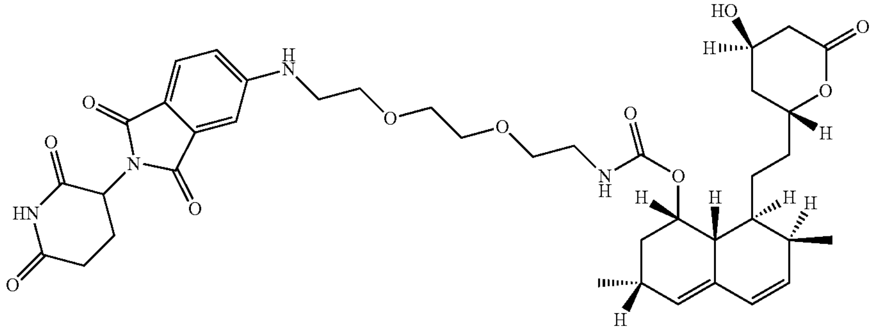

Compound 68

To a stirred solution of (1S,3R,7S,8S,8aR)-8-(2-((2R,4R)-4-((tert-butyldimethylsilyl)oxy)-6-oxotetrahydro-2H-pyran-2-yl)ethyl)-3,7-dimethyl-1,2,3,7,8,8a-hexahydronaphthalen-1-yl (2-(2-(2-((2-(2,6-dioxopiperidin-3-yl)-1,3-dioxoisoindolin-5-yl)amino)ethoxy)ethoxy)ethyl)carbamate (250 mg, 288.99 μmol) in THF (5 mL) was added a premixed solution of TBAF (1 M, 1.16 mL) and AcOH (83.30 mg, 1.39 mmol, 79.33 μL) and the resulting solution was heated at 25° C. for 12 h. LCMS showed that starting material was consumed and 85% desired mass was detected. The mixture was poured into water (50 mL) and extracted with EtOAc (50 mL×3). The combined organic layer was washed with brine (100 mL), dried over $Na_2SO_4$, filtered and concentrated. The residue was purified by silica gel column (Petroleum ether:Ethyl acetate=1:1-0:1). Compound (1S,3R,7S,8S,8aR)-8-(2-((2R,4R)-4-hydroxy-6-oxotetrahydro-2H-pyran-2-yl)ethyl)-3,7-dimethyl-1,2,3,7,8,8a-hexahydronaphthalen-1-yl (2-(2-(2-((2-(2,6-dioxopiperidin-3-yl)-1,3-dioxoisoindolin-5-yl)amino)ethoxy)ethoxy)ethyl) carbamate (70.2 mg, 89.76 μmol, 31.06% yield, 96% purity) was obtained as yellow solid.

MS $(M+H)^+$=751.6

$^1H$ NMR (400 MHz, $CDCl_3$) δ=8.17 (br s, 1H), 7.61 (d, J=8.3 Hz, 1H), 7.01 (d, J=1.7 Hz, 1H), 6.79 (br d, J=7.8 Hz, 1H), 5.98 (d, J=9.8 Hz, 1H), 5.79 (dd, J=6.4, 9.5 Hz, 1H), 5.53 (br s, 1H), 5.31 (br s, 1H), 5.22 (br s, 1H), 4.93 (dd, J=5.3, 12.0 Hz, 1H), 4.64 (br s, 1H), 4.32 (br s, 1H), 3.72 (t, J=5.0 Hz, 2H), 3.67-3.51 (m, 6H), 3.40 (br s, 4H), 2.94-2.66 (m, 5H), 2.63-2.54 (m, 1H), 2.48-2.32 (m, 2H), 2.26 (br d, J=10.6 Hz, 1H), 2.17-2.04 (m, 2H), 2.00-1.80 (m, 3H), 1.77-1.69 (m, 2H), 1.46-1.35 (m, 2H), 1.08 (d, J=7.3 Hz, 3H), 0.90 (br d, J=6.8 Hz, 3H).

Example 69. Synthesis of (1S,3R,7S,8S,8aR)-8-(2-((2R,4R)-4-methoxy-6-oxotetrahydro-2H-pyran-2-yl)ethyl)-3,7-dimethyl-1,2,3,7,8,8a-hexahydronaphthalen-1-yl (2-(2-(2-((2-(2,6-dioxopiperidin-3-yl)-1,3-dioxoisoindolin-4-yl)amino)ethoxy)ethoxy)ethyl) carbamate (Compound 69)

Step 1: Synthesis of [(1S,3R,7S,8S,8aR)-8-[2-[(2R,4R)-4-methoxy-6-oxo-tetrahydropyran-2-yl]ethyl]-3,7-dimethyl-1,2,3,7,8,8a-hexahydronaphthalen-1-yl] (4-nitrophenyl) carbonate (56)

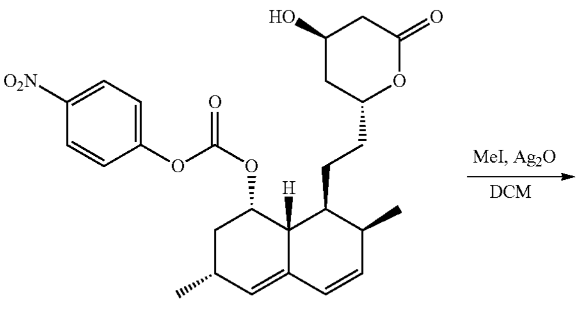

55

-continued

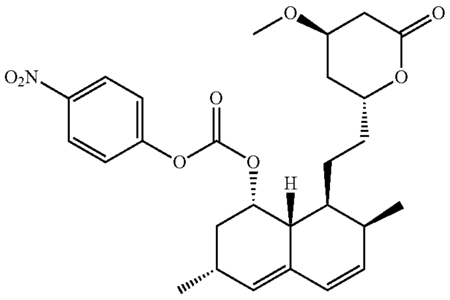

56

To the mixture of [(1S,3R,7S,8S,8aR)-8-[2-[(2R,4R)-4-hydroxy-6-oxo-tetrahydropyran-2-yl]ethyl]-3,7-dimethyl-1,2,3,7,8,8a-hexahydronaphthalen-1-yl] (4-nitrophenyl) carbonate (1 g, 2.06 mmol), $MgSO_4$ (495.83 mg, 4.12 mmol) and $Ag_2O$ (954.60 mg, 4.12 mmol) in DCM (20 mL) was added MeI (584.68 mg, 4.12 mmol, 256.44 μL) and the resulting mixture was stirred at 25° C. for 12 hr. LCMS showed that 47% starting material remained and 45% desired mass was detected. The mixture was filtered and the filtrate was concentrated. The residue was purified by silica gel column (Petroleum ether:Ethyl acetate=5:1-1:1). Compound [(1S,3R,7S,8S,8aR)-8-[2-[(2R,4R)-4-methoxy-6-oxo-tetrahydropyran-2-yl]ethyl]-3,7-dimethyl-1,2,3,7,8,8a-hexahydronaphthalen-1-yl] (4-nitrophenyl) carbonate (0.24 g, 442.00 μmol, 21.46% yield, 92% purity) was obtained as white solid.

MS $(M+H)^+$=500.3

Step 2: Synthesis of (1S,3R,7S,8S,8aR)-8-(2-((2R,4R)-4-methoxy-6-oxotetrahydro-2H-pyran-2-yl)ethyl)-3,7-dimethyl-1,2,3,7,8,8a-hexahydronaphthalen-1-yl (2-(2-(2-((2-(2,6-dioxopiperidin-3-yl)-1,3-dioxoisoindolin-4-yl)amino)ethoxy)ethoxy)ethyl) carbamate (Compound 69)

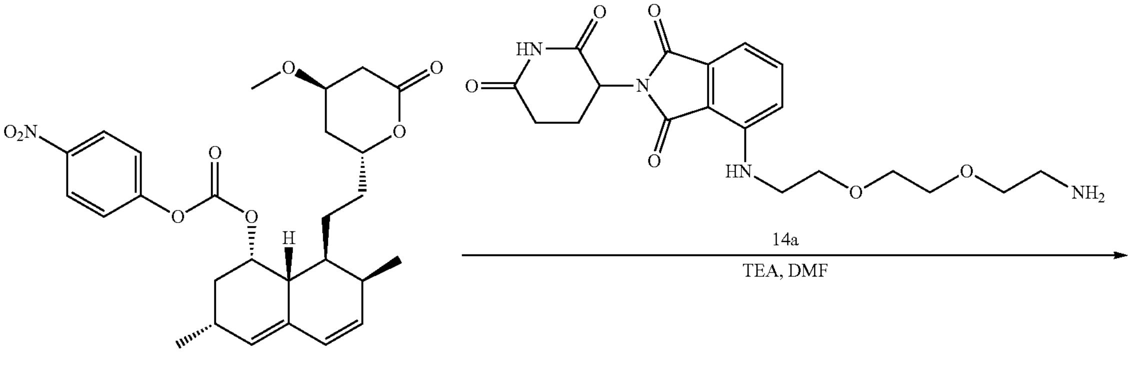

56

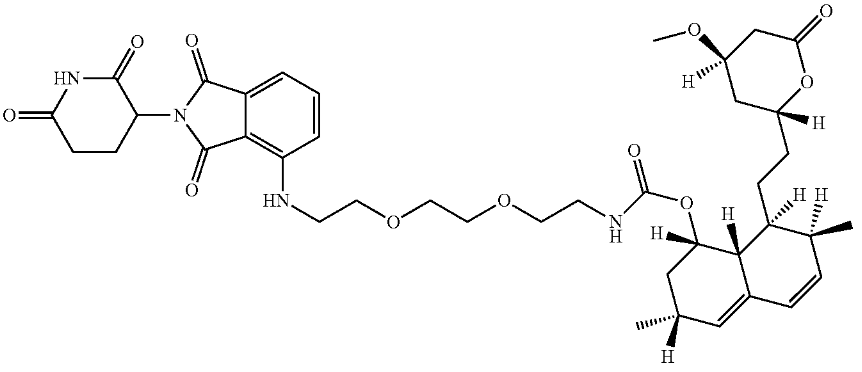

Compound 69

To the solution of [(1S,3R,7S,8S,8aR)-8-[2-[(2R,4R)-4-methoxy-6-oxo-tetrahydropyran-2-yl]ethyl]-3,7-dimethyl-1,2,3,7,8,8a-hexahydronaphthalen-1-yl] (4-nitrophenyl) carbonate (240 mg, 480.43 μmol) and 4-[2-[2-(2-aminoethoxy)ethoxy]ethylamino]-2-(2,6-dioxo-3-piperidyl)isoindoline-1,3-dione (254.17 mg, 576.52 μmol, HCl salt) in DMF (5 mL) was added TEA (145.84 mg, 1.44 mmol, 200.61 μL) and the resulting mixture was stirred at 20° C. for 12 hr. LCMS showed the starting material was consumed and 79% desired mass was detected. The mixture was poured into water (50 mL) and extracted with EtOAc (50 mL×3), the combined organic layer was washed with brine (100 mL), dried over $Na_2SO_4$, filtered and concentrated. The residue was purified by prep-HPLC (column: Phenomenex Luna C18 150*25 mm*10 μm; mobile phase: [water (0.225% FA)-ACN]; B %: 47%-77%, 11 min). Compound (1S,3R,7S,8S,8aR)-8-(2-((2R,4R)-4-methoxy-6-oxotetrahydro-2H-pyran-2-yl)ethyl)-3,7-dimethyl-1,2,3,7,8,8a-hexahydronaphthalen-1-yl (2-(2-(2-((2-(2,6-dioxopiperidin-3-yl)-1,3-dioxoisoindolin-4-yl)amino)ethoxy)ethoxy)ethyl)carbamate (125.7 mg, 159.41 μmol, 33.18% yield, 97% purity) was obtained as yellow solid.

MS $(M+H)^+$=765.4

$^1$H NMR (400 MHz, $CDCl_3$) δ=8.64-8.26 (m, 1H), 7.50 (t, J=7.8 Hz, 1H), 7.12 (d, J=7.1 Hz, 1H), 6.91 (d, J=8.6 Hz, 1H), 6.51 (br s, 1H), 5.96 (d, J=9.8 Hz, 1H), 5.81-5.71 (m, 1H), 5.50 (br s, 1H), 5.22 (br d, J=13.3 Hz, 2H), 4.93 (br s, 1H), 4.51 (br d, J=7.3 Hz, 1H), 3.81-3.69 (m, 3H), 3.64 (s, 4H), 3.61-3.50 (m, 2H), 3.49-3.39 (m, 3H), 3.33 (d, J=5.4 Hz, 4H), 2.92-2.64 (m, 5H), 2.49-2.31 (m, 2H), 2.24 (br d, J=11.5 Hz, 1H), 2.18-2.03 (m, 3H), 1.93-1.69 (m, 3H), 1.68-1.61 (m, 2H), 1.42-1.31 (m, 2H), 1.07 (d, J=7.3 Hz, 3H), 0.89 (br d, J=5.6 Hz, 3H).

Example 70. Synthesis of (1S,3R,7S,8S,8aR)-3,7-dimethyl-8-(2-((2R,4R)-6-oxo-4-((triisopropylsilyl)oxy)tetrahydro-2H-pyran-2-yl)ethyl)-1,2,3,7,8,8a-hexahydronaphthalen-1-yl (2-(2-(2-((2-(2,6-dioxopiperidin-3-yl)-1,3-dioxoisoindolin-4-yl)amino)ethoxy)ethoxy)ethyl)carbamate (Compound 70)

Step 1: Synthesis of (4R,6R)-6-(2-((1S,2S,6R,8S,8aR)-8-hydroxy-2,6-dimethyl-1,2,6,7,8,8a-hexahydronaphthalen-1-yl)ethyl)-4-((triisopropylsilyl)oxy)tetrahydro-2H-pyran-2-one (57)

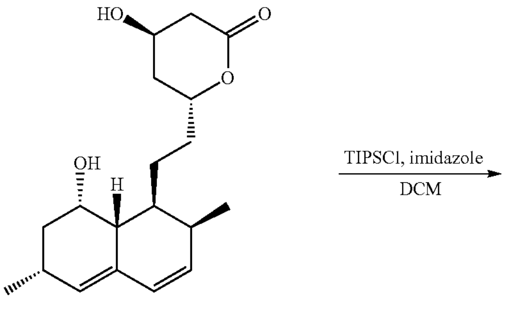

20

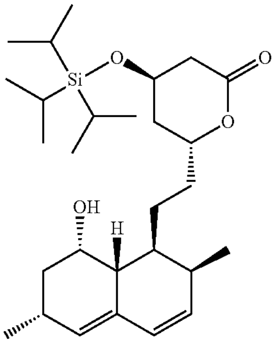

57

To a solution (4R,6R)-4-hydroxy-6-(2-((1S,2S,6R,8S,8aR)-8-hydroxy-2,6-dimethyl-1,2,6,7,8,8a-hexahydronaphthalen-1-yl)ethyl)tetrahydro-2H-pyran-2-one (1 g, 2.90 mmol), DMAP (17.73 mg, 145.00 µmol) in DCM (15 mL) was added imidazole (592.77 mg, 8.70 mmol) followed by triisopropylsilyl chloride (531.61 mg, 2.75 mmol, 590.02 µL), the mixture was stirred at 40° C. for 16 hours. Additional triisopropylsilyl chloride (167.74 mg, 870.00 µmol, 186.17 µL) was added and the resulting mixture was stirred at 40° C. for 16 hours. LCMS showed 25% of starting material remained and 35% of desired mass was detected. The mixture was concentrated under reduced pressure. The residue was purified by column chromatography ($SiO_2$, Petroleum ether/Ethyl acetate=15/1 to 4/1). Compound (4R,6R)-6-(2-((1S,2S,6R,8S,8aR)-8-hydroxy-2,6-dimethyl-1,2,6,7,8,8a-hexahydronaphthalen-1-yl)ethyl)-4-((triisopropylsilyl)oxy)tetrahydro-2H-pyran-2-one (690 mg, 1.42 mmol, 48.91% yield, 98% purity)) was obtained a yellowish oil. MS $(M+H)^+$=477.3.

Step 2: Synthesis of (1S,3R,7S,8S,8aR)-3,7-dimethyl-8-(2-((2R,4R)-6-oxo-4-((triisopropylsilyl)oxy)tetrahydro-2H-pyran-2-yl)ethyl)-1,2,3,7,8,8a-hexahydronaphthalen-1-yl (4-nitrophenyl) carbonate (58)

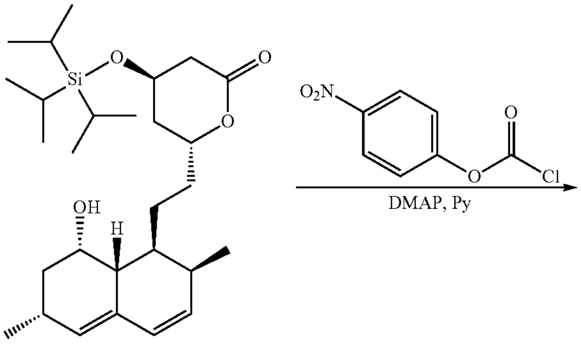

57

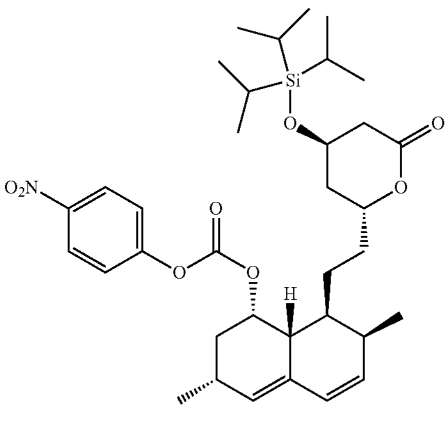

58

To a solution of (4R,6R)-6-(2-((1S,2S,6R,8S,8aR)-8-hydroxy-2,6-dimethyl-1,2,6,7,8,8a-hexahydronaphthalen-1-yl)ethyl)-4-((triisopropylsilyl)oxy)tetrahydro-2H-pyran-2-one (690 mg, 1.42 mmol) in Py (15 mL) was added DMAP (1.23 g, 10.10 mmol) followed by (4-nitrophenyl) carbonochloridate (2.00 g, 9.93 mmol). The mixture was stirred at 25° C. for 16 hours. LCMS showed 15% of desired mass was detected. The mixture was added HCl (5 M) to adjust pH=5-6 and extracted with EtOAc (40 mL×2). The combined organic layers were washed with $NaHCO_3$ solution (40 mL) and brine (40 mL), dried over $Na_2SO_4$, filtered and concentrated under reduced pressure. The residue was purified by column chromatography ($SiO_2$, Petroleum ether/Ethyl acetate=20/1). Compound (1S,3R,7S,8S,8aR)-3,7-dimethyl-8-(2-((2R,4R)-6-oxo-4-((triisopropylsilyl)oxy)tetrahydro-2H-pyran-2-yl)ethyl)-1,2,3,7,8,8a-hexahydronaphthalen-1-yl (4-nitrophenyl) carbonate (1.7 g, 794.56 µmol, 56.02% yield, 30% purity)) was obtained as a yellow solid. MS $(M+H)^+$=642.4.

Step 3: Synthesis of (1S,3R,7S,8S,8aR)-3,7-dimethyl-8-(2-((2R,4R)-6-oxo-4-((triisopropylsilyl)oxy)tetrahydro-2H-pyran-2-yl)ethyl)-1,2,3,7,8,8a-hexahydronaphthalen-1-yl (2-(2-(2-((2-(2,6-dioxopiperidin-3-yl)-1,3-dioxoisoindolin-4-yl)amino)ethoxy)ethoxy)ethyl)carbamate (Compound 70)

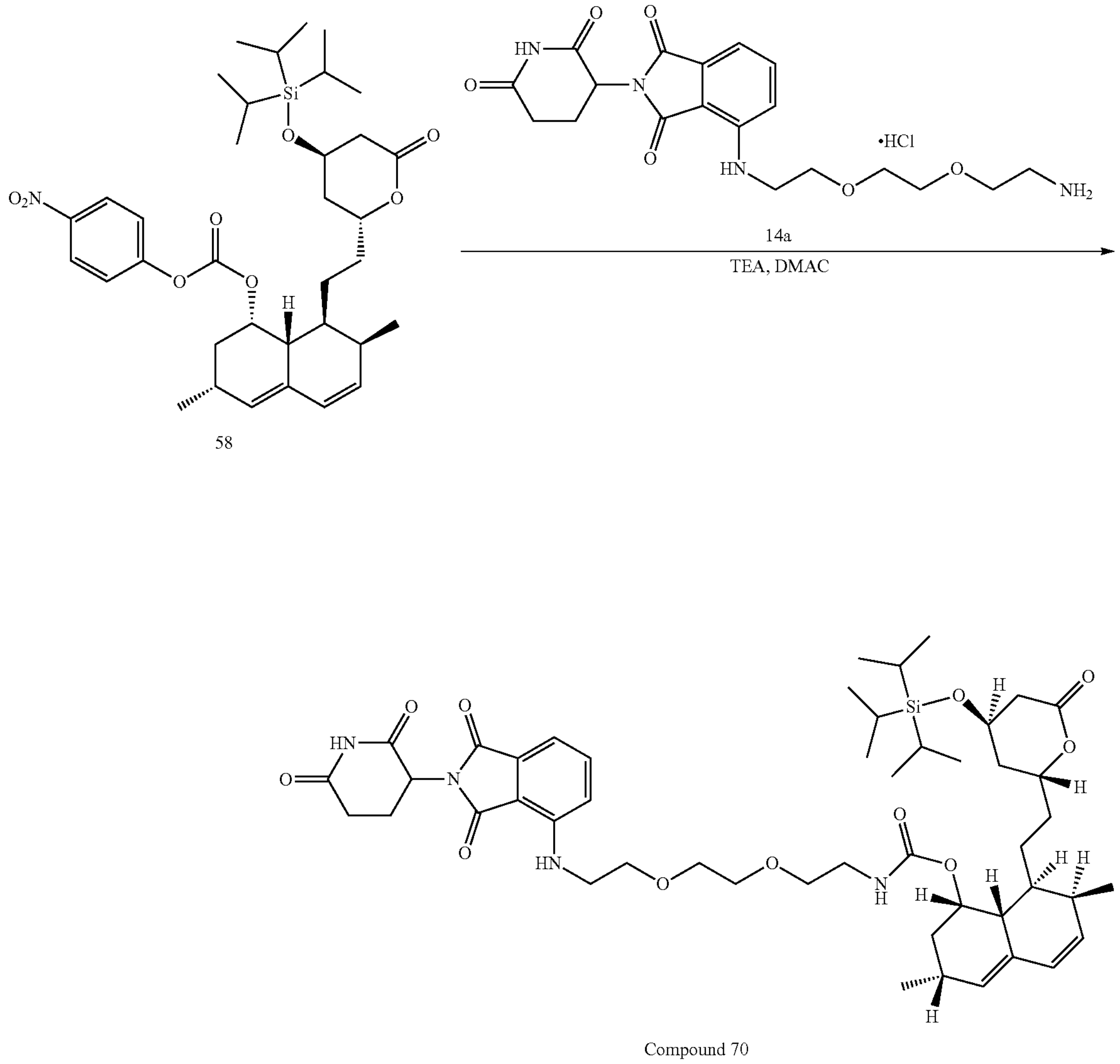

58

Compound 70

To a solution of (1S,3R,7S,8S,8aR)-3,7-dimethyl-8-(2-((2R,4R)-6-oxo-4-((triisopropylsilyl)oxy)tetrahydro-2H-pyran-2-yl)ethyl)-1,2,3,7,8,8a-hexahydronaphthalen-1-yl (4-nitrophenyl) carbonate (460 mg, 630.66 μmol), 4-((2-(2-(2-aminoethoxy)ethoxy)ethyl)amino)-2-(2,6-dioxopiperidin-3-yl)isoindoline-1,3-dione (278.04 mg, 630.66 μmol, HCl salt) in DMAC (3 mL) was added TEA (255.26 mg, 2.52 mmol, 351.12 μL). The mixture was stirred at 25° C. for 16 hours. LCMS showed 55% of desired mass was detected. The reaction mixture was purified by prep-HPLC (column: Phenomenex luna C18 150*40 mm*15 μm; mobile phase: [water (0.225% FA)-ACN]; B %: 80%-100%, 10 min). Compound (1S,3R,7S,8S,8aR)-3,7-dimethyl-8-(2-((2R,4R)-6-oxo-4-((triisopropylsilyl)oxy)tetrahydro-2H-pyran-2-yl)ethyl)-1,2,3,7,8,8a-hexahydronaphthalen-1-yl (2-(2-(2-((2-(2,6-dioxopiperidin-3-yl)-1,3-dioxoisoindolin-4-yl)amino)ethoxy)ethoxy)ethyl)carbamate (182.6 mg, 195.25 μmol, 30.96% yield, 97% purity)) was obtained as a yellow solid. MS $(M+H)^+$=907.6.

$^1$H NMR (400 MHz, $CDCl_3$) δ=8.56-8.22 (m, 1H), 7.57-7.41 (m, 1H), 7.11 (d, J=7.1 Hz, 1H), 6.91 (d, J=8.5 Hz, 1H), 6.49 (s, 1H), 5.96 (d, J=9.8 Hz, 1H), 5.77 (dd, $J_1$=9.5 Hz, $J_2$=6.0 Hz, 1H), 5.50 (s, 1H), 5.21 (s, 2H), 4.91 (m, 1H), 4.74-4.63 (m, 1H), 4.45-4.34 (m, 1H), 3.71 (t, J=5.3 Hz, 2H), 3.63 (s, 4H), 3.56 (m, 2H), 3.46 (q, J=5.4 Hz, 3H), 3.31 (m, 1H), 2.95-2.69 (m, 3H), 2.63 (dd, $J_1$=5.9 Hz, $J_2$=4.2 Hz, 2H), 2.48-2.30 (m, 2H), 2.24 (d, J=11.5 Hz, 1H), 2.17-2.04 (m, 2H), 1.98-1.91 (m, 1H), 1.89-1.63 (m, 6H), 1.49-1.39 (m, 1H), 1.37-1.28 (m, 1H), 1.10-1.01 (m, 23H), 0.89 (d, J=6.9 Hz, 3H).

Example 71. Synthesis of (1S,3R,7S,8S,8aR)-8-(2-((2R,4R)-4-((tert-butyldiphenylsilyl)oxy)-6-oxotetrahydro-2H-pyran-2-yl)ethyl)-3,7-dimethyl-1,2,3,7,8,8a-hexahydronaphthalen-1-yl (2-(2-(2-((2-(2,6-dioxopiperidin-3-yl)-1,3-dioxoisoindolin-4-yl)amino)ethoxy)ethoxy)ethyl)carbamate (Compound 71)

Step 1: Synthesis of (4R,6R)-4-((tert-butyldiphenylsilyl)oxy)-6-(2-((1S,2S,6R,8S,8aR)-8-hydroxy-2,6-dimethyl-1,2,6,7,8,8a-hexahydronaphthalen-1-yl)ethyl)tetrahydro-2H-pyran-2-one (59)

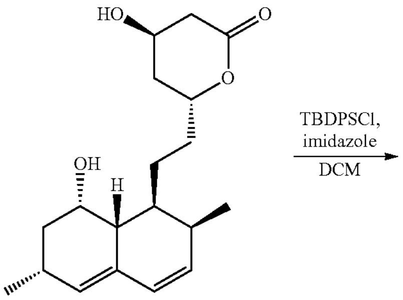

20

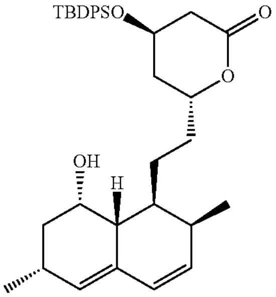

59

To a solution (4R,6R)-4-hydroxy-6-(2-((1S,2S,6R,8S,8aR)-8-hydroxy-2,6-dimethyl-1,2,6,7,8,8a-hexahydronaphthalen-1-yl)ethyl)tetrahydro-2H-pyran-2-one (1 g, 2.90 mmol) in DCM (15 mL) was added imidazole (592.77 mg, 8.71 mmol) followed by tert-butyl-chloro-diphenyl-silane (757.87 mg, 2.76 mmol, 708.29 μL). The mixture was stirred at 25° C. for 16 hours. LCMS showed 39% of desired mass was detected. The mixture was concentrated under reduced pressure. The residue was purified by ($SiO_2$, Petroleum ether/Ethyl acetate=10/1 to 4/1). Compound (4R,6R)-4-((tert-butyldiphenylsilyl)oxy)-6-(2-((1S,2S,6R,8S,8aR)-8-hydroxy-2,6-dimethyl-1,2,6,7,8,8a-hexahydronaphthalen-1-yl)ethyl)tetrahydro-2H-pyran-2-one (1.1 g, 1.04 mmol, 35.94% yield, 53% purity)) was obtained as a brown oil.

MS $(M+H)^+$=559.3

Step 2: Synthesis of (1S,3R,7S,8S,8aR)-8-(2-((2R,4R)-4-((tert-butyldiphenylsilyl)oxy)-6-oxotetrahydro-2H-pyran-2-yl)ethyl)-3,7-dimethyl-1,2,3,7,8,8a-hexahydronaphthalen-1-yl (4-nitrophenyl) carbonate (60)

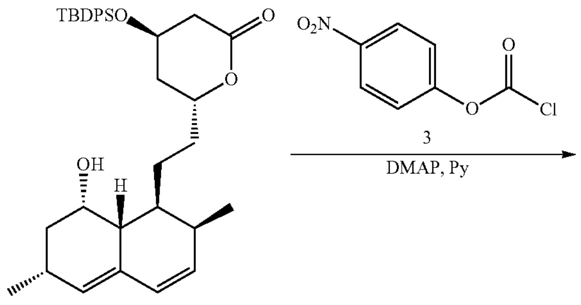

59

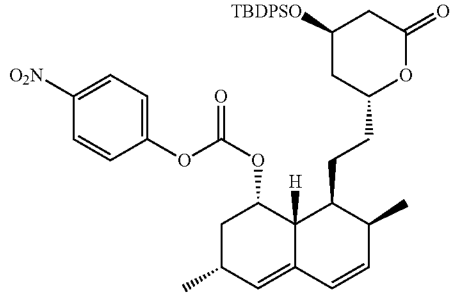

60

To a solution of (4R,6R)-4-((tert-butyldiphenylsilyl)oxy)-6-(2-((1S,2S,6R,8S,8aR)-8-hydroxy-2,6-dimethyl-1,2,6,7,8,8a-hexahydronaphthalen-1-yl)ethyl)tetrahydro-2H-pyran-2-one (1.1 g, 1.04 mmol) in Py (15 mL) was added DMAP (907.47 mg, 7.43 mmol) followed by (4-nitrophenyl) carbonochloridate (1.47 g, 7.30 mmol). The mixture was stirred at 25° C. for 16 hours. LCMS showed 30% of desired mass was detected. To this mixture was added HCl solution (5 M) to adjust pH=5-6, and then the resulting mixture was extracted with EtOAc (40 mL×2). The combined organic layers were washed with $NaHCO_3$ solution (40 mL) and brine (40 mL), dried over $Na_2SO_4$, filtered and concentrated under reduced pressure. The residue was purified by column chromatography ($SiO_2$, Petroleum ether/Ethyl acetate=15/1 to 4/1). Compound (1S,3R,7S,8S,8aR)-8-(2-((2R,4R)-4-((tert-butyldiphenylsilyl)oxy)-6-oxotetrahydro-2H-pyran-2-yl)ethyl)-3,7-dimethyl-1,2,3,7,8,8a-hexahydronaphthalen-1-yl (4-nitrophenyl) carbonate (1.7 g, 798.43 μmol, 76.53% yield, 34% purity)) was obtained as a yellow solid. MS $(M+H)^+$=724.4.

Step 3: Synthesis of (1S,3R,7S,8S,8aR)-8-(2-((2R,4R)-4-((tert-butyldiphenylsilyl)oxy)-6-oxotetrahydro-2H-pyran-2-yl)ethyl)-3,7-dimethyl-1,2,3,7,8,8a-hexahydronaphthalen-1-yl (2-(2-(2-((2-(2,6-dioxopiperidin-3-yl)-1,3-dioxoisoindolin-4-yl)amino)ethoxy)ethoxy)ethyl)carbamate (Compound 71)

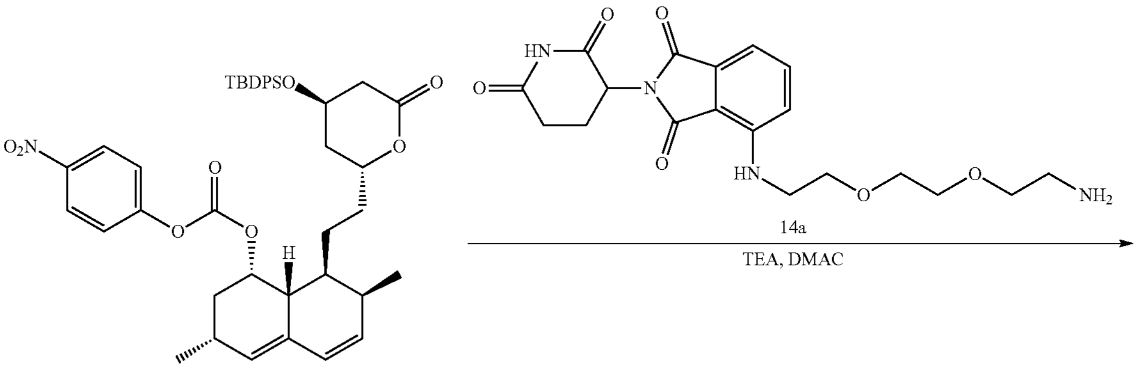

60

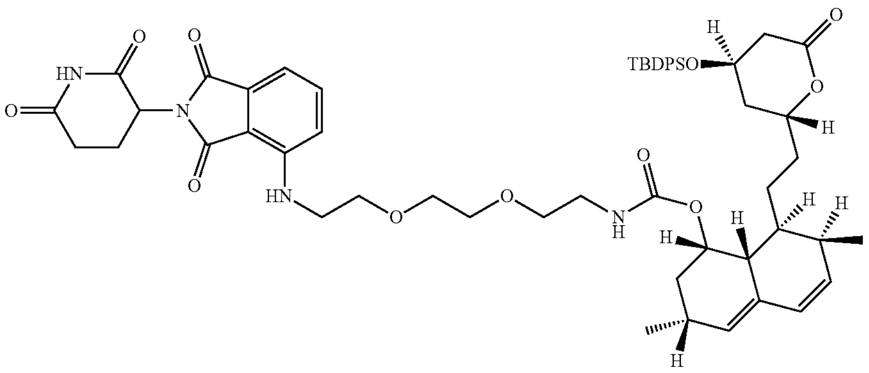

Compound 71

A mixture of (1S,3R,7S,8S,8aR)-8-(2-((2R,4R)-4-((tert-butyldiphenylsilyl)oxy)-6-oxotetrahydro-2H-pyran-2-yl)ethyl)-3,7-dimethyl-1,2,3,7,8,8a-hexahydronaphthalen-1-yl (4-nitrophenyl) carbonate (700 mg, 328.76 μmol), 4-[2-[2-(2-aminoethoxy) ethoxy] ethylamino]-2-(2, 6-dioxo-3-piperidyl) isoindoline-1, 3-dione (132.96 mg, 328.76 μmol), TEA (133.07 mg, 1.32 mmol, 183.04 μL) in DMAC (3 mL) was stirred at 25° C. for 16 hours. Then to this mixture was added 4-[2-[2-(2-aminoethoxy) ethoxy] ethylamino]-2-(2, 6-dioxo-3-piperidyl) isoindoline-1, 3-dione (132.96 mg, 328.76 μmol) and the resulting mixture was stirred at 25° C. for 32 hours. LCMS showed 31% of desired mass was detected. The mixture was purified by (column: Phenomenex luna C18 150*40 mm*15 μm; mobile phase: [water (0.225% FA)-ACN]; B %: 80%-100%, 11 min). Compound ((1S,3R,7S,8S,8aR)-8-(2-((2R,4R)-4-((tert-butyldiphenylsilyl)oxy)-6-oxotetrahydro-2H-pyran-2-yl)ethyl)-3,7-dimethyl-1,2,3,7,8,8a-hexahydronaphthalen-1-yl (2-(2-(2-((2-(2,6-dioxopiperidin-3-yl)-1,3-dioxoisoindolin-4-yl)amino)ethoxy)ethoxy)ethyl)carbamate (85.8 mg, 85.87 μmol, 26.12% yield, 99% purity)) was obtained as a yellow solid. MS $[M+H]^+$=989.2.

$^1$H NMR (400 MHz, $CDCl_3$) δ=8.44-8.15 (m, 1H), 7.67-7.59 (m, 4H), 7.52-7.38 (m, 7H), 7.11 (d, J=7.1 Hz, 1H), 6.90 (d, J=8.6 Hz, 1H), 6.49 (s, 1H), 5.97 (d, J=9.7 Hz, 1H), 5.78 (dd, $J_1$=9.4 Hz, $J_2$=6.1 Hz, 1H), 5.51 (s, 1H), 5.20 (s, 2H), 4.97-4.84 (m, 1H), 4.82-4.70 (m, 1H), 4.28 (s, 1H), 3.70 (t, J=5.4 Hz, 2H), 3.61 (d, J=3.9 Hz, 4H), 3.53 (d, J=4.8 Hz, 2H), 3.45-3.53 (m, 3H), 3.32-3.26 (m, 1H), 2.90-2.67 (m, 3H), 2.61-2.52 (m, 1H), 2.49-2.39 (m, 2H), 2.38-2.30 (m, 1H), 2.24 (d, J=11.7 Hz, 1H), 2.16-2.07 (m, 2H), 1.92-1.81 (m, 2H), 1.78-1.69 (m, 2H), 1.53-1.46 (m, 1H), 1.46-1.17 (m, 3H), 1.11-1.03 (m, 12H), 0.89 (d, J=6.8 Hz, 3H).

Example 72 & Example 73. Synthesis of (1S,3R,7S,8S,8aR)-8-(2-((2R,4R)-4-((tert-butyldimethylsilyl)oxy)-6-oxotetrahydro-2H-pyran-2-yl)ethyl)-3,7-dimethyl-1,2,3,7,8,8a-hexahydronaphthalen-1-yl (4-(4-((2-(2,6-dioxopiperidin-3-yl)-1,3-dioxoisoindolin-4-yl)amino)piperidin-1-yl)butyl)carbamate (Compound 72) and (1S,3R,7S,8S,8aR)-8-(2-((2R,4R)-4-hydroxy-6-oxotetrahydro-2H-pyran-2-yl)ethyl)-3,7-dimethyl-1,2,3,7,8,8a-hexahydronaphthalen-1-yl (4-(4-((2-(2,6-dioxopiperidin-3-yl)-1,3-dioxoisoindolin-4-yl)amino)piperidin-1-yl)butyl)carbamate (Compound 73)

Step 1: Synthesis of tert-butyl (4-bromobutyl)carbamate (62)

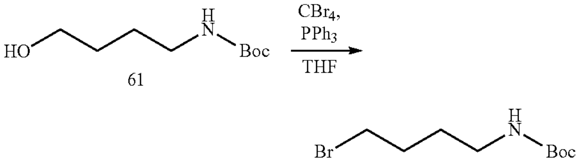

61

62

To a mixture of tert-butyl N-(4-hydroxybutyl)carbamate (1 g, 5.28 mmol) in THF (10 mL) was added $PPh_3$ (2.63 g, 10.04 mmol), then a solution of $CBr_4$ (3.33 g, 10.04 mmol) in THF (10 mL) was added drop-wise at 0° C. and the resulting mixture was stirred at 15° C. for 4 h. TLC indicated starting material was consumed completely and three new spots were detected. The reaction mixture was diluted with $H_2O$ (40 mL) and extracted with EtOAc (40 mL×3). The combined organic layer was dried over $Na_2SO_4$, filtrated and concentrated. The residue was purified by column chromatography ($SiO_2$, Petroleum ether/Ethyl acetate=1/0 to 5/1) to afford tert-butyl (4-bromobutyl)carbamate (1.3 g, 5.16 mmol, 97.57% yield) as a white oil.

$^1H$ NMR (400 MHz, $CDCl_3$) δ=4.60 (br s, 1H), 3.41 (t, J=6.7 Hz, 2H), 3.14 (q, J=6.2 Hz, 2H), 1.92-1.83 (m, 2H), 1.66-1.60 (m, 2H), 1.43 (s, 9H).

Step 2: Synthesis of tert-butyl 4-((2-(2,6-dioxopiperidin-3-yl)-1,3-dioxoisoindolin-4-yl)amino)piperidine-1-carboxylate (63)

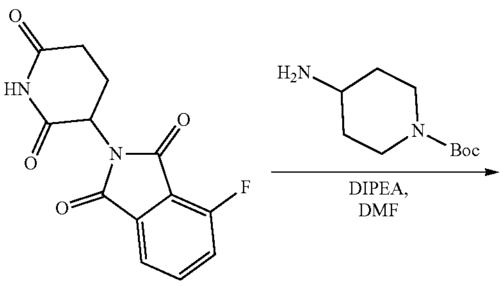

11

-continued

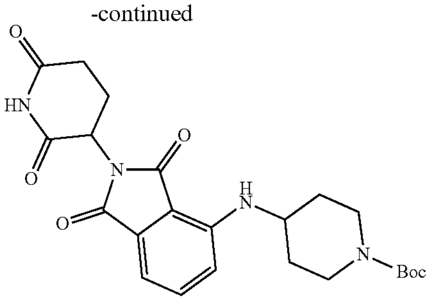

63

To a mixture of 2-(2,6-dioxopiperidin-3-yl)-4-fluoroisoindoline-1,3-dione (2 g, 7.24 mmol) and tert-butyl 4-aminopiperidine-1-carboxylate (1.60 g, 7.96 mmol) in DMF (10 mL) was added DIPEA (2.81 g, 21.72 mmol, 3.78 mL) in one portion at 25° C. and the resulting mixture was stirred at 90° C. for 16 h. LCMS showed starting material remained and desired mass was detected. The reaction mixture was diluted with $H_2O$ (30 mL) and extracted with EtOAc (30 mL×3). The combined organic layer was washed with brine (30 mL×3), dried over $Na_2SO_4$, filtrated and concentrated. The residue was purified by column chromatography ($SiO_2$, Petroleum ether/Ethyl acetate=1/0 to 1/1) to afford tert-butyl 4-((2-(2,6-dioxopiperidin-3-yl)-1,3-dioxoisoindolin-4-yl)amino)piperidine-1-carboxylate (2.1 g, 4.60 mmol, 63.53% yield) as a yellow solid.

MS $(M+H)^+$=457.2

Step 3: Synthesis of 2-(2,6-dioxopiperidin-3-yl)-4-(piperidin-4-ylamino)isoindoline-1,3-dione (64)

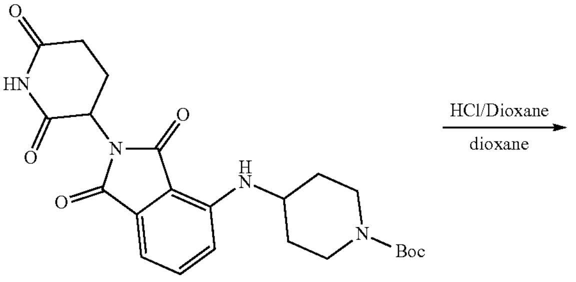

63

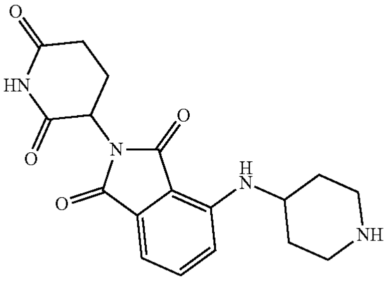

64

To a mixture of tert-butyl 4-((2-(2,6-dioxopiperidin-3-yl)-1,3-dioxoisoindolin-4-yl)amino)piperidine-1-carboxylate (2.1 g, 4.60 mmol) in dioxane (20 mL) was added HCl/dioxane (4 M, 40 mL) at 25° C. and the resulting mixture was stirred at 25° C. for 1 h. LCMS showed starting material was consumed completely and desired mass was detected.

The reaction mixture was concentrated in vacuum to afford 2-(2,6-dioxopiperidin-3-yl)-4-(piperidin-4-ylamino)isoindoline-1,3-dione (1.81 g, crude, HCl salt) as a yellow solid.

MS $(M+H)^+$=357.2

Step 4: Synthesis of tert-butyl (4-(4-((2-(2,6-dioxopiperidin-3-yl)-1,3-dioxoisoindolin-4-yl)amino)piperidin-1-yl)butyl)carbamate (65)

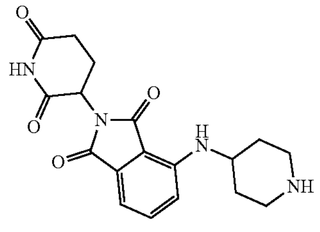

64

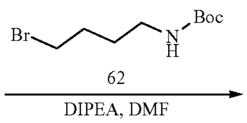

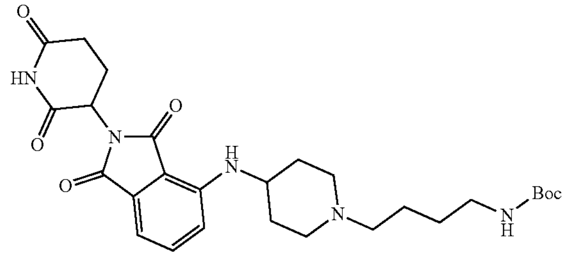

65

To a mixture of 2-(2,6-dioxopiperidin-3-yl)-4-(piperidin-4-ylamino)isoindoline-1,3-dione (1 g, 2.55 mmol, HCl salt) in DMF (10 mL) was added DIPEA (1.97 g, 15.27 mmol, 2.66 mL) and tert-butyl (4-bromobutyl)carbamate (641.87 mg, 2.55 mmol, 521.84 μL) in one portion at 25° C. and the resulting mixture was stirred at 90° C. for 16 h. LCMS showed starting material was consumed completely and desired mass was detected. TLC indicated starting material was consumed completely and three new spots were detected. The reaction mixture was combined with another batch (0.5 g, scale) for work-up, the combined reaction mixture was diluted with $H_2O$ (30 mL) and extracted with EtOAc (30 mL×3). The combined organic layer was washed with brine (30 mL×3), dried over $Na_2SO_4$, filtrated and concentrated. The residue was purified by column chromatography ($SiO_2$, Petroleum ether/Ethyl acetate=2/1 to 0/1) to afford tert-butyl (4-(4-((2-(2,6-dioxopiperidin-3-yl)-1,3-dioxoisoindolin-4-yl)amino)piperidin-1-yl)butyl)carbamate (510 mg, 966.62 μmol, 36.02% yield, 98% purity) as a yellow solid.

MS $(M+H)^+$=528.3

Step 5: Synthesis of 4-((1-(4-aminobutyl)piperidin-4-yl)amino)-2-(2,6-dioxopiperidin-3-yl)isoindoline-1,3-dione (66)

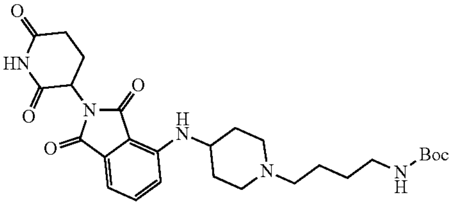

65

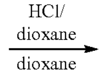

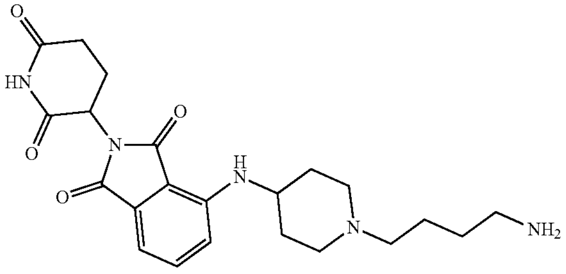

66

To a mixture of tert-butyl (4-(4-((2-(2,6-dioxopiperidin-3-yl)-1,3-dioxoisoindolin-4-yl)amino)piperidin-1-yl)butyl)carbamate (510 mg, 966.62 μmol) in dioxane (2 mL) was added HCl/dioxane (4 M, 10 mL) in one portion at 15° C. and the resulting mixture was stirred at 15° C. for 1 h. LCMS indicated starting material was consumed completely and desired mass was detected. The reaction mixture was concentrated in vacuum to afford 4-((1-(4-aminobutyl)piperidin-4-yl)amino)-2-(2,6-dioxopiperidin-3-yl)isoindoline-1,3-dione (450 mg, crude, HCl salt) as a yellow solid.

MS $(M+H)^+$=428.2

Step 6: Synthesis of (1S,3R,7S,8S,8aR)-8-(2-((2R, 4R)-4-((tert-butyldimethylsilyl)oxy)-6-oxotetrahydro-2H-pyran-2-yl)ethyl)-3,7-dimethyl-1,2,3,7,8, 8a-hexahydronaphthalen-1-yl (4-(4-((2-(2,6-dioxopiperidin-3-yl)-1,3-dioxoisoindolin-4-yl) amino)piperidin-1-yl)butyl)carbamate (Compound 72)

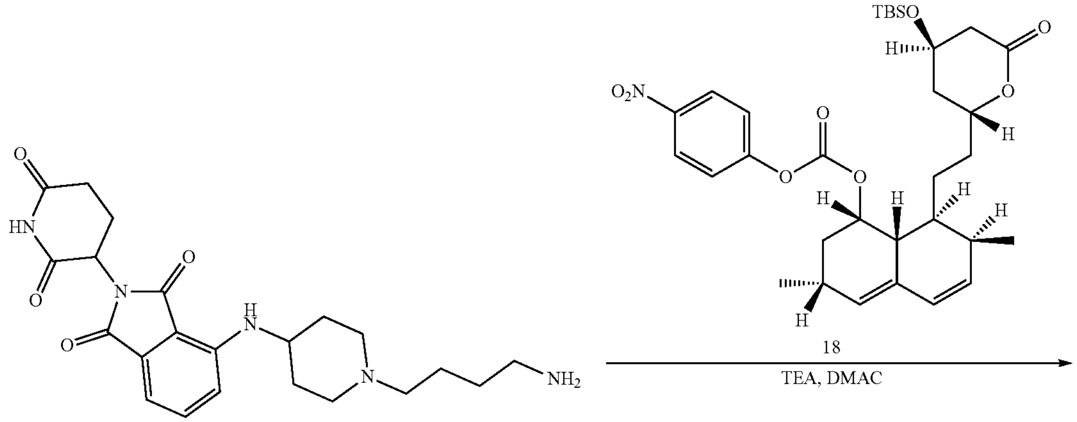

66

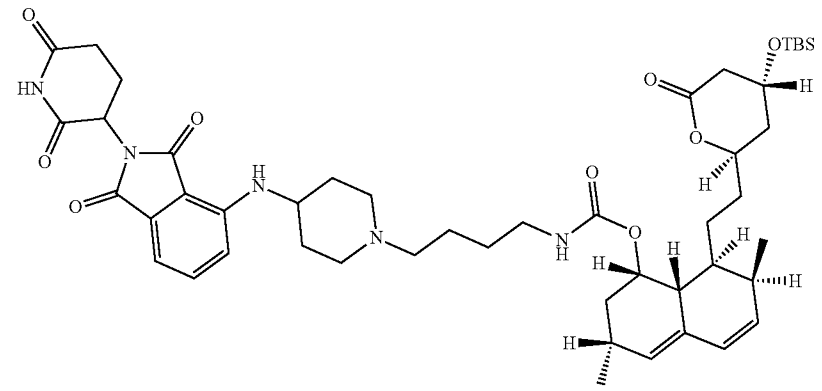

Compound 72

To a mixture of 4-((1-(4-aminobutyl)piperidin-4-yl) amino)-2-(2,6-dioxopiperidin-3-yl)isoindoline-1,3-dione (450 mg, 969.92 μmol, HCl salt) in DMAC (4 mL) was added TEA (392.58 mg, 3.88 mmol, 540.01 μL) and (1S, 3R,7S,8S,8aR)-8-(2-((2R,4R)-4-((tert-butyldimethylsilyl) oxy)-6-oxotetrahydro-2H-pyran-2-yl)ethyl)-3,7-dimethyl-1, 2,3,7,8,8a-hexahydronaphthalen-1-yl (4-nitrophenyl) carbonate (465.39 mg, 775.93 μmol) in one portion at 15° C. and the resulting mixture was stirred at 15° C. for 16 h. LCMS showed starting material was consumed completely and desired mass was detected. The reaction mixture was diluted with $H_2O$ (12 mL) and extracted with EtOAc (12 mL×3). The combined organic layer was washed with brine (12 mL×3), dried over $Na_2SO_4$, filtrated and concentrated. The residue was purified by prep-HPLC (column: Waters Xbridge C18 150*50 mm*10 μm; mobile phase: [water (10 mM $NH_4HCO_3$)-ACN]; B %: 75%-100%, 11.5 min) to afford (1S,3R,7S,8S,8aR)-8-(2-((2R,4R)-4-((tert-butyldimethylsilyl)oxy)-6-oxotetrahydro-2H-pyran-2-yl)ethyl)-3,7-dimethyl-1,2,3,7,8,8a-hexahydronaphthalen-1-yl (4-(4-((2-(2,6-dioxopiperidin-3-yl)-1,3-dioxoisoindolin-4-yl)amino) piperidin-1-yl)butyl)carbamate (611.3 mg, 660.74 μmol, 68.12% yield, 96% purity) as a yellow solid.

MS $(M+H)^+$=888.6

$^1H$ NMR (400 MHz, $CDCl_3$) δ=8.07 (br s, 1H), 7.53-7.46 (m, 1H), 7.10 (d, J=7.1 Hz, 1H), 6.88 (d, J=8.6 Hz, 1H), 6.24 (br d, J=7.7 Hz, 1H), 6.01-5.87 (m, 2H), 5.73 (m, 1H), 5.52 (br s, 1H), 5.18 (br s, 1H), 4.96-4.89 (m, 1H), 4.72-4.65 (m, 1H), 4.33-4.26 (m, 1H), 3.49 (br d, J=9.7 Hz, 1H), 3.26 (br s, 1H), 3.12 (br s, 1H), 2.94-2.70 (m, 4H), 2.66-2.56 (m, 2H), 2.48-2.33 (m, 4H), 2.28-2.09 (m, 5H), 2.03-1.98 (m, 2H), 1.93-1.81 (m, 3H), 1.80-1.58 (m, 8H), 1.51-1.25 (m, 3H), 1.10 (d, J=7.5 Hz, 3H), 0.92-0.89 (m, 12H), 0.09 (s, 6H).

Step 7: Synthesis of (1S,3R,7S,8S,8aR)-8-(2-((2R,4R)-4-hydroxy-6-oxotetrahydro-2H-pyran-2-yl)ethyl)-3,7-dimethyl-1,2,3,7,8,8a-hexahydronaphthalen-1-yl (4-(4-((2-(2,6-dioxopiperidin-3-yl)-1,3-dioxoisoindolin-4-yl)amino)piperidin-1-yl)butyl)carbamate (Compound 73)

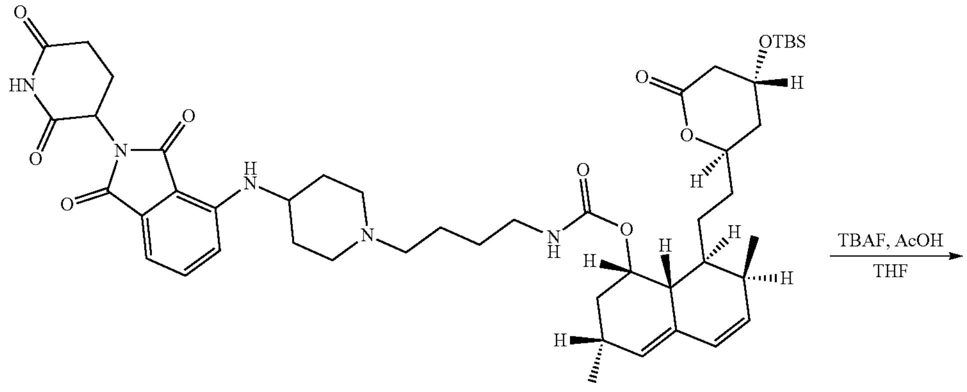

Compound 72

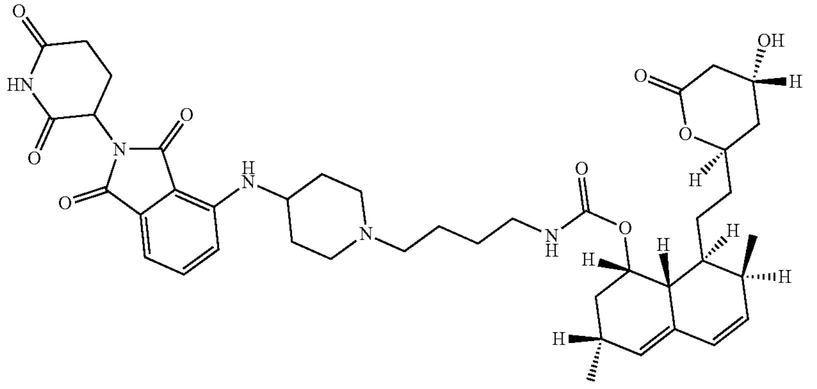

Compound 73

To a mixture of (1S,3R,7S,8S,8aR)-8-(2-((2R,4R)-4-((tert-butyldimethylsilyl)oxy)-6-oxotetrahydro-2H-pyran-2-yl)ethyl)-3,7-dimethyl-1,2,3,7,8,8a-hexahydronaphthalen-1-yl (4-(4-((2-(2,6-dioxopiperidin-3-yl)-1,3-dioxoisoindolin-4-yl)amino)piperidin-1-yl)butyl)carbamate (510 mg, 574.21 μmol) in THE (6 mL) was added AcOH (172.41 mg, 2.87 mmol, 164.20 μL), TBAF (1 M, 2.30 mL) in one portion at 15° C. and the resulting mixture was stirred at 15° C. for 16 h. LCMS showed starting material was consumed completely and desired mass was detected. The reaction mixture was quenched with $NH_4Cl$ (sat.aq, 12 mL) and extracted with EtOAc (12 mL×3). The organic layer was washed with $NH_4Cl$ (sat.aq, 12 mL×3), dried over $Na_2SO_4$, filtrated and concentrated. The residue was purified by prep-HPLC (column: Phenomenex luna C18 150*40 mm*15 μm; mobile phase: [water (0.225% FA)-ACN]; B %: 22%-52%, 11 min) to afford (1S,3R,7S,8S,8aR)-8-(2-((2R,4R)-4-hydroxy-6-oxotetrahydro-2H-pyran-2-yl)ethyl)-3,7-dimethyl-1,2,3,7,8,8a-hexahydronaphthalen-1-yl (4-(4-((2-(2,6-dioxopiperidin-3-yl)-1,3-dioxoisoindolin-4-yl)amino)piperidin-1-yl)butyl)carbamate (36.8 mg, 44.22 μmol, 7.70% yield, 93% purity, FA salt) as a yellow solid.

MS $(M+H)^+=774.5$ $^1H$ NMR (400 MHz, Chloroform-d) δ 8.52-8.09 (m, 1H), 7.55-7.46 (m, 1H), 7.11 (d, J=7.1 Hz, 1H), 6.87 (d, J=8.6 Hz, 1H), 6.25 (d, J=7.6 Hz, 1H), 5.93 (d, J=9.5 Hz, 1H), 5.73 (t, J=8.0 Hz, 1H), 5.51 (s, 2H), 5.19 (s, 1H), 4.92 (dd, J=12.0, 5.4 Hz, 1H), 4.74-4.58 (m, 1H), 4.37-4.26 (m, 1H), 3.61-3.54 (m, 1H), 3.33-3.21 (m, 2H), 3.20-3.09 (m, 1H), 3.08-2.95 (m, 2H), 2.93-2.83 (m, 2H), 2.83-2.72 (m, 3H), 2.70-2.67 (m, 1H), 2.65-2.62 (m, 1H), 2.62-2.55 (m, 2H), 2.52-2.40 (m, 3H), 2.39-2.32 (m, 1H), 2.24 (d, J=11.8 Hz, 1H), 2.18-2.07 (m, 3H), 1.97 (d, J=14.3 Hz, 1H), 1.90-1.82 (m, 1H), 1.79-1.71 (m, 3H), 1.69-1.60 (m, 4H), 1.48-1.37 (m, 3H), 1.08 (d, J=7.4 Hz, 3H), 0.89 (d, J=6.9 Hz, 3H).

Example 74 & Example 75. Synthesis of (1S,3R,7S,8S,8aR)-8-(2-((2R,4R)-4-((tert-butyldimethylsilyl)oxy)-6-oxotetrahydro-2H-pyran-2-yl)ethyl)-3,7-dimethyl-1,2,3,7,8,8a-hexahydronaphthalen-1-yl (5-(2-((2-(2,6-dioxopiperidin-3-yl)-1,3-dioxoisoindolin-4-yl)oxy)acetamido)pentyl)carbamate (Compound 74) and (1S,3R,7S,8S,8aR)-8-(2-((2R,4R)-4-hydroxy-6-oxotetrahydro-2H-pyran-2-yl)ethyl)-3,7-dimethyl-1,2,3,7,8,8a-hexahydronaphthalen-1-yl (5-(2-((2-(2,6-dioxopiperidin-3-yl)-1,3-dioxoisoindolin-4-yl)oxy)acetamido)pentyl)carbamate (Compound 75)

Step 1: Synthesis of 2-((2-(2,6-dioxopiperidin-3-yl)-1,3-dioxoisoindolin-4-yl)oxy)acetic acid (68)

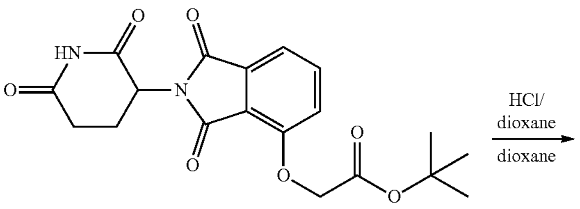

67

-continued

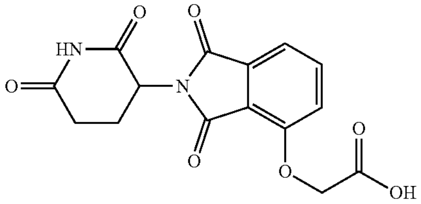

68

To a mixture of tert-butyl 2-((2-(2,6-dioxopiperidin-3-yl)-1,3-dioxoisoindolin-4-yl)oxy)acetate (7 g, 18.02 mmol) in dioxane (10 mL) was added HCl/dioxane (4 M, 35.00 mL) in one portion at 15° C. and the resulting mixture was stirred at 15° C. for 6 h. LCMS showed starting material was consumed completely and desired mass was detected. The reaction mixture was concentrated in vacuum to afford 2-((2-(2,6-dioxopiperidin-3-yl)-1,3-dioxoisoindolin-4-yl)oxy)acetic acid (6.8 g, crude) as a white solid.

MS $(M+H)^+$=333.3

Step 2: Synthesis of tert-butyl N-[5-[[2-[2-(2,6-dioxo-3-piperidyl)-1,3-dioxo-isoindolin-4-yl]oxyacetyl]amino]pentyl]carbamate (69)

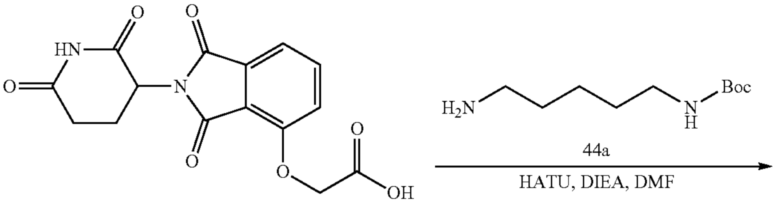

68

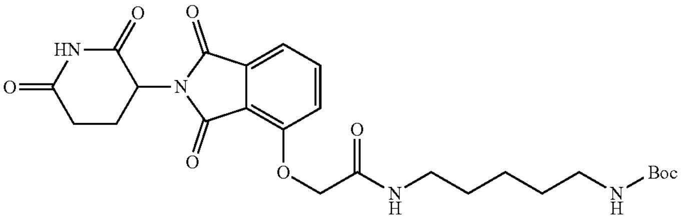

69

To the solution of 2-[2-(2,6-dioxo-3-piperidyl)-1,3-dioxo-isoindolin-4-yl]oxyacetic acid (1 g, 3.01 mmol) and HATU (2.29 g, 6.02 mmol), DIPEA (1.17 g, 9.03 mmol, 1.57 mL) in DMF (10 mL) was added tert-butyl N-(5-aminopentyl) carbamate (669.72 mg, 3.31 mmol, 689.01 μL) and the resulting mixture was stirred at 25° C. for 2 h. LCMS showed 31% desired mass was detected. The mixture was poured into water (50 mL) and extracted with EtOAc (50 mL×2), Combined extracts were washed with brine (100 mL), dried over $Na_2SO_4$, filtered and concentrated. The residue was purified by silica gel chromatography (Petroleum ether:Ethyl acetate 1:1 to 1:4) to afford tert-butyl N-[5-[[2-[2-(2,6-dioxo-3-piperidyl)-1,3-dioxo-isoindolin-4-yl]oxyacetyl]amino]pentyl]carbamate (0.7 g, 1.19 mmol, 39.62% yield, 88% purity) as white solid. MS $(M+H)^+$=417.1

Step 3: Synthesis of N-(5-aminopentyl)-2-[2-(2,6-dioxo-3-piperidyl)-1,3-dioxo-isoindolin-4-yl]oxy-acetamide (70)

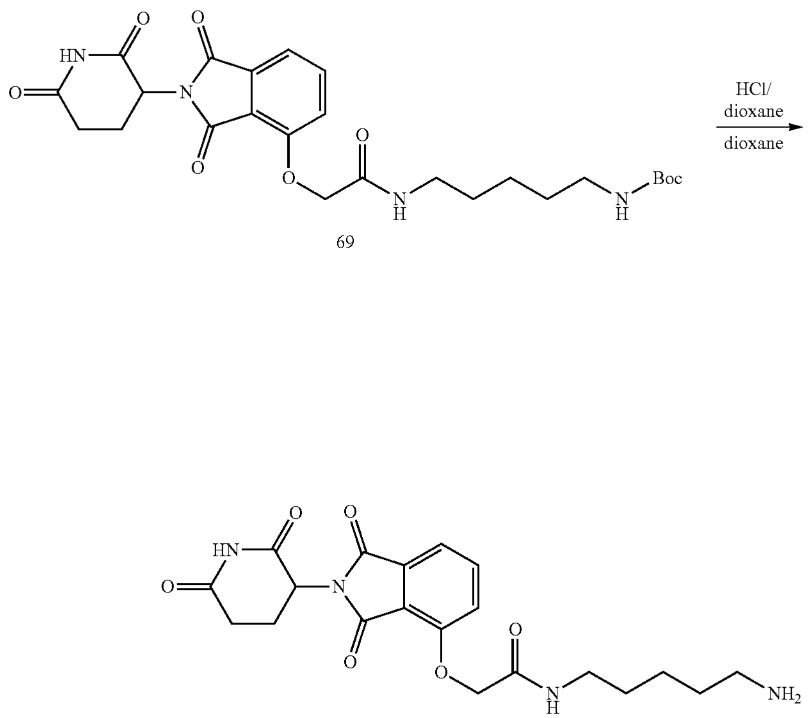

69

70

To a solution of tert-butyl N-[5-[[2-[2-(2,6-dioxo-3-piperidyl)-1,3-dioxo-isoindolin-4-yl]oxyacetyl]amino]pentyl] carbamate (0.7 g, 1.36 mmol) in dioxane (10 mL) was added HCl/dioxane (4 M, 10 mL) and the resulting mixture was stirred at 25° C. for 12 h. LCMS showed 97% desired mass was detected. The mixture was concentrated under vacuum to afford N-(5-aminopentyl)-2-[2-(2,6-dioxo-3-piperidyl)-1,3-dioxo-isoindolin-4-yl]oxy-acetamide (0.6 g, 1.32 mmol, 97.76% yield, HCl salt) as yellow solid. MS $(M+H)^+$=417.1

Step 4: Synthesis of (1S,3R,7S,8S,8aR)-8-(2-((2R,4R)-4-((tert-butyldimethylsilyl)oxy)-6-oxotetrahydro-2H-pyran-2-yl)ethyl)-3,7-dimethyl-1,2,3,7,8,8a-hexahydronaphthalen-1-yl (5-(2-((2-(2,6-dioxopiperidin-3-yl)-1,3-dioxoisoindolin-4-yl)oxy)acetamido)pentyl)carbamate (Compound 74)

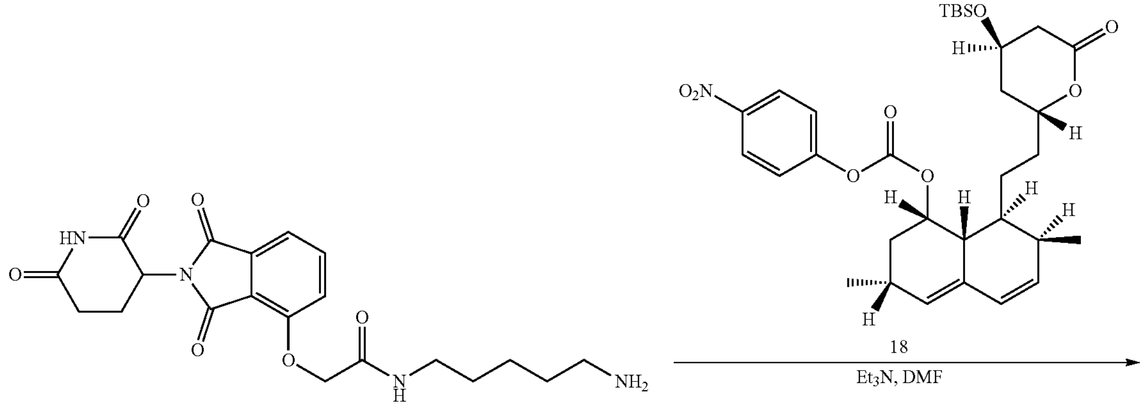

70

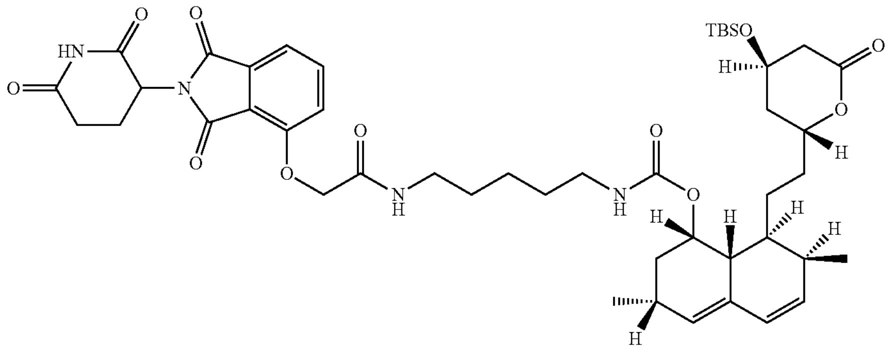

Compound 74

To the solution of [(1S,3R,7S,8S,8aR)-8-[2-[(2R,4R)-4-[tert-butyl(dimethyl)silyl]oxy-6-oxo-tetrahydropyran-2-yl]ethyl]-3,7-dimethyl-1,2,3,7,8,8a-hexahydronaphthalen-1-yl] (4-nitrophenyl) carbonate (794.61 mg, 1.32 mmol) and N-(5-aminopentyl)-2-[2-(2,6-dioxo-3-piperidyl)-1,3-dioxo-isoindolin-4-yl]oxy-acetamide (600 mg, 1.32 mmol, HCl salt) in DMF (10 mL) was added TEA (402.18 mg, 3.97 mmol, 553.20 μL) and the resulting mixture was stirred at 25° C. for 12 h. LCMS showed 57% desired mass was detected. The mixture was poured into water (50 mL) and extracted with EtOAc (50 mL×3). The combined organic layer was washed with brine (50 mL), dried over $Na_2SO_4$, filtered and concentrated. The residue was purified by prep-HPLC (column: Phenomenex luna C18 150*40 mm*15 μm; mobile phase: [water (0.225% FA)-ACN]; B %: 66%-96%, 10 min) to afford (1S,3R,7S,8S,8aR)-8-(2-((2R,4R)-4-((tert-butyldimethylsilyl)oxy)-6-oxotetrahydro-2H-pyran-2-yl)ethyl)-3,7-dimethyl-1,2,3,7,8,8a-hexahydronaphthalen-1-yl (5-(2-((2-(2,6-dioxopiperidin-3-yl)-1,3-dioxoisoindolin-4-yl)oxy)acetamido)pentyl)carbamate (308.2 mg, 326.79 μmol, 24.67% yield, 93% purity) as white solid.

MS $(M+H)^+$=877.2.

$^1H$ NMR (400 MHz, $CDCl_3$) δ=8.85 (br s, 1H), 7.76 (t, J=7.8 Hz, 1H), 7.56 (br d, J=7.2 Hz, 2H), 7.20 (d, J=8.2 Hz, 1H), 5.97 (br d, J=9.8 Hz, 1H), 5.81-5.72 (m, 1H), 5.51 (br s, 1H), 5.16 (br s, 1H), 5.05 (br s, 1H), 4.91 (br s, 1H), 4.71-4.58 (m, 3H), 4.33-4.23 (m, 1H), 3.54-3.41 (m, 1H), 3.36-3.04 (m, 3H), 2.94-2.75 (m, 3H), 2.69-2.49 (m, 2H), 2.47-2.07 (m, 5H), 1.90-1.72 (m, 4H), 1.72-1.63 (m, 3H), 1.54-1.37 (m, 6H), 1.35-1.23 (m, 1H), 1.07 (br d, J=7.2 Hz, 3H), 0.92-0.85 (m, 12H), 0.07 (s, 6H).

Step 5: Synthesis of (1S,3R,7S,8S,8aR)-8-(2-((2R,4R)-4-hydroxy-6-oxotetrahydro-2H-pyran-2-yl)ethyl)-3,7-dimethyl-1,2,3,7,8,8a-hexahydronaphthalen-1-yl (5-(2-((2-(2,6-dioxopiperidin-3-yl)-1,3-dioxoisoindolin-4-yl)oxy)acetamido)pentyl) carbamate (Compound 75)

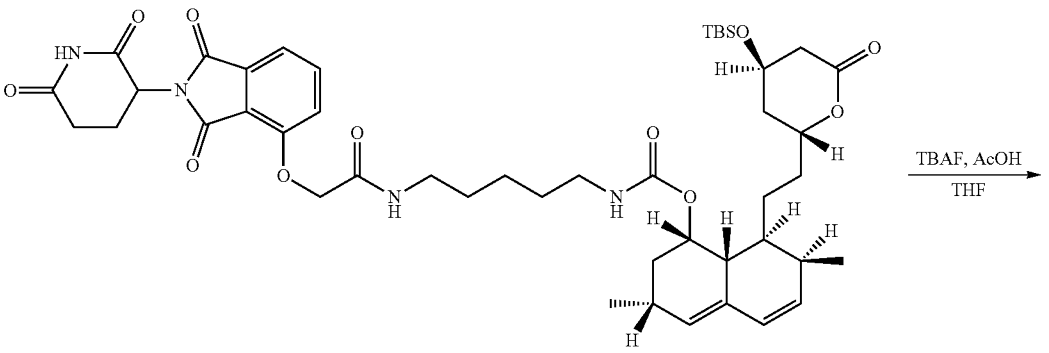

Compound 74

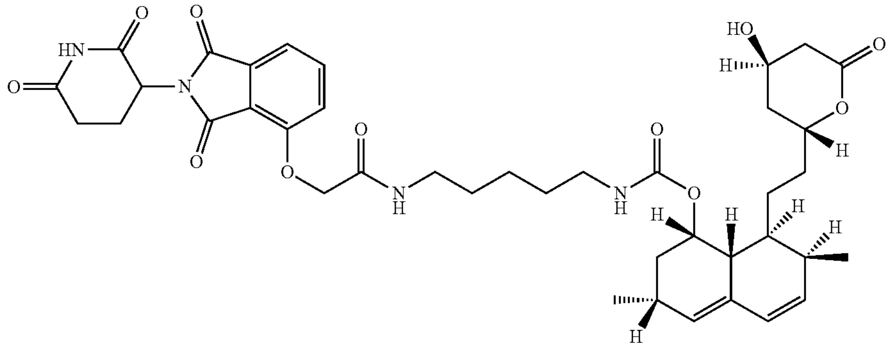

Compound 75

To the solution of (1S,3R,7S,8S,8aR)-8-(2-((2R,4R)-4-((tert-butyldimethylsilyl)oxy)-6-oxotetrahydro-2H-pyran-2-yl)ethyl)-3,7-dimethyl-1,2,3,7,8,8a-hexahydronaphthalen-1-yl (5-(2-((2-(2,6-dioxopiperidin-3-yl)-1,3-dioxoisoindolin-4-yl)oxy)acetamido)pentyl)carbamate (0.2 g, 228.02 μmol) in THF (3 mL) was added AcOH (68.47 mg, 1.14 mmol, 65.21 μL), TBAF (1 M, 912.09 μL) and the resulting mixture was stirred at 25° C. for 12 h. LCMS showed 82% desired mass was detected. The mixture was poured into water (20 mL) and extracted with EtOAc (20 mL×3). The combined organic layer was washed by brine (50 mL), dried over $Na_2SO_4$, filtered and concentrated. The residue was purified by prep-TLC (Petroleum ether/Ethyl acetate=10/1) to afford (1S,3R,7S,8S,8aR)-8-(2-((2R,4R)-4-hydroxy-6-oxotetrahydro-2H-pyran-2-yl)ethyl)-3,7-dimethyl-1,2,3,7,8,8a-hexahydronaphthalen-1-yl (5-(2-((2-(2,6-dioxopiperidin-3-yl)-1,3-dioxoisoindolin-4-yl)oxy)acetamido)pentyl)carbamate (105.5 mg, 132.77 μmol, 58.23% yield, 96% purity) as white solid.

MS $(M+H)^+$=763.4

(m, 2H), 7.24-7.16 (m, 1H), 5.97 (d, J=9.6 Hz, 1H), 5.83-5.72 (m, 1H), 5.51 (br s, 1H), 5.30-5.17 (m, 1H), 5.15-4.96 (m, 1H), 4.75 (br s, 1H), 4.70-4.55 (m, 3H), 4.36-4.20 (m, 1H), 3.50-3.41 (m, 1H), 3.33-3.16 (m, 3H), 2.95-2.74 (m, 3H), 2.73-2.51 (m, 2H), 2.48-2.31 (m, 2H), 2.29-2.12 (m, 2H), 2.10-1.93 (m, 2H), 1.92-1.78 (m, 2H), 1.76-1.64 (m, 3H), 1.61-1.24 (m, 8H), 1.11-1.02 (m, 3H), 0.84-0.80 (m, 3H)

Example 76 & Example 77. Synthesis of (1S,3R,7S,8S,8aR)-8-(2-((2R,4R)-4-((tert-butyldimethylsilyl)oxy)-6-oxotetrahydro-2H-pyran-2-yl)ethyl)-3,7-dimethyl-1,2,3,7,8,8a-hexahydronaphthalen-1-yl (8-((2-(2,6-dioxopiperidin-3-yl)-1,3-dioxoisoindolin-4-yl)amino)-8-oxooctyl)carbamate (Compound 76) and Synthesis of (1S,3R,7S,8S,8aR)-8-(2-((2R,4R)-4-hydroxy-6-oxotetrahydro-2H-pyran-2-yl)ethyl)-3,7-dimethyl-1,2,3,7,8,8a-hexahydronaphthalen-1-yl (8-((2-(2,6-dioxopiperidin-3-yl)-1,3-dioxoisoindolin-4-yl)amino)-8-oxooctyl)carbamate (Compound 77)

Step 1: Synthesis of tert-butyl (8-((2-(2,6-dioxopiperidin-3-yl)-1,3-dioxoisoindolin-4-yl)amino)-8-oxooctyl)carbamate (72)

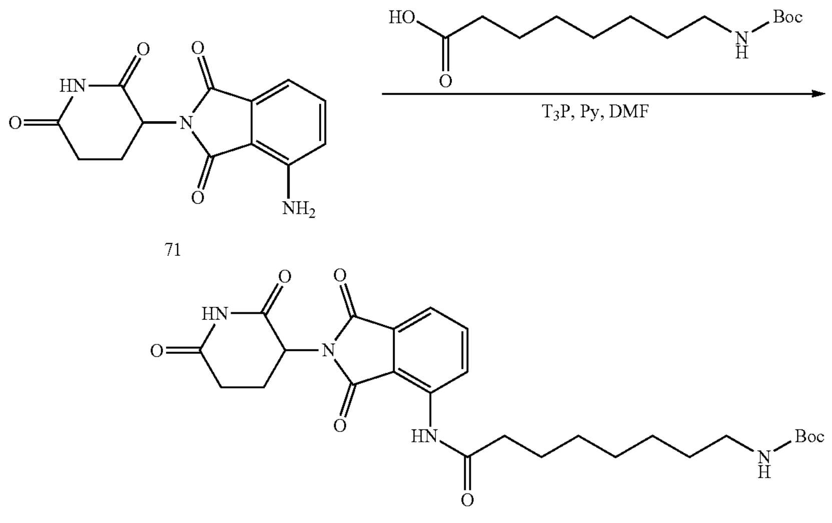

71

72

To a mixture of 4-amino-2-(2,6-dioxopiperidin-3-yl) isoindoline-1,3-dione (1 g, 3.66 mmol) in DMF (50 mL) was added 8-((tert-butoxycarbonyl)amino)octanoic acid (1.90 g, 7.32 mmol) at 15° C., then $T_3P$ (13.97 g, 21.96 mmol, 13.06 mL, 50% purity) and Py (2.89 g, 36.60 mmol, 2.95 mL) was added. The reaction mixture was stirred at 80° C. for 16 h. LCMS showed starting material was consumed completely and desired mass was detected. TLC ($SiO_2$, Petroleum ether:Ethyl acetate=1:1) indicated starting material was consumed completely and two new spots were detected. The reaction mixture was diluted with $H_2O$ (150 mL) and extracted with EtOAc (150 mL×3). The organic layer was washed with brine (150 mL×3). The organic layer was dried over $Na_2SO_4$, filtrated and concentrated. The residue was purified by column chromatography ($SiO_2$, Petroleum ether/Ethyl acetate=8/1 to 1/1) to afford tert-butyl (8-((2-(2,6-dioxopiperidin-3-yl)-1,3-dioxoisoindolin-4-yl)amino)-8-oxooctyl)carbamate (1.7 g, 3.30 mmol, 90.27% yield) as a yellow solid.

MS $(M+H)^+$=515.2

Step 2: Synthesis of 8-amino-N-(2-(2,6-dioxopiperidin-3-yl)-1,3-dioxoisoindolin-4-yl)octanamide (73)

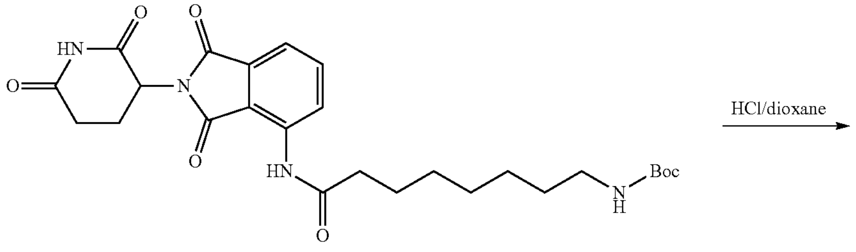

72

-continued

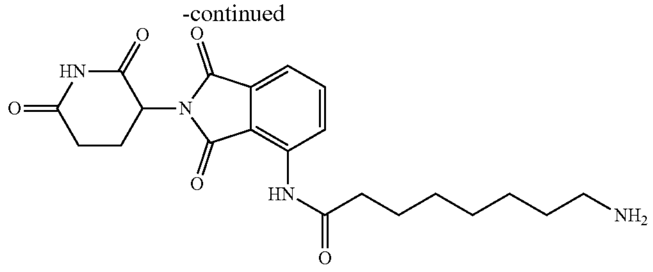

73

To a mixture of tert-butyl (8-((2-(2,6-dioxopiperidin-3-yl)-1,3-dioxoisoindolin-4-yl)amino)-8-oxooctyl)carbamate (1.7 g, 3.30 mmol) in dioxane (10 mL) was added HCl/dioxane (4 M, 20 mL) in one portion at 25° C. and the resulting mixture was stirred at 25° C. for 1 h. LCMS showed starting material was consumed completely and desired mass was detected. The reaction mixture was concentrated in vacuum to afford 8-amino-N-(2-(2,6-dioxopiperidin-3-yl)-1,3-dioxoisoindolin-4-yl)octanamide (1.49 g, crude, HCl salt) as a yellow oil.

MS $(M+H)^+$=415.2

Step 3: Synthesis of (1S,3R,7S,8S,8aR)-8-(2-((2R,4R)-4-((tert-butyldimethylsilyl)oxy)-6-oxotetrahydro-2H-pyran-2-yl)ethyl)-3,7-dimethyl-1,2,3,7,8,8a-hexahydronaphthalen-1-yl (8-((2-(2,6-dioxopiperidin-3-yl)-1,3-dioxoisoindolin-4-yl)amino)-8-oxooctyl)carbamate (Compound 76)

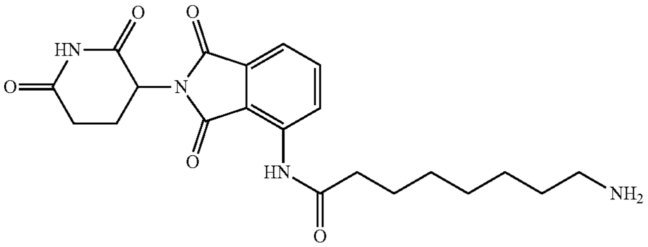

73

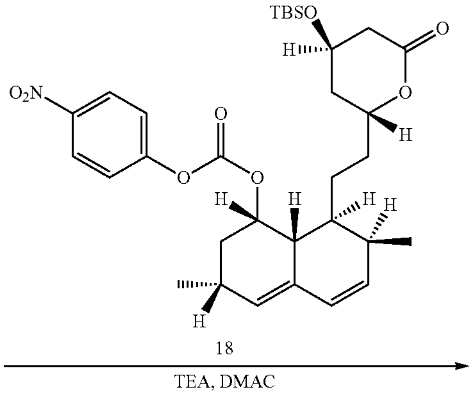

18

TEA, DMAC

-continued

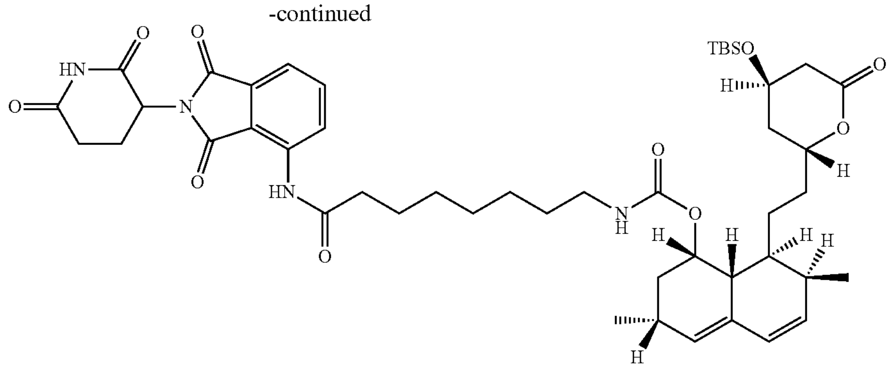

Compound 76

To a mixture of 8-amino-N-(2-(2,6-dioxopiperidin-3-yl)-1,3-dioxoisoindolin-4-yl)octanamide (1.49 g, 3.30 mmol, HCl salt) and (1S,3R,7S,8S,8aR)-8-(2-((2R,4R)-4-((tert-butyldimethylsilyl)oxy)-6-oxotetrahydro-2H-pyran-2-yl) ethyl)-3,7-dimethyl-1,2,3,7,8,8a-hexahydronaphthalen-1-yl (4-nitrophenyl) carbonate (3.37 g, 3.60 mmol) in DMAC (15 mL) was added TEA (1.00 g, 9.91 mmol, 1.38 mL) in one portion at 15° C. and the resulting mixture was stirred at 15° C. for 16 h. LCMS showed starting material was consumed completely and desired mass was detected. The reaction mixture was diluted with $H_2O$ (30 mL) and extracted with EtOAc (30 mL×3). The organic layer was dried over $Na_2SO_4$, filtrated and concentrated. The residue was purified by prep-HPLC (column: Waters Xbridge C18 150*50 mm*10 μm; mobile phase: [water (10 mM $NH_4HCO_3$)-ACN]; %: 70%-100%, 11.5 min) to afford (1S,3R,7S,8,8aR)-8-(2-((2R,4R)-4-((tert-butyldimethylsilyl)oxy)-6-oxo-tetrahydro-2H-pyran-2-yl)ethyl)-3,7-dimethyl-1,2,3,7,8,8a-hexahydronaphthalen-1-yl (8-((2-(2,6-dioxopiperidin-3-yl)-1,3-dioxoisoindolin-4-yl)amino)-8-oxooctyl)carbamate (560 mg, 620.71 μmol, 18.78% yield, 97% purity) as a white solid.

MS $(M+H)^+$=875.8

$^1H$ NMR (400 MHz, Chloroform-d) δ 9.43 (s, 1H), 8.82 (d, J=8.4 Hz, 1H), 8.29-8.15 (m, 1H), 7.71 (dd, J=8.5, 7.3 Hz, 1H), 7.55 (d, J=7.3 Hz, 1H), 5.97 (d, J=9.6 Hz, 1H), 5.81-5.73 (m, 1H), 5.51 (s, 1H), 5.17 (s, 1H), 5.02-4.91 (m, 1H), 4.85-4.74 (m, 1H), 4.69-4.57 (m, 1H), 4.28 (s, 1H), 3.28-3.16 (m, 1H), 3.12-3.03 (m, 1H), 2.93-2.86 (m, 1H), 2.84-2.75 (m, 2H), 2.64-2.52 (m, 2H), 2.48-2.33 (m, 4H), 2.27-2.15 (m, 2H), 2.10 (d, J=14.9 Hz, 1H), 1.92-1.80 (m, 3H), 1.79-1.70 (m, 3H), 1.69-1.62 (m, 2H), 1.50-1.43 (m, 2H), 1.40-1.28 (m, 8H), 1.07 (dd, J=7.4, 2.2 Hz, 3H), 0.90-0.86 (m, 12H), 0.08 (s, 6H).

Step 4: Synthesis of (1S,3R,7S,8S,8aR)-8-(2-((2R,4R)-4-hydroxy-6-oxotetrahydro-2H-pyran-2-yl) ethyl)-3,7-dimethyl-1,2,3,7,8,8a-hexahydronaphthalen-1-yl (8-((2-(2,6-dioxopiperidin-3-yl)-1,3-dioxoisoindolin-4-yl)amino)-8-oxooctyl)carbamate (Compound 77)

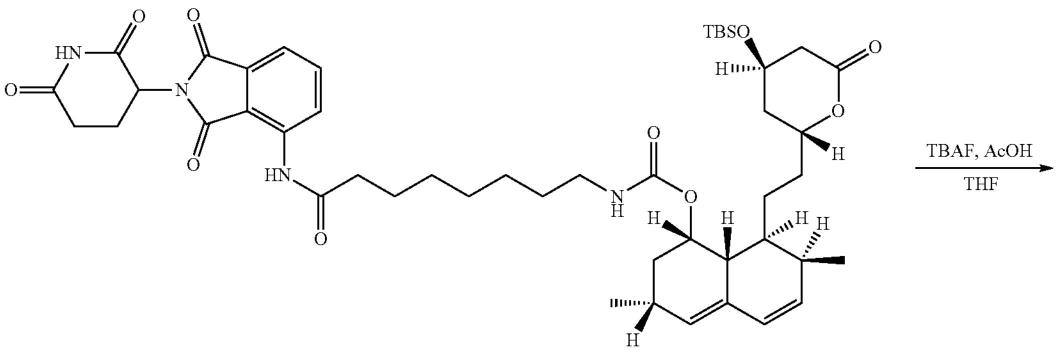

Compound 76

-continued

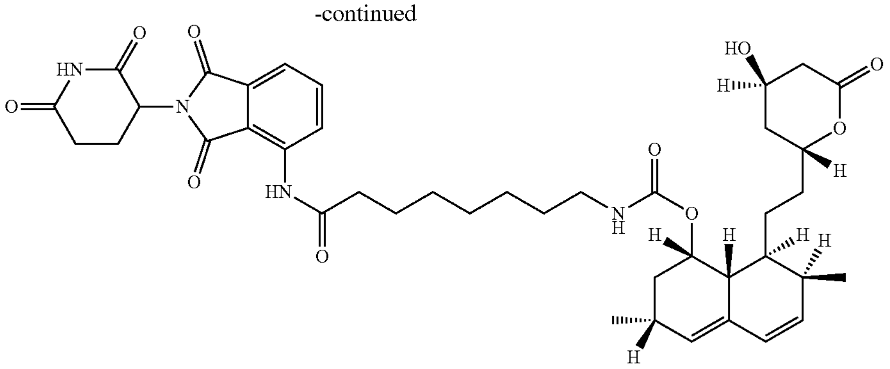

Compound 77

To a mixture of (1S,3R,7S,8S,8aR)-8-(2-((2R,4R)-4-((tert-butyldimethylsilyl)oxy)-6-oxotetrahydro-2H-pyran-2-yl)ethyl)-3,7-dimethyl-1,2,3,7,8,8a-hexahydronaphthalen-1-yl (8-((2-(2,6-dioxopiperidin-3-yl)-1,3-dioxoisoindolin-4-yl)amino)-8-oxooctyl)carbamate (456 mg, 521.06 μmol) in THE (5 mL) was added TBAF (1 M, 2.08 mL), AcOH (156.45 mg, 2.61 mmol, 149.00 μL) drop-wise at 15° C. and the resulting mixture was stirred at 15° C. for 16 h. LCMS showed starting material was consumed completely and desired mass was detected. TLC ($SiO_2$, Dichloromethane: Methanol=10:1) indicated starting material was consumed completely and one major new spot was detected. The reaction mixture was quenched with saturated $NH_4Cl$ (15 mL) and extracted with EtOAc (15 mL×3). The organic layer was dried over $Na_2SO_4$, filtrated and concentrated. The residue was purified by column chromatography ($SiO_2$, Dichloromethane/Methanol=1/0 to 8/1) followed by prep-HPLC (column: Phenomenex luna C18 150*40 mm*15 μm; mobile phase: [water (0.225% FA)-ACN]; B %: 49%-79%, 10 min) to afford (1S,3R,7S,8S,8aR)-8-(2-((2R,4R)-4-hydroxy-6-oxotetrahydro-2H-pyran-2-yl)ethyl)-3,7-dimethyl-1,2,3,7,8,8a-hexahydronaphthalen-1-yl (8-((2-(2,6-dioxopiperidin-3-yl)-1,3-dioxoisoindolin-4-yl)amino)-8-oxooctyl) carbamate (132.4 mg, 163.57 μmol, 31.39% yield, 94% purity) as a white solid.

MS $(M+H)^+$=761.7

$^1H$ NMR (400 MHz, Chloroform-d) δ 9.50-9.39 (m, 1H), 8.79 (d, J=8.5 Hz, 1H), 7.71 (t, J=7.9 Hz, 1H), 7.55 (d, J=7.3 Hz, 1H), 5.96 (d, J=9.6 Hz, 1H), 5.77 (t, J=7.5 Hz, 1H), 5.54-5.45 (m, 1H), 5.35-5.15 (m, 1H), 5.09-4.91 (m, 1H), 4.81 (s, 1H), 4.70-4.55 (m, 1H), 4.40-4.18 (m, 1H), 3.22-3.03 (m, 2H), 2.97-2.86 (m, 1H), 2.86-2.66 (m, 3H), 2.66-2.55 (m, 1H), 2.51-2.30 (m, 4H), 2.26-2.11 (m, 2H), 2.09-1.91 (m, 3H), 1.90-1.77 (m, 4H), 1.67-1.58 (m, 2H), 1.50-1.41 (m, 2H), 1.40-1.25 (m, 8H), 1.06 (d, J=7.3 Hz, 3H), 0.88 (dd, J=7.0, 2.2 Hz, 3H).

Example 78 & Example 79. Synthesis of (1S,3R,7S,8S,8aR)-8-(2-((2R,4R)-4-((tert-butyldimethylsilyl)oxy)-6-oxotetrahydro-2H-pyran-2-yl)ethyl)-3,7-dimethyl-1,2,3,7,8,8a-hexahydronaphthalen-1-yl (3-((2-((2-(2,6-dioxopiperidin-3-yl)-1,3-dioxoisoindolin-4-yl)oxy)acetamido)methyl)benzyl)carbamate (Compound 78) and (1S,3R,7S,8S,8aR)-8-(2-((2R,4R)-4-hydroxy-6-oxotetrahydro-2H-pyran-2-yl)ethyl)-3,7-dimethyl-1,2,3,7,8,8a-hexahydronaphthalen-1-yl (3-((2-((2-(2,6-dioxopiperidin-3-yl)-1,3-dioxoisoindolin-4-yl)oxy)acetamido)methyl)benzyl)carbamate (Compound 79)

Step 1: Synthesis of tert-butyl (3-((2-((2-(2,6-dioxopiperidin-3-yl)-1,3-dioxoisoindolin-4-yl)oxy)acetamido)methyl)benzyl)carbamate (74)

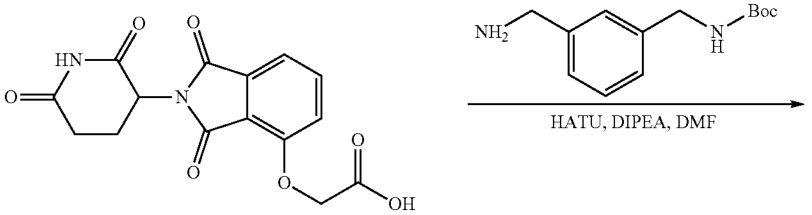

-continued

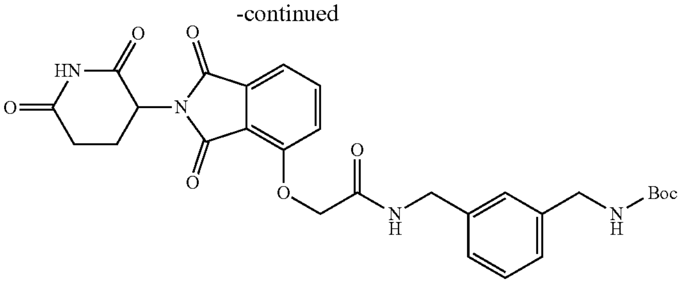

74

To a mixture of 2-((2-(2,6-dioxopiperidin-3-yl)-1,3-dioxoisoindolin-4-yl)oxy)acetic acid (790 mg, 2.38 mmol) and tert-butyl (3-(aminomethyl)benzyl)carbamate (674.23 mg, 2.85 mmol) in DMF (10 mL) was added HATU (994.45 mg, 2.62 mmol) and DIPEA (921.87 mg, 7.13 mmol, 1.24 mL) in one portion at 25° C. and the resulting mixture was stirred at 25° C. for 2 h. LCMS showed the starting material was consumed completely and desired mass was detected. TLC ($SiO_2$, Dichloromethane:Methanol=20:1) indicated the starting material was consumed completely and three new spots were detected. The reaction mixture was diluted with $H_2O$ (30 mL) and extracted with EtOAc (30 mL×3). The organic layer was washed with brine (30 mL×3). The organic layer was dried over $Na_2SO_4$, filtrated and concentrated. The residue was purified by column chromatography ($SiO_2$, Petroleum ether/Ethyl acetate=5/1 to 1/3) to afford tert-butyl (3-((2-((2-(2,6-dioxopiperidin-3-yl)-1,3-dioxoisoindolin-4-yl)oxy)acetamido)methyl)benzyl)carbamate (1.2 g, 2.05 mmol, 86.17% yield, 94% purity) as a yellow solid.

MS $(M+H)^+$=551.2

Step 2: Synthesis of N-(3-(aminomethyl)benzyl)-2-((2-(2,6-dioxopiperidin-3-yl)-1,3-dioxoisoindolin-4-yl)oxy)acetamide (75)

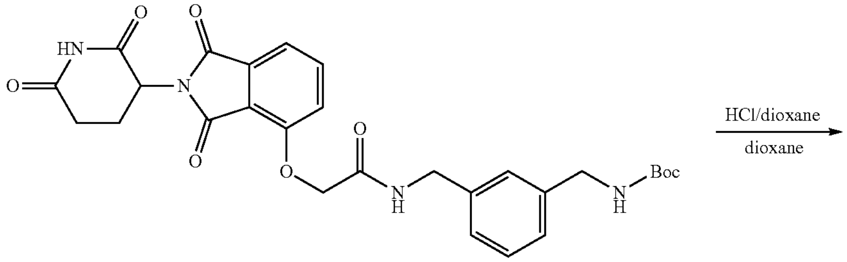

74

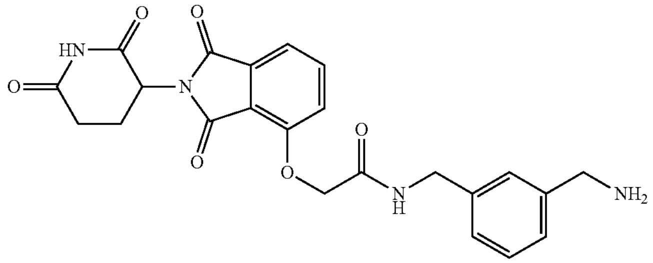

75

To a mixture of tert-butyl (3-((2-((2-(2,6-dioxopiperidin-3-yl)-1,3-dioxoisoindolin-4-yl)oxy)acetamido)methyl)benzyl)carbamate (1.2 g, 2.18 mmol) in dioxane (10 mL) was added HCl/dioxane (4 M, 20 mL) in one portion at 25° C. and the resulting mixture was stirred at 25° C. for 1 h. LCMS showed starting material was consumed completely and desired mass was detected. The reaction mixture was concentrated in vacuum to afford N-(3-(aminomethyl)benzyl)-2-((2-(2,6-dioxopiperidin-3-yl)-1,3-dioxoisoindolin-4-yl)oxy)acetamide (1.06 g, crude, HCl) as a yellow solid.

MS $(M+H)^+$=451.2

Step 3: Synthesis of (1S,3R,7S,8S,8aR)-8-(2-((2R,4R)-4-((tert-butyldimethylsilyl)oxy)-6-oxotetrahydro-2H-pyran-2-yl)ethyl)-3,7-dimethyl-1,2,3,7,8,8a-hexahydronaphthalen-1-yl (3-((2-((2-(2,6-dioxopiperidin-3-yl)-1,3-dioxoisoindolin-4-yl)oxy)acetamido)methyl)benzyl)carbamate (Compound 78)

(2.04 g, 2.18 mmol, 34.02 μL) in DMAC (15 mL) was added TEA (660.87 mg, 6.53 mmol, 909.04 μL) in one portion at 25° C. and the resulting mixture was stirred at 25° C. for 16 h. LCMS showed starting material was consumed completely and desired mass was detected. The reaction mixture was diluted with $H_2O$ (30 mL) and extracted with EtOAc (30 mL×3). The organic layer was dried over $Na_2SO_4$, filtrated and concentrated. The residue was purified by prep-HPLC (column: Waters Xbridge C18 150*50 mm*10 μm; mobile phase: [water (10 mM $NH_4HCO_3$)-ACN]; B %: 60%-90%, 11.5 min) to afford (1S,3R,7S,8S,8aR)-8-(2-((2R,4R)-4-((tert-butyldimethylsilyl)oxy)-6-oxotetrahydro-2H-pyran-2-yl)ethyl)-3,7-dimethyl-1,2,3,7,8,8a-hexahydronaphthalen-1-yl (3-((2-((2-(2,6-dioxopiperidin-3-yl)-1,3-dioxoisoindolin-4-yl)oxy)acetamido)methyl)benzyl) carbamate (965 mg, 1.01 mmol, 46.22% yield, 95% purity) as a white solid.

MS $(M+H)^+$=911.9

$^1H$ NMR (400 MHz, $CDCl_3$) δ=7.88 (br s, 1H), 7.77-7.72 (m, 1H), 7.55 (d, J=7.4 Hz, 1H), 7.27-7.04 (m, 5H), 5.96 (br

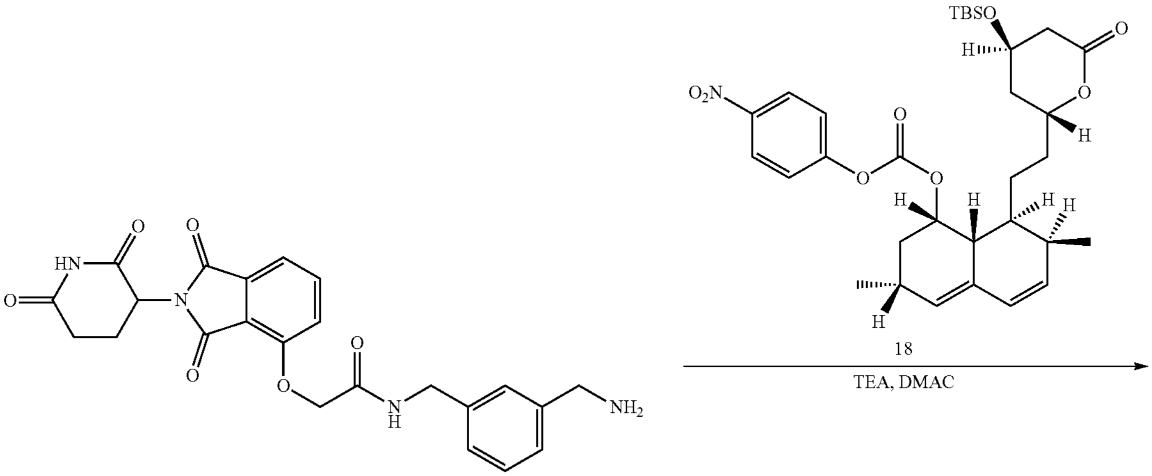

75

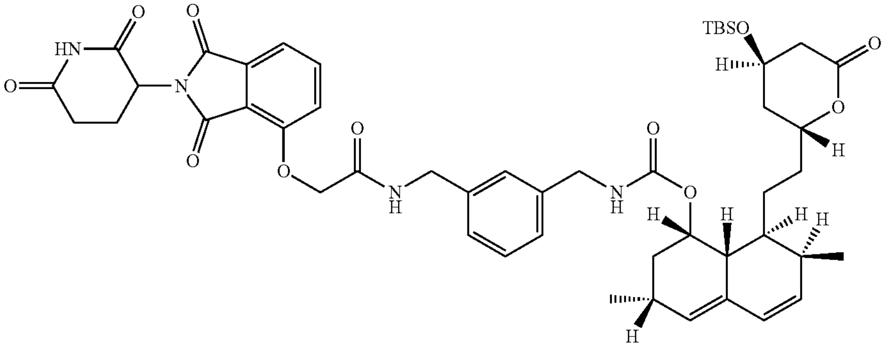

Compound 78

To a mixture of tert-butyl (3-((2-((2-(2,6-dioxopiperidin-3-yl)-1,3-dioxoisoindolin-4-yl)oxy)acetamido)methyl)benzyl)carbamate (1.06 g, 2.18 mmol, HCl salt) and (1S,3R,7S,8,8aR)-8-(2-((2R,4R)-4-((tert-butyldimethylsilyl)oxy)-6-oxotetrahydro-2H-pyran-2-yl)ethyl)-3,7-dimethyl-1,2,3,7,8,8a-hexahydronaphthalen-1-yl (4-nitrophenyl) carbonate d, J=9.2 Hz, 1H), 5.77 (br dd, J=6.1, 9.4 Hz, 1H), 5.52 (br s, 1H), 5.39-5.17 (m, 2H), 5.14-4.88 (m, 1H), 4.75-4.64 (m, 3H), 4.62-4.41 (m, 3H), 4.39-4.12 (m, 3H), 2.92-2.14 (m, 10H), 1.91-1.46 (m, 7H), 1.28-1.24 (m, 1H), 1.12-1.02 (m, 3H), 0.90-0.87 (m, 12H), 0.07 (s, 6H).

Step 4: Synthesis of (1S,3R,7S,8S,8aR)-8-(2-((2R,4R)-4-hydroxy-6-oxotetrahydro-2H-pyran-2-yl)ethyl)-3,7-dimethyl-1,2,3,7,8,8a-hexahydronaphthalen-1-yl (3-((2-((2-(2,6-dioxopiperidin-3-yl)-1,3-dioxoisoindolin-4-yl)oxy)acetamido)methyl)benzyl) carbamate (Compound 79)

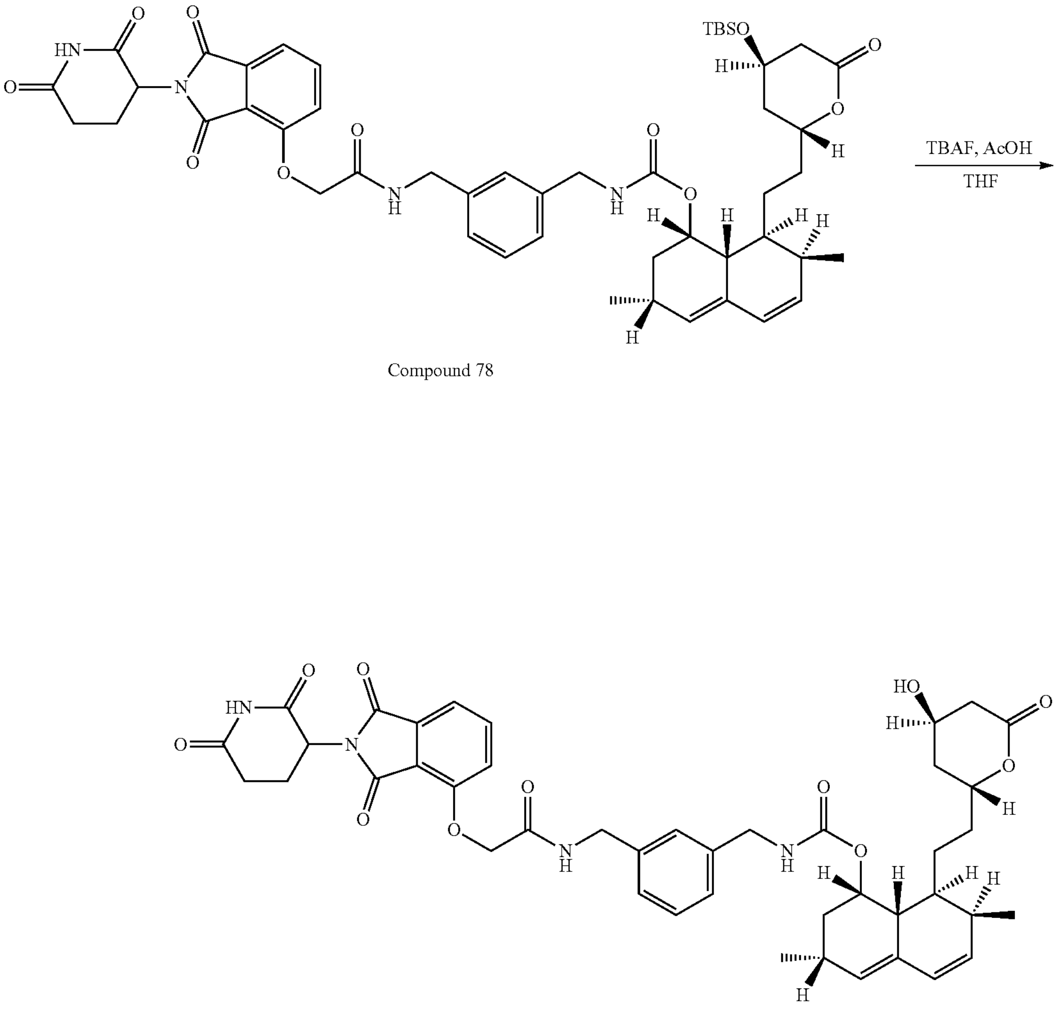

Compound 78

Compound 79

To a mixture of (1S,3R,7S,8S,8aR)-8-(2-((2R,4R)-4-((tert-butyldimethylsilyl)oxy)-6-oxotetrahydro-2H-pyran-2-yl)ethyl)-3,7-dimethyl-1,2,3,7,8,8a-hexahydronaphthalen-1-yl (3-((2-((2-(2,6-dioxopiperidin-3-yl)-1,3-dioxoisoindolin-4-yl)oxy)acetamido)methyl)benzyl) carbamate (162 mg, 177.80 μmol) in THF (3 mL) was added AcOH (53.39 mg, 889.02 μmol, 50.84 μL), TBAF (1 M, 711.21 μL) in one portion at 15° C. and the resulting mixture was stirred at 15° C. for 32 h. The reaction mixture was quenched with $NH_4Cl$ (sat.aq, 10 mL) and extracted with EtOAc (10 mL×3). The organic layer was washed with $NH_4Cl$ (sat.aq, 10 mL×3), dried over $Na_2SO_4$, filtrated and concentrated. The residue was purified by prep-HPLC (column: Unisil 3-100 C18 Ultra 150*50 mm*3 μm; mobile phase: [water (0.225% FA)-ACN]; B %: 43%-63%, 10 min) to afford (1S,3R,7S,8S,8aR)-8-(2-((2R,4R)-4-hydroxy-6-oxotetrahydro-2H-pyran-2-yl)ethyl)-3,7-dimethyl-1,2,3,7,8,8a-hexahydronaphthalen-1-yl (3-((2-((2-(2,6-dioxopiperidin-3-yl)-1,3-dioxoisoindolin-4-yl)oxy)acetamido)methyl)benzyl)carbamate (57.2 mg, 65.32 μmol, 36.74% yield, 91% purity) as a white solid.

MS $(M+H)^+$=797.5

$^1$H NMR (400 MHz, $CDCl_3$) δ=8.07-7.86 (m, 1H), 7.79-7.73 (m, 1H), 7.57 (d, J=7.3 Hz, 1H), 7.31 (br d, J=12.3 Hz, 1H), 7.25-6.97 (m, 4H), 6.03-5.93 (m, 1H), 5.82-5.74 (m, 1H), 5.52 (s, 1H), 5.40-5.11 (m, 2H), 5.09-4.96 (m, 1H), 4.76-4.68 (m, 2H), 4.67-4.45 (m, 3H), 4.44-4.26 (m, 2H), 4.25-4.15 (m, 1H), 3.20-2.89 (m, 1H), 2.89-2.51 (m, 4H), 2.50-2.42 (m, 1H), 2.39-2.30 (m, 1H), 2.29-2.20 (m, 1H), 2.16-2.02 (m, 2H), 1.93-1.83 (m, 2H), 1.78-1.69 (m, 1H), 1.64-1.57 (m, 3H), 1.44-1.28 (m, 2H), 1.11 (br d, J=6.3 Hz, 3H), 0.92-0.83 (m, 3H).

Example 80 & Example 81. Synthesis of (1S,3R,7S,8S,8aR)-8-(2-((2R,4R)-4-((tert-butyldimethylsilyl)oxy)-6-oxotetrahydro-2H-pyran-2-yl)ethyl)-3,7-dimethyl-1,2,3,7,8,8a-hexahydronaphthalen-1-yl (2-(1-(2-((2-(2,6-dioxopiperidin-3-yl)-1,3-dioxoisoindolin-4-yl)oxy)acetyl)piperidin-4-yl)ethyl)carbamate (Compound 80) and (1S,3R,7S,8S,8aR)-8-(2-((2R,4R)-4-hydroxy-6-oxotetrahydro-2H-pyran-2-yl)ethyl)-3,7-dimethyl-1,2,3,7,8,8a-hexahydronaphthalen-1-yl (2-(1-(2-((2-(2,6-dioxopiperidin-3-yl)-1,3-dioxoisoindolin-4-yl)oxy)acetyl)piperidin-4-yl)ethyl)carbamate (Compound 81)

Step 1: Synthesis of tert-butyl (2-(1-(2-((2-(2,6-dioxopiperidin-3-yl)-1,3-dioxoisoindolin-4-yl)oxy)acetyl)piperidin-4-yl)ethyl)carbamate (76)

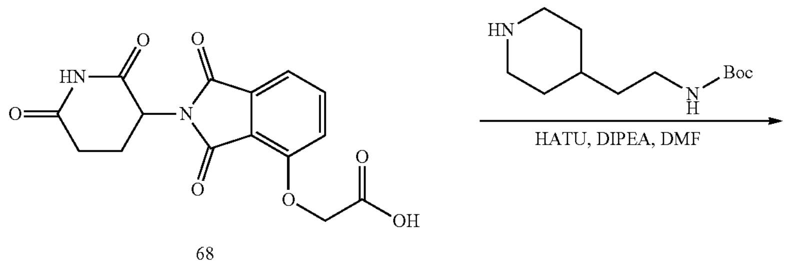

68

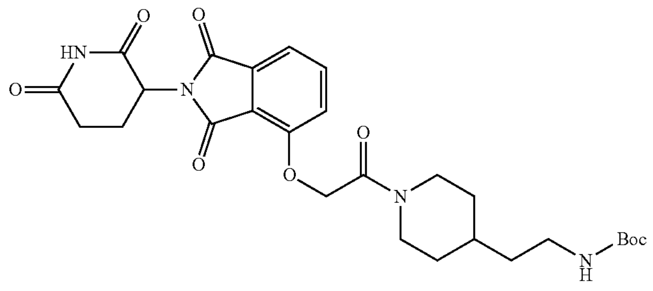

76

To a mixture of 2-((2-(2,6-dioxopiperidin-3-yl)-1,3-dioxoisoindolin-4-yl)oxy)acetic acid (800 mg, 2.41 mmol) and tert-butyl (2-(piperidin-4-yl)ethyl)carbamate (604.73 mg, 2.65 mmol) in DMF (10 mL) was added HATU (915.49 mg, 2.41 mmol), DIPEA (933.54 mg, 7.22 mmol, 1.26 mL) in one portion at 15° C. and the resulting mixture was stirred at 15° C. for 1 h. LCMS showed starting material was consumed completely and desired mass was detected. TLC ($SiO_2$, Petroleum ether:Ethyl acetate=1:2) indicated starting material was consumed completely and one major new spot was detected. The reaction mixture was diluted with $H_2O$ (30 mL) and extracted with EtOAc (30 mL×3). The organic layer was washed with brine (30 mL×3), dried over $Na_2SO_4$, filtrated and concentrated. The residue was purified by column chromatography ($SiO_2$, Petroleum ether/Ethyl acetate=1/1 to 0/1) to afford tert-butyl (2-(1-(2-((2-(2,6-dioxopiperidin-3-yl)-1,3-dioxoisoindolin-4-yl)oxy)acetyl)piperidin-4-yl)ethyl)carbamate (1.1 g, 1.99 mmol, 82.52% yield, 98% purity) as an off-white solid.

MS $(M+H)^+$=543.2

Step 2: Synthesis of 4-(2-(4-(2-aminoethyl)piperidin-1-yl)-2-oxoethoxy)-2-(2,6-dioxopiperidin-3-yl)isoindoline-1,3-dione (77)

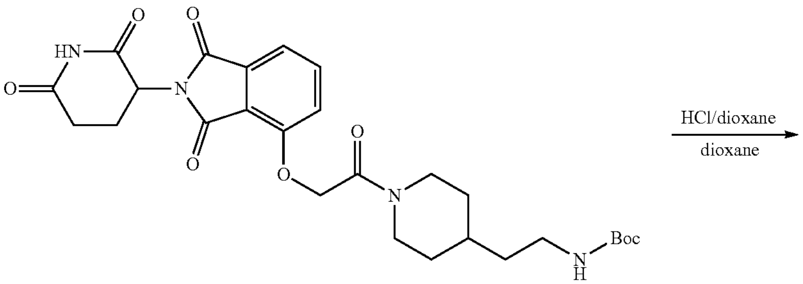

76

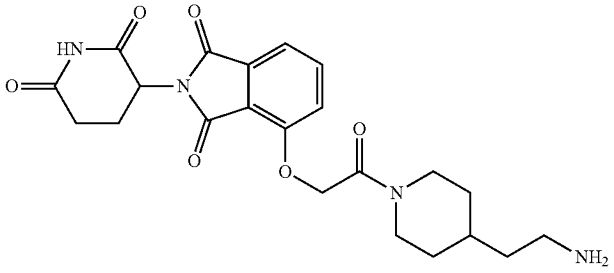

77

To solution of tert-butyl (2-(1-(2-((2-(2,6-dioxopiperidin-3-yl)-1,3-dioxoisoindolin-4-yl)oxy)acetyl)piperidin-4-yl)ethyl)carbamate (1.1 g, 2.03 mmol) in dioxane (10 mL) was added HCl/dioxane (4 M, 20 mL) in on portion at 15° C. and the resulting mixture was stirred at 15° C. for 1 h. LCMS showed starting material was consumed completely and desired mass was detected. The reaction mixture was concentrated in vacuum to afford 4-(2-(4-(2-aminoethyl)piperidin-1-yl)-2-oxoethoxy)-2-(2,6-dioxopiperidin-3-yl)isoindoline-1,3-dione (972 mg, crude, HCl salt) as a white solid. MS (M+H)=443.1

Step 3: Synthesis of (1S,3R,7S,8S,8aR)-8-(2-((2R,4R)-4-((tert-butyldimethylsilyl)oxy)-6-oxotetrahydro-2H-pyran-2-yl)ethyl)-3,7-dimethyl-1,2,3,7,8,8a-hexahydronaphthalen-1-yl (2-(1-(2-((2-(2,6-dioxopiperidin-3-yl)-1,3-dioxoisoindolin-4-yl)oxy)acetyl)piperidin-4-yl)ethyl)carbamate (Compound 80)

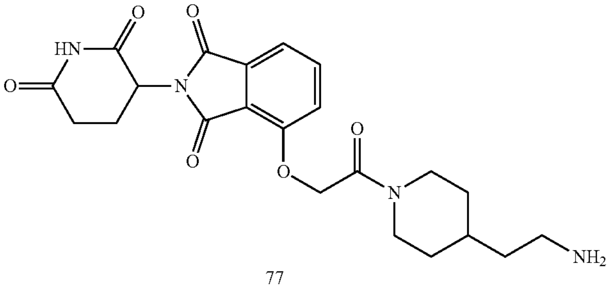

77

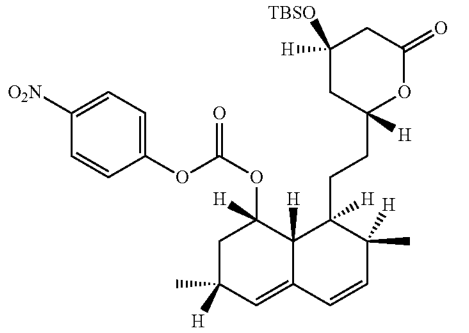

18

TEA, DMAC

-continued

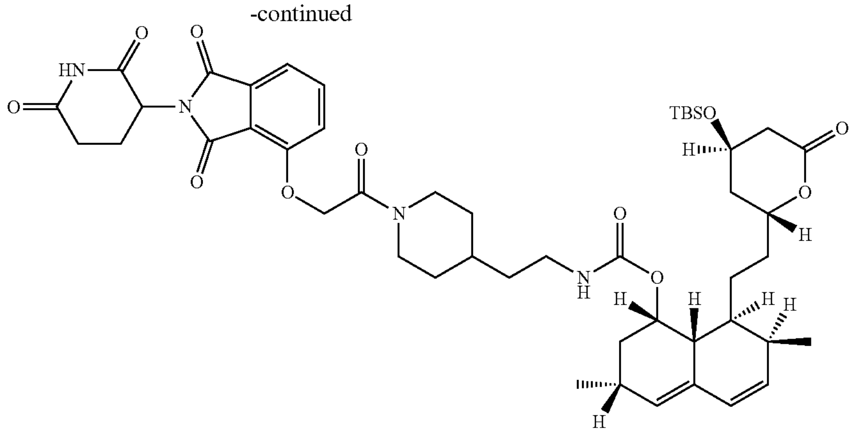

Compound 80

To a mixture of 4-(2-(4-(2-aminoethyl)piperidin-1-yl)-2-oxoethoxy)-2-(2,6-dioxopiperidin-3-yl)isoindoline-1,3-dione (872 mg, 1.82 mmol, HCl salt) in DMAC (10 mL) was added TEA (552.72 mg, 5.46 mmol, 760.28 µL) and (1S,3R,7S,8S,8aR)-8-(2-((2R,4R)-4-((tert-butyldimethylsilyl)oxy)-6-oxotetrahydro-2H-pyran-2-yl)ethyl)-3,7-dimethyl-1,2,3,7,8,8a-hexahydronaphthalen-1-yl (4-nitrophenyl) carbonate (3.74 g, 2.18 mmol) in one portion at 15° C. and the resulting mixture was stirred at 15° C. for 16 h. LCMS showed starting material was consumed completely and desired mass was detected. The reaction mixture was diluted with $H_2O$ (30 mL) and extracted with EtOAc (30 mL×3). The organic layer was dried over $Na_2SO_4$, filtrated and concentrated. The residue was purified by prep-HPLC (column: Waters Xbridge C18 150*50 mm*10 µm; mobile phase: [water (10 mM $NH_4HCO_3$)-ACN]; B %: 57%-87%, 11.5 min) followed by prep-HPLC (column: Unisil 3-100 C18 Ultra 150*50 mm*3 µm; mobile phase: [water (0.225% FA)-ACN]; B %: 70%-90%, 10 min) to afford (1S,3R,7S,8S,8aR)-8-(2-((2R,4R)-4-((tert-butyldimethylsilyl)oxy)-6-oxotetrahydro-2H-pyran-2-yl)ethyl)-3,7-dimethyl-1,2,3,7,8,8a-hexahydronaphthalen-1-yl (2-(1-(2-((2-(2,6-dioxopiperidin-3-yl)-1,3-dioxoisoindolin-4-yl)oxy)acetyl)piperidin-4-yl)ethyl)carbamate (464.8 mg, 478.62 µmol, 26.29% yield, 93% purity) as a white solid.

MS $(M+H)^+$=903.5

$^1H$ NMR (400 MHz, $CDCl_3$) δ=7.68 (t, J=8.0 Hz, 1H), 7.51 (d, J=7.2 Hz, 1H), 7.40-7.28 (m, 1H), 5.98 (d, J=9.8 Hz, 1H), 5.78 (br dd, J=5.8, 9.3 Hz, 1H), 5.53 (br s, 1H), 5.14 (br s, 1H), 5.08-4.99 (m, 1H), 4.99-4.88 (m, 3H), 4.74-4.63 (m, 1H), 4.68 (br s, 1H), 4.47 (br s, 1H), 4.29 (br s, 1H), 4.15-3.92 (m, 1H), 3.20-2.95 (m, 2H), 2.94-2.69 (m, 3H), 2.65-2.51 (m, 3H), 2.43 (br s, 1H), 2.34 (br s, 1H), 2.26 (br d, J=11.4 Hz, 1H), 2.16-2.12 (m, 2H), 1.93-1.74 (m, 5H), 1.72-1.36 (m, 9H), 1.35-1.12 (m, 2H), 1.08 (br d, J=7.6 Hz, 3H), 0.97-0.88 (m, 12H), 0.08 (s, 6H)

Step 4: Synthesis of (1S,3R,7S,8S,8aR)-8-(2-((2R,4R)-4-hydroxy-6-oxotetrahydro-2H-pyran-2-yl)ethyl)-3,7-dimethyl-1,2,3,7,8,8a-hexahydronaphthalen-1-yl (2-(1-(2-((2-(2,6-dioxopiperidin-3-yl)-1,3-dioxoisoindolin-4-yl)oxy)acetyl)piperidin-4-yl)ethyl)carbamate (Compound 81)

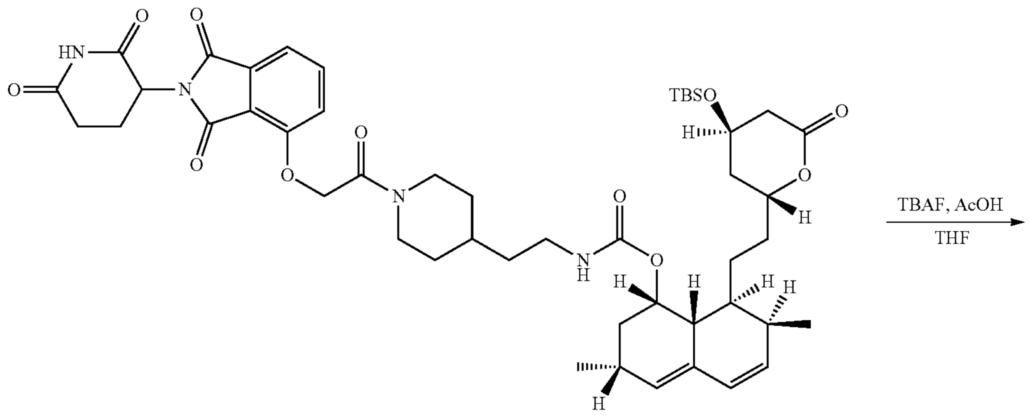

Compound 80

-continued

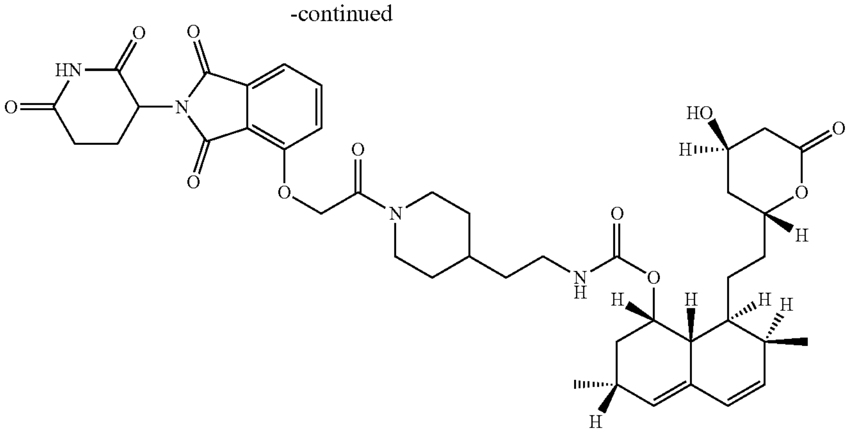

Compound 81

To a mixture of (1S,3R,7S,8S,8aR)-8-(2-((2R,4R)-4-((tert-butyldimethylsilyl)oxy)-6-oxotetrahydro-2H-pyran-2-yl)ethyl)-3,7-dimethyl-1,2,3,7,8,8a-hexahydronaphthalen-1-yl (2-(1-(2-((2-(2,6-dioxopiperidin-3-yl)-1,3-dioxoisoindolin-4-yl)oxy)acetyl)piperidin-4-yl)ethyl) carbamate (360 mg, 398.61 μmol) in THF (8 mL) was added TBAF (1 M, 1.59 mL) and AcOH (119.69 mg, 1.99 mmol, 113.99 μL) in one portion at 15° C. and the mixture was stirred at 15° C. for 16 h. LCMS showed starting material was consumed completely and desired mass was detected. The reaction mixture was quenched with $NH_4Cl$ (sat.aq, 30 mL) and extracted with EtOAc (30 mL×3). The organic layer was washed with $NH_4Cl$ (sat.aq, 30 mL×3). The organic layer was dried over $Na_2SO_4$, filtrated and concentrated. The residue was purified by column chromatography ($SiO_2$, Petroleum ether/Ethyl acetate=1/1 to 0/1) followed by prep-HPLC (column: Waters Xbridge C18 150*50 mm*10 μm; mobile phase: [water (10 mM $NH_4HCO_3$)-ACN]; B %: 32%-62%, 11.5 min) to afford 312 mg impure product, which was re-purified by prep-TLC ($SiO_2$, Ethyl acetate:Methanol=10:1) to afford (1S,3R,7S,8S,8aR)-8-(2-((2R,4R)-4-hydroxy-6-oxotetrahydro-2H-pyran-2-yl)ethyl)-3,7-dimethyl-1,2,3,7,8,8a-hexahydronaphthalen-1-yl (2-(1-(2-((2-(2,6-dioxopiperidin-3-yl)-1,3-dioxoisoindolin-4-yl)oxy)acetyl)piperidin-4-yl)ethyl)carbamate (67.6 mg, 83.12 μmol, 20.85% yield, 97% purity) as a white solid.

MS $(M+H)^+=789.5$ $^1H$ NMR (400 MHz, $CDCl_3$) δ=7.73-7.67 (m, 1H), 7.52 (d, J=7.2 Hz, 1H), 7.46-7.29 (m, 1H), 6.01-5.95 (m, 1H), 5.83-5.75 (m, 1H), 5.56-5.49 (m, 1H), 5.23-5.07 (m, 1H), 5.00-4.92 (m, 2H), 4.91-4.78 (m, 1H), 4.72-4.54 (m, 1H), 4.51-4.39 (m, 1H), 4.36-4.26 (m, 1H), 4.22-3.91 (m, 1H), 3.40-2.96 (m, 3H), 2.92-2.53 (m, 7H), 2.47-2.32 (m, 2H), 2.30-2.22 (m, 1H), 2.21-2.03 (m, 2H), 2.03-1.82 (m, 3H), 1.79-1.55 (m, 10H), 1.48-1.35 (m, 4H), 1.10-1.04 (m, 3H), 0.93-0.88 (m, 3H).

Example 82 & Example 83. Synthesis of (1S,3R,7S,8S,8aR)-8-(2-((2R,4R)-4-((tert-butyldimethylsilyl)oxy)-6-oxotetrahydro-2H-pyran-2-yl)ethyl)-3,7-dimethyl-1,2,3,7,8,8a-hexahydronaphthalen-1-yl (2-(2-(2-((2-(2,6-dioxopiperidin-3-yl)-1,3-dioxoisoindolin-4-yl)amino)ethoxy)ethoxy)ethyl)(methyl) carbamate (Compound 82) and (1S,3R,7S,8S,8aR)-8-(2-((2R,4R)-4-hydroxy-6-oxotetrahydro-2H-pyran-2-yl)ethyl)-3,7-dimethyl-1,2,3,7,8,8a-hexahydronaphthalen-1-yl (2-(2-(2-((2-(2,6-dioxopiperidin-3-yl)-1,3-dioxoisoindolin-4-yl)amino)ethoxy)ethoxy)ethyl)(methyl)carbamate (Compound 83)

Step 1: Synthesis of 2-(2,6-dioxopiperidin-3-yl)-4-((2-(2-(2-hydroxyethoxy)ethoxy)ethyl)amino)isoindoline-1,3-dione (78)

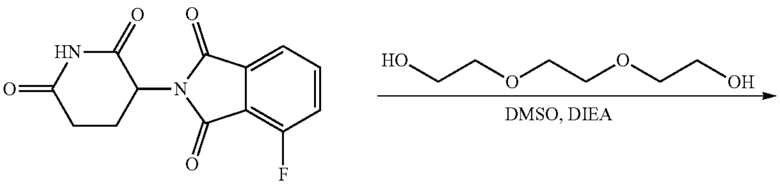

11

-continued
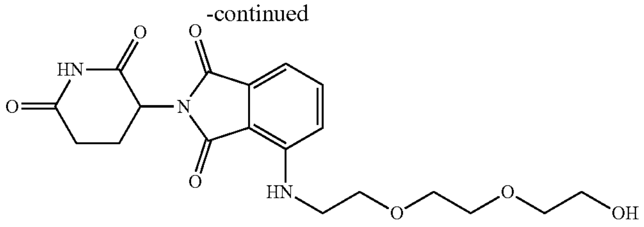
78
Step 2: Synthesis of 2-(2-(2-((2-(2,6-dioxopiperidin-3-yl)-1,3-dioxoisoindolin-4-yl)amino)ethoxy)ethoxy)ethyl 4-methylbenzenesulfonate (79)
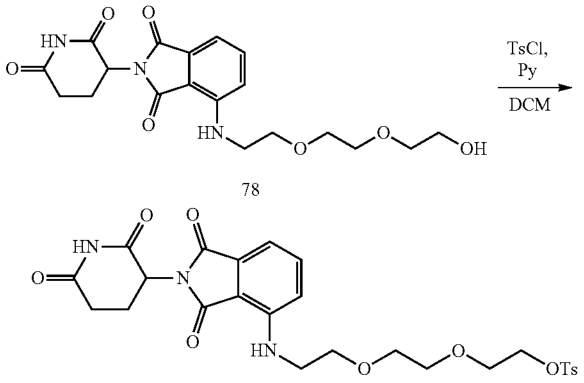
78
79
Step 3: Synthesis of 4-((2-(2-(2-(benzyl(methyl)amino)ethoxy)ethoxy)ethyl)amino)-2-(2,6-dioxopiperidin-3-yl)isoindoline-1,3-dione (80)
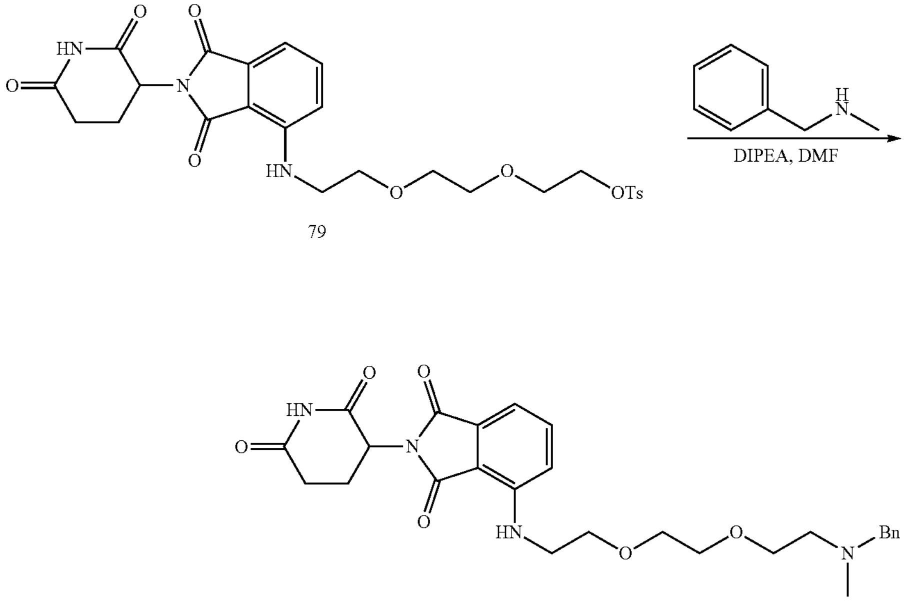
79
80

Step 4: Synthesis of 2-(2,6-dioxopiperidin-3-yl)-4-((2-(2-(2-(methylamino)ethoxy)ethoxy)ethyl)amino)isoindoline-1,3-dione (81)
-continued
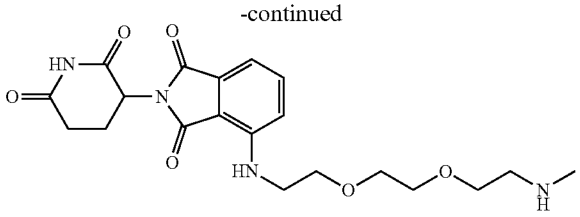
81
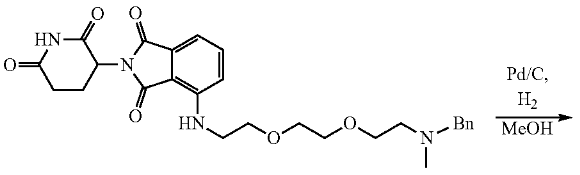
80
Step 5: Synthesis of (1S,3R,7S,8S,8aR)-8-(2-((2R,4R)-4-((tert-butyldimethylsilyl)oxy)-6-oxotetrahydro-2H-pyran-2-yl)ethyl)-3,7-dimethyl-1,2,3,7,8,8a-hexahydronaphthalen-1-yl (2-(2-(2-((2-(2,6-dioxopiperidin-3-yl)-1,3-dioxoisoindolin-4-yl)amino)ethoxy)ethoxy)ethyl)(methyl)carbamate (Compound 82)
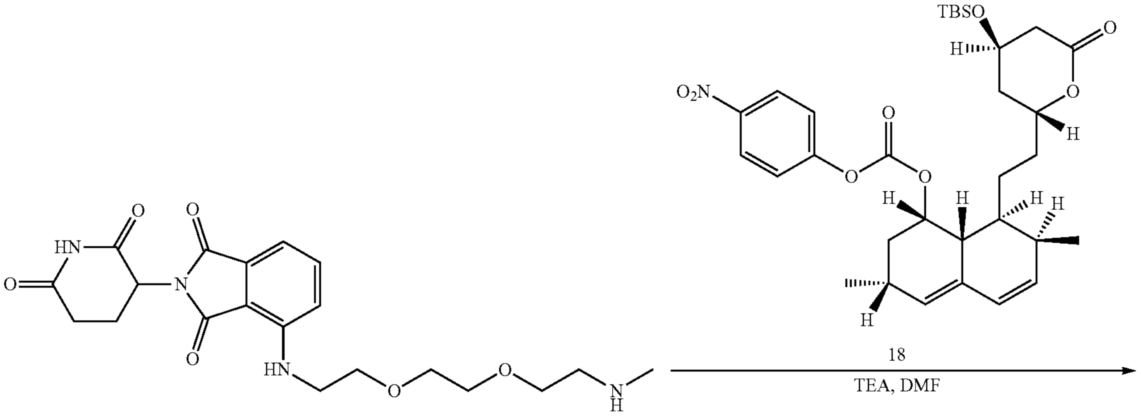
81
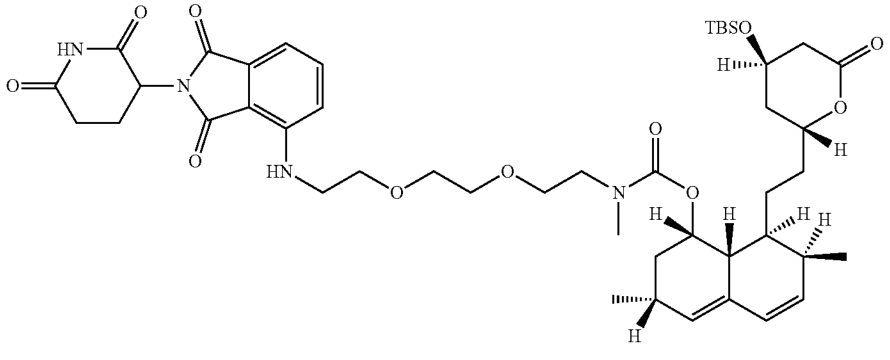
Compound 82

According to the above reaction scheme, in a manner similar to the other examples, the titled compound (83.7 mg, 91.40 μmol, 8.50% yield, 96% purity) was obtained as a yellow solid.

MS $(M+H)^+$=879.3

$^1$H NMR (400 MHz, $CDCl_3$) δ=8.28-7.90 (m, 1H), 7.59-7.44 (m, 1H), 7.13 (d, J=7.1 Hz, 1H), 6.94 (d, J=8.4 Hz, 1H), 6.51 (br s, 1H), 5.99 (br d, J=8.8 Hz, 1H), 5.78 (br s, 1H), 5.52 (br s, 1H), 5.27-5.12 (m, 1H), 5.02-4.88 (m, 1H), 4.67 (br s, 1H), 4.30 (br s, 1H), 3.75-3.70 (m, 2H), 3.66-3.53 (m, 6H), 3.48 (br d, J=5.4 Hz, 2H), 3.31 (br s, 1H), 2.98 (s, 1H), 2.95-2.85 (m, 3H), 2.85-2.73 (m, 2H), 2.67-2.53 (m, 2H), 2.49-2.34 (m, 2H), 2.27 (br d, J=11.9 Hz, 1H), 2.19-2.08 (m, 2H), 1.95-1.61 (m, 6H), 1.46-1.22 (m, 3H), 1.07 (d, J=7.3 Hz, 3H), 0.94-0.87 (m, 12H), 0.09 (s, 6H).

Step 6: Synthesis of (1S,3R,7S,8S,8aR)-8-(2-((2R,4R)-4-hydroxy-6-oxotetrahydro-2H-pyran-2-yl)ethyl)-3,7-dimethyl-1,2,3,7,8,8a-hexahydronaphthalen-1-yl (2-(2-(2-((2-(2,6-dioxopiperidin-3-yl)-1,3-dioxoisoindolin-4-yl)amino)ethoxy)ethoxy)ethyl)(methyl)carbamate (Compound 83)

combined organic layer was washed with brine (100 mL), dried over $Na_2SO_4$, filtered and concentrated. The residue was purified by prep-HPLC (column: Phenomenex Luna C18 150*25 mm*10 μm; mobile phase: [water (0.225% FA)-ACN]; B %: 45%-75%, 11 min) to afford 200 mg of product with 90% purity, which was re-purified by prep-HPLC (column: Unisil 3-100 C18 Ultra 150*50 mm*3 μm; mobile phase: [water (0.225% FA)-ACN]; B %: 50%-70%, 10 min) to afford 100 mg of crude product with 81% purity, then the product was re-purified by prep-TLC (Ethyl acetate: Methanol=10:1) and the eluent was concentrated then lyophilized to get 50 mg of crude product with 84% purity, which was re-purified by prep-HPLC (column: Unisil 3-100 C18 Ultra 150*50 mm*3 μm; mobile phase: [water (0.225% FA)-ACN]; B %: 45%-65%, 10 min) to afford (1S,3R,7S,8S,8aR)-8-(2-((2R,4R)-4-hydroxy-6-oxotetrahydro-2H-pyran-2-yl)ethyl)-3,7-dimethyl-1,2,3,7,8,8a-hexahydronaphthalen-1-yl(2-(2-(2-((2-(2,6-dioxopiperidin-3-yl)-1,3-dioxoisoindolin-4-yl)amino)ethoxy)ethoxy)ethyl)(methyl)carbamate (16.6 mg, 21.70 μmol, 6.36% yield) as white solid.

MS $(M+H)^+$=765.5

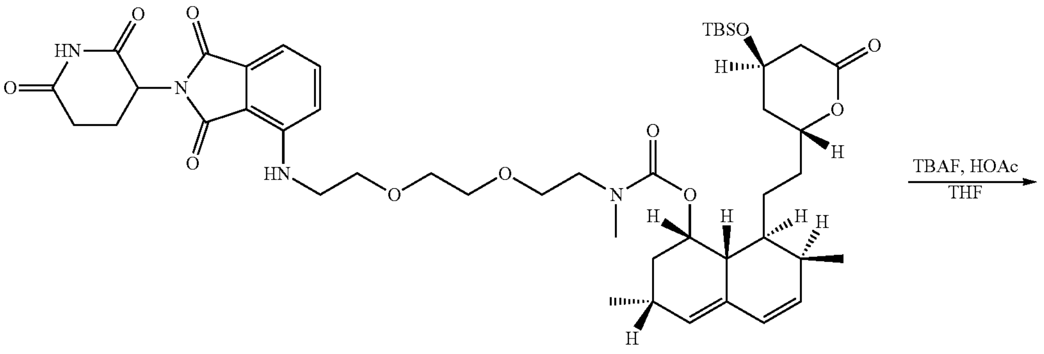

Compound 82

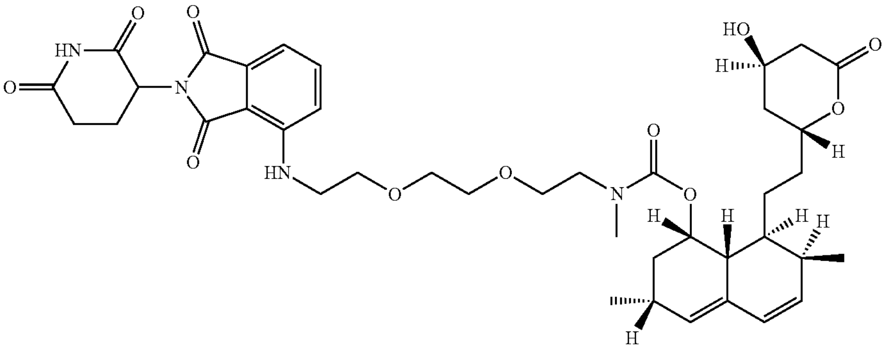

Compound 83

To the solution of (1S,3R,7S,8S,8aR)-8-(2-((2R,4R)-4-((tert-butyldimethylsilyl)oxy)-6-oxotetrahydro-2H-pyran-2-yl)ethyl)-3,7-dimethyl-1,2,3,7,8,8a-hexahydronaphthalen-1-yl(2-(2-(2-((2-(2,6-dioxopiperidin-3-yl)-1,3-dioxoisoindolin-4-yl)amino)ethoxy)ethoxy)ethyl)(methyl)carbamate (0.3 g, 341.25 μmol) in THF (10 mL) was added AcOH (102.46 mg, 1.71 mmol, 97.58 μL) and TBAF (1 M, 1.37 mL) and the resulting mixture was stirred at 25° C. for 12 h. LCMS showed the starting material was consumed and 66% desired mass was detected. The mixture was poured into water (50 mL) and extracted by EtOAc (50 mL×3). The $^1$H NMR (400 MHz, Chloroform-d) δ 7.50 (t, J=7.7 Hz, 1H), 7.17-7.05 (m, 1H), 6.90 (d, J=8.5 Hz, 1H), 6.61-6.43 (m, 1H), 5.97 (d, J=9.7 Hz, 1H), 5.83-5.73 (m, 1H), 5.50 (s, 1H), 5.28-5.16 (m, 1H), 5.03-4.88 (m, 1H), 4.68-4.56 (m, 1H), 4.35-4.19 (m, 1H), 3.71 (t, J=5.2 Hz, 2H), 3.68-3.59 (m, 4H), 3.59-3.49 (m, 2H), 3.47-3.41 (m, 2H), 2.97 (d, J=6.5 Hz, 1H), 2.89 (s, 3H), 2.80-2.67 (m, 3H), 2.66-2.59 (m, 1H), 2.59-2.48 (m, 1H), 2.48-2.30 (m, 2H), 2.25 (d, J=11.9 Hz, 1H), 2.18-2.05 (m, 2H), 2.03-1.82 (m, 3H), 1.77-1.62 (m, 3H), 1.42-1.24 (m, 3H), 1.05 (d, J=7.2 Hz, 3H), 0.94-0.85 (m, 3H)

Example 84 & Example 85. Synthesis of (1S,3R,7S,8S,8aR)-8-(2-((2R,4R)-4-((tert-butyldimethylsilyl)oxy)-6-oxotetrahydro-2H-pyran-2-yl)ethyl)-3,7-dimethyl-1,2,3,7,8,8a-hexahydronaphthalen-1-yl4-(2-(2-((2-(2,6-dioxopiperidin-3-yl)-1,3-dioxoisoindolin-4-yl)amino)ethoxy)ethyl)piperidine-1-carboxylate (Compound 84) and (1S,3R,7S,8S,8aR)-8-(2-((2R,4R)-4-hydroxy-6-oxotetrahydro-2H-pyran-2-yl)ethyl)-3,7-dimethyl-1,2,3,7,8,8a-hexahydronaphthalen-1-yl4-(2-(2-((2-(2,6-dioxopiperidin-3-yl)-1,3-dioxoisoindolin-4-yl)amino)ethoxy)ethyl)piperidine-1-carboxylate (Compound 85)

Step 1: Synthesis of tert-butyl 4-(2-((methylsulfonyl)oxy)ethyl)piperidine-1-carboxylate (83)

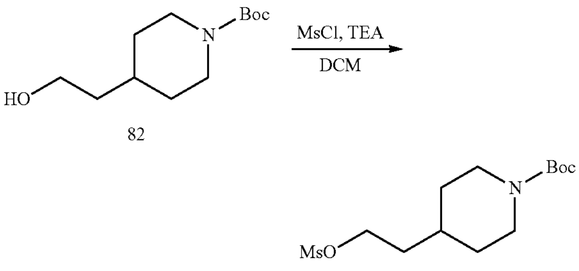

82

83

To a mixture of tert-butyl 4-(2-hydroxyethyl) piperidine-1-carboxylate (5 g, 21.80 mmol) and TEA (6.62 g, 65.41 mmol, 9.10 mL) in DCM (50 mL) was added MsCl (2.75 g, 23.98 mmol, 1.86 mL) drop-wise at 0° C. and the resulting mixture was stirred at 15° C. for 16 h. TLC ($SiO_2$, Petroleum ether:Ethyl acetate=1:1) indicated starting material was consumed completely and one new spot was detected. The reaction mixture was diluted $H_2O$ (150 mL) and extracted with DCM (150 mL×3). The organic layer was dried over $Na_2SO_4$, filtrated and concentrated in vacuum to afford tert-butyl 4-(2-((methylsulfonyl) oxy) ethyl) piperidine-1-carboxylate (6.6 g, crude) as a yellow solid.

$^1$H NMR (400 MHz, $CDCl_3$) δ=4.26 (t, J=6.4 Hz, 2H), 4.14-3.98 (m, 2H), 3.01-2.95 (m, 3H), 2.67 (br t, J=12.2 Hz, 2H), 1.71-1.55 (m, 5H), 1.43 (s, 9H), 1.18-1.05 (m, 2H).

Step 2: Synthesis of tert-butyl 4-(2-(2-(1,3-dioxoisoindolin-2-yl)ethoxy)ethyl)piperidine-1-carboxylate (84)

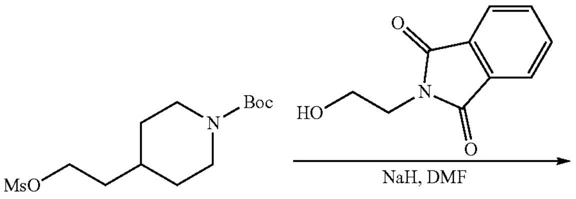

83

-continued

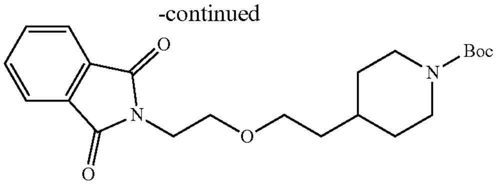

84

To a mixture of 2-(2-hydroxyethyl)isoindoline-1,3-dione (1.86 g, 9.73 mmol) in DMF (20 mL) was added NaH (598.50 mg, 14.96 mmol, 60% purity) at 0° C., after stirring at 15° C. for 0.5 h, the reaction mixture cool to 0° C., then a solution of tert-butyl 4-(2-methylsulfonyloxyethyl)piperidine-1-carboxylate (2.3 g, 7.48 mmol) in DMF (10 mL) was added drop-wise and the resulting mixture was stirred at 15° C. for 16 h. LCMS showed starting material was consumed completely and desired mass was detected. TLC ($SiO_2$, Petroleum ether:Ethyl acetate=3:1) indicated starting material was consumed completely and three new spots were detected. The reaction mixture was combined with another batch (1.5 g scale) for work-up, the reaction mixture was quenched with saturated $NH_4Cl$ (100 mL) and extracted with EtOAc (100 mL×3). The organic layer was washed with brine (100 mL×3), dried over $Na_2SO_4$, filtrated and concentrated. The crude product was purified by column chromatography ($SiO_2$, Petroleum ether/Ethyl acetate=10/1 to 2/1) to afford tert-butyl (2-(2-(3-((2-(2, 6-dioxopiperidin-3-yl)-1, 3-dioxoisoindolin-4-yl) amino) propoxy) ethoxy) ethyl) carbamate (1.02 g, 2.53 mmol, 33.87% yield) as a yellow oil.

MS $(M+H)^+$=403.4

Step 3: Synthesis of tert-butyl 4-(2-(2-aminoethoxy)ethyl)piperidine-1-carboxylate (85)

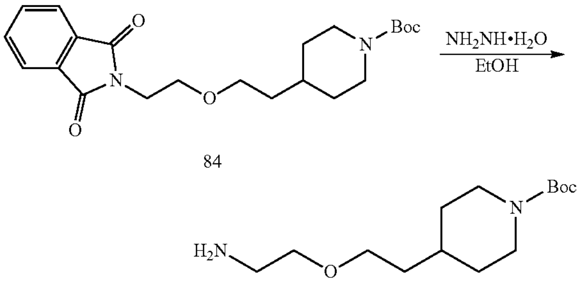

84

85

To a mixture of tert-butyl (2-(2-(3-((2-(2,6-dioxopiperidin-3-yl)-1,3-dioxoisoindolin-4-yl) amino) propoxy) ethoxy) ethyl) carbamate (1.02 g, 2.53 mmol) in EtOH (10 mL) was added $NH_2NH_2 \cdot H_2O$ (1.49 g, 25.34 mmol, 1.45 mL, 85% purity) in one portion at 15° C. and the resulting mixture was stirred at 80° C. for 16 h. LCMS showed starting material was consumed completely and desired mass was detected. The reaction mixture was filtrated and the filtrate was concentrated in vacuum. The residue was diluted with DCM (30 mL) and filtrated, the filtrated was concentrated in vacuum to afford tert-butyl 4-(2-(2-amino-ethoxy) ethyl) piperidine-1-carboxylate (625 mg, crude) as a yellow oil.

MS $(M+H)^+$=273.6

Step 4: Synthesis of tert-butyl 4-(2-(2-((2-(2,6-dioxopiperidin-3-yl)-1,3-dioxoisoindolin-4-yl)amino)ethoxy)ethyl)piperidine-1-carboxylate (86)

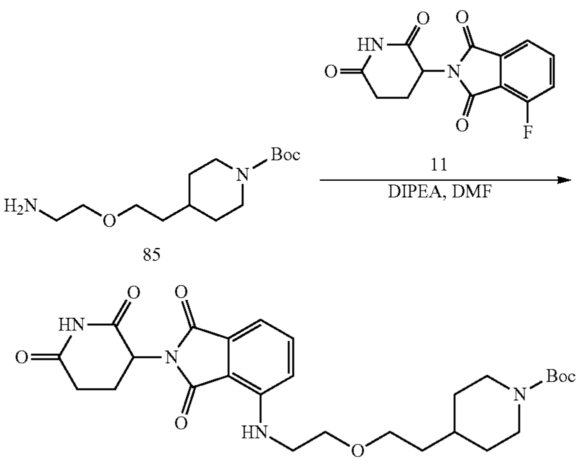

11

85

86

To a mixture of 2-(2,6-dioxo-3-piperidyl)-4-fluoro-isoindoline-1,3-dione (600 mg, 2.17 mmol) and tert-butyl 4-(2-(2-((2-(2,6-dioxopiperidin-3-yl)-1,3-dioxoisoindolin-4-yl)amino)ethoxy)ethyl)piperidine-1-carboxylate (591.67 mg, 2.17 mmol) in DMF (6 mL) was added DIPEA (842.22 mg, 6.52 mmol, 1.14 mL) at 15° C. and the mixture was stirred at 90° C. for 16 h. LCMS showed starting material was consumed completely and desired mass was detected. TLC ($SiO_2$, Petroleum ether:Ethyl acetate=1:1) indicated starting material was consumed completely and four new spots were detected. The reaction mixture was diluted with $H_2O$ (30 ml) and extracted with EtOAc (30 mL×3). The organic layer was washed with brine (30 mL×3), dried over $Na_2SO_4$, filtrated and concentrated. The residue was purified by column chromatography ($SiO_2$, Petroleum ether/Ethyl acetate=10/1 to 1/1) followed by prep-HPLC (column: Phenomenex luna C18 150*40 mm*15 μm; mobile phase: [water (0.225% FA)-ACN]; B %: 49%-79%, 11 min) to afford tert-butyl 4-(2-(2-((2-(2,6-dioxopiperidin-3-yl)-1,3-dioxoisoindolin-4-yl)amino)ethoxy)ethyl)piperidine-1-carboxylate (248 mg, 469.17 μmol, 21.60% yield, 100% purity) as a yellow solid.

MS $(M+H)^+$=529.3

Step 5: Synthesis of 2-(2,6-dioxopiperidin-3-yl)-4-((2-(2-(piperidin-4-yl)ethoxy)ethyl)amino)isoindoline-1,3-dione (87)

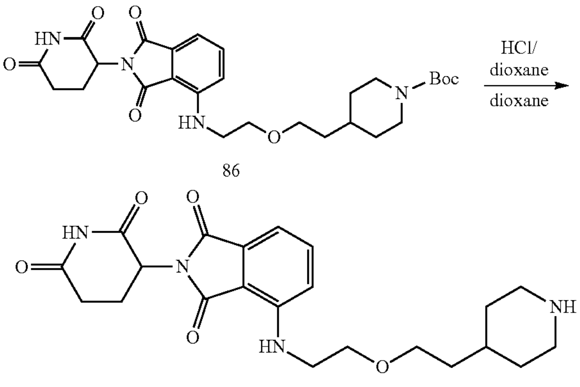

86

87

To a mixture of tert-butyl 4-(2-(2-((2-(2,6-dioxopiperidin-3-yl)-1,3-dioxoisoindolin-4-yl)amino)ethoxy)ethyl)piperidine-1-carboxylate (248 mg, 469.17 μmol) in dioxane (4 mL) was added HCl/dioxane (4 M, 8 mL) in one portion at 15° C. and the resulting mixture was stirred at 15° C. for 1 h. LCMS showed starting material was consumed completely and desired mass was detected. The reaction mixture was concentrated in vacuum to afford 2-(2, 6-dioxopiperidin-3-yl)-4-((2-(2-(piperidin-4-yl) ethoxy) ethyl) amino) isoindoline-1, 3-dione (220 mg, crude, HCl salt) as a yellow solid.

MS $(M+H)^+$=429.3

Step 6: Synthesis of (1S,3R,7S,8S,8aR)-8-(2-((2R,4R)-4-((tert-butyldimethylsilyl)oxy)-6-oxotetrahydro-2H-pyran-2-yl)ethyl)-3,7-dimethyl-1,2,3,7,8,8a-hexahydronaphthalen-1-yl4-(2-(2-((2-(2,6-dioxopiperidin-3-yl)-1,3-dioxoisoindolin-4-yl)amino)ethoxy)ethyl)piperidine-1-carboxylate (Compound 84)

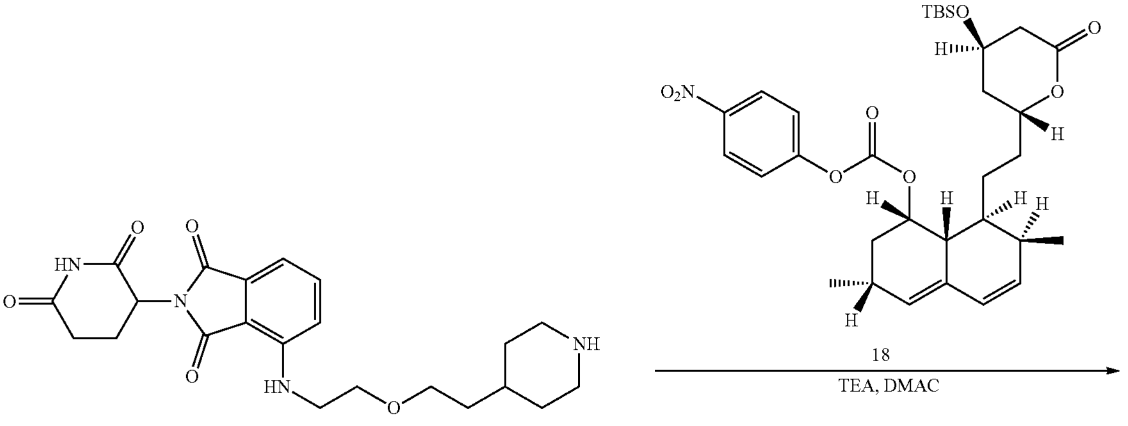

87

18

-continued

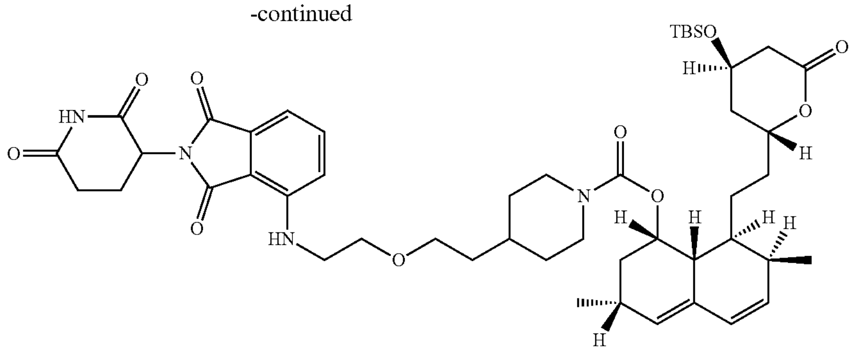

Compound 84

To a mixture of 2-(2, 6-dioxopiperidin-3-yl)-4-((2-(2-(piperidin-4-yl) ethoxy) ethyl) amino) isoindoline-1, 3-dione (220 mg, 473.18 μmol, HCl salt) in DMAC (5 mL) was added TEA (143.64 mg, 1.42 mmol, 197.58 μL) and [(1S, 3R,7S,8S,8aR)-8-[2-[(2R,4R)-4-[tert-butyl(dimethyl)silyl] oxy-6-oxo-tetrahydropyran-2-yl]ethyl]-3,7-dimethyl-1,2,3, 7,8,8a-hexahydronaphthalen-1-yl] (4-nitrophenyl) carbonate (283.81 mg, 473.18 μmol) in one portion at 15° C. and the resulting mixture was stirred at 15° C. for 16 h. LCMS showed starting material was consumed completely and desired mass was detected. TLC ($SiO_2$, Petroleum ether:Ethyl acetate=1:2) indicated starting material was consumed completely and two new spots were detected. The reaction mixture was diluted with $H_2O$ (15 mL) and extracted with EtOAc (15 mL×3). The organic layer was washed with brine (15 mL×3), dried over $Na_2SO_4$, filtrated and concentrated. The residue was purified by column chromatography ($SiO_2$, Petroleum ether/Ethyl acetate=5/1 to 1/3) to afford (1S, 3R, 7S, 8S, 8aR)-8-(2-((2R,4R)-4-((tert-butyldimethylsilyl)oxy)-6-oxotetrahydro-2H-pyran-2-yl)ethyl)-3,7-dimethyl-1,2,3,7,8,8a-hexahydronaphthalen-1-yl4-(2-(2-((2-(2,6-dioxopiperidin-3-yl)-1,3-dioxoisoindolin-4-yl)amino)ethoxy)ethyl)piperidine-1-carboxylate (345.8 mg, 377.24 μmol, 79.72% yield, 97% purity) as a yellow solid.

MS $(M+H)^+$=889.5

$^1H$ NMR (400 MHz, $CDCl_3$) δ=8.71-8.34 (m, 1H), 7.50 (t, J=7.8 Hz, 1H), 7.11 (d, J=7.1 Hz, 1H), 6.91 (d, J=8.4 Hz, 1H), 6.54-6.41 (m, 1H), 5.98 (d, J=9.8 Hz, 1H), 5.81-5.74 (m, 1H), 5.51 (br s, 1H), 5.22 (br s, 1H), 4.95-4.87 (m, 1H), 4.68-4.58 (m, 1H), 4.32-4.25 (m, 1H), 4.20-3.92 (m, 2H), 3.65 (br t, J=4.8 Hz, 2H), 3.52 (br s, 2H), 3.44 (br d, J=4.6 Hz, 2H), 3.02 (s, 1H), 2.95 (s, 1H), 2.90-2.81 (m, 1H), 2.79-2.68 (m, 4H), 2.60-2.50 (m, 2H), 2.46-2.34 (m, 2H), 2.26 (br d, J=12.0 Hz, 1H), 2.16-2.07 (m, 3H), 1.94-1.80 (m, 3H), 1.71-1.59 (m, 6H), 1.39-1.21 (m, 3H), 1.06-1.04 (m, 3H), 0.92-0.84 (m, 12H), 0.07 (d, J=3.8 Hz, 6H).

Step 7: Synthesis of (1S,3R,7S,8S,8aR)-8-(2-((2R, 4R)-4-hydroxy-6-oxotetrahydro-2H-pyran-2-yl) ethyl)-3,7-dimethyl-1,2,3,7,8,8a-hexahydronaphthalen-1-yl4-(2-(2-((2-(2,6-dioxopiperidin-3-yl)-1,3-dioxoisoindolin-4-yl)amino)ethoxy)ethyl)piperidine-1-carboxylate (Compound 85)

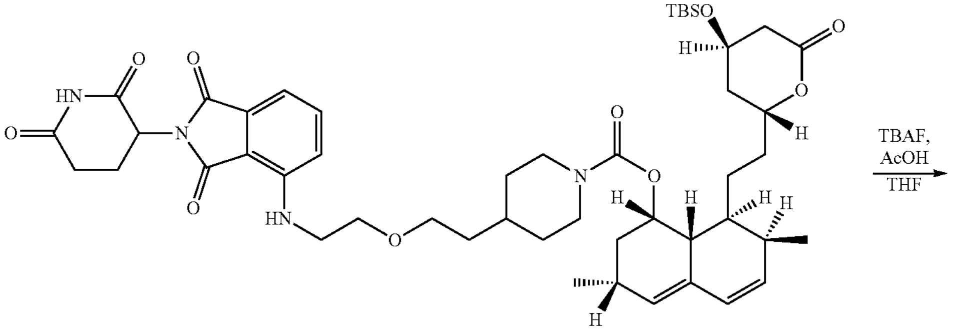

Compound 84

-continued

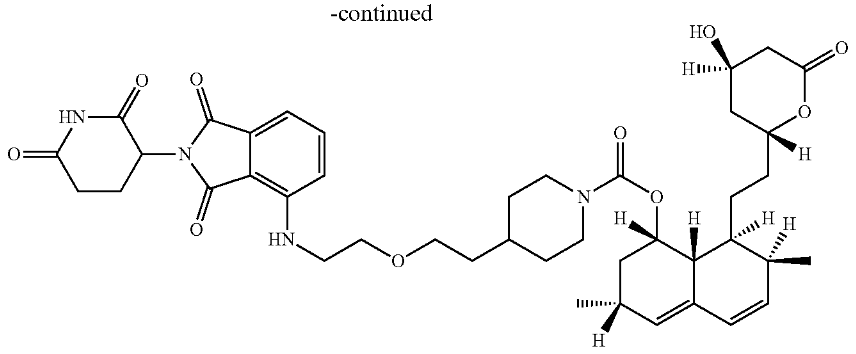

Compound 85

To a mixture of (1S,3R,7S,8S,8aR)-8-(2-((2R,4R)-4-((tert-butyldimethylsilyl)oxy)-6-oxotetrahydro-2H-pyran-2-yl)ethyl)-3,7-dimethyl-1,2,3,7,8,8a-hexahydronaphthalen-1-yl4-(2-(2-((2-(2,6-dioxopiperidin-3-yl)-1,3-dioxoisoindolin-4-yl)amino)ethoxy)ethyl)piperidine-1-carboxylate (244 mg, 274.42 μmol) in THF (5 mL) was added AcOH (82.40 mg, 1.37 mmol, 78.47 μL) and TBAF (1 M, 1.10 mL) in one portion at 15° C. and the resulting mixture was stirred at 15° C. for 16 h. LCMS showed 7% of starting material remained and 84% desired mass was detected. The reaction mixture was quenched with saturated $NH_4Cl$ (15 mL) and extracted with EtOAc (15 mL×3). The organic layer was washed with saturated $NH_4Cl$ (15 mL×3), dried over $Na_2SO_4$, filtrated and concentrated. The residue was purified by prep-HPLC (column: Phenomenex luna C18 150*40 mm*15 μm; mobile phase: [water (0.225% FA)-ACN]; B %: 52%-82%, 11 min) to afford (1S,3R,7S,8S,8aR)-8-(2-((2R,4R)-4-hydroxy-6-oxotetrahydro-2H-pyran-2-yl)ethyl)-3,7-dimethyl-1,2,3,7,8,8a-hexahydronaphthalen-1-yl4-(2-(2-((2-(2,6-dioxopiperidin-3-yl)-1,3-dioxoisoindolin-4-yl)amino)ethoxy)ethyl)piperidine-1-carboxylate (83.6 mg, 102.49 μmol, 37.35% yield, 95% purity) as a yellow solid.

MS $(M+H)^+$=775.5

$^1$H NMR (400 MHz, $CDCl_3$) δ 7.56-7.46 (m, 1H), 7.12 (d, J=7.0 Hz, 1H), 6.88 (dd, J=8.6, 5.2 Hz, 1H), 6.53-6.42 (m, 1H), 6.03-5.94 (m, 1H), 5.83-5.71 (m, 1H), 5.55-5.45 (m, 1H), 5.36-5.18 (m, 1H), 5.00-4.85 (m, 1H), 4.74-4.38 (m, 1H), 4.38-4.22 (m, 1H), 4.22-3.91 (m, 2H), 3.85-3.50 (m, 4H), 3.50-3.30 (m, 2H), 3.02-2.48 (m, 8H), 2.48-1.99 (m, 6H), 1.99-1.76 (m, 3H), 1.75-1.60 (m, 4H), 1.53-1.20 (m, 5H), 1.11-0.96 (m, 5H), 0.89 (t, J=6.7 Hz, 3H).

Example 86 & Example 87. Synthesis of (1S,3R,7S,8S,8aR)-8-(2-((2R,4R)-4-((tert-butyldimethylsilyl)oxy)-6-oxotetrahydro-2H-pyran-2-yl)ethyl)-3,7-dimethyl-1,2,3,7,8,8a-hexahydronaphthalen-1-yl (2-(2-((2-(2,6-dioxopiperidin-3-yl)-1,3-dioxoisoindolin-4-yl)amino)ethoxy)ethyl)carbamate (Compound 86) and (1S,3R,7S,8S,8aR)-8-(2-((2R,4R)-4-hydroxy-6-oxotetrahydro-2H-pyran-2-yl)ethyl)-3,7-dimethyl-1,2,3,7,8,8a-hexahydronaphthalen-1-yl (2-(2-((2-(2,6-dioxopiperidin-3-yl)-1,3-dioxoisoindolin-4-yl)amino)ethoxy)ethyl)carbamate (Compound 87)

Step 1: Synthesis of tert-butyl (2-(2-((2-(2,6-dioxopiperidin-3-yl)-1,3-dioxoisoindolin-4-yl)amino)ethoxy)ethyl)carbamate (13f)

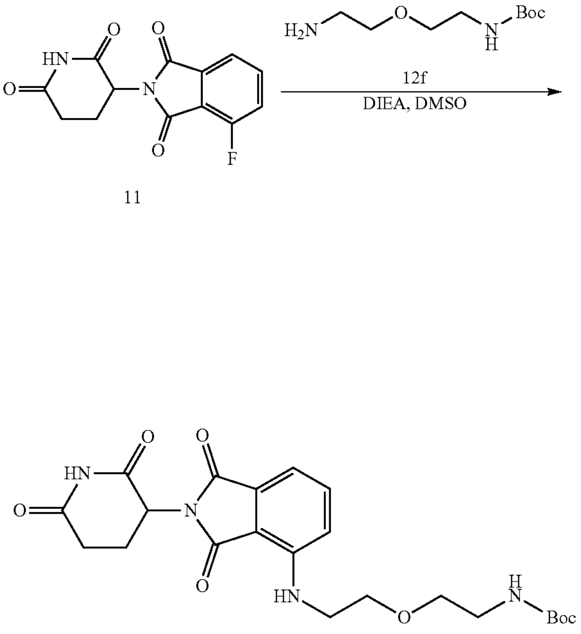

11

13f

In a manner similar to Step 1 of Example 2, the titled compound (1.8 g, 3.71 mmol, 41.03% yield, 95% purity) was obtained as a green solid.

MS $[M+H]^+$=461.2

Step 2: Synthesis of 4-((2-(2-aminoethoxy)ethyl) amino)-2-(2,6-dioxopiperidin-3-yl)isoindoline-1,3-dione (14f)

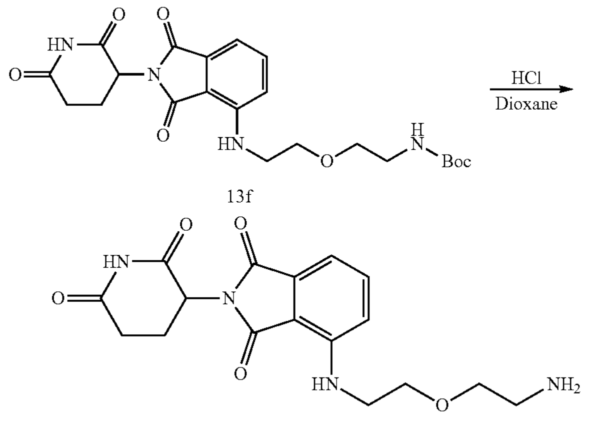

13f

14f

In a manner similar to Step 2 of Example 2, the titled compound (2.2 g, crude, HCl salt) was obtained as a green solid.

Step 3: Synthesis of (1S,3R,7S,8S,8aR)-8-(2-((2R, 4R)-4-((tert-butyldimethylsilyl)oxy)-6-oxotetrahydro-2H-pyran-2-yl)ethyl)-3,7-dimethyl-1,2,3,7,8,8a-hexahydronaphthalen-1-yl (2-(2-((2-(2,6-dioxopiperidin-3-yl)-1,3-dioxoisoindolin-4-yl) amino)ethoxy)ethyl)carbamate (Compound 86)

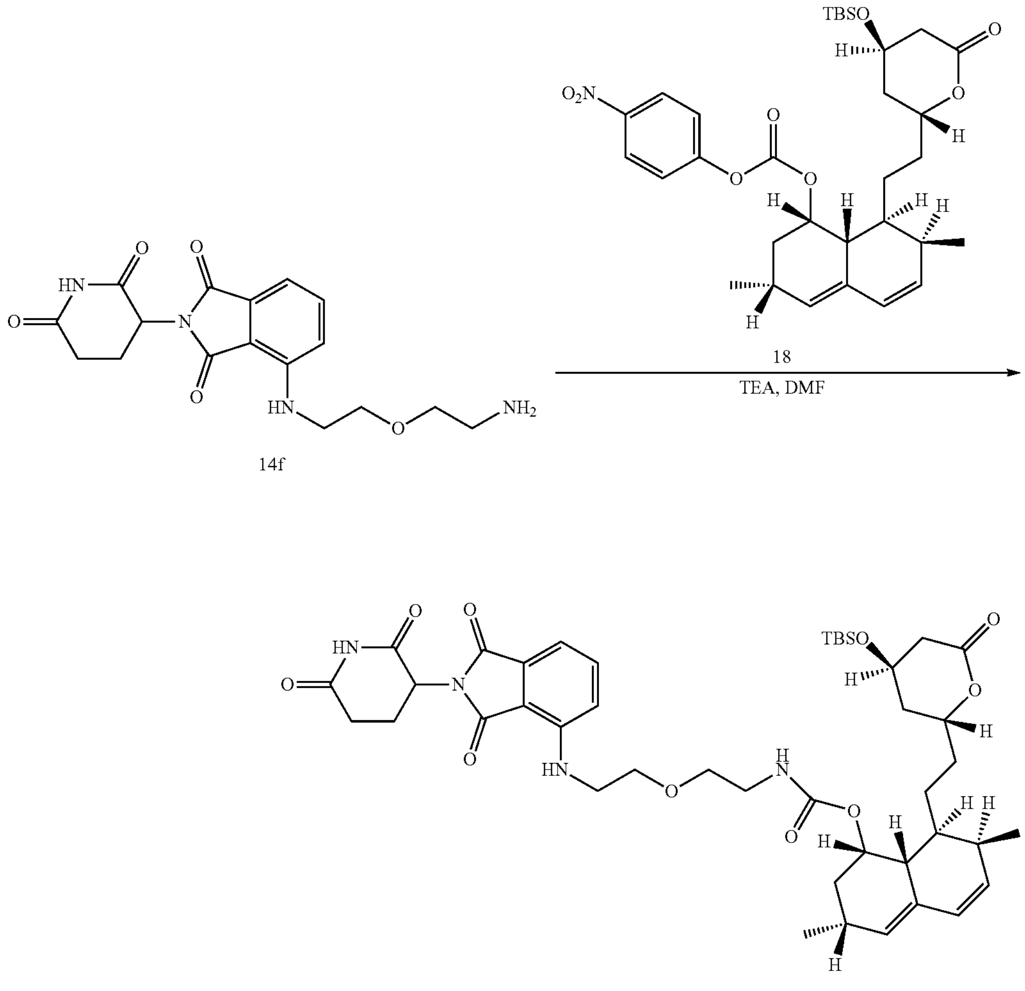

14f

18

Compound 86

To a solution of 4-((2-(2-aminoethoxy)ethyl)amino)-2-(2,6-dioxopiperidin-3-yl)isoindoline-1,3-dione (800 mg, 2.02 mmol, HCl salt) in DMAC (8 mL) was added TEA (611.99 mg, 6.05 mmol, 841.80 μL) followed by (1S,3R,7S,8S,8aR)-8-(2-((2R,4R)-4-((tert-butyldimethylsilyl)oxy)-6-oxotetrahydro-2H-pyran-2-yl)ethyl)-3,7-dimethyl-1,2,3,7,8,8a-hexahydronaphthalen-1-yl (4-nitrophenyl) carbonate (3.45 g, 2.02 mmol). The mixture was stirred at 20° C. for 16 hours. LCMS showed 14% of desired mass was detected. The reaction mixture was filtered and the filtrate was purified by prep-HPLC (column: Phenomenex luna C18 150*40 mm*15 μm; mobile phase: [water (0.225% FA)-ACN]; B %: 70%-100%, 10 min). Compound (1S,3R,7S,8S,8aR)-8-(2-((2R,4R)-4-((tert-butyldimethylsilyl)oxy)-6-oxotetrahydro-2H-pyran-2-yl)ethyl)-3,7-dimethyl-1,2,3,7,8,8a-hexahydronaphthalen-1-yl (2-(2-((2-(2,6-dioxopiperidin-3-yl)-1,3-dioxoisoindolin-4-yl)amino)ethoxy)ethyl)carbamate (450.8 mg, 538.08 μmol, 26.69% yield, 98% purity)) was obtained as a yellow solid.

MS $[M+H]^+$=821.6.

$^1H$ NMR (400 MHz, DMSO-$d_6$) δ=11.09 (s, 1H), 7.57 (dd, $J_1$=8.4 Hz, $J_2$=7.3 Hz, 1H), 7.13 (d, J=8.7 Hz, 1H), 7.07-6.96 (m, 2H), 6.59 (t, J=5.5 Hz, 1H), 5.91 (d, J=9.7 Hz, 1H), 5.81-5.67 (m, 1H), 5.46 (s, 1H), 5.11-4.96 (m, 2H), 4.52-4.41 (m, 1H), 4.31-4.23 (m, 1H), 3.63-3.51 (m, 2H), 3.57-3.40 (m, 4H), 3.11 (m, 2H), 2.95-2.83 (m, 1H), 2.70-2.64 (m, 1H), 2.63-2.52 (m, 2H), 2.39-2.28 (m, 3H), 2.26-2.20 (m, 1H), 2.06-1.98 (m, 1H), 1.89-1.73 (m, 3H), 1.66 (t, J=11.7 Hz, 3H), 1.51-1.41 (m, 1H), 1.36-1.20 (m, 2H), 1.02 (d, J=7.3 Hz, 3H), 0.83-0.73 (m, 12H), 0.04 (s, 6H).

Step 4: Synthesis of (1S,3R,7S,8S,8aR)-8-(2-((2R,4R)-4-hydroxy-6-oxotetrahydro-2H-pyran-2-yl)ethyl)-3,7-dimethyl-1,2,3,7,8,8a-hexahydronaphthalen-1-yl (2-(2-((2-(2,6-dioxopiperidin-3-yl)-1,3-dioxoisoindolin-4-yl)amino)ethoxy)ethyl)carbamate (Compound 87)

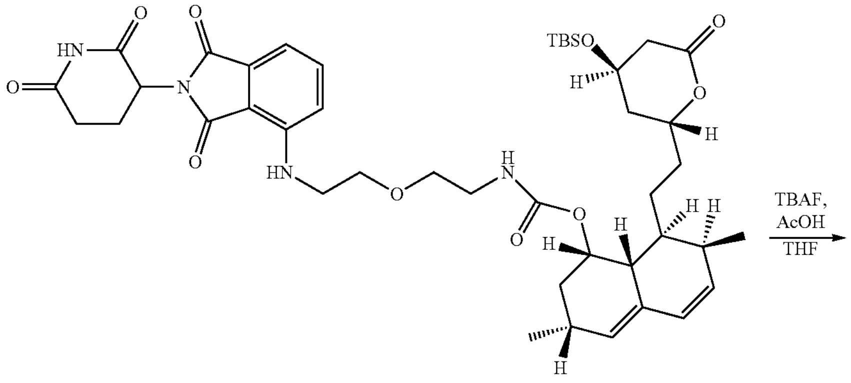

Compound 86

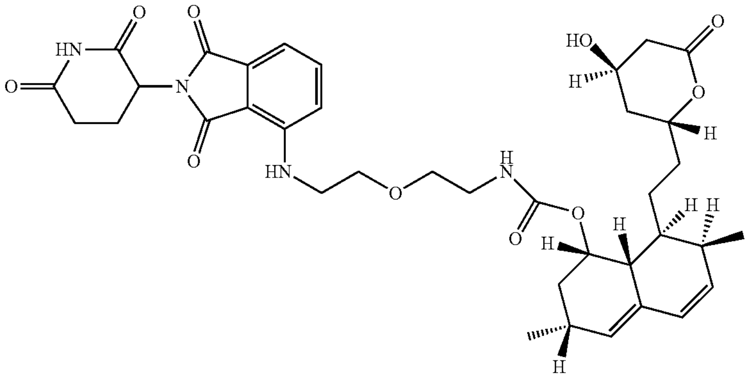

Compound 87

To a solution of (1S,3R,7S,8S,8aR)-8-(2-((2R,4R)-4-((tert-butyldimethylsilyl)oxy)-6-oxotetrahydro-2H-pyran-2-yl)ethyl)-3,7-dimethyl-1,2,3,7,8,8a-hexahydronaphthalen-1-yl (2-(2-((2-(2,6-dioxopiperidin-3-yl)-1,3-dioxoisoindolin-4-yl)amino)ethoxy)ethyl)carbamate (250 mg, 298.40 μmol) in THF (5 mL) was added AcOH (89.60 mg, 1.49 mmol, 85.33 μL) followed by TBAF (1 M, 1.19 mL). The mixture was stirred at 20° C. for 16 hours. LCMS showed 93% of desired mass was detected. The reaction mixture was diluted with $H_2O$ (20 mL) and extracted with EtOAc (30 mL×3). The combined organic layers were washed with $NH_4Cl$ (sat.aq, 50 mL×3), dried over $Na_2SO_4$, filtered and concentrated under reduced pressure. The residue was purified by prep-HPLC (column: Phenomenex Luna C18 150*25 mm*10 μm; mobile phase: [water (0.225% FA)-ACN]; B %: 42%-72%, 9 min). Compound (1S,3R,7S,8S,8aR)-8-(2-((2R,4R)-4-hydroxy-6-oxotetrahydro-2H-pyran-2-yl)ethyl)-3,7-dimethyl-1,2,3,7,8,8a-hexahydronaphthalen-1-yl (2-(2-((2-(2,6-dioxopiperidin-3-yl)-1,3-dioxoisoindolin-4-yl)amino)ethoxy)ethyl)carbamate (100.9 mg, 134.19 μmol, 44.97% yield, 94% purity)) was obtained as a yellow solid.

MS $[M+H]^+$=707.1.

$^1$H NMR (400 MHz, DMSO-$d_6$) δ=11.09 (s, 1H), 7.57 (dd, $J_1$=8.4 Hz, $J_2$=7.3 Hz, 1H), 7.14 (d, J=8.7 Hz, 1H), 7.07-6.93 (m, 2H), 6.59 (t, J=5.4 Hz, 1H), 5.91 (d, J=9.7 Hz, 1H), 5.81-5.68 (m, 1H), 5.46 (s, 1H), 5.17 (d, J=3.4 Hz, 1H), 5.10-4.98 (m, 2H), 4.54-4.38 (m, 1H), 4.13-3.93 (m, 1H), 3.63-3.51 (m, 2H), 3.49-3.36 (m, 4H), 3.19-3.05 (m, 2H), 2.94-2.82 (m, 1H), 2.69-2.52 (m, 3H), 2.40 (s, 3H), 2.23 (d, J=12.4 Hz, 1H), 2.06-1.98 (m, 1H), 1.90-1.75 (m, 3H), 1.72-1.56 (m, 3H), 1.51-1.43 (m, 1H), 1.35-1.21 (m, 2H), 1.02 (d, J=7.3 Hz, 3H), 0.83 (d, J=6.7 Hz, 3H).

Example 88 & Example 89. Synthesis of (1S,3R,7S,8S,8aR)-8-(2-((2R,4R)-4-((tert-butyldimethylsilyl)oxy)-6-oxotetrahydro-2H-pyran-2-yl)ethyl)-3,7-dimethyl-1,2,3,7,8,8a-hexahydronaphthalen-1-yl (4-(4-((2-(2,6-dioxopiperidin-3-yl)-1,3-dioxoisoindolin-4-yl)amino)butoxy)butyl)carbamate (Compound 88) and (1S,3R,7S,8S,8aR)-8-(2-((2R,4R)-4-hydroxy-6-oxotetrahydro-2H-pyran-2-yl)ethyl)-3,7-dimethyl-1,2,3,7,8,8a-hexahydronaphthalen-1-yl (4-(4-((2-(2,6-dioxopiperidin-3-yl)-1,3-dioxoisoindolin-4-yl)amino)butoxy)butyl)carbamate (Compound 89)

Step 1: Synthesis of 2-[4-[4-(1,3-dioxoisoindolin-2-yl)butoxy]butyl]isoindoline-1,3-dione (89)

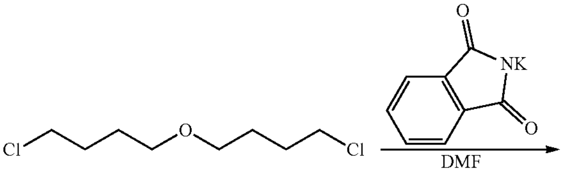

88

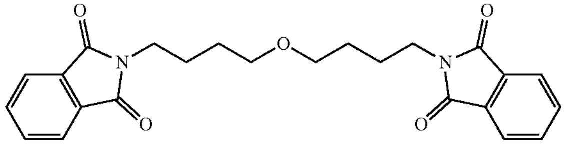

89

Step 2: Synthesis of 4-(4-aminobutoxy)butan-1-amine (90)

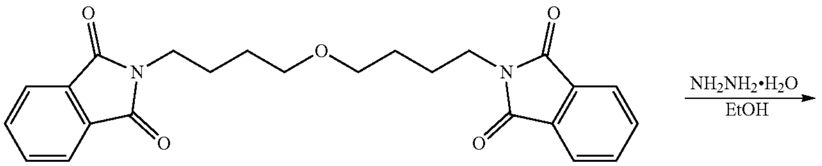

89

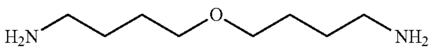

90

Step 3: Synthesis of tert-butyl N-[4-(4-aminobutoxy)butyl]carbamate (91)
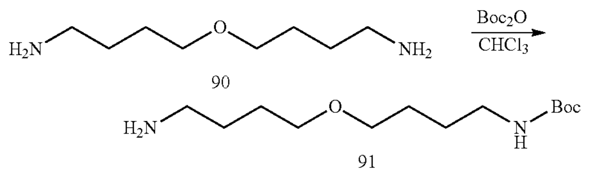
90
91
Step 4: Synthesis of tert-butyl N-[4-[4-[[2-(2,6-dioxo-3-piperidyl)-1,3-dioxo-isoindolin-4-yl]amino]butoxy]butyl]carbamate (92)
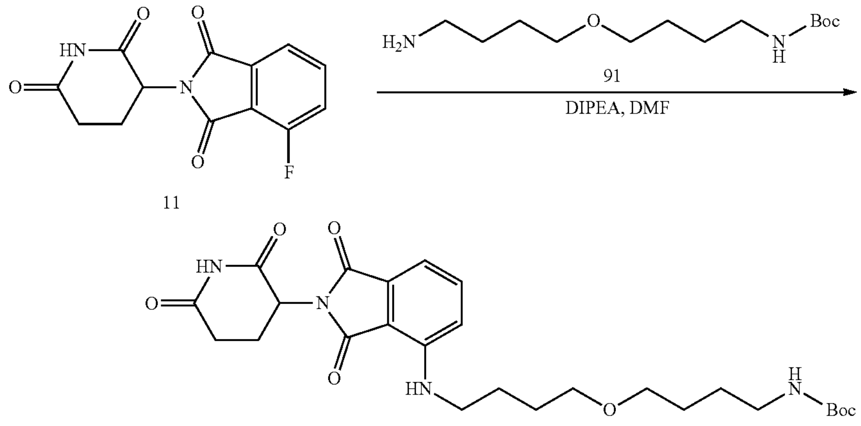
91
11
92
Step 5: Synthesis of 4-[4-(4-aminobutoxy)butylamino]-2-(2,6-dioxo-3-piperidyl)isoindoline-1,3-dione (93)
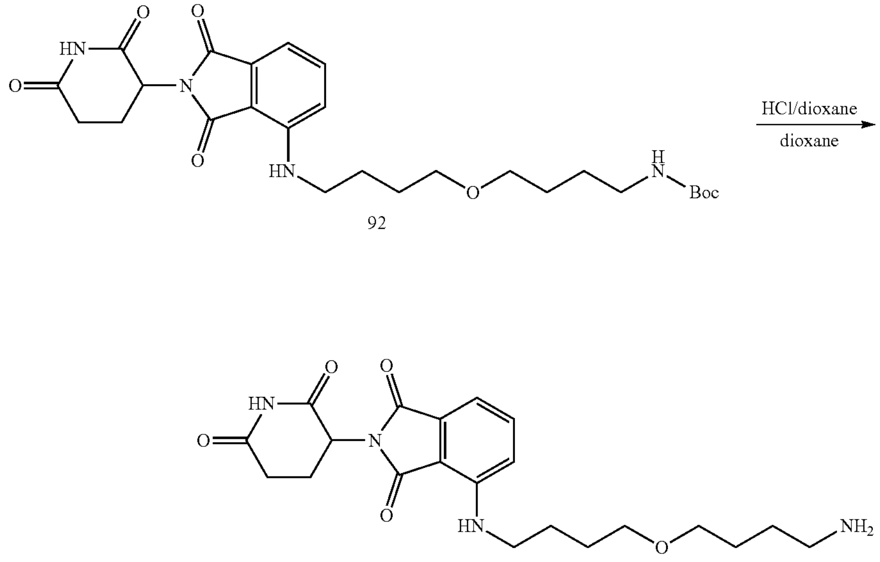
92
93

According to the above reaction scheme, in a manner similar to the other examples, the titled compound (964 mg, crude, HCl salt) as a white solid. MS $(M+H)^+$=417.2

Step 6: Synthesis of (1S,3R,7S,8S,8aR)-8-(2-((2R, 4R)-4-((tert-butyldimethylsilyl)oxy)-6-oxotetrahydro-2H-pyran-2-yl)ethyl)-3,7-dimethyl-1,2,3,7,8, 8a-hexahydronaphthalen-1-yl (4-(4-((2-(2,6-dioxopiperidin-3-yl)-1,3-dioxoisoindolin-4-yl) amino)butoxy)butyl)carbamate (Compound 88)

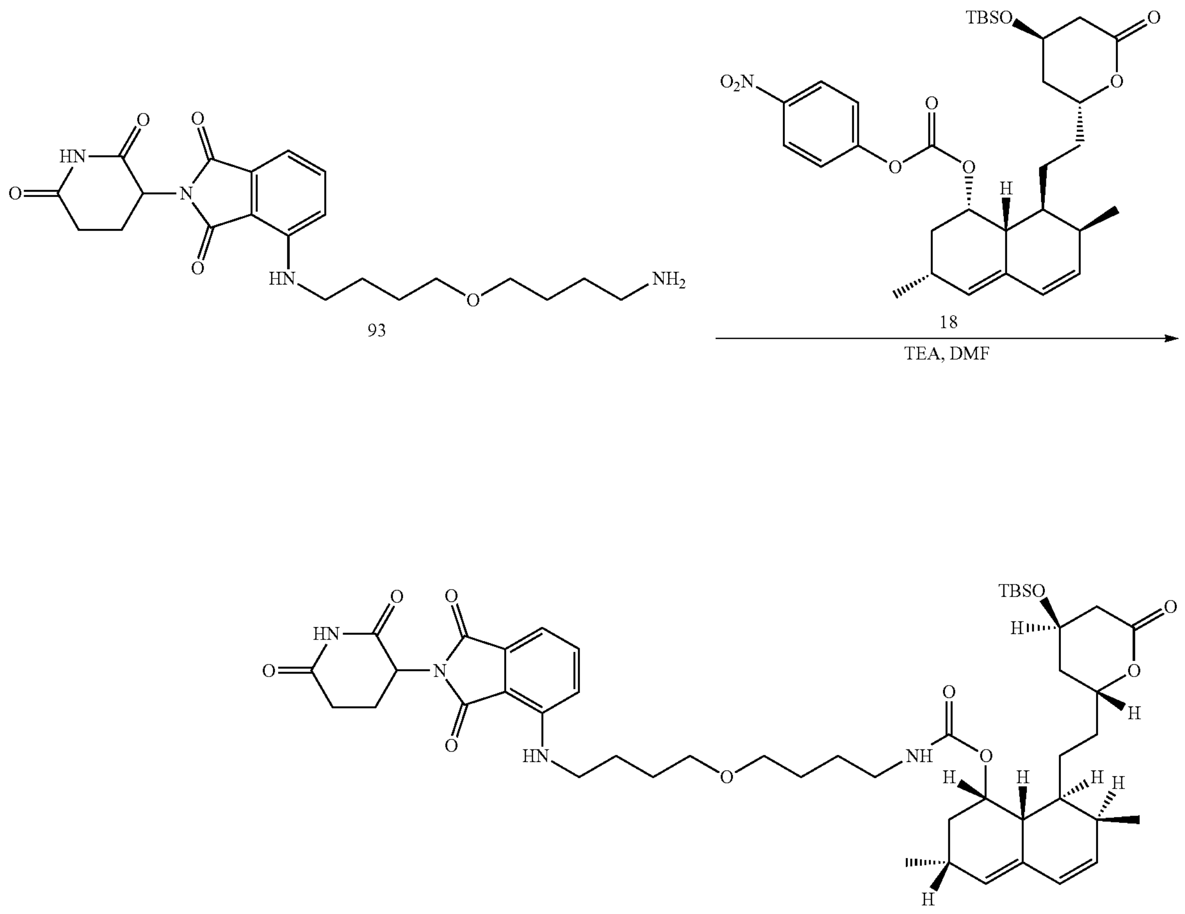

93

18

Compound 88

In a manner similar to Step 3 of Example 51, 58, the titled compound (574.7 mg, 642.09 μmol, 30.29% yield, 98% purity) was obtained as a yellow solid.

MS $(M+H)^+$=877.6

$^1$H NMR (400 MHz, Chloroform-d) δ 8.04 (s, 1H), 7.49 (dd, J=8.5, 7.1 Hz, 1H), 7.09 (d, J=7.0 Hz, 1H), 6.89 (d, J=8.5 Hz, 1H), 6.35-6.23 (m, 1H), 5.97 (d, J=9.6 Hz, 1H), 5.77 (dd, J=9.6, 6.0 Hz, 1H), 5.51 (s, 1H), 5.18 (s, 1H), 5.02-4.86 (m, 2H), 4.68-4.58 (m, 1H), 4.35-4.22 (m, 1H), 3.42 (dt, J=12.0, 6.0 Hz, 4H), 3.36-3.18 (m, 3H), 3.18-3.01 (m, 1H), 2.98-2.66 (m, 3H), 2.66-2.50 (m, 2H), 2.50-2.29 (m, 2H), 2.24 (d, J=12.0 Hz, 1H), 2.19-2.06 (m, 2H), 1.94-1.58 (m, 11H), 1.47-1.23 (m, 2H), 1.07 (d, J=7.4 Hz, 3H), 0.88 (d, J=2.4 Hz, 12H), 0.07 (d, J=0.8 Hz, 6H)

Step 7: Synthesis of (1S,3R,7S,8S,8aR)-8-(2-((2R,4R)-4-hydroxy-6-oxotetrahydro-2H-pyran-2-yl)ethyl)-3,7-dimethyl-1,2,3,7,8,8a-hexahydronaphthalen-1-yl (4-(4-((2-(2,6-dioxopiperidin-3-yl)-1,3-dioxoisoindolin-4-yl)amino)butoxy)butyl)carbamate (Compound 89)

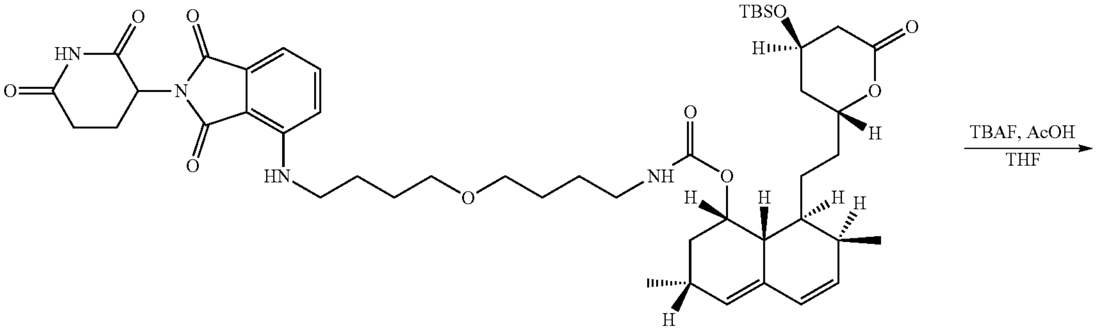

Compound 88

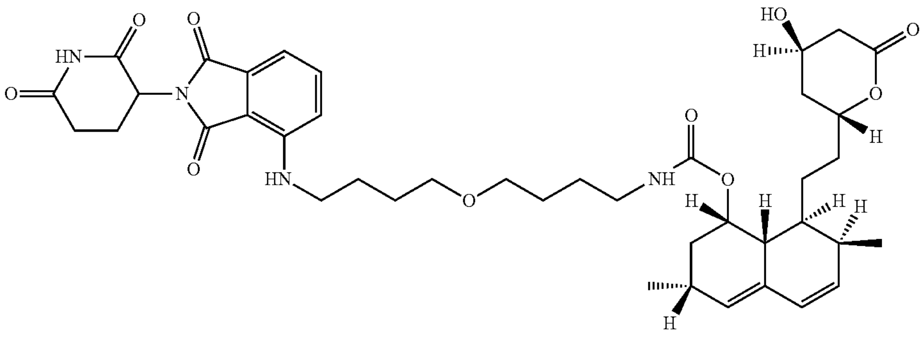

Compound 89

In a manner similar to Step 4 of Example 51, 58, the titled compound (178.4 mg, 215.14 μmol, 47.18% yield, 92% purity) was obtained as a yellow solid.

MS $(M+H)^+=763.5$ $^1H$ NMR (400 MHz, $CDCl_3$) δ=8.36 (br d, J=15.0 Hz, 1H), 7.50 (t, J=7.8 Hz, 1H), 7.10 (d, J=6.8 Hz, 1H), 6.90 (d, J=8.6 Hz, 1H), 6.30 (br s, 1H), 5.98 (d, J=9.6 Hz, 1H), 5.85-5.73 (m, 1H), 5.52 (br s, 1H), 5.22 (br s, 1H), 4.93 (br s, 2H), 4.62 (br s, 1H), 4.30 (br s, 1H), 3.45 (td, J=5.4, 10.4 Hz, 4H), 3.31 (br d, J=5.4 Hz, 2H), 3.20 (br d, J=5.8 Hz, 2H), 2.94-2.68 (m, 4H), 2.64-2.50 (m, 2H), 2.49-2.33 (m, 2H), 2.25 (br d, J=10.4 Hz, 1H), 2.18-2.02 (m, 2H), 2.00-1.83 (m, 3H), 1.78-1.65 (m, 7H), 1.58-1.51 (m, 4H), 1.42-1.31 (m, 2H), 1.08 (d, J=7.4 Hz, 3H), 0.90 (br d, J=7.0 Hz, 3H).

Example 90 & Example 91. Synthesis of (1S,3R,7S,8S,8aR)-8-(2-((2R,4R)-4-((tert-butyldimethylsilyl)oxy)-6-oxotetrahydro-2H-pyran-2-yl)ethyl)-3,7-dimethyl-1,2,3,7,8,8a-hexahydronaphthalen-1-yl (2-(3-(2-((2-(2,6-dioxopiperidin-3-yl)-1,3-dioxoisoindolin-4-yl)amino)ethoxy)propoxy)ethyl)carbamate (Compound 90) and (1S,3R,7S,8S,8aR)-8-(2-((2R,4R)-4-hydroxy-6-oxotetrahydro-2H-pyran-2-yl)ethyl)-3,7-dimethyl-1,2,3,7,8,8a-hexahydronaphthalen-1-yl (2-(3-(2-((2-(2,6-dioxopiperidin-3-yl)-1,3-dioxoisoindolin-4-yl)amino)ethoxy)propoxy)ethyl)carbamate (Compound 91)

Step 1: Synthesis of ethyl 2-[3-(2-ethoxy-2-oxo-ethoxy)propoxy]acetate (95)

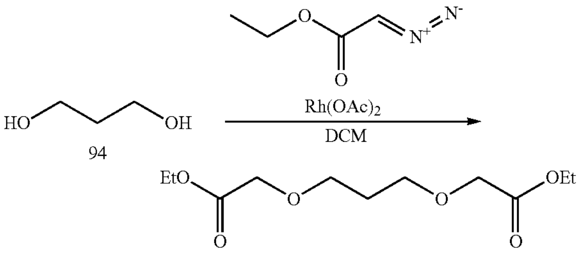

94

95

Step 2: Synthesis of 2-[3-(2-hydroxyethoxy)propoxy]ethanol (96)

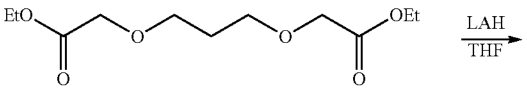

95

-continued

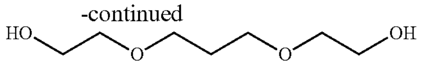

96

Step 3: Synthesis of 2-[3-(2-methylsulfonyloxy-ethoxy)propoxy]ethyl methanesulfonate (97)

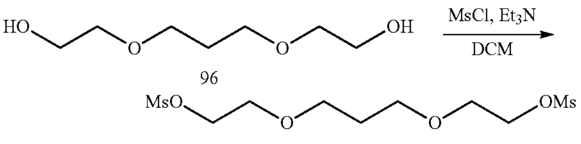

96

97

Step 4: Synthesis of 2-[2-[3-[2-(1,3-dioxoisoindolin-2-yl)ethoxy]propoxy]ethyl]isoindoline-1,3-dione (98)

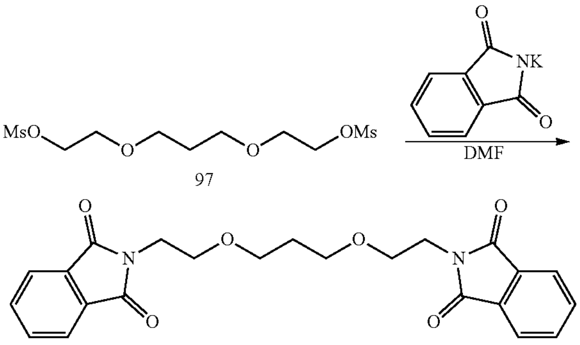

97

98

Step 5: Synthesis of 2-[3-(2-aminoethoxy)propoxy]ethanamine (99)

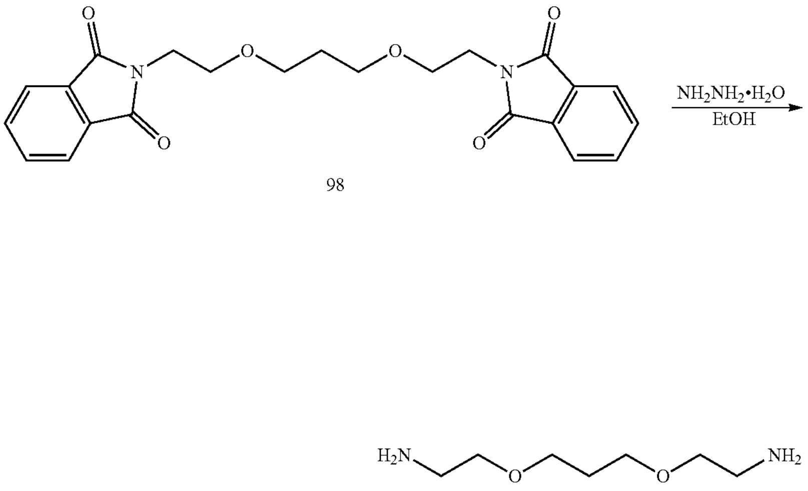

98

99

Step 6: Synthesis of tert-butyl N-[2-[3-(2-aminoethoxy)propoxy]ethyl]carbamate (100)
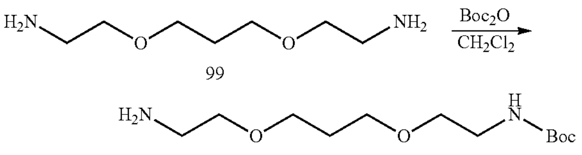
99
100
Step 7: Synthesis of tert-butyl N-[2-[3-[2-[[2-(2,6-dioxo-3-piperidyl)-1,3-dioxo-isoindolin-4-yl]amino]ethoxy]propoxy]ethyl]carbamate (101)
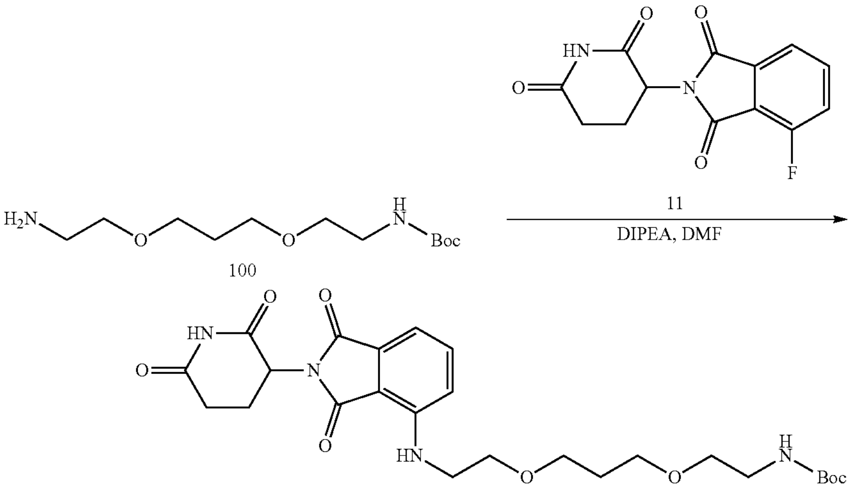
11
100
101
Step 8: Synthesis of 4-[2-[3-(2-aminoethoxy)propoxy]ethylamino]-2-(2,6-dioxo-3-piperidyl)isoindoline-1,3-dione (102)
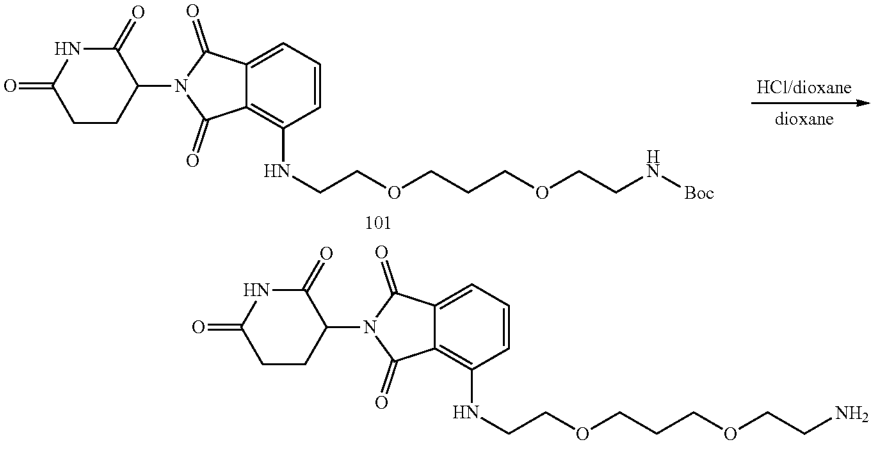
101
102

Step 9: Synthesis of (1S,3R,7S,8S,8aR)-8-(2-((2R,4R)-4-((tert-butyldimethylsilyl)oxy)-6-oxotetrahydro-2H-pyran-2-yl)ethyl)-3,7-dimethyl-1,2,3,7,8,8a-hexahydronaphthalen-1-yl (2-(3-(2-((2-(2,6-dioxopiperidin-3-yl)-1,3-dioxoisoindolin-4-yl)amino)ethoxy)propoxy)ethyl)carbamate (Compound 90)

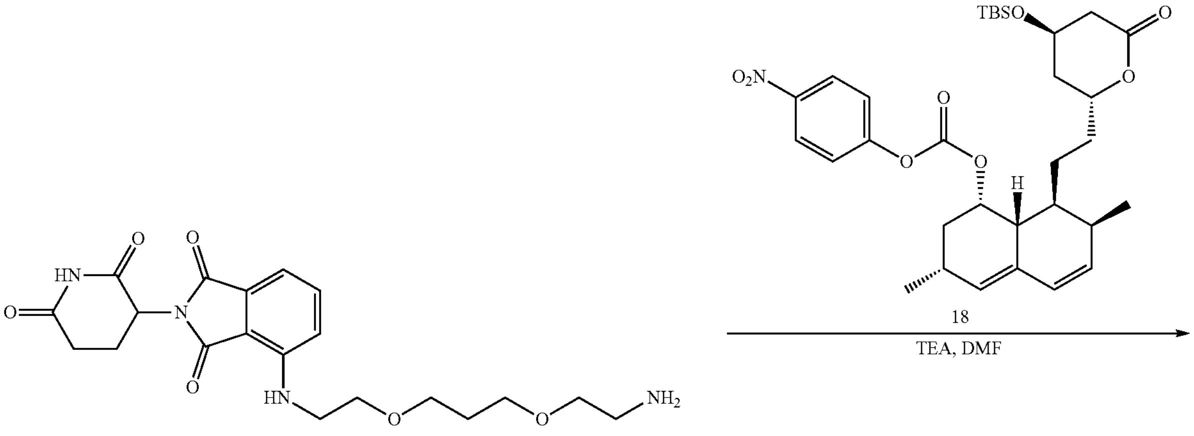

102

18

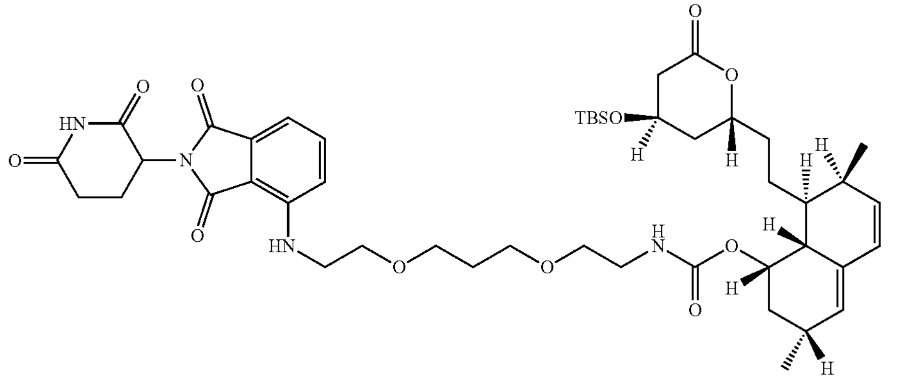

Compound 90

In a manner similar to Step 3 of Example 51, 58, the titled compound (520.7 mg, 586.37 μmol, 29.92% yield, 99% purity) was obtained as a yellow solid.

MS $(M+H)^+=879.5$ $^1H$ NMR (400 MHz, $CDCl_3$) δ=8.34 (br s, 1H), 7.50 (t, J=7.8 Hz, 1H), 7.12 (d, J=7.0 Hz, 1H), 6.92 (d, J=8.6 Hz, 1H), 6.51 (br s, 1H), 5.98 (d, J=9.7 Hz, 1H), 5.82-5.74 (m, 1H), 5.52 (br s, 1H), 5.22 (br s, 1H), 5.13 (br s, 1H), 4.98-4.86 (m, 1H), 4.68-4.55 (m, 1H), 4.32-4.25 (m, 1H), 3.68-3.63 (m, 2H), 3.58-3.51 (m, 4H), 3.49-3.38 (m, 5H), 3.32-3.23 (m, 1H), 2.92-2.72 (m, 3H), 2.62-2.52 (m, 2H), 2.46-2.34 (m, 2H), 2.25 (br d, J=9.2 Hz, 1H), 2.18-2.07 (m, 2H), 1.92-1.74 (m, 6H), 1.70-1.62 (m, 2H), 1.46-1.30 (m, 2H), 1.08 (d, J=6.8 Hz, 3H), 0.92-0.88 (m, 12H), 0.08 (s, 6H).

Step 10: Synthesis of (1S,3R,7S,8S,8aR)-8-(2-((2R,4R)-4-hydroxy-6-oxotetrahydro-2H-pyran-2-yl)ethyl)-3,7-dimethyl-1,2,3,7,8,8a-hexahydronaphthalen-1-yl (2-(3-(2-((2-(2,6-dioxopiperidin-3-yl)-1,3-dioxoisoindolin-4-yl)amino)ethoxy)propoxy)ethyl) carbamate (Compound 91)

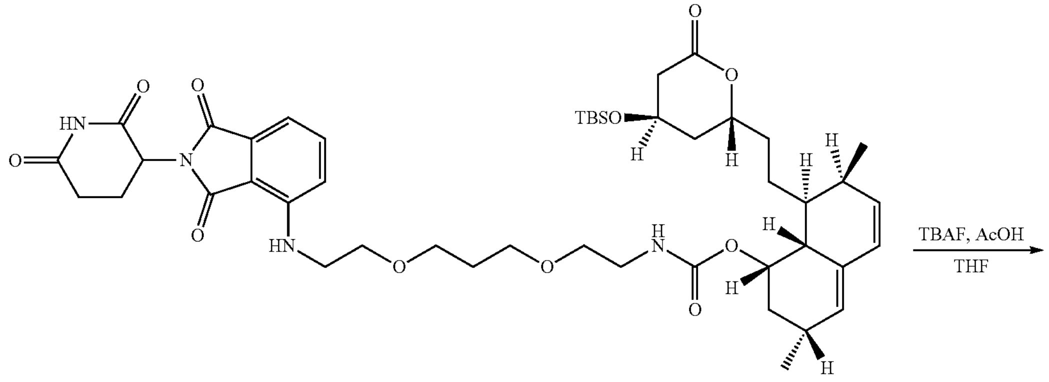

Compound 90

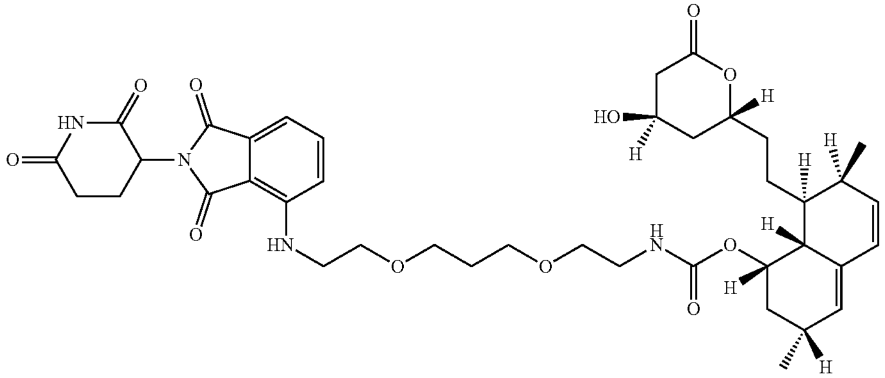

Compound 91

In a manner similar to Step 4 of Example 51, 58, the titled compound (326.8 mg, 405.90 μmol, 89.21% yield, 95% purity) was obtained as a yellow solid.

MS $(M+H)^+$=765.4

$^1$H NMR (400 MHz, $CDCl_3$) δ=7.55-7.48 (m, 1H), 7.13 (t, J=6.9 Hz, 1H), 6.91 (d, J=8.5 Hz, 1H), 6.58-6.46 (m, 1H), 5.97 (d, J=9.6 Hz, 1H), 5.85-5.70 (m, 1H), 5.52 (br s, 1H), 5.25 (br s, 1H), 5.21-5.09 (m, 1H), 4.99-4.89 (m, 1H), 4.67-4.50 (m, 1H), 4.36-4.11 (m, 1H), 3.74-3.40 (m, 11H), 3.36-3.17 (m, 1H), 3.01-2.69 (m, 4H), 2.66-2.55 (m, 1H), 2.45-2.34 (m, 2H), 2.25 (br d, J=12.3 Hz, 1H), 2.17-2.11 (m, 1H), 2.11-2.02 (m, 1H), 2.02-1.94 (m, 1H), 1.91-1.80 (m, 4H), 1.72 (br d, J=10.8 Hz, 2H), 1.65-1.52 (m, 3H), 1.40-1.29 (m, 2H), 1.08 (d, J=7.4 Hz, 3H), 0.89 (dd, J=4.6, 6.9 Hz, 3H).

Example 92 & Example 93. Synthesis of (1S,3R,7S,8S,8aR)-8-(2-((2R,4R)-4-((tert-butyldimethylsilyl)oxy)-6-oxotetrahydro-2H-pyran-2-yl)ethyl)-3,7-dimethyl-1,2,3,7,8,8a-hexahydronaphthalen-1-yl (2-(2-(3-((2-(2,6-dioxopiperidin-3-yl)-1,3-dioxoisoindolin-4-yl)amino)propoxy)ethoxy)ethyl)carbamate (Compound 92) and (1S,3R,7S,8S,8aR)-8-(2-((2R,4R)-4-hydroxy-6-oxotetrahydro-2H-pyran-2-yl)ethyl)-3,7-dimethyl-1,2,3,7,8,8a-hexahydronaphthalen-1-yl (2-(2-(3-((2-(2,6-dioxopiperidin-3-yl)-1,3-dioxoisoindolin-4-yl)amino)propoxy)ethoxy)ethyl)carbamate (Compound 93)

Step 1: Synthesis of tert-butyl (2-(2-(2-cyanoethoxy)ethoxy)ethyl)carbamate (104)

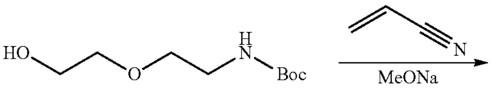

103

-continued
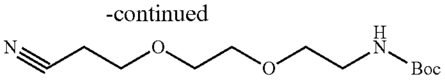
104
Step 2: Synthesis of tert-butyl (2-(2-(3-aminopropoxy)ethoxy)ethyl)carbamate (105)
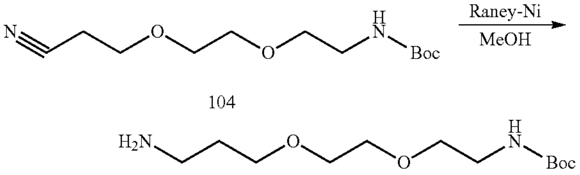
104
105
Step 3: Synthesis of tert-butyl (2-(2-(3-((2-(2,6-dioxopiperidin-3-yl)-1,3-dioxoisoindolin-4-yl)amino)propoxy)ethoxy)ethyl)carbamate (106)
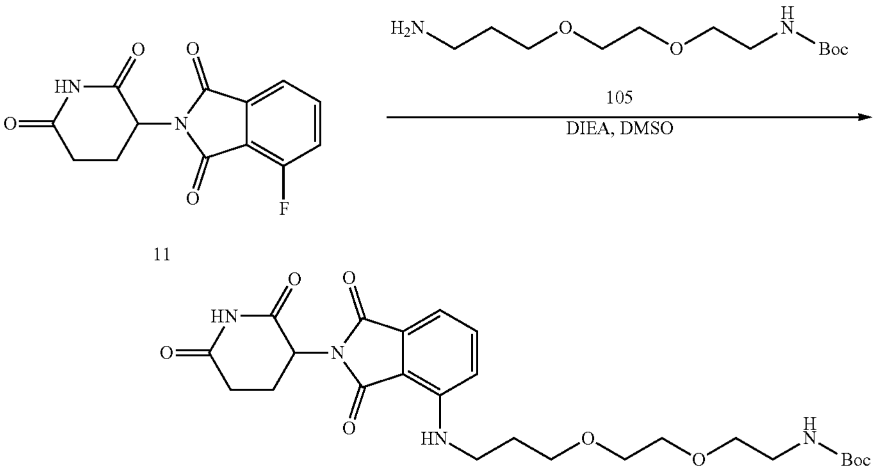
105
11
106
Step 4: Synthesis of 4-((3-(2-(2-aminoethoxy)ethoxy)propyl)amino)-2-(2,6-dioxopiperidin-3-yl)isoindoline-1,3-dione (107)
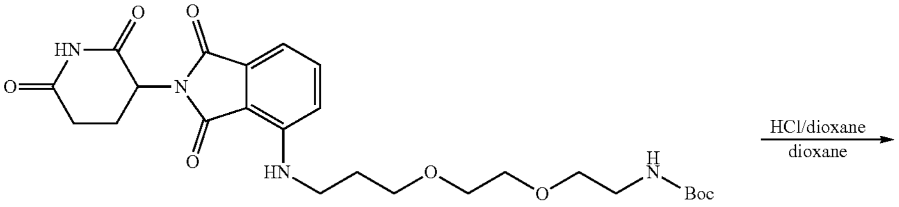
106

-continued
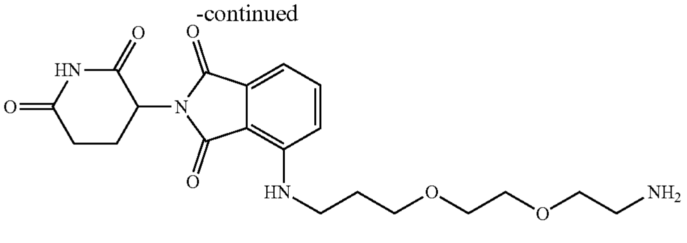
107
Step 5: Synthesis of (1S,3R,7S,8S,8aR)-8-(2-((2R,4R)-4-((tert-butyldimethylsilyl)oxy)-6-oxotetrahydro-2H-pyran-2-yl)ethyl)-3,7-dimethyl-1,2,3,7,8,8a-hexahydronaphthalen-1-yl (2-(2-(3-((2-(2,6-dioxopiperidin-3-yl)-1,3-dioxoisoindolin-4-yl)amino)propoxy)ethoxy)ethyl)carbamate (Compound 92)
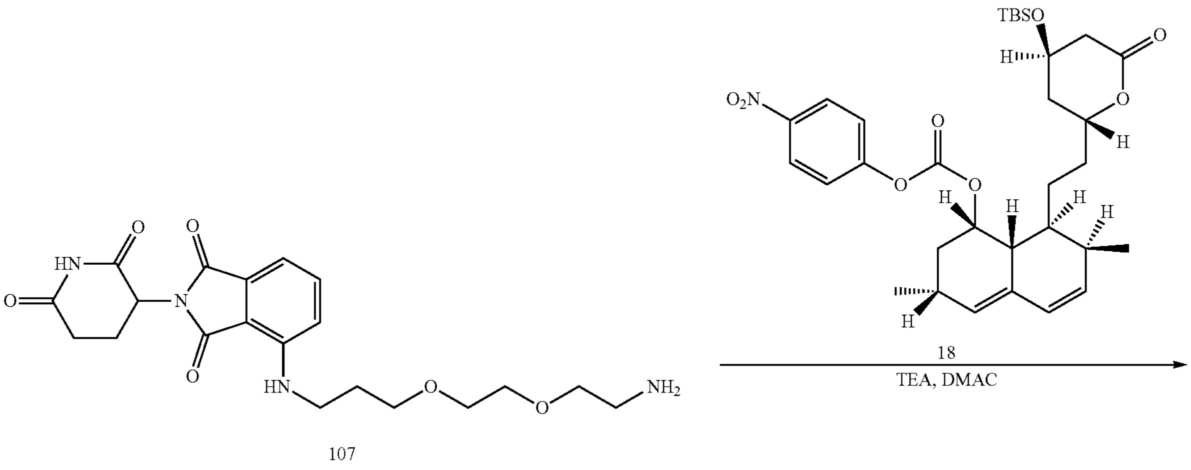
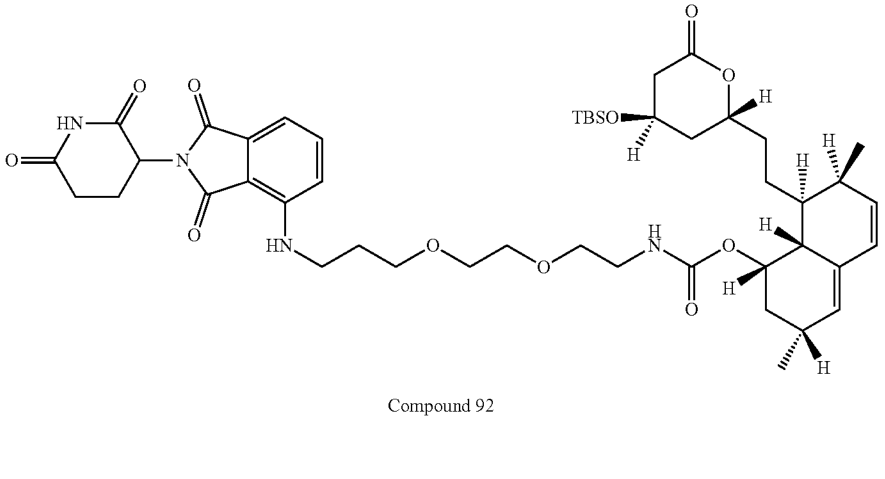
Compound 92

In a manner similar to Step 3 of Example 51, 58, the titled compound (942.3 mg, 1.06 mmol, 50.28% yield, 99% purity) was obtained as a yellow solid.

MS $(M+H)^+$=879.6

$^1$H NMR (400 MHz, $CDCl_3$) δ=8.13 (br s, 1H), 7.54-7.47 (m, 1H), 7.09 (d, J=6.8 Hz, 1H), 6.92 (d, J=8.6 Hz, 1H), 6.45 (br s, 1H), 5.97 (d, J=9.8 Hz, 1H), 5.78 (dd, J=6.1, 9.6 Hz, 1H), 5.51 (br s, 1H), 5.22 (br s, 2H), 4.92 (br dd, J=5.0, 11.6 Hz, 1H), 4.70-4.60 (m, 1H), 4.32-4.24 (m, 1H), 3.65-3.61 (m, 2H), 3.61-3.52 (m, 6H), 3.40 (q, J=6.0 Hz, 2H), 3.35-3.27 (m, 1H), 2.93-2.84 (m, 1H), 2.82-2.69 (m, 2H), 2.64-2.51 (m, 2H), 2.46-2.33 (m, 2H), 2.25 (br d, J=11.2 Hz, 1H), 2.17-2.06 (m, 2H), 1.97-1.74 (m, 6H), 1.68-1.59 (m, 2H), 1.46-1.27 (m, 2H), 1.07 (d, J=7.4 Hz, 3H), 0.93-0.83 (m, 12H), 0.08 (s, 6H).

Step 6: Synthesis of (1S,3R,7S,8S,8aR)-8-(2-((2R,4R)-4-hydroxy-6-oxotetrahydro-2H-pyran-2-yl)ethyl)-3,7-dimethyl-1,2,3,7,8,8a-hexahydronaphthalen-1-yl (2-(2-(3-((2-(2,6-dioxopiperidin-3-yl)-1,3-dioxoisoindolin-4-yl)amino)propoxy)ethoxy)ethyl) carbamate (Compound 93)

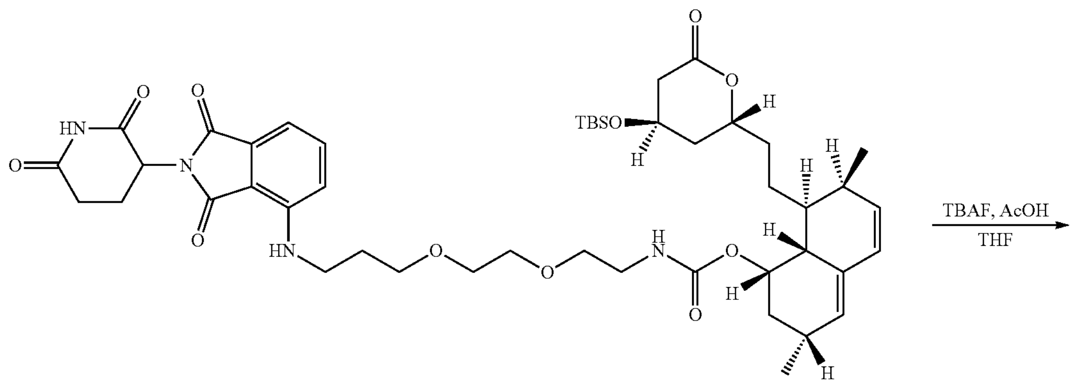

Compound 92

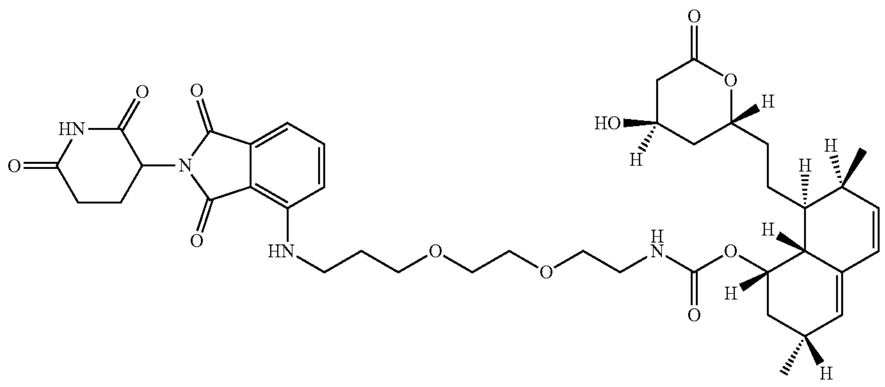

Compound 93

In a manner similar to Step 4 of Example 51, 58, the titled compound (389.4 mg, 468.38 μmol, 49.02% yield, 92% purity) was obtained as a yellow solid.

MS $(M+H)^+$=765.5

$^1$H NMR (400 MHz, $CDCl_3$) δ=8.77-8.47 (m, 1H), 7.53-7.47 (m, 1H), 7.09 (dd, J=1.4, 7.0 Hz, 1H), 6.91 (d, J=8.6 Hz, 1H), 6.55 (br s, 1H), 5.97 (d, J=9.6 Hz, 1H), 5.81-5.74 (m, 1H), 5.51 (br s, 1H), 5.38-5.14 (m, 2H), 4.99-4.89 (m, 1H), 4.68-4.54 (m, 1H), 4.34-4.24 (m, 1H), 3.71-3.54 (m, 8H), 3.45-3.32 (m, 4H), 2.96-2.63 (m, 5H), 2.63-2.52 (m, 1H), 2.47-2.31 (m, 2H), 2.28-2.22 (m, 1H), 2.18-2.11 (m, 1H), 2.08-2.04 (m, 1H), 1.95-1.92 (m, 3H), 1.90-1.78 (m, 2H), 1.72-1.60 (m, 3H), 1.42-1.30 (m, 2H), 1.07 (d, J=7.4 Hz, 3H), 0.89 (dd, J=1.6, 6.9 Hz, 3H).

Example 94 & Example 95. Synthesis of (1S,3R,7S,8S,8aR)-8-(2-((2R,4R)-4-((tert-butyldimethylsilyl)oxy)-6-oxotetrahydro-2H-pyran-2-yl)ethyl)-3,7-dimethyl-1,2,3,7,8,8a-hexahydronaphthalen-1-yl (3-(3-(3-((2-(2,6-dioxopiperidin-3-yl)-1,3-dioxoisoindolin-4-yl)amino)propoxy)propoxy)propyl)carbamate (Compound 94) and (1S,3R,7S,8S,8aR)-8-(2-((2R,4R)-4-hydroxy-6-oxotetrahydro-2H-pyran-2-yl)ethyl)-3,7-dimethyl-1,2,3,7,8,8a-hexahydronaphthalen-1-yl (3-(3-(3-((2-(2,6-dioxopiperidin-3-yl)-1,3-dioxoisoindolin-4-yl)amino)propoxy)propoxy)propyl)carbamate (Compound 95)

Step 1: Synthesis of 3,3'-(propane-1,3-diylbis(oxy))dipropanenitrile (109)

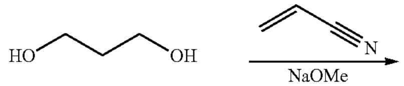

108

-continued

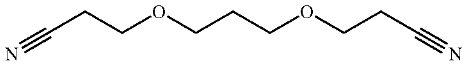

109

Step 2: Synthesis of 3,3'-(propane-1,3-diylbis(oxy))bis(propan-1-amine) (110)

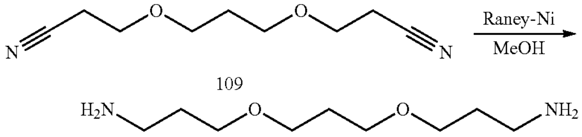

109

110

Step 3: Synthesis of tert-butyl (3-(3-(3-aminopropoxy)propoxy)propyl)carbamate (111)

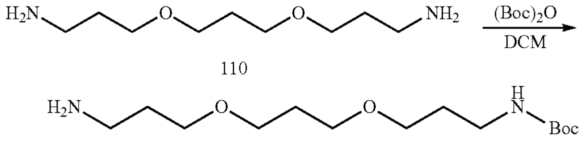

110

111

Step 4: Synthesis of tert-butyl (3-(3-(3-((2-(2,6-dioxopiperidin-3-yl)-1,3-dioxoisoindolin-4-yl)amino)propoxy)propoxy)propyl)carbamate (112)

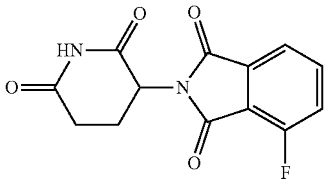

11

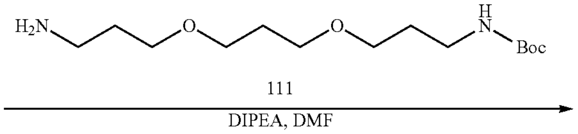

111

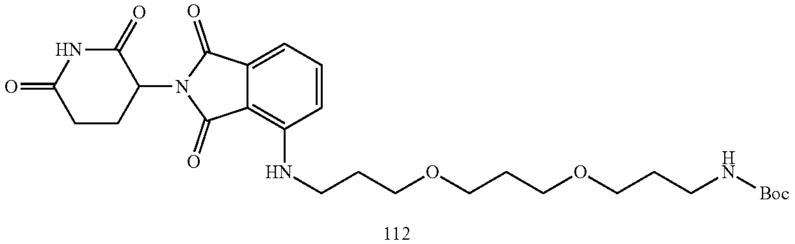

112

Step 5: Synthesis of 4-((3-(3-(3-aminopropoxy)propoxy)propyl)amino)-2-(2,6-dioxopiperidin-3-yl)isoindoline-1,3-dione (113)
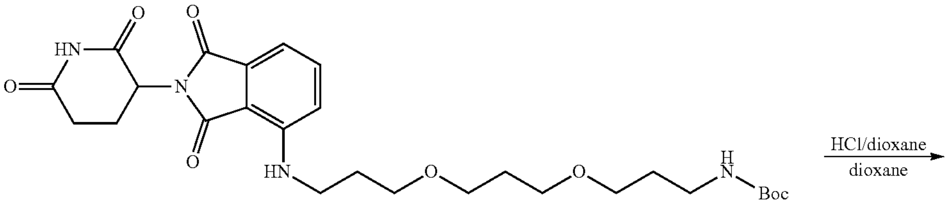
112
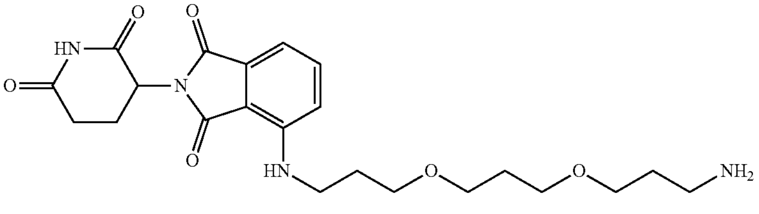
113
Step 6: Synthesis of (1S,3R,7S,8S,8aR)-8-(2-((2R,4R)-4-((tert-butyldimethylsilyl)oxy)-6-oxotetrahydro-2H-pyran-2-yl)ethyl)-3,7-dimethyl-1,2,3,7,8,8a-hexahydronaphthalen-1-yl (3-(3-(3-((2-(2,6-dioxopiperidin-3-yl)-1,3-dioxoisoindolin-4-yl)amino)propoxy)propoxy)propyl)carbamate (Compound 94)
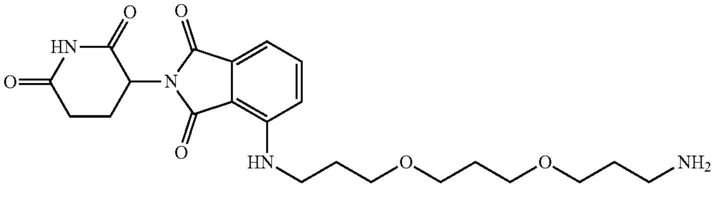
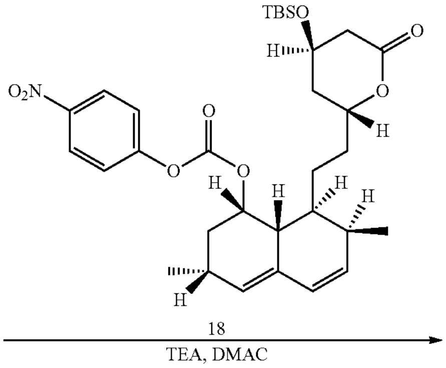
113

-continued

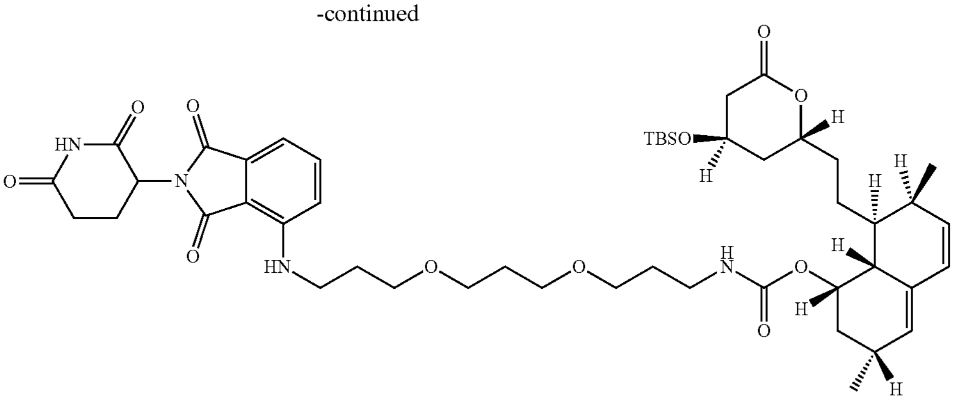

Compound 94

In a manner similar to Step 3 of Example 51, 58, the titled compound (620 mg, 656.10 μmol, 27.55% yield, 96% purity) was obtained as a yellow solid.

MS $(M+H)^+=907.6$ $^1H$ NMR (400 MHz, $CDCl_3$) δ=8.15 (br s, 1H), 7.50 (dd, J=7.4, 8.4 Hz, 1H), 7.09 (d, J=7.0 Hz, 1H), 6.92 (d, J=8.6 Hz, 1H), 6.52-6.40 (m, 1H), 5.97 (d, J=9.8 Hz, 1H), 5.77 (dd, J=6.2, 9.5 Hz, 1H), 5.58-5.49 (m, 1H), 5.28-5.15 (m, 1H), 5.14-5.03 (m, 1H), 4.95-4.88 (m, 1H), 4.64 (br dd, J=3.2, 8.0 Hz, 1H), 4.29 (br s, 1H), 3.55-3.37 (m, 10H), 3.35-3.25 (m, 1H), 3.25-3.15 (m, 1H), 2.92-2.84 (m, 1H), 2.83-2.69 (m, 2H), 2.64-2.55 (m, 2H), 2.46-2.33 (m, 2H), 2.25 (br dd, J=2.0, 12.2 Hz, 1H), 2.17-2.07 (m, 2H), 1.89-1.89 (m, 1H), 1.97-1.81 (m, 7H), 1.76-1.71 (m, 2H), 1.69-1.62 (m, 2H), 1.47-1.37 (m, 1H), 1.36-1.27 (m, 1H), 1.08 (d, J=7.4 Hz, 3H), 0.91-0.89 (m, 12H), 0.08 (s, 6H).

Step 7: Synthesis of (1S,3R,7S,8S,8aR)-8-(2-((2R,4R)-4-hydroxy-6-oxotetrahydro-2H-pyran-2-yl)ethyl)-3,7-dimethyl-1,2,3,7,8,8a-hexahydronaphthalen-1-yl (3-(3-(3-((2-(2,6-dioxopiperidin-3-yl)-1,3-dioxoisoindolin-4-yl)amino)propoxy)propoxy)propyl)carbamate (Compound 95)

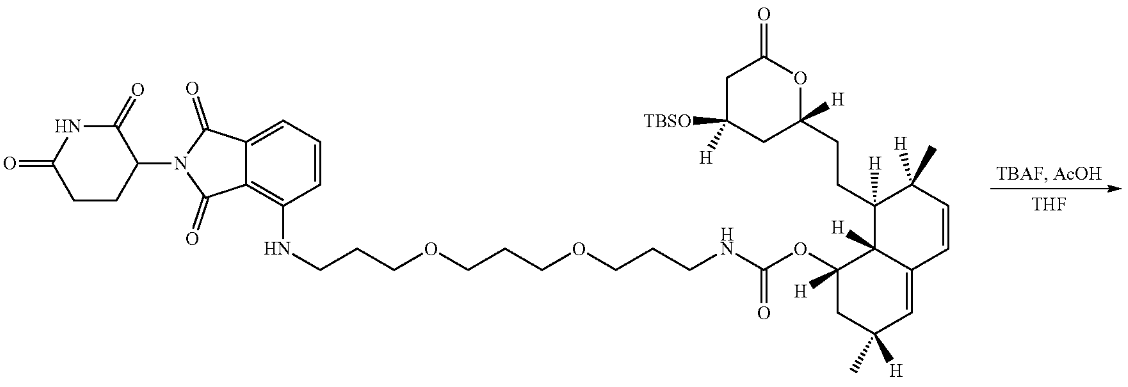

Compound 94

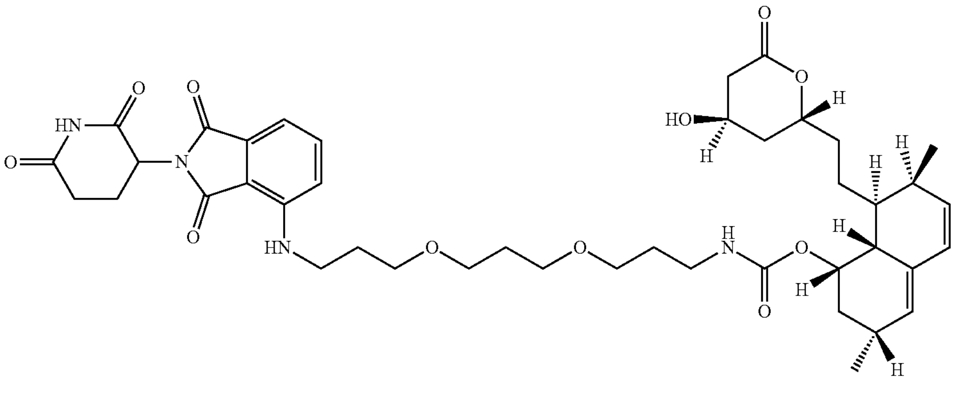

Compound 95

In a manner similar to Step 4 of Example 51, 58, the titled compound (188.9 mg, 223.94 μmol, 39.83% yield, 94% purity) was obtained as a yellow solid.

MS $(M+H)^+$=793.5

$^1H$ NMR (400 MHz, $CDCl_3$) δ=8.73-8.47 (m, 1H), 7.53-7.47 (m, 1H), 7.09 (d, J=7.1 Hz, 1H), 6.91 (d, J=8.6 Hz, 1H), 6.60-6.49 (m, 1H), 5.97 (d, J=9.8 Hz, 1H), 5.78 (dd, J=6.2, 9.6 Hz, 1H), 5.51 (br s, 1H), 5.33-5.21 (m, 1H), 5.19-4.98 (m, 1H), 4.98-4.88 (m, 1H), 4.69-4.55 (m, 1H), 4.36-4.25 (m, 1H), 3.57-3.37 (m, 10H), 3.25 (br d, J=6.2 Hz, 2H), 2.98-2.65 (m, 5H), 2.64-2.52 (m, 1H), 2.48-2.33 (m, 2H), 2.25 (br d, J=11.0 Hz, 1H), 2.17-2.10 (m, 1H), 2.08-2.01 (m, 1H), 1.97-1.81 (m, 7H), 1.75-1.62 (m, 5H), 1.43-1.30 (m, 2H), 1.08 (d, J=7.4 Hz, 3H), 0.90 (d, J=7.0 Hz, 3H).

Example 96 & Example 97. Synthesis of (1S,3R,7S,8S,8aR)-8-(2-((2R,4R)-4-((tert-butyldimethylsilyl)oxy)-6-oxotetrahydro-2H-pyran-2-yl)ethyl)-3,7-dimethyl-1,2,3,7,8,8a-hexahydronaphthalen-1-yl (8-(2-((2-(2,6-dioxopiperidin-3-yl)-1,3-dioxoisoindolin-4-yl)oxy)acetamido)octyl)carbamate (Compound 96) and (1S,3R,7S,8S,8aR)-8-(2-((2R,4R)-4-hydroxy-6-oxotetrahydro-2H-pyran-2-yl)ethyl)-3,7-dimethyl-1,2,3,7,8,8a-hexahydronaphthalen-1-yl (8-(2-((2-(2,6-dioxopiperidin-3-yl)-1,3-dioxoisoindolin-4-yl)oxy)acetamido)octyl)carbamate (Compound 97)

Step 1: Synthesis of tert-butyl (8-(2-((2-(2,6-dioxopiperidin-3-yl)-1,3-dioxoisoindolin-4-yl)oxy)acetamido)octyl)carbamate (114)

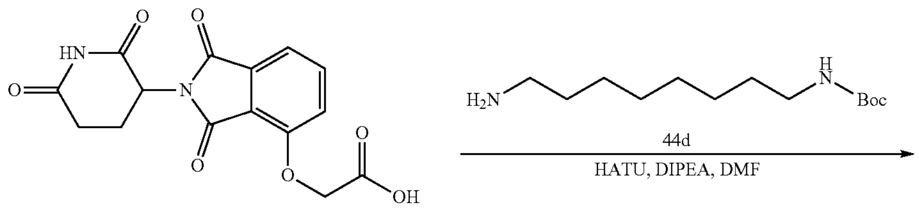

68

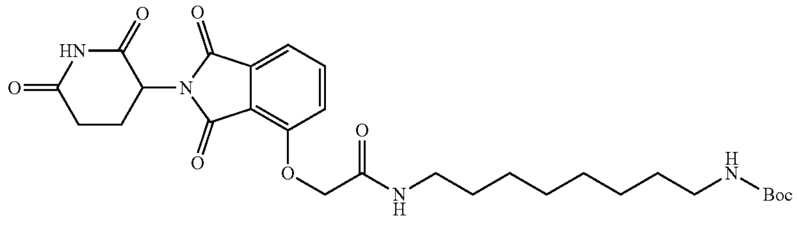

114

Step 2: Synthesis of N-(8-aminooctyl)-2-((2-(2,6-dioxopiperidin-3-yl)-1,3-dioxoisoindolin-4-yl)oxy)acetamide (115)

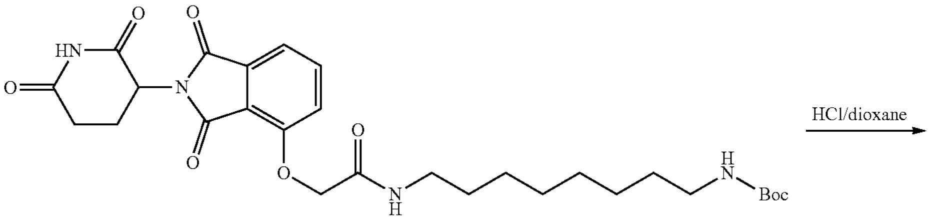

114

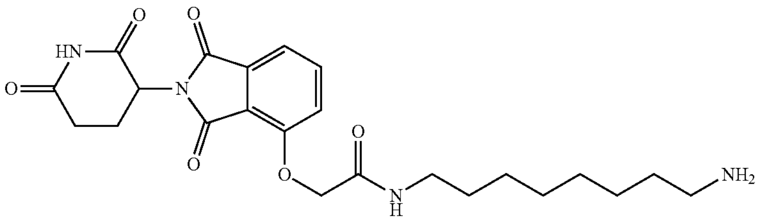

115

Step 3: Synthesis of (1S,3R,7S,8S,8aR)-8-(2-((2R,4R)-4-((tert-butyldimethylsilyl)oxy)-6-oxotetrahydro-2H-pyran-2-yl)ethyl)-3,7-dimethyl-1,2,3,7,8,8a-hexahydronaphthalen-1-yl (8-(2-((2-(2,6-dioxopiperidin-3-yl)-1,3-dioxoisoindolin-4-yl)oxy)acetamido)octyl)carbamate (Compound 96)

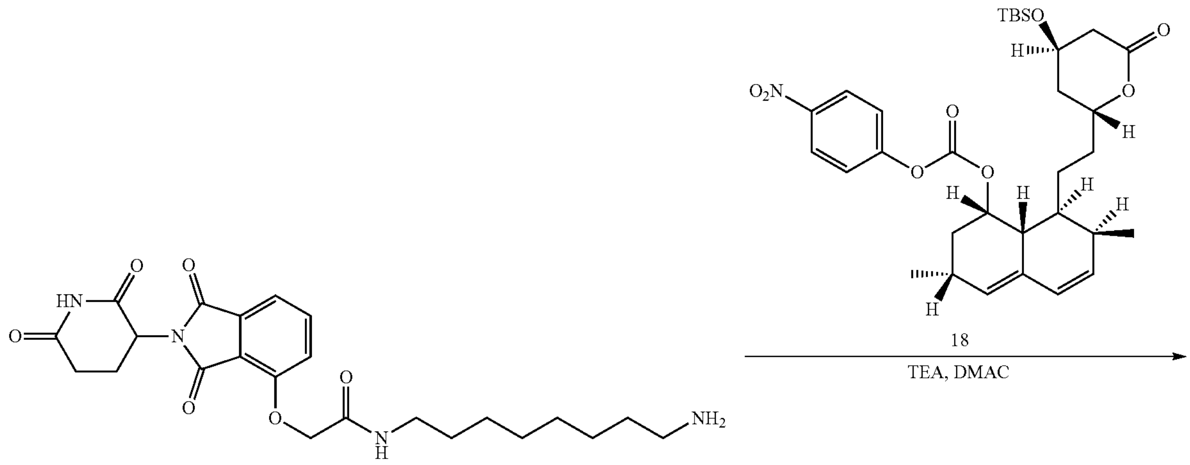

115

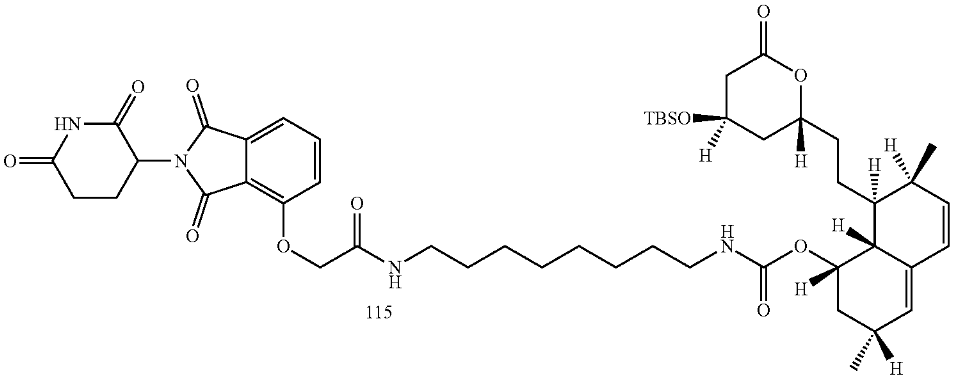
115

Compound 96

In a manner similar to Step 3 of Example 51, 58, the titled compound (628.6 mg, 642.84 μmol, 32.43% yield, 94% purity) was obtained as a white solid.

MS $(M+H)^+$=919.8

$^1$H NMR (400 MHz, Chloroform-d) δ 8.38 (d, J=18.3 Hz, 1H), 7.75 (t, J=7.9 Hz, 1H), 7.55 (d, J=7.3 Hz, 1H), 7.47-7.35 (m, 1H), 7.19 (d, J=8.4 Hz, 1H), 5.97 (d, J=9.6 Hz, 1H), 5.78 (t, J=7.8 Hz, 1H), 5.52 (s, 1H), 5.17 (s, 1H), 4.97 (dd, J=12.4, 5.1 Hz, 1H), 4.90-4.82 (m, 1H), 4.72-4.58 (m, 3H), 4.33-4.24 (m, 1H), 3.36 (q, J=6.6 Hz, 2H), 3.29-3.15 (m, 1H), 3.15-2.99 (m, 1H), 2.99-2.71 (m, 3H), 2.66-2.48 (m, 2H), 2.48-2.31 (m, 2H), 2.24 (d, J=11.8 Hz, 1H), 2.20-2.06 (m, 2H), 1.92-1.71 (m, 4H), 1.70-1.63 (m, 2H), 1.50-1.40 (m, 3H), 1.40-1.21 (m, 11H), 1.07 (d, J=7.3 Hz, 3H), 0.92-0.86 (m, 12H), 0.07 (d, J=1.5 Hz, 6H).

Step 4: Synthesis of (1S,3R,7S,8S,8aR)-8-(2-((2R, 4R)-4-hydroxy-6-oxotetrahydro-2H-pyran-2-yl) ethyl)-3,7-dimethyl-1,2,3,7,8,8a-hexahydronaphthalen-1-yl (8-(2-((2-(2,6-dioxopiperidin-3-yl)-1,3-dioxoisoindolin-4-yl)oxy)acetamido)octyl)carbamate (Compound 97)

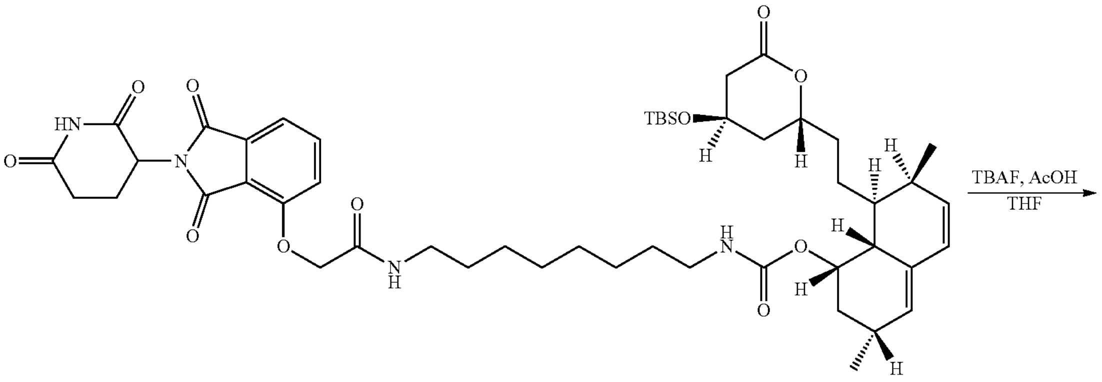

Compound 96

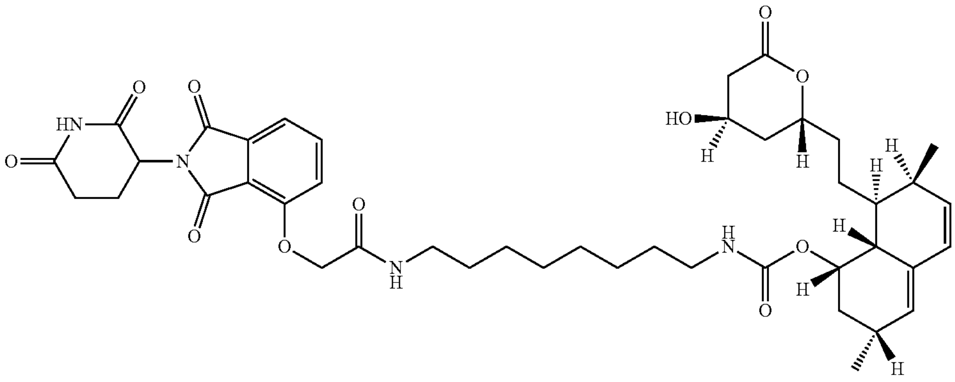

Compound 97

In a manner similar to Step 4 of Example 51, 58, the titled compound (50.5 mg, 60.23 μmol, 17.30% yield, 96% purity) was obtained as a white solid.

MS $(M+H)^+$=805.6

$^1$H NMR (400 MHz, $CDCl_3$) δ=7.79-7.74 (m, 1H), 7.57 (d, J=7.2 Hz, 1H), 7.52-7.45 (m, 1H), 7.21 (d, J=8.4 Hz, 1H), 5.98 (d, J=9.5 Hz, 1H), 5.79 (dd, J=6.1, 9.6 Hz, 1H), 5.52 (br s, 1H), 5.28-5.20 (m, 1H), 5.03-4.96 (m, 1H), 4.88-4.76 (m, 1H), 4.70-4.60 (m, 3H), 4.36-4.22 (m, 1H), 3.46-3.29 (m, 2H), 3.24-3.07 (m, 2H), 3.05-2.78 (m, 4H), 2.71-2.62 (m, 1H), 2.60-2.51 (m, 1H), 2.49-2.33 (m, 2H), 2.29-2.21 (m, 1H), 2.17 (br dd, J=5.7, 7.6 Hz, 1H), 2.09-1.98 (m, 2H), 1.92-1.81 (m, 2H), 1.73-1.59 (m, 4H), 1.49-1.23 (m, 14H), 1.08 (d, J=7.3 Hz, 3H), 0.90 (dd, J=2.3, 7.0 Hz, 3H).

Example 98 & Example 99. Synthesis of (1S,3R,7S,8S,8aR)-8-(2-((2R,4R)-4-((tert-butyldimethylsilyl)oxy)-6-oxotetrahydro-2H-pyran-2-yl)ethyl)-3,7-dimethyl-1,2,3,7,8,8a-hexahydronaphthalen-1-yl (2-(2-(2-(2-((2-(2,6-dioxopiperidin-3-yl)-1,3-dioxoisoindolin-4-yl)amino)-2-oxoethoxy)ethoxy)ethoxy)ethyl)carbamate (Compound 98) and (1S,3R,7S,8S,8aR)-8-(2-((2R,4R)-4-hydroxy-6-oxotetrahydro-2H-pyran-2-yl)ethyl)-3,7-dimethyl-1,2,3,7,8,8a-hexahydronaphthalen-1-yl (2-(2-(2-(2-((2-(2,6-dioxopiperidin-3-yl)-1,3-dioxoisoindolin-4-yl)amino)-2-oxoethoxy)ethoxy)ethoxy)ethyl)carbamate (Compound 99)

Step 1: Synthesis of tert-butyl (2-(2-(2-(2-((2-(2,6-dioxopiperidin-3-yl)-1,3-dioxoisoindolin-4-yl)amino)-2-oxoethoxy)ethoxy)ethoxy)ethyl)carbamate (116)

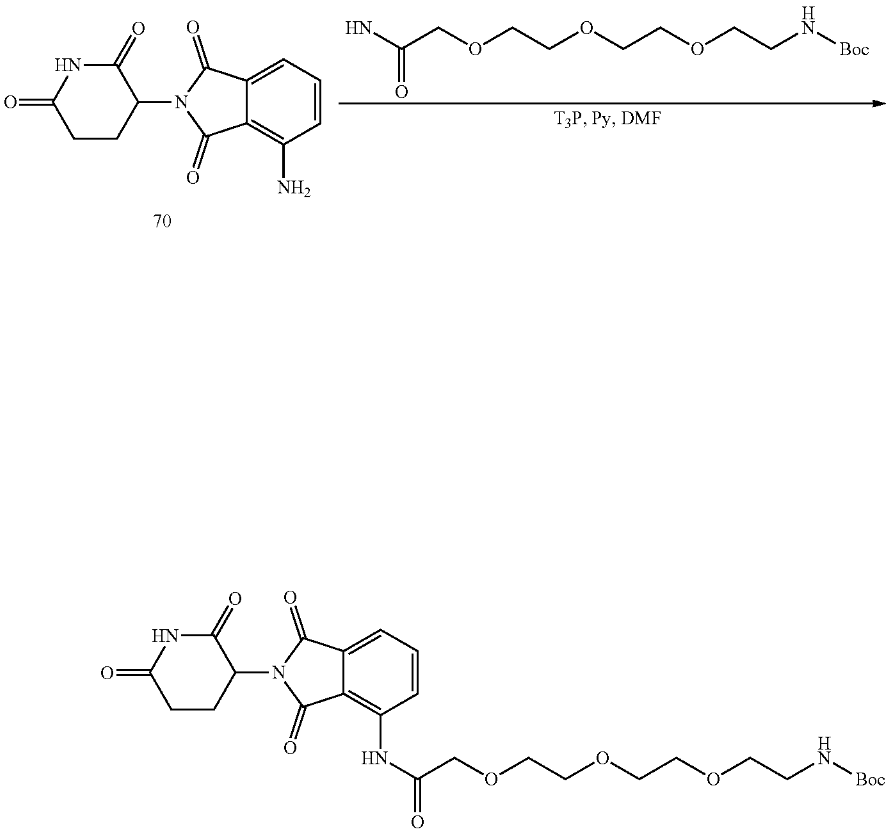

70

116

To a mixture of 4-amino-2-(2,6-dioxopiperidin-3-yl)isoindoline-1,3-dione (800 mg, 2.93 mmol) and 2-[2-[2-[2-(tert-butoxycarbonylamino)ethoxy]ethoxy]ethoxy]acetic acid (899.82 mg, 2.93 mmol) in DMF (10 mL) was added T3P (11.18 g, 17.57 mmol, 10.45 mL, 50% purity), Py (2.32 g, 29.28 mmol, 2.36 mL) in one portion at 25° C. The mixture was stirred at 80° C. for 16 h. LCMS showed starting material was consumed completely and 87% desired mass (MS-100) was detected.

TLC ($SiO_2$, Petroleum ether:Ethyl acetate=10:1) indicated starting material was consumed completely and one major new spot was detected. The reaction mixture was combined with another batch (100 mg scale) for work-up, the reaction mixture was diluted with $H_2O$ (30 mL) and extracted with EtOAc (30 mL×3). The organic layer was washed with brine (30 mL×3), dried over $Na_2SO_4$, filtrated and concentrated. The residue was purified by column chromatography ($SiO_2$, Petroleum ether/Ethyl acetate=3/1 to 0/1). Compound tert-butyl (2-(2-(2-(2-((2-(2,6-dioxopiperidin-3-yl)-1,3-dioxoisoindolin-4-yl)amino)-2-oxoethoxy)ethoxy)ethoxy)ethyl)carbamate (1.42 g, 2.45 mmol, 83.63% yield, 97% purity) was obtained as a yellow solid.

MS $(M+H)^+$=563.2

Step 2: Synthesis of 2-(2-(2-(2-aminoethoxy)ethoxy)ethoxy)-N-(2-(2,6-dioxopiperidin-3-yl)-1,3-dioxoisoindolin-4-yl)acetamide (117)

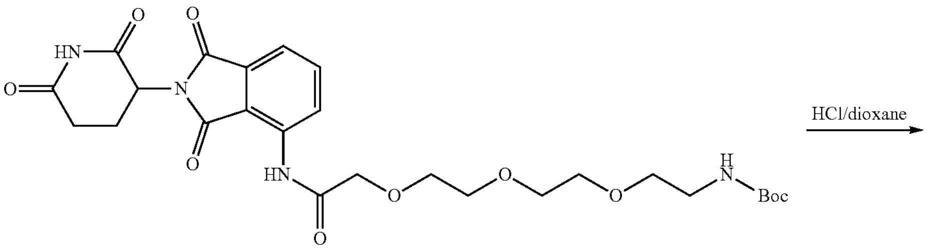

116

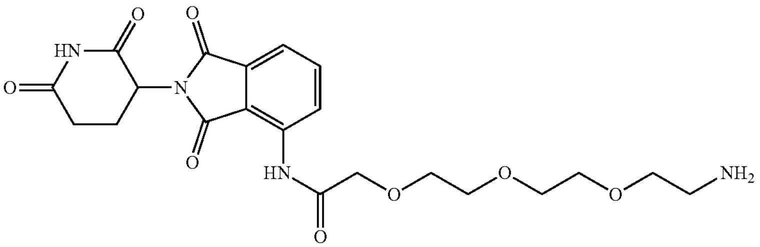

117

In a manner similar to Step 2 of Example 2, the titled compound (1.22 g, crude, HCl salt) was obtained as a yellow solid.

MS $(M+H)^+$=463.2

Step 3: Synthesis of (1S,3R,7S,8S,8aR)-8-(2-((2R,4R)-4-((tert-butyldimethylsilyl)oxy)-6-oxotetrahydro-2H-pyran-2-yl)ethyl)-3,7-dimethyl-1,2,3,7,8,8a-hexahydronaphthalen-1-yl (2-(2-(2-(2-((2-(2,6-dioxopiperidin-3-yl)-1,3-dioxoisoindolin-4-yl)amino)-2-oxoethoxy)ethoxy)ethoxy)ethyl)carbamate (Compound 98)

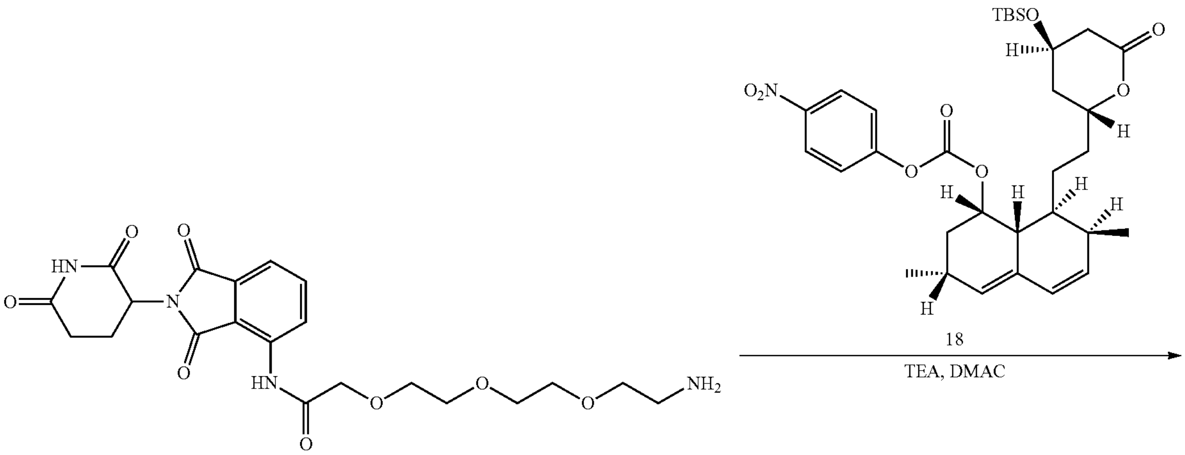

117

18

-continued

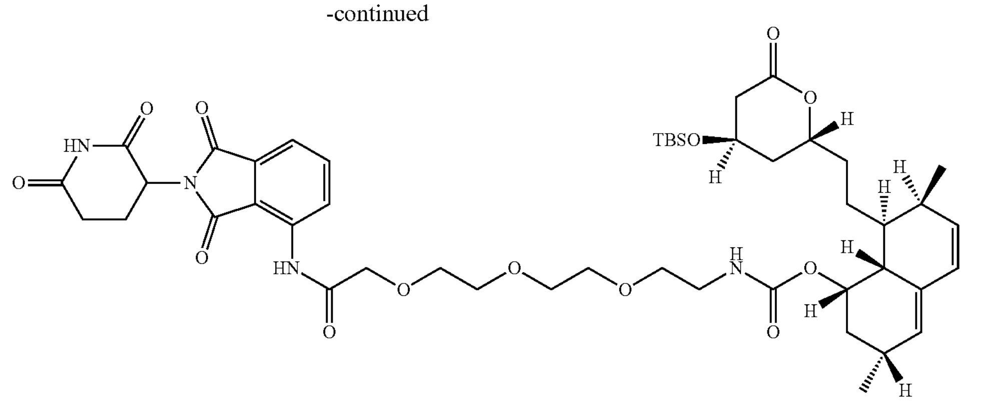

Compound 98

In a manner similar to Step 3 of Example 51, 58, the titled compound (821.3 mg, 827.41 μmol, 31.36% yield, 93% purity) was obtained as a white solid.

MS $(M+H)^+$=923.6

$^1$H NMR (400 MHz, Chloroform-d) δ 10.48 (s, 1H), 8.85 (d, J=8.4 Hz, 1H), 8.52 (s, 1H), 7.73 (dd, J=8.5, 7.3 Hz, 1H), 7.58 (d, J=7.3 Hz, 1H), 5.96 (dd, J=9.7, 3.5 Hz, 1H), 5.82-5.70 (m, 1H), 5.57-5.39 (m, 2H), 5.19 (s, 1H), 5.02-4.91 (m, 1H), 4.70-4.57 (m, 1H), 4.33-4.24 (m, 1H), 4.19 (d, J=3.5 Hz, 2H), 3.79 (s, 4H), 3.71-3.47 (m, 6H), 3.44-3.24 (m, 2H), 2.95-2.83 (m, 1H), 2.83-2.70 (m, 2H), 2.64-2.49 (m, 2H), 2.46-2.31 (m, 2H), 2.27-2.12 (m, 2H), 2.07 (dd, J=14.6, 3.8 Hz, 1H), 1.92-1.76 (m, 3H), 1.74-1.63 (m, 3H), 1.49-1.22 (m, 2H), 1.05 (dd, J=7.4, 3.2 Hz, 3H), 0.93-0.81 (m, 12H), 0.07 (s, 6H).

Step 4: Synthesis of (1S,3R,7S,8S,8aR)-8-(2-((2R, 4R)-4-hydroxy-6-oxotetrahydro-2H-pyran-2-yl) ethyl)-3,7-dimethyl-1,2,3,7,8,8a-hexahydronaphthalen-1-yl (2-(2-(2-(2-((2-(2,6-dioxopiperidin-3-yl)-1, 3-dioxoisoindolin-4-yl)amino)-2-oxoethoxy)ethoxy) ethoxy)ethyl)carbamate (Compound 99)

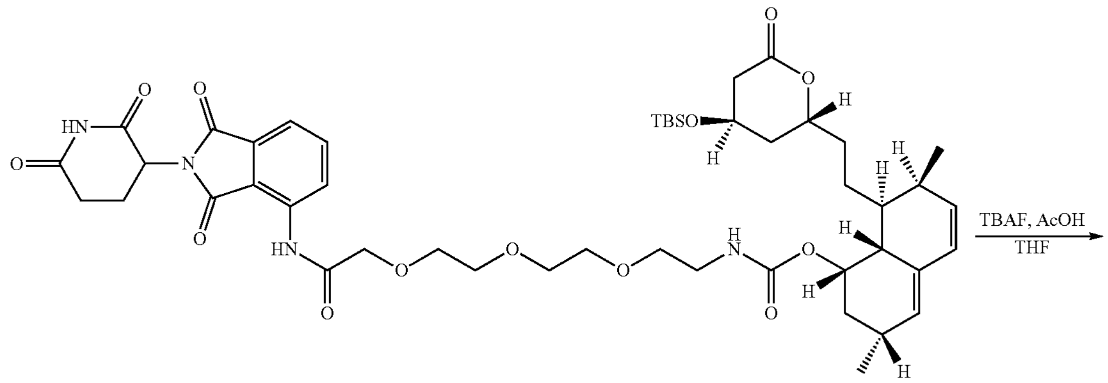

Compound 98

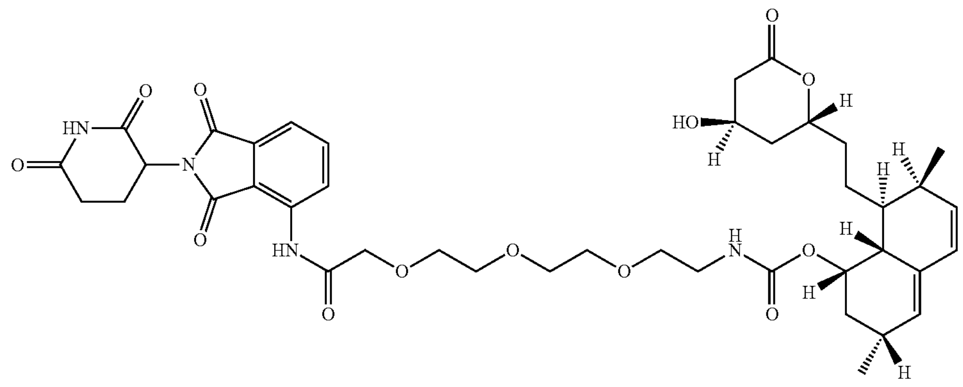

Compound 99

In a manner similar to Step 4 of Example 51, 58, the titled compound (102.6 mg, 124.31 μmol, 16.16% yield, 98% purity) was obtained as a white solid.

MS $(M+H)^+$=809.5

$^1H$ NMR (400 MHz, Chloroform-d) δ 10.47 (s, 1H), 9.06-8.82 (m, 2H), 7.79-7.69 (m, 1H), 7.59 (d, J=7.3 Hz, 1H), 5.96 (t, J=8.9 Hz, 1H), 5.76 (t, J=7.7 Hz, 1H), 5.51 (d, J=11.6 Hz, 1H), 5.47-5.30 (m, 1H), 5.22 (s, 1H), 5.05-4.92 (m, 1H), 4.61 (s, 1H), 4.36-4.25 (m, 1H), 4.25-4.13 (m, 2H), 3.80 (s, 4H), 3.74-3.65 (m, 2H), 3.64-3.44 (m, 4H), 3.41-3.25 (m, 2H), 2.99-2.66 (m, 5H), 2.63-2.50 (m, 1H), 2.50-2.28 (m, 2H), 2.28-2.10 (m, 2H), 2.10-1.92 (m, 2H), 1.92-1.77 (m, 2H), 1.77-1.68 (m, 2H), 1.47-1.29 (m, 2H), 1.05 (t, J=7.4 Hz, 3H), 0.88 (d, J=6.8 Hz, 3H).

Example 100 & Example 101. Synthesis of (1S,3R,7S,8S,8aR)-8-(2-((2R,4R)-4-((tert-butyldimethylsilyl)oxy)-6-oxotetrahydro-2H-pyran-2-yl)ethyl)-3,7-dimethyl-1,2,3,7,8,8a-hexahydronaphthalen-1-yl (3-((2-(2-((2-(2,6-dioxopiperidin-3-yl)-1,3-dioxoisoindolin-4-yl)amino)ethoxy)ethyl)amino)-3-oxopropyl)carbamate (Compound 100) and (1S,3R,7S,8S,8aR)-8-(2-((2R,4R)-4-hydroxy-6-oxotetrahydro-2H-pyran-2-yl)ethyl)-3,7-dimethyl-1,2,3,7,8,8a-hexahydronaphthalen-1-yl (3-((2-(2-((2-(2,6-dioxopiperidin-3-yl)-1,3-dioxoisoindolin-4-yl)amino)ethoxy)ethyl)amino)-3-oxopropyl)carbamate (Compound 101)

Step 1: Synthesis of tert-butyl (3-((2-(2-((2-(2,6-dioxopiperidin-3-yl)-1,3-dioxoisoindolin-4-yl)amino)ethoxy)ethyl)amino)-3-oxopropyl)carbamate (118)

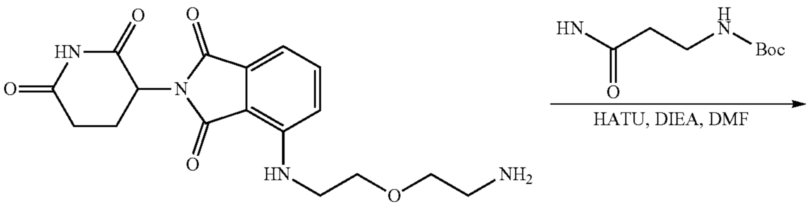

14f

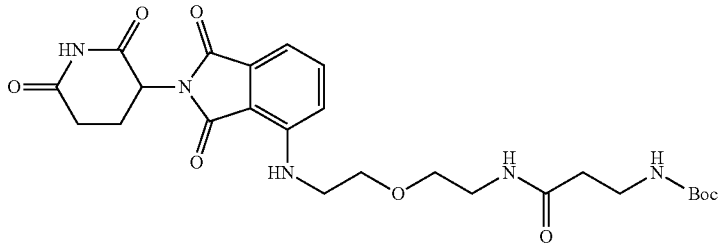

118

To a solution of 3-(tert-butoxycarbonylamino) propanoic acid (1.47 g, 2.72 mmol) in DMF (15 mL) was added DIEA (2.51 g, 19.42 mmol, 3.38 mL) and HATU (2.22 g, 5.83 mmol). The mixture was stirred at 20° C. for 25 minutes, then to this mixture was added 4-((2-(2-aminoethoxy)ethyl) amino)-2-(2,6-dioxopiperidin-3-yl)isoindoline-1,3-dione (1.4 g, 3.88 mmol). The mixture was stirred at 20° C. for 2 hours. LCMS showed 87% of desired mass was detected. The reaction mixture was diluted with $H_2O$ (40 mL) and extracted with EtOAc (40 mL×3). The combined organic layers were washed with brine (80 mL×3), dried over $Na_2SO_4$, filtered and concentrated. The residue was purified by column chromatography ($SiO_2$, Petroleum ether/Ethyl acetate=5/1 to 1/1). Compound tert-butyl (3-((2-(2-((2-(2,6-dioxopiperidin-3-yl)-1,3-dioxoisoindolin-4-yl)amino) ethoxy)ethyl)amino)-3-oxopropyl)carbamate (2.1 g, 3.79 mmol, 97.62% yield, 96% purity)) was obtained as a green solid. MS $[M+H]^+$=532.4.

Step 2: Synthesis of 3-amino-N-(2-(2-((2-(2,6-dioxopiperidin-3-yl)-1,3-dioxoisoindolin-4-yl)amino) ethoxy)ethyl)propanamide (119)

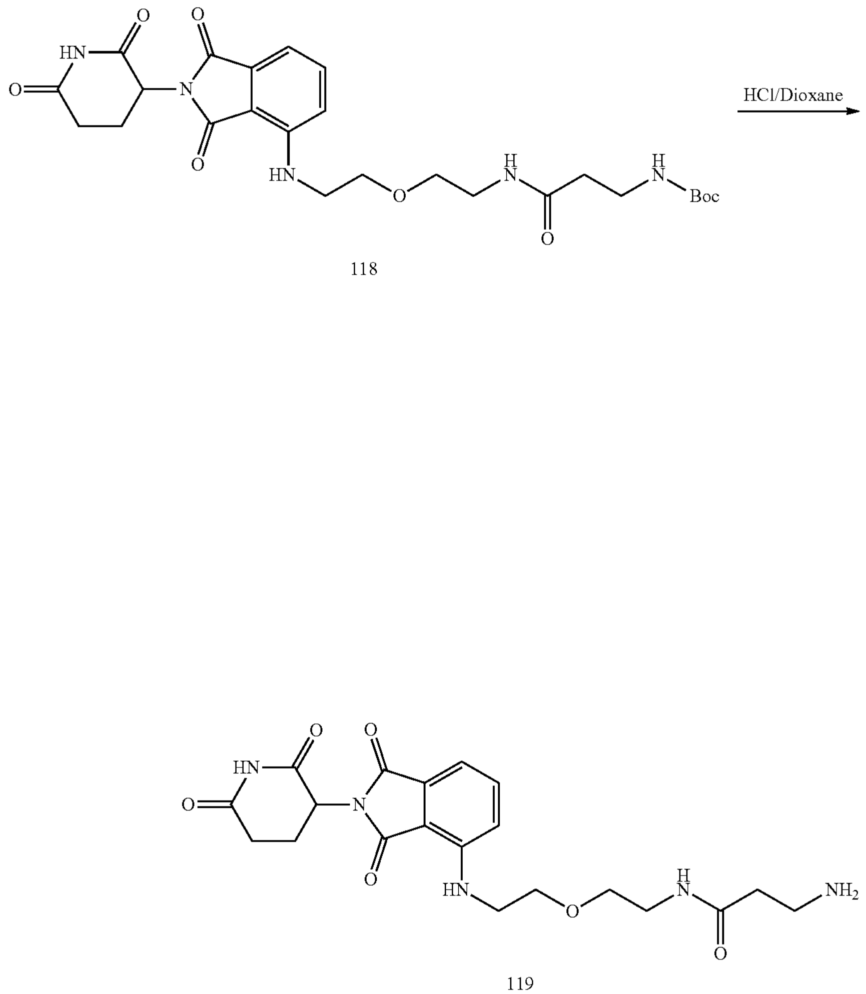

118

119

In a manner similar to Step 2 of Example 2, the titled compound (3.5 g, crude, HCl salt) was obtained as a yellow solid.

Step 3: Synthesis of (1S,3R,7S,8S,8aR)-8-(2-((2R, 4R)-4-((tert-butyldimethylsilyl)oxy)-6-oxotetrahydro-2H-pyran-2-yl)ethyl)-3,7-dimethyl-1,2,3,7,8,8a-hexahydronaphthalen-1-yl (3-((2-(2-((2-(2,6-dioxopiperidin-3-yl)-1,3-dioxoisoindolin-4-yl)amino)ethoxy)ethyl)amino)-3-oxopropyl)carbamate (Compound 100)

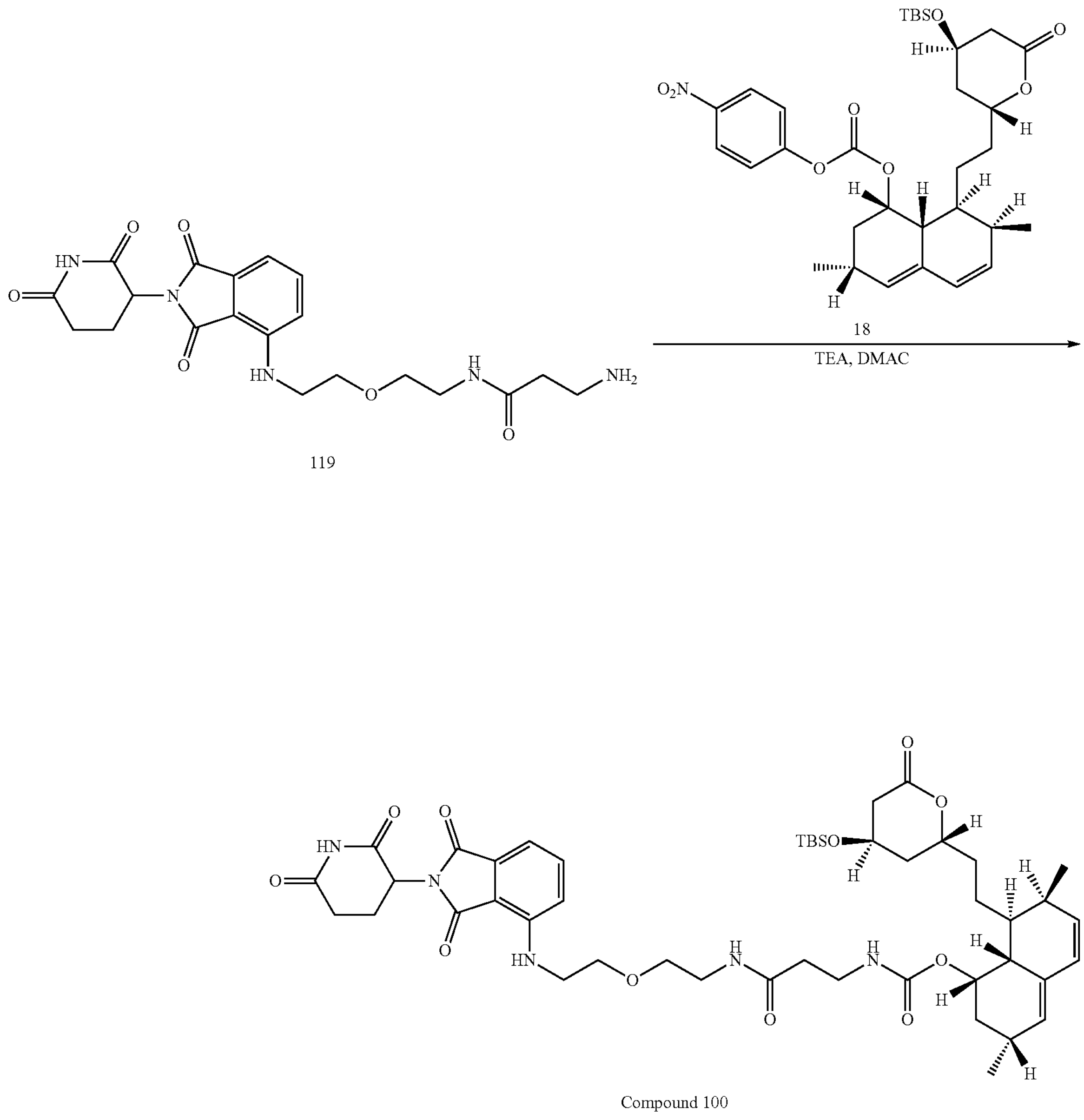

In a manner similar to Step 3 of Example 51, 58, the titled compound (1.13 g, 1.22 mmol, 17.70% yield, 96% purity) was obtained as a yellow solid.

MS $[M+H]^+$=892.6

$^1$H NMR (400 MHz, DMSO-$d_6$) δ=11.09 (s, 1H), 7.83 (t, J=5.5 Hz, 1H), 7.58 (dd, $J_1$=9.5 Hz, $J_2$=7.2 Hz, 1H), 7.14 (d, J=8.7 Hz, 1H), 7.04 (d, J=7.0 Hz, 1H), 6.92 (t, J=5.5 Hz, 1H), 6.61 (t, J=5.6 Hz, 1H), 5.90 (d, J=9.8 Hz, 1H), 5.75 (dd, $J_1$=9.5 Hz, $J_2$=6.0 Hz, 1H), 5.45 (s, 1H), 5.15-4.96 (m, 2H), 4.54-4.42 (m, 1H), 4.33-4.24 (m, 1H), 3.65-3.54 (m, 2H), 3.50-3.39 (m, 4H), 3.22-3.07 (m, 4H), 2.95-2.82 (m, 1H), 2.68 (dd, $J_1$=17.2 Hz, $J_2$=4.1 Hz, 1H), 2.63-2.52 (m, 2H), 2.39-2.30 (m, 3H), 2.22 (t, J=7.2 Hz, 3H), 2.06-1.98 (m, 1H), 1.88-1.76 (m, 3H), 1.74-1.61 (m, 3H), 1.52-1.42 (m, 1H), 1.40-1.31 (m, 1H), 1.29-1.20 (m, 1H), 1.02 (d, J=7.4 Hz, 3H), 0.86-0.81 (m, 12H), 0.05 (s, 6H).

Step 4: Synthesis of (1S,3R,7S,8S,8aR)-8-(2-((2R,4R)-4-hydroxy-6-oxotetrahydro-2H-pyran-2-yl)ethyl)-3,7-dimethyl-1,2,3,7,8,8a-hexahydronaphthalen-1-yl (3-((2-(2-((2-(2,6-dioxopiperidin-3-yl)-1,3-dioxoisoindolin-4-yl)amino)ethoxy)ethyl)amino)-3-oxopropyl)carbamate (Compound 101)

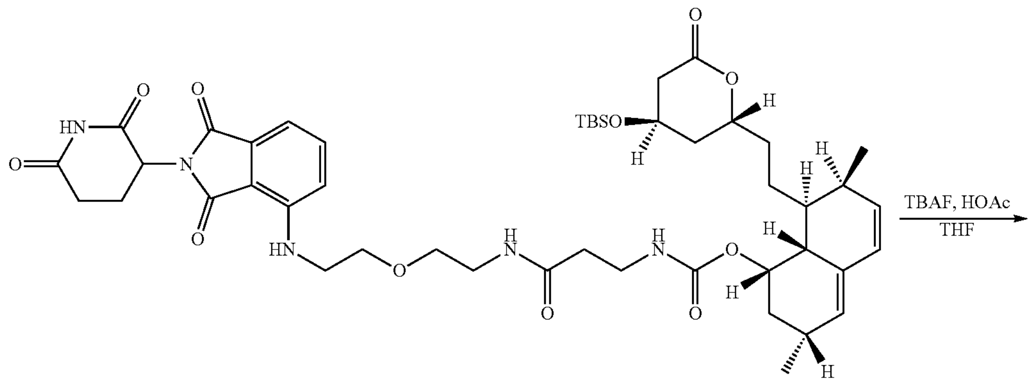

Compound 100

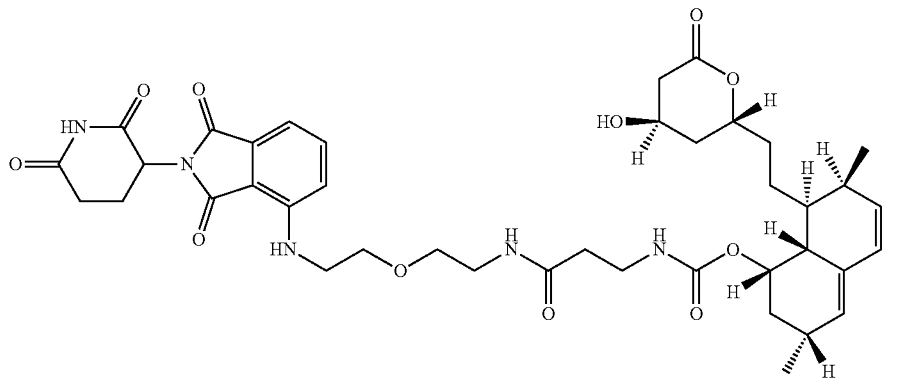

Compound 101

In a manner similar to Step 4 of Example 51, 58, the titled compound (122.6 mg, 146.58 μmol, 45.40% yield, 93% purity) was obtained as a yellow solid.

MS $[M+H]^+$=778.1

$^1$H NMR (400 MHz, DMSO-$d_6$) δ=11.09 (s, 1H), 7.90-7.75 (m, 1H), 7.59 (dd, $J_1$=8.4 Hz, $J_2$=7.2 Hz, 1H), 7.14 (d, J=8.5 Hz, 1H), 7.04 (d, J=7.0 Hz, 1H), 6.93 (t, J=5.7 Hz, 1H), 6.61 (t, J=5.8 Hz, 1H), 5.90 (d, J=9.8 Hz, 1H), 5.76 (dd, $J_1$=9.5 Hz, $J_2$=6.0 Hz, 1H), 5.45 (s, 1H), 5.18 (d, J=2.9 Hz, 1H), 5.10-4.98 (m, 2H), 4.46-4.51 (m, 1H), 4.15-4.04 (m, 1H), 3.64-3.55 (m, 2H), 3.49-3.40 (m, 4H), 3.22-3.09 (m, 4H), 2.93-2.82 (m, 1H), 2.68-2.52 (m, 3H), 2.41-2.31 (m, 3H), 2.26-2.18 (m, 3H), 2.06-1.98 (m, 1H), 1.89-1.76 (m, 3H), 1.71-1.56 (m, 3H), 1.52-1.43 (m, 1H), 1.38-1.21 (m, 2H), 1.02 (d, J=7.4 Hz, 3H), 0.83 (d, J=6.9 Hz, 3H).

Example 102 & Example 103. (1S,3R,7S,8S,8aR)-8-(2-((2R,4R)-4-((tert-butyldimethylsilyl)oxy)-6-oxotetrahydro-2H-pyran-2-yl)ethyl)-3,7-dimethyl-1,2,3,7,8,8a-hexahydronaphthalen-1-yl (3-(4-(((2-(2,6-dioxopiperidin-3-yl)-1,3-dioxoisoindolin-4-yl)amino)methyl)-1H-imidazol-1-yl)propyl)carbamate (Compound 102) and (1S,3R,7S,8S,8aR)-8-(2-((2R,4R)-4-hydroxy-6-oxotetrahydro-2H-pyran-2-yl)ethyl)-3,7-dimethyl-1,2,3,7,8,8a-hexahydronaphthalen-1-yl (3-(4-(((2-(2,6-dioxopiperidin-3-yl)-1,3-dioxoisoindolin-4-yl)amino)methyl)-1H-imidazol-1-yl)propyl)carbamate (Compound 103)

Step 1: Synthesis of Methyl 1H-imidazole-4-carboxylate (121)

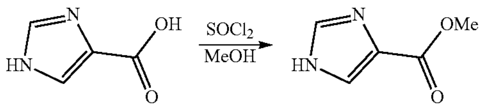

120 121

To a solution of 1H-imidazole-4-carboxylic acid (23 g, 205.20 mmol) in MeOH (180 mL) was added $SOCl_2$ (122.06 g, 1.03 mol, 74.43 mL). The reaction mixture was stirred at 70° C. for 16 h.

The reaction mixture was concentrated under reduced pressure. Compound (Methyl 1H-imidazole-4-carboxylate (33 g, crude, HCl salt) was obtained as a black solid.

$^1$H NMR (400 MHz, DMSO-$d_6$) δ=14.78-12.34 (m, 2H), 9.30 (s, 1H), 8.35 (s, 1H), 8.27 (s, 1H), 3.84 (s, 3H).

Step 2: Synthesis of Methyl 1-[3-(tert-butoxycarbonylamino)propyl]imidazole-4-carboxylate (122)

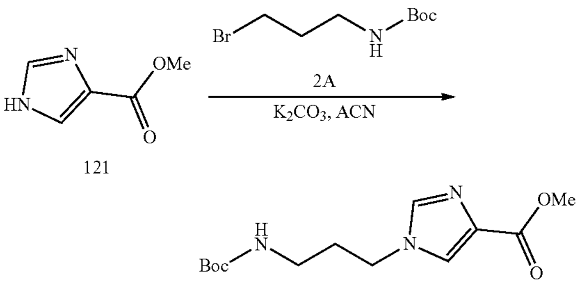

121

122

To a solution of methyl 1H-imidazole-4-carboxylate (3.3 g, 20.30 mmol, HCl salt) in ACN (50 mL) was added $K_2CO_3$ (14.03 g, 101.49 mmol) and tert-butyl N-(3-bromopropyl) carbamate (6.77 g, 28.42 mmol). The mixture was stirred at 15° C. for 16 h. TLC ($SiO_2$, Ethyl acetate/MeOH=10/1) indicated 30% of starting material remained and two new spots with lower polarity were detected. The reaction mixture was concentrated under reduced pressure, the residue was then diluted with $H_2O$ (30 mL) and extracted with EtOAc (80 mL×3). The combined organic layers were washed with brine (80 mL×2), dried over $Na_2SO_4$, filtered and concentrated under reduced pressure. The residue was purified by column chromatography ($SiO_2$, Petroleum ether/Ethyl acetate=4/3 to 0/1). Compound (methyl 1-[3-(tert-butoxycarbonylamino)propyl]imidazole-4-carboxylate (2.9 g, 9.31 mmol, 45.89% yield, 91% purity) was obtained as a colorless oil.

MS (M+H)$^+$=284.2

$^1$H NMR (400 MHz, DMSO-$d_6$) δ=7.94 (s, 1H), 7.76 (s, 1H), 6.93 (t, J=4.7 Hz, 1H), 4.02-3.98 (m, 2H), 3.73 (s, 3H), 2.87 (q, J=6.2 Hz, 2H), 1.86-1.78 (m, 2H), 1.37 (s, 9H).

Step 3: Synthesis of tert-butyl N-[3-[4-(hydroxymethyl)imidazol-1-yl]propyl]carbamate (123)

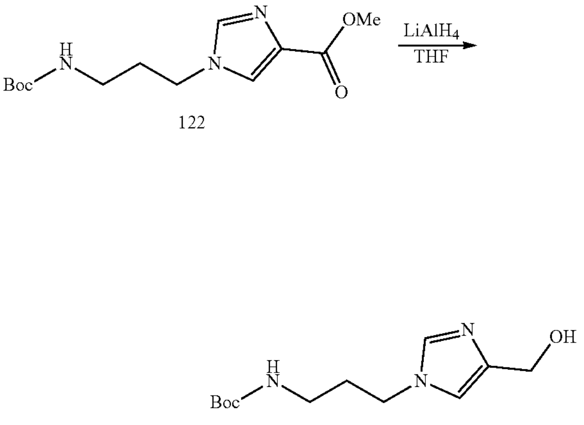

122

123

A mixture of Methyl 1-[3-(tert-butoxycarbonylamino)propyl]imidazole-4-carboxylate (2.9 g, 9.31 mmol) in THF (45 mL) was added $LiAlH_4$ (636.34 mg, 16.77 mmol) slowly at 0° C. After addition, the resulting mixture was stirred at 20° C. for 2 h. LCMS showed starting material was consumed completely and desired mass was detected. The reaction mixture was quenched with $H_2O$ (4 mL) and NaOH solution (15%, 6 mL) at 0° C. The suspension was dried over $Na_2SO_4$, filtered and the filtrate was concentrated under reduced pressured. Compound (tert-butyl N-[3-[4-(hydroxymethyl)imidazol-1-yl]propyl]carbamate (2.4 g, 8.55 mmol, 91.84% yield, 91% purity) was obtained as a colorless oil.

MS (M+H)$^+$=256.2

Step 4: Synthesis of tert-butyl N-[3-[4-(azidomethyl)imidazol-1-yl]propyl]carbamate (124)

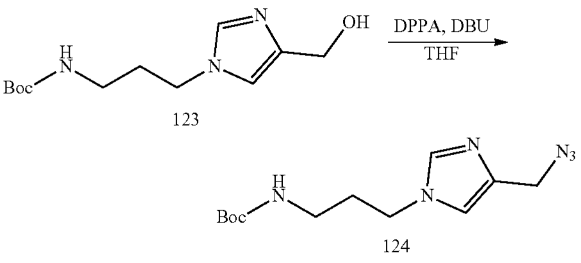

123

124

To a solution of tert-butyl N-[3-[4-(hydroxymethyl)imidazol-1-yl]propyl]carbamate (2.4 g, 8.55 mmol) in THE (50 mL) was added DPPA (3.53 g, 12.83 mmol, 2.78 mL) and DBU (3.26 g, 21.39 mmol, 3.22 mL) at 0° C. and the reaction mixture was stirred at 20° C. for 16 h. LCMS showed starting material was consumed completely and 60% of desired mass was detected. The mixture was diluted with $H_2O$ (100 mL) and extracted with EtOAc (100 mL×3). The combined organic layers were washed with brine (200 mL×2), dried over $Na_2SO_4$, filtered and concentrated under reduced pressure. The residue was purified by column chromatography ($SiO_2$, Petroleum ether/MeOH=20/1). Compound (tert-butyl N-[3-[4-(azidomethyl)imidazol-1-yl]propyl]carbamate (2.3 g, 5.74 mmol, 67.14% yield, 70% purity) was obtained as a colorless oil.

MS $(M+H)^+$=281.1

Step 5: Synthesis of tert-butyl N-[3-[4-(aminomethyl)imidazol-1-yl]propyl]carbamate (125)

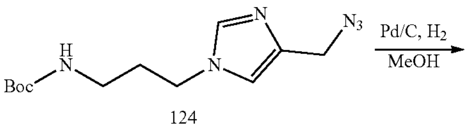

124

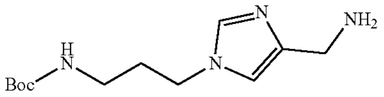

125

To a solution of tert-butyl N-[3-[4-(azidomethyl)imidazol-1-yl]propyl]carbamate (2.3 g, 5.74 mmol) in MeOH (40 mL) was added Pd/C (600 mg, 5.74 mmol, 10% purity). The mixture was then degassed and purged with $N_2$ for 3 times and then degassed and purged with $H_2$ for 3 times. The reaction mixture was stirred at 20° C. for 12 hours at $H_2$ atmosphere. The reaction mixture was filtered and concentrated under reduced pressure. Compound (tert-butyl N-[3-[4-(aminomethyl)imidazol-1-yl]propyl]carbamate (1.85 g, crude)) was obtained as a colorless oil.

Step 6: Synthesis of tert-butyl N-[3-[4-[[[2-(2,6-dioxo-3-piperidyl)-1,3-dioxo-isoindolin-4-yl]amino]methyl]imidazol-1-yl]propyl]carbamate (126)

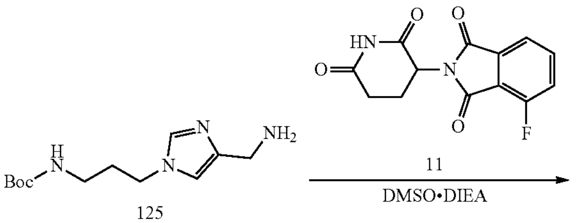

125

-continued

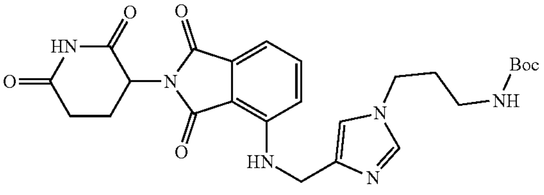

126

In a manner similar to Step 1 of Example 2, the titled compound (1.05 g, 2.02 mmol, 31.07% yield, 98% purity) was obtained as a yellow solid.

MS $(M+H)^+$=511.2

Step 7: Synthesis of 4-(((1-(3-aminopropyl)-1H-imidazol-4-yl)methyl)amino)-2-(2,6-dioxopiperidin-3-yl)isoindoline-1,3-dione (127)

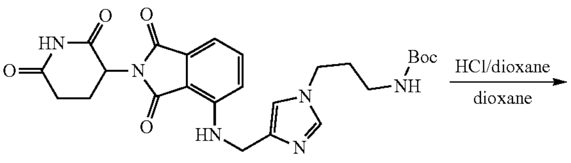

126

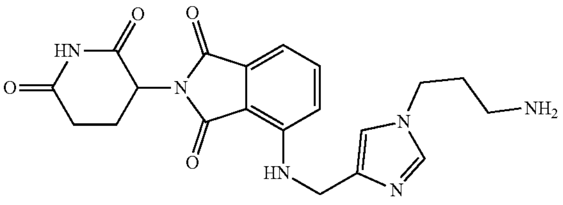

127

In a manner similar to Step 2 of Example 2, the titled compound (1.34 g, crude, HCl salt) was obtained as a yellow solid.

MS $(M+H)^+$=411.2

Step 8: Synthesis of (1S,3R,7S,8S,8aR)-8-(2-((2R,4R)-4-((tert-butyldimethylsilyl)oxy)-6-oxotetrahydro-2H-pyran-2-yl)ethyl)-3,7-dimethyl-1,2,3,7,8,8a-hexahydronaphthalen-1-yl (3-(4-(((2-(2,6-dioxopiperidin-3-yl)-1,3-dioxoisoindolin-4-yl)amino)methyl)-1H-imidazol-1-yl)propyl)carbamate (Compound 102)

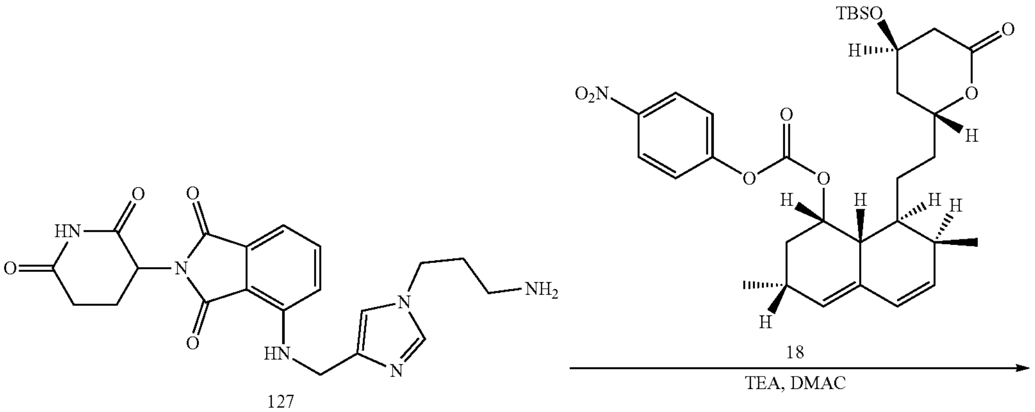

127

18

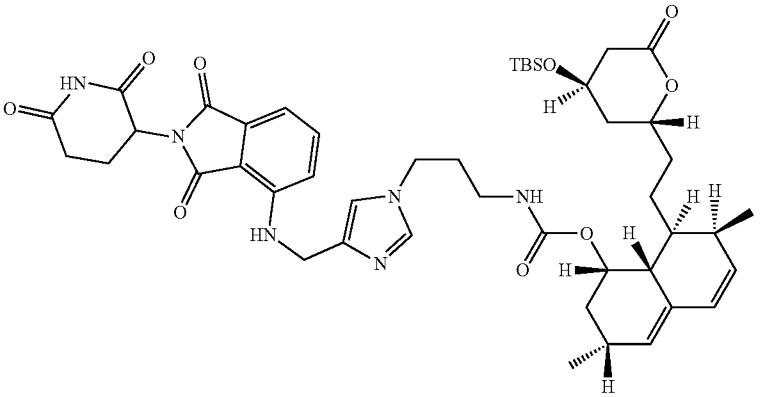

Compound 102

In a manner similar to Step 3 of Example 51, 58, the titled compound (1.08 g, 1.19 mmol, 41.28% yield, 96% purity) was obtained as a yellow solid.

MS $(M+H)^+=871.3$ $^1H$ NMR (400 MHz, Chloroform-d) δ 8.81 (s, 1H), 7.54-7.40 (m, 2H), 7.08 (d, J=7.1 Hz, 1H), 6.97 (d, J=8.6 Hz, 1H), 6.85 (s, 1H), 6.67 (t, J=5.8 Hz, 1H), 5.97 (d, J=9.6 Hz, 1H), 5.76 (dd, J=9.6, 6.0 Hz, 1H), 5.53 (s, 1H), 5.27 (s, 1H), 5.09 (s, 1H), 4.96-4.86 (m, 1H), 4.78-4.62 (m, 1H), 4.42 (d, J=5.7 Hz, 2H), 4.26 (p, J=3.4 Hz, 1H), 3.91 (t, J=7.1 Hz, 2H), 3.32-3.02 (m, 2H), 2.90-2.66 (m, 4H), 2.61-2.50 (m, 2H), 2.50-2.37 (m, 1H), 2.37-2.16 (m, 2H), 2.16-2.05 (m, 1H), 2.02-1.89 (m, 2H), 1.89-1.70 (m, 5H), 1.69-1.60 (m, 1H), 1.55-1.40 (m, 1H), 1.36-1.19 (m, 1H), 1.07 (d, J=7.4 Hz, 3H), 0.91-0.85 (m, 12H), 0.06 (d, J=3.8 Hz, 6H).

Step 9: Synthesis of (1S,3R,7S,8S,8aR)-8-(2-((2R, 4R)-4-hydroxy-6-oxotetrahydro-2H-pyran-2-yl) ethyl)-3,7-dimethyl-1,2,3,7,8,8a-hexahydronaphthalen-1-yl (3-(4-(((2-(2,6-dioxopiperidin-3-yl)-1,3-dioxoisoindolin-4-yl)amino)methyl)-1H-imidazol-1-yl)propyl)carbamate (Compound 103)

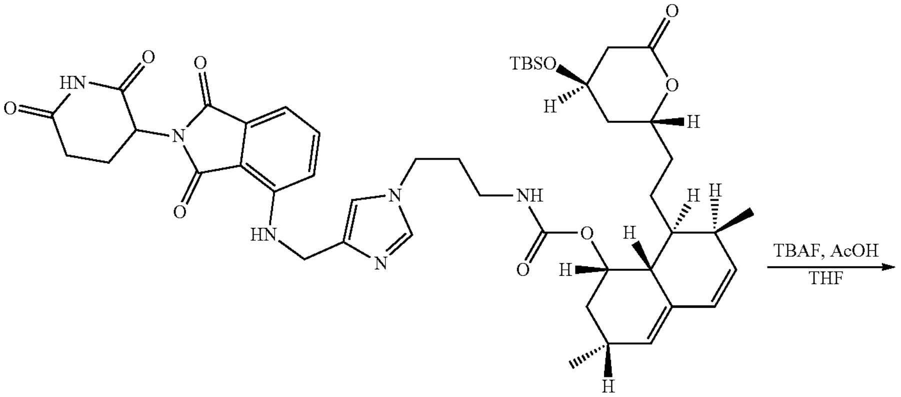

Compound 102

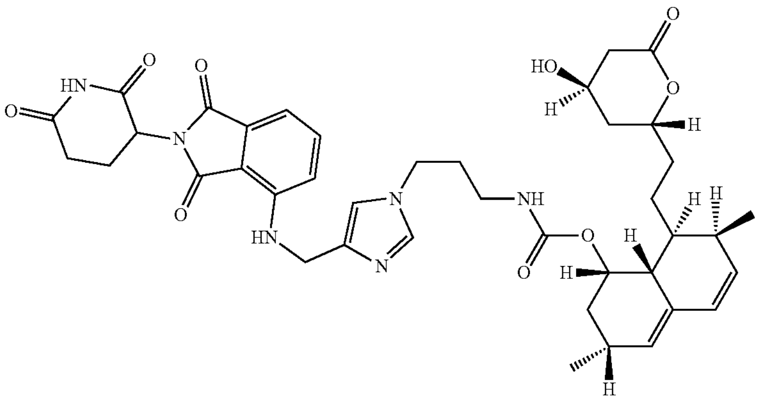

Compound 103

In a manner similar to Step 4 of Example 51, 58, the titled compound (164.3 mg, 204.06 μmol, 37.03% yield, 94% purity, FA salt) was obtained as a yellow solid.

MS $(M+H)^+$=757.2

$^1$H NMR (400 MHz, Chloroform-d) δ 9.25 (s, 1H), 8.22 (s, 1H), 7.66 (s, 1H), 7.45 (t, J=7.8 Hz, 1H), 7.07 (d, J=7.1 Hz, 1H), 7.02-6.87 (m, 2H), 6.65 (s, 1H), 5.96 (d, J=9.6 Hz, 1H), 5.76 (dd, J=9.5, 5.9 Hz, 1H), 5.57-5.44 (m, 1H), 5.37-5.10 (m, 2H), 4.99-4.86 (m, 1H), 4.71-4.49 (m, 4H), 4.49-4.38 (m, 2H), 4.32-4.15 (m, 1H), 3.94 (t, J=7.0 Hz, 2H), 3.25-3.07 (m, 2H), 2.90-2.67 (m, 3H), 2.67-2.49 (m, 2H), 2.46-2.21 (m, 3H), 2.18-2.03 (m, 2H), 1.99-1.82 (m, 4H), 1.69-1.59 (m, 2H), 1.49-1.28 (m, 2H), 1.05 (d, J=7.3 Hz, 3H), 0.87 (d, J=6.9 Hz, 3H).

Example 104 & Example 105. Synthesis of (1S,3R,7S,8S,8aR)-8-(2-((2R,4R)-4-((tert-butyldimethylsilyl)oxy)-6-oxotetrahydro-2H-pyran-2-yl)ethyl)-3,7-dimethyl-1,2,3,7,8,8a-hexahydronaphthalen-1-yl (4-(2-((2-(2,6-dioxopiperidin-3-yl)-1,3-dioxoisoindolin-4-yl)amino)ethoxy)benzyl)carbamate (Compound 104) and (1S,3R,7S,8S,8aR)-8-(2-((2R,4R)-4-hydroxy-6-oxotetrahydro-2H-pyran-2-yl)ethyl)-3,7-dimethyl-1,2,3,7,8,8a-hexahydronaphthalen-1-yl (4-(2-((2-(2,6-dioxopiperidin-3-yl)-1,3-dioxoisoindolin-4-yl)amino)ethoxy)benzyl)carbamate (Compound 105)

Step 1: Synthesis of tert-butyl N-[[4-[2-(benzyloxycarbonylamino)ethoxy]phenyl]methyl]carbamate (129)

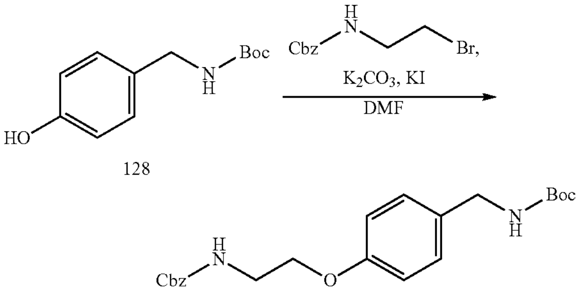

128

129

To a solution of tert-butyl N-[(4-hydroxyphenyl)methyl] carbamate (3 g, 13.44 mmol) in DMF (30 mL) was added $K_2CO_3$ (5.57 g, 40.31 mmol) and KI (2.23 g, 13.44 mmol) followed by benzyl N-(2-bromoethyl)carbamate (3.82 g, 14.78 mmol). The mixture was stirred under nitrogen at 60° C. for 16 hours. LCMS showed starting material was consumed completely and 60% of desired mass was detected. The reaction mixture was diluted with $H_2O$ (100 mL) and extracted with EtOAc (100 mL×3). The combined organic layers were washed with brine (200 mL×3), dried over $Na_2SO_4$, filtered and concentrated under reduced pressure. The residue was purified by column chromatography ($SiO_2$, Petroleum ether/Ethyl acetate=5/1 to 3/1). Compound (tert-butyl N-[[4-[2-(benzyloxycarbonylamino)ethoxy]phenyl] methyl]carbamate (4.58 g, 10.64 mmol, 79.16% yield, 93% purity) was obtained as a brown solid.

$^1$H NMR (400 MHz, DMSO-$d_6$) δ=7.36-7.29 (m, 5H), 7.14 (d, J=8.4 Hz, 2H), 6.86 (d, J=8.4 Hz, 2H), 5.03 (s, 2H), 4.08-4.01 (m, 2H), 3.96 (t, J=5.8 Hz, 2H), 3.36 (q, J=5.9 Hz, 2H), 2.89 (s, 1H), 2.73 (s, 1H), 1.38 (s, 9H).

Step 2: Synthesis of tert-butyl N-[[4-(2-aminoethoxy)phenyl]methyl]carbamate (130)

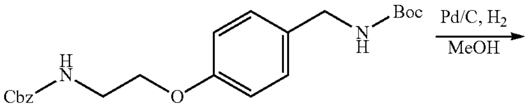

129

-continued

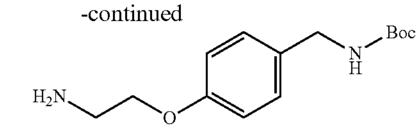

130

To a solution of tert-butyl N-[[4-[2-(benzyloxycarbonylamino)ethoxy]phenyl]methyl]carbamate (4.58 g, 10.64 mmol) in MeOH (80 mL) was added Pd/C (0.8 g, 10.64 mmol, 10% purity). The mixture was stirred under $H_2$ (15 psi) at 20° C. for 16 hours. LCMS showed starting material was consumed completely and 78% of desired mass was detected. The reaction mixture was filtered and concentrated under reduced pressure. Compound (tert-butyl N-[[4-(2-aminoethoxy)phenyl]methyl]carbamate (2.9 g, 8.49 mmol, 79.85% yield, 78% purity) was obtained as a colorless oil.

MS $(M+H)^+$=267.3

Step 3: Synthesis of tert-butyl N-[[4-[2-[[2-(2,6-dioxo-3-piperidyl)-1,3-dioxo-isoindolin-4-yl]amino] ethoxy]phenyl]methyl]carbamate (131)

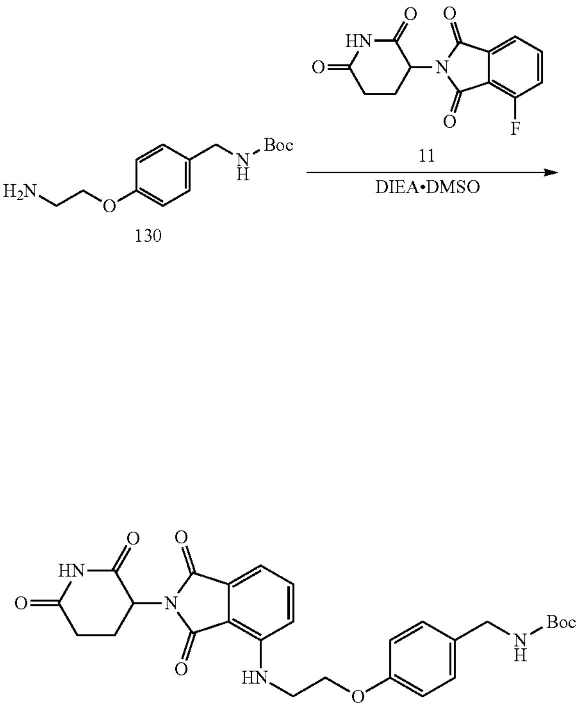

11

130

131

In a manner similar to Step 1 of Example 2, the titled compound (1.78 g, 2.96 mmol, 34.89% yield, 87% purity) was obtained as a yellow solid.

LCMS: MS $(M+H)^+$=523.2

Step 4: Synthesis of 4-[2-[4-(aminomethyl)phenoxy]ethylamino]-2-(2,6-dioxo-3-piperidyl)isoindoline-1,3-dione (132)

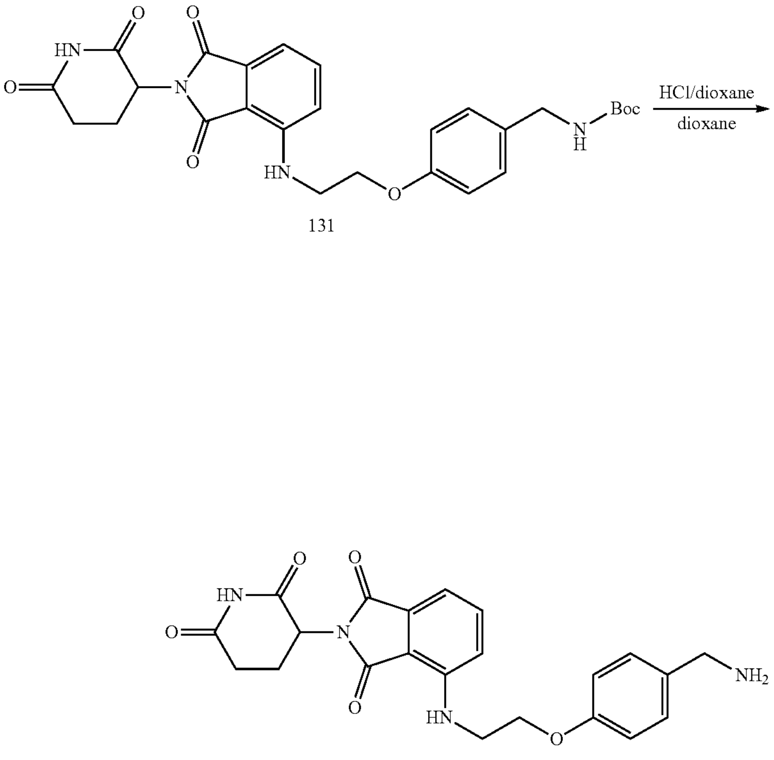

131

132

In a manner similar to Step 2 of Example 2, the titled compound (2.4 g, crude, HCl salt) was obtained as a green solid.

MS $(M+H)^+=423.2$

Step 5: Synthesis of (1S,3R,7S,8S,8aR)-8-(2-((2R,4R)-4-((tert-butyldimethylsilyl)oxy)-6-oxotetrahydro-2H-pyran-2-yl)ethyl)-3,7-dimethyl-1,2,3,7,8,8a-hexahydronaphthalen-1-yl (4-(2-((2-(2,6-dioxopiperidin-3-yl)-1,3-dioxoisoindolin-4-yl)amino)ethoxy)benzyl)carbamate (Compound 104)

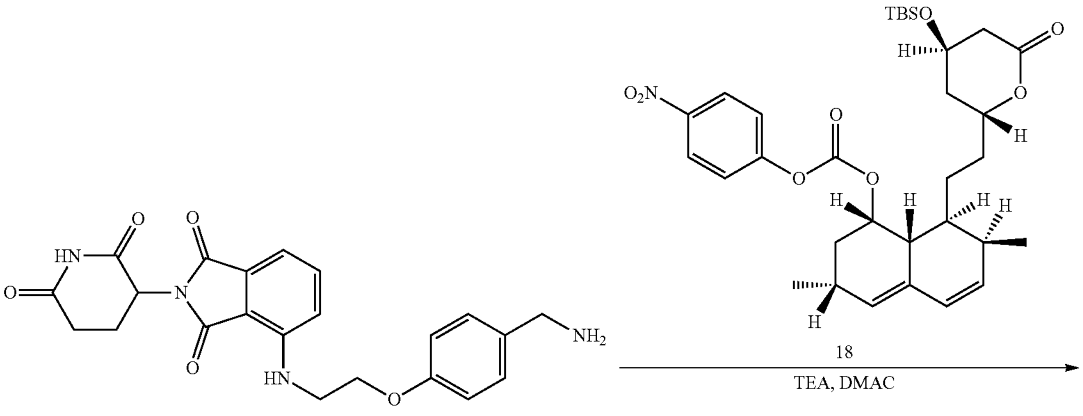

18

132

-continued

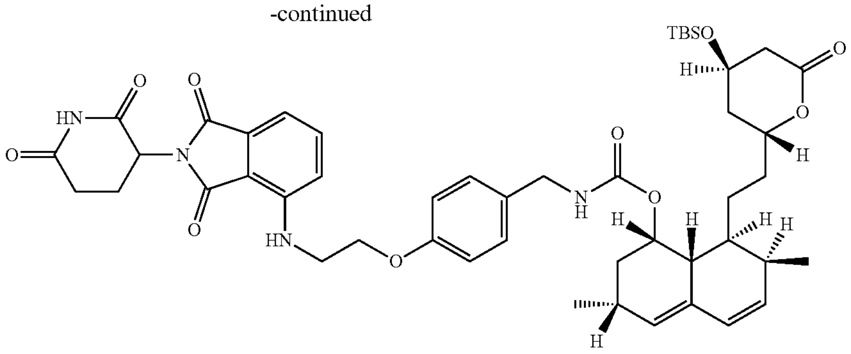

Compound 104

In a manner similar to Step 3 of Example 51, 58, the titled compound (620.5 mg, 681.55 μmol, 26.06% yield, 97% purity) was obtained as a yellow solid.

MS $(M+H)^+$=883.3

$^1$H NMR (400 MHz, Chloroform-d) δ 8.06 (s, 1H), 7.52 (dd, J=8.5, 7.1 Hz, 1H), 7.15 (dd, J=15.2, 7.6 Hz, 3H), 7.00 (d, J=8.5 Hz, 1H), 6.83 (d, J=8.3 Hz, 2H), 6.62-6.53 (m, 1H), 5.96 (d, J=9.6 Hz, 1H), 5.77 (t, J=8.0 Hz, 1H), 5.51 (s, 1H), 5.30-5.20 (m, 1H), 5.16 (t, J=6.0 Hz, 1H), 4.91 (dd, J=12.0, 5.3 Hz, 1H), 4.72-4.56 (m, 1H), 4.37-4.26 (m, 1H), 4.25-4.21 (m, 1H), 4.15 (t, J=5.3 Hz, 2H), 3.69 (q, J=5.6 Hz, 2H), 2.97-2.65 (m, 3H), 2.64-2.51 (m, 2H), 2.51-2.31 (m, 2H), 2.25 (d, J=12.2 Hz, 1H), 2.17-2.05 (m, 2H), 1.95-1.53 (m, 6H), 1.53-1.30 (m, 2H), 1.29-1.16 (m, 1H), 1.08 (d, J=7.4 Hz, 3H), 0.97-0.79 (m, 12H), 0.07 (s, 6H).

Step 6: Synthesis of (1S,3R,7S,8S,8aR)-8-(2-((2R,4R)-4-hydroxy-6-oxotetrahydro-2H-pyran-2-yl)ethyl)-3,7-dimethyl-1,2,3,7,8,8a-hexahydronaphthalen-1-yl (4-(2-((2-(2,6-dioxopiperidin-3-yl)-1,3-dioxoisoindolin-4-yl)amino)ethoxy)benzyl) carbamate (Compound 105)

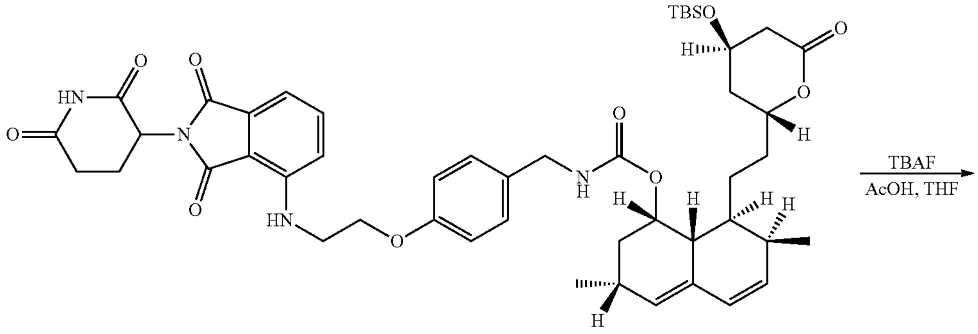

Compound 104

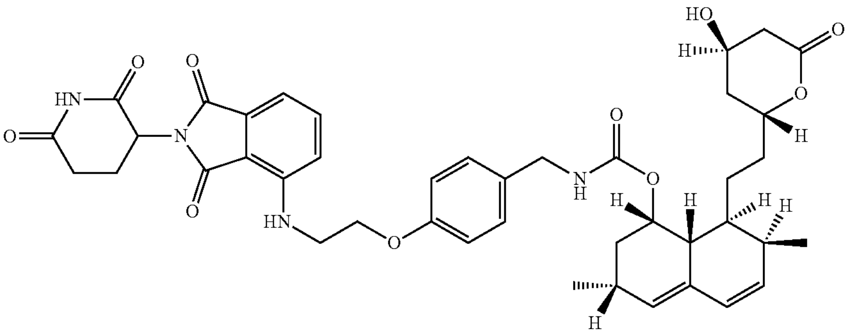

Compound 105

In a manner similar to Step 4 of Example 51, 58, the titled compound (103.5 mg, 130.58 μmol, 22.86% yield, 97% purity) was obtained as a yellow solid.

MS $(M+H)^+=769.2$ $^1$H NMR (400 MHz, $CDCl_3$) δ=8.43 (s, 1H), 7.53 (t, J=7.8 Hz, 1H), 7.15 (dd, $J_1$=17.4 Hz, $J_2$=7.5 Hz, 3H), 7.00 (d, J=8.4 Hz, 1H), 6.85 (d, J=7.9 Hz, 2H), 6.57 (t, J=5.7 Hz, 1H), 5.97 (d, J=9.7 Hz, 1H), 5.85-5.64 (m, 1H), 5.52 (s, 1H), 5.24 (s, 2H), 4.92 (dd, $J_1$=11.6 Hz, $J_2$=5.1 Hz, 1H), 4.69-4.46 (m, 1H), 4.37 (dd, $J_1$=14.5 Hz, $J_2$=5.5 Hz, 1H), 4.27-4.03 (m, 4H), 3.81-3.49 (m, 2H), 2.90-2.71 (m, 3H), 2.68-2.52 (m, 2H), 2.50-2.29 (m, 2H), 2.27-2.05 (m, 3H), 1.78 (s, 7H), 1.42-1.19 (m, 2H), 1.09 (d, J=7.3 Hz, 3H), 0.95-0.77 (m, 3H).

Example 106. Synthesis of (3R,5R)-7-((1S,2S,6R,8S,8aR)-8-(((2-(2-(2-((2-(2,6-dioxopiperidin-3-yl)-1,3-dioxoisoindolin-4-yl)amino)ethoxy)ethoxy)ethyl)carbamoyl)oxy)-2,6-dimethyl-1,2,6,7,8,8a-hexahydronaphthalen-1-yl)-3,5-dihydroxyheptanoic acid (Compound 106)

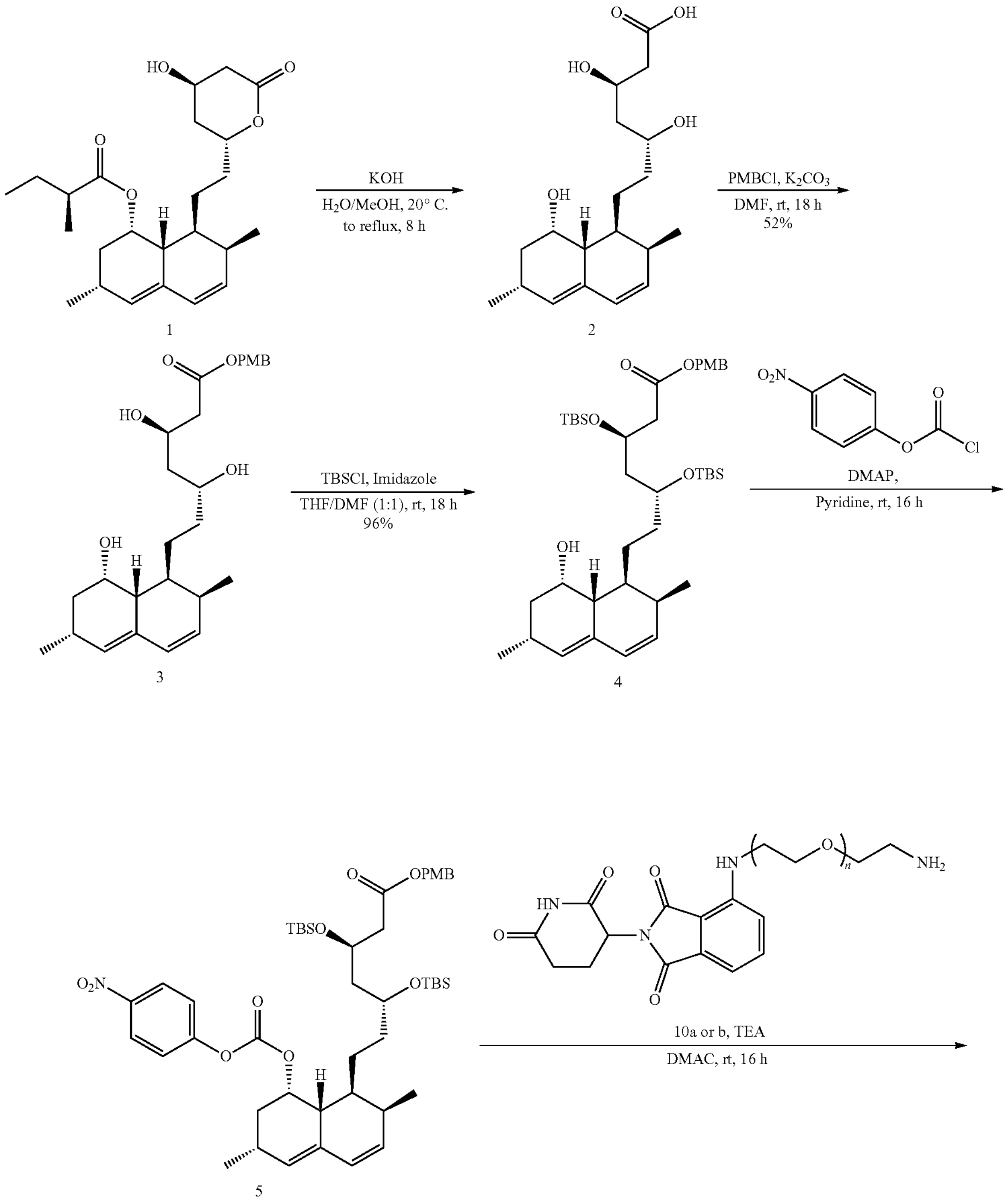

-continued
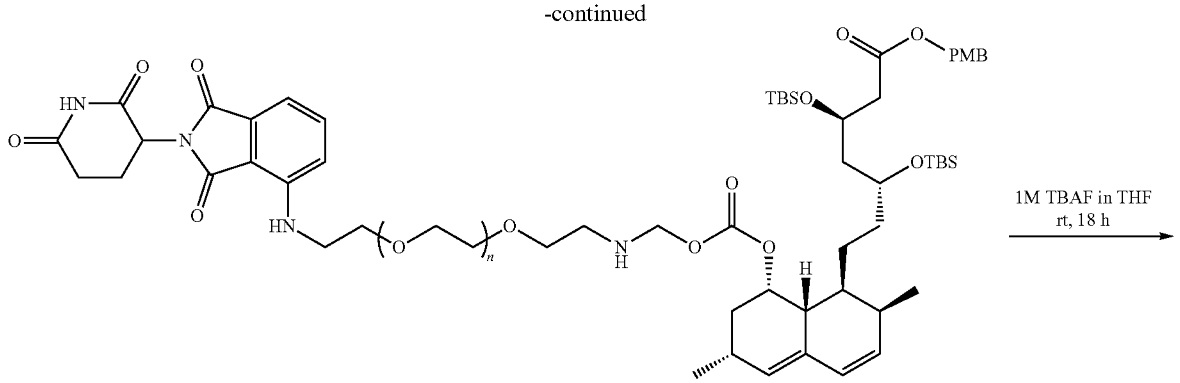
n = 1, 2
6a, 6b
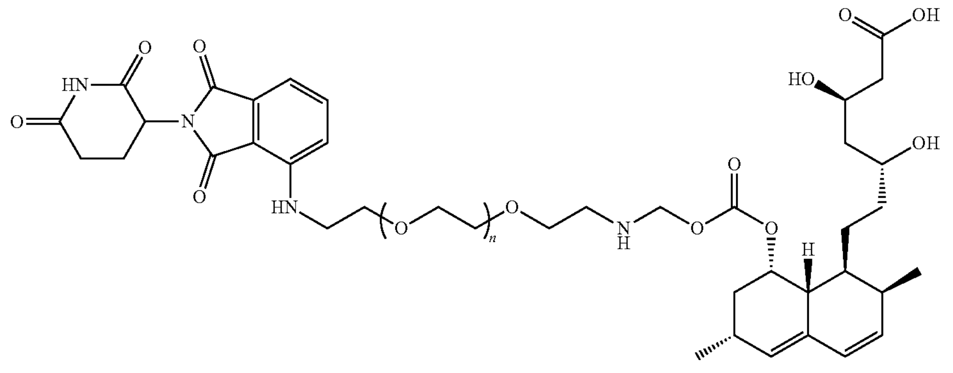
n = 1, 2
Compound 106, 107
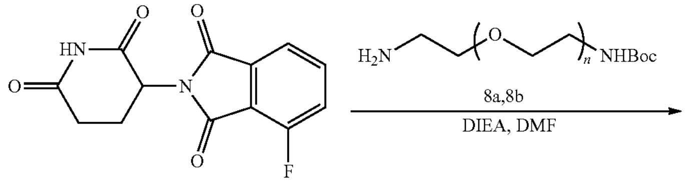
7
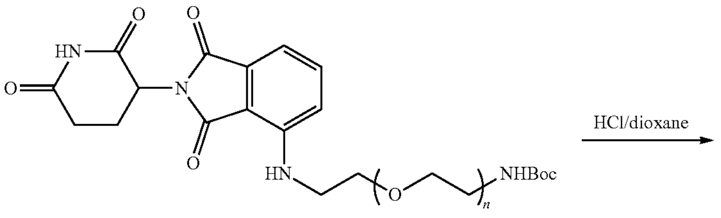
n = 1, 2
9a,9b
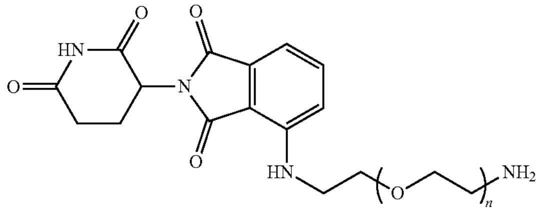
10a,10b Step 1: (3R,5R)-3,5-dihydroxy-7-((1S,2S,6R,8S,8aR)-8-hydroxy-2,6-dimethyl-1,2,6,7,8,8a-hexahydronaphthalen-1-yl)heptanoic acid (2)

KOH (13.87 g, 247 mmol) was dissolved in water (10 mL), and methanol (60 mL) was slowly added dropwise while stirring at 0° C. while maintaining an internal temperature of 20° C. After the dropwise addition was completed, lovastatin (10.00 g, 24.72 mmol) was added, and the resulting mixture was stirred at 100° C. for 8 h. TLC (EA 100%) shows starting material was consumed. The solvent of the mixture was concentrated under reduced pressure, and 1N HCl was slowly added dropwise to the residue to adjust the pH to 5-6. The reaction mixture was extracted with EtOAc (100 mL) and concentrated under reduced pressure. The residue was vacuum-dried to give the title compound (10.68 g, crude) as a black oil.

MS $(M+K)^+$=378.3

Step 2: Synthesis of 4-methoxybenzyl (3R,5R)-3,5-dihydroxy-7-((1S,2S,6R,8S,8aR)-8-hydroxy-2,6-dimethyl-1, Synthesis of 2,6,7,8,8a-hexahydronaphthalen-1-yl)heptanoate (3)

To a solution of (3R,5R)-3,5-dihydroxy-7-((1S,2S,6R,8S,8aR)-8-hydroxy-2,6-dimethyl-1,2,6,7,8,8a-hexahydronaphthalen-1-yl)heptanoic acid (10.68 g, crude) and K2CO3 (15.37 g, 111.23 mmol) in DMF (100 mL) was added PMBCl (103.82 mmol, 14.02 mL), and the mixture was stirred at 25° C. for 18 hours. LCMS showed a main peak of the desired mass. Water (50 mL) was added to the mixture, extracted with EtOAc (100 mL×3), and the organic phase was washed with brine (50 mL×2) and concentrated under reduced pressure. The residue was purified by silica gel column chromatography (Hex:EtOAc=1:1) to afford the title compound (5.89 g, 12.84 mmol, 52% yield) as a clear oil.

MS $(M+Na)^+$=481.3

Step 3: 4-methoxybenzyl (3R,5R)-3,5-bis((tert-butyldimethylsilyl)oxy)-7-((1S,2S,6R,8S,8aR)-8-hydroxy-2,6-dimethyl-1,2,6,7,8,8a-hexahydronaphthalen-1-yl)heptanoate (4)

To a solution of 4-methoxybenzyl (3R,5R)-3,5-dihydroxy-7-((1S,2S,6R,8S,8aR)-8-hydroxy-2,6-dimethyl-1,2,6,7,8,8a-hexahydronaphthalen-1-yl)heptanoate (5.85 g, 12.76 mmol) and imidazole (3.47 g, 51.02 mmol) in DMF/THF (1:1) (82 mL) was added TBDMSCl (44.65 mmol, 7.73 mL) and the resulting mixture was stirred at 25° C. for 18 hours. LCMS showed a main peak of the desired mass. The reaction mixture was concentrated under reduced pressure, water (50 mL) was poured into the residue, extracted with EtOAc (100 mL×3), dried over $Na_2SO_4$, filtered, and concentrated under reduced pressure. The residue was purified by silica gel column chromatography (Hex:EtOAc=95:5 to 9:1) to afford the title compound (8.45 g, 12.30 mmol, 96% yield) as a white solid.

MS $(M+Na)^+$=710.3

Step 4: Synthesis of 4-methoxybenzyl(3R,5R)-3,5-bis((tert-butyldimethylsilyl)oxy)-7-((1S,2S,6R,8S,8aR)-2,6-dimethyl-8-((4-nitrophenoxy)carbonyl)oxy)-1,2,6,7,8,8a-hexahydronaphthalen-1-yl)heptanoate (5)

To a mixture of 4-methoxybenzyl(3R,5R)-3,5-bis((tert-butyldimethylsilyl)oxy)-7-((1S,2S,6R,8S,8aR)-8-hydroxy-2,6-dimethyl-1,2,6,7,8,8a-hexahydronaphthalen-1-yl)heptanoate (8.40 g, 12.22 mmol) and DMAP (9.11 g, 74.57 mmol) was added (4-nitrophenyl)carbonochloridate (14.78 g, 73.35 mmol), and the resulting mixture was stirred at 25° C. for 16 hours. LCMS showed a peak of the desired mass and the starting material was consumed. Water (100 mL) was poured into the mixture, extracted with EtOAc (100 mL×3), and the organic phase was washed with 1N HCl (50 mL×3) and brine (50 mL), and concentrated under reduced pressure. The residue was purified by silica gel column chromatography (Hex: EtOAc=9:1 to 4:1) to afford the title compound (8.65 g, crude, 78% purity) as a yellow oil.

MS $(M+H)^+$=852.2

Step 5: Synthesis of tert-butyl (2-(2-(2-((2-(2,6-dioxopiperidin-3-yl)-1,3-dioxoisoindolin-4-yl)amino))oxy)ethoxy)ethyl)carbamate (9a)

To a solution of 2-(2,6-dioxo-3-piperidyl)-4-fluoro-isoindoline-1,3-dione (1.67 g, 6.04 mmol, 1 eq) and tert-butyl (2-(2-(2-aminoethoxy)ethoxy)ethyl)carbamate (1.50 g, 6.04 mmol) in DMF (15 mL) was added DIEA (12.08 mmol, 1.72 mL), and the mixture was stirred at 90° C. for 12 hours. LCMS showed a main peak of the desired mass. Water (40 mL) was poured into the mixture, extracted with EtOAc (40 mL×3), and the organic phase was washed with 1N HCl (20 mL×3), brine (20 mL×2), and concentrated under reduced pressure. The residue was purified by silica gel column chromatography (Hex:EtOAc=1:1 to 1:3) to afford the title compound (0.79 g, 1.57 mmol, 26% yield) as a green oil.

MS $(M+Na)^+$=527.2

Step 6: Synthesis of 4-((2-(2-(2-(2-aminoethoxy)ethoxy)ethyl)amino)-2-(2,6-dioxopiperidin-3-yl)isoindoline-1,3-dione (10a)

To a solution of tert-butyl (2-(2-(2-((2-(2,6-dioxopiperidin-3-yl)-1,3-dioxoisoindolin-4-yl))amino)ethoxy)ethoxy)ethyl)carbamate (0.75 g, 1.49 mmol) in DCM (3.5 mL) was added HCl/dioxane (4 M, 0.743 mL), and the resulting mixture was stirred at 25° C. for 4 hours. LCMS showed a main peak of the desired mass. The reaction mixture was concentrated in vacuo to afford the title compound (0.530 g, crude, HCl salt) as a yellow solid.

MS $(M+H)^+$=405.2

Step 7: Synthesis of 4-methoxybenzyl(3R,5R)-3,5-bis((tert-butyldimethylsilyl)oxy)-7-((1S,2S,6R,8S,8aR)-8-((2-(2-(2-(2-(2-(2-(2-(2,6-dioxopiperidin-3-yl)-1,3-dioxoisoindolin-4-yl)amino))oxy)ethoxy)ethyl)carbamoyl)oxy)-2,6-dimethyl-1,2,6,7,8,8a-hexahydronaphthalen-1-yl)heptanoate (6a)

To a solution of 4-((2-(2-(2-(2-aminoethoxy)ethoxy)ethyl)amino)-2-(2,6-dioxopiperidin-3-yl)isoindoline-1,3-dione (10a) (534 mg, 1.32 mmol, HCl salt) and (4-methoxybenzyl (3R,5R)-3,5-bis((tert-butyldimethylsilyl)oxy)-7-((1S,2S,6R,8S,8aR)-2,6-dimethyl-8-((4-nitrophenoxy)carbonyl)oxy)-1,2,6,7,8,8a-hexahydronaphthalen-1-yl)heptanoate (900 mg, 1.06 mmol) in DMAC (10.8 mL) was added TEA (4.22 mmol, 590 μL), and the resulting mixture was stirred at 25° C. for 16 hours. LCMS showed a peak of the desired mass.

The reaction mixture was quenched by adding $H_2O$ (10 mL) and extracted with EtOAc (20 mL×3). The organic layer was washed with brine (sat.aq, 10 mL×2), dried over $Na_2SO_4$, and filtered. The residue was purified by silica gel column chromatography (Hex:EtOAc=1:9 to 1:1) to afford the title compound (899 mg, 804 μmol, 76% yield) as a yellow solid.

MS $(M)^+$=1117.5

$^1$H NMR (600 MHz, DMSO-$d_6$) δ 11.10 (s, 1H), 7.58 (t, J=7.7 Hz, 1H), 7.30-7.25 (m, 2H), 7.13 (d, J=8.6 Hz, 1H), 7.04 (dd, J=7.0, 1.5 Hz, 1H), 6.97-6.89 (m, 3H), 6.60 (t, J=5.8 Hz, 1H), 5.90 (d, J=9.5 Hz, 1H), 5.78-5.73 (m, 1H), 5.44 (s, 1H), 5.08-5.03 (m, 1H), 5.02-4.94 (m, 3H), 4.13 (t, J=6.3 Hz, 1H), 3.77-3.72 (m, 3H), 3.69-3.56 (m, 4H), 3.54-3.43 (m, 6H), 3.36 (t, J=6.5 Hz, 2H), 3.19 (dd, J=13.4, 6.7 Hz, 1H), 3.00-2.96 (m, 1H), 2.88 (t, J=12.8 Hz, 1H), 2.60-2.53 (m, 2H), 2.38-2.32 (m, 2H), 2.29-2.25 (m, 1H), 2.17 (d, J=12.2 Hz, 1H), 2.04-2.00 (m, 1H), 1.89-1.79 (m, 2H), 1.65-1.50 (m, 4H), 1.41 (s, 2H), 1.19-1.15 (m, 1H), 1.09 (d, J=10.0 Hz, 1H), 1.01 (d, J=7.4 Hz, 3H), 0.92-0.68 (m, 21H), 0.07--0.09 (m, 12H).

Step 8: Synthesis of (3R,5R)-7-((1S,2S,6R,8S,8aR)-8-((2-(2-(2-(2-(2-(2,6-dioxopiperidin-3-yl)-1,3-dioxoisoindolin-4-yl)amino)ethoxy)ethoxy)ethyl)carbamoyl)oxy)-2,6-dimethyl-1,2,6,7,8,8,8a-hexahydronaphthalen-1-yl)-3,5-dihydroxyheptanoic acid (Compound 106)

To a solution of 4-methoxybenzyl(3R,5R)-3,5-bis((tert-butyldimethylsilyl)oxy)-7-((1S,2S,6R,8S,8aR)-8-((2-(2-(2-(2-(2-(2-(2-(2,6-dioxopiperidin-3-yl)-1,3-dioxoisoindolin-4-yl)amino)ethoxy)oxy)ethyl)carbamoyl)oxy)-2,6-dimethyl-1,2,6,7,8,8a-hexahydronaphthalen-1-yl) heptanoate (350 mg, 313 μmol) was added TBAF (1 M, 6.26 mL) in one portion at room temperature and the resulting mixture was stirred for 18 h. LCMS showed complete consumption of starting material and the desired mass was detected. The reaction mixture was quenched with $H_2O$ (5 mL) and extracted with EtOAc (5 mL×3). The organic layer was dried over $Na_2SO_4$, filtered and concentrated. The residue was purified by silica gel column chromatography (Hex: EtOAc=0:100, MC:MeOH=9:1) to afford the title compound (235 mg, 306 μmol, 98% yield, 96% purity) was obtained as a yellow solid.

MS $(M+Na)^+$=791.4

$^1$H NMR (600 MHz, DMSO-$d_6$) δ 11.06 (s, 1H), 7.59-7.53 (m, 1H), 7.11 (d, J=8.6 Hz, 1H), 7.01 (d, J=7.0 Hz, 1H), 6.92 (t, J=5.8 Hz, 1H), 6.57 (d, J=6.0 Hz, 1H), 5.86 (d, J=9.5 Hz, 1H), 5.76-5.69 (m, 1H), 5.40 (s, 1H), 5.06-4.94 (m, 2H), 4.49-4.35 (m, 2H), 3.98-3.90 (m, 1H), 3.62-3.33 (m, 10H), 3.15-3.03 (m, 3H), 2.88-2.82 (m, 1H), 2.61-2.50 (m, 3H), 2.39-2.25 (m, 3H), 2.15 (d, J=12.3 Hz, 1H), 2.02-1.95 (m, 1H), 1.86-1.74 (m, 2H), 1.65-1.49 (m, 3H), 1.46-1.36 (m, 2H), 1.32-1.25 (m, 2H), 0.99 (d, J=7.1 Hz, 3H), 0.79 (d, J=6.7 Hz, 3H).

Example 107. Synthesis of (3R,5R)-7-((1S,2S,6R,8S,8aR)-8-(((2-(2-(2-(2-((2-(2,6-dioxopiperidin-3-yl)-1,3-dioxoisoindolin-4-yl)amino)ethoxy)ethoxy)ethoxy)ethyl)carbamoyl)oxy)-2,6-dimethyl-1,2,6,7,8,8a-hexahydronaphthalen-1-yl)-3,5-dihydroxyheptanoic acid (Compound 107)

Step 1-2 are Described in the Above Reaction Scheme

Step 3: Synthesis of 4-methoxybenzyl(3R,5R)-3,5-bis((tert-butyldimethylsilyl)oxy)-7-((1S,2S,6R,8S,8aR)-8-((2-(2-(2-(2-(2-(2-(2-(2-(2,6-dioxopiperidin-3-yl))-1,3-dioxoisoindolin-4-yl))amino)ethoxy)ethoxy)ethoxy)ethyl)carbamoyl)oxy)-2,6-dimethyl-1,2,6,7,8,8a-hexahydronaphthalen-1-yl)heptanoate (6b)

In a manner similar to Step 7 of Example 106, the titled compound (207 mg, 178 μmol, 51% yield) was obtained as a yellow solid.

MS $(M)^+$=1161.6

$^1$H NMR (600 MHz, DMSO-$d_6$) δ 11.07 (s, 1H), 7.58-7.54 (m, 1H), 7.26 (dt, J=8.8, 2.5 Hz, 2H), 7.12 (d, J=8.6 Hz, 1H), 7.02 (dd, J=7.0, 1.6 Hz, 1H), 6.93-6.87 (m, 3H), 6.58 (t, J=5.9 Hz, 1H), 5.88 (d, J=9.6 Hz, 1H), 5.74 (dd, J=9.6, 6.0 Hz, 1H), 5.42 (s, 1H), 5.04 (dd, J=12.9, 5.5 Hz, 1H), 4.99-4.95 (m, 2H), 4.13-4.09 (m, 1H), 3.72 (d, J=1.5 Hz, 3H), 3.65-3.57 (m, 4H), 3.53-3.48 (m, 4H), 3.46-3.43 (m, 4H), 3.37-3.32 (m, 4H), 3.18-3.13 (m, 1H), 2.97-2.92 (m, 1H), 2.86 (t, J=12.8 Hz, 1H), 2.53 (d, J=14.8 Hz, 2H), 2.33 (dd, J=14.8, 7.5 Hz, 2H), 2.26 (d, J=6.8 Hz, 1H), 2.15 (d, J=12.4 Hz, 1H), 2.03-1.98 (m, 1H), 1.86-1.78 (m, 2H), 1.60-1.48 (m, 4H), 1.39 (d, J=7.0 Hz, 2H), 1.16 (td, J=6.9, 1.8 Hz, 1H), 1.08 (t, J=10.2 Hz, 1H), 1.00 (d, J=7.3 Hz, 3H), 0.80 (dd, J=19.5, 1.8 Hz, 21H), 0.01-0.07 (m, 12H).

Step 4: Synthesis of (3R,5R)-7-((1S,2S,6R,8S,8aR)-8-((2-(2-(2-(2-(2-(2-(2-(2,6-dioxopiperidin-3-yl)-1,3-dioxoisoindolin-4-yl)amino)ethoxy)ethoxy)ethoxy)ethyl)carbamoyl)-2,6-dimethyl-1,2,6,7,8,8a-hexahydronaphthalen-1-yl)-3,5-dihydroxyheptanoic acid (compound 107)

In a manner similar to Step 8 of Example 106, the titled compound (20 mg, 24.6 μmol, 8% yield, 91% purity) was obtained as a yellow solid.

MS $(M+Na)^+$=835.4

$^1$H NMR (600 MHz, DMSO-d6) δ 11.08 (s, 2H), 7.60-7.56 (m, 1H), 7.14 (d, J=8.6 Hz, 1H), 7.04 (d, J=7.0 Hz, 1H), 6.94 (t, J=5.8 Hz, 1H), 6.60 (t, J=5.9 Hz, 1H), 5.89 (d, J=9.6 Hz, 1H), 5.77-5.73 (m, 1H), 5.43 (s, 1H), 5.08-5.01 (m, 2H), 4.59-4.41 (m, 2H), 3.97-3.90 (m, 1H), 3.61 (t, J=5.5 Hz, 2H), 3.56-3.44 (m, 10H), 3.18-3.14 (m, 1H), 3.08 (dq, J=13.5, 6.8 Hz, 2H), 2.88 (ddd, J=17.1, 13.9, 5.4 Hz, 1H), 2.64-2.53 (m, 3H), 2.35-2.25 (m, 3H), 2.21-2.16 (m, 1H), 2.04-2.00 (m, 1H), 1.87-1.78 (m, 2H), 1.67-1.53 (m, 3H), 1.44-1.38 (m, 2H), 1.28-1.21 (m, 2H), 1.01 (d, J=7.4 Hz, 3H), 0.82 (d, J=6.9 Hz, 3H).

Examples 108-113. Compound 108-113 are Synthesized in a Similar Manner to the Other Examples

Examples 114 & 115. Synthesis of (1S,3R,7S,8S,8aR)-8-(2-((2R,4R)-4-((tert-butyldimethylsilyl)oxy)-6-oxotetrahydro-2H-pyran-2-yl)ethyl)-3,7-dimethyl-1,2,3,7,8,8a-hexahydronaphthalen-1-yl (2-(2-((3-(2-(2,6-dioxopiperidin-3-yl)-1,3-dioxoisoindolin-4-yl)prop-2-yn-1-yl)oxy)ethoxy)ethyl)carbamate (Compound 114) and (1S,3R,7S,8S,8aR)-8-(2-((2R,4R)-4-hydroxy-6-oxotetrahydro-2H-pyran-2-yl)ethyl)-3,7-dimethyl-1,2,3,7,8,8a-hexahydronaphthalen-1-yl (2-(2-((3-(2-(2,6-dioxopiperidin-3-yl)-1,3-dioxoisoindolin-4-yl)prop-2-yn-1-yl)oxy)ethoxy)ethyl)carbamate (Compound 115)

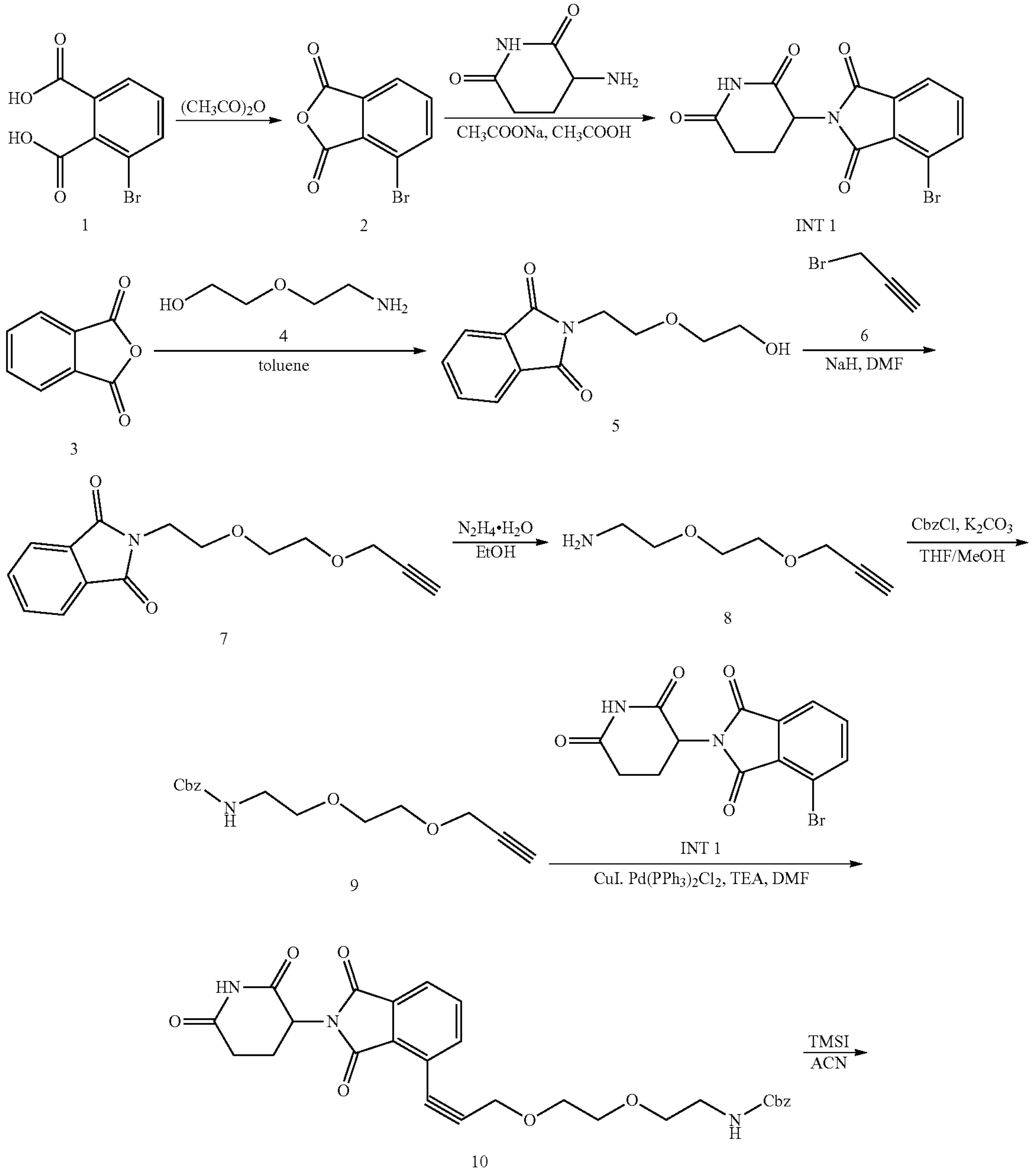

-continued

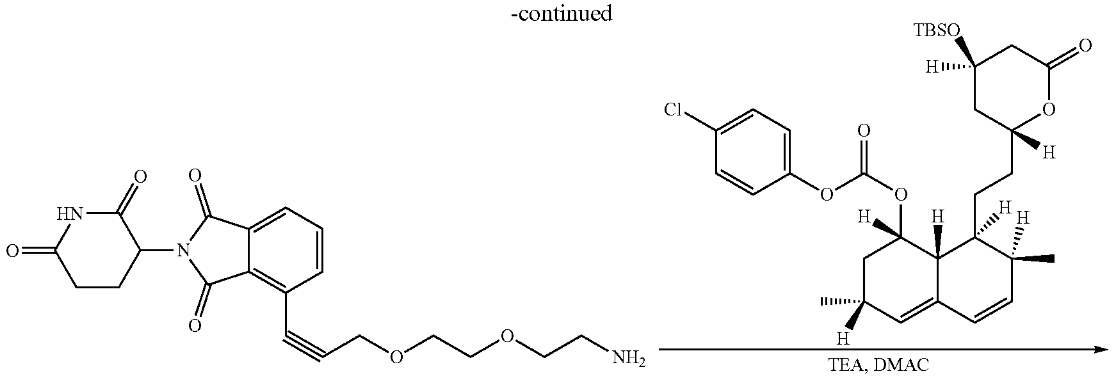

11

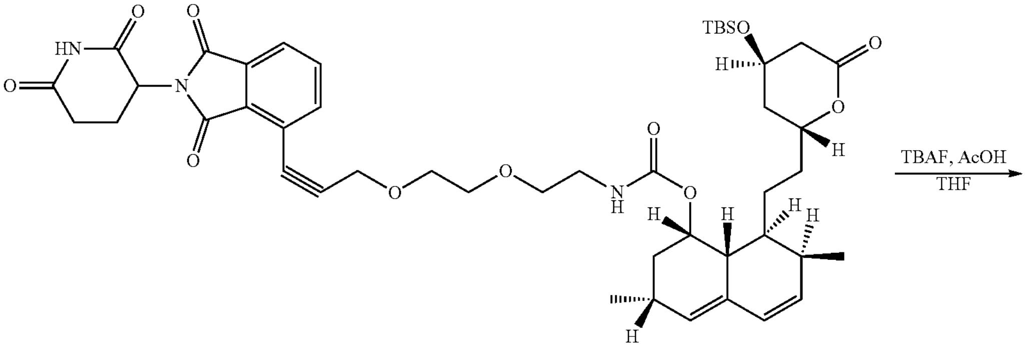

Compound 114

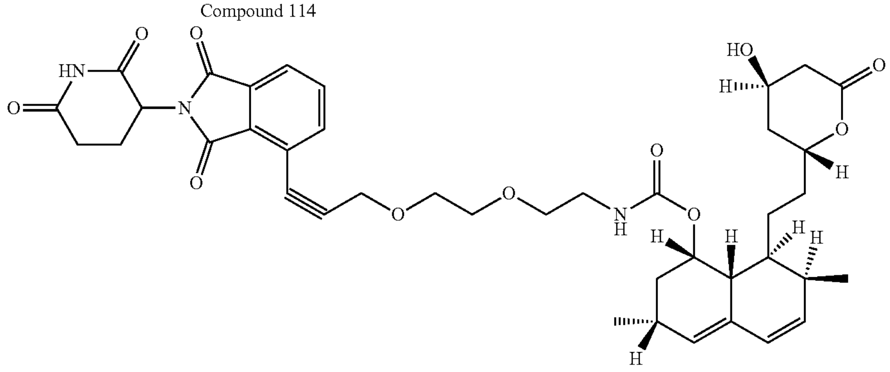

Compound 115

Step 1-6 are Described in the Above Reaction Scheme

Step 7: Synthesis of benzyl (2-(2-((3-(2-(2,6-dioxopiperidin-3-yl)-1,3-dioxoisoindolin-4-yl)prop-2-yn-1-yl)oxy)ethoxy)ethyl)carbamate (10)

To a mixture of 4-bromo-2-(2,6-dioxopiperidin-3-yl) isoindoline-1,3-dione (2 g, 5.93 mmol) and benzyl (2-(2-(prop-2-yn-1-yloxy)ethoxy)ethyl)carbamate (1.81 g, 6.53 mmol) in DMF (15 mL) were added $Pd(PPh_3)_2Cl_2$ (416.40 mg, 593.25 μmol), CuI (225.97 mg, 1.19 mmol) and TEA (6.00 g, 59.33 mmol, 8.26 mL) in one portion at 15° C. under $N_2$ and the resulting mixture was stirred at 80° C. for 16 h. LCMS showed 4-bromo-2-(2,6-dioxopiperidin-3-yl)isoindoline-1,3-dione was consumed completely and one peak with desired mass was detected. TLC ($SiO_2$, Petroleum ether:Ethyl acetate=1:1) indicated 4-bromo-2-(2,6-dioxopiperidin-3-yl)isoindoline-1,3-dione was consumed completely and four new spots were detected. The reaction mixture was diluted with $H_2O$ (50 mL) and extracted with EtOAc (50 mL×3). The organic layer was washed with brine (50 mL×3), dried over $Na_2SO_4$, filtered and concentrated. The residue was purified by column chromatography ($SiO_2$, Petroleum ether/Ethyl acetate=3/1 to 1/2) to afford the titled compound (761 mg, 1.07 mmol, 18.03% yield, 75% purity) as a yellow oil. MS $(M+H)^+$=534.2

Step 8: Synthesis of 4-(3-(2-(2-aminoethoxy)ethoxy)prop-1-yn-1-yl)-2-(2,6-dioxopiperidin-3-yl)isoindoline-1,3-dione (11)

To a mixture of benzyl (2-(2-((3-(2-(2,6-dioxopiperidin-3-yl)-1,3-dioxoisoindolin-4-yl) prop-2-yn-1-yl)oxy)ethoxy)ethyl)carbamate (400 mg, 562.29 μmol) in ACN (4 mL) was added TMSI (247.52 mg, 1.24 mmol, 168.38 μL) in one portion at 15° C. and the resulting mixture was stirred at 15° C. for 2 h. LCMS showed starting material remained and one peak with desired mass was detected and the mixture was stirred at 15° C. for 2 h. LCMS showed starting material was consumed completely and one peak with desired mass was detected. The reaction mixture was combined with other batches (0.3 g scale) for work-up. The reaction mixture was concentrated in vacuum. The residue was purified by prep-HPLC (column: Phenomenex luna $C_{18}$ 150*40 mm*15 μm; mobile phase: [water (0.225% FA)-ACN]; B %: 1%-30%, 11 min) and then lyophilized to afford the titled compound (267 mg, 409.77 μmol, 72.87% yield, 98% purity) as a white solid. MS $(M+H)^+$=400.1

Step 9: Synthesis of (1S,3R,7S,8S,8aR)-8-(2-((2R, 4R)-4-((tert-butyldimethylsilyl)oxy)-6-oxotetra-hydro-2H-pyran-2-yl)ethyl)-3,7-dimethyl-1,2,3,7,8, 8a-hexahydronaphthalen-1-yl (2-(2-((3-(2-(2,6-dioxopiperidin-3-yl)-1,3-dioxoisoindolin-4-yl)prop-2-yn-1-yl)oxy)ethoxy)ethyl)carbamate (Compound 114)

To a mixture of 4-(3-(2-(2-aminoethoxy)ethoxy) prop-1-yn-1-yl)-2-(2,6-dioxopiperidin-3-yl)isoindoline-1,3-dione (167 mg, 418.13 μmol) in DMAC (4 mL) were added TEA (84.62 mg, 836.26 μmol, 116.40 μL) and (1S,3R,7S,8S, 8aR)-8-(2-((2R,4R)-4-((tert-butyldimethylsilyl)oxy)-6-oxo-tetrahydro-2H-pyran-2-yl)ethyl)-3,7-dimethyl-1,2,3,7,8,8a-hexahydronaphthalen-1-yl (4-nitrophenyl) carbonate (250.79 mg, 418.13 μmol) in one portion at 15° C. and the resulting mixture was stirred at 15° C. for 16 h. LCMS showed all starting material was consumed completely and one peak with desired mass was detected. The reaction mixture was diluted with $H_2O$ (12 mL) and extracted with EtOAc (12 mL×3). The organic layer was washed with brine (12 mL×3), dried over $Na_2SO_4$, filtered and concentrated. The residue was purified by prep-HPLC (column: Phenomenex luna $C_{18}$ 150*40 mm*15 μm; mobile phase: [water (0.225% FA)-ACN]; B %: 68%-98%, 11 min) and then lyophilized to afford the titled compound (96.2 mg, 109.61 mol, 26.22% yield, 98% purity) as a white solid. MS $(M+H)^+$=860.5

$^1$H NMR (400 MHz, $CDCl_3$) δ=8.89-8.44 (m, 1H), 7.83 (dd, J=0.8, 7.2 Hz, 1H), 7.78-7.66 (m, 2H), 5.96 (d, J=9.7 Hz, 1H), 5.76 (dd, J=6.1, 9.4 Hz, 1H), 5.50 (br s, 1H), 5.32-5.14 (m, 2H), 5.01-4.96 (m, 1H), 4.69-4.57 (m, 1H), 4.49 (s, 2H), 4.32-4.23 (m, 1H), 3.91-3.76 (m, 2H), 3.74-3.66 (m, 2H), 3.61-3.49 (m, 2H), 3.47-3.36 (m, 1H), 3.35-3.26 (m, 1H), 2.93-2.71 (m, 3H), 2.64-2.49 (m, 2H), 2.45-2.30 (m, 2H), 2.27-2.20 (m, 1H), 2.17-2.04 (m, 2H), 1.90-1.63 (m, 6H), 1.48-1.27 (m, 2H), 1.06 (d, J=7.5 Hz, 3H), 0.88 (m, 12H), 0.07 (s, 6H)

Step 10: Synthesis of (1S,3R,7S,8S,8aR)-8-(2-((2R, 4R)-4-hydroxy-6-oxotetrahydro-2H-pyran-2-yl) ethyl)-3,7-dimethyl-1,2,3,7,8,8a-hexahydronaphthalen-1-yl (2-(2-((3-(2-(2,6-dioxopiperidin-3-yl)-1,3-dioxoisoindolin-4-yl)prop-2-yn-1-yl)oxy)ethoxy) ethyl)carbamate (Compound 115)

To a mixture of (1S,3R,7S,8S,8aR)-8-(2-((2R,4R)-4-((tert-butyldimethylsilyl) oxy)-6-oxotetrahydro-2H-pyran-2-yl)ethyl)-3,7-dimethyl-1,2,3,7,8,8a-hexahydronaphthalen-1-yl (2-(2-((3-(2-(2,6-dioxopiperidin-3-yl)-1,3-dioxoisoindolin-4-yl)prop-2-yn-1-yl)oxy)ethoxy)ethyl) carbamate (182 mg, 211.61 μmol) in THE (3 mL) were added AcOH (63.54 mg, 1.06 mmol, 60.51 μL) and TBAF (1 M, 846.44 μL) in one portion at 15° C. and the resulting mixture was stirred at 15° C. for 16 h. LCMS showed starting material was consumed completely and desired mass was detected. The reaction mixture was quenched with saturated $NH_4Cl$ (10 mL) and extracted with EtOAc (10 mL×3). The organic layer was washed with saturated $NH_4Cl$ (10 mL×3), dried over $Na_2SO_4$, filtered and concentrated. The residue was purified by prep-HPLC (column: Unisil 3-100 $C_{18}$ μLtra 150*50 mm*3 μm; mobile phase: [water (0.225% FA)-ACN]; B %: 43%-63%, 10 min) and then lyophilized to afford the titled compound (51.3 mg, 62.59 μmol, 29.58% yield, 91% purity) as a white solid. MS $(M+H)^+$=746.5

$^1$H NMR (400 MHz, $CDCl_3$) δ=8.95-8.66 (m, 1H), 7.88-7.82 (m, 1H), 7.78-7.69 (m, 2H), 5.98 (d, J=9.6 Hz, 1H), 5.83-5.74 (m, 1H), 5.52 (s, 1H), 5.36-5.15 (m, 2H), 5.08-4.94 (m, 1H), 4.68-4.45 (m, 3H), 4.37-4.21 (m, 1H), 3.94-3.78 (m, 2H), 3.75-3.66 (m, 2H), 3.65-3.48 (m, 2H), 3.46-3.25 (m, 2H), 3.00-2.48 (m, 7H), 2.46-2.32 (m, 2H), 2.23-2.26 (m, 1H), 2.21-2.13 (m, 1H), 2.12-2.04 (m, 1H), 2.03-1.94 (m, 1H), 1.92-1.81 (m, 2H), 1.78-1.67 (m, 2H), 1.44-1.31 (m, 2H), 1.12-1.06 (m, 3H), 0.93-0.87 (m, 3H)

Examples 116 to 119. In a Manner Similar to the Other Examples, Compounds 116 to 119 were Obtained Examples 120 & 121. Synthesis of (1S,3R,7S,8S, 8aR)-8-(2-((2R,4R)-4-((tert-butyldimethylsilyl)oxy)-6-oxotetrahydro-2H-pyran-2-yl)ethyl)-3,7-dimethyl-1,2,3,7,8,8a-hexahydronaphthalen-1-yl (3-(4-((2-(2, 6-dioxopiperidin-3-yl)-1,3-dioxoisoindolin-4-yl) amino)butoxy)propyl)carbamate (Compound 120) and (1S,3R,7S,8S,8aR)-8-(2-((2R,4R)-4-hydroxy-6-oxotetrahydro-2H-pyran-2-yl)ethyl)-3,7-dimethyl-1, 2,3,7,8,8a-hexahydronaphthalen-1-yl (3-(4-((2-(2,6-dioxopiperidin-3-yl)-1,3-dioxoisoindolin-4-yl) amino)butoxy)propyl)carbamate (Compound 121)

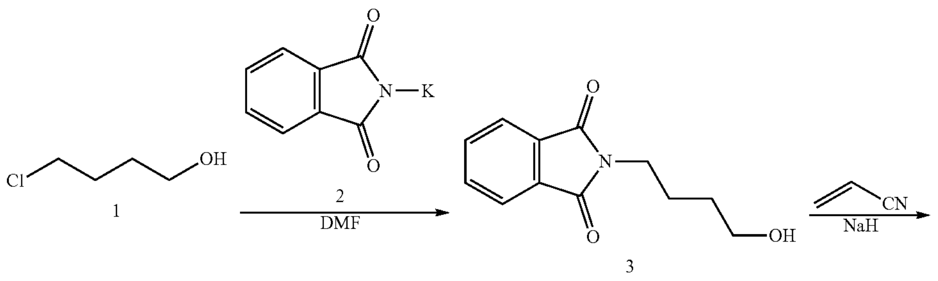

-continued
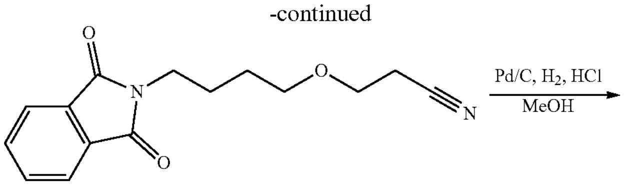
4
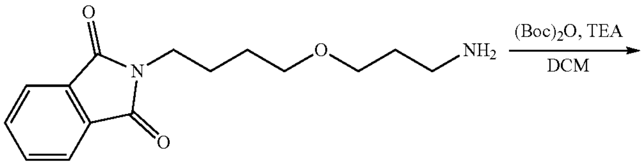
5
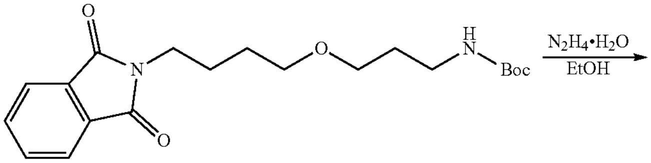
6
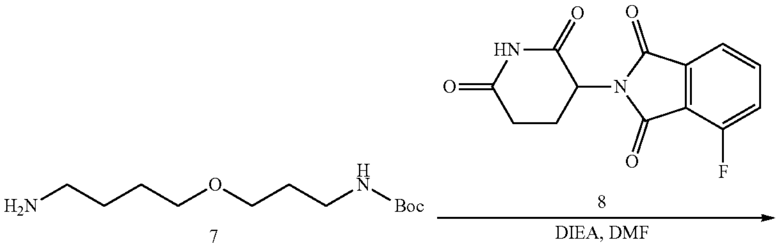
7
8
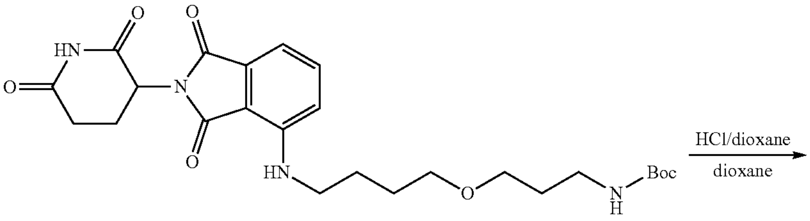
9
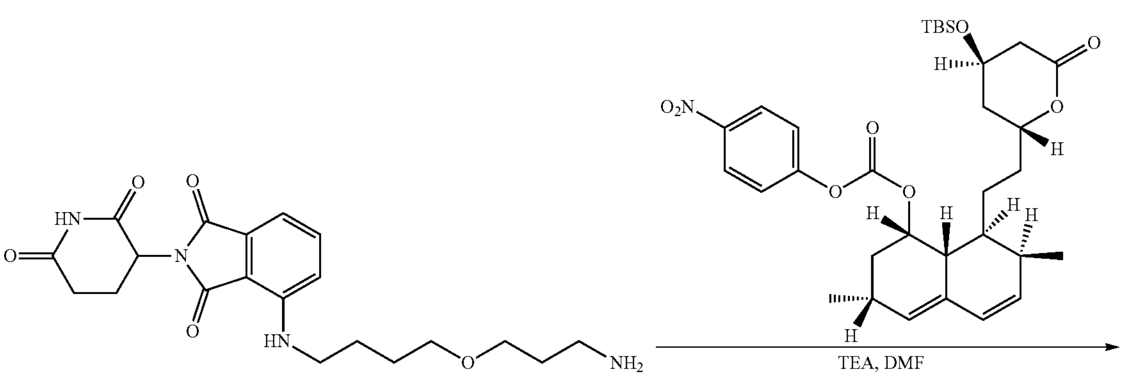
10

-continued

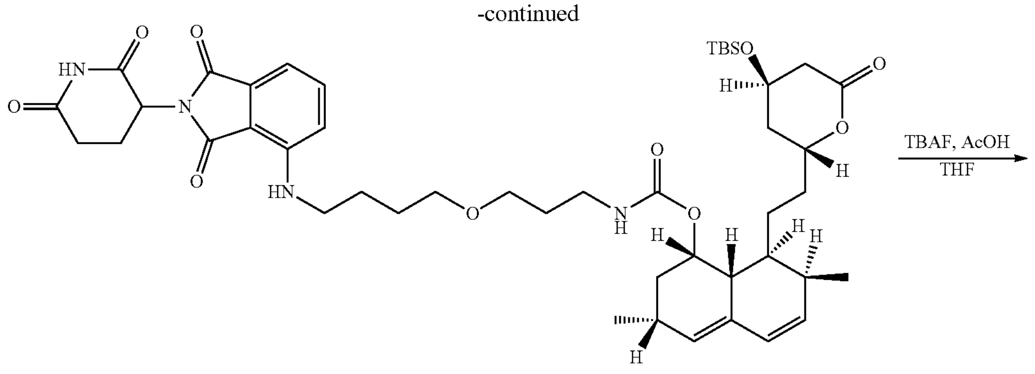

Compound 120

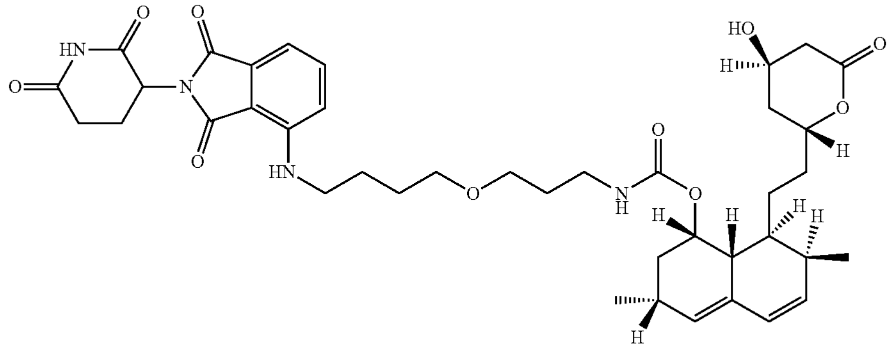

Compound 121

Step 1-7 are Described in the Above Reaction Scheme

Step 8: Synthesis of (1S,3R,7S,8S,8aR)-8-(2-((2R, 4R)-4-((tert-butyldimethylsilyl)oxy)-6-oxotetrahydro-2H-pyran-2-yl)ethyl)-3,7-dimethyl-1,2,3,7,8, 8a-hexahydronaphthalen-1-yl (3-(4-((2-(2,6-dioxopiperidin-3-yl)-1,3-dioxoisoindolin-4-yl) amino)butoxy)propyl)carbamate (Compound 120)

According to the above reaction scheme, in a manner similar to the other examples, obtained the titled compound (156 mg, 177.12 μmol, 20.95% yield, 98% purity) as a yellow solid. MS $(M+H)^+$=863.7

$^1H$ NMR (400 MHz, $CDCl_3$) δ=8.09-7.97 (m, 1H), 7.54-7.46 (m, 1H), 7.10 (d, J=7.0 Hz, 1H), 6.90 (d, J=8.5 Hz, 1H), 6.32-6.22 (m, 1H), 5.97 (d, J=9.6 Hz, 1H), 5.76 (dd, J=6.1, 9.4 Hz, 1H), 5.51 (br s, 1H), 5.25-5.05 (m, 2H), 4.98-4.87 (m, 1H), 4.70-4.60 (m, 1H), 4.27-4.30 (m, 1H), 3.51-3.42 (m, 4H), 3.38-3.16 (m, 4H), 2.93-2.69 (m, 3H), 2.65-2.50 (m, 2H), 2.48-2.31 (m, 2H), 2.29-2.21 (m, 1H), 2.18-2.05 (m, 2H), 1.91-1.62 (m, 12H), 1.53-1.13 (m, 3H), 1.08 (d, J=7.4 Hz, 3H), 0.88 (m, 12H), 0.07 (s, 6H)

Step 9: Synthesis of (1S,3R,7S,8S,8aR)-8-(2-((2R, 4R)-4-hydroxy-6-oxotetrahydro-2H-pyran-2-yl) ethyl)-3,7-dimethyl-1,2,3,7,8,8a-hexahydronaphthalen-1-yl (3-(4-((2-(2,6-dioxopiperidin-3-yl)-1,3-dioxoisoindolin-4-yl)amino)butoxy)propyl) carbamate (Compound 121)

To a mixture of (1S,3R,7S,8S,8aR)-8-(2-((2R,4R)-4-((tert-butyldimethylsilyl) oxy)-6-oxotetrahydro-2H-pyran-2-yl)ethyl)-3,7-dimethyl-1,2,3,7,8,8a-hexahydronaphthalen-1-yl(3-(4-((2-(2,6-dioxopiperidin-3-yl)-1,3-dioxoisoindolin-4-yl)amino)butoxy)propyl)carbamate (100 mg, 115.86 μmol) in THF (2 mL) were was added AcOH (34.79 mg, 579.29 μmol, 33.13 μL) and TBAF (1 M, 463.44 μL) in one portion at 15° C. and the resulting mixture was stirred at 15° C. for 16 h. LCMS showed starting material was consumed completely and one peak with desired mass was detected. The reaction mixture was quenched with saturated $NH_4Cl$ (10 mL) and extracted with EtOAc (10 mL×3). The organic layer was washed with saturated $NH_4Cl$ (10 mL×3), dried over $Na_2SO_4$, filtered and concentrated. The residue was purified by prep-HPLC (column: Phenomenex Luna $C_{18}$ 150*25 mm*10 μm; mobile phase: [water (0.225% FA)-ACN]; B %: 46%-76%, 10 min) to afford the titled compound (81.2 mg, 103.01 μmol, 88.91% yield, 95% purity) as a yellow solid. MS $(M+H)^+$=749.5

$^1H$ NMR (400 MHz, $CDCl_3$) δ=8.42-8.20 (m, 1H), 7.54-7.47 (m, 1H), 7.10 (d, J=7.1 Hz, 1H), 6.90 (d, J=8.6 Hz, 1H), 6.41-6.21 (m, 1H), 5.96 (d, J=9.6 Hz, 1H), 5.81-5.71 (m, 1H), 5.54-5.47 (m, 1H), 5.37-5.17 (m, 1H), 5.15-5.01 (m, 1H), 4.98-4.88 (m, 1H), 4.69-4.57 (m, 1H), 4.36-4.25 (m, 1H), 3.52-3.42 (m, 4H), 3.36-3.20 (m, 4H), 2.93-2.67 (m, 4H), 2.62-2.54 (m, 1H), 2.48-2.31 (m, 2H), 2.29-2.21 (m, 1H), 2.18-2.11 (m, 1H), 2.10-2.02 (m, 1H), 2.00-1.92 (m, 1H), 1.91-1.81 (m, 2H), 1.78-1.62 (m, 10H), 1.40-1.33 (m, 2H), 1.08 (d, J=7.4 Hz, 3H), 0.89 (d, J=7.0 Hz, 3H)

Examples 122 to 123. In a Manner Similar to the Other Examples, Compounds 122 to 123 were Obtained

Examples 124 & 126. Synthesis of (1S,3R,7S,8S,8aR)-8-(2-((2R,4R)-4-((tert-butyldimethylsilyl)oxy)-6-oxotetrahydro-2H-pyran-2-yl)ethyl)-3,7-dimethyl-1,2,3,7,8,8a-hexahydronaphthalen-1-yl (5-(4-((2-(2,6-dioxopiperidin-3-yl)-1,3-dioxoisoindolin-4-yl)amino)piperidin-1-yl)pentyl)carbamate (Compound 124) and (1S,3R,7S,8S,8aR)-8-(2-((2R,4R)-4-hydroxy-6-oxotetrahydro-2H-pyran-2-yl)ethyl)-3,7-dimethyl-1,2,3,7,8,8a-hexahydronaphthalen-1-yl (5-(4-((2-(2,6-dioxopiperidin-3-yl)-1,3-dioxoisoindolin-4-yl)amino)piperidin-1-yl)pentyl)carbamate (Compound 126)

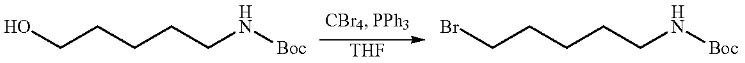

1 linker

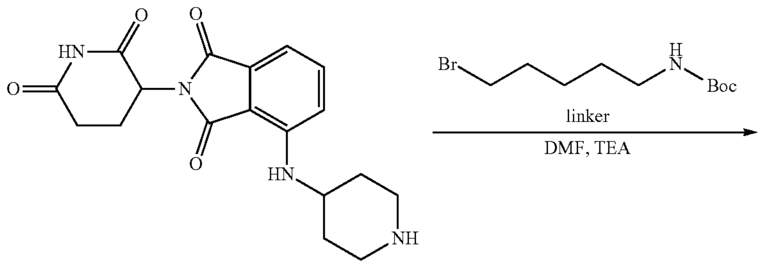

2

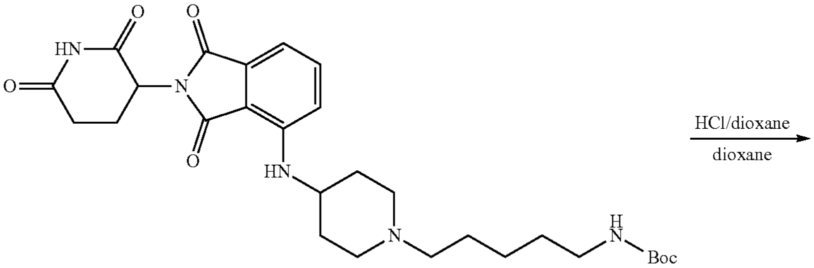

3

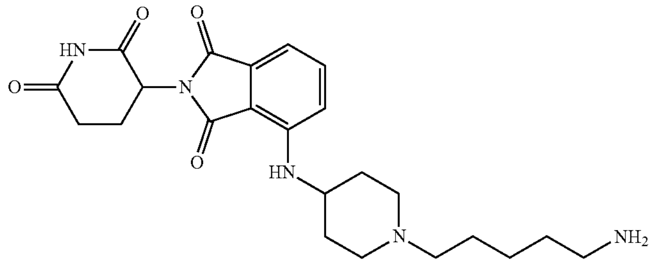

4

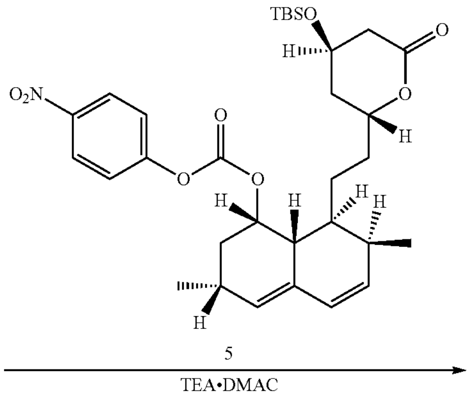

5

TEA•DMAC

-continued

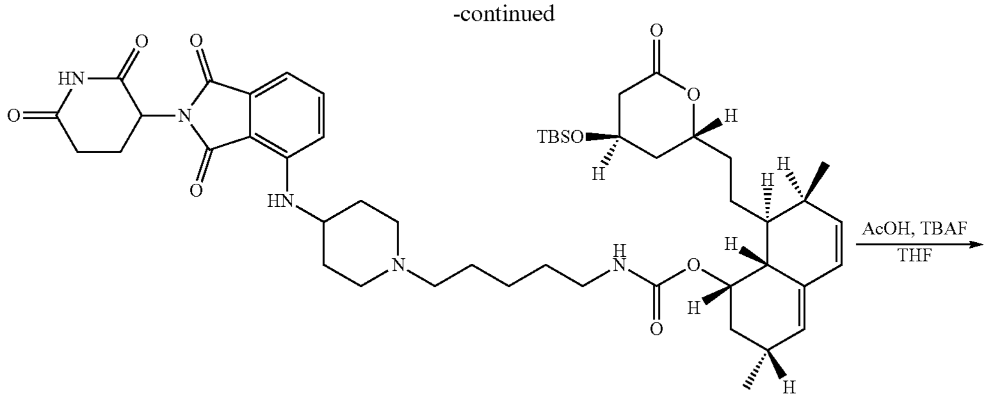

Compound 124

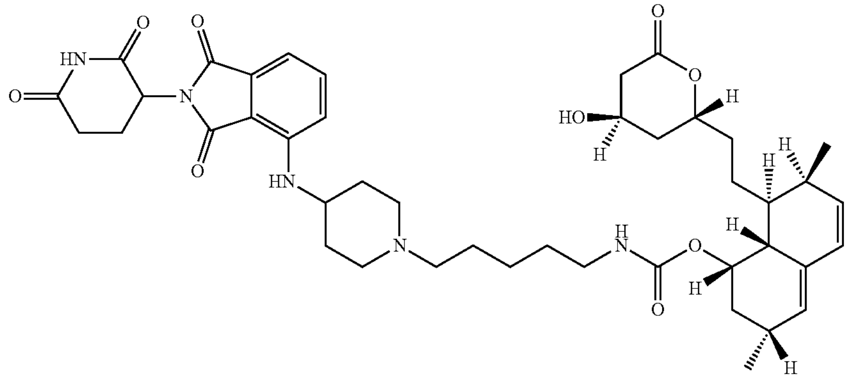

Compound 126

Step 1-3 are Described in the Above Reaction Scheme

Step 4: Synthesis of (1S,3R,7S,8S,8aR)-8-(2-((2R, 4R)-4-((tert-butyldimethylsilyl)oxy)-6-oxotetrahydro-2H-pyran-2-yl)ethyl)-3,7-dimethyl-1,2,3,7,8, 8a-hexahydronaphthalen-1-yl (5-(4-((2-(2,6-dioxopiperidin-3-yl)-1,3-dioxoisoindolin-4-yl) amino)piperidin-1-yl)pentyl)carbamate (Compound 124)

According to the above reaction scheme, in a manner similar to the other examples, obtained the titled compound (1.02 g, 1.02 mmol, 34.72% yield, 90% purity) as a yellow solid. MS $(M+H)^+$=902.7.

$^1$H NMR (400 MHz, $CDCl_3$) δ=8.46 (s, 1H), 7.50-7.47 (m, 1H), 7.10 (d, J=7.0 Hz, 1H), 6.88 (d, J=8.5 Hz, 1H), 6.25 (d, J=7.8 Hz, 1H), 5.98 (d, J=9.7 9.6 Hz, 1H), 5.78 (dd, J 1=9.5 Hz, $J_2$=6.1 Hz, 1H), 5.53 (s, 1H), 5.17 (s, 1H), 5.06-4.76 (m, 2H), 4.66-4.65 (m, 1H), 4.34-4.26 (m, 1H), 3.70-3.49 (m, 2H), 3.30-3.15 (m, 1H), 3.05-2.95 (m, 3H), 2.93-2.84 (m, 1H), 2.83-2.66 (m, 2H), 2.64-2.54 (m, 2H), 2.54-2.31 (m, 6H), 2.29-2.21 (m, 1H), 2.20-2.00 (m, 4H), 1.91-1.80 (m, 3H), 1.76-1.61 (m, 5H), 1.58-1.43 (m, 4H), 1.32 (m, 3H), 1.08 (d, J=7.3 Hz, 3H), 0.93-0.85 (m, 12H), 0.08 (s, 6H).

Step 5: Synthesis of (1S,3R,7S,8S,8aR)-8-(2-((2R, 4R)-4-hydroxy-6-oxotetrahydro-2H-pyran-2-yl) ethyl)-3,7-dimethyl-1,2,3,7,8,8a-hexahydronaphthalen-1-yl (5-(4-((2-(2,6-dioxopiperidin-3-yl)-1,3-dioxoisoindolin-4-yl)amino)piperidin-1-yl)pentyl)carbamate (Compound 126)

According to the above reaction scheme, in a manner similar to the other examples, obtained the titled compound (140.5 mg, 167.61 μmol, 21.60% yield, 94% purity) as a yellow solid. MS $(M+H)^+$=788.6.

$^1$H NMR (400 MHz, $CDCl_3$) δ=8.52 (s, 1H), 7.50 (t, J=7.8 Hz, 1H), 7.12 (d, J=7.1 Hz, 1H), 6.89 (d, J=8.7 Hz, 1H), 6.26 (d, J=7.2 Hz, 1H), 5.98 (d, J=9.7 Hz, 1H), 5.80-5.76 (m, 1H), 5.52 (s, 1H), 5.20 (s, 1H), 4.64 (br s, 2H), 4.64 (s, 1H), 4.38-4.30 (m, 1H), 3.77-3.55 (m, 2H), 3.42-3.21 (m, 1H), 3.15-3.02 (m, 2H), 2.96-2.74 (m, 3H), 2.73-2.46 (m, 6H), 2.45-2.33 (m, 2H), 2.29-2.04 (m, 5H), 1.99-1.77 (m, 5H), 1.76-1.58 (m, 5H), 1.55-1.27 (m, 7H), 1.07 (d, J=7.5 Hz, 3H), 0.90 (d, J=7.0 Hz, 3H).

Examples 125 & 127. Synthesis of (1S,3R,7S,8S,8aR)-8-(2-((2R,4R)-4-((tert-butyldimethylsilyl)oxy)-6-oxotetrahydro-2H-pyran-2-yl)ethyl)-3,7-dimethyl-1,2,3,7,8,8a-hexahydronaphthalen-1-yl (6-(4-((2-(2,6-dioxopiperidin-3-yl)-1,3-dioxoisoindolin-4-yl)amino)piperidin-1-yl)hexyl)carbamate (Compound 125) and (1S,3R,7S,8S,8aR)-8-(2-((2R,4R)-4-hydroxy-6-oxotetrahydro-2H-pyran-2-yl)ethyl)-3,7-dimethyl-1,2,3,7,8,8a-hexahydronaphthalen-1-yl (6-(4-((2-(2,6-dioxopiperidin-3-yl)-1,3-dioxoisoindolin-4-yl)amino)piperidin-1-yl)hexyl)carbamate (Compound 127)

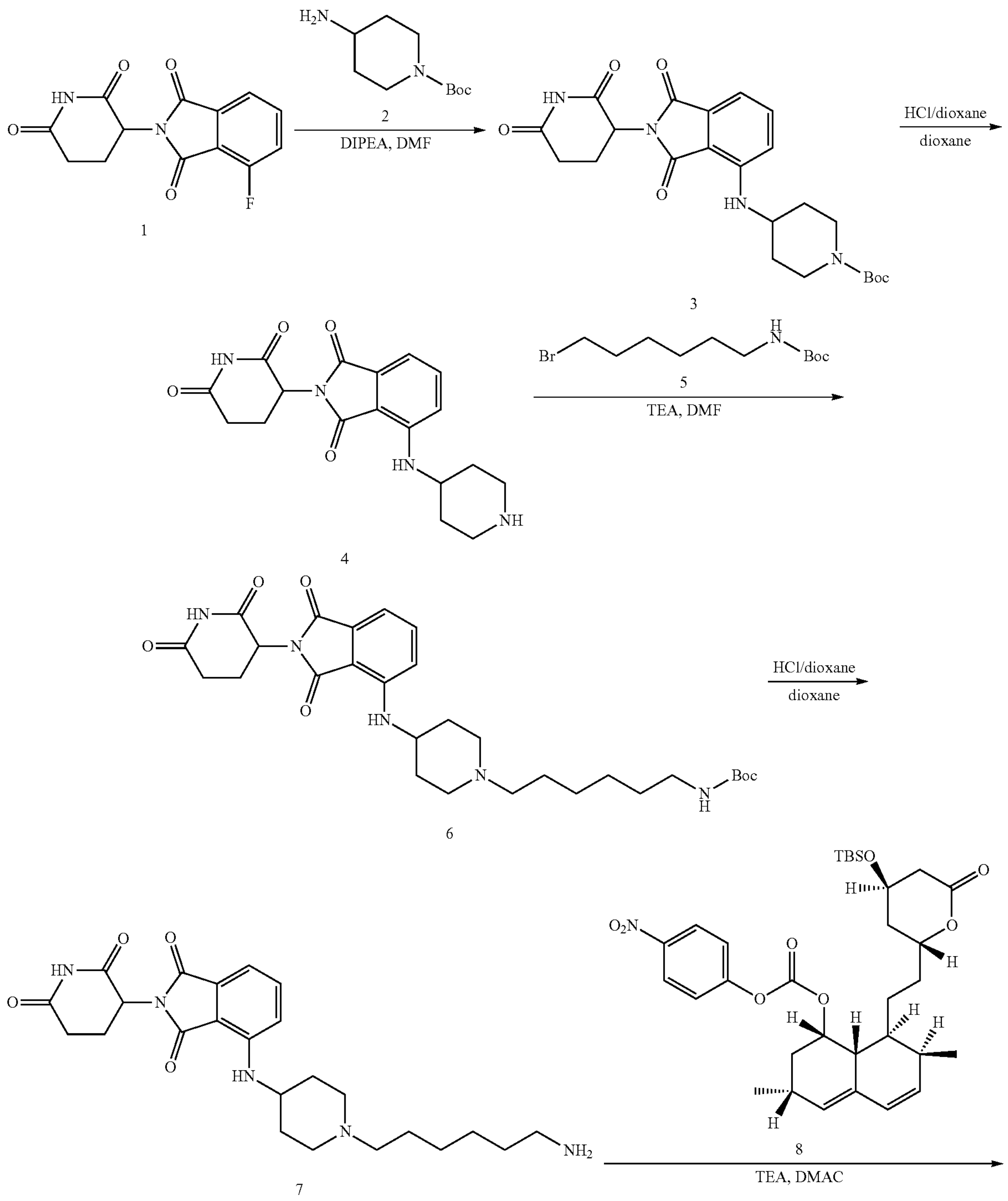

-continued

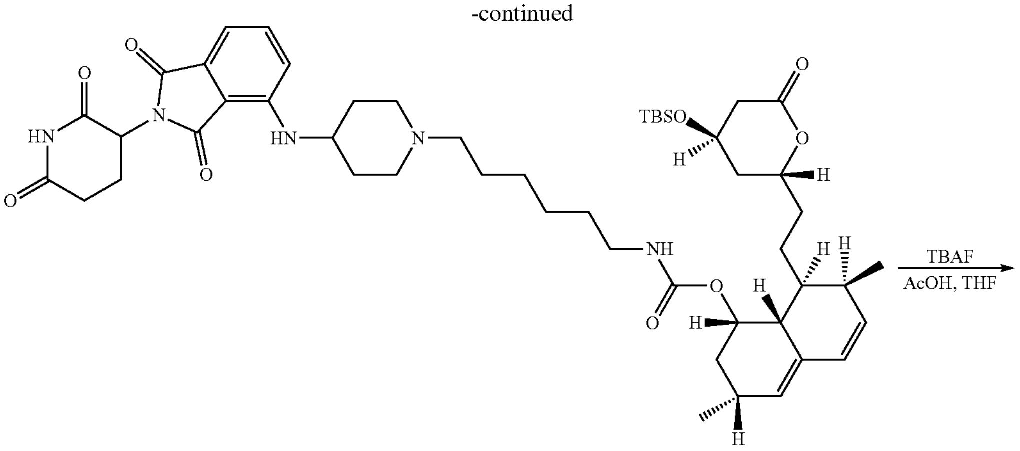

Compound 125

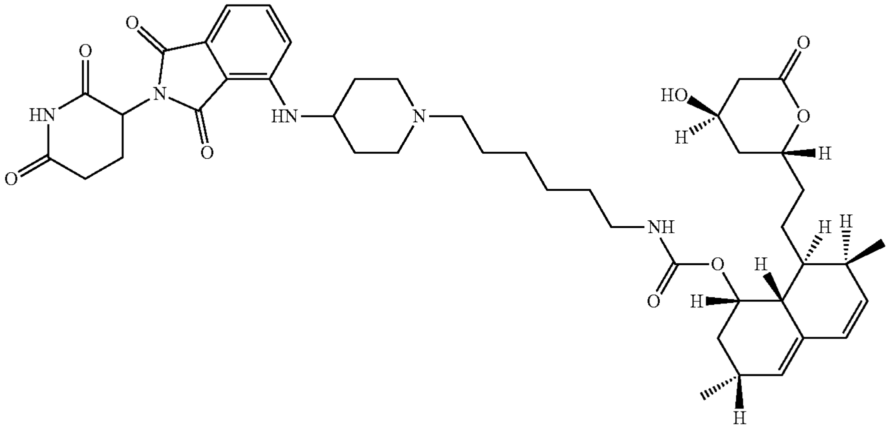

Compound 127

Step 1-4 are Described in the Above Reaction Scheme

Step 5: Synthesis of (1S,3R,7S,8S,8aR)-8-(2-((2R, 4R)-4-((tert-butyldimethylsilyl)oxy)-6-oxotetrahydro-2H-pyran-2-yl)ethyl)-3,7-dimethyl-1,2,3,7,8, 8a-hexahydronaphthalen-1-yl (6-(4-((2-(2,6-dioxopiperidin-3-yl)-1,3-dioxoisoindolin-4-yl) amino)piperidin-1-yl)hexyl)carbamate (Compound 125)

According to the above reaction scheme, in a manner similar to the other examples, obtained the titled compound (527.6 mg, 541.29 μmol, 37.51% yield, 94% purity) as a yellow solid. MS $(M+H)^+$=916.7.

$^1$H NMR (400 MHz, $CDCl_3$) δ=8.44 (s, 1H), 7.49 (t, J=7.8 Hz, 1H), 7.12 (d, J=7.1 Hz, 1H), 6.88 (d, J=8.6 Hz, 1H), 6.28 (d, J=7.6 Hz, 1H), 5.97 (d, J=9.6 Hz, 1H), 5.78 (dd, J 1=9.5 Hz, $J_2$=6.0 Hz, 1H), 5.52 (s, 1H), 5.17 (s, 1H), 4.99-4.84 (m, 2H), 4.83-4.61 (m, 1H), 4.30-4.28 (m, 1H), 3.68-3.59 (m, 1H), 3.27-3.17 (m, 1H), 3.17-3.00 (m, 3H), 2.93-2.85 (m, 1H), 2.83-2.73 (m, 2H), 2.72-2.49 (m, 6H), 2.46-2.33 (m, 2H), 2.29-2.16 (m, 3H), 2.16-2.06 (m, 2H), 1.94-1.73 (m, 6H), 1.71-1.59 (m, 4H), 1.51-1.41 (m, 3H), 1.36-1.24 (m, 5H), 1.08 (d, J=7.4 Hz, 3H), 0.95-0.83 (m, 12H), 0.08 (s, 6H).

Step 6: Synthesis of (1S,3R,7S,8S,8aR)-8-(2-((2R, 4R)-4-hydroxy-6-oxotetrahydro-2H-pyran-2-yl) ethyl)-3,7-dimethyl-1,2,3,7,8,8a-hexahydronaphthalen-1-yl (6-(4-((2-(2,6-dioxo piperidin-3-yl)-1,3-dioxoisoindolin-4-yl)amino)piperidin-1-yl)hexyl) carbamate (Compound 127)

According to the above reaction scheme, in a manner similar to the other examples, obtained the titled compound (39.5 mg, 44.33 μmol, 11.60% yield, 90% purity) as a yellow solid. MS $(M+H)^+$=802.6.

$^1$H NMR (400 MHz, $CDCl_3$) δ=7.49 (t, J=7.6 Hz, 1H), 7.11 (d, J=7.1 Hz, 1H), 6.89 (d, J=8.5 Hz, 1H), 6.27 (d, J=7.6 Hz, 1H), 5.98 (d, J=9.5 Hz, 1H), 5.79 (dd, J=6.0, 9.6 Hz, 1H), 5.53 (s, 1H), 5.23 (s, 1H), 4.92 (dd, J=5.2, 12.0 Hz, 1H), 4.79-4.56 (m, 2H), 4.32-4.31 (m, 1H), 3.58-3.45 (m, 1H), 3.36-3.19 (m, 1H), 3.15-3.00 (m, 1H), 2.94-2.83 (m, 3H), 2.81-2.69 (m, 3H), 2.65-2.58 (m, 1H), 2.47-2.41 (m, 1H), 2.41-2.32 (m, 3H), 2.30-2.19 (m, 3H), 2.16-2.12 (m, 1H), 2.11-2.03 (m, 3H), 1.96-1.82 (m, 5H), 1.78-1.71 (m, 5H), 1.53-1.44 (m, 5H), 1.41-1.26 (m, 5H), 1.08 (d, J=7.3 Hz, 3H), 0.91 (d, J=7.0 Hz, 3H).

Examples 128 & 129. Synthesis of (1S,3R,7S,8S,8aR)-8-(2-((2R,4R)-4-((tert-butyldimethylsilyl)oxy)-6-oxotetrahydro-2H-pyran-2-yl)ethyl)-3,7-dimethyl-1,2,3,7,8,8a-hexahydronaphthalen-1-yl (2-(2-(2-((2-(2,6-dioxopiperidin-3-yl)-1,3-dioxoisoindolin-4-yl)oxy)acetamido)ethoxy)ethyl)carbamate (Compound 128) and (1S,3R,7S,8S,8aR)-8-(2-((2R,4R)-4-hydroxy-6-oxotetrahydro-2H-pyran-2-yl)ethyl)-3,7-dimethyl-1,2,3,7,8,8a-hexahydronaphthalen-1-yl (2-(2-(2-((2-(2,6-dioxopiperidin-3-yl)-1,3-dioxoisoindolin-4-yl)oxy)acetamido)ethoxy)ethyl)carbamate (Compound 129)

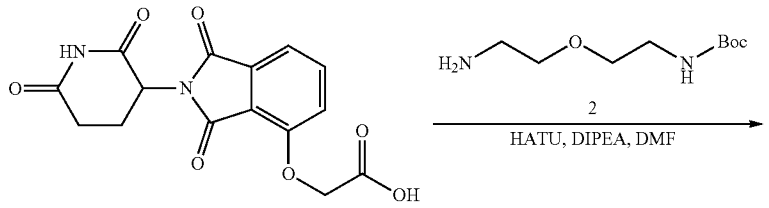

1

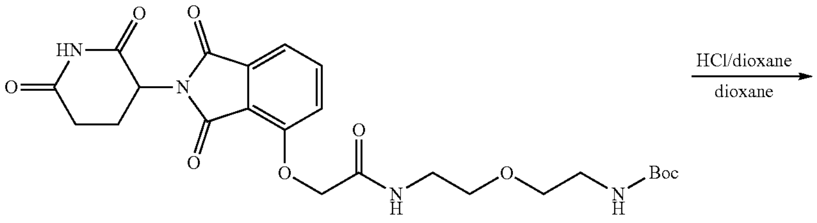

3

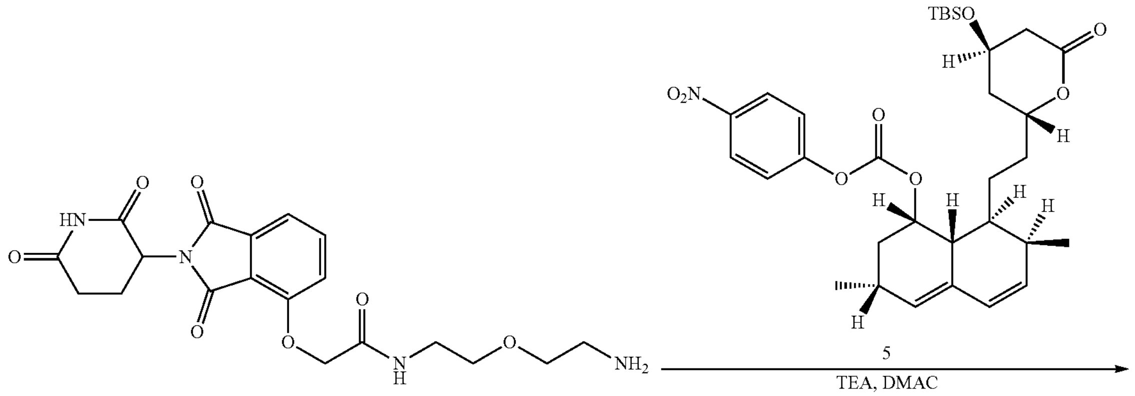

4

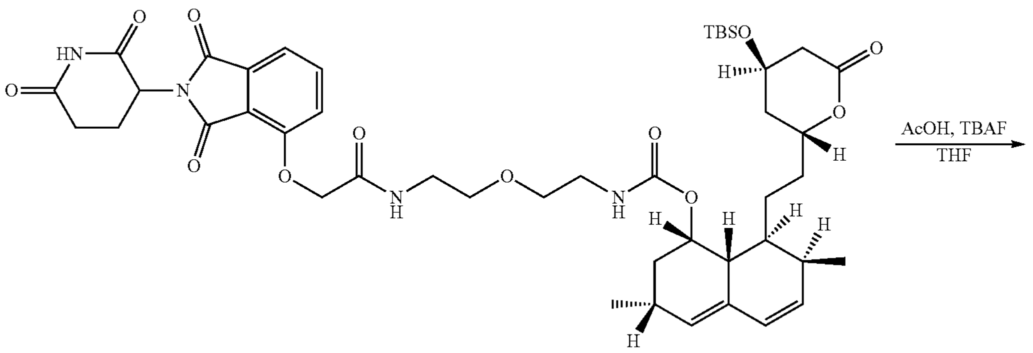

Compound 128

-continued

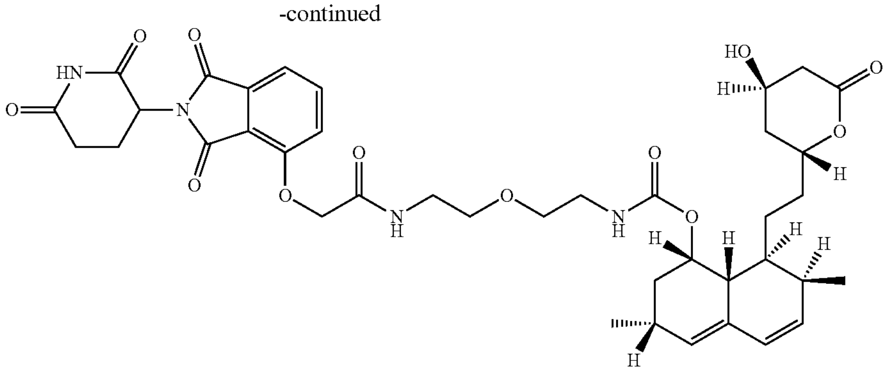

Compound 129

Step 1-2 are Described in the Above Reaction Scheme

Step 3: Synthesis of (1S,3R,7S,8S,8aR)-8-(2-((2R, 4R)-4-((tert-butyldimethylsilyl)oxy)-6-oxotetrahydro-2H-pyran-2-yl)ethyl)-3,7-dimethyl-1,2,3,7,8, 8a-hexahydronaphthalen-1-yl (2-(2-(2-((2-(2,6-dioxopiperidin-3-yl)-1,3-dioxoisoindolin-4-yl)oxy) acetamido)ethoxy)ethyl)carbamate (Compound 128)

According to the above reaction scheme, in a manner similar to the other examples, obtained the titled compound (491.7 mg, 542.56 μmol, 24.68% yield, 97% purity) as a off-white solid. MS $(M+H)^+$=879.5.

$^1$H NMR (400 MHz, $CDCl_3$) δ=8.84-8.35 (m, 1H), 7.90-7.61 (m, 2H), 7.55 (d, J=7.3 Hz, 1H), 7.18 (d, J=8.4 Hz, 1H), 6.03-5.82 (m, 1H), 5.81-5.66 (m, 1H), 5.62-5.25 (m, 2H), 5.23-5.12 (m, 1H), 5.02 (d, J=4.6 Hz, 1H), 4.76-4.52 (m, 3H), 4.28 (d, J=2.8 Hz, 1H), 3.68-3.24 (m, 8H), 3.02-2.67 (m, 3H), 2.66-2.49 (m, 2H), 2.46-2.14 (m, 4H), 2.08 (m, 1H), 1.90-1.62 (m, 6H), 1.51-1.39 (m, 1H), 1.36-1.24 (m, 1H), 1.12-0.96 (m, 3H), 0.89-0.76 (m, 12H), 0.07 (s, 6H).

Step 4: Synthesis of (1S,3R,7S,8S,8aR)-8-(2-((2R, 4R)-4-hydroxy-6-oxotetrahydro-2H-pyran-2-yl) ethyl)-3,7-dimethyl-1,2,3,7,8,8a-hexahydronaphthalen-1-yl (2-(2-(2-((2-(2,6-dioxopiperidin-3-yl)-1,3-dioxoisoindolin-4-yl)oxy)acetamido)ethoxy)ethyl) carbamate (Compound 129)

According to the above reaction scheme, in a manner similar to the other examples, obtained the titled compound (104 mg, 130.54 μmol, 32.79% yield, 96% purity) as a off-white solid. MS $(M+H)^+$=765.2.

$^1$H NMR (400 MHz, DMSO-$d_6$) δ 11.12 (s, 1H), 8.02 (t, J=5.6 Hz, 1H), 7.82 (dd, J=8.5, 7.3 Hz, 1H), 7.50 (d, J=7.3 Hz, 1H), 7.40 (d, J=8.5 Hz, 1H), 7.04-6.95 (m, 1H), 5.89 (d, J=9.6 Hz, 1H), 5.45 (s, 1H), 5.19 (d, J=3.2 Hz, 1H), 5.17-5.08 (m, 1H), 5.04 (d, J=3.3 Hz, 1H), 4.79 (s, 2H), 4.55-4.44 (m, 1H), 4.15-4.04 (m, 1H), 3.50-3.41 (m, 2H), 3.41-3.36 (m, 2H), 3.33-3.26 (m, 3H), 3.22-3.06 (m, 2H), 2.98-2.82 (m, 1H), 2.72-2.55 (m, 2H), 2.44-2.27 (m, 3H), 2.23 (d, J=12.2 Hz, 1H), 2.11-1.96 (m, 1H), 1.94-1.75 (m, 3H), 1.75-1.55 (m, 3H), 1.55-1.40 (m, 1H), 1.37-1.17 (m, 2H), 1.03 (d, J=7.3 Hz, 3H), 0.84 (d, J=6.9 Hz, 3H).

Examples 130 to 133. In a Manner Similar to the Other Examples, Compounds 130 to 133 were Obtained Examples 134 & 135. Synthesis of (1S,3R,7S,8S, 8aR)-8-(2-((2R,4R)-4-((tert-butyldimethylsilyl)oxy)-6-oxotetrahydro-2H-pyran-2-yl)ethyl)-3,7-dimethyl-1,2,3,7,8,8a-hexahydronaphthalen-1-yl (3-((1-(2-((2-(2,6-dioxopiperidin-3-yl)-1,3-dioxoisoindolin-4-yl) oxy)acetyl)piperidin-4-yl)oxy)propyl)carbamate (Compound 134) and (1S,3R,7S,8S,8aR)-8-(2-((2R, 4R)-4-hydroxy-6-oxotetrahydro-2H-pyran-2-yl) ethyl)-3,7-dimethyl-1,2,3,7,8,8a-hexahydronaphthalen-1-yl (3-((1-(2-((2-(2,6-dioxopiperidin-3-yl)-1,3-dioxoisoindolin-4-yl)oxy)acetyl)piperidin-4-yl)oxy) propyl)carbamate (Compound 135)

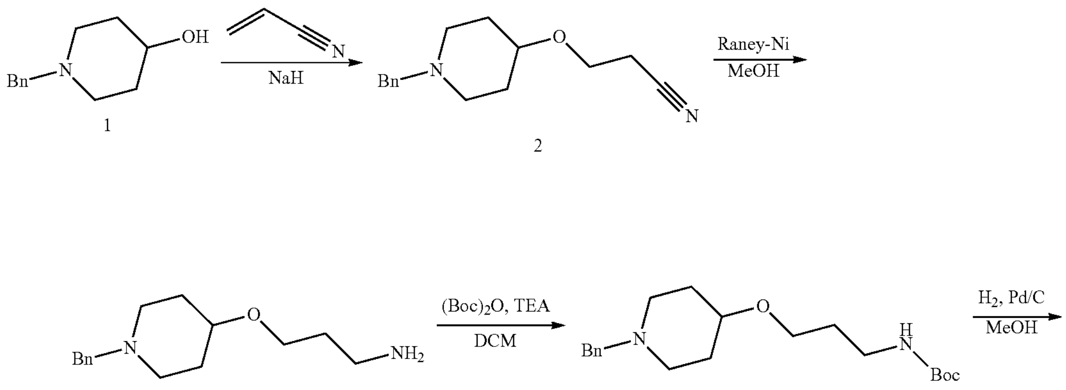

1 2 3 4

-continued
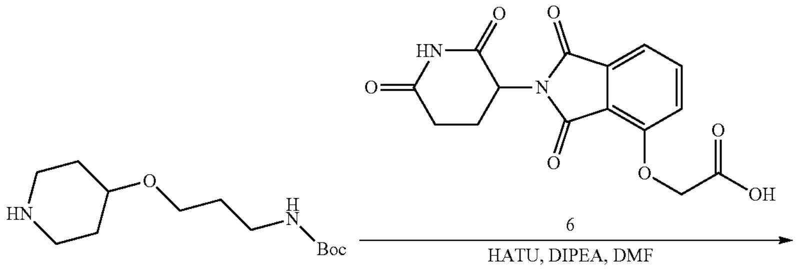
5
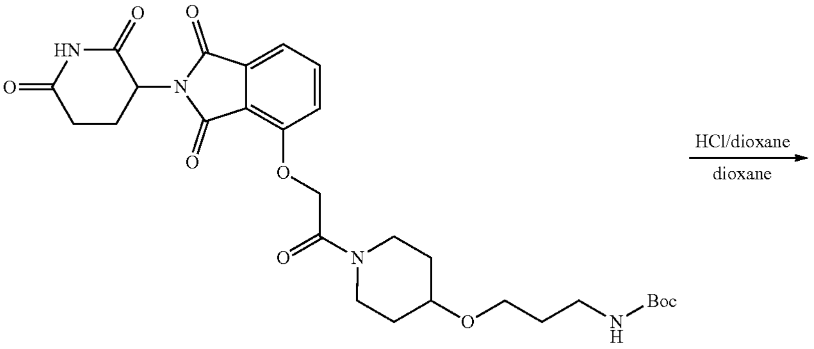
7
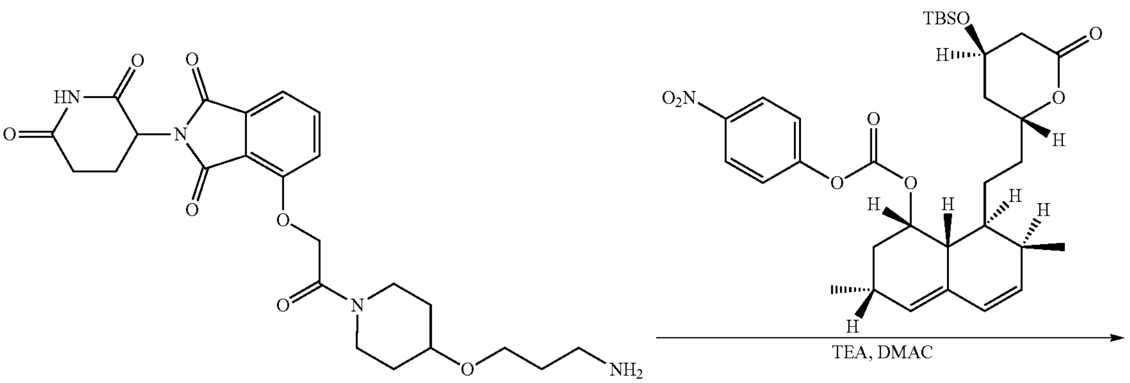
8
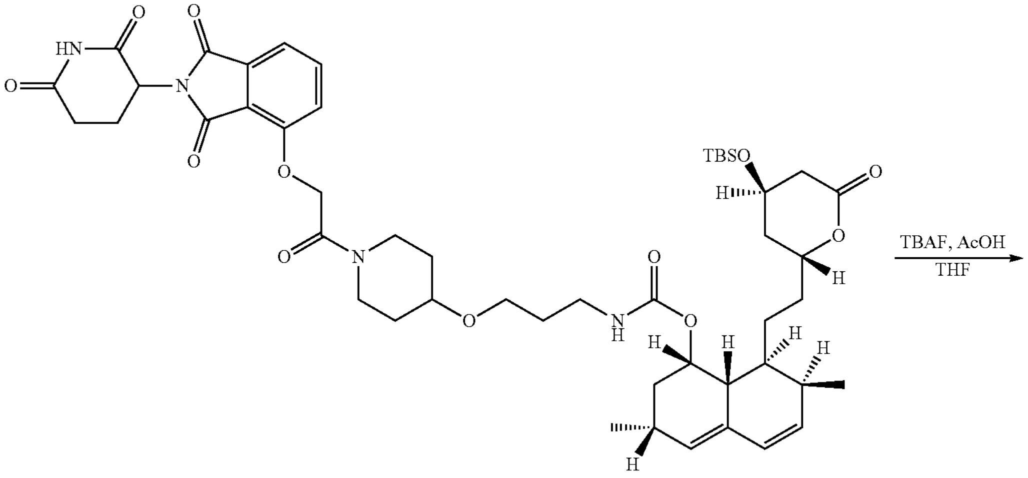
Compound 134

-continued

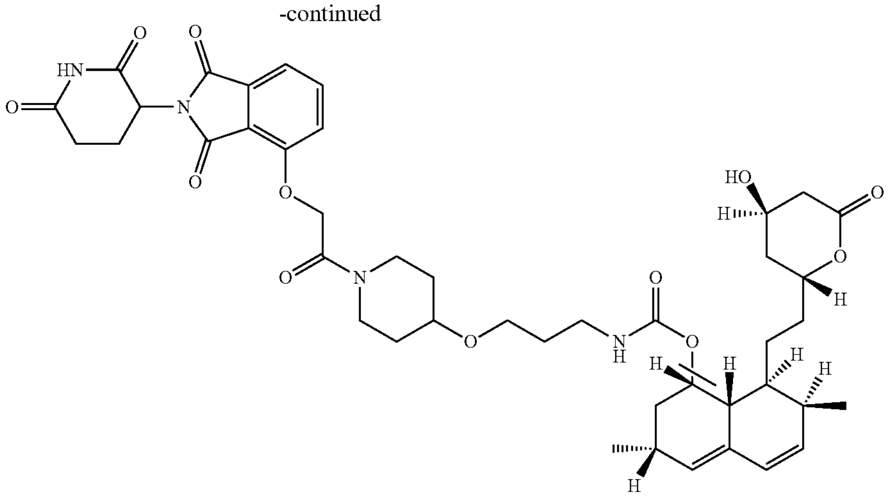

Compound 135

Step 1: Synthesis of 3-((1-benzylpiperidin-4-yl)oxy)propanenitrile (2)

To a mixture of 1-benzylpiperidin-4-ol (10 g, 52.28 mmol) and prop-2-enenitrile (13.25 g, 249.71 mmol, 16.56 mL) was added NaH (100 mg, 2.50 mmol, 60% purity) in one portion at 0° C. and the resulting mixture was stirred at 15° C. for 16 h. TLC ($SiO_2$, Ethyl acetate:Methanol=10:1) indicated 1-benzylpiperidin-4-ol was consumed completely and one new spot was detected. The reaction mixture was diluted with i-PrOH (400 mL) and filtered. The filtrate was concentrated to afford the titled compound (11.1 g, 45.43 mmol, 86.89% yield) as a yellow oil.

$^1$H NMR (400 MHz, $CDCl_3$) δ=7.33-7.23 (m, 5H), 3.70-3.60 (m, 2H), 3.52-3.47 (m, 2H), 3.45-3.35 (m, 1H), 2.80-2.66 (m, 2H), 2.61-2.51 (m, 2H), 2.24-2.08 (m, 2H), 1.92-1.82 (m, 2H), 1.70-1.52 (m, 2H)

Step 2: Synthesis of 3-((1-benzylpiperidin-4-yl)oxy) propan-1-amine (3)

To a solution of 3-((1-benzylpiperidin-4-yl)oxy)propanenitrile (11 g, 45.02 mmol) in MeOH (100 mL) was added Raney-Ni (7.71 g, 90.04 mmol) under $N_2$. The suspension was degassed under vacuum and purged with $H_2$ several times. The mixture was stirred under $H_2$ (50 psi) at 25° C. for 16 h. TLC ($SiO_2$, Ethyl acetate:Methanol=8:1) indicated starting material was consumed completely and one new spot was detected. The reaction mixture was diluted with MeOH (150 mL) and filtered. The filtrate was concentrated in vacuum to afford the titled compound (9.3 g, 37.45 mmol, 83.17% yield) as a yellow oil.

Step 3: Synthesis of tert-butyl (3-((1-benzylpiperidin-4-yl)oxy)propyl)carbamate (4)

To a solution of 3-((1-benzylpiperidin-4-yl) oxy) propan-1-amine (5 g, 20.13 mmol) in DCM (50 mL) was added TEA (6.11 g, 60.40 mmol, 8.41 mL), then a solution of $(Boc)_2O$ (4.83 g, 22.15 mmol, 5.09 mL) in DCM (50 mL) was added drop-wise at 0° C. and the resulting mixture was stirred at 15° C. for 16 h. LCMS showed starting material was consumed completely and one peak with desired mass was detected. TLC ($SiO_2$, Petroleum ether:Ethyl acetate=1:1) indicated starting material was consumed completely and two new spots were detected. The reaction mixture was concentrated in vacuum. The residue was purified by column chromatography ($SiO_2$, Petroleum ether/Ethyl acetate=5/1 to 1/1) to afford the titled compound (3.4 g, 9.76 mmol, 48.46% yield) as a yellow oil. MS $(M+H)^+$=349.4

Step 4: Synthesis of tert-butyl (3-(piperidin-4-yloxy)propyl)carbamate (5)

To a solution of tert-butyl (3-((1-benzylpiperidin-4-yl) oxy)propyl)carbamate (3.4 g, 9.76 mmol) in MeOH (34 mL) was added Pd/C (340 mg, 975.67 μmol, 10% purity) under $N_2$. The suspension was degassed under vacuum and purged with $H_2$ several times. The mixture was stirred under $H_2$ (15 psi) at 15° C. for 16 h. TLC ($SiO_2$, Petroleum ether:Ethyl acetate=1:1) indicated starting material was consumed completely and one new spot was detected. The reaction mixture was filtered. The filtrate was concentrated in vacuum to afford the titled compound (2.7 g, crude) as a yellow oil.

$^1$H NMR (400 MHz, $CDCl_3$) δ=4.96 (br s, 1H), 3.51 (t, J=6.0 Hz, 2H), 3.39-3.31 (m, 1H), 3.25-3.18 (m, 2H), 3.07 (td, J=4.6, 12.7 Hz, 2H), 2.69-2.53 (m, 2H), 1.97-1.86 (m, 2H), 1.77-1.70 (m, 2H), 1.50-1.44 (m, 2H), 1.43 (s, 9H)

Step 5: Synthesis of tert-butyl (3-((1-(2-((2-(2,6-dioxopiperidin-3-yl)-1,3-dioxoisoindolin-4-yl)oxy) acetyl)piperidin-4-yl)oxy)propyl)carbamate (7)

To a mixture of 2-[2-(2,6-dioxo-3-piperidyl)-1,3-dioxoisoindolin-4-yl]oxyacetic acid (700 mg, 2.11 mmol) and tert-butyl (3-(piperidin-4-yloxy)propyl)carbamate (598.72 mg, 2.32 mmol) in DMF (7 mL) were added HATU (881.16 mg, 2.32 mmol) and DIPEA (816.85 mg, 6.32 mmol, 1.10 mL) in one portion at 15° C. and the resulting mixture was stirred at 15° C. for 2 h. LCMS showed all starting material was consumed completely and one peak with desired mass was detected. TLC ($SiO_2$, Petroleum ether:Ethyl acetate=0:1) indicated all starting material was consumed completely and three new spots were detected. The reaction mixture was diluted with $H_2O$ (30 mL) and extracted with EtOAc (30 mL×3). The organic layer was washed with brine (30 mL×3), dried over $Na_2SO_4$, filtered and concentrated. The residue was purified by column chromatography ($SiO_2$, Petroleum ether/Ethyl acetate=3/1 to 0/1) to afford the titled compound (860 mg, 1.35 mmol, 64.16% yield, 90% purity) as a off-white solid. MS $(M-100+H)^+$=473.3

Step 6: Synthesis of 4-(2-(4-(3-aminopropoxy)piperidin-1-yl)-2-oxoethoxy)-2-(2,6-dioxopiperidin-3-yl)isoindoline-1,3-dione (8)

To a mixture of tert-butyl (3-((1-(2-((2-(2,6-dioxopiperidin-3-yl)-1,3-dioxoisoindolin-4-yl)oxy) acetyl)piperidin-4-yl)oxy)propyl)carbamate (860 mg, 1.50 mmol) in dioxane (8 mL) was added HCl/dioxane (4 M, 16 mL) in one portion at 15° C. and the resulting mixture was stirred at 15° C. for 2 h. LCMS showed starting material was consumed completely and one peak with desired mass was detected. The reaction mixture was concentrated in vacuum to afford the titled compound (770 mg, crude, HCl) as an off-white solid. MS $(M+H)^+$=473.3

Step 7: Synthesis of (1S,3R,7S,8S,8aR)-8-(2-((2R,4R)-4-((tert-butyldimethylsilyl)oxy)-6-oxotetrahydro-2H-pyran-2-yl)ethyl)-3,7-dimethyl-1,2,3,7,8,8a-hexahydronaphthalen-1-yl (3-((1-(2-((2-(2,6-dioxopiperidin-3-yl)-1,3-dioxoisoindolin-4-yl)oxy)acetyl)piperidin-4-yl)oxy)propyl)carbamate (Compound 134)

To a mixture of 4-(2-(4-(3-aminopropoxy)piperidin-1-yl)-2-oxoethoxy)-2-(2,6-dioxopiperidin-3-yl)isoindoline-1,3-dione (770 mg, 1.51 mmol, HCl) in DMAc (10 mL) were added TEA (459.28 mg, 4.54 mmol) and (1S,3R,7S,8S,8aR)-8-(2-((2R,4R)-4-((tert-butyldimethylsilyl)oxy)-6-oxotetrahydro-2H-pyran-2-yl)ethyl)-3,7-dimethyl-1,2,3,7,8,8a-hexahydronaphthalen-1-yl (4-nitrophenyl) carbonate (907.42 mg, 1.51 mmol) in one portion at 15° C. and the resulting mixture was stirred at 15° C. for 32 h. LCMS showed a little of 4-(2-(4-(3-aminopropoxy)piperidin-1-yl)-2-oxoethoxy)-2-(2,6-dioxopiperidin-3-yl)isoindoline-1,3-dione remained and one peak with desired mass was detected. The reaction mixture was diluted with $H_2O$ (30 mL) and extracted with EtOAc (30 mL×3). The organic layer was washed with brine (30 mL×3), dried over $Na_2SO_4$, filtered and concentrated. The residue was purified by prep-HPLC (column: Phenomenex luna C18 150*40 mm*15 μm; mobile phase: [water (0.225% FA)-ACN]; B %: 67%-97%, 11 min) and then lyophilized to afford the titled compound (623 mg, 640.91 μmol, 42.36% yield, 96% purity) as a white solid. MS $(M+H)^+$=933.6

$^1H$ NMR (400 MHz, $CDCl_3$) δ=8.35-7.99 (m, 1H), 7.72-7.65 (m, 1H), 7.52 (d, J=7.4 Hz, 1H), 7.41-7.29 (m, 1H), 5.98 (d, J=9.8 Hz, 1H), 5.81-5.74 (m, 1H), 5.51 (s, 1H), 5.18-5.12 (m, 1H), 4.99-4.93 (m, 2H), 4.75-4.59 (m, 1H), 4.35-4.25 (m, 1H), 3.79-3.70 (m, 1H), 3.53-3.28 (m, 5H), 3.23-3.16 (m, 1H), 2.93-2.70 (m, 3H), 2.63-2.50 (m, 2H), 2.46-2.31 (m, 2H), 2.25 (d, J=10.4 Hz, 1H), 2.19-2.06 (m, 2H), 1.93-1.51 (m, 16H), 1.49-1.40 (m, 1H), 1.36-1.26 (m, 1H), 1.07 (d, J=7.4 Hz, 3H), 0.88 (m, 12H), 0.07 (s, 6H)

Step 8: Synthesis of (1S,3R,7S,8S,8aR)-8-(2-((2R,4R)-4-hydroxy-6-oxotetrahydro-2H-pyran-2-yl)ethyl)-3,7-dimethyl-1,2,3,7,8,8a-hexahydronaphthalen-1-yl (3-((1-(2-((2-(2,6-dioxopiperidin-3-yl)-1,3-dioxoisoindolin-4-yl)oxy)acetyl)piperidin-4-yl)oxy)propyl)carbamate (Compound 135)

To a mixture of (1S,3R,7S,8S,8aR)-8-(2-((2R,4R)-4-((tert-butyldimethylsilyl)oxy)-6-oxotetrahydro-2H-pyran-2-yl)ethyl)-3,7-dimethyl-1,2,3,7,8,8a-hexahydronaphthalen-1-yl (3-((1-(2-((2-(2,6-dioxopiperidin-3-yl)-1,3-dioxoisoindolin-4-yl)oxy)acetyl)piperidin-4-yl)oxy)propyl) carbamate (589 mg, 631.18 μmol) in THF (8 mL) were added AcOH (189.52 mg, 3.16 mmol, 180.49 μL) and TBAF (1 M, 2.52 mL) in one portion at 15° C. and the resulting mixture was stirred at 15° C. for 32 h. LCMS showed starting material was consumed completely and one peak with desired mass was detected. The reaction mixture was quenched with saturated $NH_4Cl$ (30 mL) and extracted with EtOAc (30 mL×3). The organic layer was dried over $Na_2SO_4$, filtered and concentrated. The residue was purified by prep-HPLC (column: Phenomenex Luna C18 150*25 mm*10 μm; mobile phase: [water (0.225% F A)-ACN]; B %: 38%-68%, 11 min) and re-purified by prep-TLC ($SiO_2$, Ethyl acetate:Methanol=10:1) to afford the titled compound (95.2 mg, 109.28 μmol, 17.31% yield, 94% purity) as a white solid. MS $(M+H)^+$=819.5

$^1H$ NMR (400 MHz, $CD_3OD$) δ=7.75 (dd, J=7.5, 8.4 Hz, 1H), 7.49 (d, J=7.2 Hz, 1H), 7.35 (d, J=8.6 Hz, 1H), 5.93 (d, J=9.9 Hz, 1H), 5.82-5.68 (m, 1H), 5.48 (br s, 1H), 5.20-5.07 (m, 4H), 4.73-4.62 (m, 1H), 4.30-4.19 (m, 1H), 3.88-3.66 (m, 2H), 3.66-3.49 (m, 3H), 3.49-3.38 (m, 2H), 3.27-3.10 (m, 2H), 2.94-2.81 (m, 1H), 2.79-2.65 (m, 3H), 2.57-2.48 (m, 1H), 2.46-2.35 (m, 2H), 2.34-2.26 (m, 1H), 2.18-2.09 (m, 1H), 2.02-1.86 (m, 4H), 1.85-1.69 (m, 6H), 1.68-1.53 (m, 3H), 1.51-1.36 (m, 2H), 1.10 (d, J=7.5 Hz, 3H), 0.91 (d, J=7.0 Hz, 3H)

Examples 136 to 137. In a Manner Similar to the Other Examples, Compounds 136 to 137 were Obtained

Examples 138 & 139. Synthesis of (1S,3R,7S,8S,8aR)-8-(2-((2R,4R)-4-((tert-butyldimethylsilyl)oxy)-6-oxotetrahydro-2H-pyran-2-yl)ethyl)-3,7-dimethyl-1,2,3,7,8,8a-hexahydronaphthalen-1-yl (2-(2-(2-(2-((2-(2,6-dioxopiperidin-3-yl)-1,3-dioxoisoindolin-4-yl)oxy)acetamido)ethoxy)ethoxy)ethyl)carbamate (Compound 138) and (1S,3R,7S,8S,8aR)-8-(2-((2R,4R)-4-hydroxy-6-oxotetrahydro-2H-pyran-2-yl)ethyl)-3,7-dimethyl-1,2,3,7,8,8a-hexahydronaphthalen-1-yl (2-(2-(2-(2-((2-(2,6-dioxopiperidin-3-yl)-1,3-dioxoisoindolin-4-yl)oxy)acetamido)ethoxy)ethoxy)ethyl)carbamate (Compound 139)

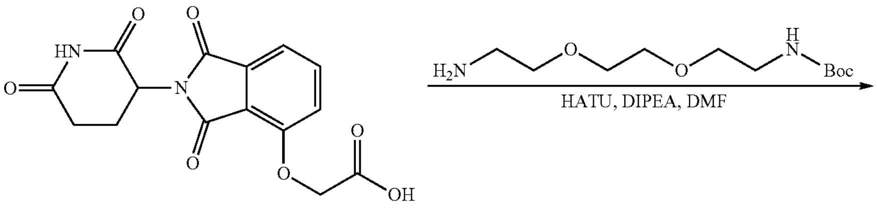

1

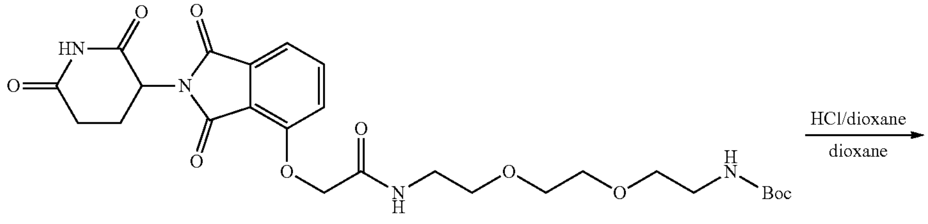

2

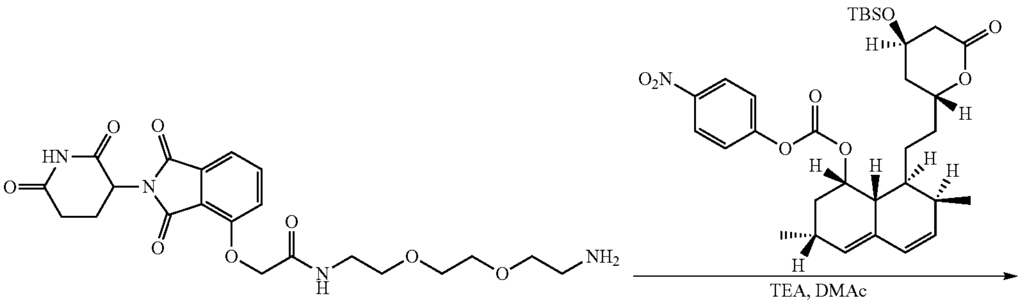

3

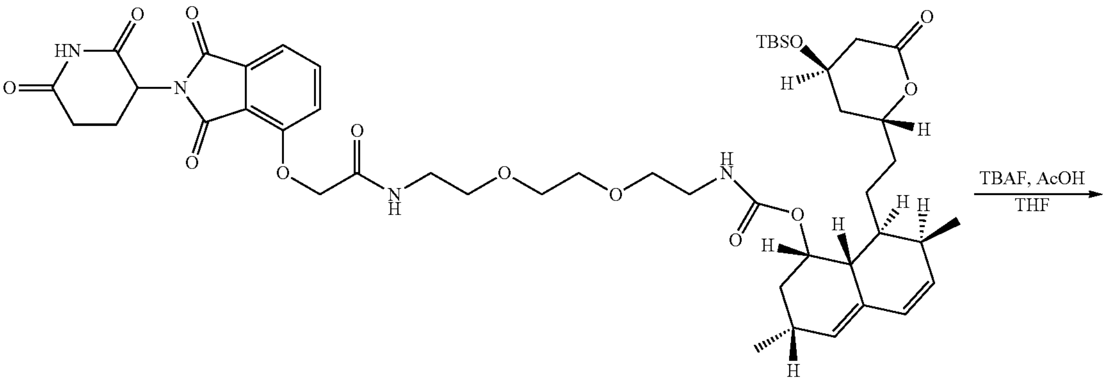

Compound 138

-continued

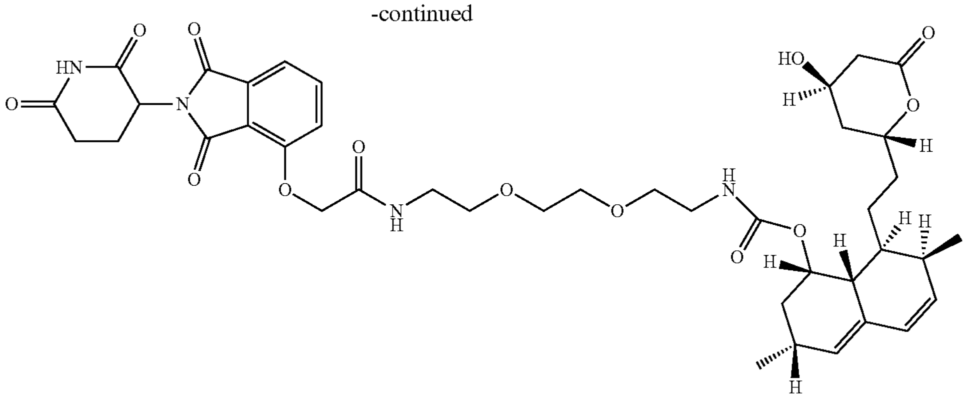

Compound 139

Step 1-2 are Described in the Above Reaction Scheme

Step 3: Synthesis of (1S,3R,7S,8S,8aR)-8-(2-((2R,4R)-4-((tert-butyldimethylsilyl)oxy)-6-oxotetrahydro-2H-pyran-2-yl)ethyl)-3,7-dimethyl-1,2,3,7,8,8a-hexahydronaphthalen-1-yl (2-(2-(2-(2-((2-(2,6-dioxopiperidin-3-yl)-1,3-dioxoisoindolin-4-yl)oxy)acetamido)ethoxy)ethoxy)ethyl)carbamate (Compound 138)

According to the above reaction scheme, in a manner similar to the other examples, obtained the titled compound (838.2 mg, 898.92 μmol, 53.39% yield, 99% purity) as a yellow solid. MS $(M+H)^+$=923.6

$^1$H NMR (400 MHz, $CDCl_3$) δ=8.75-8.54 (m, 1H), 7.78-7.71 (m, 1H), 7.64-7.52 (m, 2H), 7.20 (d, J=8.4 Hz, 1H), 5.97 (d, J=9.8 Hz, 1H), 5.84-5.75 (m, 1H), 5.51 (s, 1H), 5.47-5.32 (m, 1H), 5.20 (br s, 1H), 5.01-4.93 (m, 1H), 4.65 (s, 3H), 4.29 (br s, 1H), 3.64-3.49 (m, 10H), 3.45-3.23 (m, 2H), 2.92-2.70 (m, 3H), 2.66-2.51 (m, 2H), 2.47-2.32 (m, 2H), 2.26-2.18 (m, 1H), 2.19-2.04 (m, 2H), 1.90-1.61 (m, 6H), 1.50-1.38 (m, 1H), 1.36-1.22 (m, 1H), 1.10-1.03 (m, 3H), 0.88 (m, 12H), 0.07 (s, 6H)

Step 4: Synthesis of (1S,3R,7S,8S,8aR)-8-(2-((2R,4R)-4-hydroxy-6-oxotetrahydro-2H-pyran-2-yl)ethyl)-3,7-dimethyl-1,2,3,7,8,8a-hexahydronaphthalen-1-yl (2-(2-(2-(2-((2-(2,6-dioxopiperidin-3-yl)-1,3-dioxoisoindolin-4-yl)oxy)acetamido)ethoxy)ethoxy)ethyl)carbamate (Compound 139)

According to the above reaction scheme, in a manner similar to the other examples, obtained the titled compound (167.7 mg, 0.201 mmol, 25.43% yield, 97% purity) as a white solid. MS $(M+H)^+$=809.5

$^1$H NMR (400 MHz, $CDCl_3$) δ=9.92-8.85 (m, 1H), 7.78-7.73 (m, 1H), 7.65 (s, 1H), 7.56 (dd, J=1.8, 7.3 Hz, 1H), 7.21 (br d, J=8.4 Hz, 1H), 5.98 (dd, J=3.2, 9.8 Hz, 1H), 5.82-5.74 (m, 1H), 5.52 (s, 1H), 5.41-5.10 (m, 2H), 5.05-4.96 (m, 1H), 4.72-4.56 (m, 3H), 4.34-4.24 (m, 1H), 3.65-3.48 (m, 10H), 3.44-3.25 (m, 2H), 2.92-2.84 (m, 1H), 2.82-2.74 (m, 2H), 2.71-2.62 (m, 1H), 2.60-2.49 (m, 1H), 2.45-2.33 (m, 2H), 2.24 (d, J=12.4 Hz, 1H), 2.19-2.11 (m, 1H), 2.08-1.95 (m, 2H), 1.90-1.82 (m, 2H), 1.76-1.58 (m, 4H), 1.42-1.31 (m, 2H), 1.01-1.01 (m, 3H), 0.93-0.85 (m, 3H)

Examples 140 to 141. In a Manner Similar to the Other Examples, Compounds 140 to 141 were Obtained Examples 142 & 143. Synthesis of (1S,3R,7S,8S,8aR)-8-(2-((2R,4R)-4-((tert-butyldimethylsilyl)oxy)-6-oxotetrahydro-2H-pyran-2-yl)ethyl)-3,7-dimethyl-1,2,3,7,8,8a-hexahydronaphthalen-1-yl (2-(2-(2-((2-(2,6-dioxopiperidin-3-yl)-1,3-dioxoisoindolin-4-yl)amino)-2-oxoethoxy)ethoxy)ethyl)carbamate (Compound 142) and (1S,3R,7S,8S,8aR)-8-(2-((2R,4R)-4-hydroxy-6-oxotetrahydro-2H-pyran-2-yl)ethyl)-3,7-dimethyl-1,2,3,7,8,8a-hexahydronaphthalen-1-yl (2-(2-(2-((2-(2,6-dioxopiperidin-3-yl)-1,3-dioxoisoindolin-4-yl)amino)-2-oxoethoxy)ethoxy)ethyl)carbamate (Compound 143)

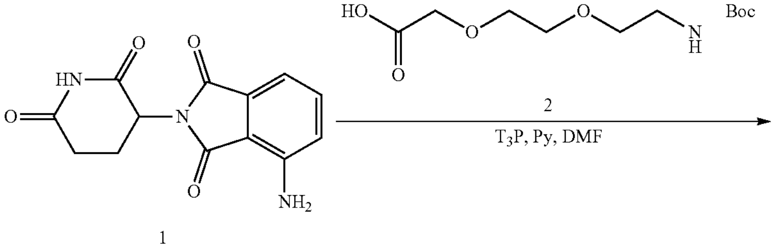

1

-continued
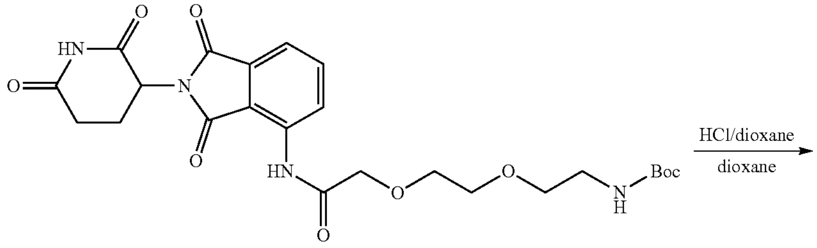
3
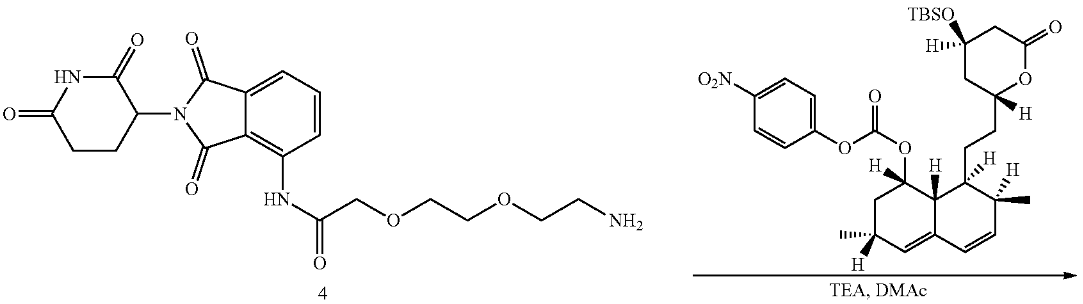
4
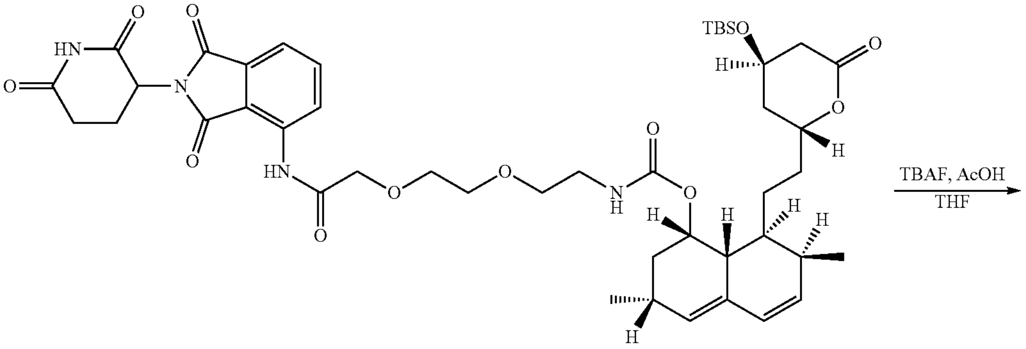
Compound 142
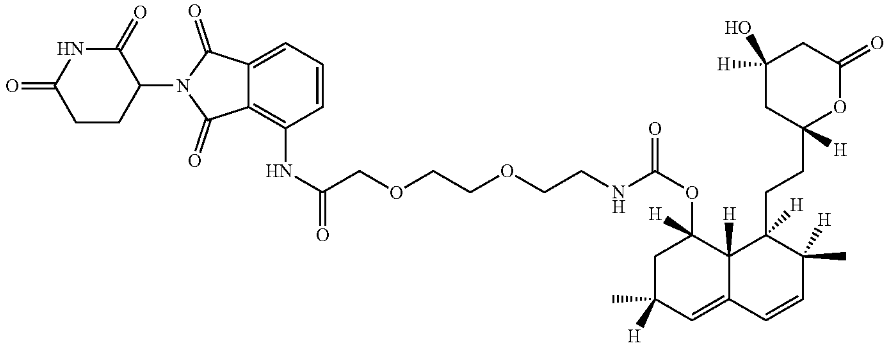
Compound 143

Step 1-2 are Described in the Above Reaction Scheme

Step 3: Synthesis of (1S,3R,7S,8S,8aR)-8-(2-((2R, 4R)-4-((tert-butyldimethylsilyl)oxy)-6-oxotetrahydro-2H-pyran-2-yl)ethyl)-3,7-dimethyl-1,2,3,7,8, 8a-hexahydronaphthalen-1-yl (2-(2-(2-((2-(2,6-dioxopiperidin-3-yl)-1,3-dioxoisoindolin-4-yl) amino)-2-oxoethoxy)ethoxy)ethyl)carbamate (Compound 142)

According to the above reaction scheme, in a manner similar to the other examples, obtained the titled compound (722 mg, 804.89 μmol, 41.60% yield, 98% purity) as a white solid. MS $(M+H)^+$=879.6

$^1$H NMR (400 MHz, Chloroform-d) δ 10.46 (s, 1H), 8.92-8.82 (m, 1H), 8.79-8.50 (m, 1H), 7.73 (t, J=7.9 Hz, 1H), 7.58 (d, J=7.3 Hz, 1H), 5.94 (d, J=9.7 Hz, 1H), 5.76 (dd, J=9.6, 6.1 Hz, 1H), 5.49 (s, 1H), 5.19 (s, 2H), 5.08-4.94 (m, 1H), 4.70-4.59 (m, 1H), 4.31-4.23 (m, 1H), 4.16 (d, J=3.9 Hz, 2H), 3.82-3.69 (m, 4H), 3.67-3.38 (m, 2H), 3.38-3.22 (m, 1H), 3.00-2.71 (m, 3H), 2.67-2.47 (m, 2H), 2.47-2.28 (m, 2H), 2.28-2.03 (m, 3H), 1.89-1.64 (m, 5H), 1.64-1.59 (m, 3H), 1.54-1.38 (m, 1H), 1.37-1.22 (m, 1H), 1.05 (d, J=7.5 Hz, 3H), 0.93-0.80 (m, 12H), 0.06 (d, J=2.2 Hz, 6H).

Step 4: Synthesis of (1S,3R,7S,8S,8aR)-8-(2-((2R, 4R)-4-hydroxy-6-oxotetrahydro-2H-pyran-2-yl) ethyl)-3,7-dimethyl-1,2,3,7,8,8a-hexahydronaphthalen-1-yl (2-(2-(2-((2-(2,6-dioxopiperidin-3-yl)-1,3-dioxoisoindolin-4-yl)amino)-2-oxoethoxy)ethoxy) ethyl)carbamate (Compound 143)

According to the above reaction scheme, in a manner similar to the other examples, obtained the titled compound (301 mg, 0.378 mmol, 54.45% yield, 96% purity) as a white solid. MS $(M+H)^+$=765.5

$^1$H NMR (400 MHz, $CDCl_3$) δ=10.45 (d, J=15.8 Hz, 1H), 9.51-9.05 (m, 1H), 8.92-8.81 (m, 1H), 7.77-7.71 (m, 1H), 7.62-7.56 (m, 1H), 5.96 (d, J=9.6 Hz, 1H), 5.80-5.74 (m, 1H), 5.50 (s, 1H), 5.29-5.20 (m, 1H), 5.19-4.92 (m, 2H), 4.72-4.52 (m, 1H), 4.35-4.25 (m, 1H), 4.23-4.11 (m, 2H), 3.79-3.70 (m, 4H), 3.69-3.53 (m, 2H), 3.50-3.29 (m, 2H), 2.95-2.80 (m, 2H), 2.80-2.74 (m, 1H), 2.72-2.52 (m, 2H), 2.49-2.38 (m, 1H), 2.36-2.32 (m, 1H), 2.25 (d, J=12.0 Hz, 1H), 2.20-2.13 (m, 1H), 2.10-1.82 (m, 4H), 1.75-1.61 (m, 4H), 1.44-1.31 (m, 2H), 1.07 (d, J=7.4 Hz, 3H), 0.93-0.85 (m, 3H)

Examples 144 & 145. Synthesis of (1S,3R,7S,8S, 8aR)-8-(2-((2R,4R)-4-((tert-butyldimethylsilyl)oxy)-6-oxotetrahydro-2H-pyran-2-yl)ethyl)-3,7-dimethyl-1,2,3,7,8,8a-hexahydronaphthalen-1-yl (2-(2-((2-((2-(2,6-dioxopiperidin-3-yl)-1,3-dioxoisoindolin-4-yl) amino)-2-oxoethyl)amino)-2-oxoethoxy)ethyl) carbamate (Compound 144) and of (1S,3R,7S,8S, 8aR)-8-(2-((2R,4R)-4-hydroxy-6-oxotetrahydro-2H-pyran-2-yl)ethyl)-3,7-dimethyl-1,2,3,7,8,8a-hexahydronaphthalen-1-yl (2-(2-((2-((2-(2,6-dioxopiperidin-3-yl)-1,3-dioxoisoindolin-4-yl) amino)-2-oxoethyl)amino)-2-oxoethoxy)ethyl) carbamate (Compound 145)

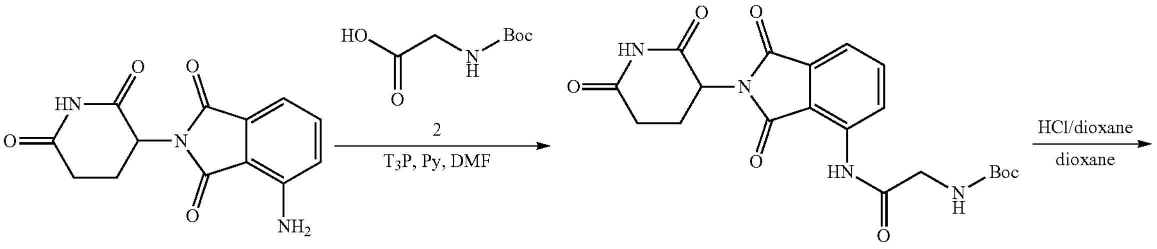

1

3

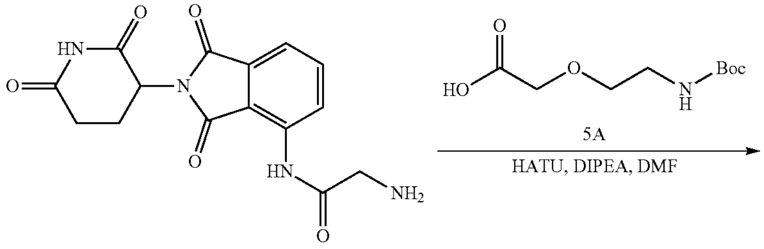

4

-continued

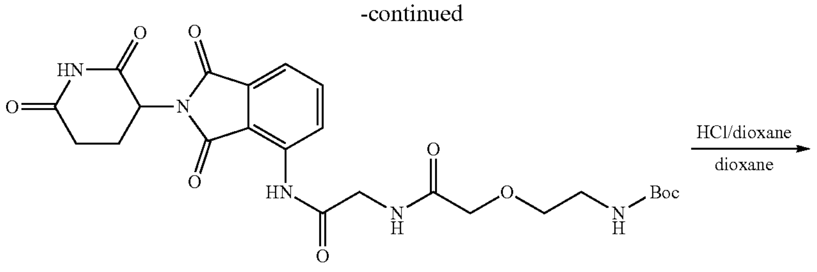

5

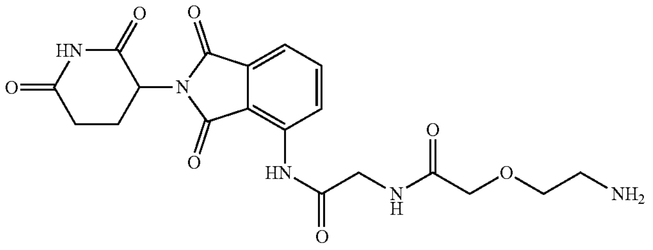

6

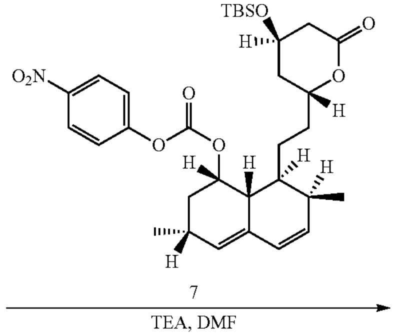

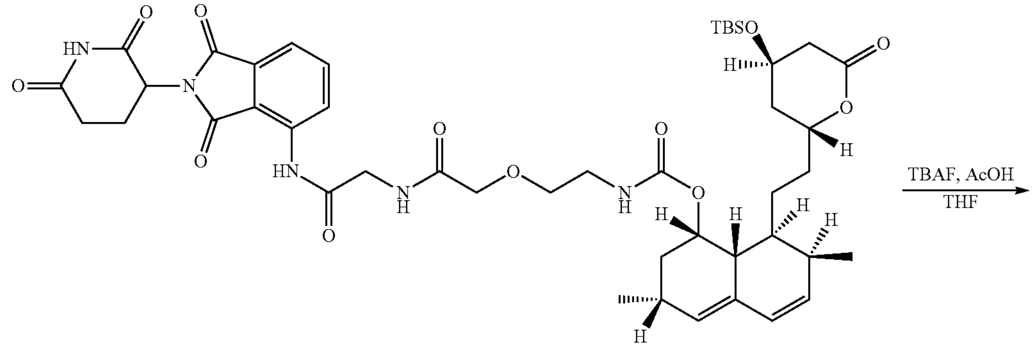

Compound 144

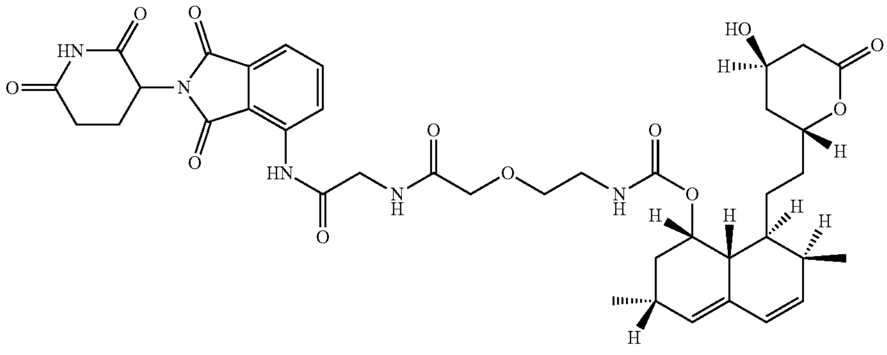

Compound 145

Step 1: Synthesis of tert-butyl (2-((2-(2,6-dioxopiperidin-3-yl)-1,3-dioxoisoindolin-4-yl)amino)-2-oxoethyl)carbamate (3)

To a mixture of 4-amino-2-(2,6-dioxopiperidin-3-yl) isoindoline-1,3-dione (2 g, 7.32 mmol) and 2-(tert-butoxycarbonylamino) acetic acid (2.56 g, 14.64 mmol) in DMF (20 mL) were added $T_3P$ (25 g, 39.29 mmol, 23.36 mL, 50% purity) and Py (5.79 g, 73.19 mmol, 5.91 mL) at 25° C. and the resulting mixture was stirred at 80° C. for 16 h. LCMS showed that the reaction was completed. The reaction mixture was quenched by addition of $H_2O$ (60 mL) and extracted with EtOAc (60 mL×3). The combined organic layers were washed with brine (50 mL×3), dried over $Na_2SO_4$, filtered and concentrated under reduced pressure. The crude product was purified by reversed-phase HPLC (method:FA condition, MeCN/water) to afford the titled compound (1.28 g, 2.97 mmol, 40.63% yield) as yellow solid. MS $(M-Boc+H)^+=331.1$ Step 2: Synthesis of 2-amino-N-(2-(2,6-dioxopiperidin-3-yl)-1,3-dioxoisoindolin-4-yl)acetamide (4)

To a solution of tert-butyl (2-((2-(2,6-dioxopiperidin-3-yl)-1,3-dioxoisoindolin-4-yl)amino)-2-oxoethyl)carbamate (1.4 g, 3.25 mmol) in dioxane (20 mL) was added HCl/dioxane (4 M, 20 mL) and the resulting mixture was stirred at 20° C. for 2 h. LCMS showed that the reaction was completed. The reaction mixture was concentrated in vacuum to afford the titled compound (1.4 g, crude, HCl) as yellow solid which was used for next step directly. MS (M+H)+=331.1

Step 3: Synthesis of tert-butyl (2-(2-((2-((2-(2,6-dioxopiperidin-3-yl)-1,3-dioxoisoindolin-4-yl)amino)-2-oxoethyl)amino)-2-oxoethoxy)ethyl)carbamate (5)

To a solution of 2-(2-((tert-butoxycarbonyl)amino)ethoxy)acetic acid (573.86 mg, 2.62 mmol) and HATU (1.66 g, 4.36 mmol) in DMF (20 mL) was added DIPEA (845.75 mg, 6.54 mmol, 1.14 mL) and the resulting mixture was stirred at 20° C. for 10 min, 2-amino-N-(2-(2,6-dioxopiperidin-3-yl)-1,3-dioxoisoindolin-4-yl)acetamide (800 mg, 2.18 mmol, HCl salt) was added and the resulting mixture was stirred at 20° C. for 1 h. LCMS showed that reaction was completed. The mixture was poured into $H_2O$ (60 mL) and extracted with EtOAc (50 mL×3), the combined organic layer was washed with brine (150 mL), dried over $Na_2SO_4$, filtered and concentrated. The residue was purified by column chromatography ($SiO_2$, Petroleum ether/Ethyl acetate=1/1 to 0/1) to afford the titled compound (1.15 g, 2.12 mmol, 97.21% yield) as yellow solid. MS (M−Boc+H)$^+$=432.1

Step 4: Synthesis of 2-(2-aminoethoxy)-N-(2-((2-(2,6-dioxopiperidin-3-yl)-1,3-dioxoisoindolin-4-yl)amino)-2-oxoethyl)acetamide (6)

To a solution of tert-butyl (2-(2-((2-((2-(2,6-dioxopiperidin-3-yl)-1,3-dioxoisoindolin-4-yl)amino)-2-oxoethyl)amino)-2-oxoethoxy)ethyl)carbamate (1.15 g, 2.12 mmol) in dioxane (15 mL) was added HCl/dioxane (4 M, 15 mL) and the resulting mixture was stirred at 20° C. for 2 h. LCMS showed that the reaction was completed. The reaction mixture was concentrated in vacuum to afford the titled compound (1 g, crude, HCl) as yellow solid which was used for next step directly. MS (M+H)$^+$=432.2

Step 5: Synthesis of (1S,3R,7S,8S,8aR)-8-(2-((2R,4R)-4-((tert-butyldimethylsilyl)oxy)-6-oxotetrahydro-2H-pyran-2-yl)ethyl)-3,7-dimethyl-1,2,3,7,8,8a-hexahydronaphthalen-1-yl (2-(2-((2-((2-(2,6-dioxopiperidin-3-yl)-1,3-dioxoisoindolin-4-yl)amino)-2-oxoethyl)amino)-2-oxoethoxy)ethyl)carbamate (Compound 144)

To the solution of 2-(2-aminoethoxy)-N-(2-((2-(2,6-dioxopiperidin-3-yl)-1,3-dioxoisoindolin-4-yl)amino)-2-oxoethyl)acetamide (1 g, 2.14 mmol, HCl) and (1S,3R,7S,8S,8aR)-8-(2-((2R,4R)-4-((tert-butyldimethylsilyl)oxy)-6-oxotetrahydro-2H-pyran-2-yl)ethyl)-3,7-dimethyl-1,2,3,7,8,8a-hexahydronaphthalen-1-yl (4-nitrophenyl) carbonate (1.03 g, 1.71 mmol) in DMF (20 mL) was added TEA (648.84 mg, 6.41 mmol, 892.49 μL) and the resulting mixture was stirred at 20° C. for 12 h. LCMS showed that the reaction was completed. The mixture was poured into water (50 mL) and extracted with EtOAc (50 mL×3), the combined organic layer was washed with brine (100 mL), dried over $Na_2SO_4$, filtered and concentrated. The residue was purified by prep-HPLC (column: Phenomenex luna $C_{18}$ 150*40 mm*15 μm; mobile phase: [water (0.225% FA)-ACN]; B %: 65%-95%, 11 min) to afford the product (800 mg, 834.01 μmol, 39.02% yield) as white solid. 500 mg of the desired product was used for next step directly, another 300 mg of the desired product was re-purified by prep-HPLC (column: Shim-pack $C_{18}$ 150*25*10 μm; mobile phase: [water (0.225% FA)-ACN]; B %: 77%-87%, 10 min) and lyophilized to afford the titled compound (66 mg, 69.55 μmol, 3.25% yield) as white solid. MS (M+H)$^+$=892.6.

$^1$H NMR (400 MHz, $CDCl_3$) δ=9.91 (brs, 1H), 8.76 (d, J=8.6 Hz, 1H), 7.69-7.65 (m, 1H), 7.51 (d, J=7.2 Hz, 1H), 5.90 (d, J=8.8 Hz, 1H), 5.73-5.66 (m, 1H), 5.52-5.33 (m, 2H), 5.16-4.83 (m, 2H), 4.74-4.59 (m, 1H), 4.27-3.99 (m, 5H), 3.68-5.37 (m, 2H), 3.48-3.27 (m, 2H), 2.89-2.66 (m, 3H), 2.58-2.32 (m, 3H), 2.26-2.08 (m, 4H), 1.88-1.56 (m, 9H), 1.22-1.15 (m, 1H), 1.02 (d, J=7.4 Hz, 3H), 0.85-0.80 (m, 12H), 0.00 (s, 6H).

Step 6: Synthesis of (1S,3R,7S,8S,8aR)-8-(2-((2R,4R)-4-hydroxy-6-oxotetrahydro-2H-pyran-2-yl)ethyl)-3,7-dimethyl-1,2,3,7,8,8a-hexahydronaphthalen-1-yl (2-(2-((2-((2-(2,6-dioxopiperidin-3-yl)-1,3-dioxoisoindolin-4-yl)amino)-2-oxoethyl)amino)-2-oxoethoxy)ethyl)carbamate (Compound 145)

To a solution of (1S,3R,7S,8S,8aR)-8-(2-((2R,4R)-4-((tert-butyldimethylsilyl)oxy)-6-oxotetrahydro-2H-pyran-2-yl)ethyl)-3,7-dimethyl-1,2,3,7,8,8a-hexahydronaphthalen-1-yl (2-(2-((2-((2-(2,6-dioxopiperidin-3-yl)-1,3-dioxoisoindolin-4-yl)amino)-2-oxoethyl)amino)-2-oxoethoxy)ethyl)carbamate (500 mg, 560.49 μmol) in THF (10 mL) were added AcOH (168.29 mg, 2.80 mmol, 160.28 μL) and TBAF (1 M, 2.24 mL) and the resulting mixture was stirred at 25° C. for 12 h. LCMS showed that the reaction was completed. The mixture was poured into water (50 mL) and extracted with EtOAc (50 mL×3), the combined organic layer was washed with brine (100 mL), dried over $Na_2SO_4$, filtered and concentrated. The residue was purified by prep-HPLC (column: Phenomenex Luna $C_{18}$ 150*25 mm*10 μm; mobile phase: [water (0.225% FA)-ACN]; B %: 35%-65%, 11 min) followed by prep-HPLC (column: Phenomenex Luna $C_{18}$ 150*25 mm*10 μm; mobile phase: [water (0.225% FA)-ACN]; B %: 35%-65%, 11 min) and the eluant was lyophilized to afford the titled compound (124.6 mg, 155.39 μmol, 27.72% yield) as white solid. MS (M+H)$^+$=778.5.

$^1$H NMR (400 MHz, $CDCl_3$) δ=9.99 (brs, 1H), 8.78 (d, J=8.4 Hz, 1H), 7.87-7.67 (m, 2H), 7.57 (d, J=7.4 Hz, 1H), 5.97 (d, J=9.8 Hz, 1H), 5.84-5.71 (m, 1H), 5.56-5.47 (m, 1H), 5.39-5.15 (m, 2H), 5.09-4.87 (brs, 1H), 4.74-4.54 (m, 1H), 4.36-4.22 (m, 2H), 4.20-4.04 (m, 3H), 3.74-3.60 (m, 2H), 3.43 (s, 2H), 2.93-2.52 (m, 5H), 2.49-2.07 (m, 5H), 1.96-1.64 (m, 6H), 1.50-1.29 (m, 2H), 1.07 (d, J=7.6 Hz, 3H), 0.95-0.85 (m, 3H).

Example 146 & 147. Synthesis of (1S,3R,7S,8S,8aR)-8-(2-((2R,4R)-4-((tert-butyldimethylsilyl)oxy)-6-oxotetrahydro-2H-pyran-2-yl)ethyl)-3,7-dimethyl-1,2,3,7,8,8a-hexahydronaphthalen-1-yl (4-(2-((2-(2,6-dioxopiperidin-3-yl)-1,3-dioxoisoindolin-4-yl)amino)-2-oxoethyl)phenethyl)carbamate (Compound 146) and Synthesis of (1S,3R,7S,8S,8aR)-8-(2-((2R,4R)-4-hydroxy-6-oxotetrahydro-2H-pyran-2-yl)ethyl)-3,7-dimethyl-1,2,3,7,8,8a-hexahydronaphthalen-1-yl (4-(2-((2-(2,6-dioxopiperidin-3-yl)-1,3-dioxoisoindolin-4-yl)amino)-2-oxoethyl)phenethyl)carbamate (Compound 147)

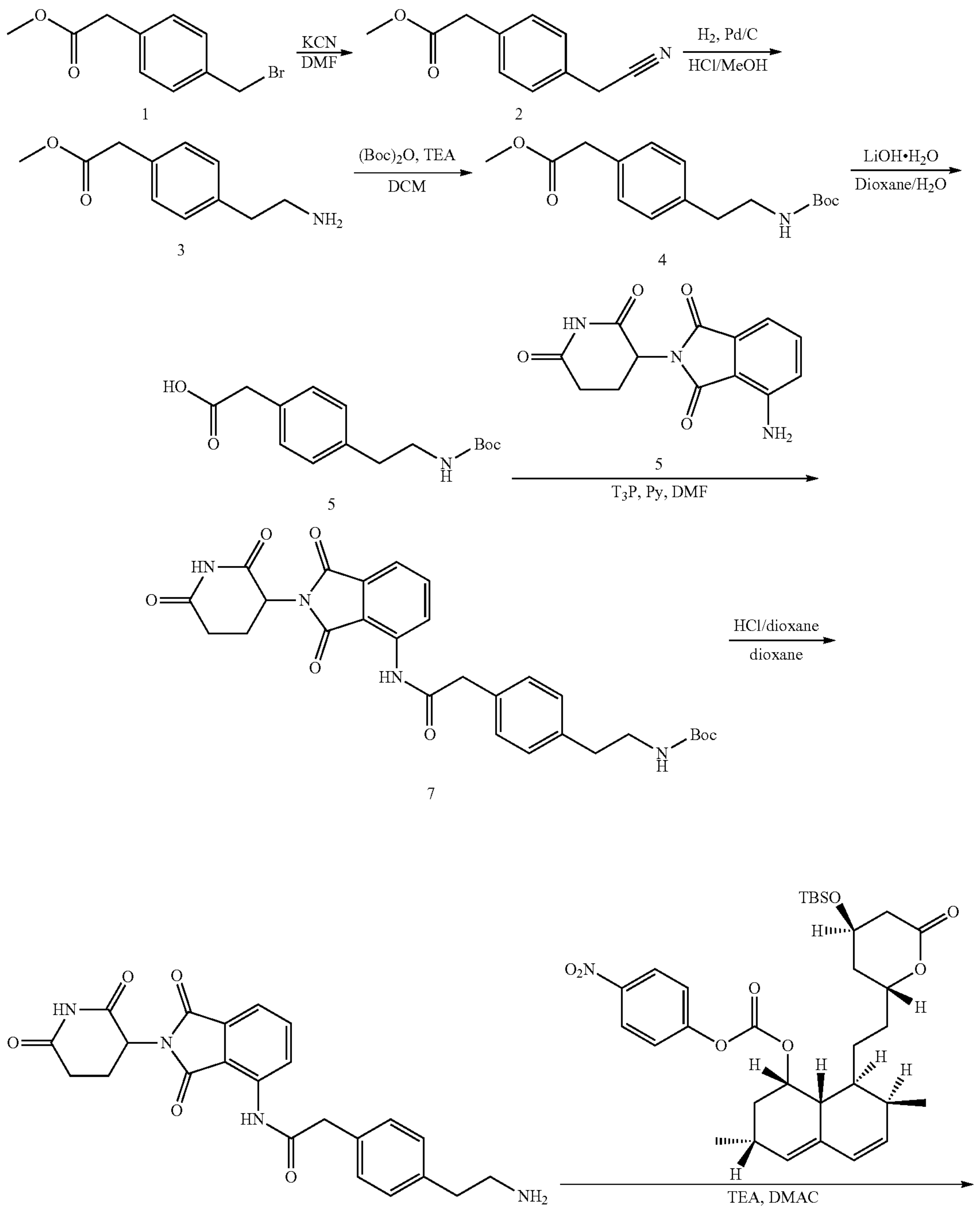

8

-continued

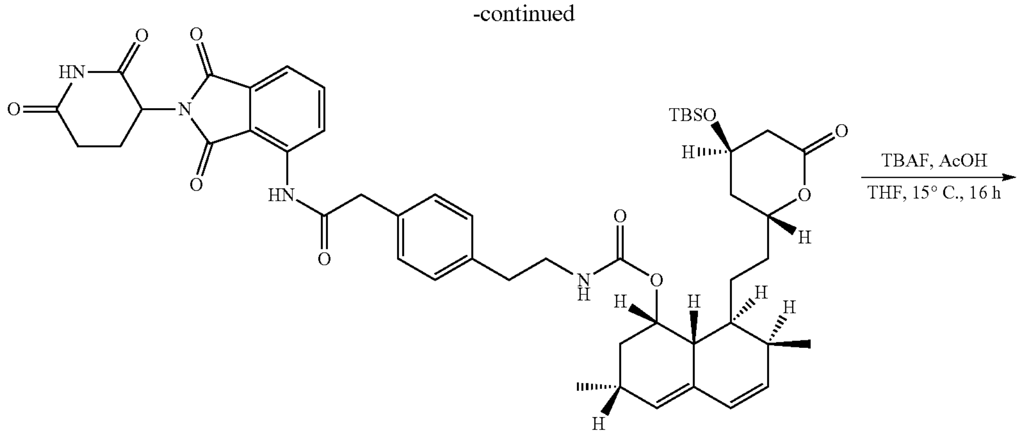

Compound 146

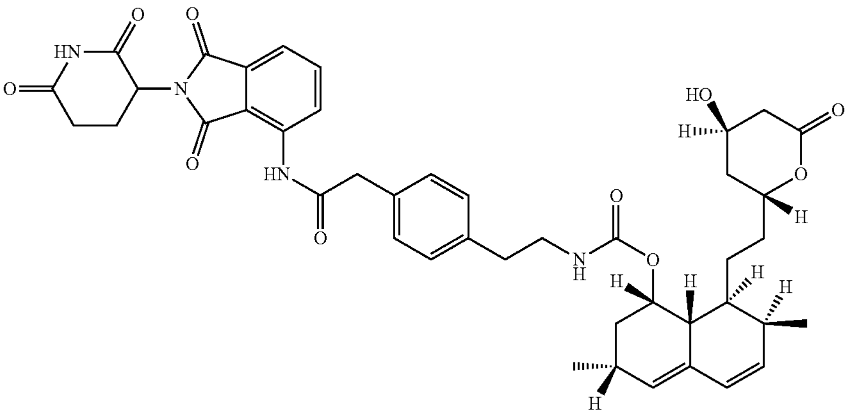

Compound 147

Step 1: Synthesis of methyl 2-(4-(cyanomethyl)phenyl)acetate (2)

To a mixture of methyl 2-[4-(bromomethyl)phenyl]acetate (3 g, 12.34 mmol) in DMF (30 mL) was added KCN (964.29 mg, 14.81 mmol) in one portion at 15° C. and the resulting mixture was stirred at 15° C. for 16 h. LCMS showed all starting material was consumed completely and no peak with desired mass was detected. TLC ($SiO_2$, Petroleum ether:Ethyl acetate=2:1) indicated starting material was consumed completely and one major new spot was detected. The reaction mixture was diluted with $H_2O$ (90 mL) and extracted with EtOAc (90 mL×3). The organic layer was washed with saturated $Na_2CO_3$ (90 mL×3) and brine (90 mL×3). The organic layer was dried over $Na_2SO_4$, filtered and concentrated to afford the titled compound (1.9 g, 10.04 mmol, 81.37% yield) as a yellow oil.

Step 2: Synthesis of methyl 2-(4-(2-aminoethyl)phenyl)acetate (3)

To a solution of methyl 2-(4-(cyanomethyl) phenyl) acetate (1.7 g, 8.98 mmol) in MeOH (17 mL) and HCl (12 M, 1.7 mL) was added Pd/C (20 mg, 10% purity) under $N_2$. The suspension was degassed under vacuum and purged with $H_2$ several times. The mixture was stirred under $H_2$ (15 psi) at 15° C. for 16 h. TLC ($SiO_2$, Petroleum ether:Ethyl acetate=10:1) indicated starting material was consumed completely and two new spots were detected. The reaction mixture was combined with other batches (0.2 g scale) for work-up. The reaction mixture was diluted with MeOH (80 mL) and filtered. The filtrate was concentrated in vacuum to afford the titled compound (2.1 g, crude, HCl) as a yellow solid.

Step 3: Synthesis of methyl 2-(4-(2-((tert-butoxycarbonyl)amino)ethyl)phenyl)acetate To a mixture of methyl 2-(4-(2-aminoethyl)phenyl)acetate (2.1 g, 10.87 mmol) in DCM (21 mL) were added TEA (3.30 g, 32.60 mmol, 4.54 mL) and $(Boc)_2O$ (2.61 g, 11.95 mmol, 2.75 mL) drop-wise at 15° C. and the resulting mixture was stirred at 15° C. for 16 h. TLC ($SiO_2$, Petroleum ether:Ethyl acetate=2:1) indicated starting material was consumed completely and three new spots were detected. The reaction mixture was concentrated in vacuum. The residue was purified by column chromatography ($SiO_2$, Petroleum ether/Ethyl acetate=10/1 to 2/1) to afford the titled compound (718 mg, 2.45 mmol, 22.52% yield) as a yellow oil. $^1H$ NMR (400 MHz, $CDCl_3$) δ=7.24-7.21 (m, 2H), 7.17-7.14 (m, 2H), 4.58 (br s, 1H), 3.70 (s, 3H), 3.61 (s, 2H), 3.37 (d, J=6.2 Hz, 2H), 2.78 (t, J=7.0 Hz, 2H), 1.44 (s, 9H)

Step 4: Synthesis of 2-(4-(2-((tert-butoxycarbonyl)amino)ethyl)phenyl)acetic acid (5)

To a mixture of methyl 2-(4-(2-((tert-butoxycarbonyl)amino)ethyl)phenyl)acetate (718 mg, 2.45 mmol) in dioxane (10 mL) and $H_2O$ (3 mL) was added LiOH $H_2O$ (205.41 mg, 4.90 mmol) in one portion at 15° C. and the resulting mixture was stirred at 15° C. for 16 h. TLC ($SiO_2$, Petroleum ether:Ethyl acetate=1:1) indicated starting material was consumed completely and one new spot was detected. The reaction mixture was concentrated in vacuum. The residue was diluted with $H_2O$ (10 mL) and the resulting solution was acidified with HCl (1 N) to adjust the PH=5-6. The reaction mixture was extracted with EtOAc (10 mL×3). The organic layer was dried over $Na_2SO_4$, filtered and concentrated to afford the titled compound (710 mg, crude) as a yellow oil. 1H NMR (400 MHz, DMSO-$d_6$) δ=12.55-11.94 (m, 1H), 7.18-7.10 (m, 4H), 3.57 (s, 1H), 3.51 (s, 2H), 3.16-3.06 (m, 2H), 2.66 (t, J=7.4 Hz, 2H), 1.37 (s, 9H)

Step 5: Synthesis of tert-butyl 4-(2-((2-(2,6-dioxopiperidin-3-yl)-1,3-dioxoisoindolin-4-yl)amino)-2-oxoethyl)phenethylcarbamate (7)

To a mixture of 4-amino-2-(2,6-dioxo-3-piperidyl)isoindoline-1,3-dione (500 mg, 1.83 mmol) and 2-(4-(2-((tert-butoxycarbonyl) amino) ethyl) phenyl) acetic acid (562.25 mg, 2.01 mmol) in DMF (5 mL) were added $T_3P$ (6.99 g, 10.98 mmol, 6.53 mL, 50% purity), Py (1.45 g, 18.30 mmol, 1.48 mL) in one portion at 15° C. and the resulting mixture was stirred at 80° C. for 16 h. LCMS showed all starting material was consumed completely and desired mass was detected. TLC ($SiO_2$, Petroleum ether:Ethyl acetate=1:1) indicated starting material was consumed completely and one major new spot was detected. The reaction mixture was diluted with $H_2O$ (20 mL) and extracted with EtOAc (20 mL×3). The organic layer was washed with brine (20 mL×3), dried over $Na_2SO_4$, filtered and concentrated. The residue was purified by column chromatography ($SiO_2$, Petroleum ether/Ethyl acetate=5/1 to 1/1) to afford the titled compound (562 mg, 1.05 mmol, 57.45% yield) as a yellow solid. MS $(M-100+H)^+$=435.3

Step 6: Synthesis of 2-(4-(2-aminoethyl)phenyl)-N-(2-(2,6-dioxopiperidin-3-yl)-1,3-dioxoisoindolin-4-yl)acetamide (8)

To a mixture of tert-butyl 4-(2-((2-(2,6-dioxopiperidin-3-yl)-1,3-dioxoisoindolin-4-yl)amino)-2-oxoethyl)phenethylcarbamate (560 mg, 1.05 mmol) in dioxane (5 mL) was added HCl/dioxane (4 M, 10 mL) in one portion at 15° C. and the resulting mixture was stirred at 15° C. for 2 h. TLC ($SiO_2$, Petroleum ether:Ethyl acetate=1:1) indicated starting material was consumed completely and one new spot were detected. The reaction mixture was concentrated in vacuum to afford the titled compound (495 mg, 0.946 mmol, 90.31% yield, 90% purity, HCl) as a yellow solid. MS $(M+H)^+$=435.1

Step 7: Synthesis of (1S,3R,7S,8S,8aR)-8-(2-((2R,4R)-4-((tert-butyldimethylsilyl)oxy)-6-oxotetrahydro-2H-pyran-2-yl)ethyl)-3,7-dimethyl-1,2,3,7,8,8a-hexahydronaphthalen-1-yl 4-(2-((2-(2,6-dioxopiperidin-3-yl)-1,3-dioxoisoindolin-4-yl)amino)-2-oxoethyl)phenethylcarbamate (Compound 146)

To a mixture of 2-(4-(2-aminoethyl) phenyl)-N-(2-(2,6-dioxopiperidin-3-yl)-1,3-dioxoisoindolin-4-yl)acetamide (495 mg, 1.05 mmol, HCl) in DMAC (8 mL) were added TEA (319.10 mg, 3.15 mmol) and (1S,3R,7S,8S,8aR)-8-(2-((2R,4R)-4-((tert-butyldimethylsilyl)oxy)-6-oxotetrahydro-2H-pyran-2-yl)ethyl)-3,7-dimethyl-1,2,3,7,8,8a-hexahydronaphthalen-1-yl (4-nitrophenyl) carbonate (693.52 mg, 1.16 mmol) in one portion at 15° C. and the resulting mixture was stirred at 15° C. for 16 h. LCMS showed all starting material was consumed completely and one peak with desired mass was detected. The reaction mixture was diluted with $H_2O$ (20 mL) and extracted with EtOAC (20 mL×3). The organic layer was washed with brine (20 mL×3), dried over $Na_2SO_4$, filtered and concentrated. The residue was purified by prep-HPLC (column: Phenomenex luna C18 150*40 mm*15 μm; mobile phase: [water (0.225% FA)-ACN]; B %: 70%-100%, 11 min) and then lyophilized to afford the titled compound (709 mg, 0.776 mmol, 73.84% yield, 98% purity) as a white solid. MS $(M+H)^+$=895.6

$^1$H NMR (400 MHz, $CDCl_3$) δ=9.30-9.18 (m, 1H), 8.88-8.81 (m, 1H), 8.57-8.41 (m, 1H), 7.69 (t, J=8.0 Hz, 1H), 7.53-7.47 (m, 1H), 7.27-7.18 (m, 4H), 6.07-5.93 (m, 1H), 5.83-5.75 (m, 1H), 5.60-5.49 (m, 1H), 5.42-5.16 (m, 2H), 5.00-4.87 (m, 1H), 4.73-4.65 (m, 1H), 4.31-4.26 (m, 1H), 3.84-3.76 (m, 2H), 3.57-3.43 (m, 1H), 3.36-3.24 (m, 1H), 2.85-2.68 (m, 5H), 2.61-2.54 (m, 2H), 2.47-2.39 (m, 1H), 2.37-2.32 (m, 1H), 2.29-2.22 (m, 1H), 2.16-2.07 (m, 2H), 1.87-1.72 (m, 5H), 1.53-1.44 (m, 1H), 1.37-1.20 (m, 2H), 1.13-1.01 (m, 3H), 0.90 (s, 12H), 0.07 (s, 6H)

Step 8: Synthesis of (1S,3R,7S,8S,8aR)-8-(2-((2R,4R)-4-hydroxy-6-oxotetrahydro-2H-pyran-2-yl)ethyl)-3,7-dimethyl-1,2,3,7,8,8a-hexahydronaphthalen-1-yl 4-(2-((2-(2,6-dioxopiperidin-3-yl)-1,3-dioxoisoindolin-4-yl)amino)-2-oxoethyl)phenethylcarbamate (Compound 147)

To a mixture of (1S,3R,7S,8S,8aR)-8-(2-((2R,4R)-4-((tert-butyldimethylsilyl)oxy)-6-oxotetrahydro-2H-pyran-2-yl)ethyl)-3,7-dimethyl-1,2,3,7,8,8a-hexahydronaphthalen-1-yl 4-(2-((2-(2,6-dioxopiperidin-3-yl)-1,3-dioxoisoindolin-4-yl)amino)-2-oxoethyl)phenethylcarbamate (607 mg, 678.12 μmol) in THF (8 mL) were added AcOH (203.61 mg, 3.39 mmol) and TBAF (1 M, 2.71 mL) in one portion at 15° C. and the resulting mixture was stirred at 15° C. for 16 h.

LCMS showed starting material was consumed completely and one peak with desired mass was detected. The reaction mixture was quenched with saturated $NH_4Cl$ (20 mL) and extracted with EtOAc (20 mL×3). The organic layer was washed with saturated $NH_4Cl$ (20 mL×3), dried over $Na_2SO_4$, filtered and concentrated. The residue was purified by prep-HPLC (column: Phenomenex luna C18 150*40 mm*15 μm; mobile phase: [water (0.225% FA)-ACN]; B %: 52%-82%, 11 min) and then lyophilized to afford 476 mg product with 86% by HPLC and LCMS. The product was re-purified by column chromatography ($SiO_2$, Ethyl acetate:Methanol=10:1) to afford the titled compound (327.1 mg, 0.402 mmol, 59.30% yield, 96% purity) as a white solid. MS $(M+H)^+$=781.4

$^1$H NMR (400 MHz, $CDCl_3$) δ=9.19 (d, J=18.6 Hz, 1H), 8.90-8.79 (m, 1H), 7.71-7.65 (m, 1H), 7.51 (d, J=7.2 Hz, 1H), 7.35-7.29 (m, 1H), 7.27-7.24 (m, 4H), 6.07-5.91 (m, 1H), 5.86-5.74 (m, 1H), 5.59-5.49 (m, 1H), 5.30-5.19 (m, 1H), 4.98-4.86 (m, 1H), 4.71-4.48 (m, 1H), 4.37-4.22 (m, 1H), 3.86-3.76 (m, 2H), 3.64-3.21 (m, 2H), 2.86-2.55 (m, 7H), 2.48-2.22 (m, 3H), 2.12-2.00 (m, 2H), 1.98-1.80 (m, 3H), 1.74-1.60 (m, 5H), 1.51-1.35 (m, 2H), 1.23-1.04 (m, 3H), 0.95-0.86 (br s, 3H) Examples 148 to 151. In a manner similar to the other examples, Compounds 148 to 151 were obtained.

Example 152. Synthesis of (1S,3R,7S,8S,8aR)-8-(2-((2R,4R)-4-hydroxy-6-oxotetrahydro-2H-pyran-2-yl)ethyl)-3,7-dimethyl-1,2,3,7,8,8a-hexahydronaphthalen-1-yl 5-((2-(2-(2-((3-(2,6-dioxopiperidin-3-yl)-4-oxo-3,4-dihydrobenzo[d][1,2,3]triazin-5-yl)amino)ethoxy)ethoxy)ethyl)amino)-2,2-dimethyl-5-oxopentanoate (Compound 152)
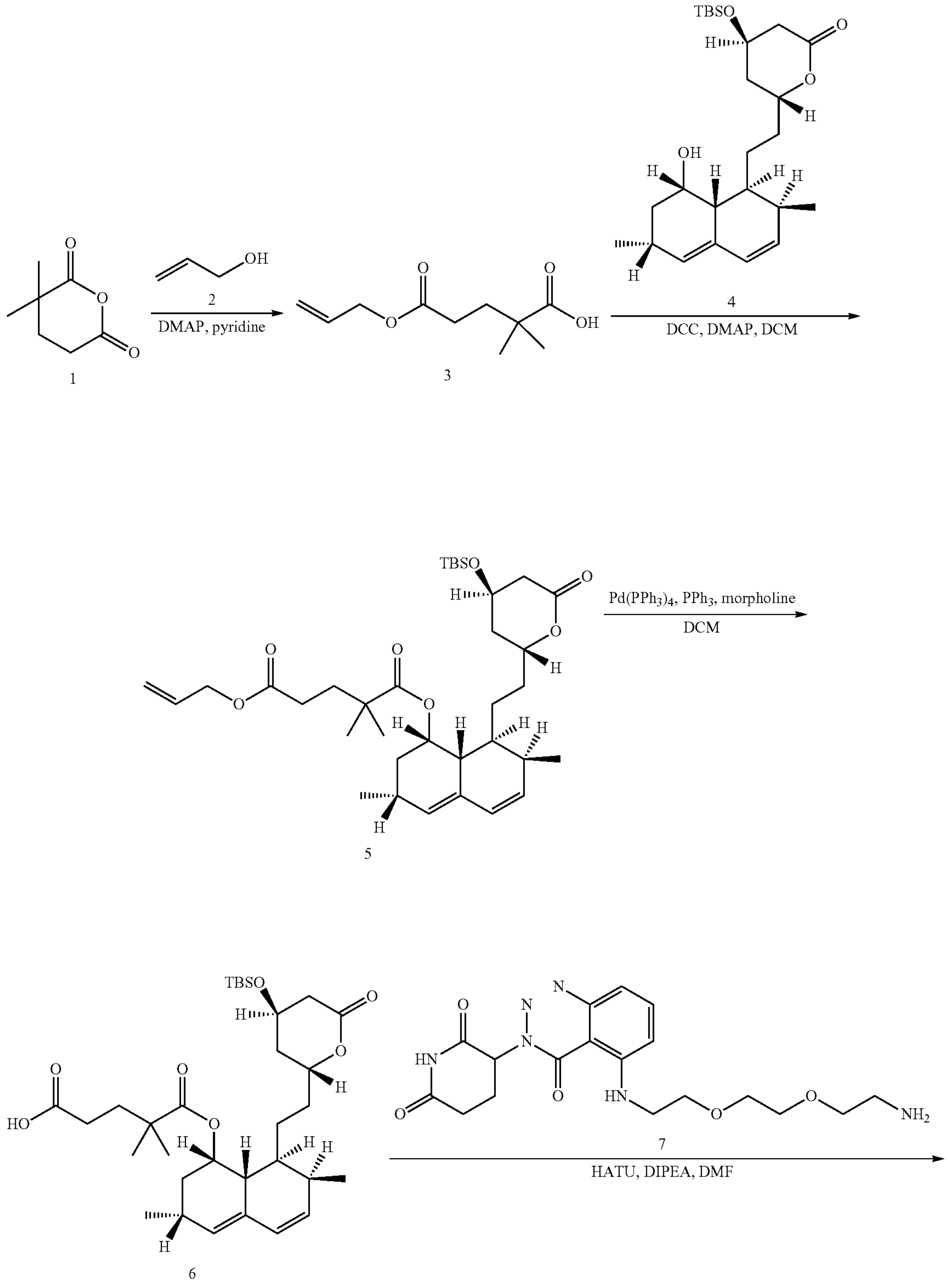

-continued

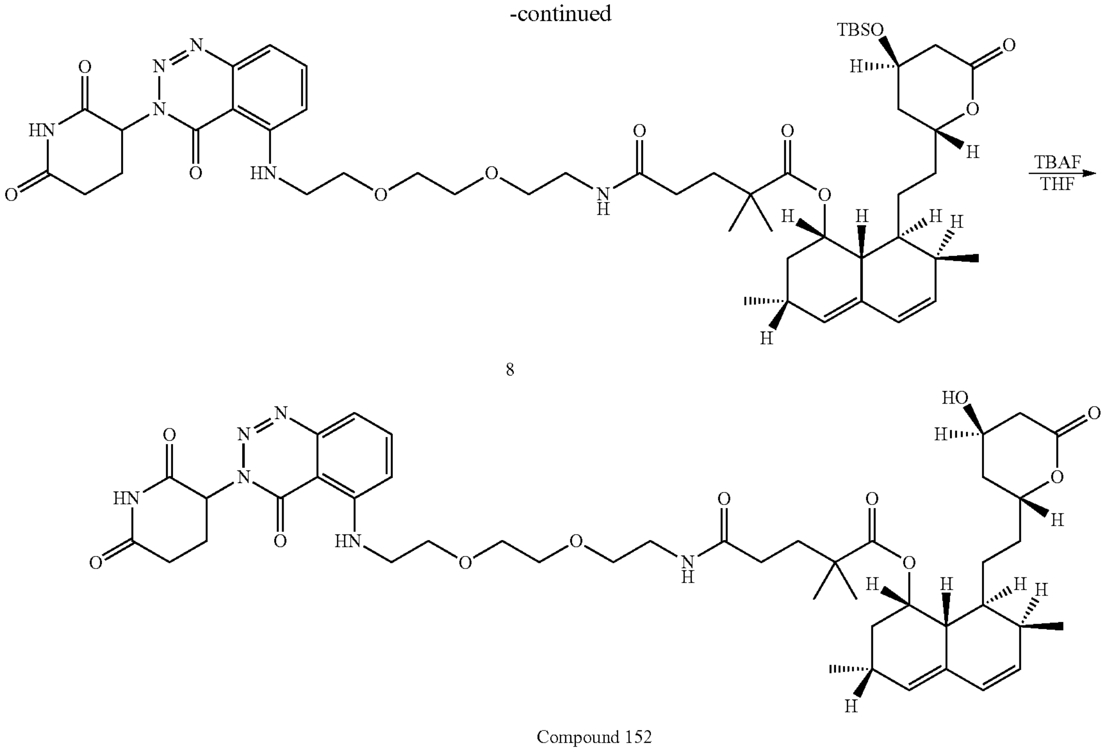

8

Compound 152

Step 1-3 are Described in the Above Reaction Scheme

Step 4: Synthesis of (1S,3R,7S,8S,8aR)-8-(2-((2R,4R)-4-((tert-butyldimethylsilyl)oxy)-6-oxotetrahydro-2H-pyran-2-yl)ethyl)-3,7-dimethyl-1,2,3,7,8,8a-hexahydronaphthalen-1-yl 5-((2-(2-(2-((3-(2,6-dioxopiperidin-3-yl)-4-oxo-3,4-dihydrobenzo[d][1,2,3]triazin-5-yl)amino)ethoxy)ethoxy)ethyl)amino)-2,2-dimethyl-5-oxopentanoate (8)

To a solution of 5-(((1S,3R,7S,8S,8aR)-8-(2-((2R,4R)-4-((tert-butyldimethylsilyl)oxy)-6-oxotetrahydro-2H-pyran-2-yl)ethyl)-3,7-dimethyl-1,2,3,7,8,8a-hexahydronaphthalen-1-yl)oxy)-4,4-dimethyl-5-oxopentanoic acid (150 mg, 260.04 μmol) in DMF (3 mL) was added HATU (150.00 mg, 394.50 μmol) and DIPEA (111.30 mg, 861.17 μmol, 150.00 μL) and the mixture was stirred at 25° C. for 15 min. Then a solution of 3-(5-((2-(2-(2-aminoethoxy)ethoxy)ethyl)amino)-4-oxobenzo[d][1,2,3]triazin-3(4H)-yl)piperidine-2,6-dione (138.00 mg, 313.01 μmol, HCl) and DIPEA (55.65 mg, 430.58 μmol, 75.00 μL) in DMF (0.4 mL) was added and the mixture was stirred at 25° C. for 1 h. LCMS showed the desired mass was detected. The mixture was diluted with $H_2O$ (10 mL) and extracted with EtOAc (10 mL×3). The combined organic layer was washed with brine (10 mL×2), dried over $Na_2SO_4$ and filtered. The filtrate was concentrated under reduced pressure. The residue was purified by flash silica gel chromatography (5 g SepaFlash® Silica Flash Column, Eluent of 20~70% Ethyl acetate/Petroleum ether gradient @ 50 mL/min) to afford the titled compound (130 mg, 128.21 mol, 49.31% yield, 95% purity) as yellow oil. MS $(M+H)^+$=963.9

Step 5: Synthesis of (1S,3R,7S,8S,8aR)-8-(2-((2R,4R)-4-hydroxy-6-oxotetrahydro-2H-pyran-2-yl)ethyl)-3,7-dimethyl-1,2,3,7,8,8a-hexahydronaphthalen-1-yl 5-((2-(2-(2-((3-(2,6-dioxopiperidin-3-yl)-4-oxo-3,4-dihydrobenzo[d][1,2,3]triazin-5-yl)amino)ethoxy)ethoxy)ethyl)amino)-2,2-dimethyl-5-oxopentanoate (Compound 152)

To a solution of (1S,3R,7S,8S,8aR)-8-(2-((2R,4R)-4-((tert-butyldimethylsilyl)oxy)-6-oxotetrahydro-2H-pyran-2-yl)ethyl)-3,7-dimethyl-1,2,3,7,8,8a-hexahydronaphthalen-1-yl 5-((2-(2-(2-((3-(2,6-dioxopiperidin-3-yl)-4-oxo-3,4-dihydrobenzo[d][1,2,3]triazin-5-yl)amino)ethoxy)ethoxy)ethyl)amino)-2,2-dimethyl-5-oxopentanoate (190 mg, 197.25 μmol) in THF (4 mL) was added TBAF (4 M, 190.00 μL) at 0° C. The mixture was stirred at 25° C. for 2 h. LCMS showed the desired mass was detected. The mixture was diluted with $H_2O$ (10 mL) at 0° C. and extracted with EtOAc (10 mL×3). The combined organic layer was washed with brine (10 mL×2), dried over $Na_2SO_4$ and filtered. The filtrate was concentrated under reduced pressure. The residue was purified by prep-TLC (Ethyl acetate:Methanol=10:1) to afford the titled compound (53.2 mg, 58.28 μmol, 29.54% yield, 93% purity) as yellow solid. MS $(M+H)^+$=849.5

$^1H$ NMR (400 MHz, $CDCl_3$) δ=9.05 (br s, 1H), 8.37 (br s, 1H), 7.70 (t, J=8.1 Hz, 1H), 7.30 (d, J=7.2 Hz, 1H), 6.81 (d, J=8.6 Hz, 1H), 6.42-6.36 (m, 1H), 5.98 (d, J=9.8 Hz, 1H), 5.81-5.75 (m, 1H), 5.70-5.63 (m, 1H), 5.53 (br s, 1H), 5.32 (br s, 1H), 4.62 (br s, 1H), 4.28 (br s, 1H), 4.15-4.04 (m, 1H), 3.77 (t, J=5.1 Hz, 2H), 3.71-3.64 (m, 4H), 3.62-3.57 (m, 2H), 3.45-3.39 (m, 4H), 2.97-2.84 (m, 3H), 2.75-2.60 (m, 2H), 2.47-2.31 (m, 3H), 2.29-2.17 (m, 3H), 2.07-2.01 (m, 1H), 2.00-1.83 (m, 3H), 1.82-1.67 (m, 4H), 1.52-1.44 (m, 1H), 1.42-1.34 (m, 2H), 1.14 (d, J=12.1 Hz, 6H), 1.07-1.02 (m, 3H), 0.91-0.86 (m, 3H).

Example 153. Synthesis of (1S,3R,7S,8S,8aR)-3,7-dimethyl-8-(2-((R)-6-oxo-3,6-dihydro-2H-pyran-2-yl)ethyl)-1,2,3,7,8,8a-hexahydronaphthalen-1-yl (2-(2-(2-((2-(2,6-dioxopiperidin-3-yl)-1,3-dioxoisoindolin-4-yl)amino)ethoxy)ethoxy)ethyl)carbamate (Compound 153)

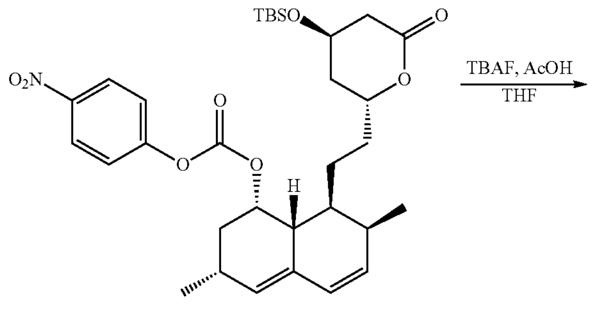

1

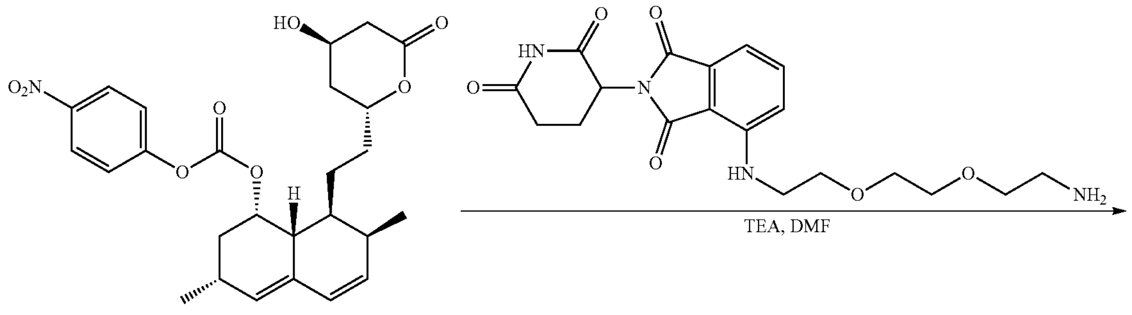

2

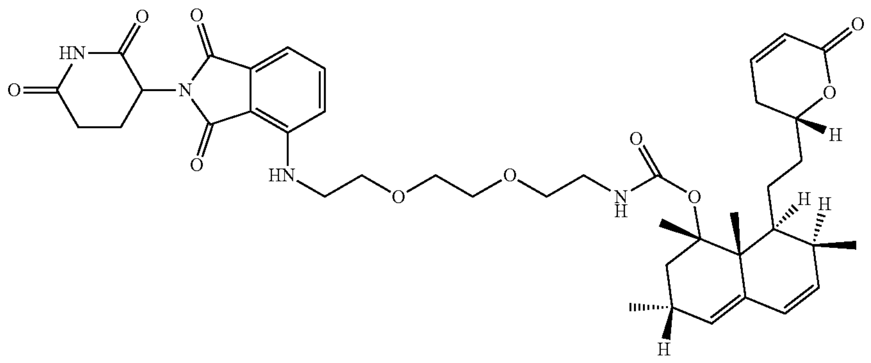

Compound 153

Step 1: Synthesis of (1S,3R,7S,8S,8aR)-8-(2-((2R,4R)-4-hydroxy-6-oxotetrahydro-2H-pyran-2-yl)ethyl)-3,7-dimethyl-1,2,3,7,8,8a-hexahydronaphthalen-1-yl (4-nitrophenyl) carbonate (2)

To the solution of (1S,3R,7S,8S,8aR)-8-(2-((2R,4R)-4-((tert-butyldimethylsilyl)oxy)-6-oxotetrahydro-2H-pyran-2-yl)ethyl)-3,7-dimethyl-1,2,3,7,8,8a-hexahydronaphthalen-1-yl (4-nitrophenyl) carbonate (4 g, 6.67 mmol) in THF (40 mL) was added TBAF (1 M, 26.68 mL, in THF) and AcOH (2.00 g, 33.35 mmol, 1.91 mL) and the resulting mixture was stirred at 25° C. for 4 h. TLC (Petroleum ether/Ethyl acetate=0/1) showed that the reaction was completed. The mixture was poured into water (200 mL) and extracted with EtOAc (100 mL×3), the combined organic layer was washed with brine (200 mL), dried over $Na_2SO_4$, filtered and concentrated. The residue was purified by silica gel column (Petroleum ether:Ethyl acetate=1:1-0:1) to afford the titled compound as white solid. MS $(M+H)^+$=486.2

Step 2: Synthesis of (1S,3R,7S,8S,8aR)-3,7-dimethyl-8-(2-((R)-6-oxo-3,6-dihydro-2H-pyran-2-yl)ethyl)-1,2,3,7,8,8a-hexahydronaphthalen-1-yl (2-(2-(2-((2-(2,6-dioxopiperidin-3-yl)-1,3-dioxoisoindolin-4-yl)amino)ethoxy)ethoxy)ethyl)carbamate (Compound 153)

To the solution of (1S,3R,7S,8S,8aR)-8-(2-((2R,4R)-4-hydroxy-6-oxotetrahydro-2H-pyran-2-yl)ethyl)-3,7-dimethyl-1,2,3,7,8,8a-hexahydronaphthalen-1-yl (4-nitrophenyl) carbonate (500 mg, 1.03 mmol) and 4-((2-(2-(2-aminoethoxy)ethoxy)ethyl)amino)-2-(2,6-dioxopiperidin-3-yl)isoindoline-1,3-dione (452.17 mg, 1.03 mmol, HCl) in DMF (5 mL) was added TEA (311.34 mg, 3.08 mmol, 428.26 μL) and the resulting mixture was stirred at 20° C. for 12 h. LCMS showed that the reaction was completed. The mixture was poured into water (50 mL) and extracted with EtOAc (50 mL×3), the combined organic layer was washed with brine (100 mL), dried over $Na_2SO_4$, filtered and concentrated. The residue was purified by prep-TLC (Petroleum ether/Ethyl acetate=1/1). The product was diluted with MeCN and water which was lyophilized to afford the titled compound (120 mg, 155.56 μmol, 26.08% yield, 95% purity) as yellow solid. MS $(M+H)^+$=733.4

$^1H$ NMR (400 MHz, $CDCl_3$) δ=8.60-8.41 (m, 1H), 7.50 (t, J=7.8 Hz, 1H), 7.11 (d, J=7.1 Hz, 1H), 6.95-6.79 (m, 2H), 6.62-6.44 (m, 1H), 6.03-5.94 (m, 2H), 5.77 (dd, J=6.1, 9.4 Hz, 1H), 5.50 (s, 1H), 5.30-5.15 (m, 2H), 4.97-4.86 (m, 1H), 4.45-4.31 (m, 1H), 3.70 (t, J=5.1 Hz, 2H), 3.66-3.51 (m, 6H), 3.49-3.29 (m, 4H), 2.92-2.71 (m, 3H), 2.47-2.32 (m, 3H), 2.31-2.20 (m, 2H), 2.19-2.04 (m, 2H), 1.96-1.82 (m, 2H), 1.77-1.66 (m, 2H), 1.48-1.30 (m, 2H), 1.07 (d, J=7.3 Hz, 3H), 0.89 (d, J=6.8 Hz, 3H).

Example 154. Synthesis of (3R,5R)-3,5-dihydroxy-7-((1S,2S,6R,8S,8aR)-8-(((11-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-11-oxoundecyl)carbamoyl)oxy)-2,6-dimethyl-1,2,6,7,8,8a-hexahydronaphthalen-1-yl)heptanoic acid (Compound 154)

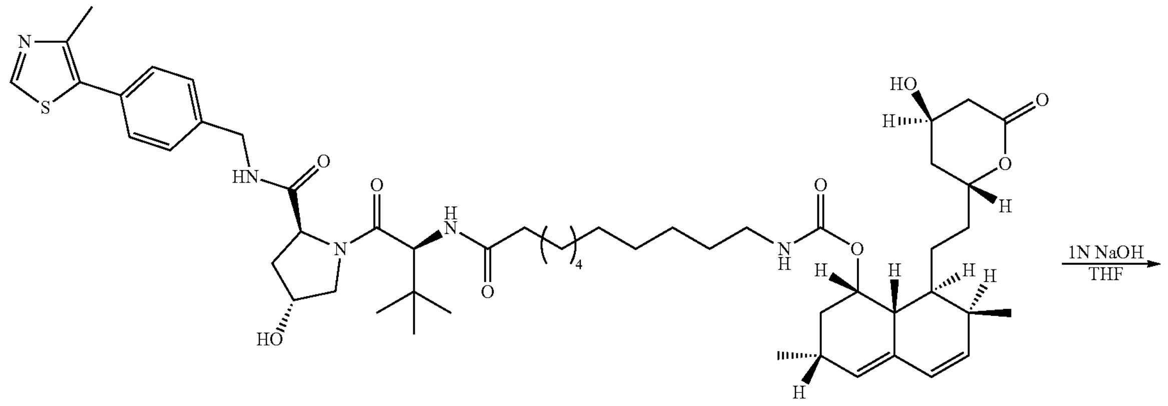

1

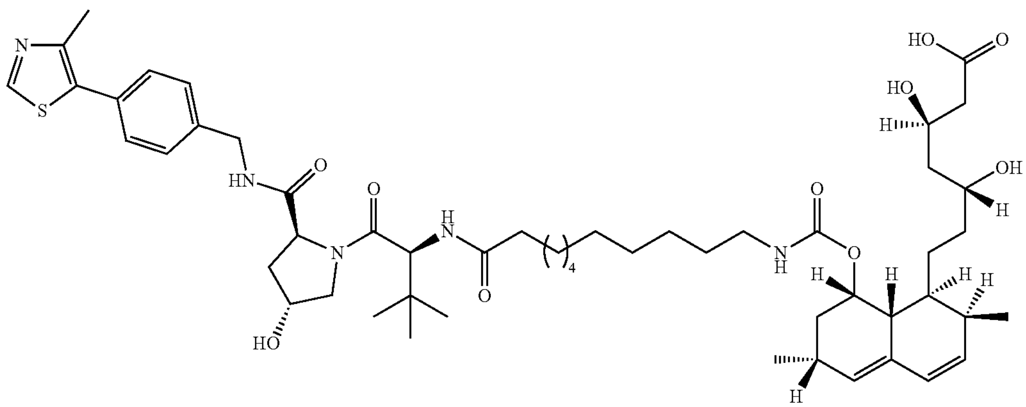

Compound 154

Step 1: Synthesis of (3R,5R)-3,5-dihydroxy-7-((1S,2S,6R,8S,8aR)-8-(((11-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-11-oxoundecyl)carbamoyl)oxy)-2,6-dimethyl-1,2,6,7,8,8a-hexahydronaphthalen-1-yl)heptanoic acid (Compound 154)

To a solution of (1S,3R,7S,8S,8aR)-8-(2-((2R,4R)-4-hydroxy-6-oxotetrahydro-2H-pyran-2-yl)ethyl)-3,7-dimethyl-1,2,3,7,8,8a-hexahydronaphthalen-1-yl (11-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-11-oxoundecyl)carbamate (100 mg, 90.60 μmol, 87% purity) in THF (1 mL) was added NaOH (1 M, 906.00 μL) and the mixture was stirred at 60° C. for 14 h. LCMS showed the desired mass was detected. The reaction mixture was adjusted the pH=7 with 1 N HCl and the solution was concentrated under reduce pressure. The crude was purified by prep-HPLC (column: Waters Xbridge 150*25 mm*5 μm; mobile phase: [water (10 mM $NH_4HCO_3$)-ACN]; B %: 31%-61%, 10 min) and the eluent was lyophilized to the titled compound (20.7 mg, 20.31 μmol, 22.42% yield, 96% purity) as a white solid. MS $(M+H)^+$=978.3.

$^1$H NMR (400 MHz, DMSO-$d_6$) δ=8.98 (s, 1H), 8.56 (t, J=5.8 Hz, 1H), 7.84 (br d, J=9.4 Hz, 1H), 7.44-7.36 (m, 4H), 6.94 (br t, J=5.5 Hz, 1H), 5.89 (br d, J=9.5 Hz, 1H), 5.79-5.73 (m, 1H), 5.44 (br s, 1H), 5.26-4.92 (m, 2H), 4.54 (d, J=9.4 Hz, 1H), 4.47-4.39 (m, 2H), 4.34 (br s, 1H), 4.25-4.17 (m, 1H), 4.01-3.93 (m, 1H), 3.70-3.60 (m, 2H), 3.52-3.44 (m, 1H), 3.31-3.28 (m, 1H), 2.99-2.86 (m, 2H), 2.44 (s, 3H), 2.35-2.27 (m, 3H), 2.25-2.15 (m, 2H), 2.14-1.99 (m, 2H), 1.94-1.77 (m, 3H), 1.69-1.58 (m, 1H), 1.51-1.30 (m, 8H), 1.26-1.09 (m, 15H), 1.03 (br d, J=7.3 Hz, 3H), 0.95-0.90 (m, 9H), 0.82 (d, J=6.9 Hz, 3H).

Examples 155 & 156. Synthesis of (1S,3R,7S,8S,8aR)-8-(2-((2R,4R)-4-((tert-butyldimethylsilyl)oxy)-6-oxotetrahydro-2H-pyran-2-yl)ethyl)-3,7-dimethyl-1,2,3,7,8,8a-hexahydronaphthalen-1-yl (2-(2-(2-((3-(2,6-dioxopiperidin-3-yl)-4-oxo-3,4-dihydrobenzo[d][1,2,3]triazin-5-yl)amino)ethoxy)ethoxy)ethyl)carbamate (Compound 155) and (1S,3R,7S,8S,8aR)-8-(2-((2R,4R)-4-hydroxy-6-oxotetrahydro-2H-pyran-2-yl)ethyl)-3,7-dimethyl-1,2,3,7,8,8a-hexahydronaphthalen-1-yl (2-(2-(2-((3-(2,6-dioxopiperidin-3-yl)-4-oxo-3,4-dihydrobenzo[d][1,2,3]triazin-5-yl)amino)ethoxy)ethoxy)ethyl)carbamate (Compound 156)

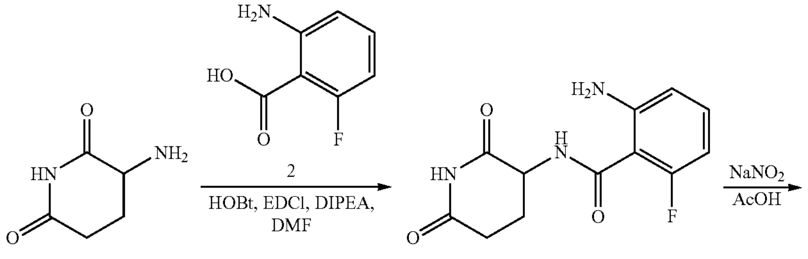

1 3

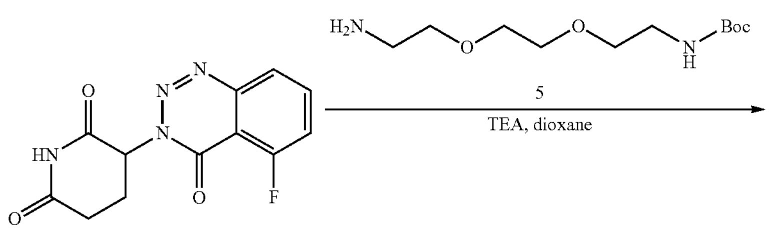

4

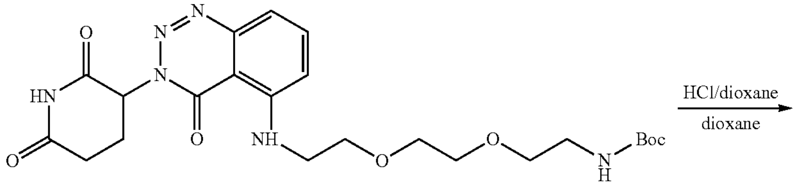

6

-continued

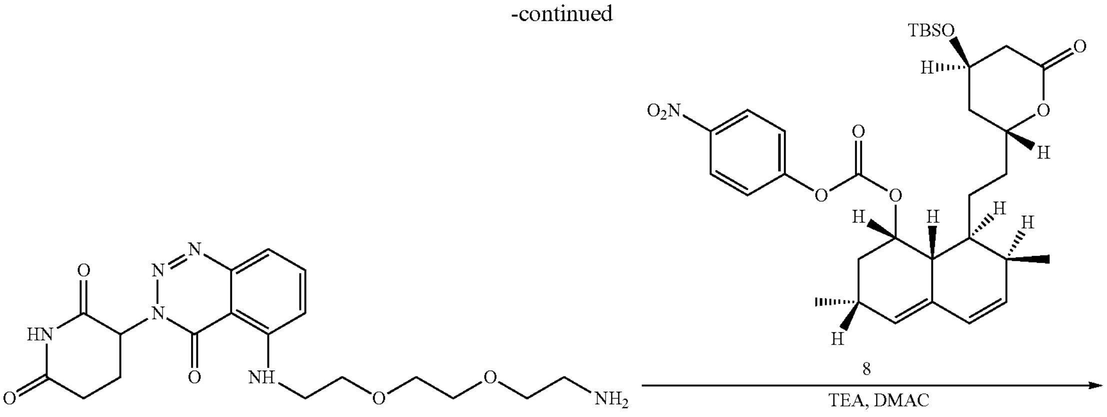

7

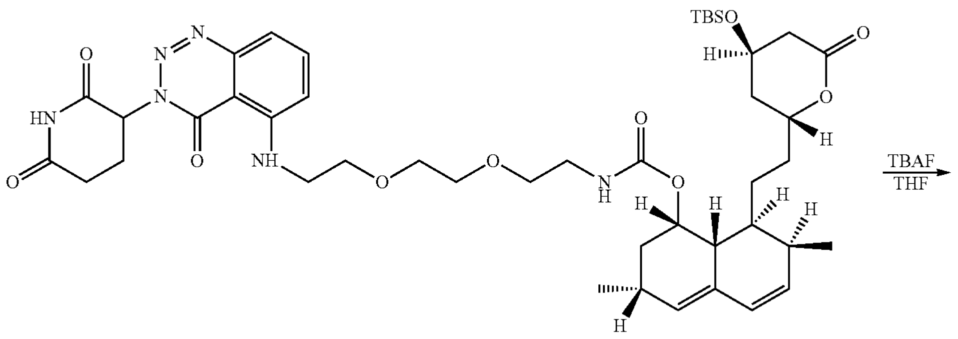

Compound 155

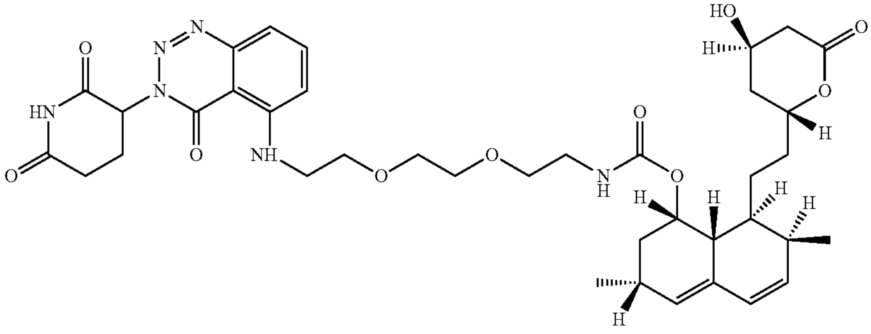

Compound 156

Step 1: Synthesis of 2-amino-N-(2,6-dioxopiperidin-3-yl)-6-fluorobenzamide (3)

To a mixture of 2-amino-6-fluoro-benzoic acid (5 g, 32.23 mmol) and 3-aminopiperidine-2, 6-dione;hydrochloride (5.84 g, 35.46 mmol) in DMF (100 mL) were added HOBt (4.79 g, 35.46 mmol), EDCI (6.80 g, 35.46 mmol) and DIPEA (12.50 g, 96.70 mmol, 16.84 mL) at 25° C. The mixture was stirred at 25° C. for 16 h. LCMS showed the 2-amino-6-fluoro-benzoic acid was consumed completely and a main peak with desired mass. The mixture was poured into water (80 mL) and filtered, the filter cake was collected and dried afford the titled compound (8 g, 29.56 mmol, 91.70% yield, 98% purity) as blue solid. MS $(M+H)^+$=266.1

Step 2: Synthesis of 3-(5-fluoro-4-oxobenzo[d][1,2,3]triazin-3(4H)-yl)piperidine-2,6-dione (4)

A mixture 2-amino-N-(2,6-dioxopiperidin-3-yl)-6-fluorobenzamide (7.9 g, 29.78 mmol) and $NaNO_2$ (3.49 g, 50.63 mmol) in AcOH (100 mL) was stirred at 25° C. for 2 hr. LCMS showed the 2-amino-N-(2, 6-dioxo-3-piperidyl)-6-fluoro-benzamide was consumed completely and a main peak with desired mass. The mixture was poured into water (80 mL) and filtered, the filter cake was collected and dried afford the titled compound (7.1 g, 24.68 mmol, 82.85% yield, 96% purity) as white solid. MS $(M+H)^+$=277.0

$^1H$ NMR (400 MHz, DMSO-$d_6$) δ=11.20 (brs, 1H), 8.19-8.03 (m, 2H), 7.81-7.77 (m, 1H), 5.97 5.99-5.94 (m, 1H), 3.04-2.88 (m, 1H), 2.76-2.60 (m, 2H), 2.33-2.22 (m, 1H).

Step 3: Synthesis of tert-butyl (2-(2-(2-((3-(2,6-dioxopiperidin-3-yl)-4-oxo-3,4-dihydrobenzo[d][1,2,3]triazin-5-yl)amino)ethoxy)ethoxy)ethyl)carbamate (6)

A solution of 3-(5-fluoro-4-oxobenzo[d][1,2,3]triazin-3(4H)-yl)piperidine-2,6-dione (3 g, 10.86 mmol), tert-butyl (2-(2-(2-aminoethoxy)ethoxy)ethyl)carbamate (3.24 g, 13.03 mmol) and TEA (3.30 g, 32.58 mmol, 4.54 mL) in dioxane (50 mL) was stirred at 100° C. for 12 h. LCMS showed the 3-(5-fluoro-4-oxobenzo[d][1,2,3]triazin-3(4H)-yl)piperidine-2,6-dione was consumed completely and a main peak with desired mass. The mixture solution was concentrated under reduced pressure. The residue was purified by flash silica gel chromatography (45 g SepaFlash® Silica Flash Column, Eluent of 0~30% Ethyl acetate/Petroleum ether gradient @ 65 mL/min) afford the titled compound (5.6 g, 10.43 mmol, 96.06% yield, 94% purity) as yellow solid. MS $(M-100+H)^+$=405.1

Step 4: Synthesis of 3-(5-((2-(2-(2-aminoethoxy)ethoxy)ethyl)amino)-4-oxobenzo[d][1,2,3]triazin-3(4H)-yl)piperidine-2,6-dione (7)

To a solution of tert-butyl (2-(2-(2-((3-(2,6-dioxopiperidin-3-yl)-4-oxo-3,4-dihydrobenzo[d][1,2,3]triazin-5-yl)amino)ethoxy)ethoxy)ethyl)carbamate (2.3 g, 4.56 mmol) in dioxane (2 mL) was added HCl/dioxane (4 M, 20 mL) at 25° C. The resulting mixture was stirred at 25° C. for 0.5 hr. TLC (petroleumether:ethylacetate=1:1; Rf=0) showed the starting material was consumed completely and found new spot. LCMS showed a main peak with desired mass. The mixture solution was concentrated under reduced pressure to give the crude product. The crude product was dissolved with cold deionized water (40 mL) and lyophilized to give the titled compound (1.6 g, crude, HCl) as brown solid. It was used for the next step directly. MS $(M+H)^+$=405.1

$^1$H NMR (400 MHz, $D_2O$) δ=7.71-7.63 (m, 1H), 7.13 (d, J=8.0 Hz, 1H), 6.88 (d, J=8.4 Hz, 1H), 5.83 (dd, J=5.6, 12.4 Hz, 1H), 3.76 (t, J=5.2 Hz, 2H), 3.70-3.66 (m, 6H), 3.39 (t, J=5.3 Hz, 2H), 3.15-3.06 (m, 2H), 2.96-2.82 (m, 2H), 2.80-2.67 (m, 1H), 2.40-2.35 (m, 1H)

Step 5: Synthesis of (1S,3R,7S,8S,8aR)-8-(2-((2R,4R)-4-((tert-butyldimethylsilyl)oxy)-6-oxotetrahydro-2H-pyran-2-yl)ethyl)-3,7-dimethyl-1,2,3,7,8,8a-hexahydronaphthalen-1-yl(2-(2-(2-((3-(2,6-dioxopiperidin-3-yl)-4-oxo-3,4-dihydrobenzo[d][1,2,3]triazin-5-yl)amino)ethoxy)ethoxy)ethyl)carbamate (Compound 155)

To a solution of 3-(5-((2-(2-(2-aminoethoxy)ethoxy)ethyl)amino)-4-oxobenzo[d][1,2,3]triazin-3(4H)-yl)piperidine-2,6-dione (1.1 g, 2.50 mmol, HCl) in DMAC (20 mL) was added TEA (1.01 g, 9.98 mmol, 1.39 mL) followed by (1S,3R,7S,8S,8aR)-8-(2-((2R,4R)-4-((tert-butyldimethylsilyl)oxy)-6-oxotetrahydro-2H-pyran-2-yl)ethyl)-3,7-dimethyl-1,2,3,7,8,8a-hexahydronaphthalen-1-yl (4-nitrophenyl) carbonate (1.50 g, 2.50 mmol). The mixture was stirred at 100° C. for 16 hours. LCMS showed (1S,3R,7S,8S,8aR)-8-(2-((2R,4R)-4-((tert-butyldimethylsilyl)oxy)-6-oxotetrahydro-2H-pyran-2-yl)ethyl)-3,7-dimethyl-1,2,3,7,8,8a-hexahydronaphthalen-1-yl (4-nitrophenyl) carbonate was consumed completely and a main peak with desired mass. The reaction mixture was diluted with $H_2O$ (50 mL) and extracted with EtOAc (80 mL×3). The combined organic layers were washed with brine (150 mL×3), dried over $Na_2SO_4$, filtered and concentrated under reduced pressure to give a residue. The residue was purified prep-HPLC (column: Phenomenex luna $C_{18}$ 150*40 mm*15 μm; mobile phase: [water (0.225% FA)-ACN]; B %: 67%-97%, 10 min) and lyophilized to afford the titled compound (1.2 g, 1.29 mmol, 51.70% yield, 93% purity) as yellow solid. MS $(M+H)^+$=864.9

$^1$H NMR (400 MHz, DMSO-$d_6$) δ=11.16 (s, 1H), 8.33-8.30 (m, 1H), 7.80 (t, J=8.2 Hz, 1H), 7.23 (d, J=8.0 Hz, 1H), 7.04-6.87 (m, 2H), 5.95-5.82 (m, 2H), 5.79-5.64 (m, 1H), 5.44 (s, 1H), 5.04 (s, 1H), 4.48-4.45 (m, 1H), 4.27 (s, 1H), 3.72-3.61 (m, 2H), 3.55-3.48 (m, 4H), 3.42-3.35 (m, 4H), 3.24-3.08 (m, 2H), 3.00-2.86 (m, 1H), 2.74-2.57 (m, 3H), 2.38-2.20 (m, 5H), 1.97-1.74 (m, 3H), 1.74-1.56 (m, 3H), 1.52-1.38 (m, 1H), 1.38-1.17 (m, 2H), 1.01 (d, J=7.2 Hz, 3H), 0.85-0.78 (m, 12H), 0.03 (s, 6H).

Step 6: Synthesis of (1S,3R,7S,8S,8aR)-8-(2-((2R,4R)-4-hydroxy-6-oxotetrahydro-2H-pyran-2-yl)ethyl)-3,7-dimethyl-1,2,3,7,8,8a-hexahydronaphthalen-1-yl(2-(2-(2-((3-(2,6-dioxopiperidin-3-yl)-4-oxo-3,4-dihydrobenzo[d][1,2,3]triazin-5-yl)amino)ethoxy)ethoxy)ethyl)carbamate (Compound 156)

To a solution of (1S,3R,7S,8S,8aR)-8-(2-((2R,4R)-4-((tert-butyldimethylsilyl)oxy)-6-oxotetrahydro-2H-pyran-2-yl)ethyl)-3,7-dimethyl-1,2,3,7,8,8a-hexahydronaphthalen-1-yl(2-(2-(2-((3-(2,6-dioxopiperidin-3-yl)-4-oxo-3,4-dihydrobenzo[d][1,2,3]triazin-5-yl)amino)ethoxy)ethoxy)ethyl)carbamate (200 mg, 231.19 μmol) in THF (5 mL) was added TBAF (1 M, 924.76 μL) at 0° C. The mixture was stirred at 15° C. for 2 hours. LCMS showed the (1S,3R,7S,8S,8aR)-8-(2-((2R,4R)-4-hydroxy-6-oxotetrahydro-2H-pyran-2-yl)ethyl)-3,7-dimethyl-1,2,3,7,8,8a-hexahydronaphthalen-1-yl(2-(2-(2-((3-(2,6-dioxopiperidin-3-yl)-4-oxo-3,4-dihydrobenzo[d][1,2,3]triazin-5-yl)amino)ethoxy)ethoxy)ethyl)carbamate was consumed completely and a main peak with desired mass. The mixture was diluted with ethyl acetate (20 mL) washed $NH_4Cl$ solution (10 mL×3), dried over $Na_2SO_4$, filtered and concentrated under reduced pressure at 15° C. The residue was purified prep-HPLC (column: Waters Xbridge 150*25 mm*5 μm; mobile phase: [water (10 mM $NH_4HCO_3$)-ACN]; B %: 37%-67%, 9 min) and lyophilized to give crude product. The crude product was purified prep-HPLC (column: Waters Xbridge 150*25 mm*5 μm; mobile phase: [water (10 mM $NH_4HCO_3$)-ACN]; B %: 37%-67%, 9 min) followed by prep-TLC (petroleumether:ethylacetate=1:1; Rf=0.5) to afford the titled compound (17.5 mg, 22.84 μmol, 9.88% yield, 98% purity) as yellow solid. MS $(M+H)^+$=751.1

$^1$H NMR (400 MHz, DMSO-$d_6$) δ=11.16 (brs, 1H), 8.33-8.30 (m, 1H), 7.80 (t, J=8.2 Hz, 1H), 7.23 (d, J=7.8 Hz, 1H), 7.00 (d, J=8.8 Hz, 2H), 5.97-5.82 (m, 2H), 5.75-5.65 (m, 1H), 5.44 (brs, 1H), 5.17 (d, J=3.2 Hz, 1H), 5.04 (d, J=2.8 Hz, 1H), 4.52-4.42 (m, 1H), 4.14-4.05 (m, 1H), 3.69-3.60 (m, 2H), 3.58-3.47 (m, 4H), 3.43-3.36 (m, 4H), 3.16-3.02 (m, 2H), 3.01-2.86 (m, 1H), 2.71-2.57 (m, 3H), 2.40-2.17 (m, 5H), 1.96-1.83 (m, 3H), 1.70-1.57 (m, 3H), 1.51-1.42 (m, 1H), 1.29-1.22 (m, 2H), 1.01 (d, J=7.6 Hz, 3H), 0.82 (d, J=6.8 Hz, 3H).

Example 157. Synthesis of (1S,3R,7S,8S,8aR)-8-(2-((2R,4R)-4-hydroxy-6-oxotetrahydro-2H-pyran-2-yl)ethyl)-3,7-dimethyl-1,2,3,7,8,8a-hexahydronaphthalen-1-yl (3-(2-(2-(3-((2-(2,6-dioxopiperidin-3-yl)-1,3-dioxoisoindolin-4-yl)amino)propoxy)ethoxy)ethoxy)propyl)carbamate (Compound 157)
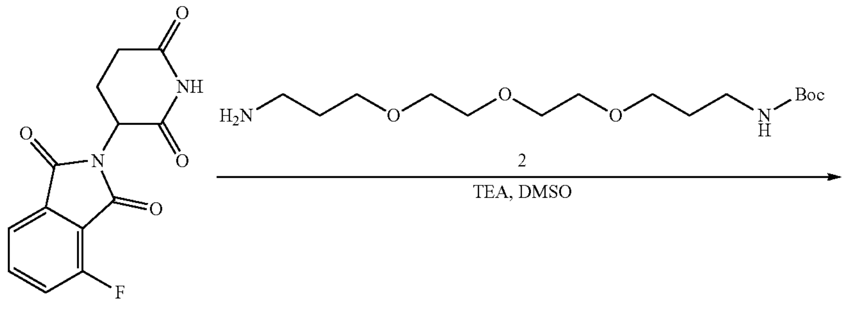
1
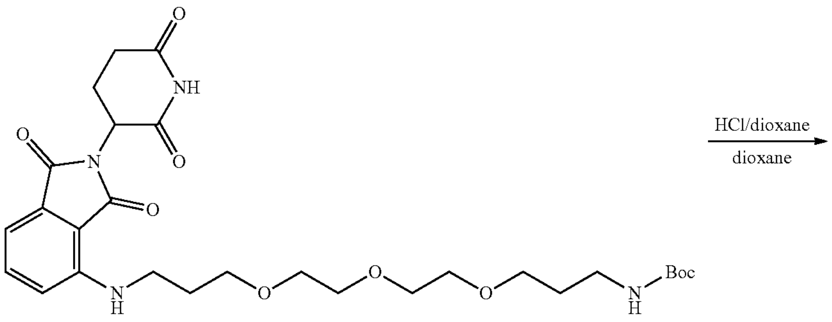
3
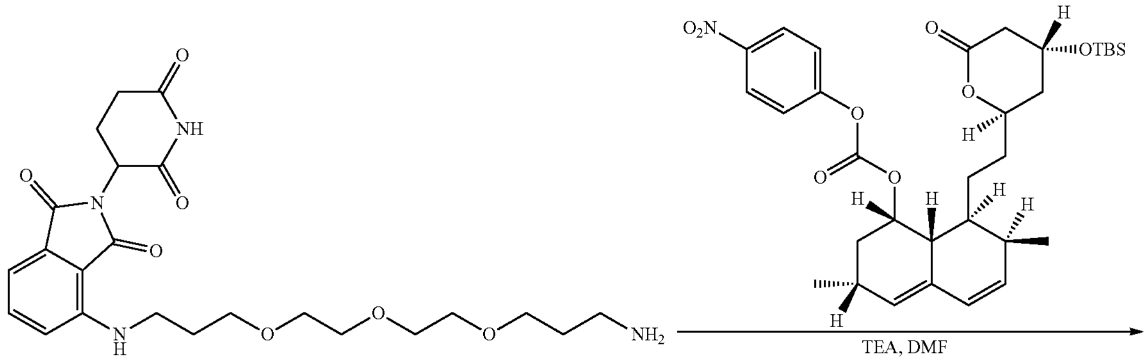
4

-continued

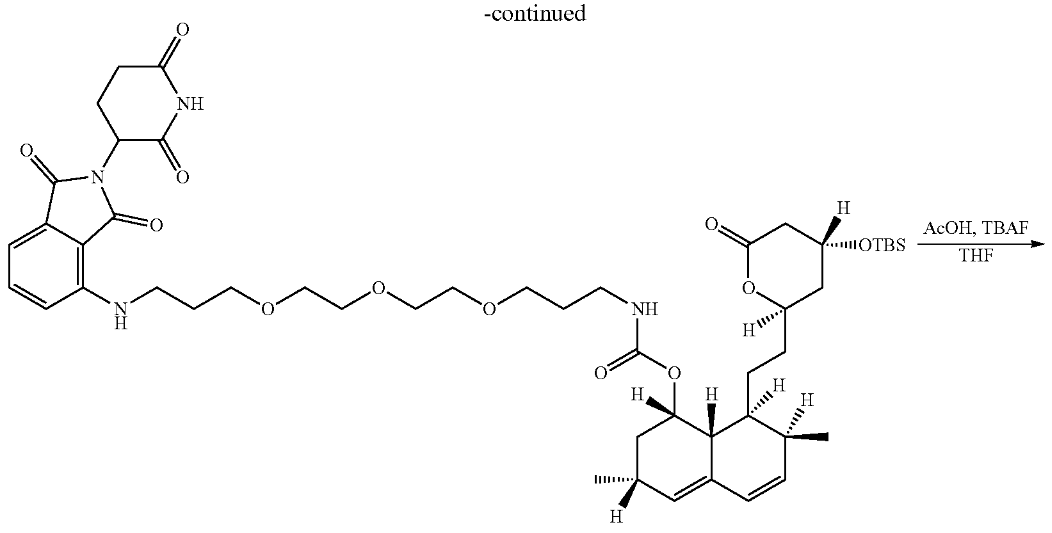

5

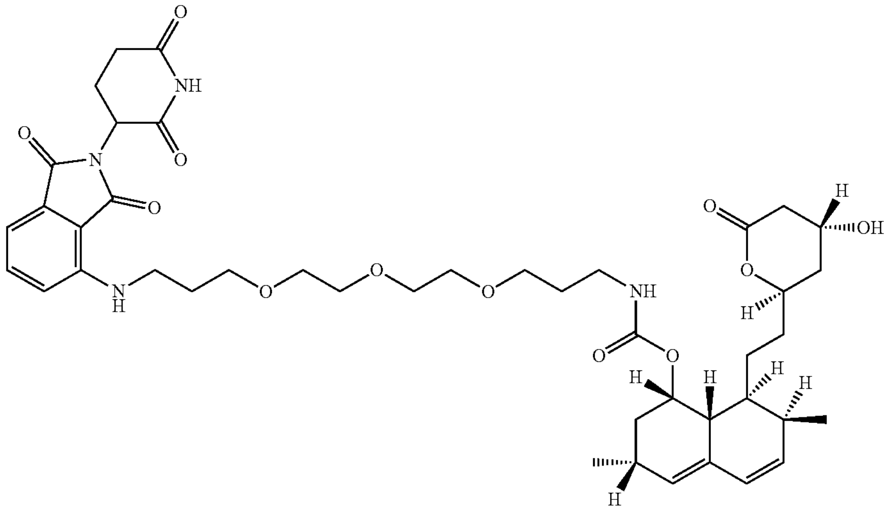

Compound 157

Step 3: Synthesis of (1S,3R,7S,8S,8aR)-8-(2-((2R,4R)-4-((tert-butyldimethylsilyl)oxy)-6-oxotetrahydro-2H-pyran-2-yl)ethyl)-3,7-dimethyl-1,2,3,7,8,8a-hexahydronaphthalen-1-yl (3-(2-(2-(3-((2-(2,6-dioxopiperidin-3-yl)-1,3-dioxoisoindolin-4-yl)amino)propoxy)ethoxy)ethoxy)propyl)carbamate (5)

To a mixture of 4-((3-(2-(2-(3-aminopropoxy) ethoxy)ethoxy)propyl)amino)-2-(2,6-dioxopiperidin-3-yl)isoindoline-1,3-dione (387 mg, crude, HCl) in DMF (5 mL) were added TEA (229.02 mg, 2.26 mmol, 315.02 μL) and (1S,3R,7S,8S,8aR)-8-(2-((2R,4R)-4-((tert-butyldimethylsilyl)oxy)-6-oxotetrahydro-2H-pyran-2-yl)ethyl)-3,7-dimethyl-1,2,3,7,8,8a-hexahydronaphthalen-1-yl (4-nitrophenyl) carbonate (497.73 mg, 829.85 μmol) in one portion at 20° C. and the resulting mixture was stirred at 20° C. for 16 h. LCMS showed all starting material was consumed completely and one peak with desired mass was detected. The reaction mixture was diluted with $H_2O$ (10 mL) and extracted with EtOAc (10 mL×3). The organic layer was washed with brine (10 mL×3), dried over $Na_2SO_4$, filtered and concentrated. The residue was purified by flash silica gel chromatography (10 g SepaFlash® Silica Flash Column, Eluent of 0-70% Ethyl acetate/Petroleum ether gradient @ 80 mL/min) to afford the titled compound (680 mg, 725.57 μmol, 96.18% yield) as a green oil. MS $(M+H)^+$=937.6

Step 4: Synthesis of (1S,3R,7S,8S,8aR)-8-(2-((2R,4R)-4-hydroxy-6-oxotetrahydro-2H-pyran-2-yl)ethyl)-3,7-dimethyl-1,2,3,7,8,8a-hexahydronaphthalen-1-yl (3-(2-(2-(3-((2-(2,6-dioxopiperidin-3-yl)-1,3-dioxoisoindolin-4-yl)amino)propoxy)ethoxy)ethoxy)propyl)carbamate (Compound 157)

To a mixture of (1S,3R,7S,8S,8aR)-8-(2-((2R,4R)-4-((tert-butyldimethylsilyl)oxy)-6-oxotetrahydro-2H-pyran-2-yl)ethyl)-3,7-dimethyl-1,2,3,7,8,8a-hexahydronaphthalen-1-yl (3-(2-(2-(3-((2-(2,6-dioxopiperidin-3-yl)-1,3-dioxoisoindolin-4-yl)amino)propoxy)ethoxy)ethoxy)propyl)carbamate (200 mg, 213.40 μmol) in THF (4 mL) were added AcOH (64.08 mg, 1.07 mmol, 61.02 μL) and TBAF (1 M in solution THF, 853.61 μL) drop-wise at 20° C. and the resulting mixture was stirred at 20° C. for 16 h. LCMS showed starting material was consumed completely and one peak desired with mass was detected. The reaction mixture was quenched with saturated $NH_4Cl$ (10 mL) and extracted with EtOAc (10 mL×3). The organic layer was washed with saturated $NH_4Cl$ (10 mL×3), dried over $Na_2SO_4$, filtered and concentrated. The residue was purified by prep-HPLC (column: Unisil 3-100 $C_{18}$ μLtra 150*50 mm*3 μm; mobile phase: [water (0.225% FA)-ACN]; B %: 43%-73%, 10 min) and then lyophilized to afford product A (101 mg) with 87% by HPLC and LCMS. The product (101 mg) was purified by prep-TLC ($SiO_2$, DCM:MeOH=20:1) to afford the titled compound (71.3 mg, 84.04 μmol, 39.38% yield, 97% purity) as a yellow solid. MS $(M+H)^+$=822.9

$^1H$ NMR (400 MHz, DMSO-$d_6$) δ=11.08 (s, 1H), 7.61-7.54 (m, 1H), 7.10 (d, J=8.7 Hz, 1H), 7.02 (d, J=7.0 Hz, 1H), 6.99-6.94 (m, 1H), 6.66 (t, J=5.7 Hz, 1H), 5.90 (d, J=9.8 Hz, 1H), 5.76 (dd, J=5.7, 9.3 Hz, 1H), 5.46 (s, 1H), 5.17 (d, J=3.3 Hz, 1H), 5.08-5.01 (m, 2H), 4.52-4.42 (m, 1H), 4.12-4.05 (m, 1H), 3.56-3.52 (m, 2H), 3.51-3.47 (m, 6H), 3.46-3.42 (m, 2H), 3.37-3.33 (m, 4H), 3.29 (s, 2H), 3.10-3.08 (m, 2H), 2.91-2.83 (m, 1H), 2.65-2.60 (m, 1H), 2.54-2.52 (m, 2H), 2.42-2.39 (m, 1H), 2.35-2.30 (m, 2H), 2.25-2.22 (m, 1H), 2.04-1.98 (m, 1H), 1.85-1.74 (m, 4H), 1.69-1.62 (m, 2H), 1.60-1.56 (m, 2H), 1.50-1.43 (m, 1H), 1.35-1.25 (m, 2H), 1.03 (br d, J=7.3 Hz, 3H), 0.83 (d, J=7.0 Hz, 3H)

Example 158. Synthesis of (1S,3R,7S,8S,8aR)-8-(2-((2R,4R)-4-hydroxy-6-oxotetrahydro-2H-pyran-2-yl)ethyl)-3,7-dimethyl-1,2,3,7,8,8a-hexahydronaphthalen-1-yl (8-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-8-oxooctyl)carbamate (Compound 158)

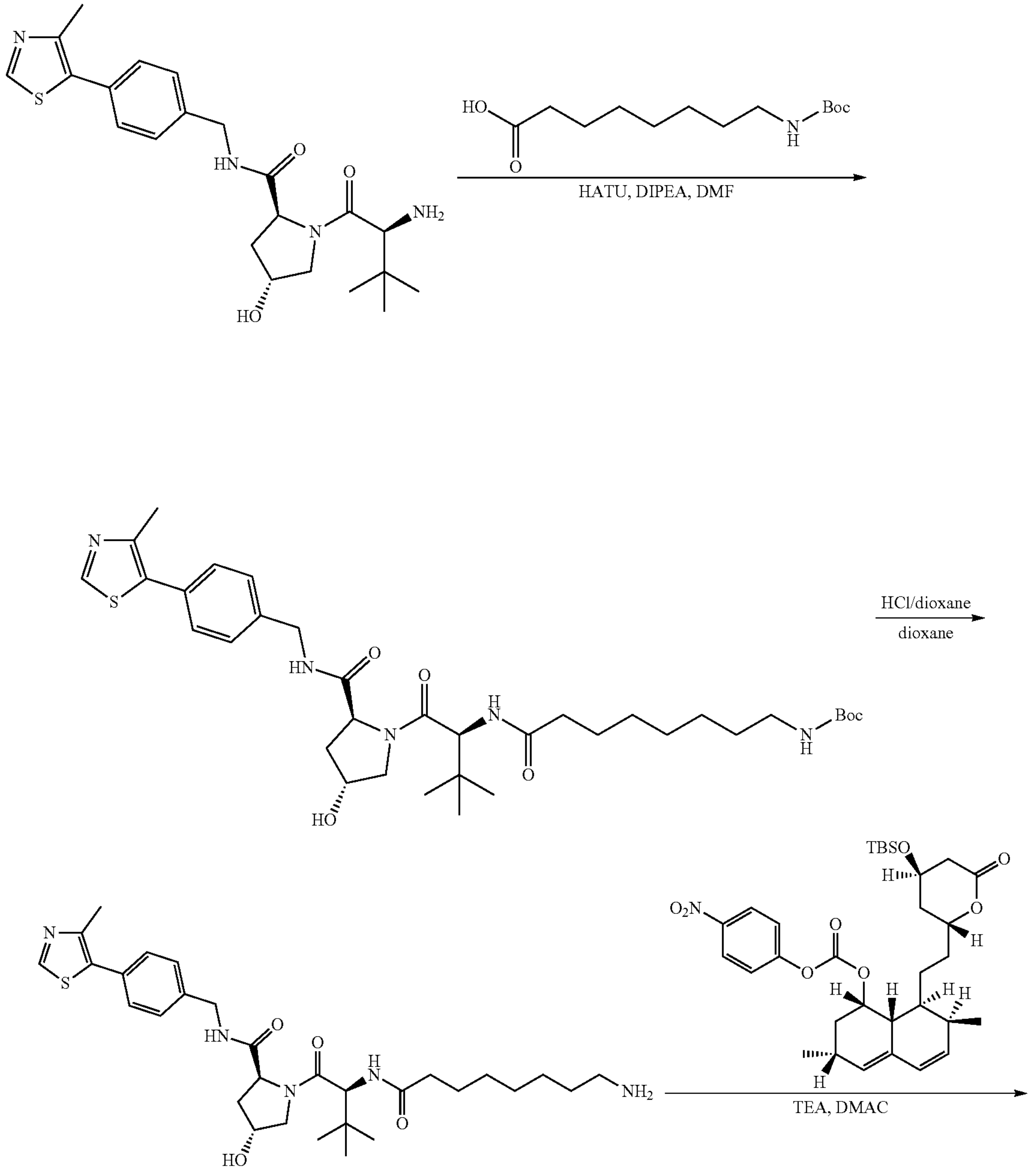

-continued

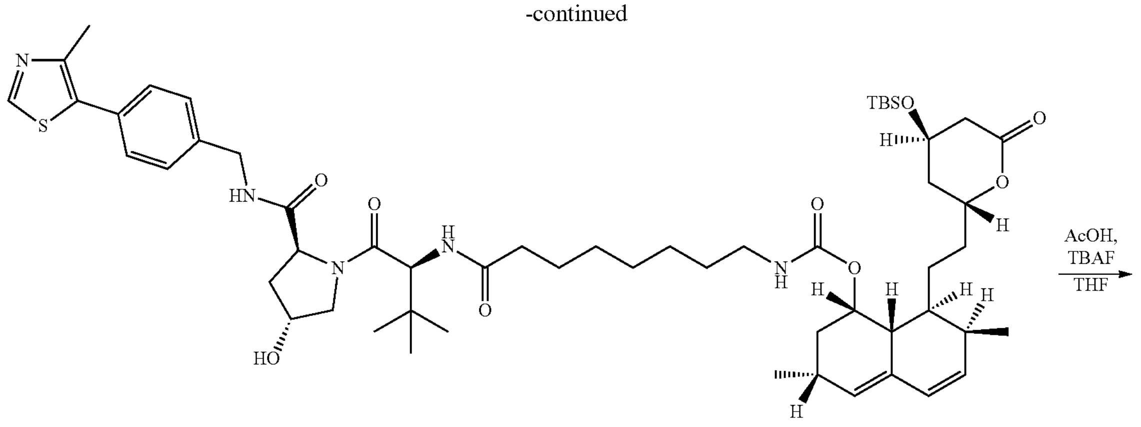

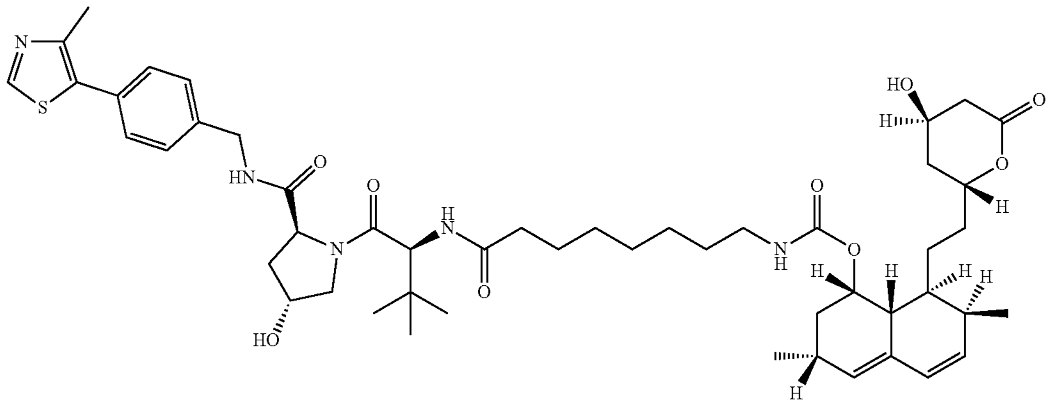

Compound 158

According to the above reaction scheme, in a manner similar to the other examples, obtained the titled compound (61.1 mg, 65.21 μmol, 23.22% yield, 98% purity) as a white solid. MS $(M+H)^+$=918.4.

$^1H$ NMR (400 MHz, DMSO-$d_6$) δ=8.98 (s, 1H), 8.57 (t, J=5.9 Hz, 1H), 7.84 (d, J=9.5 Hz, 1H), 7.46-7.33 (m, 4H), 6.99 (br t, J=5.6 Hz, 1H), 5.91 (d, J=9.5 Hz, 1H), 5.76 (dd, $J_1$=6.1, $J_2$=9.4 Hz, 1H), 5.46 (br s, 1H), 5.19 (d, J=3.3 Hz, 1H), 5.12 (d, J=3.5 Hz, 1H), 5.03 (br d, J=2.9 Hz, 1H), 4.54 (d, J=9.4 Hz, 1H), 4.51-4.38 (m, 3H), 4.37-4.32 (m, 1H), 4.21 (dd, $J_1$=5.4, $J_2$=15.9 Hz, 1H), 4.13-4.05 (m, 1H), 3.73-3.56 (m, 2H), 3.03-2.85 (m, 2H), 2.67-2.59 (m, 1H), 2.53-2.51 (m, 1H), 2.44 (s, 3H), 2.37-2.33 (m, 2H), 2.28-2.19 (m, 2H), 2.12-2.00 (m, 2H), 1.93-1.88 (m, 1H), 1.87-1.75 (m, 3H), 1.72-1.57 (m, 3H), 1.54-1.40 (m, 3H), 1.25-1.39 (m, 4H), 1.21 (br s, 6H), 1.04 (br d, J=7.3 Hz, 3H), 0.93 (s, 9H), 0.84 (d, J=6.9 Hz, 3H).

Example 159. Synthesis of (1S,3R,7S,8S,8aR)-8-(2-((2R,4R)-4-hydroxy-6-oxotetrahydro-2H-pyran-2-yl)ethyl)-3,7-dimethyl-1,2,3,7,8,8a-hexahydronaphthalen-1-yl (6-(4-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)carbamoyl)piperazin-1-yl)hexyl)carbamate (Compound 159)

In a manner similar to the other examples, Compound 159 was obtained.

Example 160. Synthesis of (1S,3R,7S,8S,8aR)-8-(2-((2R,4R)-4-hydroxy-6-oxotetrahydro-21H-pyran-2-yl)ethyl)-3,7-dimethyl-1,2,3,7,8,8a-hexahydronaphthalen-1-yl (11-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-11-oxoundecyl)carbamate (Compound 160)

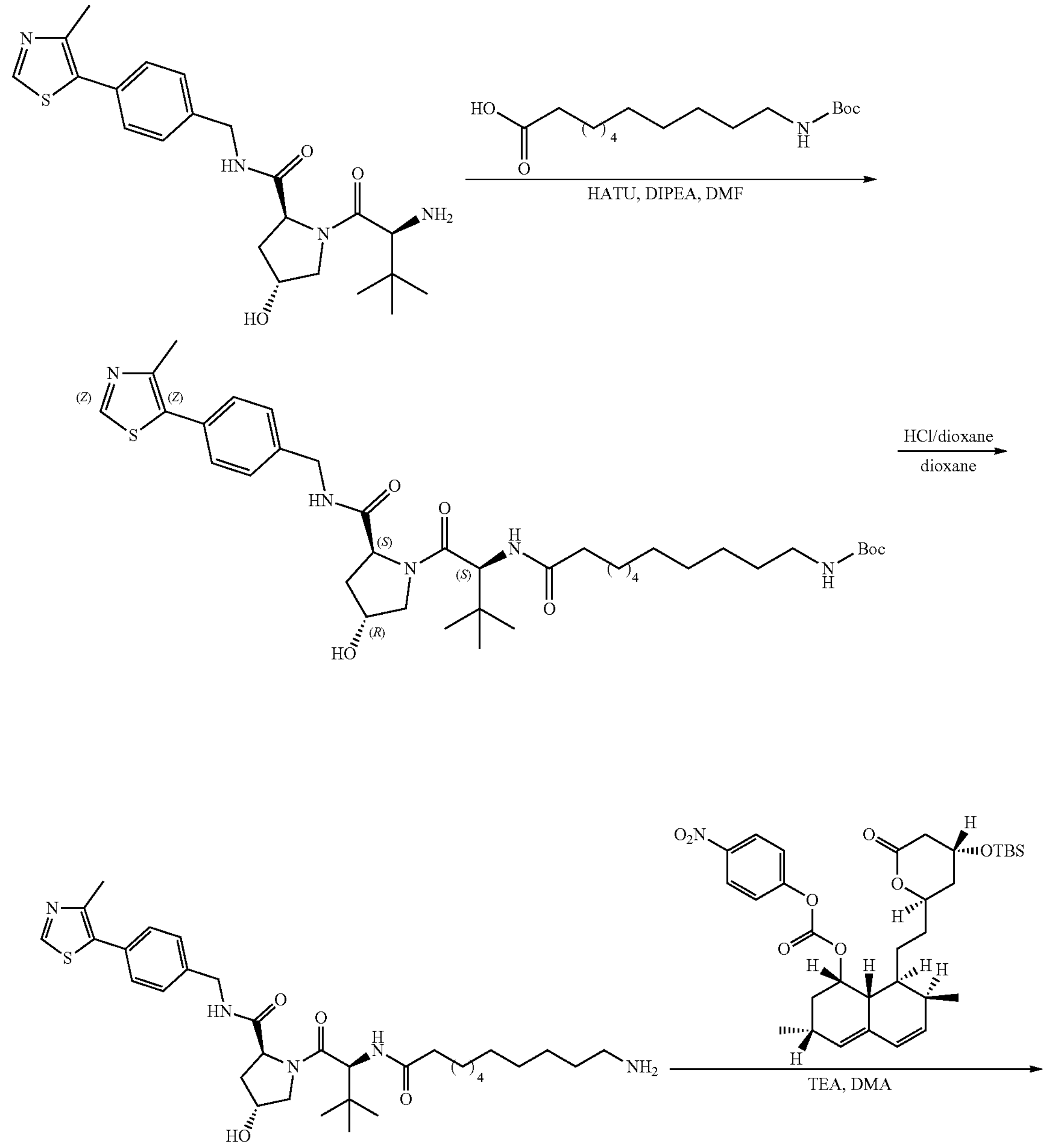

-continued

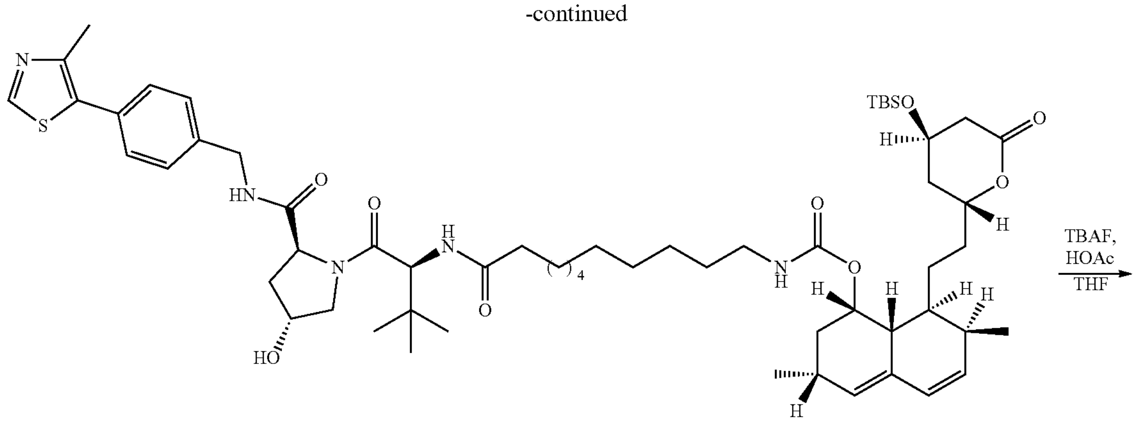

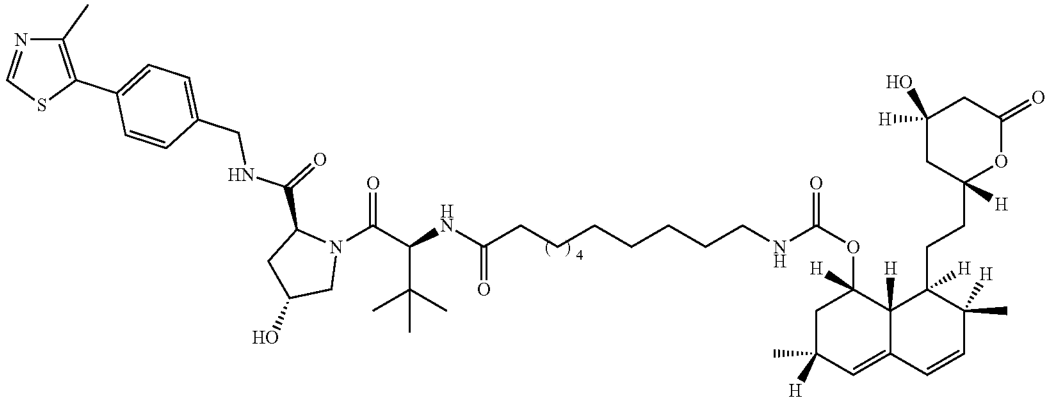

Compound 160

According to the above reaction scheme, in a manner similar to the other examples, obtained the titled compound (460.8 mg, 463.07 μmol, 38.28% yield, 96.5% purity) as a white solid and another the titled compound (173.8 mg, 178.28 μmol, 14.74% yield, 98.5% purity) as a white solid. MS $(M+H)^+$=960.7.

$^1$H NMR (400 MHz, DMSO-$d_6$) δ=8.98 (s, 1H), 8.56 (br t, J=5.9 Hz, 1H), 7.84 (br d, J=9.4 Hz, 1H), 7.44-7.35 (m, 4H), 6.97 (br t, J=5.3 Hz, 1H), 5.91 (br d, J=9.5 Hz, 1H), 5.79-5.73 (m, 1H), 5.46 (br s, 1H), 5.20-5.17 (m, 1H), 5.13-5.10 (m, 1H), 5.06-5.01 (m, 1H), 4.56-4.40 (m, 4H), 4.35 (br s, 1H), 4.25-4.18 (m, 1H), 4.12-4.06 (m, 1H), 3.70-3.61 (m, 2H), 3.30-3.29 (m, 1H), 3.01-2.85 (m, 2H), 2.64-2.58 (m, 1H), 2.47-2.40 (m, 4H), 2.39-2.19 (m, 5H), 2.14-2.00 (m, 2H), 1.94-1.76 (m, 4H), 1.71-1.59 (m, 2H), 1.50-1.44 (m, 2H), 1.37-1.17 (m, 16H), 1.04 (br d, J=7.1 Hz, 3H), 0.93 (s, 9H), 0.84 (br d, J=6.8 Hz, 3H).

Example 161. Synthesis of (1S,3R,7S,8S,8aR)-8-(2-((2R,4R)-4-hydroxy-6-oxotetrahydro-2H-pyran-2-yl)ethyl)-3,7-dimethyl-1,2,3,7,8,8a-hexahydronaphthalen-1-yl (4-(4-(4-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-4-oxobutyl)-1H-1,2,3-triazol-1-yl)butyl)carbamate (Compound 161)

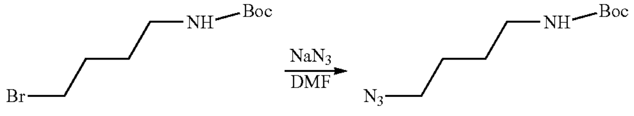

2C 2A

-continued
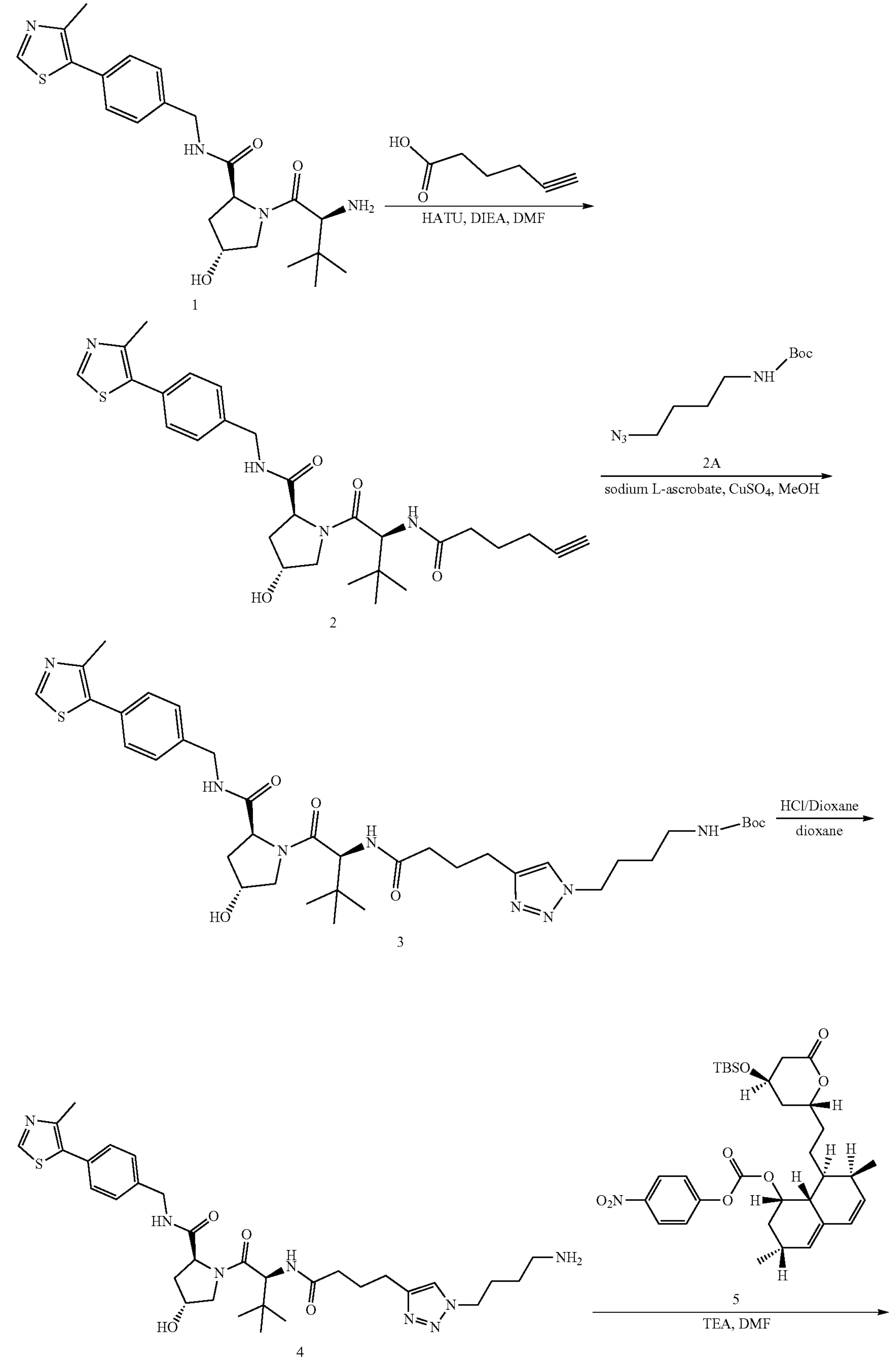
1
2
3
4
5

-continued

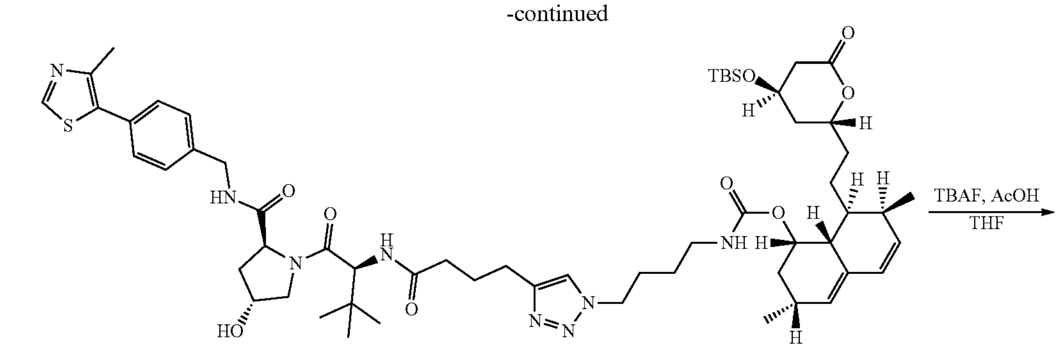

6

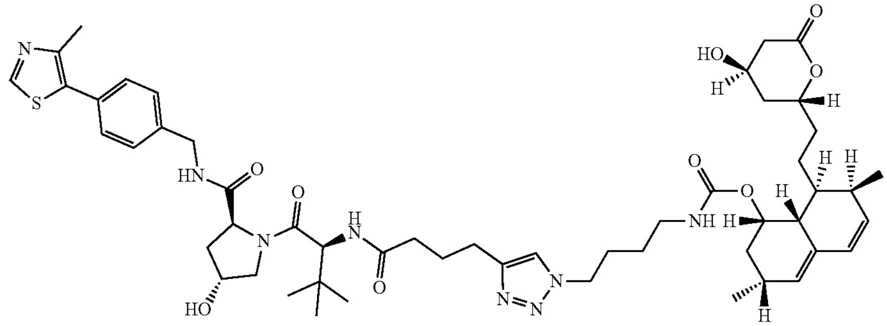

Compound 161

Step 1: Synthesis of (2S,4R)-1-((S)-2-(hex-5-ynamido)-3,3-dimethylbutanoyl)-4-hydroxy-N-(4-(4-methylthiazol-5-yl)benzyl)pyrrolidine-2-carboxamide (2)

To a solution of hex-5-ynoic acid (132.05 mg, 1.18 mmol, 128.20 μL) in DMF (4 mL) were added HATU (447.79 mg, 1.18 mmol) and DIPEA (276.74 mg, 2.14 mmol, 372.96 μL). The mixture was stirred at 20° C. for 10 min and a solution of (2S,4R)-1-((S)-2-amino-3,3-dimethylbutanoyl)-4-hydroxy-N-(4-(4-methylthiazol-5-yl)benzyl)pyrrolidine-2-carboxamide (0.5 g, 1.07 mmol, HCl salt) in DMF (4 mL) with DIPEA (276.74 mg, 2.14 mmol, 372.96 μL) was added drop-wise at 20° C. and the resulting mixture was stirred at 20° C. for 1 h. LCMS showed all starting material was consumed completely and one peak with peak with desired mass. The reaction mixture was diluted with $H_2O$ (15 mL) and extracted with EtOAc (15 mL×3). The combined organic layer was washed with brine (15 mL×3), dried over $Na_2SO_4$, filtered. The filtrate was concentrated. The residue was purified by flash silica gel chromatography (10 g SepaFlash® Silica Flash Column, Eluent of 0~100% Ethyl acetate/Petroleum to 0~10% Dichloromethane/Methanol gradient @ 80 mL/min) to afford the titled compound (568 mg, 1.06 mmol, 99.10% yield, 98% purity) as a colorless oil. MS $(M+H)^+$=525.3

Step 2: Synthesis of tert-butyl (4-azidobutyl)carbamate (2A)

A mixture of tert-butyl N-(4-bromobutyl) carbamate (0.5 g, 1.98 mmol, 406.50 μL) and $NaN_3$ (154.69 mg, 2.38 mmol) in DMF (10 mL) was stirred at 80° C. for 16 h. TLC ($SiO_2$, Petroleum ether:Ethyl acetate=5:1) indicated the starting material was consumed completely and one major new spot was detected. The reaction mixture was diluted with $H_2O$ (15 mL) and extracted with EtOAc (15 mL×3). The combined organic layer was washed with brine (15 mL×3), dried over $Na_2SO_4$, filtered. The filtrate was concentrated to afford the titled compound (425 mg, crude) as a yellow oil.

Step 3: Synthesis of tert-butyl (4-(4-(4-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-4-oxobutyl)-1H-1,2,3-triazol-1-yl)butyl)carbamate (3)

To a mixture of (2S,4R)-1-((S)-2-(hex-5-ynamido)-3,3-dimethylbutanoyl)-4-hydroxy-N-(4-(4-methylthiazol-5-yl)benzyl)pyrrolidine-2-carboxamide (518 mg, 987.28 μmol) and tert-butyl (4-azidobutyl)carbamate (253.85 mg, 1.18 mmol) in MeOH (10 mL) were added $CuSO_4$ (189.09 mg, 1.18 mmol, 181.82 μL) and sodium L-ascorbate (254.26 mg, 1.28 mmol) in one portion at 20° C. and the resulting mixture was stirred at 20° C. for 16 h. LCMS showed all starting material was consumed completely and one peak with desired mass. The reaction mixture was diluted with MeOH (20 mL) and filtered. The filtrate was concentrated in vacuum. The residue was purified by flash silica gel chromatography (10 g SepaFlash® Silica Flash Column, Eluent of 0-10% Dichloromethane/Methanol gradient @ 80 mL/min) to afford the titled compound (687 mg, 892.52 μmol, 90.40% yield, 96% purity) as a yellow oil. MS $(M+H)^+$=739.2

Step 4: Synthesis of (2S,4R)-1-((S)-2-(4-(1-(4-aminobutyl)-1H-1,2,3-triazol-4-yl)butanamido)-3,3-dimethylbutanoyl)-4-hydroxy-N-(4-(4-methylthiazol-5-yl)benzyl)pyrrolidine-2-carboxamide (4)

To a mixture of tert-butyl (4-(4-(4-(((S)-1-((2S,4R)-4-hydroxy-2-((4-(4-methylthiazol-5-yl)benzyl)carbamoyl)

pyrrolidin-1-yl)-3,3-dimethyl-1-oxobutan-2-yl)amino)-4-oxobutyl)-1H-1,2,3-triazol-1-yl)butyl)carbamate (687 mg, 929.71 μmol) in dioxane (6 mL) was added HCl/dioxane (4 M, 12 mL) in one portion at 20° C. and the resulting mixture was stirred at 20° C. for 0.5 h. LCMS showed starting material was consumed completely and one peak with desired mass was detected. The reaction mixture was concentrated in vacuum to afford the titled compound (720 mg, crude, HCl salt) as a yellow solid. MS $(M+H)^+$=639.3

Step 5: Synthesis of (1S,3R,7S,8S,8aR)-8-(2-((2R,4R)-4-((tert-butyldimethylsilyl)oxy)-6-oxotetrahydro-2H-pyran-2-yl)ethyl)-3,7-dimethyl-1,2,3,7,8,8a-hexahydronaphthalen-1-yl (4-(4-(4-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-4-oxobutyl)-1H-1,2,3-triazol-1-yl)butyl)carbamate (6)

To a mixture of (2S,4R)-1-((S)-2-(4-(1-(4-aminobutyl)-1H-1,2,3-triazol-4-yl)butanamido)-3,3-dimethylbutanoyl)-4-hydroxy-N-(4-(4-methylthiazol-5-yl)benzyl)pyrrolidine-2-carboxamide (720 mg, 1.13 mmol, HCl salt) in DMF (7 mL) were added TEA (342.14 mg, 3.38 mmol, 470.62 μL) and (1S,3R,7S,8S,8aR)-8-(2-((2R,4R)-4-((tert-butyldimethylsilyl)oxy)-6-oxotetrahydro-2H-pyran-2-yl)ethyl)-3,7-dimethyl-1,2,3,7,8,8a-hexahydronaphthalen-1-yl (4-nitrophenyl) carbonate (743.60 mg, 1.24 mmol) in one portion at 20° C. and the resulting mixture was stirred at 30° C. for 16 h. LCMS showed all starting material was consumed completely and one peak with desired mass was detected. The reaction mixture was diluted with $H_2O$ (14 mL) and extracted with EtOAc (14 mL×3). The organic layer was washed with brine (14 mL×3), dried over $Na_2SO_4$, filtered. The filtrate was concentrated. The residue was purified by flash silica gel chromatography (10 g SepaFlash® Silica Flash Column, Eluent of 0~100% Ethyl acetate/Petroleum to 0~10% Dichloromethane/Methanol gradient @ 80 mL/min) to afford the titled compound (576 mg, 471.49 μmol, 41.83% yield, 90% purity) as a colorless oil. MS $(M+H)^+$=1099.8

Step 6: Synthesis of (1S,3R,7S,8S,8aR)-8-(2-((2R,4R)-4-hydroxy-6-oxotetrahydro-2H-pyran-2-yl)ethyl)-3,7-dimethyl-1,2,3,7,8,8a-hexahydronaphthalen-1-yl (4-(4-(4-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-4-oxobutyl)-1H-1,2,3-triazol-1-yl)butyl)carbamate (Compound 161)

To a mixture of (1S,3R,7S,8S,8aR)-8-(2-((2R,4R)-4-((tert-butyldimethylsilyl)oxy)-6-oxotetrahydro-2H-pyran-2-yl)ethyl)-3,7-dimethyl-1,2,3,7,8,8a-hexahydronaphthalen-1-yl (4-(4-(4-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-4-oxobutyl)-1H-1,2,3-triazol-1-yl)butyl)carbamate (556 mg, 505.68 μmol) in THF (10 mL) were added AcOH (151.83 mg, 2.53 mmol, 144.60 μL) and TBAF (1 M, 2.02 mL) in one portion at 20° C. and the resulting mixture was stirred at 30° C. for 16 h. LCMS showed starting material was consumed completely and one peak with desired mass was detected. The reaction mixture was quenched with saturated $NH_4Cl$ (15 mL) and extracted with EtOAc (15 mL×3). The combined organic layer was washed with saturated $NH_4Cl$ (15 mL×3), dried over $Na_2SO_4$, filtered and concentrated. The residue was purified by prep-HPLC (column: Phenomenex luna $C_{18}$ 150*40 mm*15 μm; mobile phase: [water (0.225% FA)-ACN]; B %: 35%-65%, 10 min) and the eluent was lyophilized to afford the titled compound (175.8 mg, 167.73 μmol, 33.17% yield, 94% purity) as a white solid. MS $(M+H)^+$=985.7

$^1$H NMR (400 MHz, DMSO-$d_6$) δ=8.98 (s, 1H), 8.56 (t, J=6.0 Hz, 1H), 7.90 (br d, J=9.3 Hz, 1H), 7.80 (s, 1H), 7.43-7.36 (m, 4H), 7.05 (br t, J=5.6 Hz, 1H), 5.91 (br d, J=9.7 Hz, 1H), 5.76 (dd, J=6.1, 9.5 Hz, 1H), 5.46 (br s, 1H), 5.25-5.08 (m, 2H), 5.04 (br d, J=3.1 Hz, 1H), 4.55 (d, J=9.3 Hz, 1H), 4.52-4.44 (m, 2H), 4.43-4.40 (m, 1H), 4.35 (br s, 1H), 4.31-4.17 (m, 4H), 4.09 (br d, J=3.2 Hz, 1H), 3.71-3.62 (m, 2H), 2.98 (br d, J=6.4 Hz, 2H), 2.62-2.55 (m, 3H), 2.44 (s, 3H), 2.41 (br d, J=1.7 Hz, 1H), 2.38-2.36 (m, 1H), 2.31-2.27 (m, 1H), 2.26-2.20 (m, 2H), 2.20-2.15 (m, 1H), 2.07-1.99 (m, 1H), 1.86-1.72 (m, 8H), 1.70-1.63 (m, 2H), 1.50-1.42 (m, 1H), 1.35-1.26 (m, 4H), 1.02 (br d, J=7.2 Hz, 3H), 0.94 (s, 9H), 0.84 (d, J=7.0 Hz, 3H).

Example 162. Synthesis of (1R,3S,7R,8R,8aS)-8-(2-((2S,4S)-4-hydroxy-6-oxotetrahydro-2H-pyran-2-yl)ethyl)-3,7-dimethyl-1,2,3,7,8,8a-hexahydronaphthalen-1-yl (3-(1-(4-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-4-oxobutyl)piperidin-4-yl)propyl)carbamate (Compound 162)

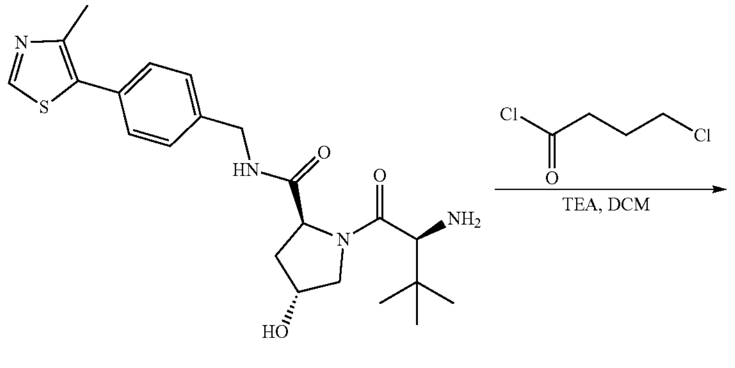

-continued
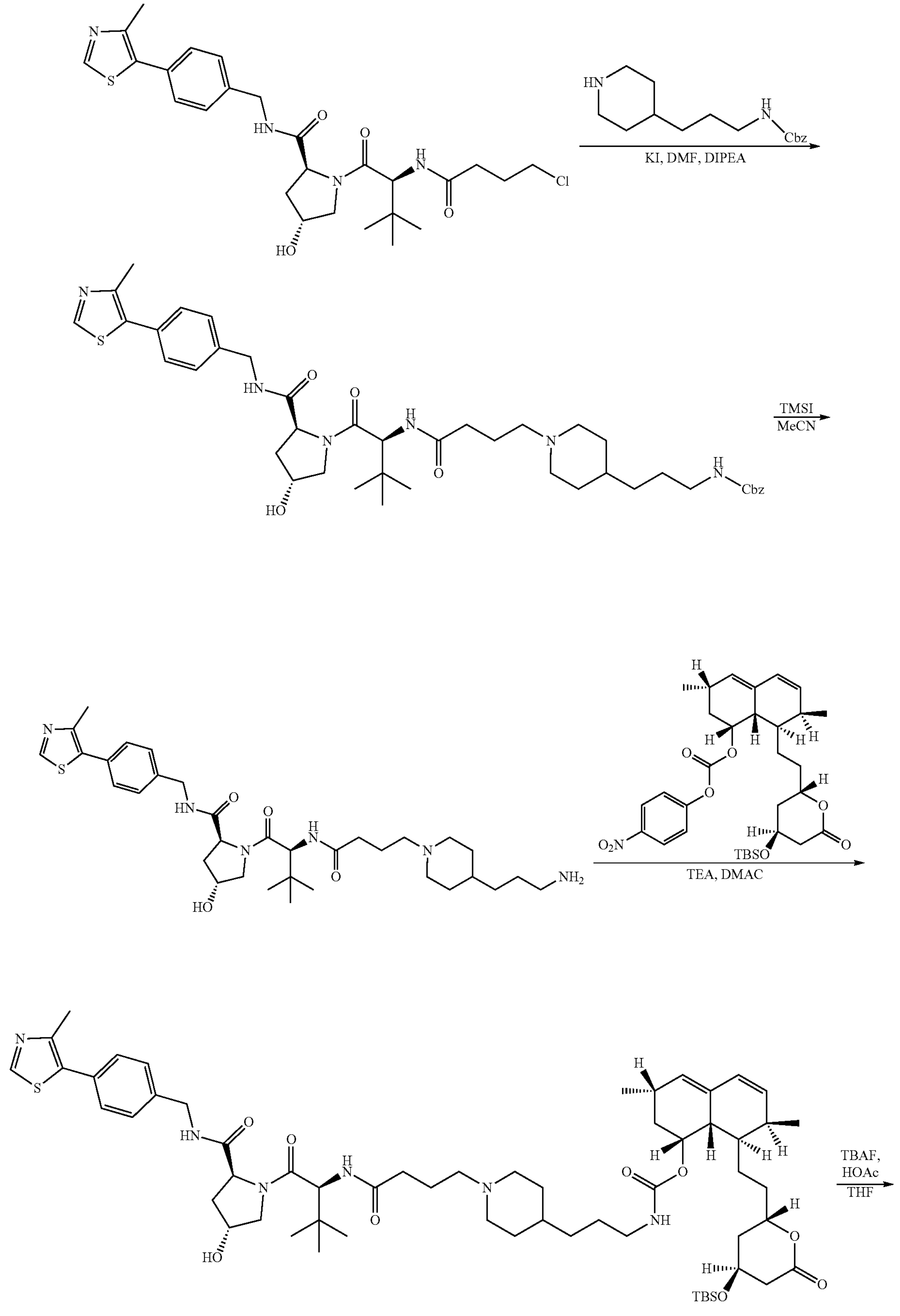

-continued

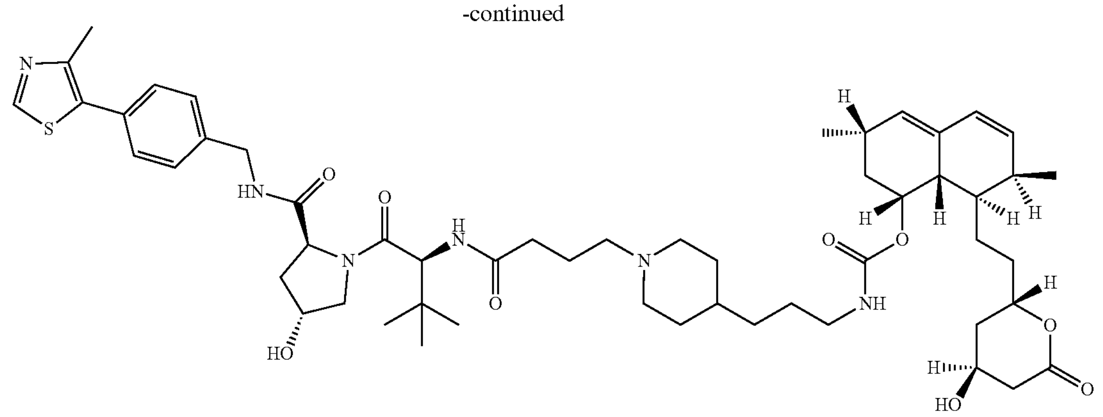

Compound 162

According to the above reaction scheme, in a manner similar to the other examples, obtained the titled compound (6.7 mg, 6.11 μmol, 8.41% yield, 90% purity) as a white solid. MS $(M+H)^+$=987.6

$^1$H NMR (400 MHz, MeOD) δ 8.88 (s, 1H), 7.49-7.40 (m, 4H), 5.98-5.89 (m, 1H), 5.80-5.71 (m, 1H), 5.49-5.42 (m, 1H), 5.18-5.10 (m, 1H), 4.91-4.87 (m, 2H), 4.73-4.63 (m, 1H), 4.58-4.48 (m, 3H), 4.36 (d, J=15.3 Hz, 1H), 4.27-4.22 (m, 1H), 3.95-3.85 (m, 1H), 3.82-3.77 (m, 1H), 3.17-3.02 (m, 2H), 3.01-2.88 (m, 2H), 2.75-2.67 (m, 1H), 2.56-2.49 (m, 1H), 2.48 (s, 3H), 2.43-2.34 (m, 4H), 2.32-2.17 (m, 4H), 2.11-1.90 (m, 4H), 1.83-1.63 (m, 7H), 1.59-1.37 (m, 5H), 1.32-1.16 (m, 6H), 1.10 (d, J=7.5 Hz, 3H), 1.06-1.01 (m, 9H), 0.91 (d, J=6.8 Hz, 3H)

Examples 163 & 164. Synthesis of (1R,3S,7R,8R,8aS)-8-(2-((2S,4S)-4-hydroxy-6-oxotetrahydro-2H-pyran-2-yl)ethyl)-3,7-dimethyl-1,2,3,7,8,8a-hexahydronaphthalen-1-yl (2-(2-(4-(3-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-3-oxopropyl)piperazin-1-yl)ethoxy)ethyl)carbamate (Compound 163) and (1R,3S,7R,8R,8aS)-8-(2-((2S,4S)-4-hydroxy-6-oxotetrahydro-2H-pyran-2-yl)ethyl)-3,7-dimethyl-1,2,3,7,8,8a-hexahydronaphthalen-1-yl (3-(4-(3-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-3-oxopropoxy)phenyl)propyl)carbamate (Compound 164)

In a manner similar to the other examples, Compounds 163 to 165 were obtained.

Example 165. Synthesis of (1S,3R,7S,8S,8aR)-8-(2-((2R,4R)-4-hydroxy-6-oxotetrahydro-2H-pyran-2-yl)ethyl)-3,7-dimethyl-1,2,3,7,8,8a-hexahydronaphthalen-1-yl (8-(2-(((2S,4R)-1-((S)-2-(1-fluorocyclopropane-1-carboxamido)-3,3-dimethylbutanoyl)-4-hydroxypyrrolidine-2-carboxamido)methyl)-5-(4-methylthiazol-5-yl)phenoxy)octyl)carbamate (Compound 165)

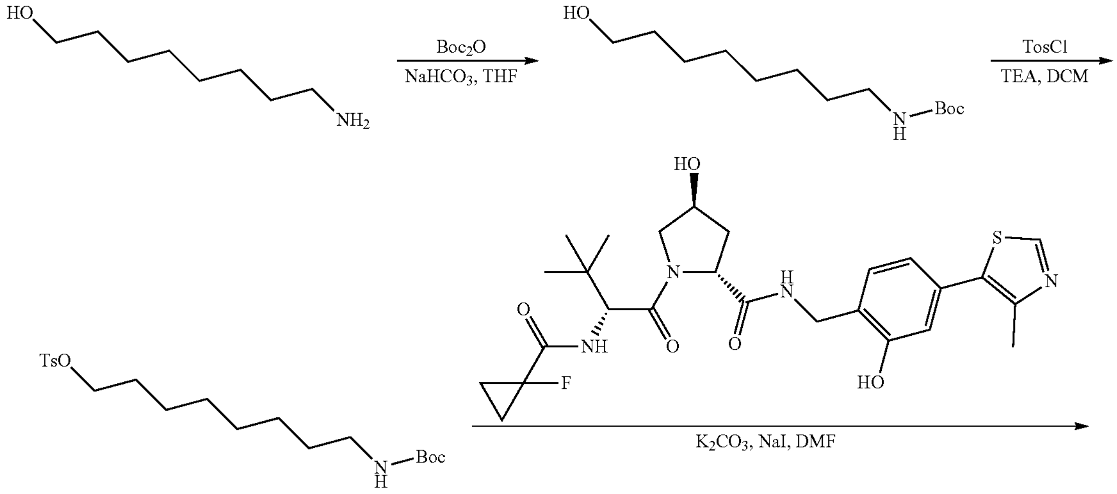

-continued
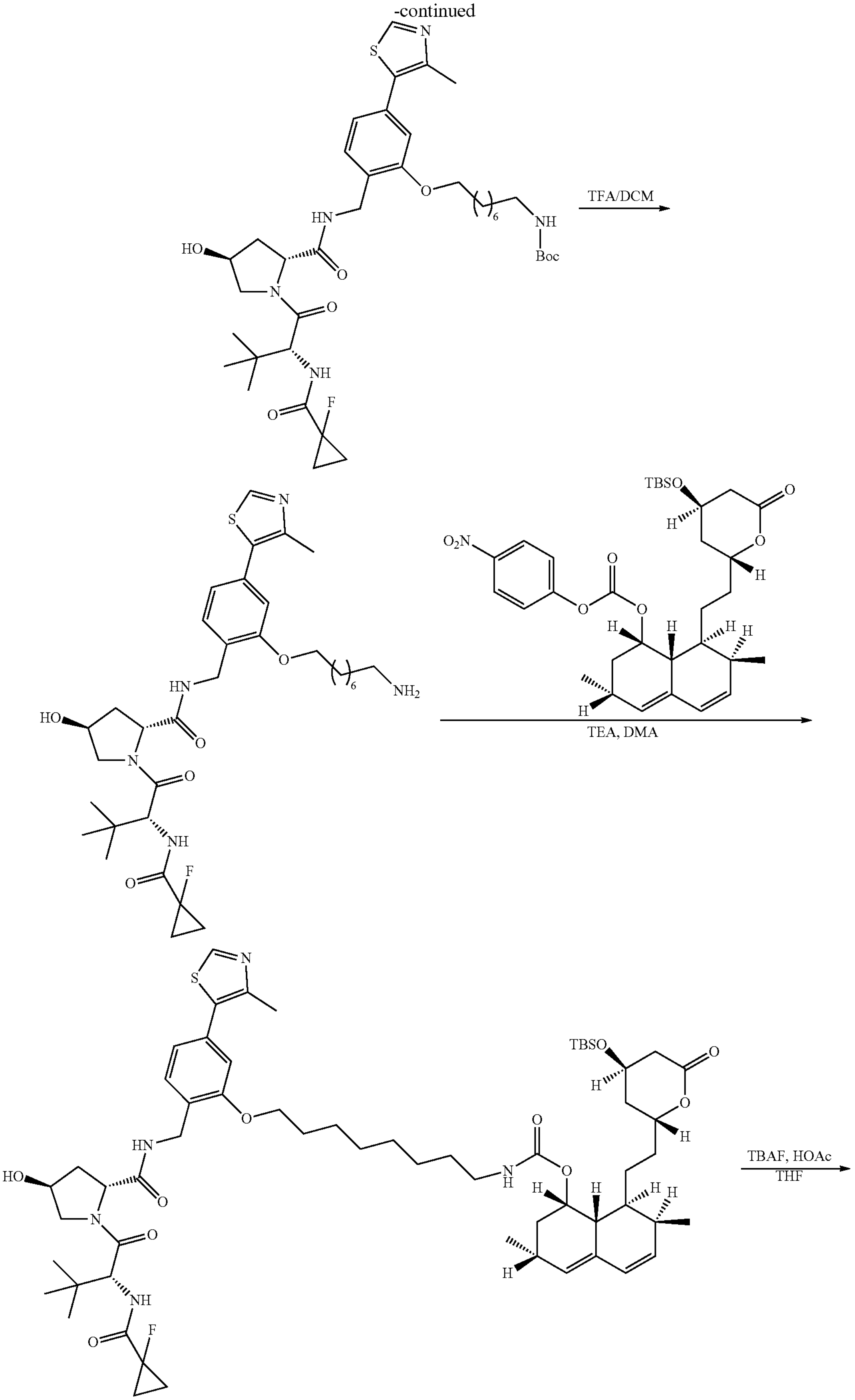

-continued

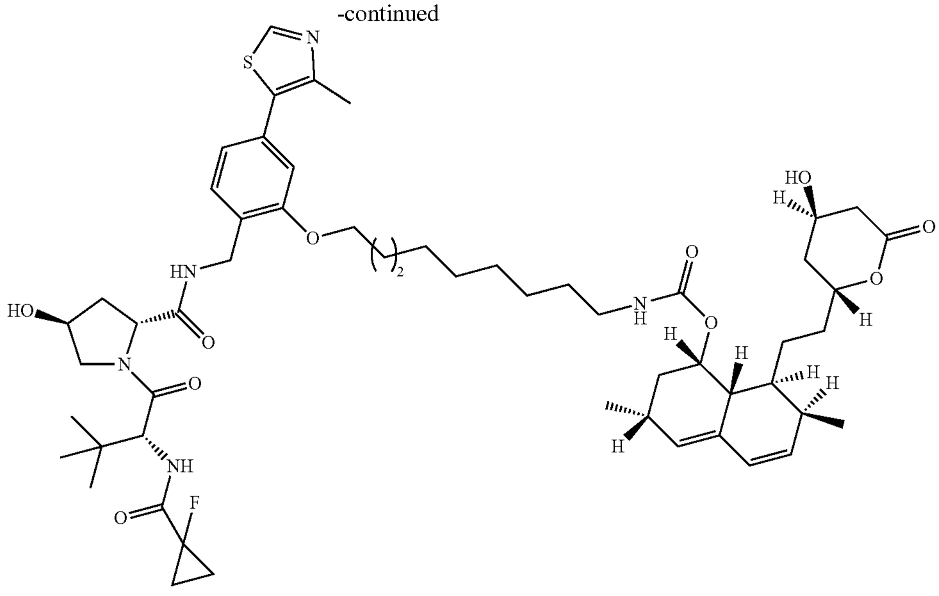

Compound 165

According to the above reaction scheme, in a manner similar to the other examples, obtained the titled compound (16 mg, 15.66 μmol, 9.75% yield, 98.9% purity) as a white solid. MS $(M+H)^+=1006.3$ $^1H$ NMR (400 MHz, DMSO-$d_6$) δ=8.98 (s, 1H), 8.49 (br t, J=5.3 Hz, 1H), 7.40 (d, J=7.6 Hz, 1H), 7.31-7.26 (m, 1H), 7.01-6.92 (m, 3H), 5.90 (br d, J=9.5 Hz, 1H), 5.78-5.71 (m, 1H), 5.45 (br s, 1H), 5.17 (t, J=3.5 Hz, 2H), 5.03 (br s, 1H), 4.59 (br d, J=9.3 Hz, 1H), 4.54-4.45 (m, 2H), 4.37-4.25 (m, 2H), 4.23-4.14 (m, 1H), 4.08 (br d, J=3.3 Hz, 1H), 4.03 (br t, J=6.2 Hz, 2H), 3.67-3.58 (m, 2H), 3.30 (br s, 2H), 2.99-2.90 (m, 2H), 2.63 (br d, J=4.5 Hz, 1H), 2.59 (br d, J=4.5 Hz, 1H), 2.45 (s, 4H), 2.40 (br d, J=1.0 Hz, 1H), 2.37-2.30 (m, 3H), 2.25-2.19 (m, 1H), 2.12-2.05 (m, 1H), 1.95-1.89 (m, 1H), 1.83 (br s, 2H), 1.79-1.71 (m, 3H), 1.67-1.55 (m, 3H), 1.42-1.25 (m, 12H), 1.03 (br d, J=7.3 Hz, 3H), 0.96 (s, 9H), 0.83 (br d, J=6.9 Hz, 3H).

Example 166. Synthesis of (1S,3R,7S,8S,8aR)-8-(2-((2R,4R)-4-hydroxy-6-oxotetrahydro-2H-pyran-2-yl)ethyl)-3,7-dimethyl-1,2,3,7,8,8a-hexahydronaphthalen-1-yl (9-(2-(((2S,4R)-1-((S)-2-(1-fluorocyclopropane-1-carboxamido)-3,3-dimethylbutanoyl)-4-hydroxypyrrolidine-2-carboxamido)methyl)-5-(4-methylthiazol-5-yl)phenoxy)nonyl)carbamate (Compound 166)

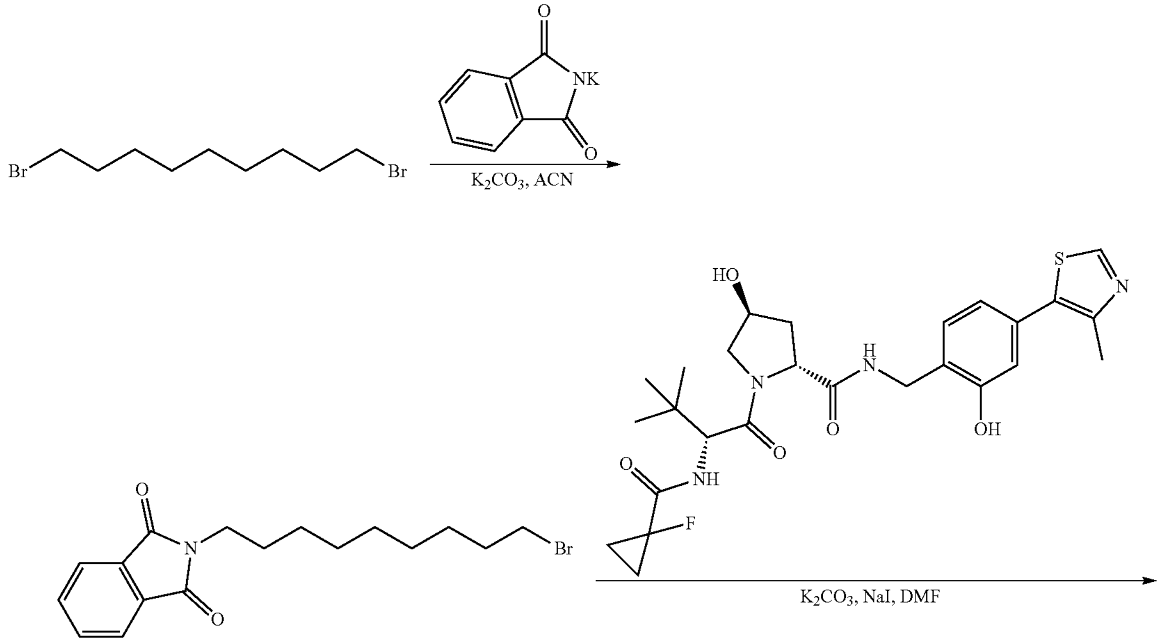

-continued
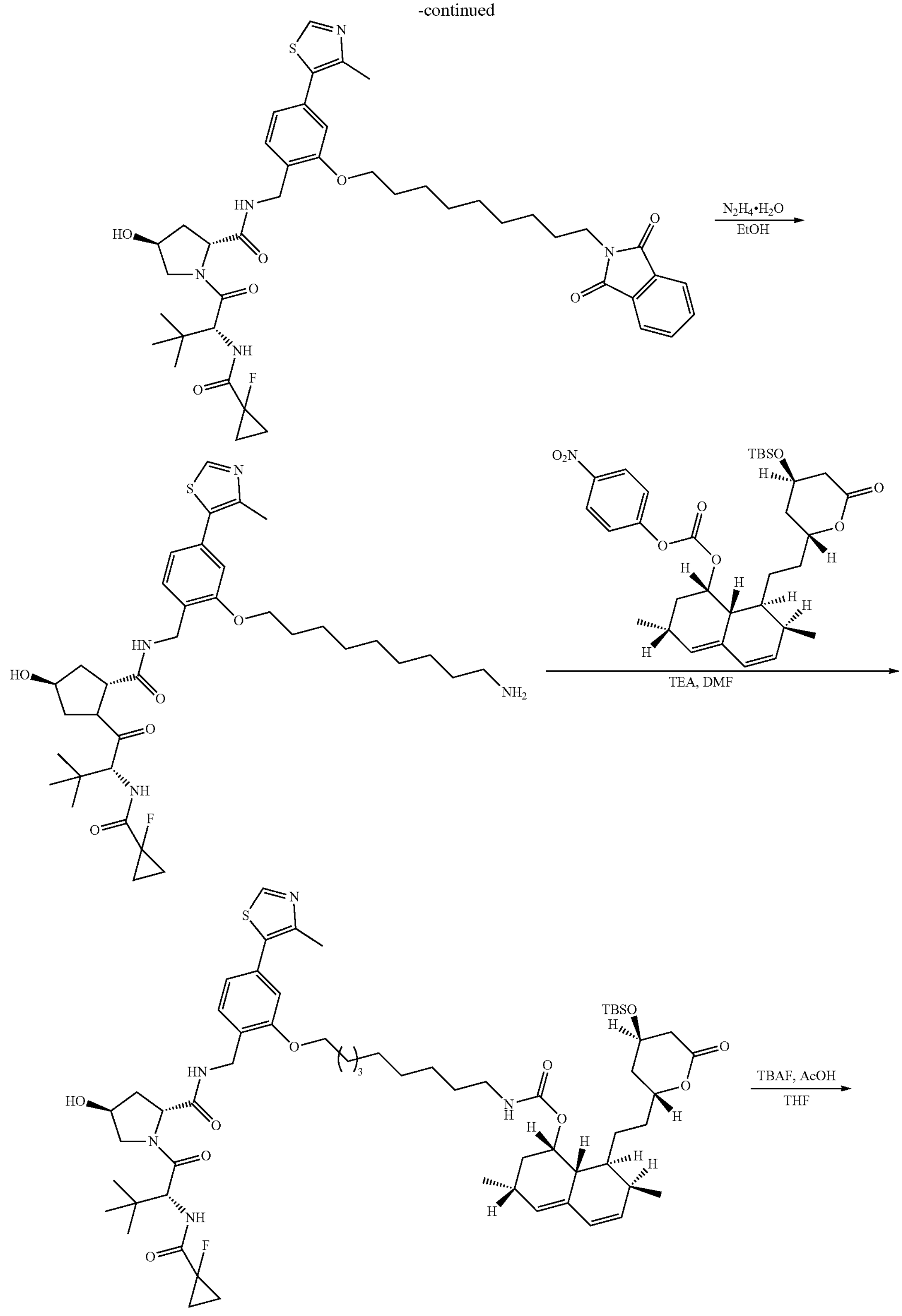

-continued

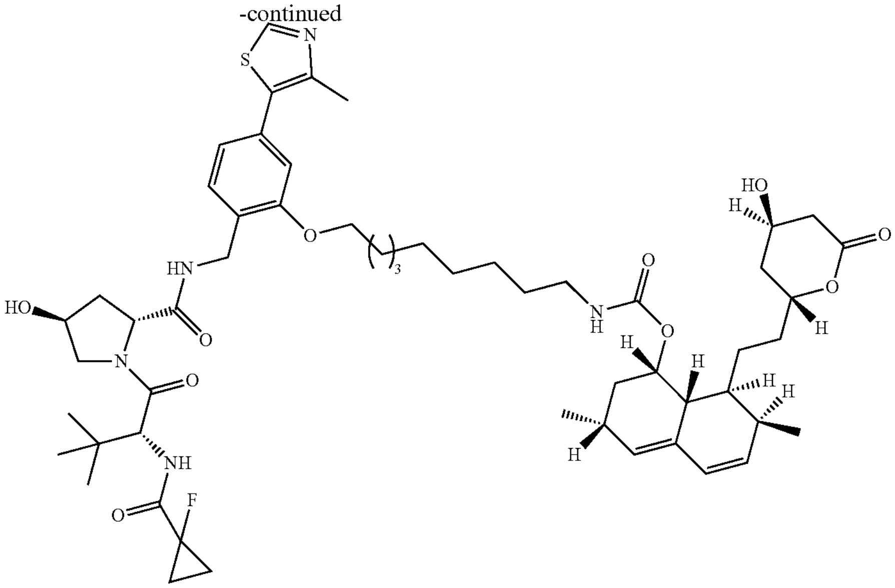

Compound 166

According to the above reaction scheme, in a manner similar to the other examples, obtained the titled compound (101.2 mg, 97.20 μmol, 33.22% yield, 98% purity) as a white solid. MS $(M+H)^+$=1020.7

$^1$H NMR (400 MHz, DMSO-$d_6$) δ=8.98 (s, 1H), 8.49 (br t, J=5.4 Hz, 1H), 7.40 (br d, J=7.8 Hz, 1H), 7.29 (br d, J=7.7 Hz, 1H), 7.05-6.91 (m, 3H), 5.90 (br d, J=9.3 Hz, 1H), 5.80-5.71 (m, 1H), 5.45 (br s, 1H), 5.27-5.10 (m, 2H), 5.04 (br d, J=1.2 Hz, 1H), 4.59 (br d, J=9.2 Hz, 1H), 4.55-4.44 (m, 2H), 4.38-4.25 (m, 2H), 4.23-4.15 (m, 1H), 4.12-4.00 (m, 3H), 3.70-3.57 (m, 2H), 3.01-2.87 (m, 2H), 2.64-2.57 (m, 2H), 2.45 (s, 3H), 2.41 (br s, 1H), 2.35 (br d, J=7.9 Hz, 3H), 2.22 (br d, J=10.1 Hz, 1H), 2.13-2.04 (m, 1H), 1.97-1.61 (in, 10H), 1.47-1.32 (m, 8H), 1.22 (br d, J=8.7 Hz, 8H), 1.04 (br d, J=6.8 Hz, 3H), 0.96 (br s, 9H), 0.83 (br d, J=6.6 Hz, 3H).

Example 167. Synthesis of (1S,3R,7S,8S,8aR)-8-(2-((2R,4R)-4-hydroxy-6-oxotetrahydro-2H-pyran-2-yl)ethyl)-3,7-dimethyl-1,2,3,7,8,8a-hexahydronaphthalen-1-yl (10-(2-(((2S,4R)-1-((S)-2-(1-fluorocyclopropane-1-carboxamido)-3,3-dimethylbutanoyl)-4-hydroxypyrrolidine-2-carboxamido)methyl)-5-(4-methylthiazol-5-yl)phenoxy)decyl)carbamate (Compound 167)

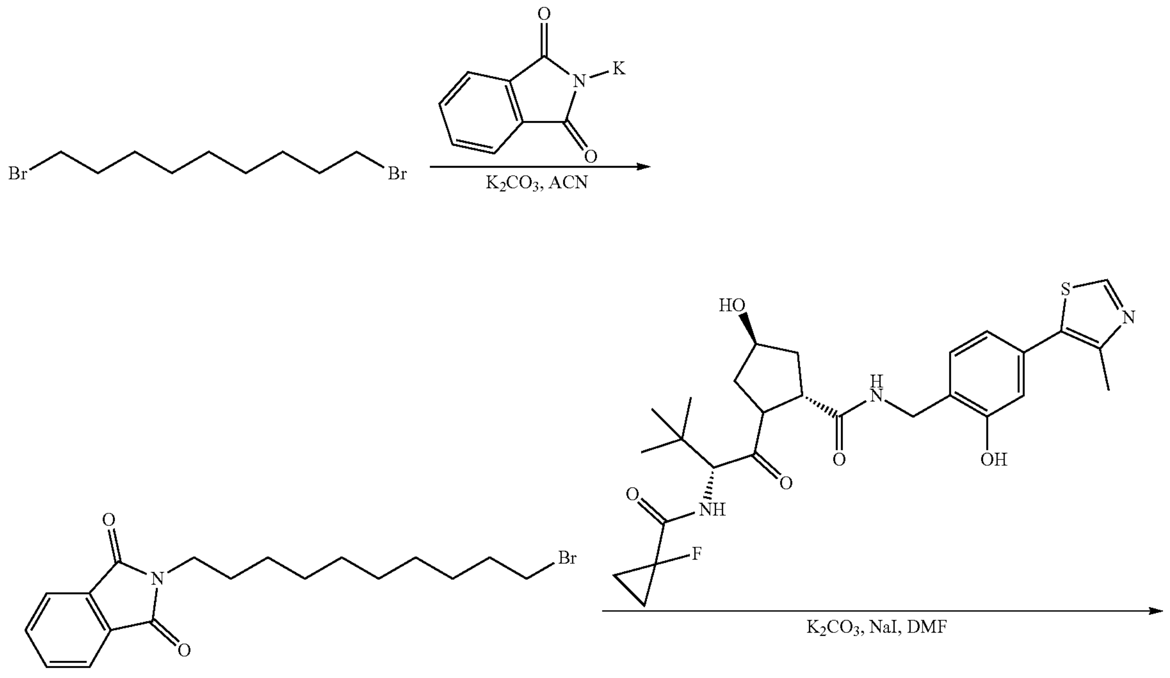

-continued
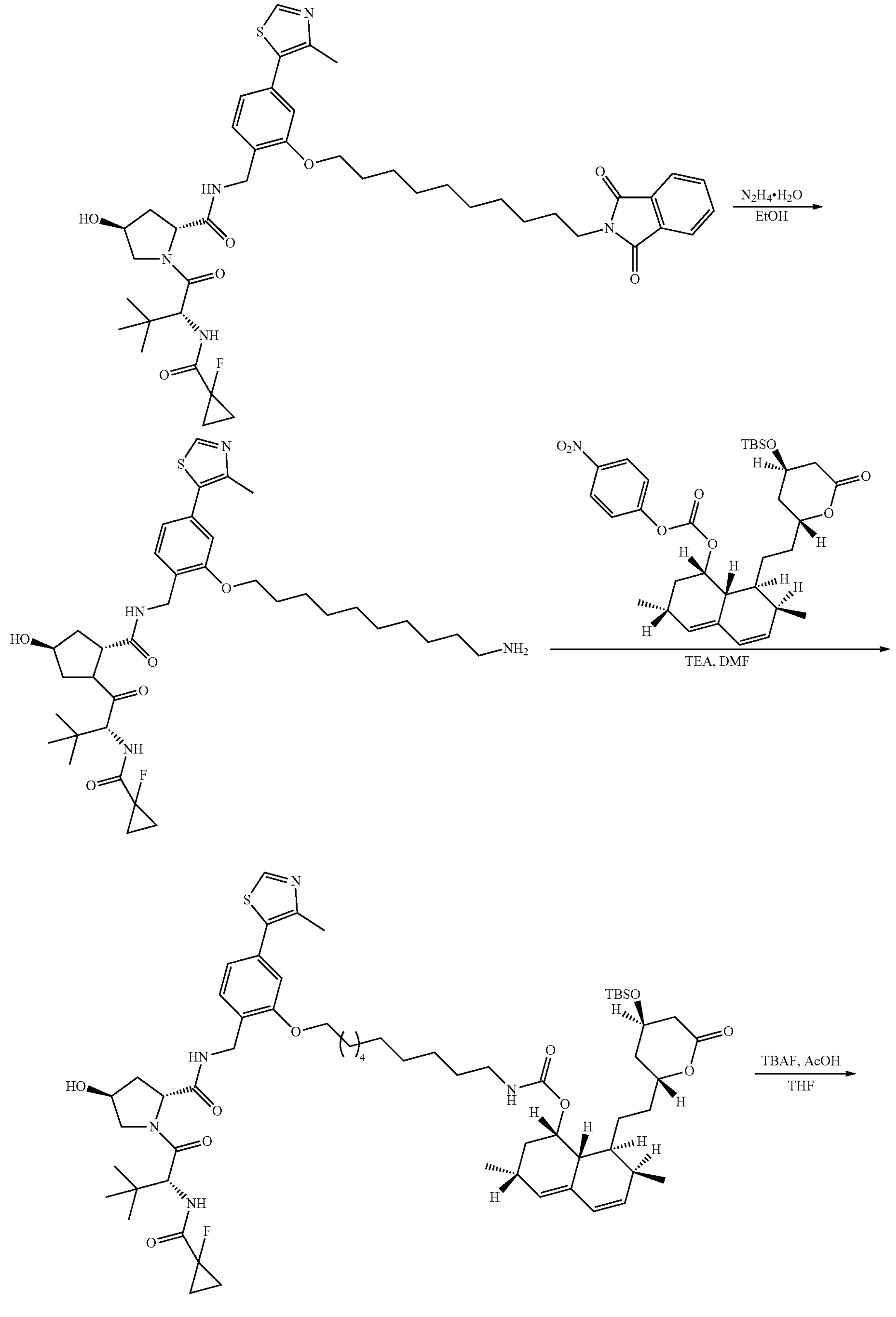

-continued

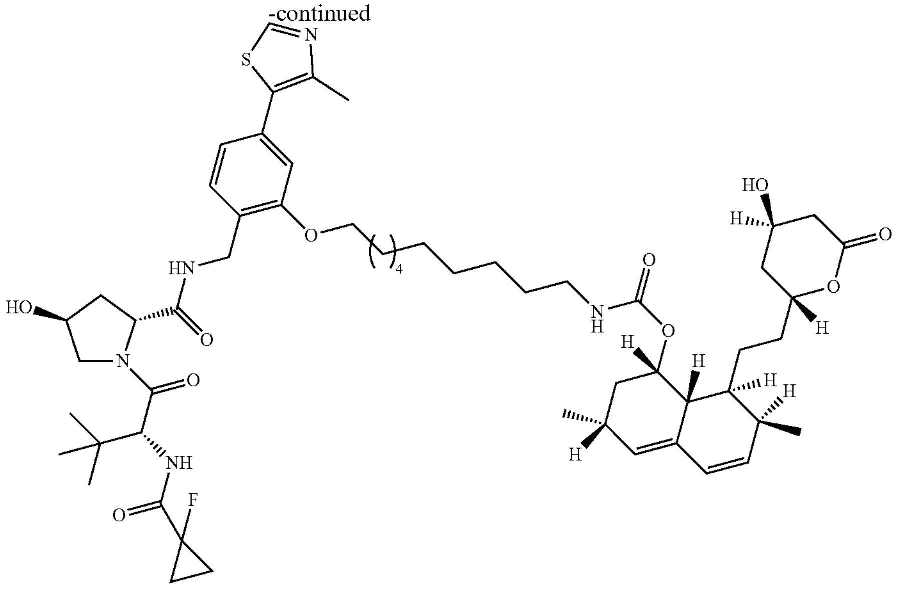

Compound 167

According to the above reaction scheme, in a manner similar to the other examples, obtained the titled compound (151.9 mg, 145.39 μmol, 37.70% yield, 98% purity) as a white solid. MS $(M+H)^+$=1033.9

$^1$H NMR (400 MHz, DMSO-$d_6$) δ=8.98 (s, 1H), 8.48 (t, J=5.9 Hz, 1H), 7.40 (d, J=7.7 Hz, 1H), 7.29 (dd, J=2.7, 9.0 Hz, 1H), 7.00-6.92 (m, 3H), 5.90 (d, J=9.4 Hz, 1H), 5.75 (dd, J=5.9, 9.4 Hz, 1H), 5.45 (s, 1H), 5.17 (t, J=3.8 Hz, 2H), 5.04 (d, J=3.1 Hz, 1H), 4.59 (d, J=9.3 Hz, 1H), 4.54-4.45 (m, 2H), 4.35 (s, 1H), 4.32-4.25 (m, 1H), 4.22-4.15 (m, 1H), 4.10-4.07 (m, 1H), 4.03 (t, J=6.3 Hz, 2H), 3.67-3.58 (m, 2H), 3.01-2.87 (m, 2H), 2.68-2.62 (m, 1H), 2.58 (d, J=4.6 Hz, 1H), 2.45 (s, 3H), 2.41 (d, J=1.8 Hz, 1H), 2.38-2.32 (m, 3H), 2.22 (d, J=12.0 Hz, 1H), 2.12-2.05 (m, 1H), 1.96-1.88 (m, 1H), 1.85-1.81 (m, 2H), 1.79-1.62 (m, 6H), 1.61-1.55 (m, 1H), 1.46-1.41 (m, 2H), 1.41-1.37 (m, 2H), 1.37-1.32 (m, 4H), 1.29-1.22 (m, 10H), 1.06-1.00 (m, 3H), 0.96 (s, 9H), 0.83 (d, J=7.0 Hz, 3H)

Example 168. Synthesis of (1S,3R,7S,8S,8aR)-8-(2-((2R,4R)-4-hydroxy-6-oxotetrahydro-2H-pyran-2-yl)ethyl)-3,7-dimethyl-1,2,3,7,8,8a-hexahydronaphthalen-1-yl (3-(1-(2-(2-(((2R,4S)-1-((R)-2-(1-fluorocyclopropane-1-carboxamido)-3,3-dimethylbutanoyl)-4-hydroxypyrrolidine-2-carboxamido)methyl)-5-(4-methylthiazol-5-yl)phenoxy)acetyl)piperidin-4-yl)propyl)carbamate (Compound 168)

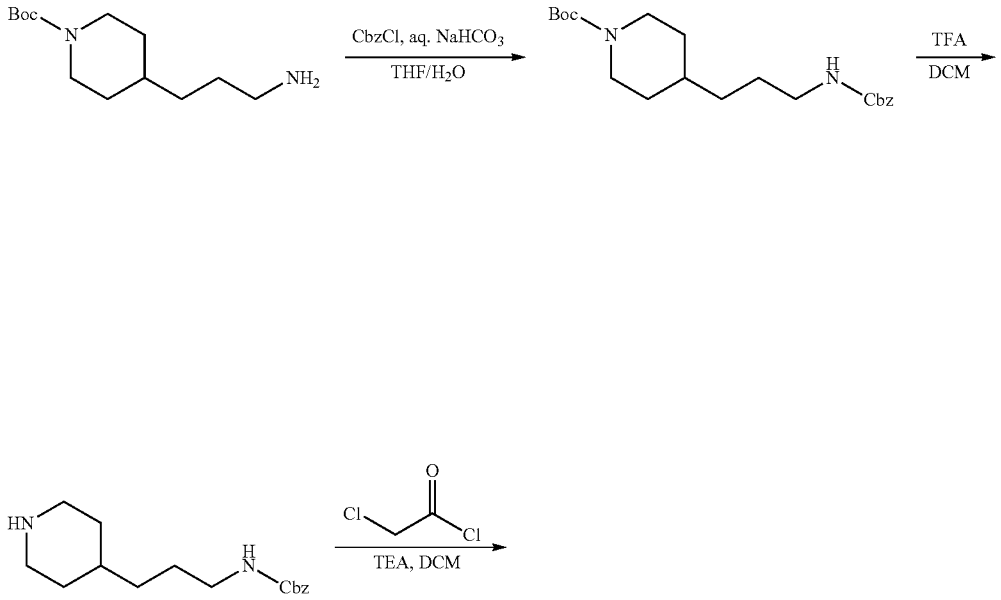

-continued
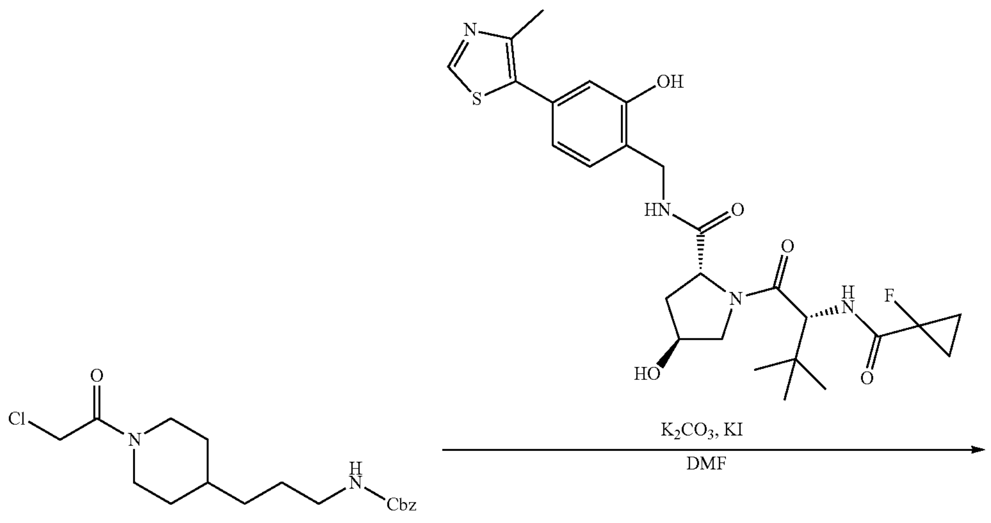
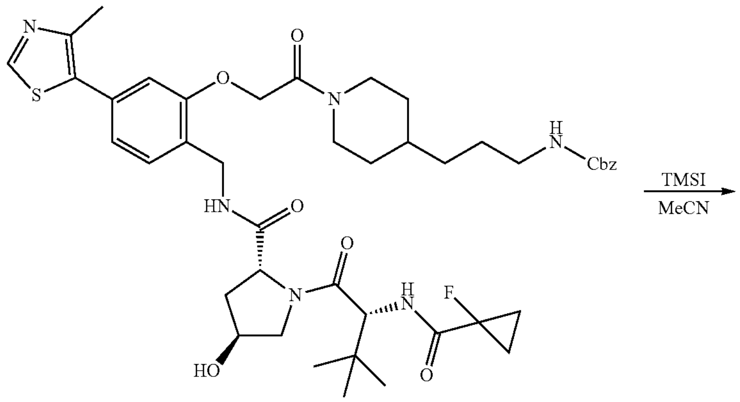
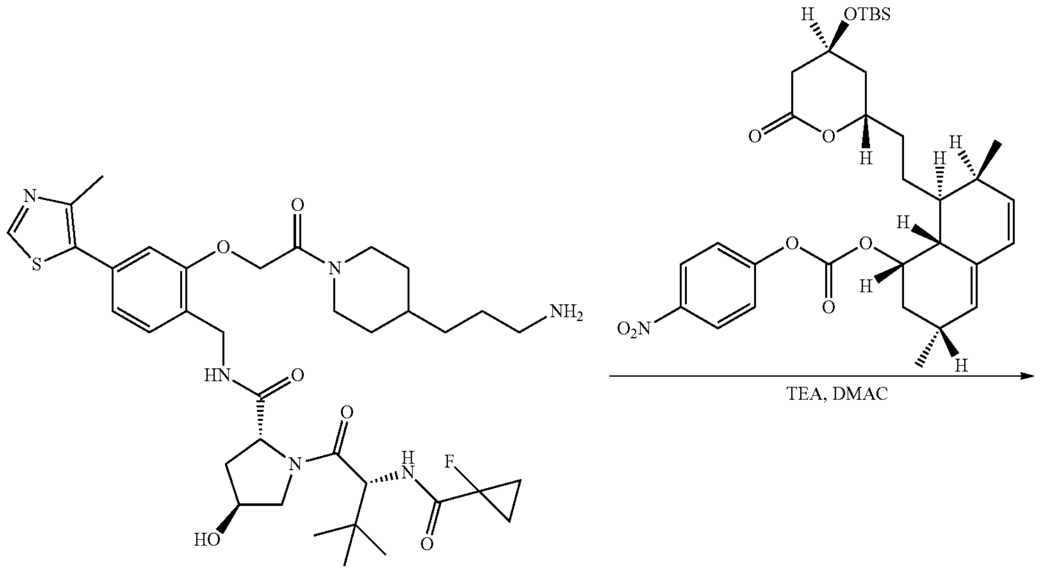

-continued

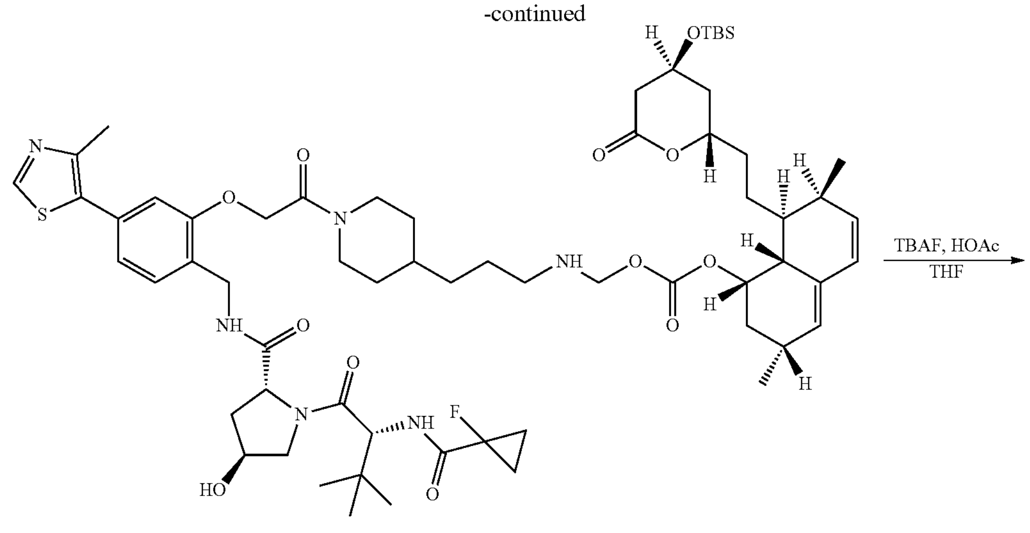

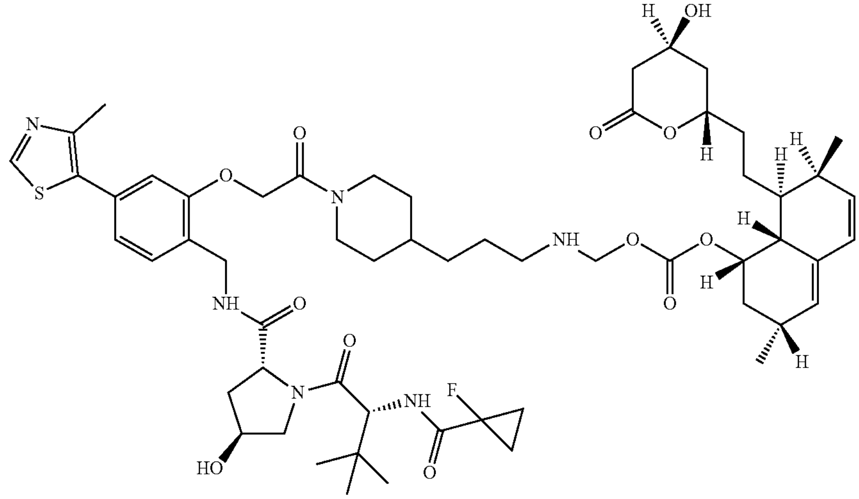

Compound 168

According to the above reaction scheme, in a manner similar to the other examples, obtained the titled compound (113.1 mg, 103.37 μmol, 46.74% yield, 97% purity) as a white solid. MS $(M+H)^+$=1061.7

$^1$H NMR (400 MHz, DMSO-$d_6$) δ 8.98 (s, 1H), 8.63-8.54 (m, 1H), 7.41 (d, J=7.7 Hz, 1H), 7.31-7.25 (m, 1H), 7.02-6.94 (m, 3H), 5.95-5.86 (m, 1H), 5.80-5.74 (m, 1H), 5.50-5.44 (m, 1H), 5.25-5.15 (m, 2H), 5.06-4.93 (m, 3H), 4.60 (d, J=9.3 Hz, 1H), 4.54-4.47 (m, 2H), 4.37-4.25 (m, 4H), 4.12-4.07 (m, 1H), 3.90-3.80 (m, 1H), 3.71-3.57 (m, 2H), 3.05-2.89 (m, 3H), 2.64-2.55 (m, 2H), 2.43 (s, 3H), 2.42-2.31 (m, 4H), 2.27-2.20 (m, 1H), 2.12-2.06 (m, 1H), 1.95-1.79 (m, 4H), 1.73-1.60 (m, 5H), 1.48-1.20 (m, 11H), 1.18-1.12 (m, 2H), 1.04 (d, J=7.3 Hz, 3H), 0.96 (s, 9H), 0.85 (d, J=6.9 Hz, 3H)

Example 169. Synthesis of (1R,3S,7R,8R,8aS)-8-(2-((2R,4R)-4-hydroxy-6-oxotetrahydro-2H-pyran-2-yl)ethyl)-3,7-dimethyl-1,2,3,7,8,8a-hexahydronaphthalen-1-yl (3-(4-(2-(2-(((2S,4R)-1-((S)-2-(1-fluorocyclopropane-1-carboxamido)-3,3-dimethylbutanoyl)-4-hydroxypyrrolidine-2-carboxamido)methyl)-5-(4-methylthiazol-5-yl)phenoxy)ethyl)-1H-1,2,3-triazol-1-yl)propyl) carbamate (Compound 169)

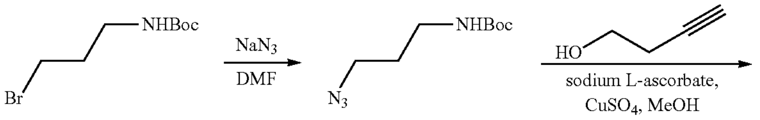

-continued
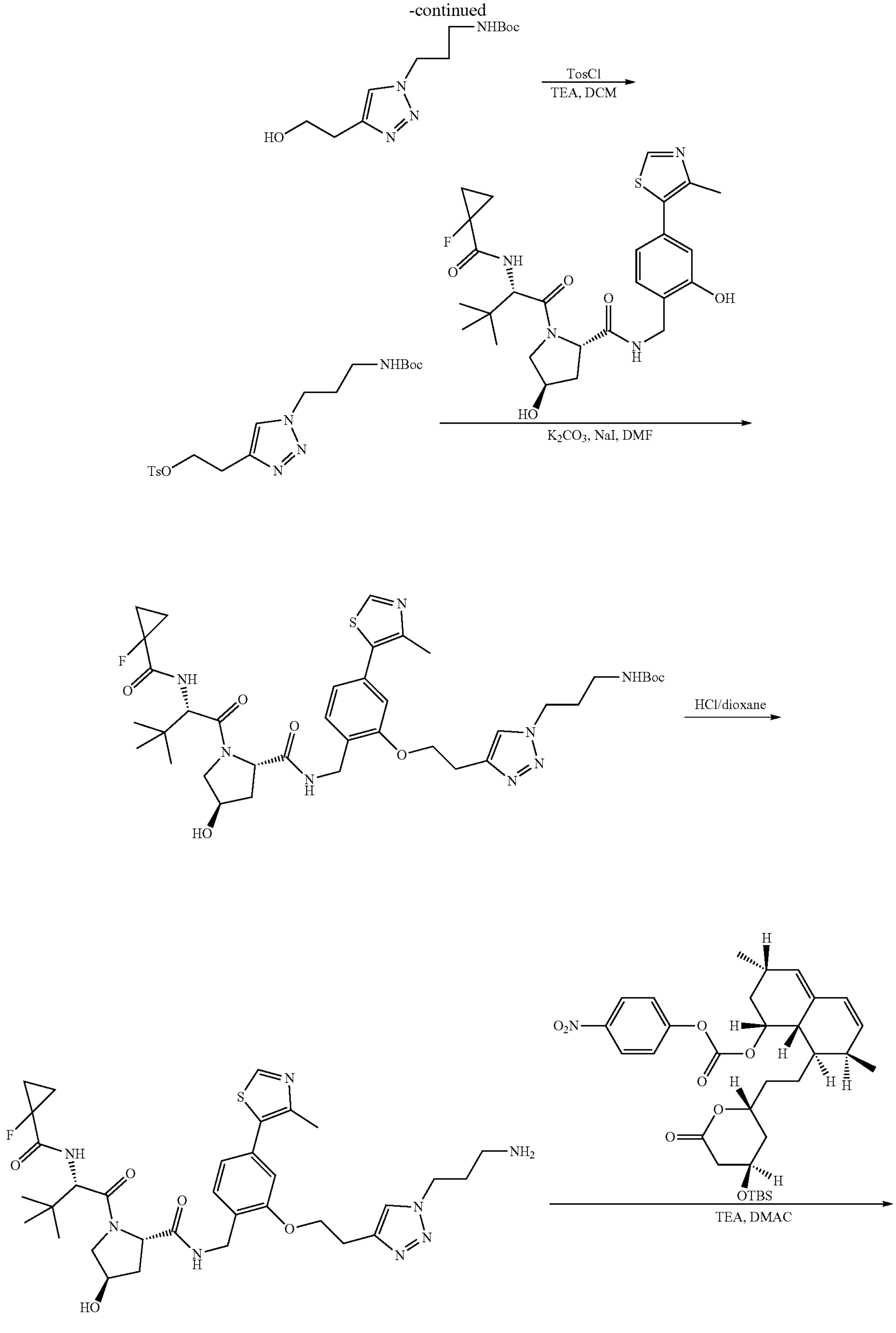

-continued

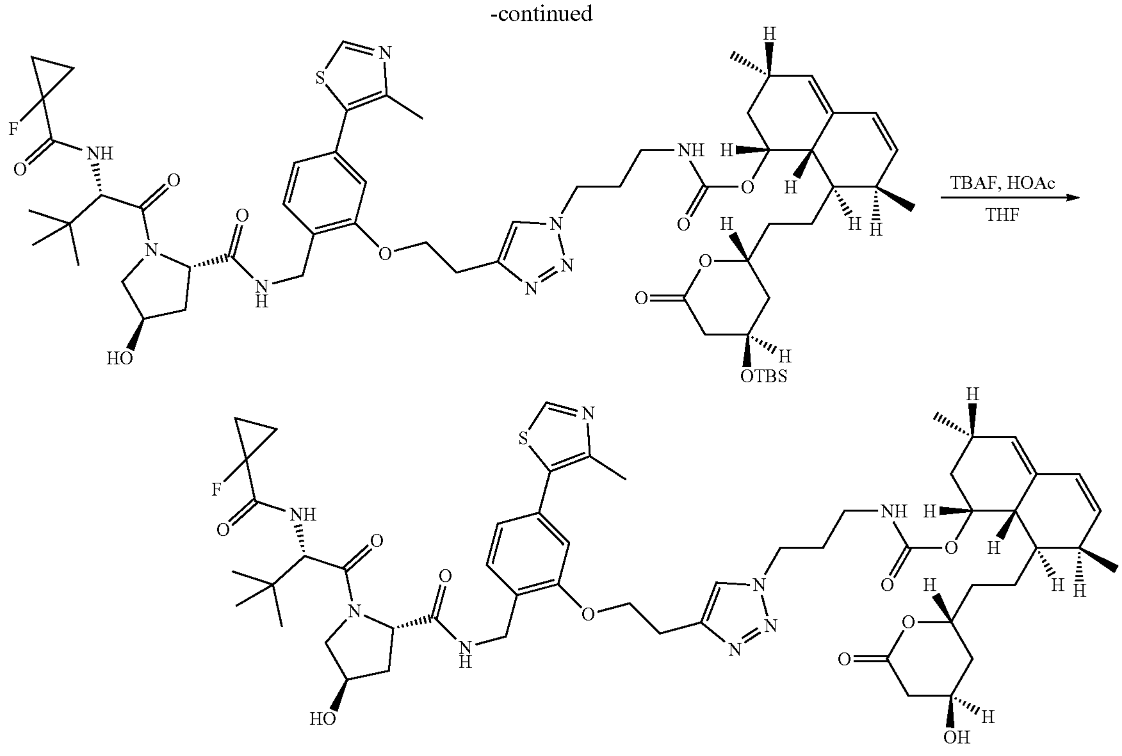

Compound 169

According to the above reaction scheme, in a manner similar to the other examples, obtained the titled compound (104.9 mg, 98.67 μmol, 37.68% yield, 97% purity) as white solid. MS $(M+H)^+$=1031.7

$^1$H NMR (400 MHz, DMSO-$d_6$) δ=8.99 (s, 1H), 8.51 (t, J=6.0 Hz, 1H), 7.99 (s, 1H), 7.41 (d, J=7.8 Hz, 1H), 7.30 (d, J=9.4 Hz, 1H), 7.22-7.16 (m, 1H), 7.03 (s, 1H), 6.96 (d, J=7.7 Hz, 1H), 5.92 (d, J=9.8 Hz, 1H), 5.82-5.73 (m, 1H), 5.48 (s, 1H), 5.20-5.15 (m, 2H), 5.10-5.01 (m, 1H), 4.60 (d, J=8.8 Hz, 1H), 4.54-4.50 (m, 1H), 4.36-4.35 (m, 1H), 4.31-4.24 (m, 4H), 4.18-4.11 (m, 1H), 4.08-4.04 (m, 1H), 3.69-3.56 (m, 2H), 3.13 (t, J=6.1 Hz, 2H), 3.02-2.95 (m, 2H), 2.65-2.55 (m, 1H), 2.46 (s, 3H), 2.40-2.35 (m, 3H), 2.25 (d, J=11.0 Hz, 1H), 2.12-2.05 (m, 1H), 1.97-1.82 (m, 6H), 1.78 (d, J=13.4 Hz, 1H), 1.74-1.64 (m, 2H), 1.62-1.45 (m, 3H), 1.41-1.17 (m, 6H), 1.05 (d, J=7.2 Hz, 3H), 0.96 (s, 9H), 0.85 (d, J=6.8 Hz, 3H).

Comparative Example 1. Synthesis of (3R,5R)-7-(3-(3-(3-(1-(14-((2-(2,6-dioxopiperidin-3-yl)-1,3-dioxoisoindolin-4-yl)amino)-3,6,9,12-tetraoxatetradecyl)-1H-1,2,3-triazol-4-yl)propoxy)phenyl)-2-(4-fluorophenyl)-5-isopropyl-4-(phenylcarbamoyl)-1H-pyrrol-1-yl)-3,5-dihydroxyheptanoic acid (Comparative Compound 1)

Comparative Compound 1 is a compound described by Formula 4 in WO 2019/109415 A1. It was synthesized according to the preparation method described in the document.

Comparative Example 2. (3R,5R)-7-(3-(3-((5-(1-(2-(2-(2-((2-(2,6-dioxopiperidin-3-yl)-1,3-dioxoisoindolin-4-yl)amino)ethoxy)ethoxy)ethyl)-1H-1,2,3-triazol-4-yl)pentyl)oxy)phenyl)-2-(4-fluorophenyl)-5-isopropyl-4-(phenylcarbamoyl)-1H-pyrrol-1-yl)-3,5-dihydroxyheptanoic acid (Comparative Compound 2)

Comparative Compound 2 is a compound described by Formula 7 in WO 2019/109415 A1. It was synthesized according to the preparation method described in the document.

Experimental Examples

1. Culture of HepG2 Cell Line

HepG2, a human liver cancer cell line, was purchased from the Korea Cell Line Bank (KCLB), Seoul, Korea. The passage in cell culture was maintained at P105 to P110.

For cell counting, cell counter (Thermo Fisher Scientific Inc., Catalog #AMQAX1000) and 0.4% trypan blue solution were used.

For cell culture, DMEM (Gibco, Cat. No. 1195-65; Lot. No. 2085318), FBS (Gibco, Cat. No. 16000-044; Lot. No. 2097593), Penicillin/Streptomycin (PS) (Gibco, Cat. No. 15140-122; Lot. No. 2058855), 100 $mm^2$ cell culture dish (SPL, Cat. No. 20100), 150 $mm^2$ cell culture dish (SPL, Cat. No. 20150), 12-well culture plate (SPL, Cat. No. 30012), PBS pH 7.4 (Gibco, Cat. No. 10010-023; Lot. No. 2085080), TrypLE™ Express (Gibco, Cat. No. 12605-010; Lot No. 2070638), Counting Chamber (Hematocytometer) (Hirschmann, Cat. No. 8100204), and 0.4% Trypan Blue Solution (DYNEBIO, Cat. No. CBT3710; Lot. No. 20190723) were used.

2. Treatment of Compounds of the Present Invention

The compounds of the present invention were completely dissolved in DMSO and used in the experiment. $2\times10^5$ cells were seeded for each well of a 12-well plate (SPL), and the cells were cultured in the culture medium in a total volume of 2 ml. Each of the compounds of the present invention and comparative compounds was diluted three folds from the highest concentration of 3 μM to the lowest concentration in 10 points and treated for 18 hours.

Each of the compounds the present invention and comparative compounds was diluted three folds from the highest concentration of 3 μM to the lowest concentration of 100 nM in 10 points and was treated for 18 hours.

3. Western Blotting

For SDS-PAGE and Western blotting, 1×RIPA lysis buffer (Rockland, Cat. No. MB-030-0050; Lot no. 39751), 100× Protease Inhibitor Cocktail (Quartett, Cat. No. PPI1015; Lot no. PCO50038424), Pierce™ BCA protein assay kit (ThermoScientific, Cat. No. 23225; Lot no. UC276876), albumin standard (ThermoScientific, Cat. No. 23209; Lot no. UB269561), 4-15% Mini-PROTEAN TGX stain-free gel (Bio-rad, Cat. No. 4568085; Lot no. L007041B), 10× Tris/Glycine/SDS buffer (Bio-rad, Cat. No. 1610732; Lot no. 10000044375B); 10×TBS (Bio-rad, Cat. No. 1706435; Lot no. 1000045140B), 10% Tween 20 (Cat. No. 1610781; Lot no. L004152B), Color protein standard broad range (NEB, Cat. No. P7719S; Lot no. 10040349), 4× Laemmli sample buffer (Bio-rad, Cat. No. 1610747; Lot no. L004133B), β-mercaptoethanol (Sigma-Aldrich, Cat. No. M3148; Lot no. 60-24-2), SuperBlock™ T20 (TBS) blocking buffer (ThermoScientific, Cat. No. 37536; Lot no. UC282578), 1M sodium azide solution (Sigma-Aldrich, Cat. No. 08591-1 mL-F; Lot no. BCBV4989), α-Rabbit pAb to Ms IgG (abcam, Cat. No. ab97046; Lot no. GR3252115-1), α-Goat pAb to Rb IgG (CST, Cat. No. 7074S; Lot no. 28), α-GAPDH (abcam, Cat. No. ab8245), α-HMGCR (GeneTex, Cat. No. GTX54088; Lot no. 821903509), ECL™ Prime western blotting reagents (GE Healthcare, Cat. No. RPN2232; Lot no. 17001655), Ponceau S solution (Sigma-Aldrich, Cat. No. P7170; Lot no. SLBV4112), Difco™ Skim milk (BD, Cat. No. 232100; Lot no. 8346795), and iBlot® 2 NC Regular stacks (Invitrogen, Cat. No. IB23001; Lot no. 2NR110619-02), were used.

For cell harvesting, the cells were first separated from the plate using trypsin and then washed with the medium and PBS. Specifically, the medium was suctioned off and washed with 1 mL of PBS, and PBS was suctioned off. The cells were treated with 0.5 mL TrypLE™ Express at 37° C. for 7 minutes to separate the cells, and then 0.5 mL of complete medium was added to collect 1 mL of cell culture solution. Then, 1 mL of the cell collection solution was centrifuged at 8,000 rpm for 120 seconds, and the supernatant was removed. After washing with 0.2 mL of PBS, the PBS was removed.

For cell lysis, a lysis buffer was added and cell debris was removed to obtain a cell lysate. Specifically, the cells were treated with 70 μL of 1×RIPA buffer containing a protease inhibitor and incubated for 30 minutes on ice. Then, the cells were centrifuged at 4° C. and 15,000 rpm for 10 minutes to obtain a cell lysate.

Then, a standard curve was obtained using the BCA assay, and the protein mass in the lysate was quantified by substituting the curve. The mixture was incubated at 37° C. for 30 minutes using 20 μL of standard or sample solution, and 200 μL of BCA or Bradford solution, and measured at 562 nm absorbance. Samples were prepared by adding 4× sample buffer so that the quantity of protein added to each well was 15 μg.

Sodium dodecyl sulfate polyacrylamide gel electrophoresis (SDS-PAGE) was performed by setting a running time of 100 minutes at 120 V on a 4-15% Mini-PROTEAN TGX stain-free gel (15 well). Transferring was performed on iBlot® 2 NC Mini stacks at P0 mode of the dry blotting system. After staining using Ponceau S solution, blocking was performed for 1 hour with a blocking buffer (Thermo). After washing with 1×TBS containing 0.05% Tween20, the product was reacted at 4° C. for 16 hours with anti-HMGCR antibody (1:500) in skim milk or anti-GAPDH (abcam) antibody (1:20000) in 1×TBS-T as the primary antibody.

After washing three times for 10 minutes with 1×TBS containing 0.05% Tween20, the product was reacted at room temperature for 1 hour with anti-mouse antibody (abcam) (1:10000) or anti-rabbit antibody (CST) (1:5000) in 1×TBS-T as a secondary antibody. Then, after washing three times for 10 minutes with 1×TBS containing 0.05% Tween 20, the product was detected with an ECL working solution (1:1).

To analyze the results, an image analyzer (GE) was used to obtain final blot data. The ratio of HMG-CoA reductase to GAPDH for each sample was calculated using the ImageQuant TL (ver. 8.2.0) program. Each calculated value was entered into each cell of the Graphpad Prism 9 program, and the graph was automatically calculated to confirm the $D_{50}$ value corresponding to the protein degradation ability (Grade A: $DC_{50}$ is 50 nM or less; B: 500 nM or less; C: more than 500 nM).

4. Confirmation of HMGCR Degradability of the Compounds of the Present Invention As a result of the experiment, $DC_{50}$ values for the compounds of the compounds of the present invention were measured as shown in the following table.

TABLE 2

| No. | $DC_{50}$ | No. | $DC_{50}$ |
|---|---|---|---|
| 1 | C | 2 | A |
| 3 | A | 4 | A |
| 5 | A | 6 | A |
| 7 | C | 8 | A |
| 9 | A | 10 | A |
| 11 | A | 12 | A |
| 13 | C | 14 | B |
| 15 | A | 16 | A |
| 17 | A | 18 | A |
| 19 | A | 20 | A |
| 21 | A | 22 | A |
| 23 | A | 24 | A |
| 25 | A | 26 | A |
| 27 | A | 28 | A |
| 29 | B | 30 | B |
| 31 | A | 32 | A |
| 33 | A | 34 | C |
| 35 | C | 36 | A |
| 37 | A | 38 | A |
| 39 | C | 40 | A |
| 41 | A | 42 | A |
| 43 | A | 44 | A |
| 45 | C | 46 | A |
| 47 | A | 48 | A |
| 49 | A | 50 | A |
| 51 | A | 52 | A |
| 53 | A | 54 | A |
| 55 | A | 56 | A |
| 57 | A | 58 | B |
| 59 | B | 60 | B |
| 61 | A | 62 | B |
| 63 | A | 64 | A |

TABLE 2-continued

| No. | $DC_{50}$ | No. | $DC_{50}$ |
|---|---|---|---|
| 65 | A | 66 | A |
| 67 | A | 68 | A |
| 69 | A | 70 | A |
| 71 | A | 72 | A |
| 73 | A | 74 | A |
| 75 | A | 76 | A |
| 77 | A | 78 | A |
| 79 | A | 80 | A |
| 81 | A | 82 | A |
| 83 | A | 84 | A |
| 85 | A | 86 | A |
| 87 | A | 88 | A |
| 89 | A | 90 | A |
| 91 | A | 92 | A |
| 93 | A | 94 | A |
| 95 | B | 96 | B |
| 97 | B | 98 | A |
| 99 | A | 100 | A |
| 101 | A | 102 | A |
| 103 | A | 104 | A |
| 105 | A | 106 | A |
| 107 | A | 114 | A |
| 115 | A | 120 | B |
| 121 | A | 124 | A |
| 125 | B | 126 | A |
| 127 | B | 128 | A |
| 129 | A | 134 | B |
| 135 | A | 138 | A |
| 139 | B | 142 | B |
| 143 | A | 144 | B |
| 145 | A | 146 | A |
| 147 | A | 152 | A |
| 153 | A | 154 | C |
| 155 | A | 156 | A |
| 157 | A | 158 | A |
| 159 | X | 160 | A |
| 161 | A | 162 | A |
| 163 | X | 164 | X |
| 165 | A | 166 | A |
| 167 | A | 168 | A |
| 169 | A | | |

As a result, it was confirmed exemplary compounds of the present invention had remarkably excellent HMGCR degradability in hepatocyte as compared to not only a negative control group (Compounds 1, 7, 13, 39, 45) that lack the E3 ubiquitin ligase ligand, but also the kwon PROTAC compounds which have atorvastatin moiety as protein target binder described in WO2019/109415 A1 (Comparative Examples 1 and 2) (see FIGS. 1 to 10).

The contents of all references, patents, pending patent applications and published patents, cited throughout this application are hereby expressly incorporated by reference.

Those skilled in the art will recognize, or be able to ascertain using no more than routine experimentation, many equivalents to the specific embodiments of the disclosure described herein. Such equivalents are intended to be encompassed by the following claims. It is understood that the detailed examples and embodiments described herein are given by way of example for illustrative purposes only, and are in no way considered to be limiting to the disclosure. Various modifications or changes in light thereof will be suggested to persons skilled in the art and are included within the spirit and purview of this application and are considered within the scope of the appended claims. For example, the relative quantities of the ingredients may be varied to optimize the desired effects, additional ingredients may be added, and/or similar ingredients may be substituted for one or more of the ingredients described. Additional advantageous features and functionalities associated with the systems, methods, and processes of the present disclosure will be apparent from the appended claims. Moreover, those skilled in the art will recognize, or be able to ascertain using no more than routine experimentation, many equivalents to the specific embodiments of the disclosure described herein. Such equivalents are intended to be encompassed by the following claims.

The invention claimed is:

1. A compound represented by Formula I, a stereoisomer thereof, or a pharmaceutically acceptable salt thereof:

ULM Linker PTM [Formula 1]

in the Formula I above,

ULM is a CRBN E3 ubiquitin ligase binding moiety represented by Formula A-2;

[Formula A-2]

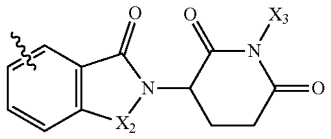

wherein:

$X_2$ is —$CH_2$—, —CO— or —N═N—;

$X_3$ is hydrogen; and indicates a covalent bond that links ULM into the Linker;

PTM is a HMG-CoA reductase binding moiety represented by Formula II:

[Formula II]

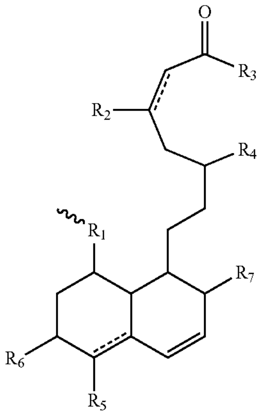

in Formula II above, $R_1$ is

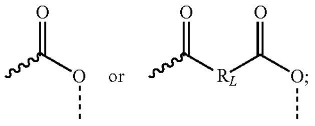

$R_L$ is a single bond or $C_{1-6}$ alkylene that is optionally substituted by 1-4 substituents selected from —$CH_3$, —CN, —$NH_2$, —OH, or halogen;

$R_2$ is selected from hydrogen, halogen, —OH, —O($C_{1-6}$ alkyl), —O($C_{3-8}$ cycloalkyl), —OCO($C_1$-$C_6$ alkyl),

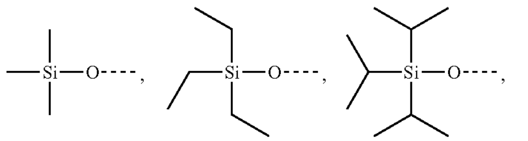

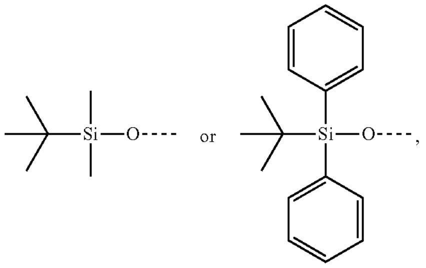

optionally substituted by one or more straight- or branched-$C_{1-4}$ alkyl, 5- to 6-membered heterocyclyl containing one or two N ring atoms, phenyl, 6-membered heteroaryl containing one or two N ring atoms, $NH_3$, OH, or $CF_3$;

$R_3$ and $R_4$ are each independently —OH or —O($C_{1-3}$ alkyl); or $R_3$ and $R_4$ together form —O—;

$R_3$ and $R_4$ are each independently hydrogen, halogen, OH, $C_{1-4}$ alkyl, $C_{1-4}$ alkenyl, O($C_{1-4}$ alkyl), $CF_3$, $NH_3$, $NO_2$, or CN;

$R_7$ is hydrogen or $C_{1-3}$ alkyl;

 is a single bond or a double bond;

indicates a covalent bond that links PTM into the Linker}; and the Linker is a chemical group that links ULM and PTM, wherein the Linker is represented by Formula L:

[Formula L]

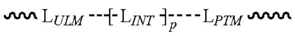

wherein:

and 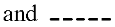 are each independently a bond;

$L_{ULM}$ is covalently bonded to a ULM moiety through 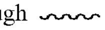 that is linked thereto, $L_{PTM}$ is covalently bonded to a PTM moiety through 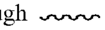 that is linked thereto, $L_{ULM}$ is

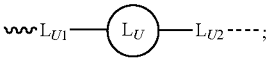

$L_{U1}$ is selected from —$CH_2$—, —$CH_2CH_2$—, —CC—, —NH—, —NHCO—, or —O—;

$L_{U2}$ is selected from a single bond, —$CH_2$—, —NH—, —O—, —CO—, and —CONH—;

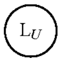

is null, $C_{1-3}$ alkyl, or 4- to 6-membered heterocycloalkyl containing one or two N ring atoms;

$L_{PTM}$ is

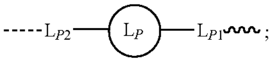

$L_{P1}$ is selected from a single bond, —NH—, —$NCH_3$, or —$CH_2NH$—;

$L_{P2}$ is selected from a single bond or —$COCH_2$—;

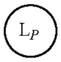

is null or 4- to 6-membered heterocycloalkyl containing one or two N ring atoms;

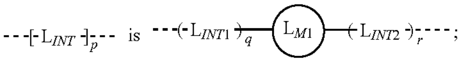

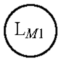

is null or a ring selected from 4- to 6-membered heterocycloalkyl containing one or two N ring atoms, phenyl, or 5- to 6-membered heteroaryl containing one or two N ring atoms;

$L_{INT1}$ and $L_{INT2}$ are each independently selected from —$CH_2$—, —NH—, —$CH_2CH_2O$—, or —$OCH_2CH_2$—; and q and r are each independently an integer from 1 to 8.

2. The compound of claim 1, wherein Formula II is represented by Formula III-1:

[Formula III-1]

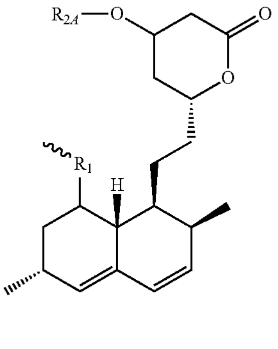

wherein:

$R_1$ is

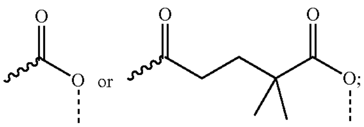

$R_{24}$ is selected from hydrogen, $C_{1-6}$ alkyl, $C_{3-6}$ cycloalkyl, 5- to 6-membered heterocyclyl containing one or two N ring atoms, phenyl, 5- to 6-membered heteroaryl containing one or two N ring atoms,

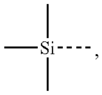, 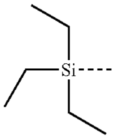, 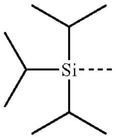, 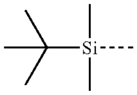 or

-continued

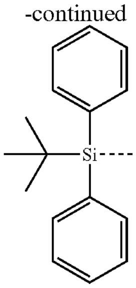;

and indicates a covalent bond that links PTM into the Linker.

3. A compound selected from following compounds, a stereoisomer thereof, or a pharmaceutically acceptable salt thereof:

TABLE 1

| Compound | Structure |
|---|---|
| 2 | 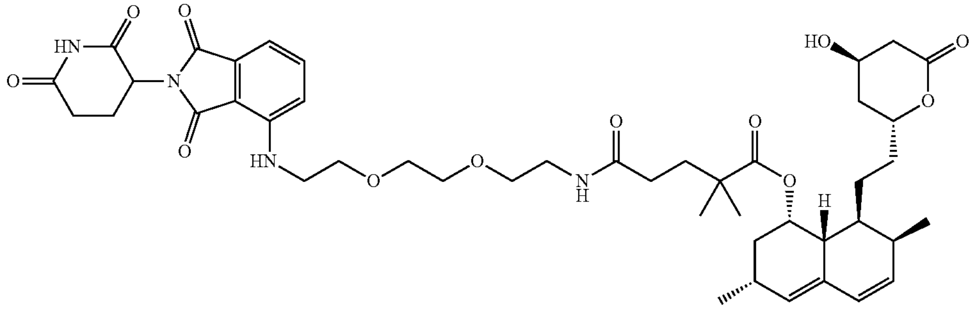 [SMILES: C[C@H]1C=C2C=C[C@H](C)[C@H](CC[C@@H]3C[C@@H](O)CC(=O)O3)[C@H]2[C@@H](OC(=O)C(C)(C)CCC(=O)NCCOCCOCCNc2cccc3c2C(=O)N(C2CCC(=O)NC2=O)C3=O)C1] |
| 3 | 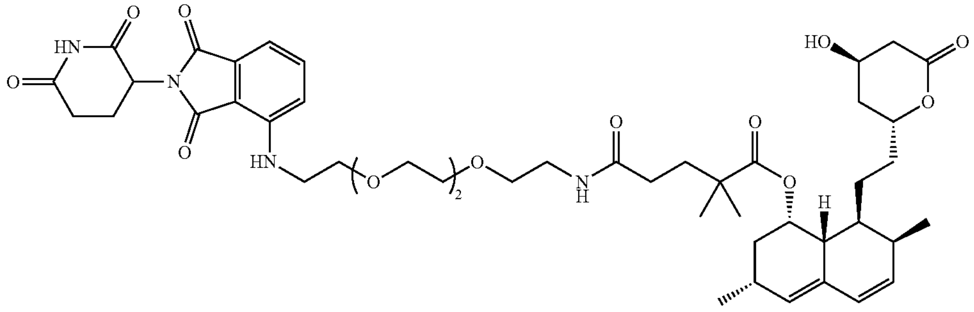 |
| 4 | 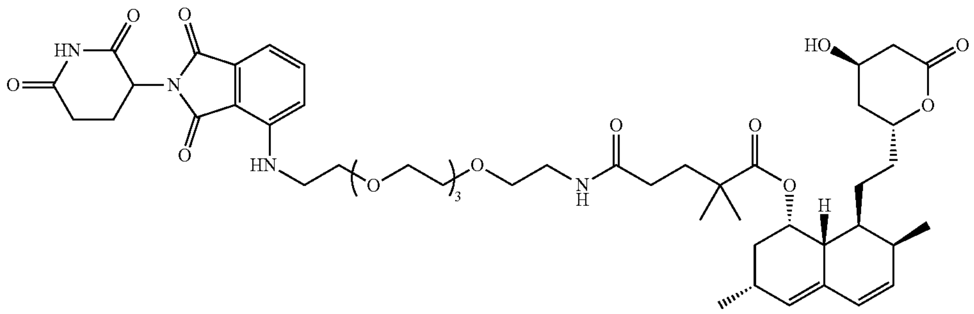 |

TABLE 1-continued
| Compound | Structure |
| --- | --- |
| 5 | 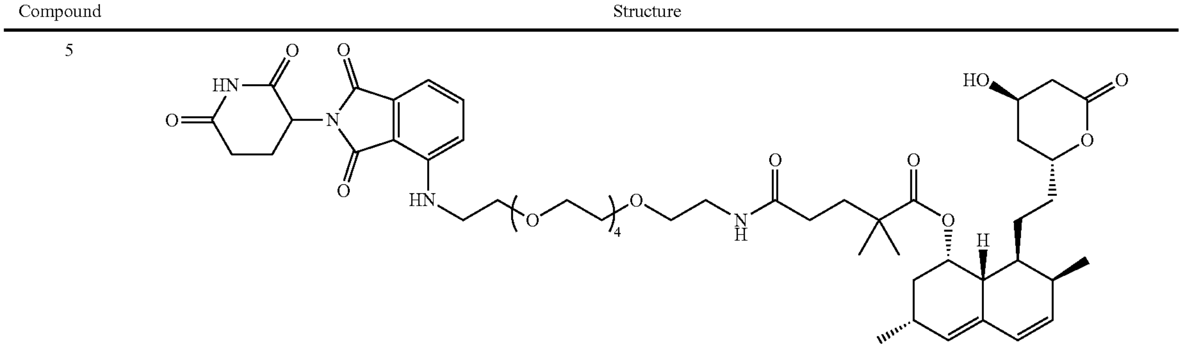 |
| 6 | 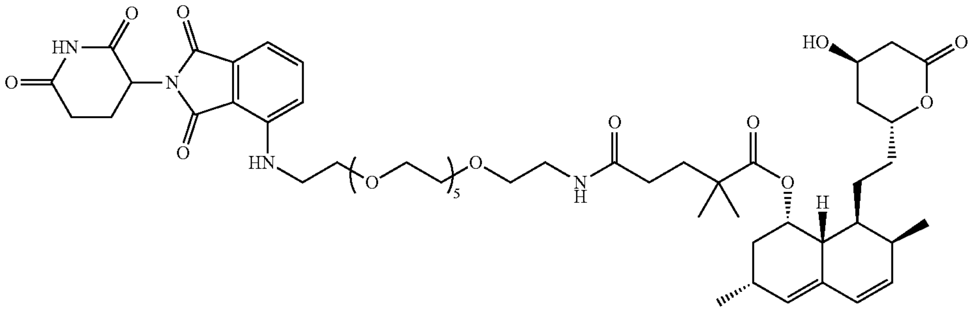 |
| 40 | 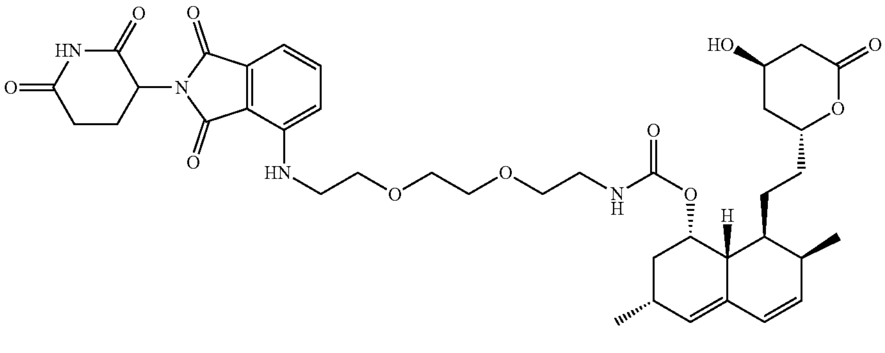 [SMILES: C[C@H]1C=C2C=C[C@H](C)[C@H](CC[C@@H]3C[C@@H](O)CC(=O)O3)[C@H]2[C@@H](OC(=O)NCCOCCOCCNc2cccc3c2C(=O)N(C2CCC(=O)NC2=O)C3=O)C1] |
| 41 | 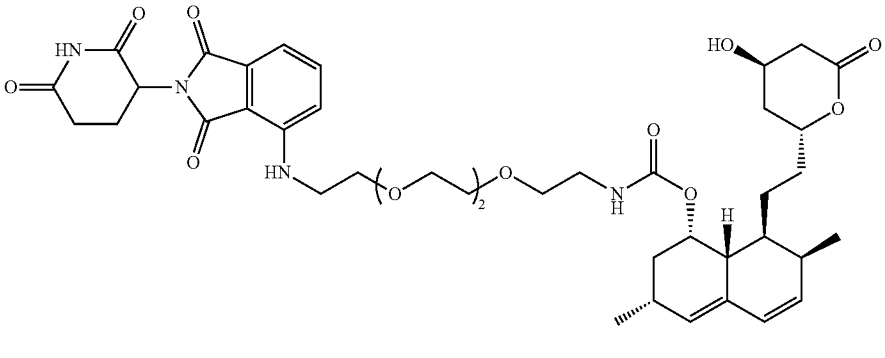 |

TABLE 1-continued
| Compound | Structure |
| --- | --- |
| 42 | 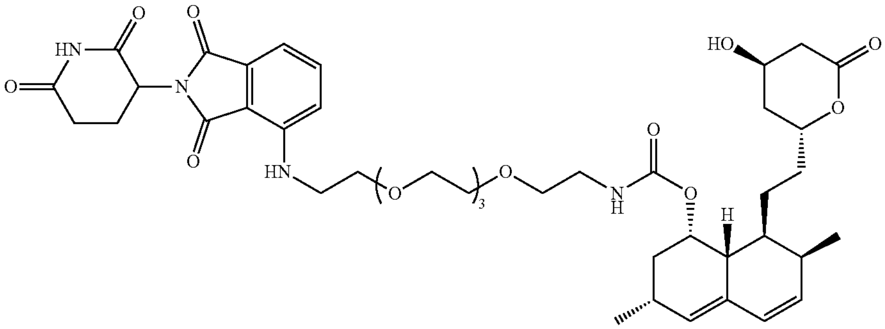 |
| 43 | 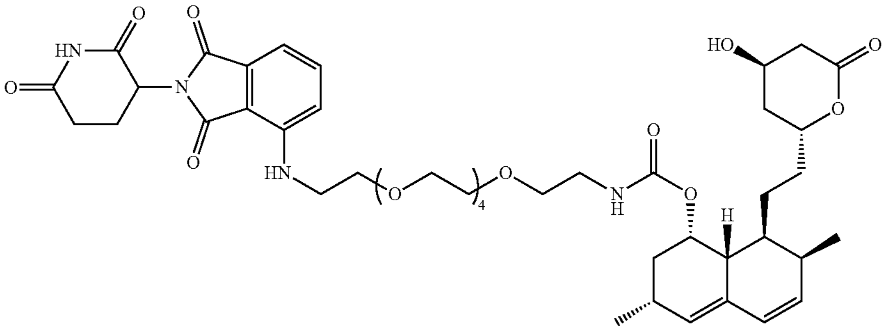 |
| 44 | 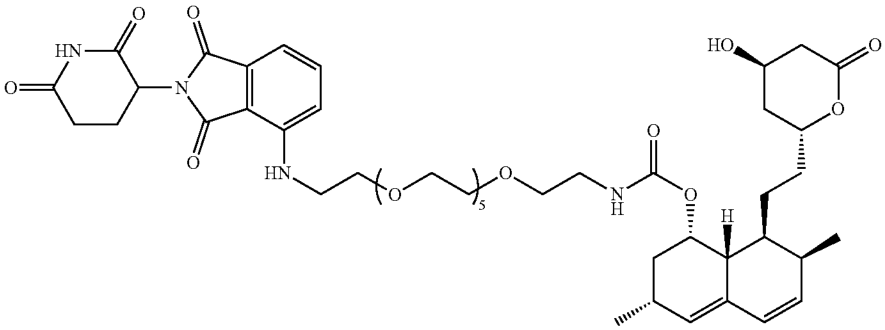 |
| 46 | 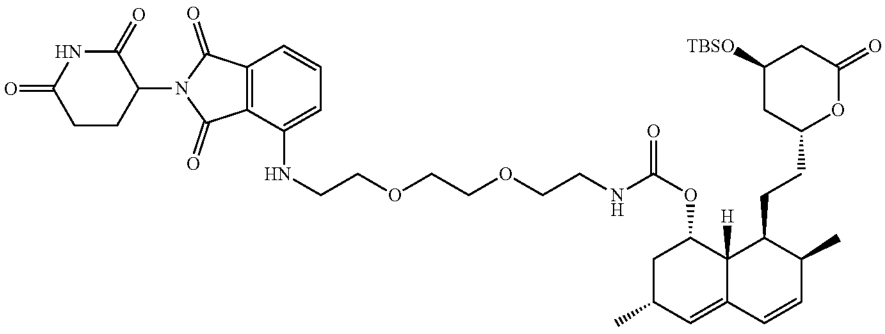 |

TABLE 1-continued
| Compound | Structure |
| --- | --- |
| 47 | 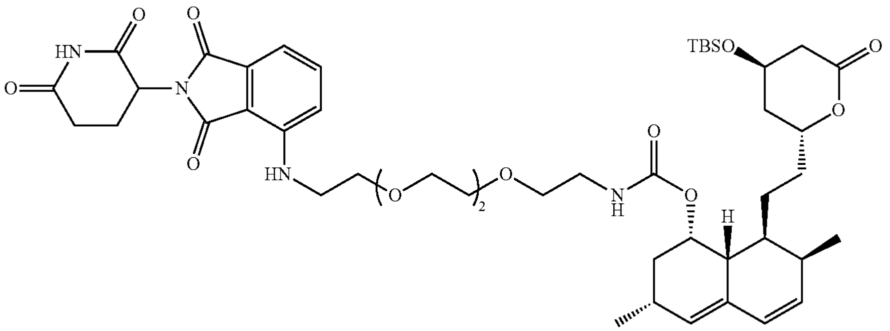 |
| 48 | 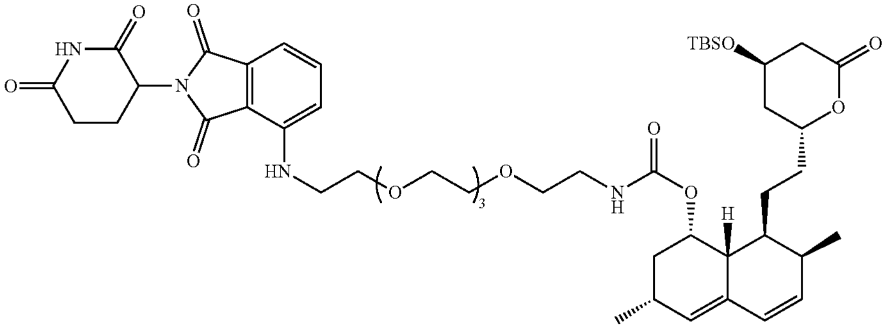 |
| 49 | 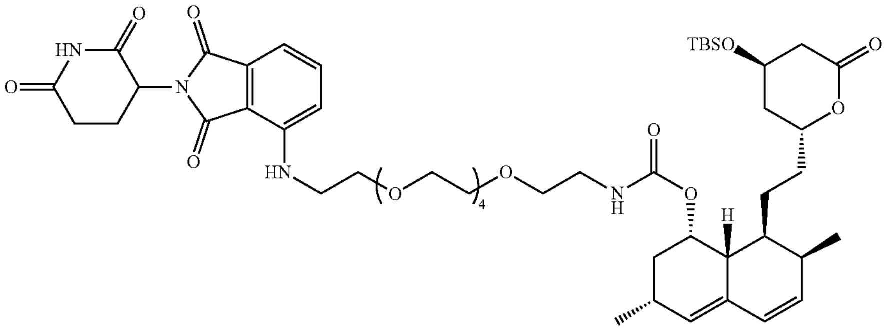 |
| 50 | 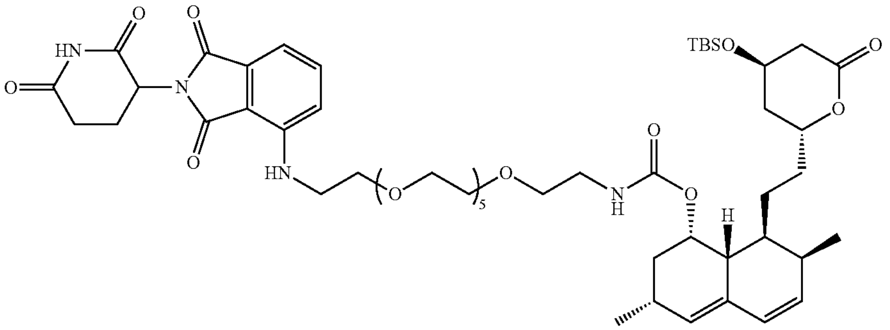 |

TABLE 1-continued
| Compound | Structure |
|---|---|
| 51 | 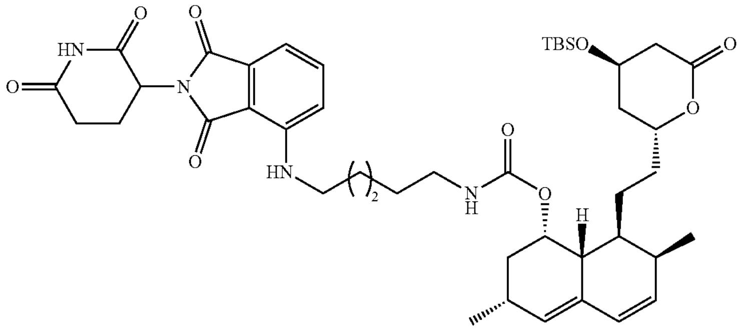 |
| 52 | 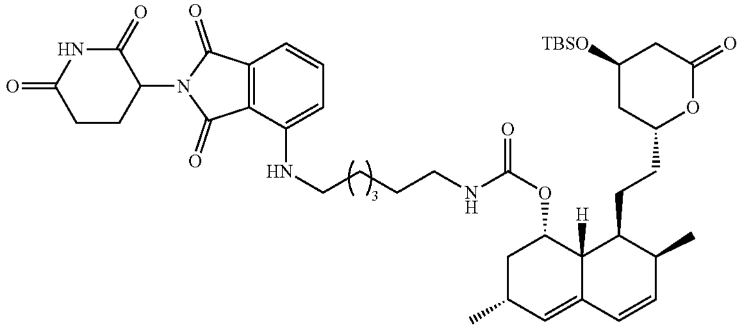 |
| 53 | 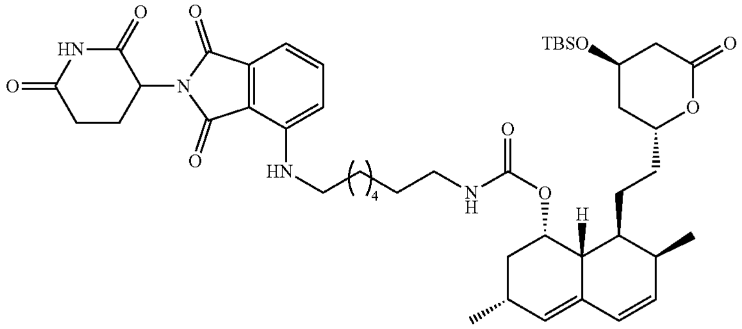 |
| 54 | 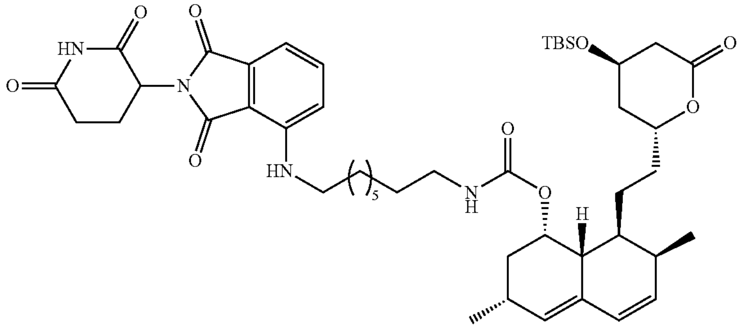 |

TABLE 1-continued
| Compound | Structure |
| --- | --- |
| 55 | 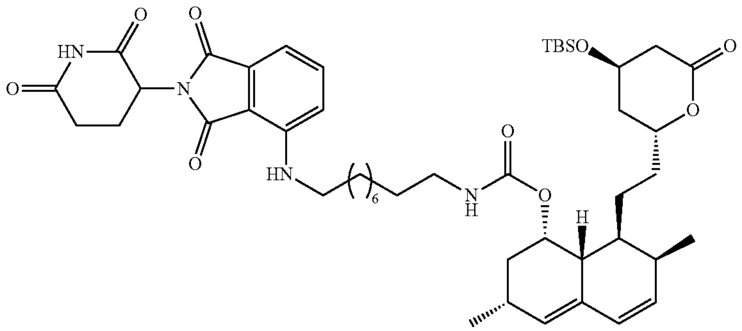 |
| 56 | 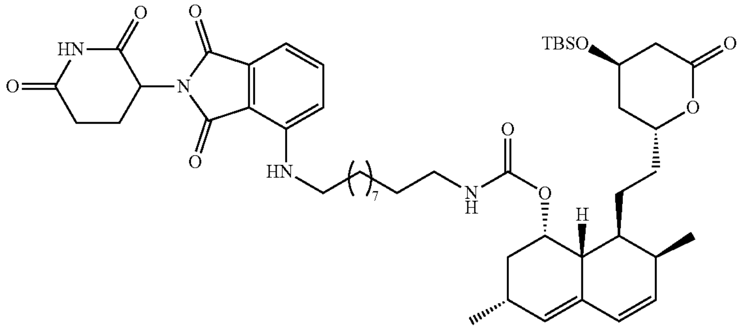 |
| 57 | 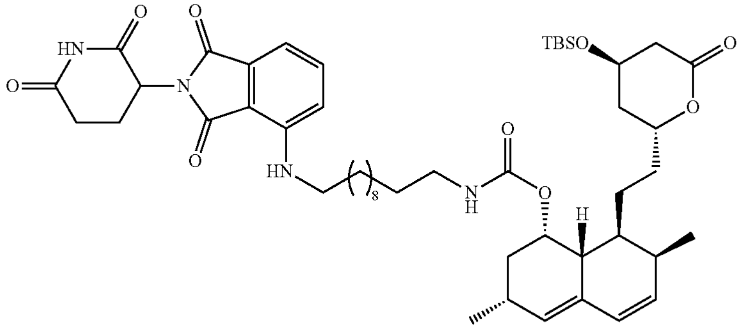 |
| 58 | 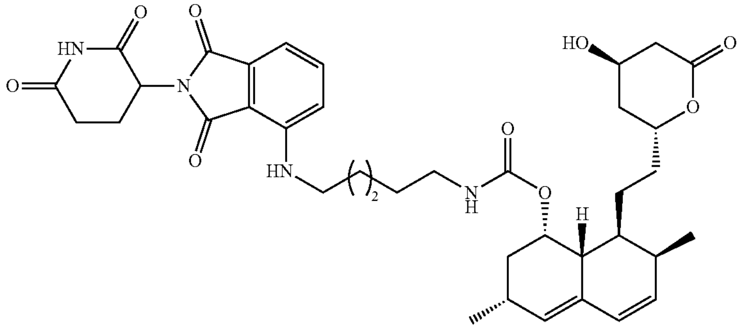 |

TABLE 1-continued
| Compound | Structure |
|---|---|
| 59 | 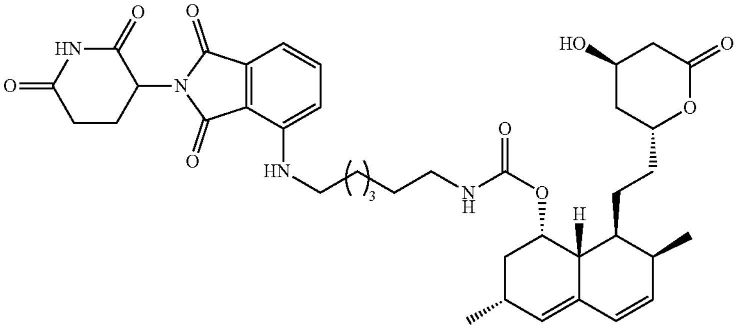 |
| 60 | 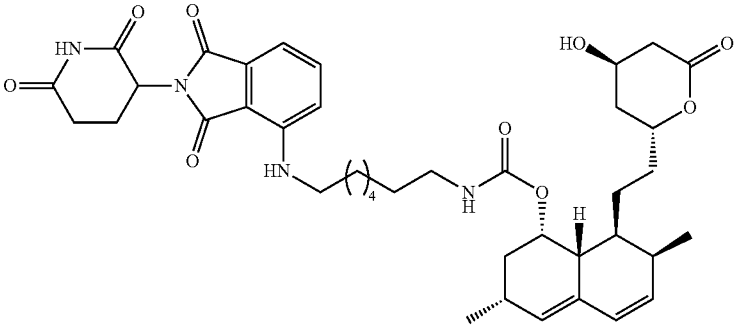 |
| 61 | 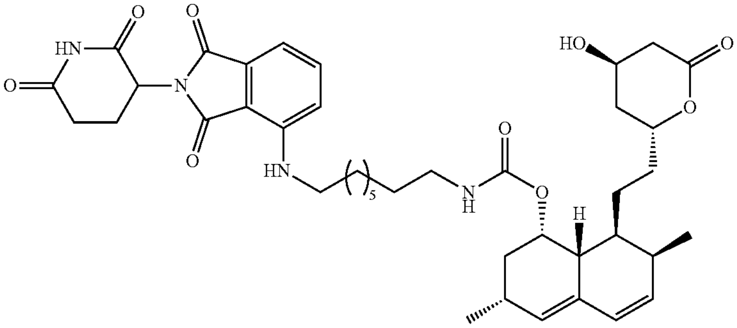 |
| 62 | 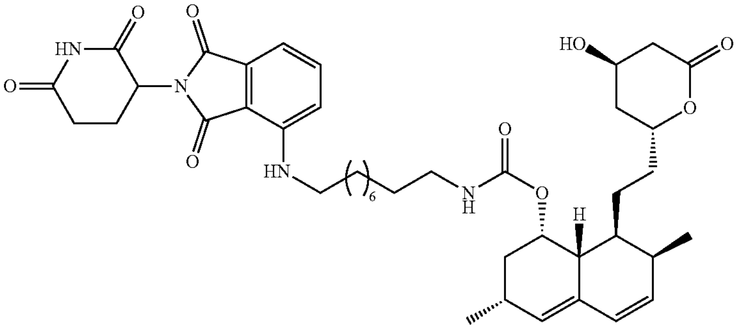 |

TABLE 1-continued
| Compound | Structure |
| --- | --- |
| 63 | 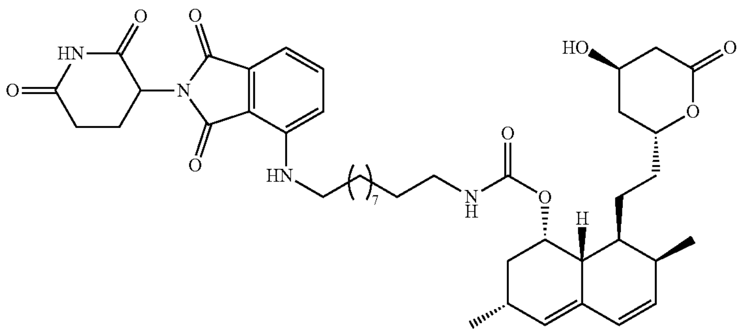 |
| 64 | 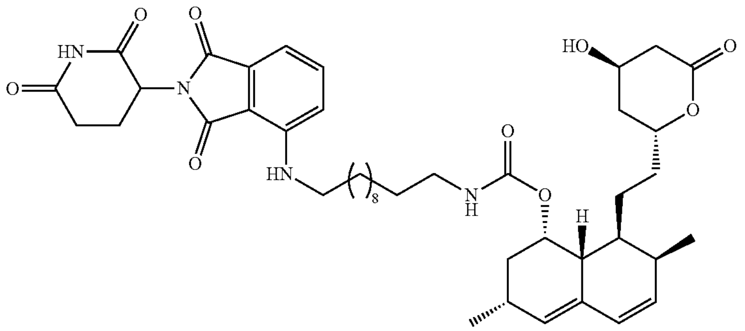 |
| 65 | 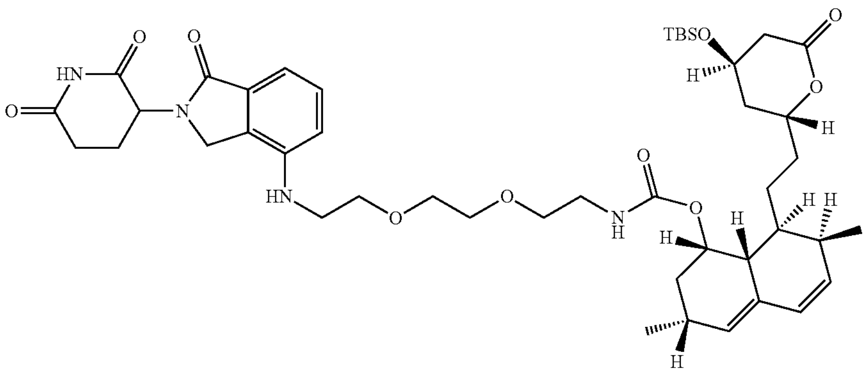 [SMILES: C[C@H]1C=C2C=C[C@H](C)[C@H](CC[C@@H]3C[C@@H](O[Si](C)(C)C(C)(C)C)CC(=O)O3)[C@H]2[C@@H](OC(=O)NCCOCCOCCNc2cccc3c2CN(C2CCC(=O)NC2=O)C3=O)C1] |
| 66 | 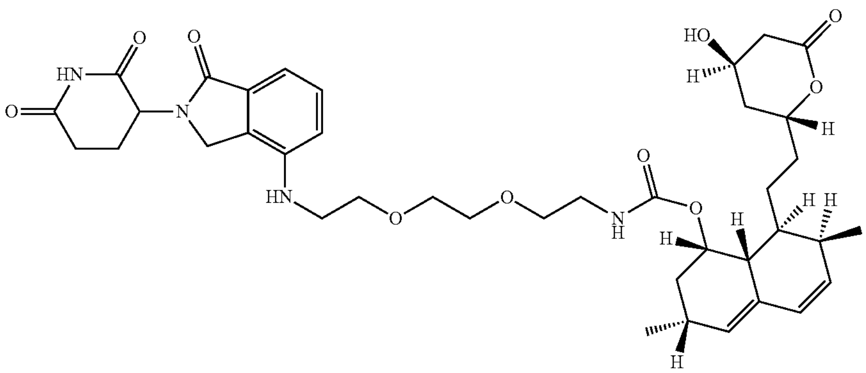 [SMILES: C[C@H]1C=C2C=C[C@H](C)[C@H](CC[C@@H]3C[C@@H](O)CC(=O)O3)[C@H]2[C@@H](OC(=O)NCCOCCOCCNc2cccc3c2CN(C2CCC(=O)NC2=O)C3=O)C1] |

TABLE 1-continued
| Compound | Structure |
| --- | --- |
| 67 | 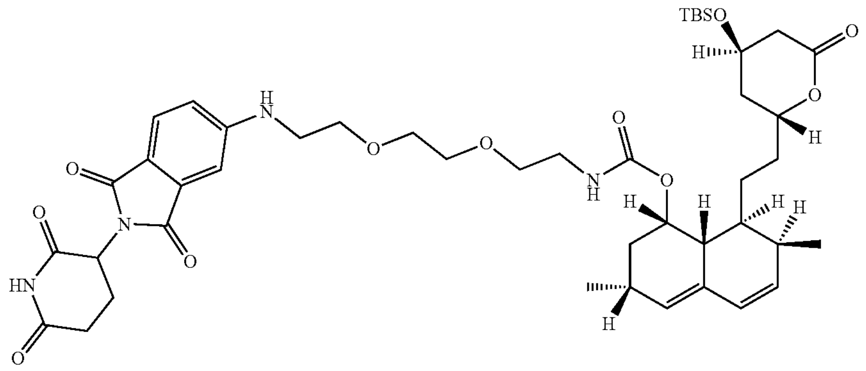 [SMILES: C[C@H]1C=C2C=C[C@H](C)[C@H](CC[C@@H]3C[C@@H](O[Si](C)(C)C(C)(C)C)CC(=O)O3)[C@H]2[C@@H](OC(=O)NCCOCCOCCNc2ccc3c(c2)C(=O)N(C2CCC(=O)NC2=O)C3=O)C1] |
| 68 | 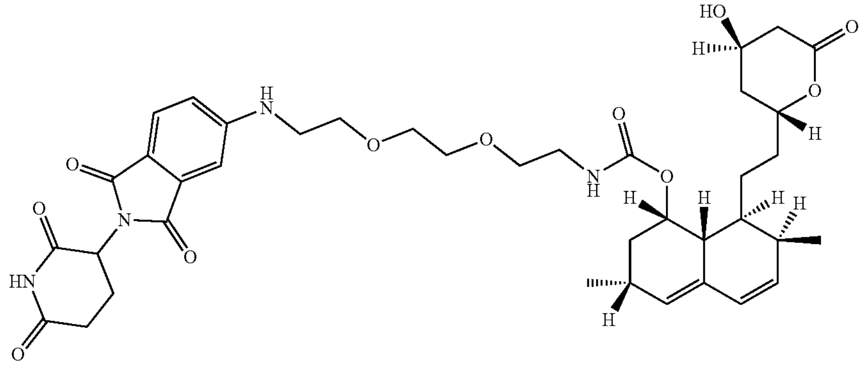 [SMILES: C[C@H]1C=C2C=C[C@H](C)[C@H](CC[C@@H]3C[C@@H](O)CC(=O)O3)[C@H]2[C@@H](OC(=O)NCCOCCOCCNc2ccc3c(c2)C(=O)N(C2CCC(=O)NC2=O)C3=O)C1] |
| 69 | 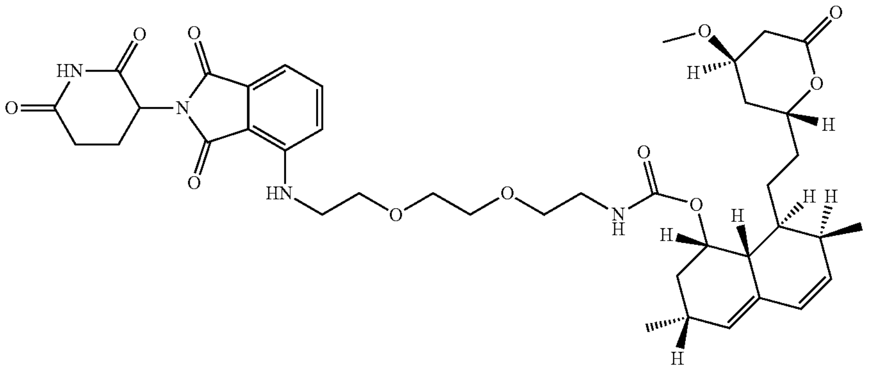 [SMILES: CO[C@H]1CC(=O)O[C@H](CC[C@@H]2[C@@H]3C(=C[C@H](C)C[C@@H]3OC(=O)NCCOCCOCCNc3cccc4c3C(=O)N(C3CCC(=O)NC3=O)C4=O)C=C[C@@H]2C)C1] |
| 70 | 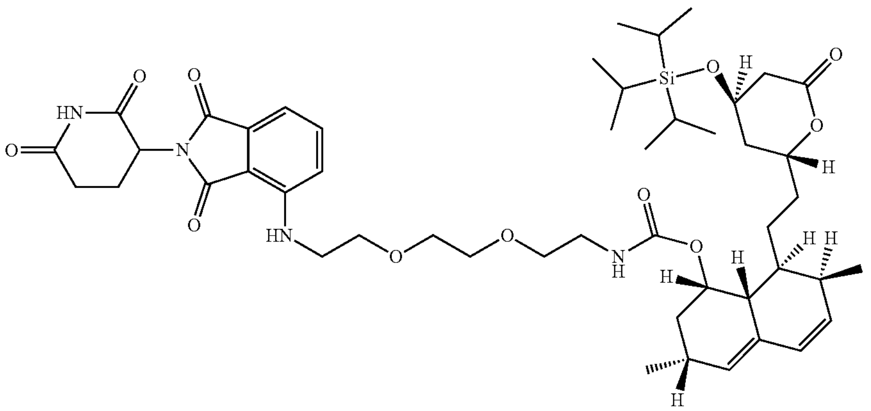 [SMILES: CC(C)[Si](O[C@H]1CC(=O)O[C@H](CC[C@@H]2[C@@H]3C(=C[C@H](C)C[C@@H]3OC(=O)NCCOCCOCCNc3cccc4c3C(=O)N(C3CCC(=O)NC3=O)C4=O)C=C[C@@H]2C)C1)(C(C)C)C(C)C] |

TABLE 1-continued
| Compound | Structure |
|---|---|
| 71 | 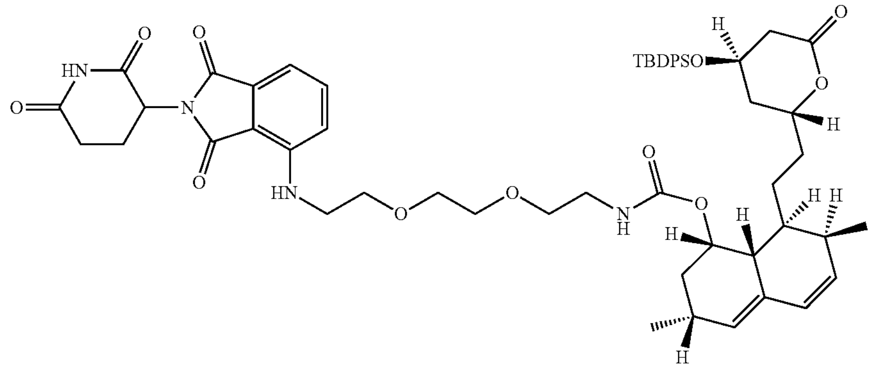 {TBDPS = tert-Butyldiphenylsilyl} |
| 72 | 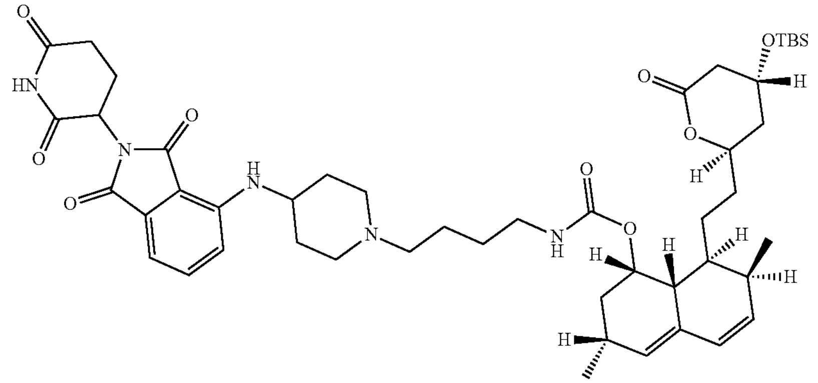 [SMILES: C[C@H]1C=C2C=C[C@H](C)[C@H](CC[C@@H]3C[C@@H](O[Si](C)(C)C(C)(C)C)CC(=O)O3)[C@H]2[C@@H](OC(=O)NCCCCN2CCC(Nc3cccc4c3C(=O)N(C3CCC(=O)NC3=O)C4=O)CC2)C1] |
| 73 | 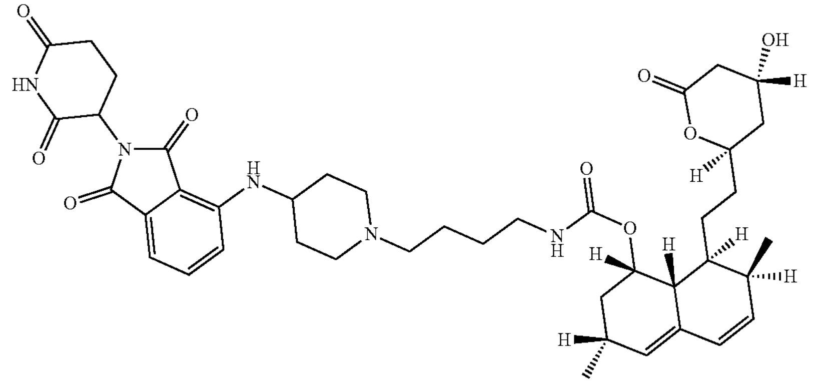 [SMILES: C[C@H]1C=C2C=C[C@H](C)[C@H](CC[C@@H]3C[C@@H](O)CC(=O)O3)[C@H]2[C@@H](OC(=O)NCCCCN2CCC(Nc3cccc4c3C(=O)N(C3CCC(=O)NC3=O)C4=O)CC2)C1] |
| 74 | 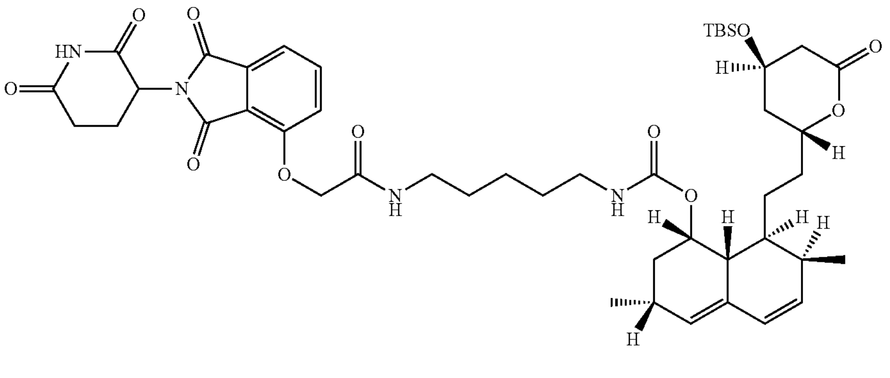 [SMILES: C[C@H]1C=C2C=C[C@H](C)[C@H](CC[C@@H]3C[C@@H](O[Si](C)(C)C(C)(C)C)CC(=O)O3)[C@H]2[C@@H](OC(=O)NCCCCCNC(=O)COc2cccc3c2C(=O)N(C2CCC(=O)NC2=O)C3=O)C1] |

TABLE 1-continued
| Compound | Structure |
| --- | --- |
| 75 | 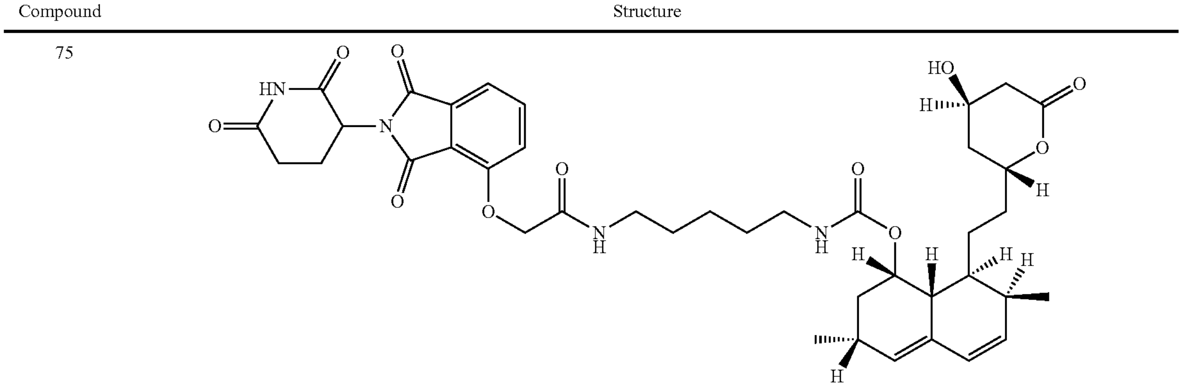 |
| 76 | 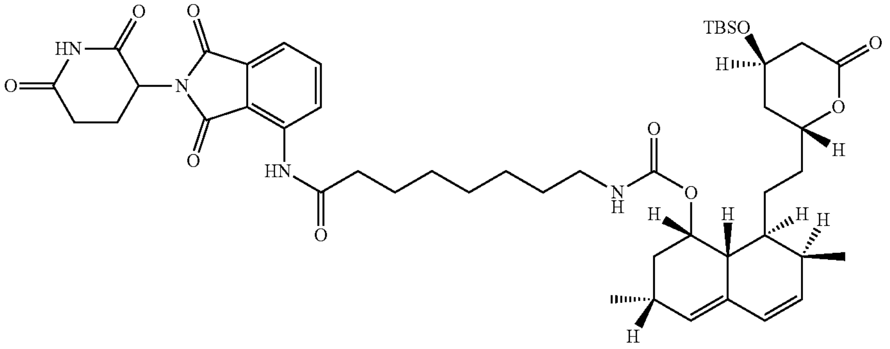 |
| 77 | 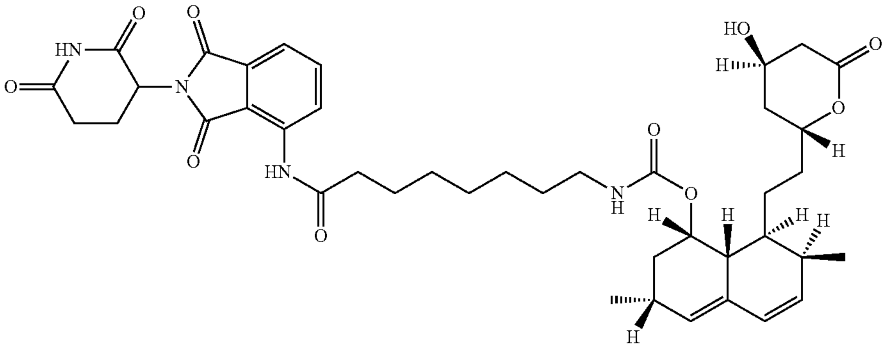 [SMILES: C[C@H]1C=C2C=C[C@H](C)[C@H](CC[C@@H]3C[C@@H](O)CC(=O)O3)[C@H]2[C@@H](OC(=O)NCCCCCCCC(=O)Nc2cccc3c2C(=O)N(C2CCC(=O)NC2=O)C3=O)C1] |
| 78 | 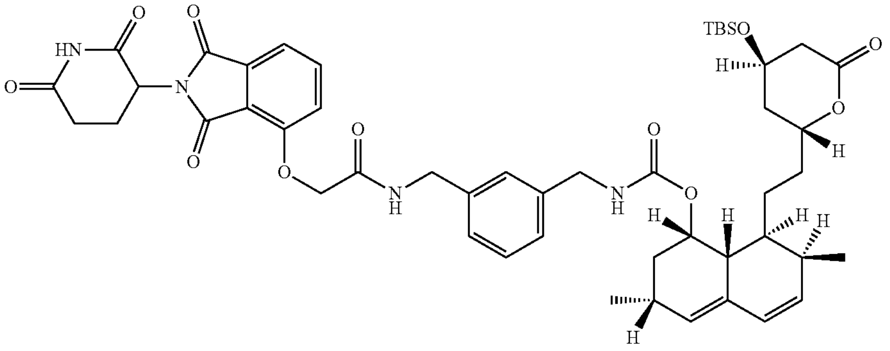 [SMILES: C[C@H]1C=C2C=C[C@H](C)[C@H](CC[C@@H]3C[C@@H](O[Si](C)(C)C(C)(C)C)CC(=O)O3)[C@H]2[C@@H](OC(=O)NCc2cccc(CNC(=O)COc3cccc4c3C(=O)N(C3CCC(=O)NC3=O)C4=O)c2)C1] |

TABLE 1-continued
| Compound | Structure |
| --- | --- |
| 79 | 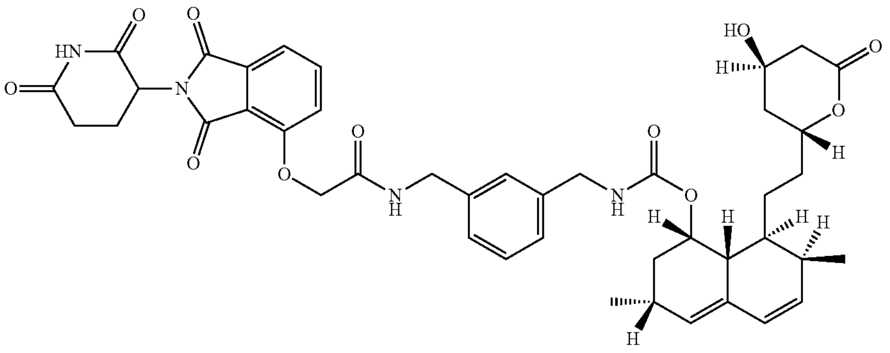 [SMILES: C[C@H]1C=C2C=C[C@H](C)[C@H](CC[C@@H]3C[C@@H](O)CC(=O)O3)[C@H]2[C@@H](OC(=O)NCc2cccc(CNC(=O)COc3cccc4c3C(=O)N(C3CCC(=O)NC3=O)C4=O)c2)C1] |
| 80 | 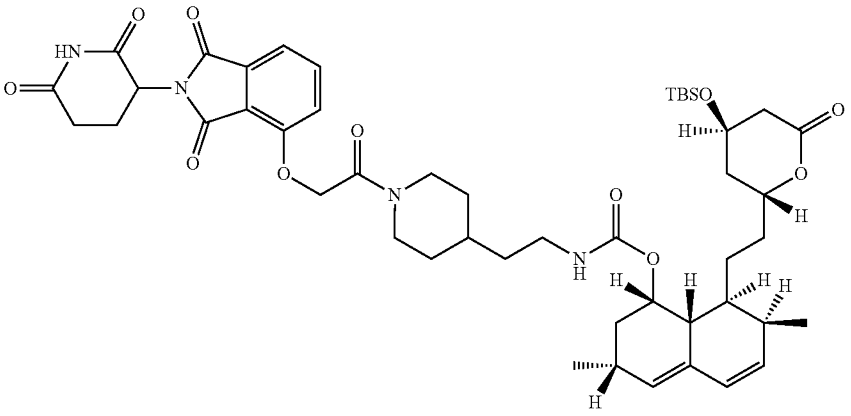 [SMILES: C[C@H]1C=C2C=C[C@H](C)[C@H](CC[C@@H]3C[C@@H](O[Si](C)(C)C(C)(C)C)CC(=O)O3)[C@H]2[C@@H](OC(=O)NCCC2CCN(C(=O)COc3cccc4c3C(=O)N(C3CCC(=O)NC3=O)C4=O)CC2)C1] |
| 81 | 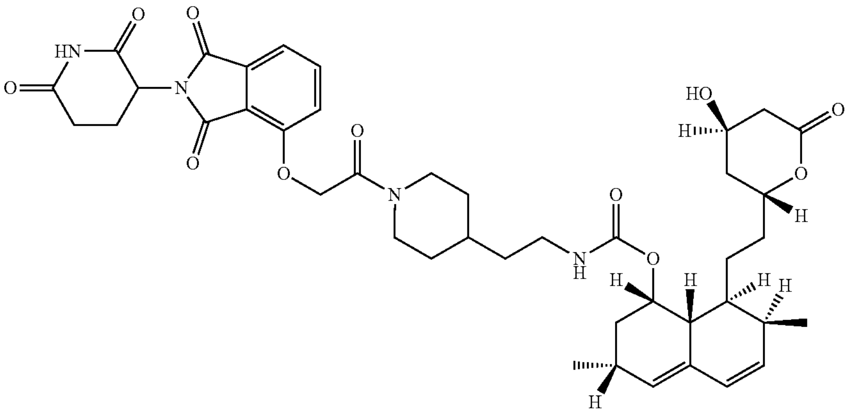 [SMILES: C[C@H]1C=C2C=C[C@H](C)[C@H](CC[C@@H]3C[C@@H](O)CC(=O)O3)[C@H]2[C@@H](OC(=O)NCCC2CCN(C(=O)COc3cccc4c3C(=O)N(C3CCC(=O)NC3=O)C4=O)CC2)C1] |
| 82 | 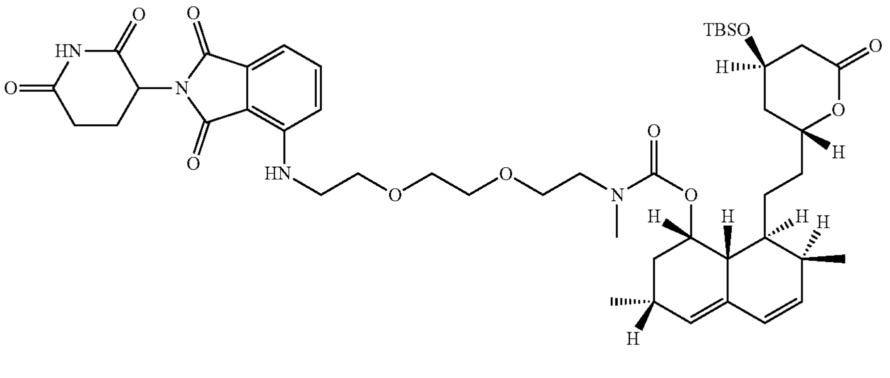 [SMILES: C[C@H]1C=C2C=C[C@H](C)[C@H](CC[C@@H]3C[C@@H](O[Si](C)(C)C(C)(C)C)CC(=O)O3)[C@H]2[C@@H](OC(=O)N(C)CCOCCOCCNc2cccc3c2C(=O)N(C2CCC(=O)NC2=O)C3=O)C1] |

TABLE 1-continued
| Compound | Structure |
| --- | --- |
| 83 | 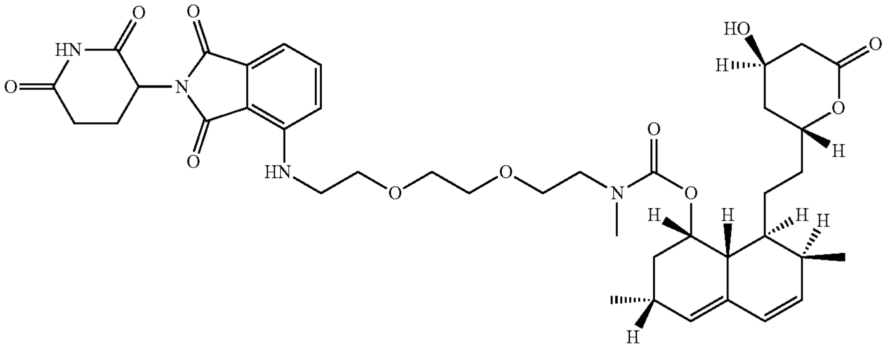 [SMILES: C[C@H]1C=C2C=C[C@H](C)[C@H](CC[C@@H]3C[C@@H](O)CC(=O)O3)[C@H]2[C@@H](OC(=O)N(C)CCOCCOCCNc2cccc3c2C(=O)N(C2CCC(=O)NC2=O)C3=O)C1] |
| 84 | 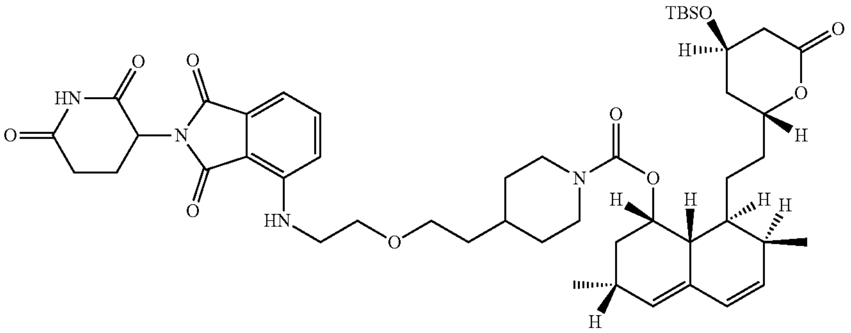 [SMILES: C[C@H]1C=C2C=C[C@H](C)[C@H](CC[C@@H]3C[C@@H](O[Si](C)(C)C(C)(C)C)CC(=O)O3)[C@H]2[C@@H](OC(=O)N2CCC(CCOCCNc3cccc4c3C(=O)N(C3CCC(=O)NC3=O)C4=O)CC2)C1] |
| 85 | 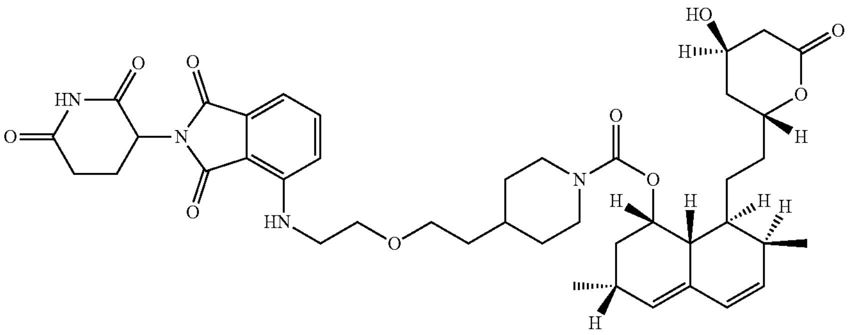 [SMILES: C[C@H]1C=C2C=C[C@H](C)[C@H](CC[C@@H]3C[C@@H](O)CC(=O)O3)[C@H]2[C@@H](OC(=O)N2CCC(CCOCCNc3cccc4c3C(=O)N(C3CCC(=O)NC3=O)C4=O)CC2)C1] |
| 86 | 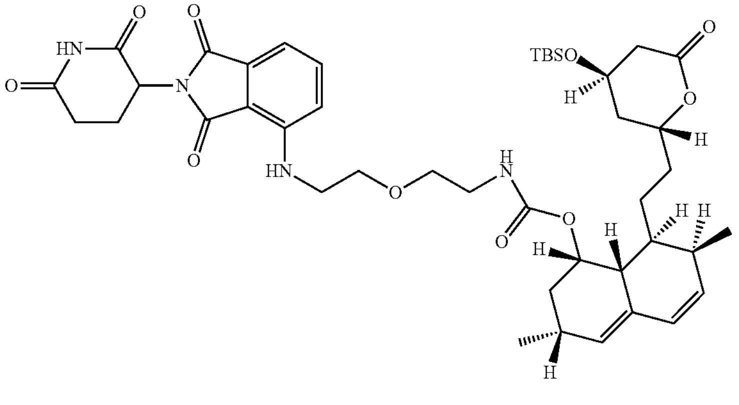 [SMILES: C[C@H]1C=C2C=C[C@H](C)[C@H](CC[C@@H]3C[C@@H](O[Si](C)(C)C(C)(C)C)CC(=O)O3)[C@H]2[C@@H](OC(=O)NCCOCCNc2cccc3c2C(=O)N(C2CCC(=O)NC2=O)C3=O)C1] |

TABLE 1-continued
| Compound | Structure |
| --- | --- |
| 87 | 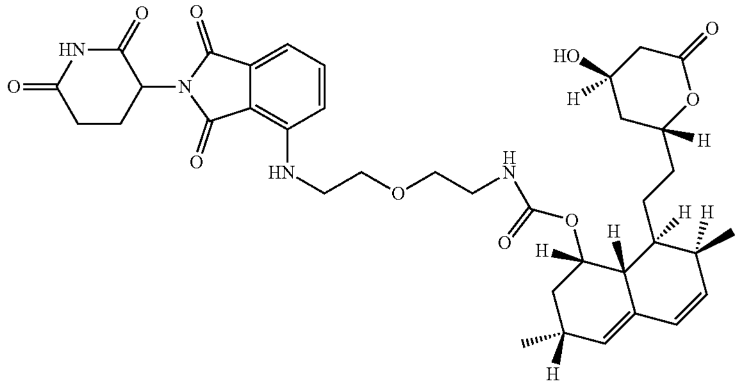 [SMILES: C[C@H]1C=C2C=C[C@H](C)[C@H](CC[C@@H]3C[C@@H](O)CC(=O)O3)[C@H]2[C@@H](OC(=O)NCCOCCNc2cccc3c2C(=O)N(C2CCC(=O)NC2=O)C3=O)C1] |
| 88 | 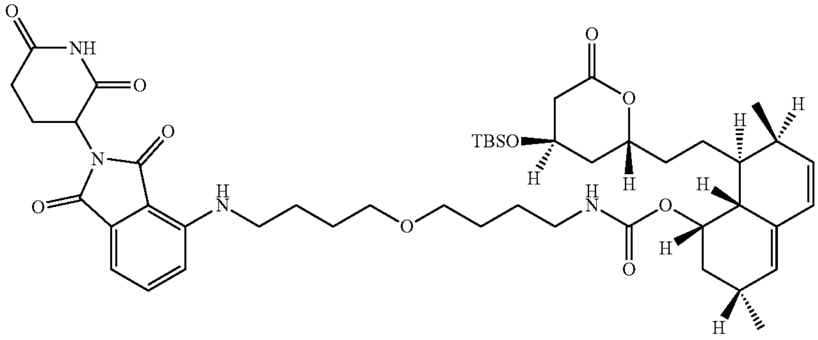 [SMILES: C[C@H]1C=C2C=C[C@H](C)[C@H](CC[C@@H]3C[C@@H](O[Si](C)(C)C(C)(C)C)CC(=O)O3)[C@H]2[C@@H](OC(=O)NCCCCOCCCCNc2cccc3c2C(=O)N(C2CCC(=O)NC2=O)C3=O)C1] |
| 89 | 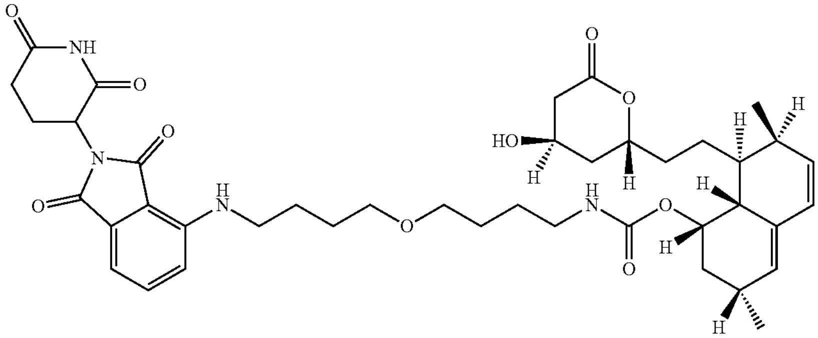 [SMILES: C[C@H]1C=C2C=C[C@H](C)[C@H](CC[C@@H]3C[C@@H](O)CC(=O)O3)[C@H]2[C@@H](OC(=O)NCCCCOCCCCNc2cccc3c2C(=O)N(C2CCC(=O)NC2=O)C3=O)C1] |
| 90 | 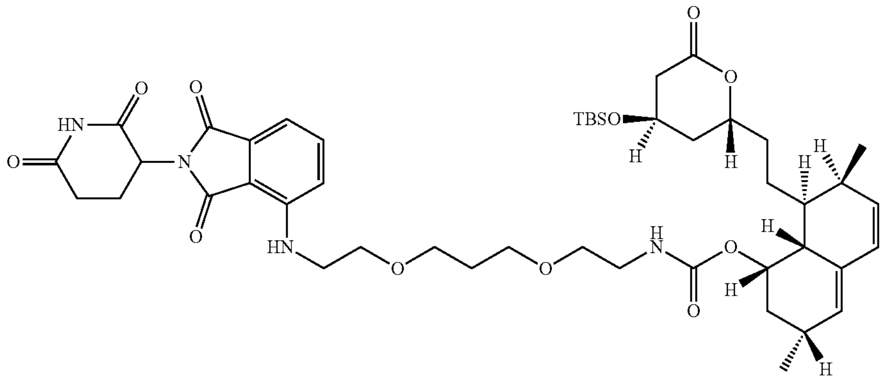 [SMILES: C[C@H]1C=C2C=C[C@H](C)[C@H](CC[C@@H]3C[C@@H](O[Si](C)(C)C(C)(C)C)CC(=O)O3)[C@H]2[C@@H](OC(=O)NCCOCCCOCCNc2cccc3c2C(=O)N(C2CCC(=O)NC2=O)C3=O)C1] |

TABLE 1-continued
| Compound | Structure |
|---|---|
| 91 | 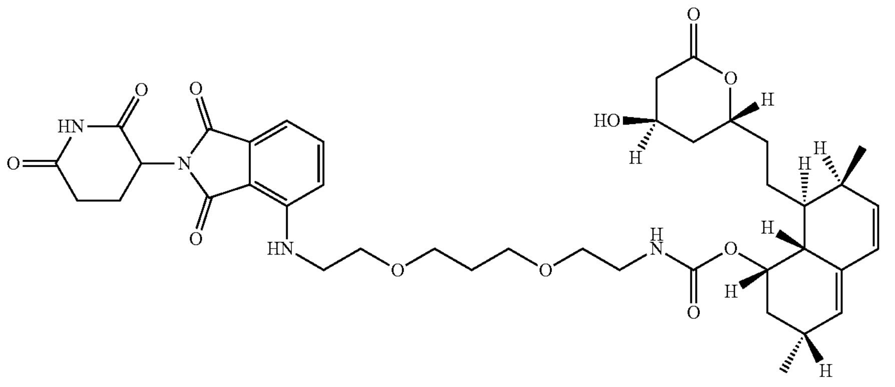 [SMILES: C[C@H]1C=C2C=C[C@H](C)[C@H](CC[C@@H]3C[C@@H](O)CC(=O)O3)[C@H]2[C@@H](OC(=O)NCCOCCCOCCNc2cccc3c2C(=O)N(C2CCC(=O)NC2=O)C3=O)C1] |
| 92 | 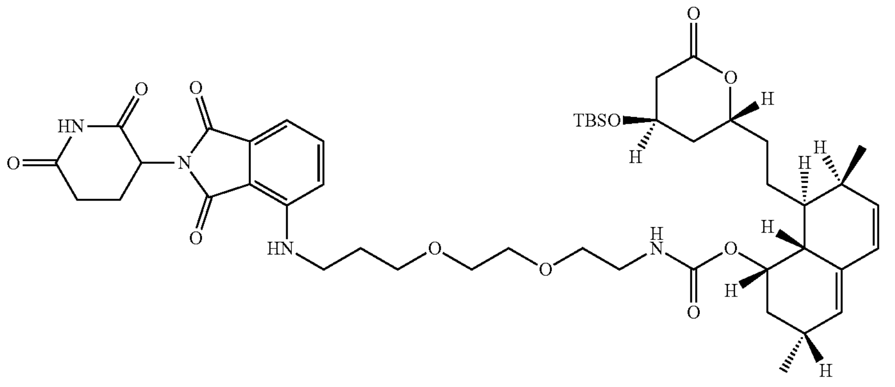 [SMILES: C[C@H]1C=C2C=C[C@H](C)[C@H](CC[C@@H]3C[C@@H](O[Si](C)(C)C(C)(C)C)CC(=O)O3)[C@H]2[C@@H](OC(=O)NCCOCCOCCCNc2cccc3c2C(=O)N(C2CCC(=O)NC2=O)C3=O)C1] |
| 93 | 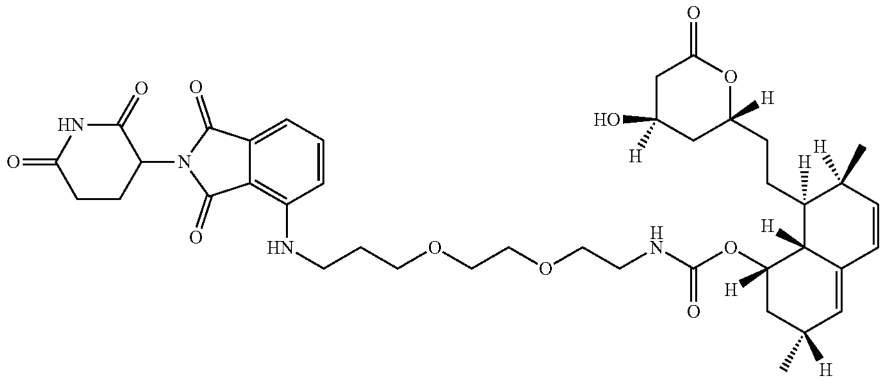 [SMILES: C[C@H]1C=C2C=C[C@H](C)[C@H](CC[C@@H]3C[C@@H](O)CC(=O)O3)[C@H]2[C@@H](OC(=O)NCCOCCOCCCNc2cccc3c2C(=O)N(C2CCC(=O)NC2=O)C3=O)C1] |
| 94 | 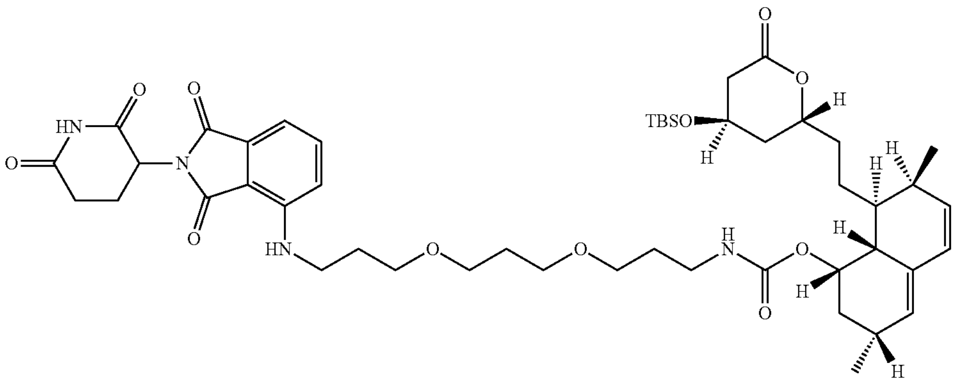 [SMILES: C[C@H]1C=C2C=C[C@H](C)[C@H](CC[C@@H]3C[C@@H](O[Si](C)(C)C(C)(C)C)CC(=O)O3)[C@H]2[C@@H](OC(=O)NCCCOCCCOCCCNc2cccc3c2C(=O)N(C2CCC(=O)NC2=O)C3=O)C1] |

TABLE 1-continued
| Compound | Structure |
| --- | --- |
| 95 | 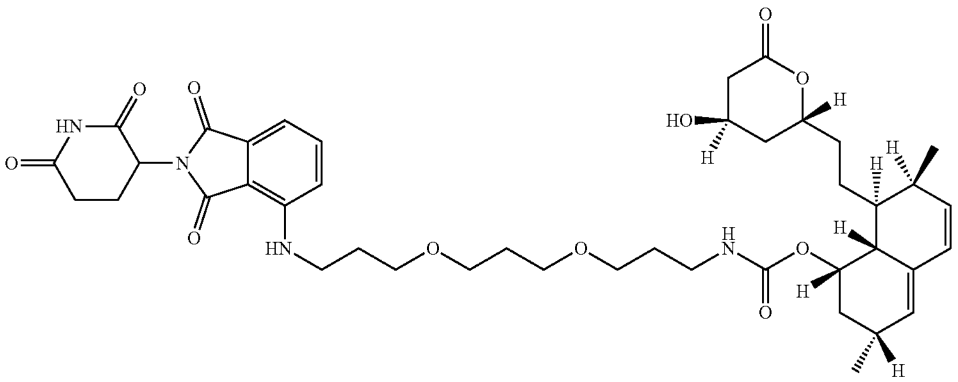 [SMILES: C[C@H]1C=C2C=C[C@H](C)[C@H](CC[C@@H]3C[C@@H](O)CC(=O)O3)[C@H]2[C@@H](OC(=O)NCCCOCCCOCCCNc2cccc3c2C(=O)N(C2CCC(=O)NC2=O)C3=O)C1] |
| 96 | 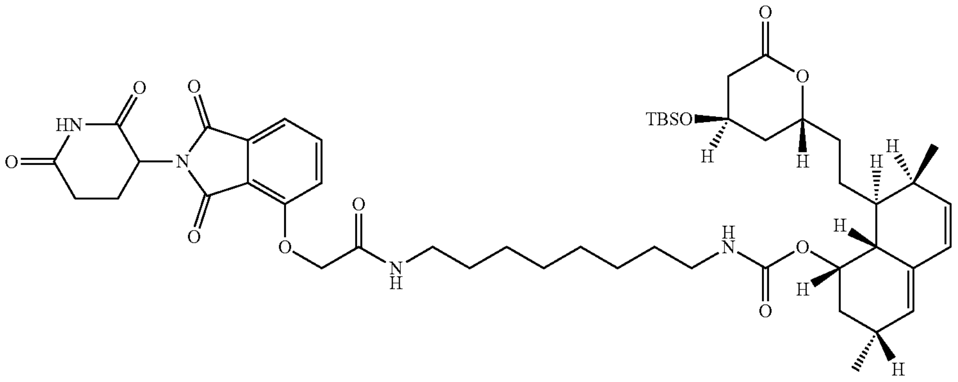 [SMILES: C[C@H]1C=C2C=C[C@H](C)[C@H](CC[C@@H]3C[C@@H](O[Si](C)(C)C(C)(C)C)CC(=O)O3)[C@H]2[C@@H](OC(=O)NCCCCCCCCNC(=O)COc2cccc3c2C(=O)N(C2CCC(=O)NC2=O)C3=O)C1] |
| 97 | 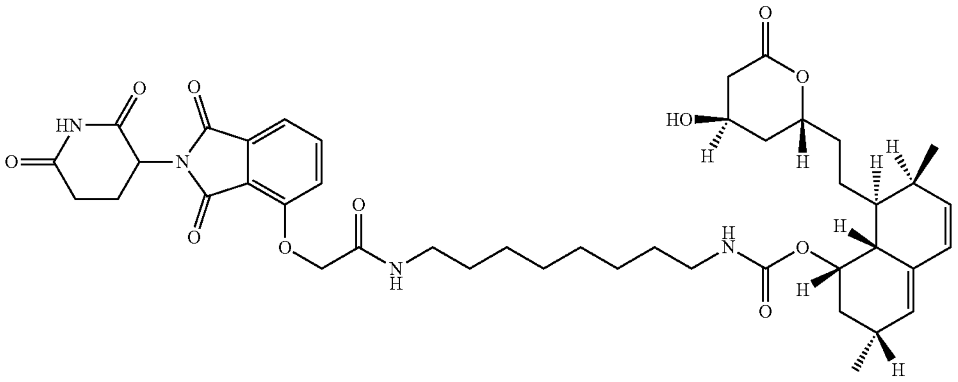 [SMILES: C[C@H]1C=C2C=C[C@H](C)[C@H](CC[C@@H]3C[C@@H](O)CC(=O)O3)[C@H]2[C@@H](OC(=O)NCCCCCCCCNC(=O)COc2cccc3c2C(=O)N(C2CCC(=O)NC2=O)C3=O)C1] |
| 98 | 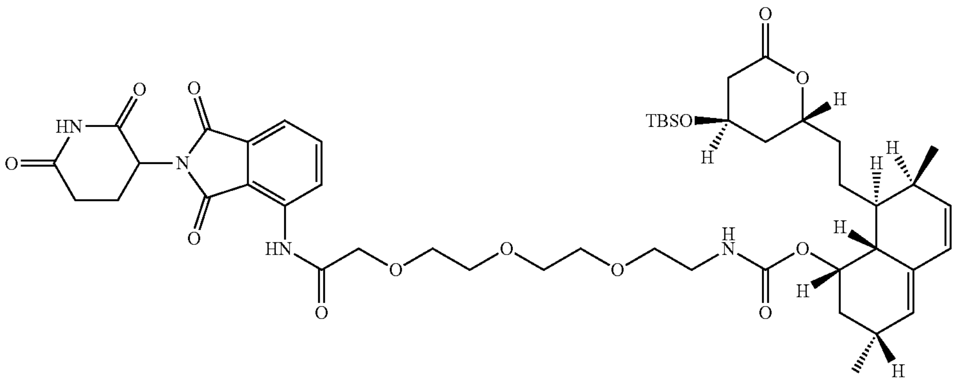 [SMILES: C[C@H]1C=C2C=C[C@H](C)[C@H](CC[C@@H]3C[C@@H](O[Si](C)(C)C(C)(C)C)CC(=O)O3)[C@H]2[C@@H](OC(=O)NCCOCCOCCOCC(=O)Nc2cccc3c2C(=O)N(C2CCC(=O)NC2=O)C3=O)C1] |

TABLE 1-continued
| Compound | Structure |
| --- | --- |
| 99 | 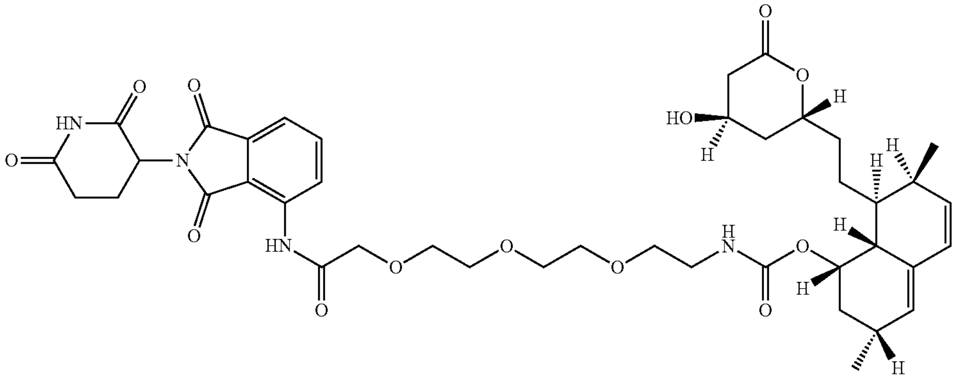 [SMILES: C[C@H]1C=C2C=C[C@H](C)[C@H](CC[C@@H]3C[C@@H](O)CC(=O)O3)[C@H]2[C@@H](OC(=O)NCCOCCOCCOCC(=O)Nc2cccc3c2C(=O)N(C2CCC(=O)NC2=O)C3=O)C1] |
| 100 | 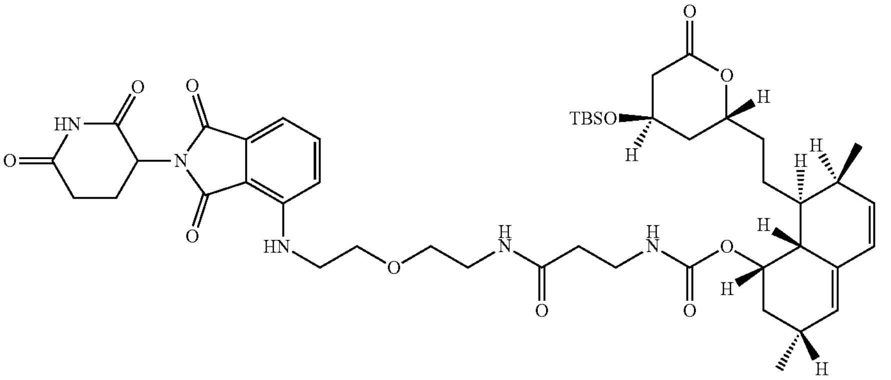 |
| 101 | 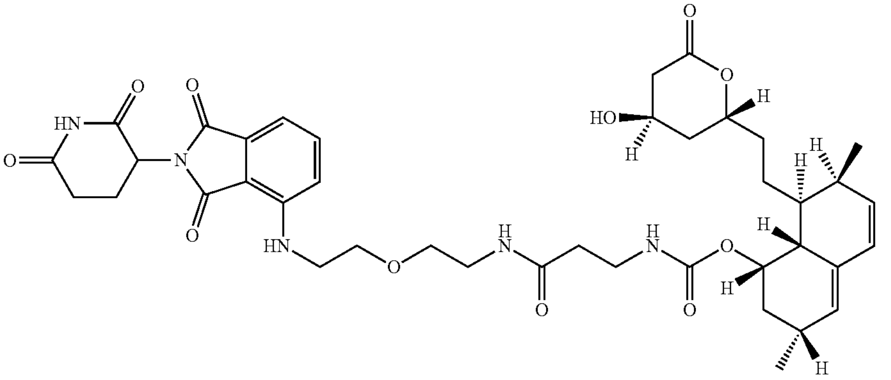 |
| 102 | 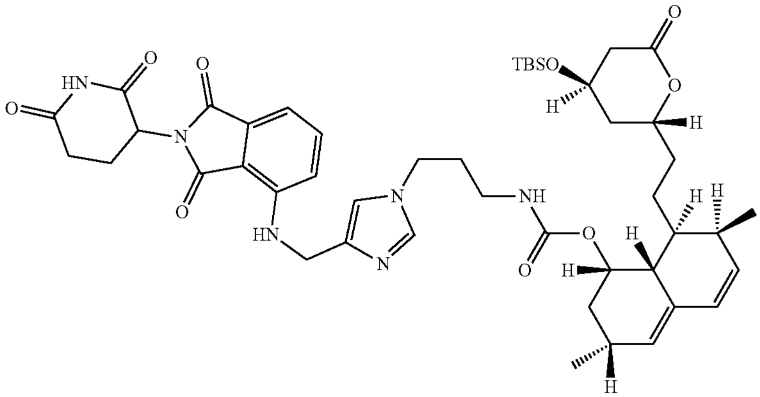 [SMILES: C[C@H]1C=C2C=C[C@H](C)[C@H](CC[C@@H]3C[C@@H](O)CC(=O)O3)[C@H]2[C@@H](OC(=O)NCCCn2cnc(CNc3cccc4c3C(=O)N(C3CCC(=O)NC3=O)C4=O)c2)C1] |

TABLE 1-continued
| Compound | Structure |
| --- | --- |
| 103 | 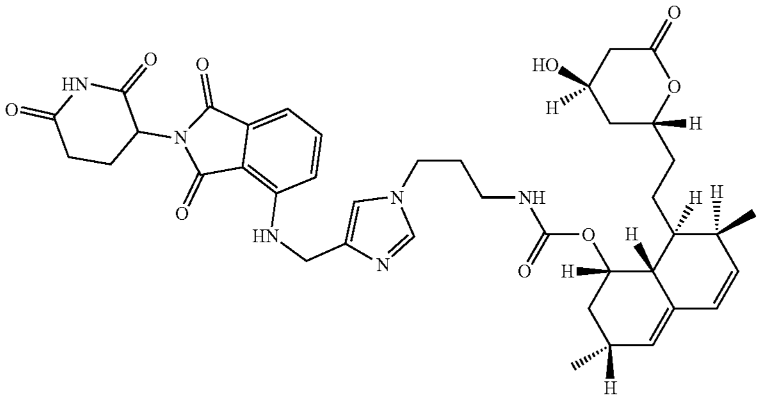 |
| 104 | 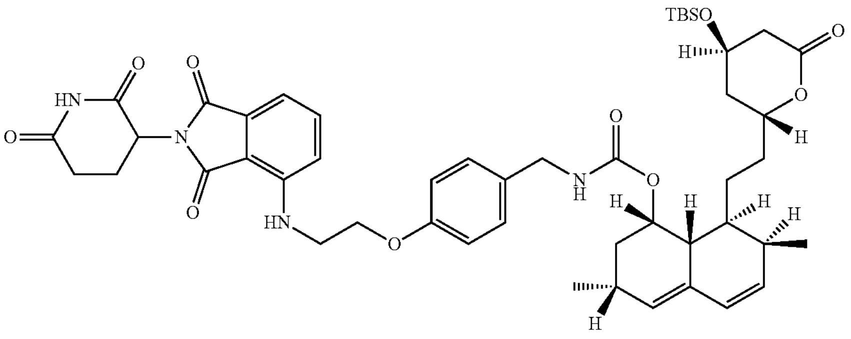 [SMILES: C[C@H]1C=C2C=C[C@H](C)[C@H](CC[C@@H]3C[C@@H](O[Si](C)(C)C(C)(C)C)CC(=O)O3)[C@H]2[C@@H](OC(=O)NCc2ccc(OCCNc3cccc4c3C(=O)N(C3CCC(=O)NC3=O)C4=O)cc2)C1] |
| 105 | 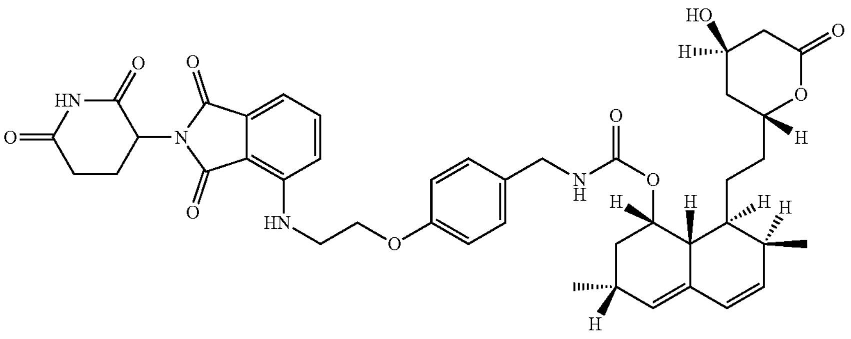 [SMILES: C[C@H]1C=C2C=C[C@H](C)[C@H](CC[C@@H]3C[C@@H](O)CC(=O)O3)[C@H]2[C@@H](OC(=O)NCc2ccc(OCCNc3cccc4c3C(=O)N(C3CCC(=O)NC3=O)C4=O)cc2)C1] |
| 106 | 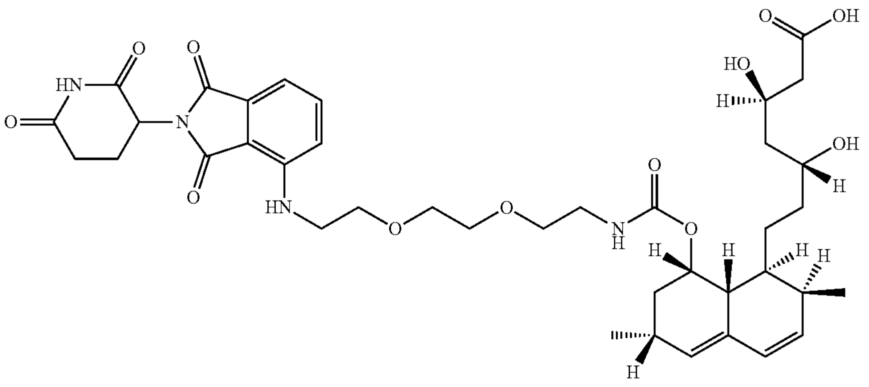 [SMILES: C[C@H]1C=C2C=C[C@H](C)[C@H](CC[C@@H](O)C[C@@H](O)CC(=O)O)[C@H]2[C@@H](OC(=O)NCCOCCOCCNc2cccc3c2C(=O)N(C2CCC(=O)NC2=O)C3=O)C1] |

TABLE 1-continued
| Compound | Structure |
| --- | --- |
| 107 | 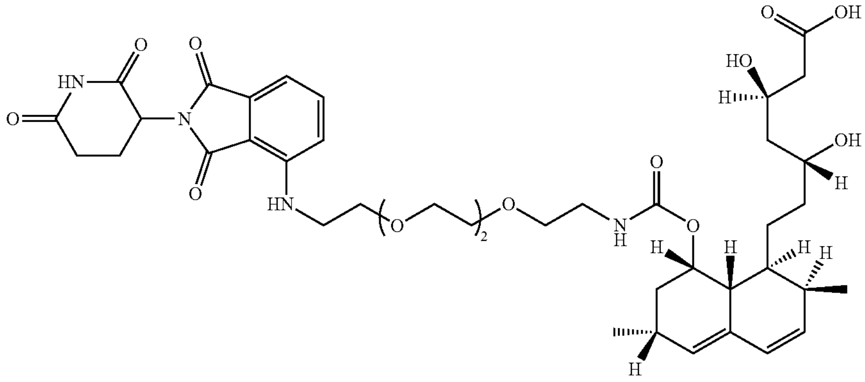 |
| 108 | 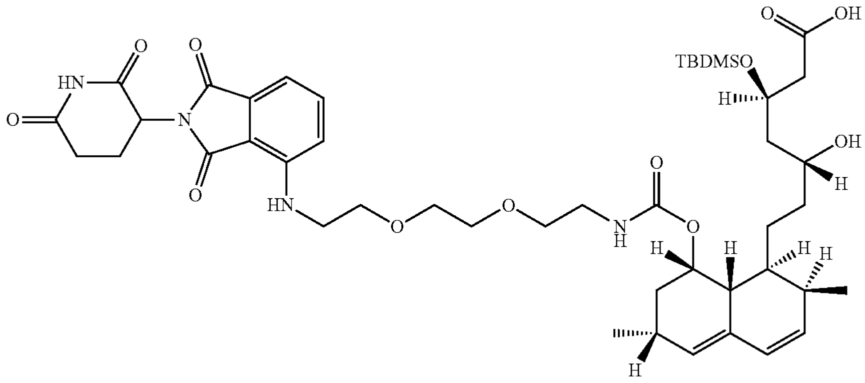 [SMILES: C[C@H]1C=C2C=C[C@H](C)[C@H](CC[C@@H](O)C[C@H](CC(=O)O)O[Si](C)(C)C(C)(C)C)[C@H]2[C@@H](OC(=O)NCCOCCOCCNc2cccc3c2C(=O)N(C2CCC(=O)NC2=O)C3=O)C1] |
| 109 | 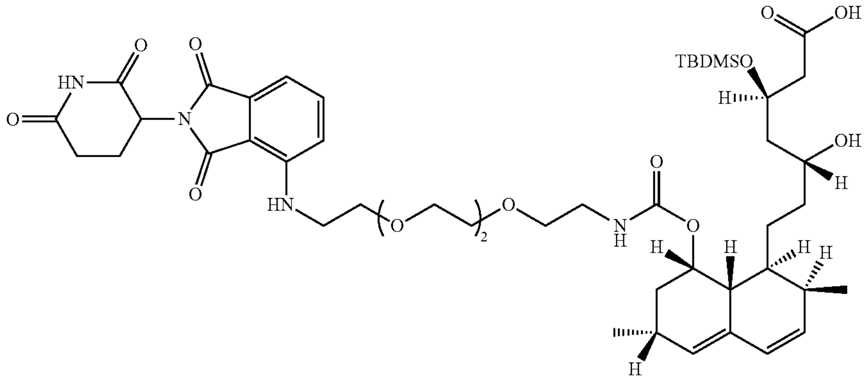 |
| 110 | 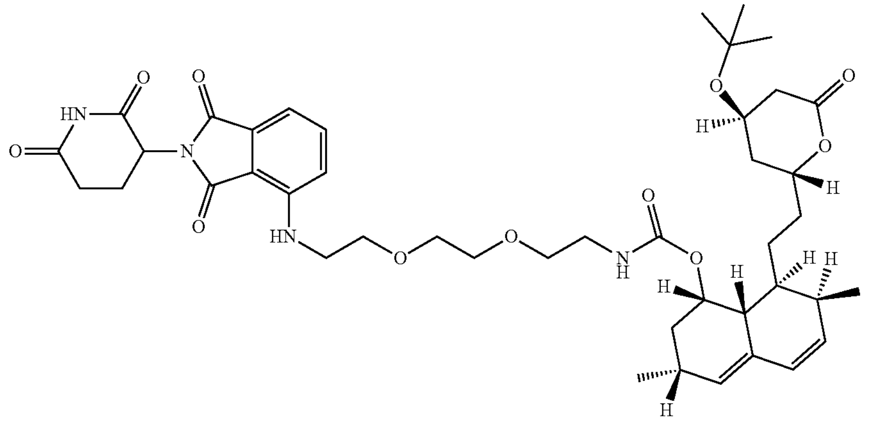 [SMILES: C[C@H]1C=C2C=C[C@H](C)[C@H](CC[C@@H]3C[C@@H](OC(C)(C)C)CC(=O)O3)[C@H]2[C@@H](OC(=O)NCCOCCOCCNc2cccc3c2C(=O)N(C2CCC(=O)NC2=O)C3=O)C1] |

TABLE 1-continued
| Compound | Structure |
|---|---|
| 111 | 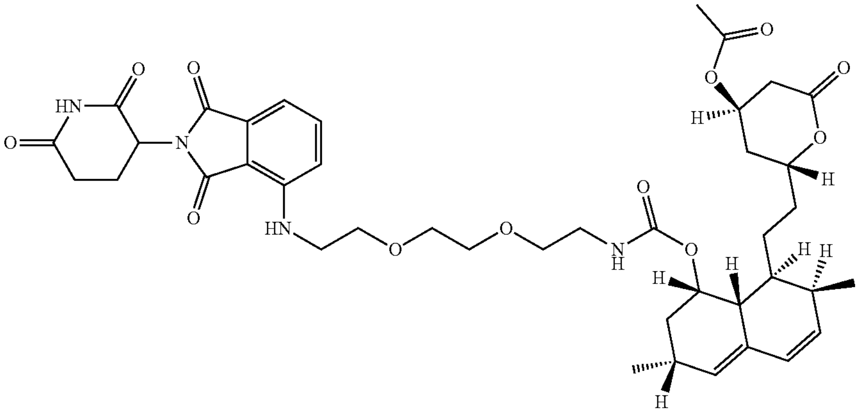 [SMILES: CC(=O)O[C@H]1CC(=O)O[C@H](CC[C@@H]2[C@@H]3C(=C[C@H](C)C[C@@H]3OC(=O)NCCOCCOCCNc3cccc4c3C(=O)N(C3CCC(=O)NC3=O)C4=O)C=C[C@@H]2C)C1] |
| 112 | 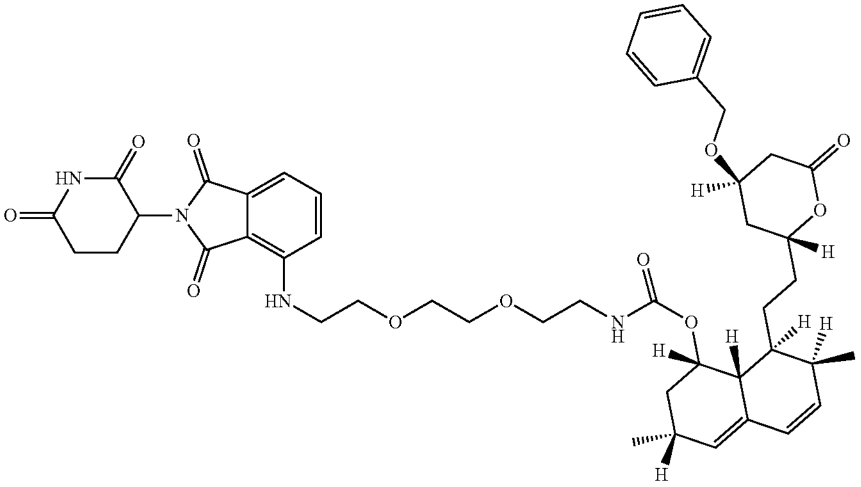 [SMILES: C[C@H]1C=C2C=C[C@H](C)[C@H](CC[C@@H]3C[C@@H](OCc4ccccc4)CC(=O)O3)[C@H]2[C@@H](OC(=O)NCCOCCOCCNc2cccc3c2C(=O)N(C2CCC(=O)NC2=O)C3=O)C1] |
| 113 | 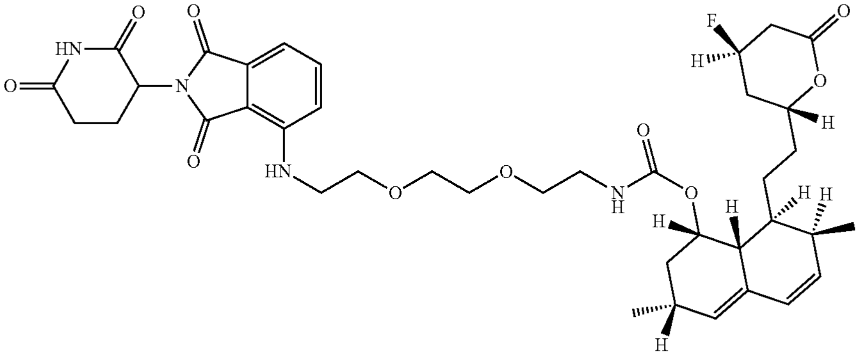 [SMILES: C[C@H]1C=C2C=C[C@H](C)[C@H](CC[C@@H]3C[C@@H](F)CC(=O)O3)[C@H]2[C@@H](OC(=O)NCCOCCOCCNc2cccc3c2C(=O)N(C2CCC(=O)NC2=O)C3=O)C1] |

TABLE 1-continued
| Compound | Structure |
|---|---|
| 114 | 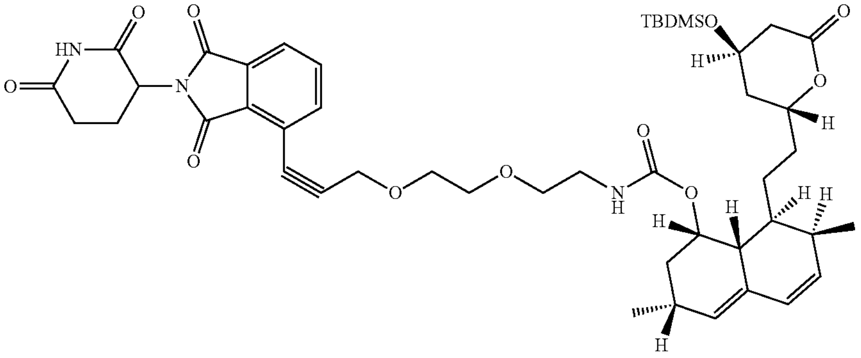 [SMILES: C[C@H]1C=C2C=C[C@H](C)[C@H](CC[C@@H]3C[C@@H](O[Si](C)(C)C(C)(C)C)CC(=O)O3)[C@H]2[C@@H](OC(=O)NCCOCCOCC#Cc2cccc3c2C(=O)N(C2CCC(=O)NC2=O)C3=O)C1] |
| 115 | 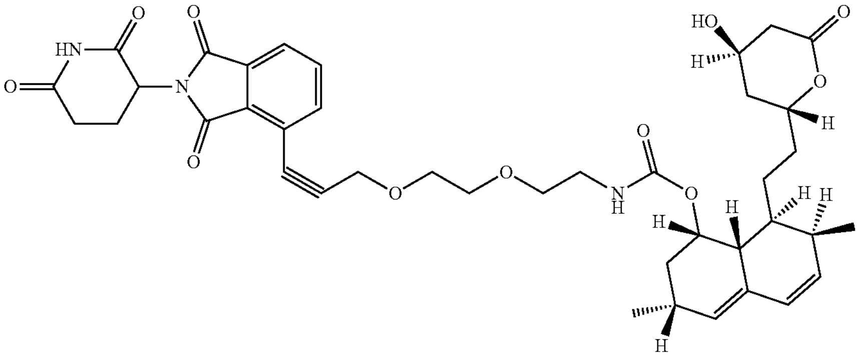 [SMILES: C[C@H]1C=C2C=C[C@H](C)[C@H](CC[C@@H]3C[C@@H](O)CC(=O)O3)[C@H]2[C@@H](OC(=O)NCCOCCOCC#Cc2cccc3c2C(=O)N(C2CCC(=O)NC2=O)C3=O)C1] |
| 116 | 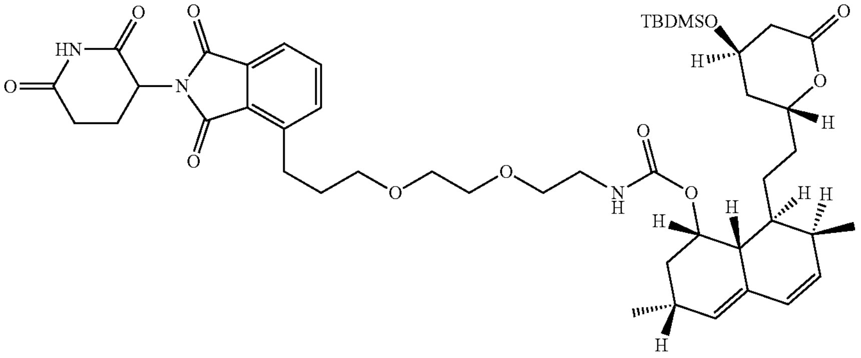 [SMILES: C[C@H]1C=C2C=C[C@H](C)[C@H](CC[C@@H]3C[C@@H](O[Si](C)(C)C(C)(C)C)CC(=O)O3)[C@H]2[C@@H](OC(=O)NCCOCCOCCCc2cccc3c2C(=O)N(C2CCC(=O)NC2=O)C3=O)C1] |
| 117 | 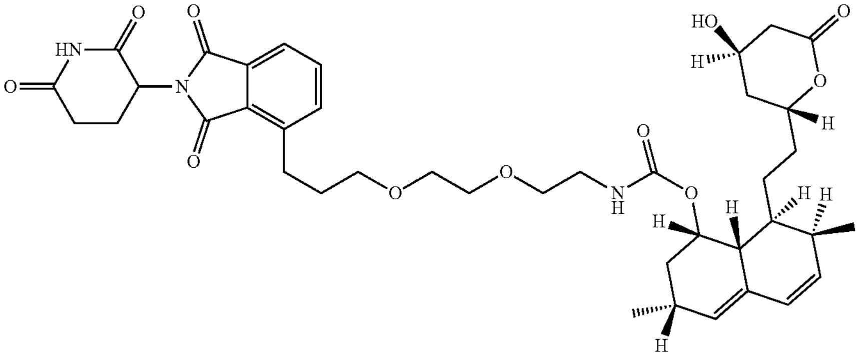 [SMILES: C[C@H]1C=C2C=C[C@H](C)[C@H](CC[C@@H]3C[C@@H](O)CC(=O)O3)[C@H]2[C@@H](OC(=O)NCCOCCOCCCc2cccc3c2C(=O)N(C2CCC(=O)NC2=O)C3=O)C1] |

TABLE 1-continued
| Compound | Structure |
| --- | --- |
| 118 | 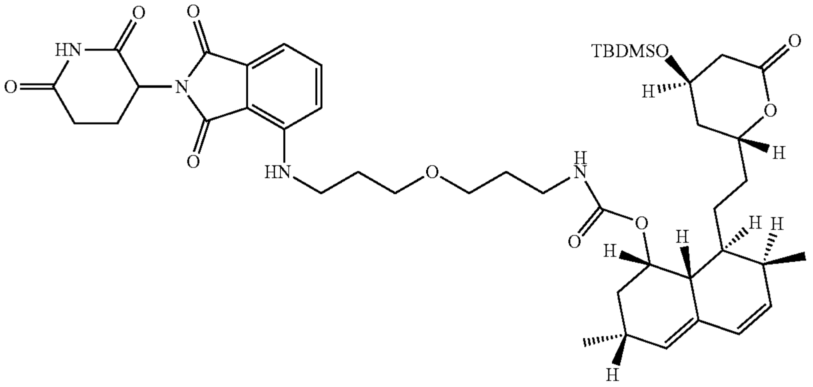 [SMILES: C[C@H]1C=C2C=C[C@H](C)[C@H](CC[C@@H]3C[C@@H](O[Si](C)(C)C(C)(C)C)CC(=O)O3)[C@H]2[C@@H](OC(=O)NCCCOCCCNc2cccc3c2C(=O)N(C2CCC(=O)NC2=O)C3=O)C1] |
| 119 | 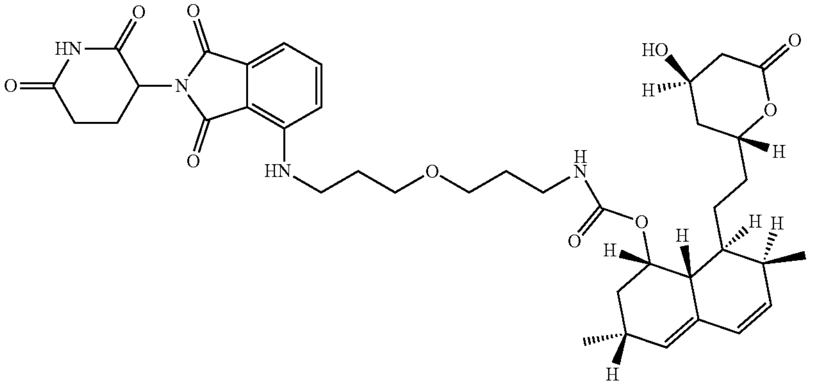 [SMILES: C[C@H]1C=C2C=C[C@H](C)[C@H](CC[C@@H]3C[C@@H](O)CC(=O)O3)[C@H]2[C@@H](OC(=O)NCCCOCCCNc2cccc3c2C(=O)N(C2CCC(=O)NC2=O)C3=O)C1] |
| 120 | 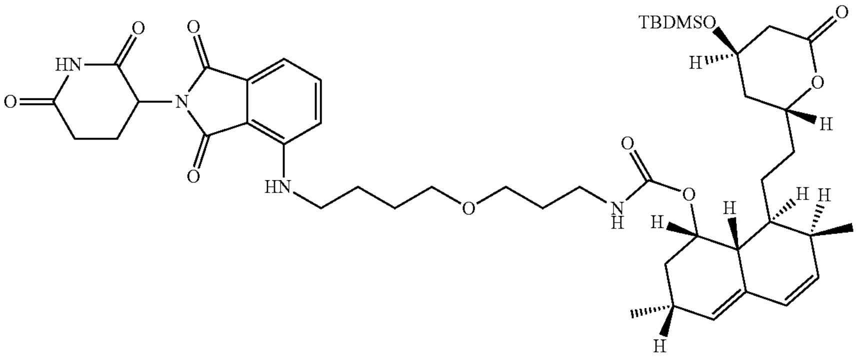 [SMILES: C[C@H]1C=C2C=C[C@H](C)[C@H](CC[C@@H]3C[C@@H](O[Si](C)(C)C(C)(C)C)CC(=O)O3)[C@H]2[C@@H](OC(=O)NCCCOCCCCNc2cccc3c2C(=O)N(C2CCC(=O)NC2=O)C3=O)C1] |
| 121 | 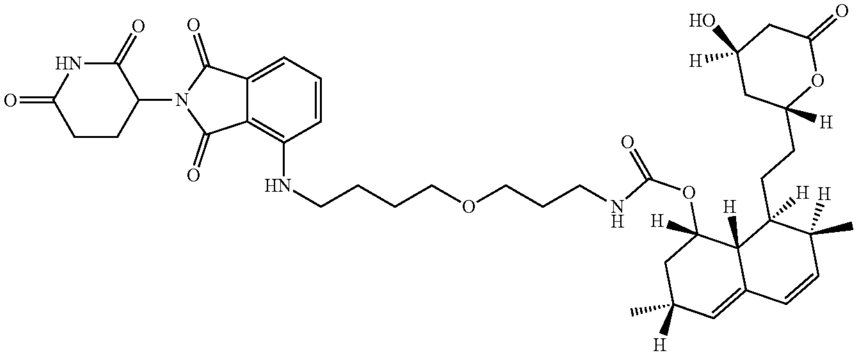 [SMILES: C[C@H]1C=C2C=C[C@H](C)[C@H](CC[C@@H]3C[C@@H](O)CC(=O)O3)[C@H]2[C@@H](OC(=O)NCCCOCCCCNc2cccc3c2C(=O)N(C2CCC(=O)NC2=O)C3=O)C1] |

TABLE 1-continued
| Compound | Structure |
| --- | --- |
| 122 | 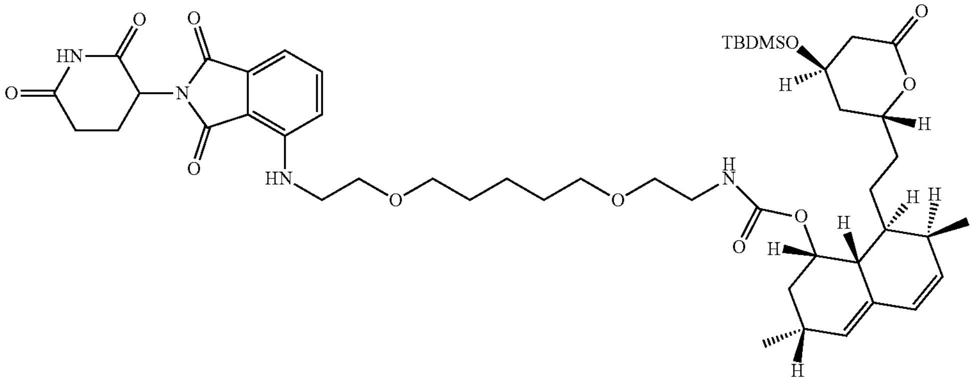 [SMILES: C[C@H]1C=C2C=C[C@H](C)[C@H](CC[C@@H]3C[C@@H](O[Si](C)(C)C(C)(C)C)CC(=O)O3)[C@H]2[C@@H](OC(=O)NCCOCCCCCOCCNc2cccc3c2C(=O)N(C2CCC(=O)NC2=O)C3=O)C1] |
| 123 | 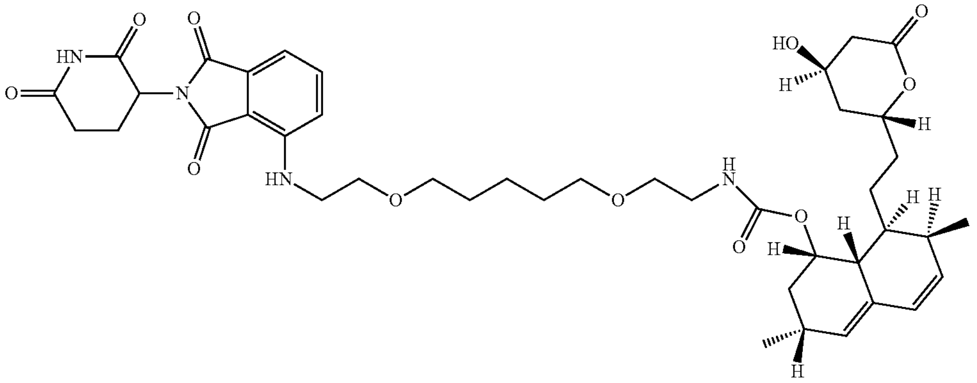 [SMILES: C[C@H]1C=C2C=C[C@H](C)[C@H](CC[C@@H]3C[C@@H](O)CC(=O)O3)[C@H]2[C@@H](OC(=O)NCCOCCCCCOCCNc2cccc3c2C(=O)N(C2CCC(=O)NC2=O)C3=O)C1] |
| 124 | 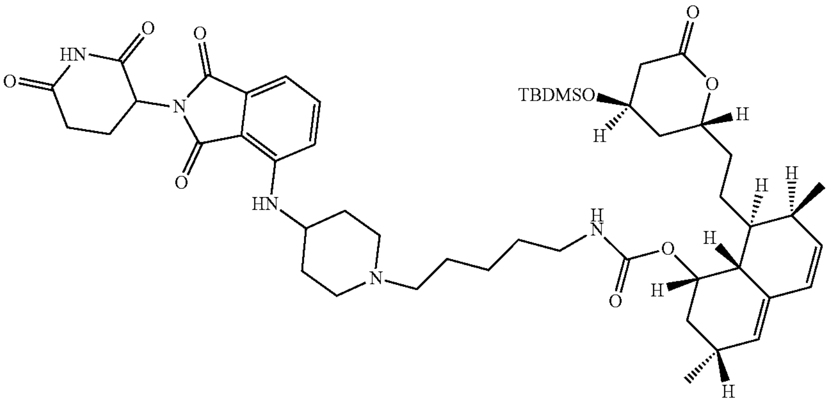 [SMILES: C[C@H]1C=C2C=C[C@H](C)[C@H](CC[C@@H]3C[C@@H](O[Si](C)(C)C(C)(C)C)CC(=O)O3)[C@H]2[C@@H](OC(=O)NCCCCCN2CCC(Nc3cccc4c3C(=O)N(C3CCC(=O)NC3=O)C4=O)CC2)C1] |
| 125 | 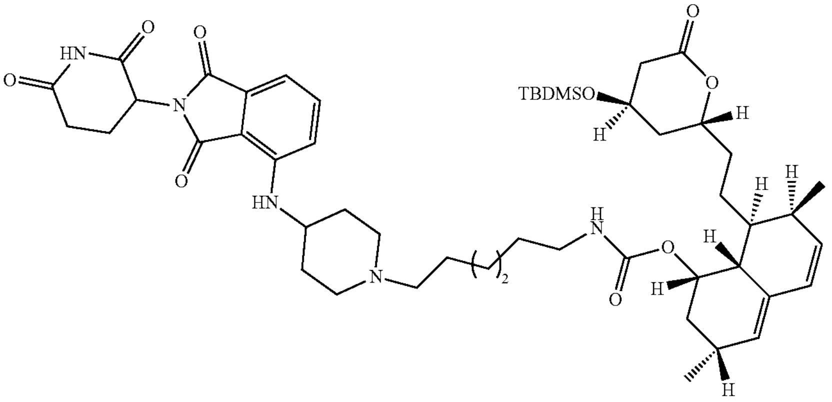 |

TABLE 1-continued
| Compound | Structure |
|---|---|
| 126 | 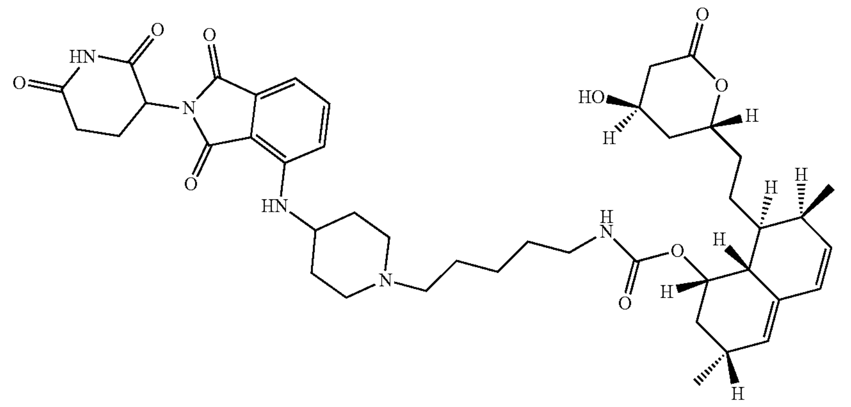 [SMILES: C[C@H]1C=C2C=C[C@H](C)[C@H](CC[C@@H]3C[C@@H](O)CC(=O)O3)[C@H]2[C@@H](OC(=O)NCCCCCN2CCC(Nc3cccc4c3C(=O)N(C3CCC(=O)NC3=O)C4=O)CC2)C1] |
| 127 | 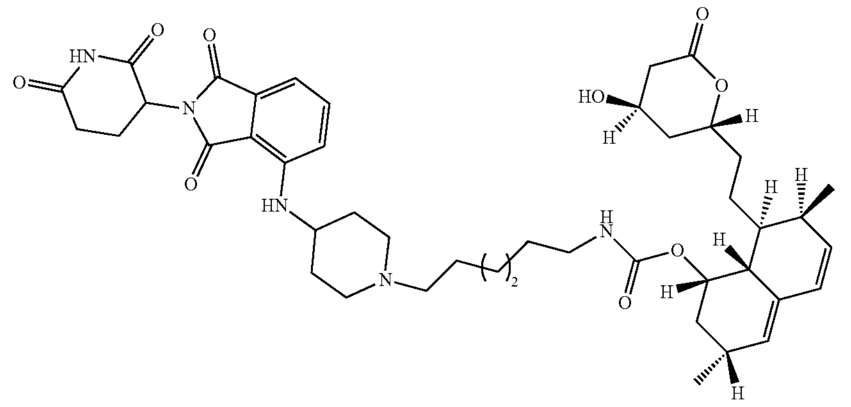 |
| 128 | 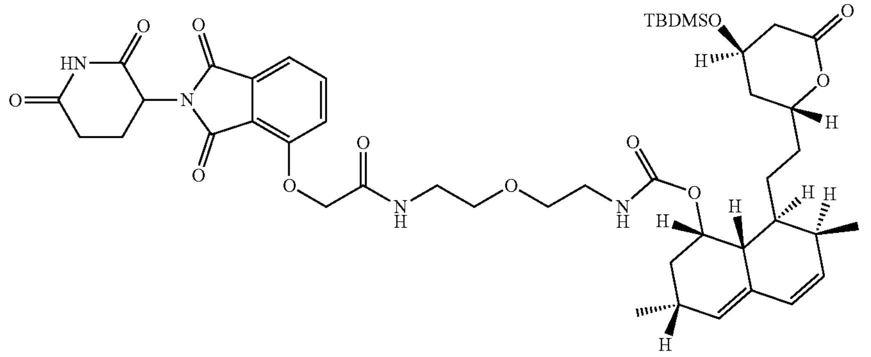 [SMILES: C[C@H]1C=C2C=C[C@H](C)[C@H](CC[C@@H]3C[C@@H](O[Si](C)(C)C(C)(C)C)CC(=O)O3)[C@H]2[C@@H](OC(=O)NCCOCCNC(=O)COc2cccc3c2C(=O)N(C2CCC(=O)NC2=O)C3=O)C1] |
| 129 | 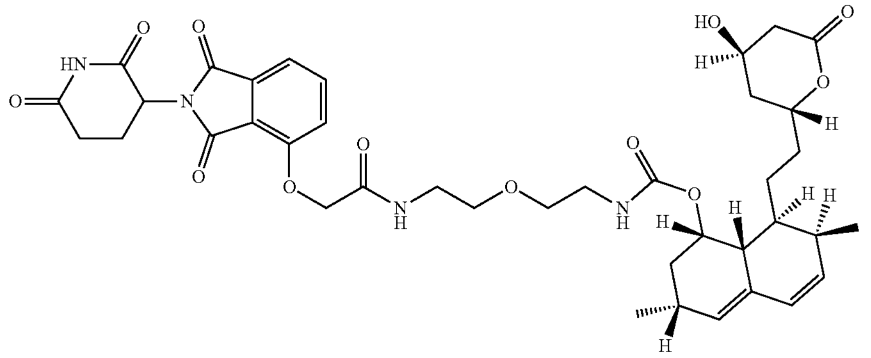 [SMILES: C[C@H]1C=C2C=C[C@H](C)[C@H](CC[C@@H]3C[C@@H](O)CC(=O)O3)[C@H]2[C@@H](OC(=O)NCCOCCNC(=O)COc2cccc3c2C(=O)N(C2CCC(=O)NC2=O)C3=O)C1] |

TABLE 1-continued
| Compound | Structure |
| --- | --- |
| 130 | 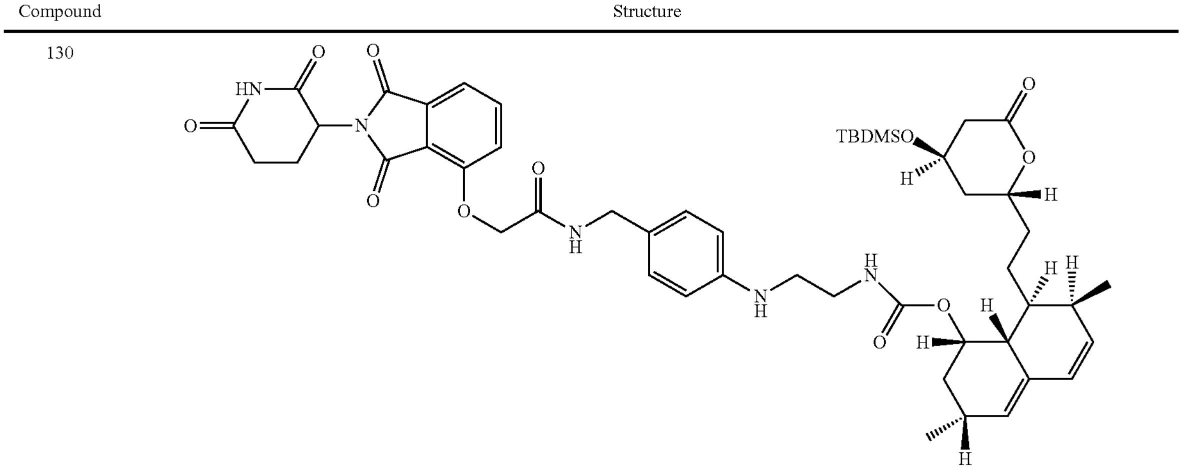 |
| 131 | 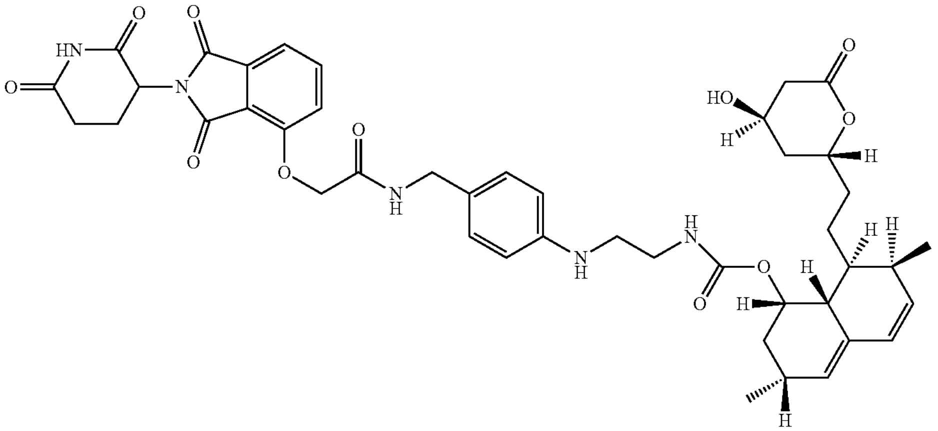 [SMILES: C[C@H]1C=C2C=C[C@H](C)[C@H](CC[C@@H]3C[C@@H](O)CC(=O)O3)[C@H]2[C@@H](OC(=O)NCCNc2ccc(CNC(=O)COc3cccc4c3C(=O)N(C3CCC(=O)NC3=O)C4=O)cc2)C1] |
| 132 | 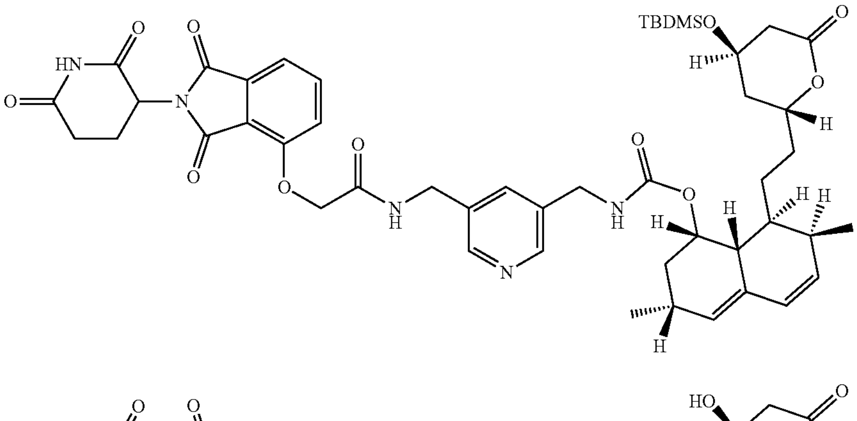 |
| 133 | 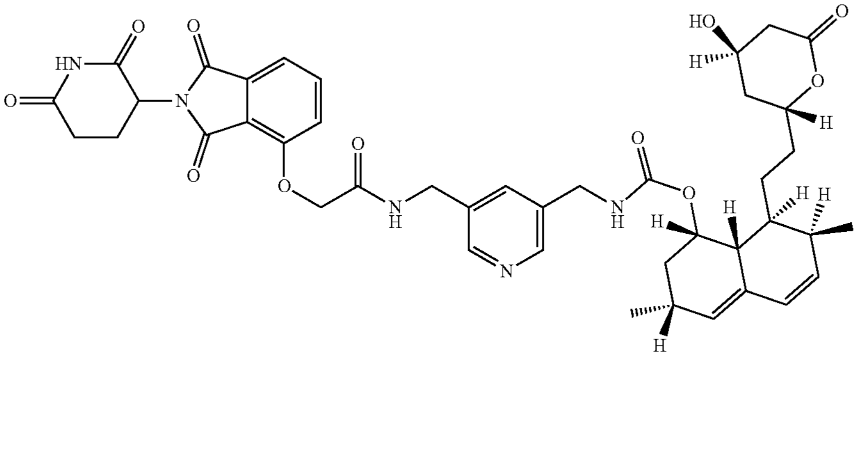 [SMILES: C[C@H]1C=C2C=C[C@H](C)[C@H](CC[C@@H]3C[C@@H](O)CC(=O)O3)[C@H]2[C@@H](OC(=O)NCc2cncc(CNC(=O)COc3cccc4c3C(=O)N(C3CCC(=O)NC3=O)C4=O)c2)C1] |

TABLE 1-continued
| Compound | Structure |
|---|---|
| 134 | 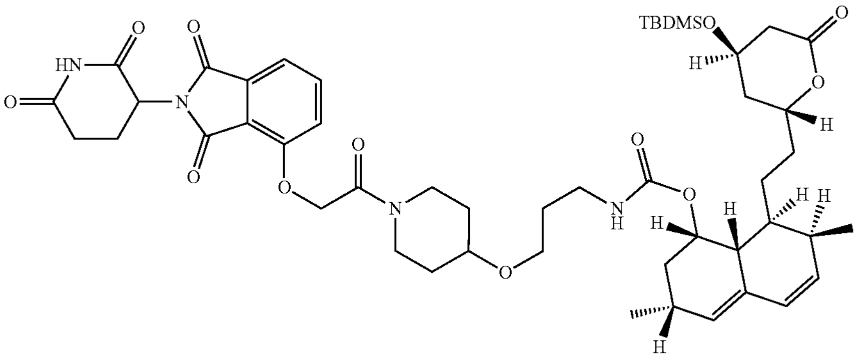 [SMILES: C[C@H]1C=C2C=C[C@H](C)[C@H](CC[C@@H]3C[C@@H](O[Si](C)(C)C(C)(C)C)CC(=O)O3)[C@H]2[C@@H](OC(=O)NCCCOC2CCN(C(=O)COc3cccc4c3C(=O)N(C3CCC(=O)NC3=O)C4=O)CC2)C1] |
| 135 | 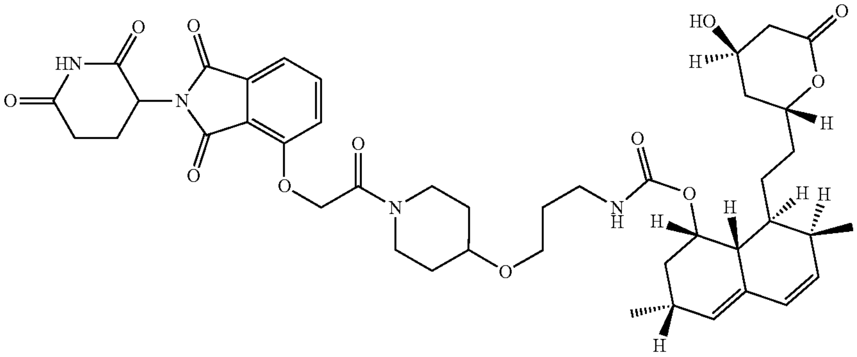 [SMILES: C[C@H]1C=C2C=C[C@H](C)[C@H](CC[C@@H]3C[C@@H](O)CC(=O)O3)[C@H]2[C@@H](OC(=O)NCCCOC2CCN(C(=O)COc3cccc4c3C(=O)N(C3CCC(=O)NC3=O)C4=O)CC2)C1] |
| 136 | 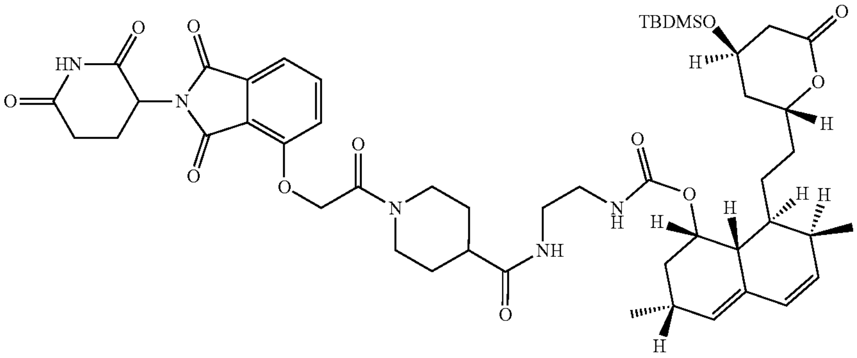 [SMILES: C[C@H]1C=C2C=C[C@H](C)[C@H](CC[C@@H]3C[C@@H](O[Si](C)(C)C(C)(C)C)CC(=O)O3)[C@H]2[C@@H](OC(=O)NCCNC(=O)C2CCN(C(=O)COc3cccc4c3C(=O)N(C3CCC(=O)NC3=O)C4=O)CC2)C1] |
| 137 | 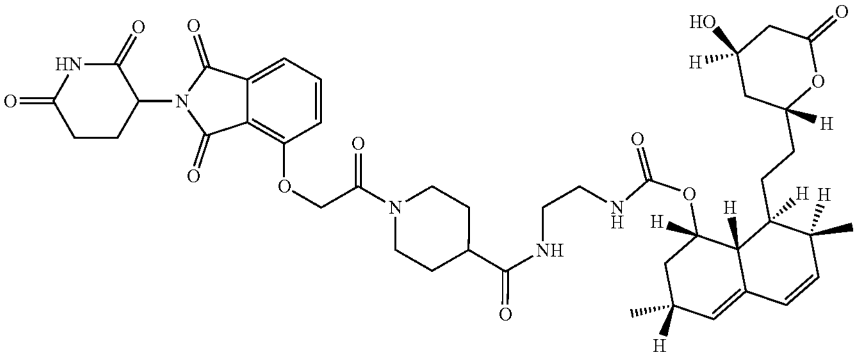 [SMILES: C[C@H]1C=C2C=C[C@H](C)[C@H](CC[C@@H]3C[C@@H](O)CC(=O)O3)[C@H]2[C@@H](OC(=O)NCCNC(=O)C2CCN(C(=O)COc3cccc4c3C(=O)N(C3CCC(=O)NC3=O)C4=O)CC2)C1] |

TABLE 1-continued
| Compound | Structure |
| --- | --- |
| 138 | 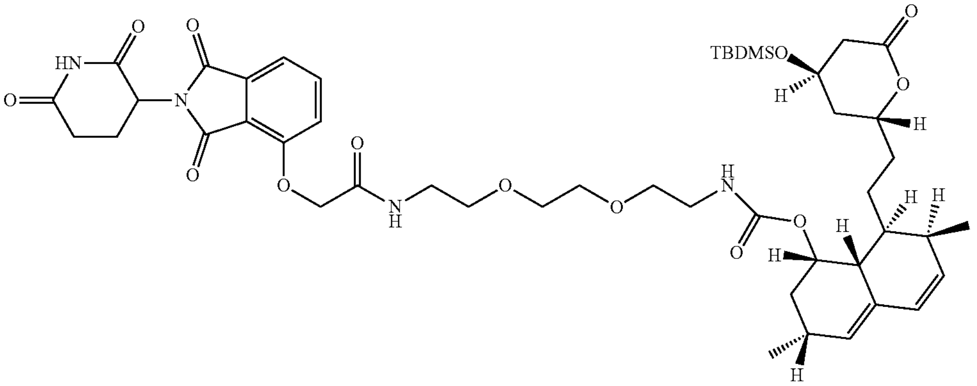 [SMILES: C[C@H]1C=C2C=C[C@H](C)[C@H](CC[C@@H]3C[C@@H](O[Si](C)(C)C(C)(C)C)CC(=O)O3)[C@H]2[C@@H](OC(=O)NCCOCCOCCNC(=O)COc2cccc3c2C(=O)N(C2CCC(=O)NC2=O)C3=O)C1] |
| 139 | 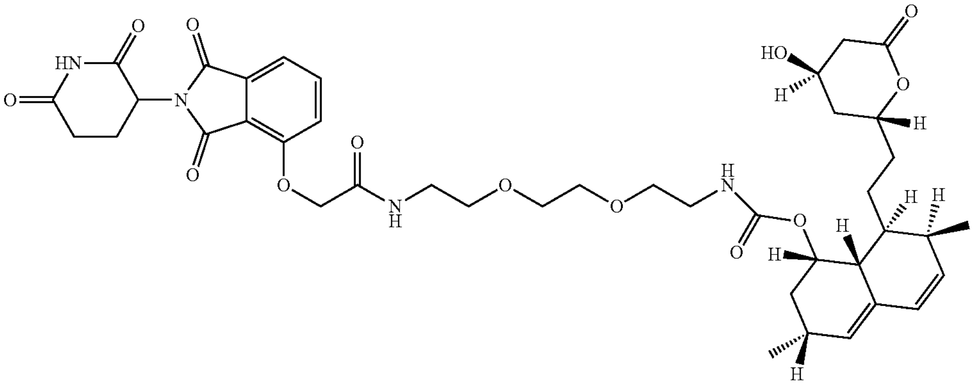 [SMILES: C[C@H]1C=C2C=C[C@H](C)[C@H](CC[C@@H]3C[C@@H](O)CC(=O)O3)[C@H]2[C@@H](OC(=O)NCCOCCOCCNC(=O)COc2cccc3c2C(=O)N(C2CCC(=O)NC2=O)C3=O)C1] |
| 140 | 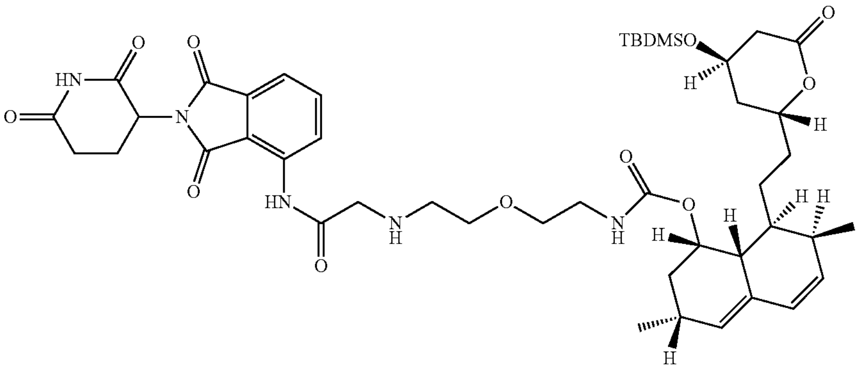 [SMILES: C[C@H]1C=C2C=C[C@H](C)[C@H](CC[C@@H]3C[C@@H](O[Si](C)(C)C(C)(C)C)CC(=O)O3)[C@H]2[C@@H](OC(=O)NCCOCCNCC(=O)Nc2cccc3c2C(=O)N(C2CCC(=O)NC2=O)C3=O)C1] |
| 141 | 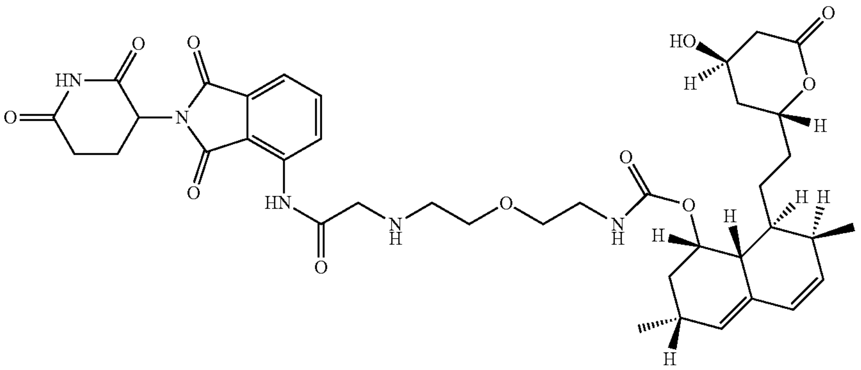 [SMILES: C[C@H]1C=C2C=C[C@H](C)[C@H](CC[C@@H]3C[C@@H](O)CC(=O)O3)[C@H]2[C@@H](OC(=O)NCCOCCNCC(=O)Nc2cccc3c2C(=O)N(C2CCC(=O)NC2=O)C3=O)C1] |

TABLE 1-continued
| Compound | Structure |
| --- | --- |
| 142 | 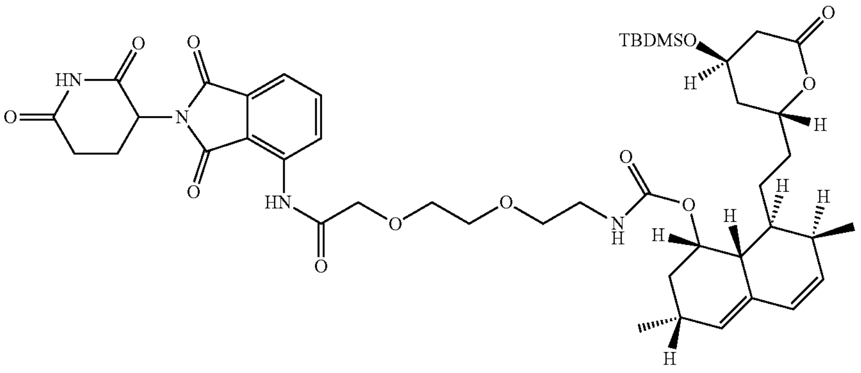 [SMILES: C[C@H]1C=C2C=C[C@H](C)[C@H](CC[C@@H]3C[C@@H](O[Si](C)(C)C(C)(C)C)CC(=O)O3)[C@H]2[C@@H](OC(=O)NCCOCCOCC(=O)Nc2cccc3c2C(=O)N(C2CCC(=O)NC2=O)C3=O)C1] |
| 143 | 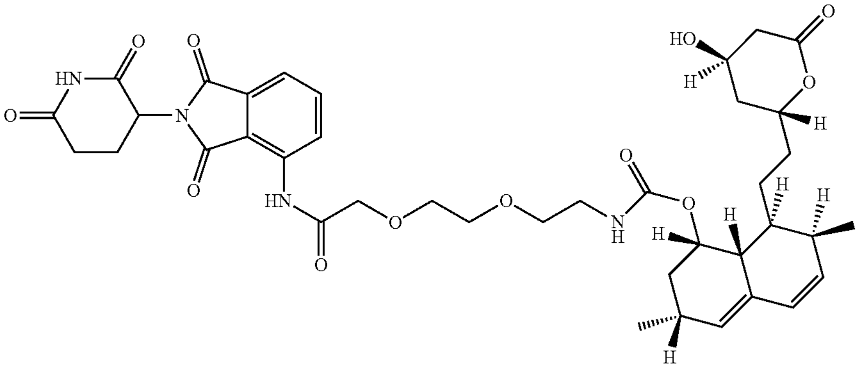 [SMILES: C[C@H]1C=C2C=C[C@H](C)[C@H](CC[C@@H]3C[C@@H](O)CC(=O)O3)[C@H]2[C@@H](OC(=O)NCCOCCOCC(=O)Nc2cccc3c2C(=O)N(C2CCC(=O)NC2=O)C3=O)C1] |
| 144 | 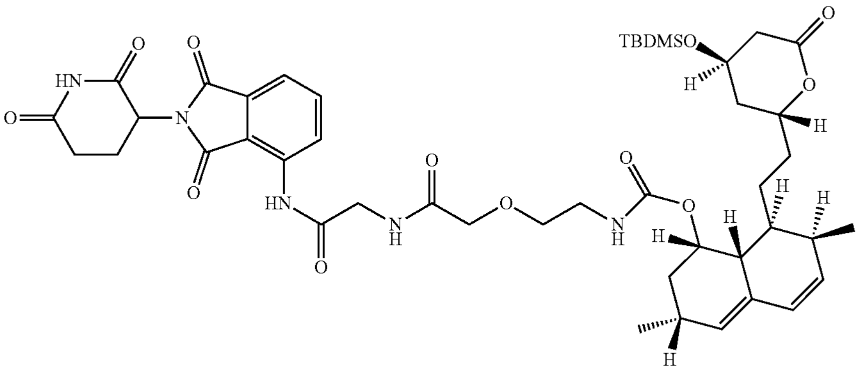 [SMILES: C[C@H]1C=C2C=C[C@H](C)[C@H](CC[C@@H]3C[C@@H](O[Si](C)(C)C(C)(C)C)CC(=O)O3)[C@H]2[C@@H](OC(=O)NCCOCC(=O)NCC(=O)Nc2cccc3c2C(=O)N(C2CCC(=O)NC2=O)C3=O)C1] |
| 145 | 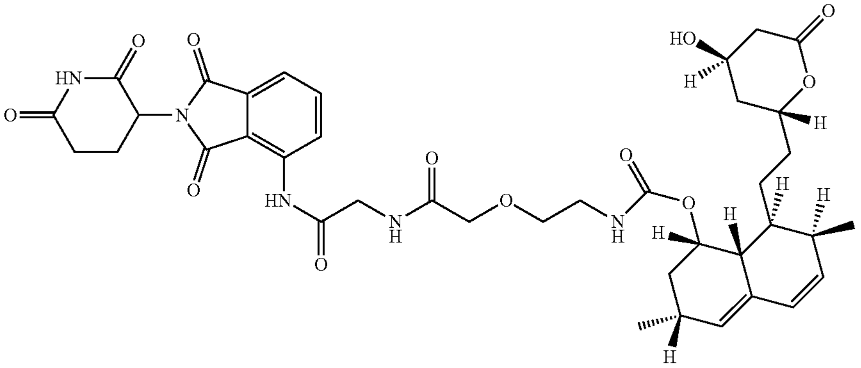 [SMILES: C[C@H]1C=C2C=C[C@H](C)[C@H](CC[C@@H]3C[C@@H](O)CC(=O)O3)[C@H]2[C@@H](OC(=O)NCCOCC(=O)NCC(=O)Nc2cccc3c2C(=O)N(C2CCC(=O)NC2=O)C3=O)C1] |

TABLE 1-continued
| Compound | Structure |
| --- | --- |
| 146 | 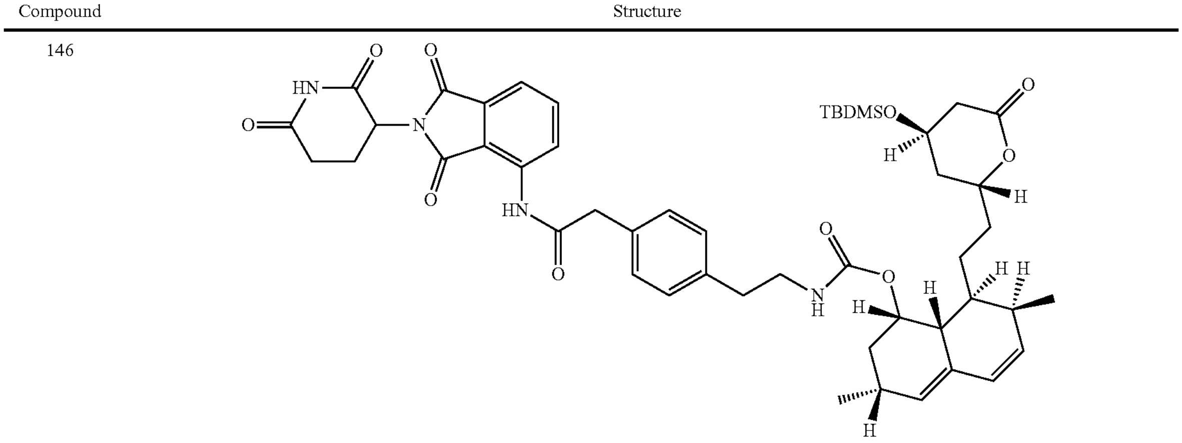 |
| 147 | 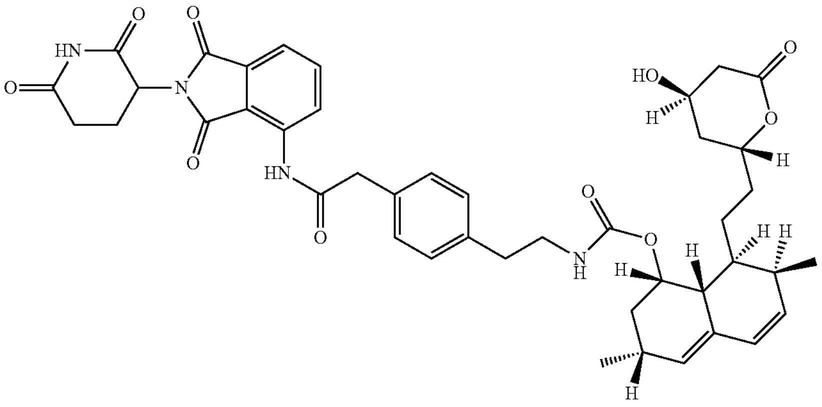 [SMILES: C[C@H]1C=C2C=C[C@H](C)[C@H](CC[C@@H]3C[C@@H](O)CC(=O)O3)[C@H]2[C@@H](OC(=O)NCCc2ccc(CC(=O)Nc3cccc4c3C(=O)N(C3CCC(=O)NC3=O)C4=O)cc2)C1] |
| 148 | 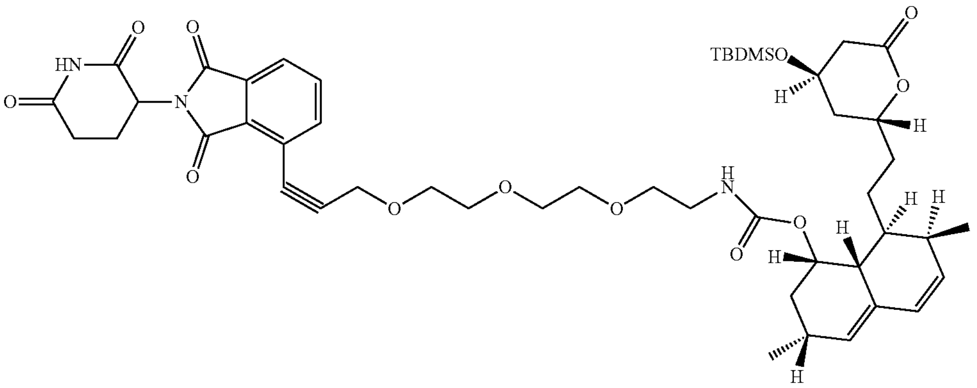 [SMILES: C[C@H]1C=C2C=C[C@H](C)[C@H](CC[C@@H]3C[C@@H](O[Si](C)(C)C(C)(C)C)CC(=O)O3)[C@H]2[C@@H](OC(=O)NCCOCCOCCOCC#Cc2cccc3c2C(=O)N(C2CCC(=O)NC2=O)C3=O)C1] |
| 149 | 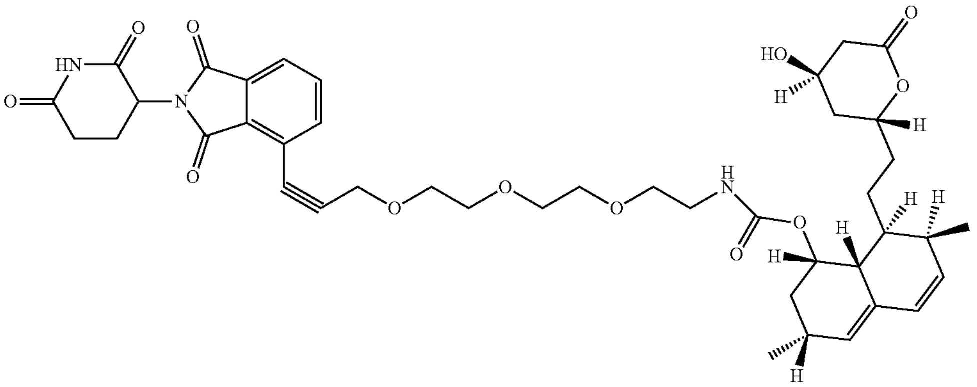 [SMILES: C[C@H]1C=C2C=C[C@H](C)[C@H](CC[C@@H]3C[C@@H](O)CC(=O)O3)[C@H]2[C@@H](OC(=O)NCCOCCOCCOCC#Cc2cccc3c2C(=O)N(C2CCC(=O)NC2=O)C3=O)C1] |

TABLE 1-continued
| Compound | Structure |
| --- | --- |
| 150 | 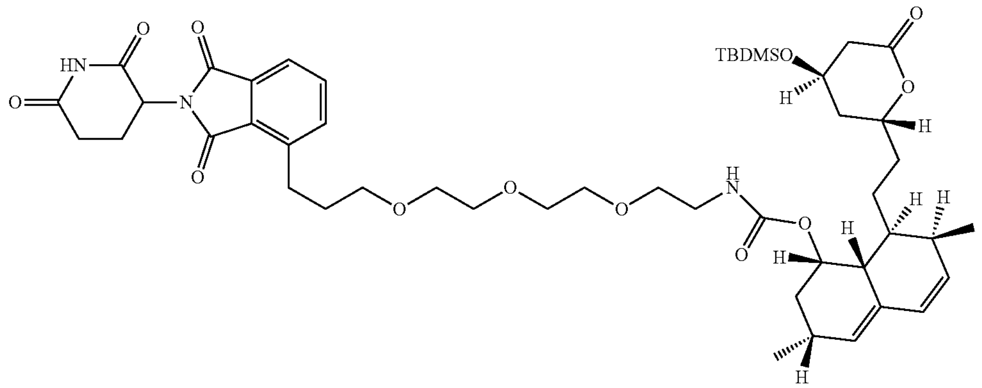 [SMILES: C[C@H]1C=C2C=C[C@H](C)[C@H](CC[C@@H]3C[C@@H](O[Si](C)(C)C(C)(C)C)CC(=O)O3)[C@H]2[C@@H](OC(=O)NCCOCCOCCOCCCc2cccc3c2C(=O)N(C2CCC(=O)NC2=O)C3=O)C1] |
| 151 | 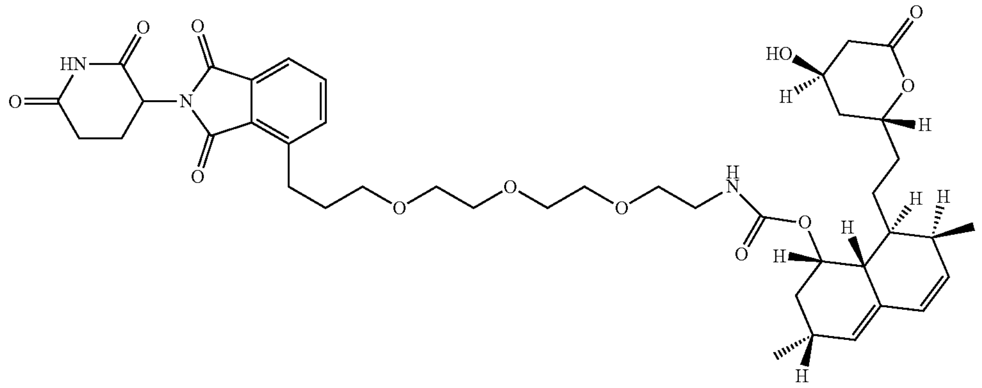 [SMILES: C[C@H]1C=C2C=C[C@H](C)[C@H](CC[C@@H]3C[C@@H](O)CC(=O)O3)[C@H]2[C@@H](OC(=O)NCCOCCOCCOCCCc2cccc3c2C(=O)N(C2CCC(=O)NC2=O)C3=O)C1] |
| 152 | 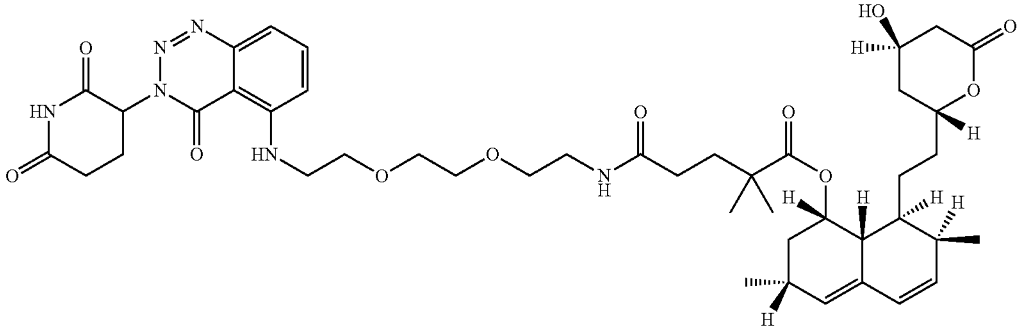 [SMILES: C[C@H]1C=C2C=C[C@H](C)[C@H](CC[C@@H]3C[C@@H](O)CC(=O)O3)[C@H]2[C@@H](OC(=O)C(C)(C)CCC(=O)NCCOCCOCCNc2cccc3nnn(C4CCC(=O)NC4=O)c(=O)c23)C1] |
| 153 | 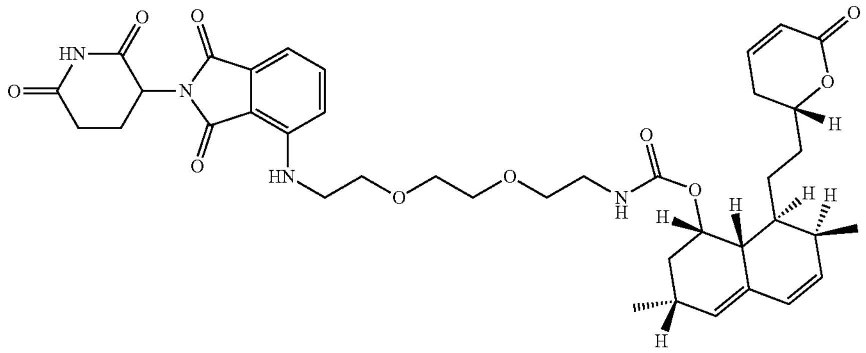 [SMILES: C[C@H]1C=C2C=C[C@H](C)[C@H](CC[C@@H]3CC=CC(=O)O3)[C@H]2[C@@H](OC(=O)NCCOCCOCCNc2cccc3c2C(=O)N(C2CCC(=O)NC2=O)C3=O)C1] |

TABLE 1-continued
| Compound | Structure |
|---|---|
| 155 | 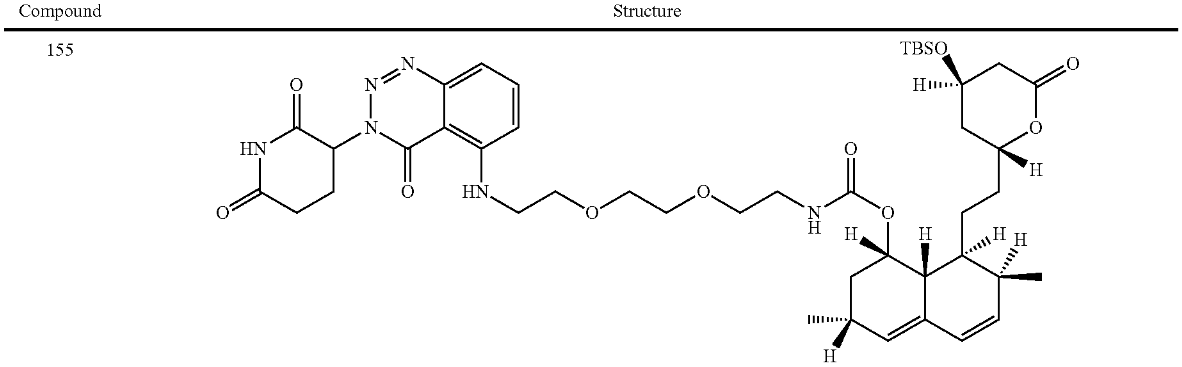 |
| 156 | 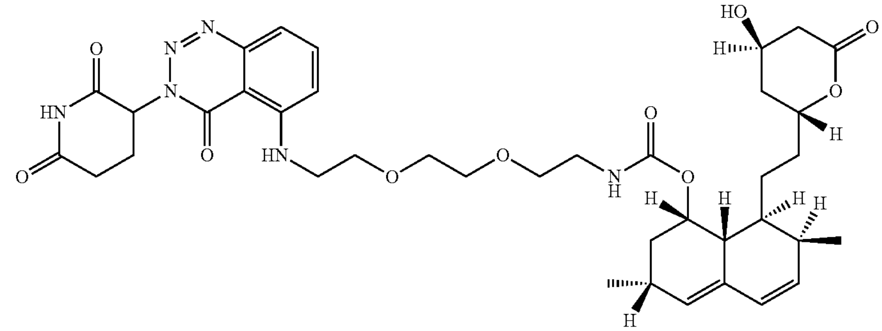 or |
| 157 | 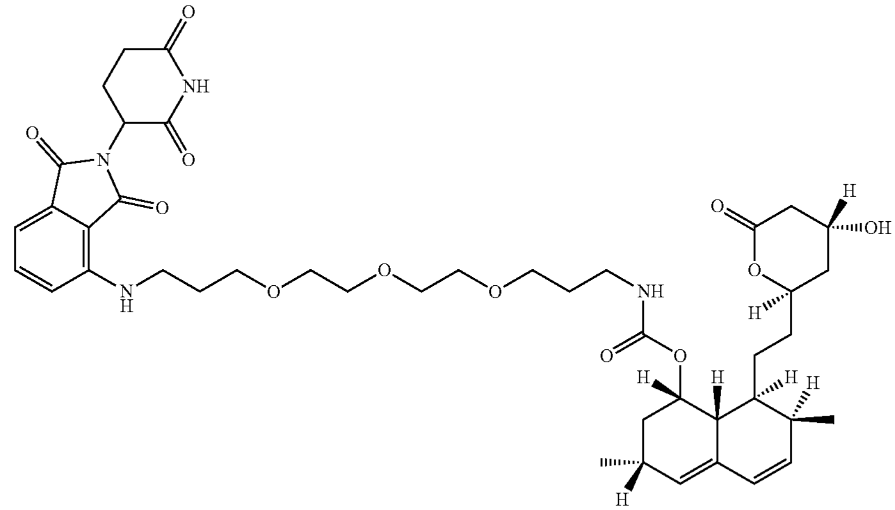 [SMILES: C[C@H]1C=C2C=C[C@H](C)[C@H](CC[C@@H]3C[C@@H](O)CC(=O)O3)[C@H]2[C@@H](OC(=O)NCCCOCCOCCOCCCNc2cccc3c2C(=O)N(C2CCC(=O)NC2=O)C3=O)C1] . |
* * * * *